United States Patent
Won et al.

(10) Patent No.: US 12,030,894 B2
(45) Date of Patent: Jul. 9, 2024

(54) COMPOSITION FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si (KR)

(72) Inventors: Jongwoo Won, Suwon-si (KR); Seonyeong Gwak, Suwon-si (KR); Mijin Lee, Suwon-si (KR); Jaehoon Kim, Suwon-si (KR); Hyung Sun Kim, Suwon-si (KR); Jinhyun Lui, Suwon-si (KR); Hayun Song, Suwon-si (KR); Chang Ju Shin, Suwon-si (KR); Hyunji Yoo, Suwon-si (KR); Seungjae Lee, Suwon-si (KR); Sung-Hyun Jung, Suwon-si (KR)

(73) Assignee: SAMSUNG SDI CO., LTD., Yongin-si (KR)

(*) Notice: Subject to any disclaimer, the term of this patent is extended or adjusted under 35 U.S.C. 154(b) by 454 days.

(21) Appl. No.: 17/466,504

(22) Filed: Sep. 3, 2021

(65) Prior Publication Data
US 2022/0081449 A1    Mar. 17, 2022

(30) Foreign Application Priority Data
Sep. 4, 2020    (KR) .................. 10-2020-0113367

(51) Int. Cl.
*C07D 498/04*    (2006.01)
*C07D 519/00*    (2006.01)
(Continued)

(52) U.S. Cl.
CPC ......... *C07D 498/04* (2013.01); *C07D 519/00* (2013.01); *H10K 85/622* (2023.02);
(Continued)

(58) Field of Classification Search
CPC .. C07D 498/04; C07D 519/00; H10K 85/654; H10K 85/6574; H10K 85/622;
(Continued)

(56) References Cited

U.S. PATENT DOCUMENTS

| | | |
|---|---|---|
| 5,061,569 A | 10/1991 | Vanslyke et al. |
| 8,987,715 B2 | 3/2015 | Nishimura et al. |

(Continued)

FOREIGN PATENT DOCUMENTS

| | | |
|---|---|---|
| CN | 107619412 A | 1/2018 |
| CN | 109791981 A | 5/2019 |

(Continued)

OTHER PUBLICATIONS

Chinese Office action dated Feb. 7, 2024.
Korean Office action dated Jan. 19, 2024.

*Primary Examiner* — Tu-Tu V Ho
(74) *Attorney, Agent, or Firm* — Lee IP Law, P.C.

(57) ABSTRACT

A composition for an organic optoelectronic device, an organic optoelectronic device including the same, and a display device, the composition including a first compound represented by a combination of Chemical Formula 1 and Chemical Formula 2, and a second compound represented by a combination of Chemical Formula 3 and Chemical Formula 4:

[Chemical Formula 1]

[Chemical Formula 2]

(Continued)

-continued

[Chemical Formula 3]

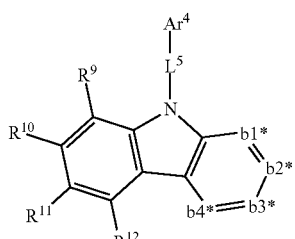

[Chemical Formula 4]

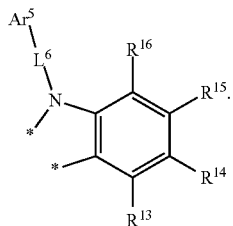

14 Claims, 2 Drawing Sheets

(51) Int. Cl.
 *H10K 85/60* (2023.01)
 *H10K 50/12* (2023.01)
 *H10K 101/30* (2023.01)
(52) U.S. Cl.
 CPC ....... H10K 85/654 (2023.02); H10K 85/6572 (2023.02); H10K 85/6574 (2023.02); H10K 85/6576 (2023.02); *H10K 50/12* (2023.02); *H10K 2101/30* (2023.02)

(58) Field of Classification Search
 CPC .......... H10K 85/6576; H10K 85/6572; H10K 50/12; H10K 2101/30
 USPC .......................................................... 257/40
 See application file for complete search history.

(56) References Cited

U.S. PATENT DOCUMENTS

| | | | |
|---|---|---|---|
| 9,293,716 | B2 | 3/2016 | Feldman et al. |
| 10,319,921 | B2* | 6/2019 | Kang ............ H10K 50/12 |
| 10,326,080 | B2 | 6/2019 | Cho et al. |
| 2019/0214573 | A1 | 7/2019 | Ryu et al. |
| 2020/0075866 | A1 | 3/2020 | Lee et al. |
| 2020/0079735 | A1 | 3/2020 | Ma et al. |

FOREIGN PATENT DOCUMENTS

| | | | |
|---|---|---|---|
| CN | 110294703 A | 10/2019 | |
| CN | 110872511 A | 3/2020 | |
| JP | 1993-009471 A | 1/1993 | |
| JP | 1995-126615 A | 5/1995 | |
| JP | 1998-095973 A | 4/1998 | |
| KR | 10-2011-0048838 A | 5/2011 | |
| KR | 10-1486561 B1 | 1/2015 | |
| KR | 10-2015-0124902 A | 11/2015 | |
| KR | 10-2017-0139443 A | 12/2017 | |
| KR | 10-2018-0008279 A | 1/2018 | |
| KR | 10-1877678 B1 | 7/2018 | |
| KR | 10-2019-0007968 A | 1/2019 | |
| KR | 10-2019-0010500 A | 1/2019 | |
| KR | 10-1959047 B1 | 3/2019 | |
| KR | 10-2019-0044338 A | 4/2019 | |
| KR | 10-2019-0055292 A | 5/2019 | |
| KR | 10-2019-0110775 A | 10/2019 | |
| KR | 10-2031300 B1 | 10/2019 | |
| KR | 10-2020-0013256 A | 2/2020 | |
| TW | I 680179 B | 12/2019 | |
| WO | WO 1995/009147 A1 | 4/1995 | |

* cited by examiner

COMPOSITION FOR ORGANIC OPTOELECTRONIC DEVICE, ORGANIC OPTOELECTRONIC DEVICE AND DISPLAY DEVICE

CROSS-REFERENCE TO RELATED APPLICATION

This application claims priority to and the benefit of Korean Patent Application No. 10-2020-0113367 filed in the Korean Intellectual Property Office on Sep. 4, 2020, the entire contents of which are incorporated herein by reference.

BACKGROUND

1. Field

Embodiments relate to a composition for an organic optoelectronic device, an organic optoelectronic device, and a display device.

2. Description of the Related Art

An organic optoelectronic device (e.g., organic optoelectronic diode) is a device capable of converting electrical energy and optical energy to each other.

Organic optoelectronic devices may be largely divided into two types according to a principle of operation. One is a photoelectric device that generates electrical energy by separating excitons formed by light energy into electrons and holes, and transferring the electrons and holes to different electrodes, respectively and the other is light emitting device that generates light energy from electrical energy by supplying voltage or current to the electrodes.

Examples of the organic optoelectronic device may include an organic photoelectric device, an organic light emitting diode, an organic solar cell, and an organic photoconductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode may be influenced by an organic material between electrodes.

SUMMARY

The embodiments may be realized by providing a composition for an organic optoelectronic device, the composition including a first compound represented by a combination of Chemical Formula 1 and Chemical Formula 2, and a second compound represented by a combination of Chemical Formula 3 and Chemical Formula 4:

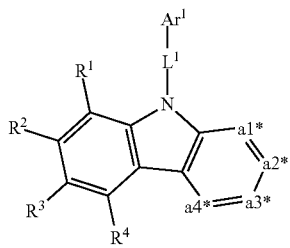

[Chemical Formula 1]

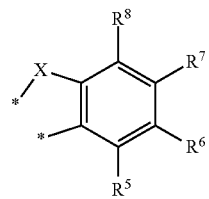

[Chemical Formula 2]

wherein, in Chemical Formula 1 and Chemical Formula 2, X is O or S, $Ar^1$ is a substituted or unsubstituted C6 to C30 aryl group or a substituted or unsubstituted C2 to C30 heterocyclic group, two adjacent ones of a1* to a4* of Chemical Formula 1 are linking carbons linked at * of Chemical Formula 2, the remaining two of a1* to a4* of Chemical Formula 1, not linked at * of Chemical Formula 2, are $CR^a$, $L^1$ is a single bond or a substituted or unsubstituted C6 to C30 arylene group, $R^a$ and $R^1$ to $R^8$ are each independently hydrogen, deuterium, a substituted or unsubstituted C1 to C30 alkyl group, a substituted or unsubstituted C6 to C30 aryl group, or a substituted or unsubstituted C2 to C30 heterocyclic group, and at least one of $R^5$ to $R^8$ is represented by Chemical Formula a, in which * is a linking point,

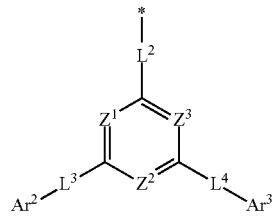

[Chemical Formula a]

wherein, in Chemical Formula a, $Z^1$ to $Z^3$ are each independently N or $CR^b$, at least two of $Z^1$ to $Z^3$ are N, $L^2$ to $L^4$ are each independently a single bond or a substituted or unsubstituted C6 to C30 arylene group, $Ar^2$ and $Ar^3$ are each independently a substituted or unsubstituted C6 to C30 aryl group or a substituted or unsubstituted C2 to C30 heterocyclic group, $R^b$ is hydrogen, deuterium, a substituted or unsubstituted C1 to C30 alkyl group, a substituted or unsubstituted C6 to C30 aryl group, or a substituted or unsubstituted C2 to C30 heterocyclic group, and * is a linking point;

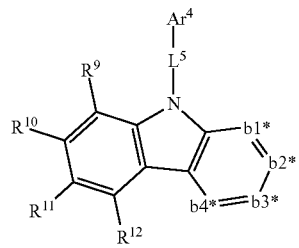

[Chemical Formula 3]

-continued

[Chemical Formula 4]

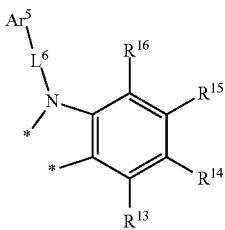

wherein, in Chemical Formula 3 and Chemical Formula 4, two adjacent ones of b1* to b4* of Chemical Formula 3 are linking carbons linked at * of Chemical Formula 4, the remaining two of b1* to b4* of Chemical Formula 3, not linked at * of Chemical Formula 4, are CRC, $Ar^4$ and $Ar^5$ are each independently a substituted or unsubstituted C6 to C30 aryl group, a substituted or unsubstituted carbazolyl group, a substituted or unsubstituted dibenzofuranyl group, or a substituted or unsubstituted dibenzothiophenyl group, $L^5$ and $L^6$ are each independently a single bond, or a substituted or unsubstituted C6 to C30 arylene group, and $R^c$ and $R^9$ to $R^{16}$ are each independently hydrogen, deuterium, a substituted or unsubstituted C1 to C30 alkyl group, or a substituted or unsubstituted C6 to C30 aryl group.

The embodiments may be realized by providing an organic optoelectronic device including an anode and a cathode facing each other, at least one organic layer between the anode and the cathode, wherein the at least one organic layer includes a light emitting layer, the light emitting layer includes the composition for an organic optoelectronic device according to an embodiment.

The embodiments may be realized by providing a display device comprising the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
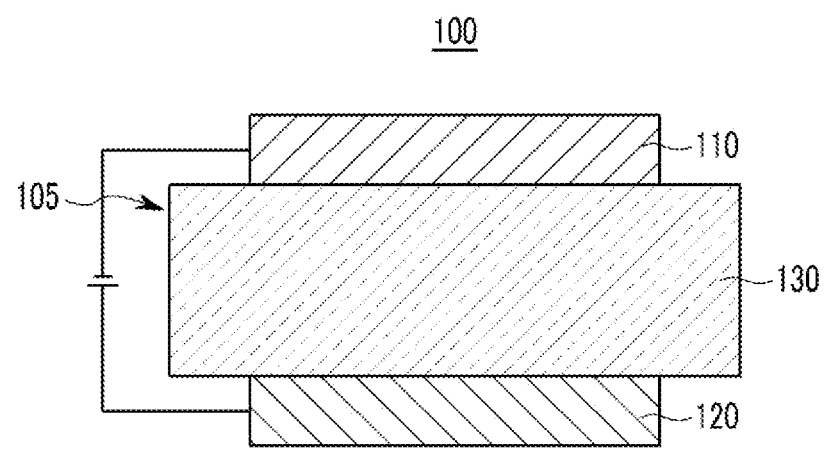
FIGS. 1 to 4 are cross-sectional views each illustrating an organic light emitting diode according to embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof. As used herein, the term "or" is not an exclusive term, e.g., "A or B" would include A, B, or A and B.

In one example, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In specific example, the "substituted" refers to replacement of at least one hydrogen of a substituent or a compound by deuterium, a C1 to C20 alkyl group, a C6 to C30 aryl group, or a cyano group. In specific example, the "substituted" refers to replacement of at least one hydrogen of a substituent or a compound by deuterium, a C1 to C5 alkyl group, a C6 to C18 aryl group, or a cyano group. In specific example, the "substituted" refers to replacement of at least one hydrogen of a substituent or a compound by deuterium, a cyano group, a methyl group, an ethyl group, a propanyl group, a butyl group, a phenyl group, a biphenyl group, a terphenyl group, or a naphthyl group.

In the present specification, when a definition is not otherwise provided, "hetero" refers to one including one to three heteroatoms selected from N, O, S, P, and Si, and remaining carbons in one functional group.

In the present specification, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic, or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectronic device according to an embodiment is described.

A composition for an organic optoelectronic device according to an embodiment may include, e.g., a first compound represented by a combination of Chemical Formula 1 and Chemical Formula 2, and a second compound represented by a combination of Chemical Formula 3 and Chemical Formula 4.

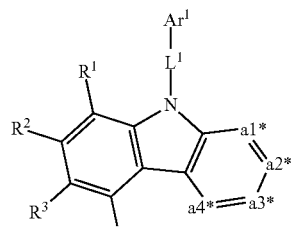

[Chemical Formula 1]

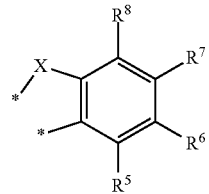

[Chemical Formula 2]

In Chemical Formula 1 and Chemical Formula 2, X may be, e.g., O or S.

$Ar^1$ may be or may include, e.g., a substituted or unsubstituted C6 to C30 aryl group or a substituted or unsubstituted C2 to C30 heterocyclic group.

Two adjacent ones of a1* to a4* of Chemical Formula 1 may be, e.g., linking carbons linked at * of Chemical Formula 2, and the remaining two of a1* to a4* of Chemical Formula 1, not linked at * of Chemical Formula 2, may be $CR^a$. As used herein, the term "linking carbon" refers to a shared carbon at which fused rings are linked.

$L^1$ may be or may include, e.g., a single bond or a substituted or unsubstituted C6 to C30 arylene group.

$R^a$ and $R^1$ to $R^8$ may each independently be or include, e.g., hydrogen, deuterium, a substituted or unsubstituted C1 to C30 alkyl group, a substituted or unsubstituted C6 to C30 aryl group or a substituted or unsubstituted C2 to C30 heterocyclic group.

In an implementation, at least one of $R^5$ to $R^8$ may be, e.g., a substituted heterocyclic group represented by Chemical Formula a.

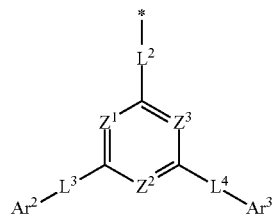

[Chemical Formula a]

In Chemical Formula a, $Z^1$ to $Z^3$ may each independently be, e.g., N or $CR^b$. In an implementation, at least two of $Z^1$ to $Z^3$ may be N.

$L^2$ to $L^4$ may each independently be or include, e.g., a single bond or a substituted or unsubstituted C6 to C30 arylene group.

$Ar^2$ and $Ar^3$ may each independently be or include, e.g., a substituted or unsubstituted C6 to C30 aryl group or a substituted or unsubstituted C2 to C30 heterocyclic group.

R$^b$ may be or include, e.g., hydrogen, deuterium, a substituted or unsubstituted C1 to C30 alkyl group, a substituted or unsubstituted C6 to C30 aryl group or a substituted or unsubstituted C2 to C30 heterocyclic group.

* is a linking point.

[Chemical Formula 3]

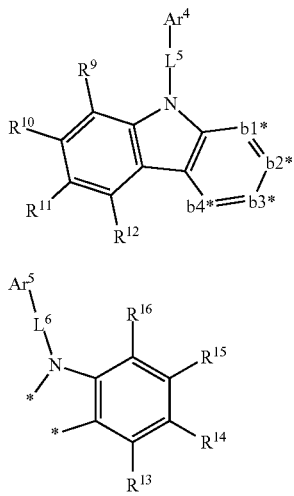

[Chemical Formula 4]

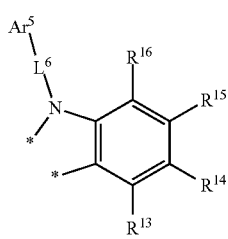

In Chemical Formula 3 and Chemical Formula 4, two adjacent ones of b1* to b4* of Chemical Formula 3 may be linking carbons linked at * of Chemical Formula 4, and the remaining two of b1* to b4* of Chemical Formula 3, not linked at * of Chemical Formula 4 may be CRC.

Ar$^4$ and Ar$^5$ may each independently be or include, e.g., a substituted or unsubstituted C6 to C30 aryl group, a substituted or unsubstituted carbazolyl group, a substituted or unsubstituted dibenzofuranyl group or a substituted or unsubstituted dibenzothiophenyl group.

L$^5$ and L$^6$ may each independently be or include, e.g., a single bond or a substituted or unsubstituted C6 to C30 arylene group.

R$^c$ and R$^9$ to R$^{16}$ may each independently be or include, e.g., hydrogen, deuterium, a substituted or unsubstituted C1 to C30 alkyl group, a substituted or unsubstituted C6 to C30 aryl group, a substituted or unsubstituted C2 to C30 heterocyclic group.

The first compound (represented by the combination of Chemical Formula 1 and Chemical Formula 2) may have a structure that includes an indolodibenzofuran (or indolodibenzothiophene) skeleton, and the indolodibenzofuran (or indolodibenzothiophene) skeleton may be substituted with a nitrogen-containing 6-membered ring.

The first compound having such a structure may have a high glass transition temperature and at the same time may be deposited at a relatively low temperature, so it may have excellent thermal stability. In an implementation, a relatively low driving voltage, and high efficiency characteristics may be realized due to improved electron transport characteristics.

In an implementation, when applied to an organic light emitting device together with the second compound having excellent hole transport characteristics, high efficiency and long life-span may be realized by charge balance.

The second compound may include an indolocarbazole skeleton, and may be included together with the aforementioned first compound to help increase the balance of holes and electrons to greatly improve the life-span characteristics of a device including them.

In an implementation, the first compound (e.g., the combination of Chemical Formula 1 and Chemical Formula 2) may be represented by, e.g., one of Chemical Formula 1A to Chemical Formula 1F.

[Chemical Formula 1A]

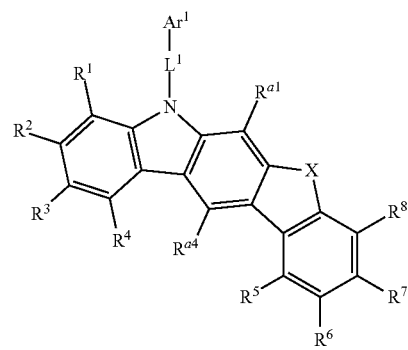

[Chemical Formula 1B]

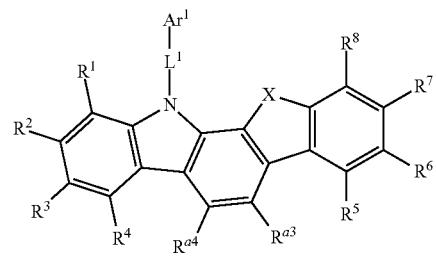

[Chemical Formula 1C]

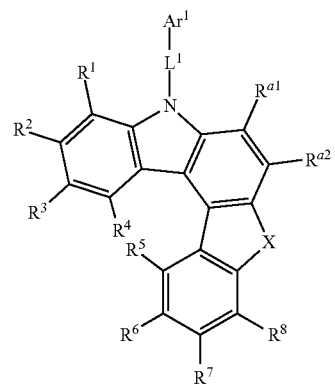

[Chemical Formula 1D]

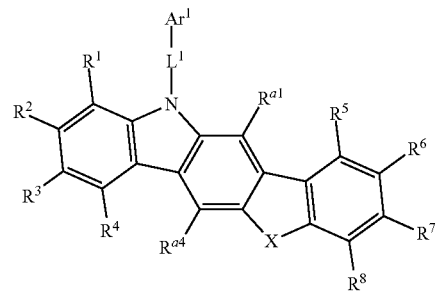

[Chemical Formula 1E]

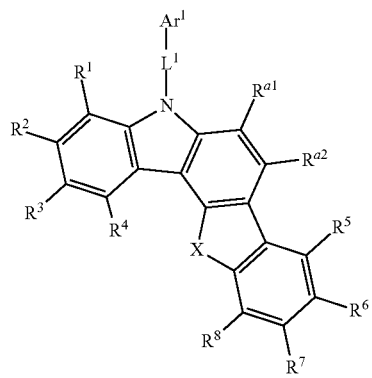

[Chemical Formula 1F]

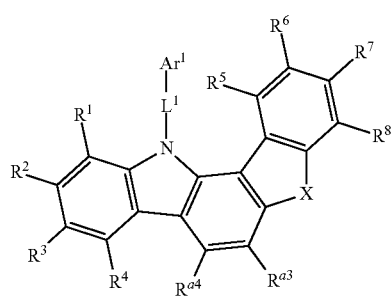

In Chemical Formula 1A to Chemical Formula 1F, X, $L^1$, $Ar^1$, and $R^1$ to $R^8$ may be defined the same as described above, and $R^{a1}$ to $R^{a4}$ may each independently be defined the same as $R^a$ described above.

In an implementation, the first compound may include the skeleton represented by Chemical Formula 1A, and, e.g., may be represented by one of Chemical Formula 1A-1 to Chemical Formula 1A-4.

[Chemical Formula 1A-1]

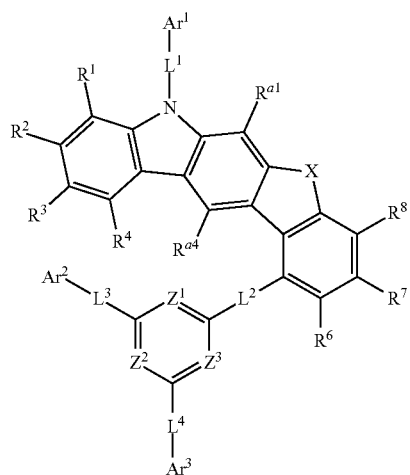

[Chemical Formula 1A-2]

[Chemical Formula 1A-3]

[Chemical Formula 1A-4]

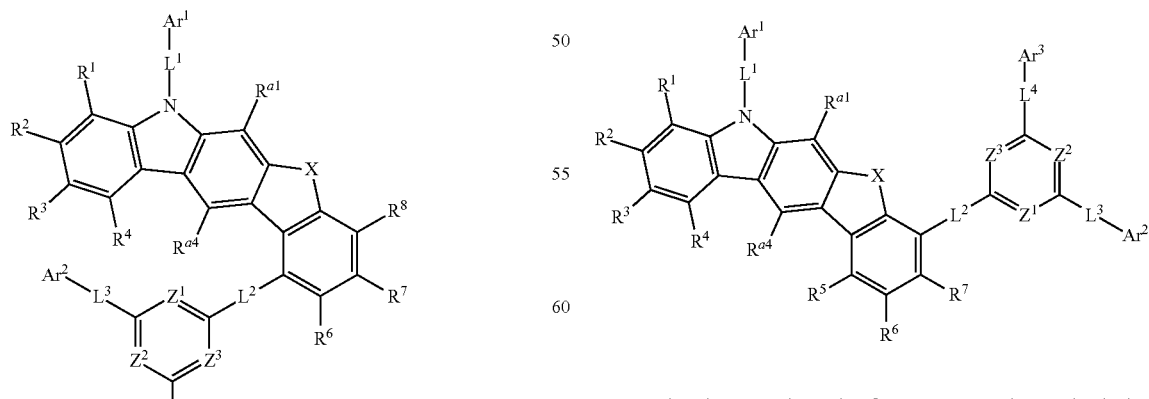

In an implementation, the first compound may include a skeleton represented by Chemical Formula 1B, and, e.g., may be represented by one of Chemical Formula 1B-1 to Chemical Formula 1B-4.

[Chemical Formula 1B-1]
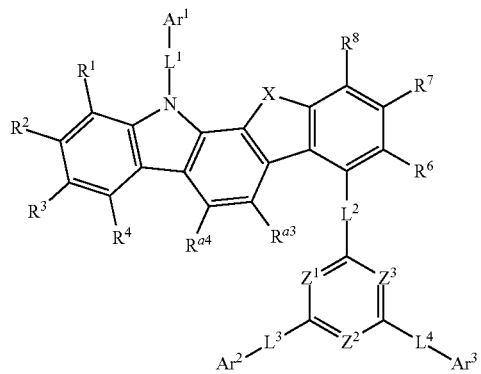
[Chemical Formula 1B-2]
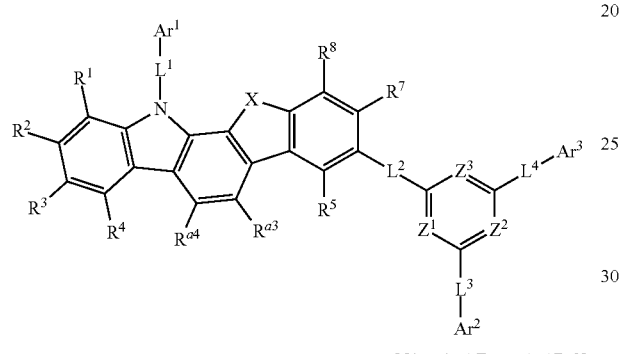
[Chemical Formula 1B-3]
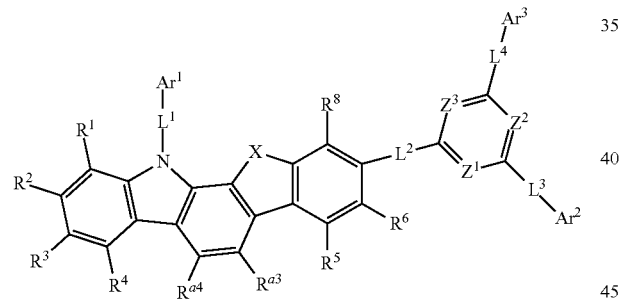
[Chemical Formula 1B-4]
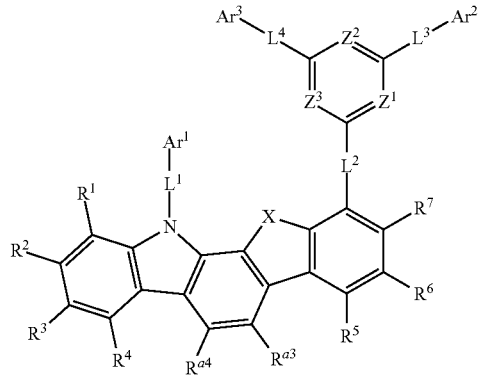
[Chemical Formula 1C-1]
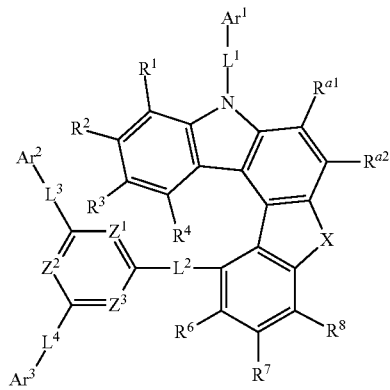
[Chemical Formula 1C-2]
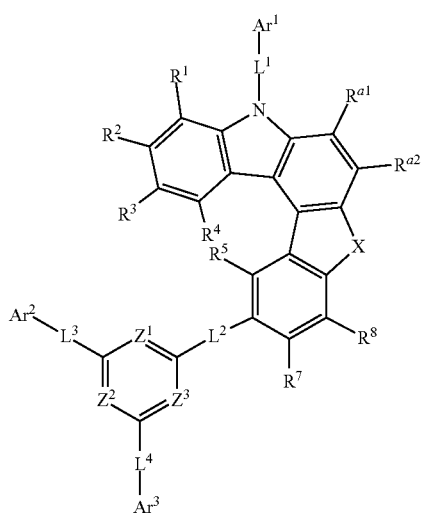
[Chemical Formula 1C-3]
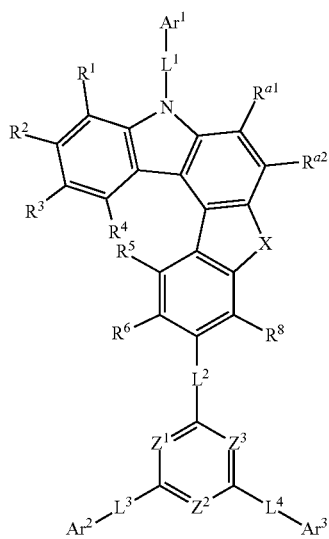
In an implementation, the first compound may include a skeleton represented by Chemical Formula 1C, and, e.g., may be represented by one of Chemical Formula 1C-1 to Chemical Formula 1C-4.

[Chemical Formula 1C-4]

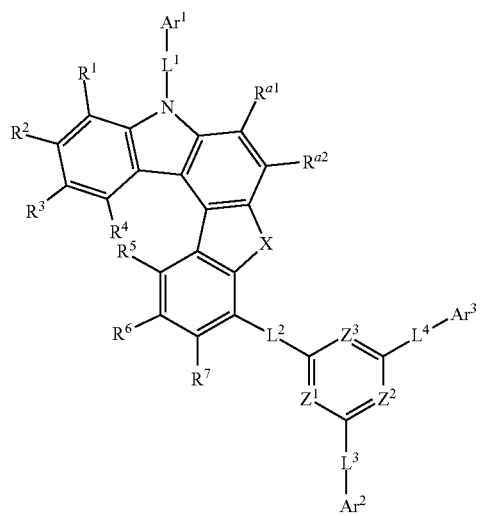

[Chemical Formula 1D-3]

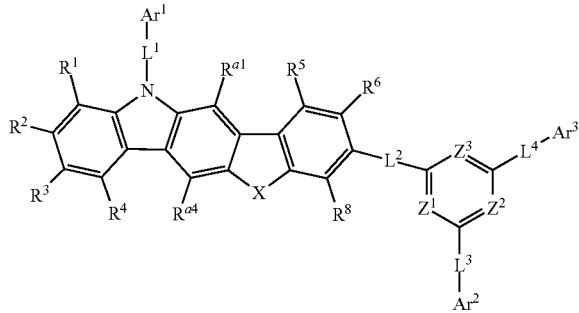

In an implementation, the first compound may include a skeleton represented by Chemical Formula 1D, and, e.g., may be represented by one of Chemical Formula 1D-1 to Chemical Formula 1D-4.

[Chemical Formula 1D-1]

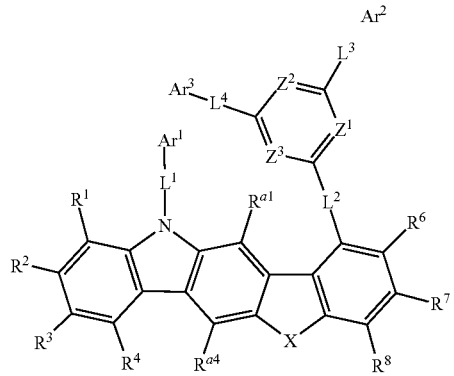

[Chemical Formula 1D-4]

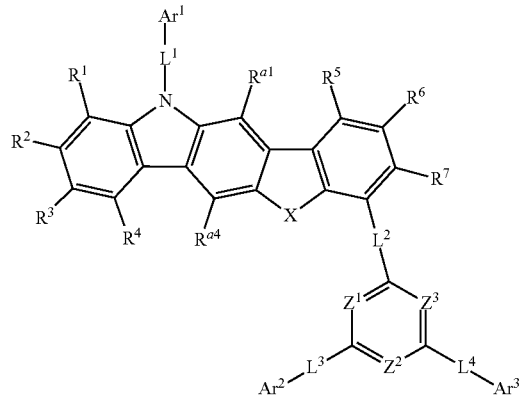

In an implementation, the first compound may include a skeleton represented by Chemical Formula 1E, and, e.g., may be represented by one of Chemical Formula 1E-1 to Chemical Formula 1E-4.

[Chemical Formula 1D-2]

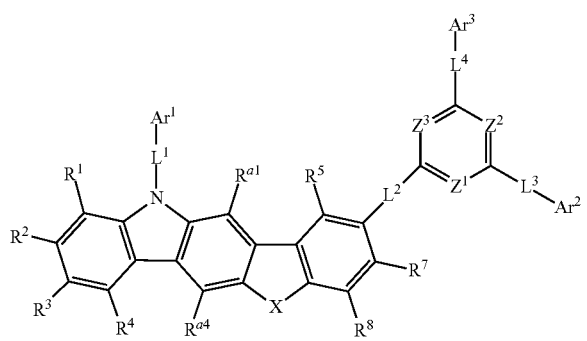

[Chemical Formula 1E-1]

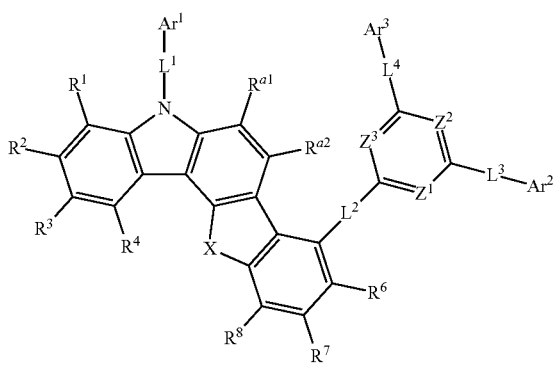

-continued
[Chemical Formula 1E-2]
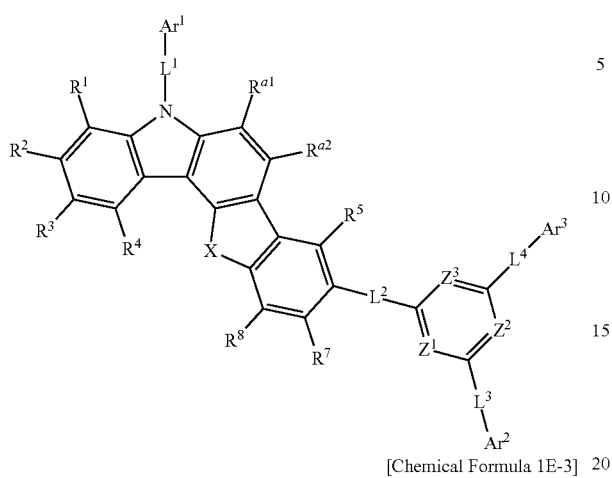
[Chemical Formula 1E-3]
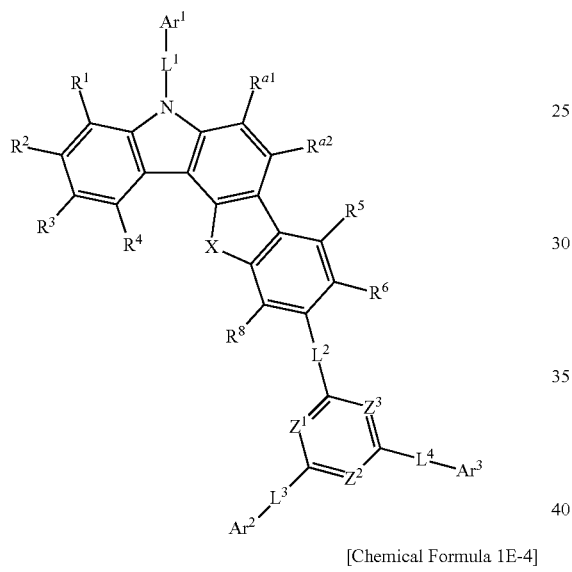
[Chemical Formula 1E-4]
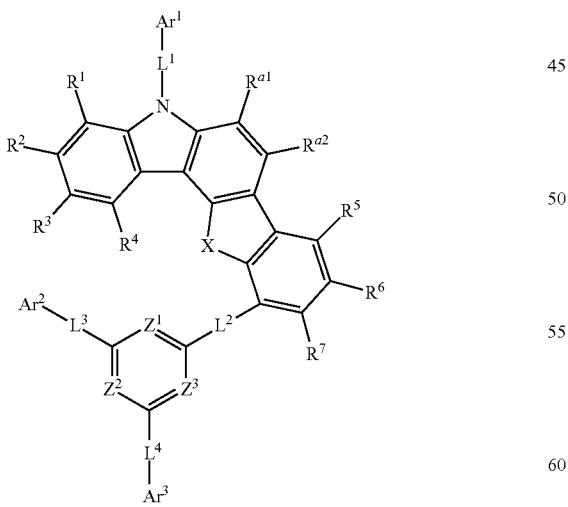
[Chemical Formula 1F-1]
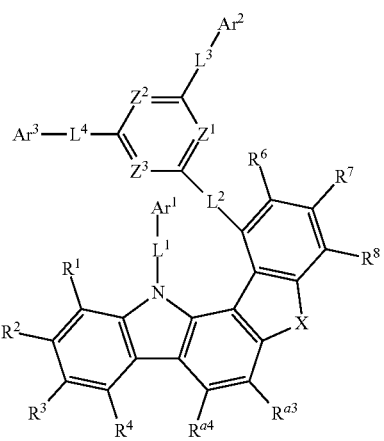
[Chemical Formula 1F-2]
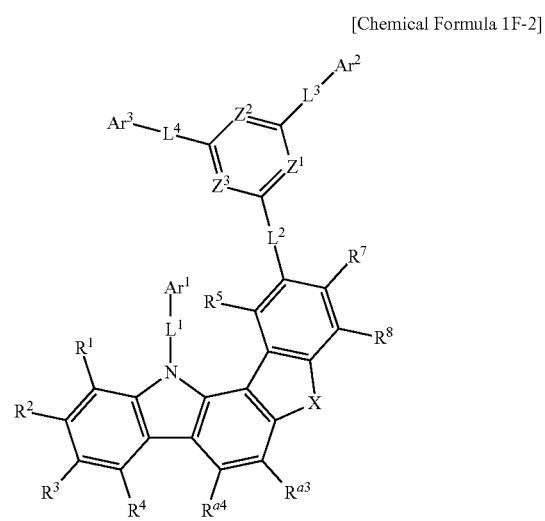
[Chemical Formula 1F-3]
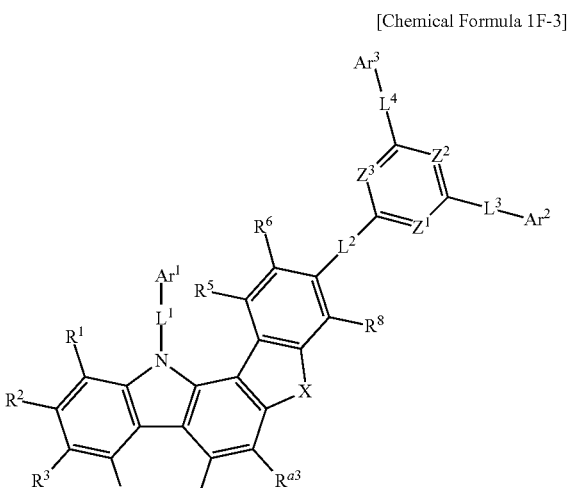
In an implementation, the first compound may include a skeleton represented by Chemical Formula 1F, and, e.g., may be represented by one of Chemical Formula 1F-1 to Chemical Formula 1F-4.

[Chemical Formula 1F-4]

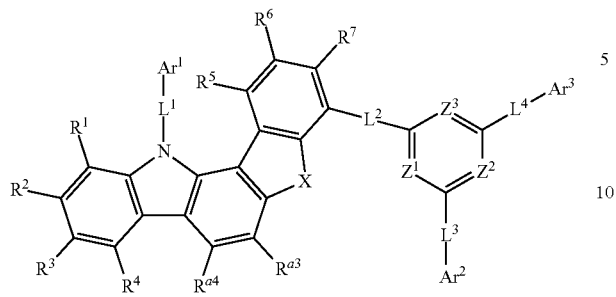

In Chemical Formula 1A-1 to Chemical Formula 1A-4, Chemical Formula 1B-1 to Chemical Formula 1B-4, Chemical Formula 1C-1 to Chemical Formula 1C-4, Chemical Formula 1D-1 to Chemical Formula 1D-4, Chemical Formula 1E-1 to Chemical Formula 1E-4, and Chemical Formula 1F-1 to Chemical Formula 1F-4, X, $Ar^1$ to $Ar^3$, and $L^1$ to $L^4$ may be defined the same as described above, and $R^{a1}$ to $R^{a4}$, and $R^1$ to $R^8$ may each independently be, e.g., hydrogen, deuterium, a substituted or unsubstituted C1 to C30 alkyl group, a substituted or unsubstituted C6 to C30 aryl group, or a substituted or unsubstituted C2 to C20 heterocyclic group.

In an implementation, AO may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group or a substituted or unsubstituted fluorene group, the $Ar^2$ and $Ar^3$ are each independently a substituted or unsubstituted phenyl group, a substituted or unsubstituted biphenyl group, a substituted or unsubstituted terphenyl group, a substituted or unsubstituted fluorene group, a substituted or unsubstituted dibenzofuranyl group, a substituted or unsubstituted dibenzothiophenyl group, a substituted or unsubstituted carbazolyl group, or a substituted or unsubstituted pyridinyl group.

In an implementation, Chemical Formula a may be, e.g., a group of the following Group I.

[Group I]

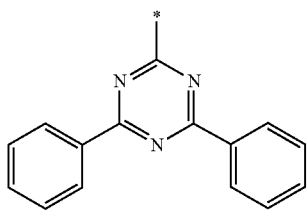

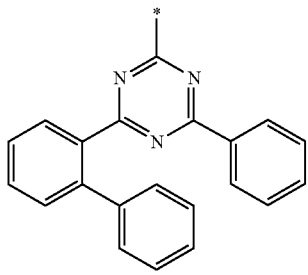

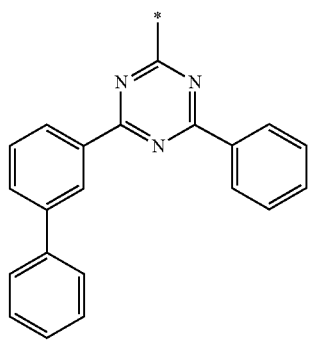

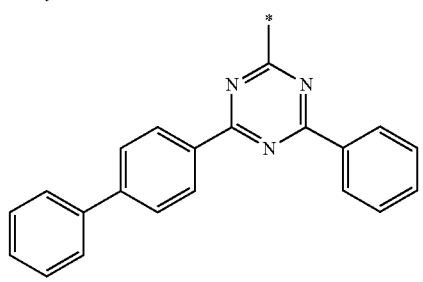

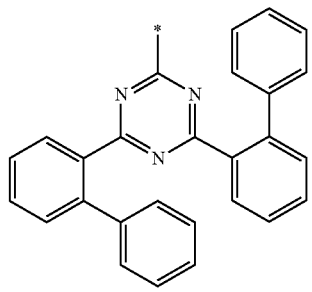

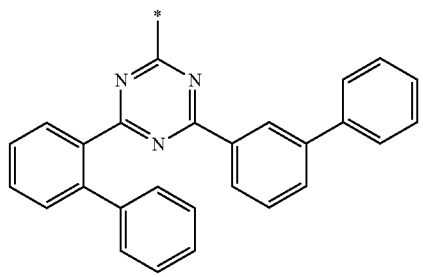

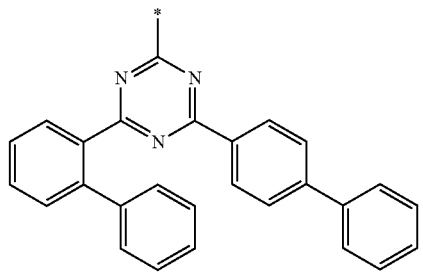

-continued
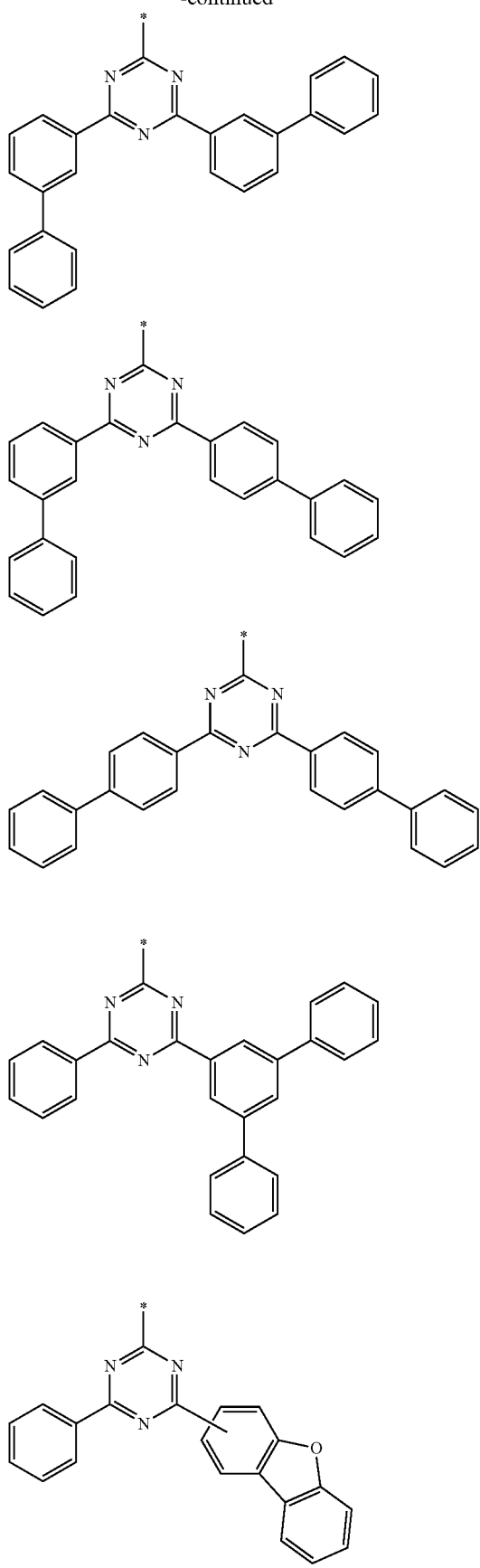
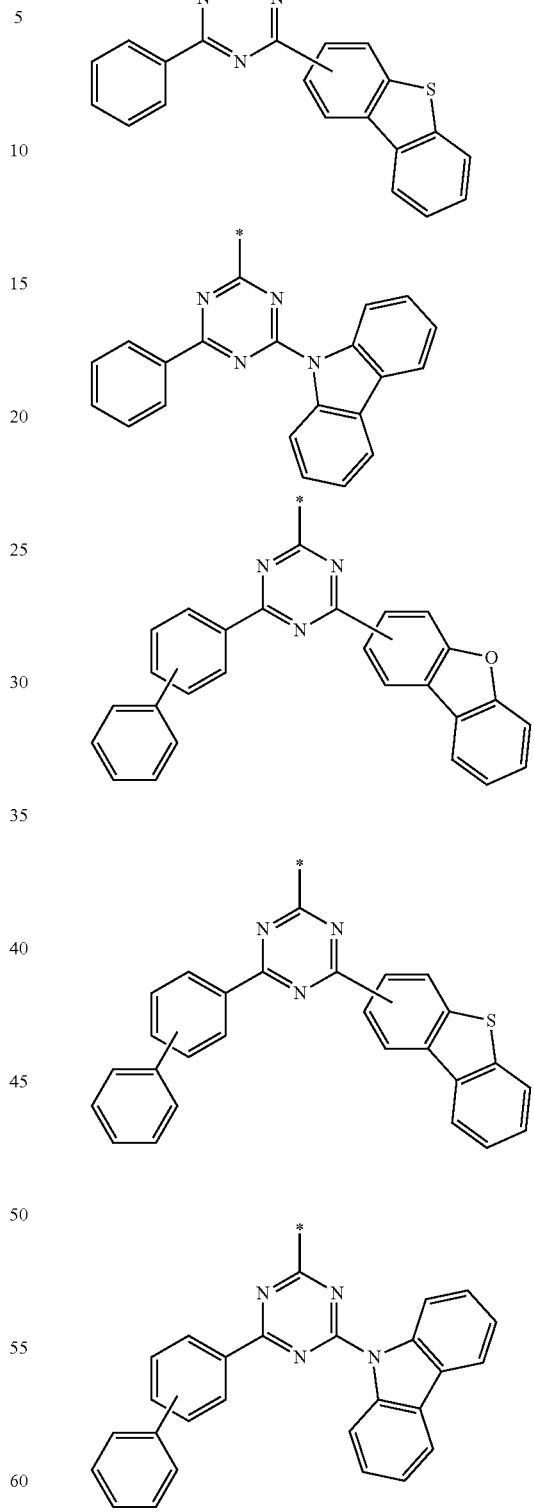
In Group I, * is a linking point.
In an implementation, $L^1$ may be, e.g., a single bond, a substituted or unsubstituted phenylene group, or a substituted or unsubstituted biphenylene group.

In an implementation, $L^2$ to $L^4$ may each independently be, e.g., a single bond or a substituted or unsubstituted phenylene group.

In an implementation, $R^a$, $R^{a1}$ to $R^{a4}$, and $R^1$ to $R^8$ may each independently be, e.g., hydrogen, deuterium, a substituted or unsubstituted C1 to C5 alkyl group, a substituted or unsubstituted phenyl group, or a substituted or unsubstituted pyridinyl group.

In an implementation, the first compound may be, e.g., represented by Chemical Formula 1B.

In an implementation, the first compound may be, e.g., represented by Chemical Formula 1B-1 or Chemical Formula 1B-4.

When the first compound is represented by Chemical Formula 1B-1 or Chemical Formula 1B-4, deposition at a lower temperature may be possible.

In an implementation, the first compound may be, e.g., represented by Chemical Formula 1B-4.

In an implementation, the first compound may be, e.g., a compound of Group 1.

[Group 1]

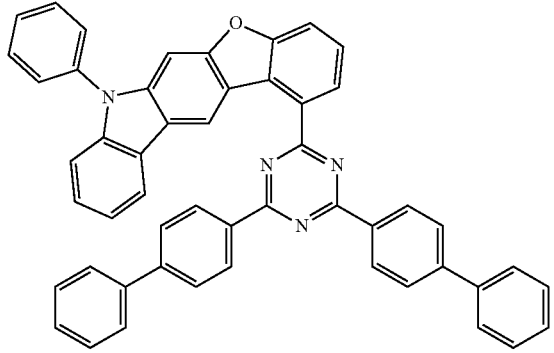

1A-1-1

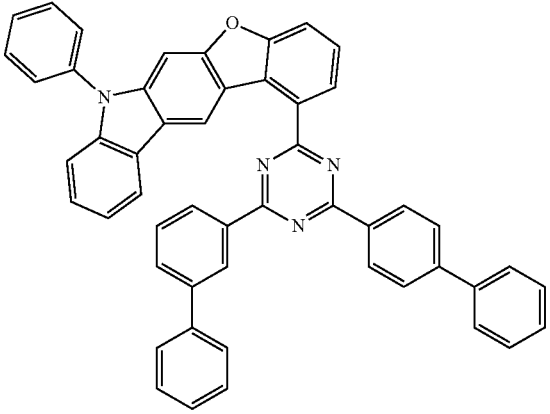

1A-1-2

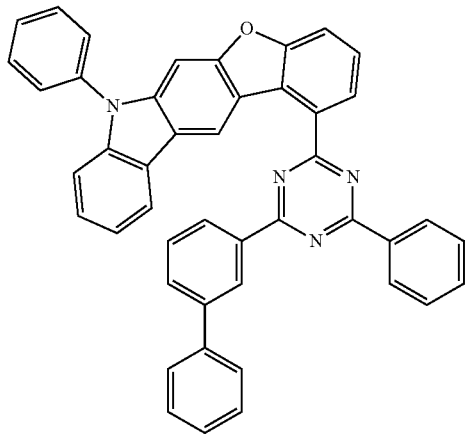

1A-1-3

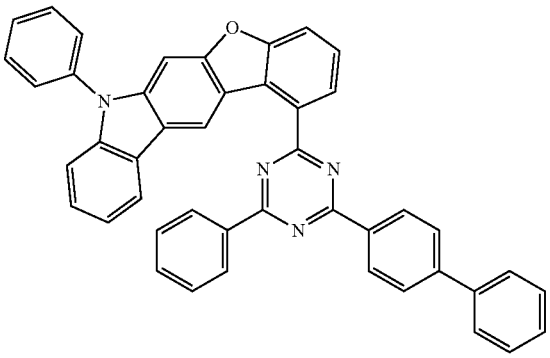

1A-1-4

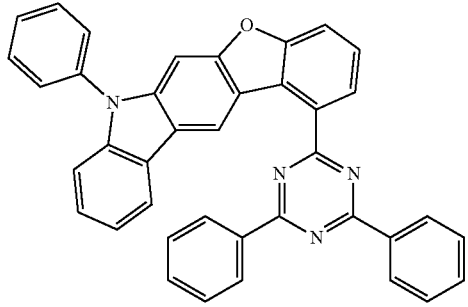

1A-1-5

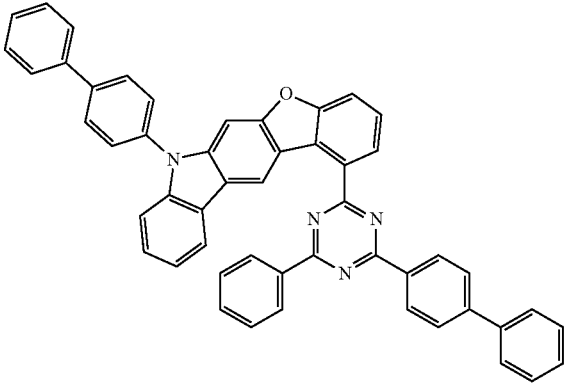

1A-1-6

-continued
1A-1-7
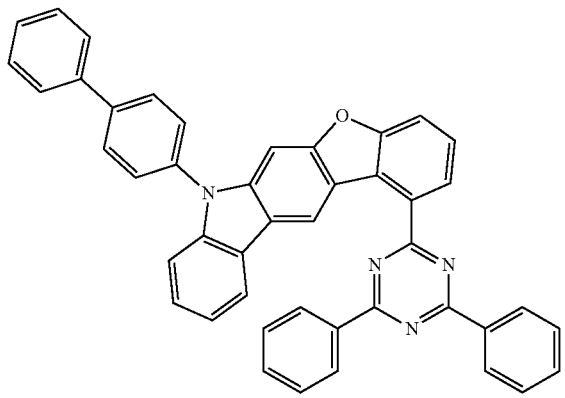
1A-1-8
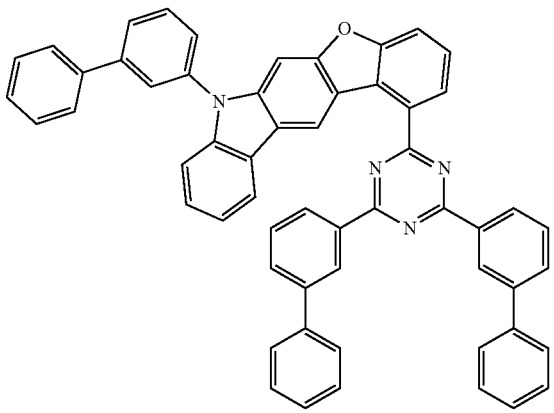
1A-1-9
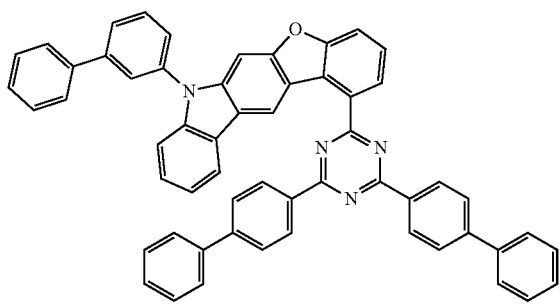
1A-1-10
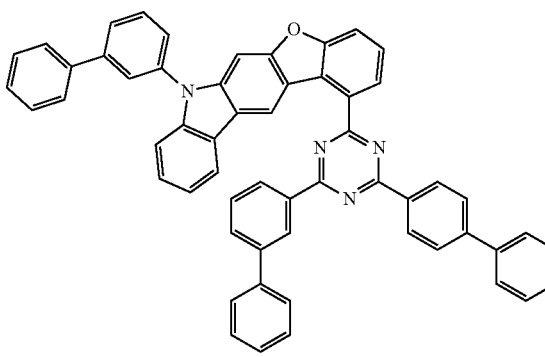
1A-1-11
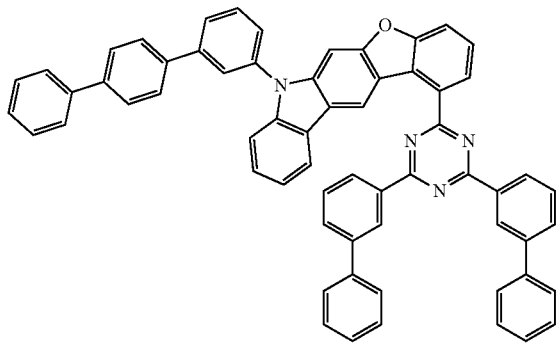
1A-1-12
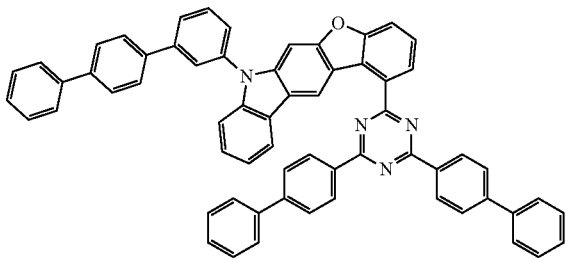
1A-1-13
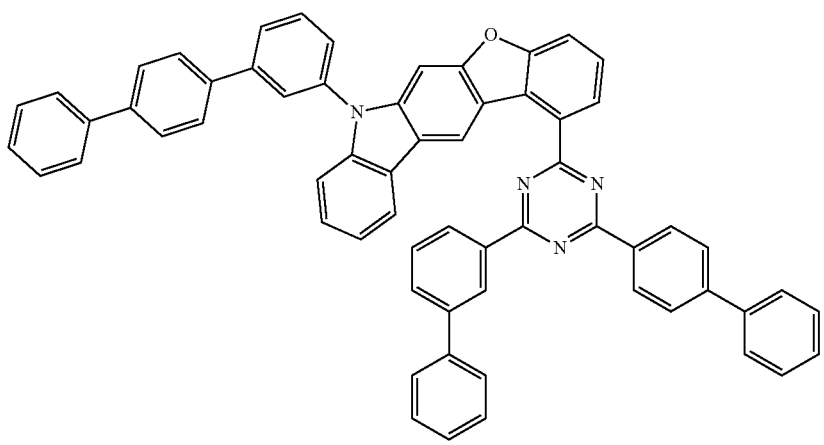

1A-1-14
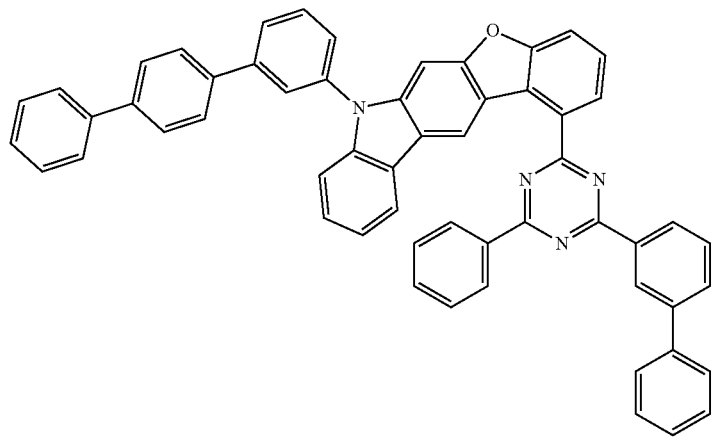
1A-1-15
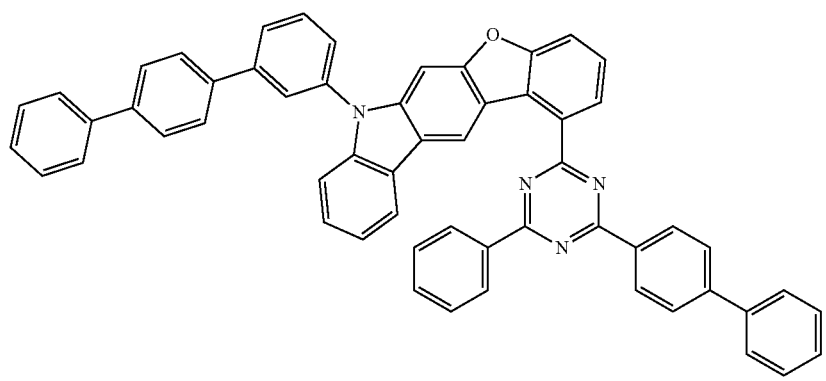
1A-1-16
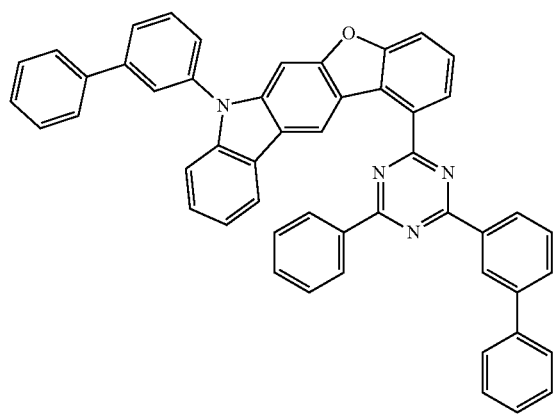
1A-1-17
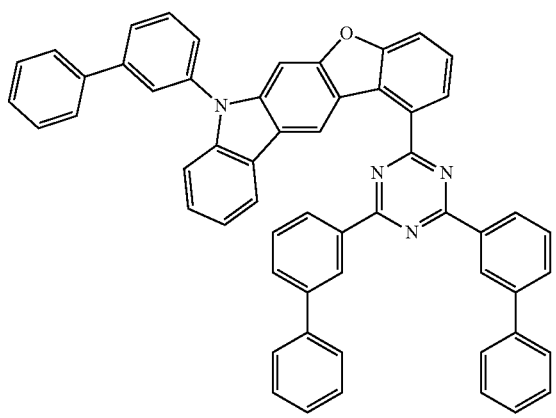

-continued
1A-1-18
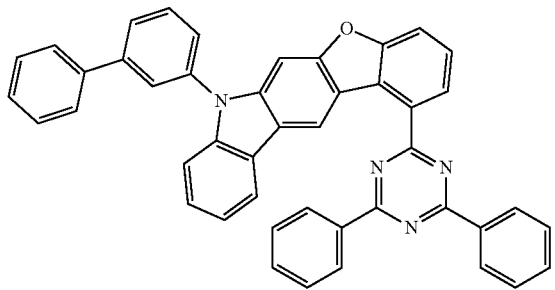
1A-1-19
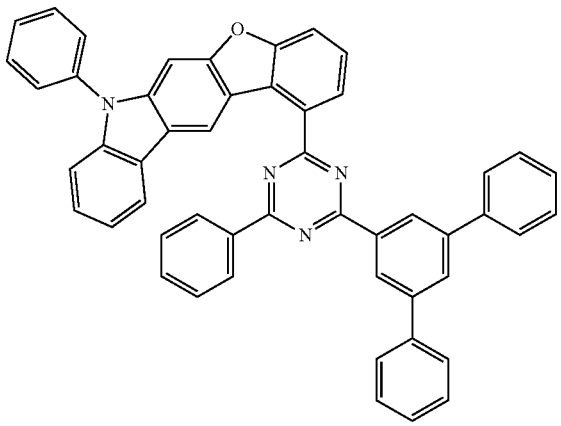
1A-1-20
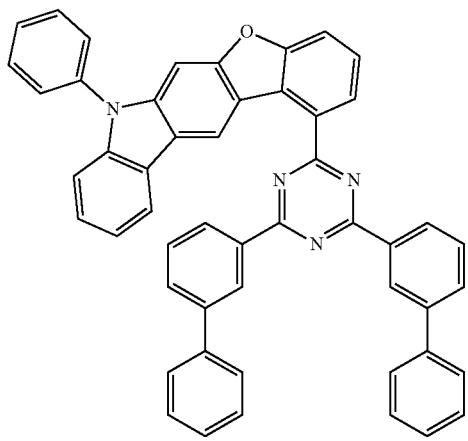
1A-1-21
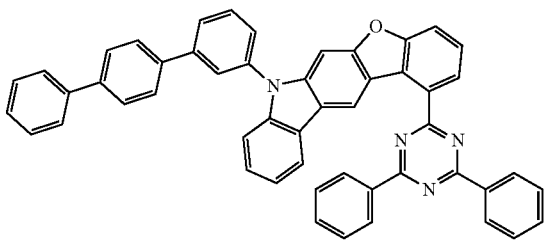
1A-1-22
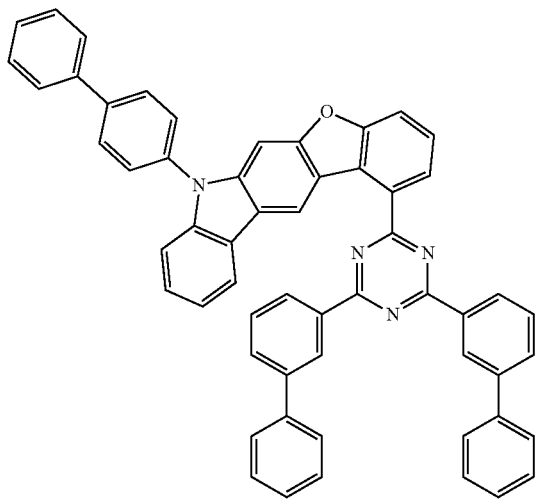
1A-1-23
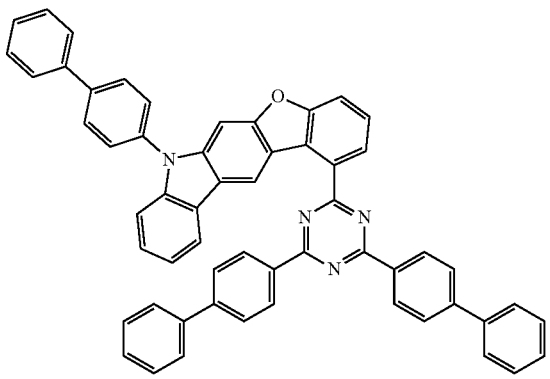

-continued
1A-1-24
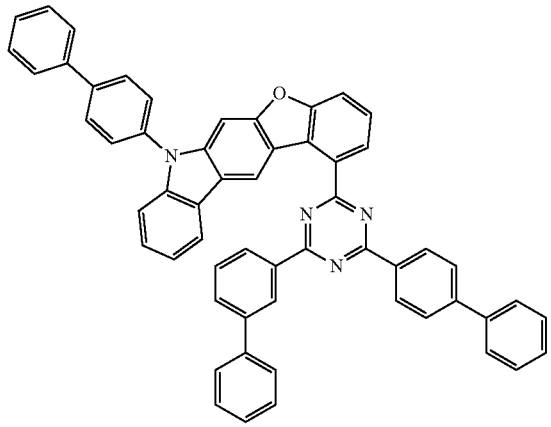
1A-1-25
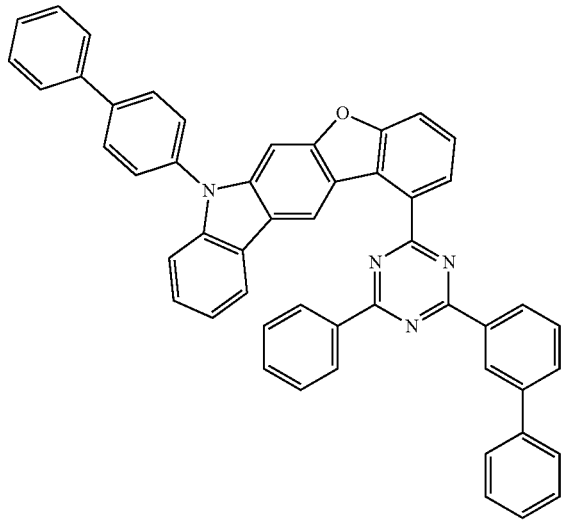
1A-1-26
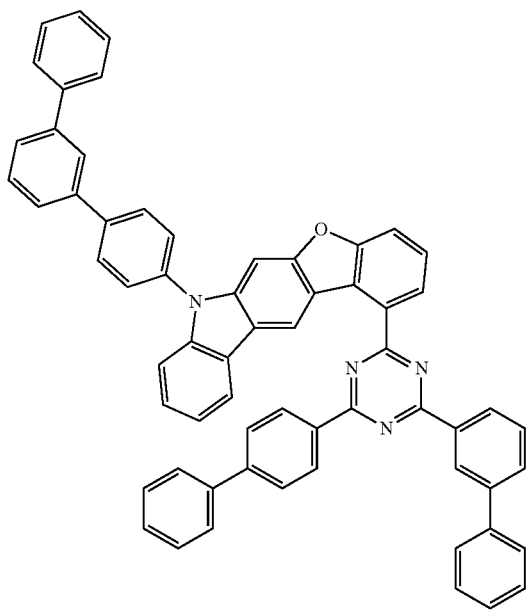
1A-1-27
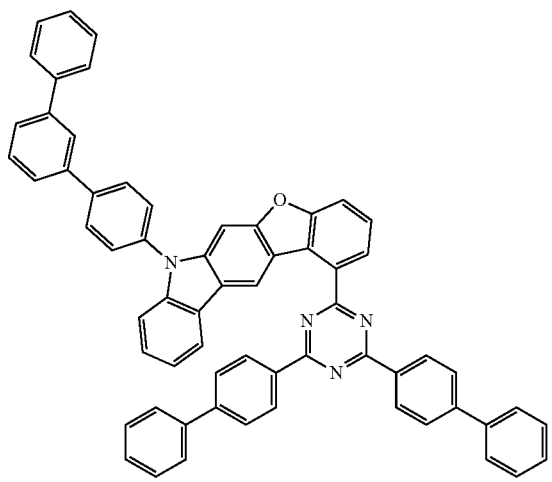

-continued
1A-1-28
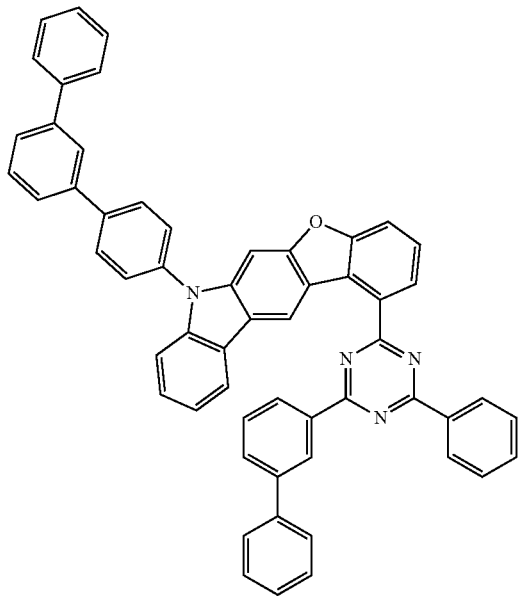
1A-1-29
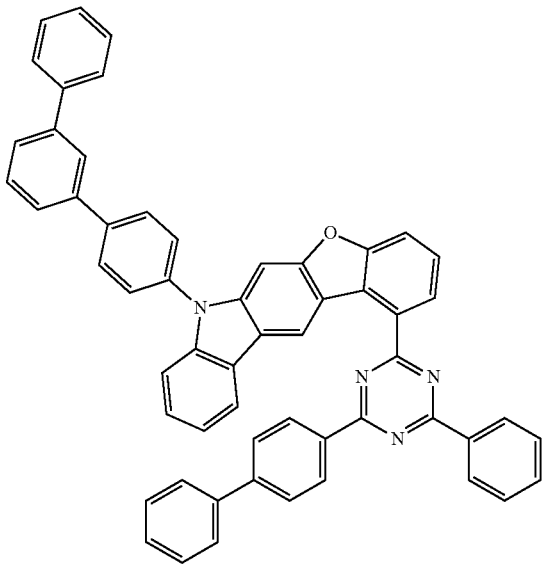
1A-1-30
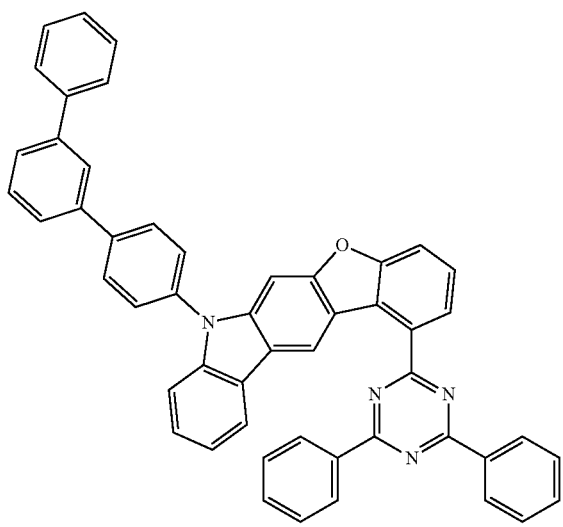
1A-1-31
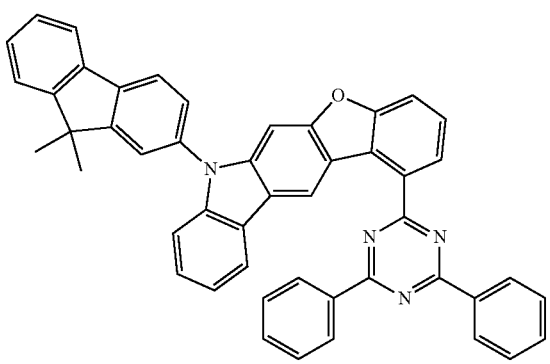
1A-1-32
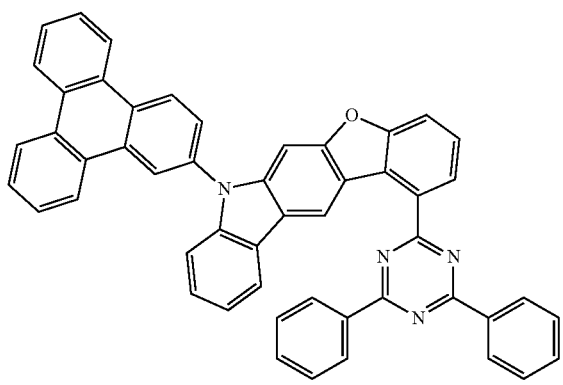
1A-1-33
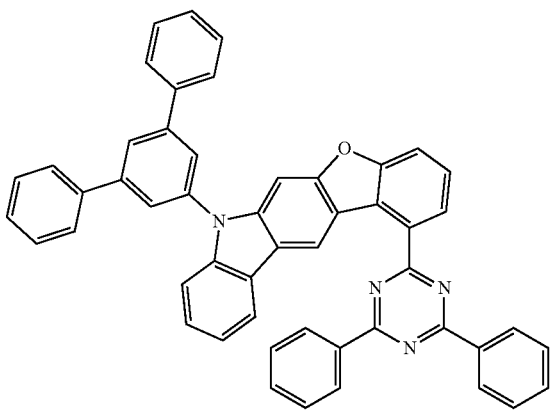

-continued
1A-1-34
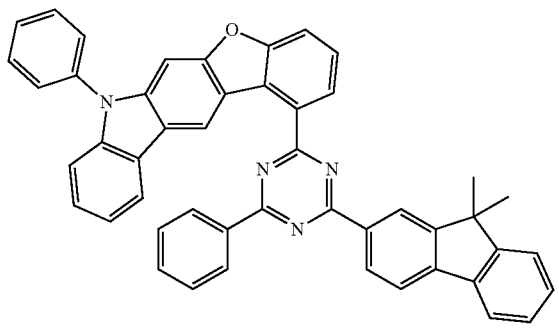
1A-1-35
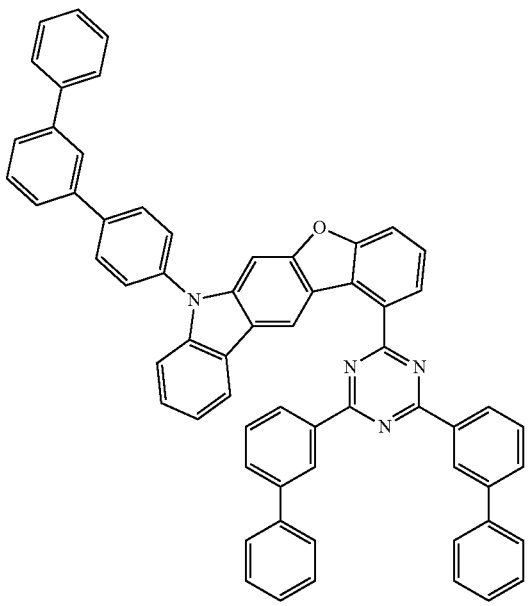
1A-1-36
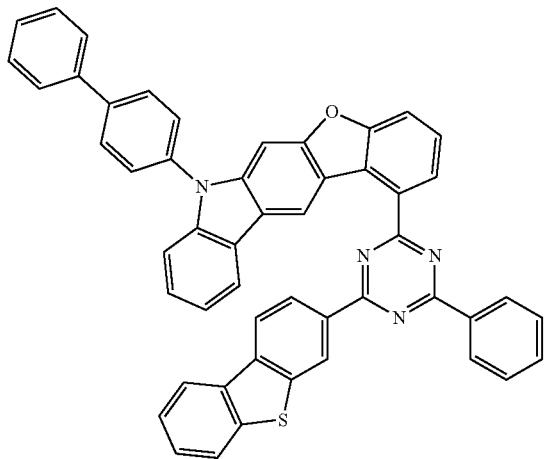
1A-1-37
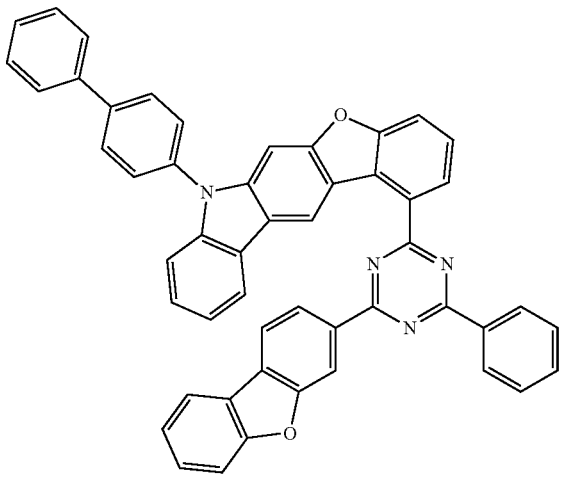
1A-1-38
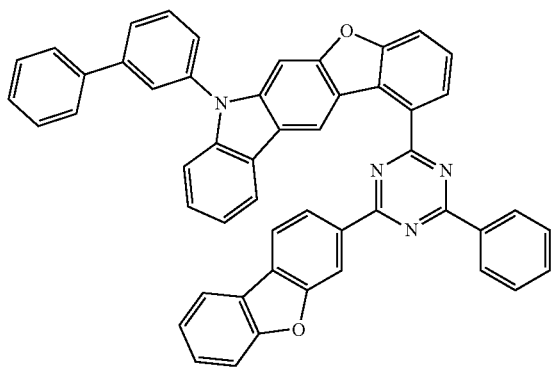
1A-1-39
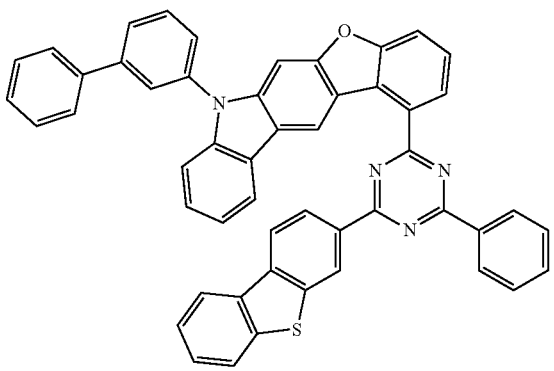

-continued
1A-1-40
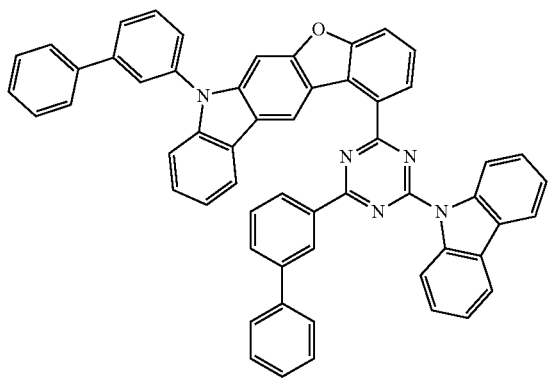
1A-1-41
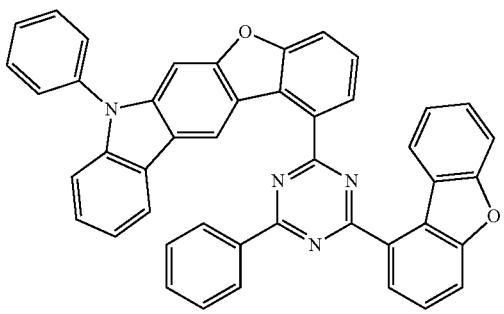
1A-1-42
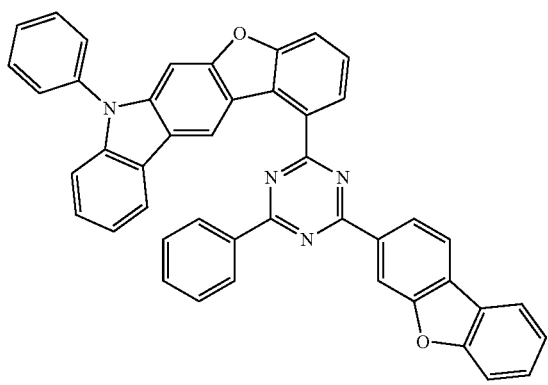
1A-1-43
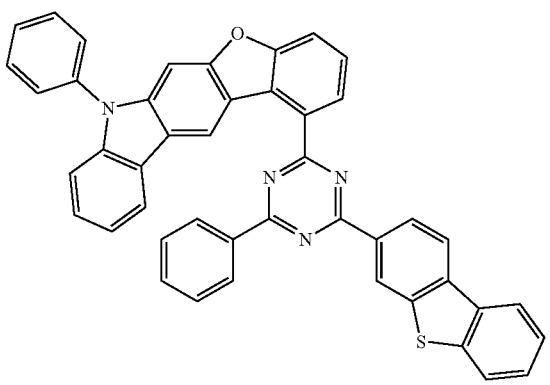
1A-1-44
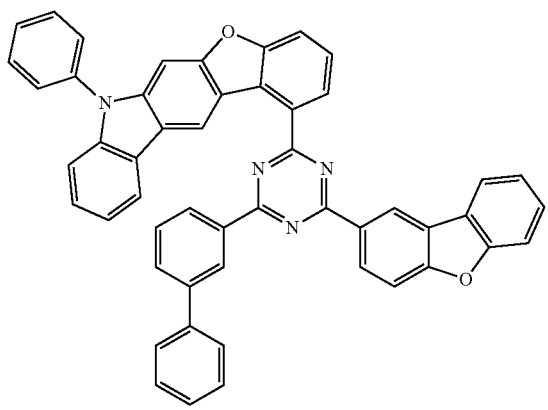
1A-1-45
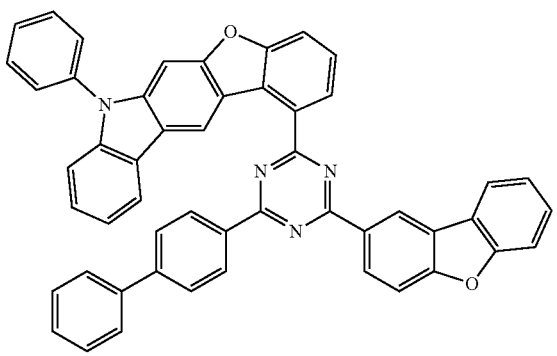
1A-1-46
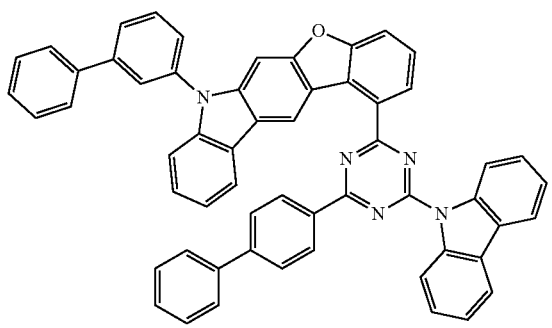
1A-1-47
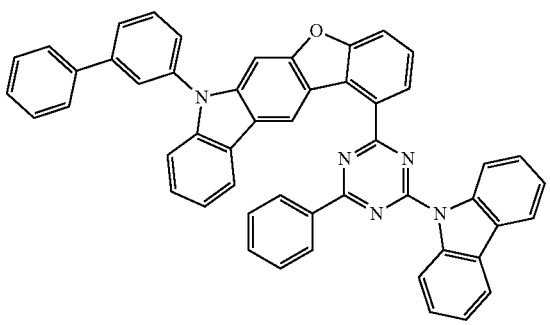

-continued
1A-1-48
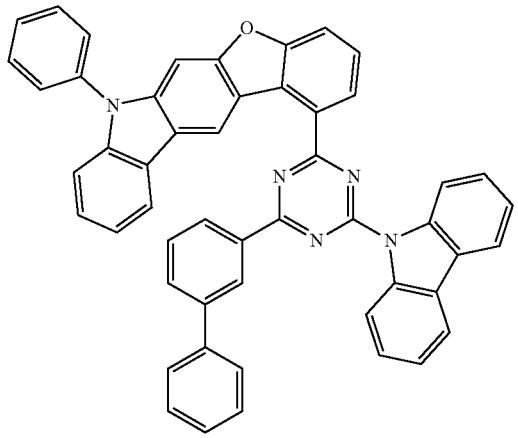
1A-1-49
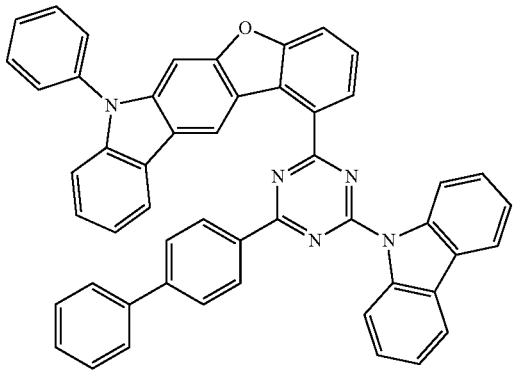
1A-1-50
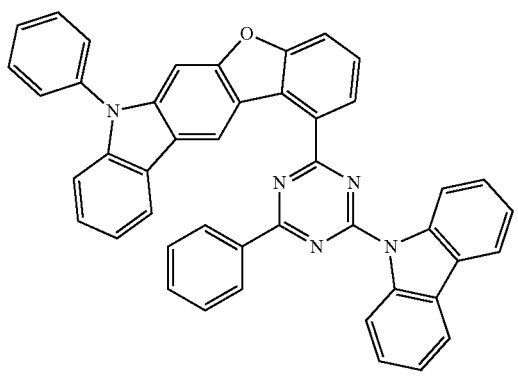
1A-1-51
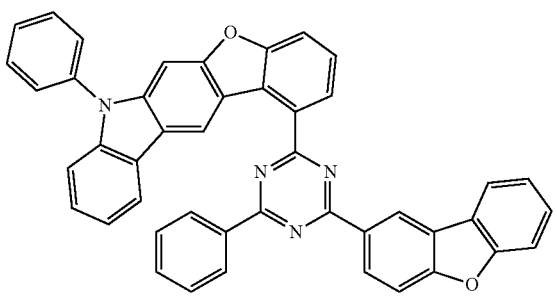
1A-1-52
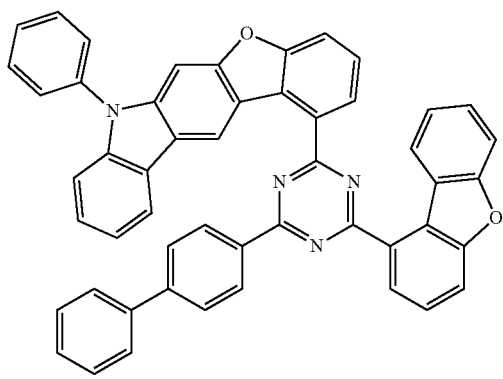
1A-1-53
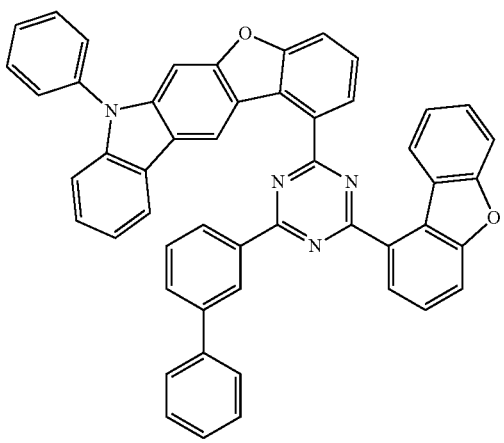

-continued
1A-1-54
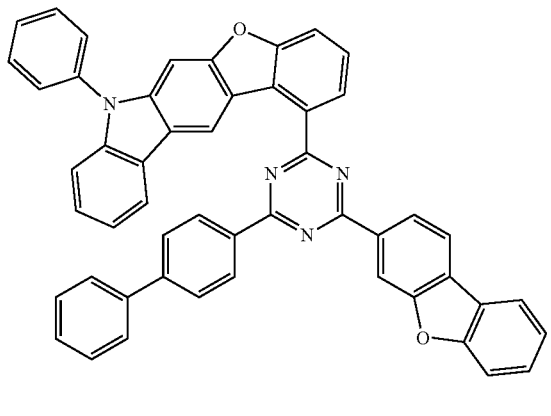
1A-1-55
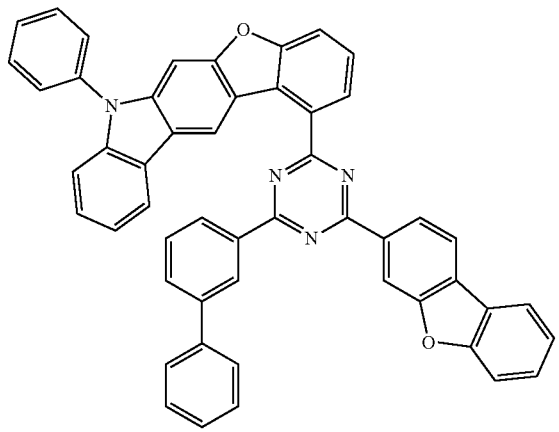
1A-1-56
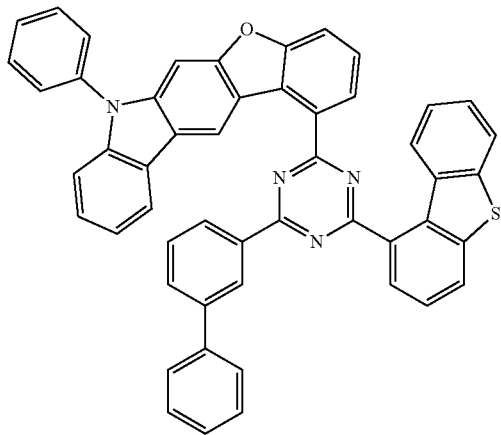
1A-1-57
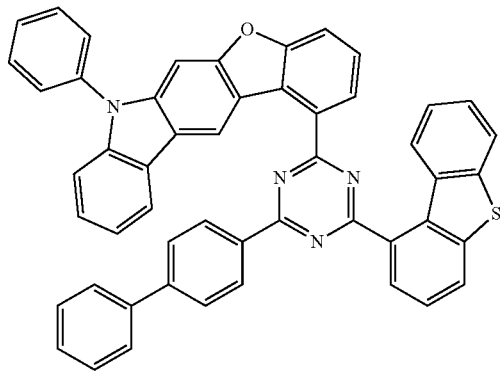
1A-1-58
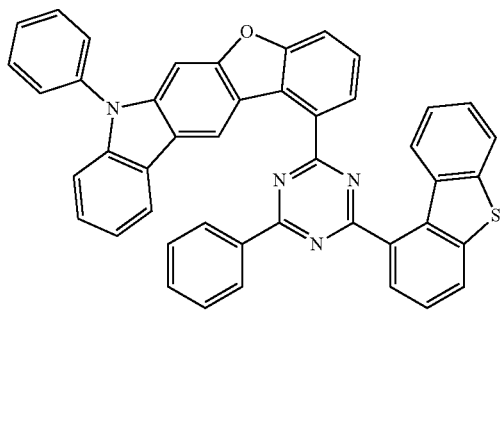
1A-1-59
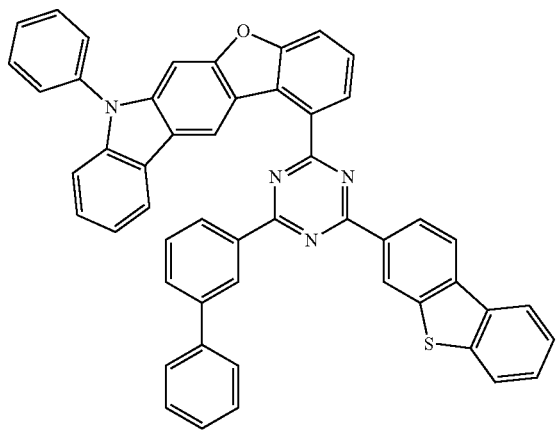

-continued
1A-1-60
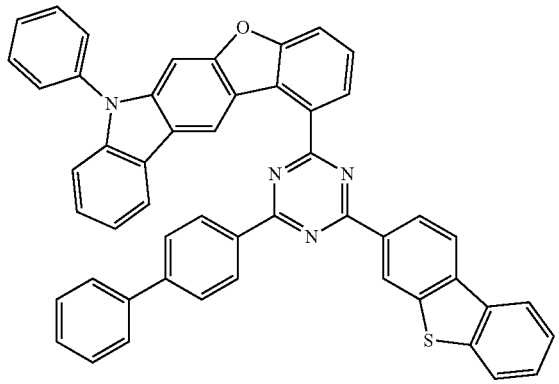
1A-1-61
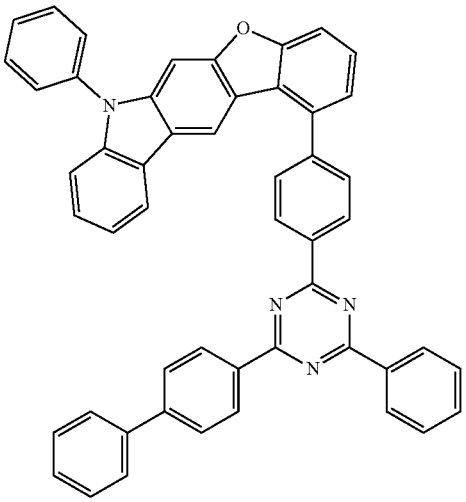
1A-1-62
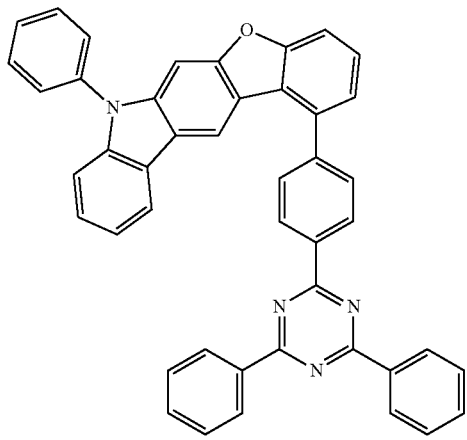
1A-1-63
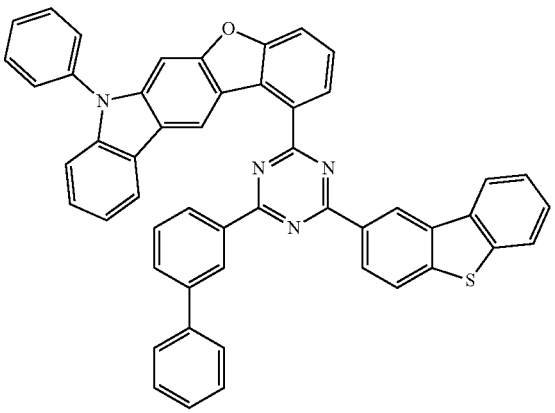
1A-1-64
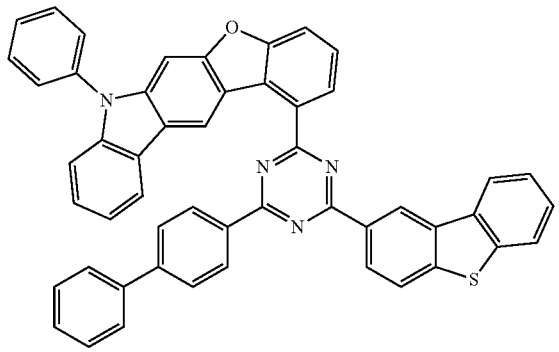
1A-1-65
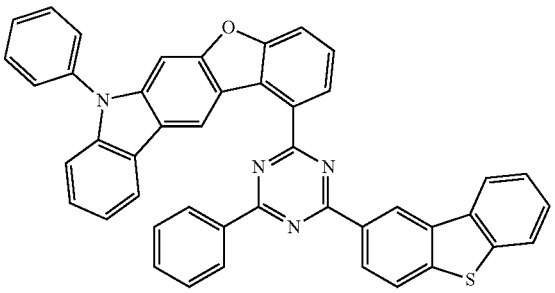

1A-1-66
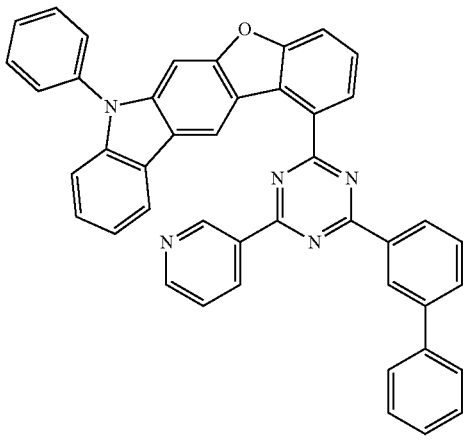
1A-1-67
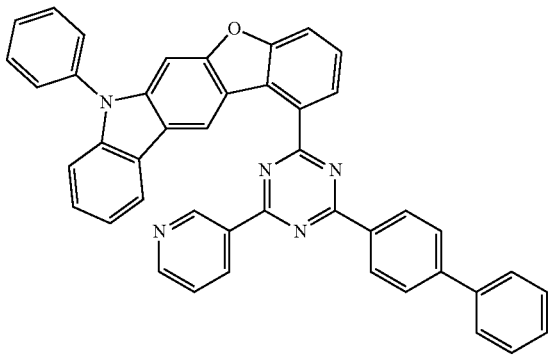
1A-1-68
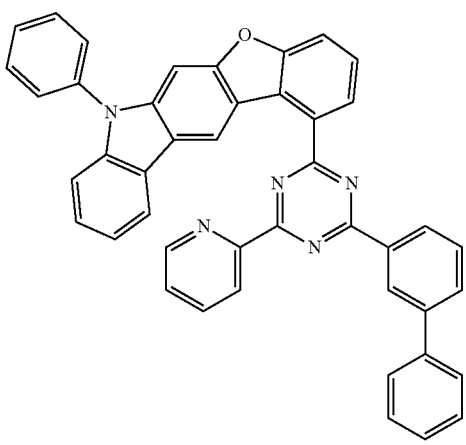
1A-1-69
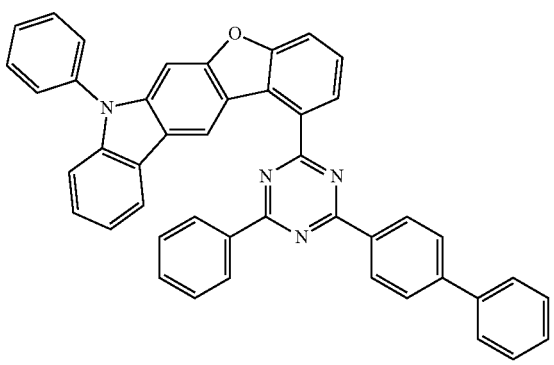
1A-1-70
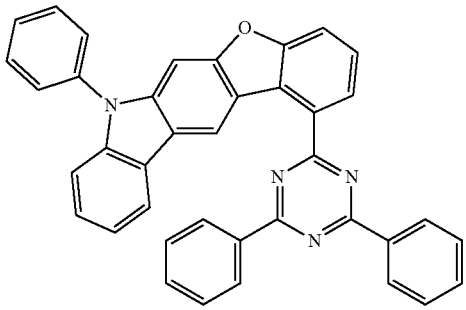
1A-1-71
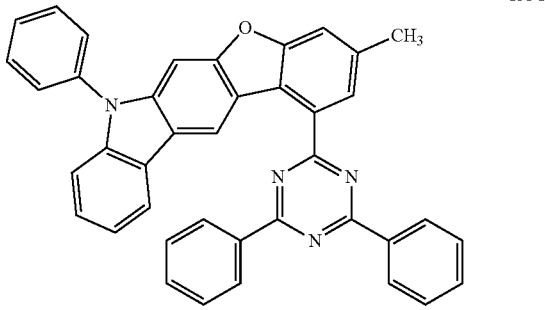
1A-1-72
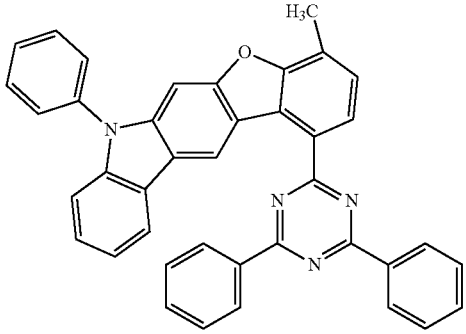
1A-1-73
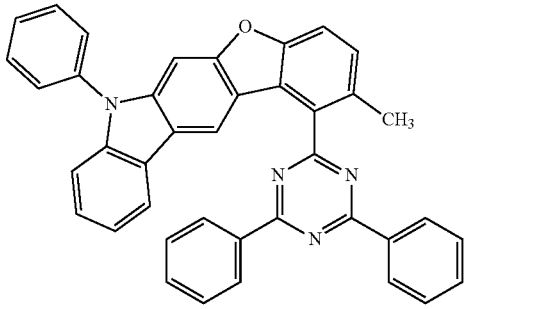

-continued
1A-1-74
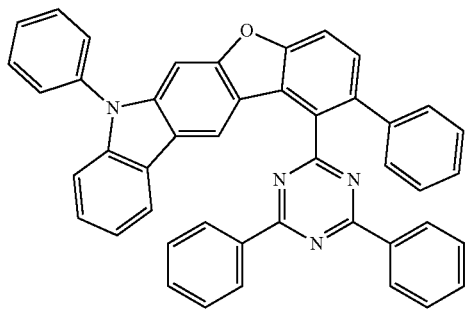
1A-1-75
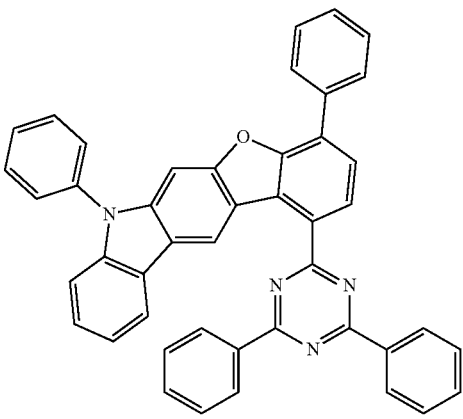
1A-1-76
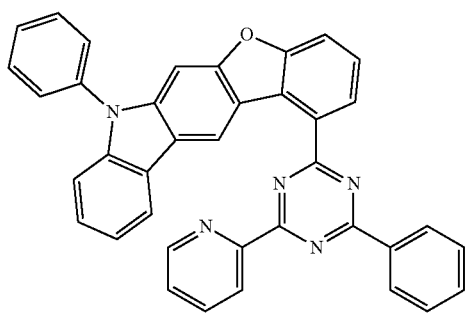
1A-1-77
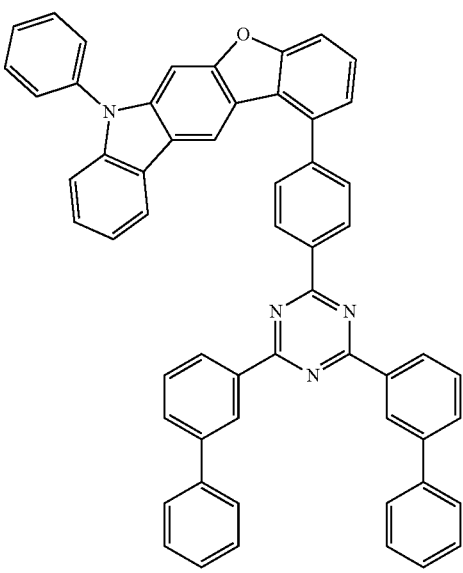
1A-1-78
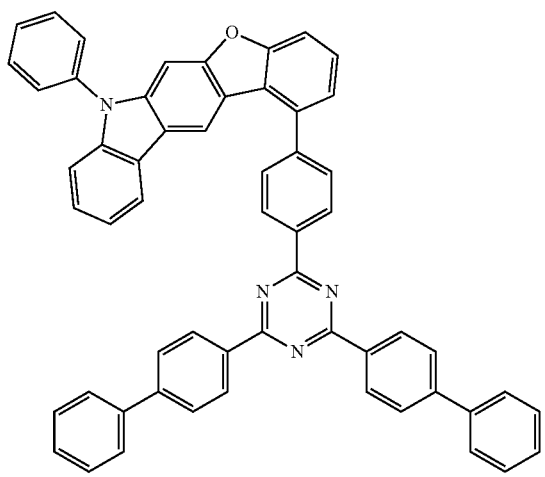
1A-1-79
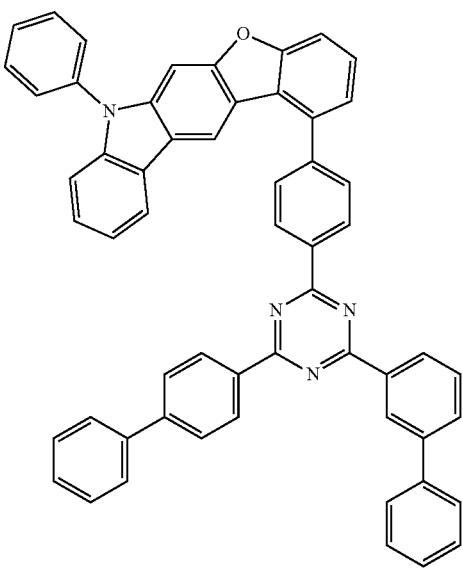

-continued
1A-1-80
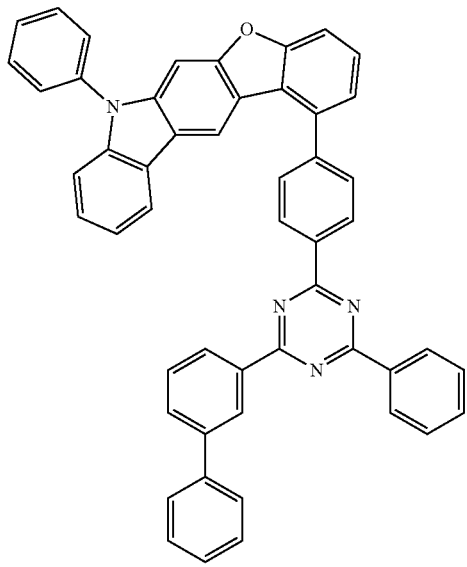
1A-1-81
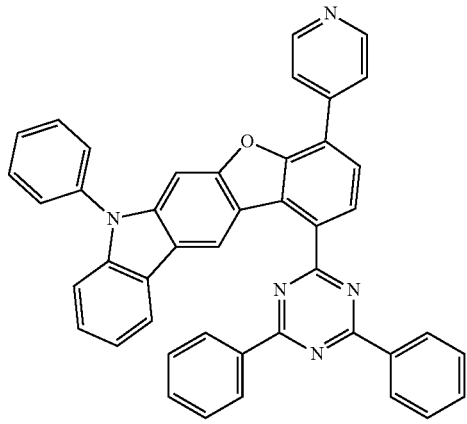
1A-1-82
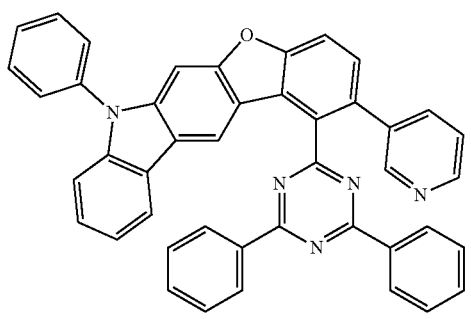
1A-1-83
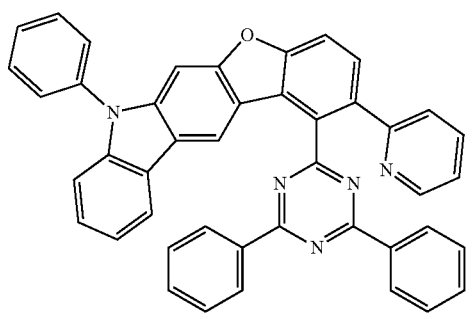
1A-2-1
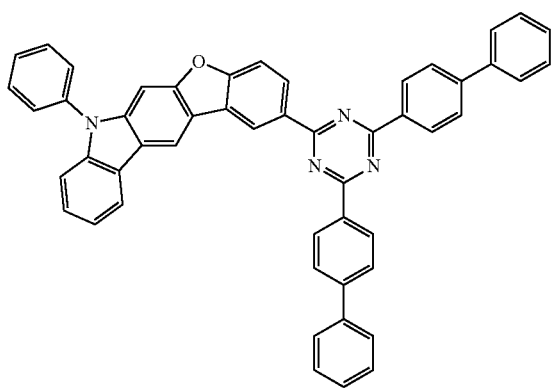
1A-2-2
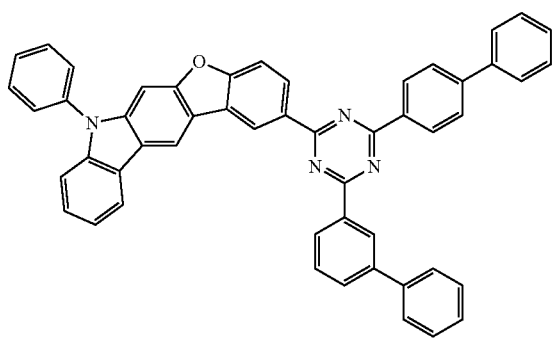

-continued
1A-2-3
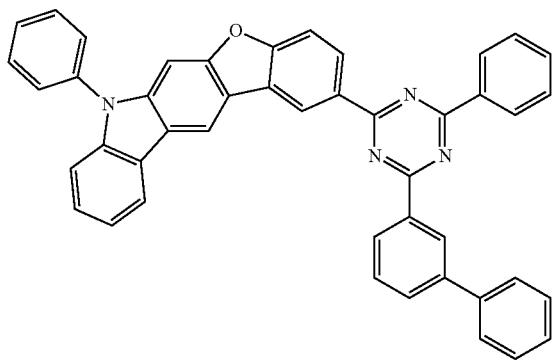
1A-2-4
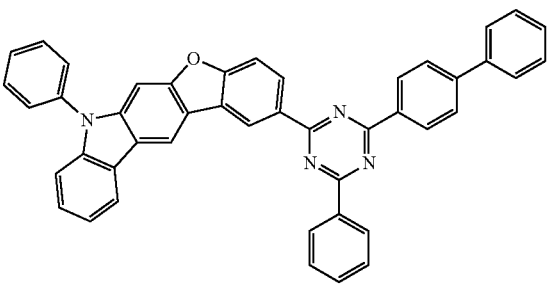
1A-2-5
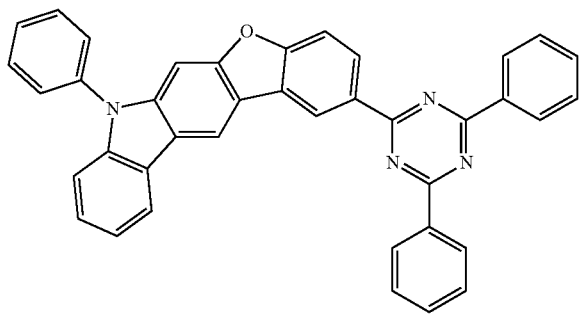
1A-2-6
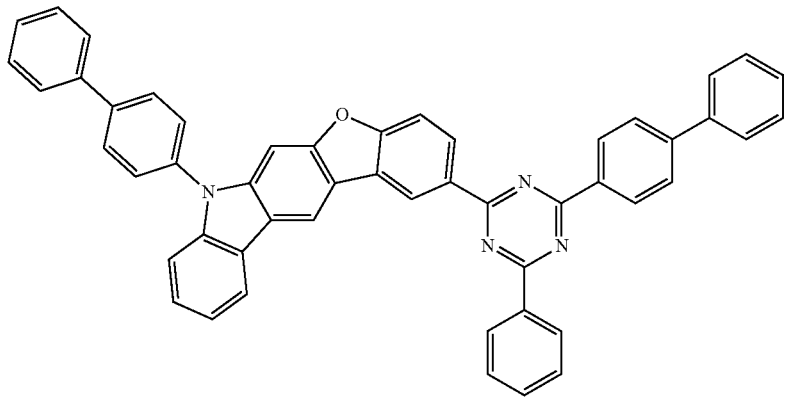
1A-2-7
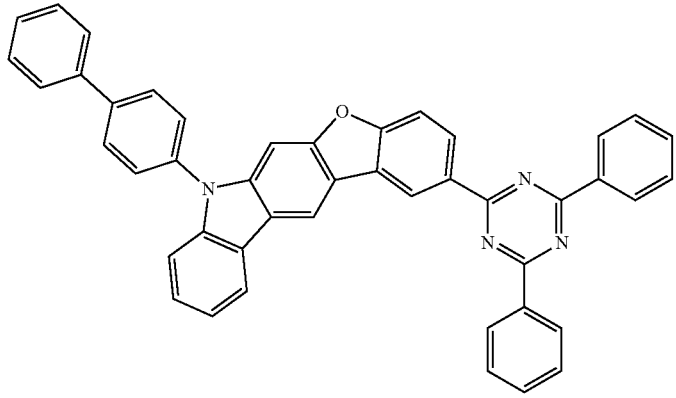

-continued
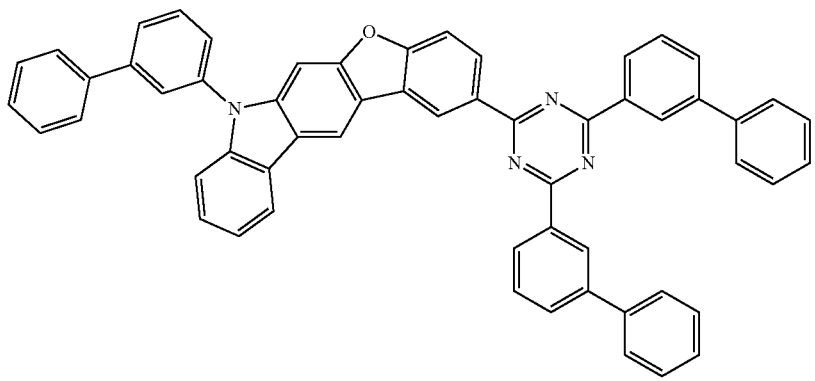
1A-2-8
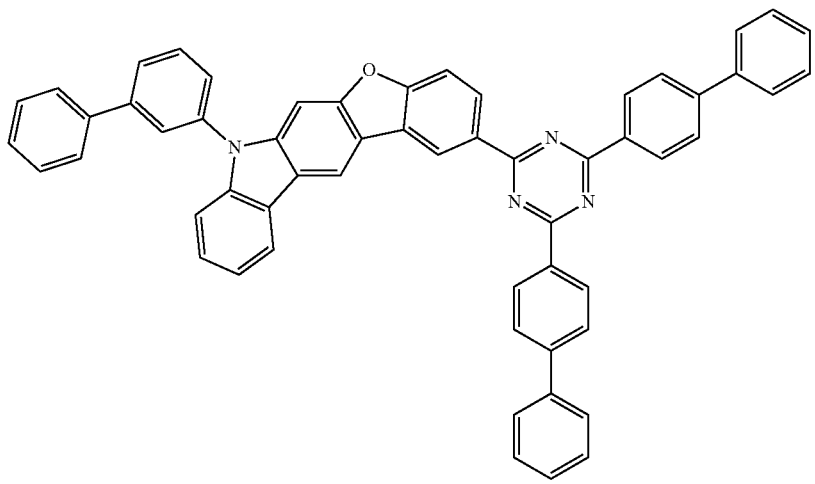
1A-2-9
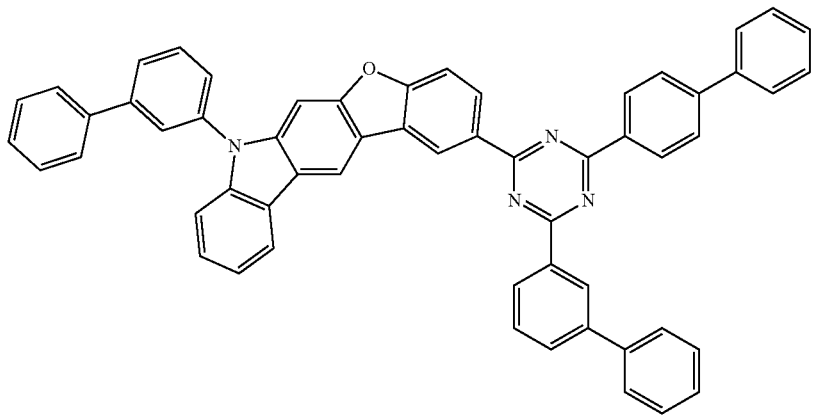
1A-2-10

-continued
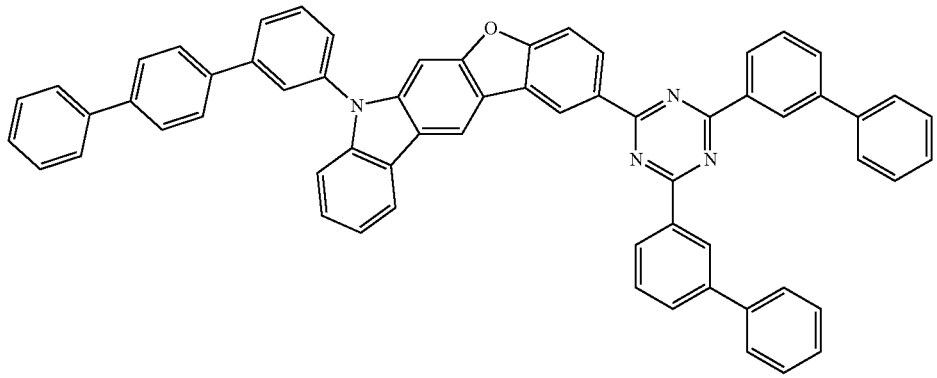
1A-2-11
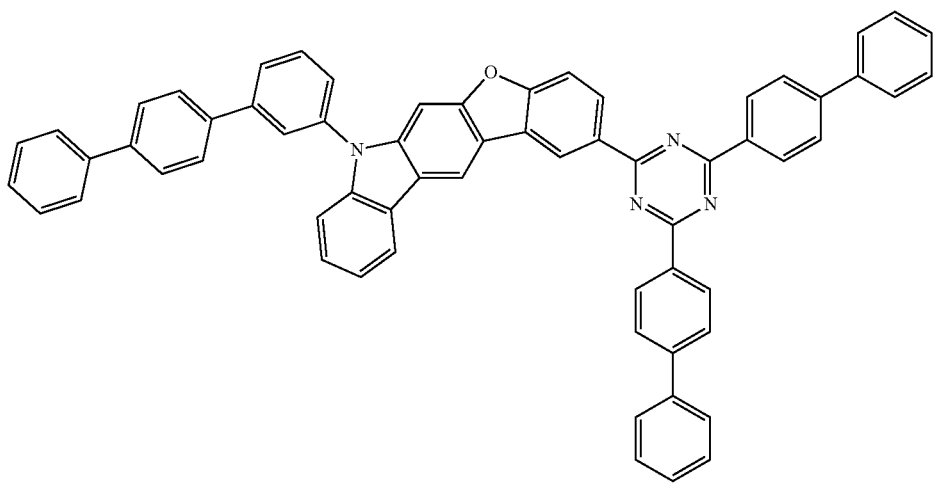
1A-2-12
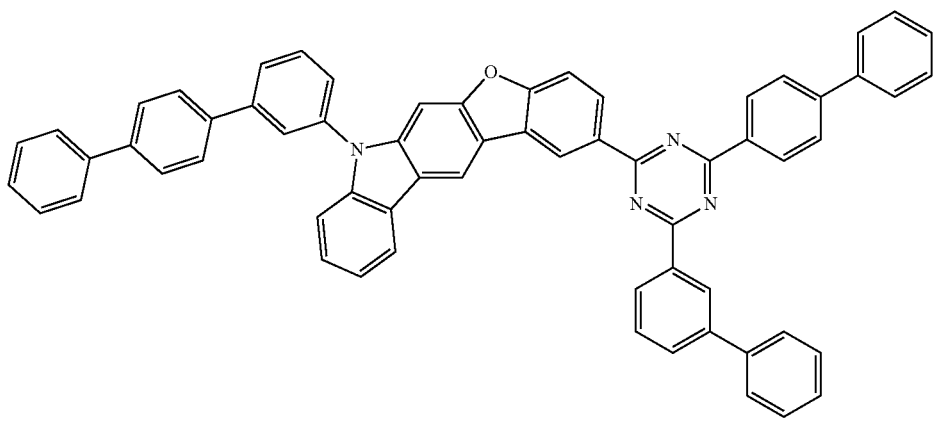
1A-2-13
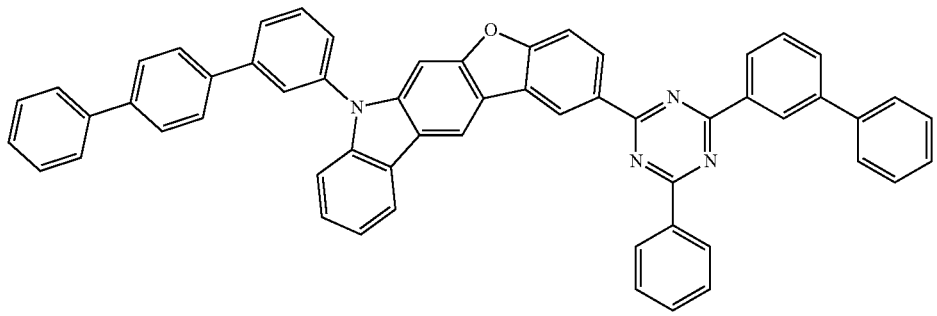
1A-2-14

1A-2-15
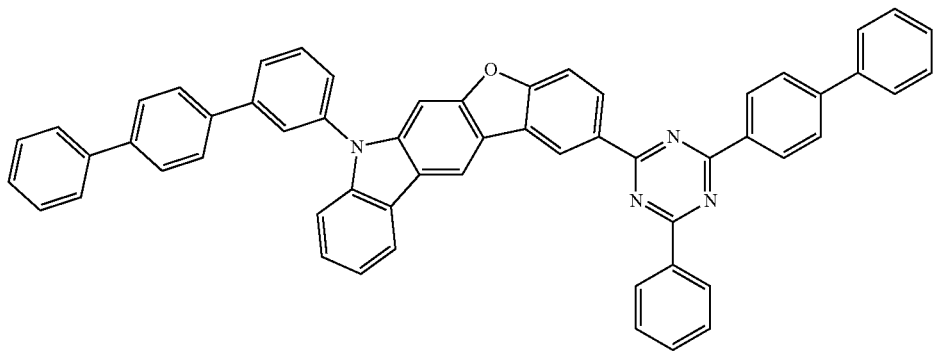
1A-2-16
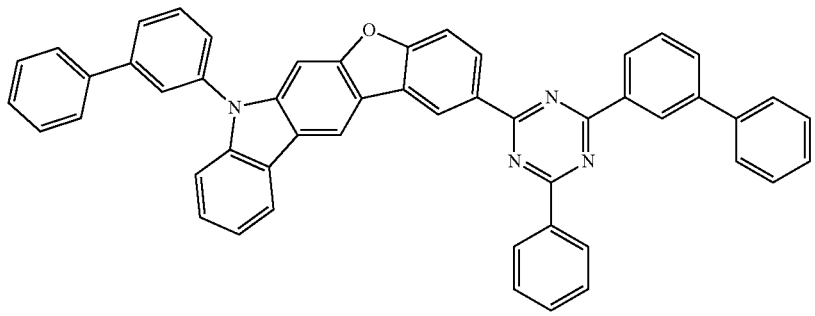
1A-2-17
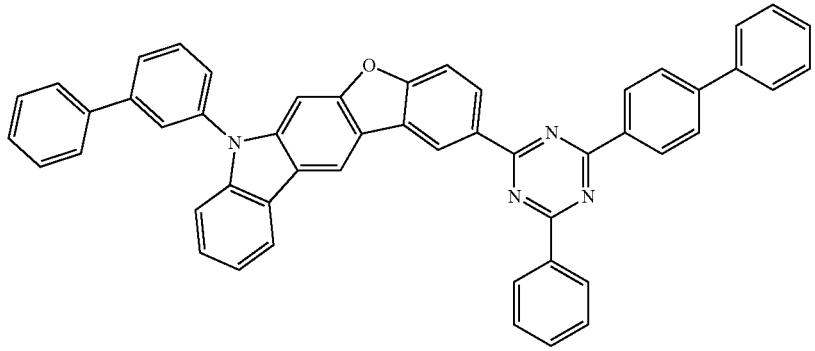
1A-2-18 1A-2-19
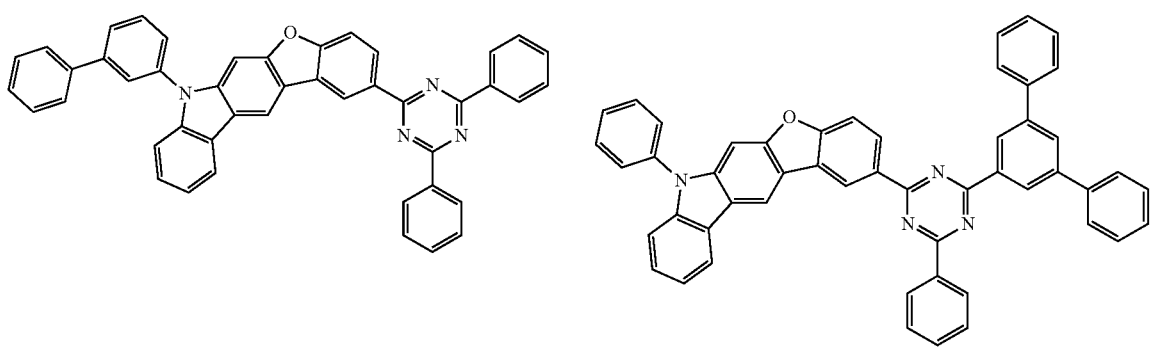

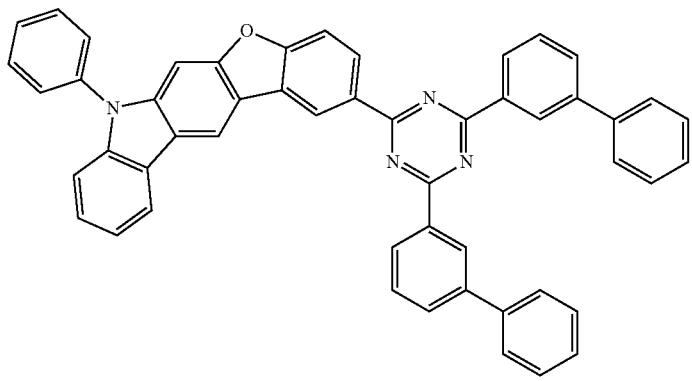
1A-2-20
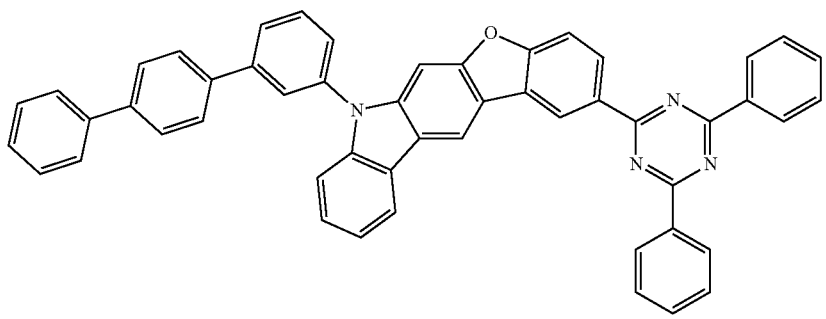
1A-2-21
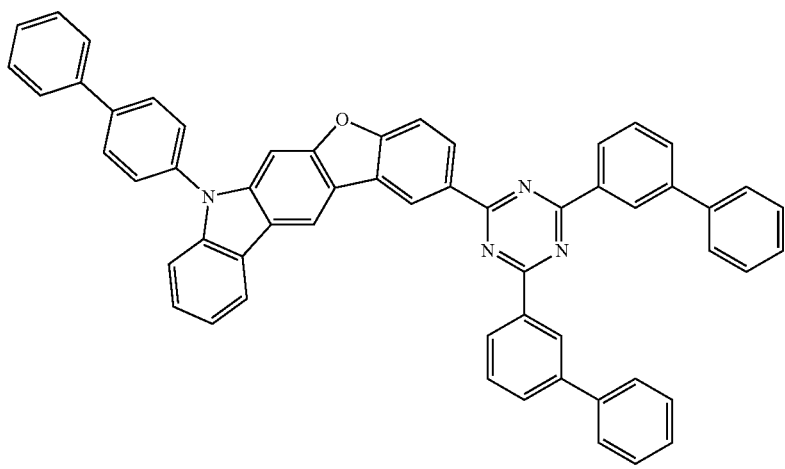
1A-2-22

-continued
1A-2-23
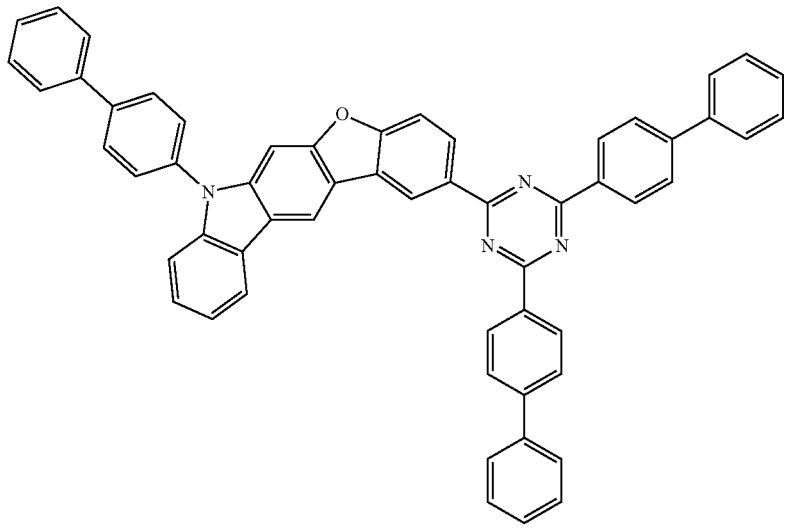
1A-2-24
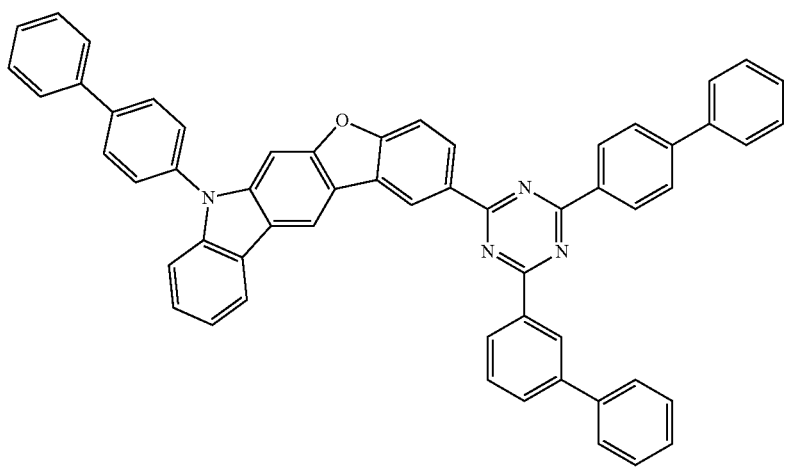
1A-2-25
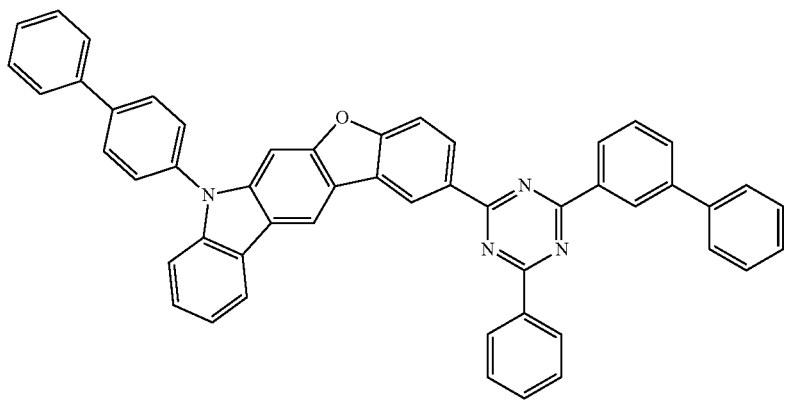

1A-2-26
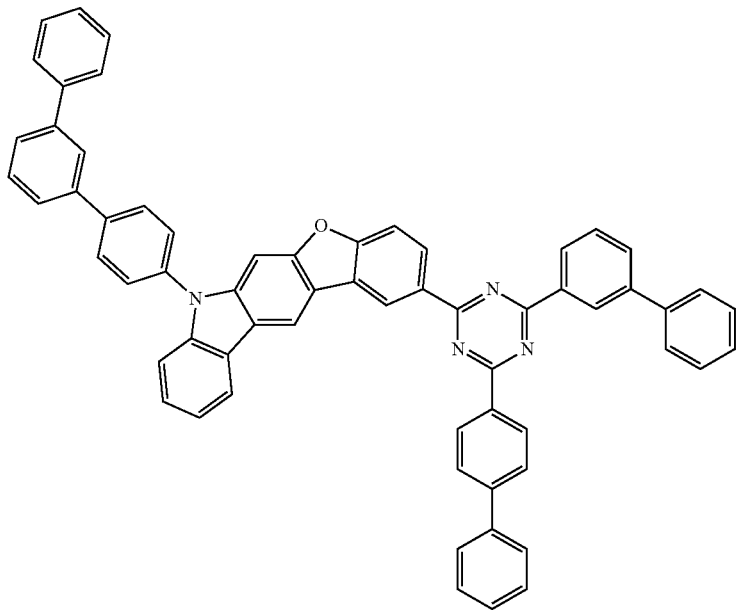
1A-2-27
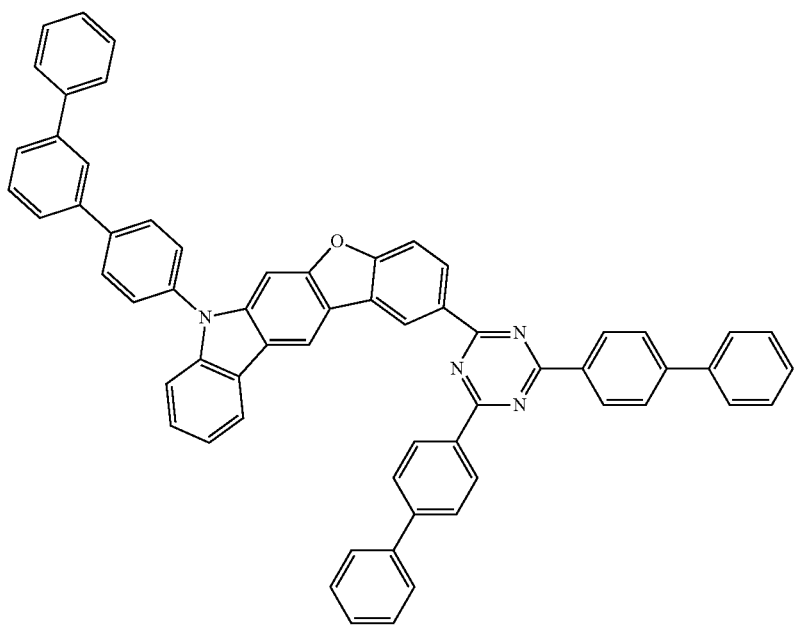

-continued
1A-2-28
1A-2-29
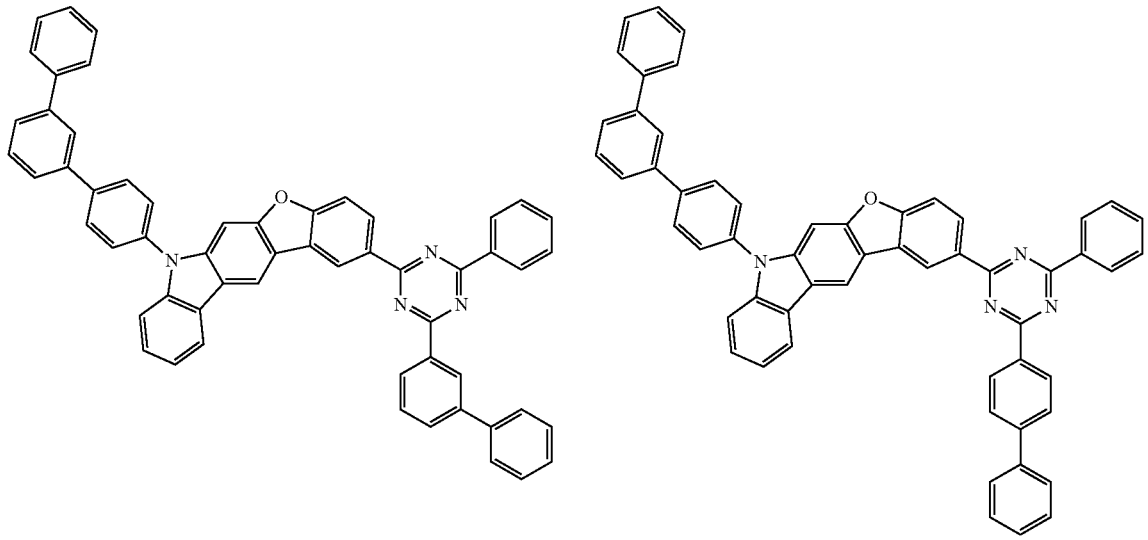
1A-2-30
1A-2-31
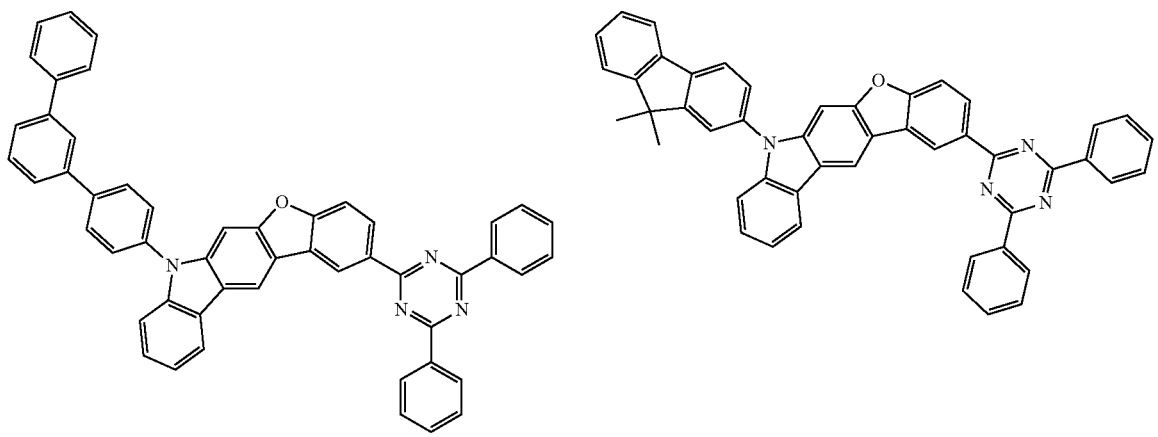
1A-2-32
1A-2-33
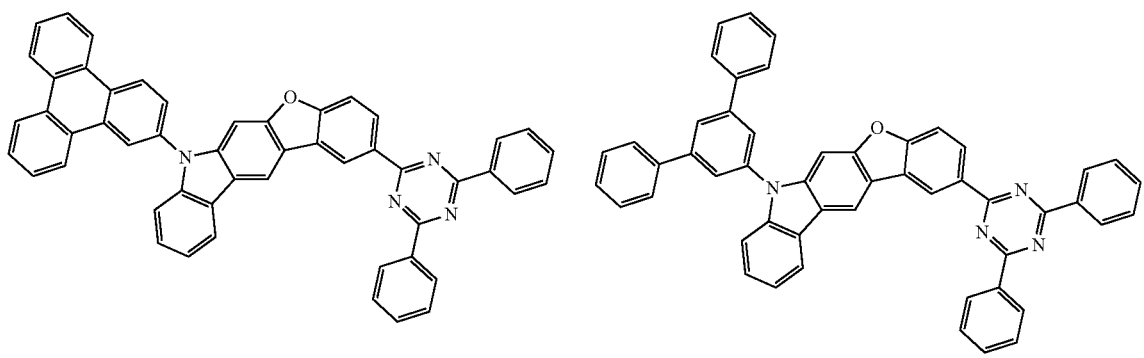

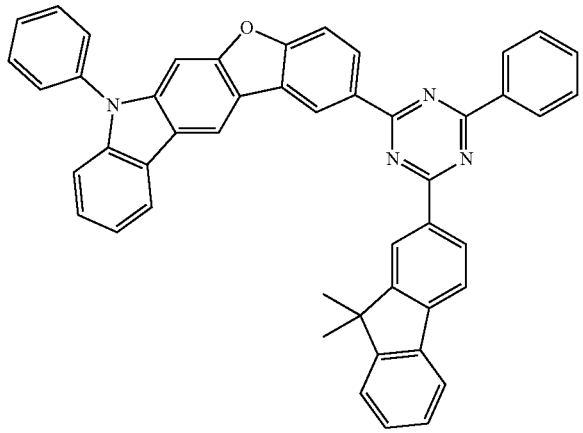
1A-2-34
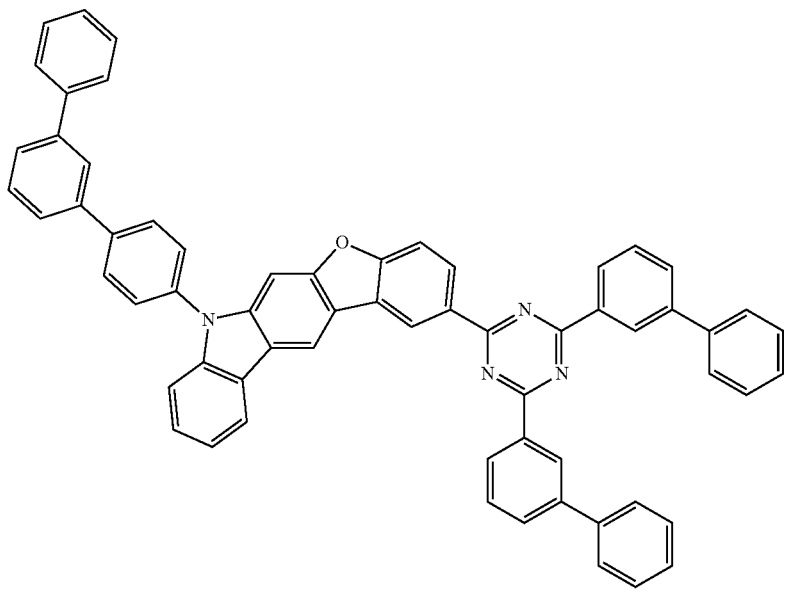
1A-2-35
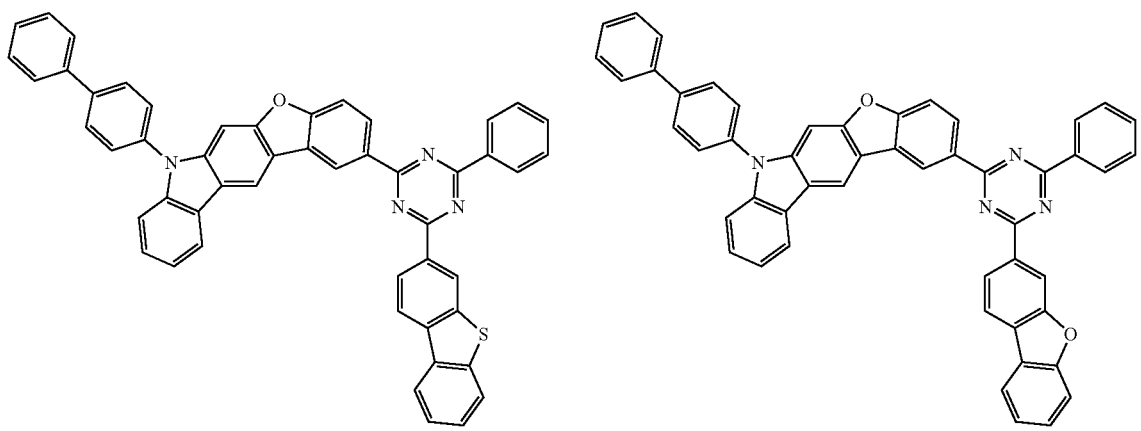
1A-2-36        1A-2-37

-continued
1A-2-38
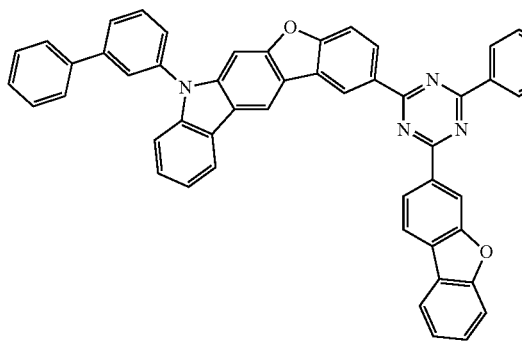
1A-2-39
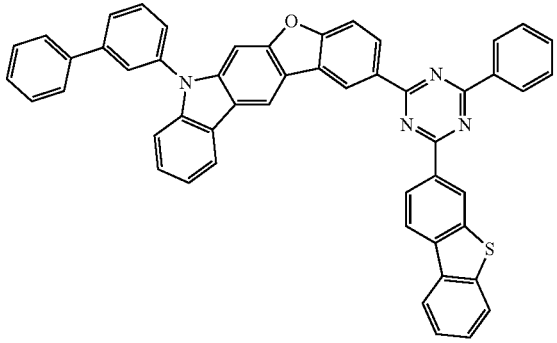
1A-2-40
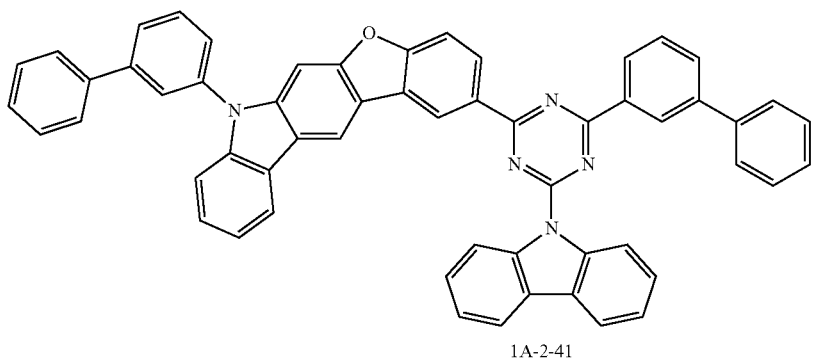
1A-2-41
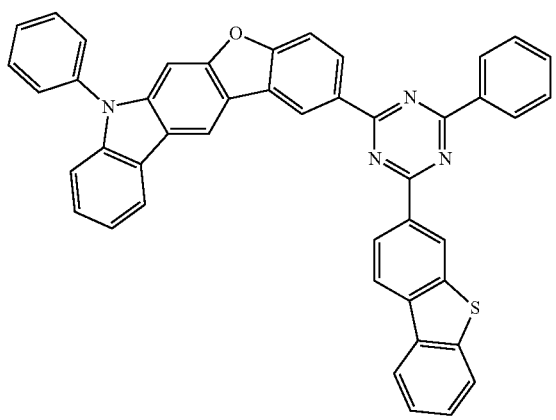
1A-2-42
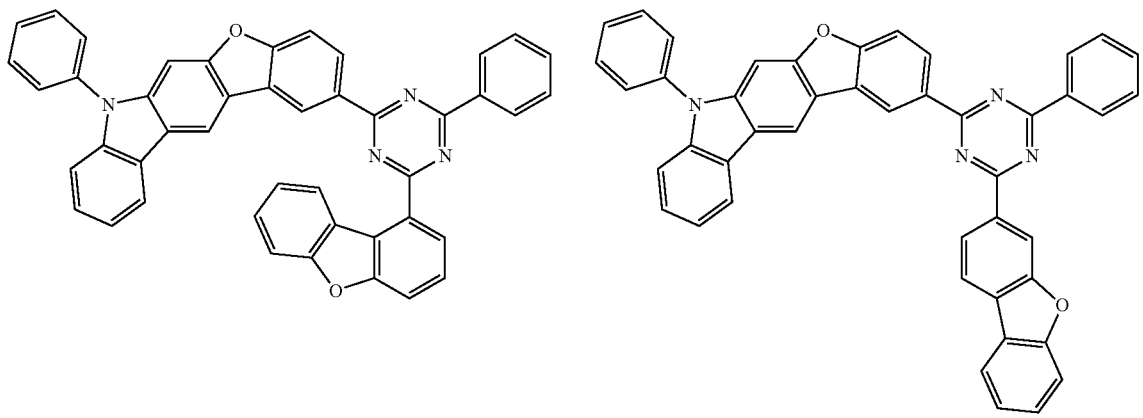
1A-2-43
1A-2-44
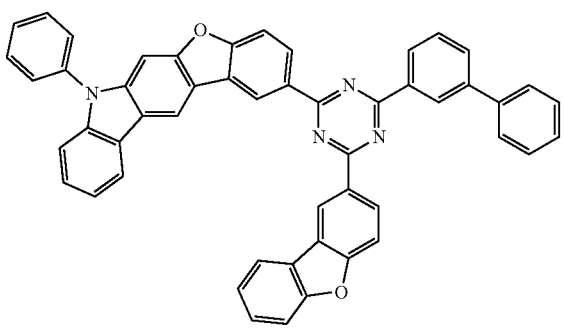

1A-2-45
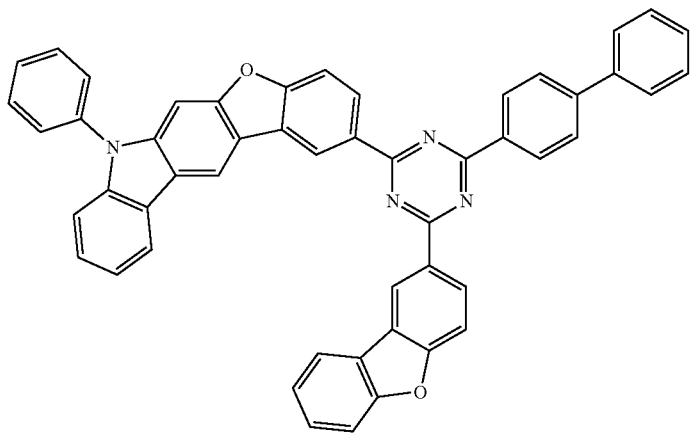
1A-2-46
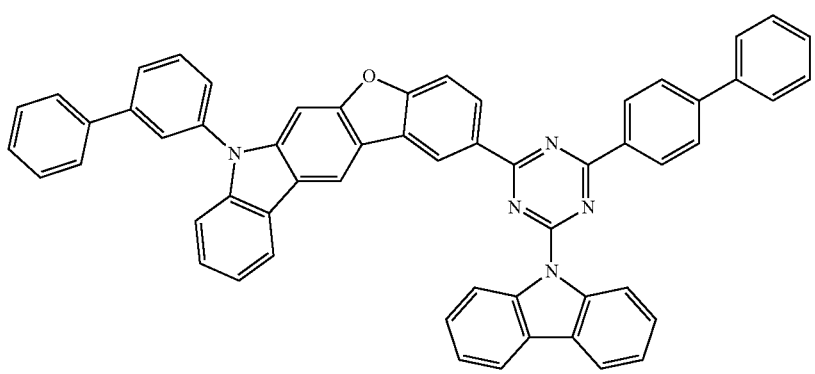
1A-2-47 1A-2-48
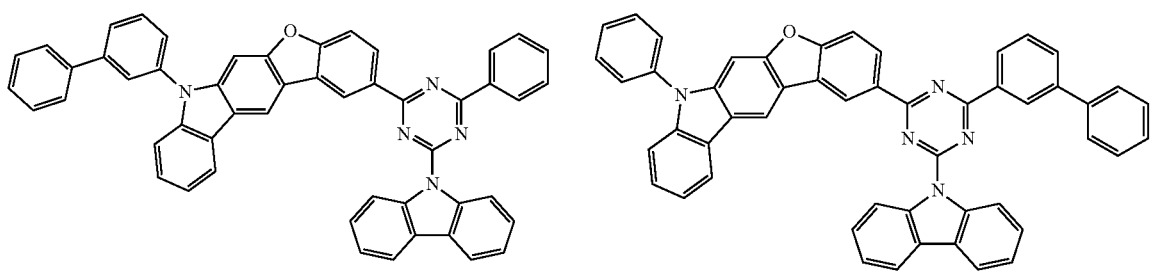
1A-2-49 1A-2-50
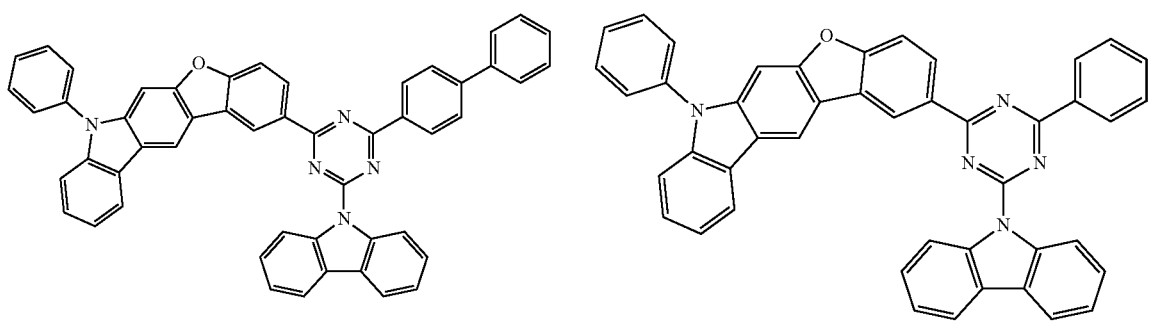

-continued
1A-2-51
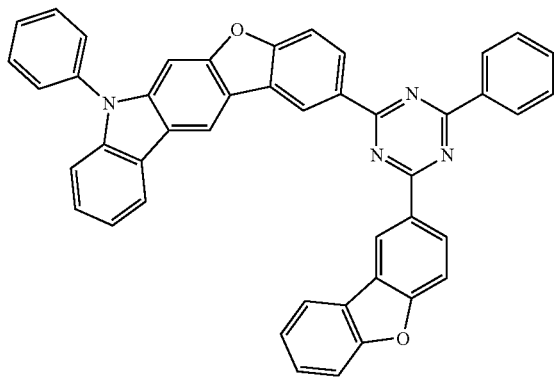
1A-2-52
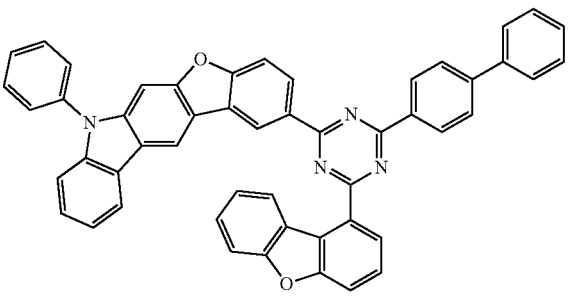
1A-2-53
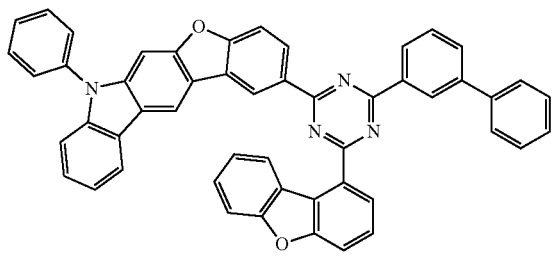
1A-2-54
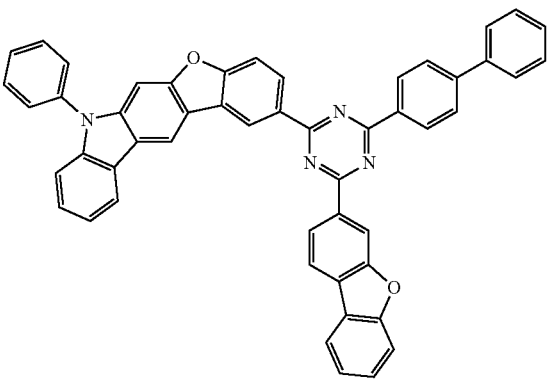
1A-2-55
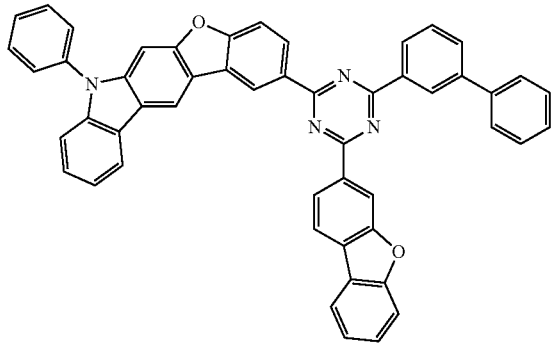
1A-2-56
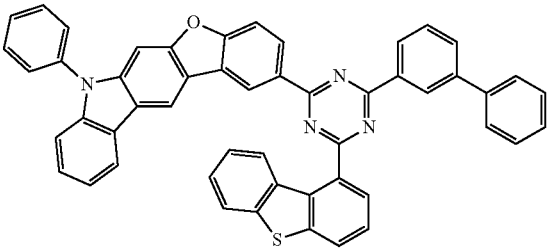
1A-2-57
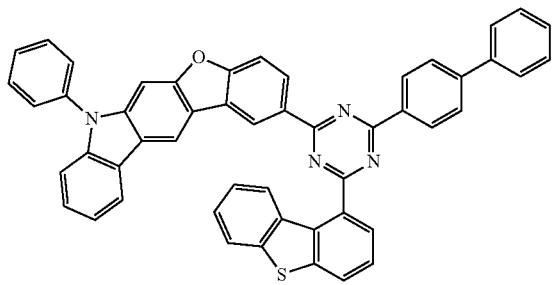
1A-2-58
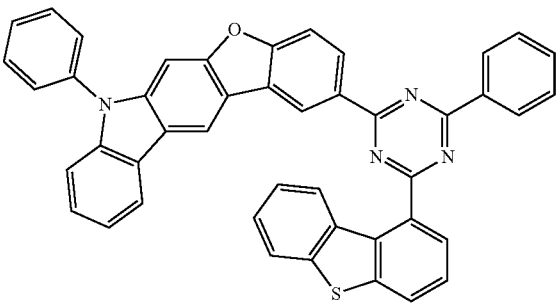

-continued
1A-2-59
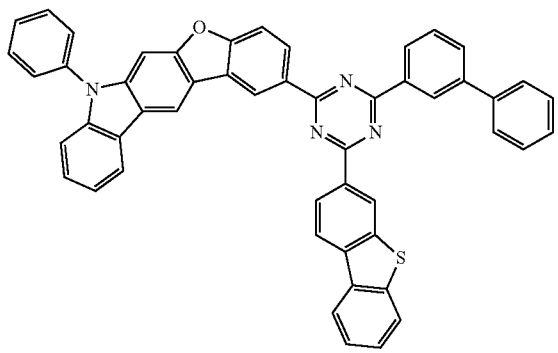
1A-2-60
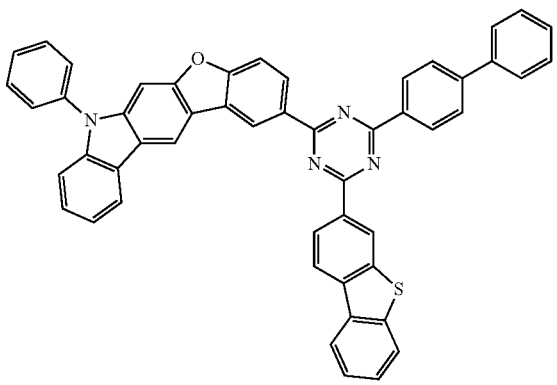
1A-2-61
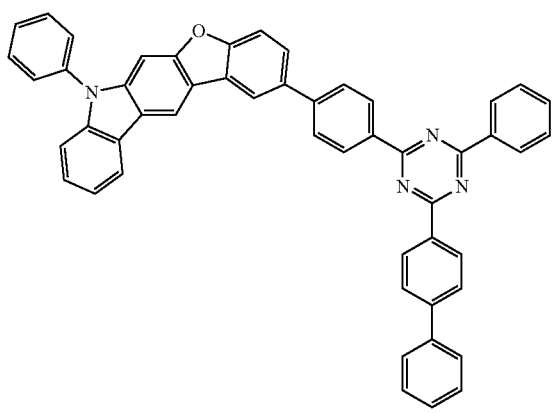
1A-2-62
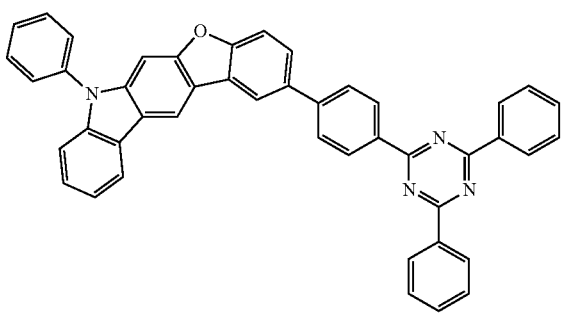
1A-2-63
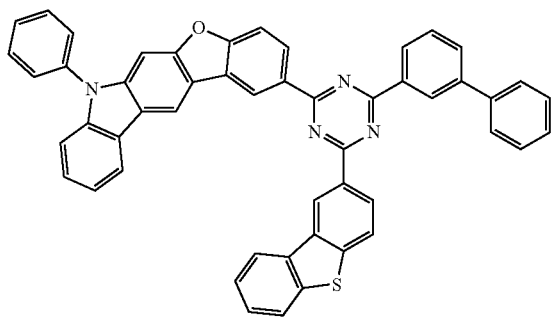
1A-2-64
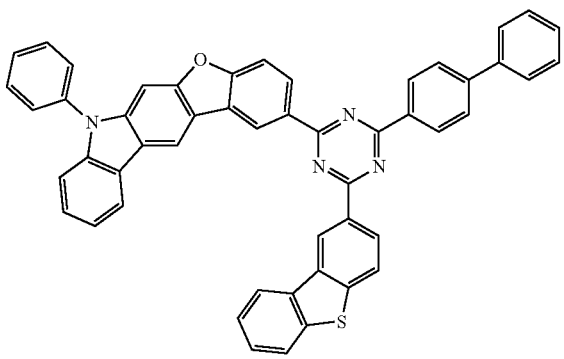
1A-2-65
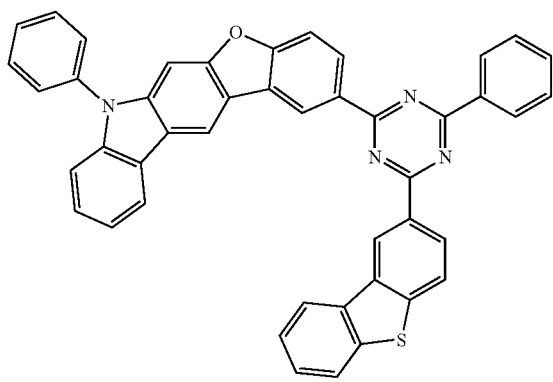
1A-2-66
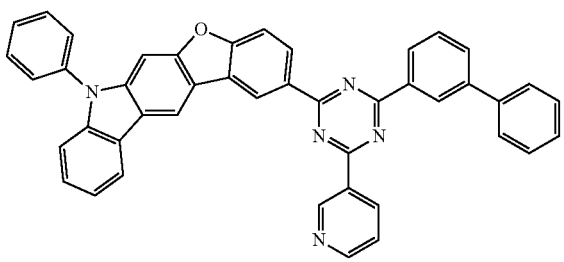

-continued
1A-2-67
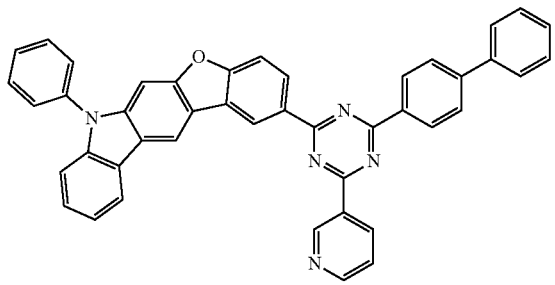
1A-2-68
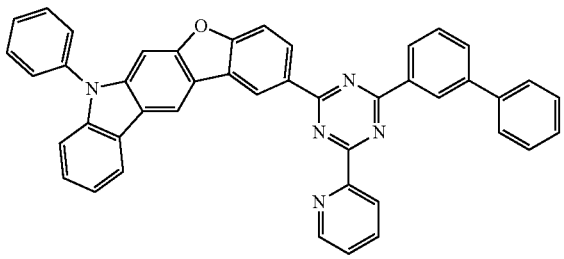
1A-2-69
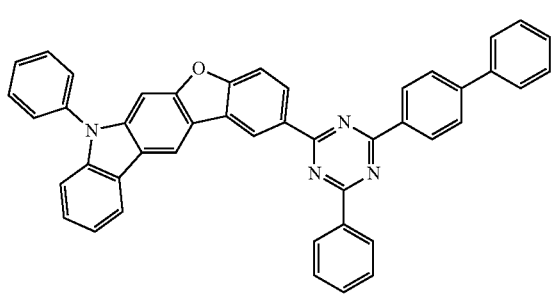
1A-2-70
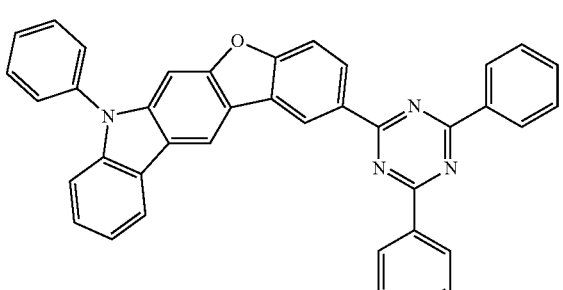
1A-2-71
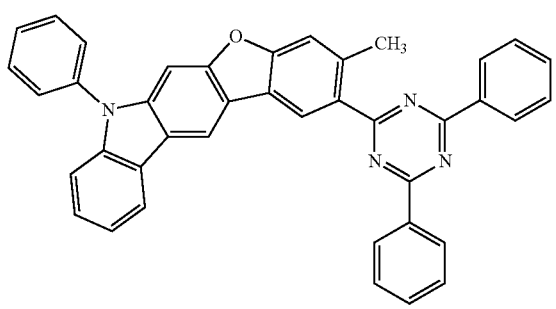
1A-2-72
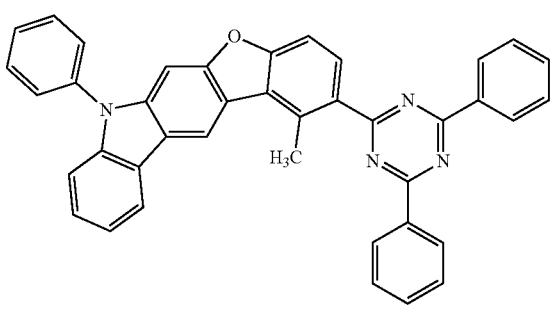
1A-2-73
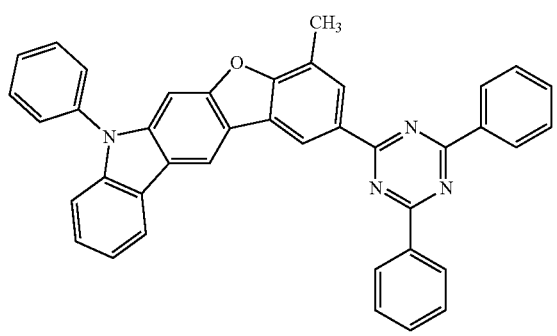
1A-2-74
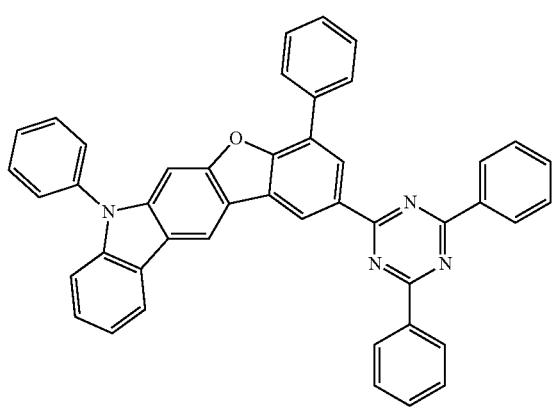

1A-2-75
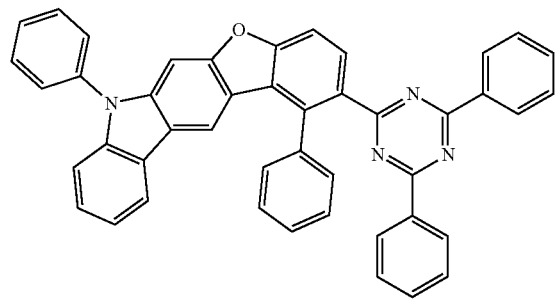
1A-2-76
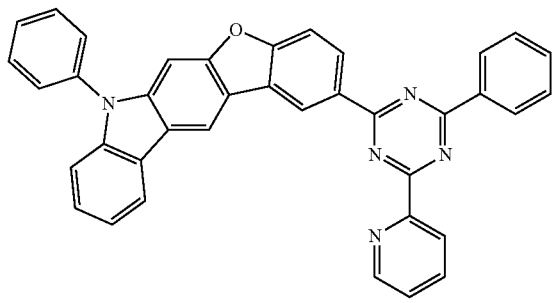
1A-2-77
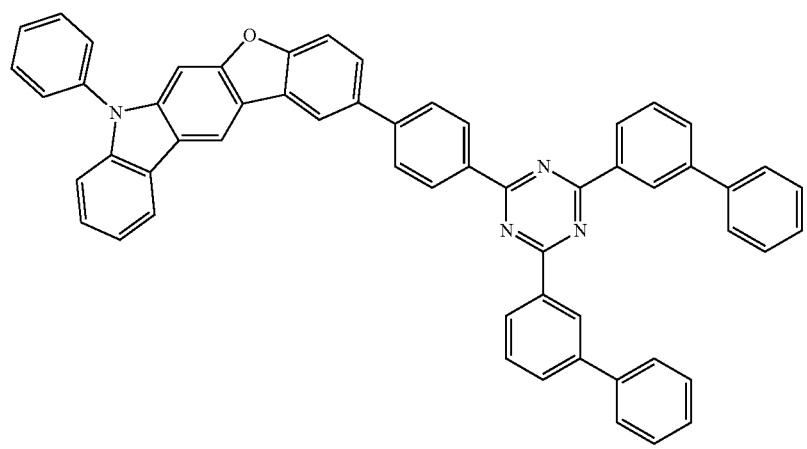
1A-2-78
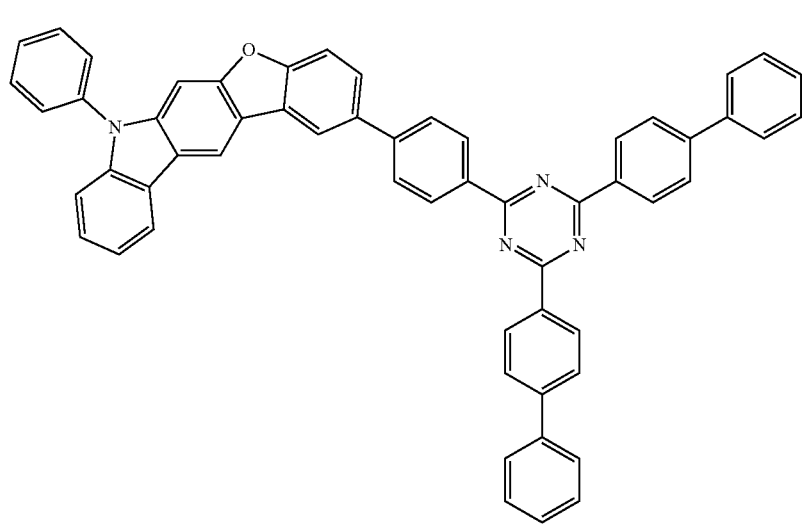

-continued
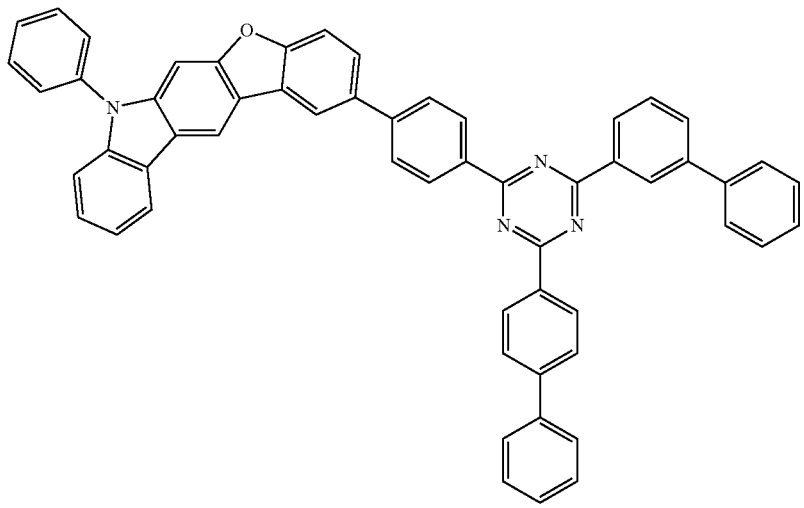
1A-2-79
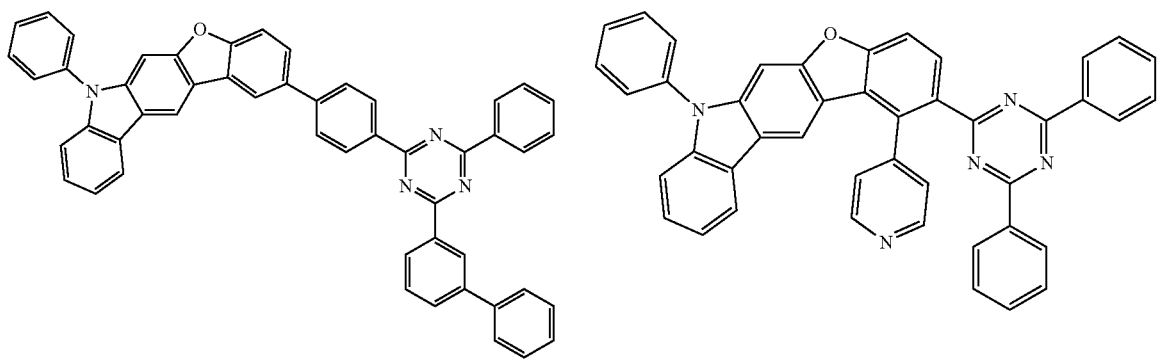
1A-2-80          1A-2-81
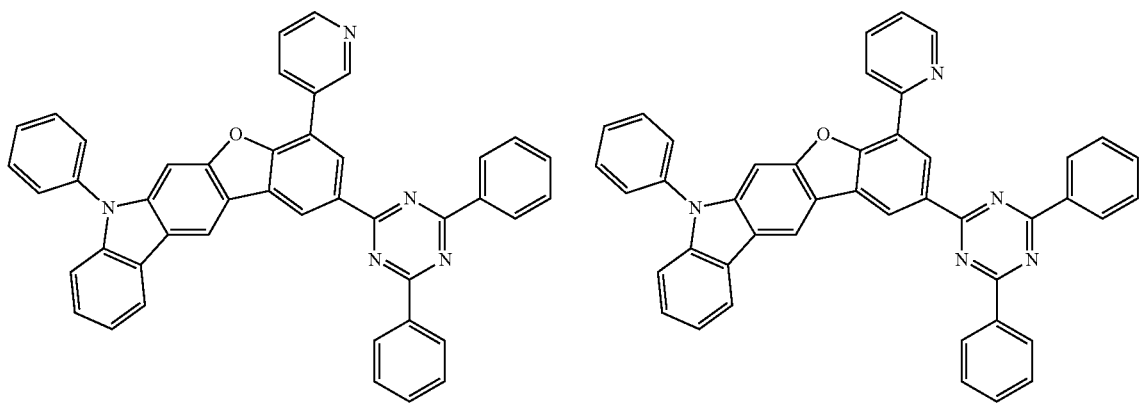
1A-2-82          1A-2-83

-continued
1A-3-1
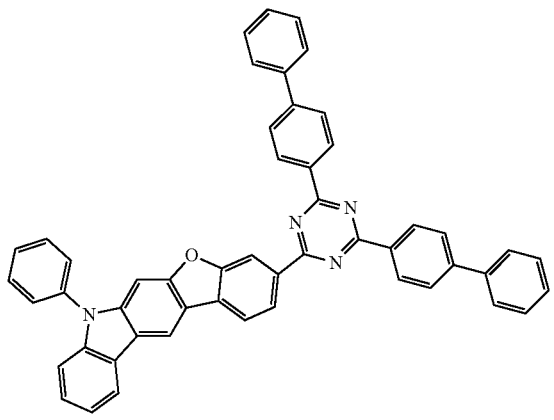
1A-3-2
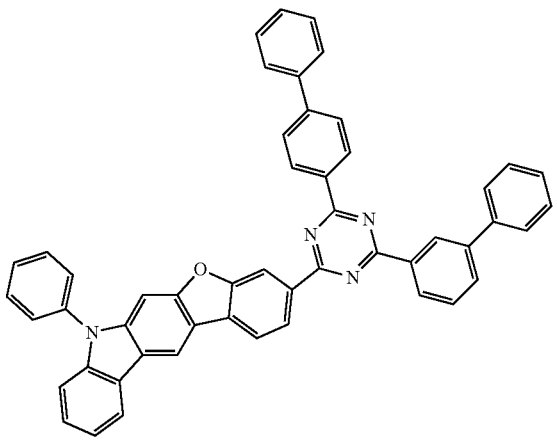
1A-3-3
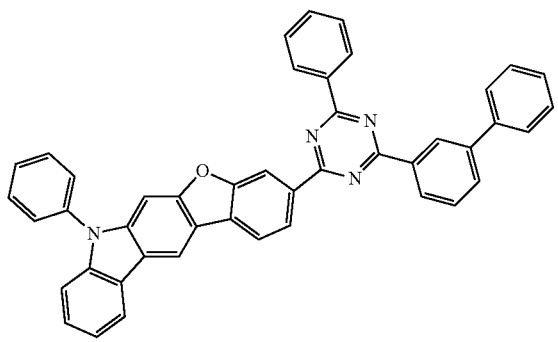
1A-3-4
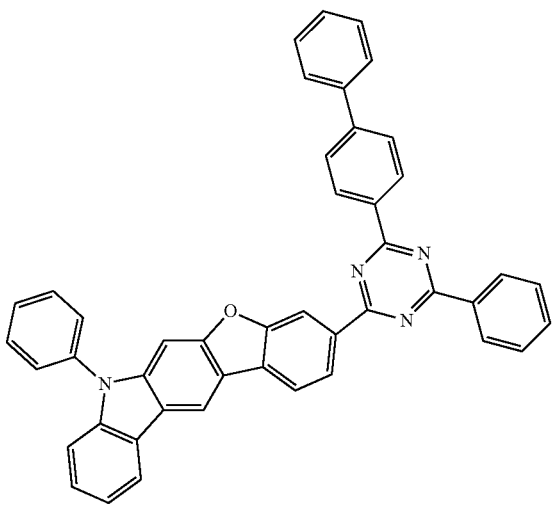
1A-3-5
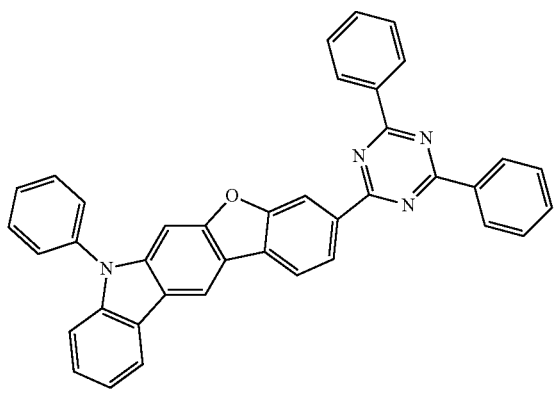
1A-3-6
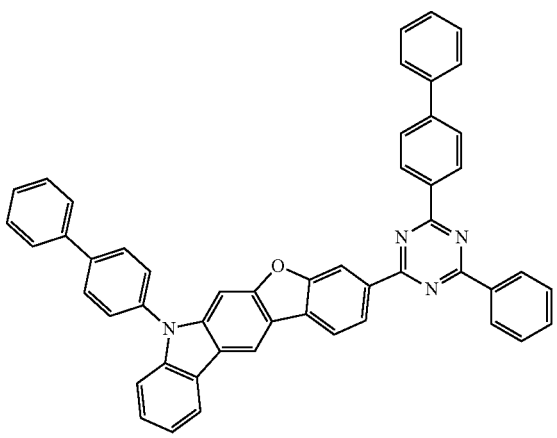

1A-3-7
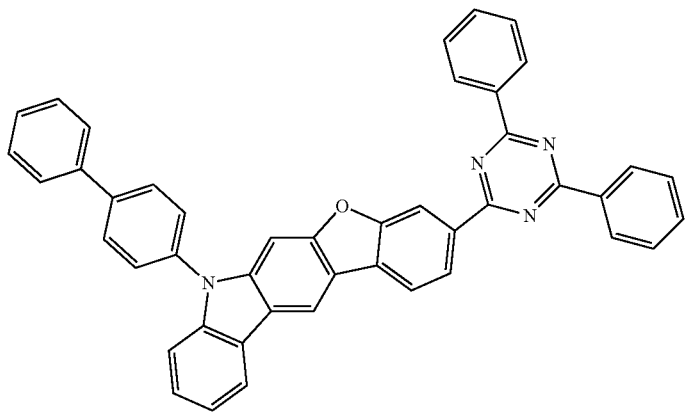
1A-3-8
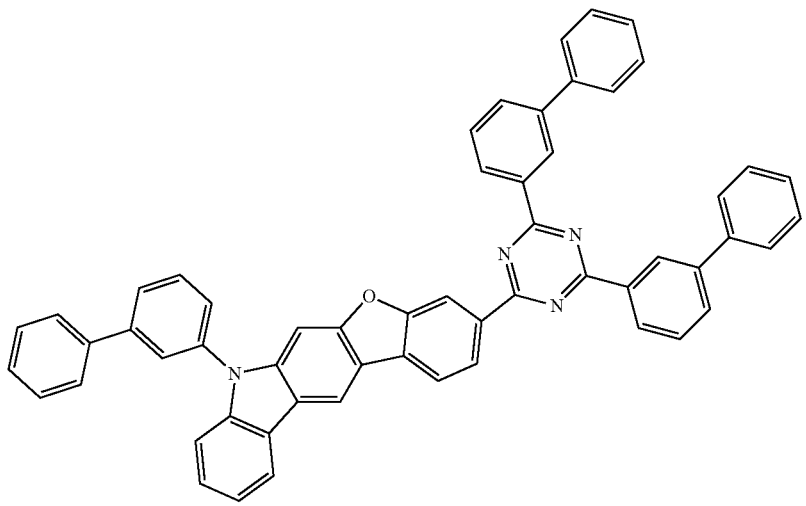
1A-3-9
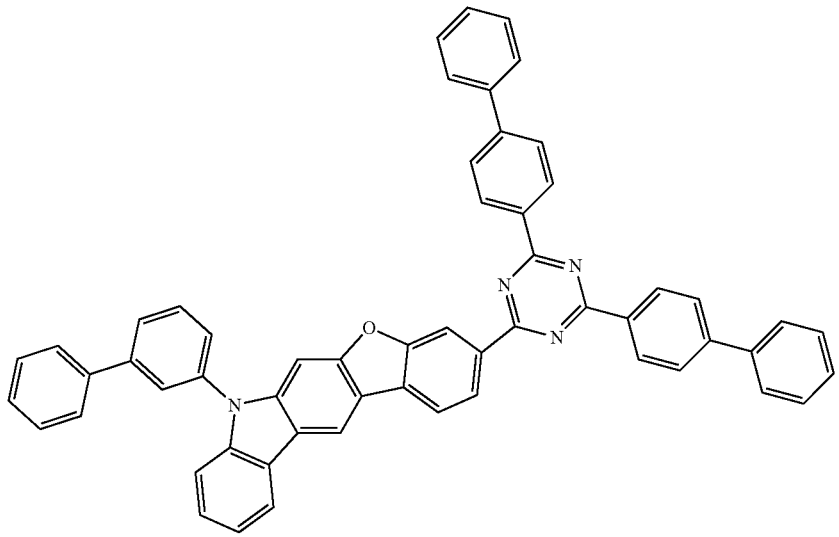

1A-3-10
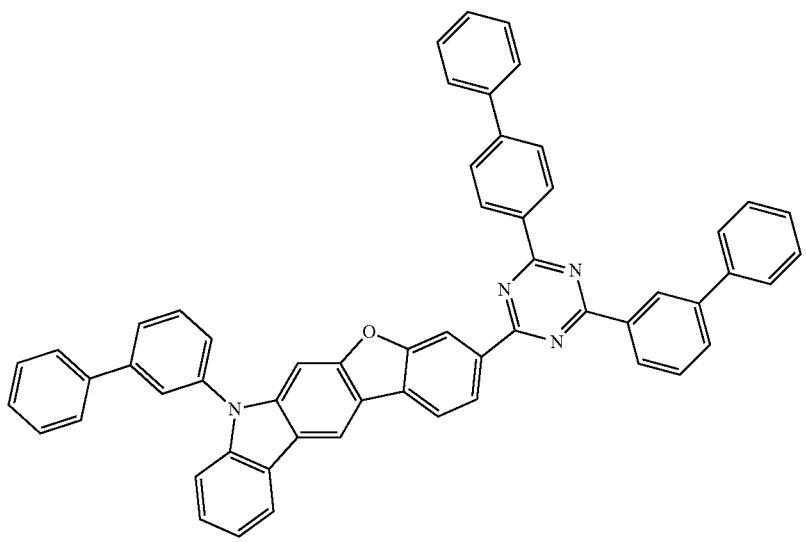
1A-3-11
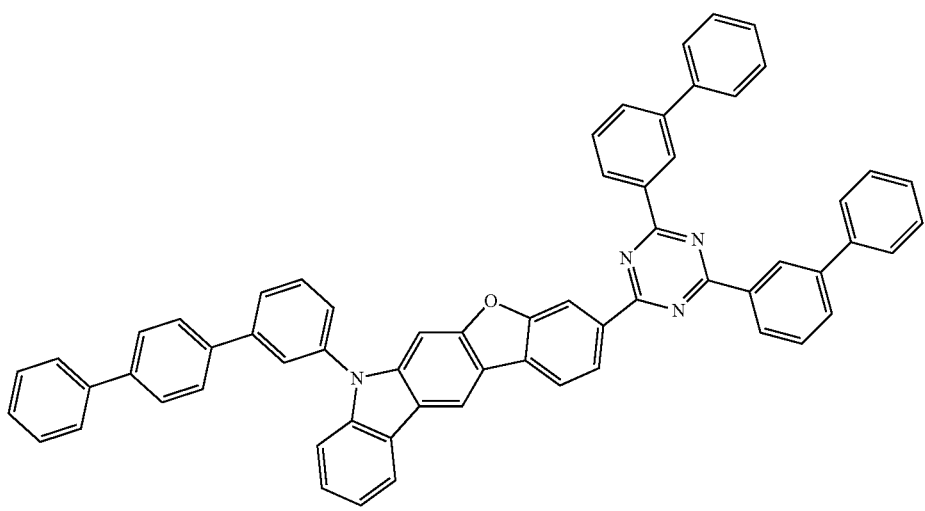
1A-3-12
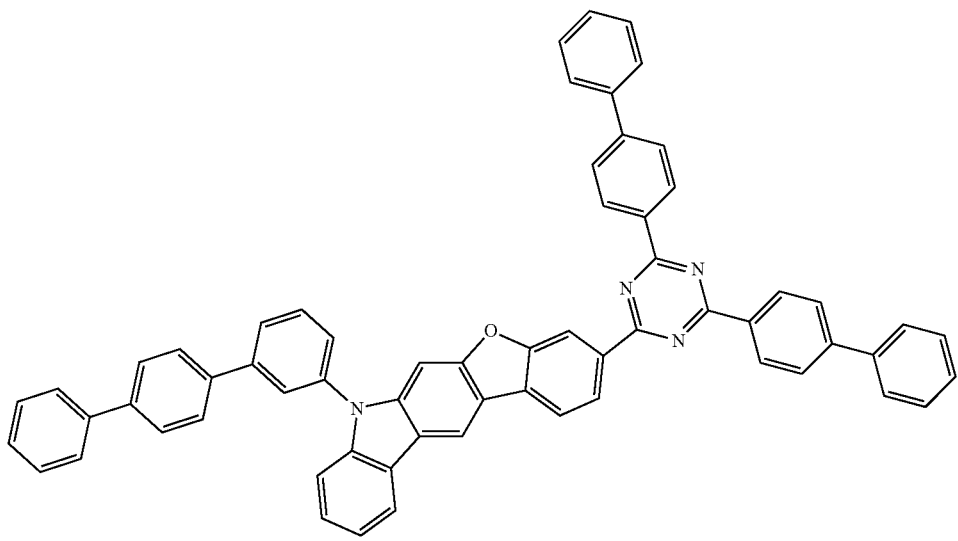

1A-3-13
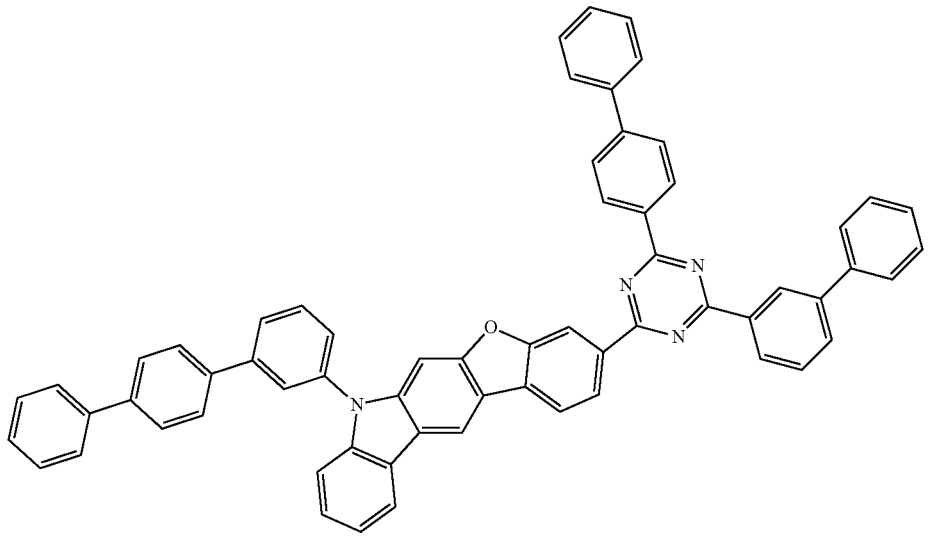
1A-3-14
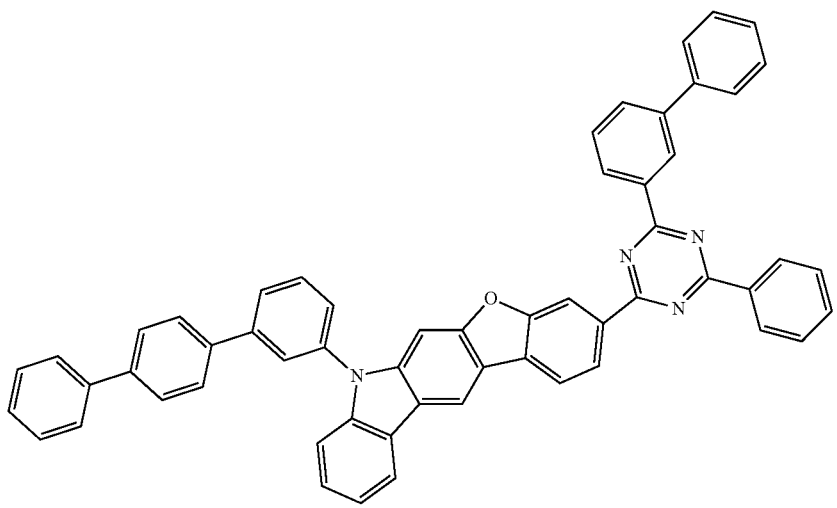
1A-3-15
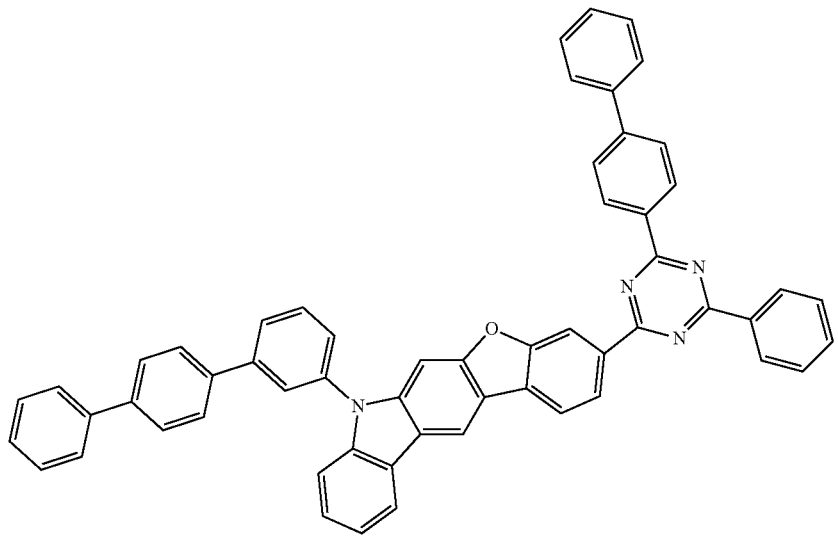

-continued
1A-3-16
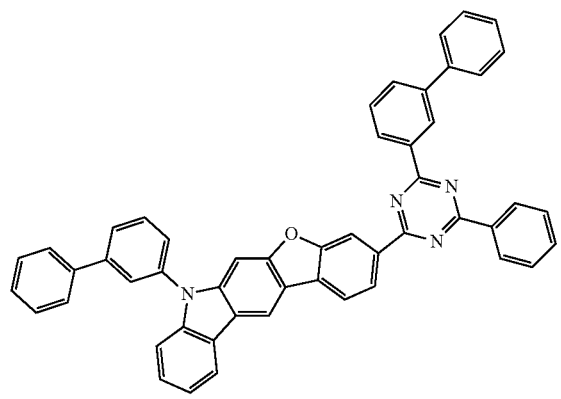
1A-3-17
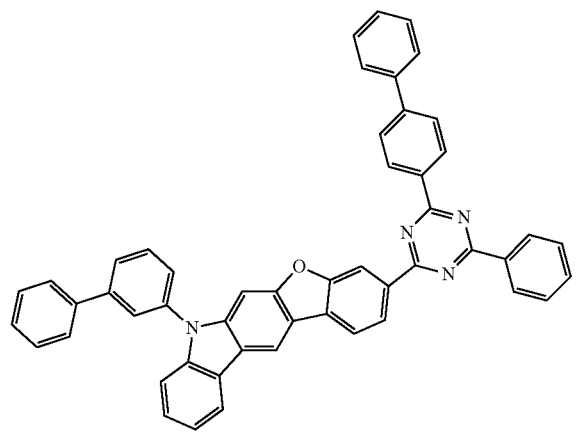
1A-3-18
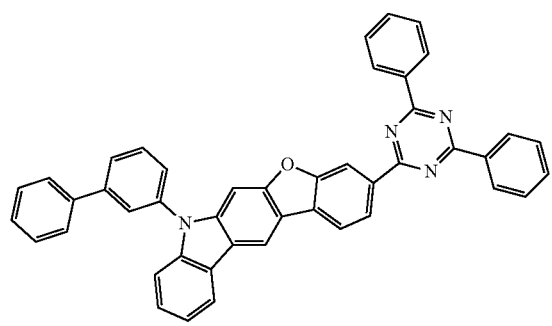
1A-3-19
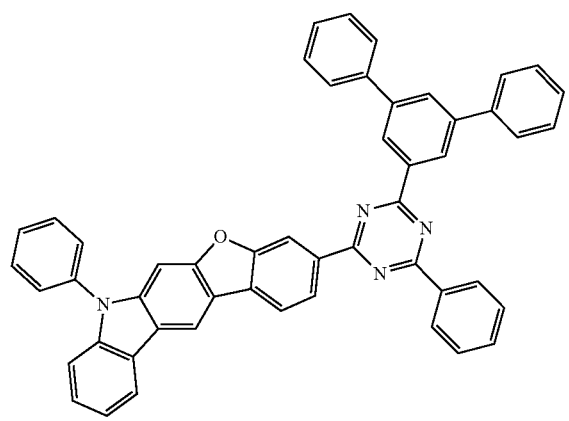
1A-3-20
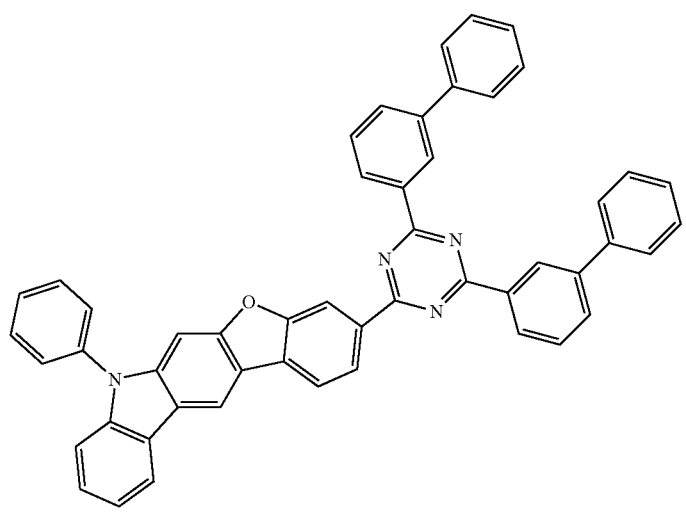

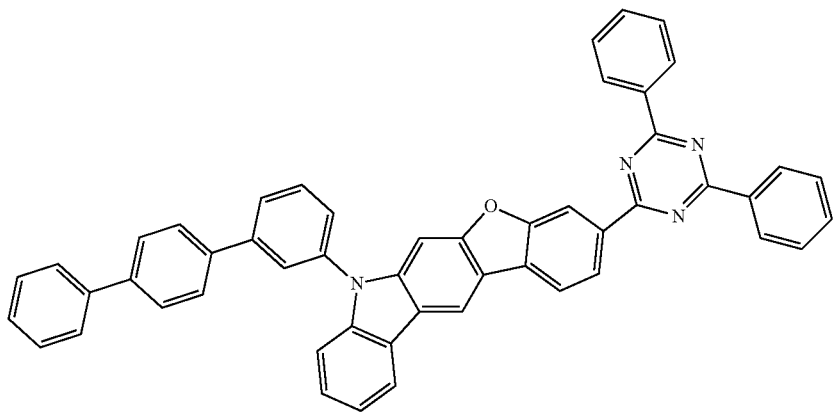
1A-3-21
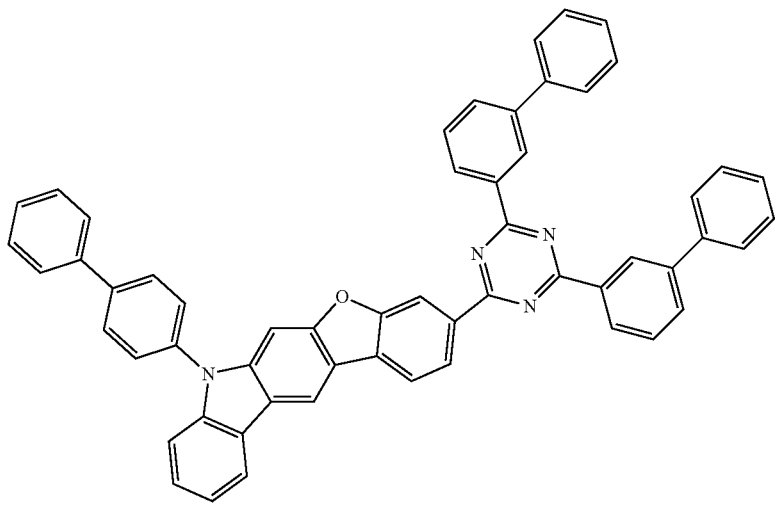
1A-3-22
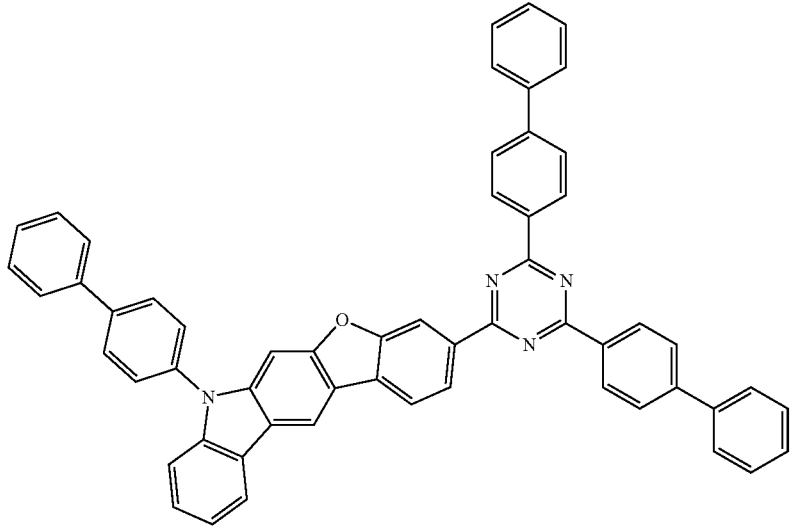
1A-3-23

-continued
1A-3-24
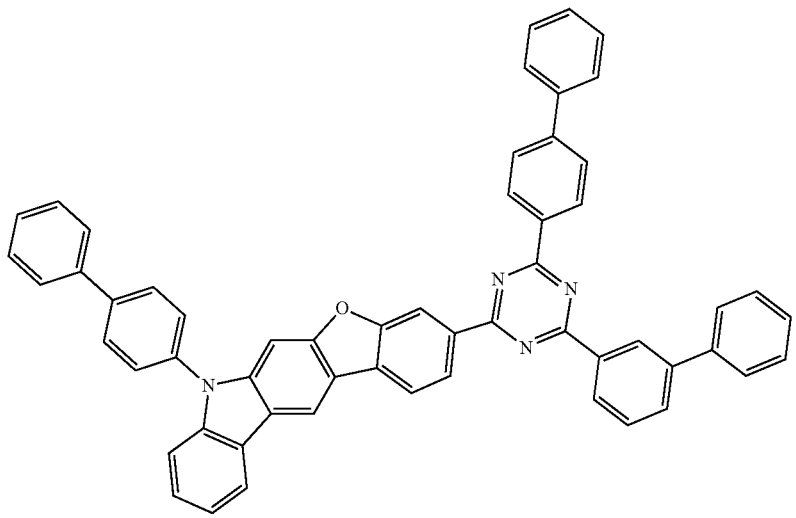
1A-3-25
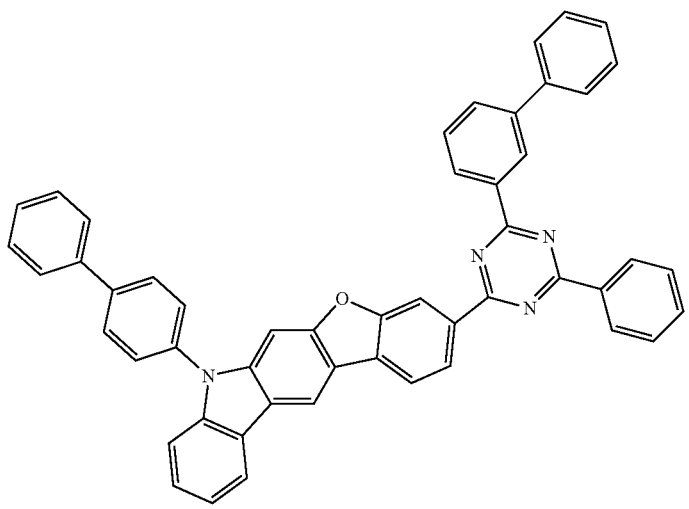
1A-3-26
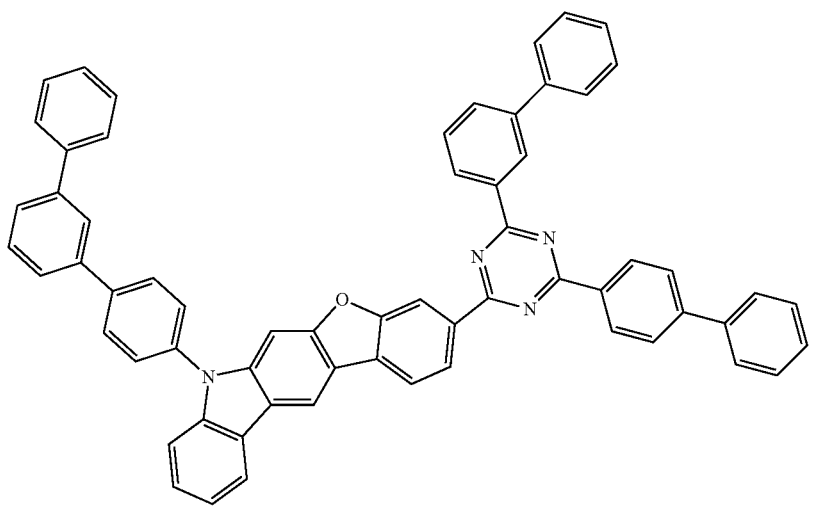

-continued
1A-3-27
1A-3-28
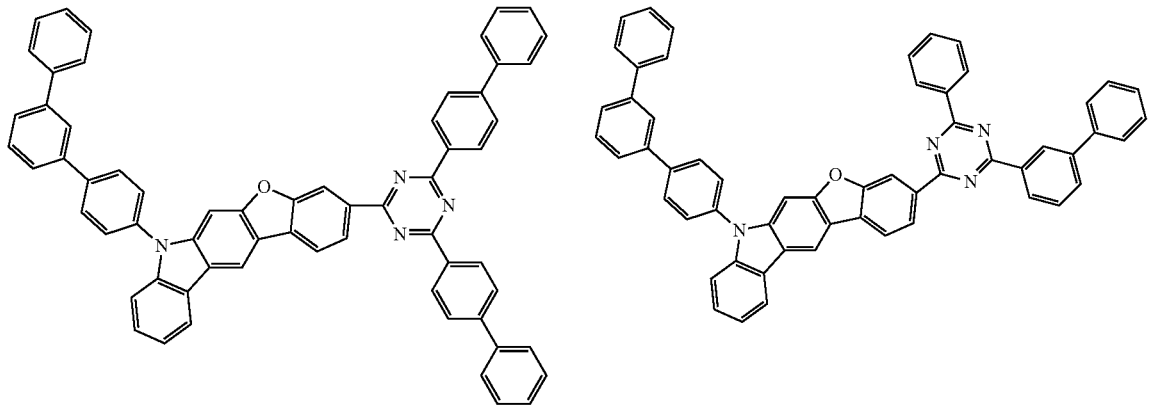
1A-3-29
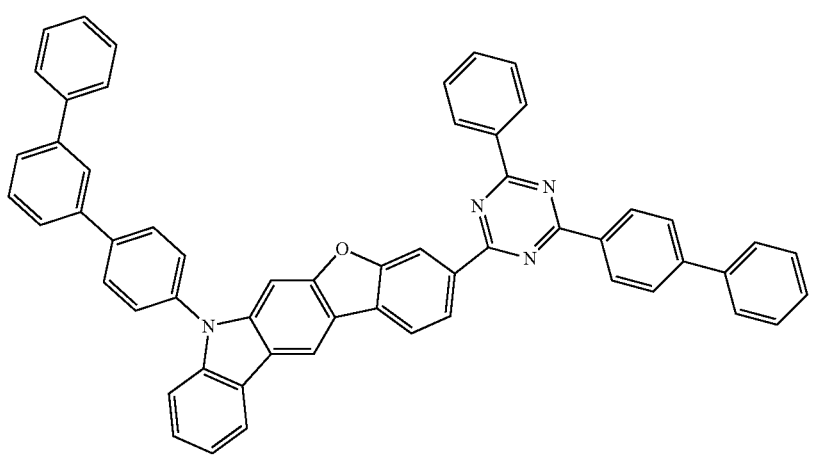
1A-3-30
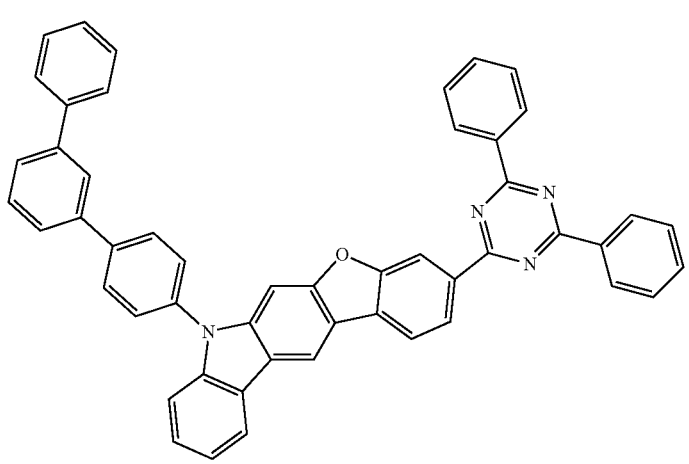

1A-3-31
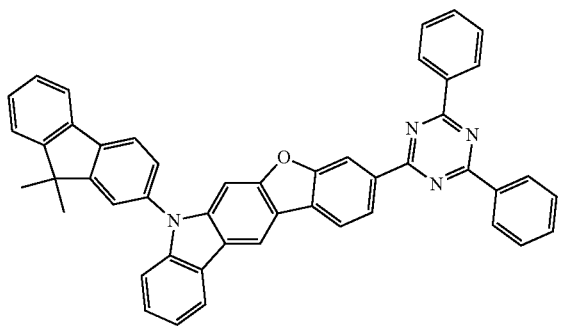
1A-3-32
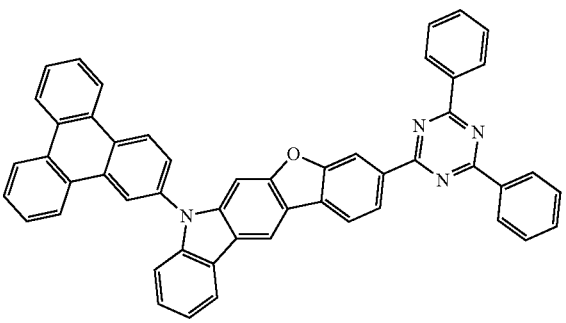
1A-3-33
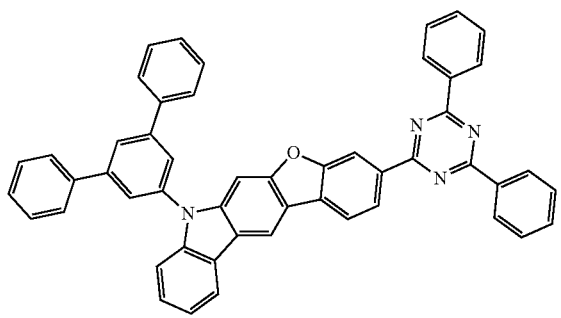
1A-3-34
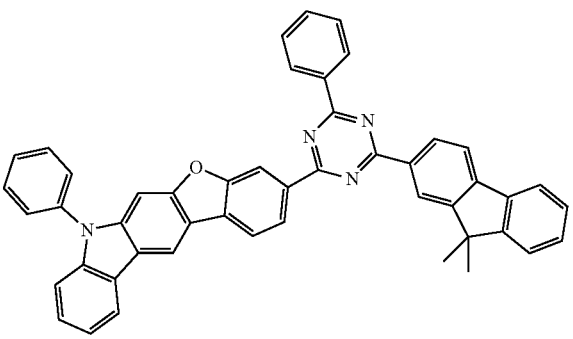
1A-3-35
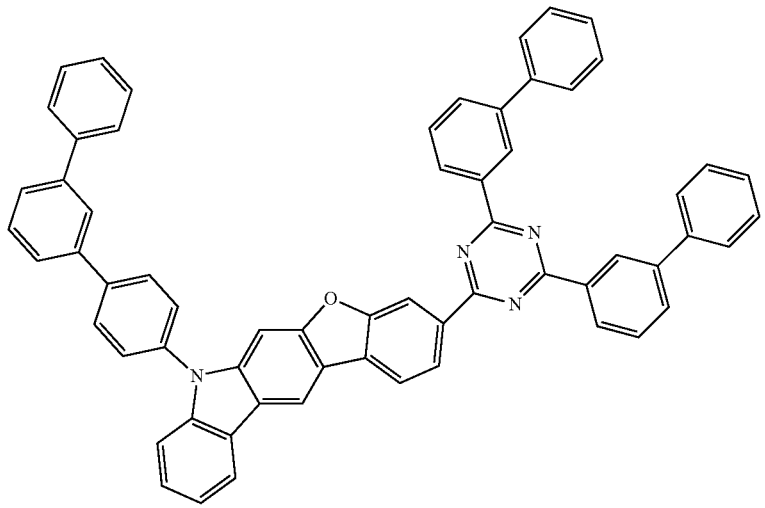
1A-3-36
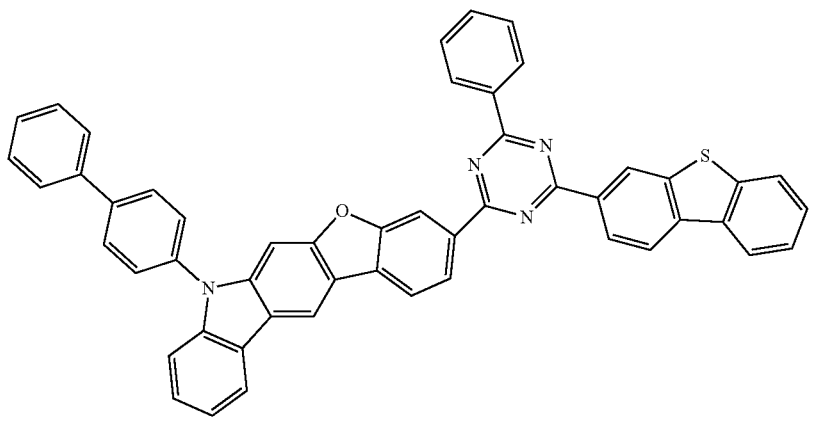

-continued
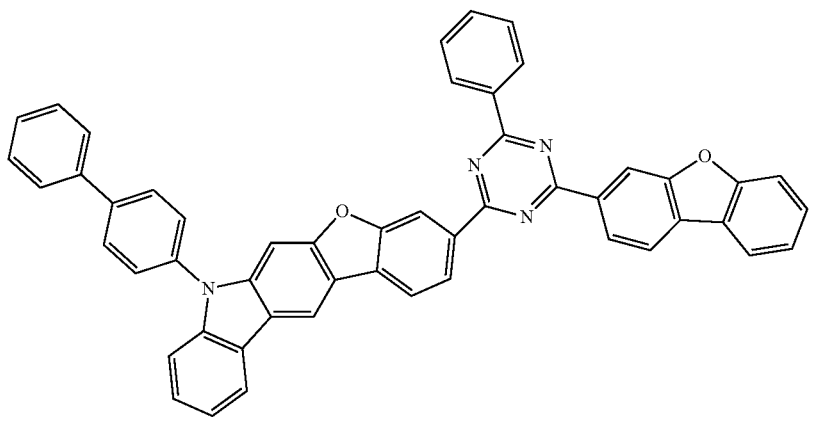
1A-3-37
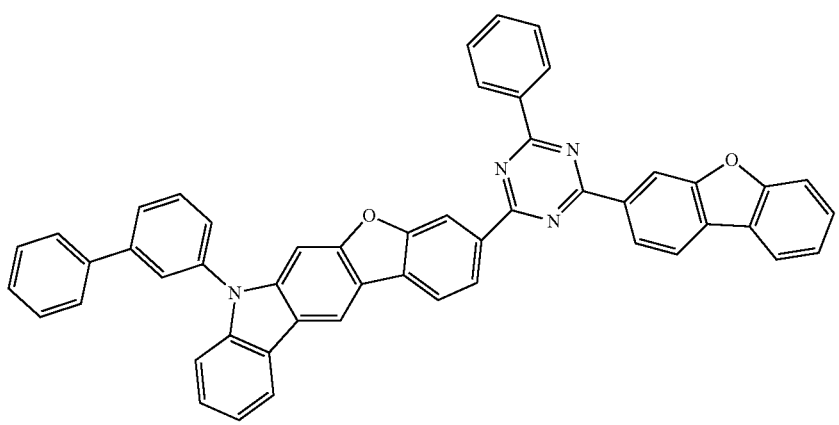
1A-3-38
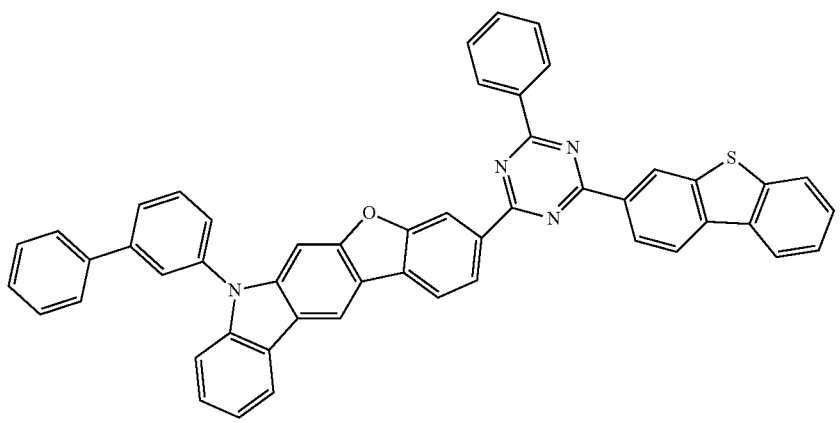
1A-3-39

-continued
1A-3-40
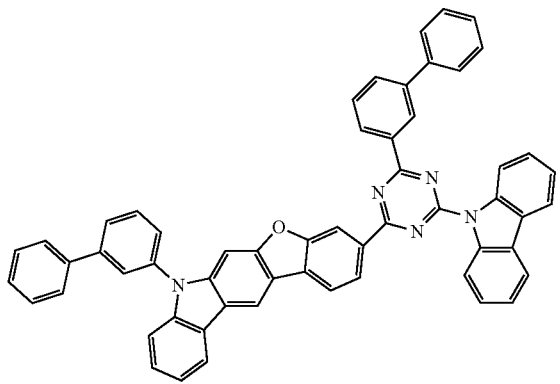
1A-3-41
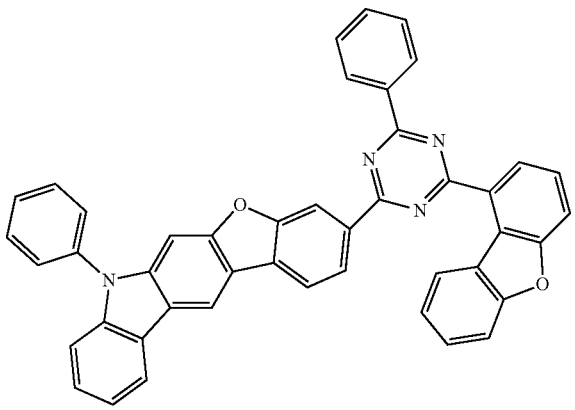
1A-3-42
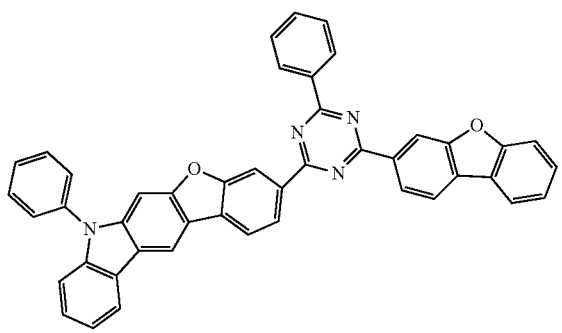
1A-3-43
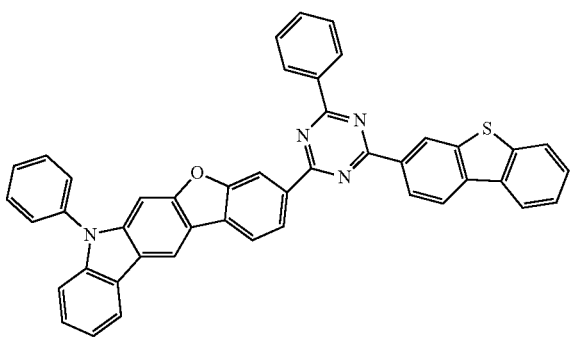
1A-3-44
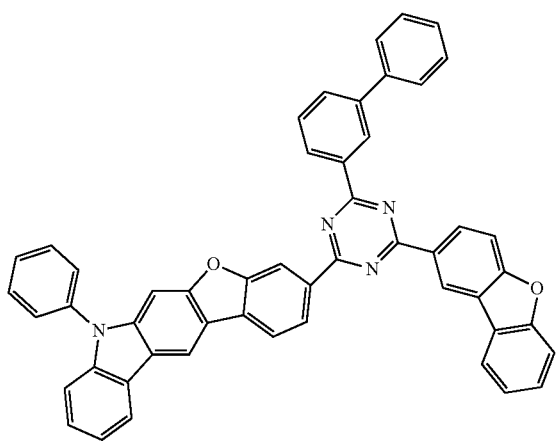
1A-3-45
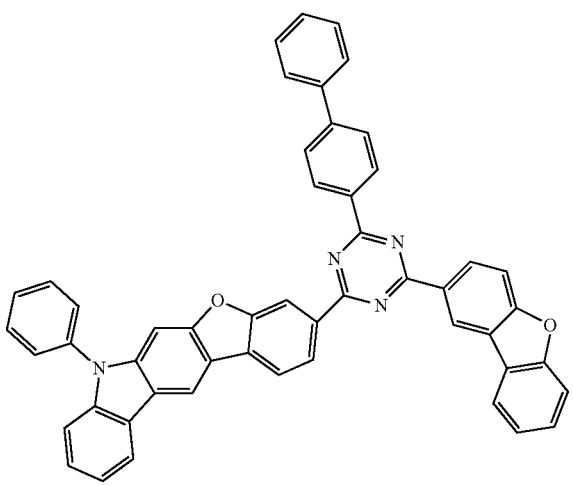

-continued
1A-3-46
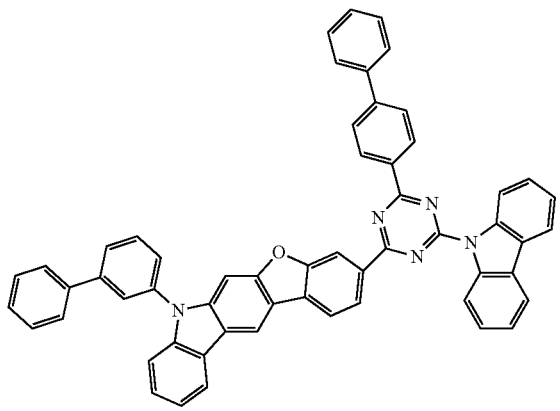
1A-3-47
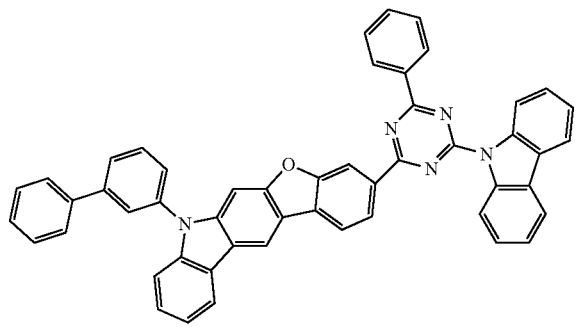
1A-3-48
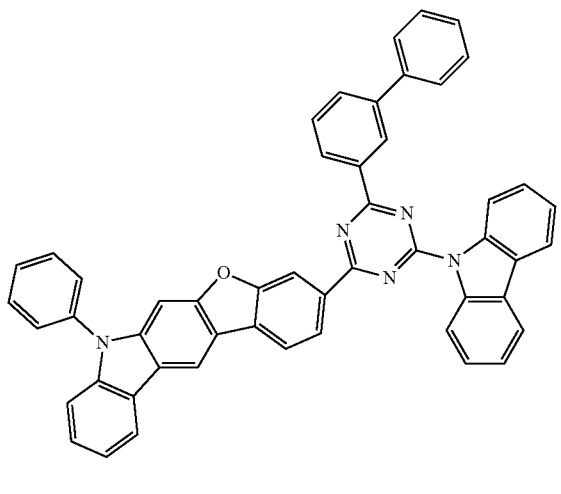
1A-3-49
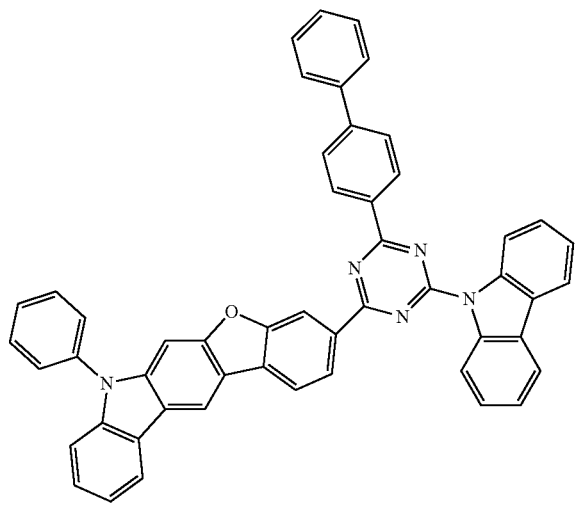
1A-3-50
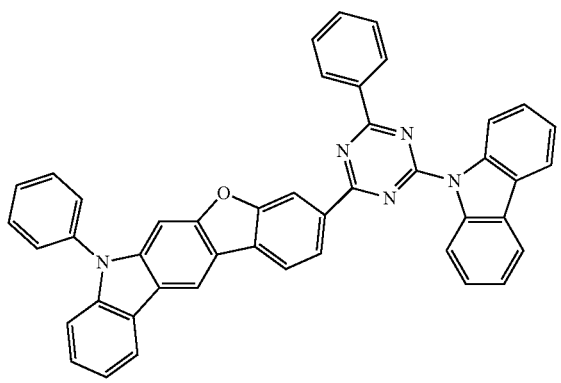
1A-3-51
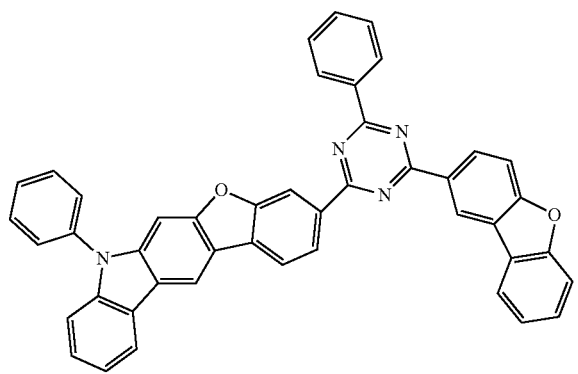

-continued
1A-3-52
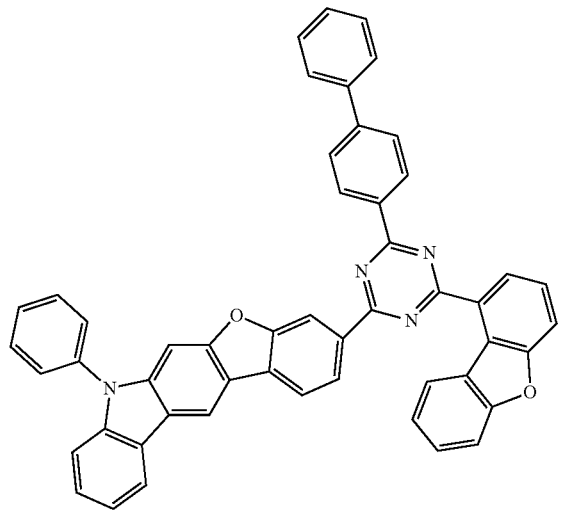
1A-3-53
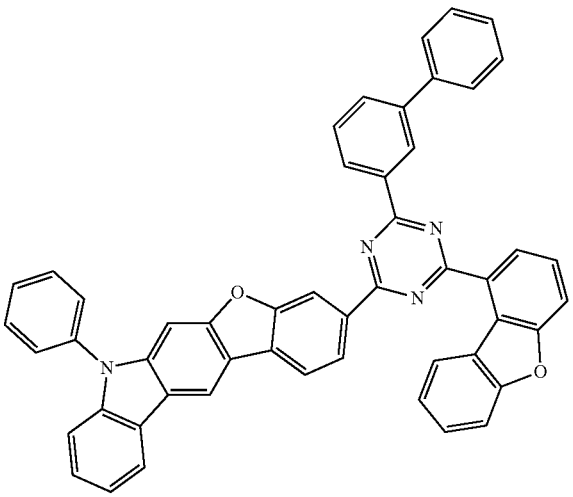
1A-3-54
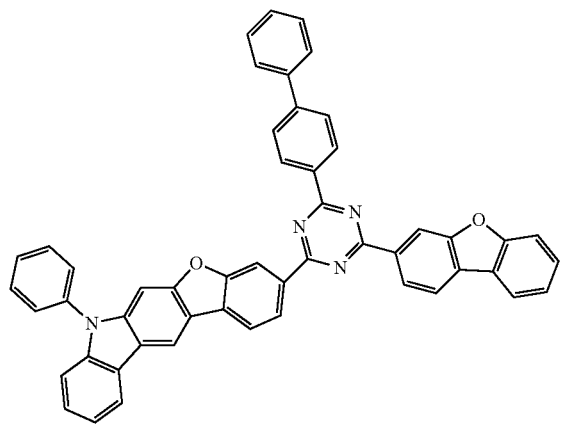
1A-3-55
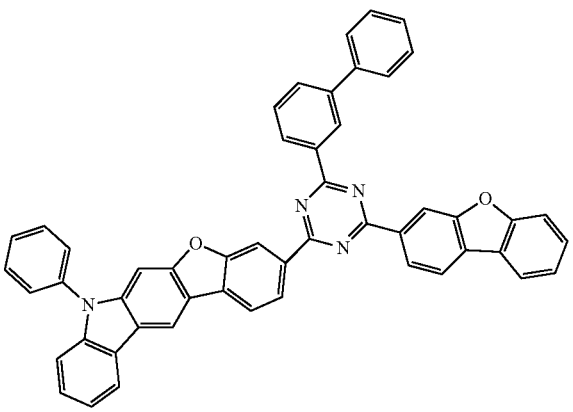
1A-3-56
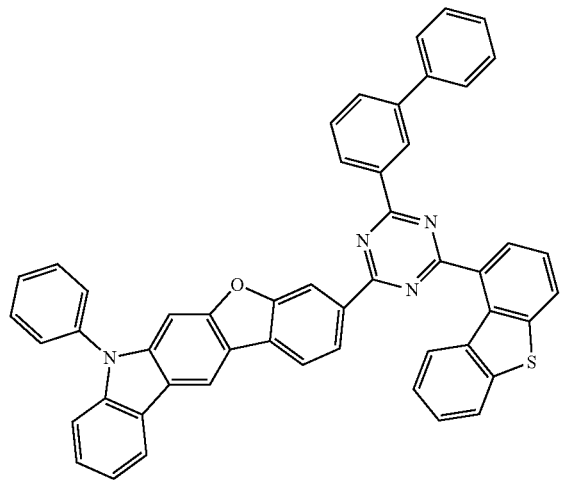
1A-3-57
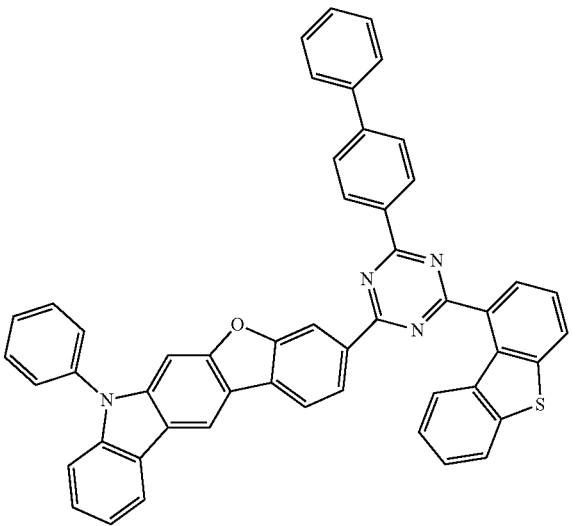

-continued
1A-3-58
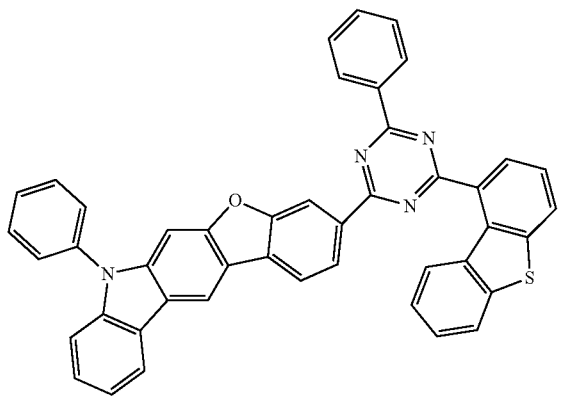
1A-3-59
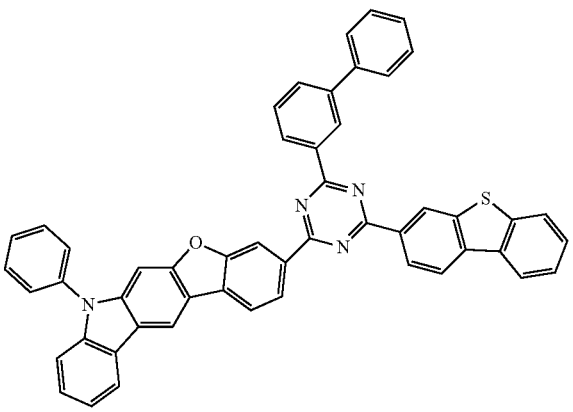
1A-3-60
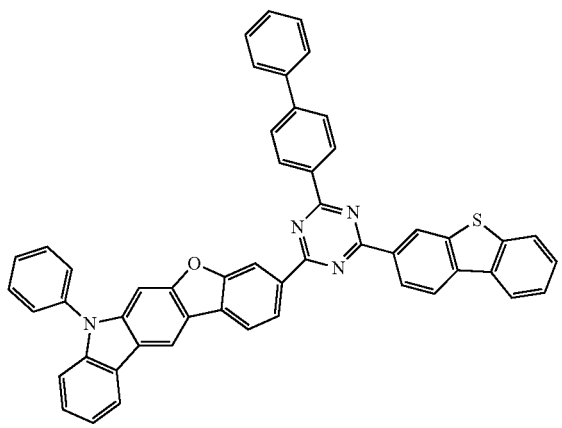
1A-3-61
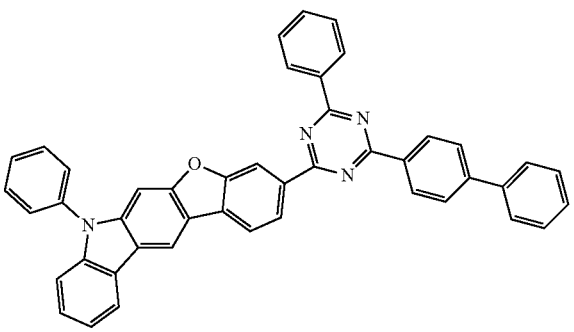
1A-3-62
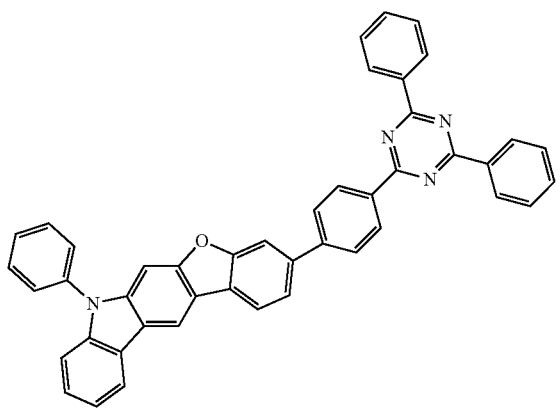
1A-3-63
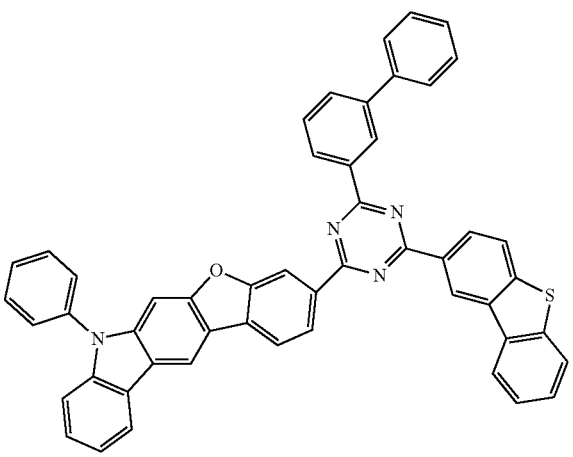

-continued
1A-3-64
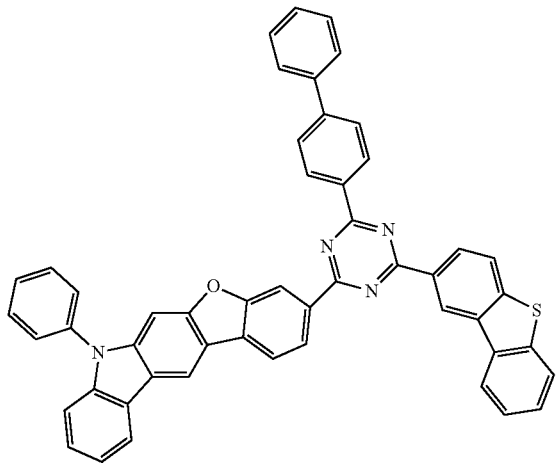
1A-3-65
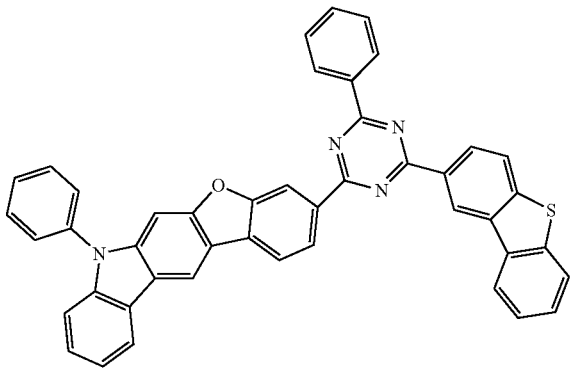
1A-3-66
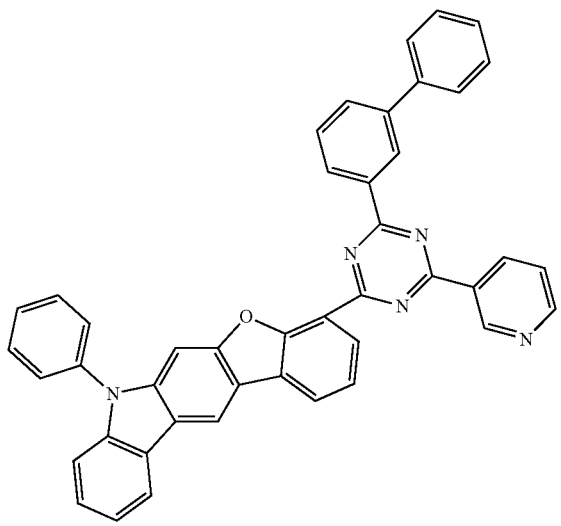
1A-3-67
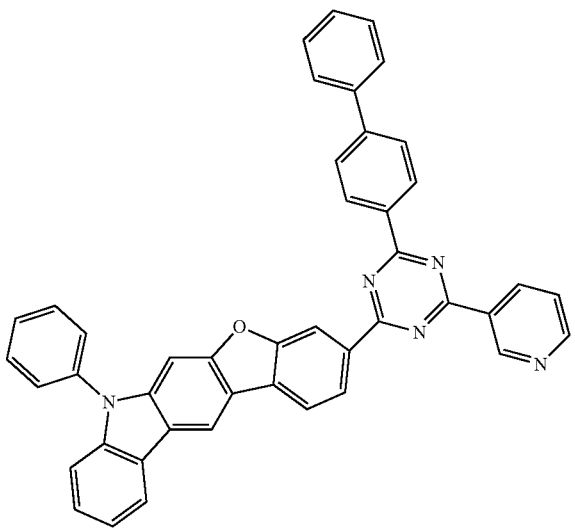
1A-3-68
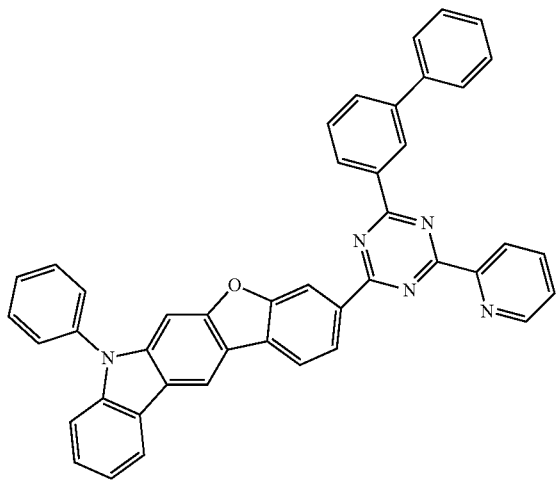
1A-3-69
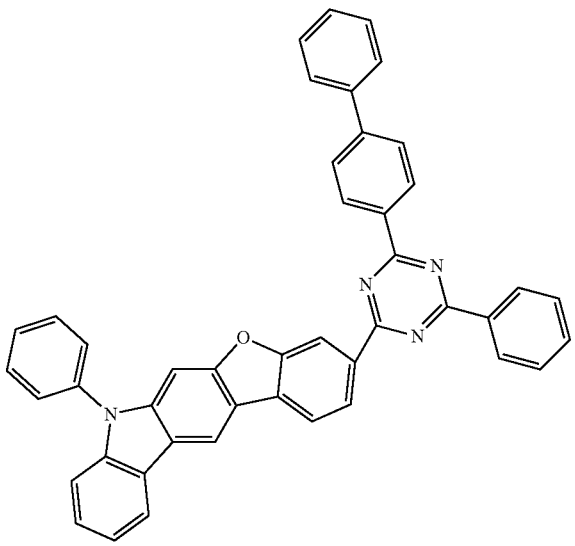

-continued
1A-3-70
1A-3-71
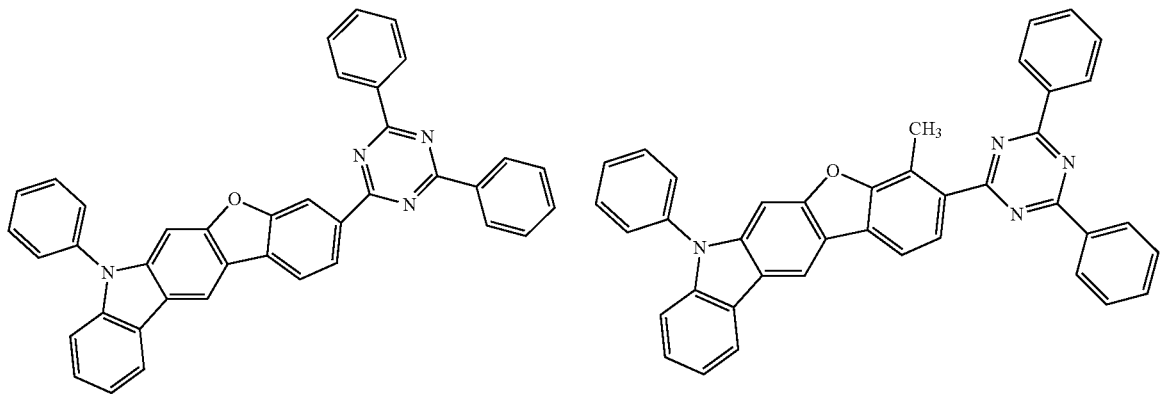
1A-3-72
1A-3-73
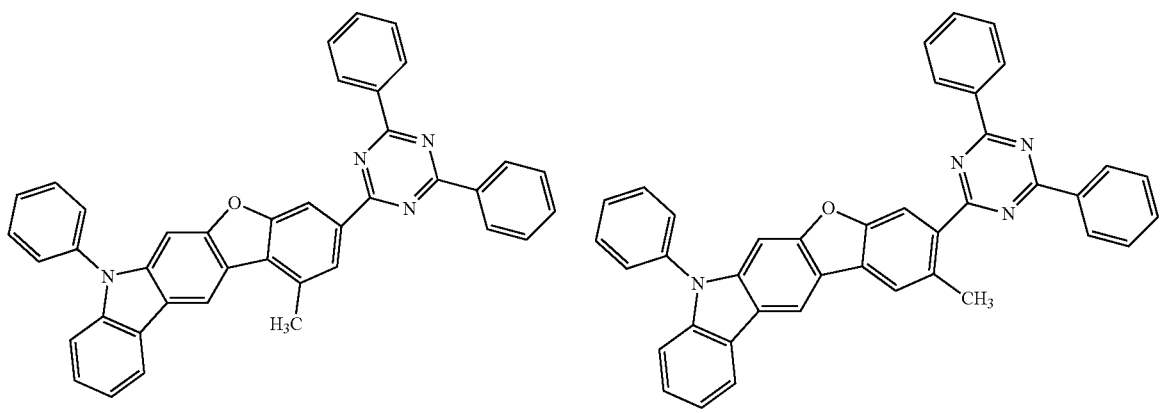
1A-3-74
1A-3-75
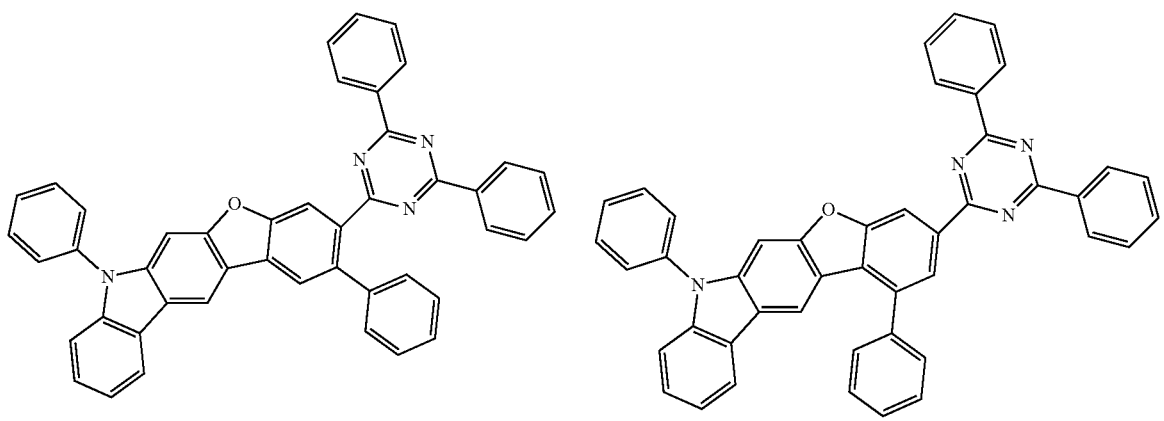

1A-3-76
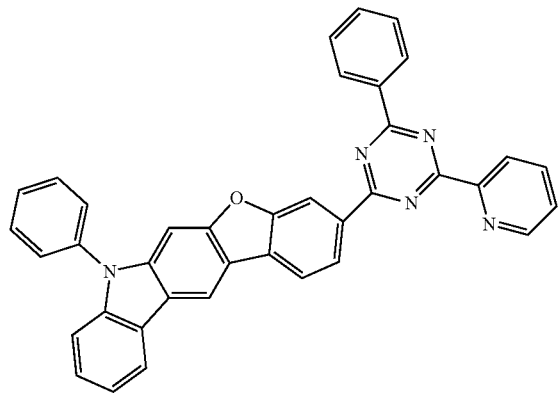
1A-3-77
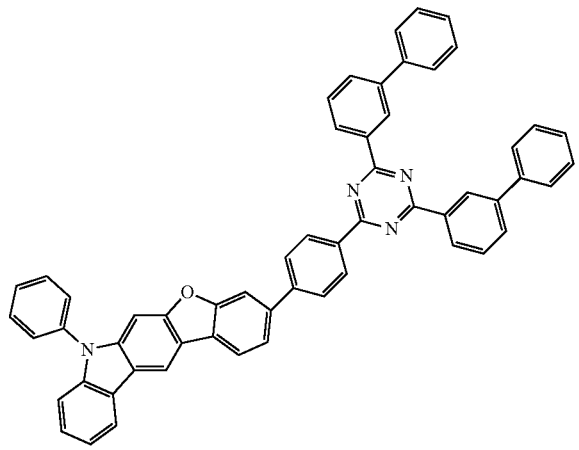
1A-3-78
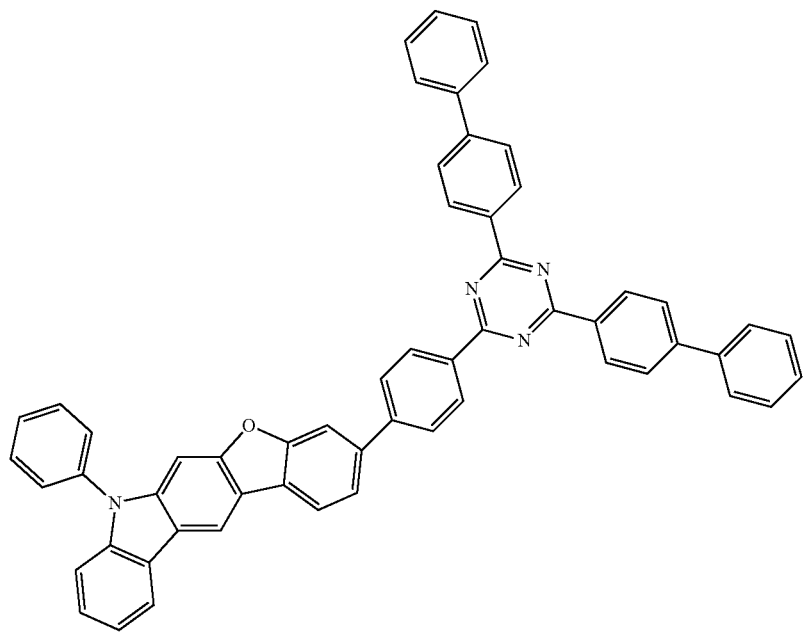

1A-3-79
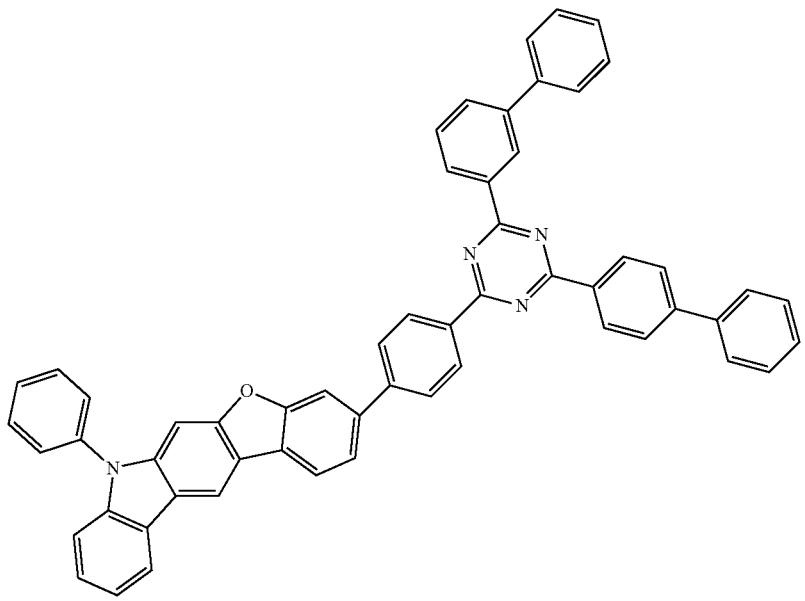
1A-3-80 1A-3-81
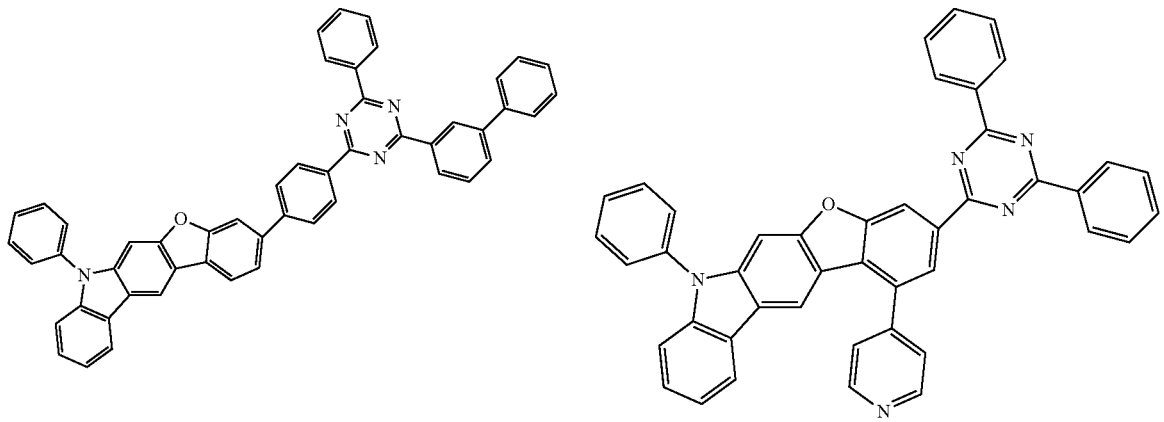
1A-3-82 1A-3-83
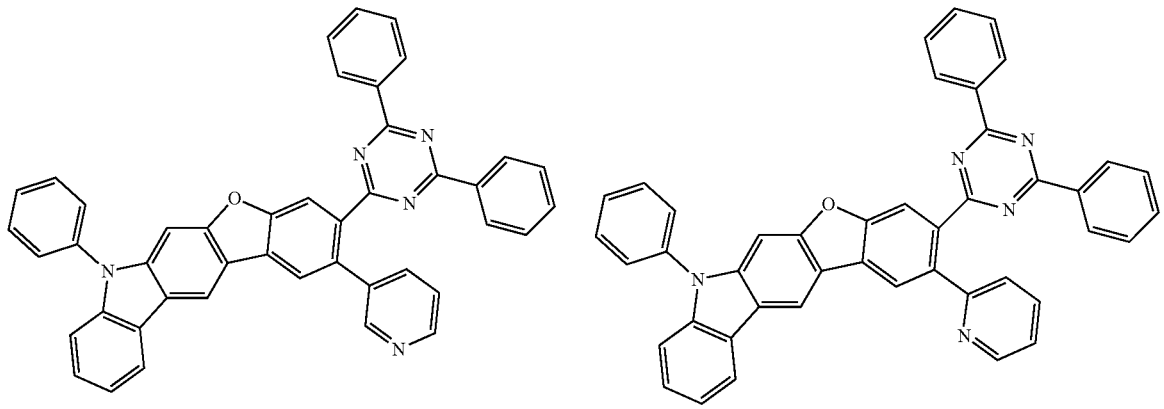

-continued
1A-4-1
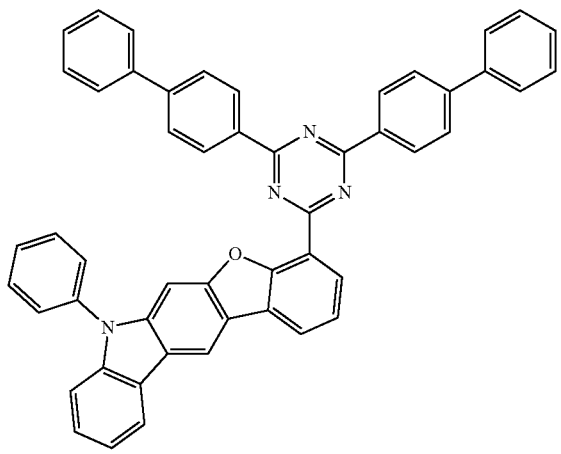
1A-4-2
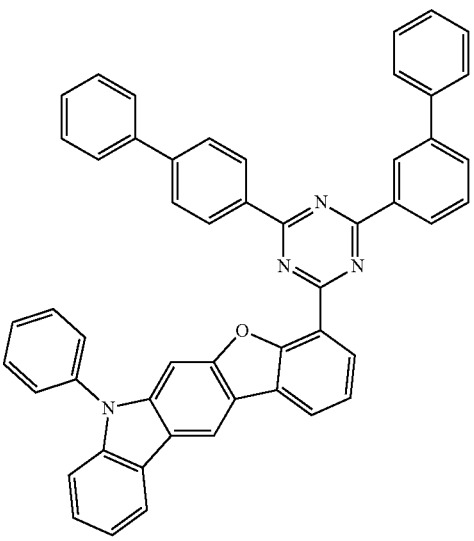
1A-4-3
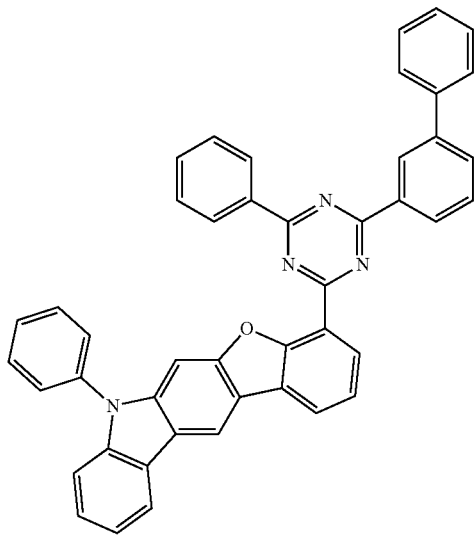
1A-4-4
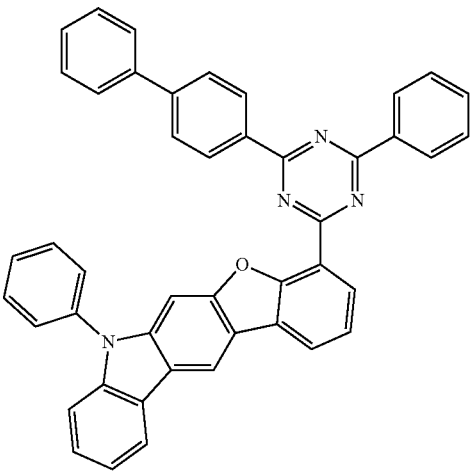
1A-4-5
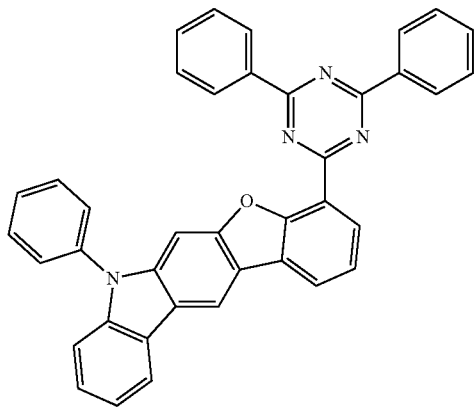
1A-4-6
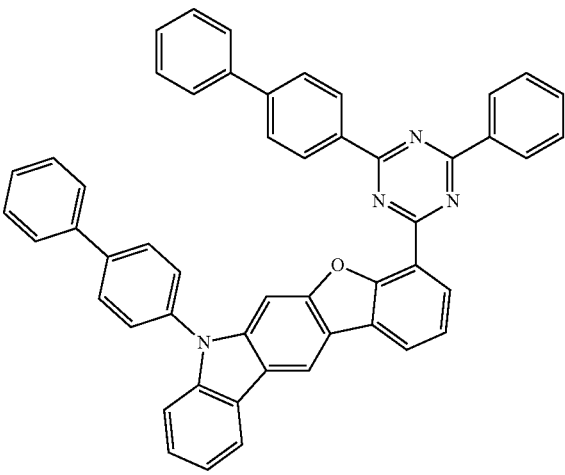

-continued
1A-4-7
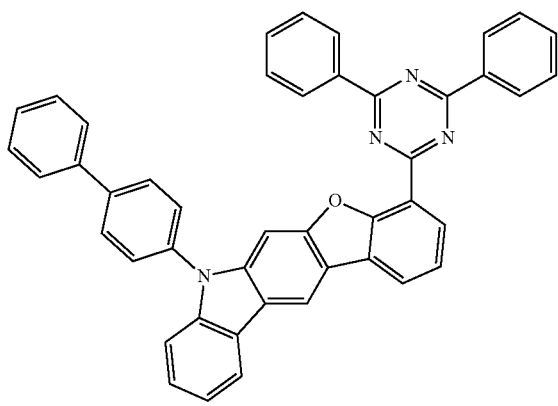
1A-4-8
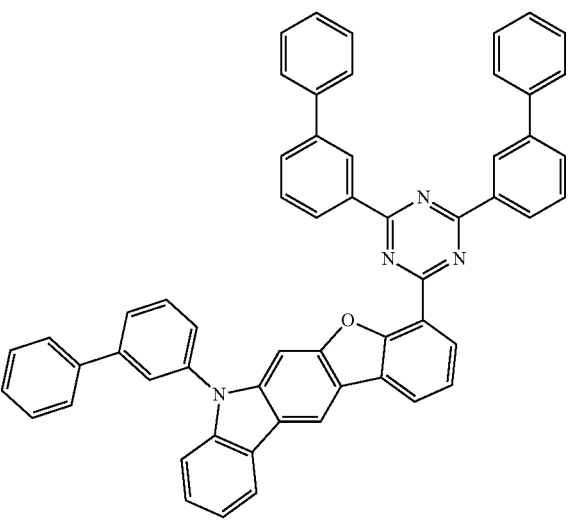
1A-4-9
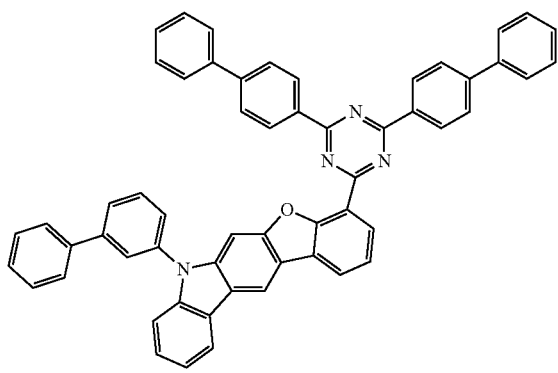
1A-4-10
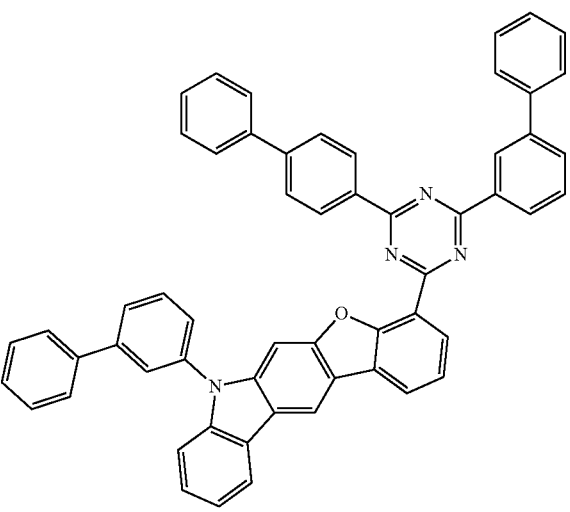
1A-4-11
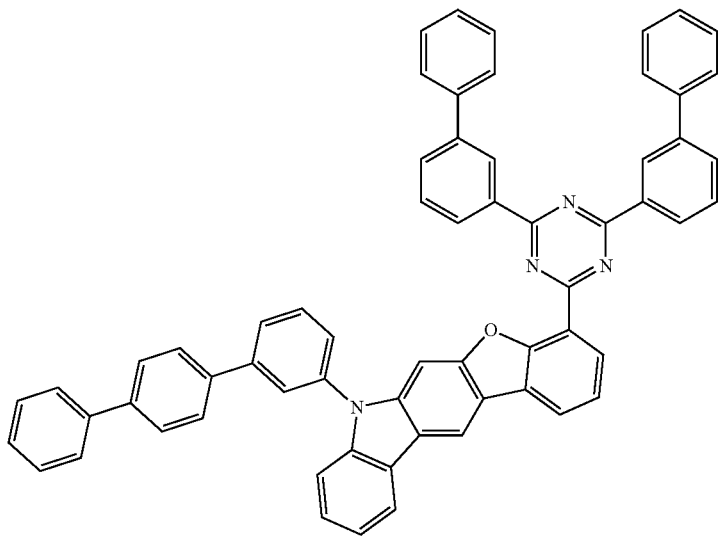

1A-4-12
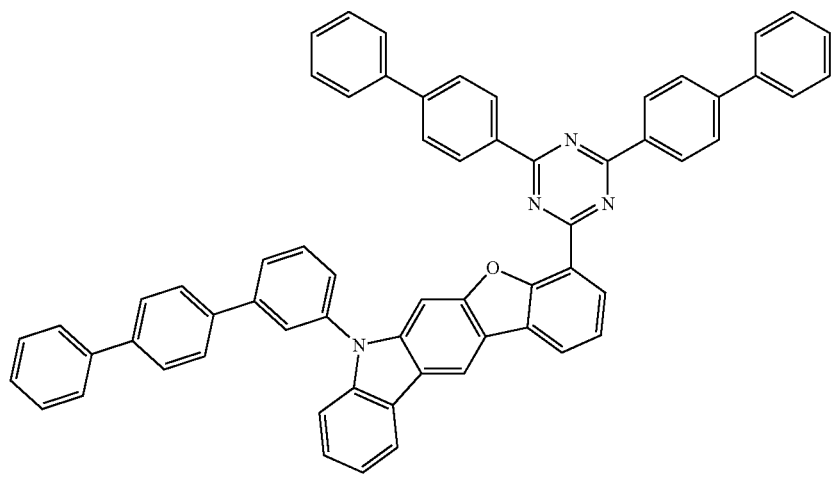
1A-4-13 1A-4-14
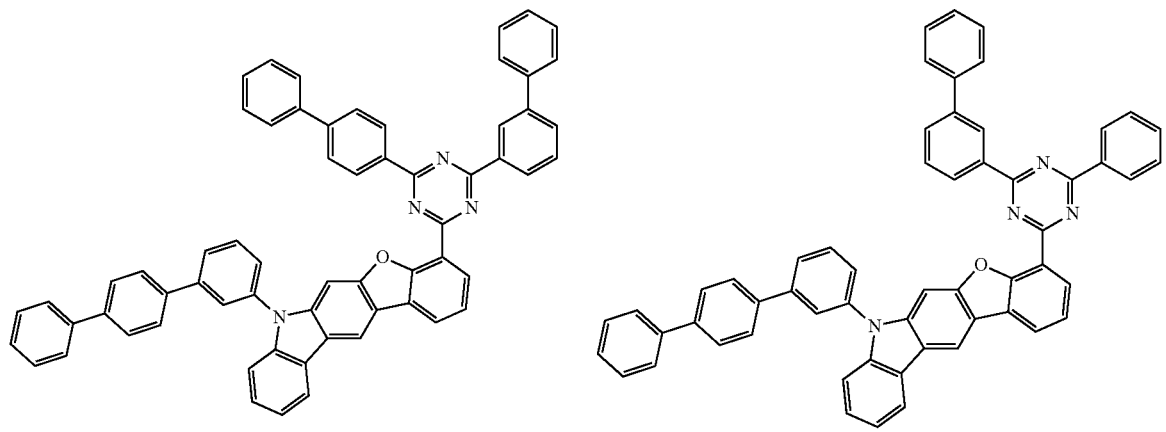
1A-4-15 1A-4-16
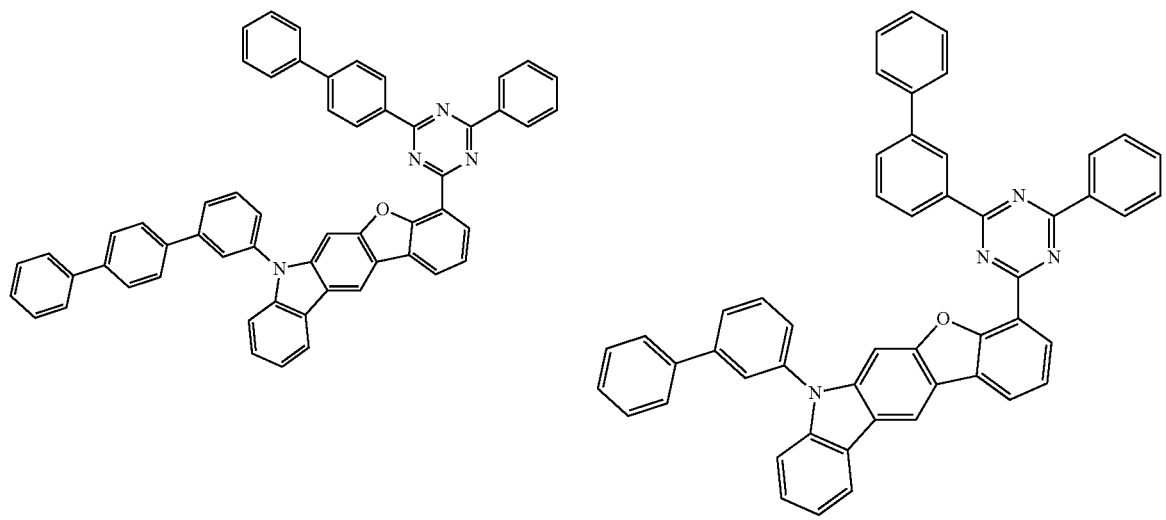

-continued
1A-4-17
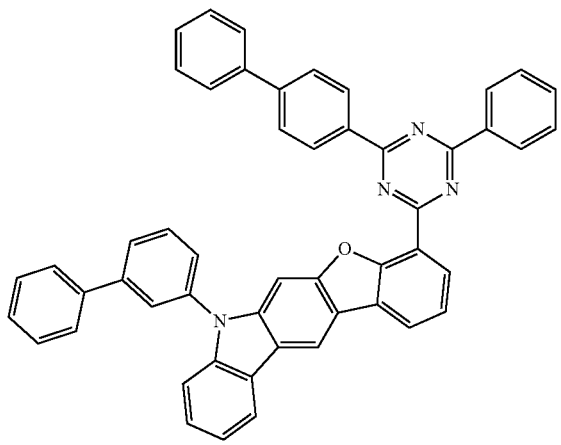
1A-4-18
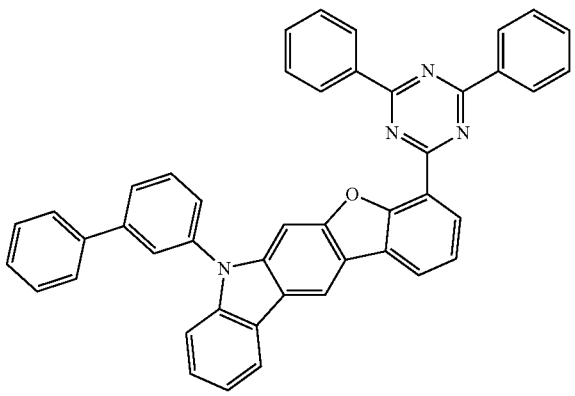
1A-4-19
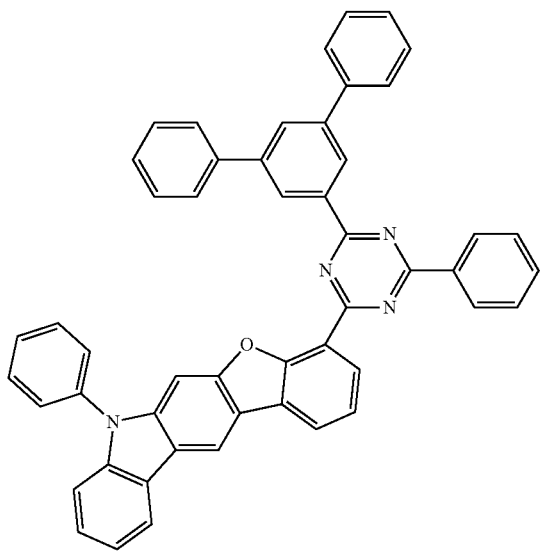
1A-4-20
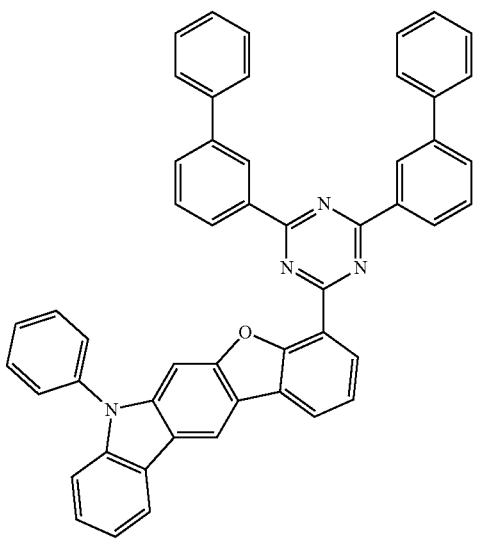
1A-4-21
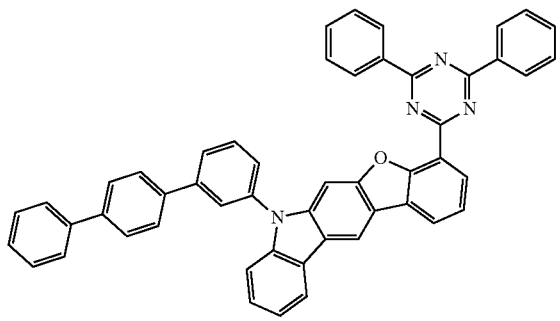
1A-4-22
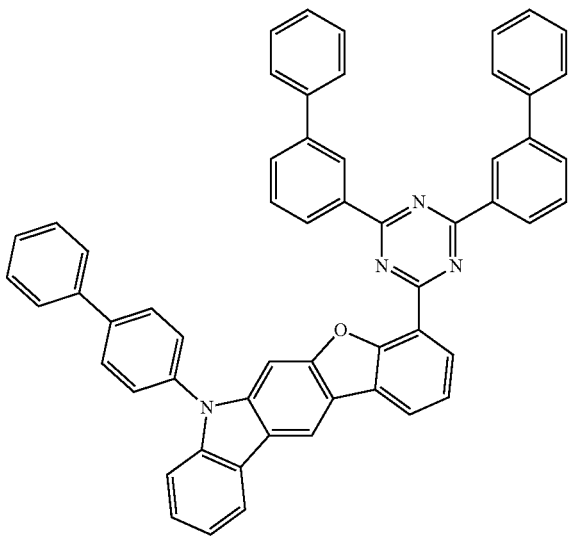

-continued
1A-4-23
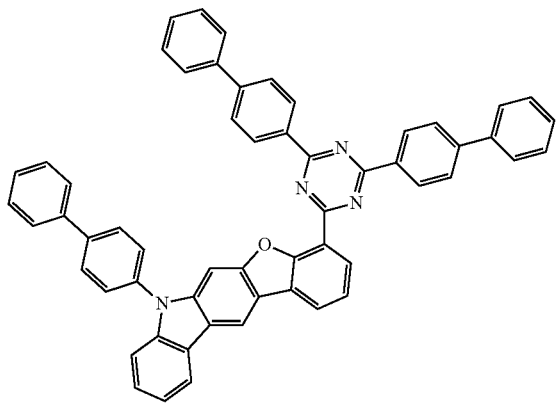
1A-4-24
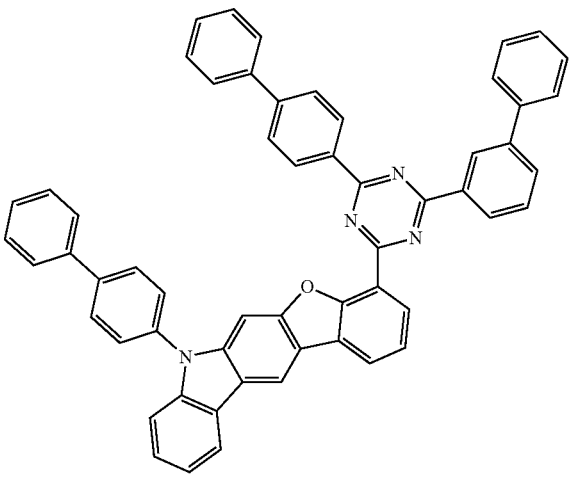
1A-4-25
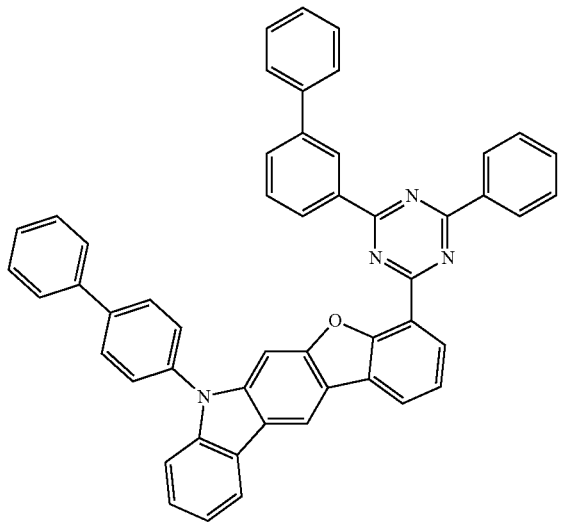
1A-4-26
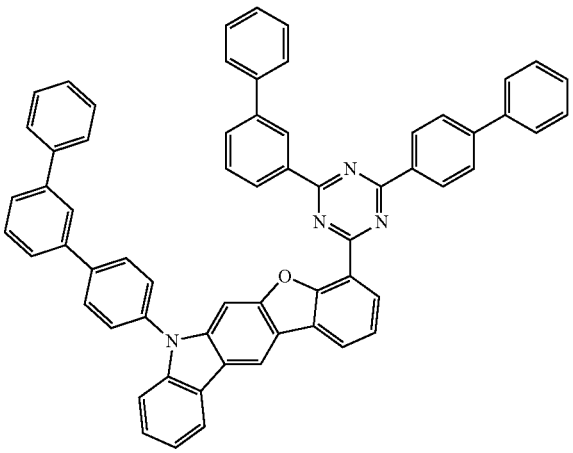
1A-4-27
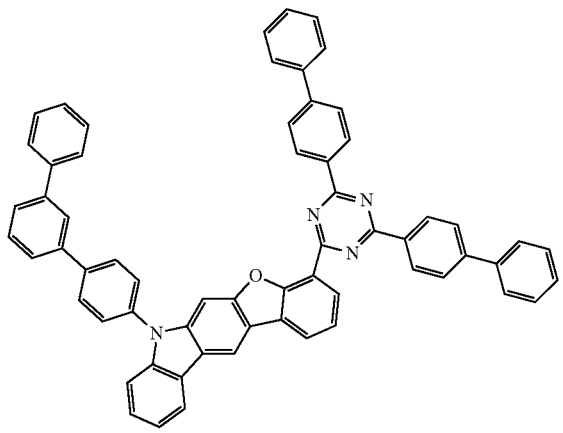
1A-4-28
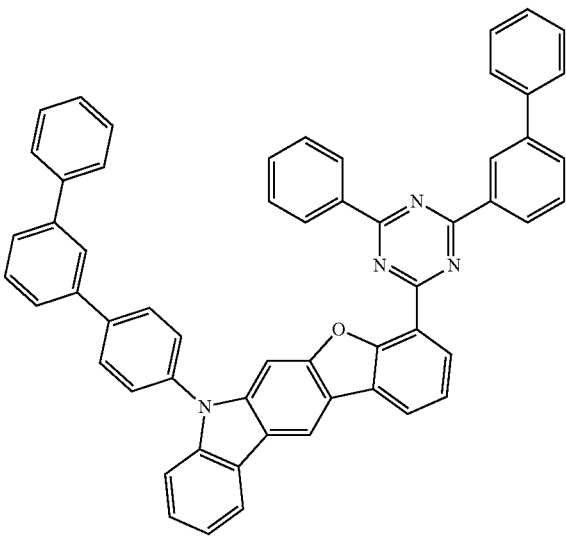

-continued
1A-4-29
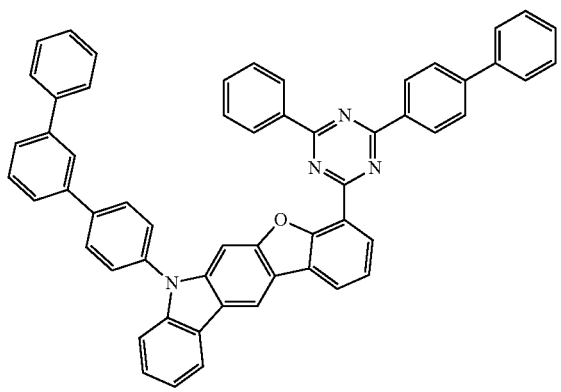
1A-4-30
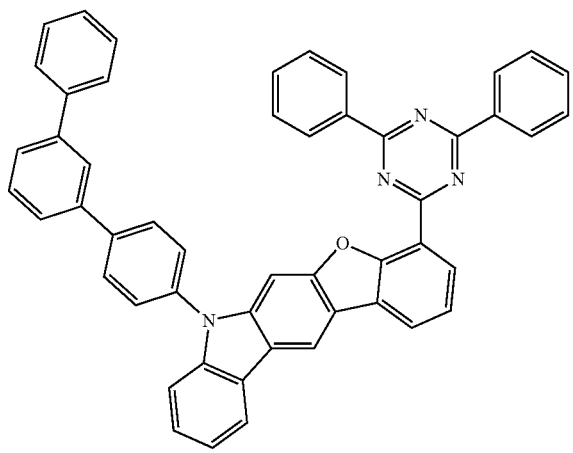
1A-4-31
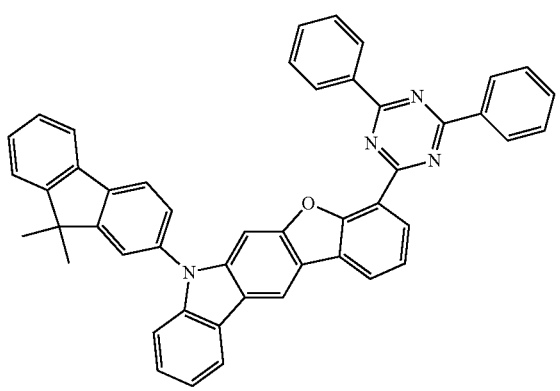
1A-4-32
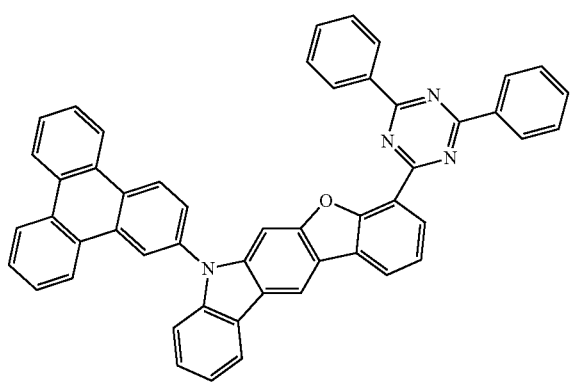
1A-4-33
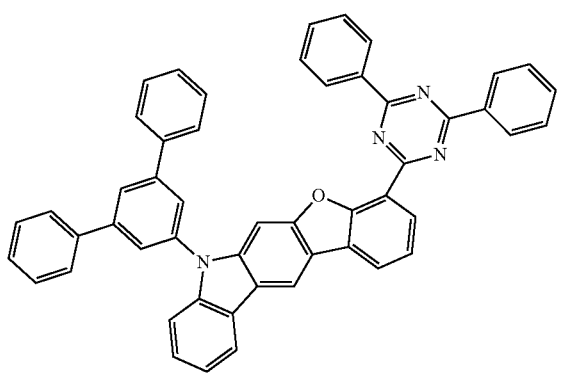
1A-4-34
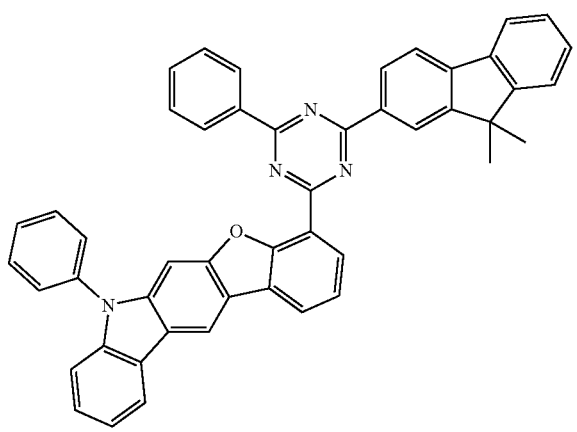

-continued
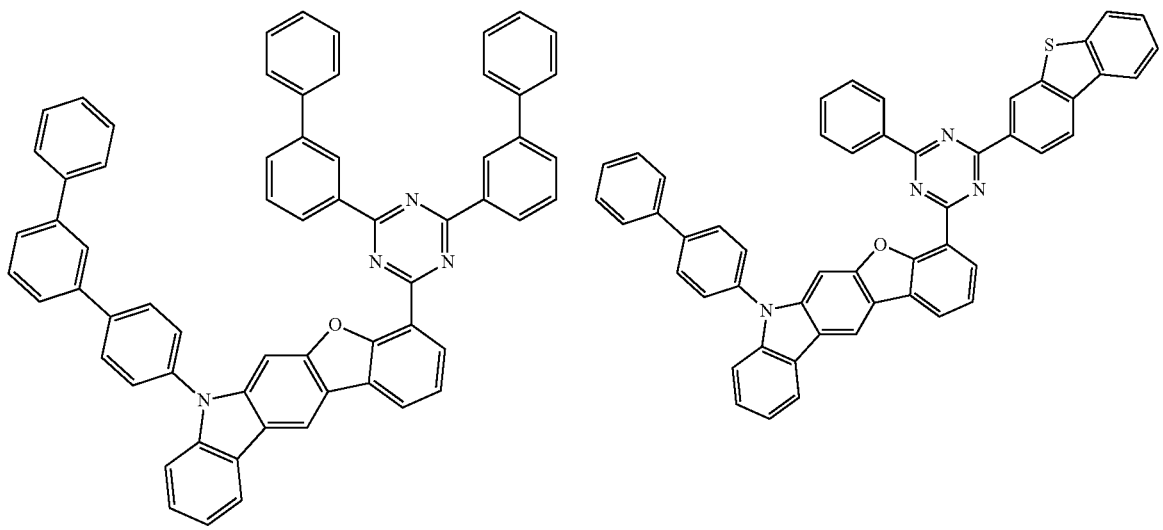
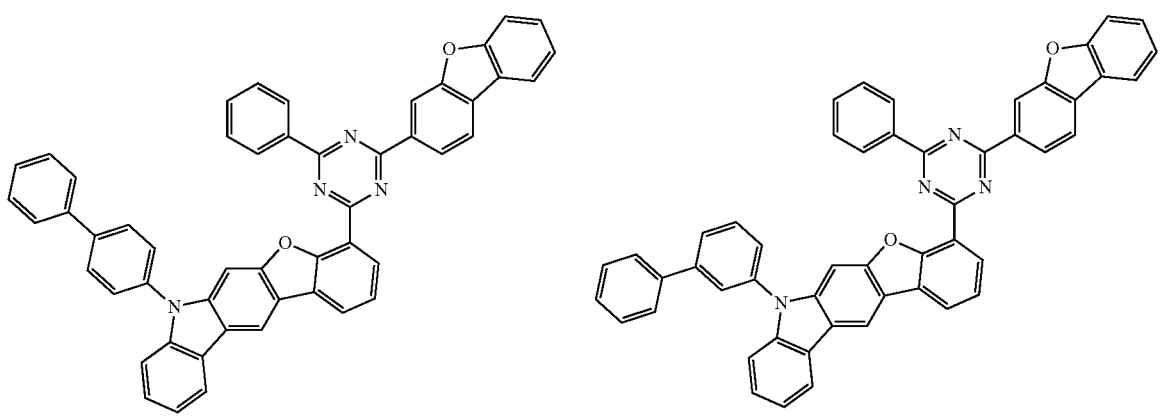
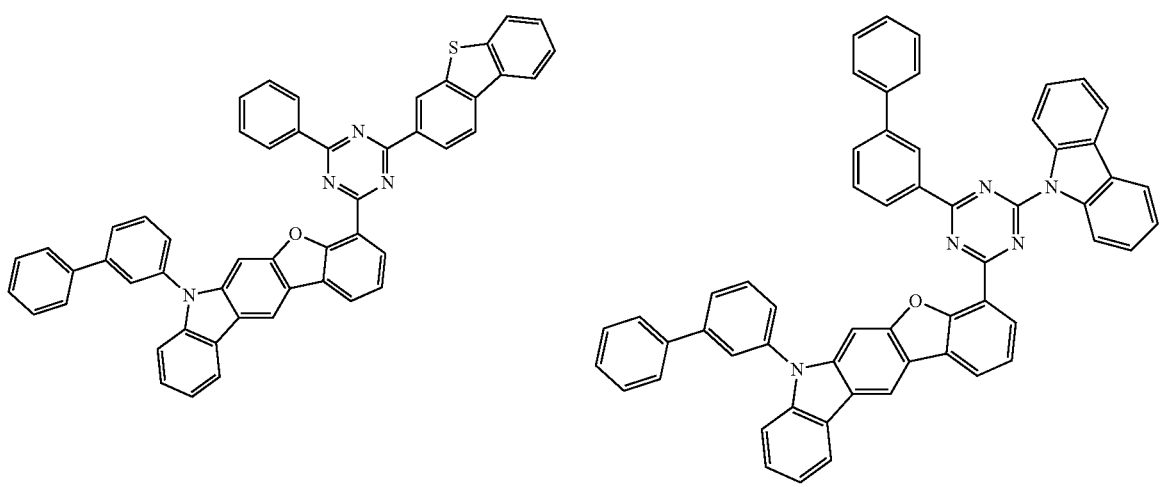

-continued
1A-4-41
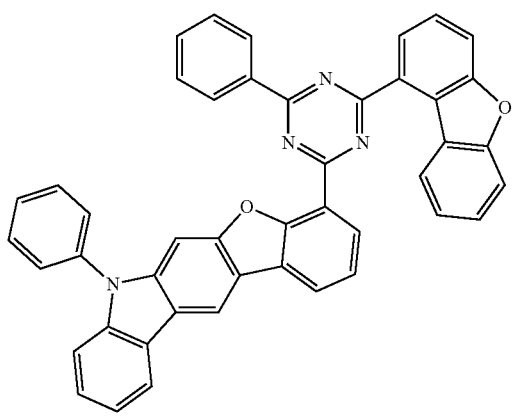
1A-4-42
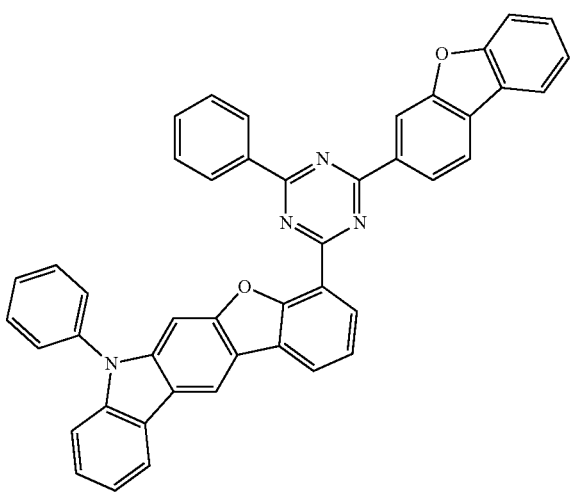
1A-4-43
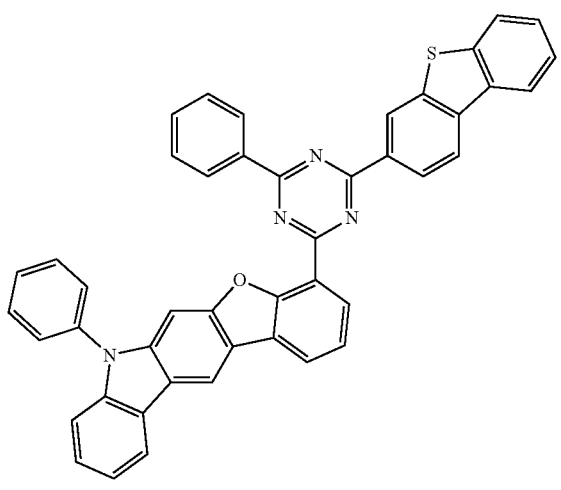
1A-4-44
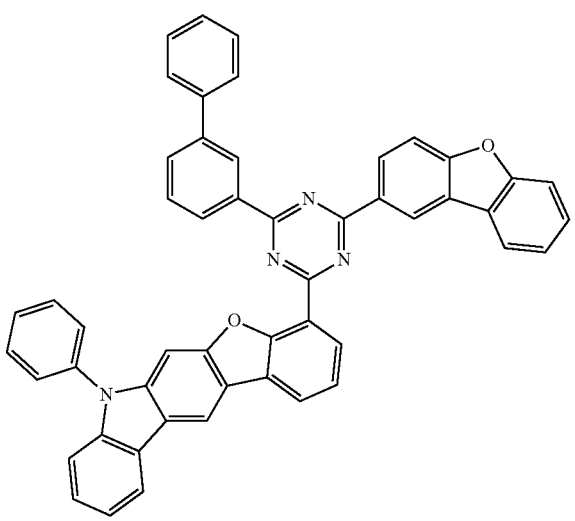
1A-4-45
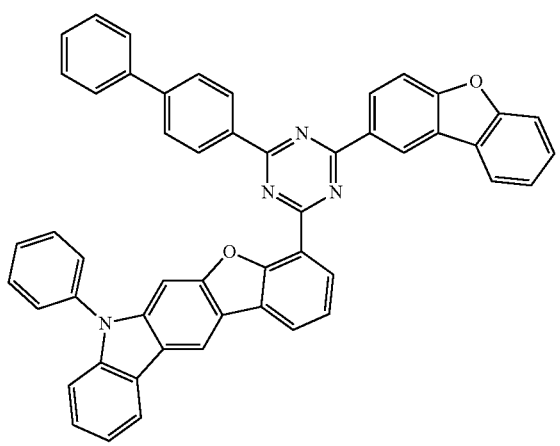
1A-4-46
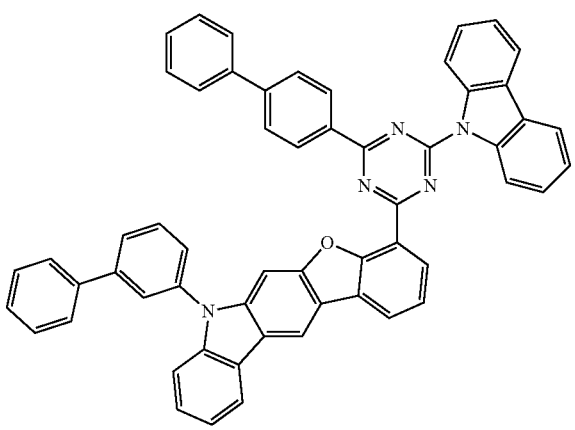

-continued
1A-4-47
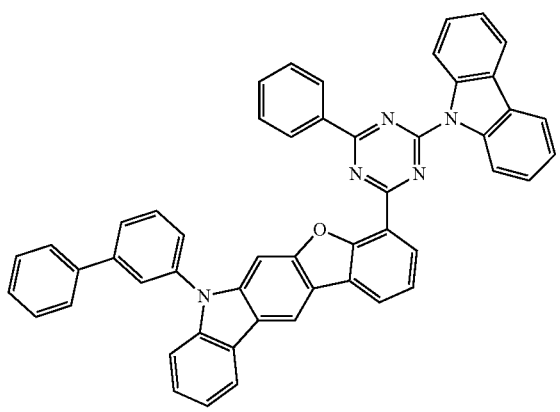
1A-4-48
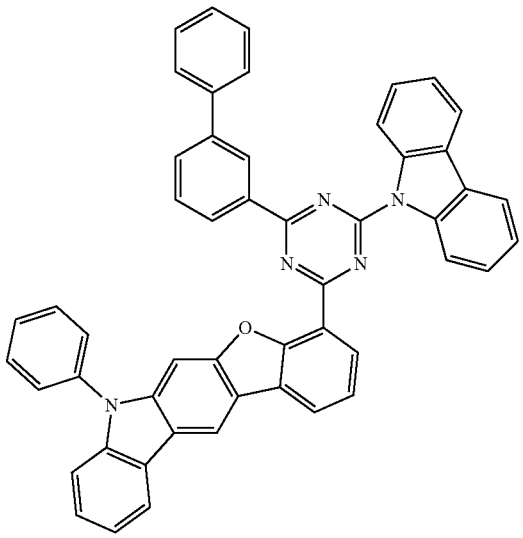
1A-4-49
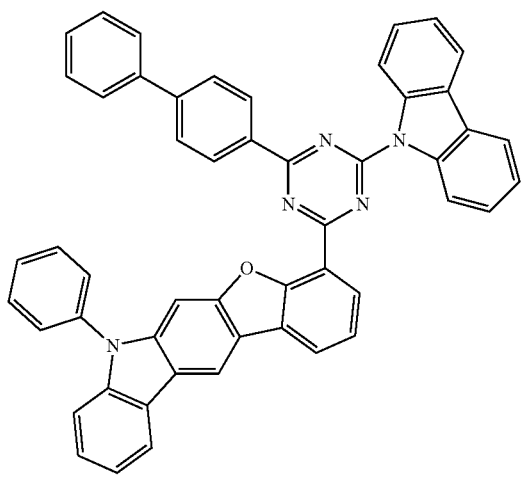
1A-4-50
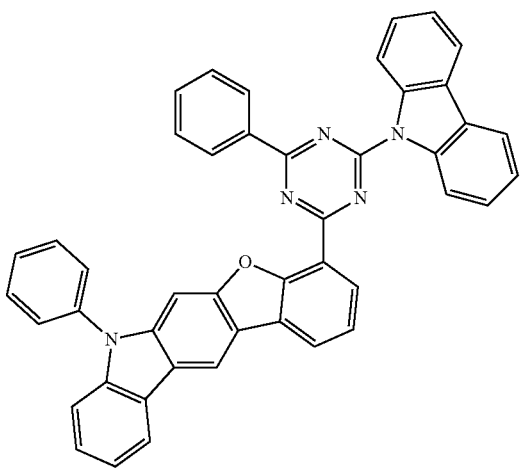
1A-4-51
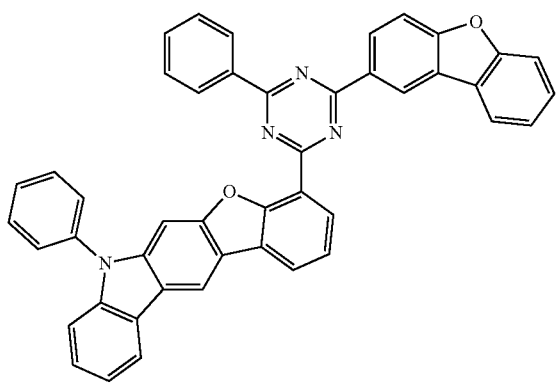
1A-4-52
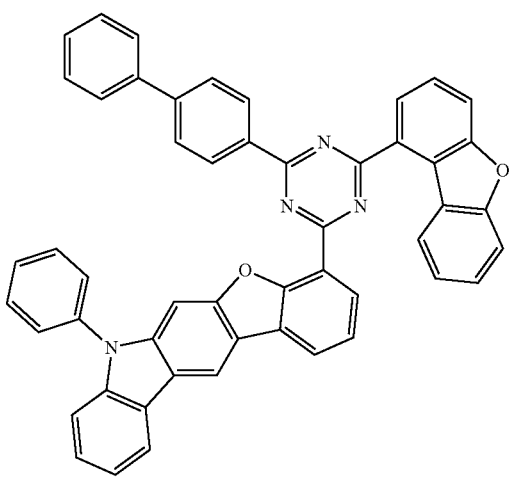

-continued
1A-4-53
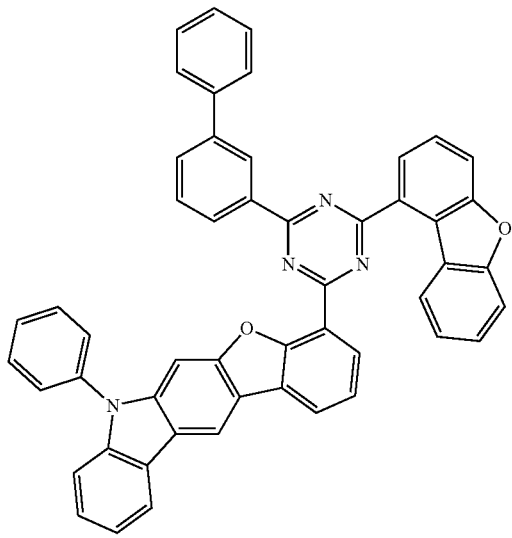
1A-4-54
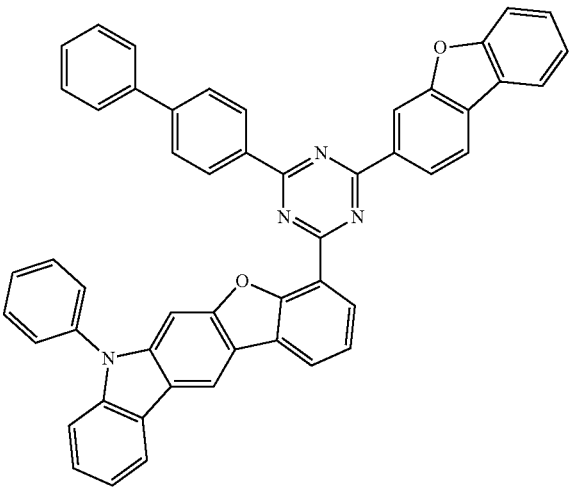
1A-4-55
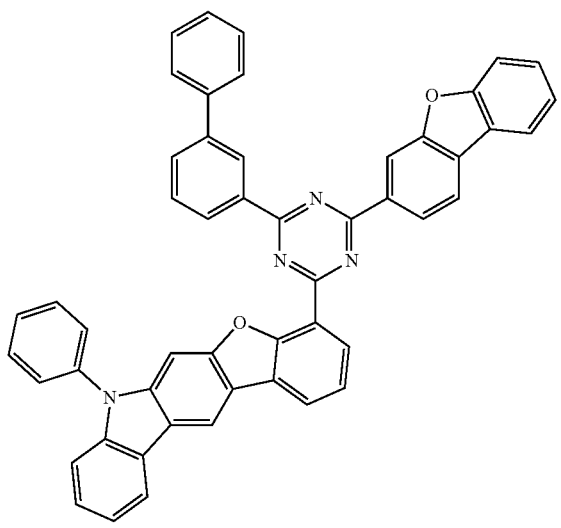
1A-4-56
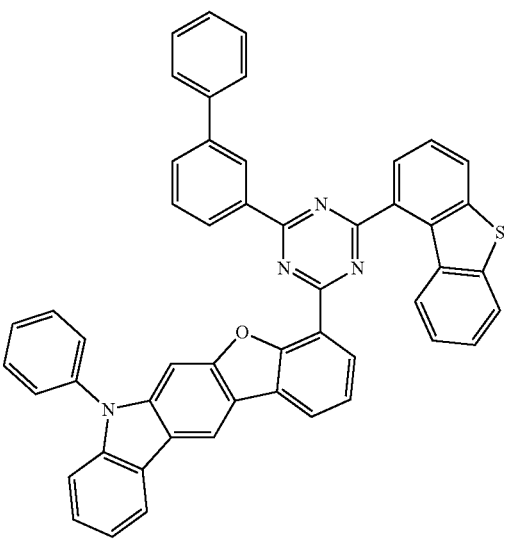
1A-4-57
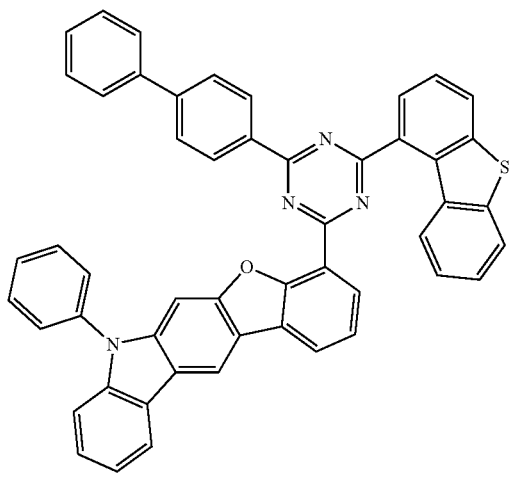
1A-4-58
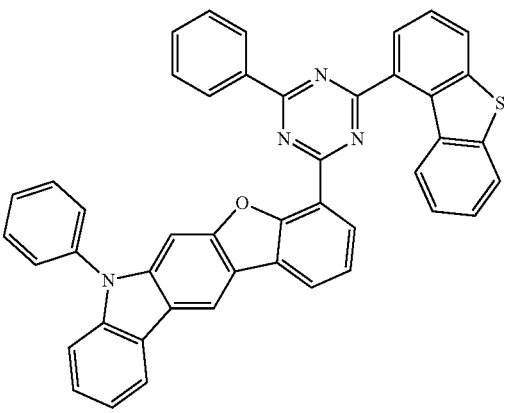

-continued
1A-5-59
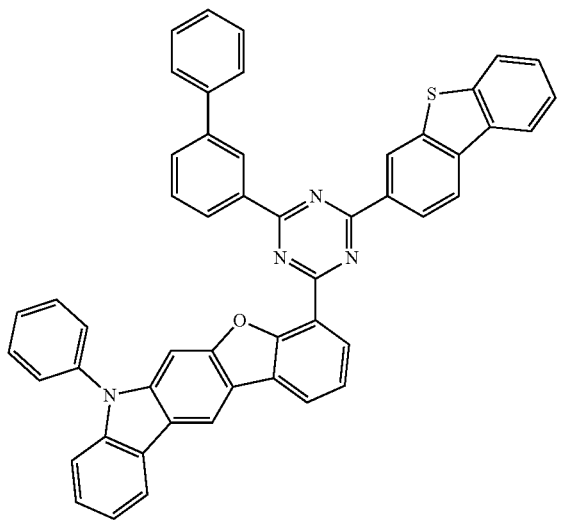
1A-4-60
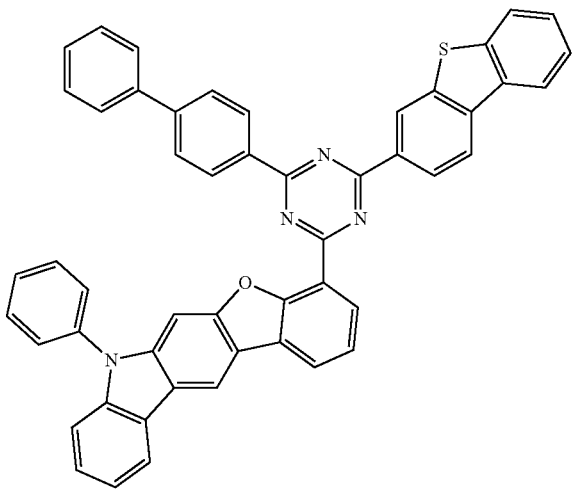
1A-4-61
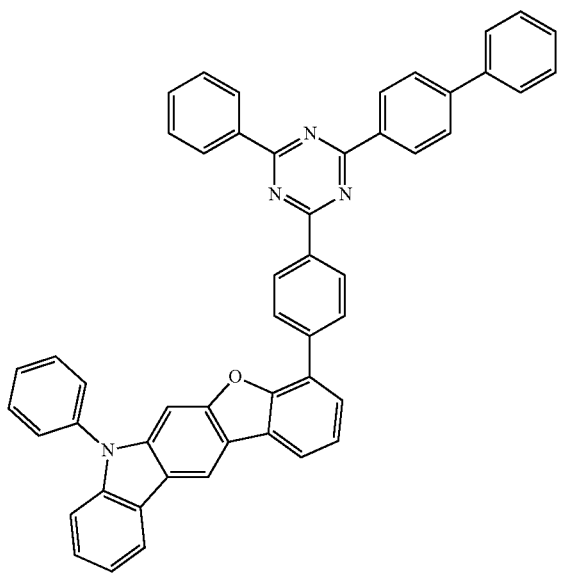
1A-4-62
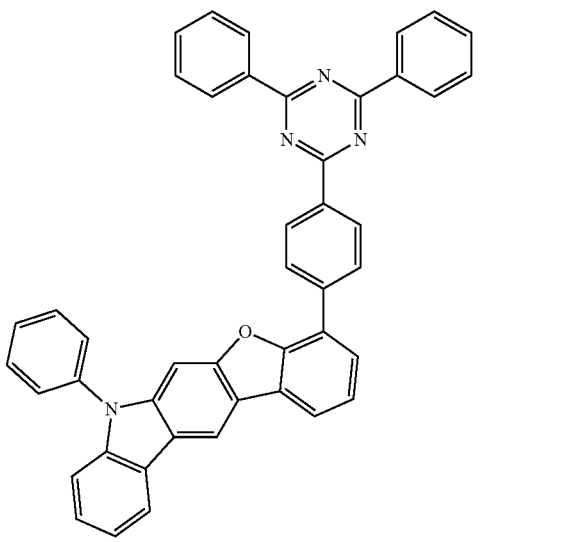
1A-4-63
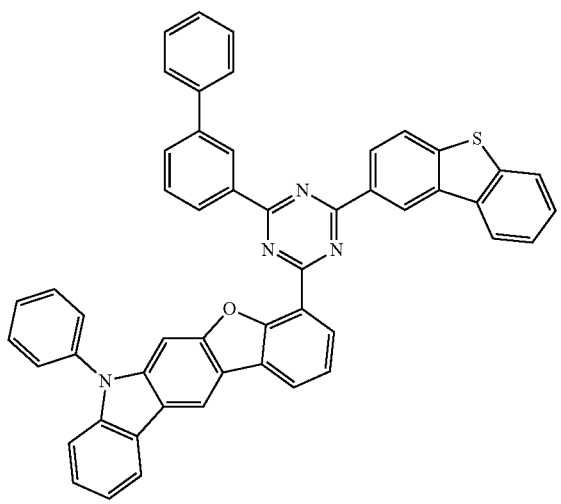
1A-4-64
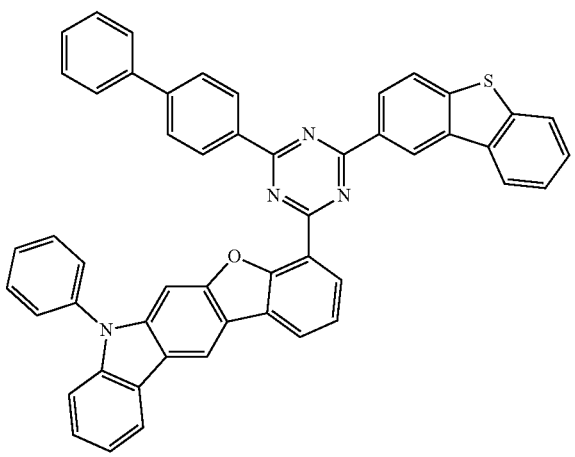

-continued
1A-4-65
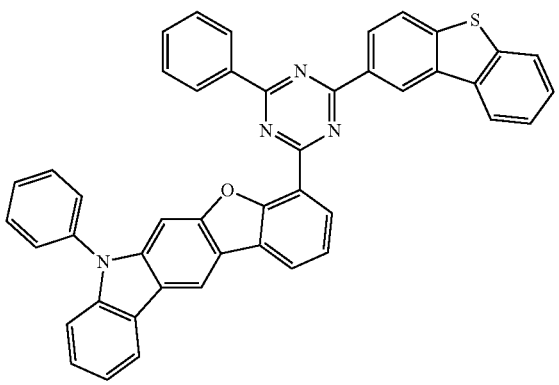
1A-4-66
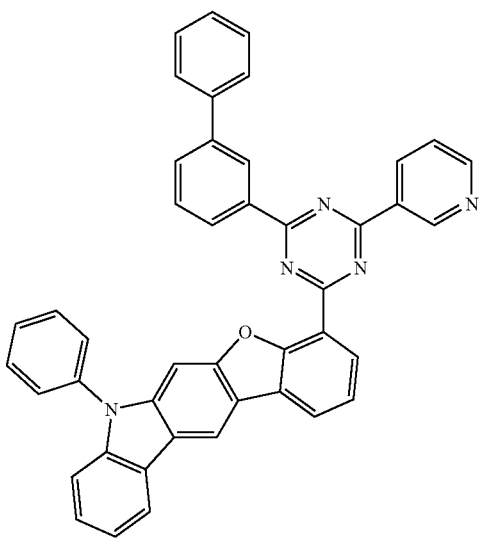
1A-4-67
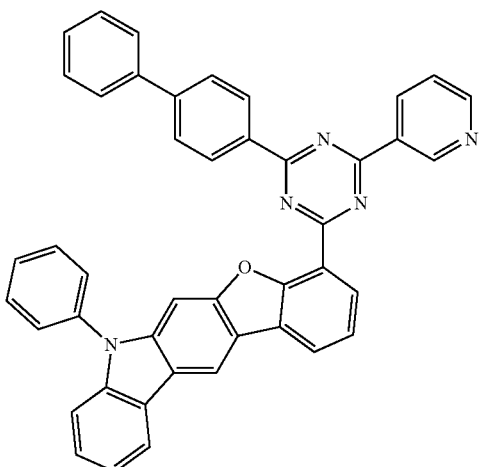
1A-4-68
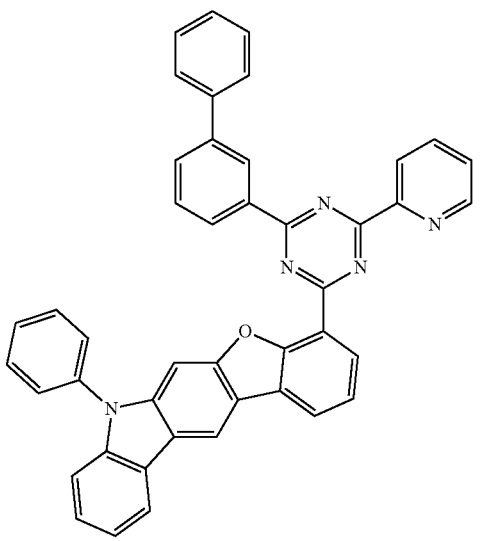
1A-4-69
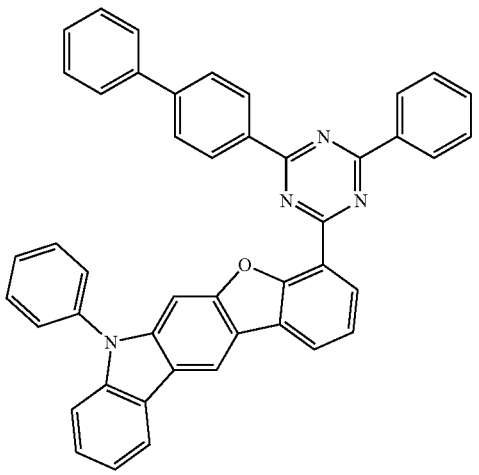
1A-4-70
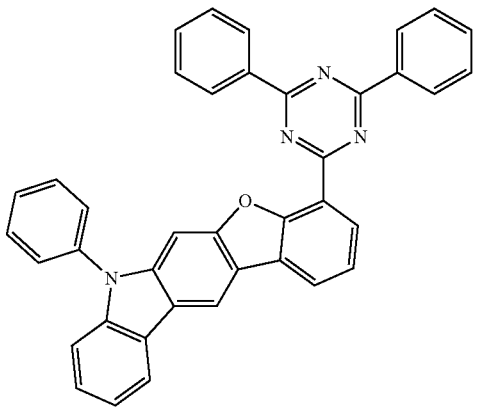

-continued
1A-4-71
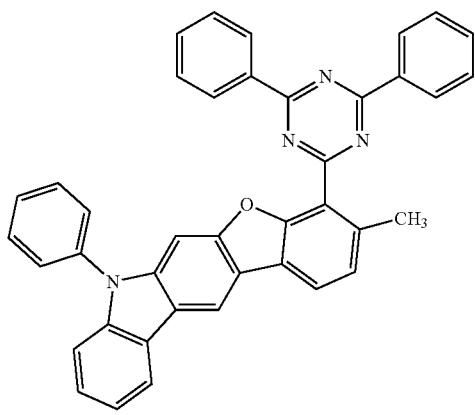
1A-4-72
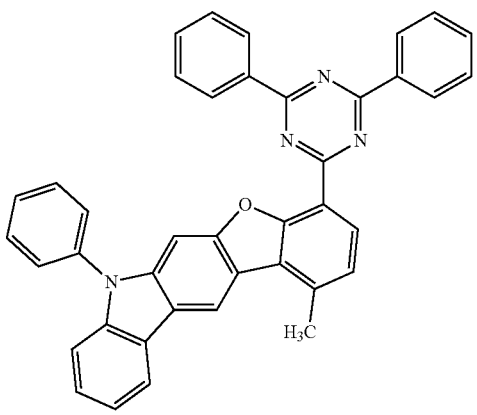
1A-4-73
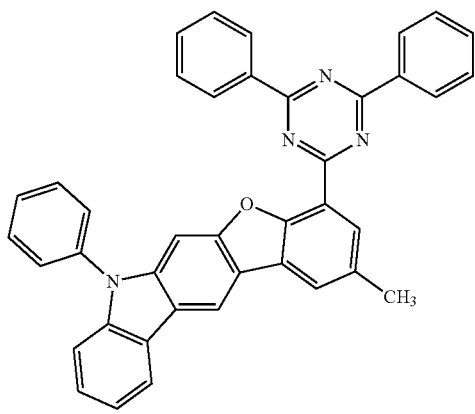
1A-4-74
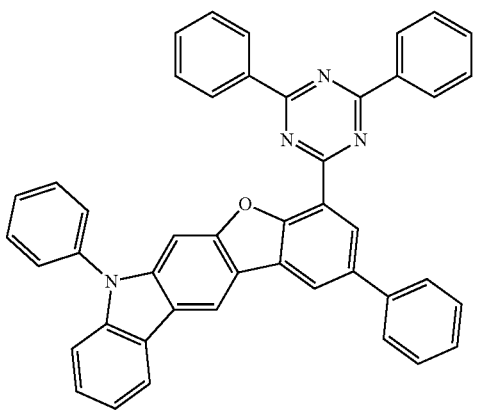
1A-4-75
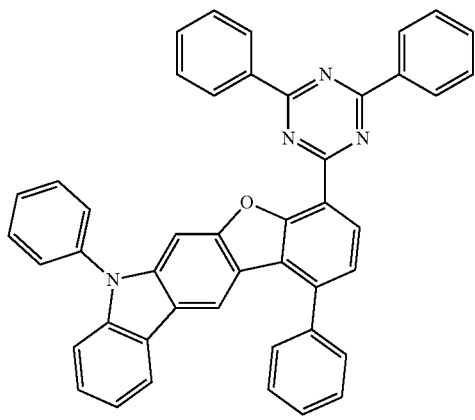
1A-4-76
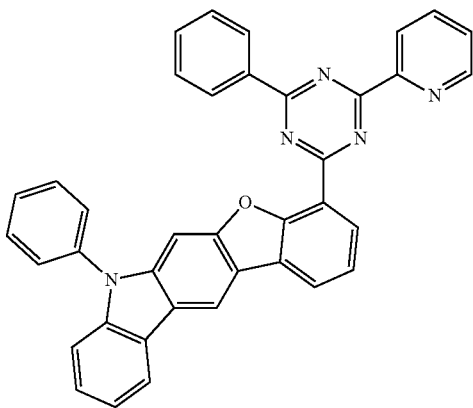

-continued
1A-4-77
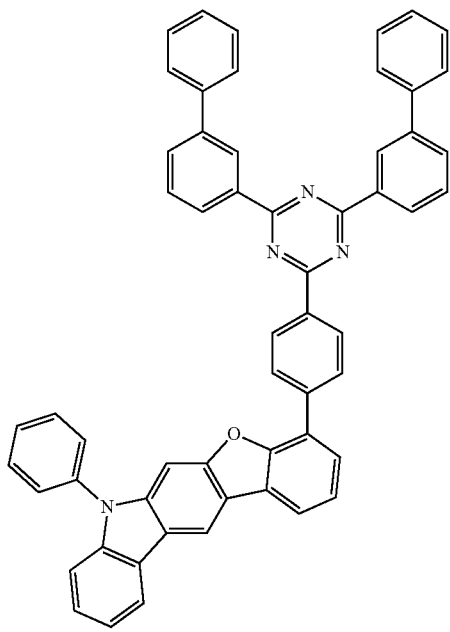
1A-4-78
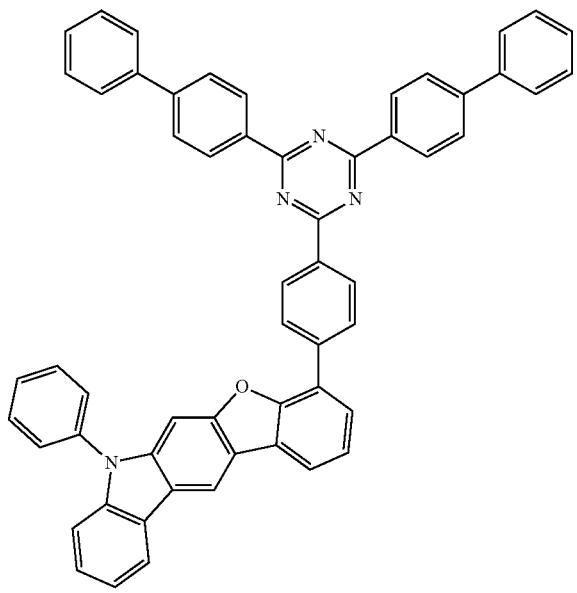
1A-4-79
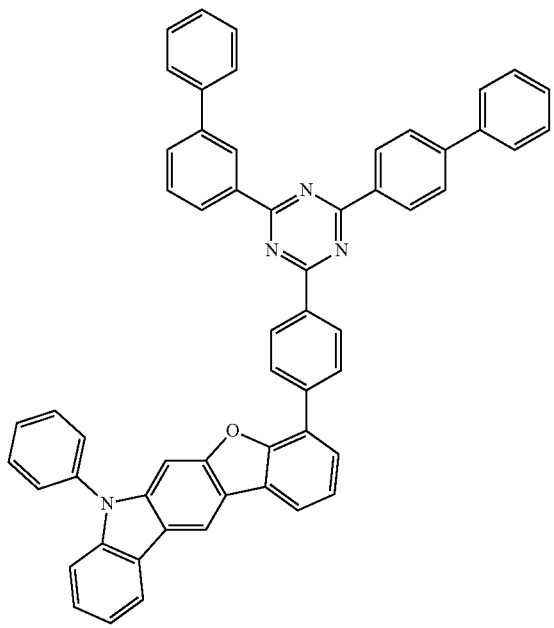
1A-4-80
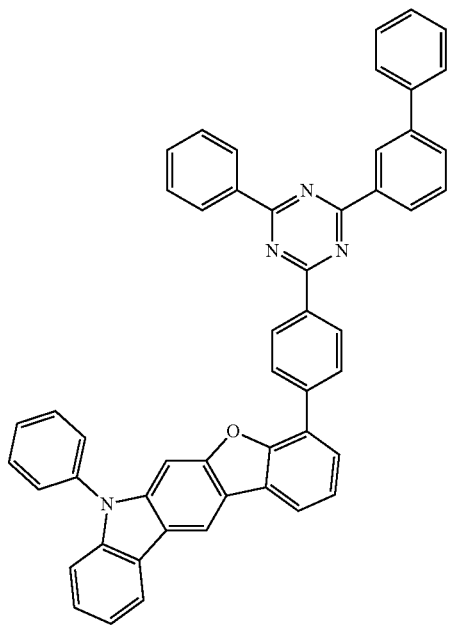

-continued
1A-4-81
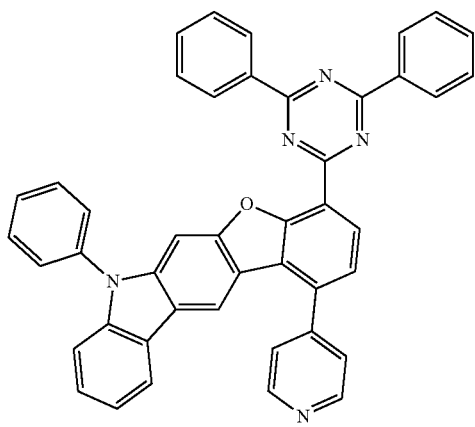
1A-4-82
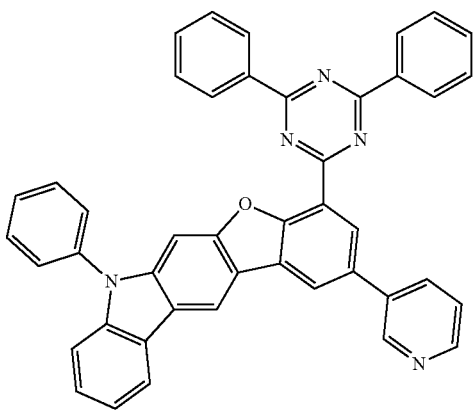
1A-4-83
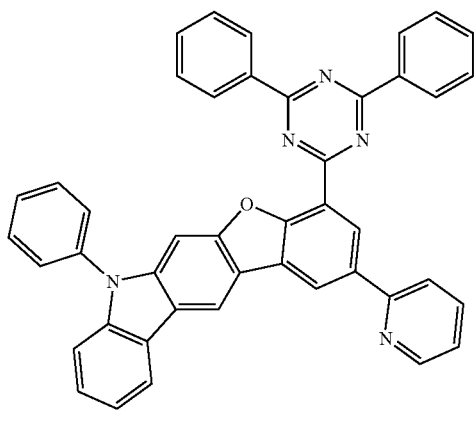
1B-1-1
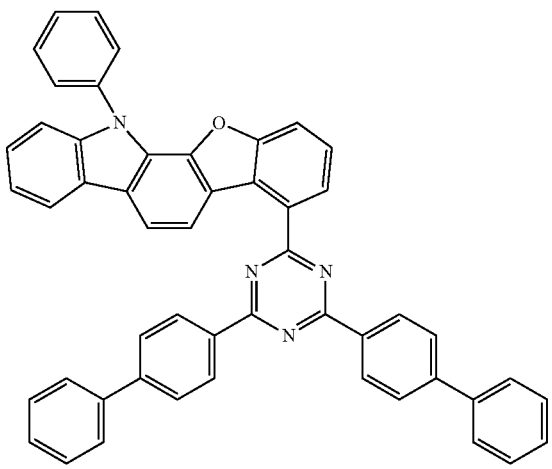
1B-1-2
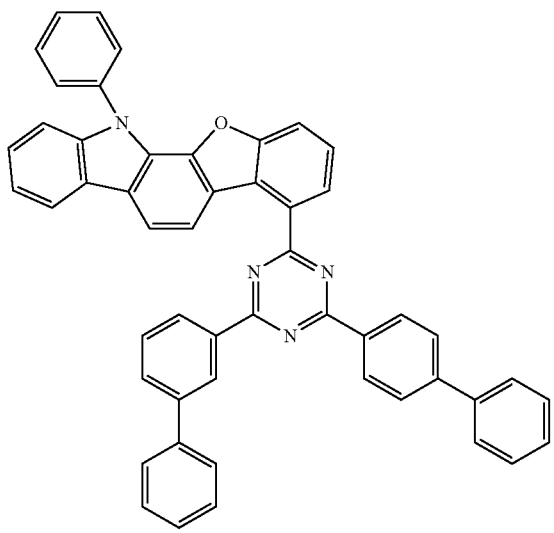
1B-1-3
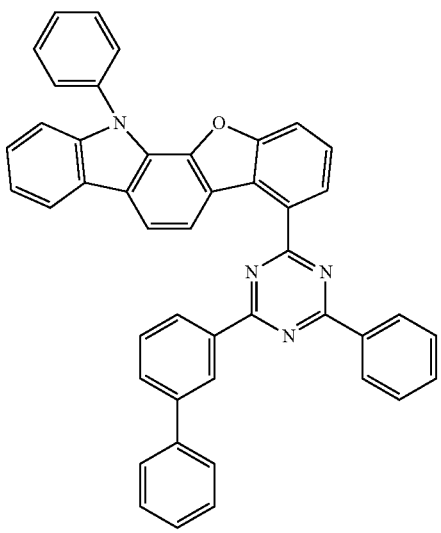

-continued
1B-1-4
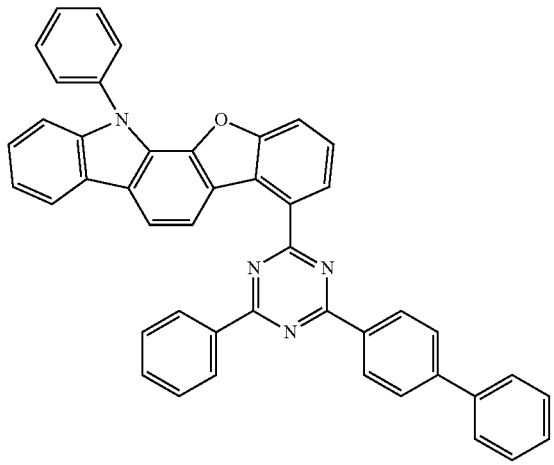
1B-1-5
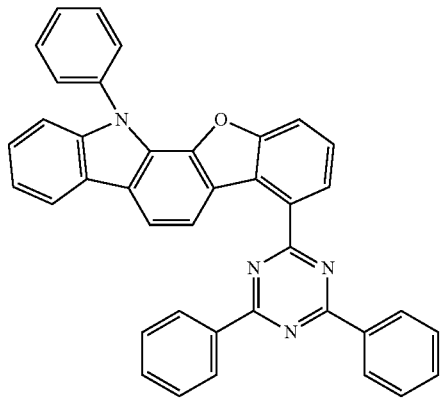
1B-1-6
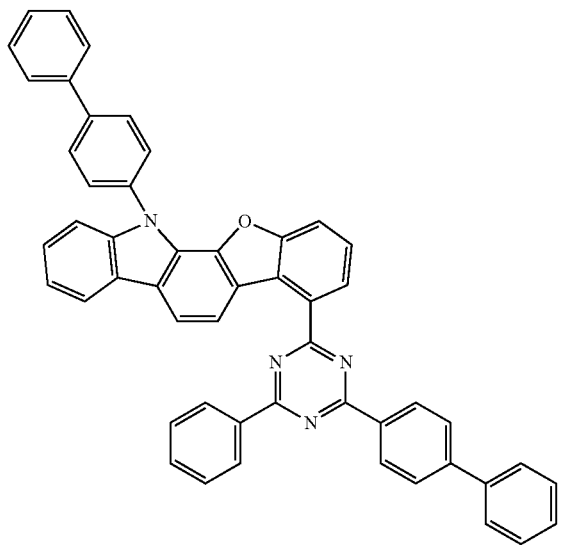
1B-1-7
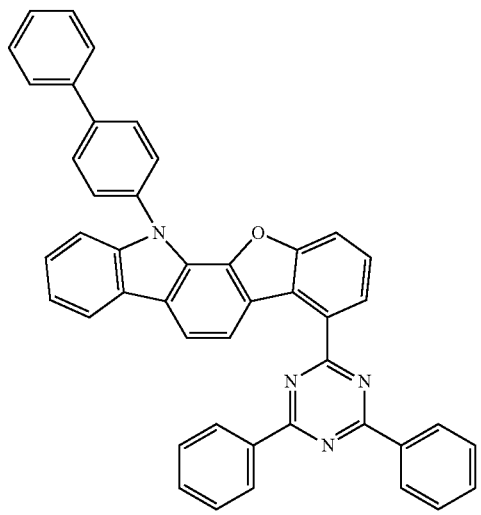
1B-1-8
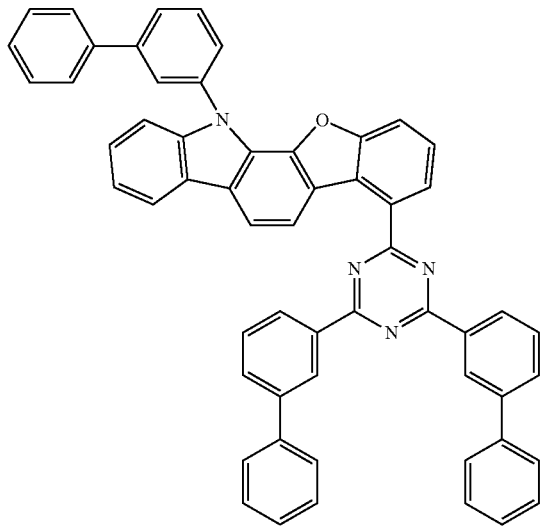
1B-1-9
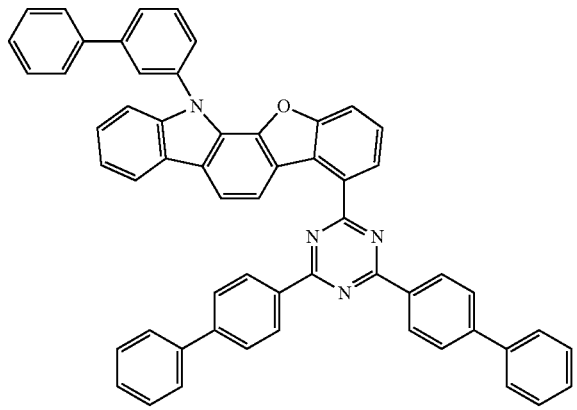

1B-1-10
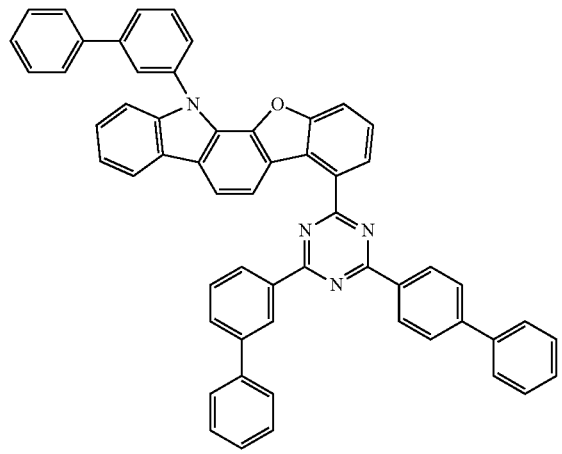
1B-1-11
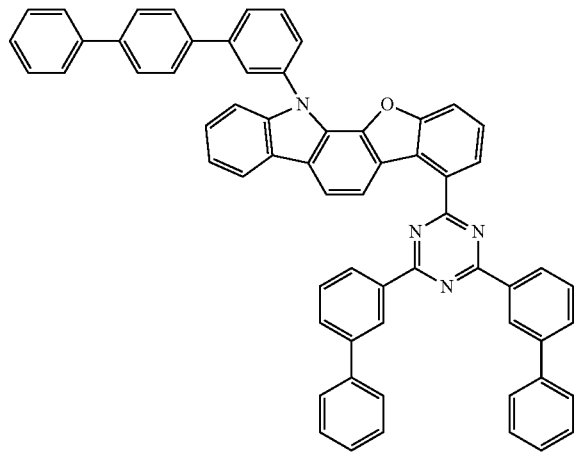
1B-1-12
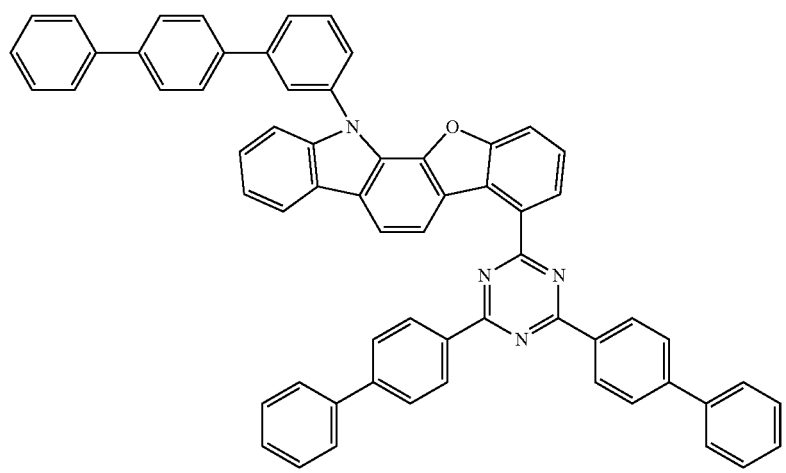
1B-1-13
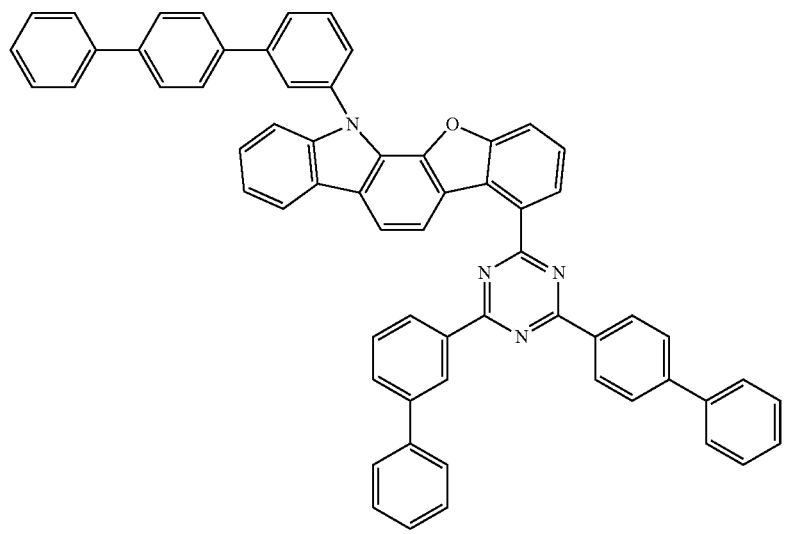

1B-1-14
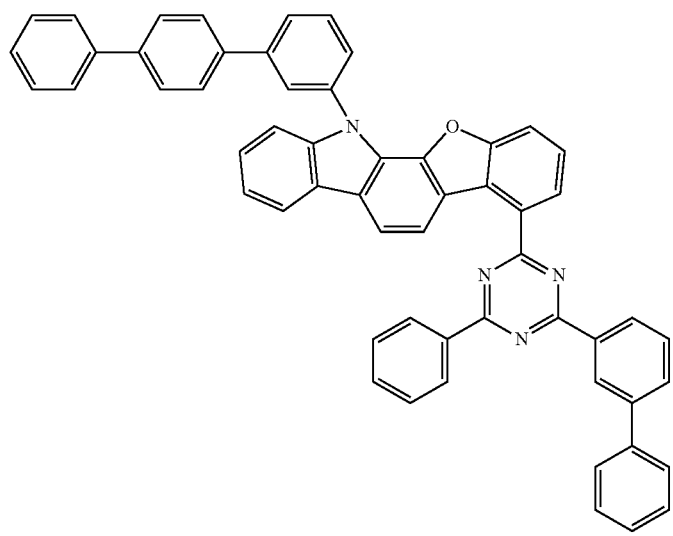
1B-1-15
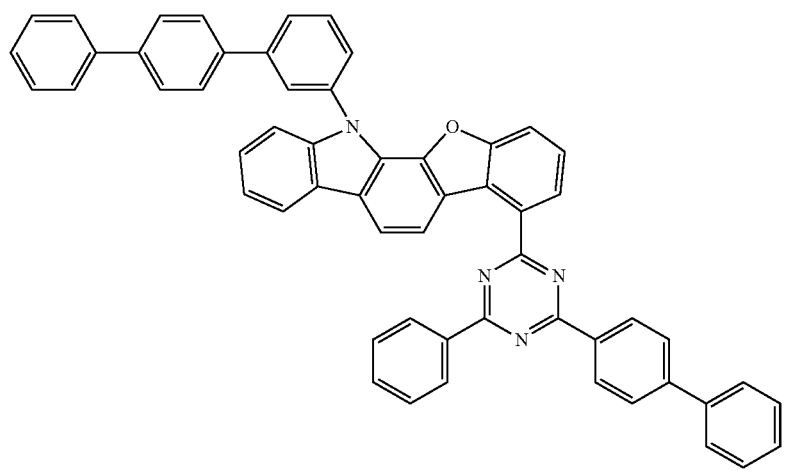
1B-1-16
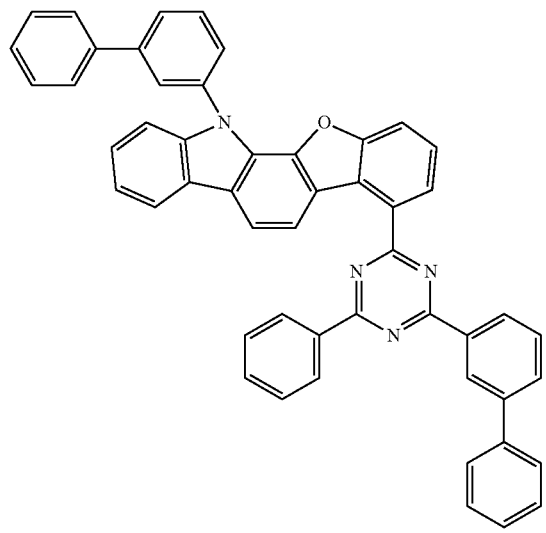
1B-1-17
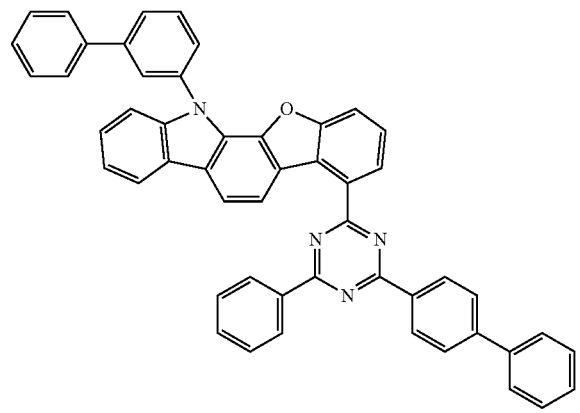

1B-1-18
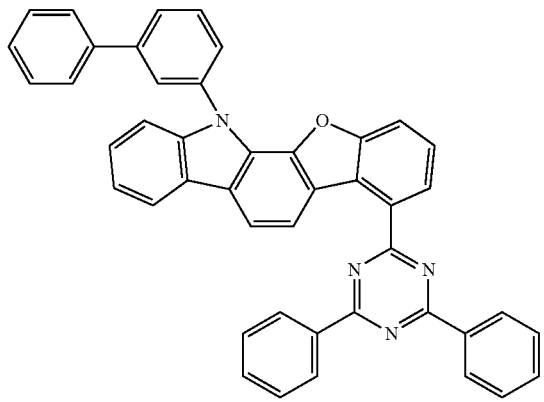
1B-1-19
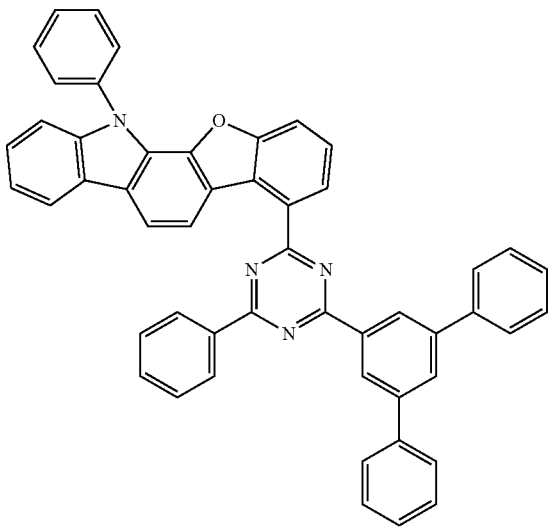
1B-1-20
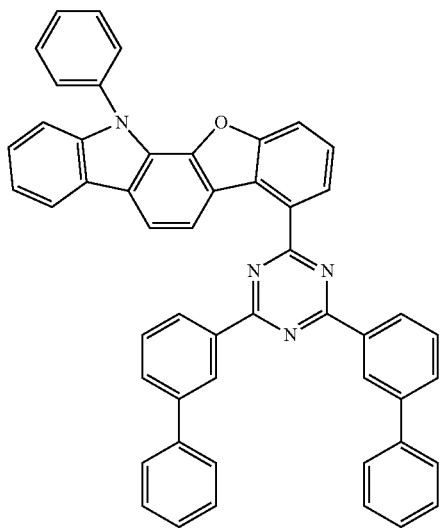
1B-1-21
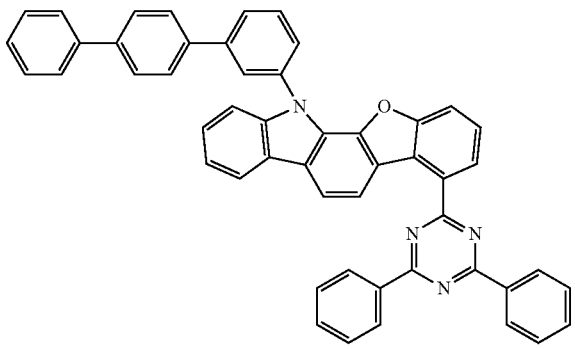

-continued
1B-1-22
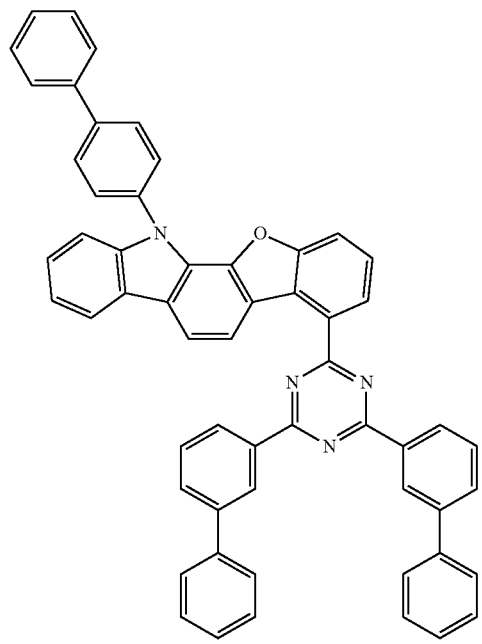
1B-1-23
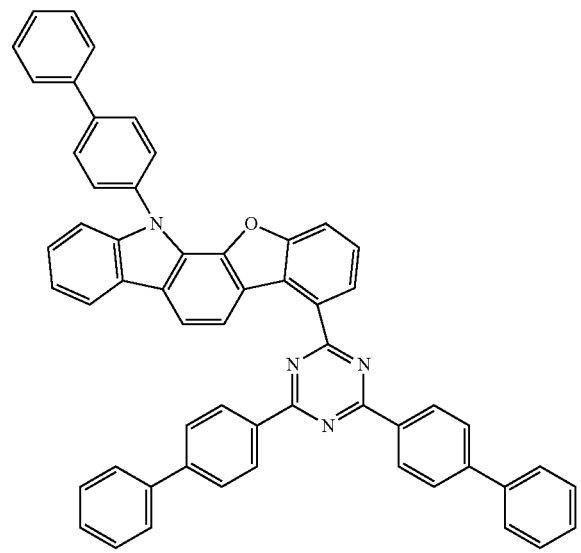
1B-1-24
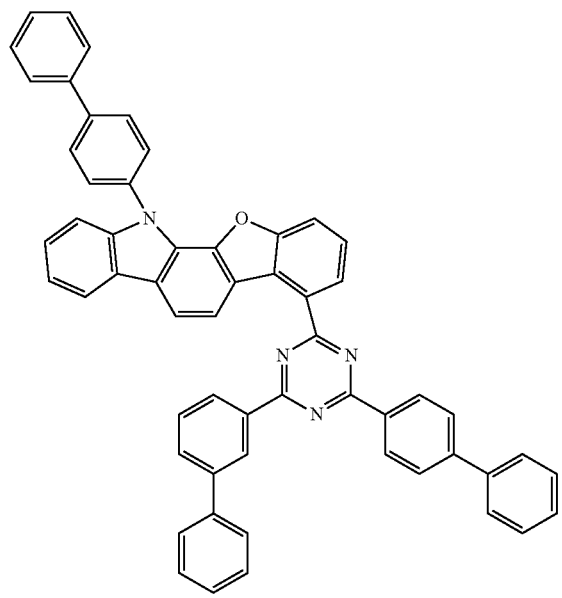
1B-1-25
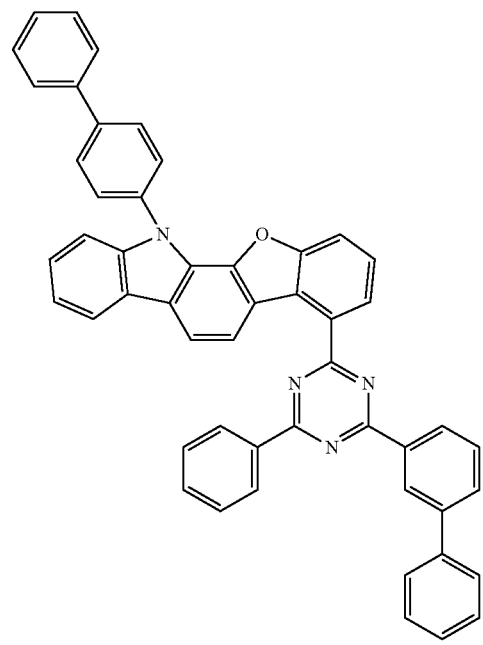

1B-1-26
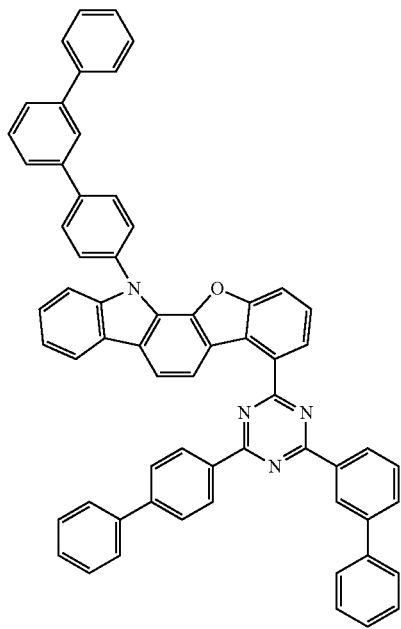
1B-1-27
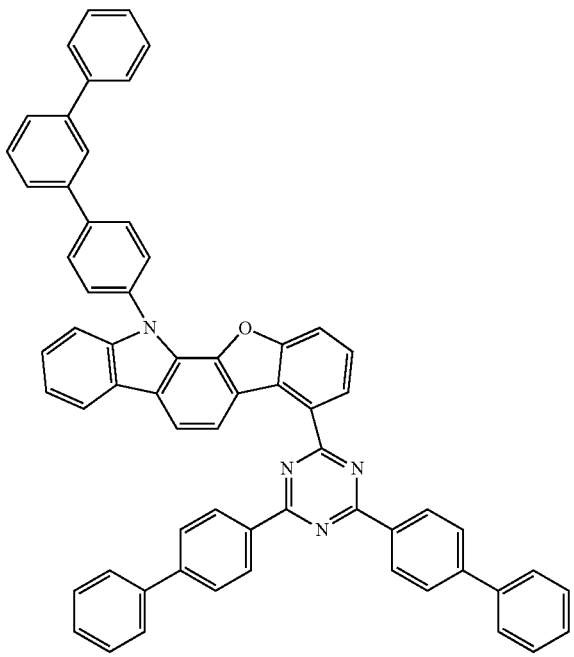
1B-1-28
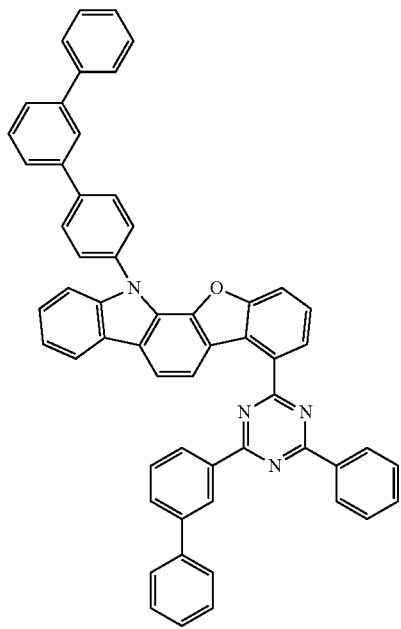
1B-1-29
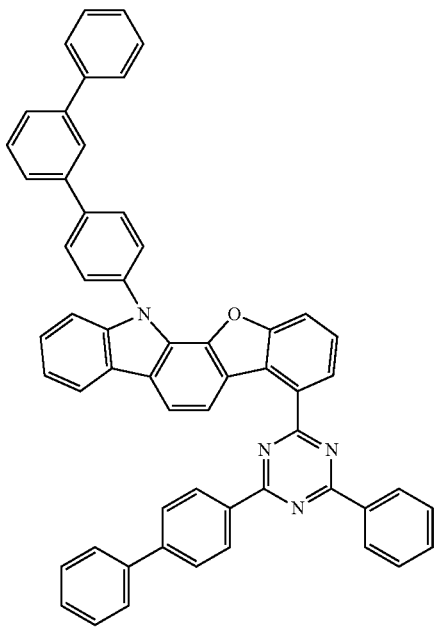

1B-1-30
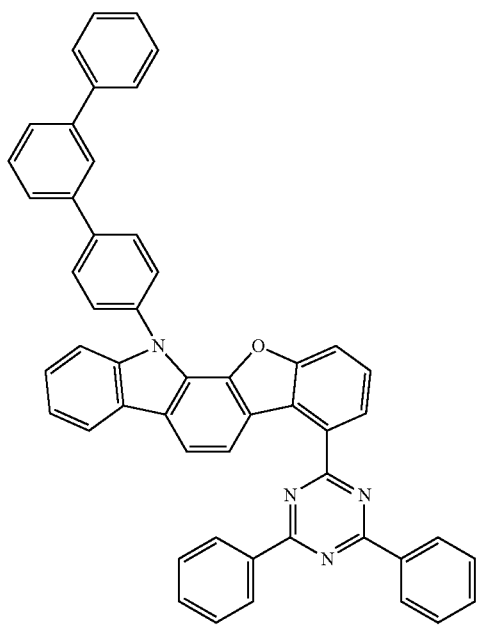
1B-1-31
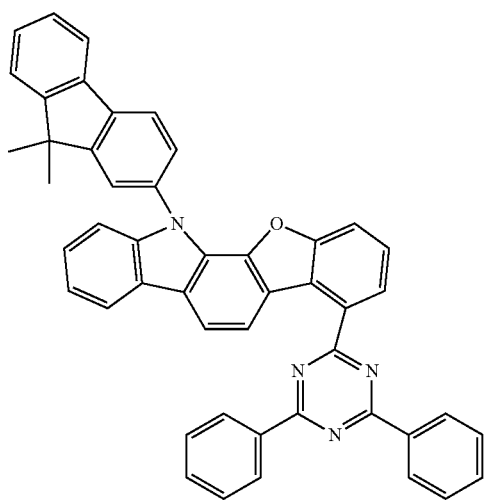
1B-1-32
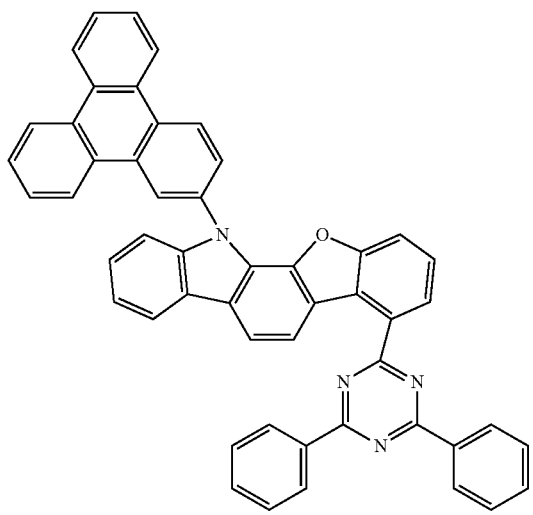
1B-1-33
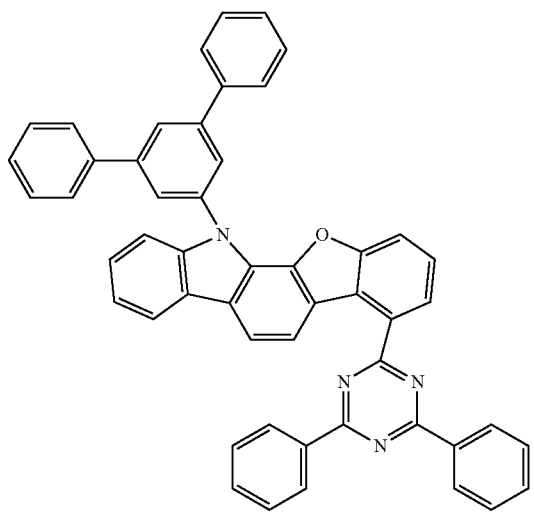
1B-1-34
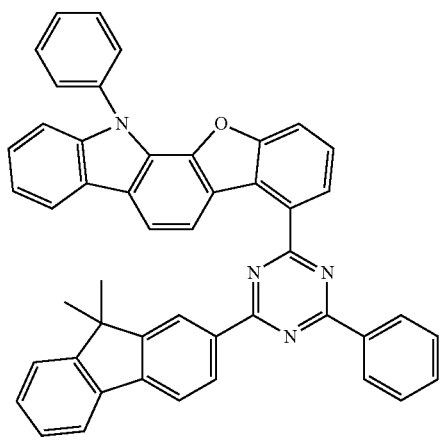
1B-1-35
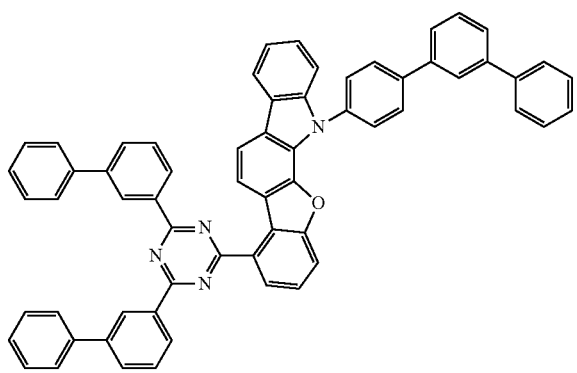

1B-1-36
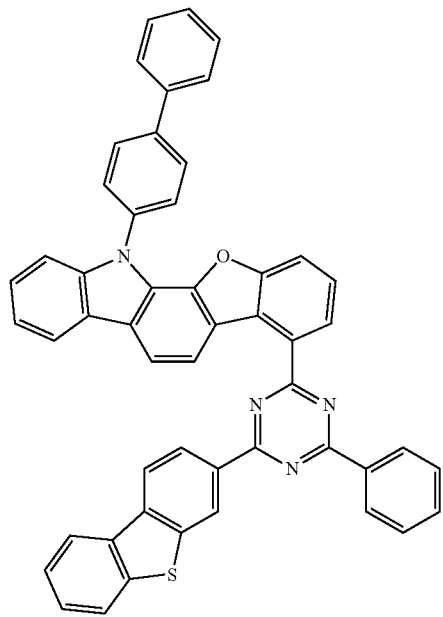
1B-1-37
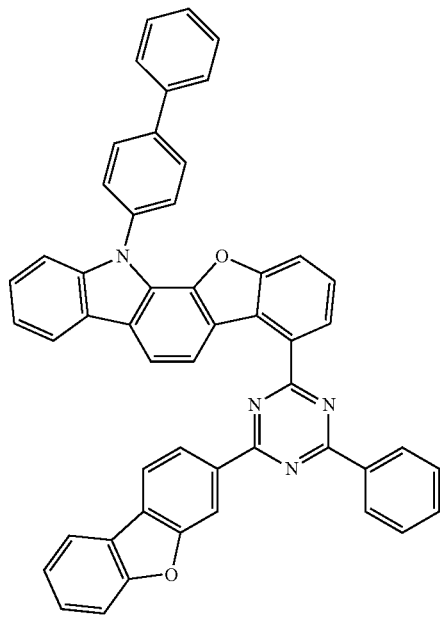
1B-1-38
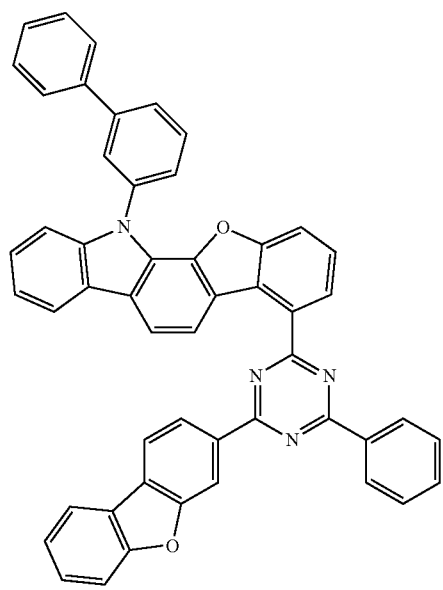
1B-1-39
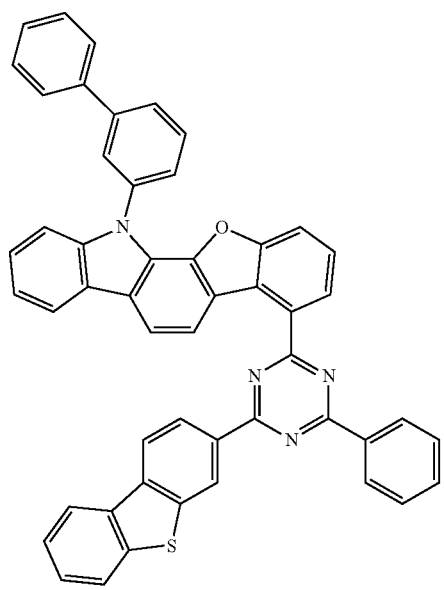

-continued
1B-1-40
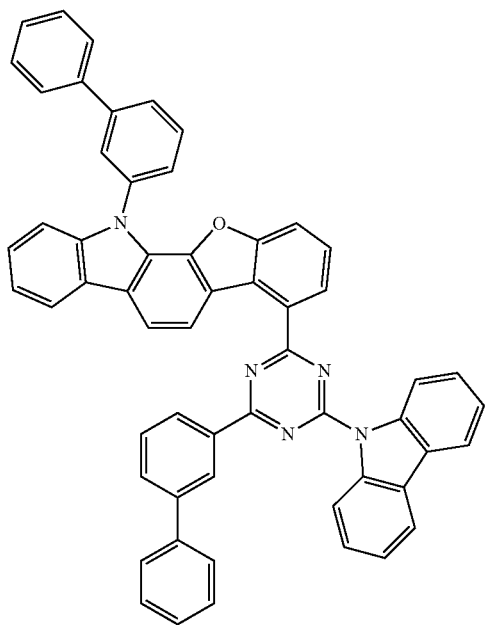
1B-1-41
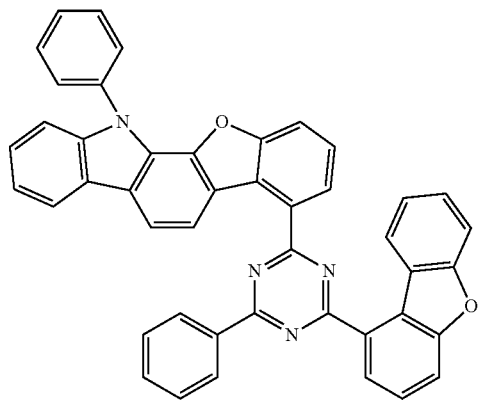
1B-1-42
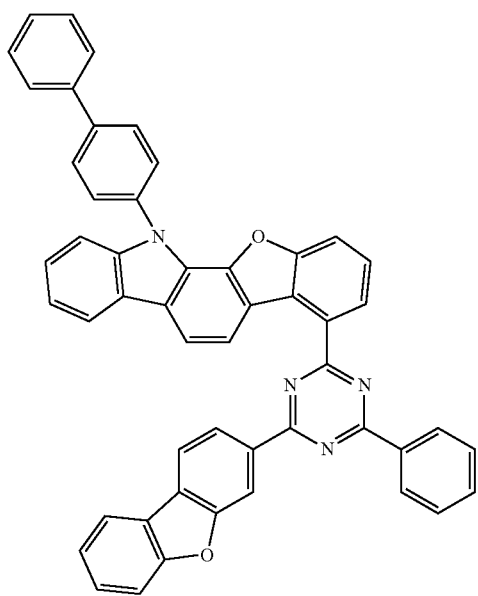
1B-1-43
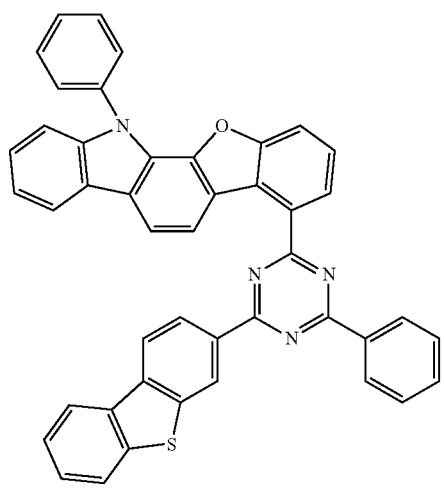

-continued
1B-1-44
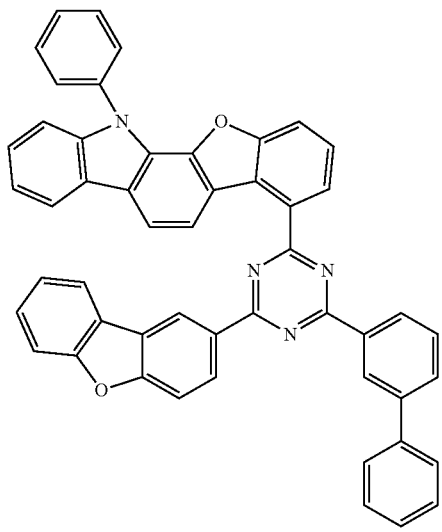
1B-1-45
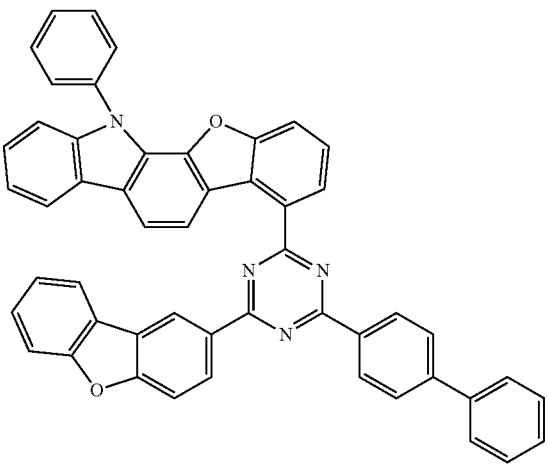
1B-1-46
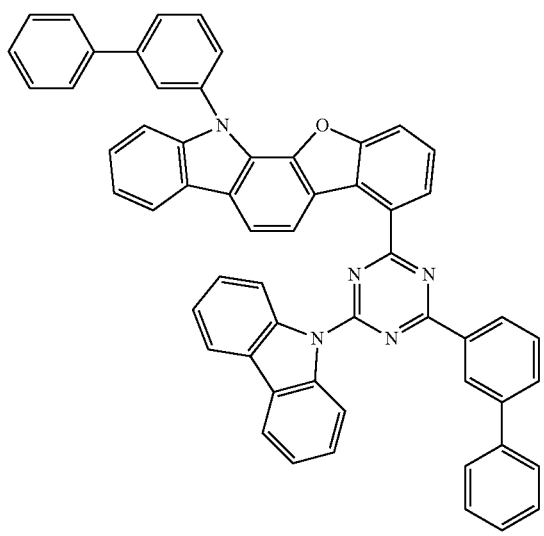
1B-1-47
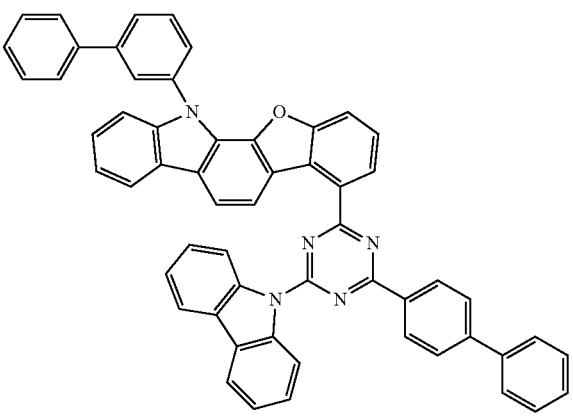
1B-1-48
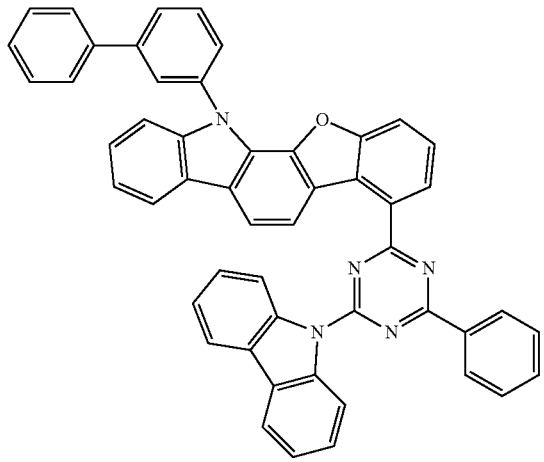
1B-1-49
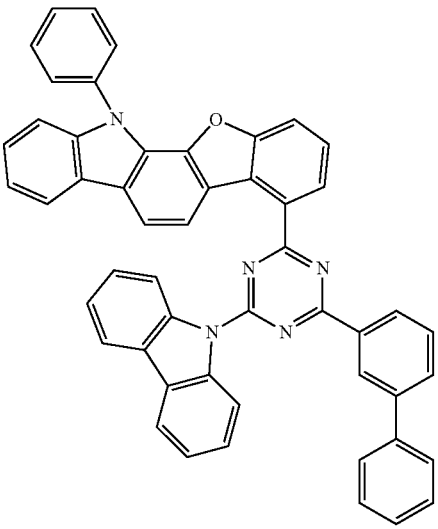

-continued
1B-1-50
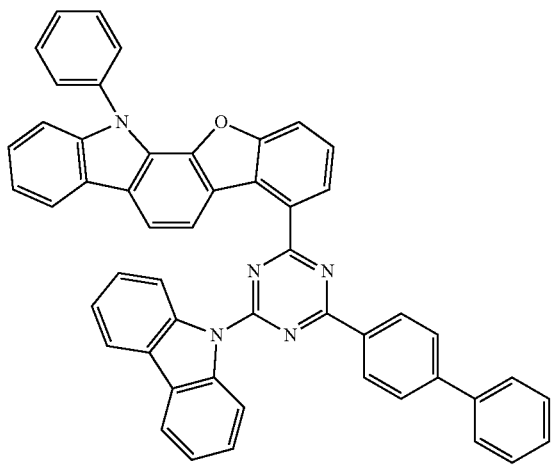
1B-1-51
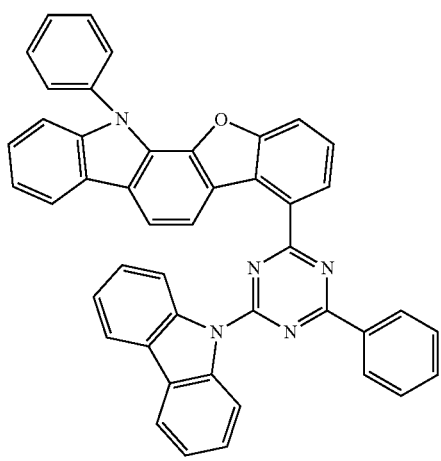
-continued
1B-1-53
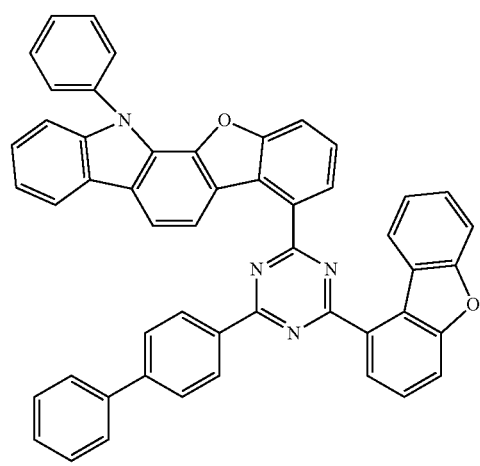
1B-1-52
1B-1-54
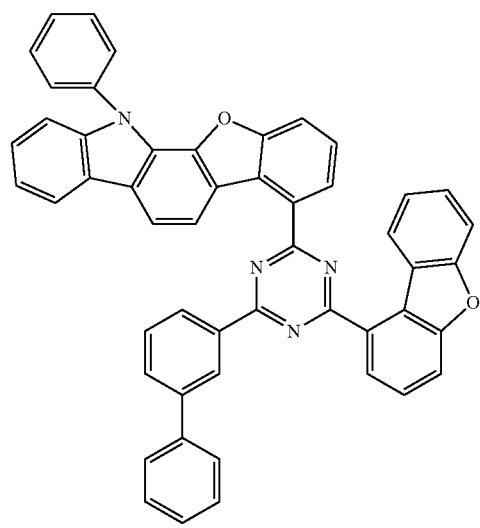

1B-1-55
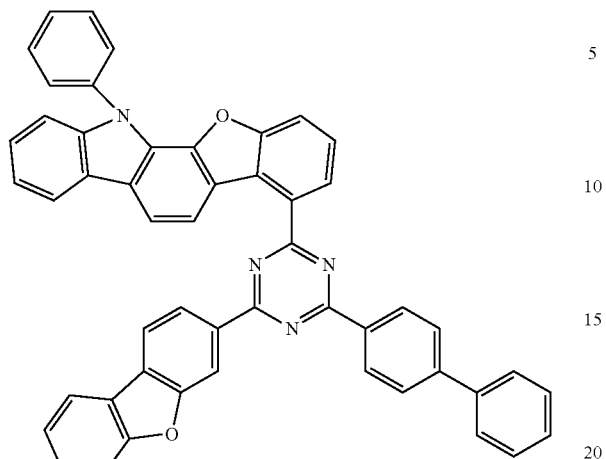
1B-1-56
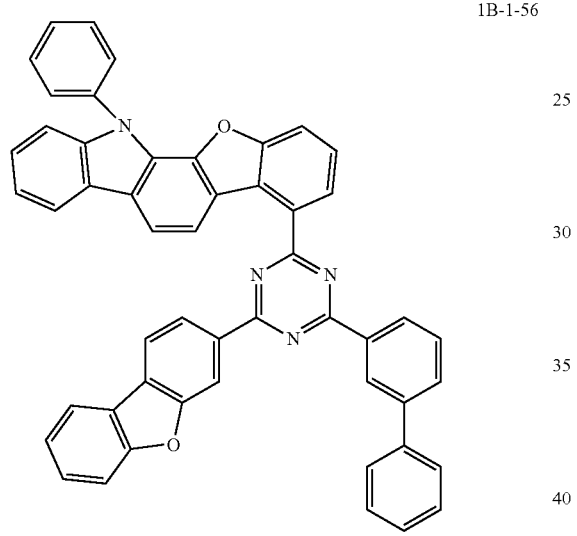
1B-1-57
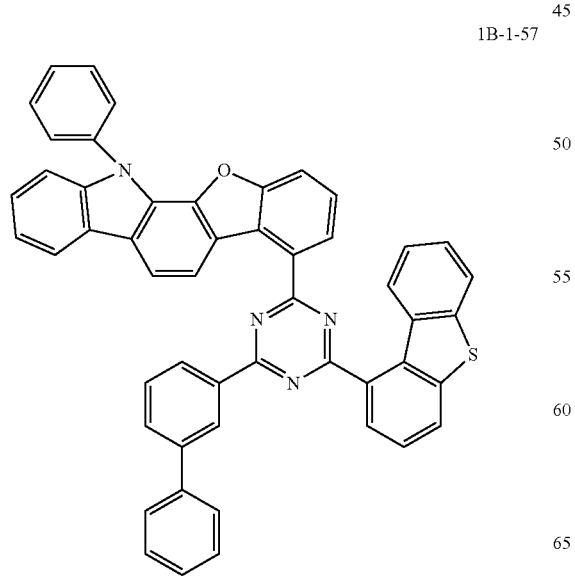
1B-1-58
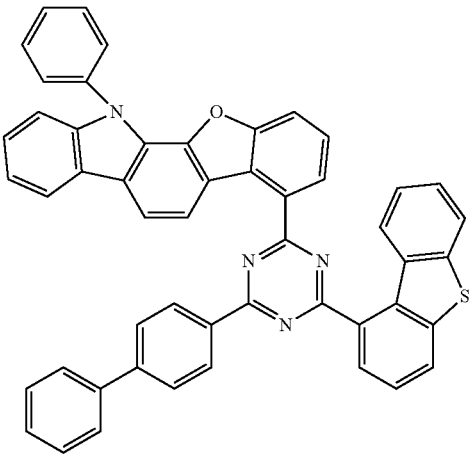
1B-1-59
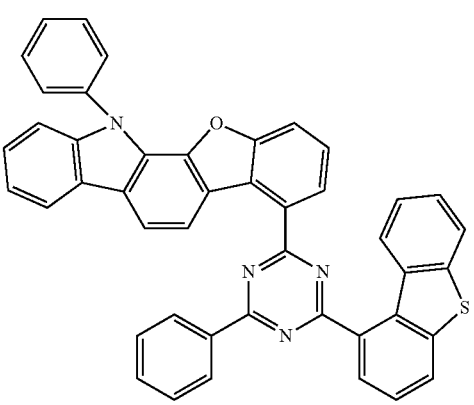
1B-1-60
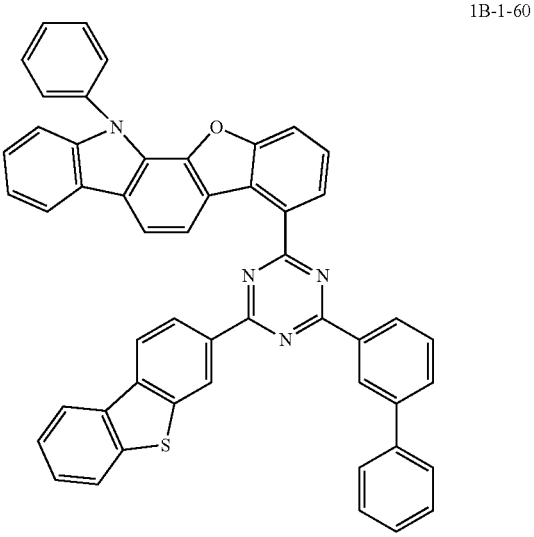

-continued
1B-1-61
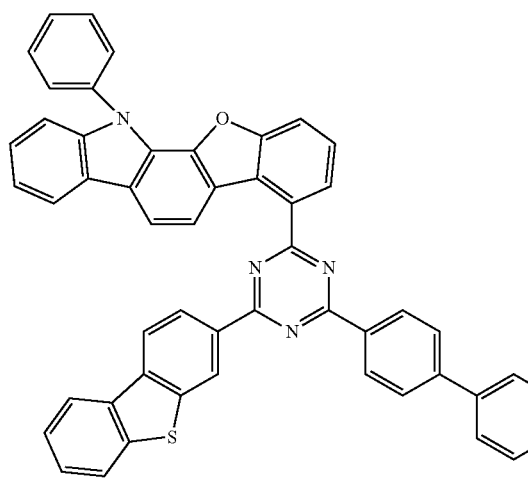
1B-1-62
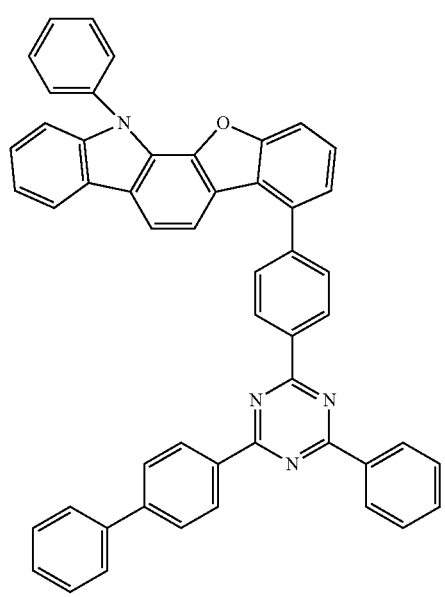
1B-1-63
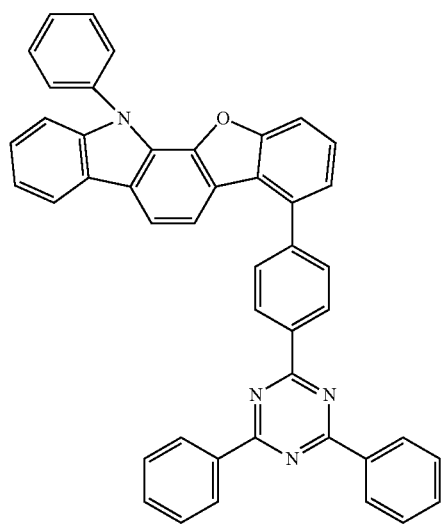
-continued
1B-1-64
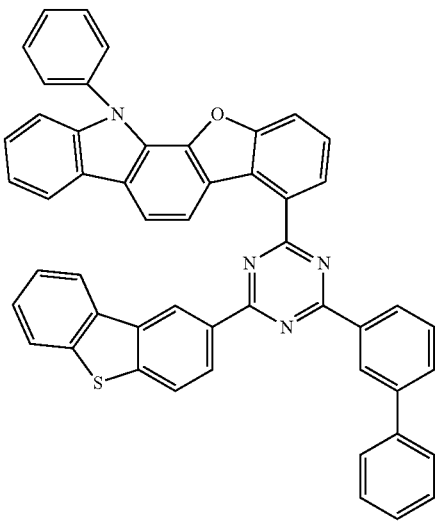
1B-1-65
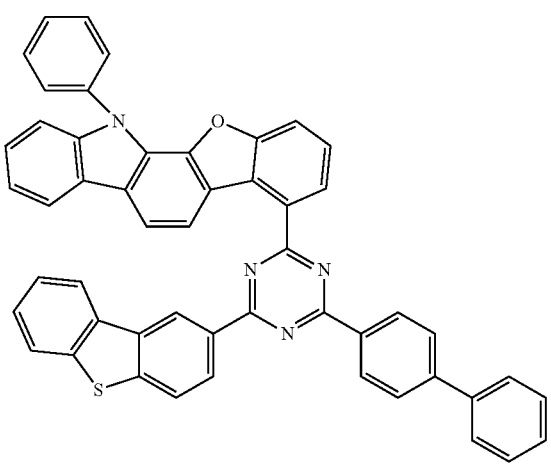
1B-1-66
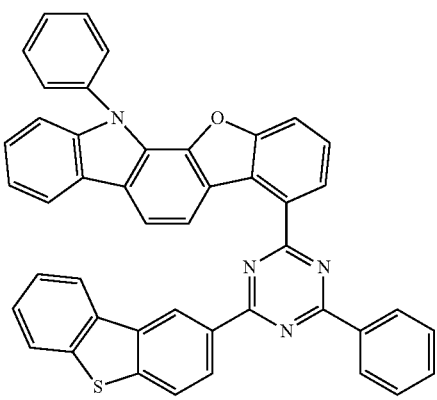

1B-1-67
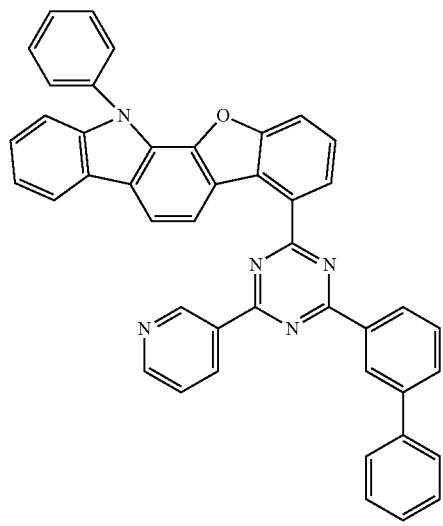
1B-1-68
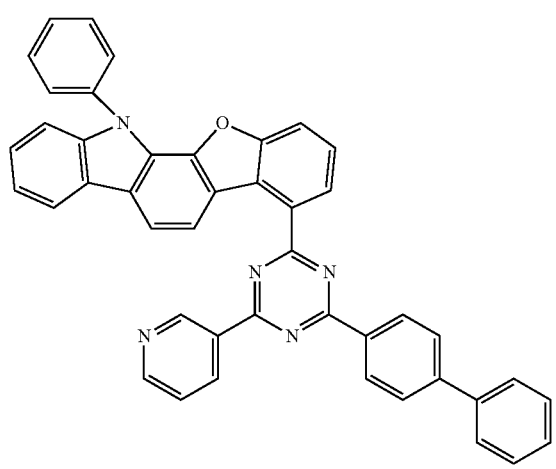
1B-1-69
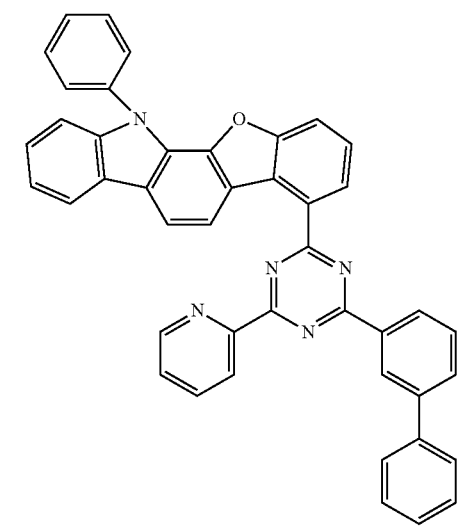
1B-1-70
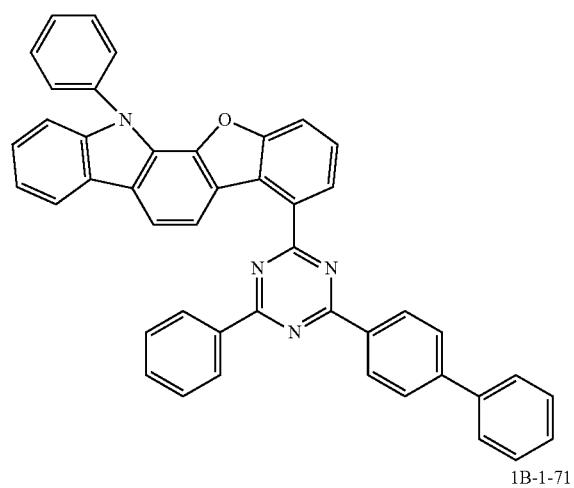
1B-1-71
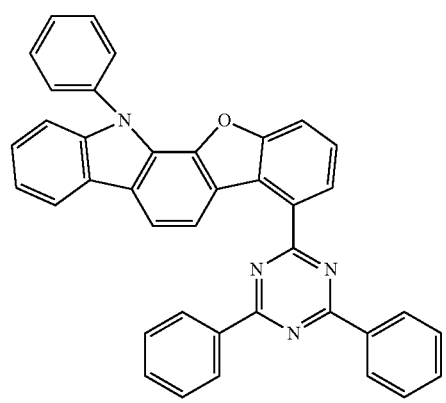
1B-1-72
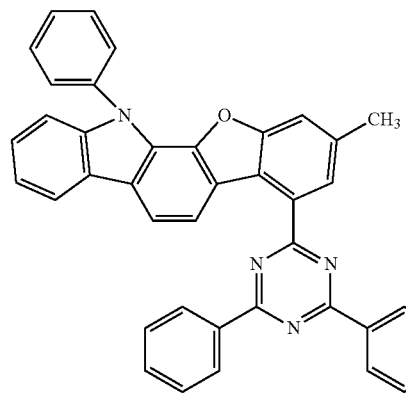
1B-1-73
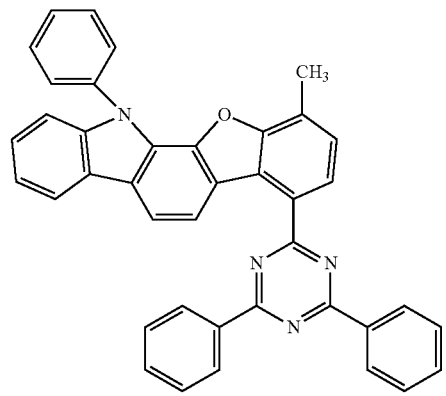

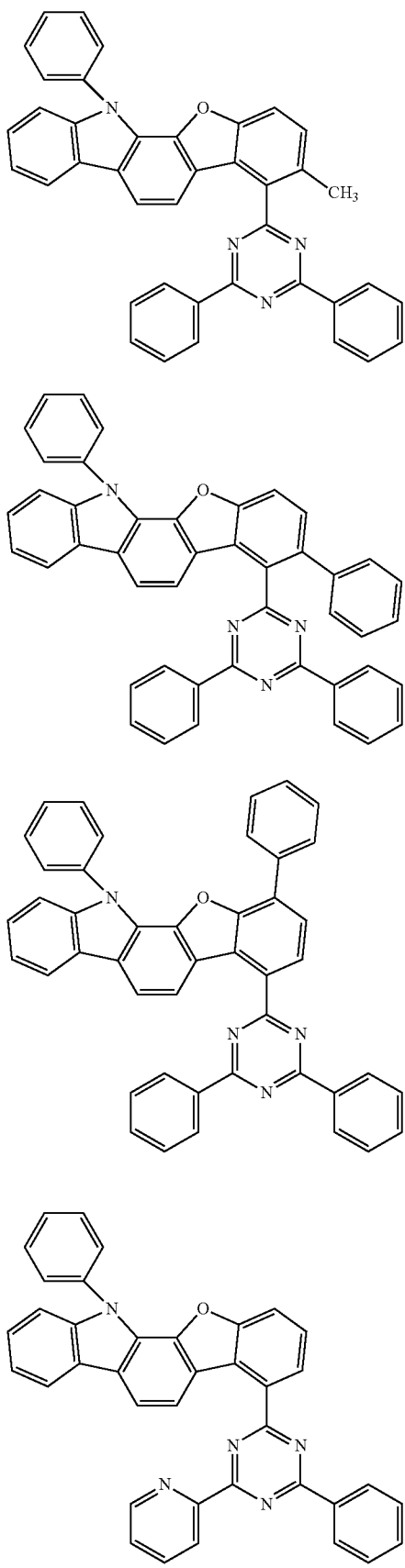
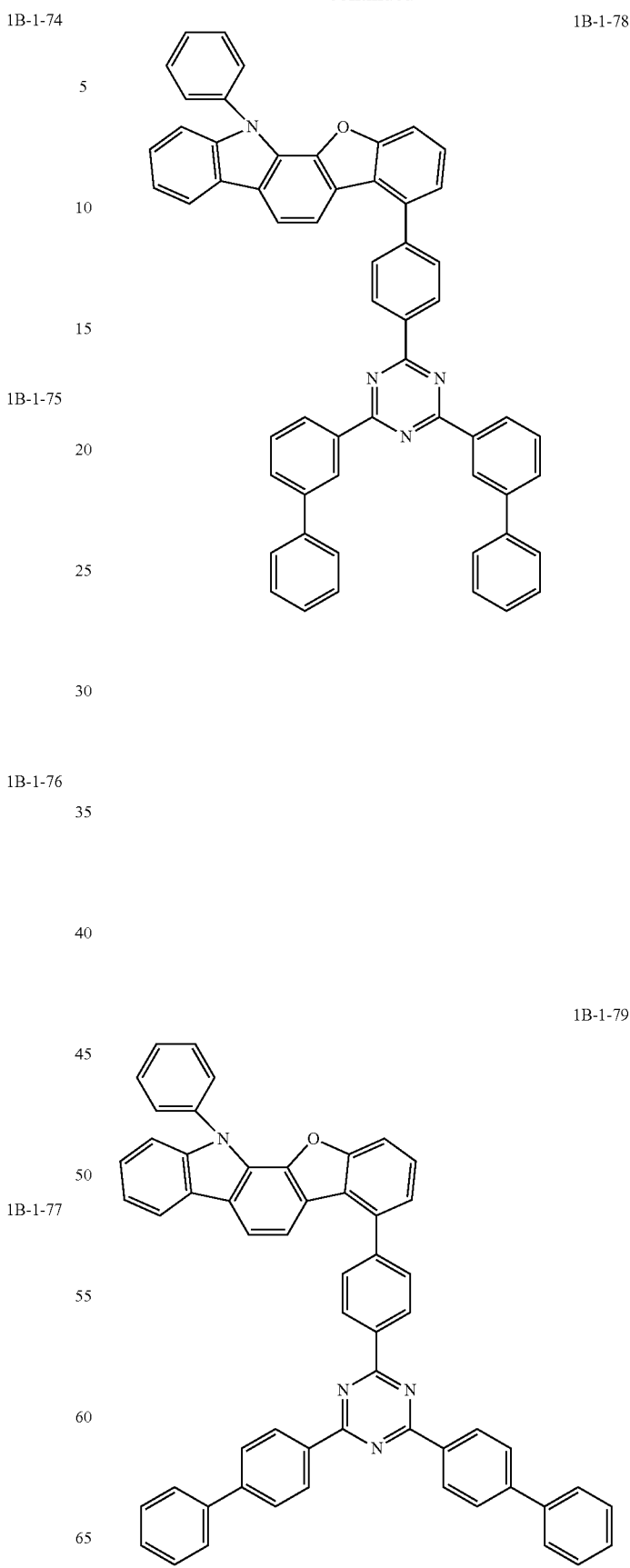

1B-1-80
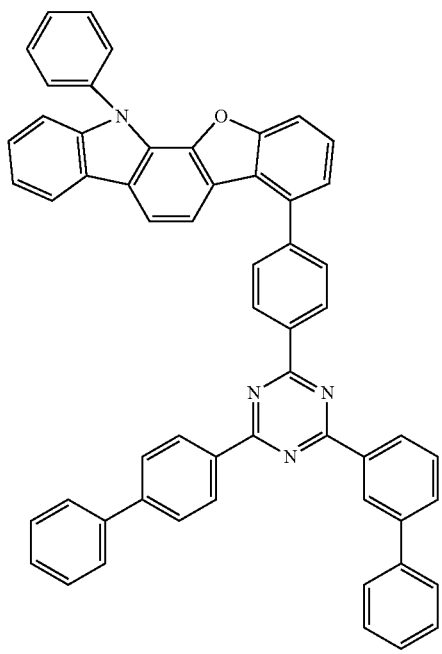
1B-1-81
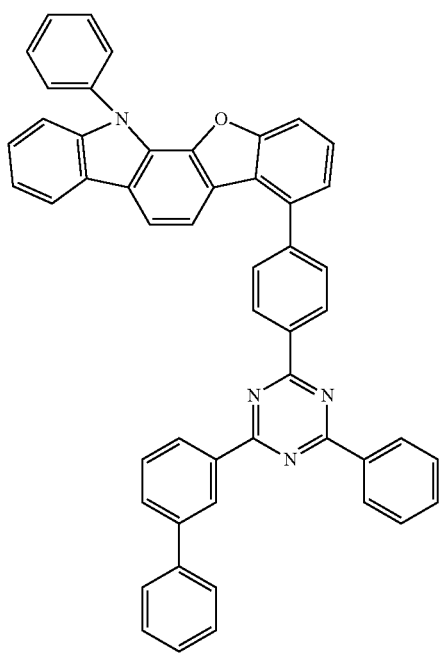
1B-1-82
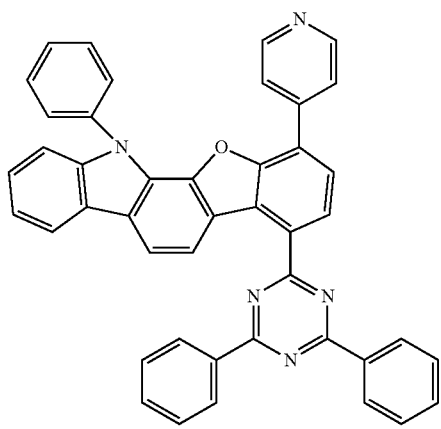
1B-1-83
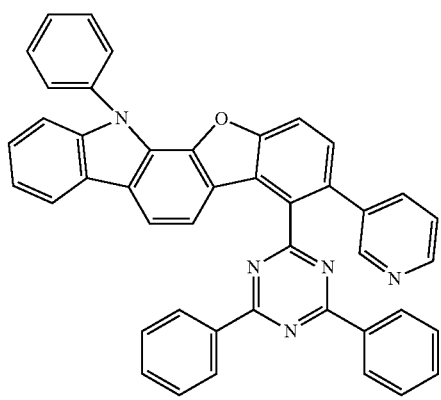
1B-1-84
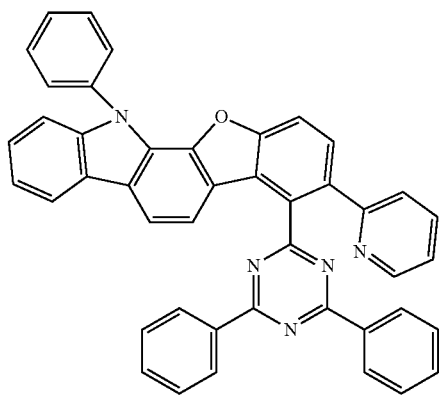

-continued
1B-2-1
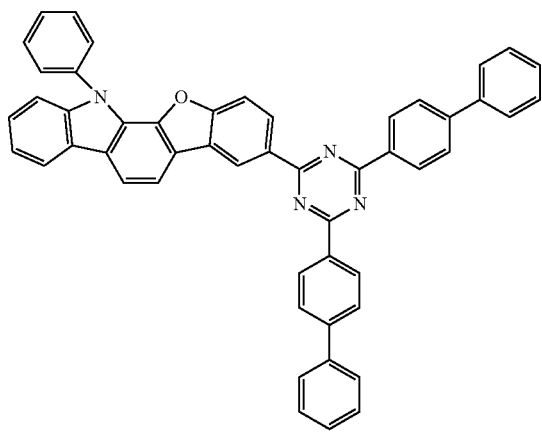
1B-2-2
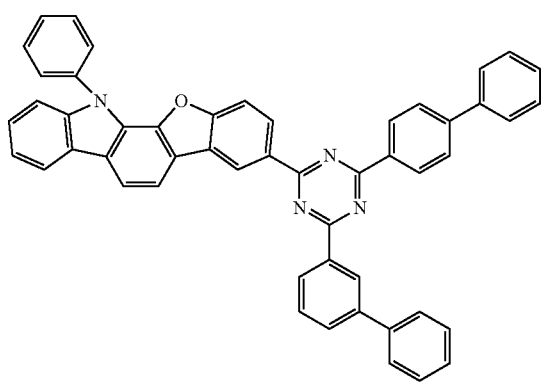
1B-2-3
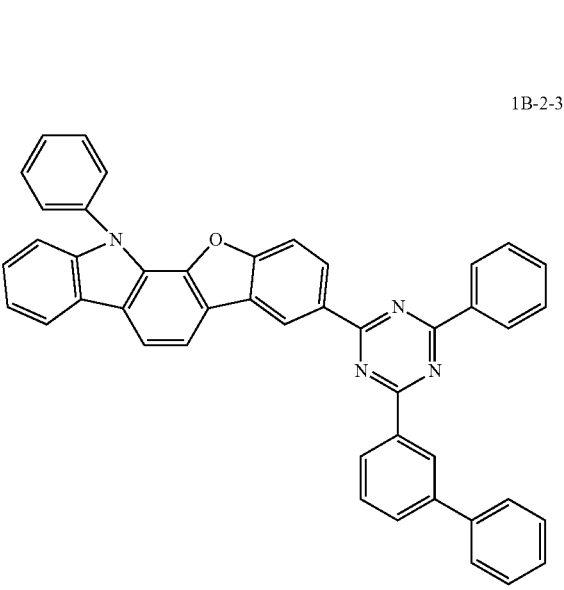
-continued
1B-2-4
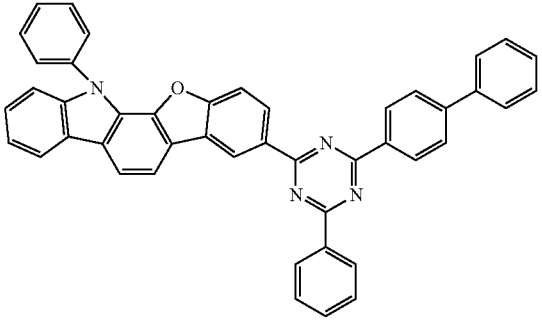
1B-2-5
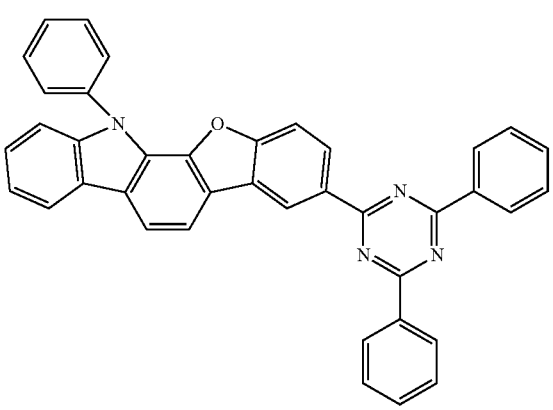
1B-2-6
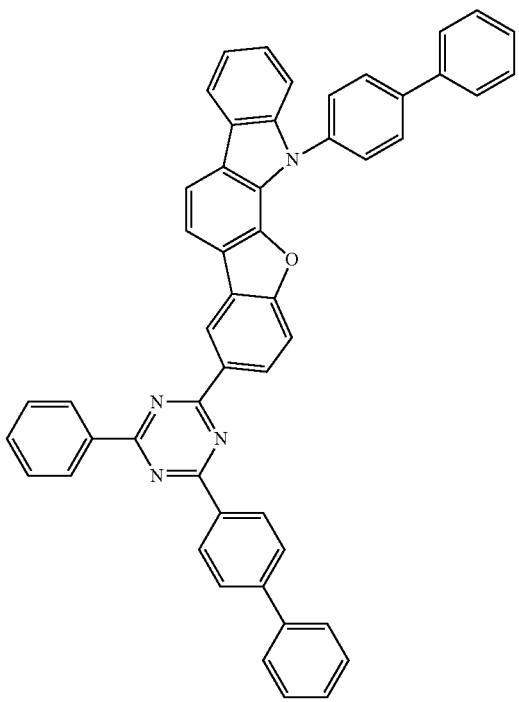

1B-2-7
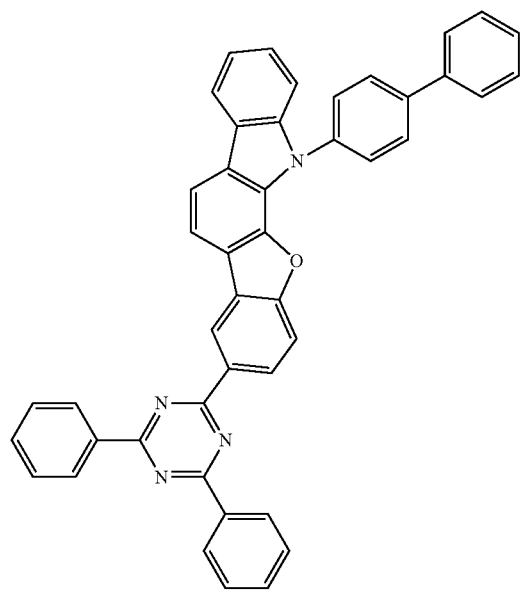
1B-2-8
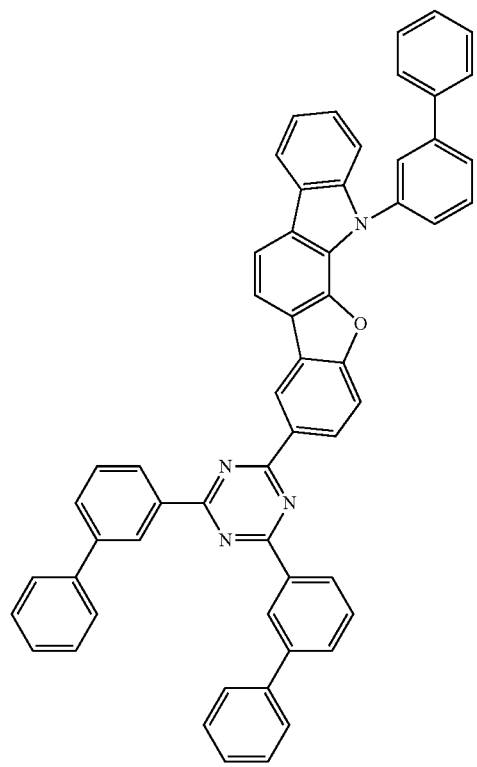
1B-2-9
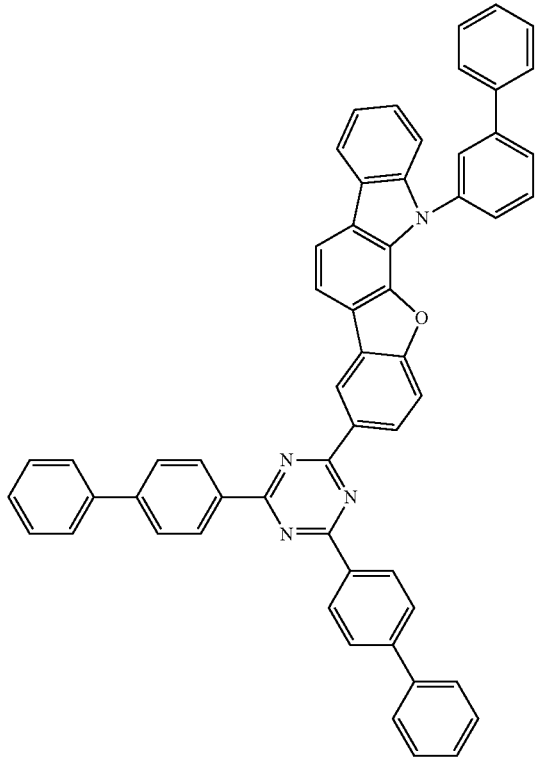
1B-2-10
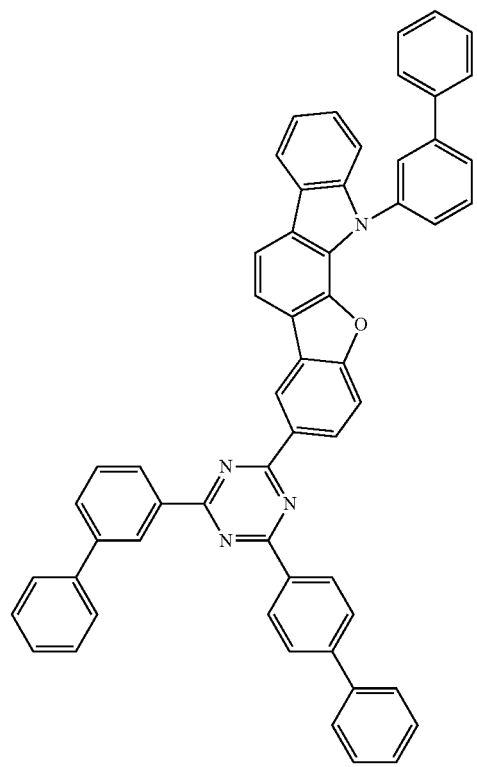

1B-2-11
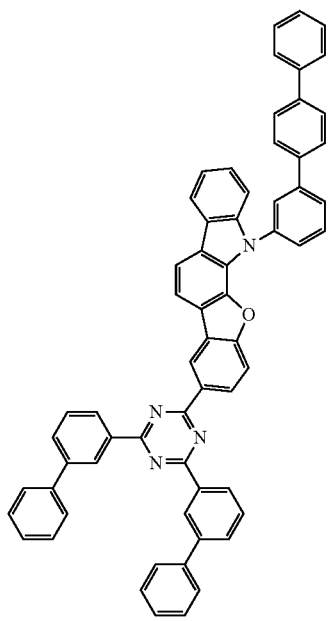
1B-2-12
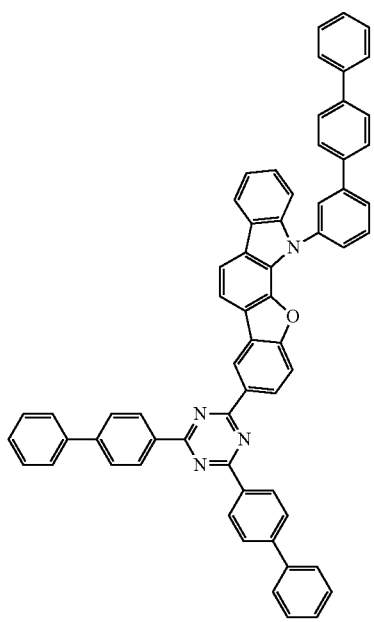
1B-2-13
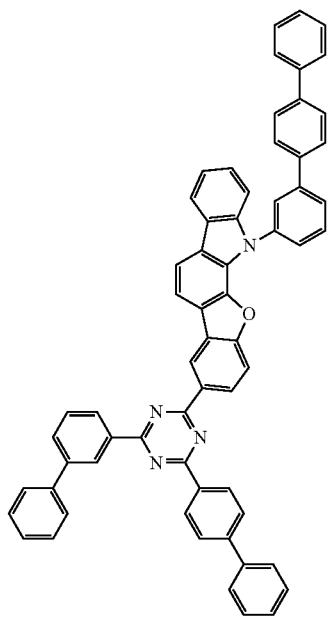
1B-2-14
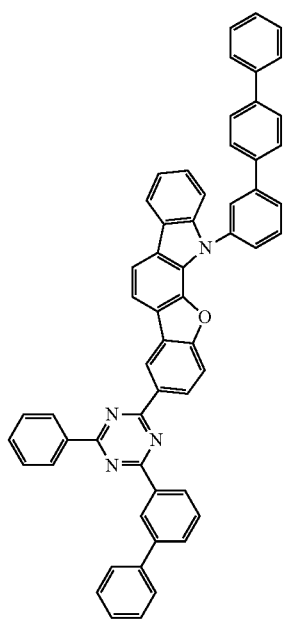

1B-2-15
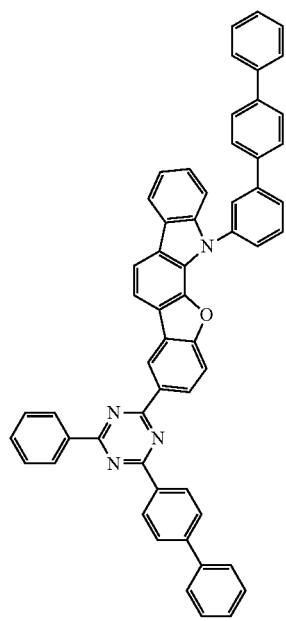
1B-2-16
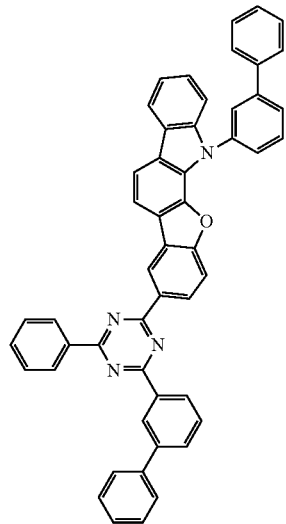
1B-2-17
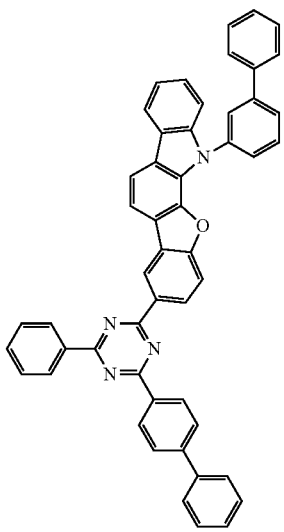
1B-2-18
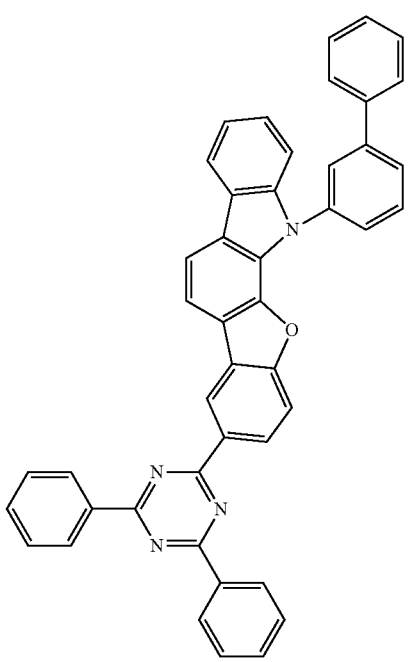

1B-2-19
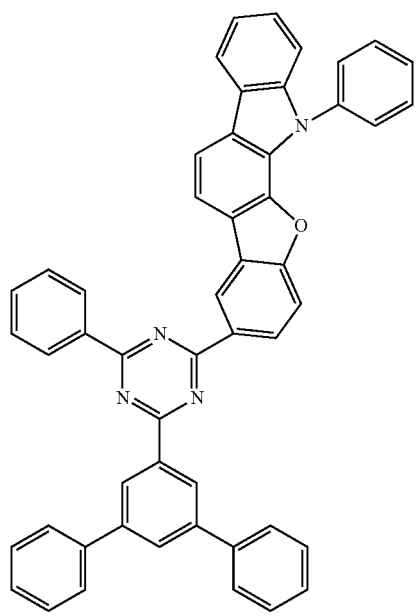
1B-2-21
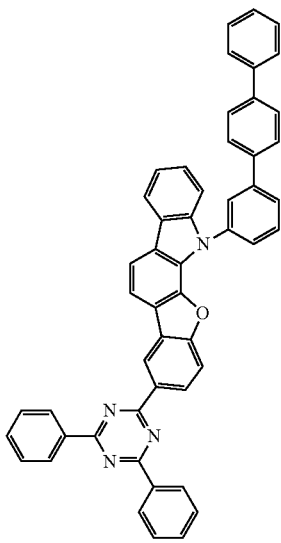
1B-2-20
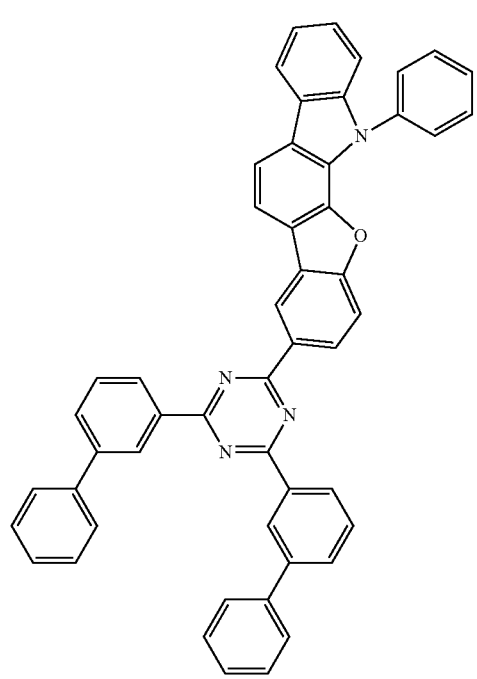
1B-2-22
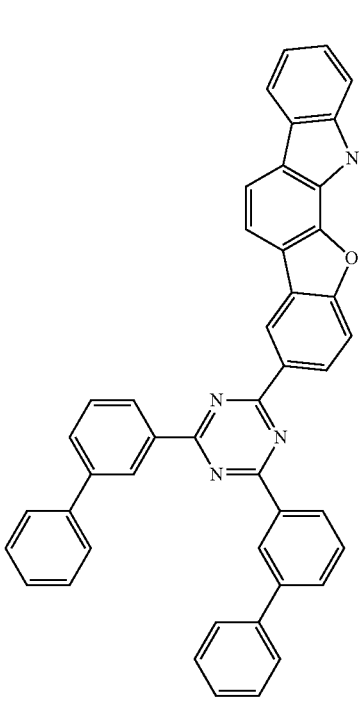

1B-2-23
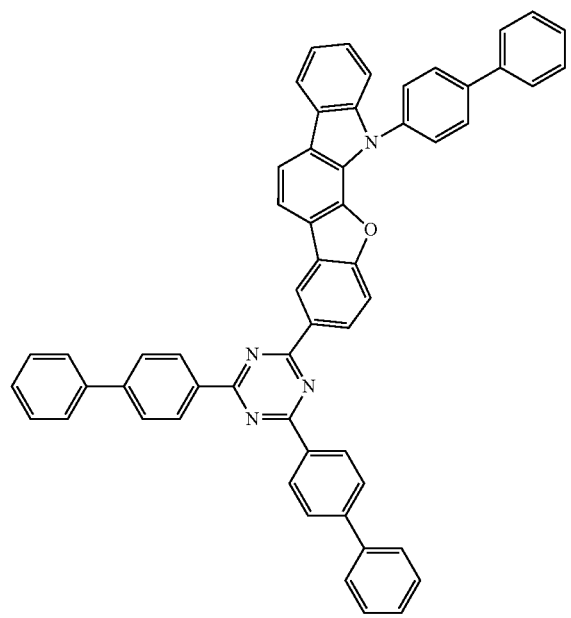
1B-2-25
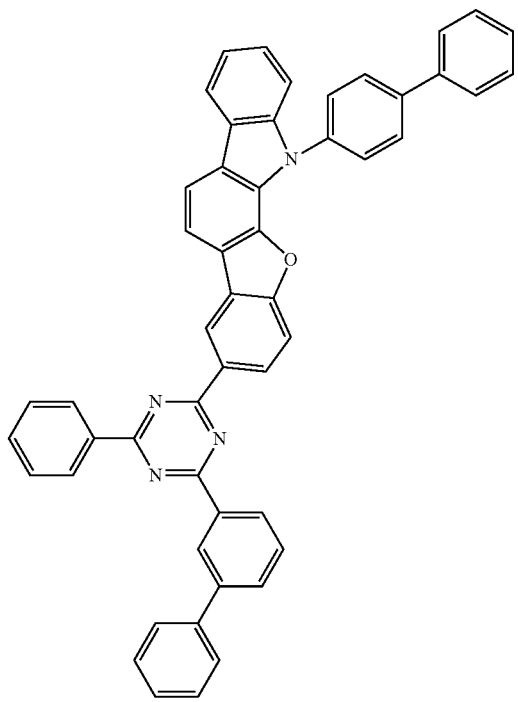
1B-2-24
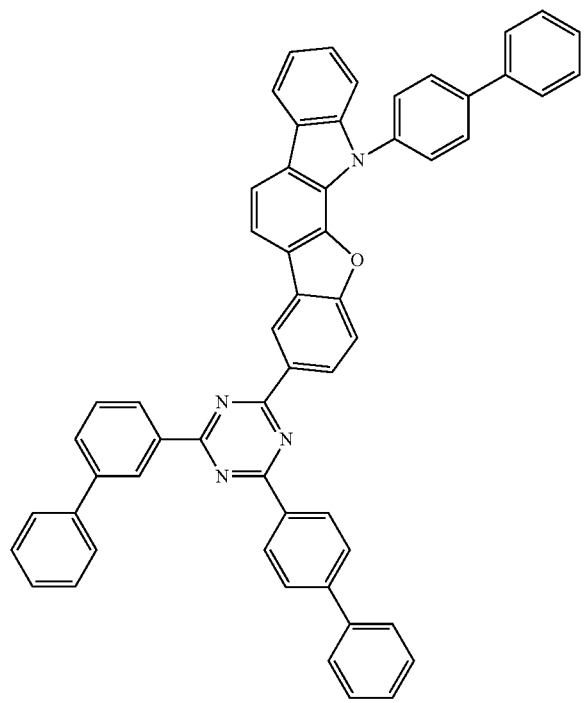
1B-2-26
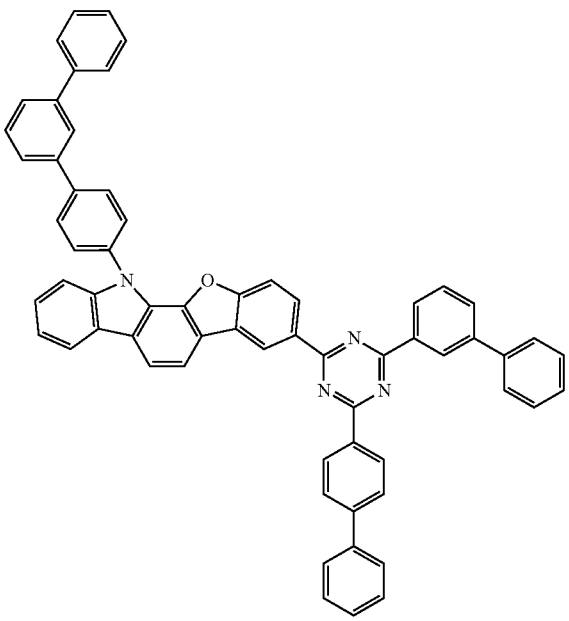

1B-2-27
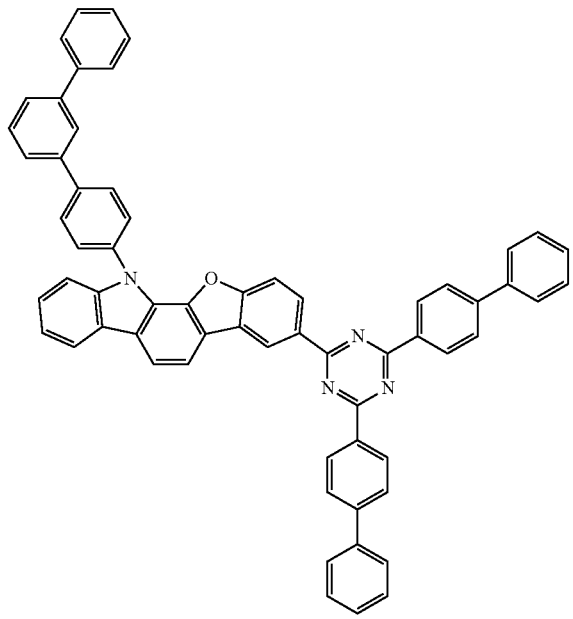
1B-2-29
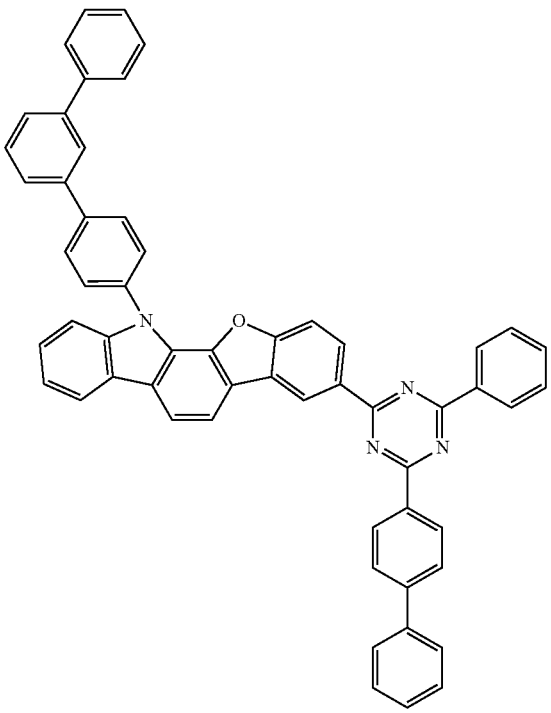
1B-2-28
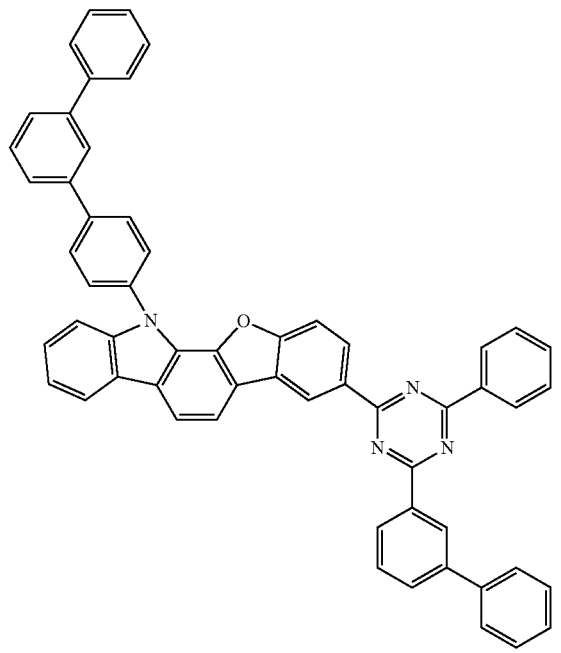
1B-2-30
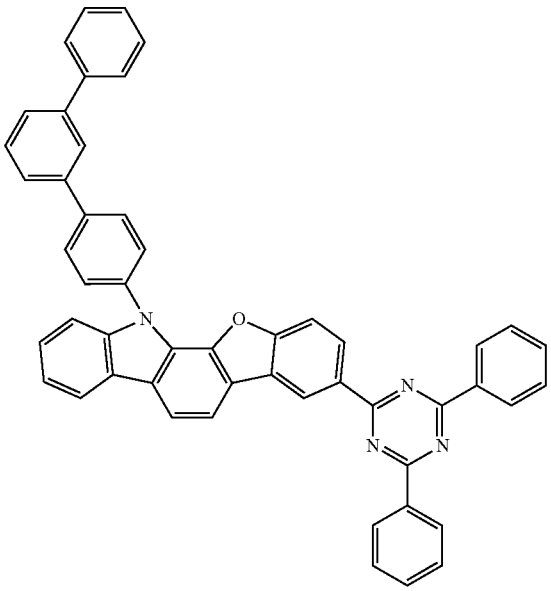

193
-continued
1B-2-31
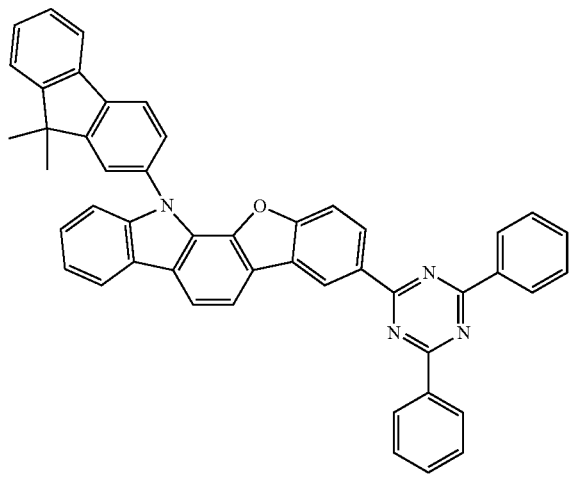
1B-2-32
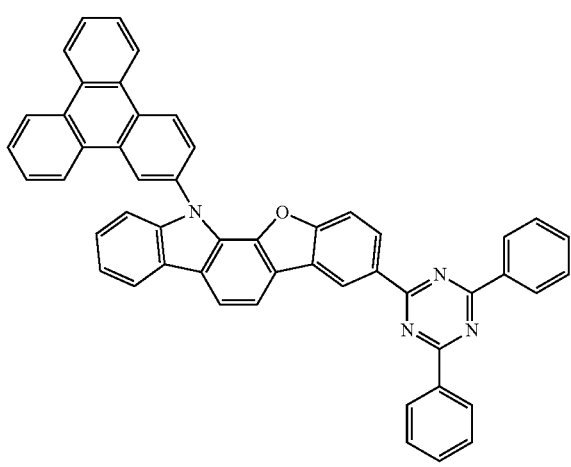
1B-2-33
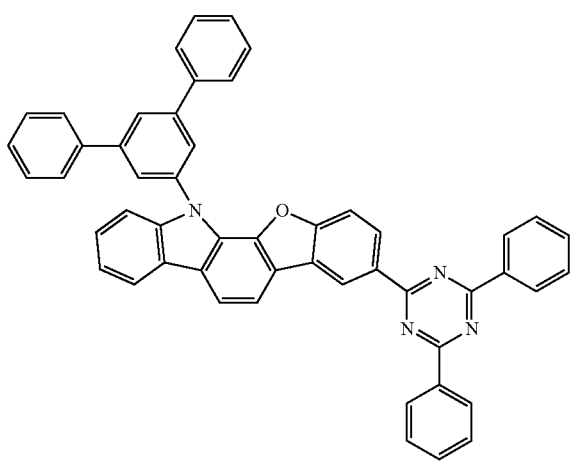
194
-continued
1B-2-34
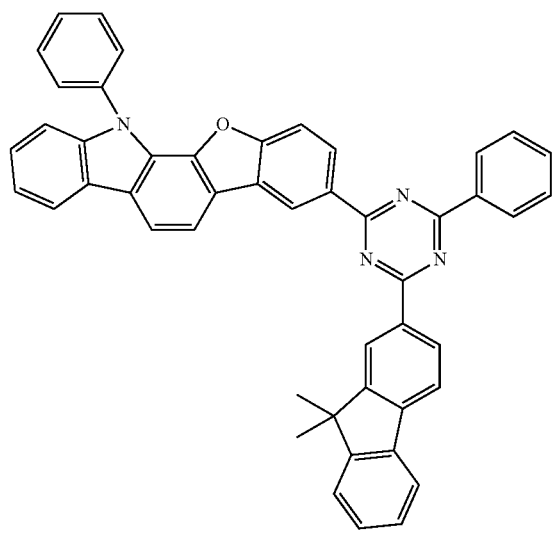
1B-2-35
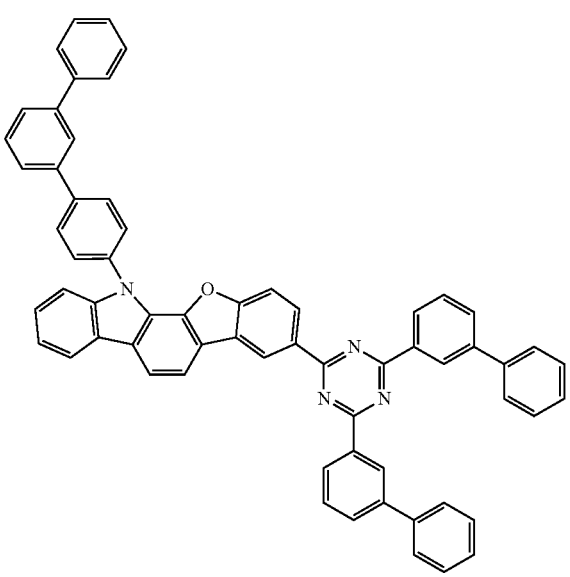
1B-2-36
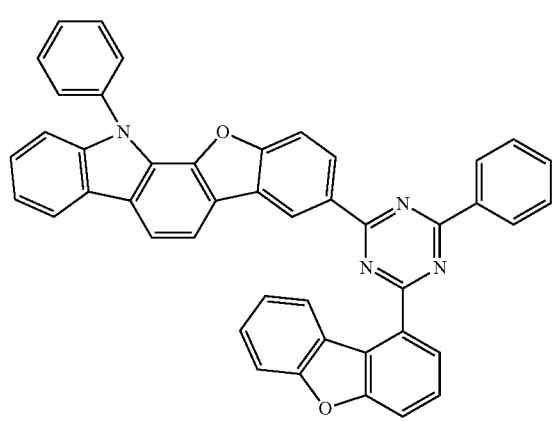

1B-2-37
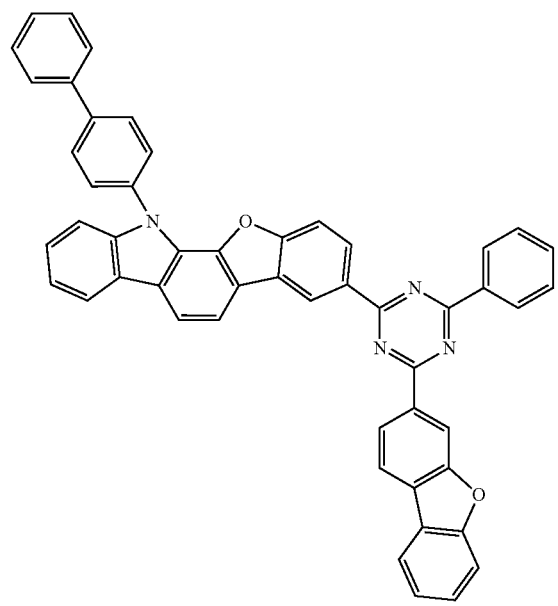
1B-2-40
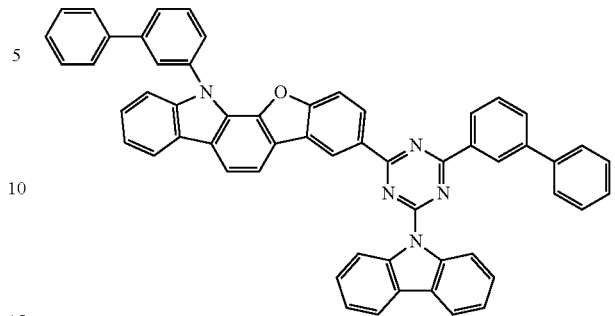
1B-2-38
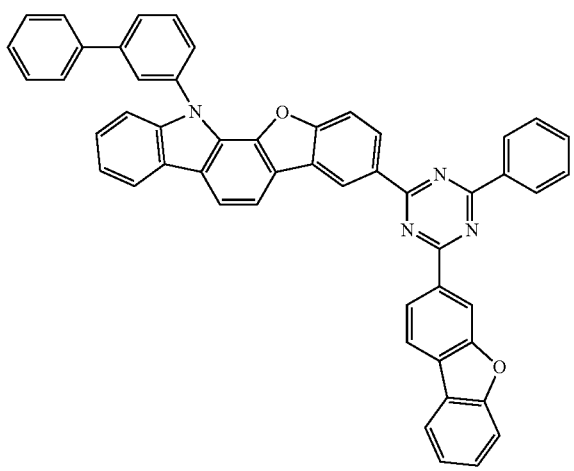
1B-2-41
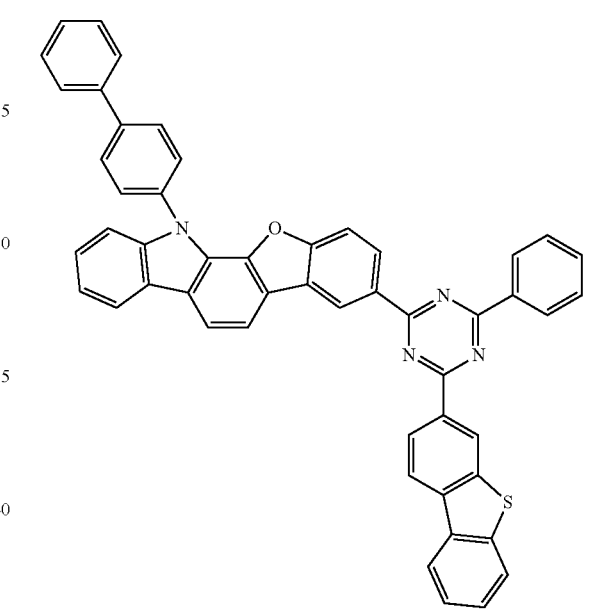
1B-2-39
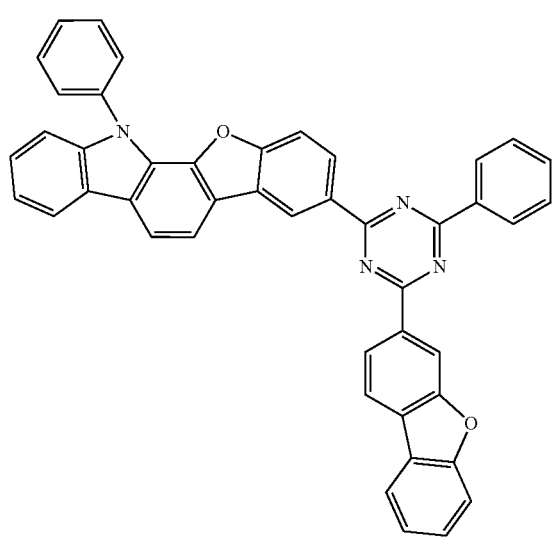
1B-2-42
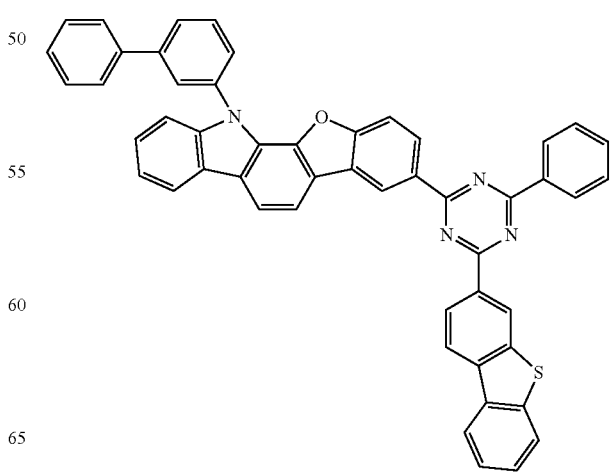

-continued
1B-2-43
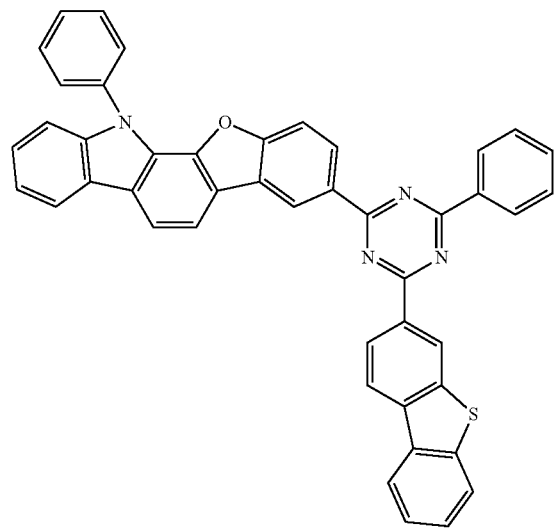
1B-2-44
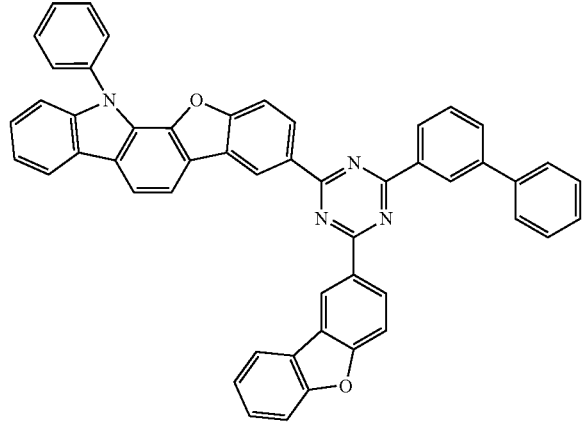
1B-2-45
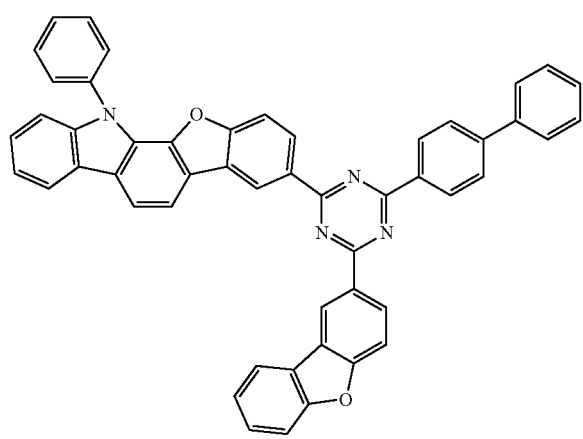
-continued
1B-2-46
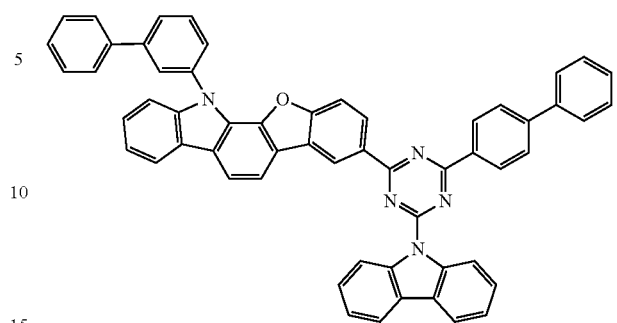
1B-2-47
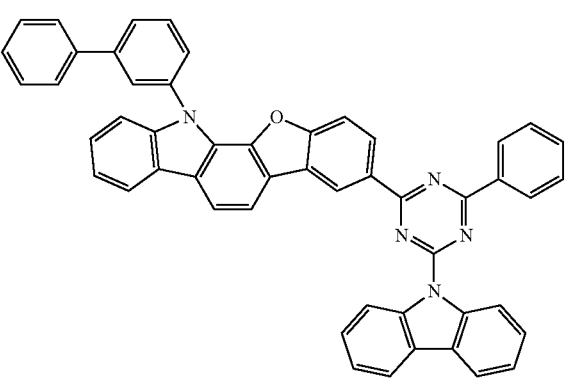
1B-2-48
1B-2-49
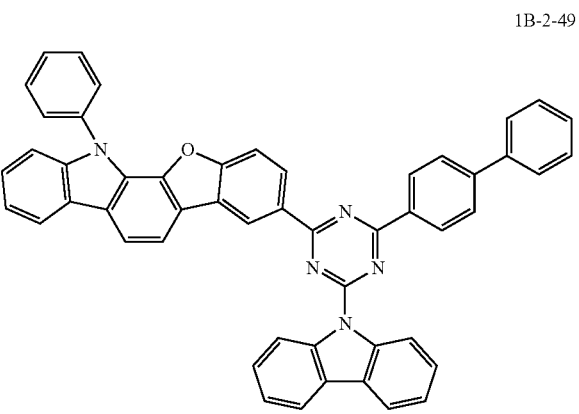

1B-2-50
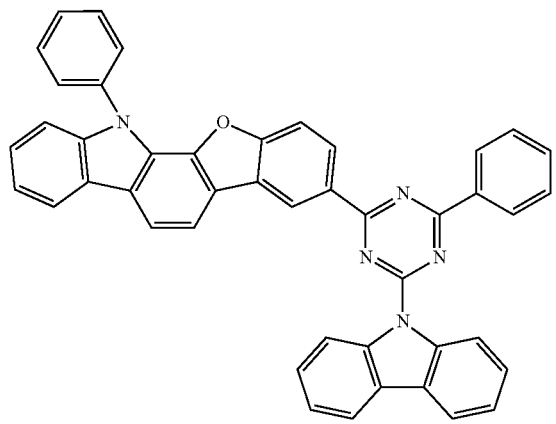
1B-2-51
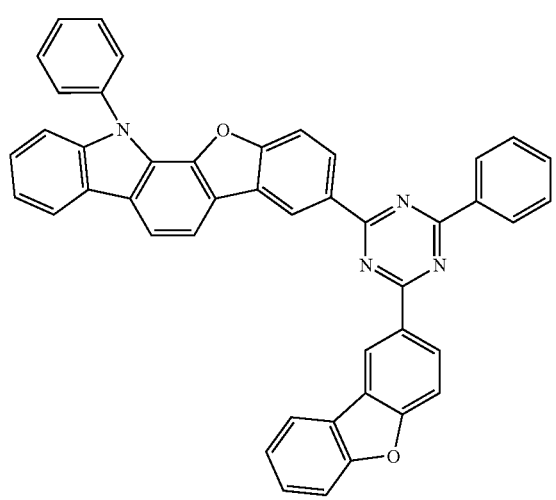
1B-2-52
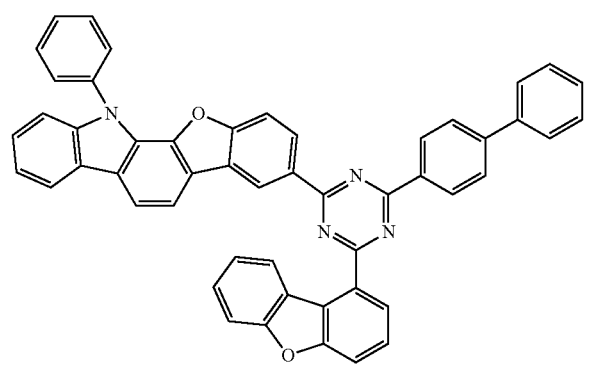
1B-2-53
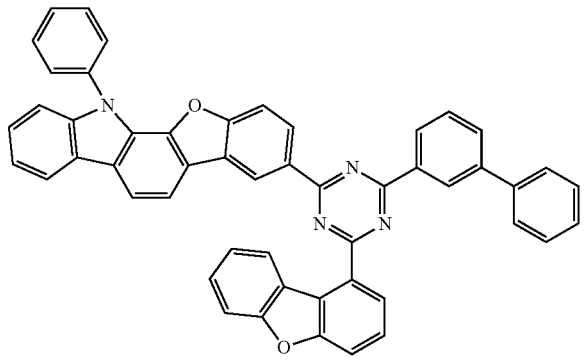
1B-2-54
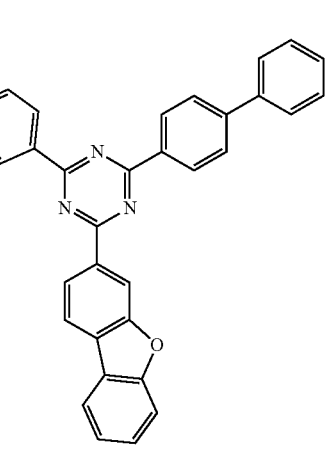
1B-2-55
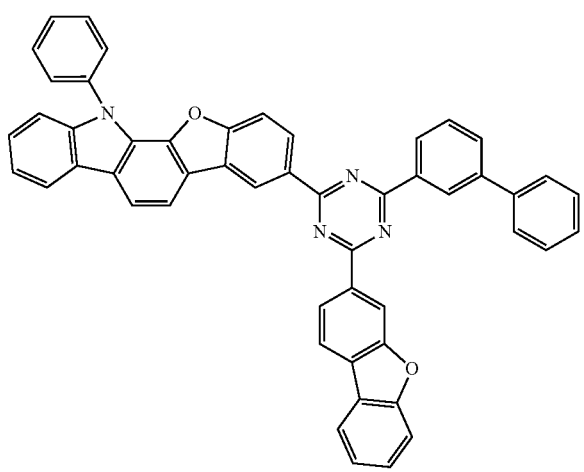

-continued
1B-2-56
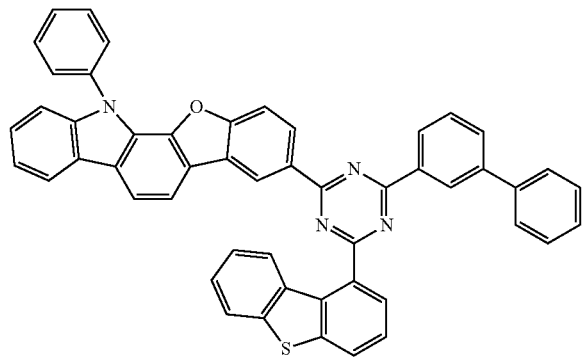
1B-2-57
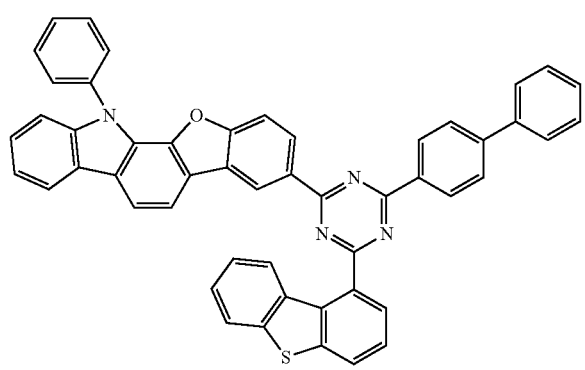
1B-2-58
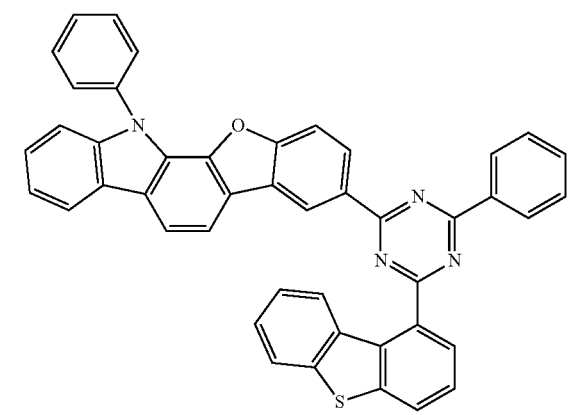
-continued
1B-2-59
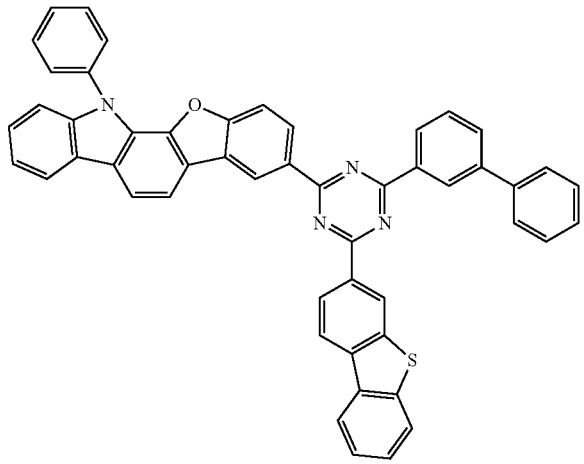
1B-2-60
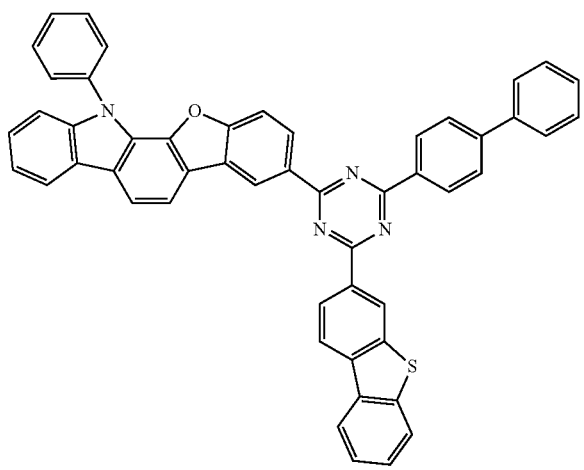
1B-2-61
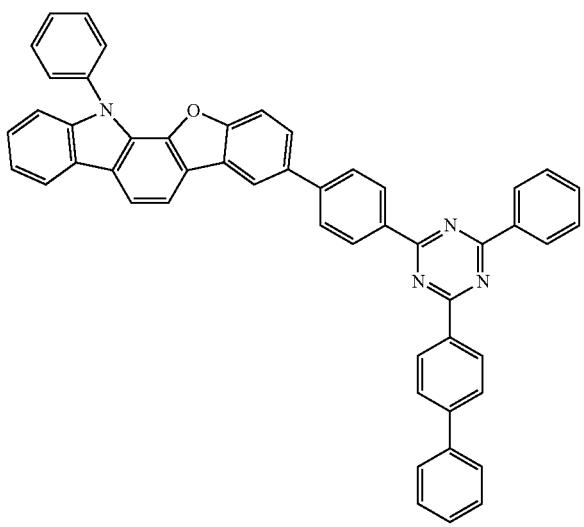

1B-2-62
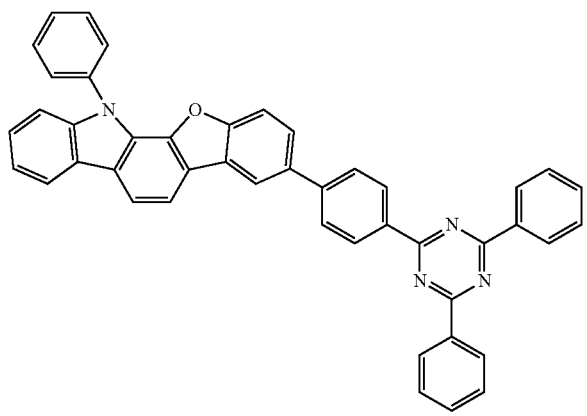
1B-2-63
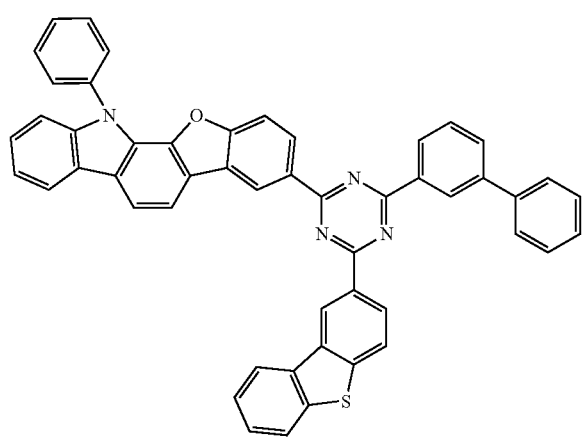
1B-2-64
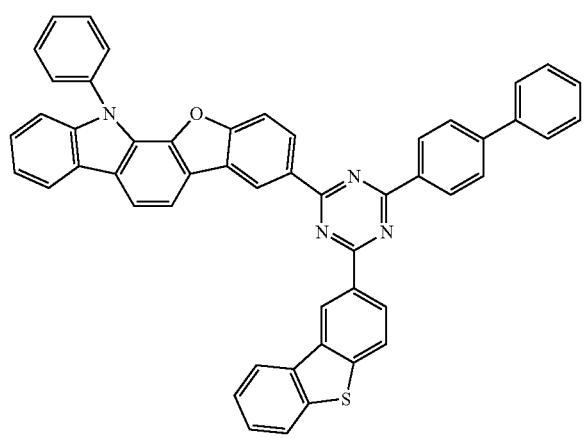
1B-2-65
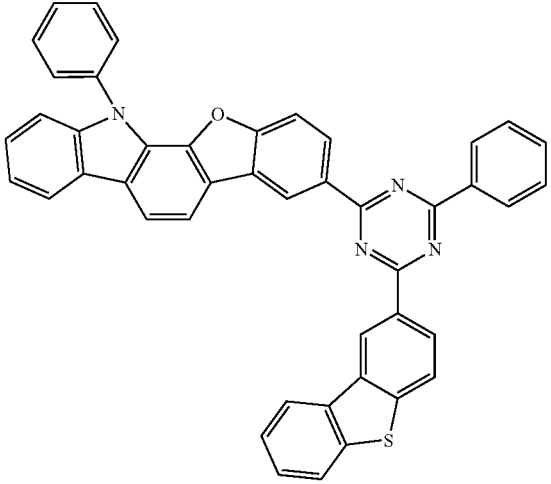
1B-2-66
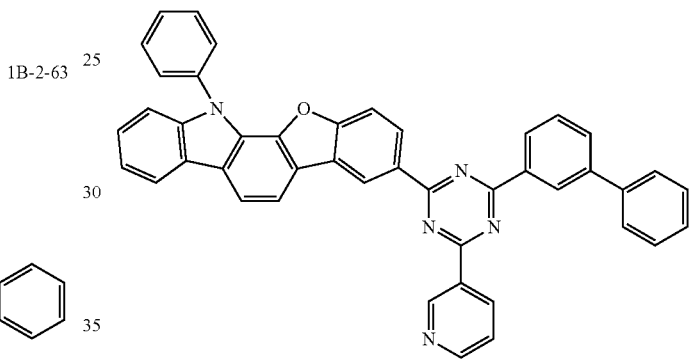
1B-2-67
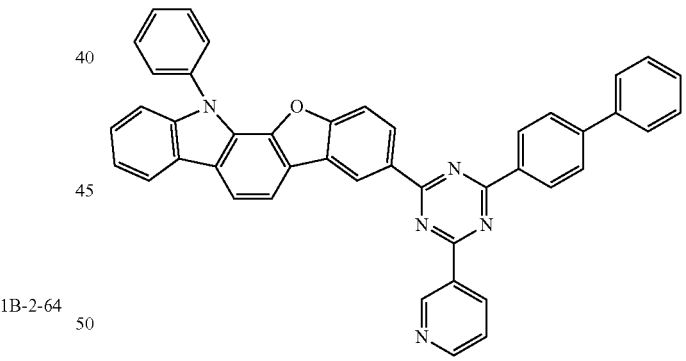
1B-2-68
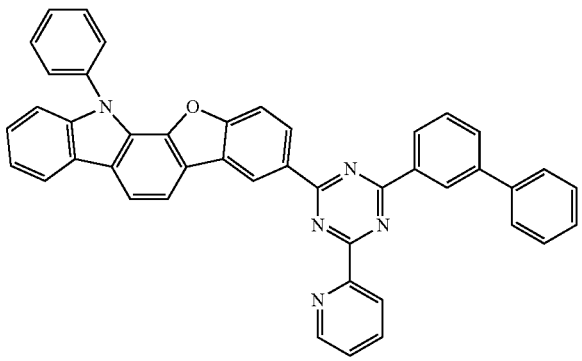

1B-2-69
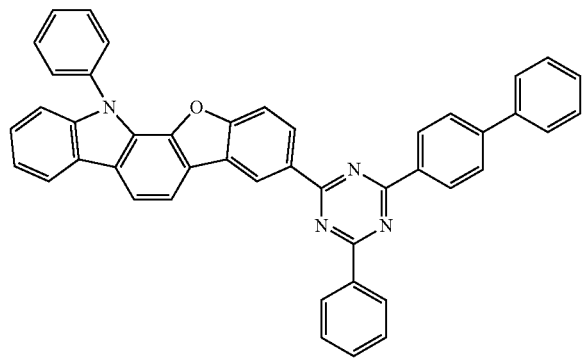
1B-2-70
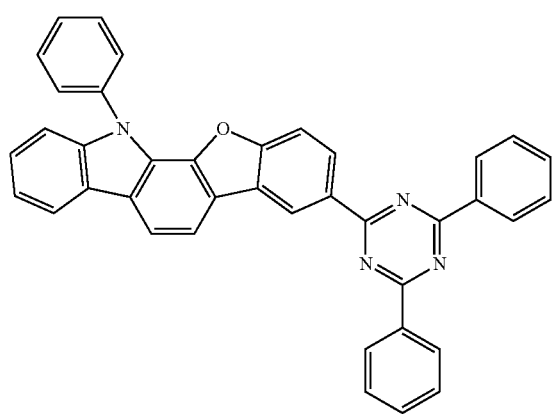
1B-2-71
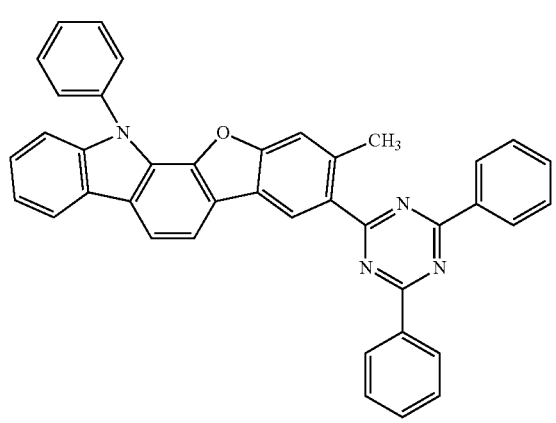
1B-2-72
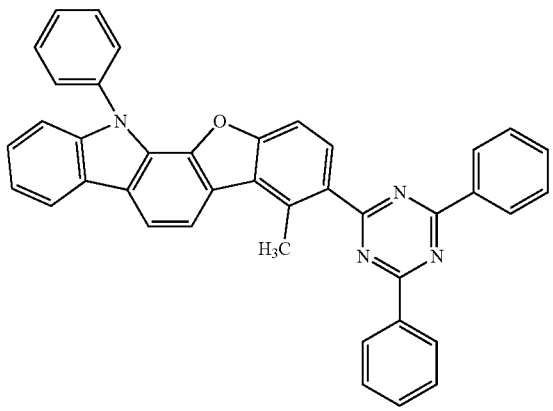
1B-2-73
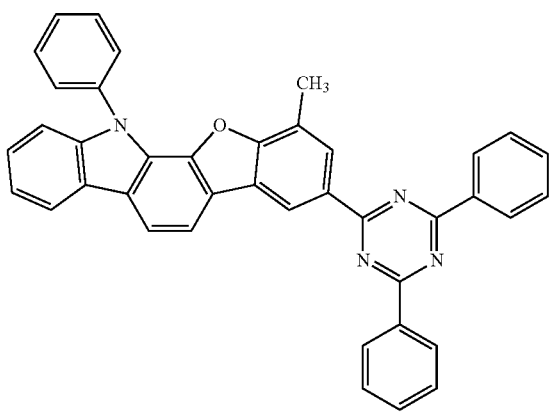
1B-2-74
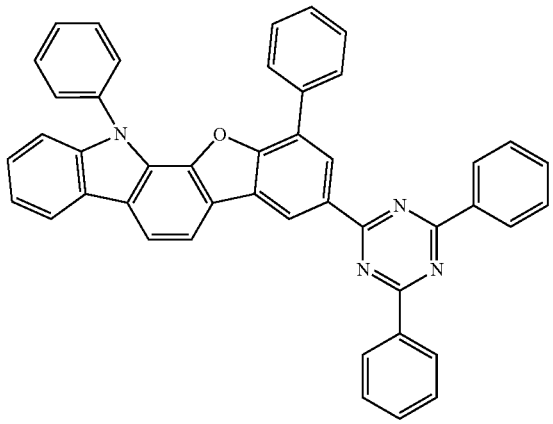

207
-continued
1B-2-75
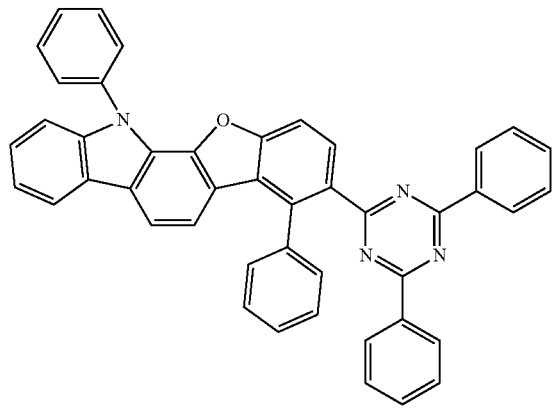
1B-2-76
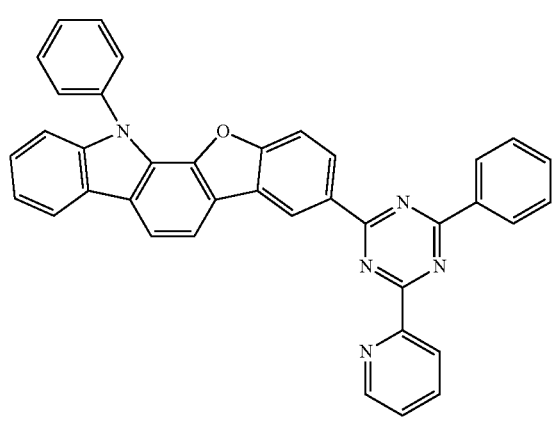
1B-2-77
208
-continued
1B-2-78
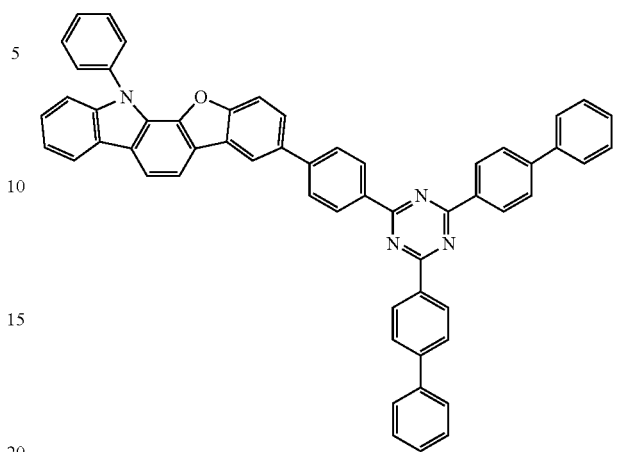
1B-2-79
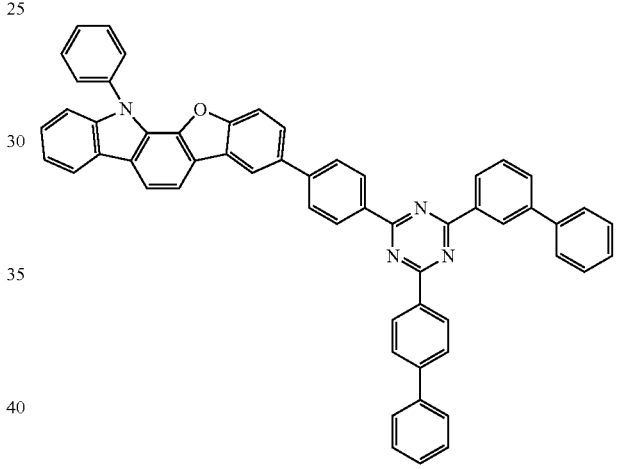
1B-2-80
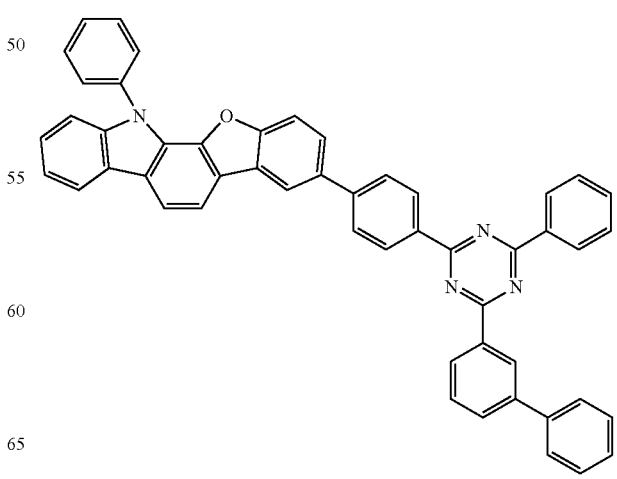

1B-2-81
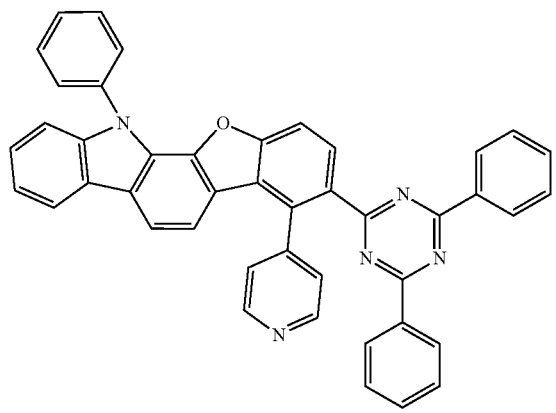
1B-3-1
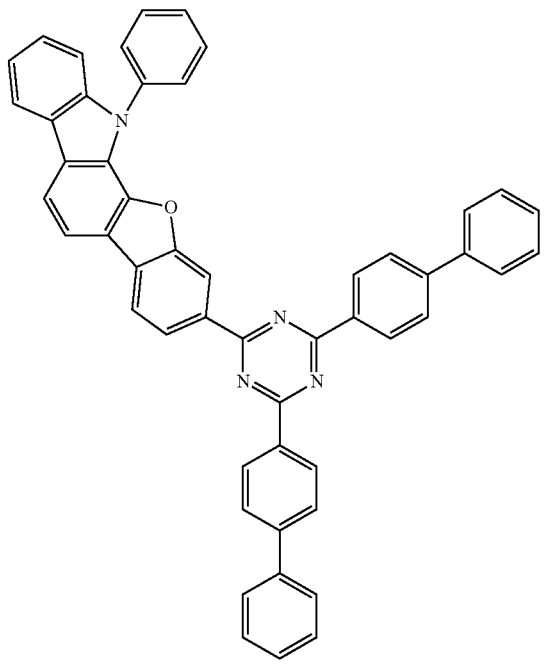
1B-2-82
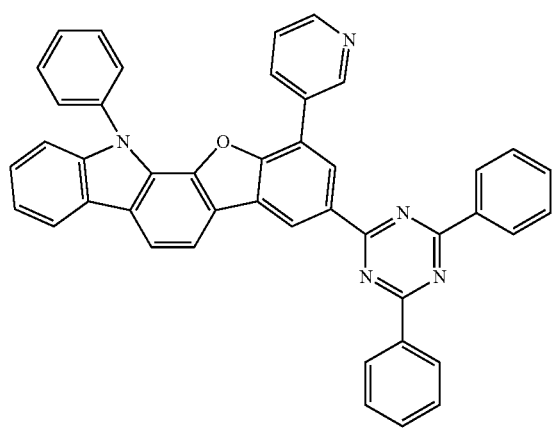
1B-2-83
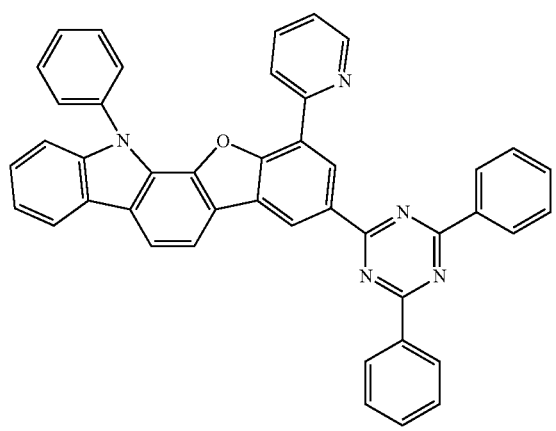
1B-3-2
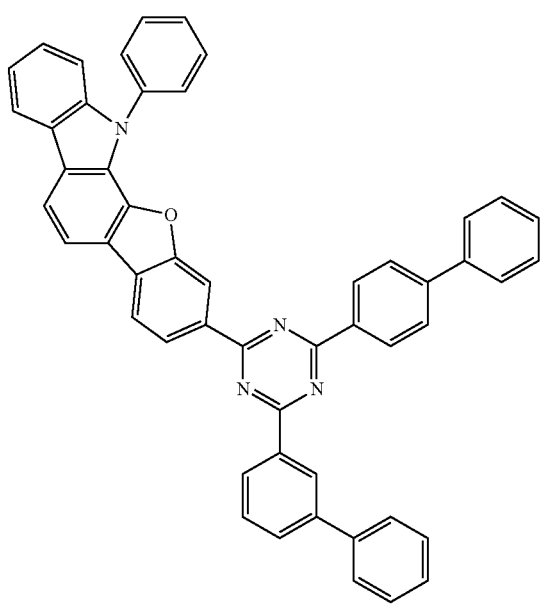

1B-3-3
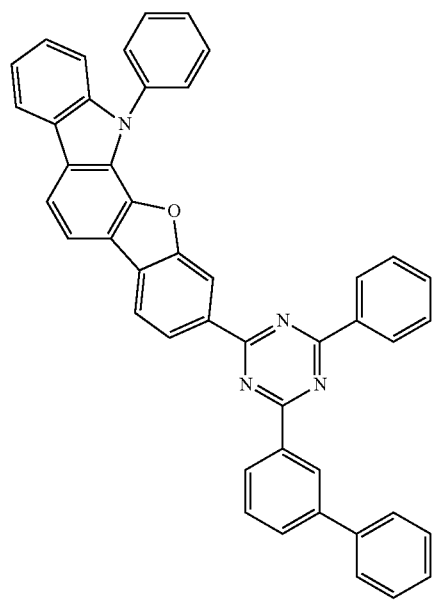
1B-3-4
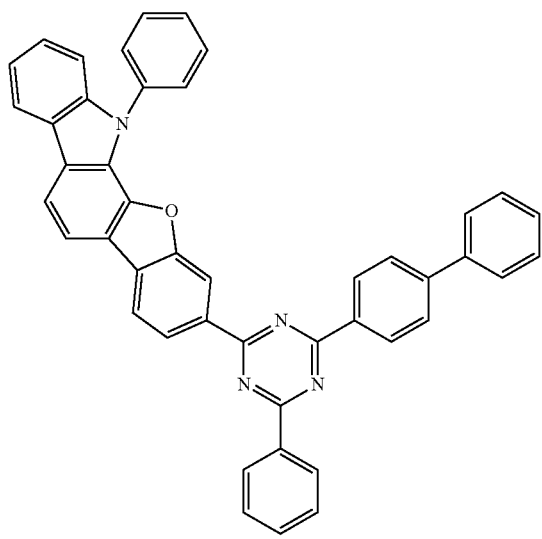
1B-3-5
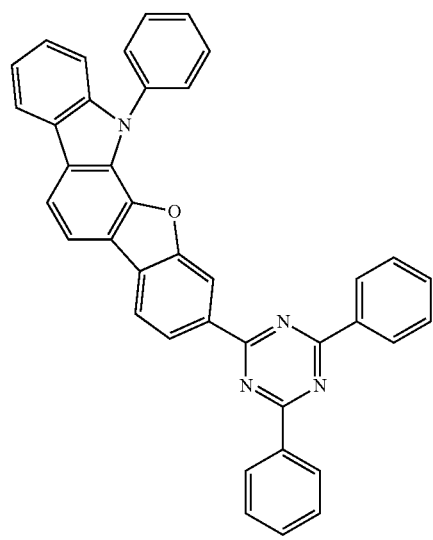
1B-3-6
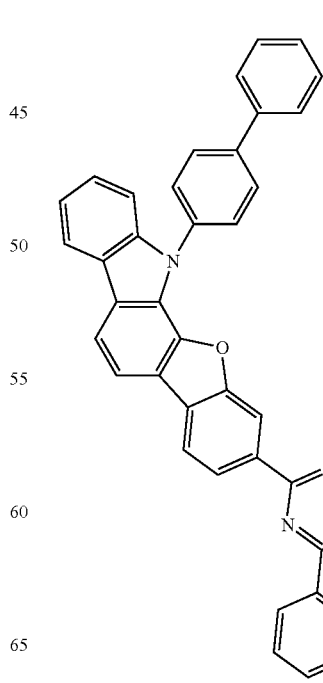

1B-3-7
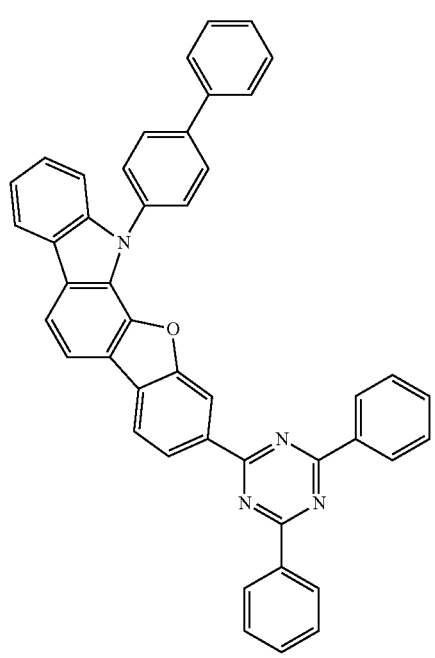
1B-3-8
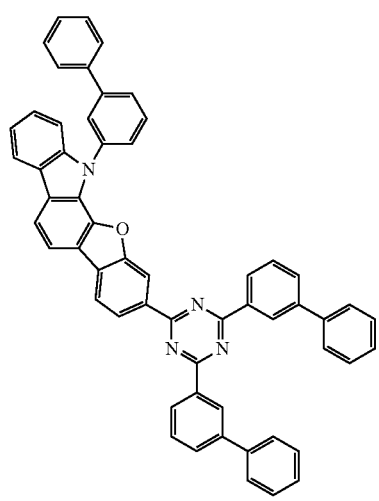
1B-3-9
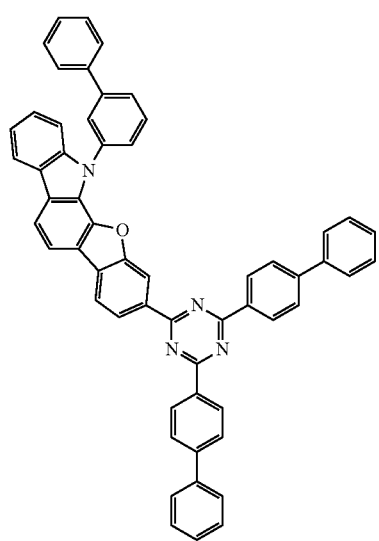
1B-3-10
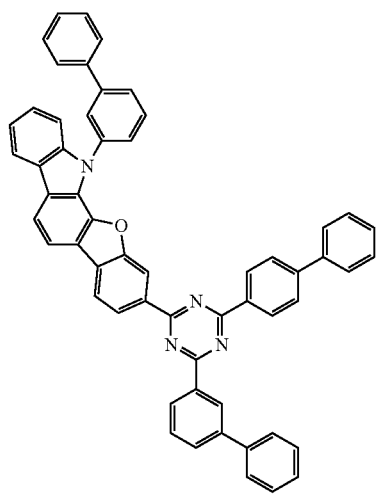
1B-3-11
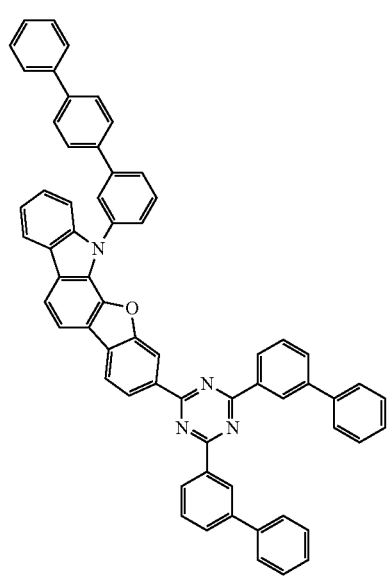
1B-3-12
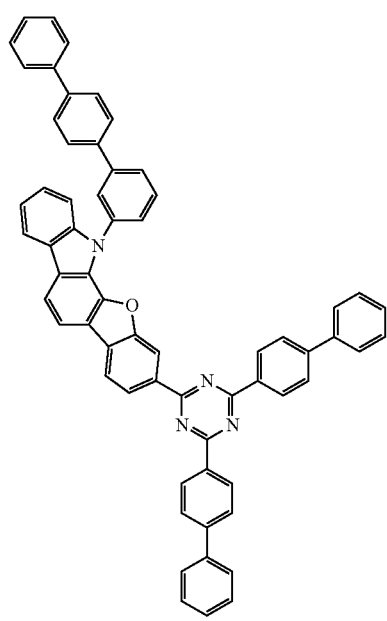

1B-3-13
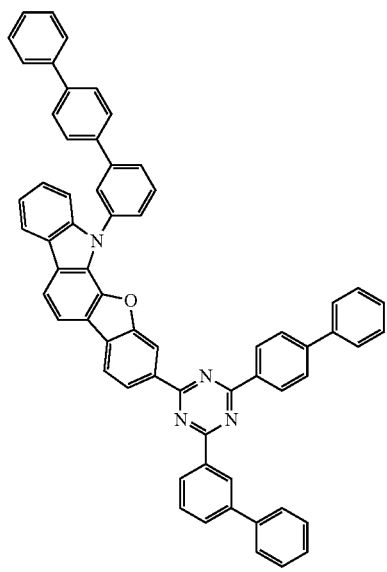
1B-3-14
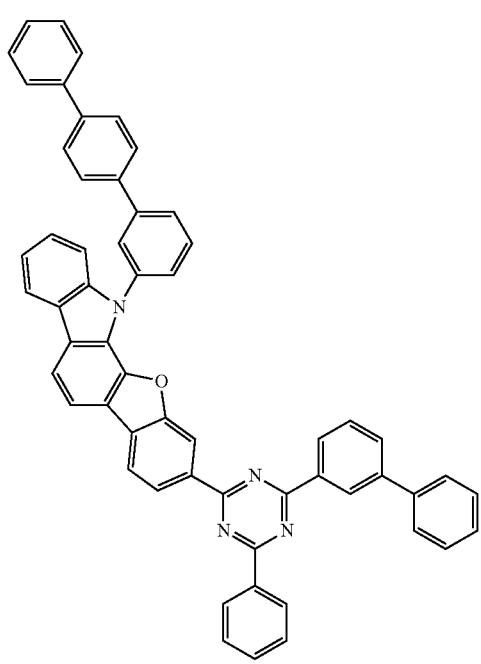
1B-3-15
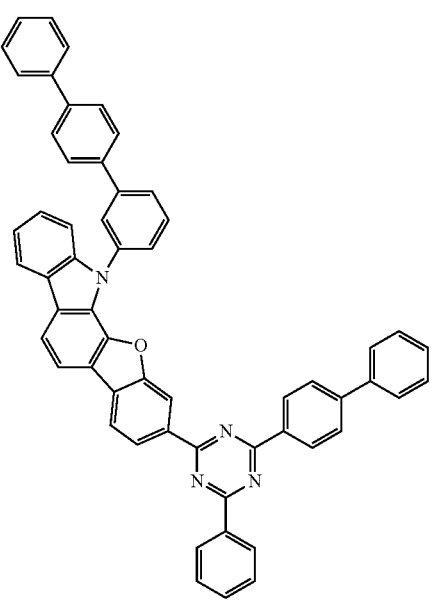
1B-3-16

217
-continued
1B-3-17
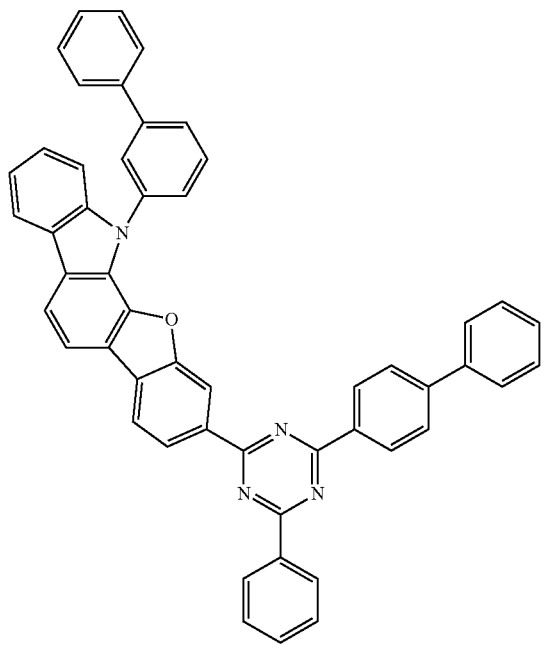
1B-3-18
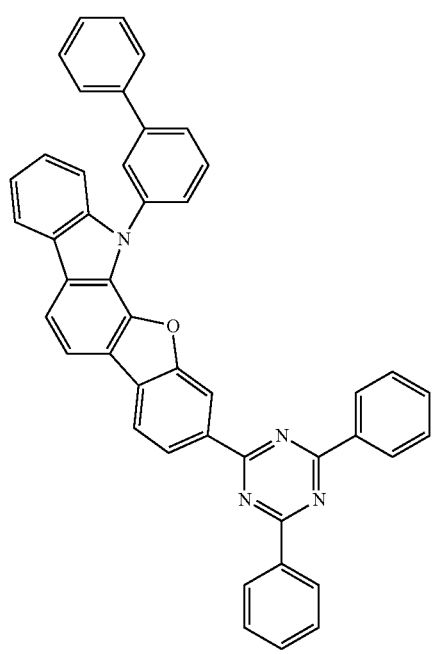
218
-continued
1B-3-19
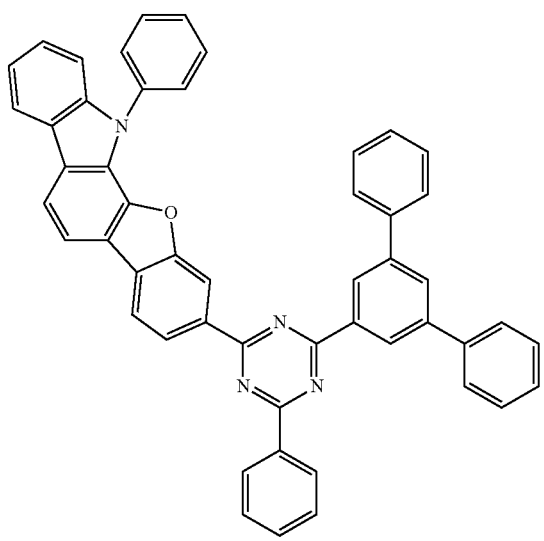
1B-3-20
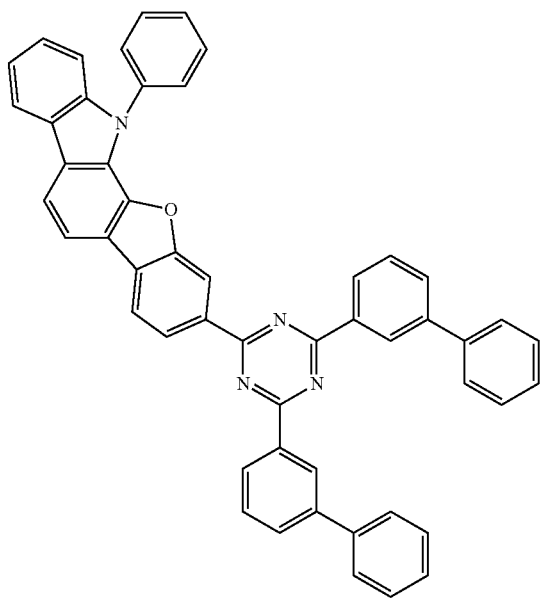

1B-3-21
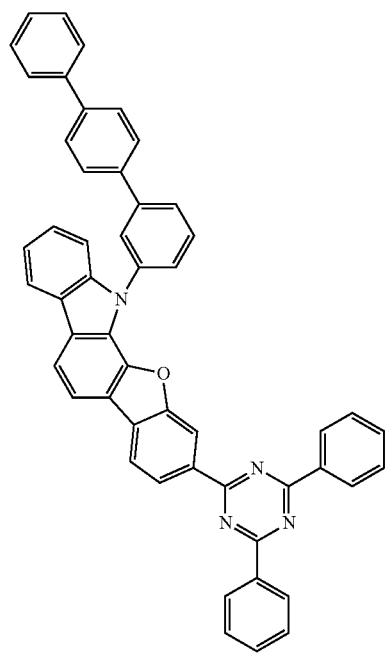
1B-3-22
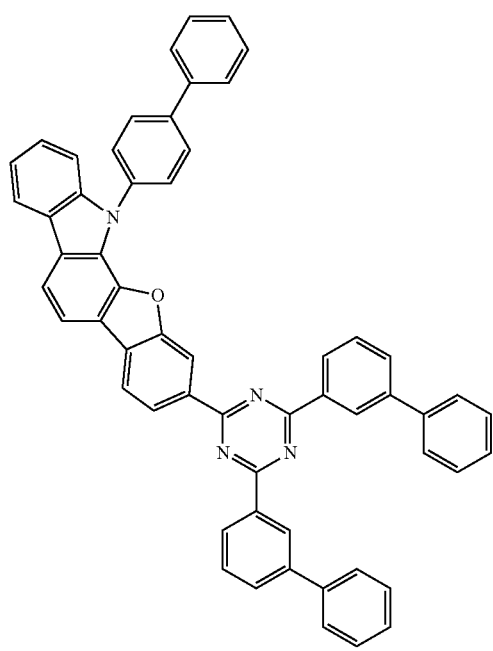
1B-3-23
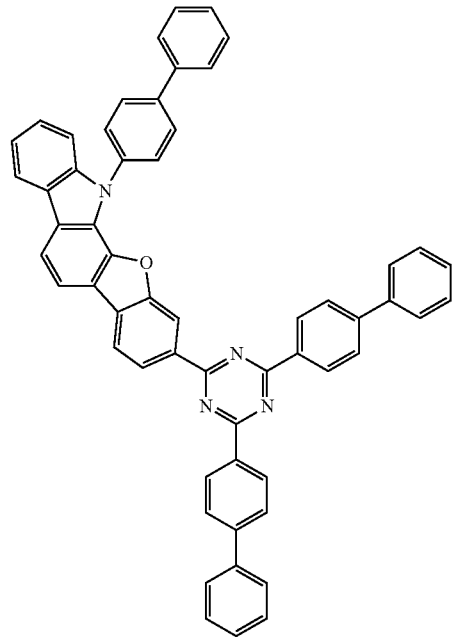
1B-3-24
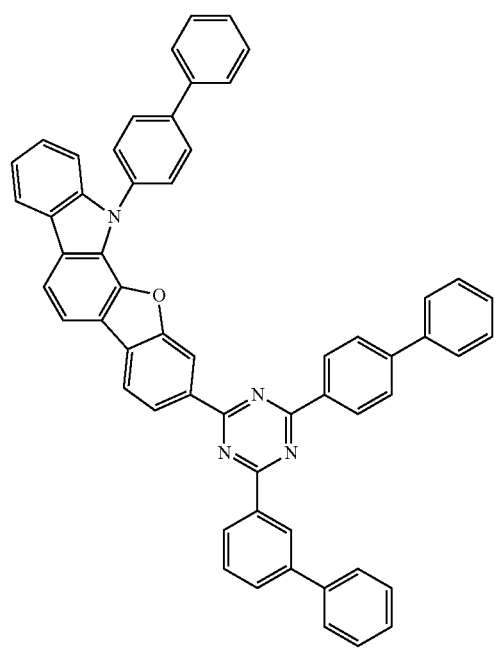

-continued
1B-3-25
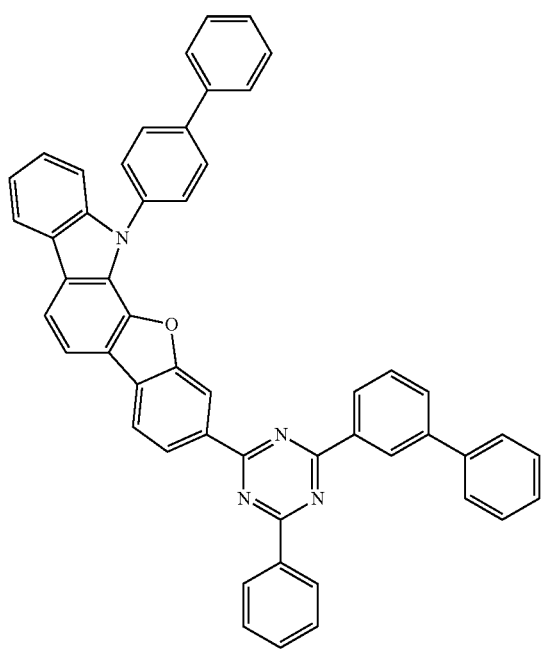
1B-3-27
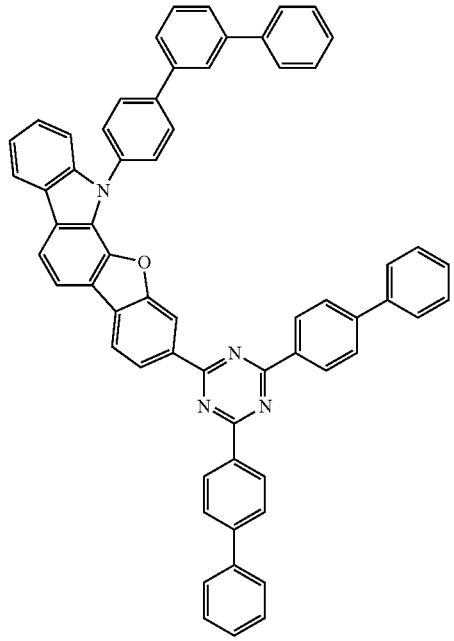
1B-3-26
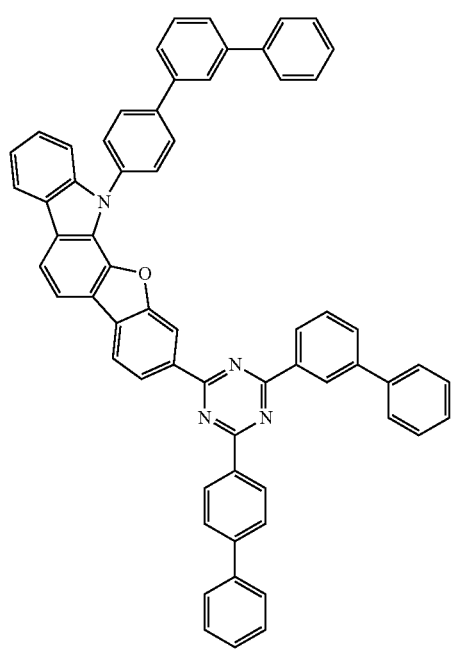
1B-3-28
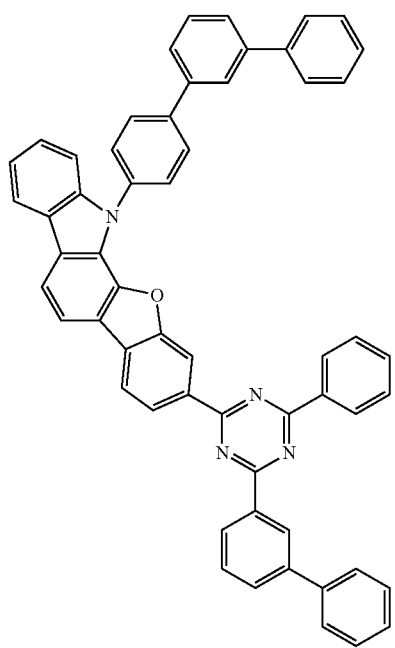

-continued
1B-3-29
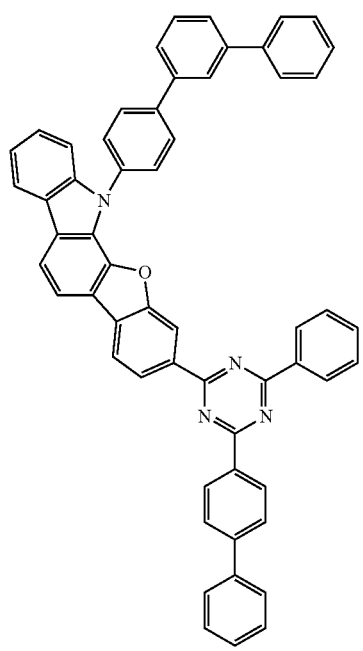
1B-3-31
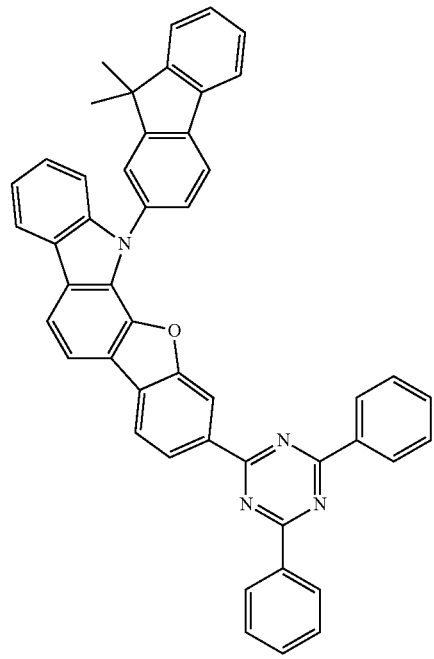
1B-3-30
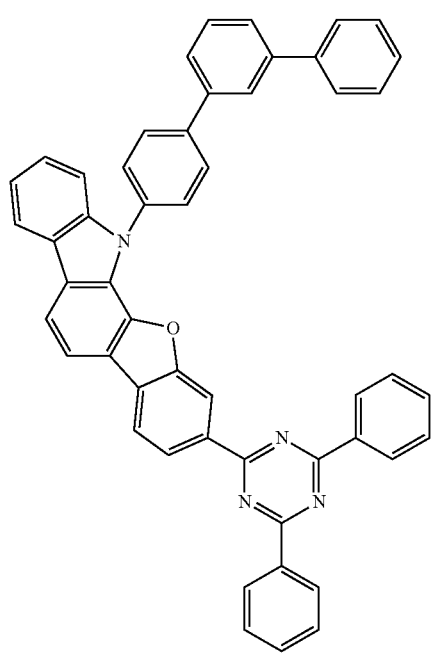
1B-3-32
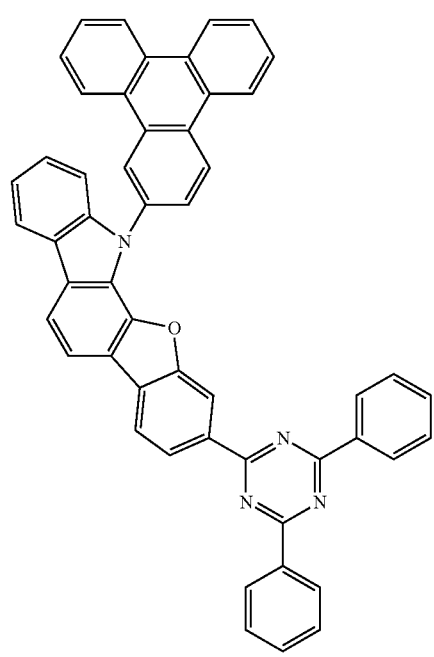

1B-3-33
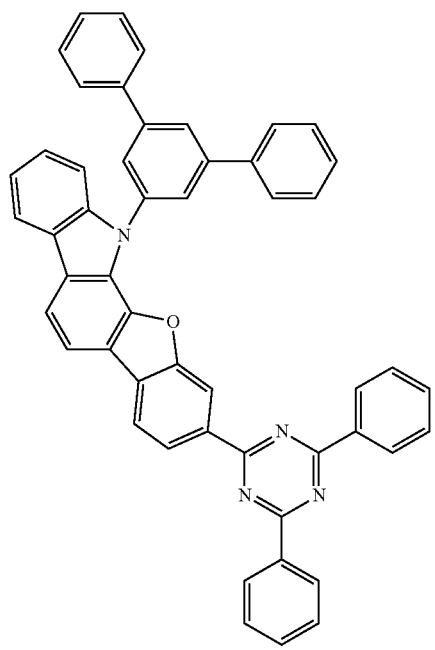
1B-3-34
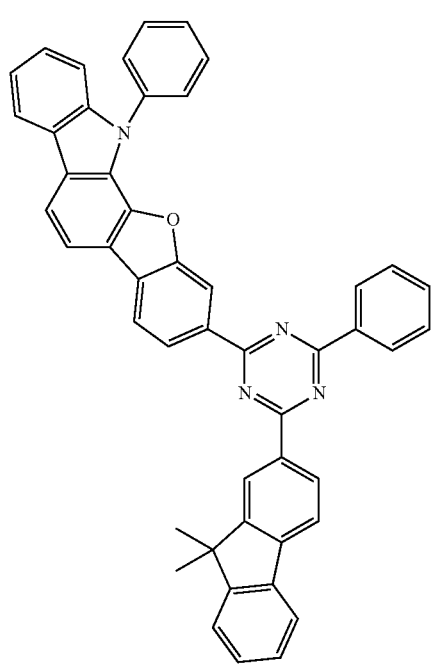
1B-3-35
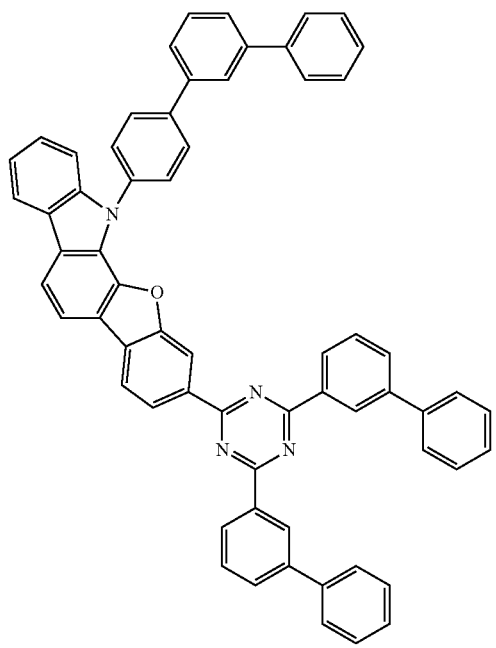
1B-3-36
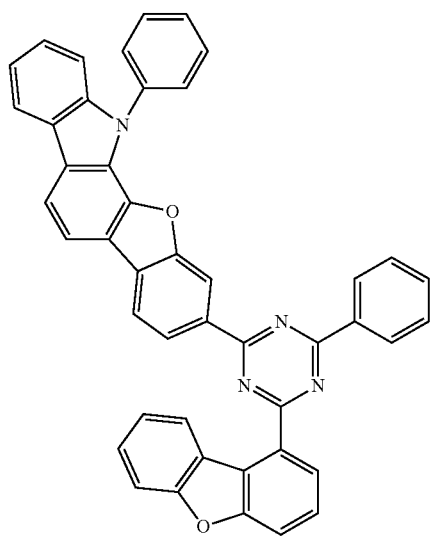

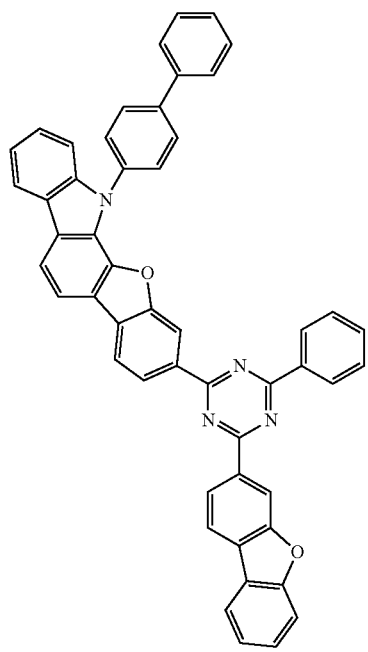
1B-3-37
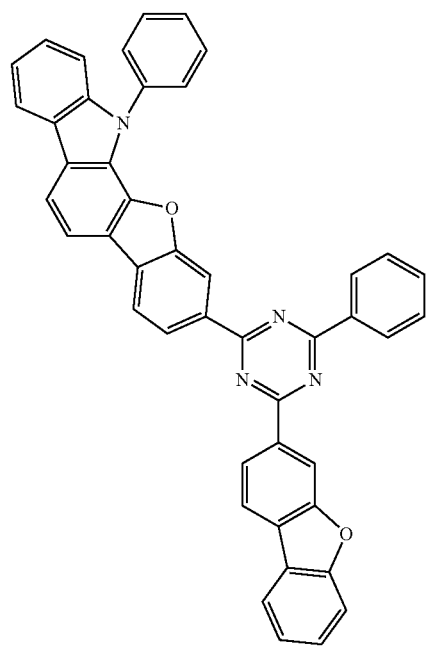
1B-3-39
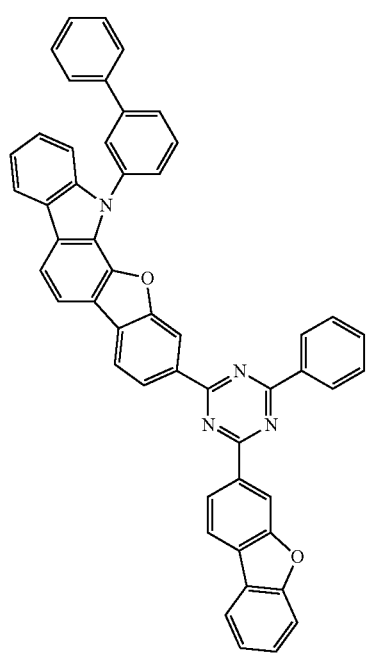
1B-3-38
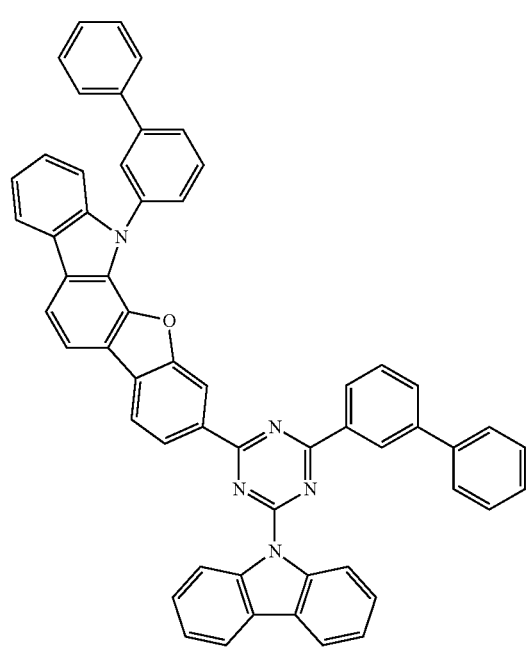
1B-3-40

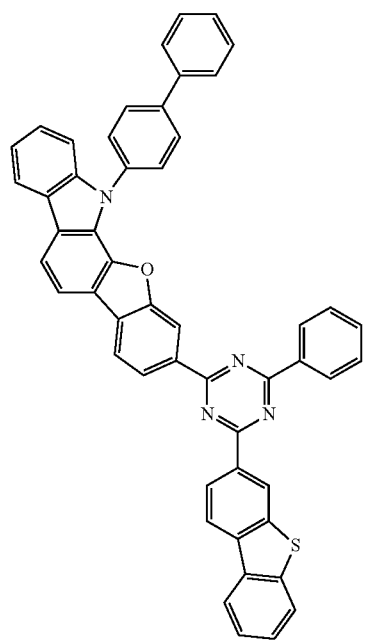
1B-3-41
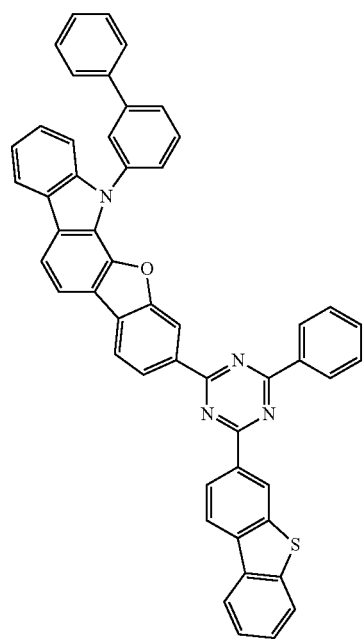
1B-3-42
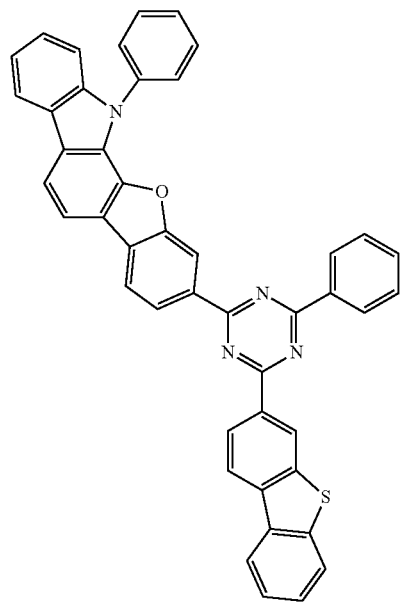
1B-3-43
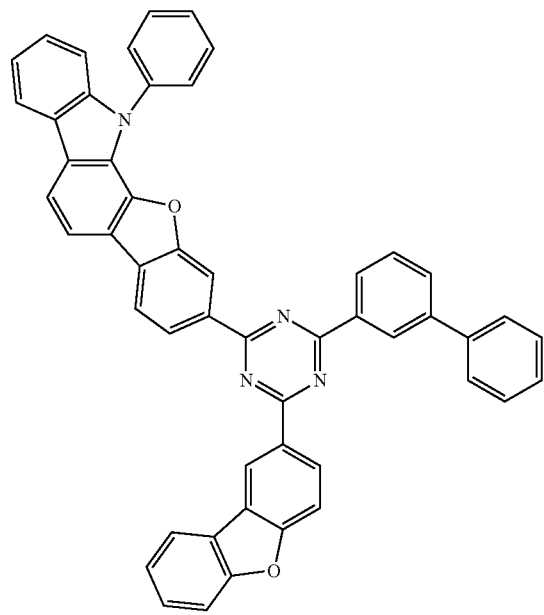
1B-3-44

1B-3-45
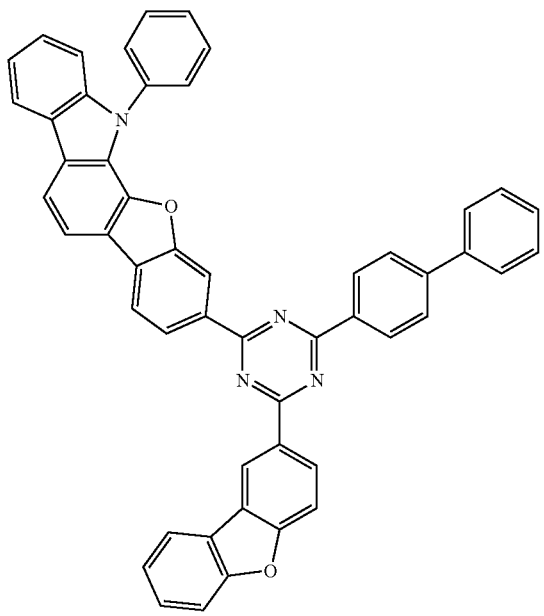
1B-3-46
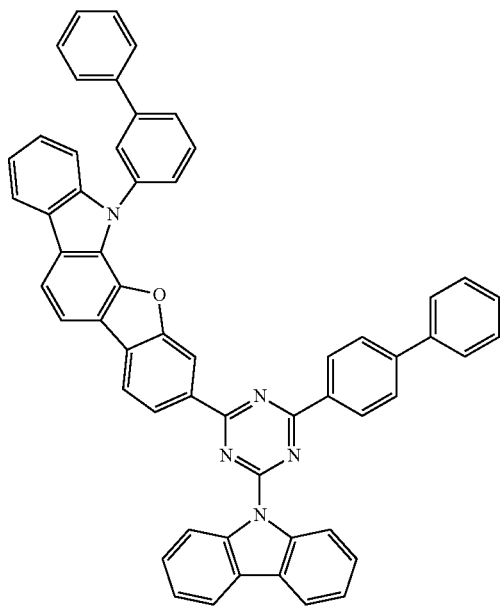
1B-3-47
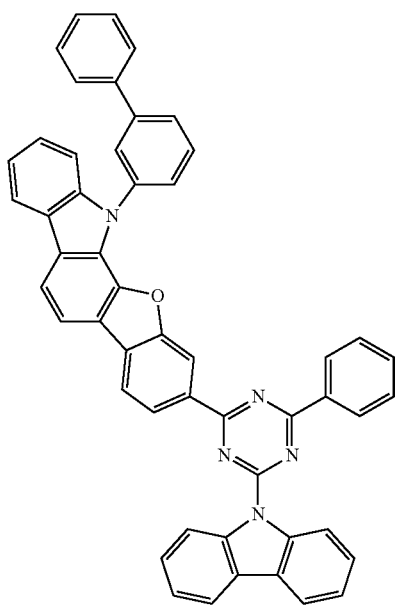
1B-3-48
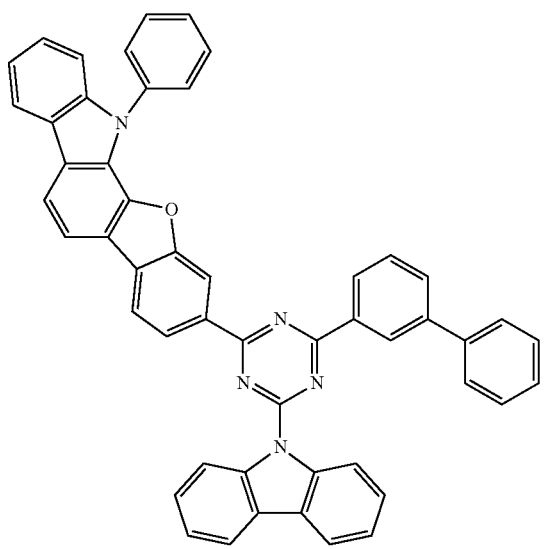

1B-3-49
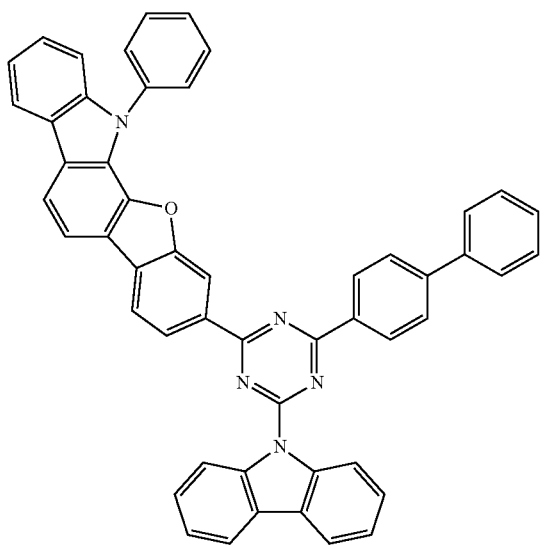
1B-3-50
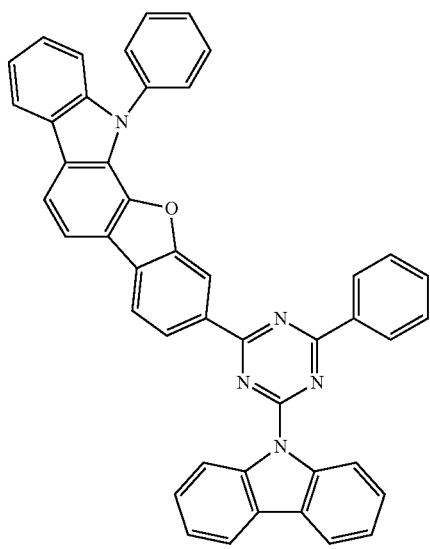
1B-3-51
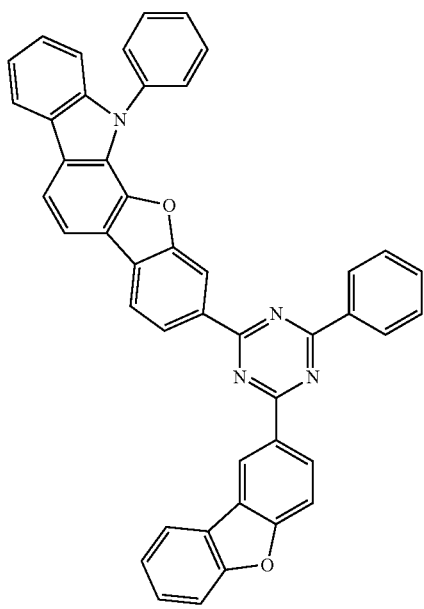
1B-3-52
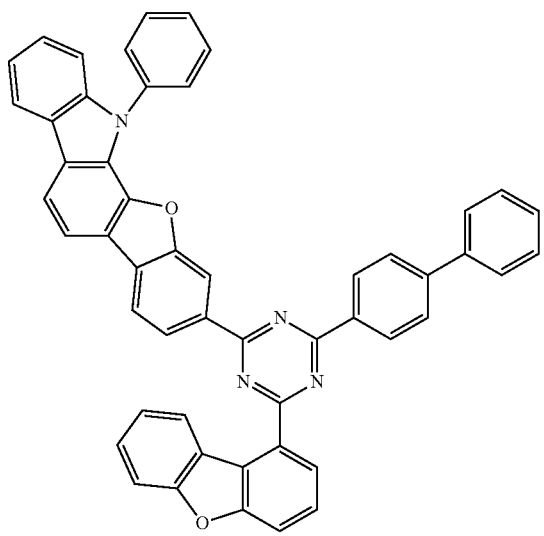

1B-3-53
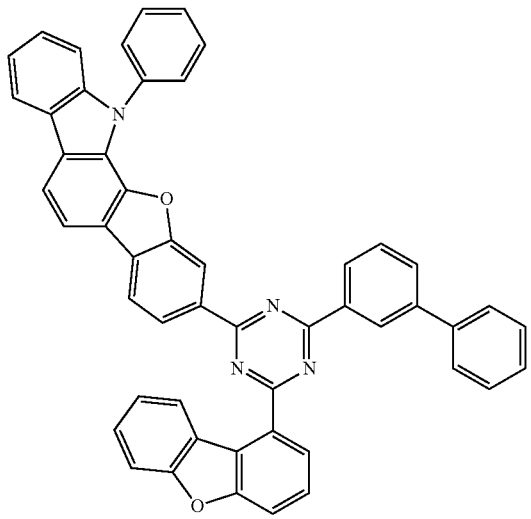
1B-3-54
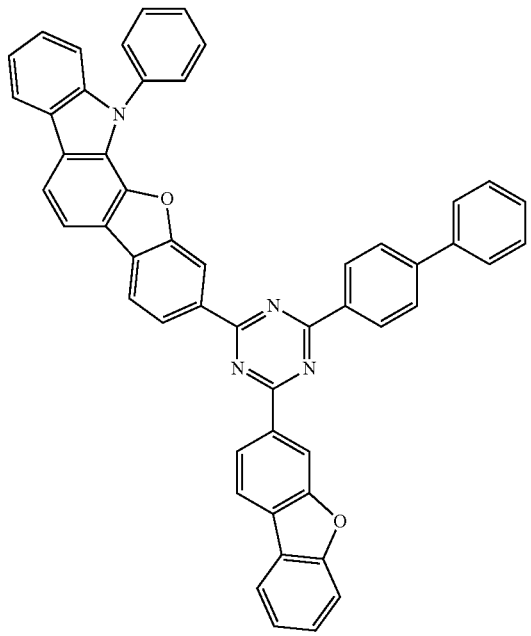
1B-3-55
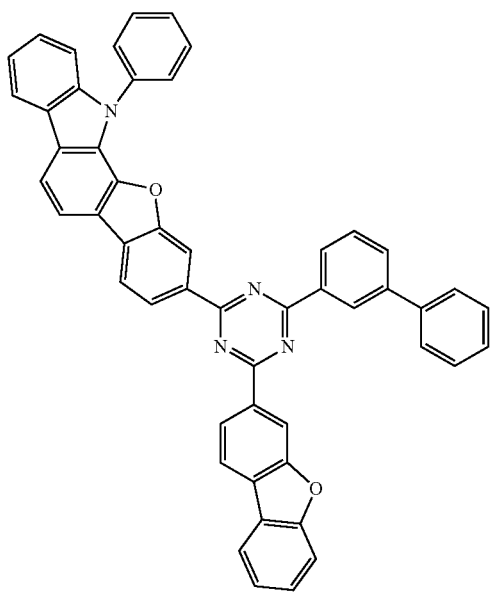
1B-3-56
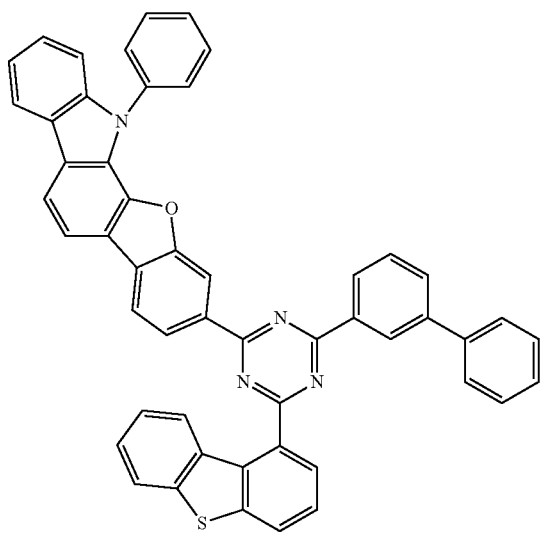

-continued
1B-3-57
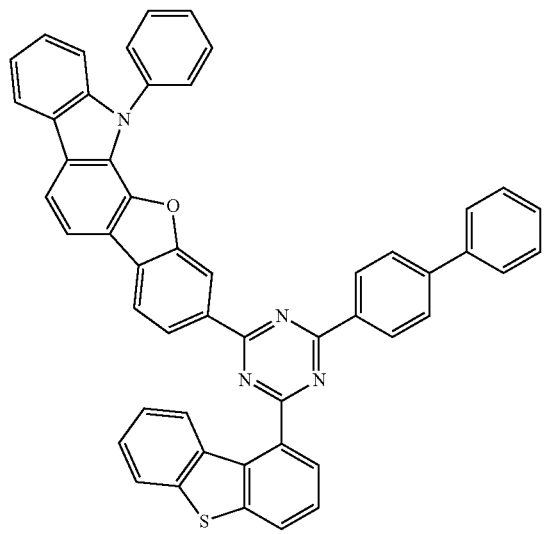
1B-3-58
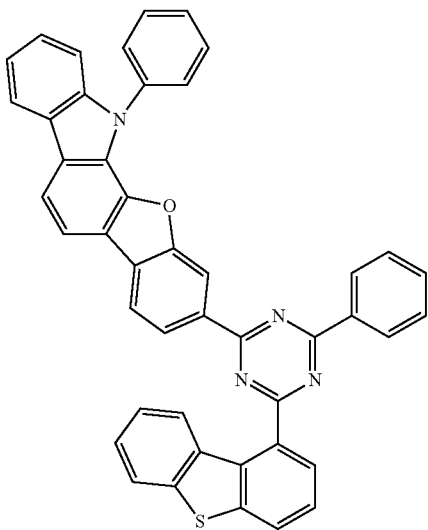
1B-3-59
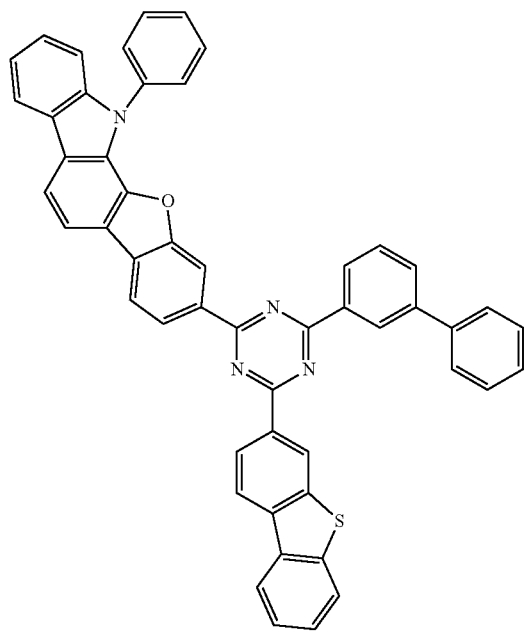
1B-3-60
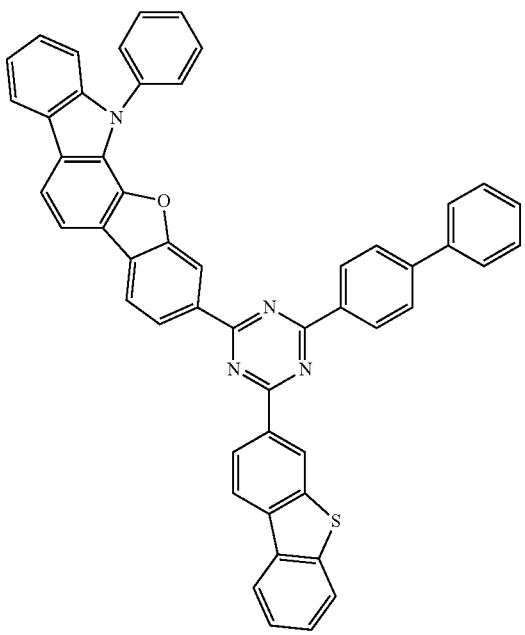

1B-3-61
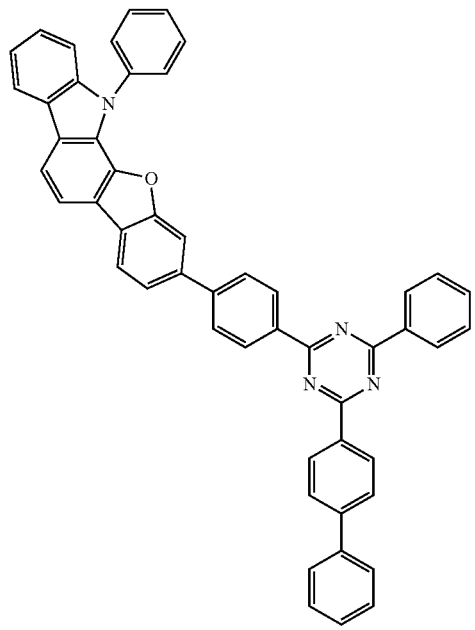
1B-3-62
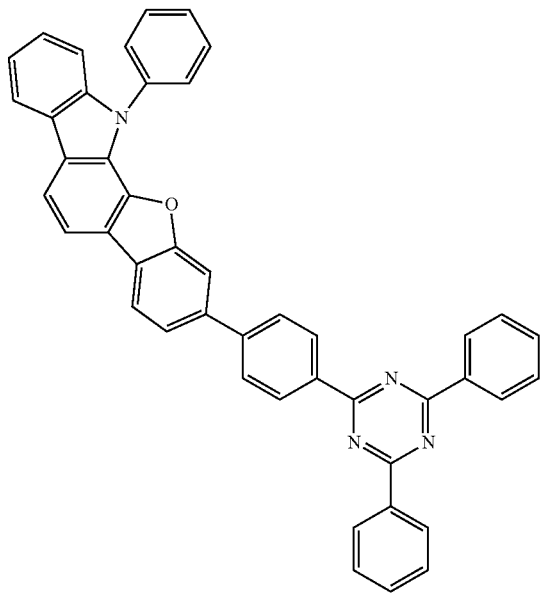
1B-3-63
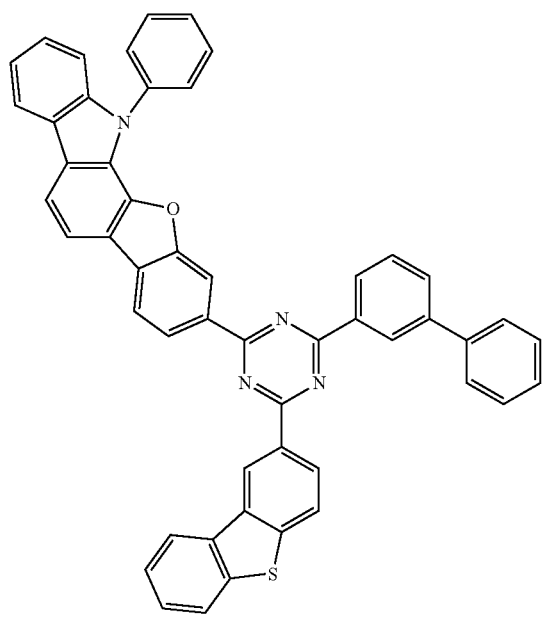
1B-3-64
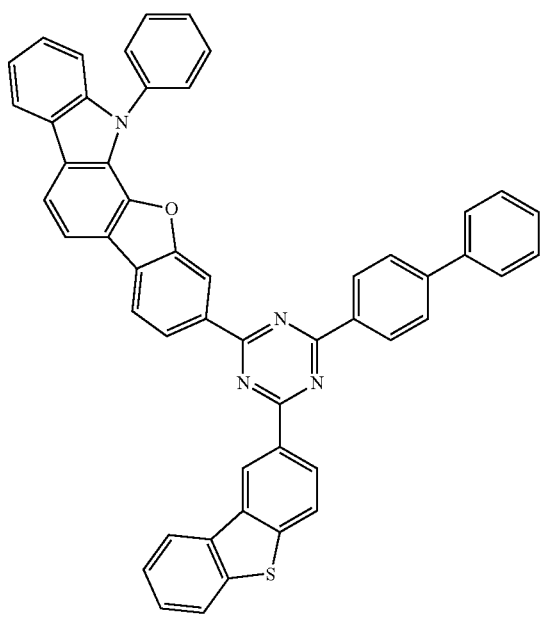

-continued
1B-3-65
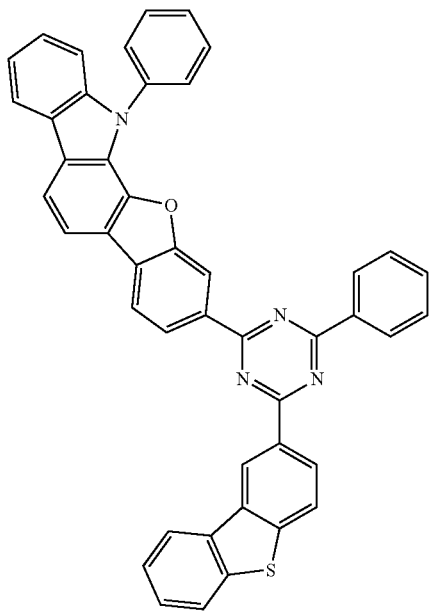
1B-3-66
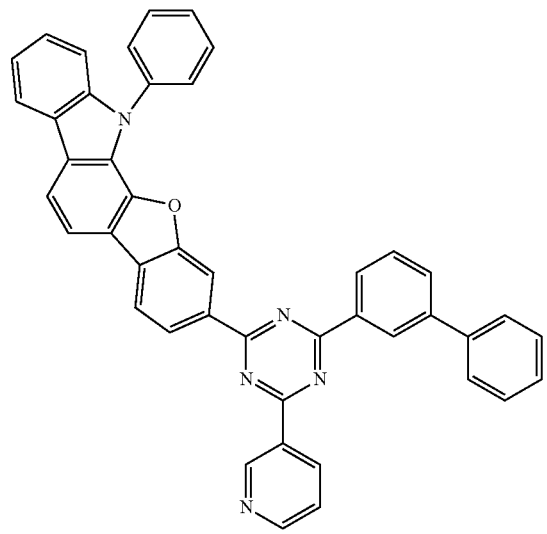
1B-3-67
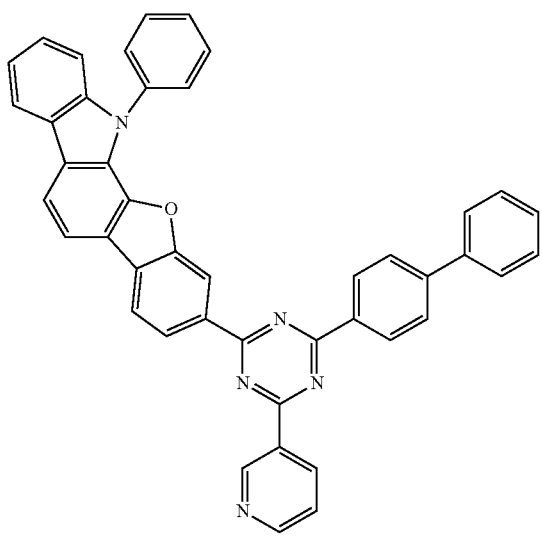
1B-3-68
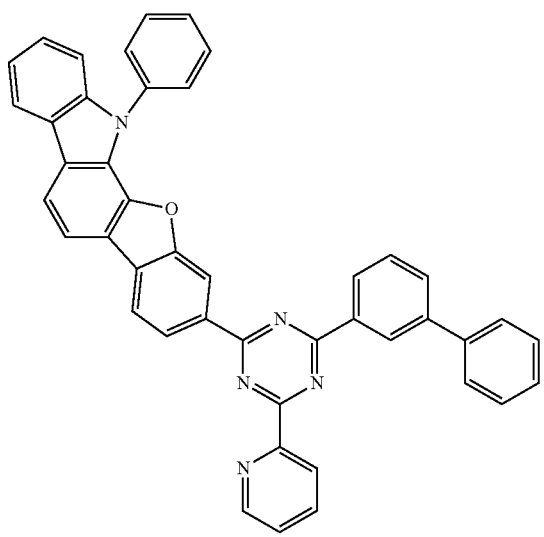

-continued
1B-3-69
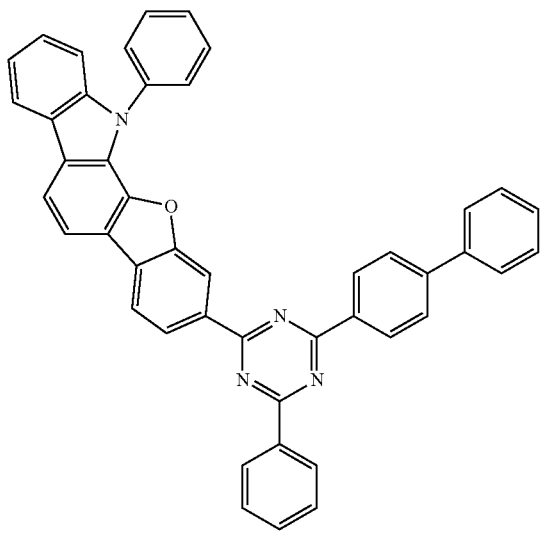
1B-3-70
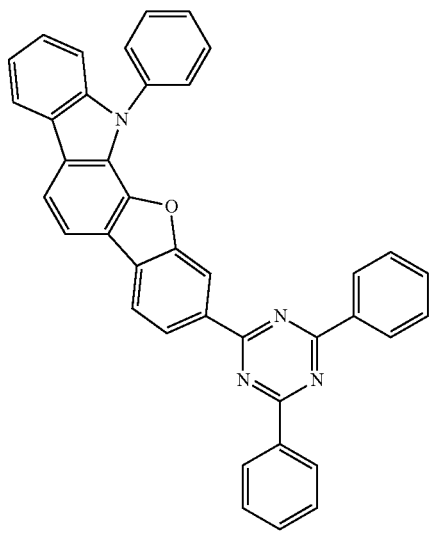
1B-3-71
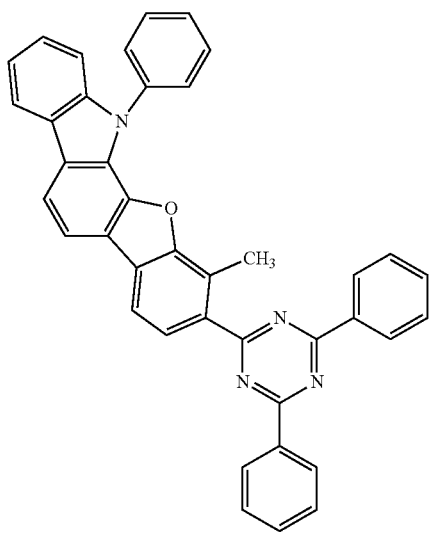
1B-3-72
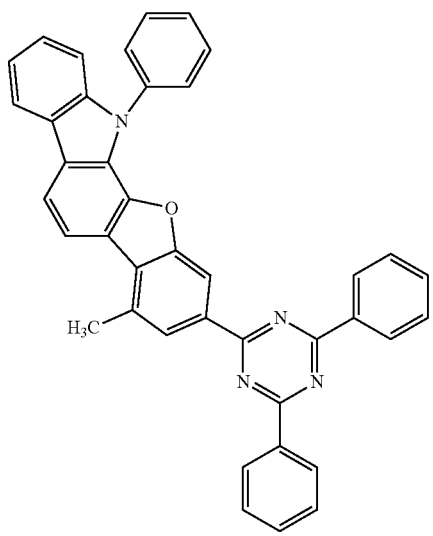
1B-3-73
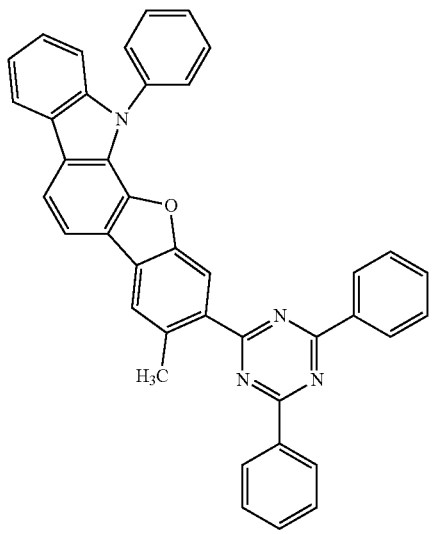
1B-3-74
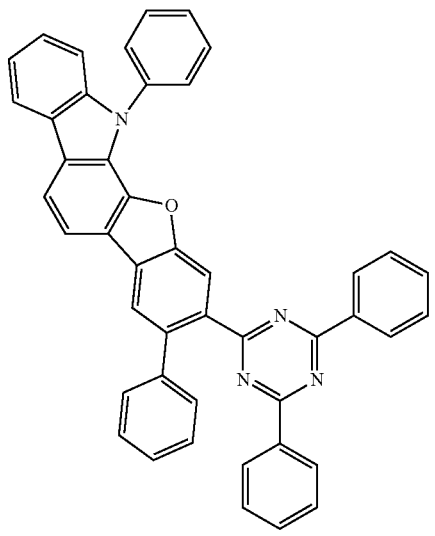

-continued
1B-3-75
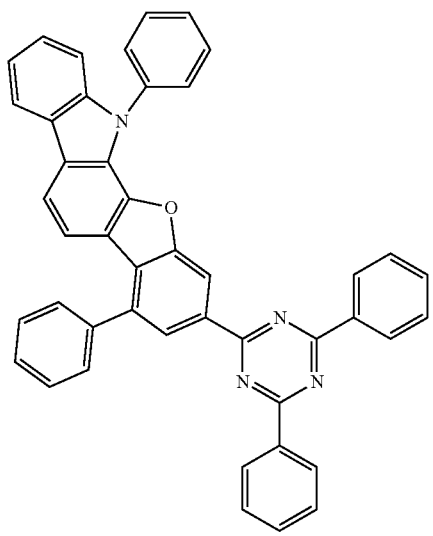
1B-3-76
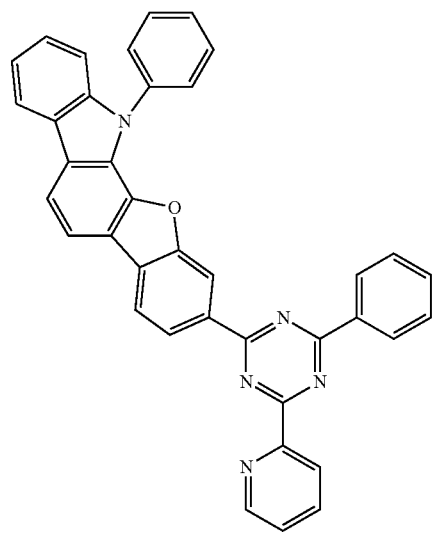
1B-3-77
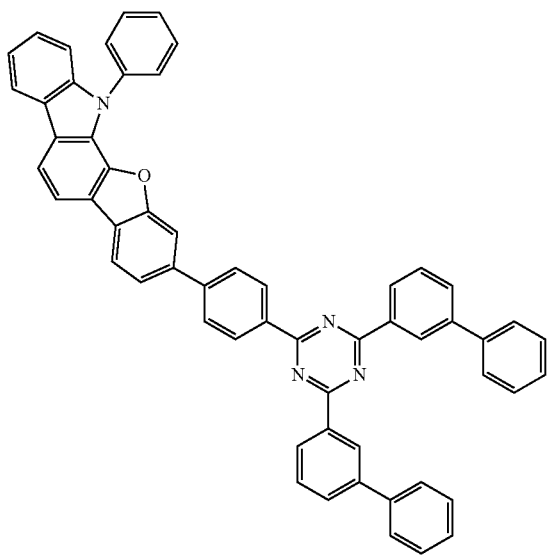
1B-3-78
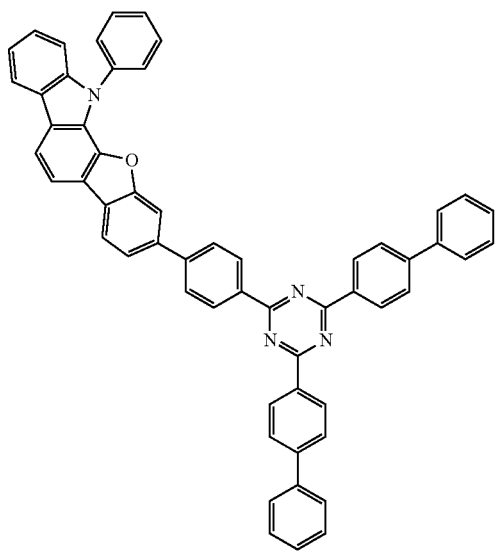

1B-3-79
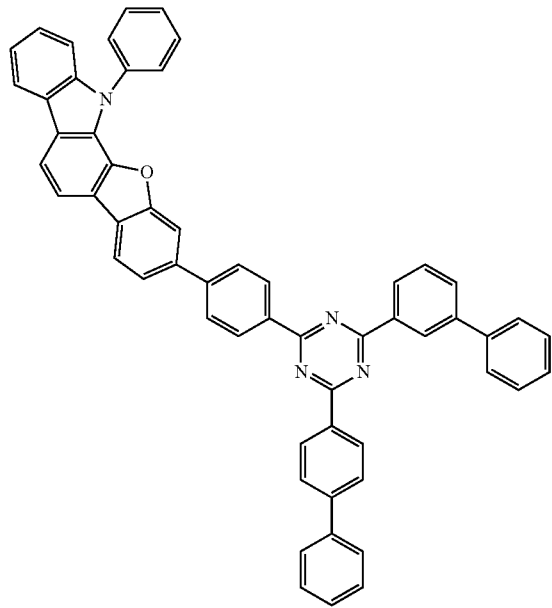
1B-3-80
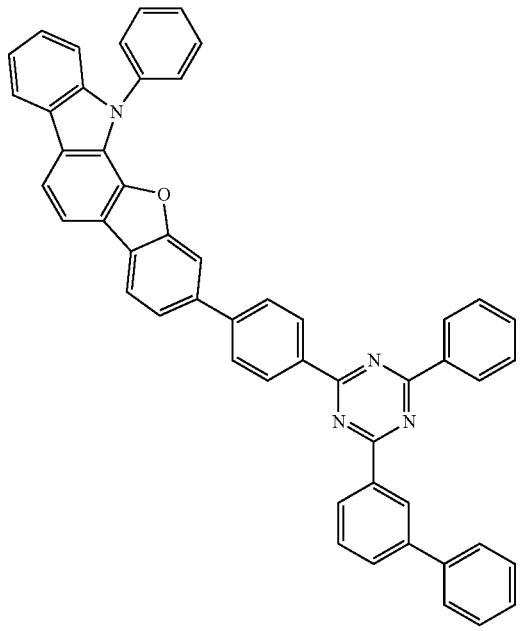
1B-3-81
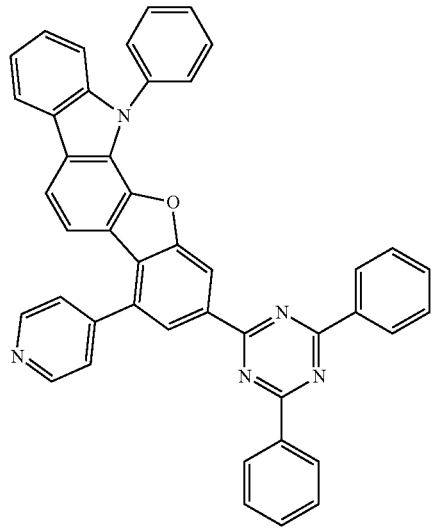
1B-3-82
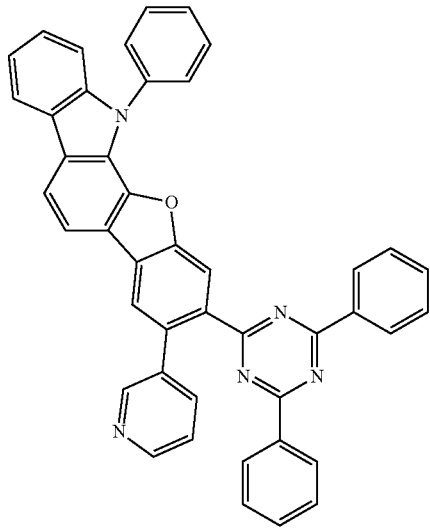

-continued
1B-3-83
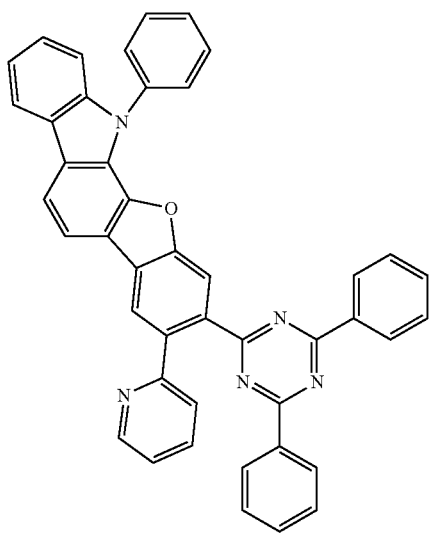
1B-4-1
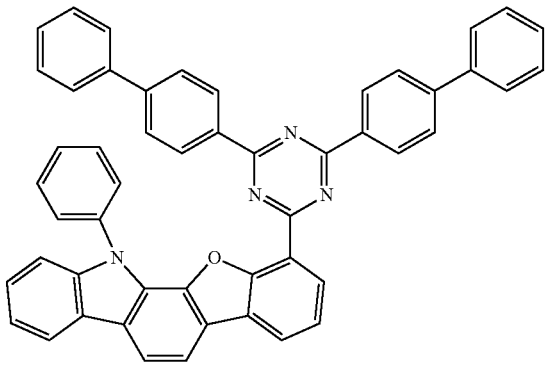
1B-4-2
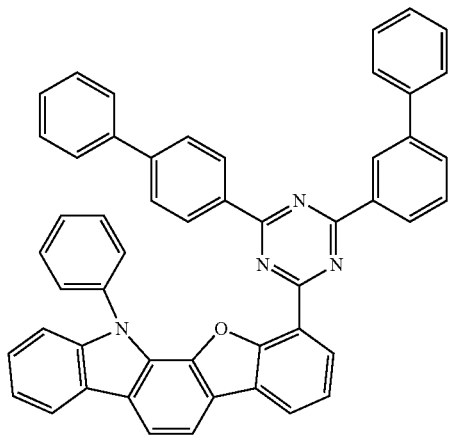
1B-4-3
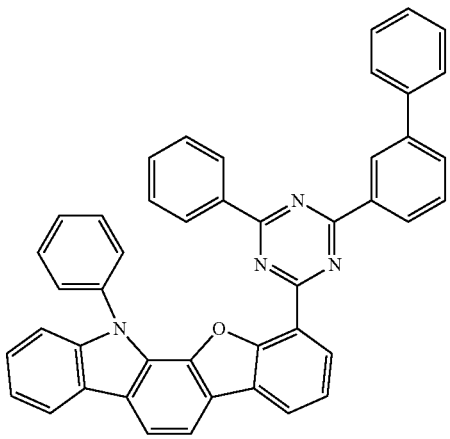
1B-4-4
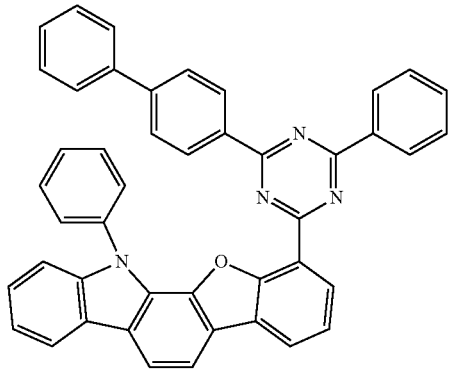
1B-4-5
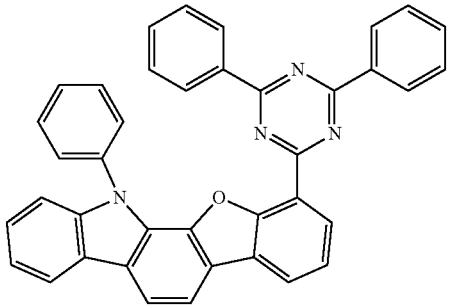

-continued
1B-4-6
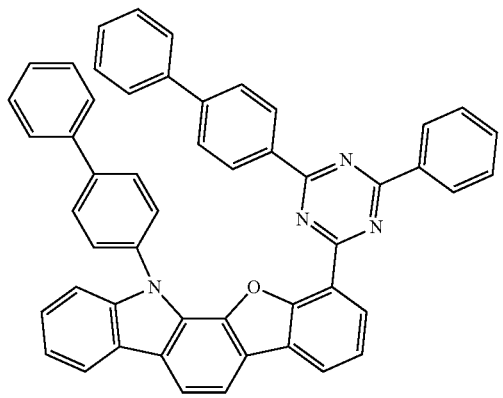
1B-4-7
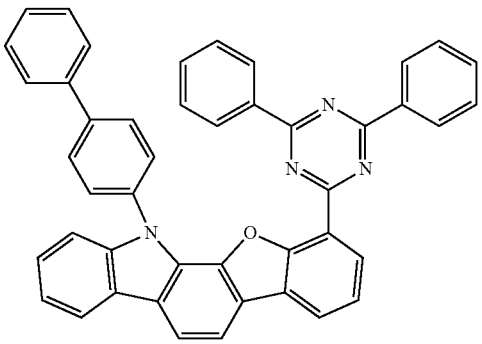
1B-4-8
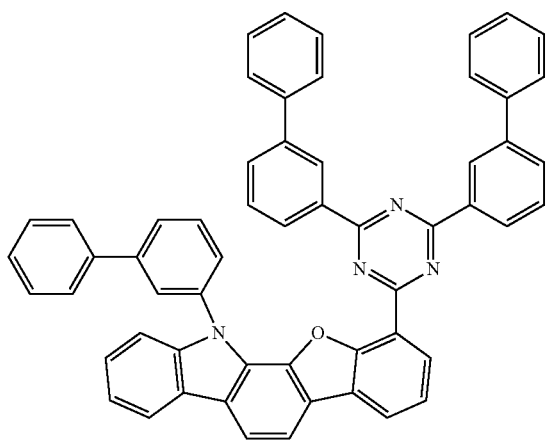
1B-4-9
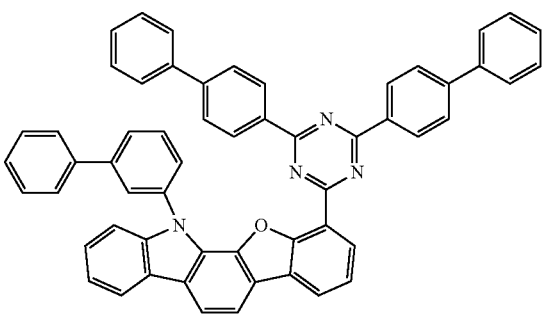
1B-4-10
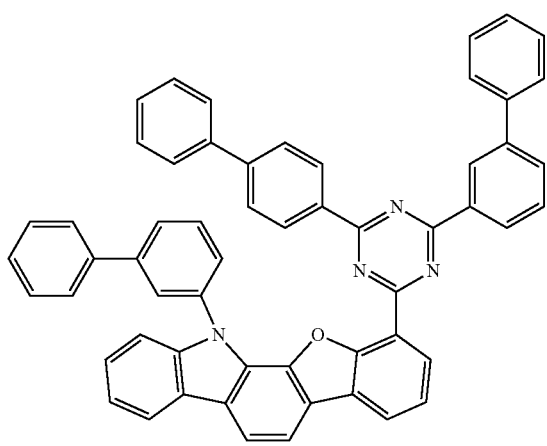
1B-4-11
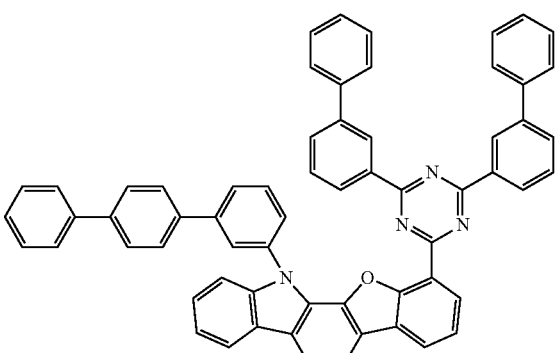

-continued
1B-4-12
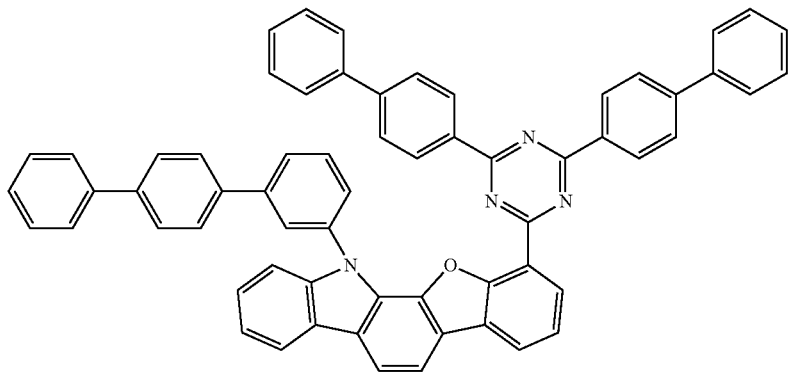
1B-4-13
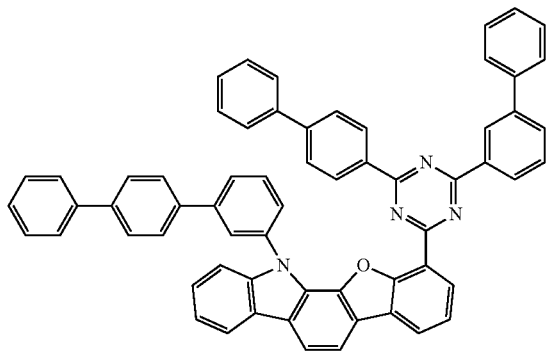
1B-4-14
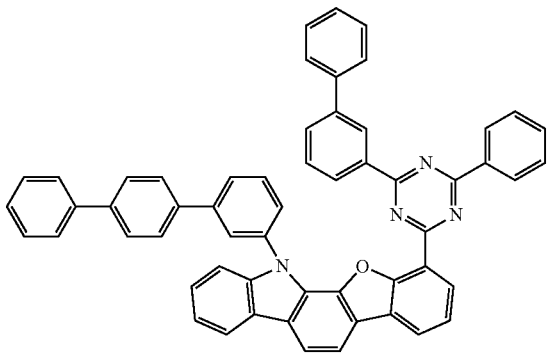
1B-4-15
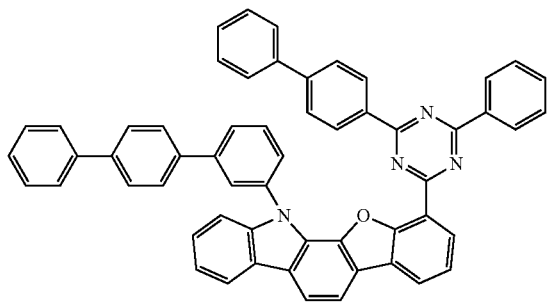
1B-4-16
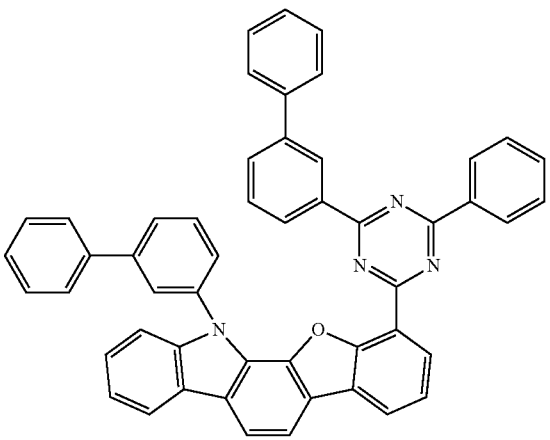
1B-4-17
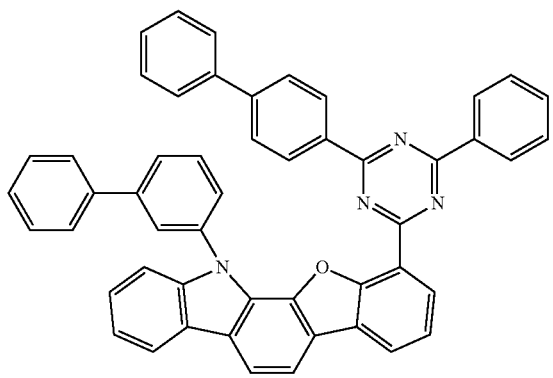
1B-4-18
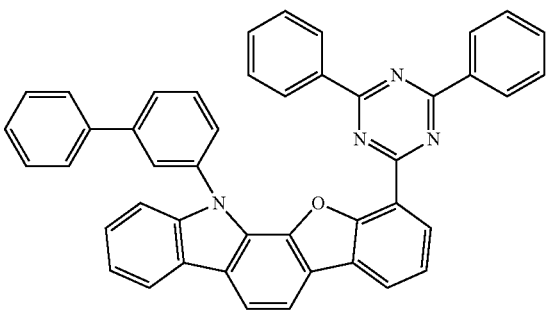

-continued
1B-4-19
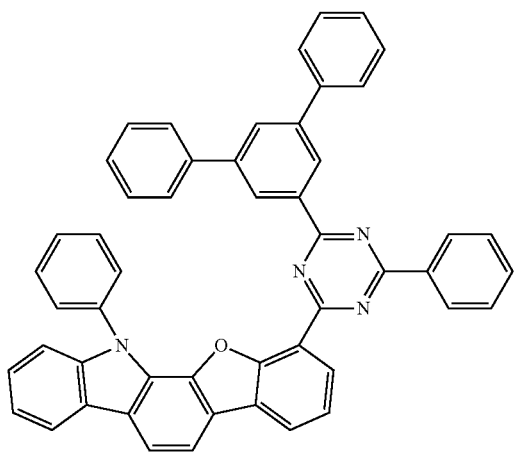
1B-4-20
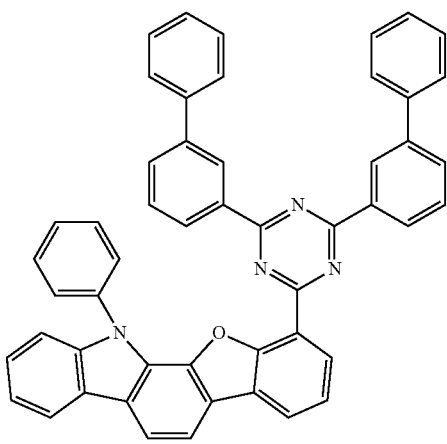
1B-4-21
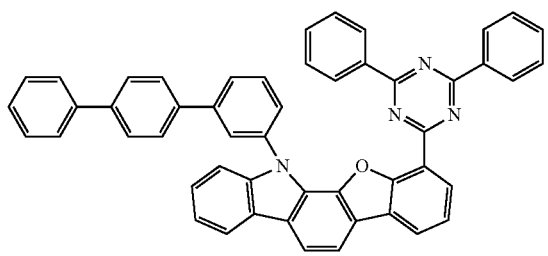
1B-4-22
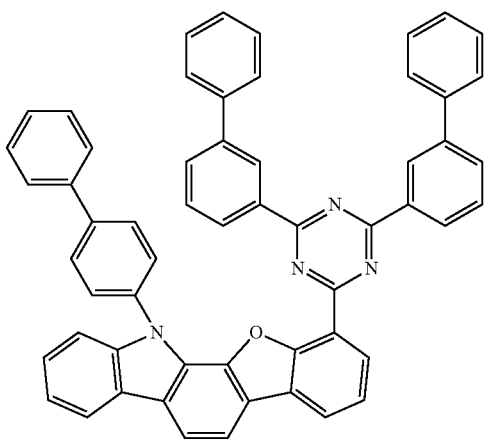
1B-4-23
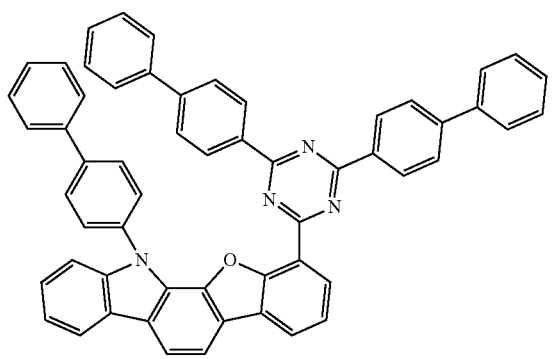
1B-4-24
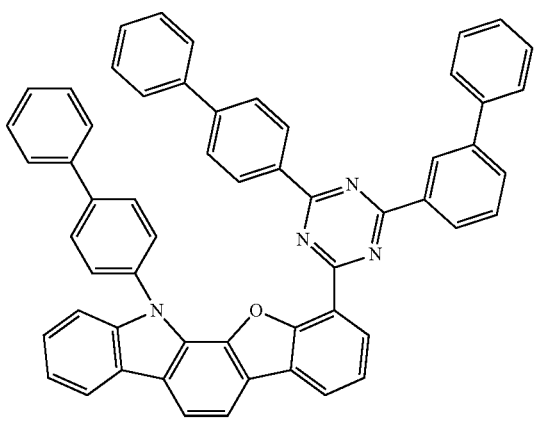

-continued
1B-4-25
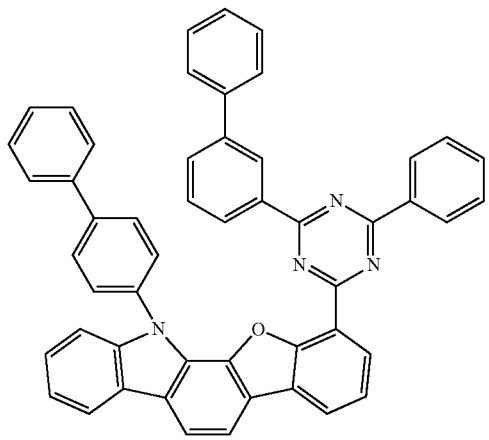
1B-4-26
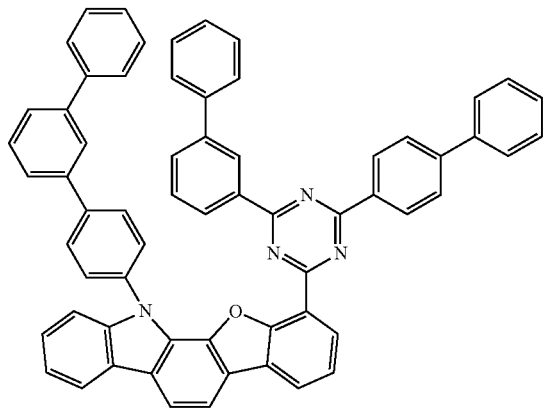
1B-4-27
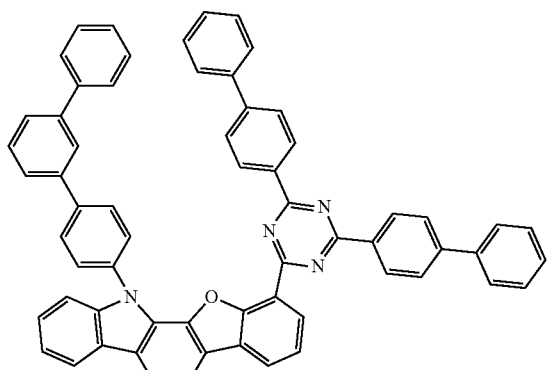
1B-4-28
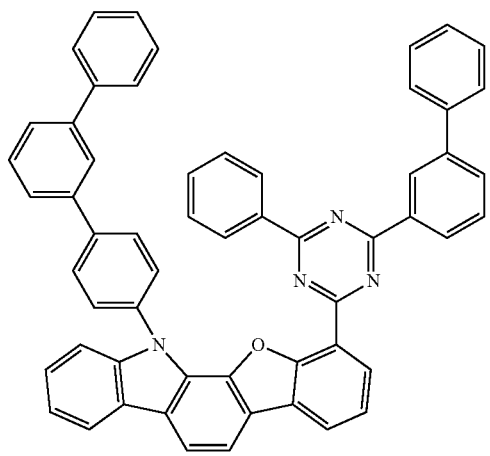
1B-4-29
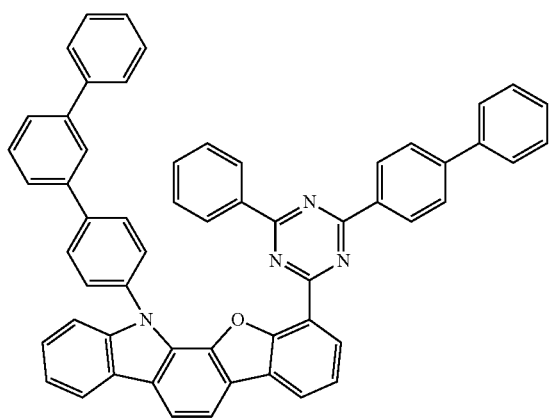
1B-4-30
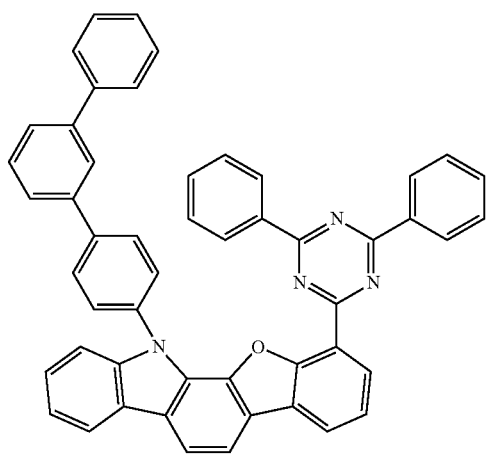

-continued
1B-4-31
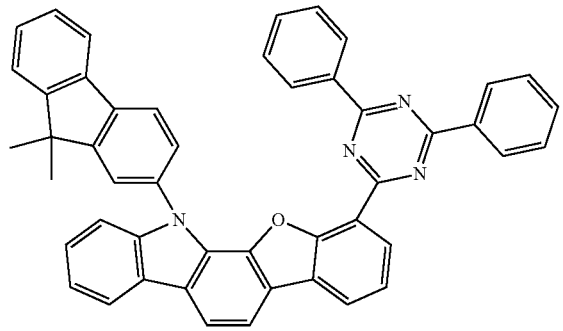
1B-4-32
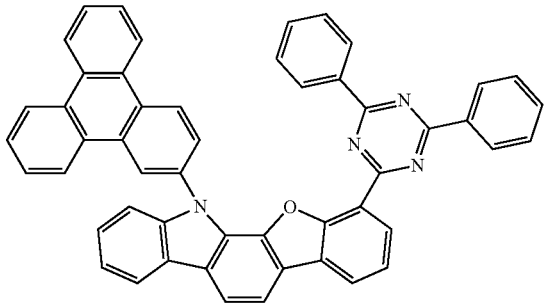
1B-4-33
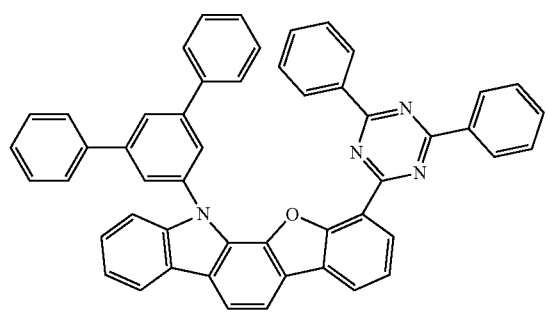
1B-4-34
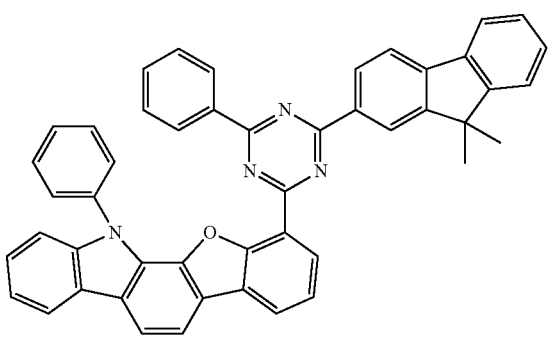
1B-4-35
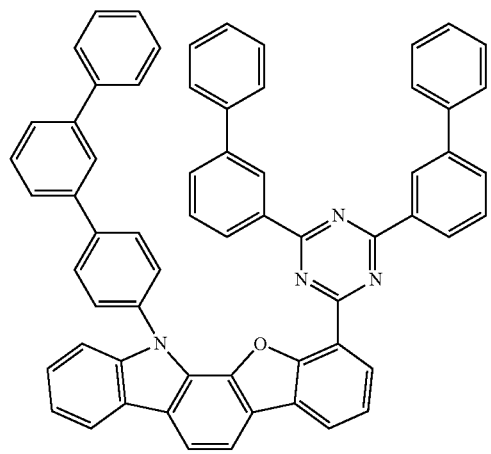
1B-4-36
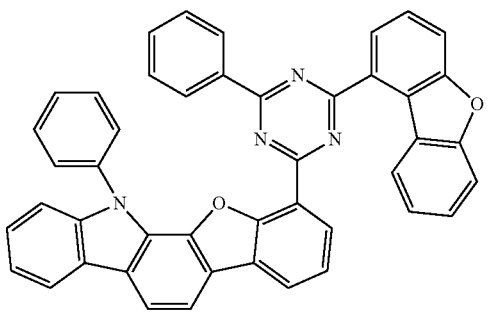
1B-4-37
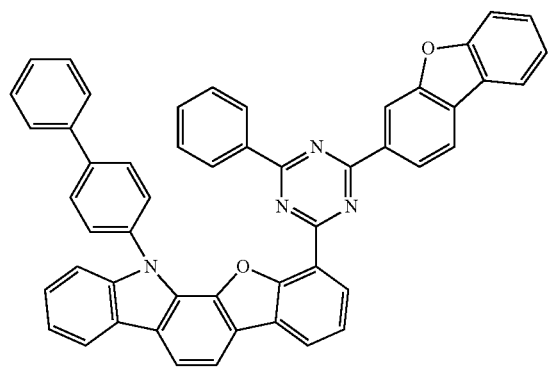
1B-4-38
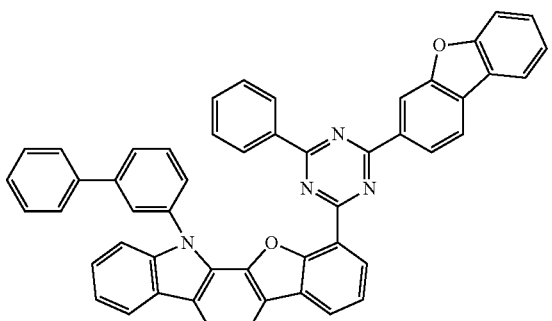

-continued
1B-4-39
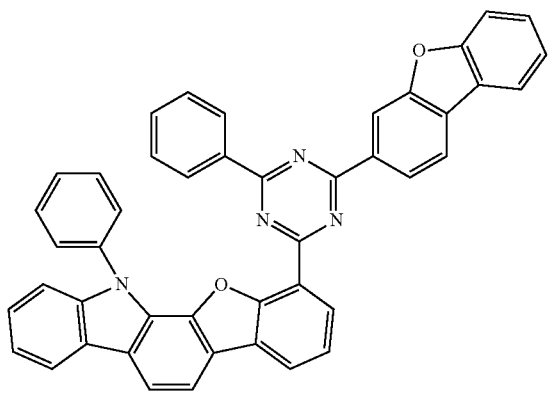
1B-4-40
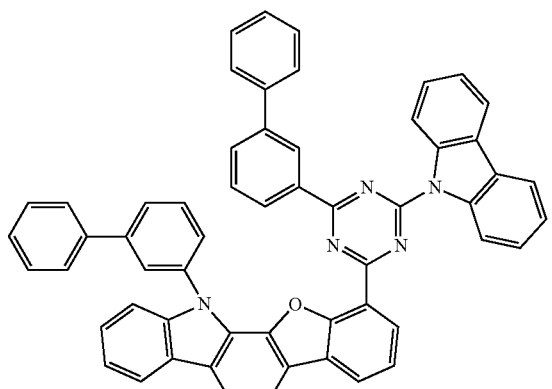
1B-4-41
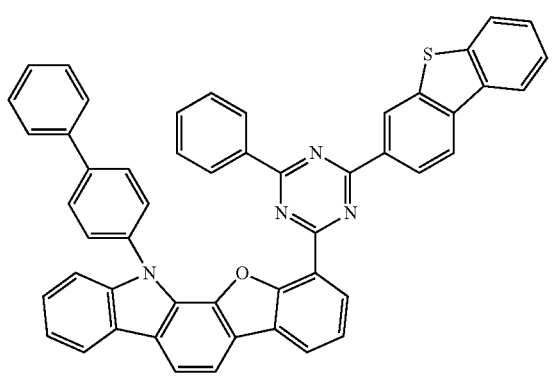
1B-4-42
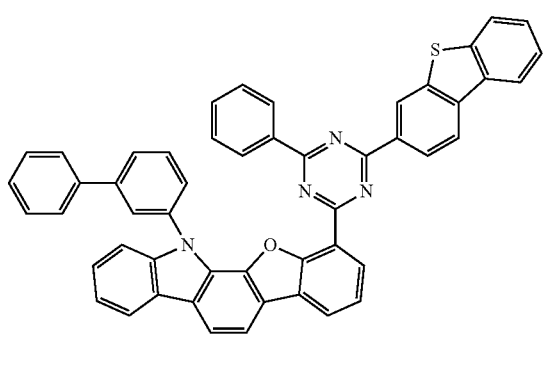
1B-4-43
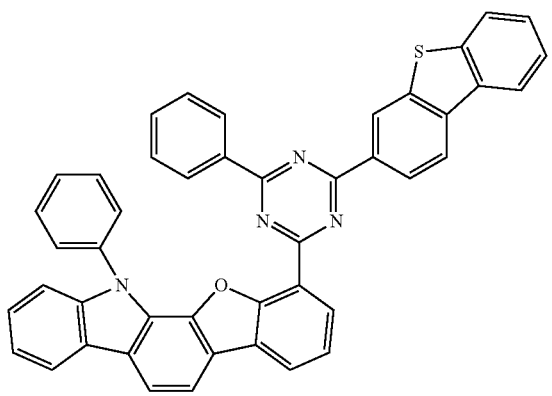
1B-4-44
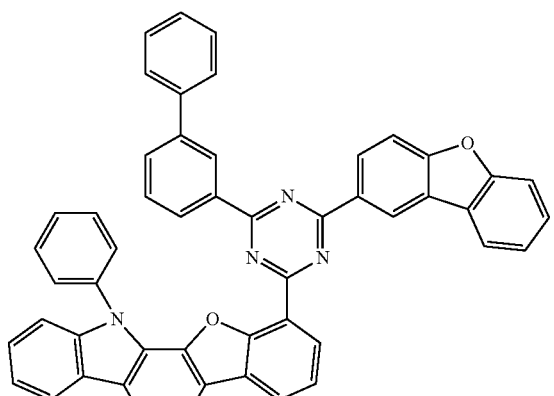
1B-4-45
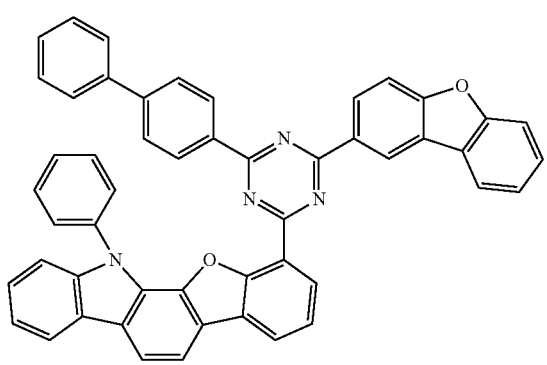
1B-4-46
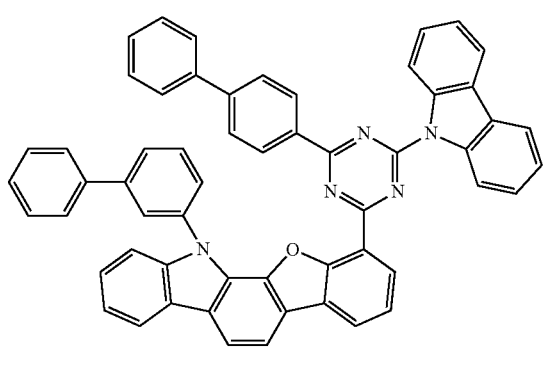

-continued
1B-4-47
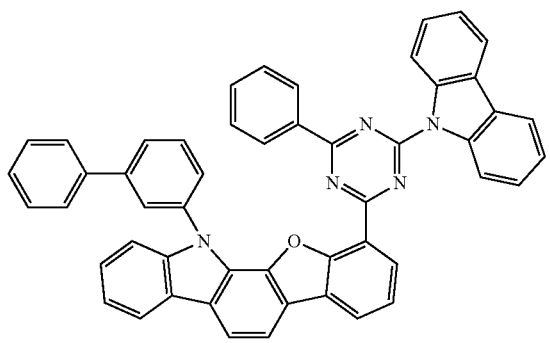
1B-4-48
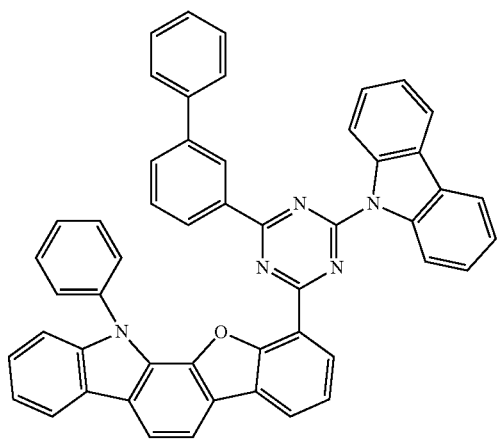
1B-4-49
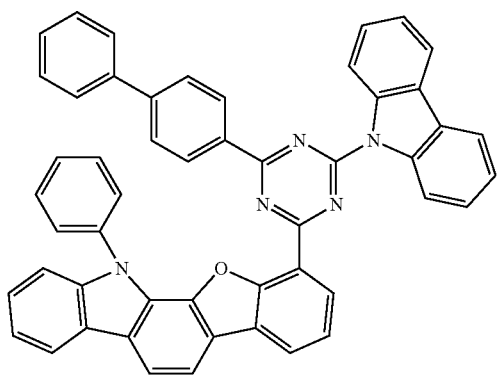
1B-4-50
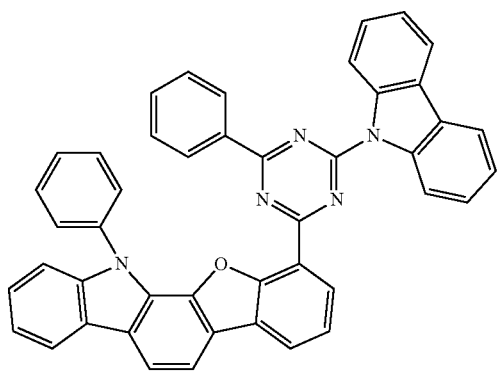
1B-4-51
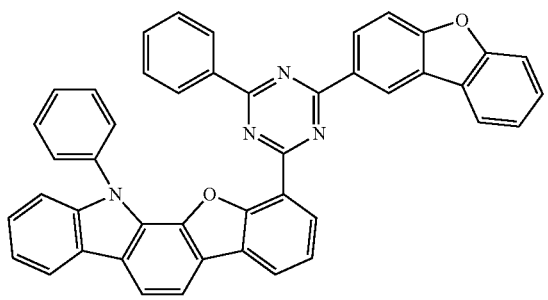
1B-4-52
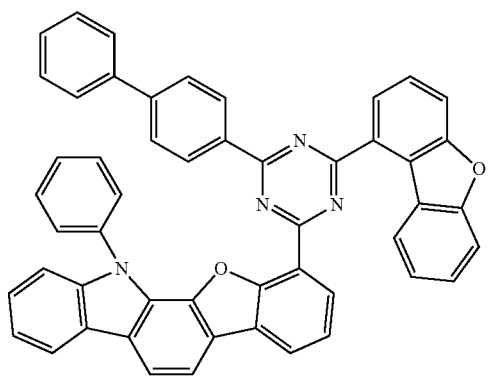

-continued
1B-4-53
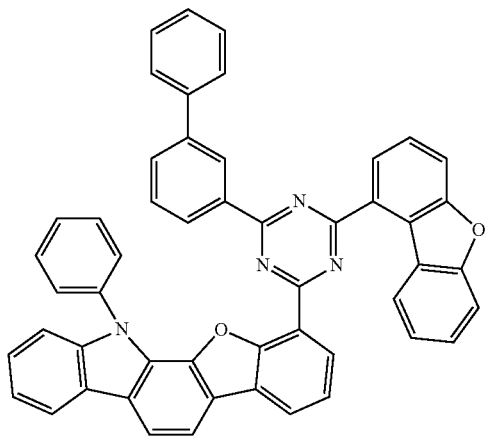
1B-4-54
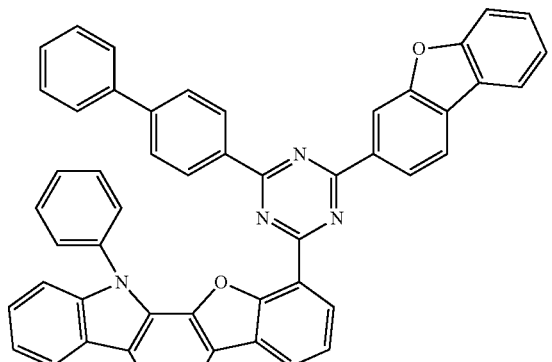
1B-4-55
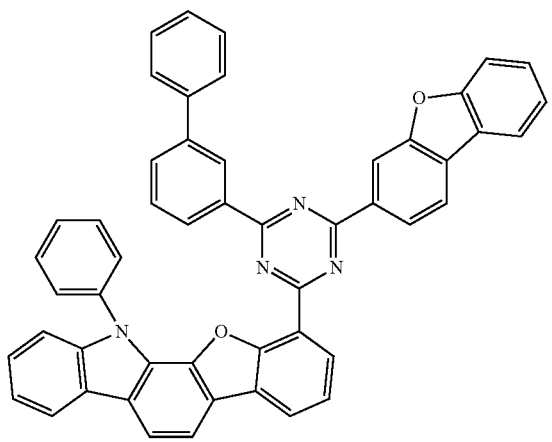
1B-4-56
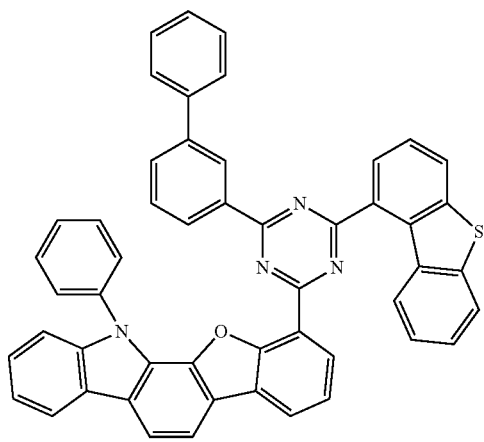
1B-4-57
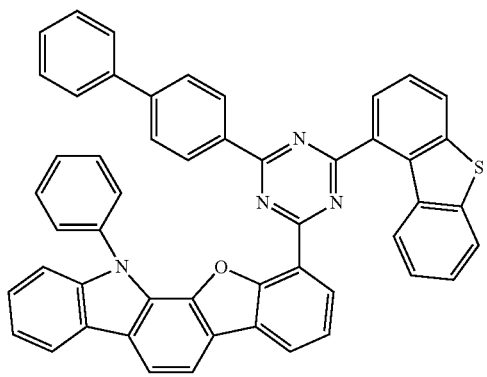
1B-4-58
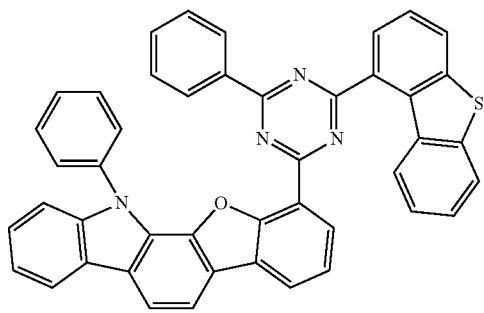

-continued
1B-4-59
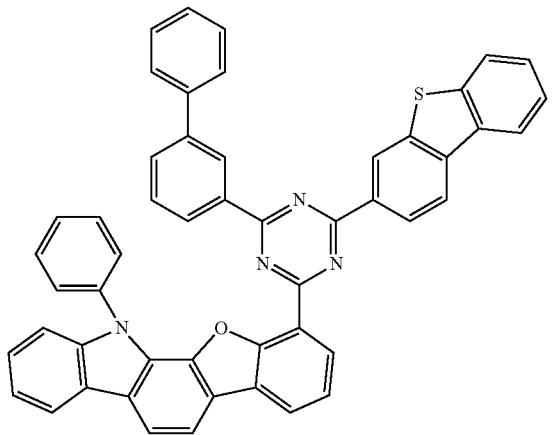
1B-4-60
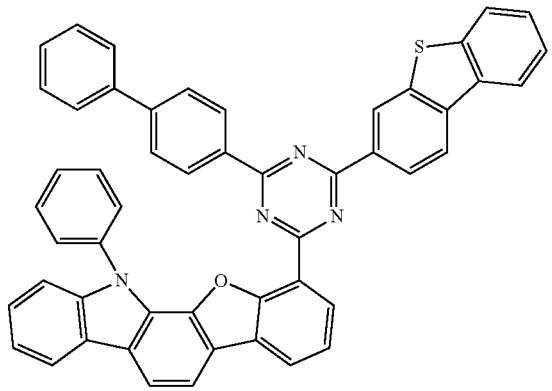
1B-4-61
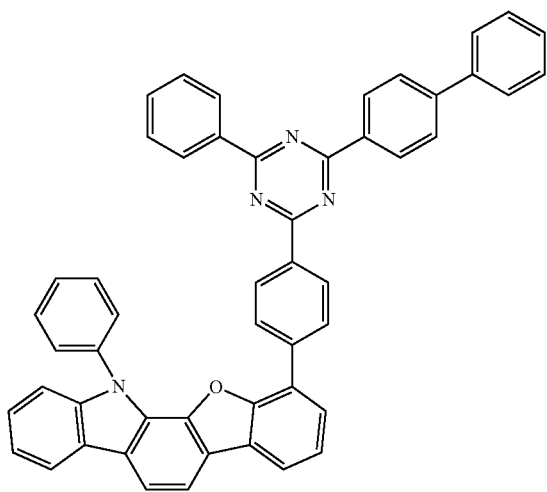
1B-4-62
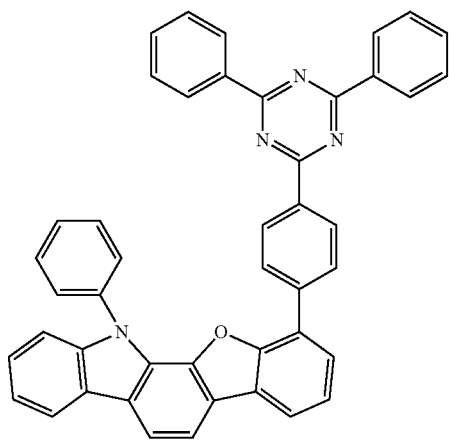
1B-4-63
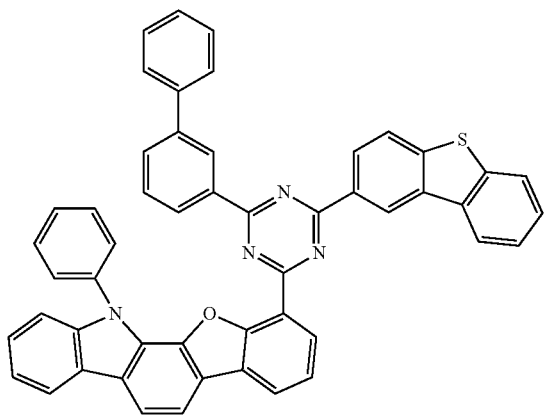
1B-4-64
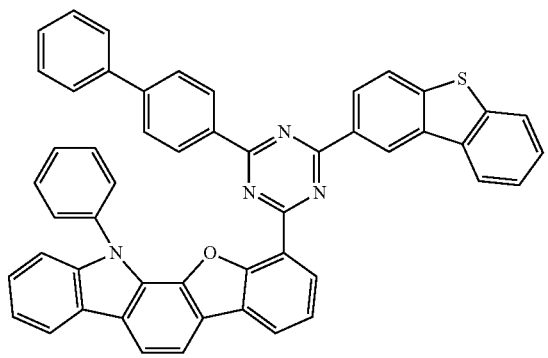

-continued
1B-4-65
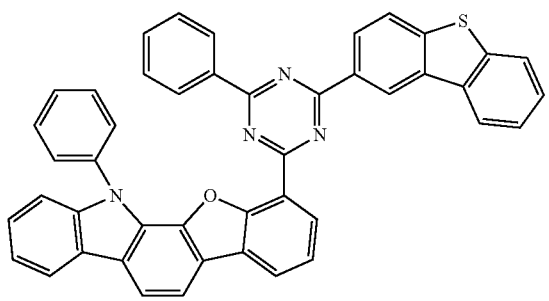
1B-4-66
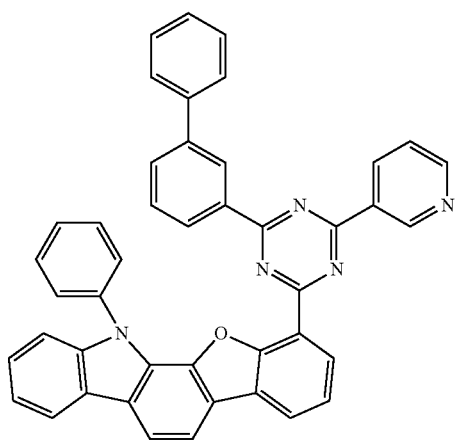
1B-4-67
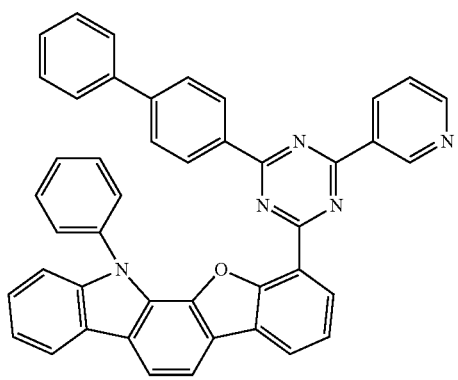
1B-4-68
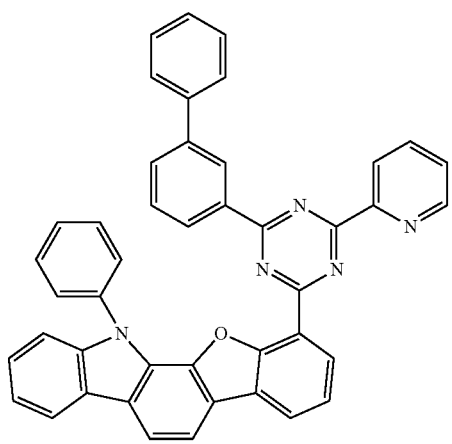
1B-4-69
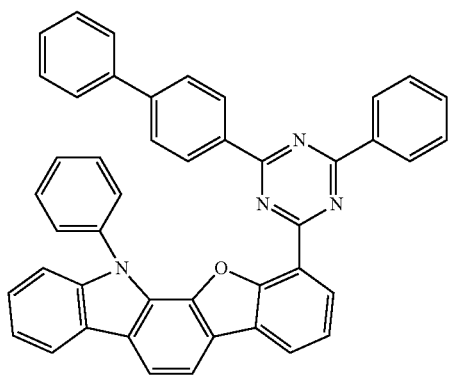
1B-4-70
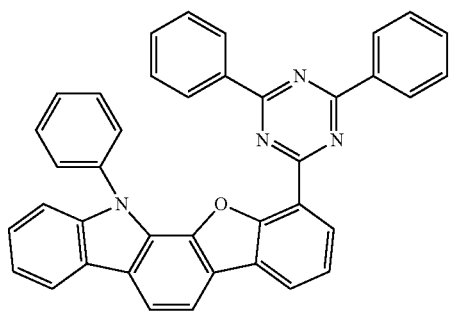
1B-4-71
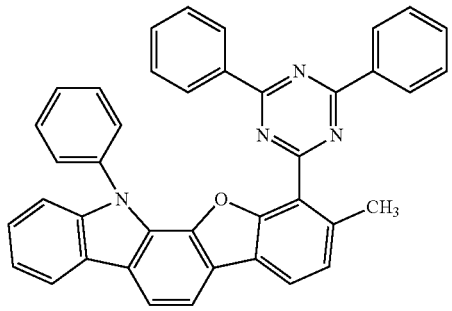
1B-4-72
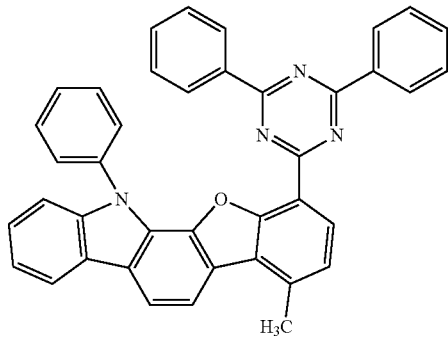

-continued
1B-4-73
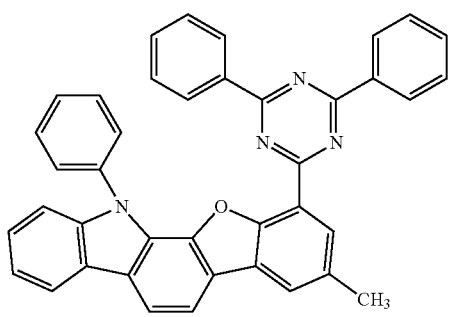
1B-4-74
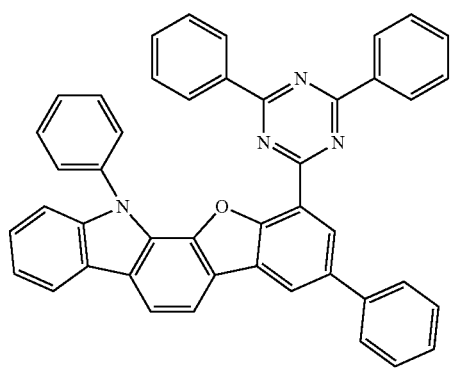
1B-4-75
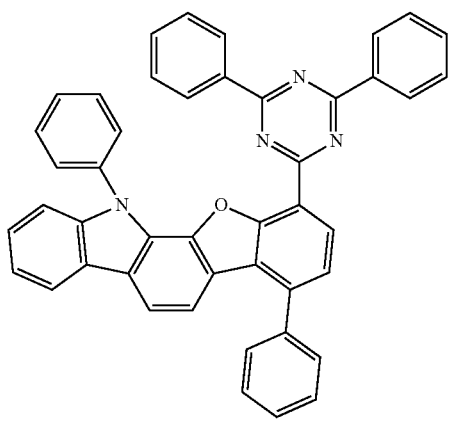
1B-4-76
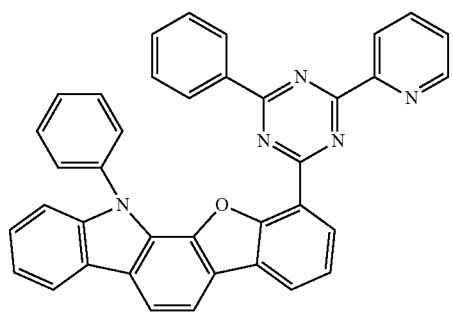
1B-4-77
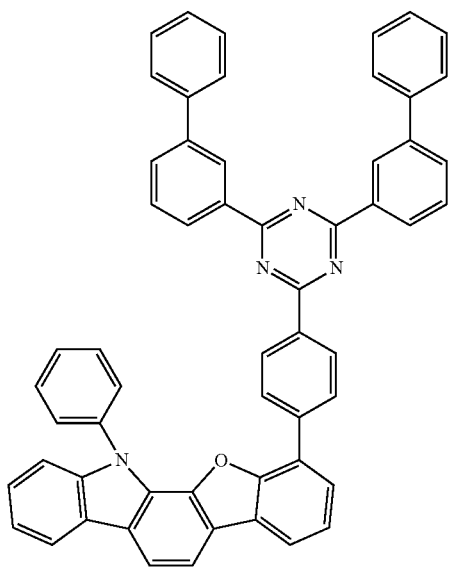
1B-4-78
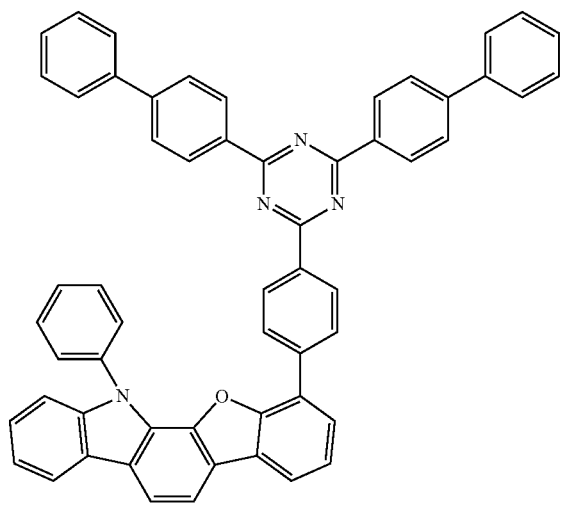

-continued
1B-4-79
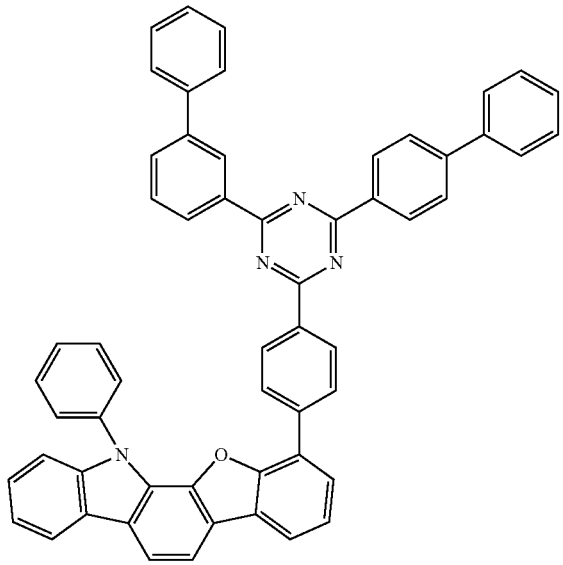
1B-4-80
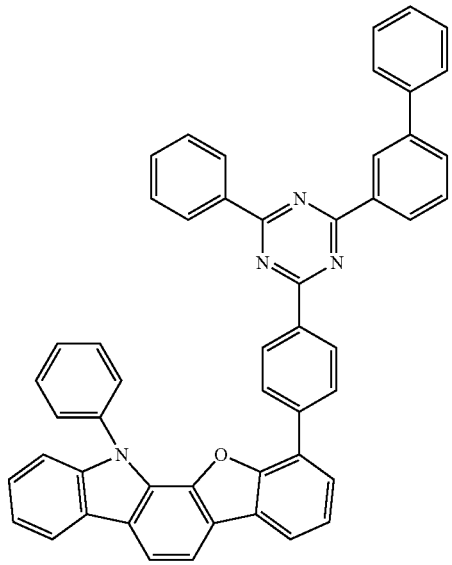
1B-4-81
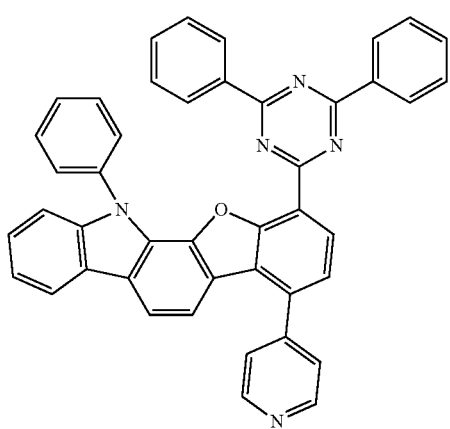
1B-4-82
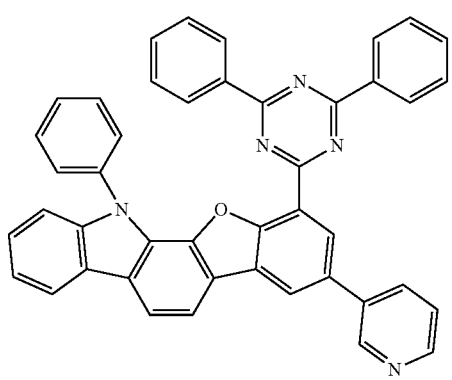
1B-4-83
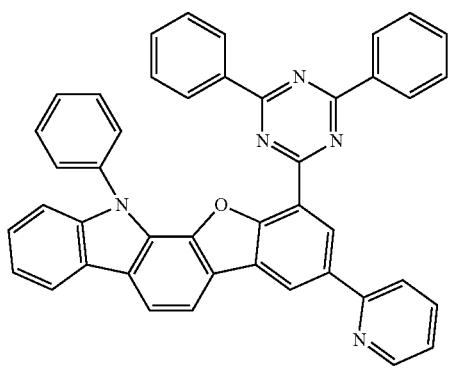
1C-1-1
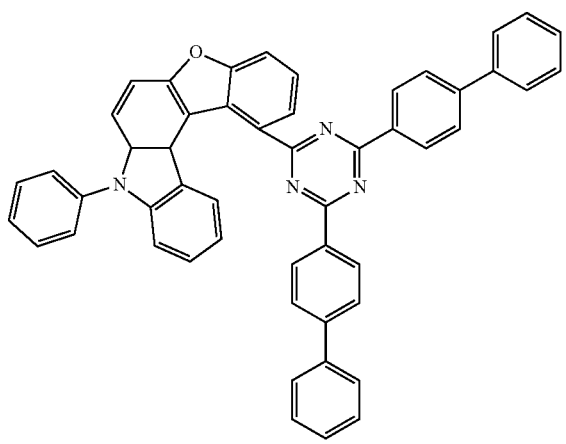

-continued
1C-1-2
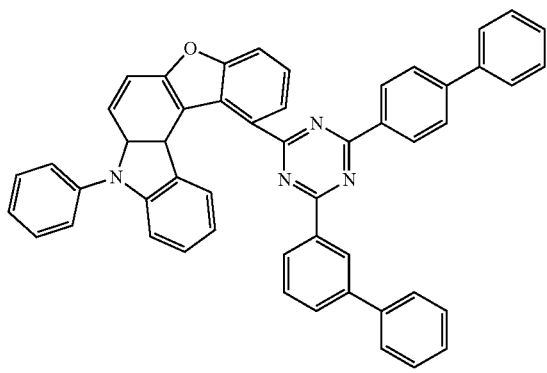
1C-1-3
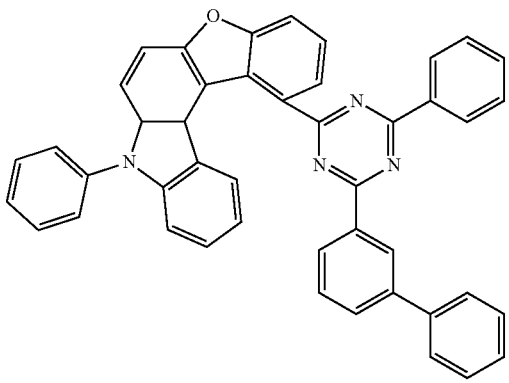
1C-1-4
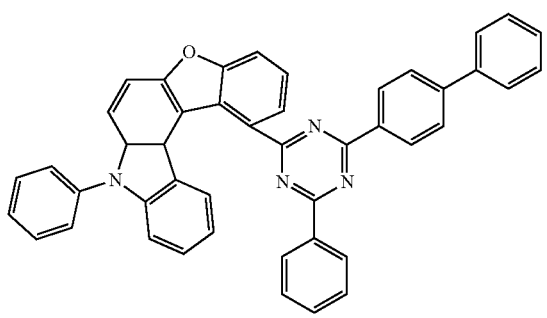
1C-1-5
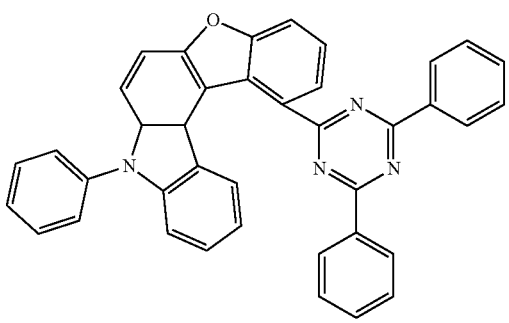
1C-1-6
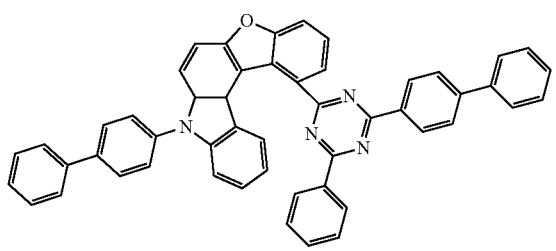
1C-1-7
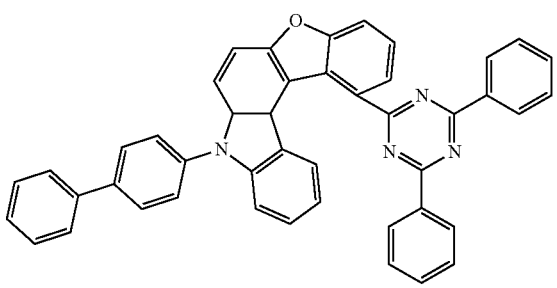
1C-1-8
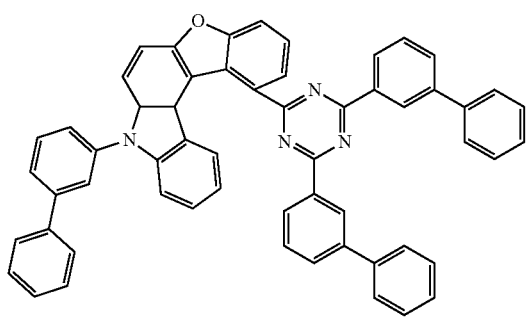
1C-1-9
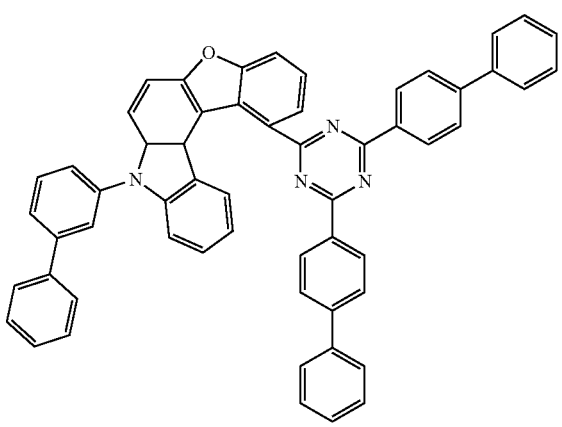

-continued
1C-1-10
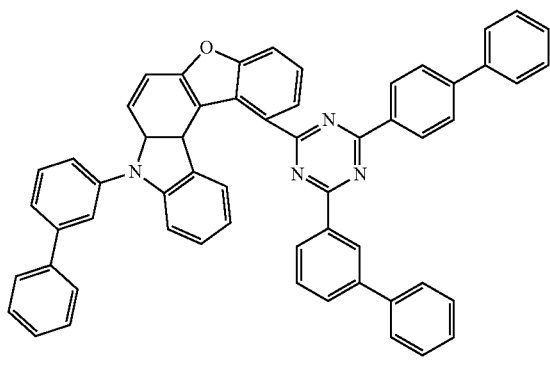
1C-1-11
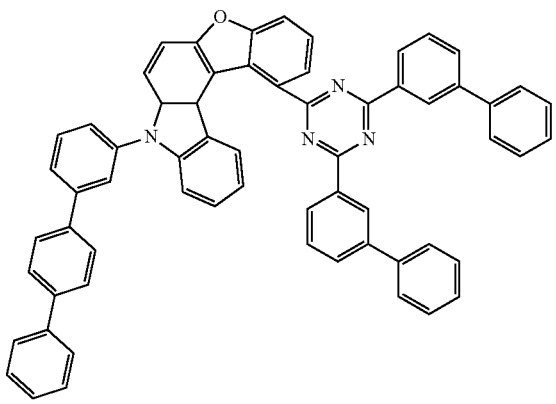
1C-1-12
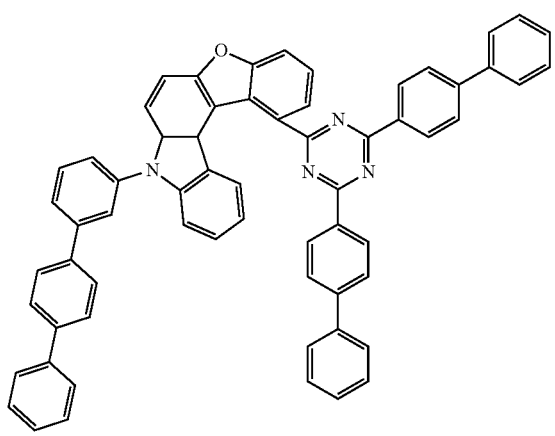
1C-1-13
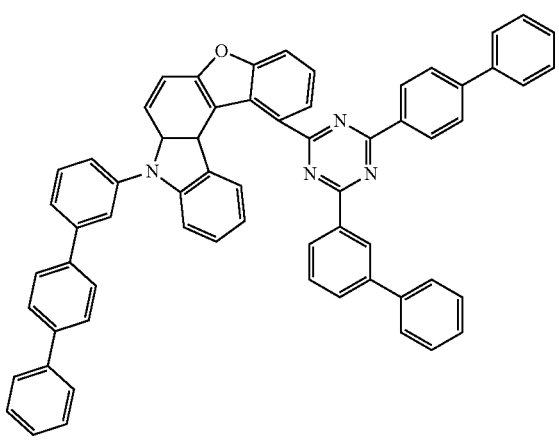
1C-1-14
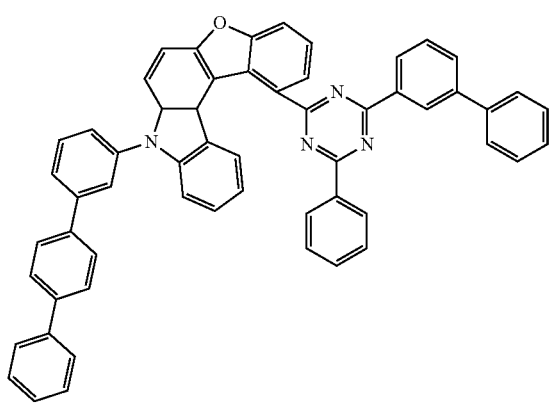
1C-1-15
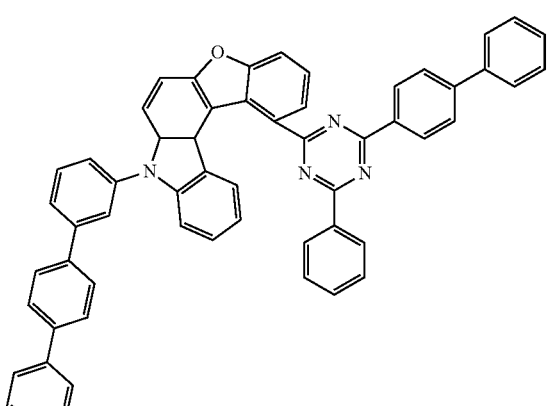

-continued
1C-1-16
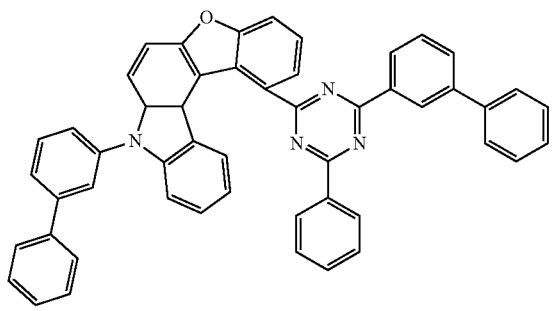
1C-1-17
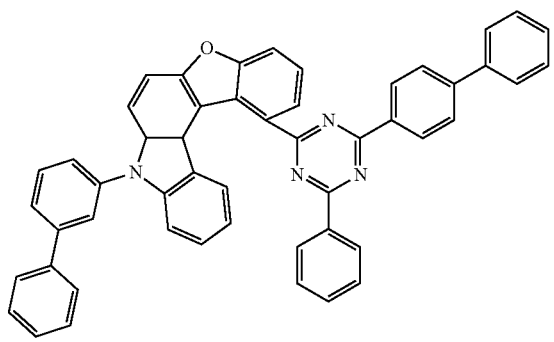
1C-1-18
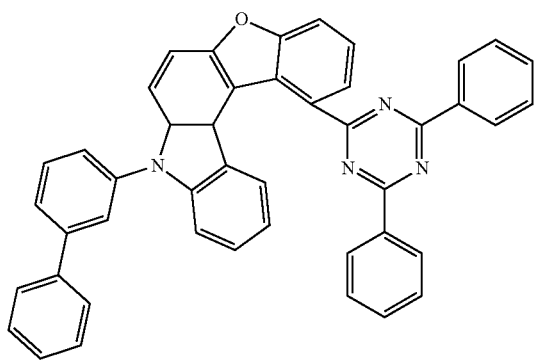
1C-1-19
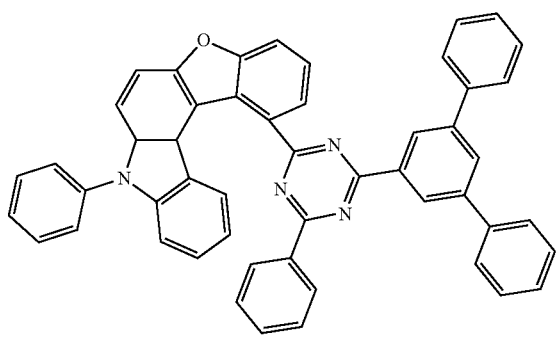
1C-1-20
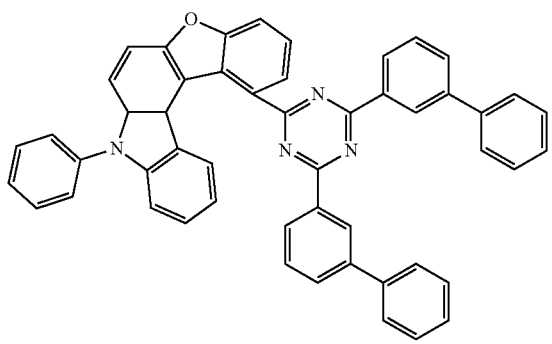
1C-1-21
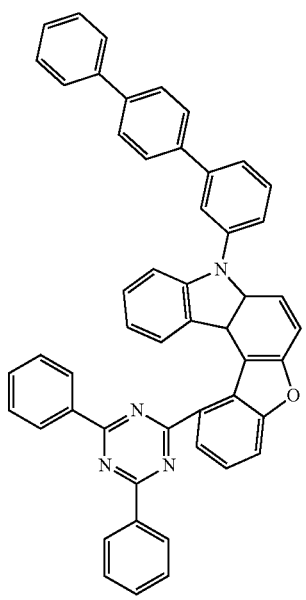

281 282
-continued
1C-1-22
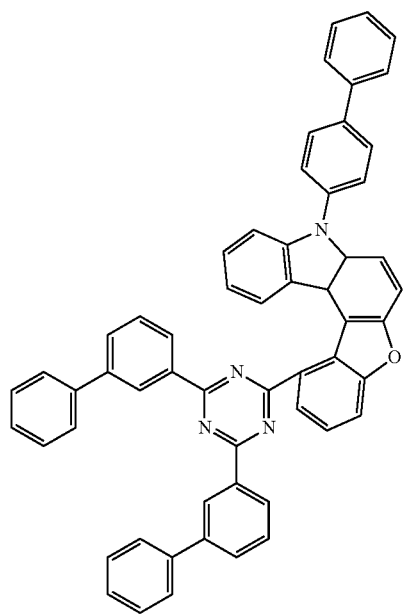
1C-1-23
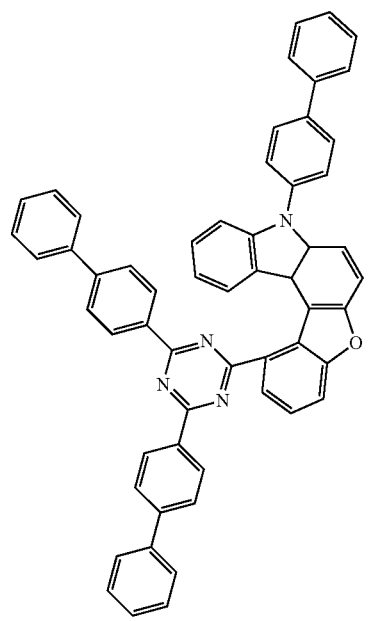
1C-1-24
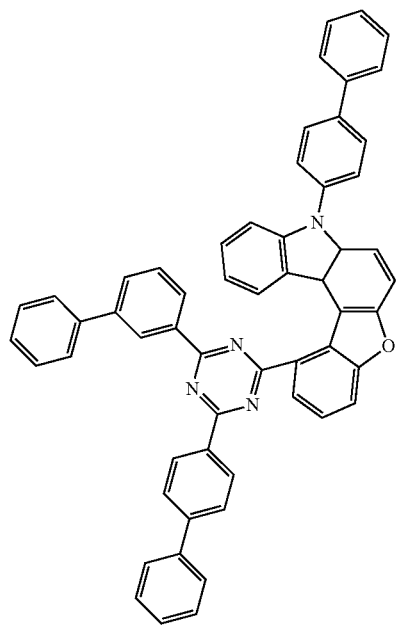
1C-1-25
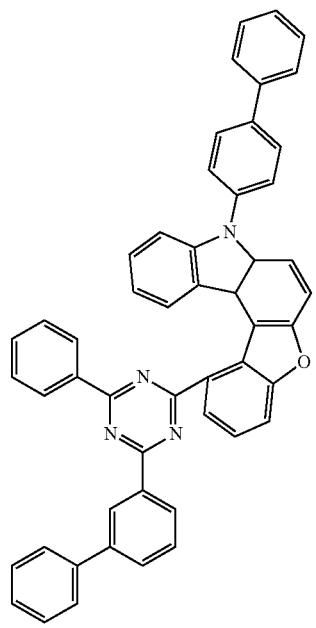

1C-1-26
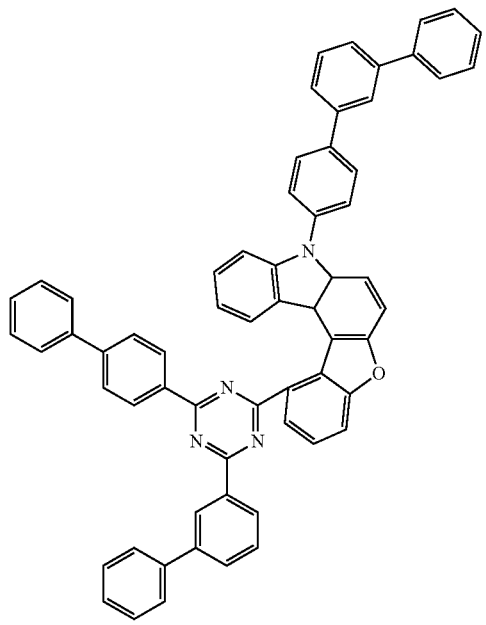
1C-1-27
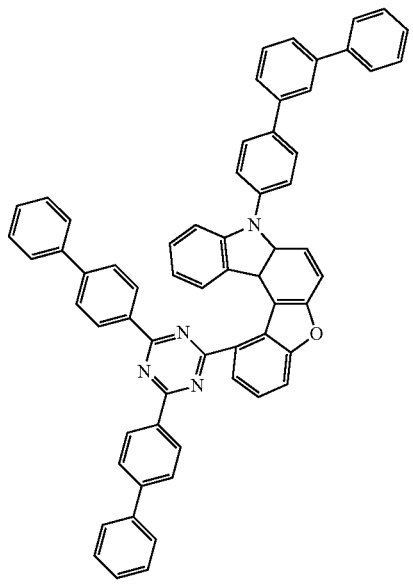
1C-1-28
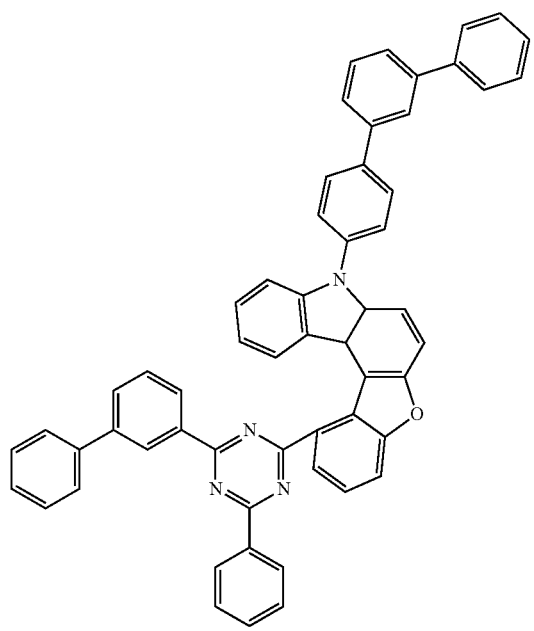
1C-1-29
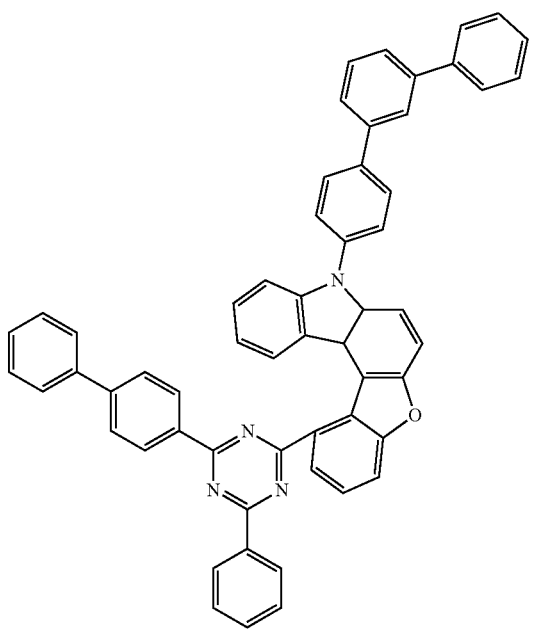

1C-1-30
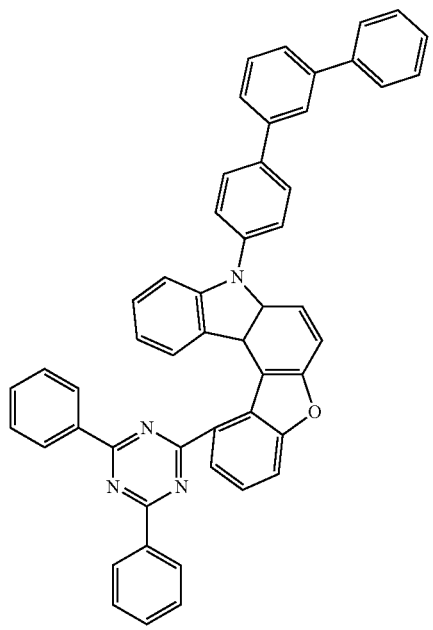
1C-1-31
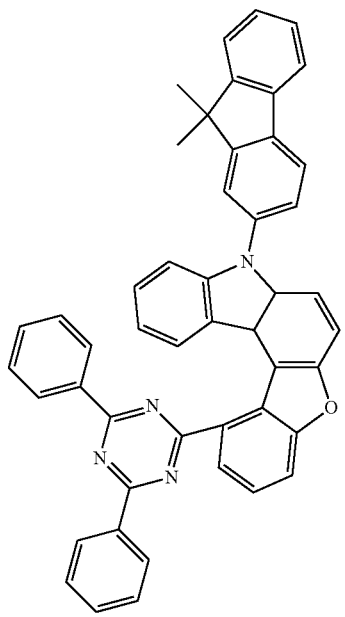
1C-1-32
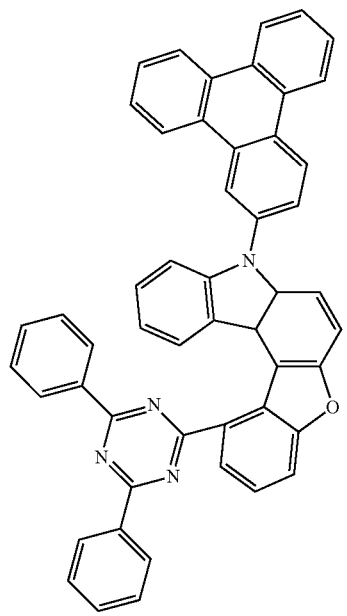
1C-1-33
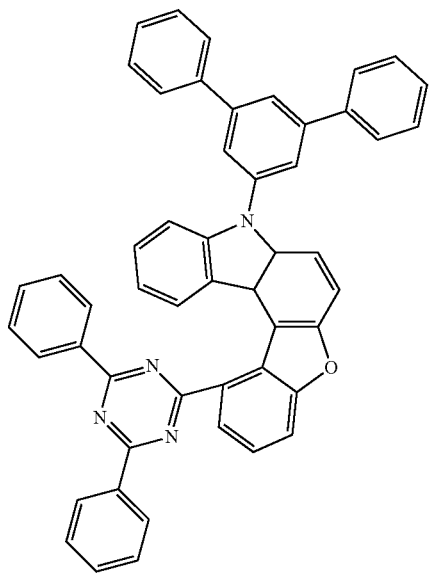

-continued
1C-1-34
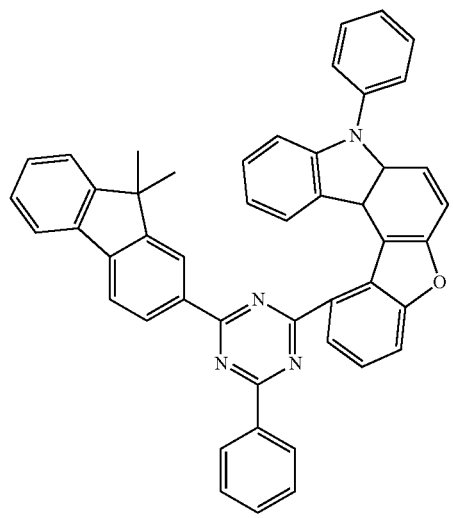
1C-1-35
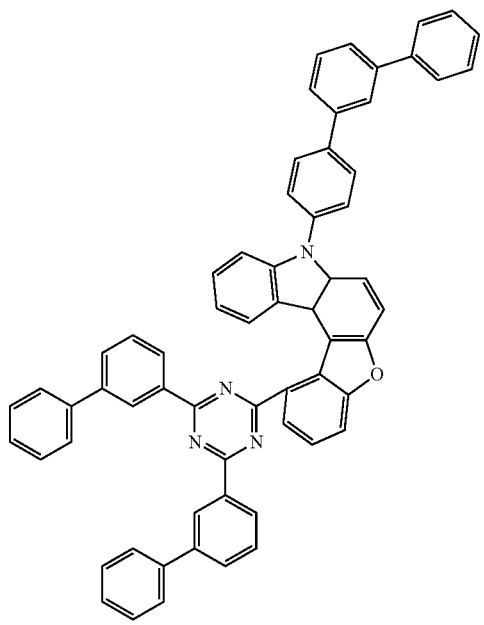
1C-1-36
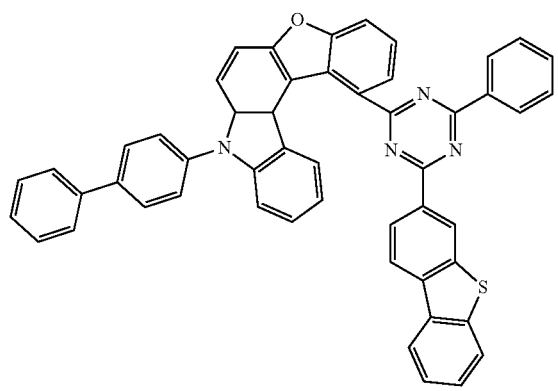
1C-1-37
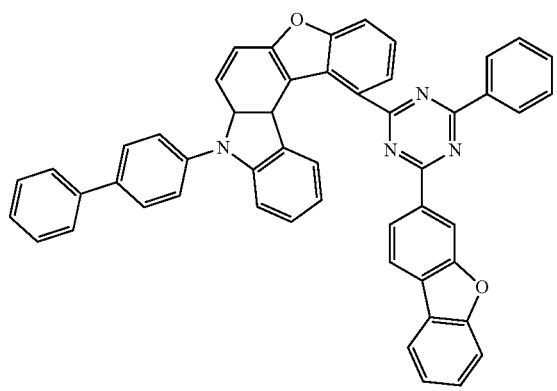
1C-1-38
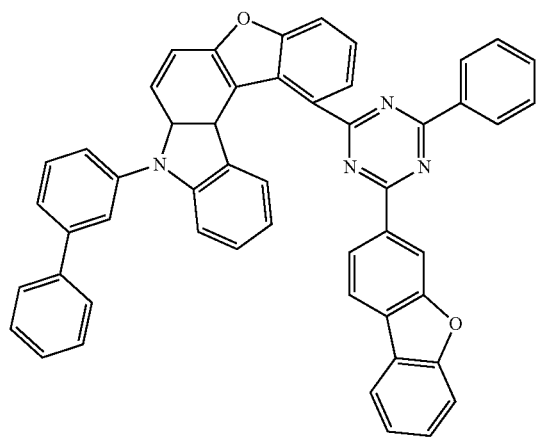
1C-1-39
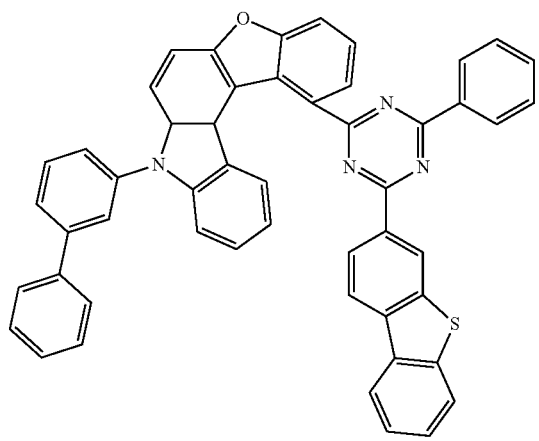

-continued
1C-1-40
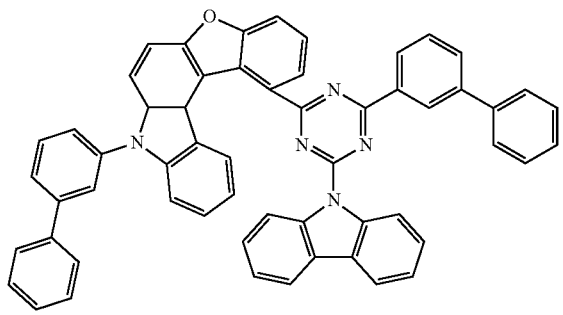
1C-1-41
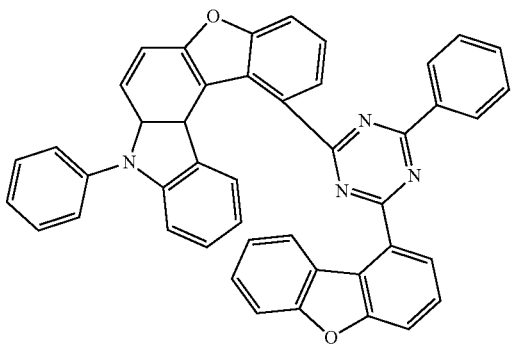
1C-1-42
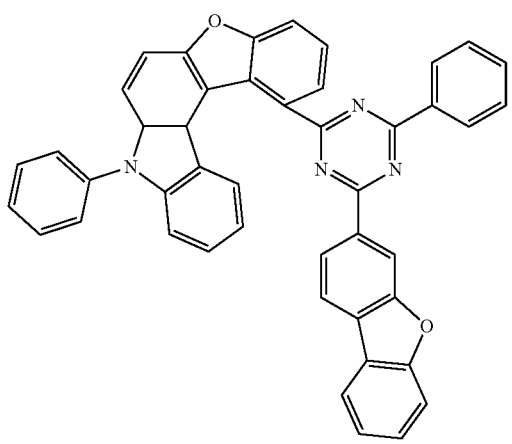
1C-1-43
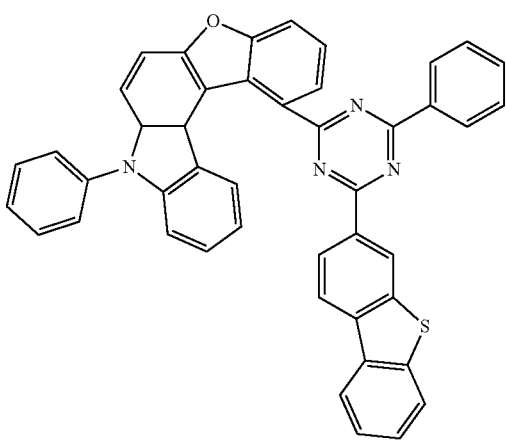
1C-1-44
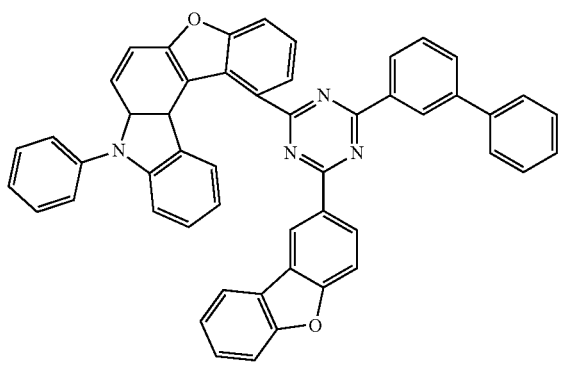
1C-1-45
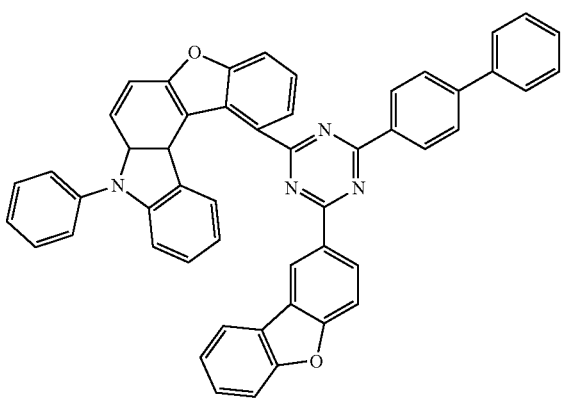
1C-1-46
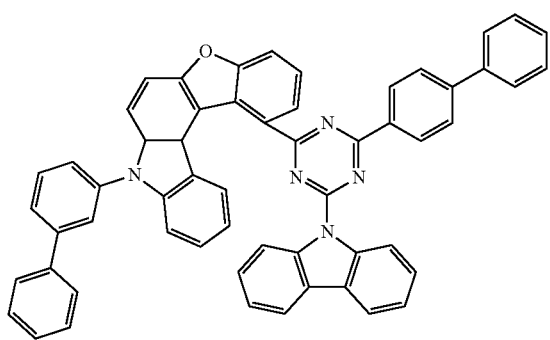
1C-1-47
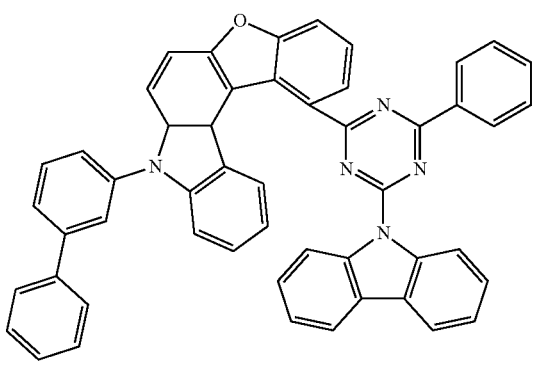

-continued
1C-1-48
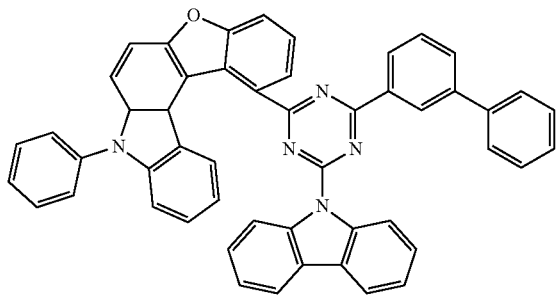
1C-1-49
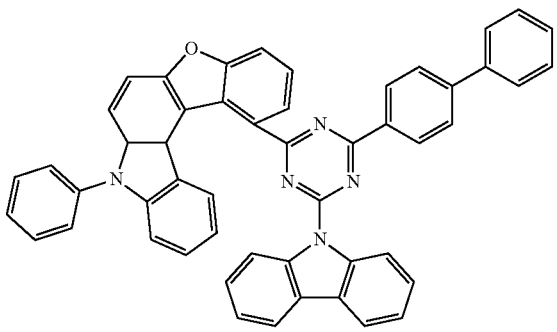
1C-1-50
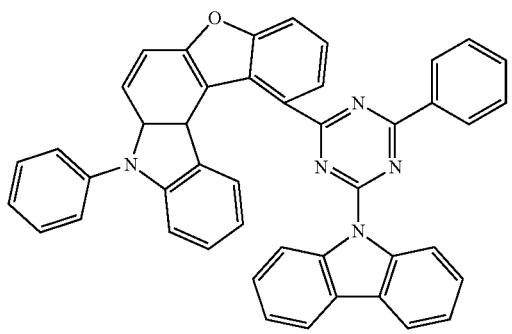
1C-1-51
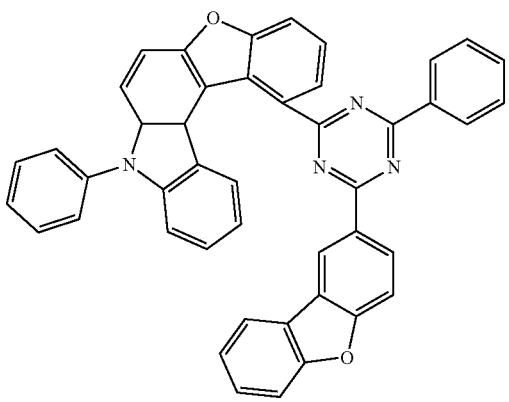
1C-1-52
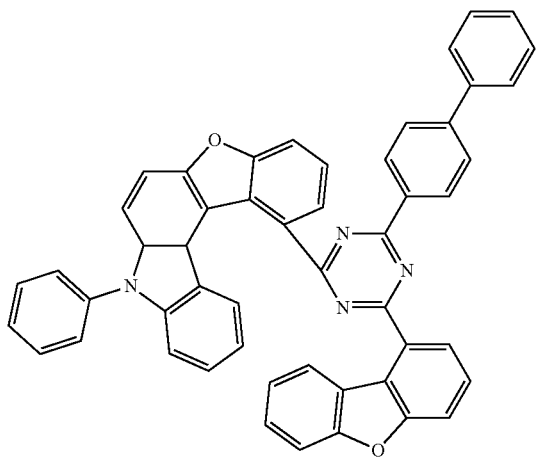
1C-1-53
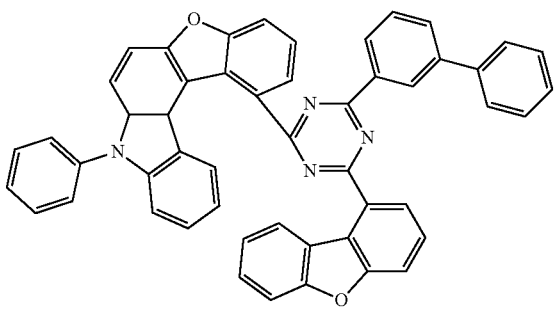

-continued
1C-1-54
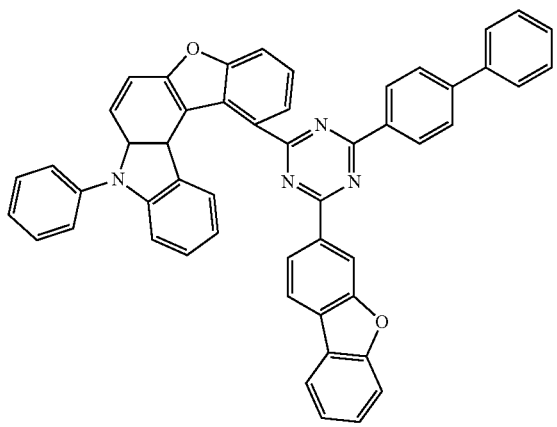
1C-1-55
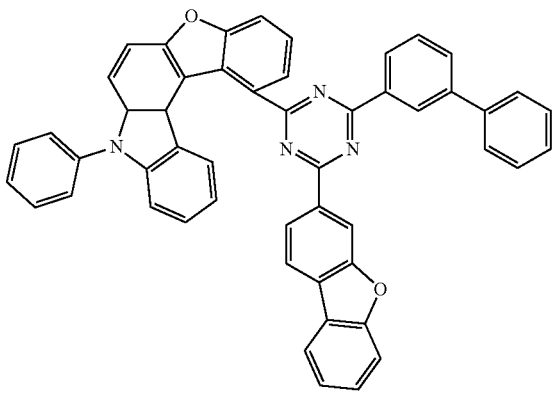
1C-1-56
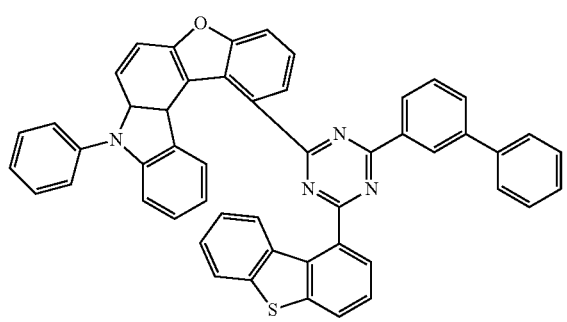
-continued
1C-1-59
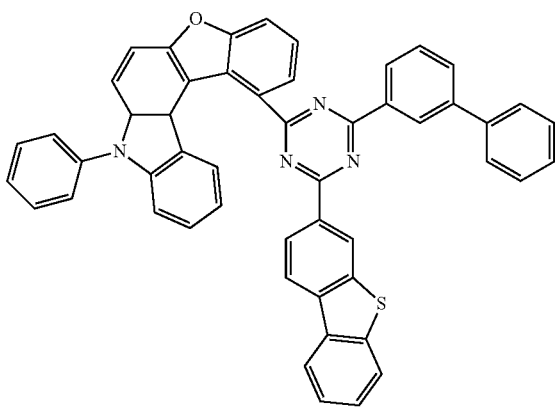
1C-1-57
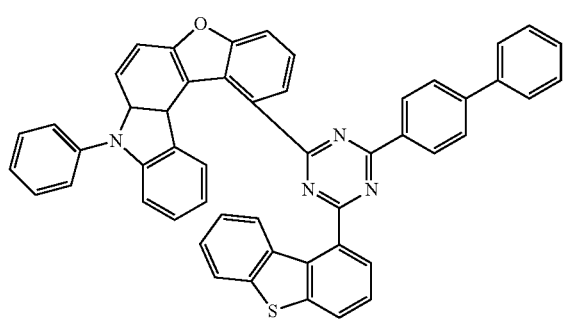
1C-1-58
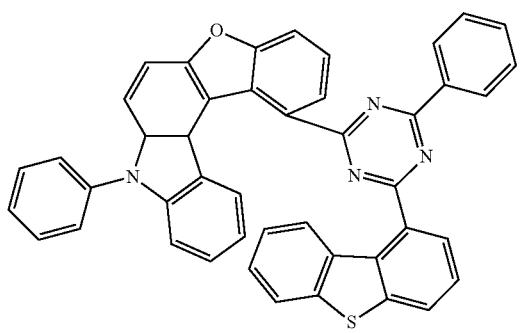
1C-1-60
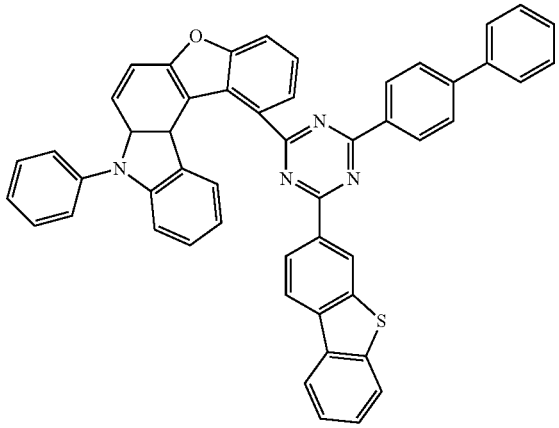

1C-1-61
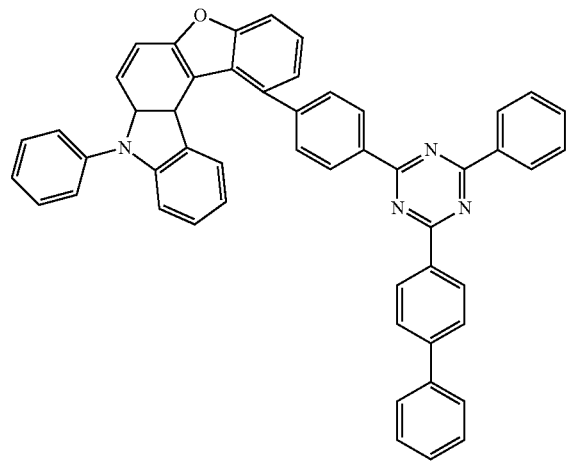
1C-1-62
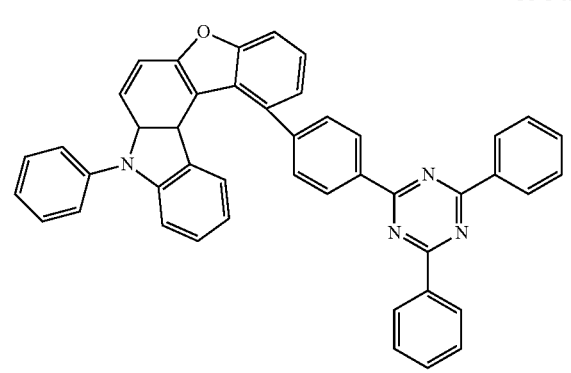
1C-1-63
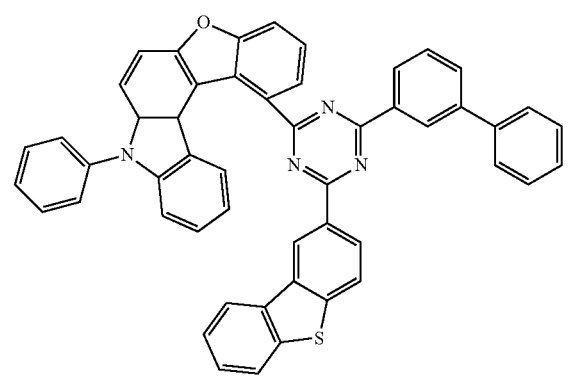
1C-1-64
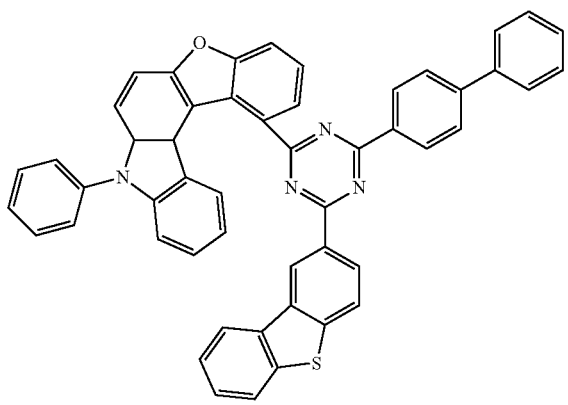
1C-1-65
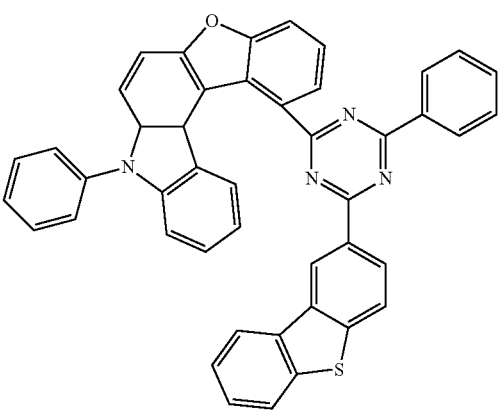
1C-1-66
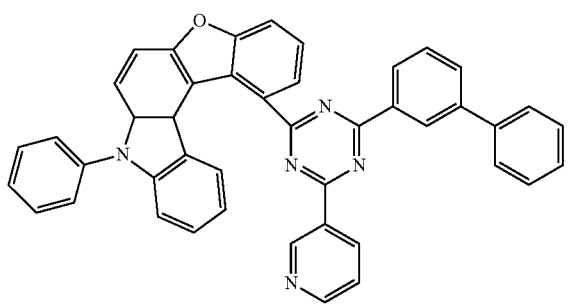
1C-1-67
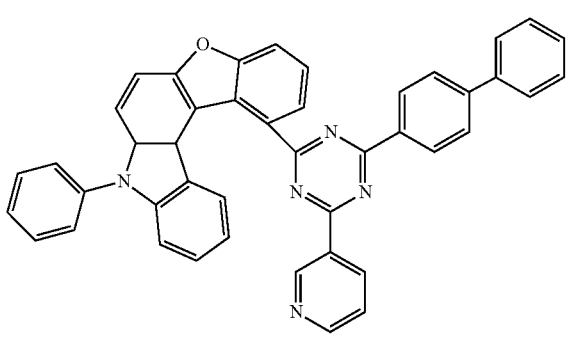

-continued
1C-1-68
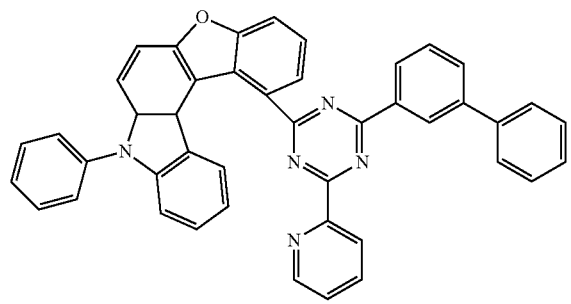
1C-1-69
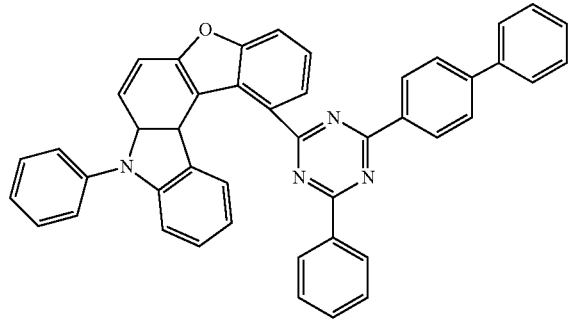
1C-1-70
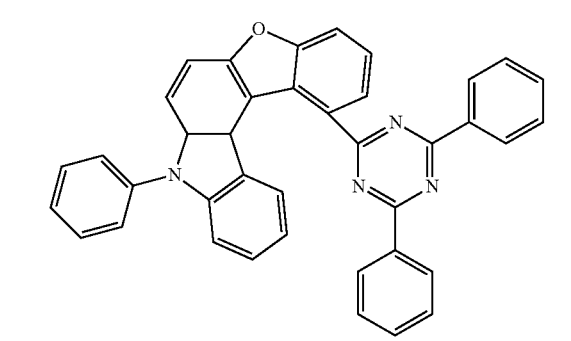
1C-1-71
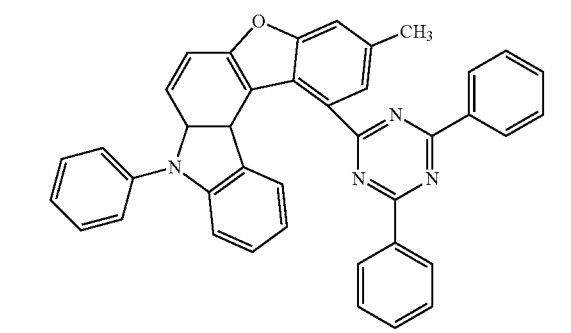
-continued
1C-1-72
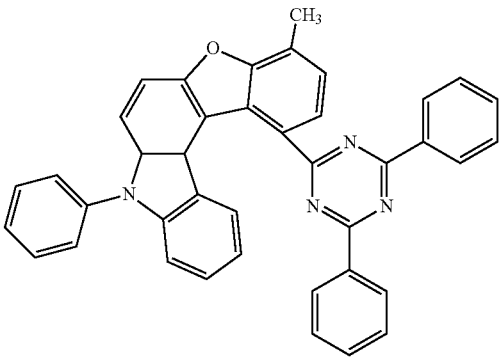
1C-1-73
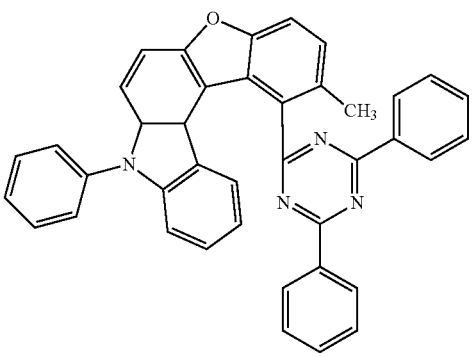
1C-1-74
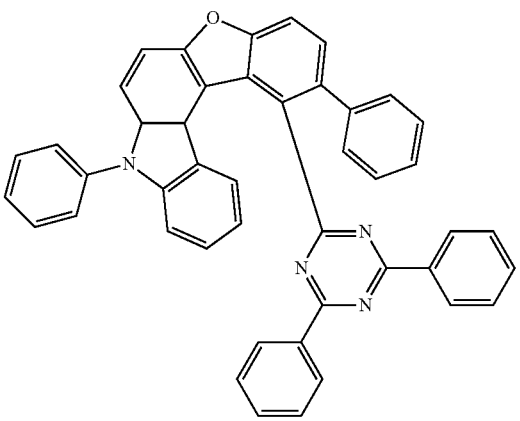
1C-1-75
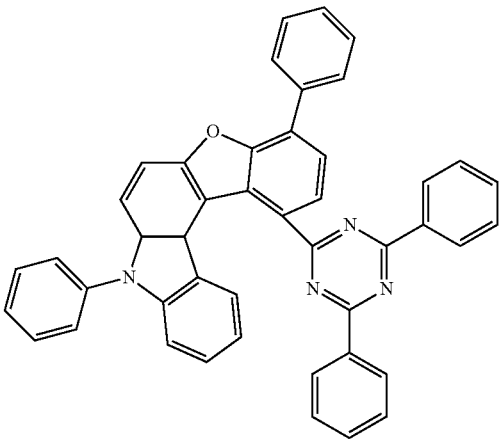

1C-1-76
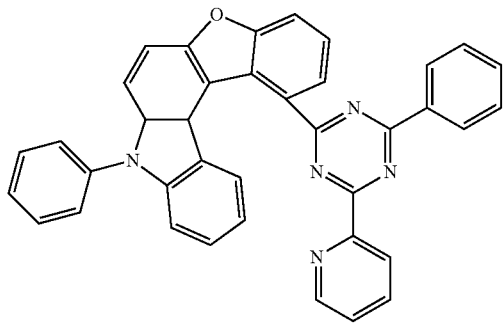
1C-1-77
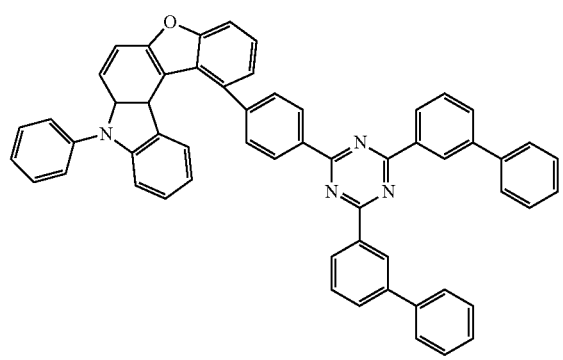
1C-1-78
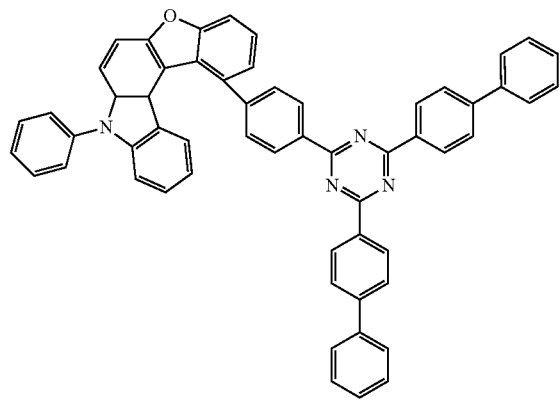
1C-1-79
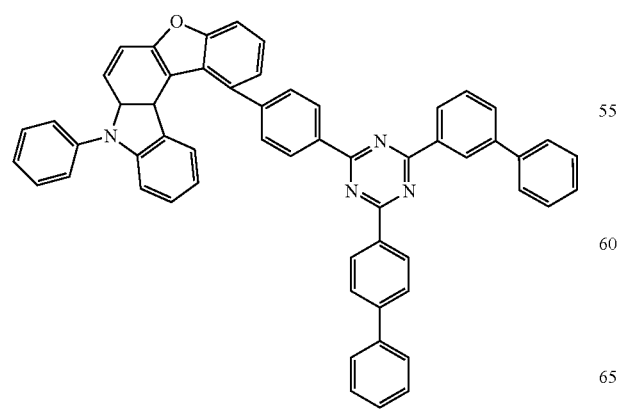
1C-1-80
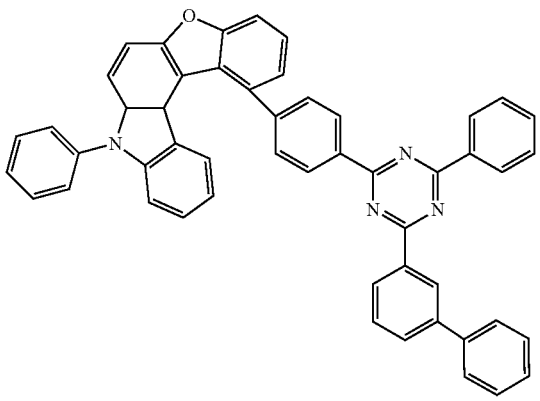
1C-1-81
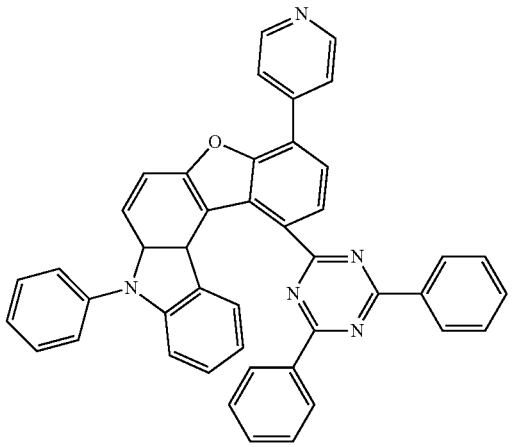
1C-1-82
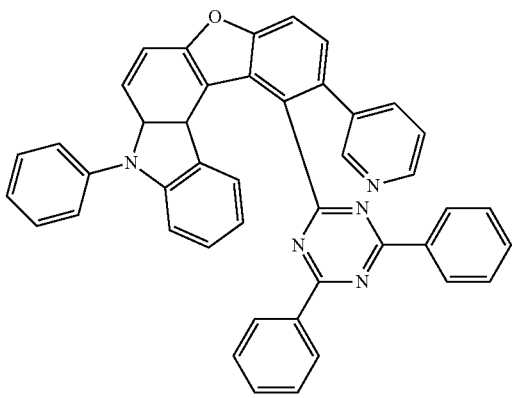

1C-1-83
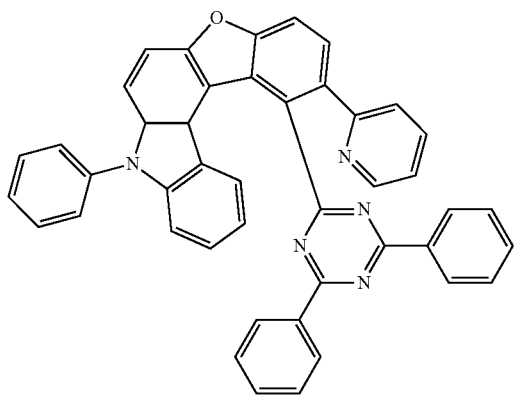
1C-2-1
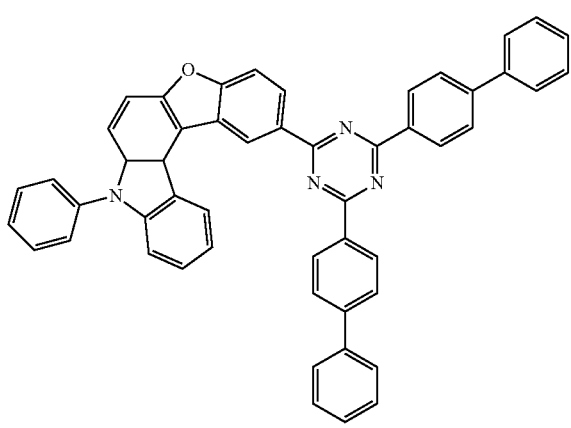
1C-2-2
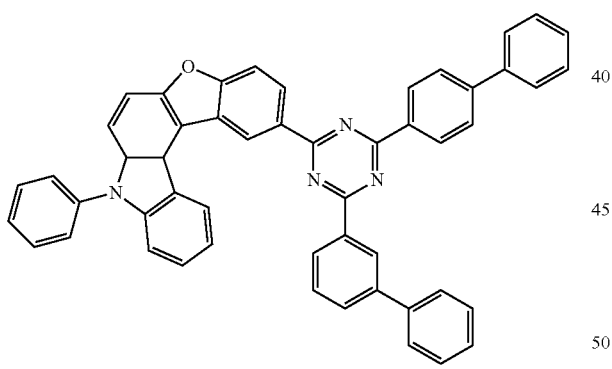
1C-2-3
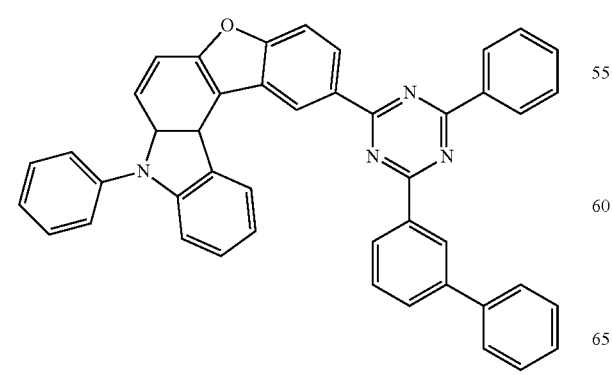
1C-2-4
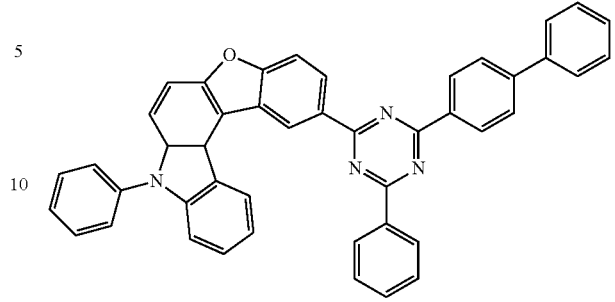
1C-2-5
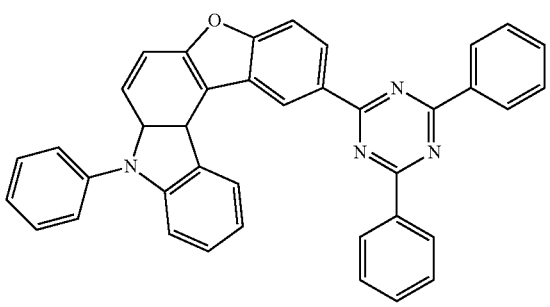
1C-2-6
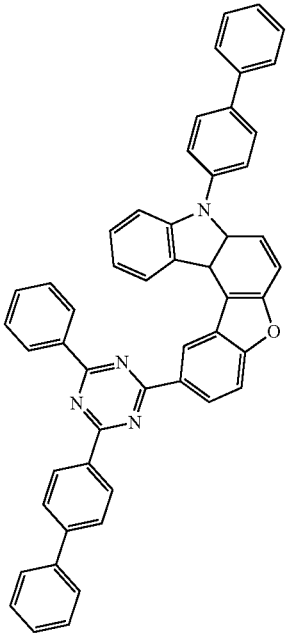

1C-2-7
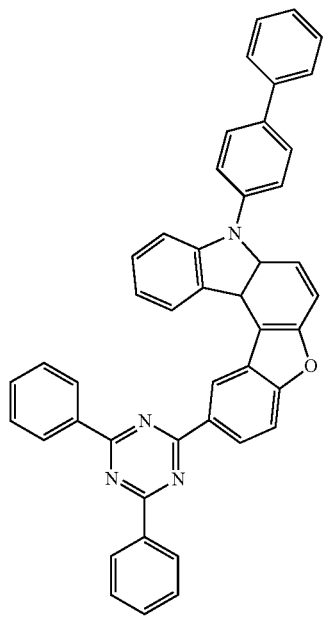
1C-2-8
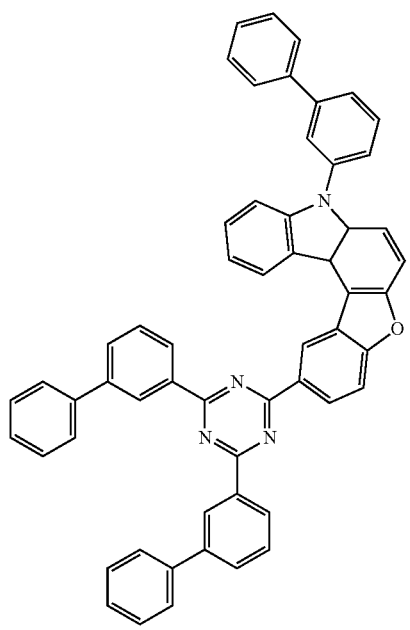
1C-2-9
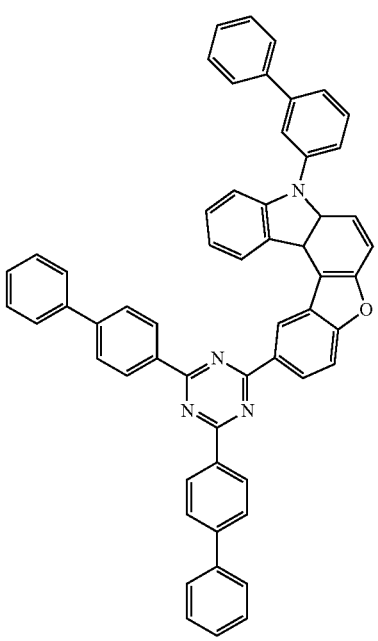
1C-2-10
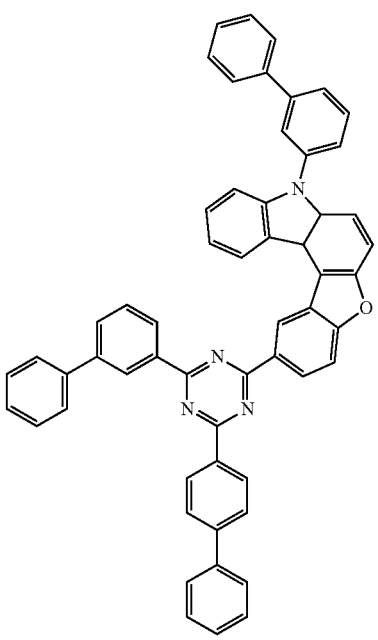
1C-2-11
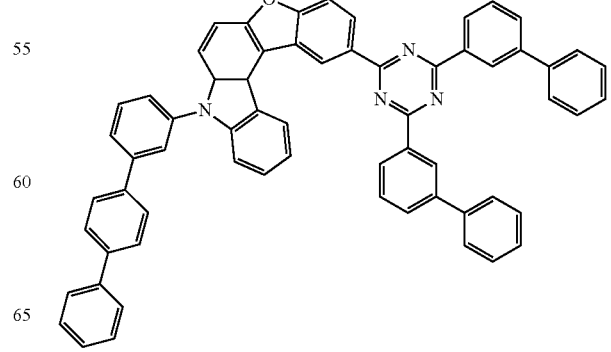

1C-2-12
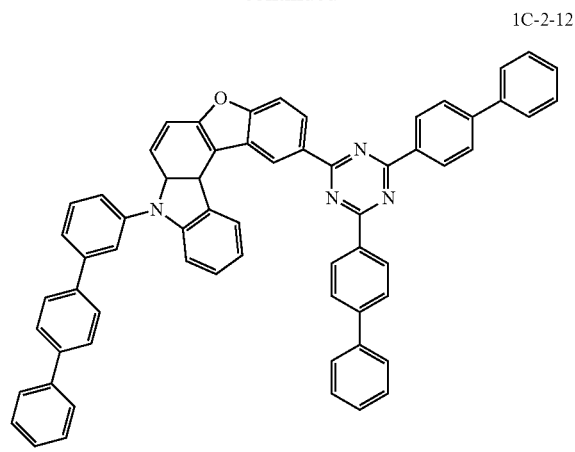
1C-2-13
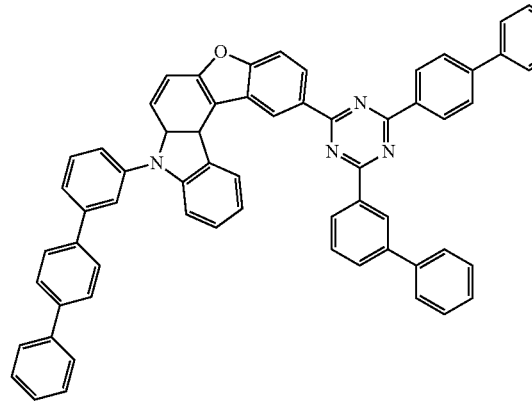
1C-2-14
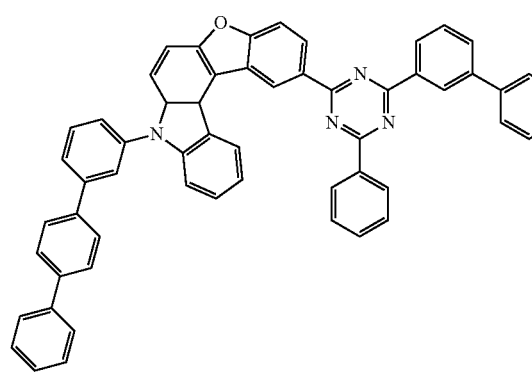
1C-2-15
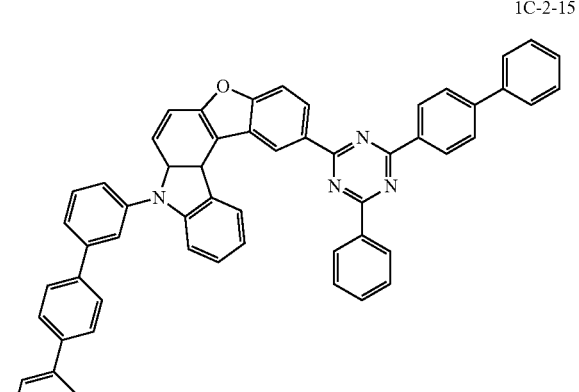
1C-2-16
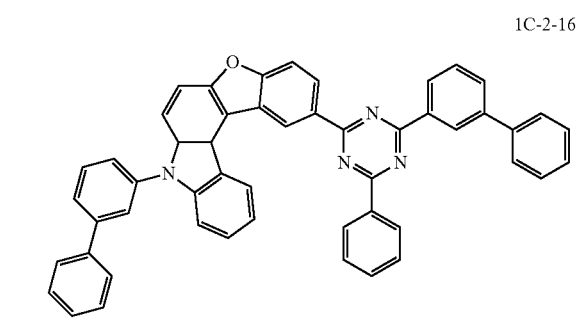
1C-2-17
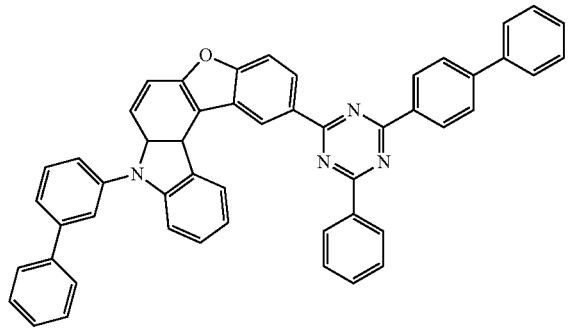
1C-2-18
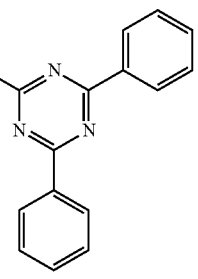

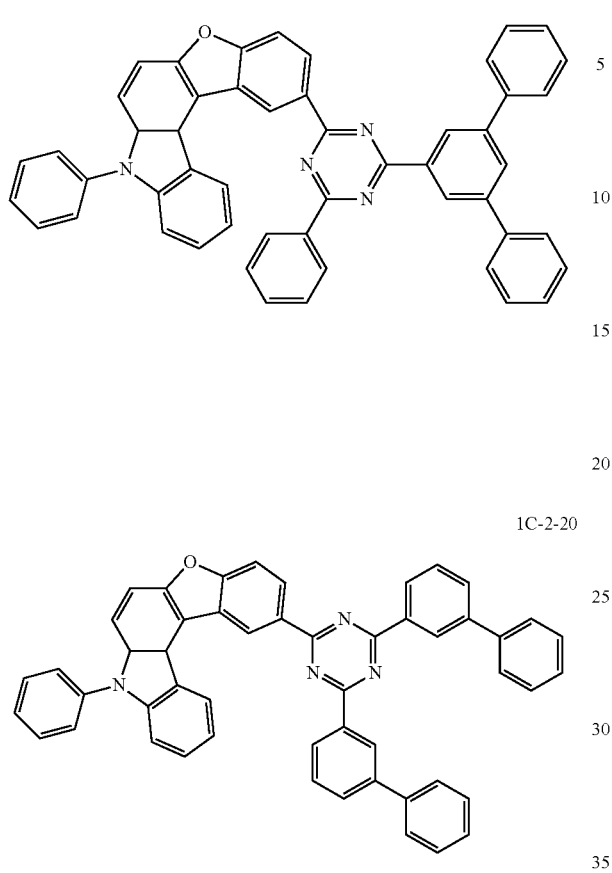
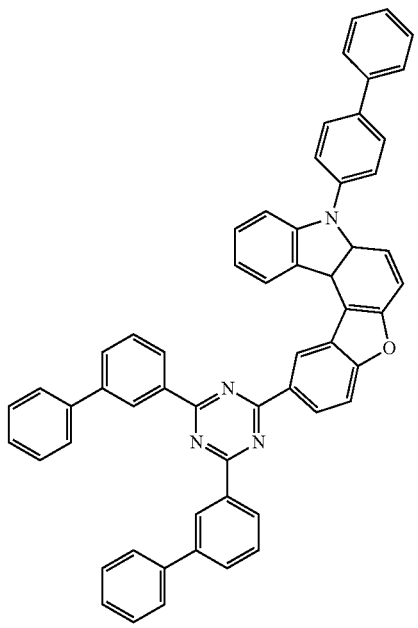
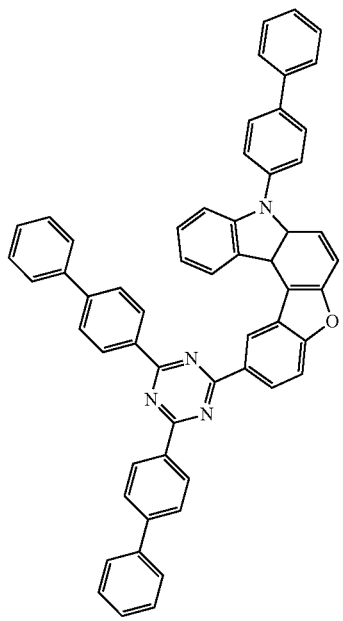

-continued
1C-2-24
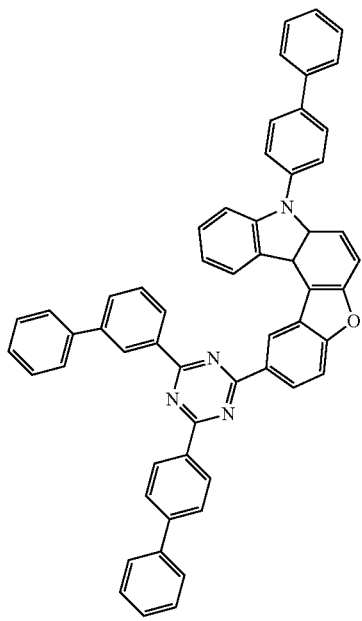
1C-2-25
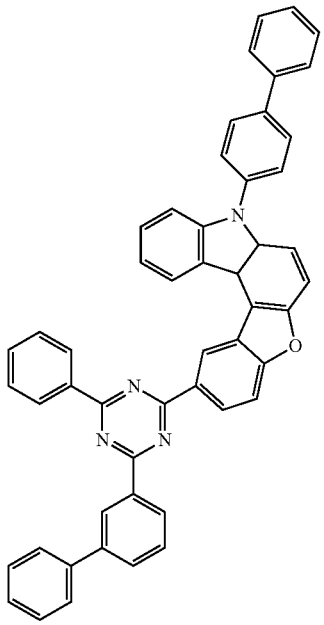
-continued
1C-2-26
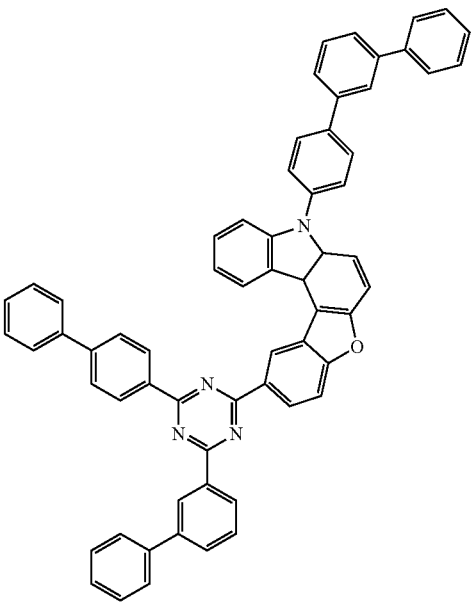
1C-2-27
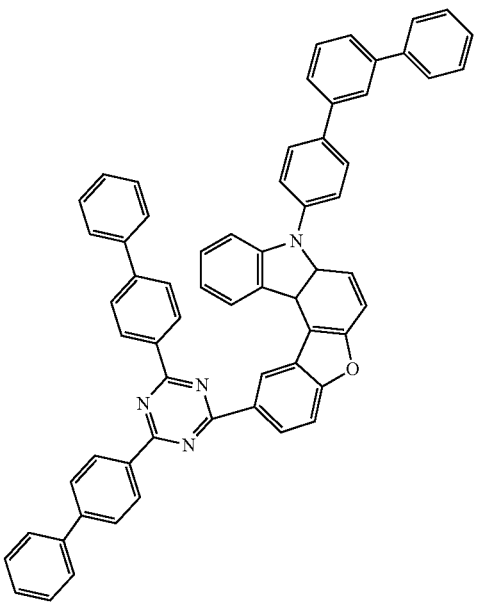

1C-2-28
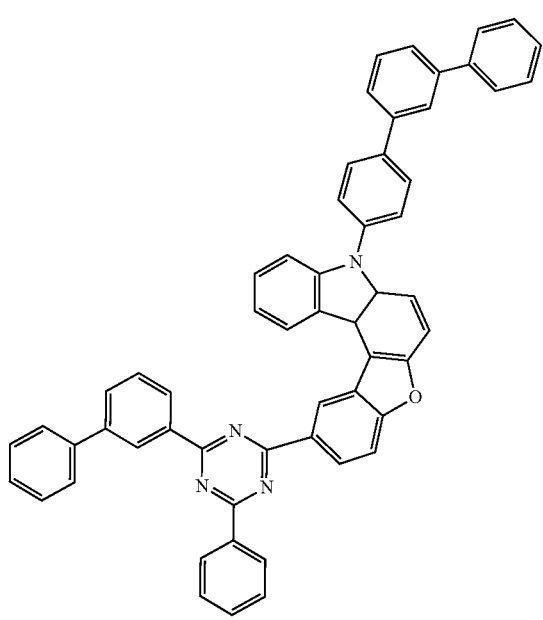
1C-2-30
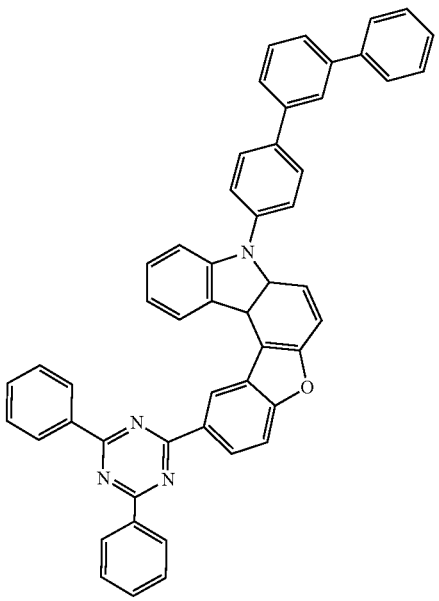
1C-2-29
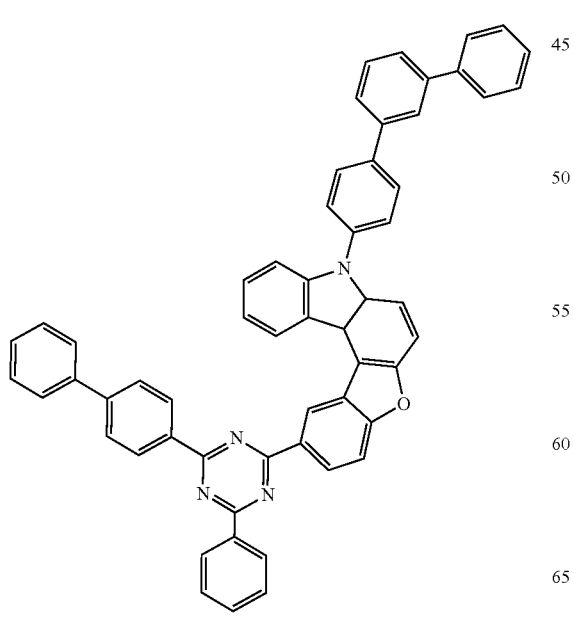
1C-2-31
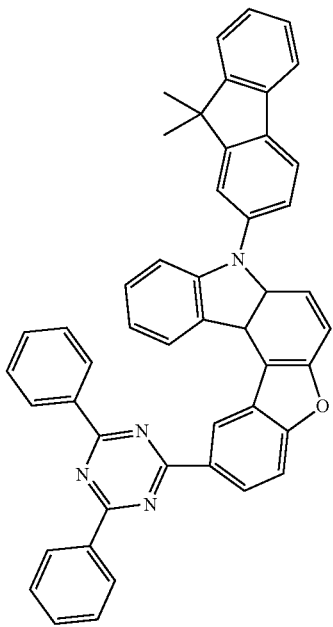

1C-2-32
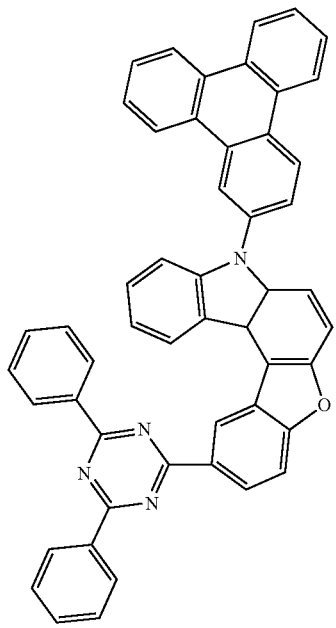
1C-2-33
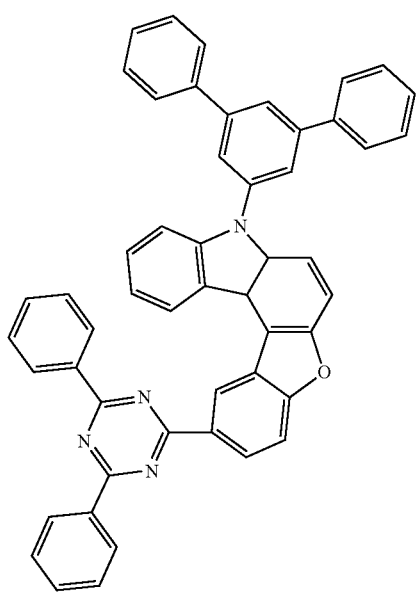
1C-2-34
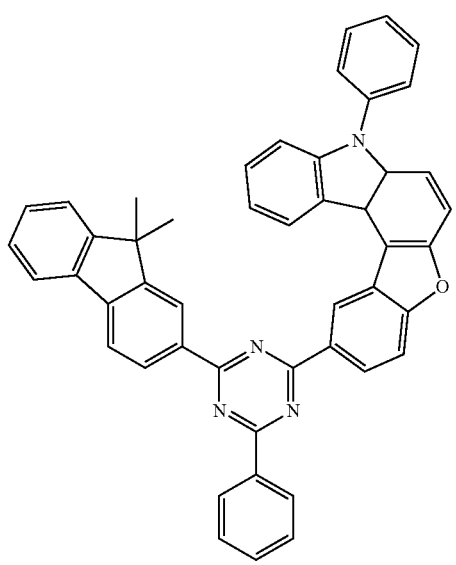
1C-2-35
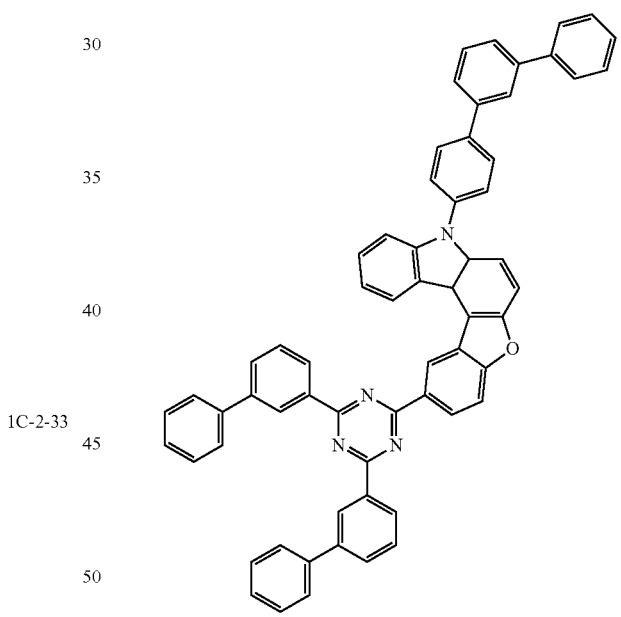
1C-2-36
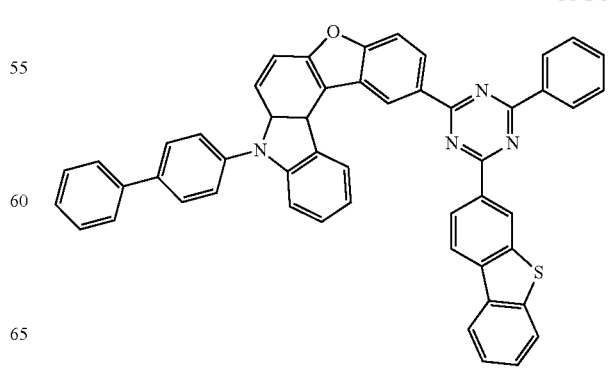

1C-2-37
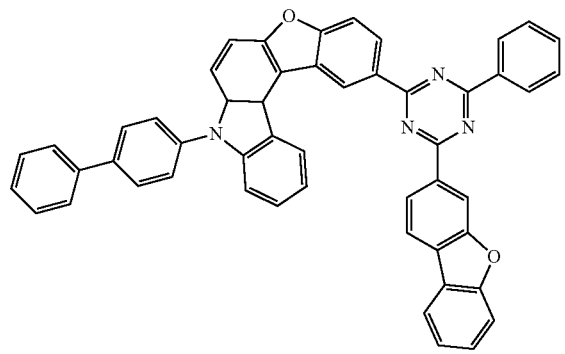
1C-2-38
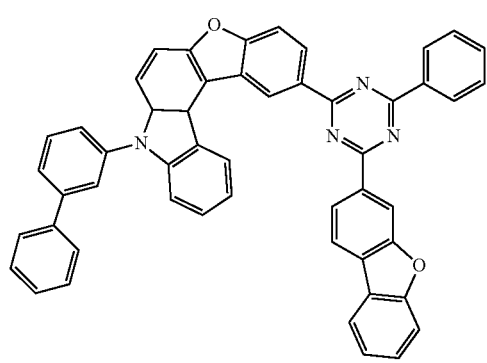
1C-2-39
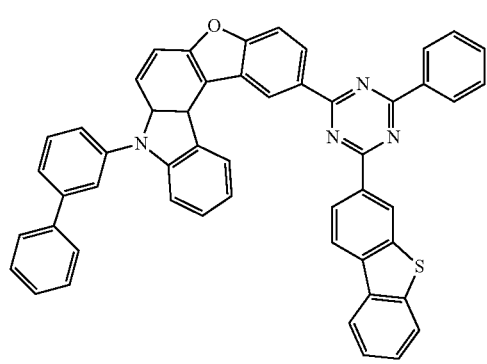
1C-2-40
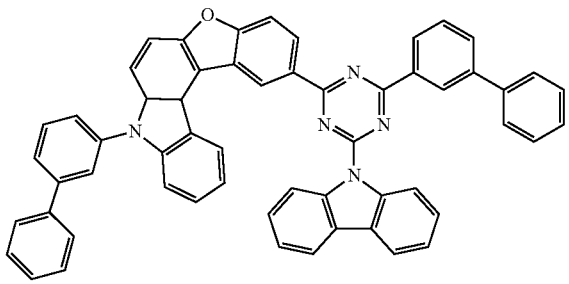
1C-2-41
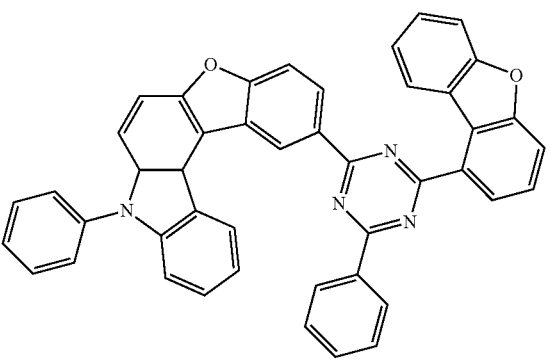
1C-2-42
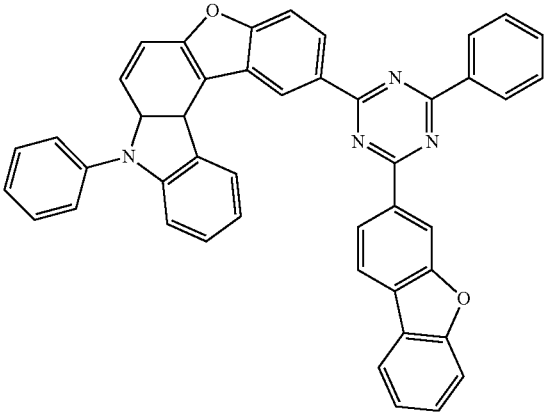
1C-2-43
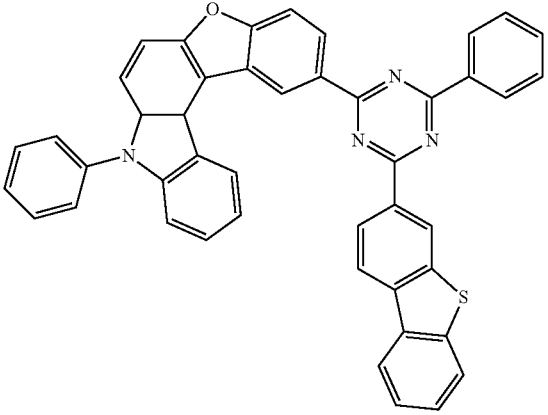
1C-2-44
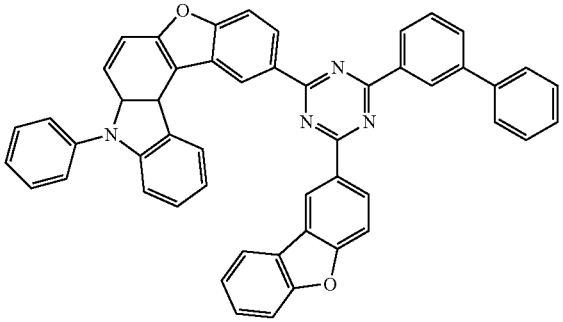

1C-2-45
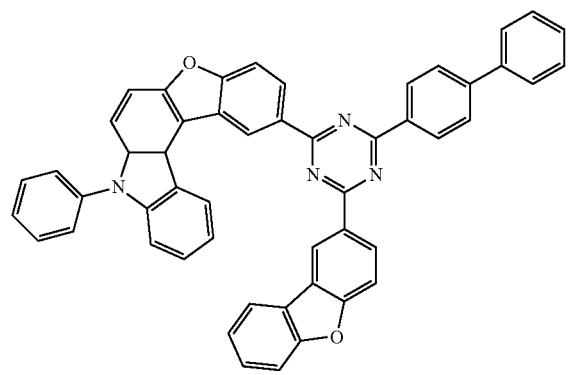
1C-2-46
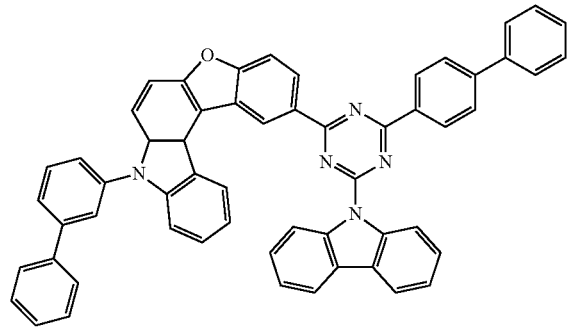
1C-2-47
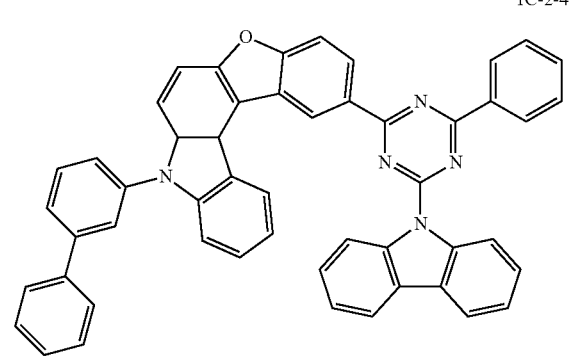
1C-2-48
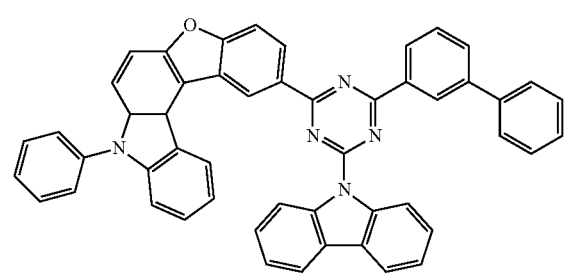
1C-2-49
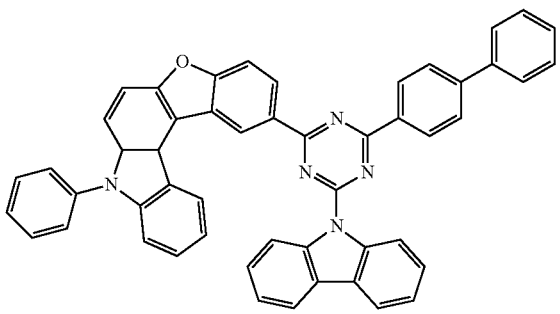
1C-2-50
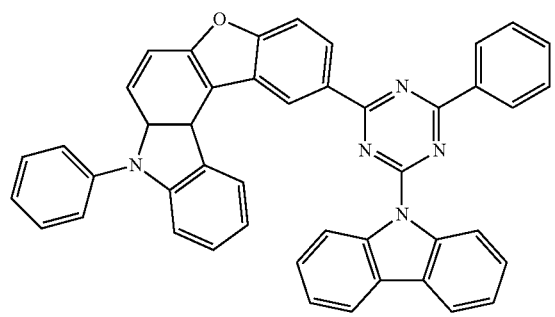
1C-2-51
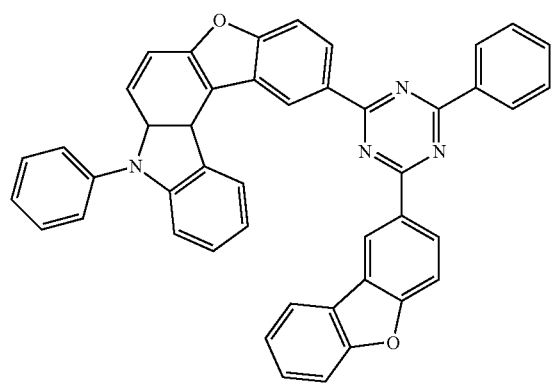
1C-2-52
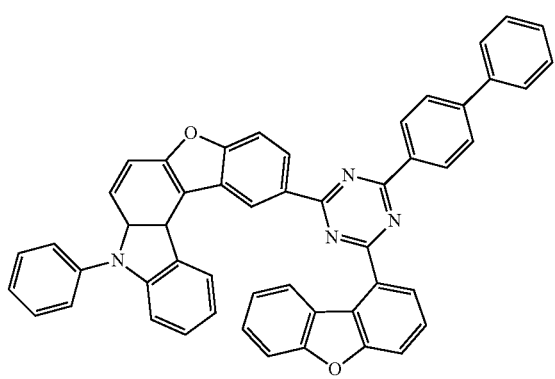

-continued
1C-2-53
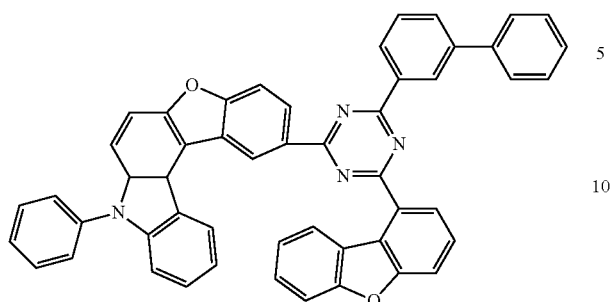
1C-2-54
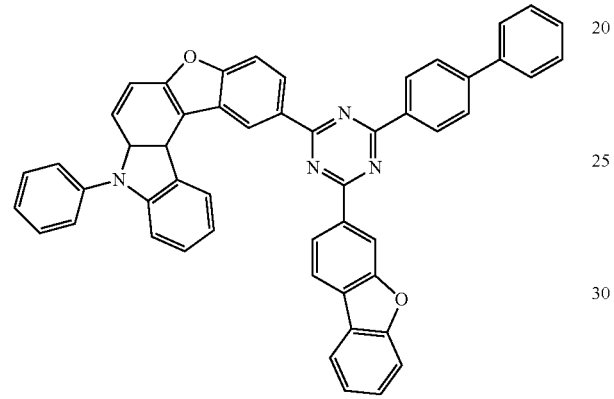
1C-2-55
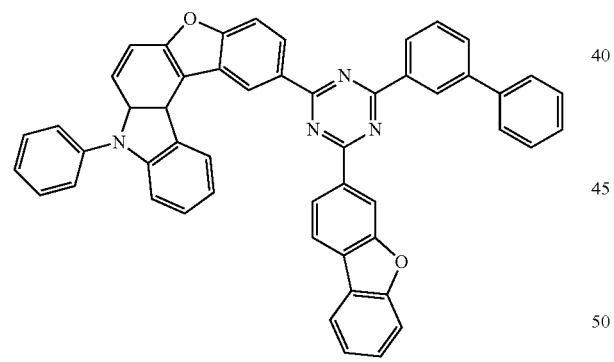
1C-2-56
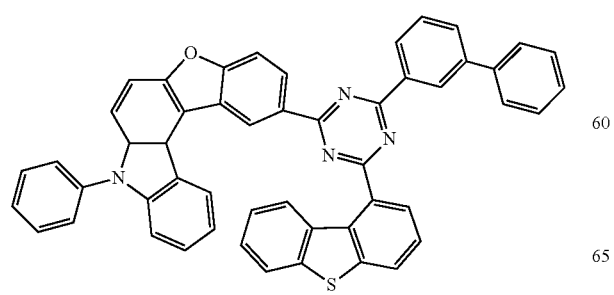
-continued
1C-2-57
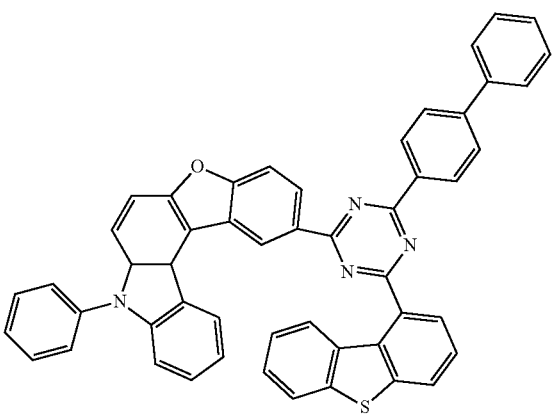
1C-2-58
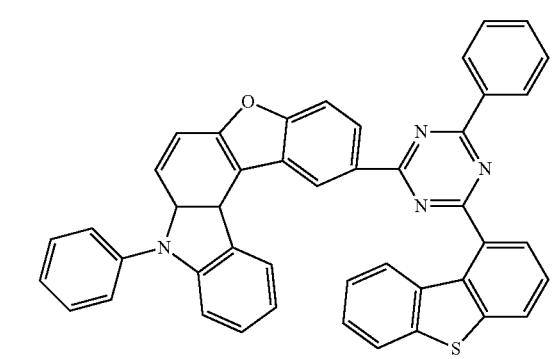
1C-2-59
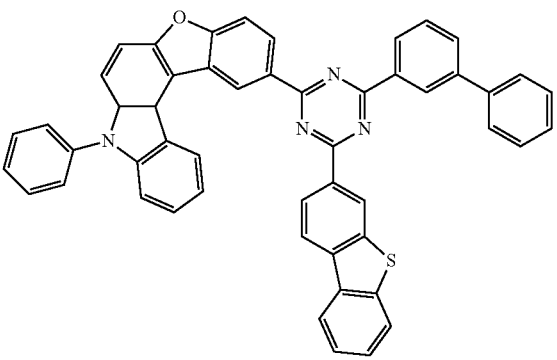
1C-2-60
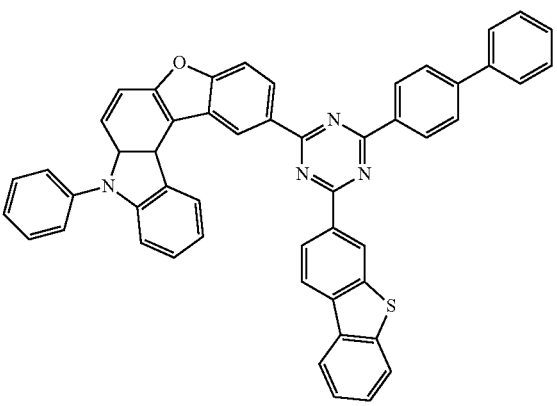

-continued
1C-2-61
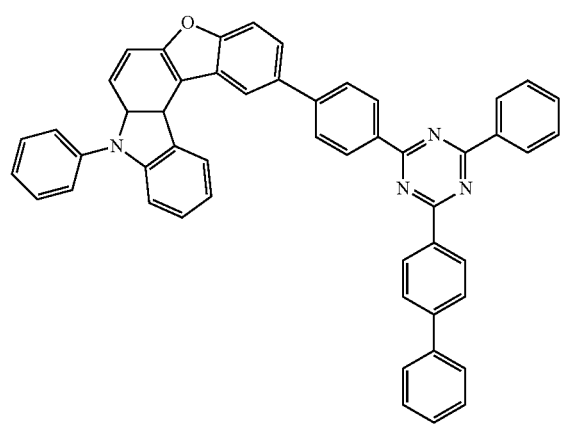
1C-2-62
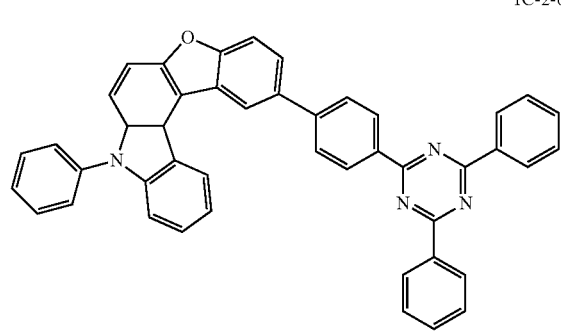
1C-2-63
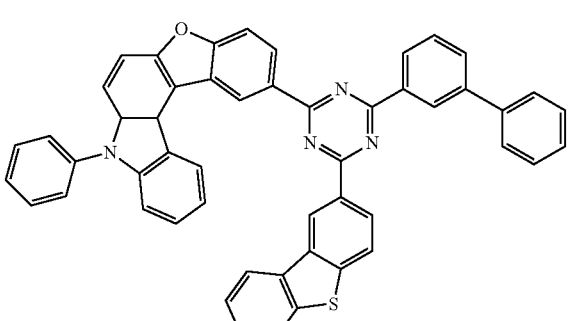
1C-2-64
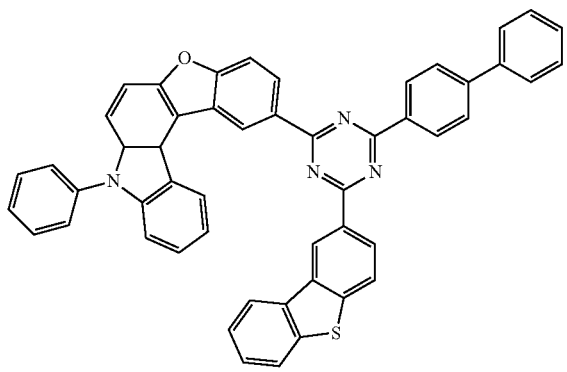
1C-2-65
1C-2-66
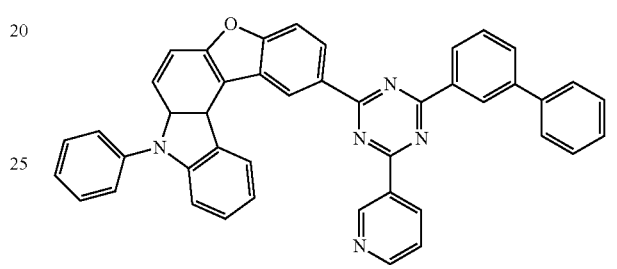
1C-2-67
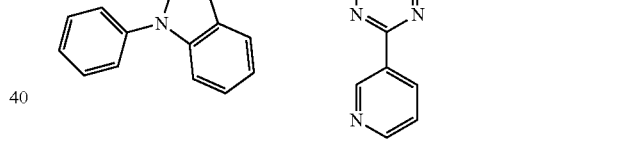
1C-2-68
1C-2-69

1C-2-70
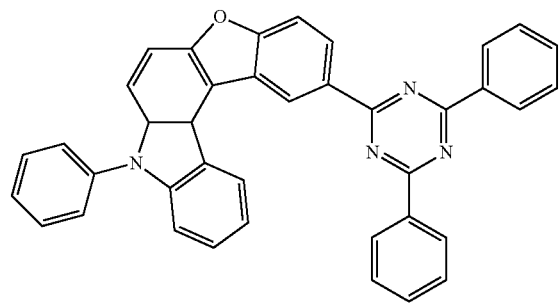
1C-2-71
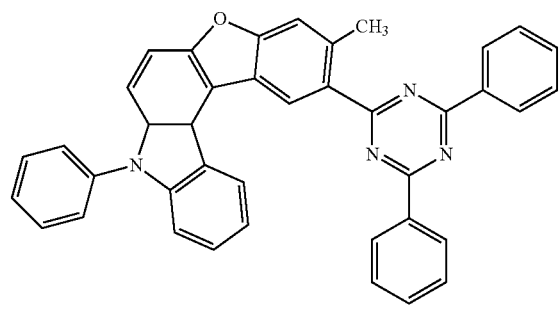
1C-2-72
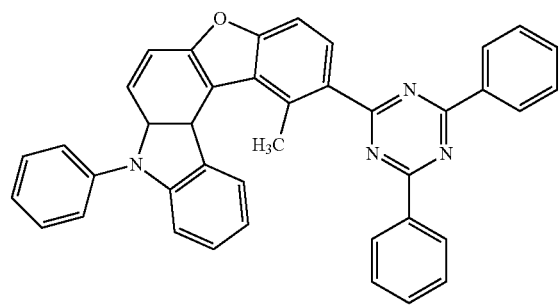
1C-2-73
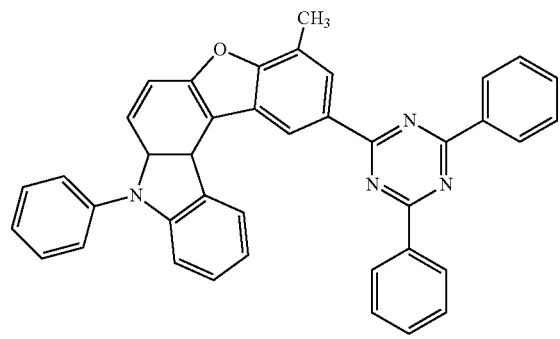
1C-2-74
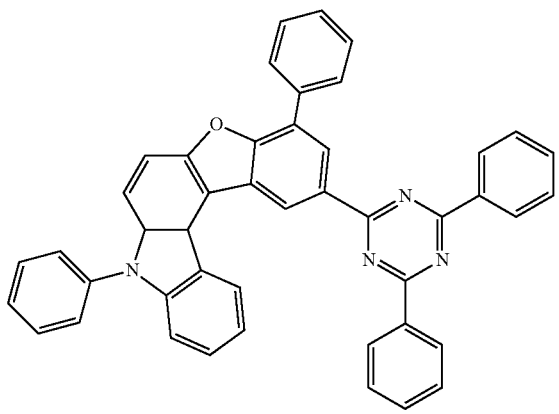
1C-2-75
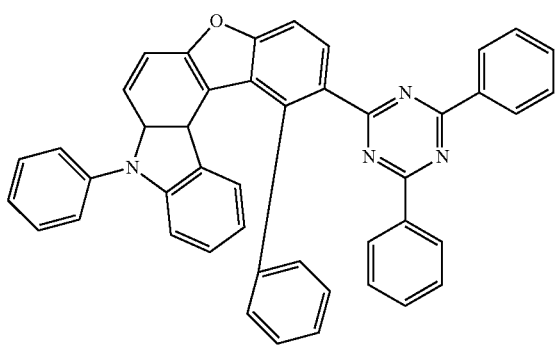
1C-2-76
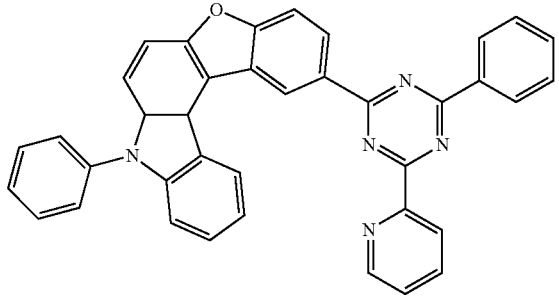
1C-2-77
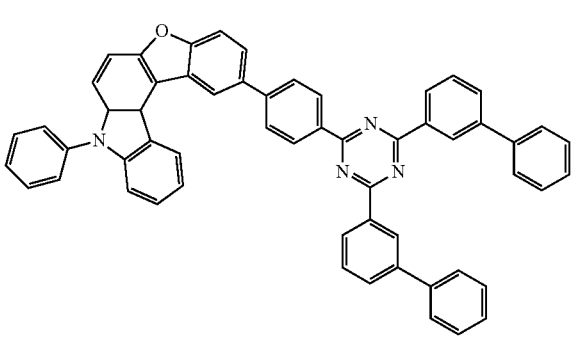

1C-2-78
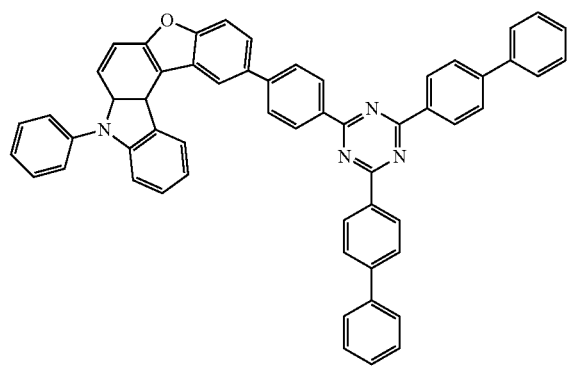
1C-2-79
1C-2-80
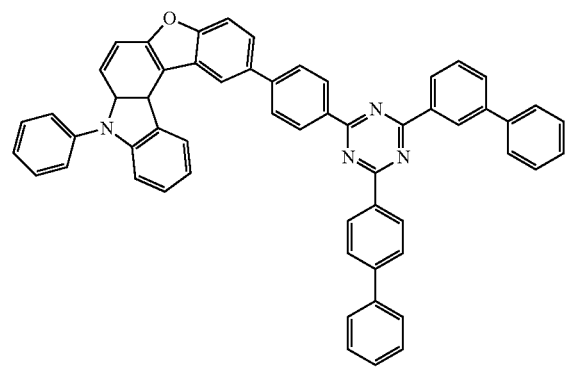
1C-2-81
1C-2-82
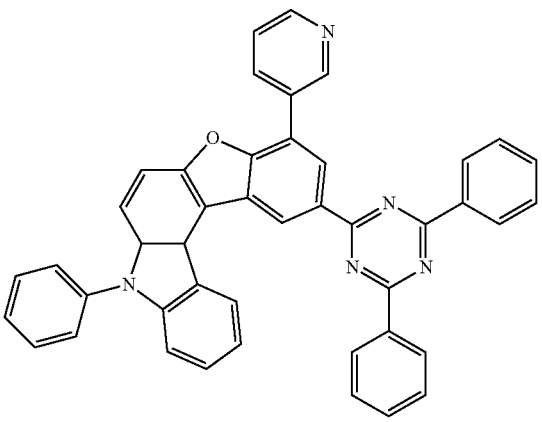
1C-2-83
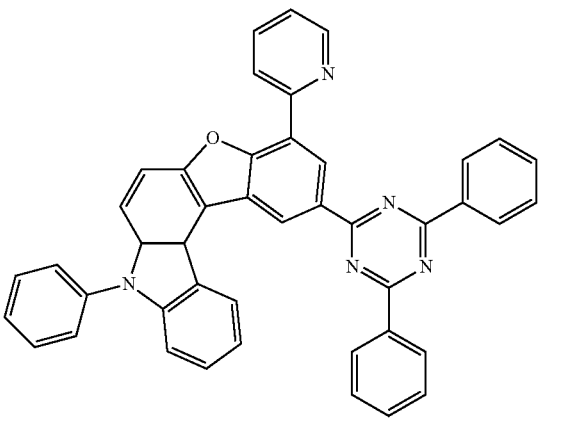
1C-3-1
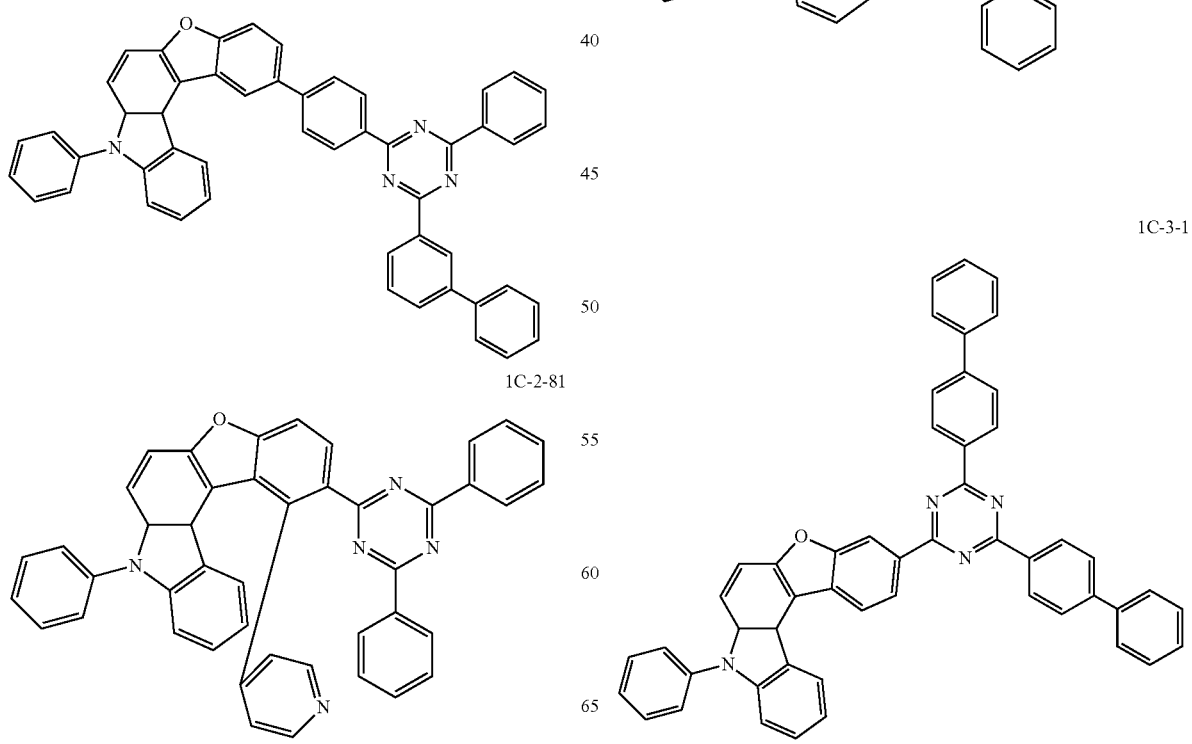

-continued
1C-3-2
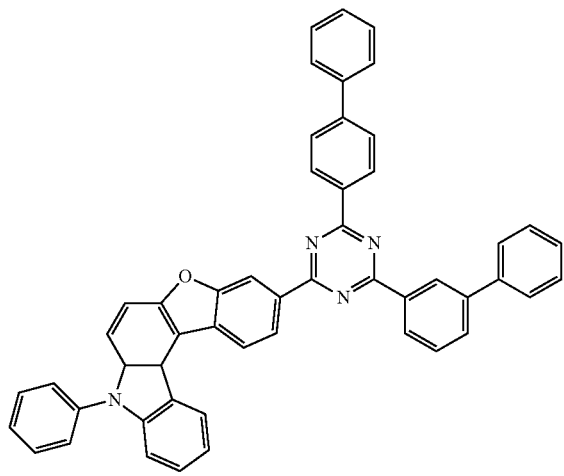
1C-3-3
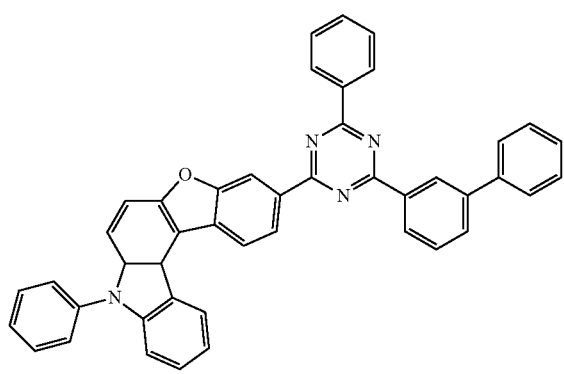
1C-3-4
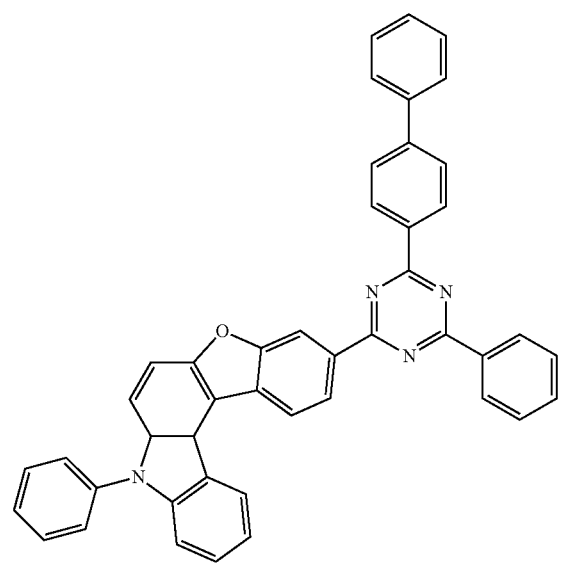
1C-3-5
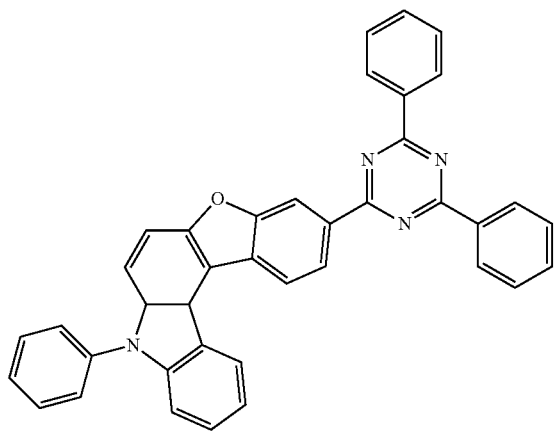
1C-3-6
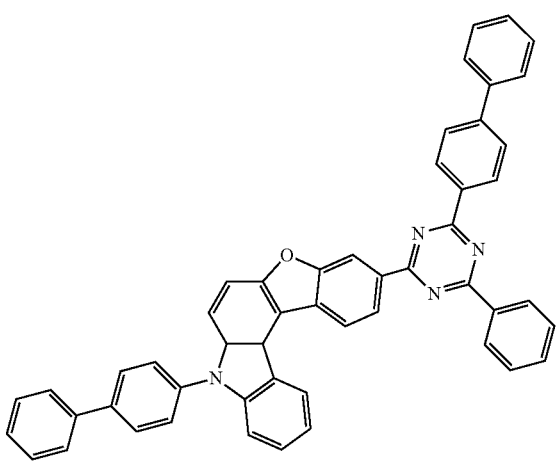
1C-3-7
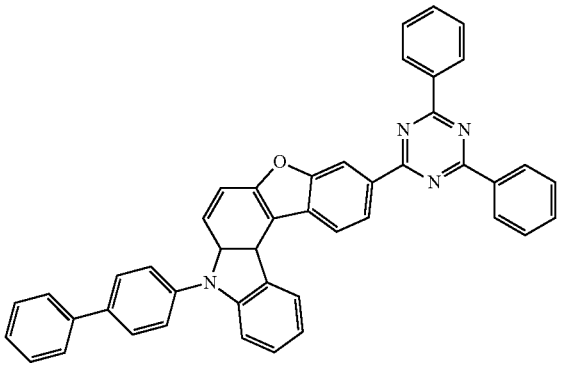

1C-3-8
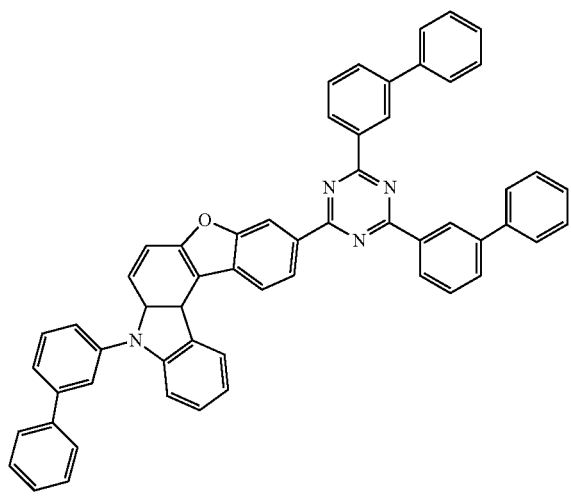
1C-3-9
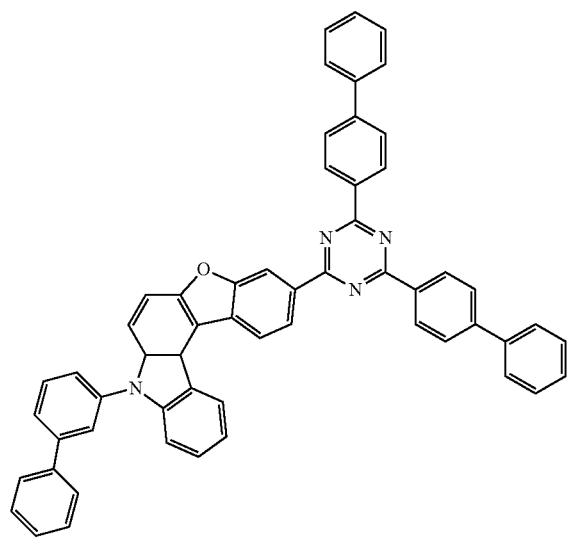
1C-3-10
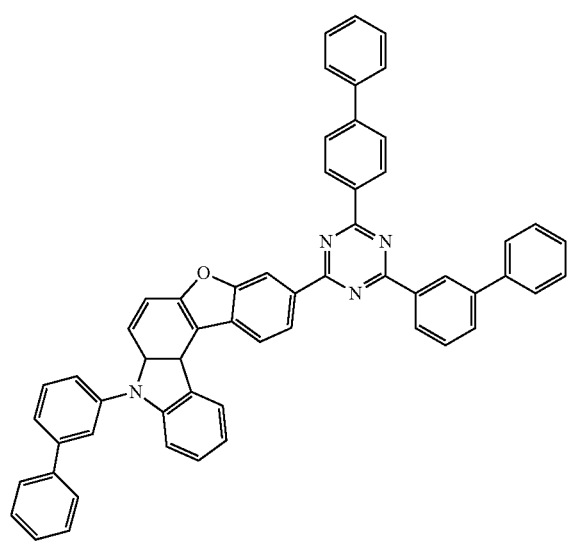
1C-3-11
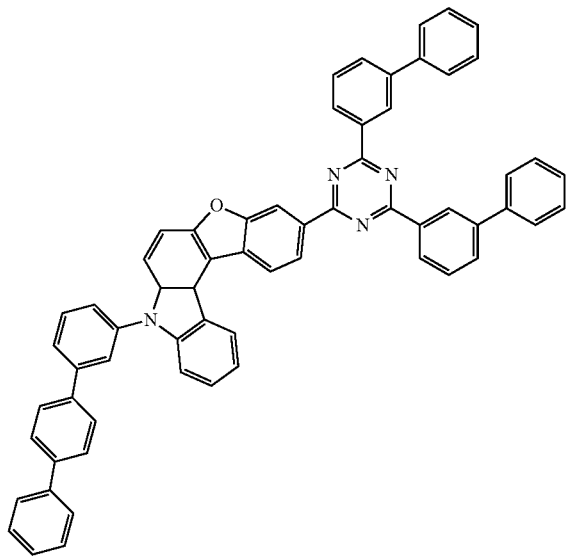
1C-3-12
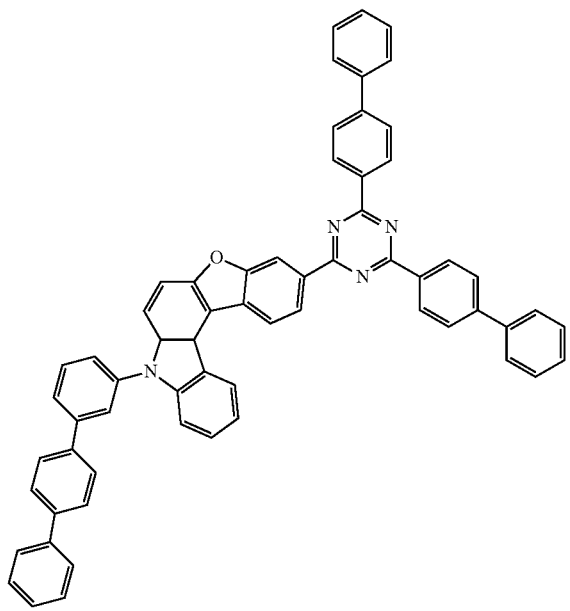

1C-3-13
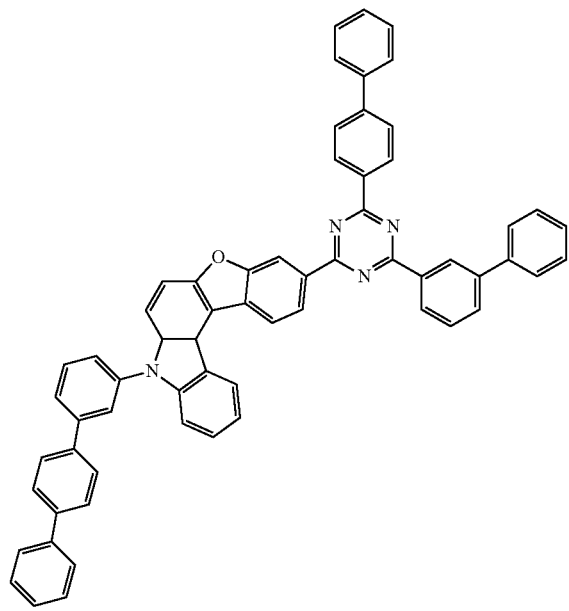
1C-3-15
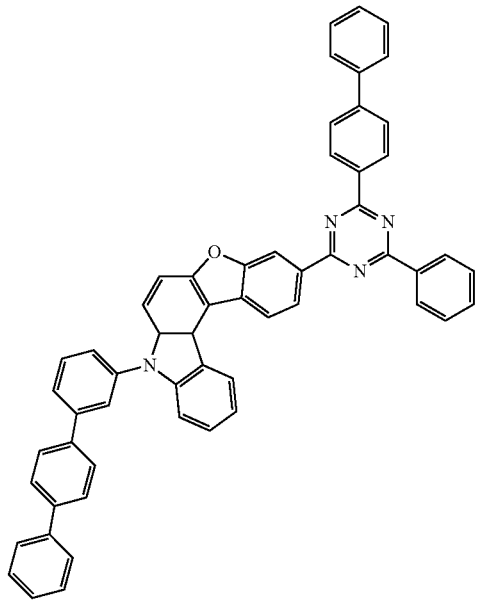
1C-3-14
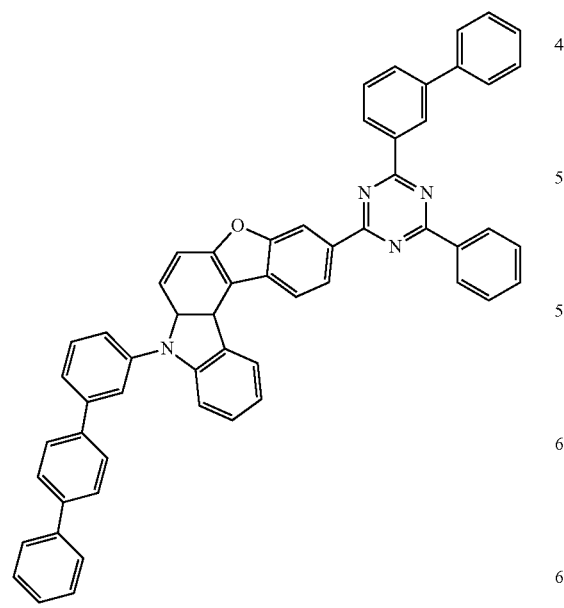
1C-3-16
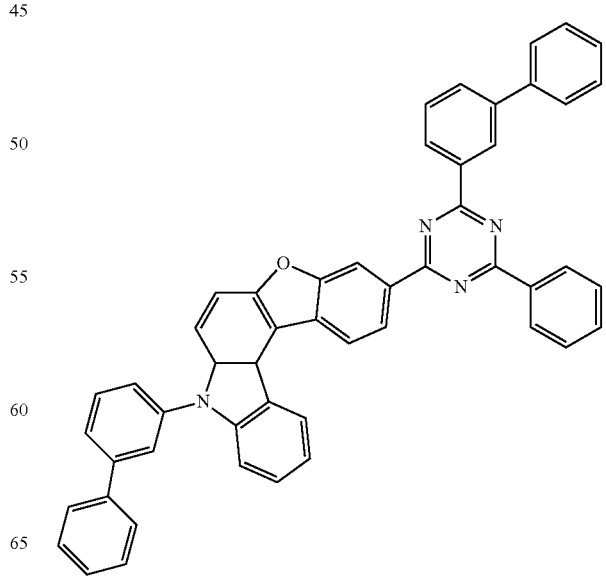

-continued
1C-3-17
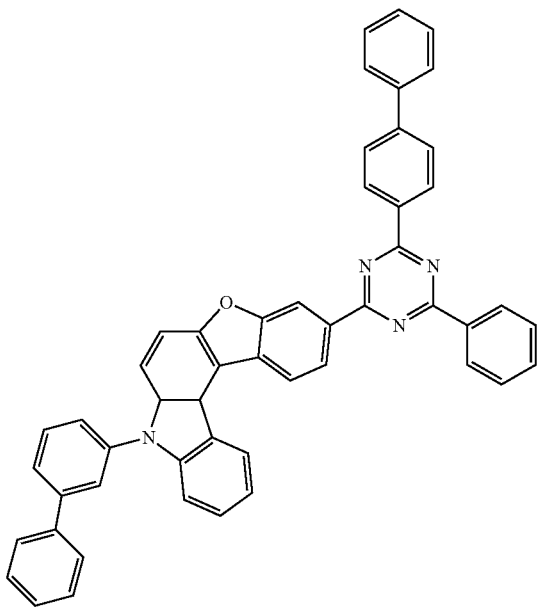
1C-3-18
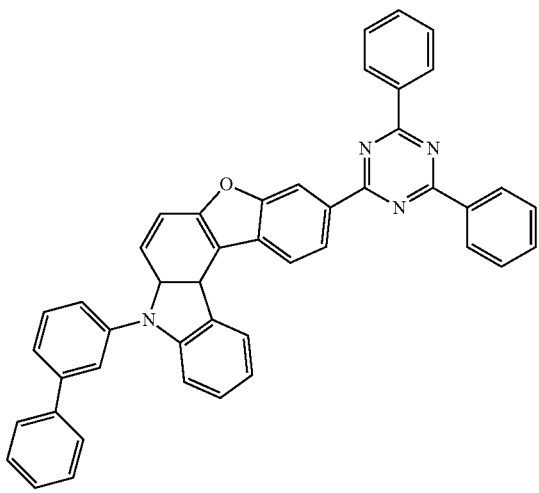
1C-3-19
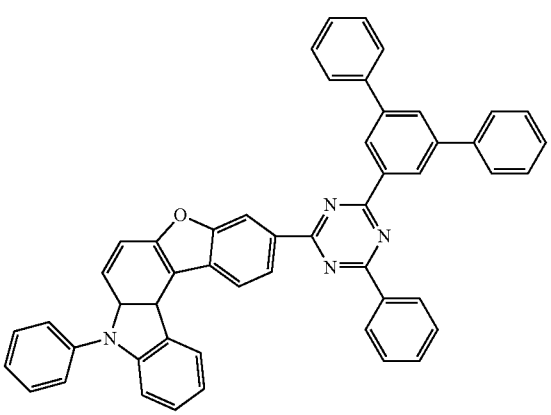
-continued
1C-3-20
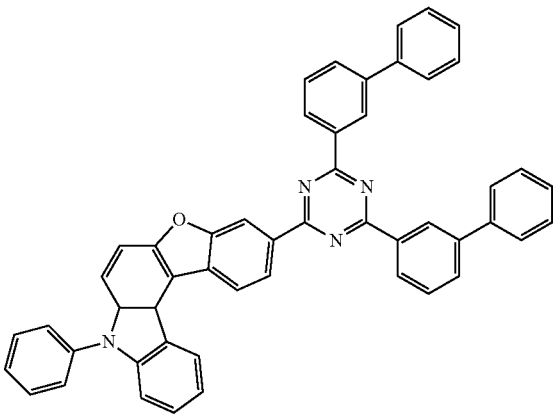
1C-3-21
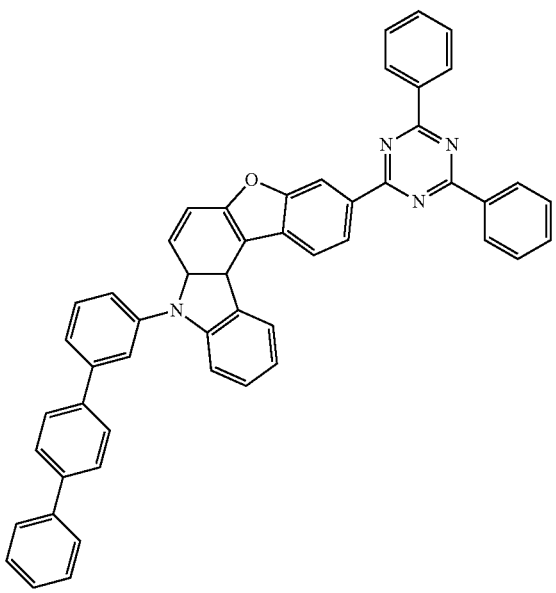
1C-3-22
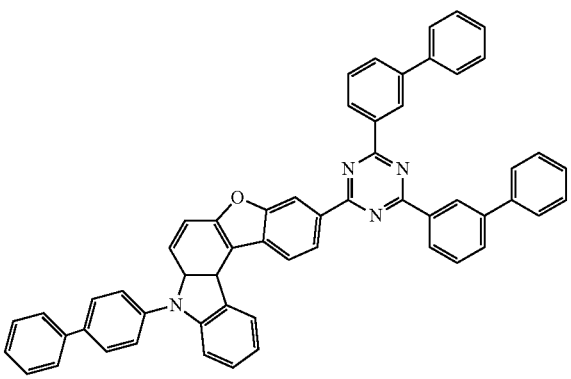

1C-3-23
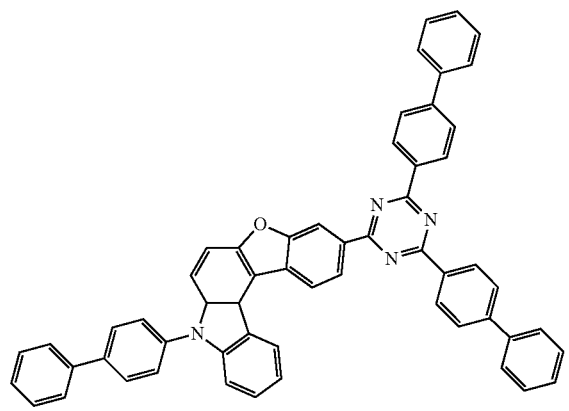
1C-3-24
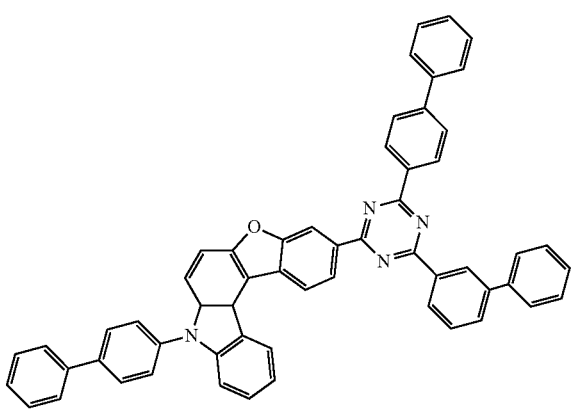
1C-3-25
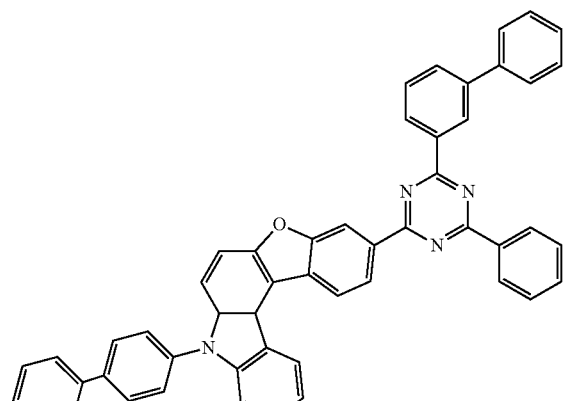
1C-3-26
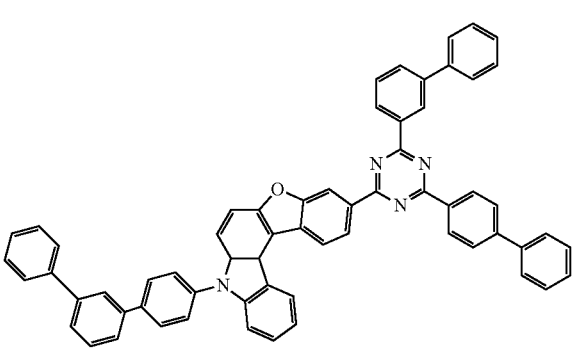
1C-3-27
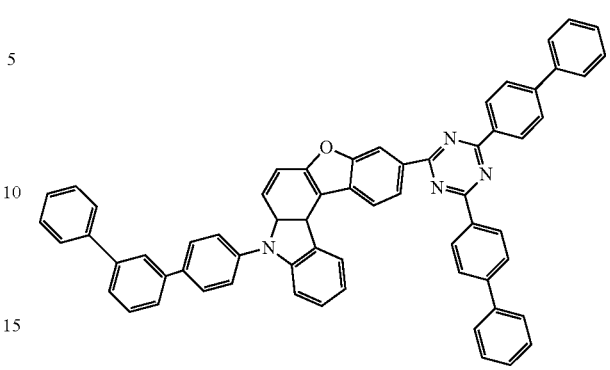
1C-3-28
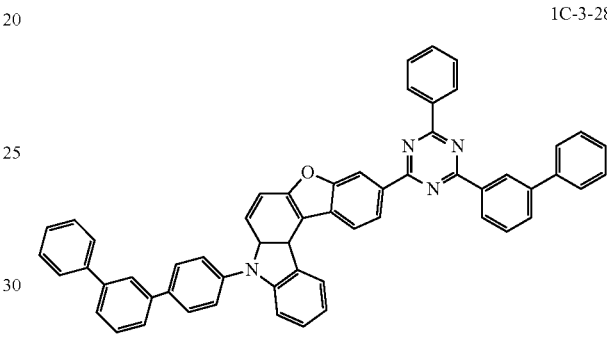
1C-3-29
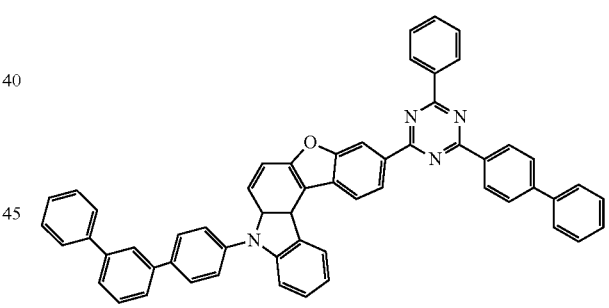
1C-3-30
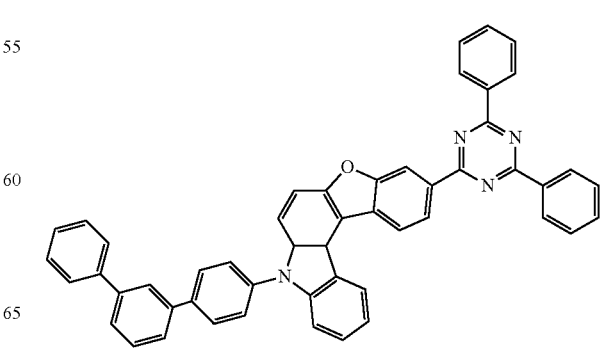

1C-3-31
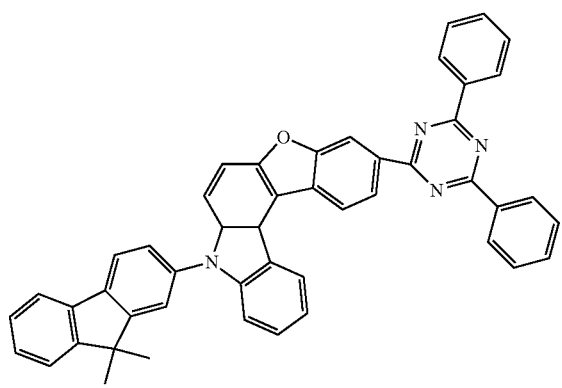
1C-3-32
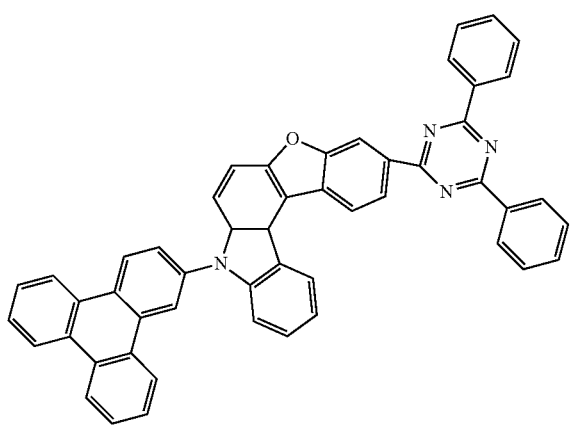
1C-3-33
1C-3-34
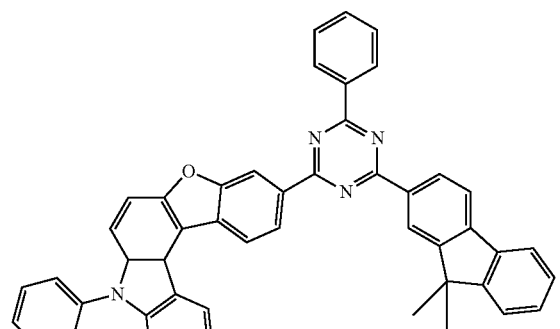
1C-3-35
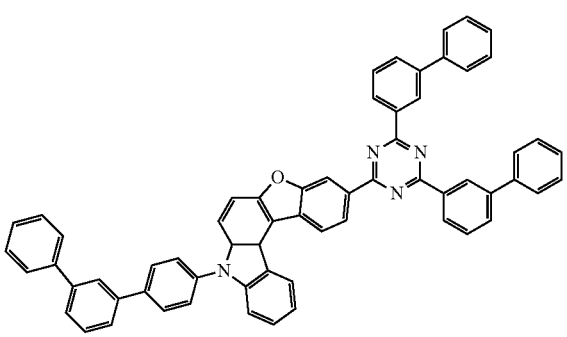
1C-3-36
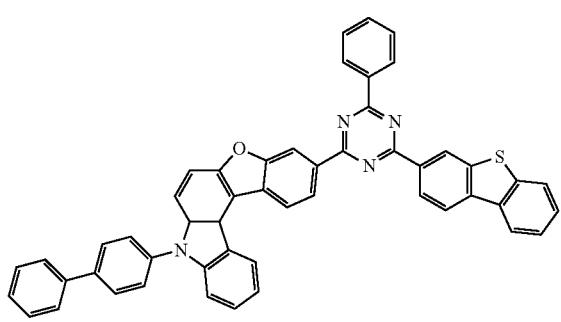
1C-3-37
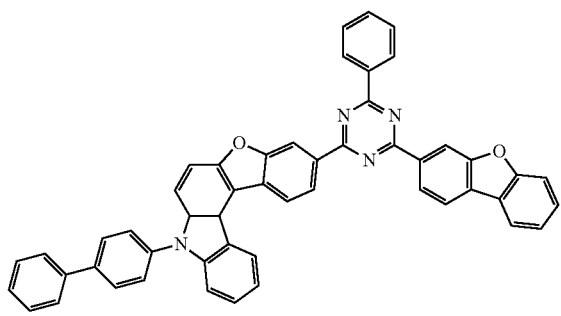

1C-3-38
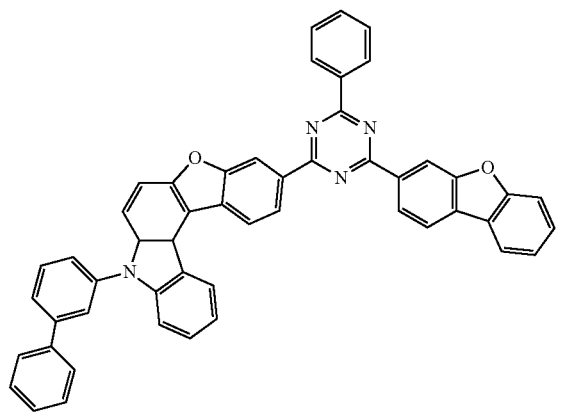
1C-3-39
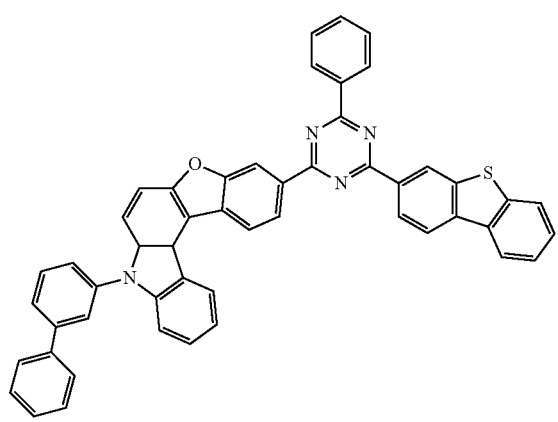
1C-3-40
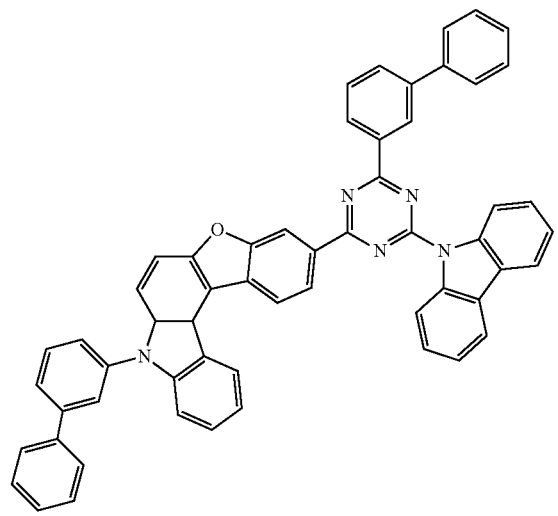
1C-3-41
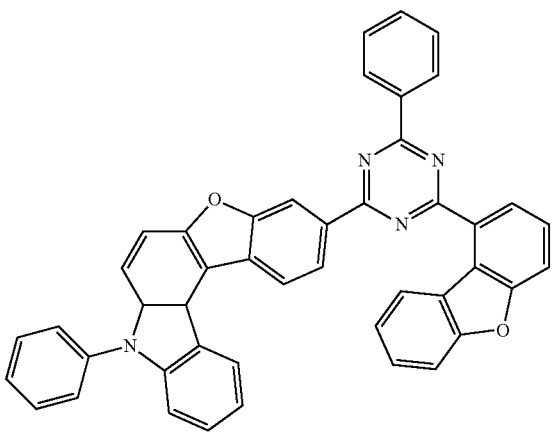
1C-3-42
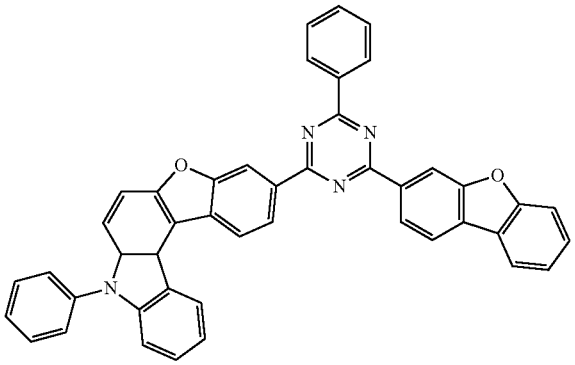
1C-3-43
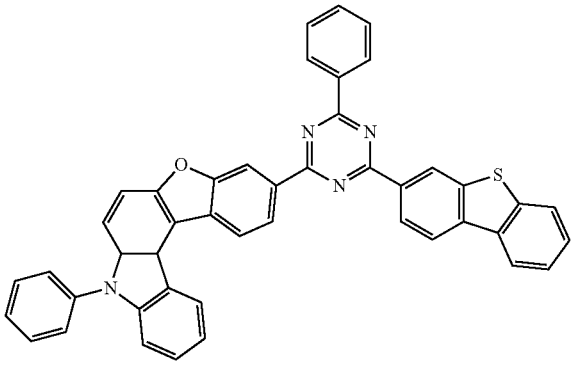

-continued
1C-3-44
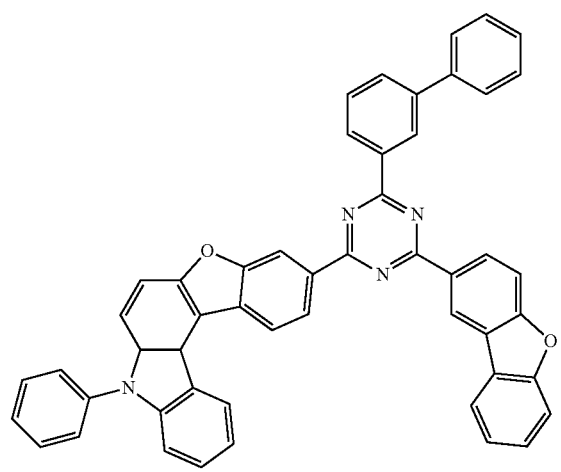
1C-3-45
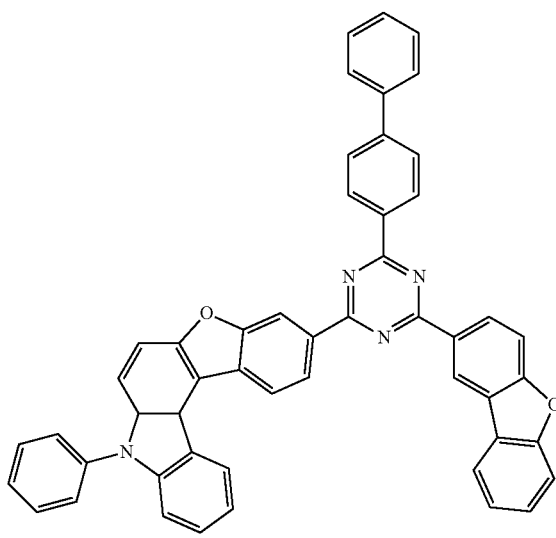
1C-3-46
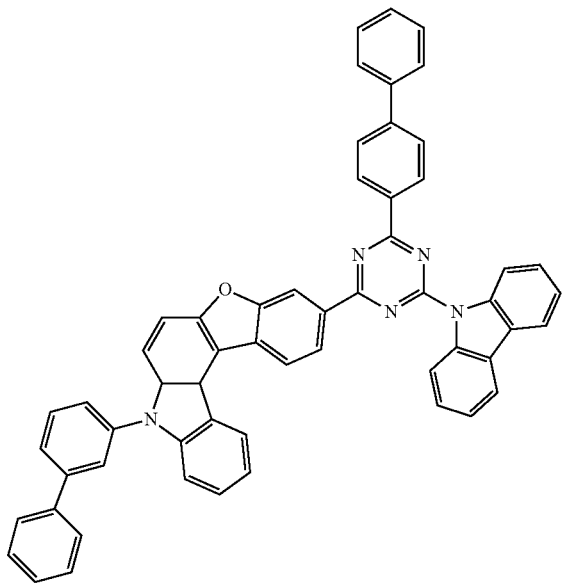
-continued
1C-3-47
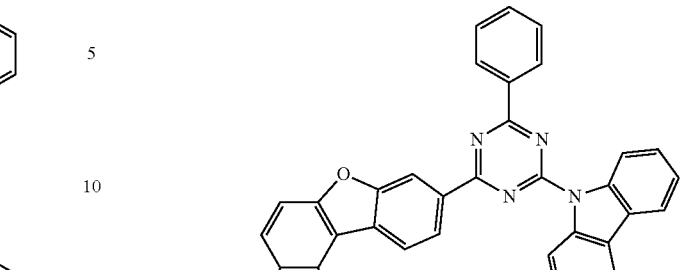
1C-3-48
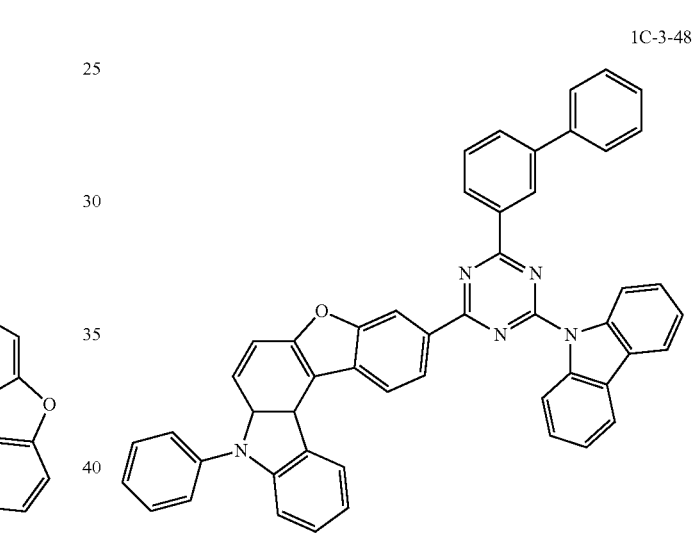
1C-3-49
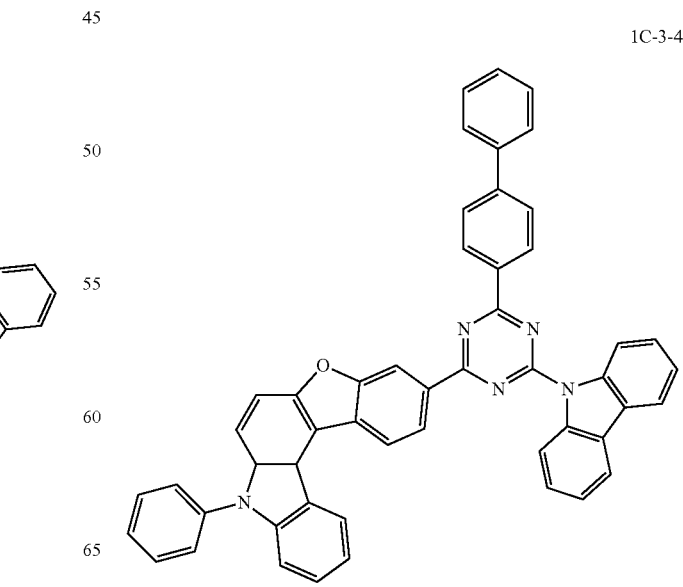

1C-3-50
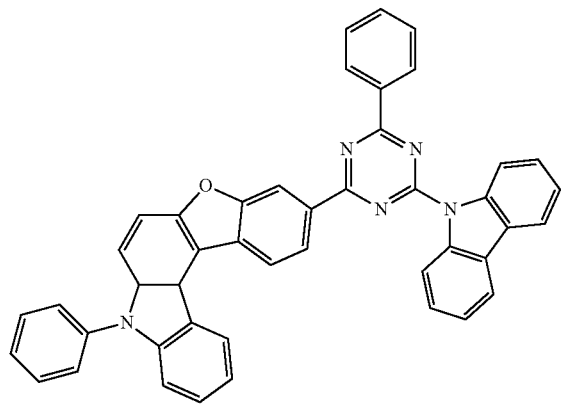
1C-3-51
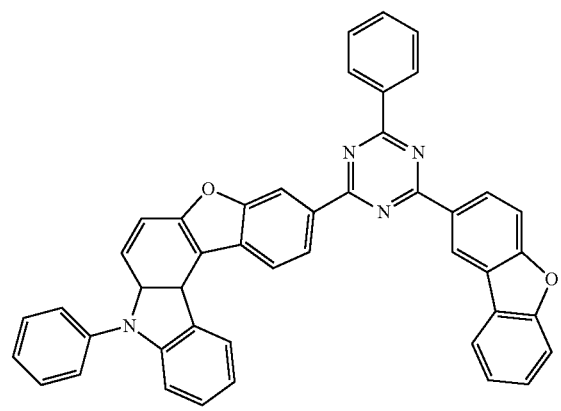
1C-3-52
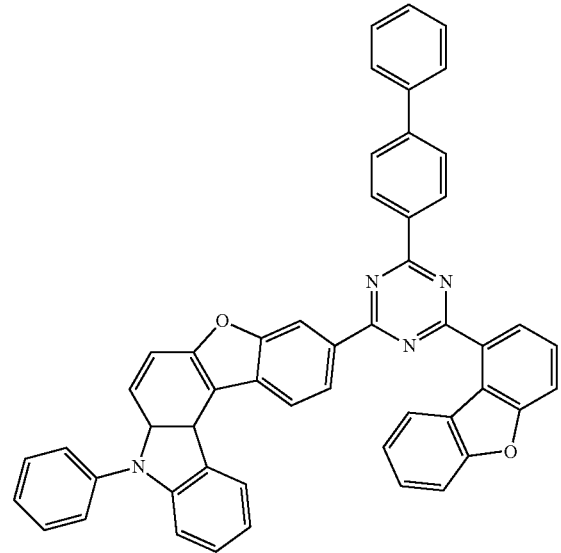
1C-3-53
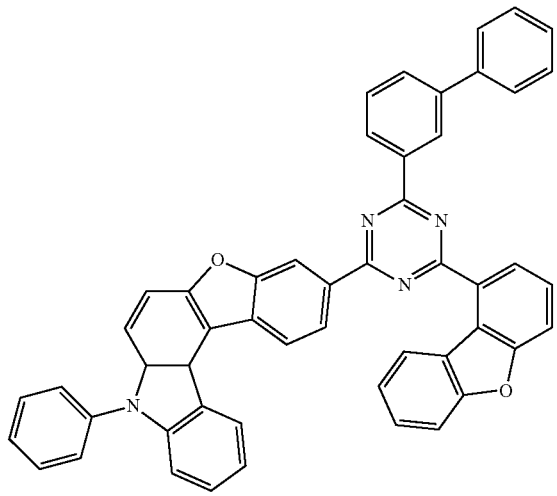
1C-3-54
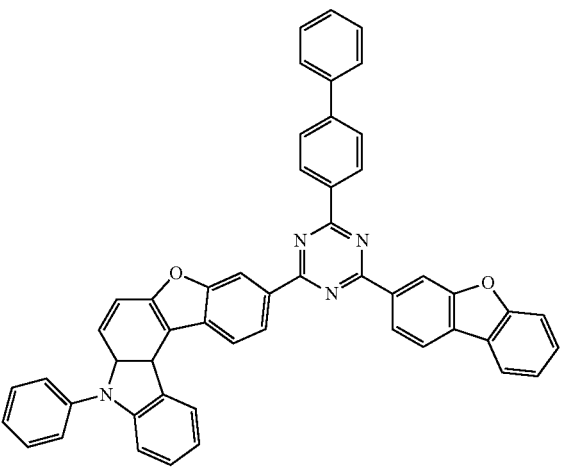
1C-3-55
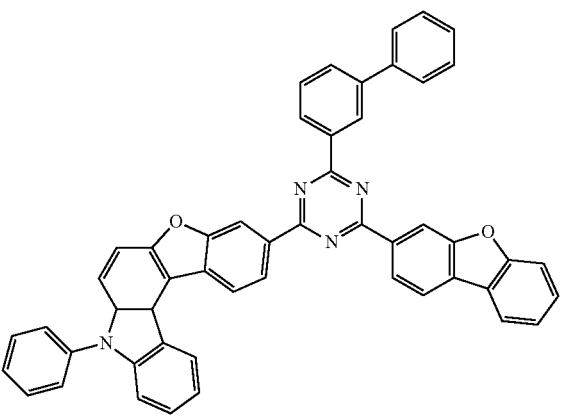

1C-3-56
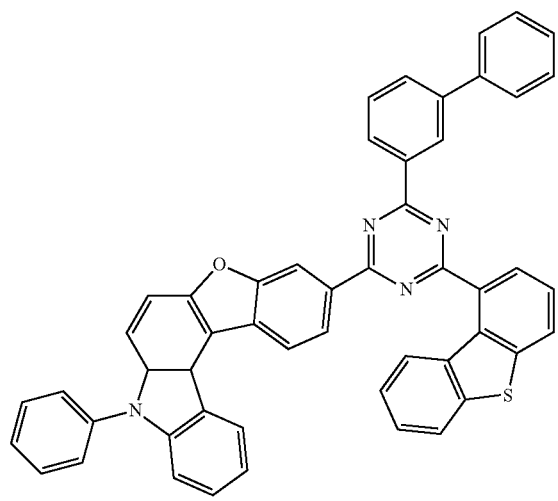
1C-3-59
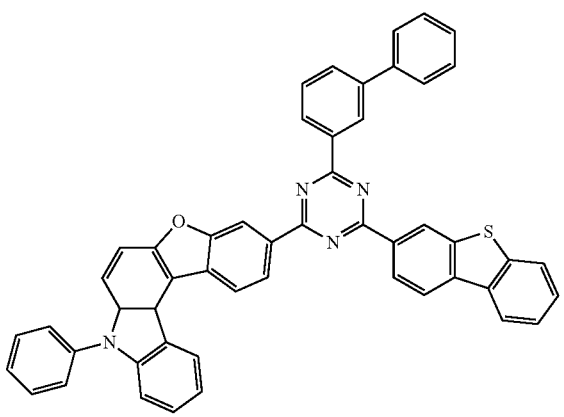
1C-3-57
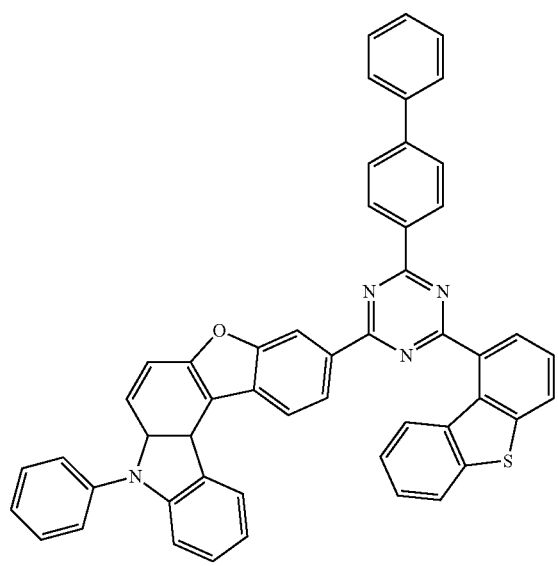
1C-3-60
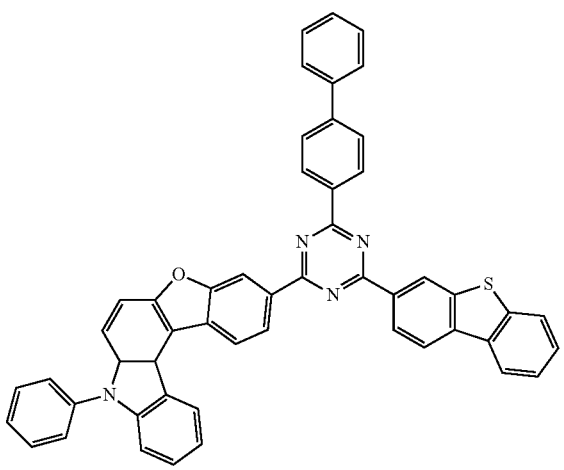
1C-3-58
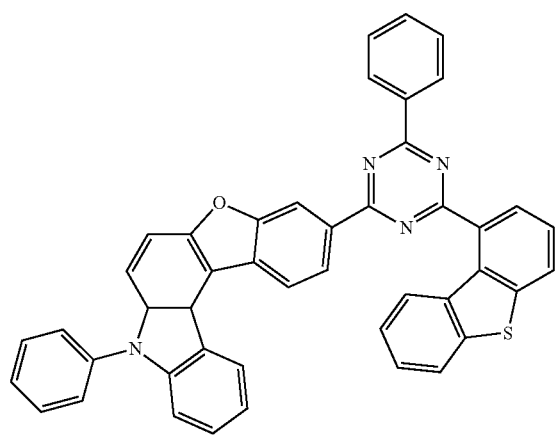
1C-3-61

-continued
1C-3-62
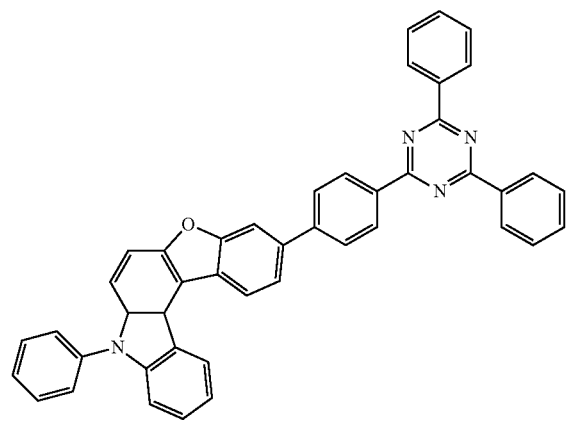
1C-3-63
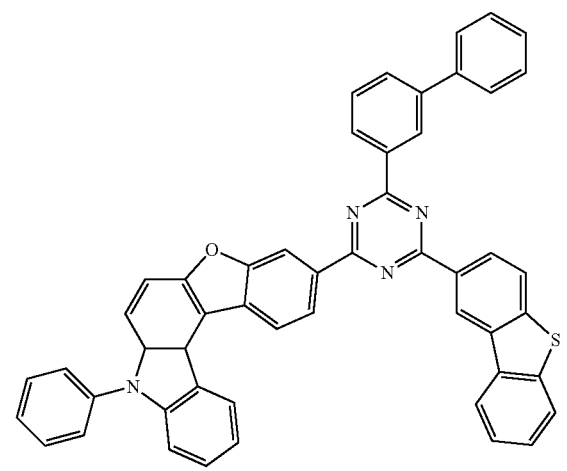
1C-3-64
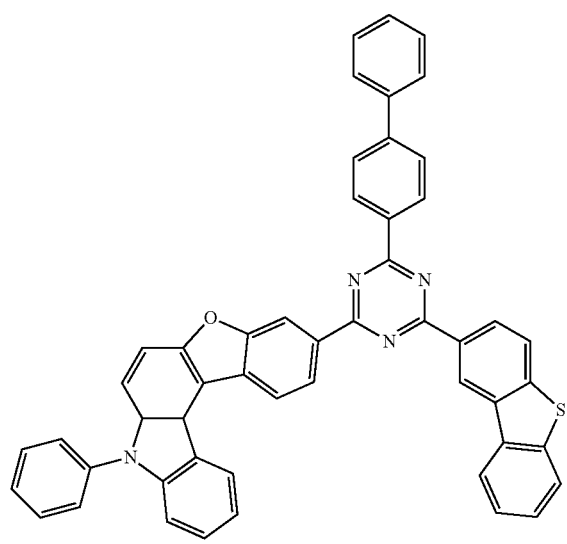
-continued
1C-3-65
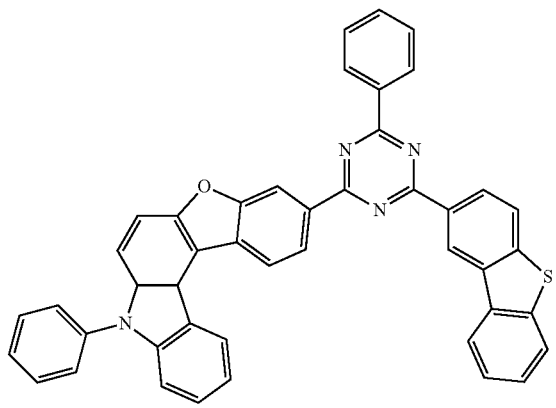
1C-3-66
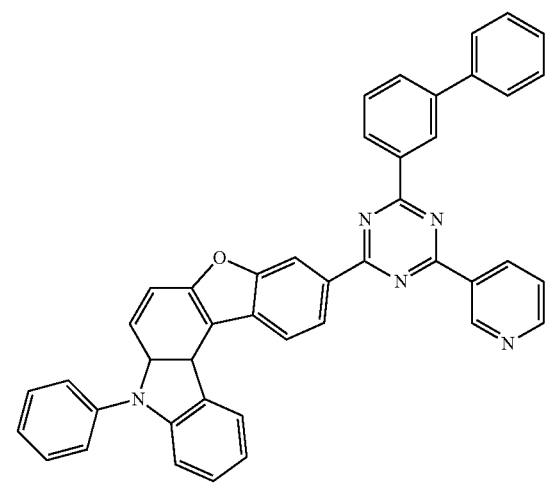
1C-3-67
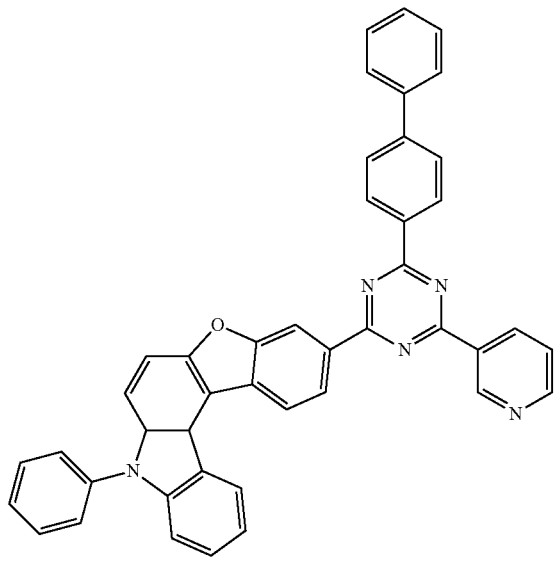

-continued
1C-3-68
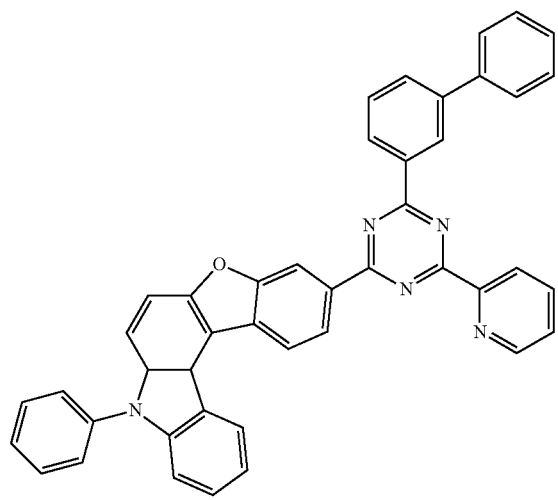
1C-3-69
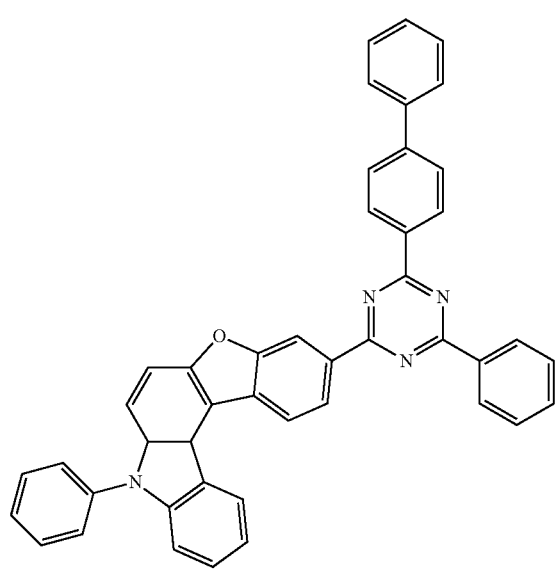
1C-3-70
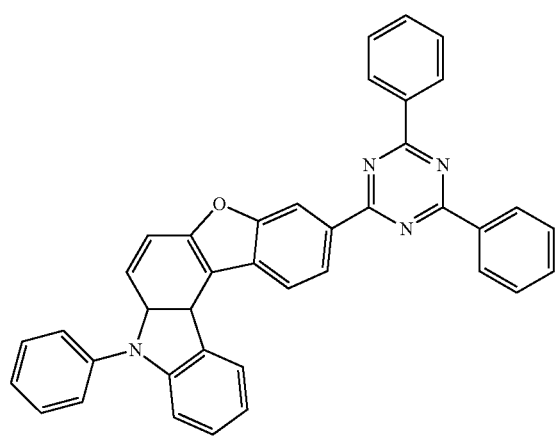
-continued
1C-3-71
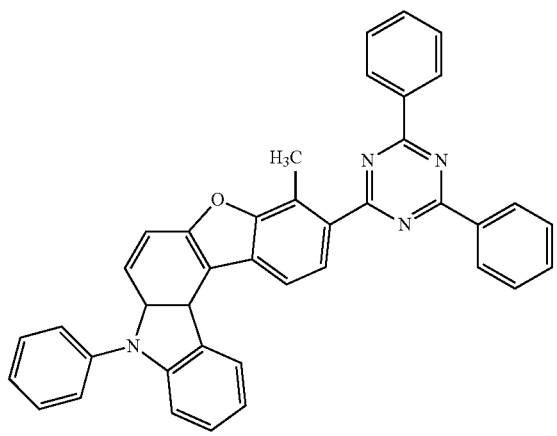
1C-3-72
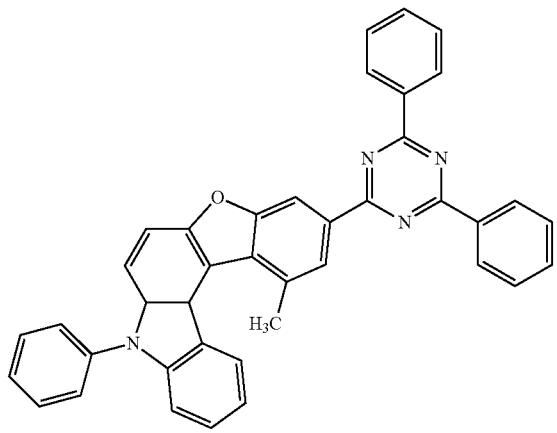
1C-3-73
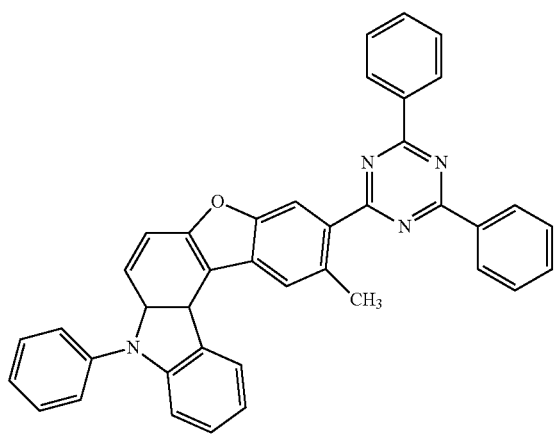

1C-3-74
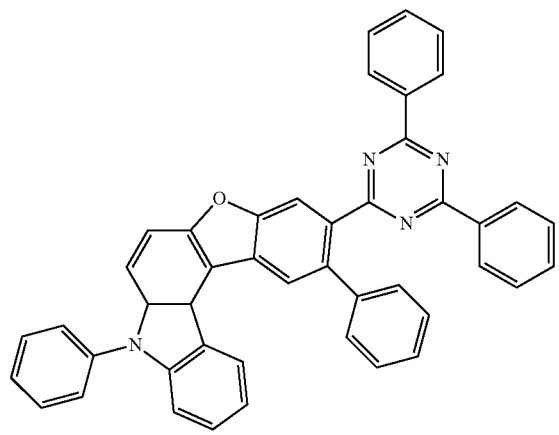
1C-3-75
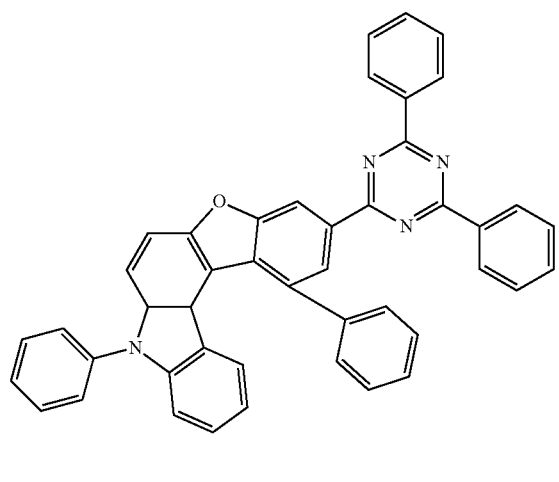
1C-3-76
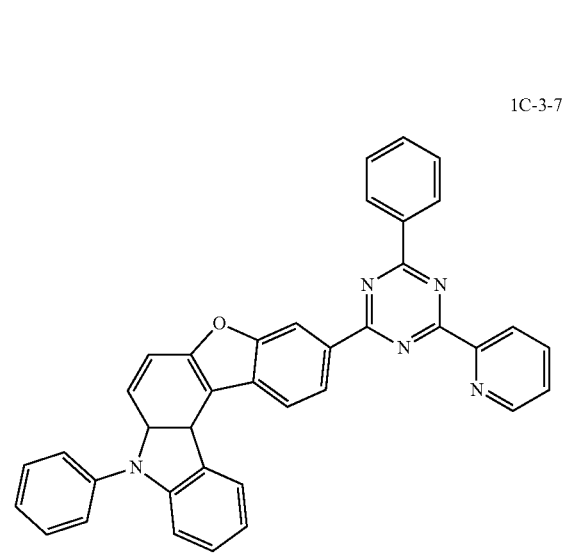
1C-3-77
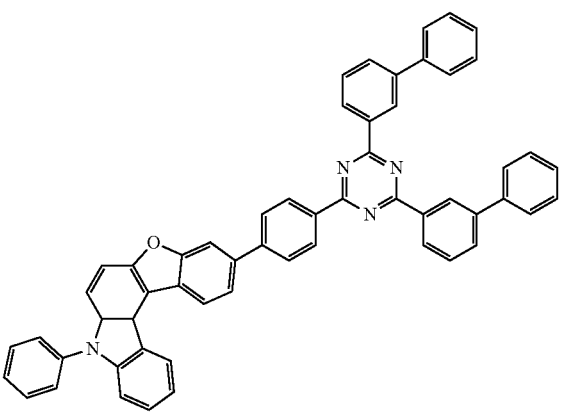
1C-3-78
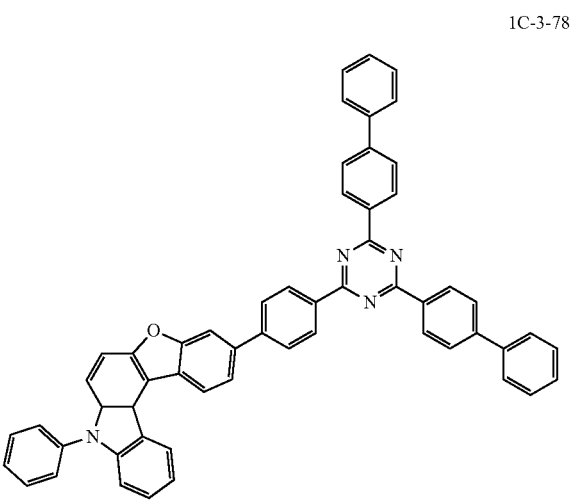
1C-3-79
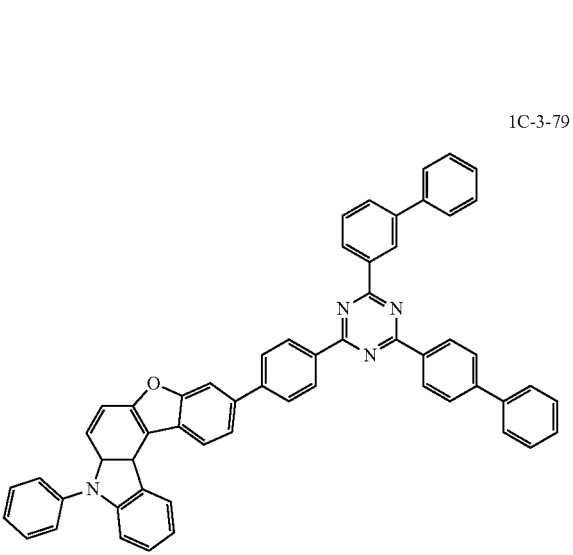

1C-3-80
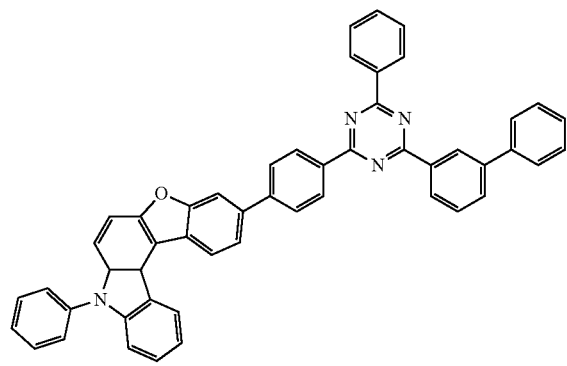
1C-3-81
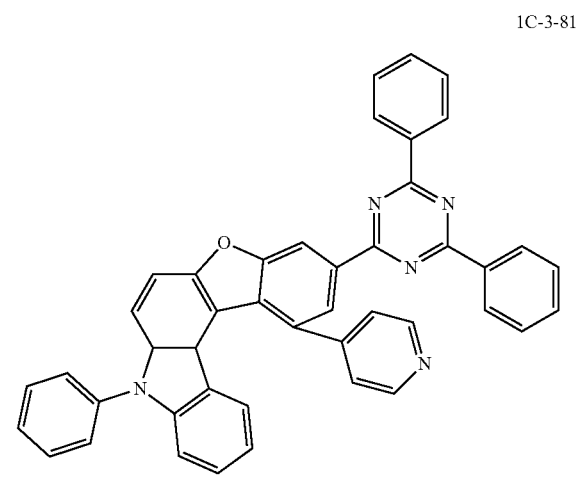
1C-3-82
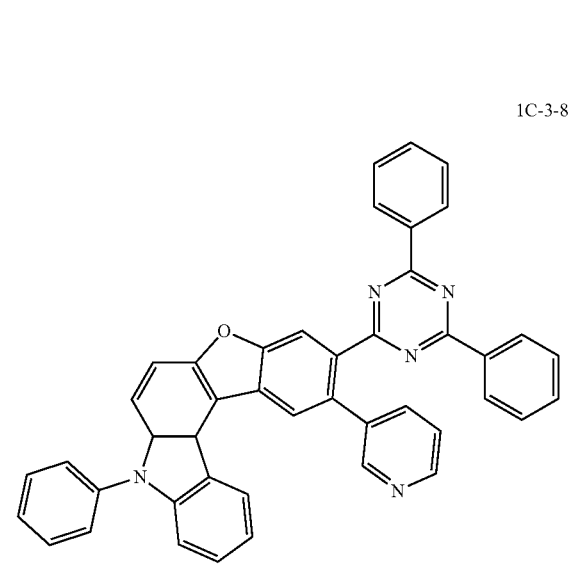
1C-3-83
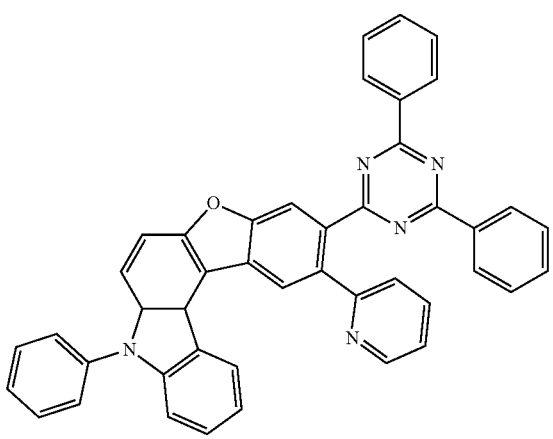
1C-4-1
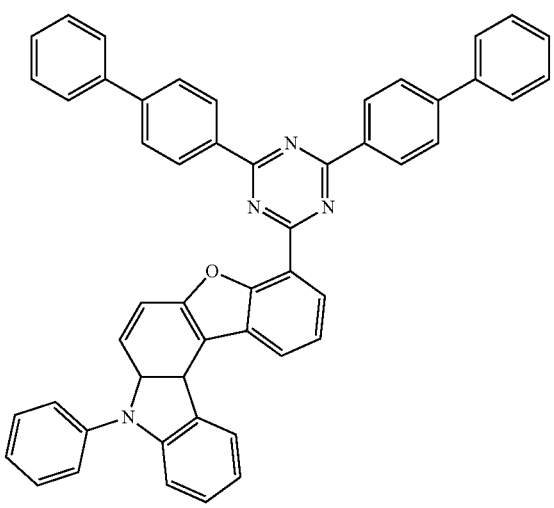
1C-4-2
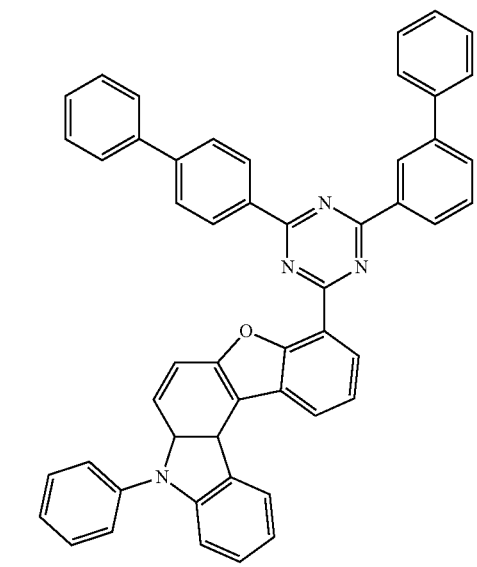

1C-4-3
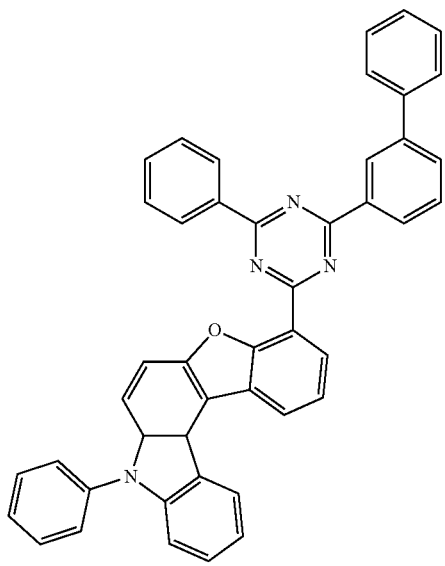
1C-4-4
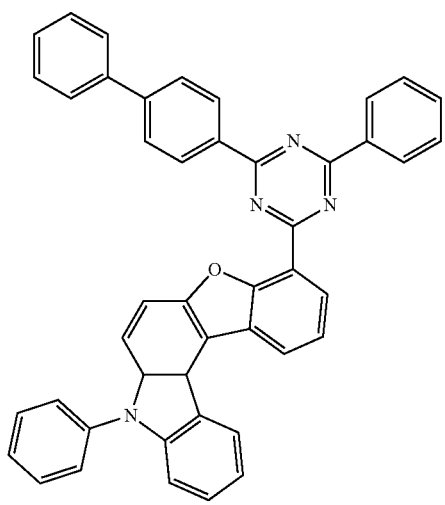
1C-4-5
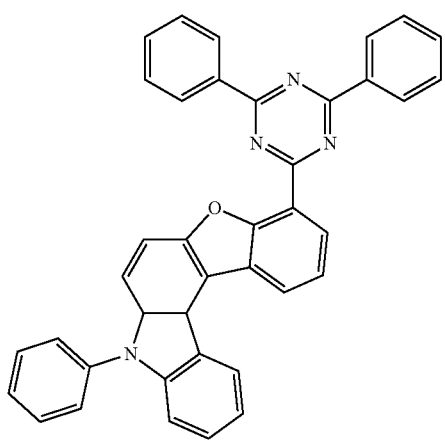
1C-4-6
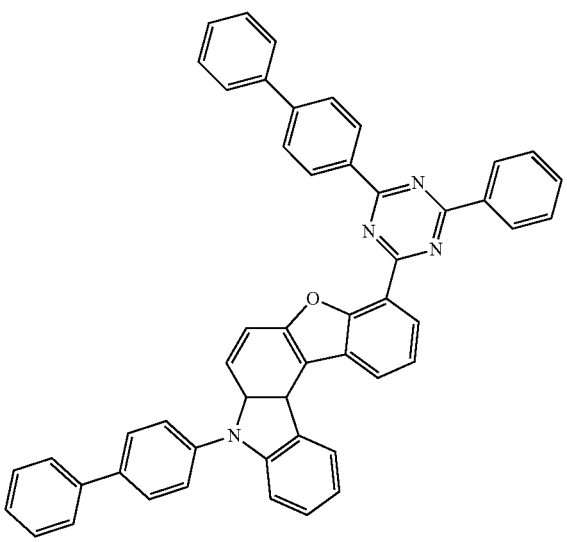
1C-4-7
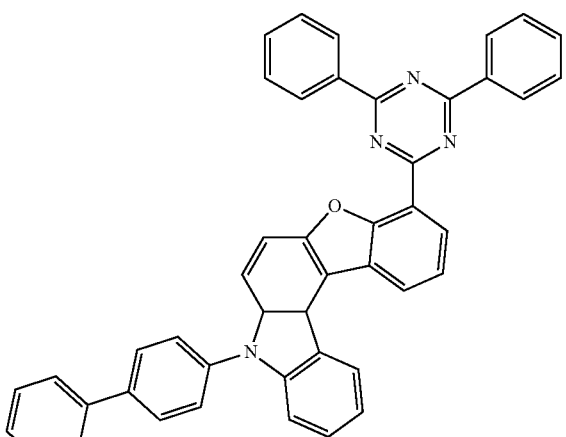
1C-4-8
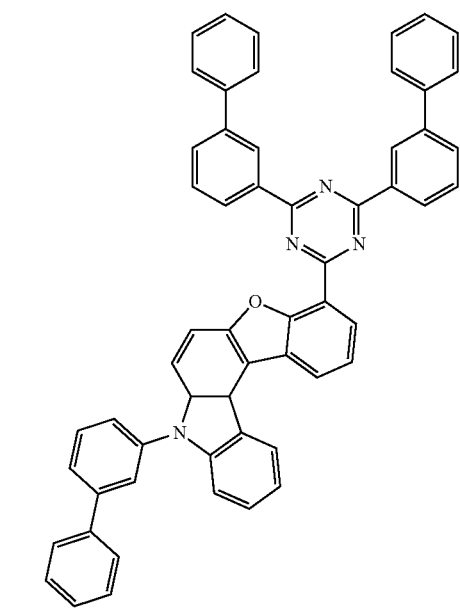

357
-continued
1C-4-9
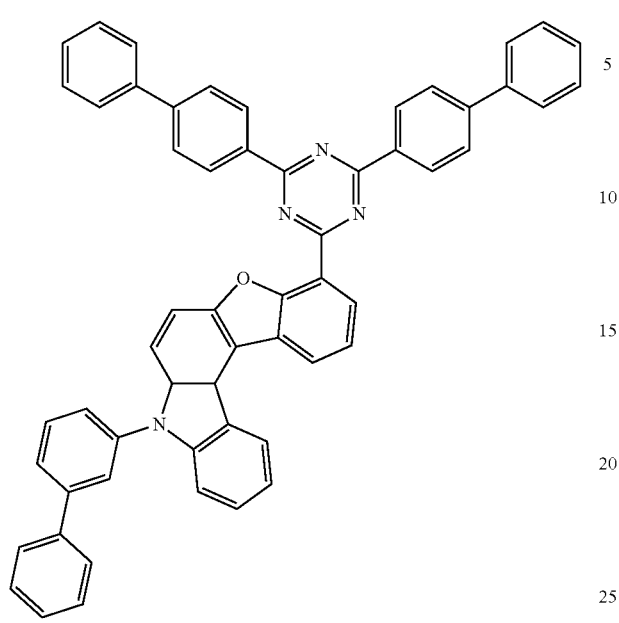
1C-4-10
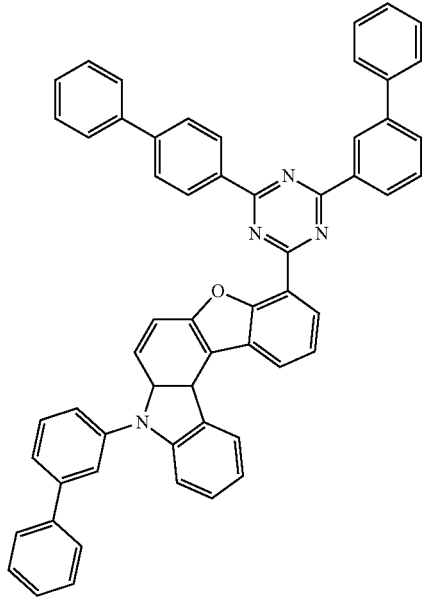
358
-continued
1C-4-11
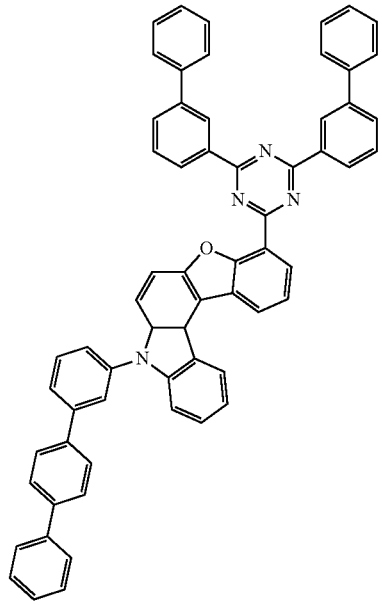
1C-4-12
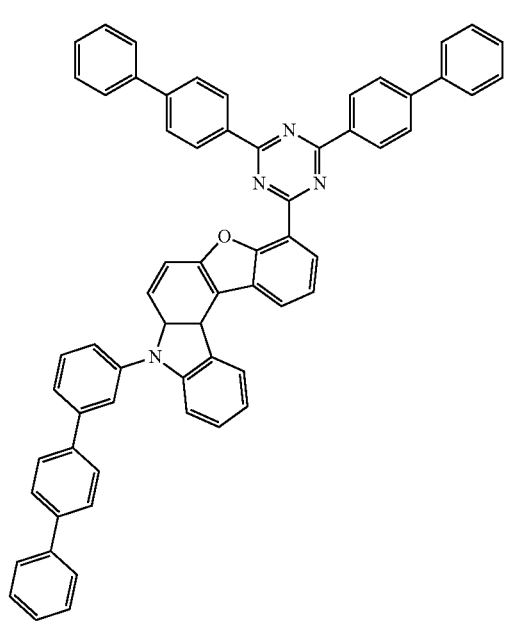

1C-4-13
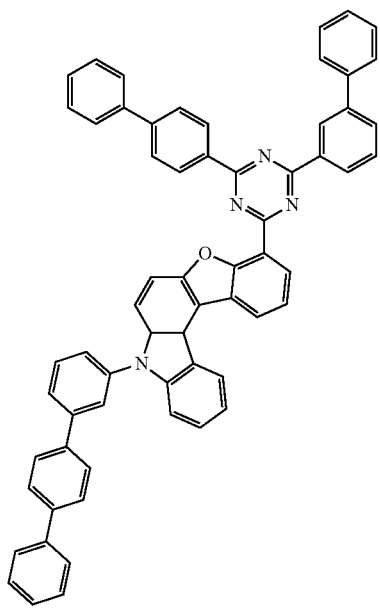
1C-4-14
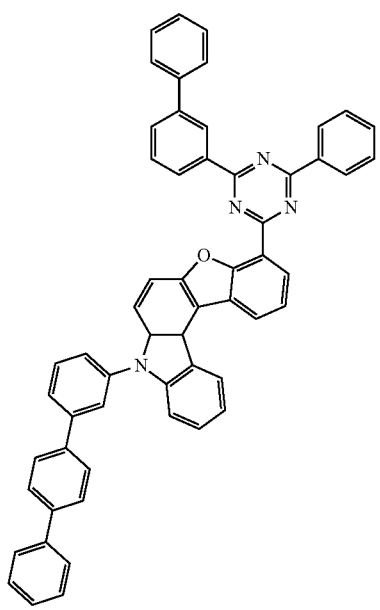
1C-4-15
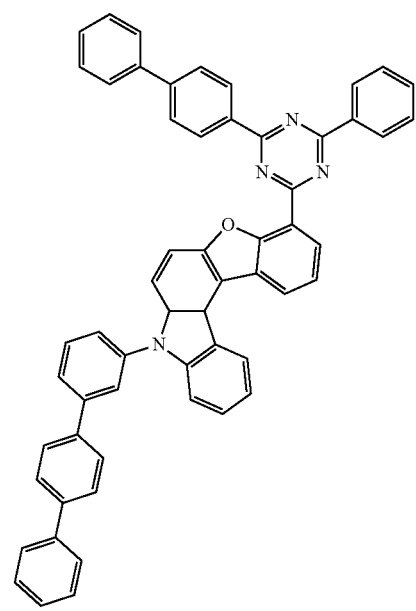
1C-4-16
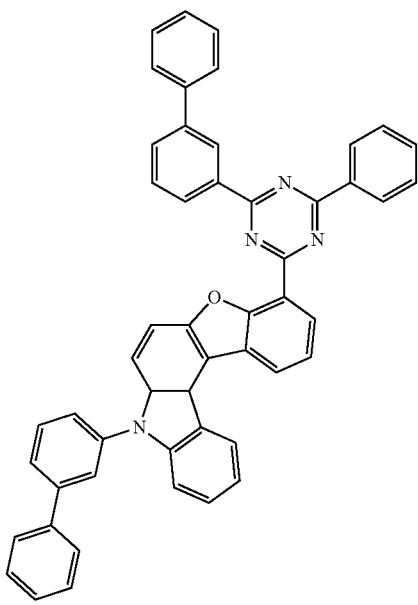

1C-4-17
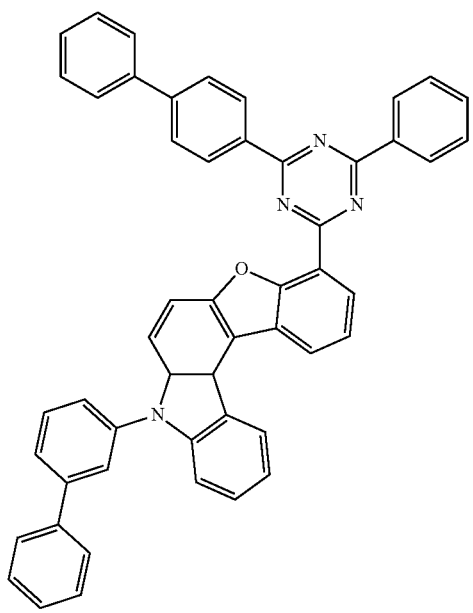
1C-4-19
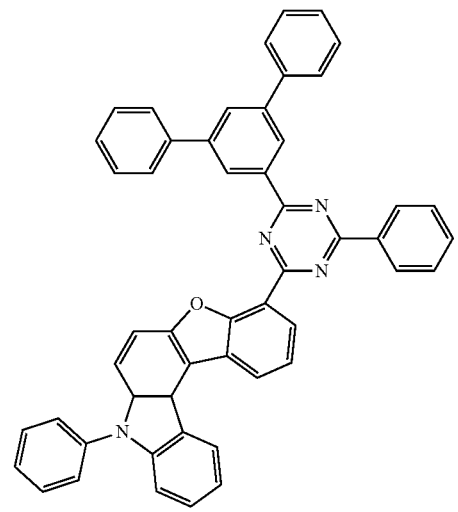
1C-4-18
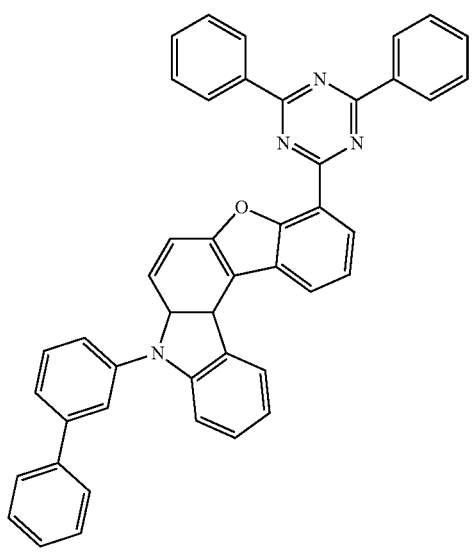
1C-4-20
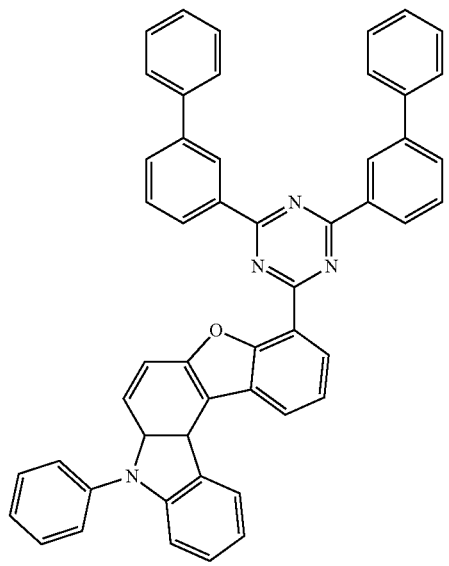

1C-4-21
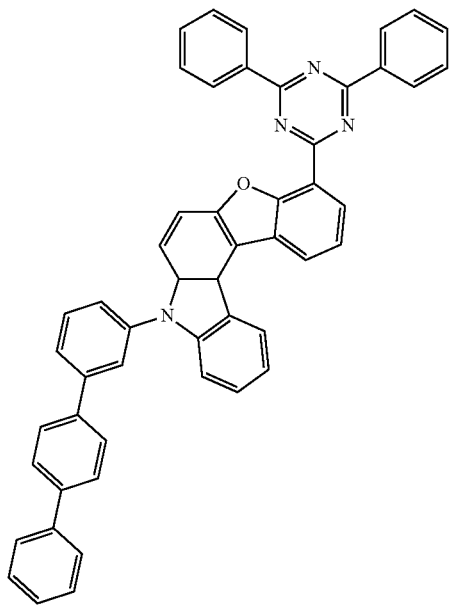
1C-4-22
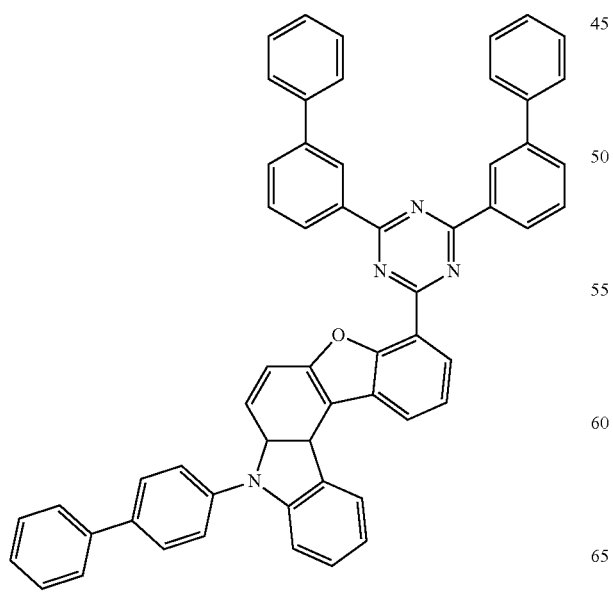
1C-4-23
1C-4-24
1C-4-25
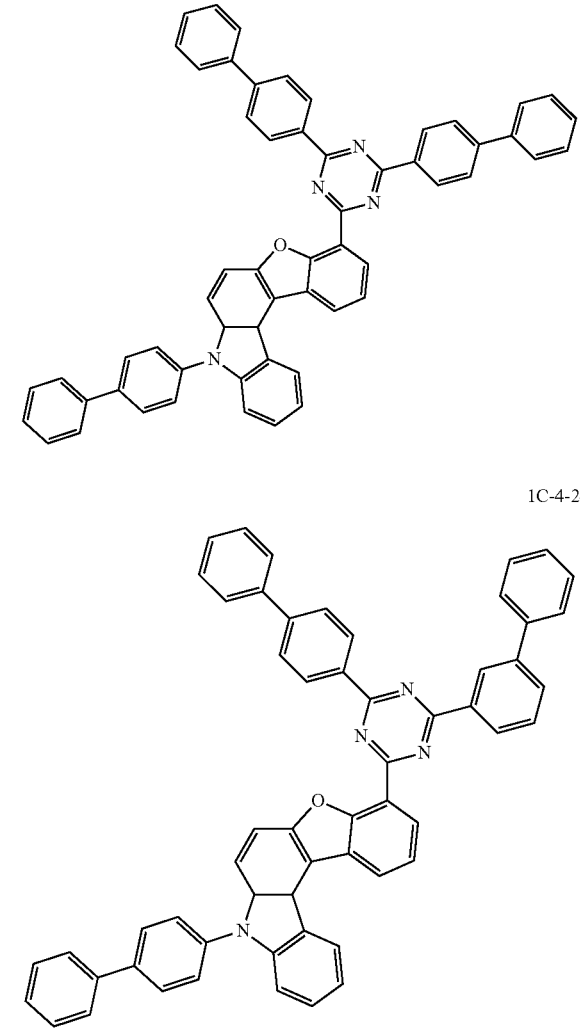
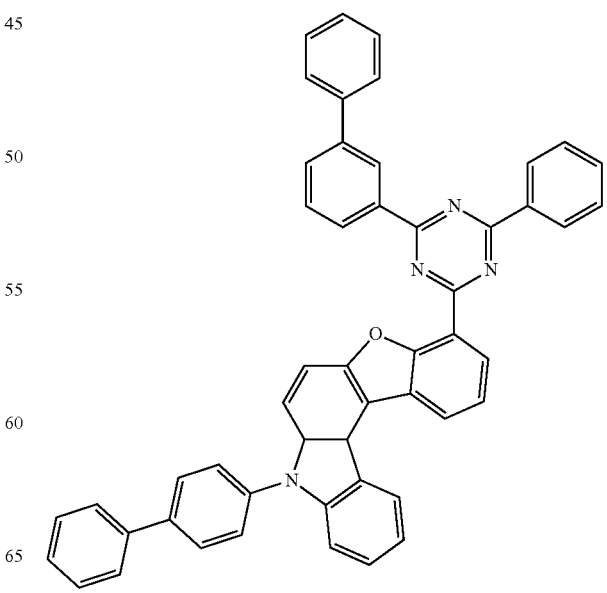

365
-continued
1C-4-26
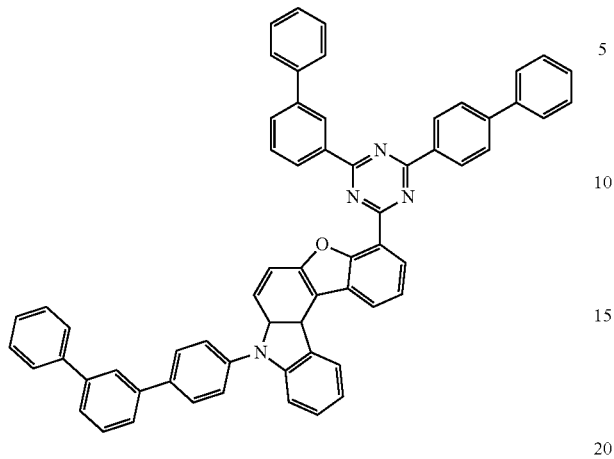
1C-4-27
1C-4-28
366
-continued
1C-4-29
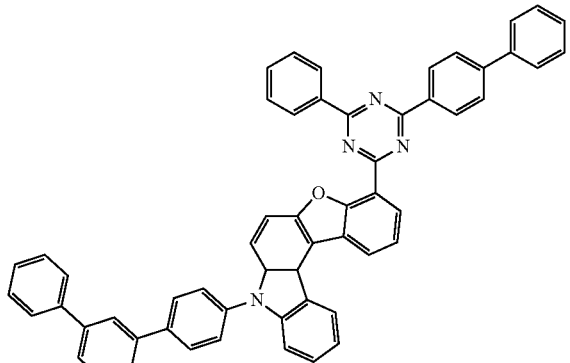
1C-4-30
1C-4-31
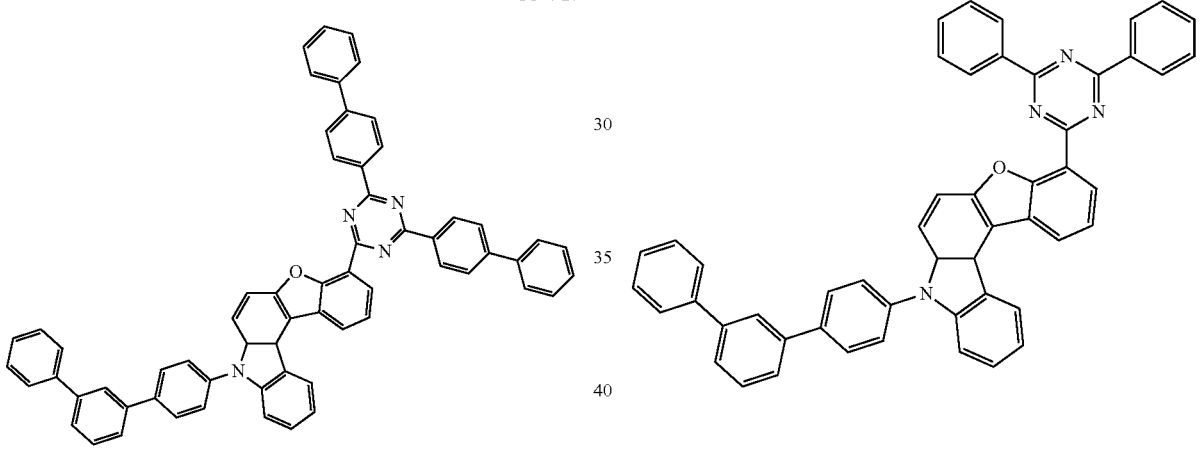
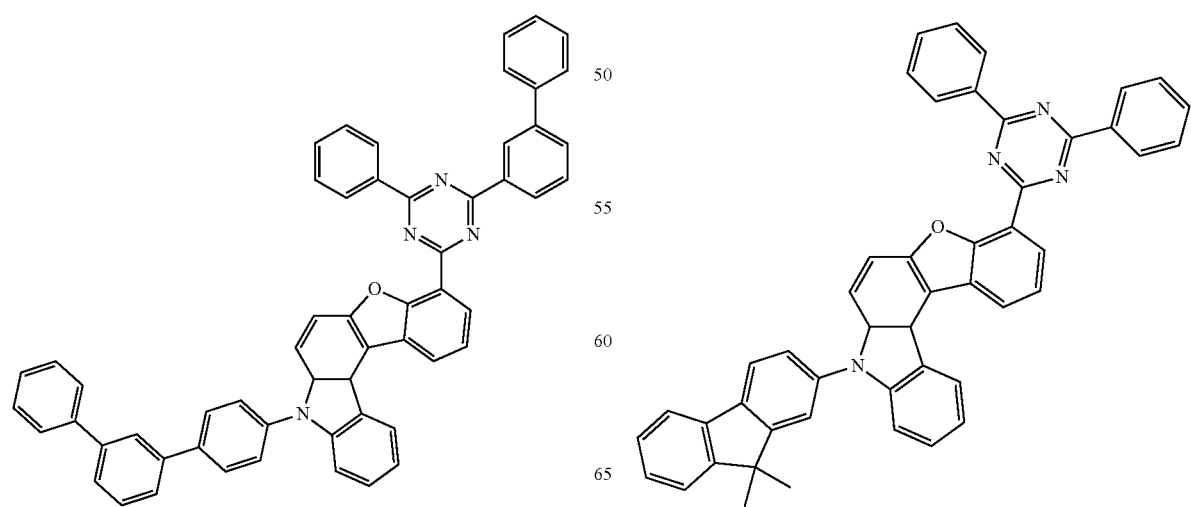

1C-4-32
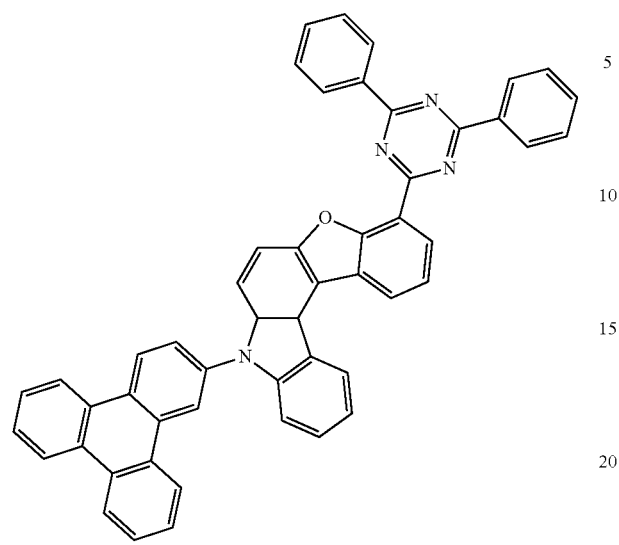
1C-4-33
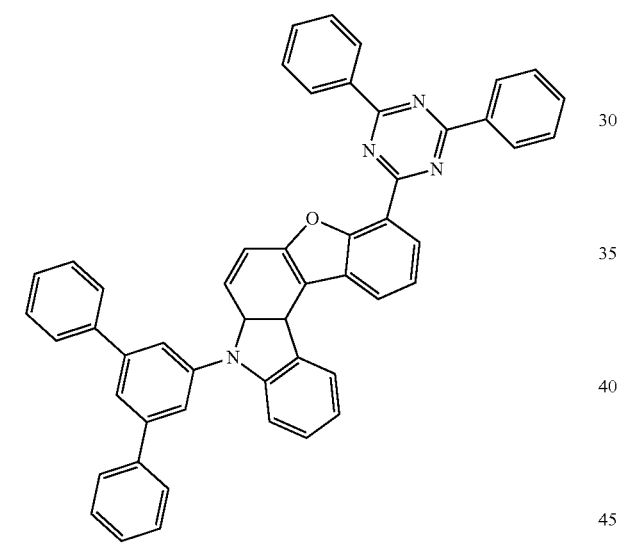
1C-4-34
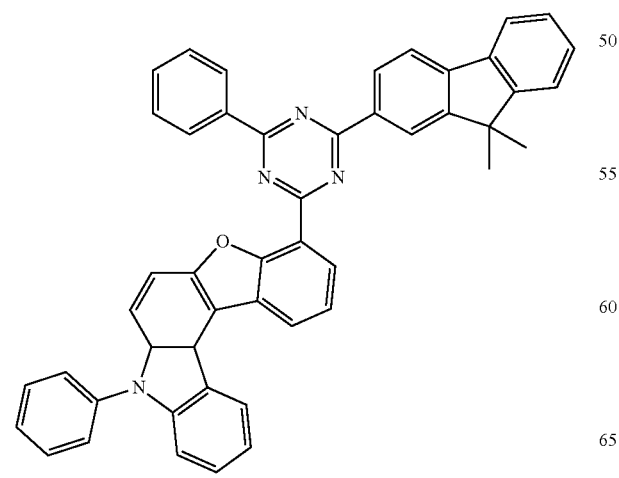
1C-4-35
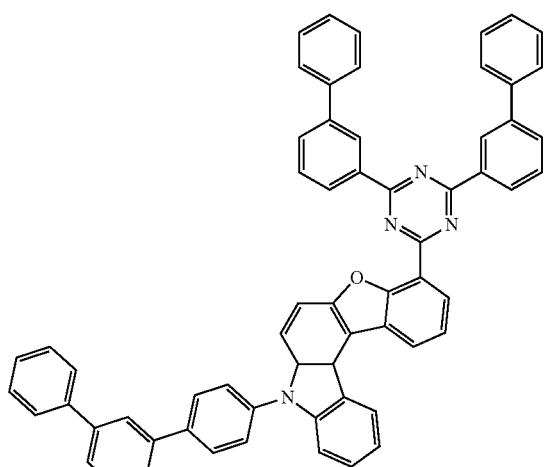
1C-4-36
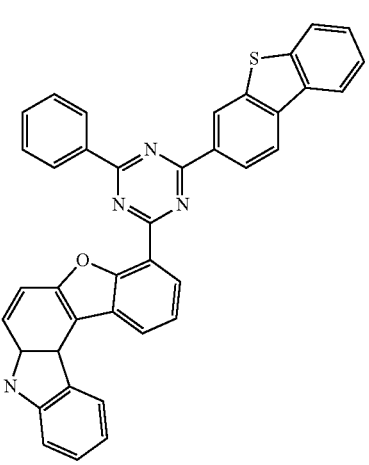
1C-4-37
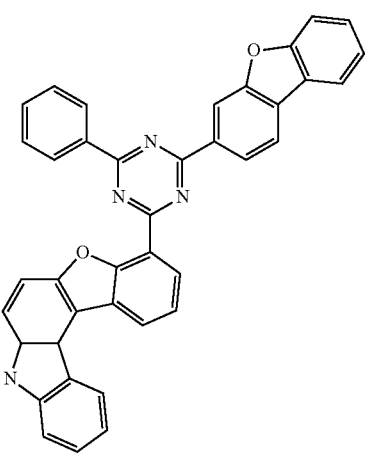

1C-4-38
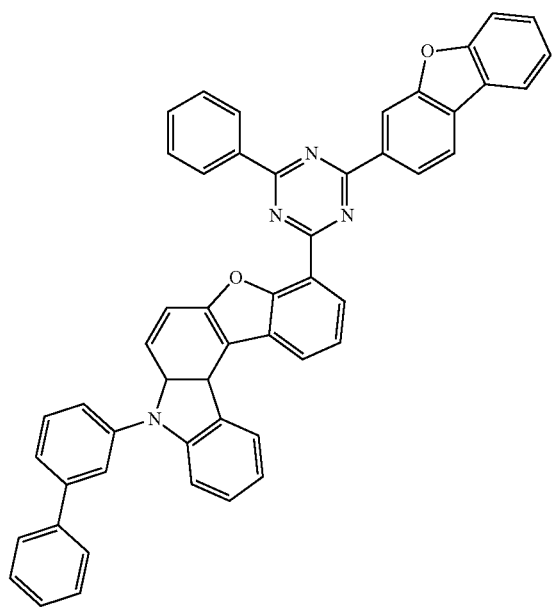
1C-4-40
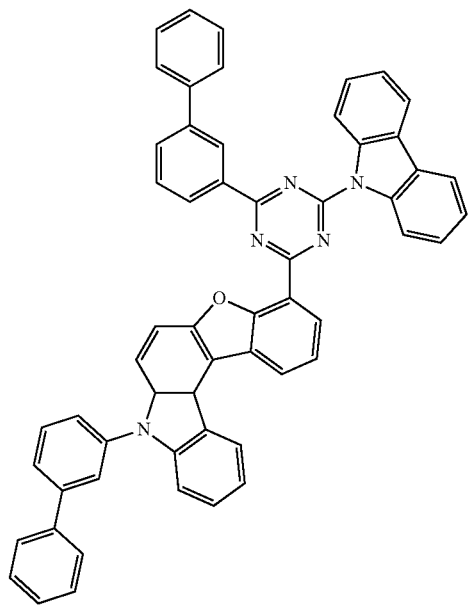
1C-4-41
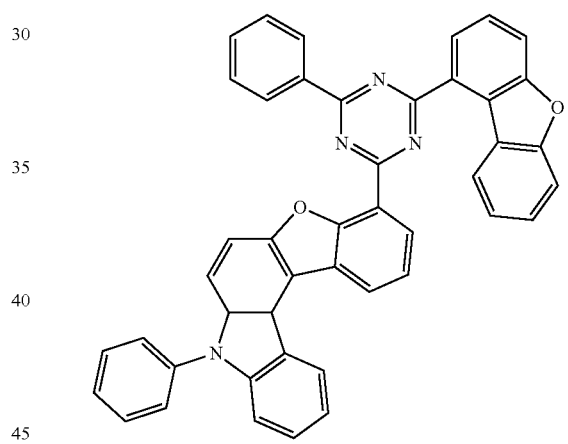
1C-4-39
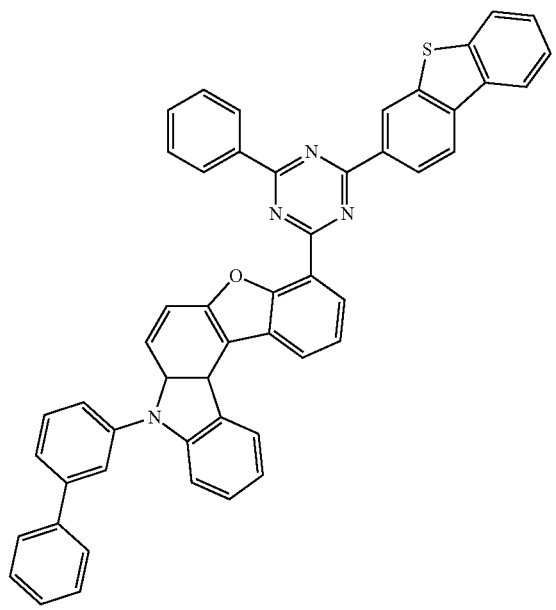
1C-4-42
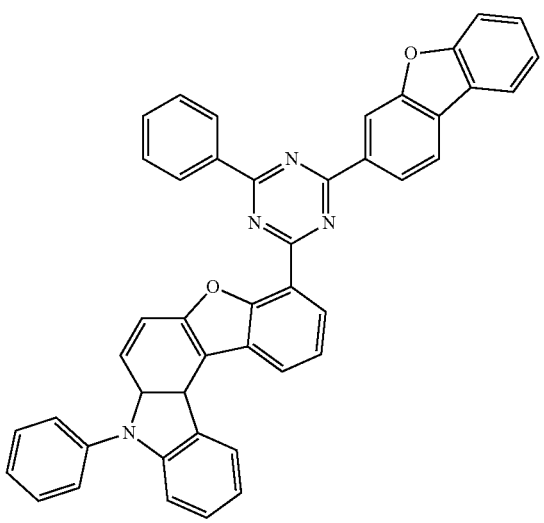

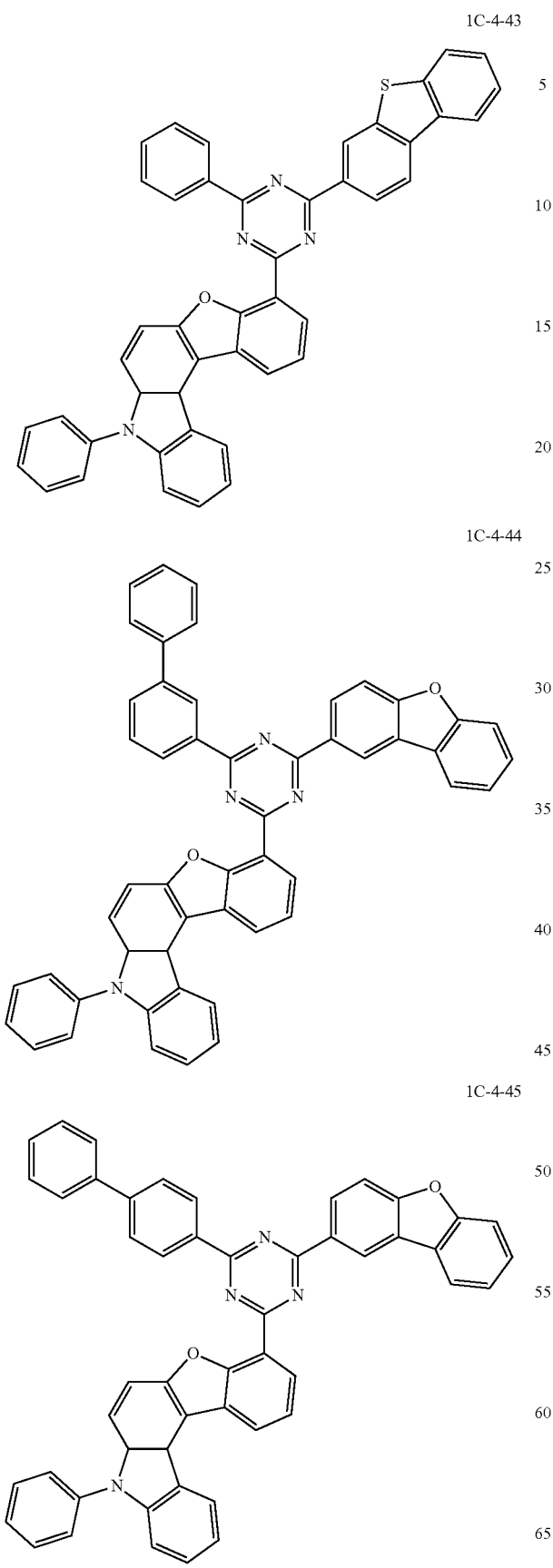
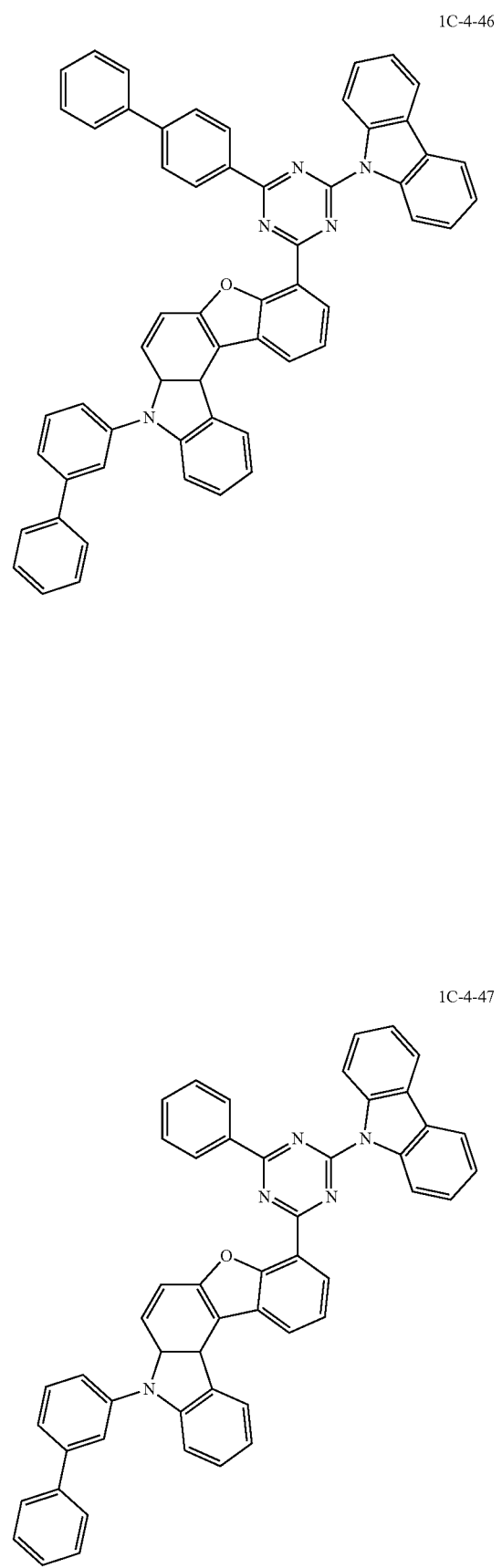

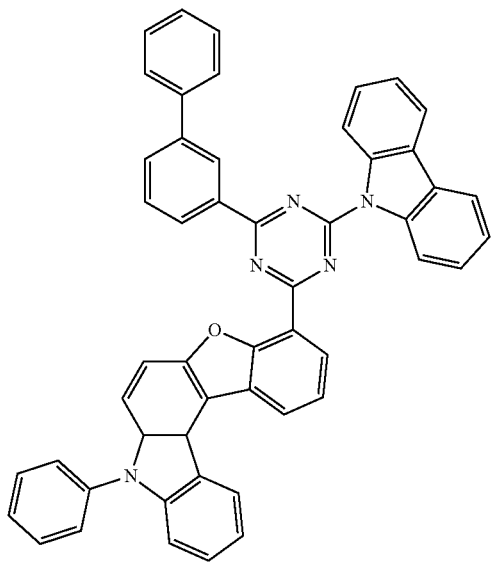

1C-4-54
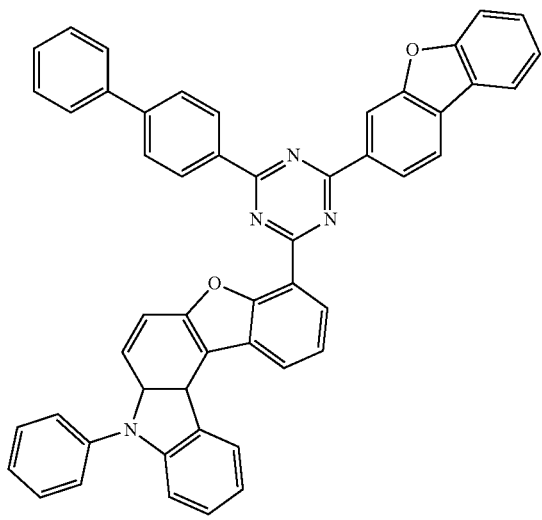
1C-4-56
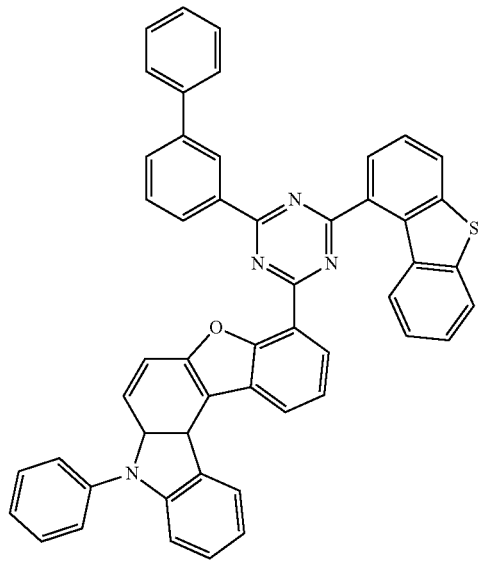
1C-4-57
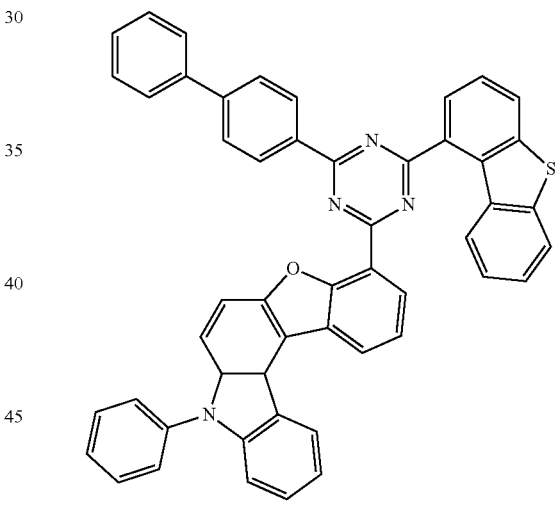
1C-4-55
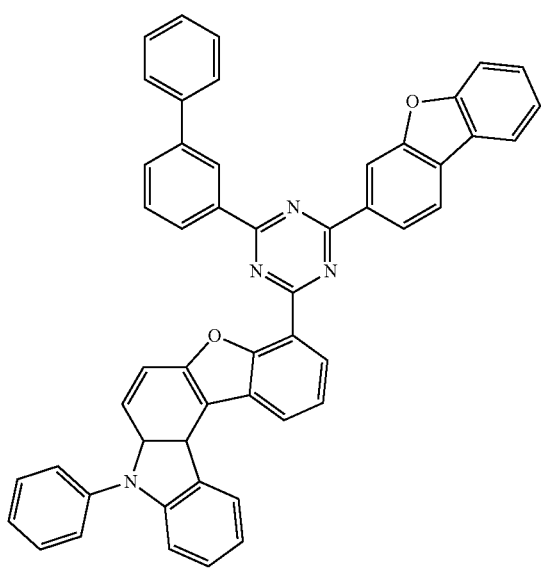
1C-4-58
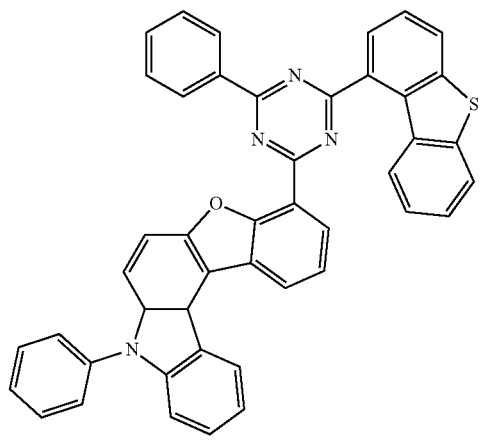

1C-4-59
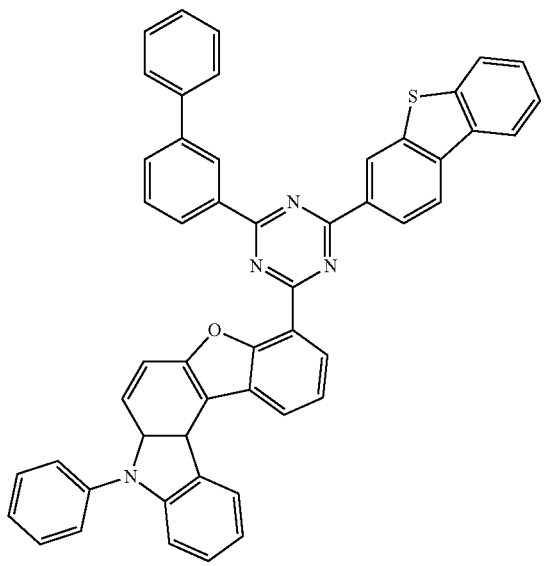
1C-4-60
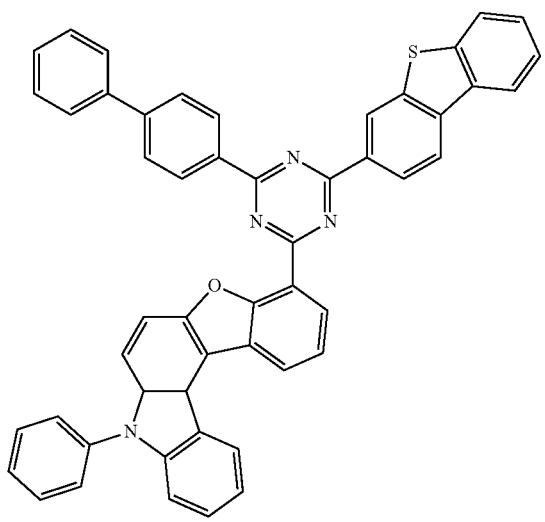
1C-4-61
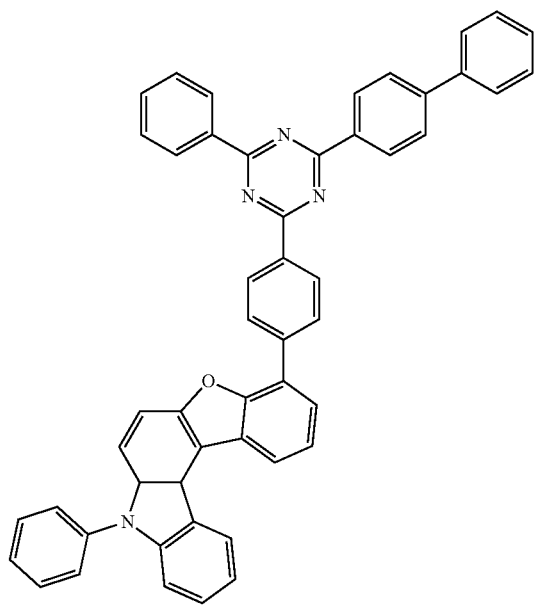
1C-4-62
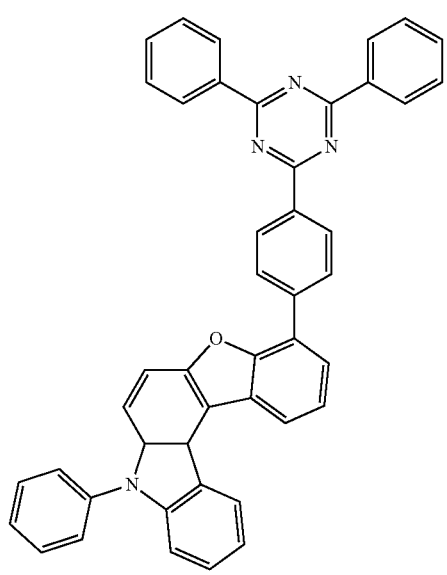

1C-4-63
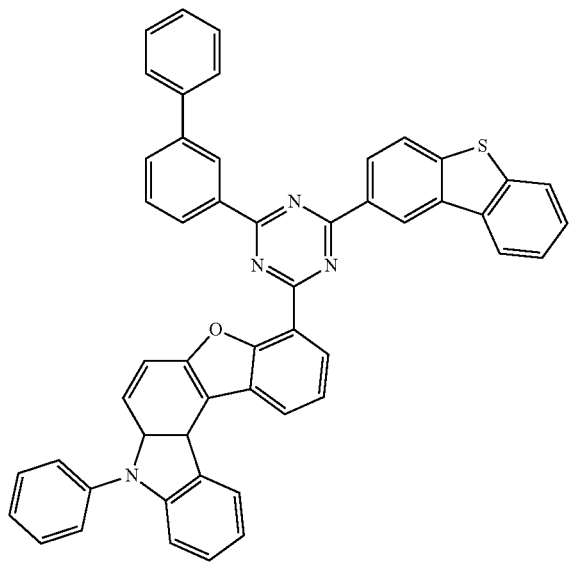
1C-4-64
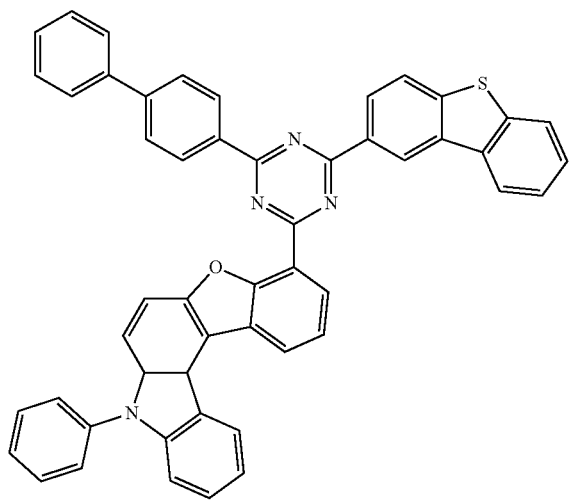
1C-4-65
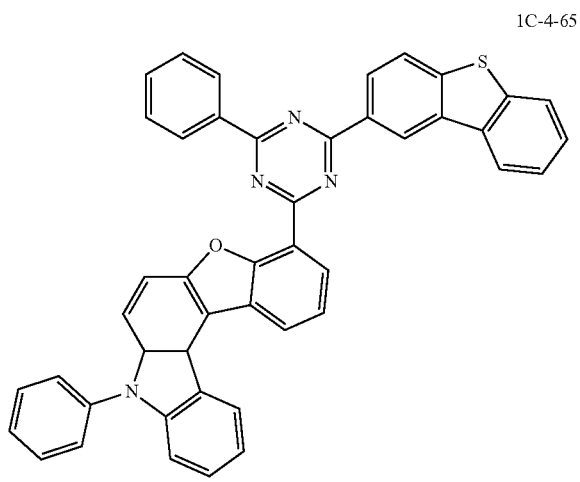 [SMILES: C1=CC2C(c3ccccc3N2c2ccccc2)c2c1oc1c(-c3nc(-c4ccccc4)nc(-c4ccc5sc6ccccc6c5c4)n3)cccc21]
1C-4-66
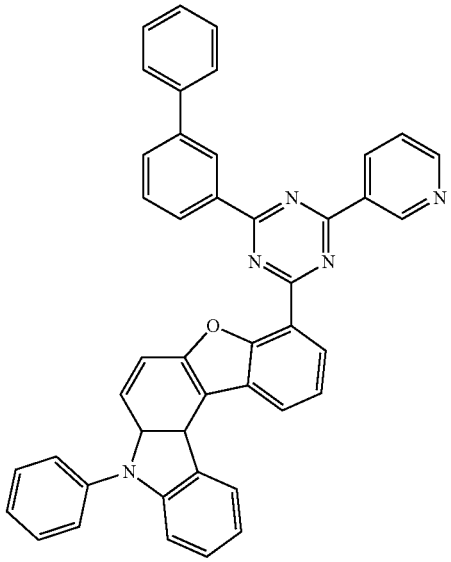
1C-4-67
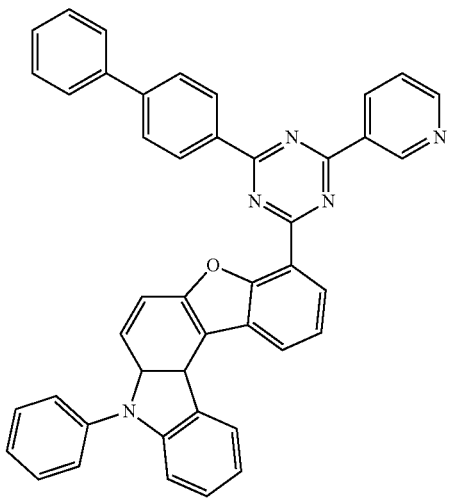
1C-4-68
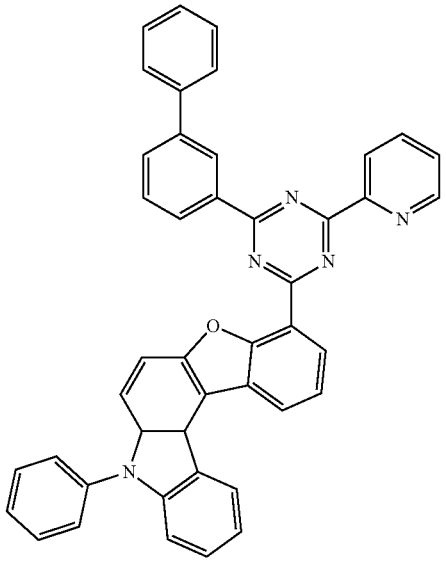

381
-continued
1C-4-69
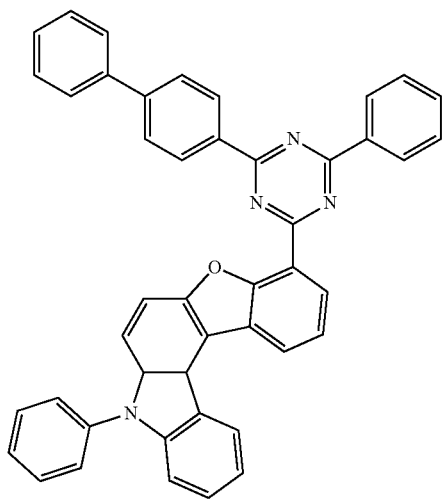
1C-4-70
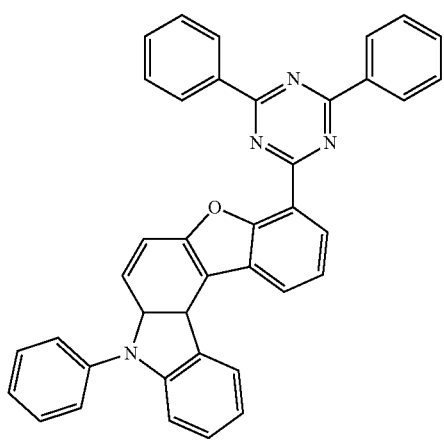
1C-4-71
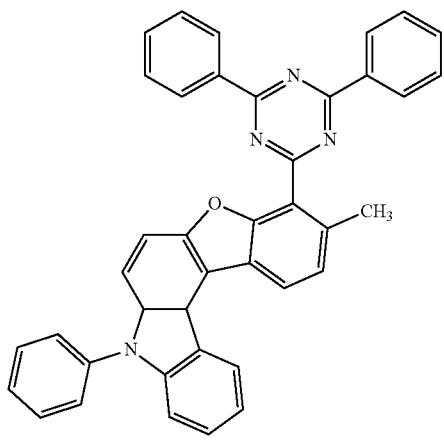
382
-continued
1C-4-72
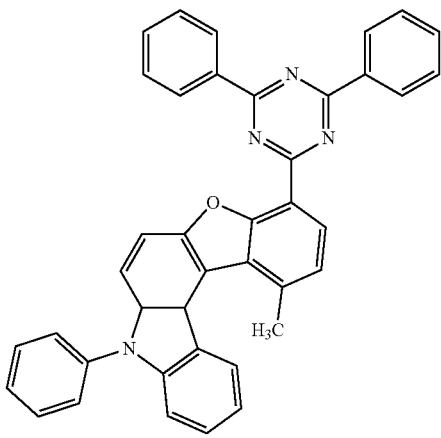
1C-4-73
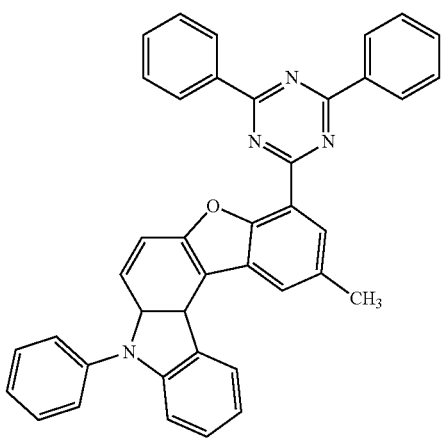
1C-4-74
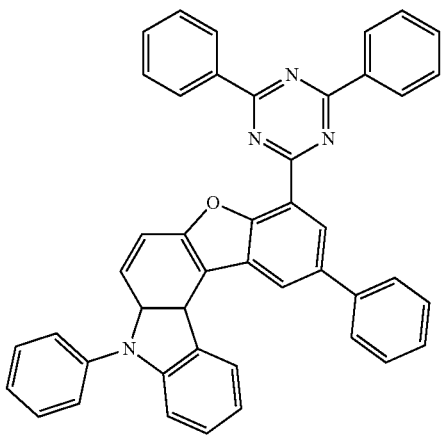

1C-4-75
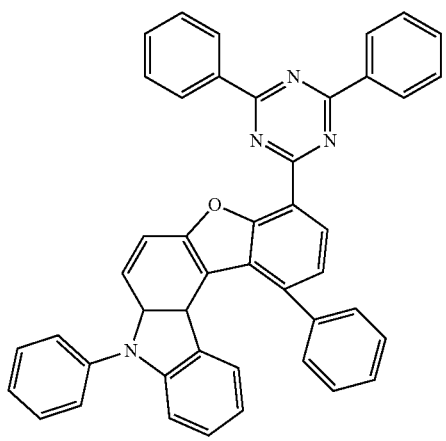
1C-4-76
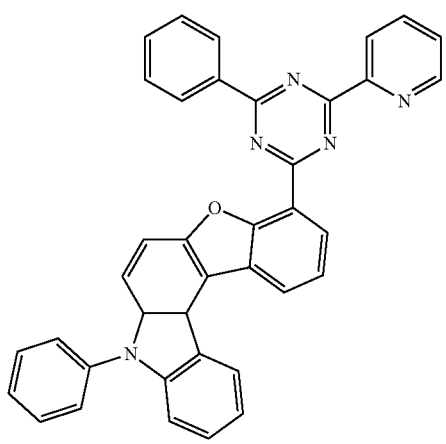
1C-4-78
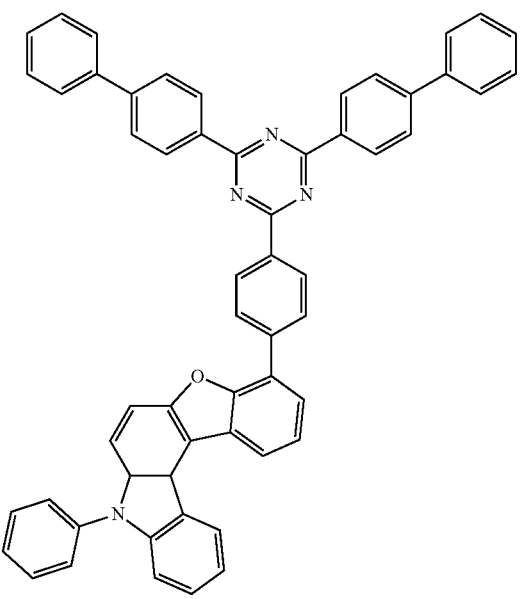
1C-4-77
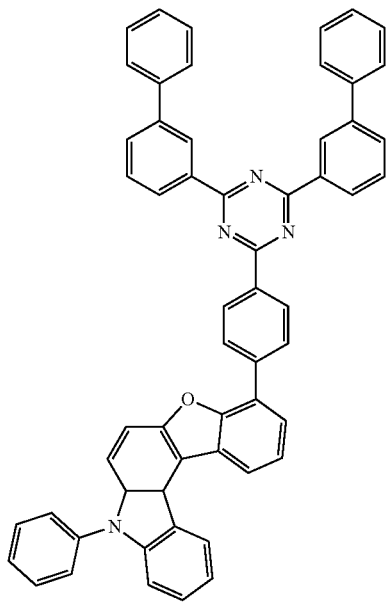
1C-4-79
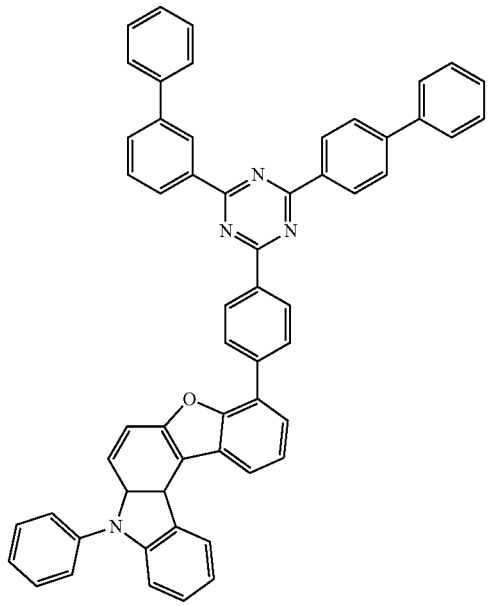

1C-4-80
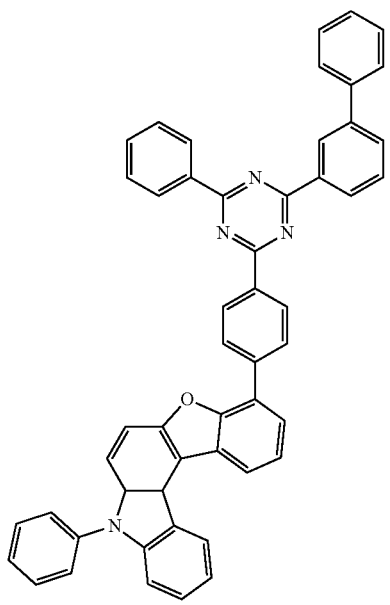
1C-4-83
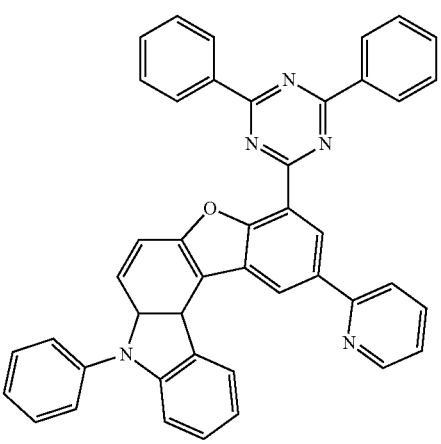
1C-4-81
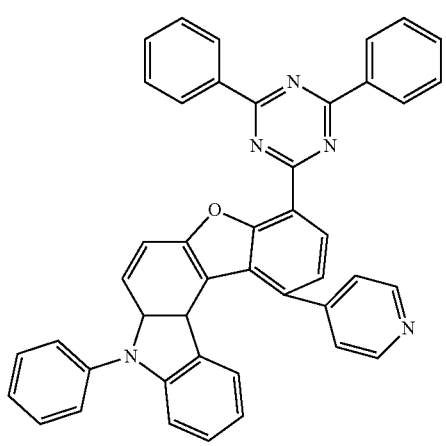
1D-1-1
1C-4-82
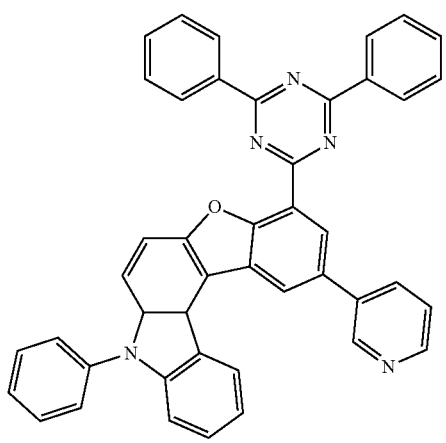
1D-1-2
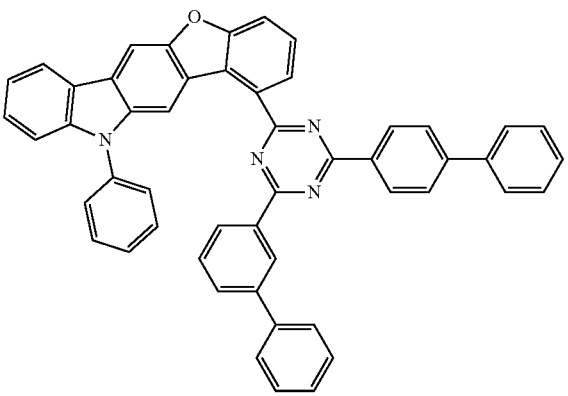

1D-1-3
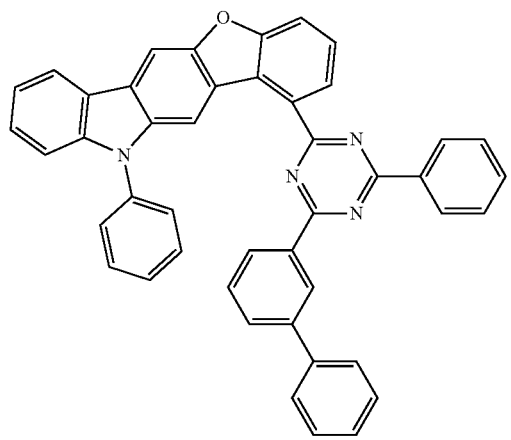
1D-1-4
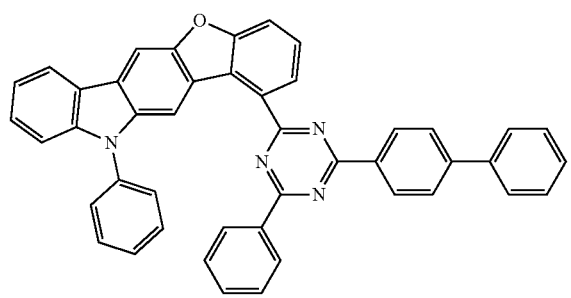
1D-1-5
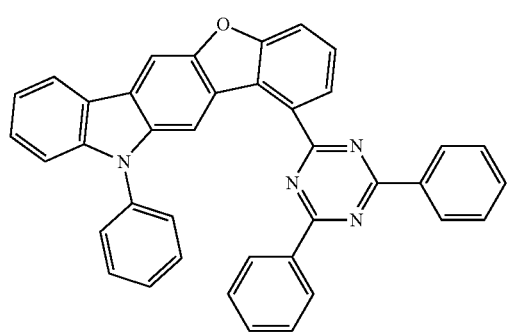
1D-1-6
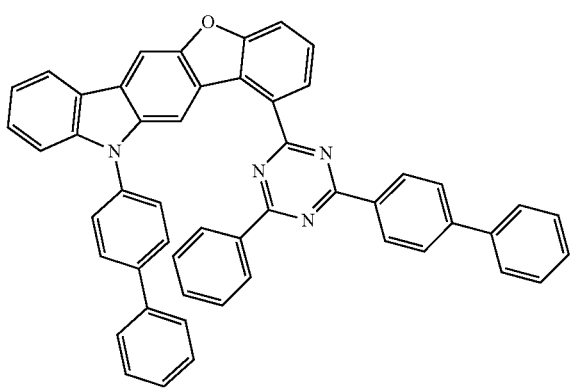
1D-1-7
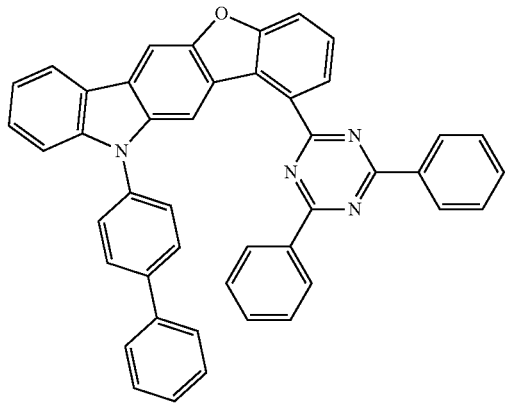
1D-1-8
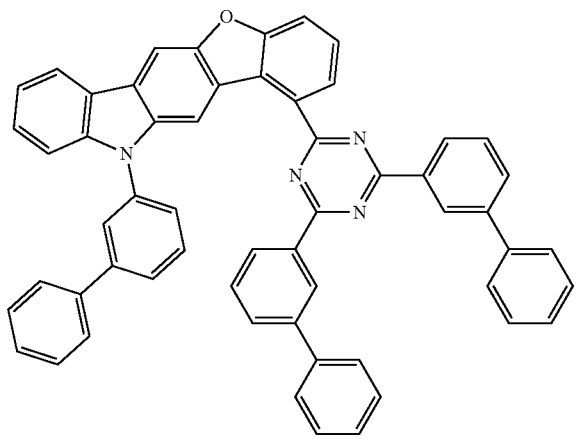
1D-1-9
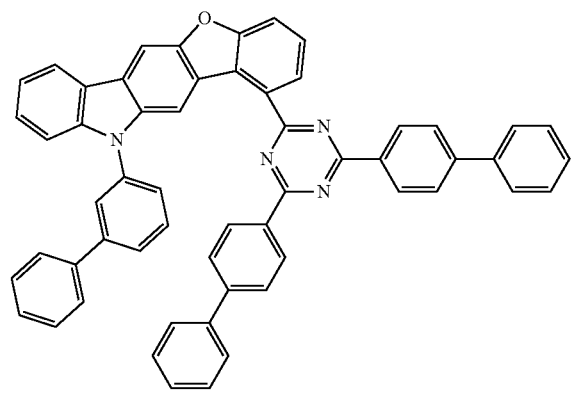

1D-1-10
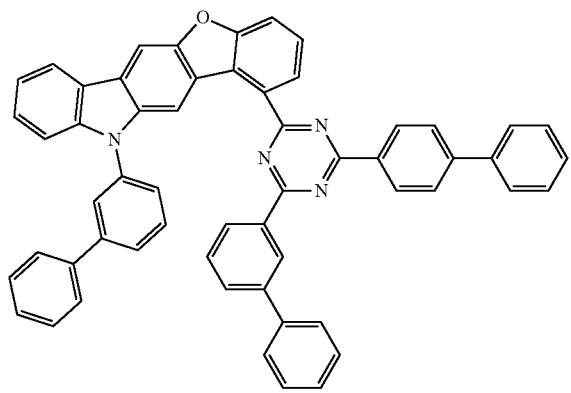
1D-1-11
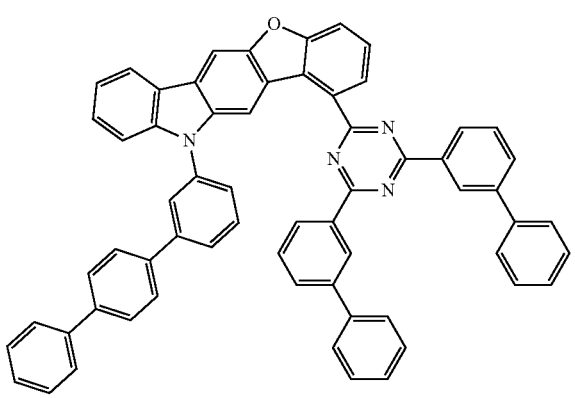
1D-1-12
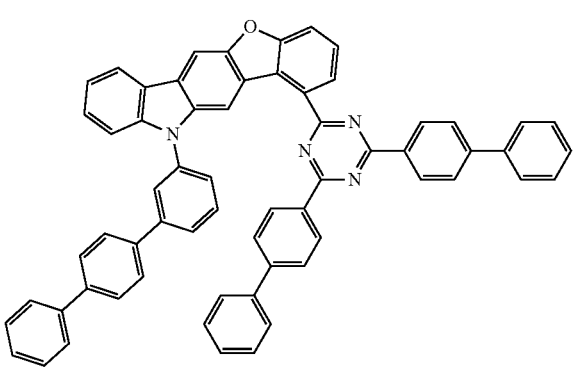
1D-1-13
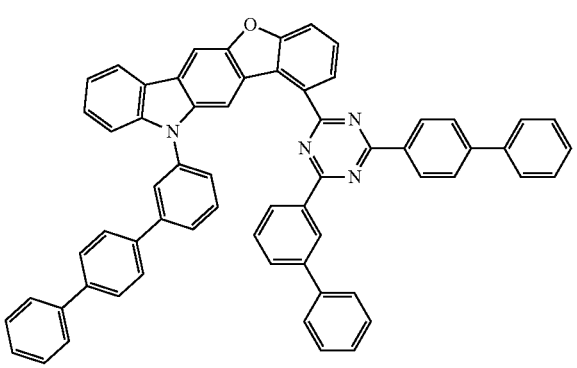
1D-1-14
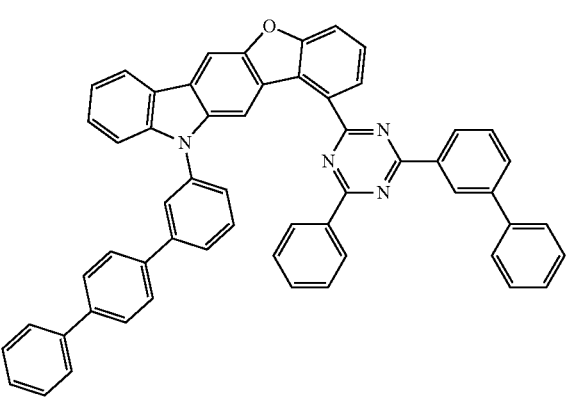
1D-1-15
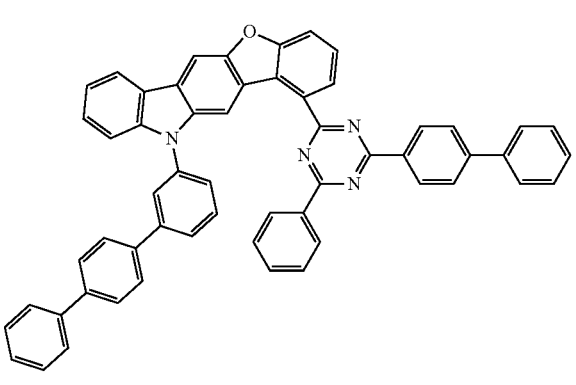
1D-1-16
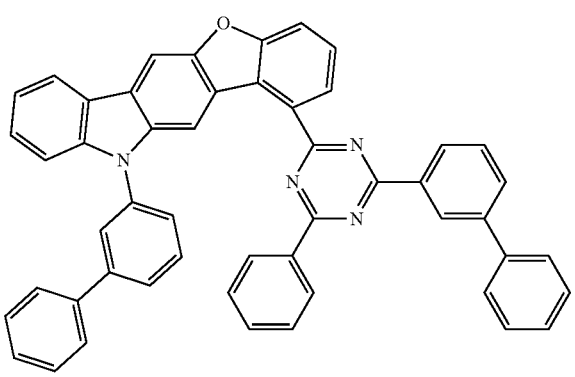
1D-1-17
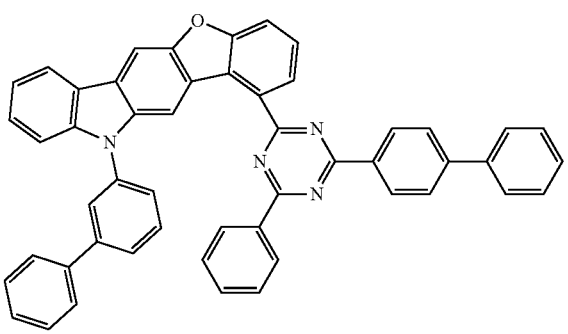

1D-1-18
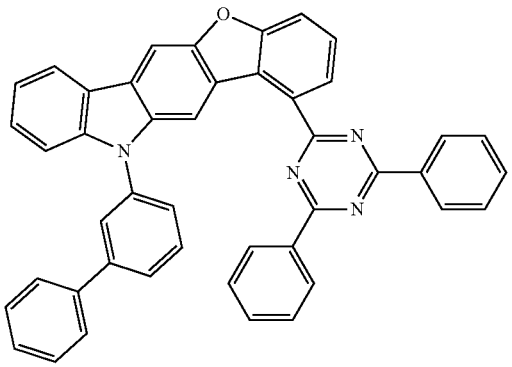
1D-1-19
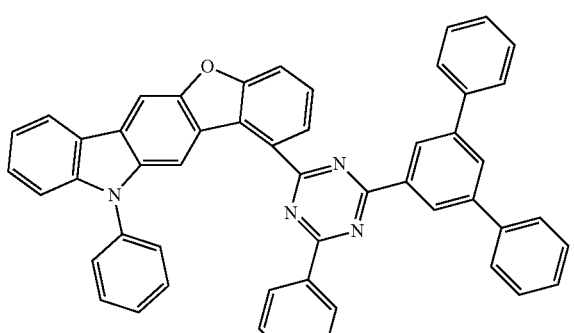
1D-1-20
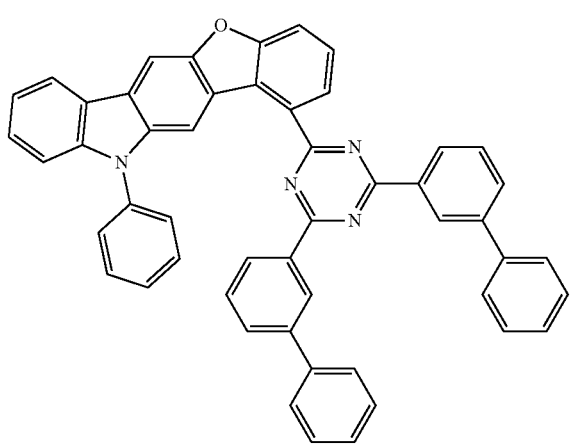
1D-1-21
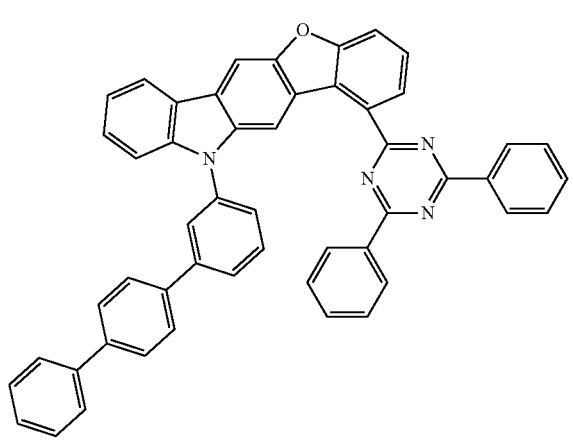
1D-1-22
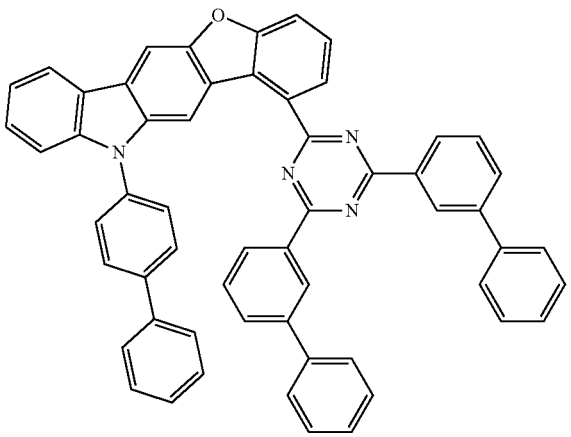
1D-1-23
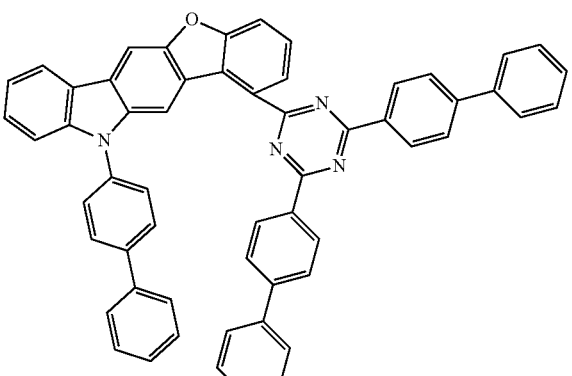
1D-1-24
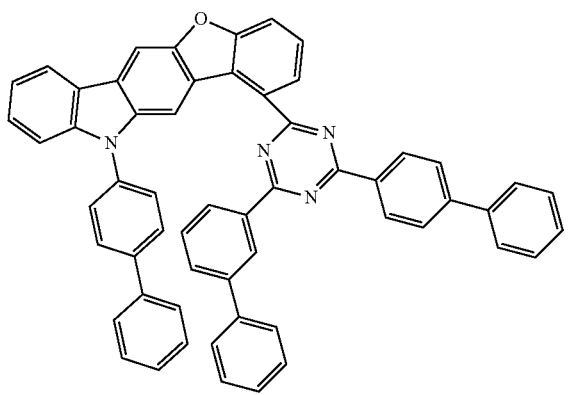

1D-1-25
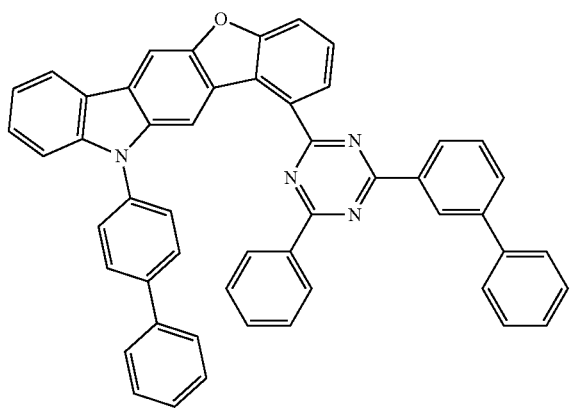
1D-1-28
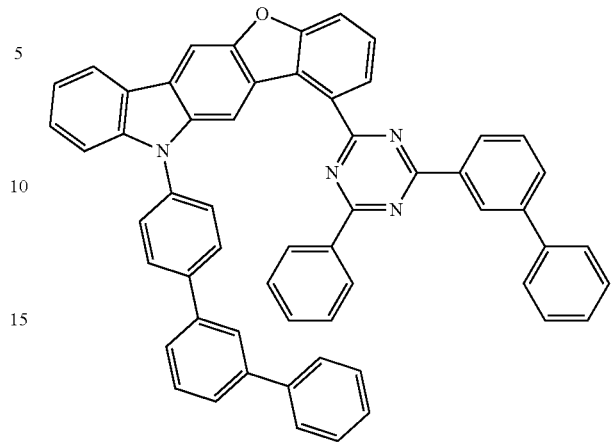
1D-1-26
1D-1-29
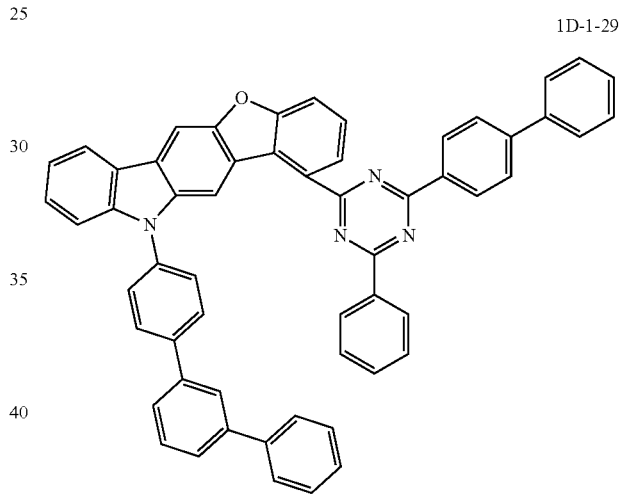
1D-1-27
1D-1-30
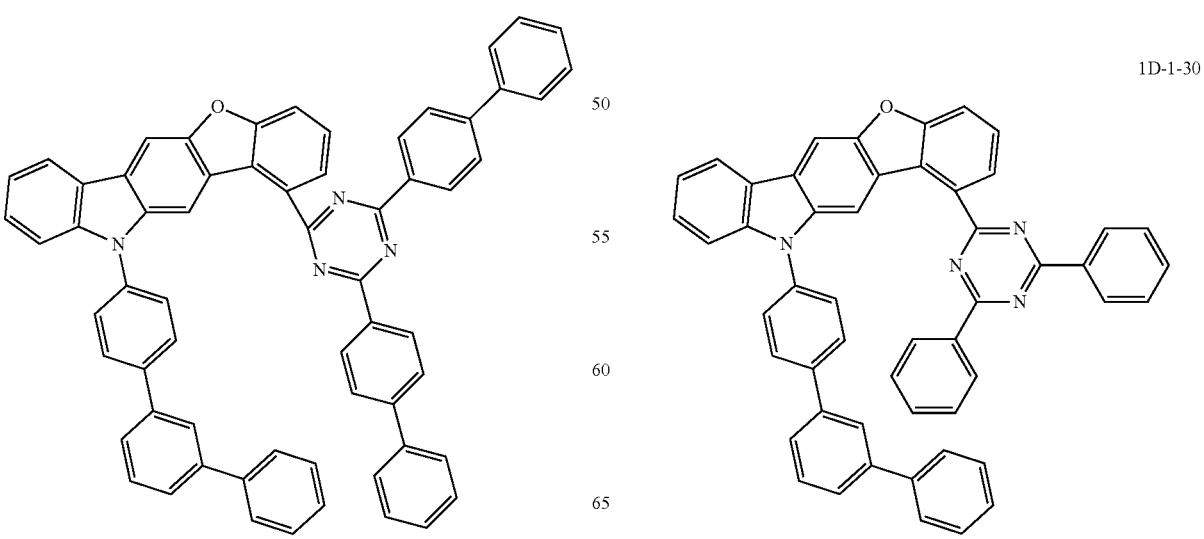

1D-1-31
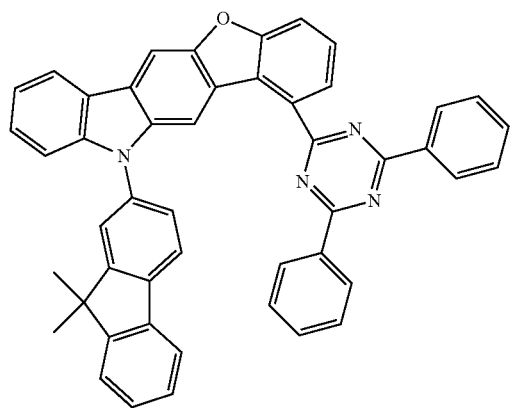
1D-1-32
1D-1-34
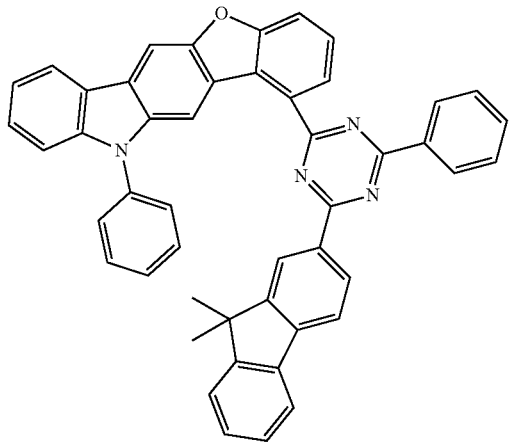
1D-1-35
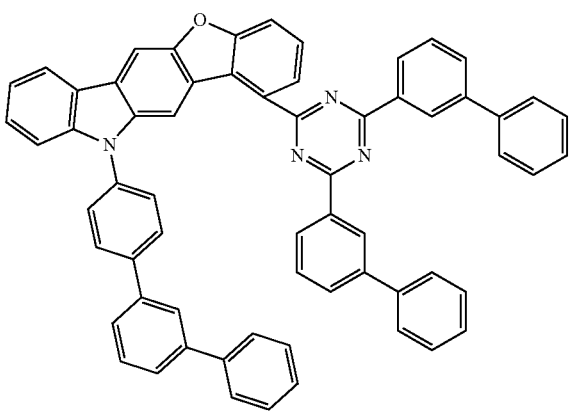
1D-1-33
1D-1-36
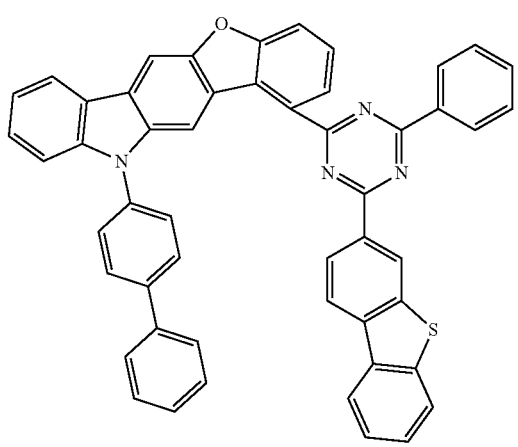

1D-1-37
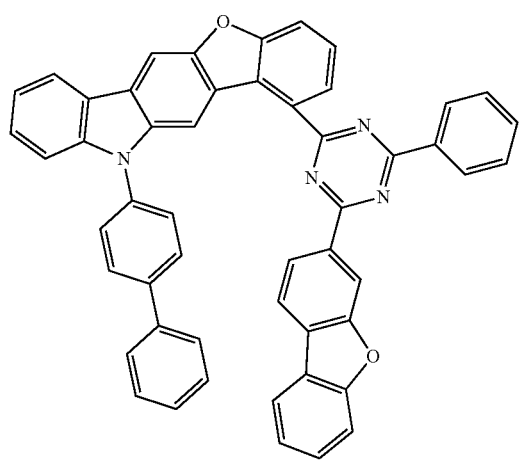
1D-1-38
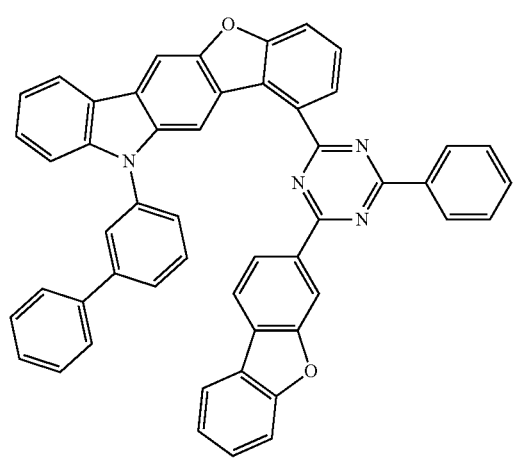
1D-1-39
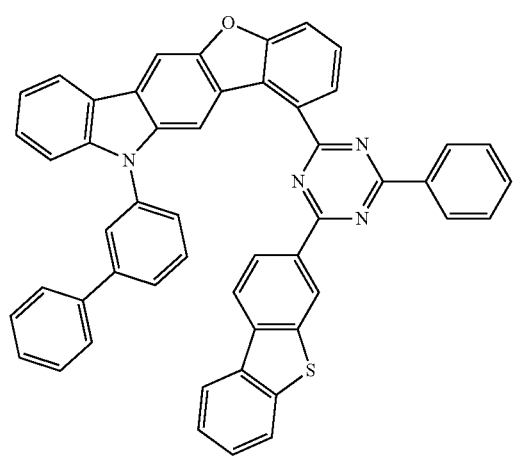
1D-1-40
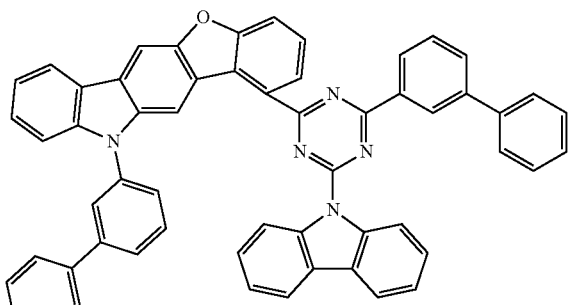
1D-1-41
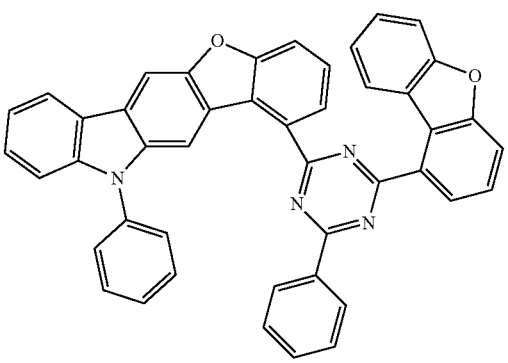
1D-1-42
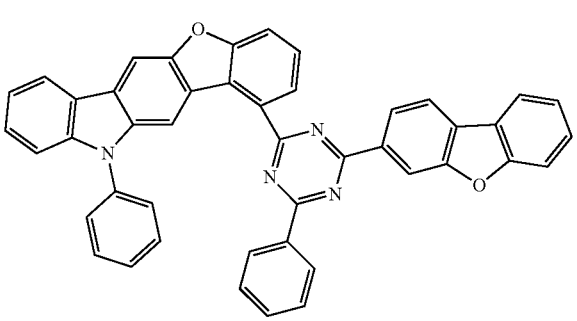
1D-1-43
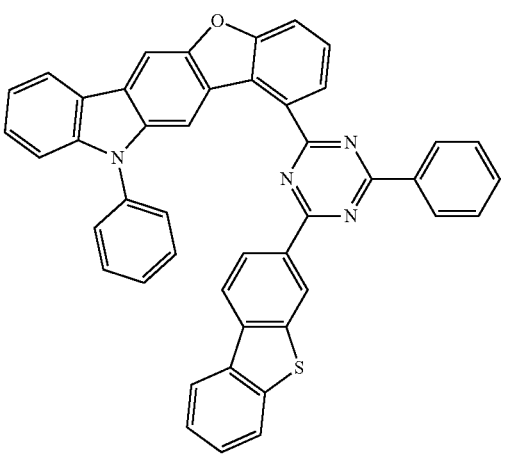

-continued
1D-1-44
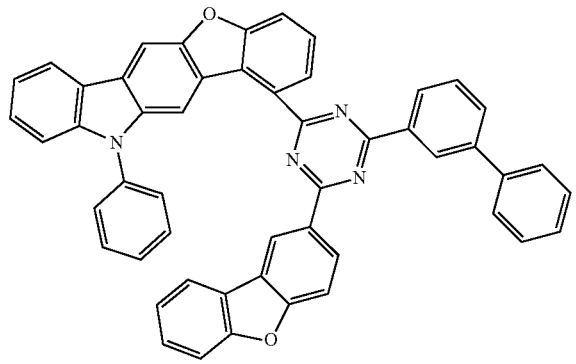
1D-1-45
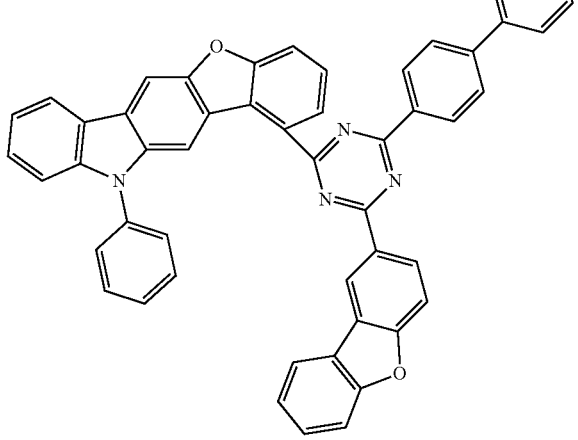
1D-1-46
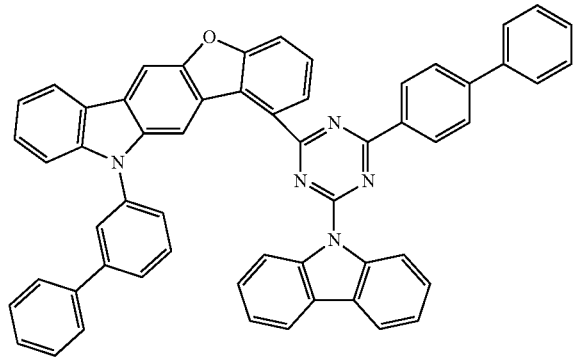
-continued
1D-1-47
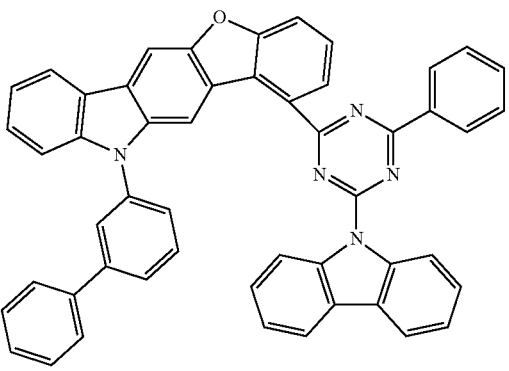
1D-1-48
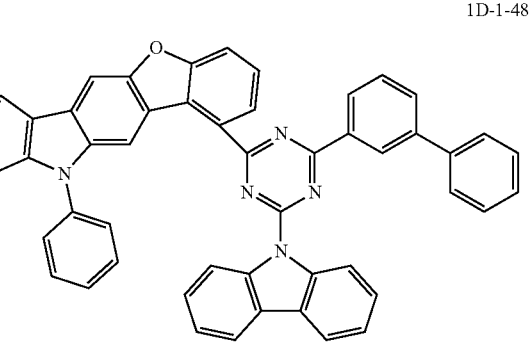
1D-1-49
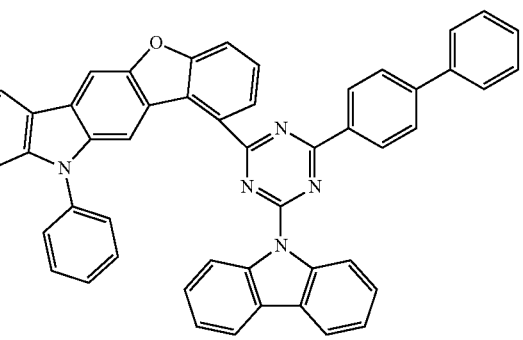
1D-1-50
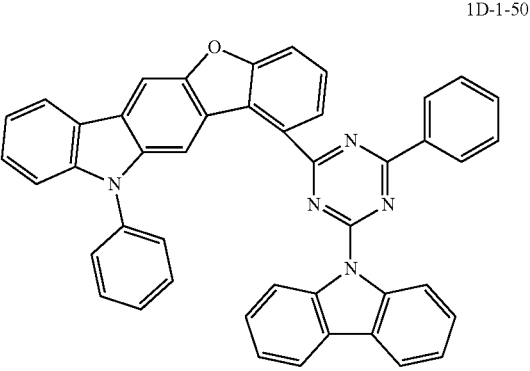

-continued
1D-1-51
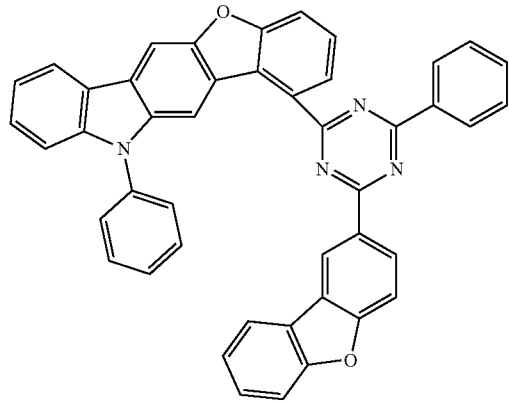
1D-1-52
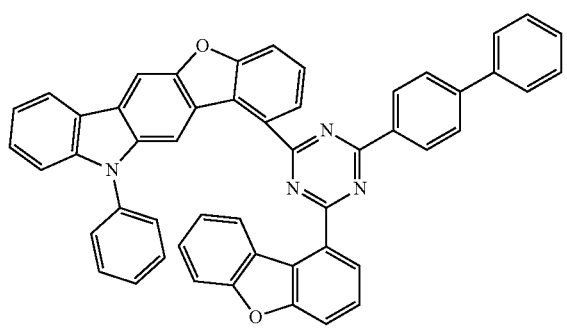
1D-1-53
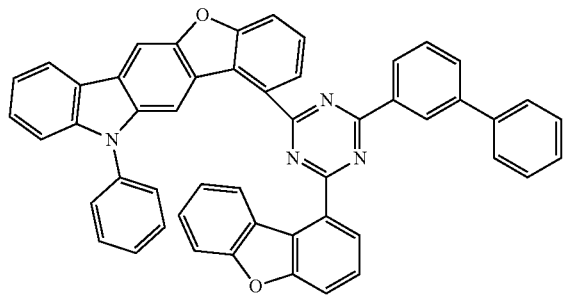
1D-1-54
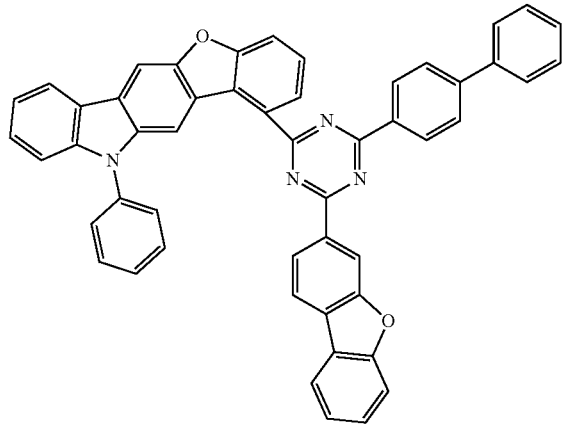
-continued
1D-1-55
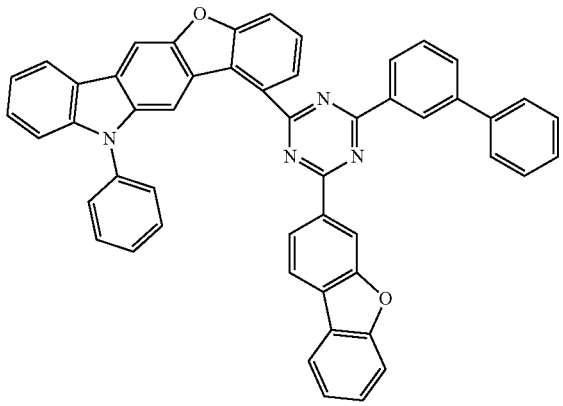
1D-1-56
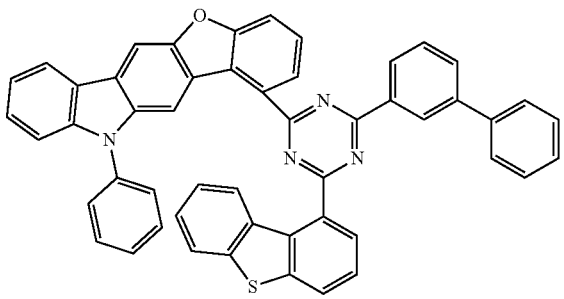
1D-1-57
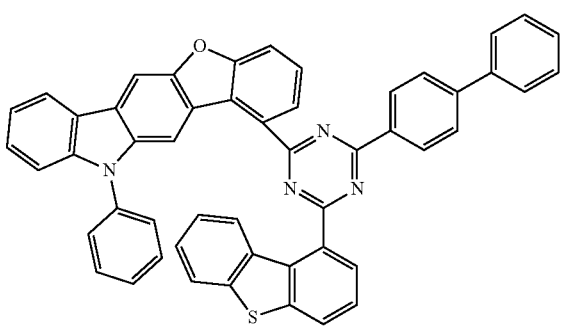
1D-1-58
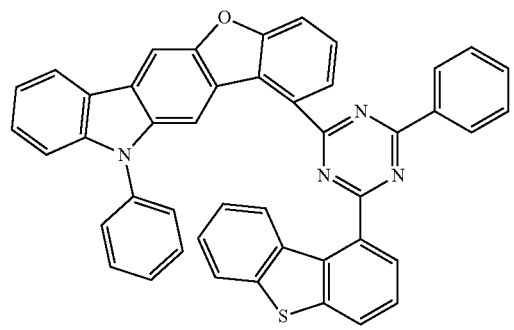

1D-1-59
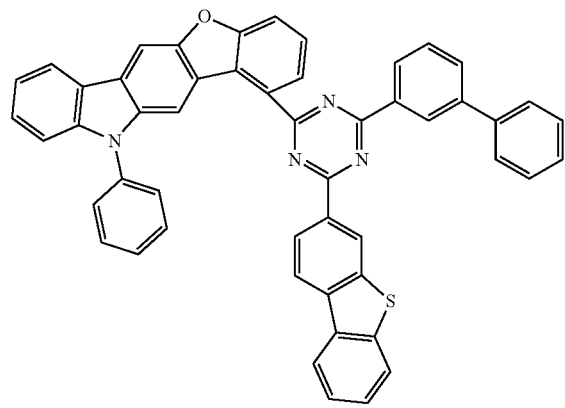
1D-1-60
1D-1-61
1D-1-62
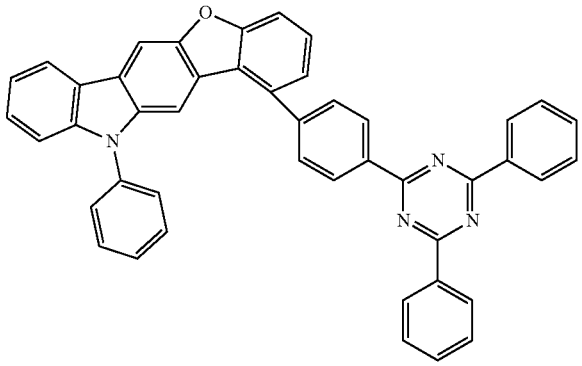
1D-1-63
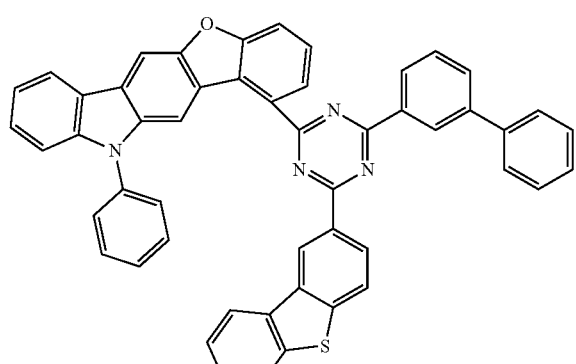
1D-1-64
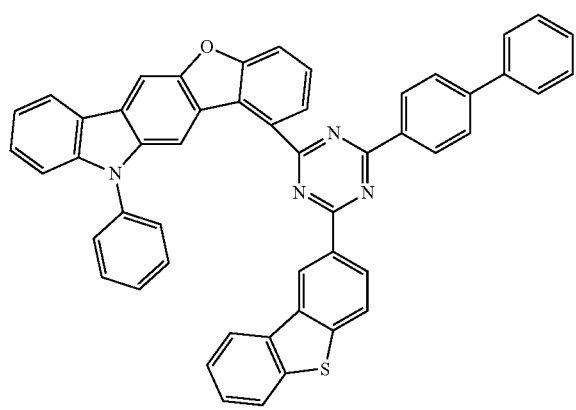
1D-1-65
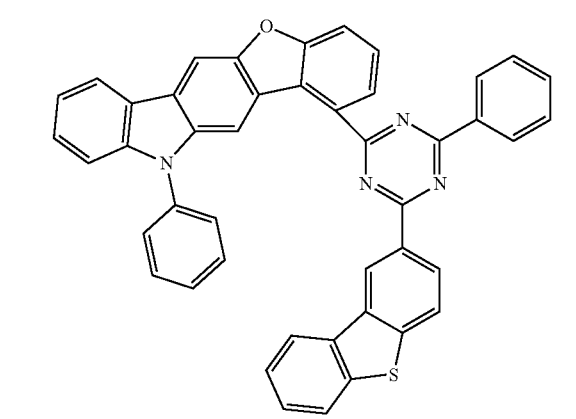

1D-1-66
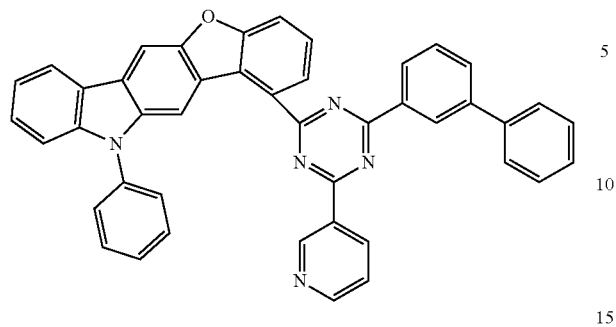
1D-1-67
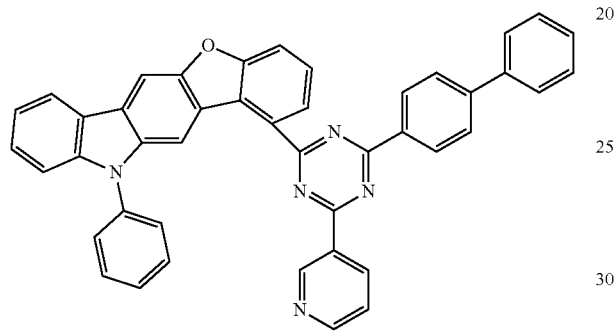
1D-1-68
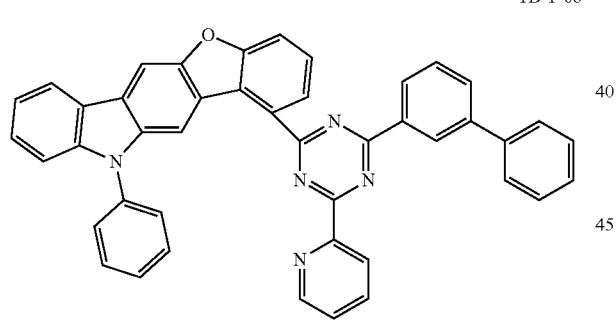
1D-1-69
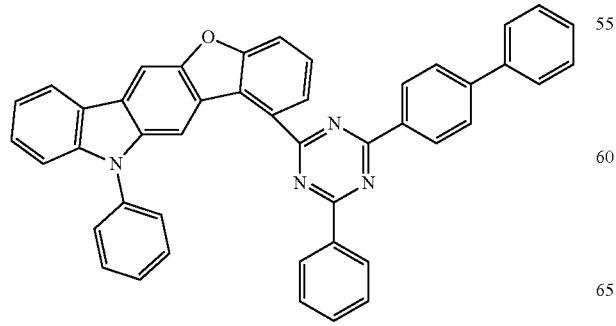
1D-1-70
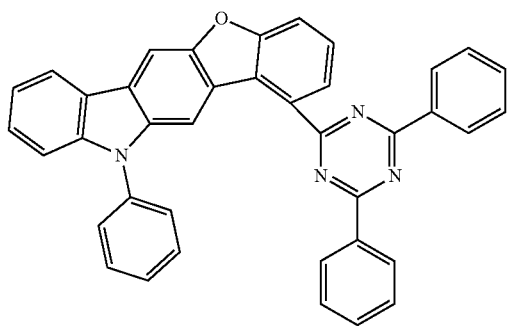
1D-1-71
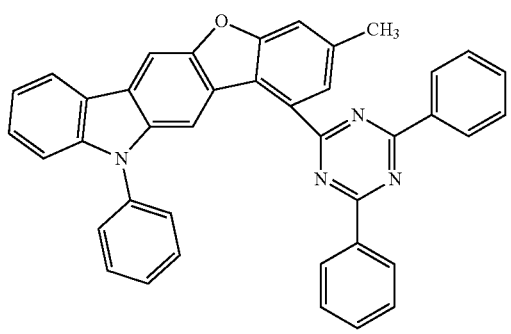
1D-1-72
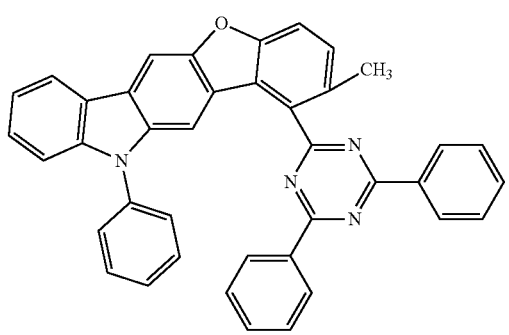
1D-1-73
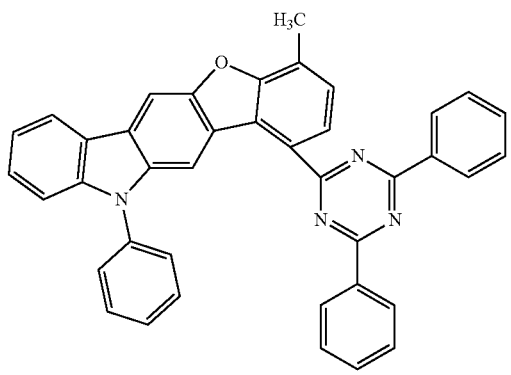

-continued
1D-1-74
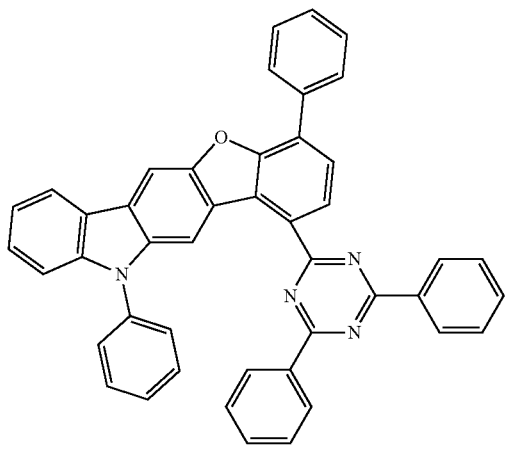
1C-1-75
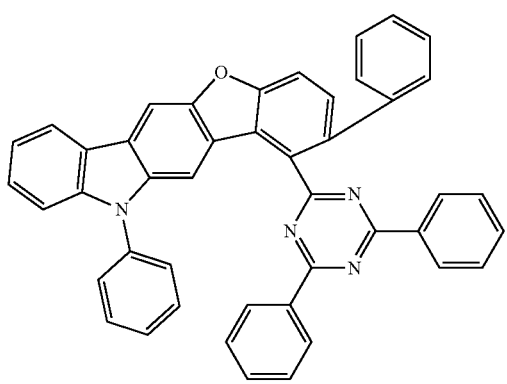
1D-1-76
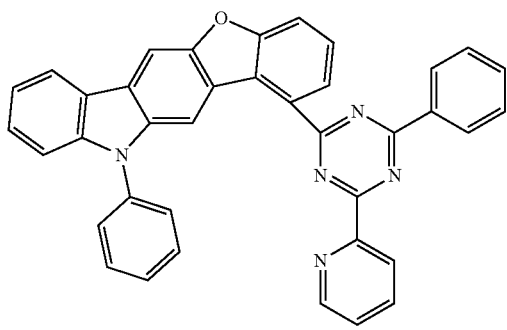
1D-1-77
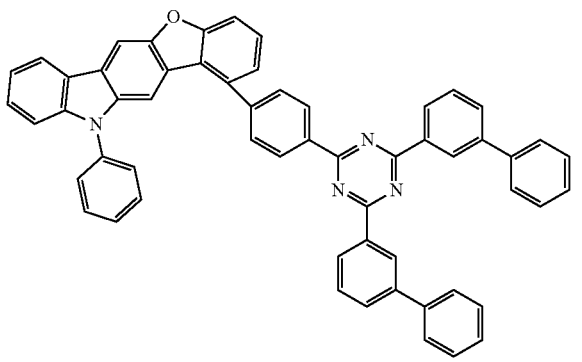
-continued
1D-1-78
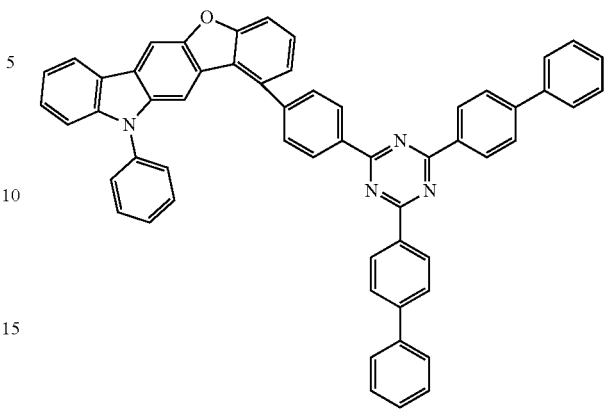
1D-1-79
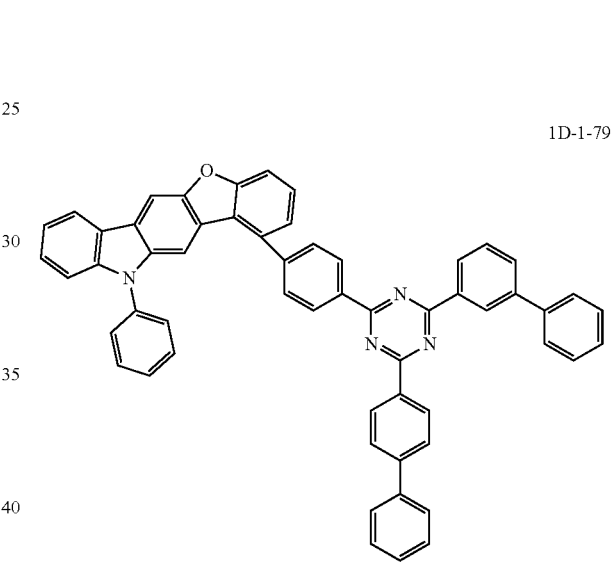
1D-1-80
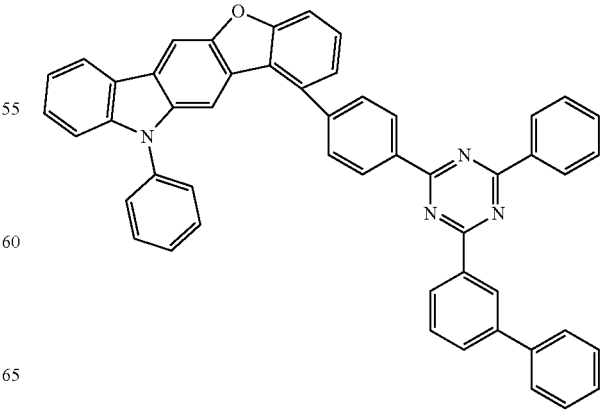

1D-1-81
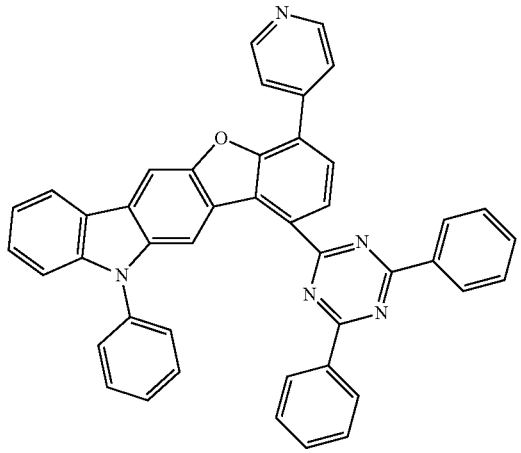
1D-1-82
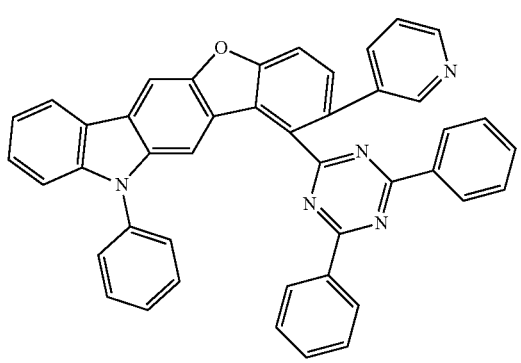
1D-1-83
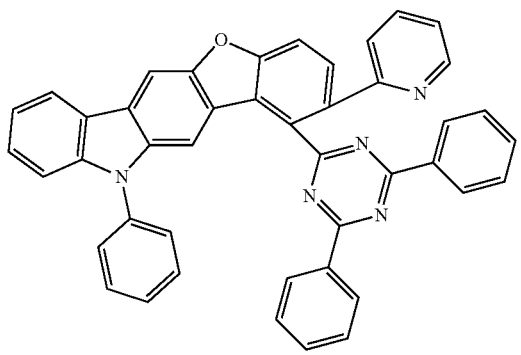
1D-2-1
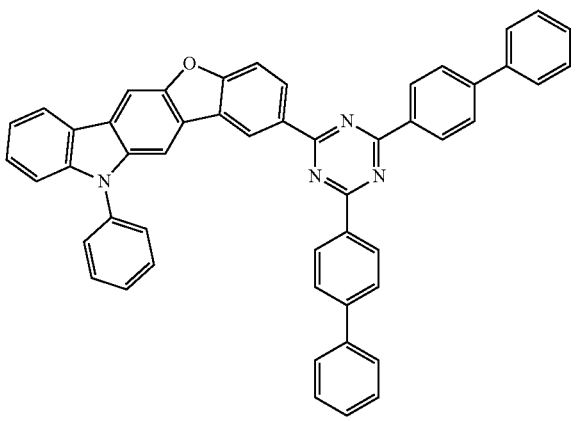
1D-2-2
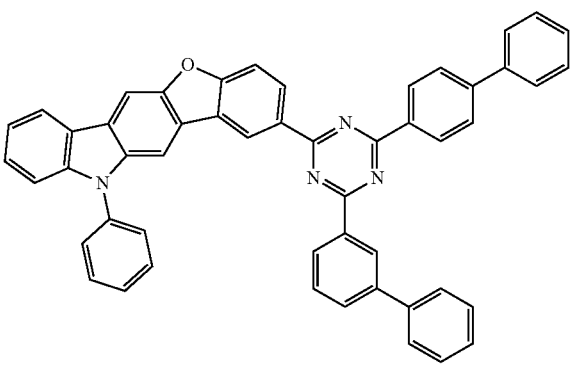
1D-2-3
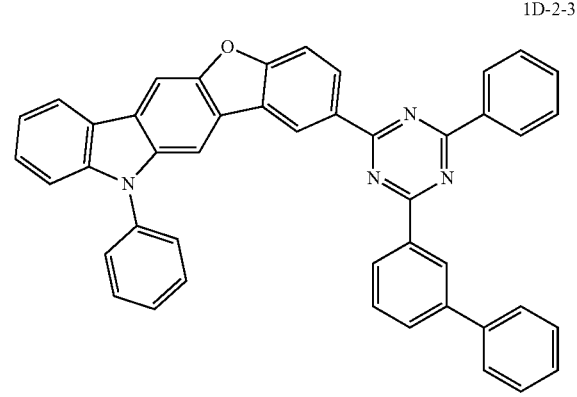
1D-2-4
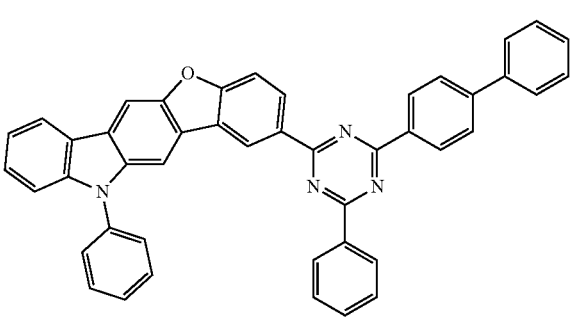
1D-2-5
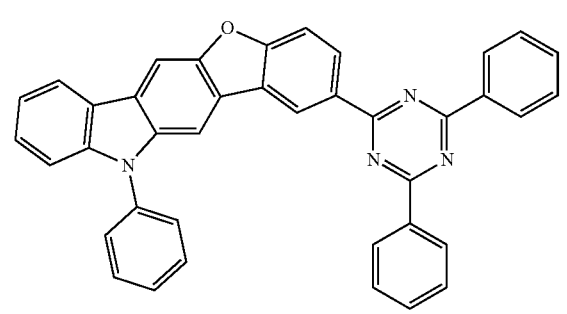

1D-2-6
1D-2-10
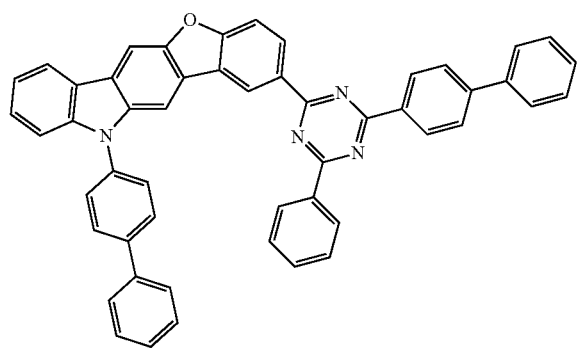
1D-2-7
1D-2-8
1D-2-9
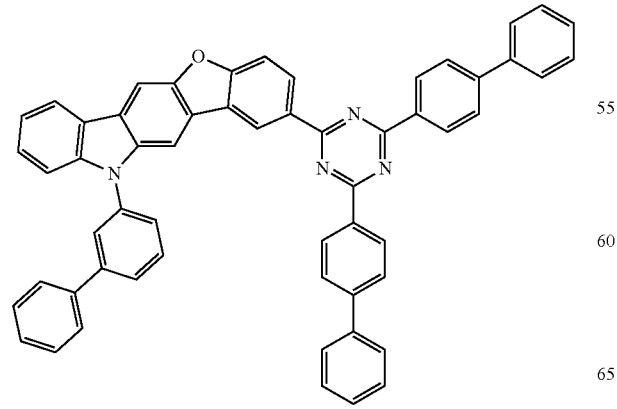
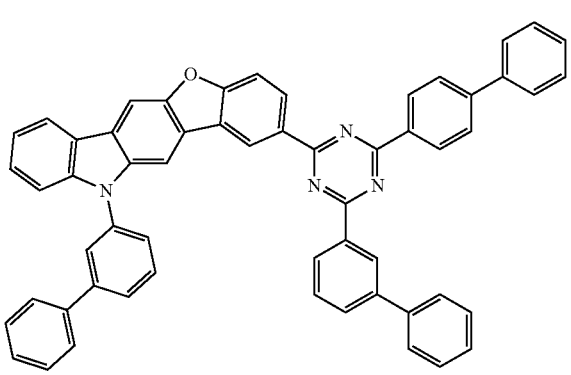
1D-2-11

1D-2-12
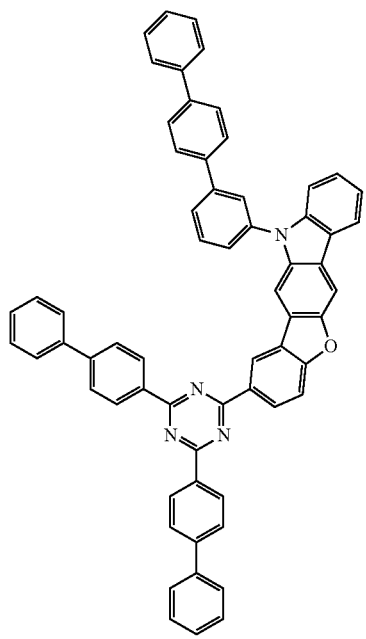
1D-2-14
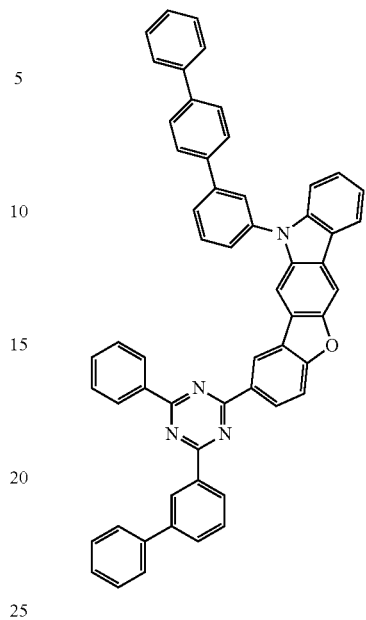
1D-2-15
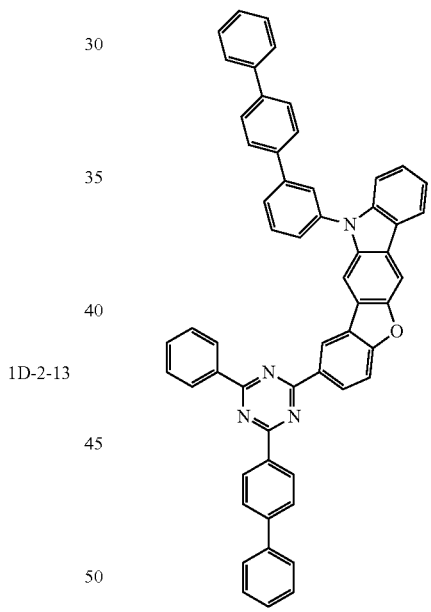
1D-2-13
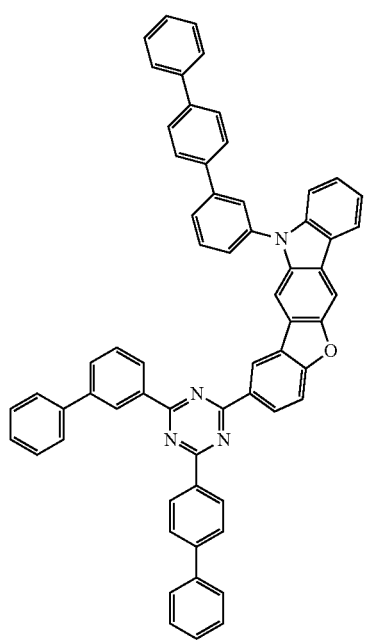
1D-2-16
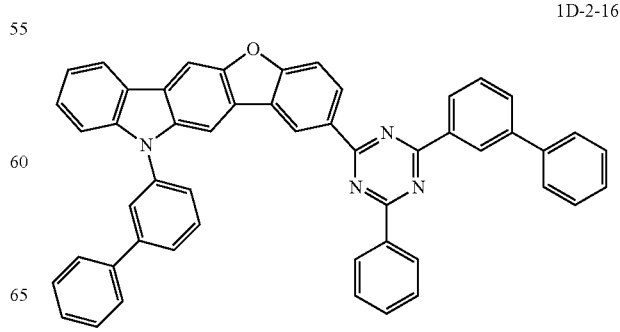

1D-2-17
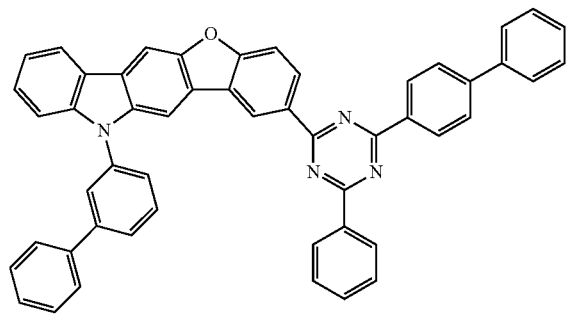
1D-2-18
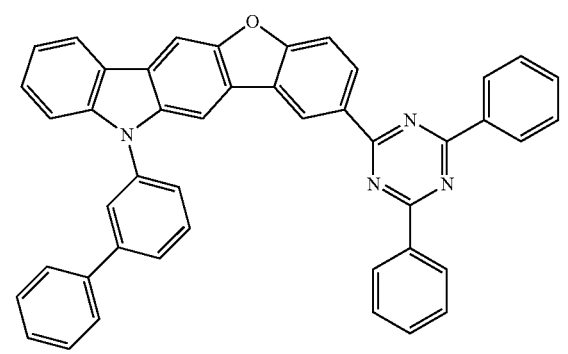
1D-2-19
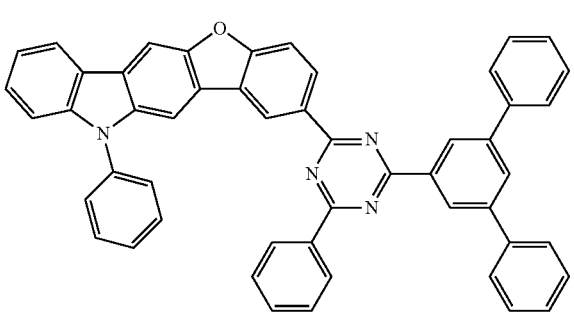
1D-2-20
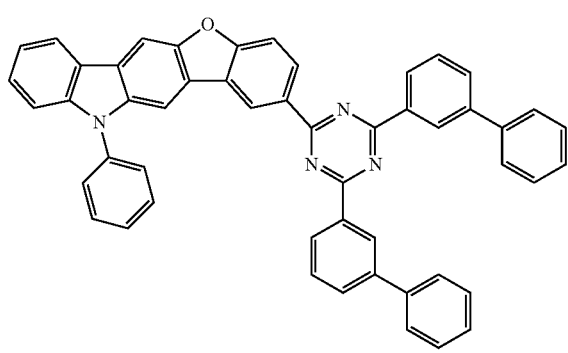
1D-2-21
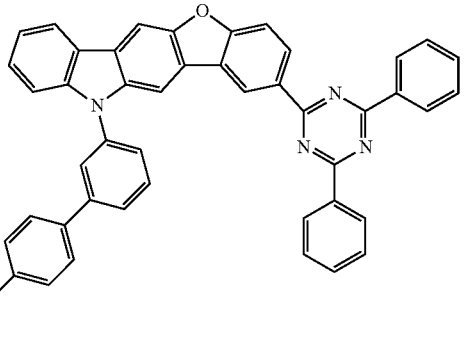
1D-2-22
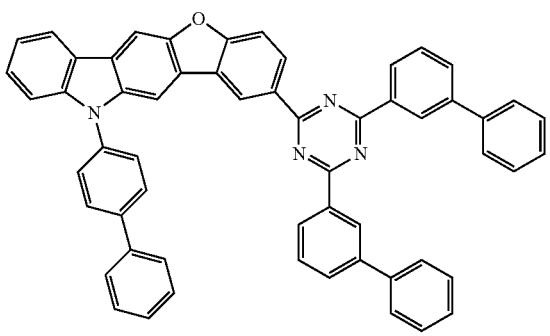
1D-2-23
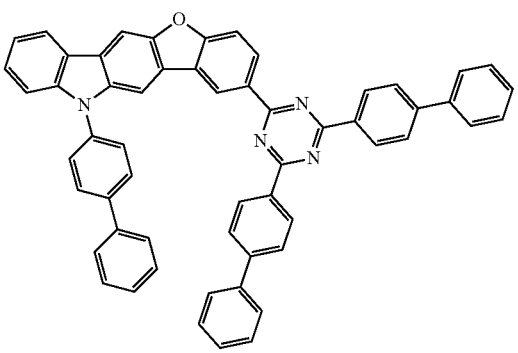
1D-2-24
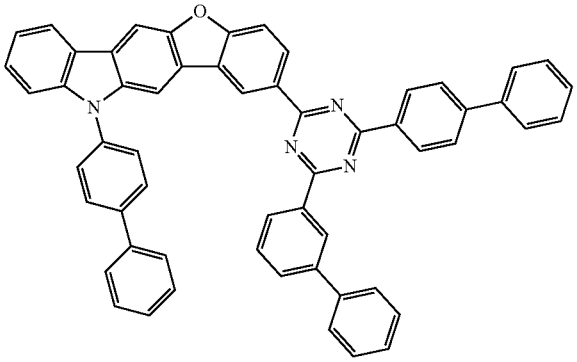

1D-2-25
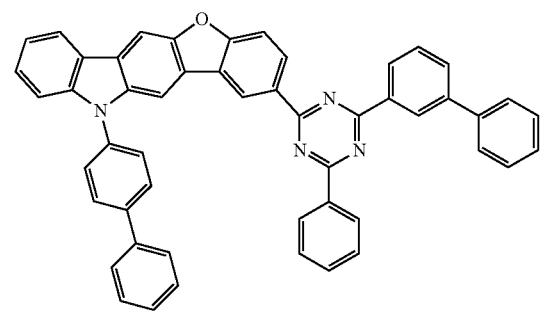
1D-2-26
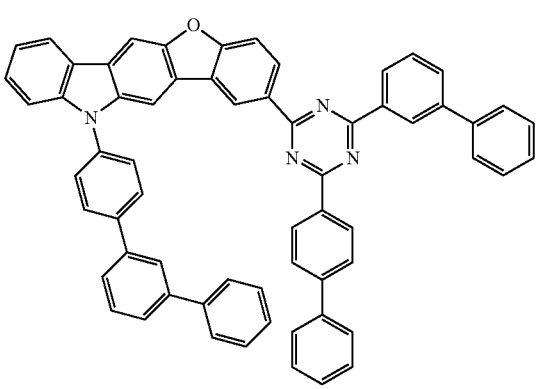
1D-2-27
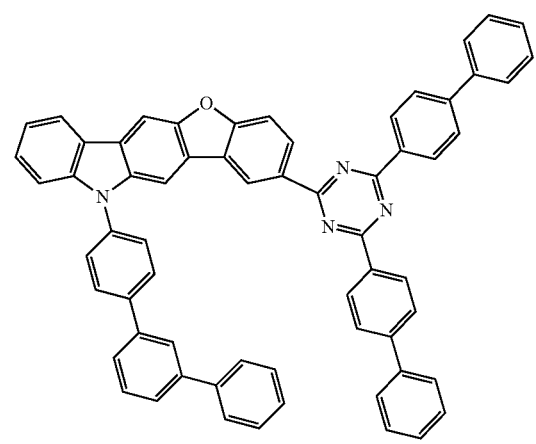
1D-2-28
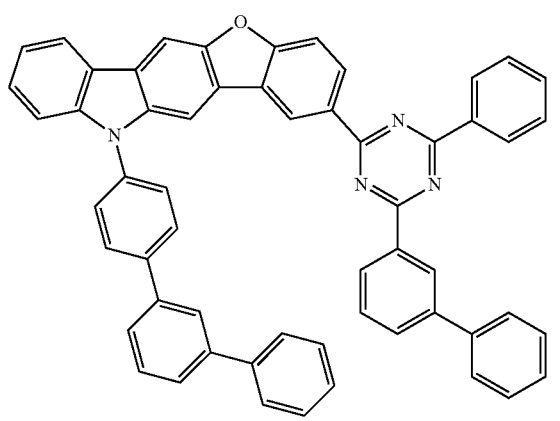
1D-2-29
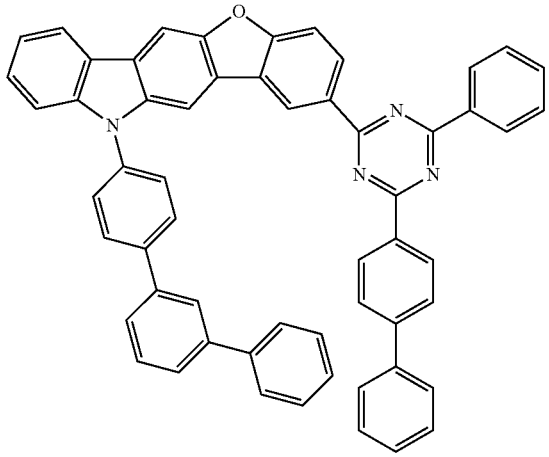
1D-2-30
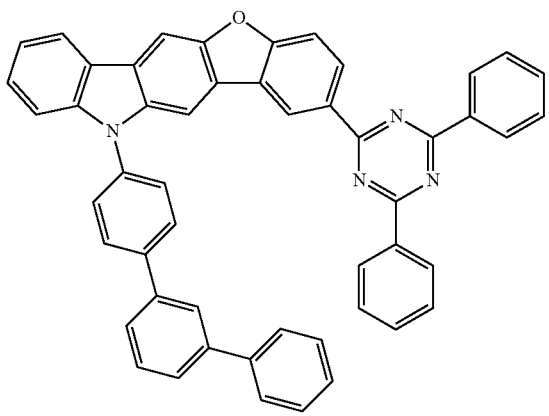
1D-2-31
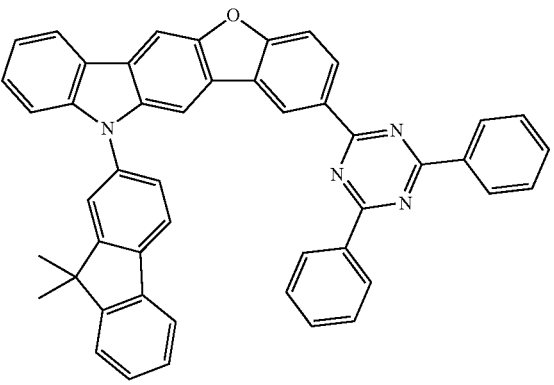

-continued
1D-2-32
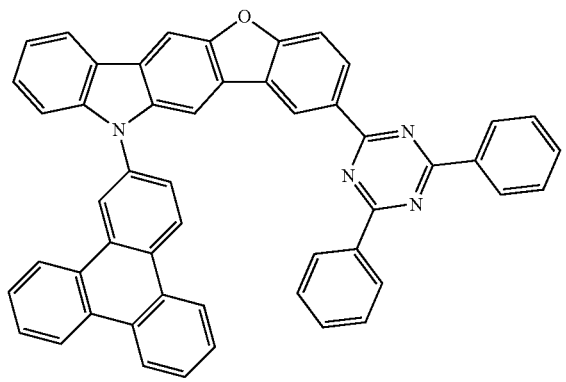
1D-2-33
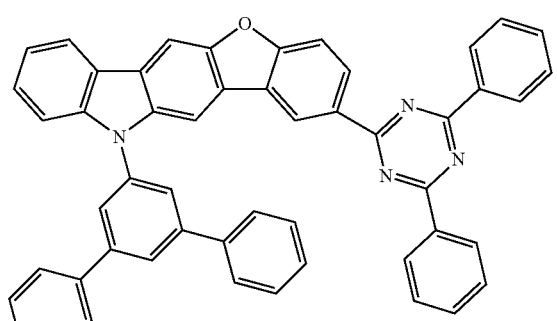
1D-2-34
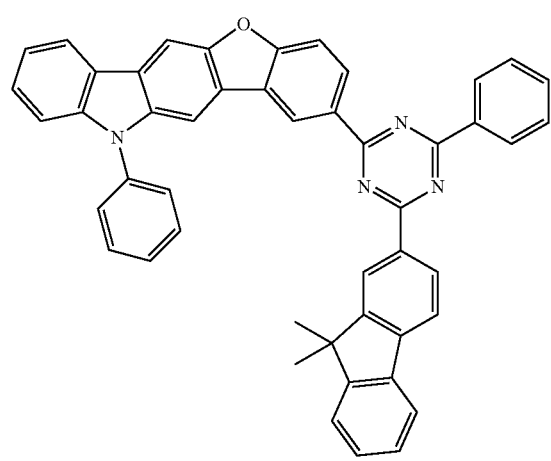
1D-2-35
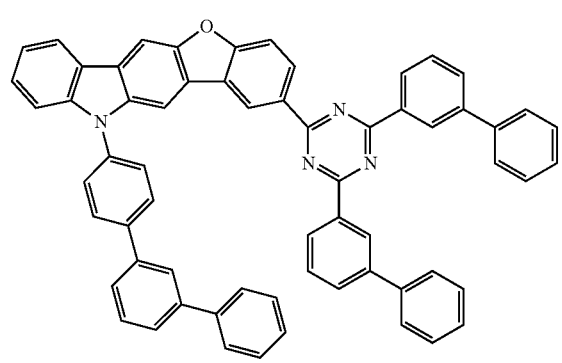
-continued
1D-2-36
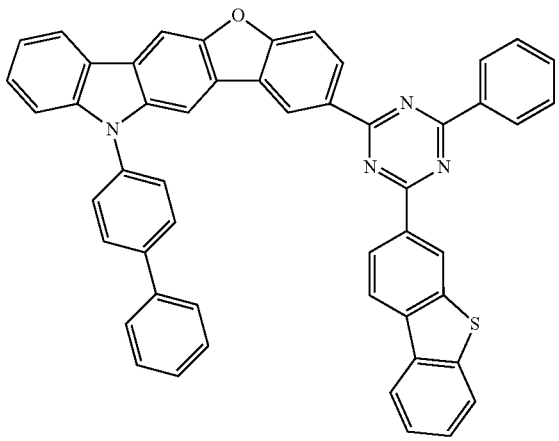
1D-2-37
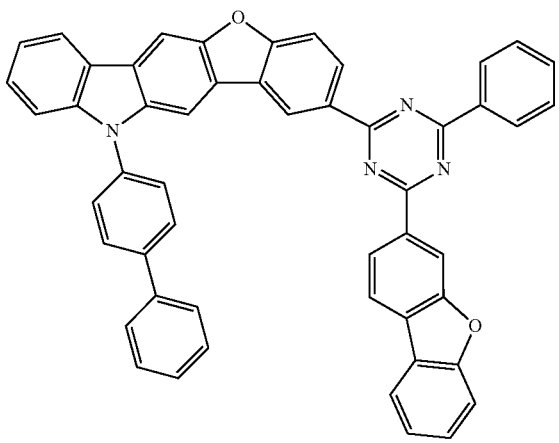
1D-2-38
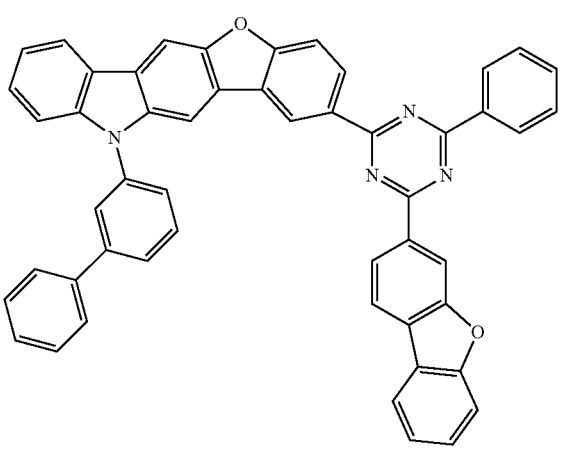

-continued
1D-2-39
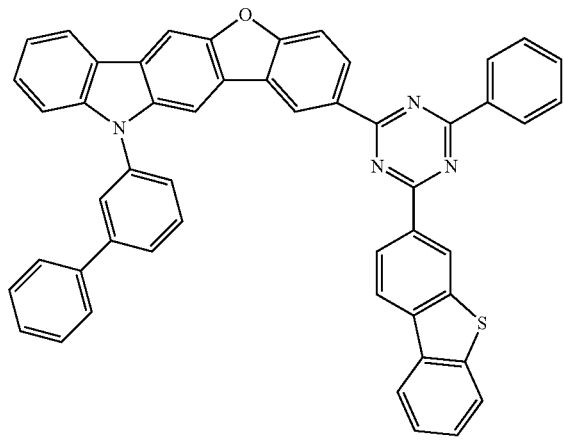
1D-2-40
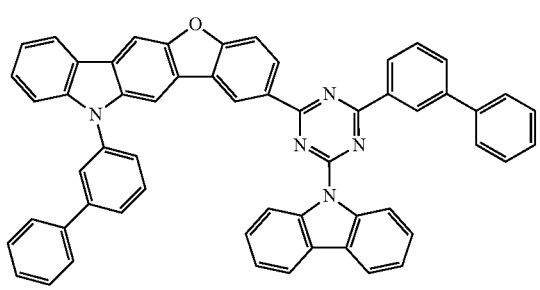
1D-2-41
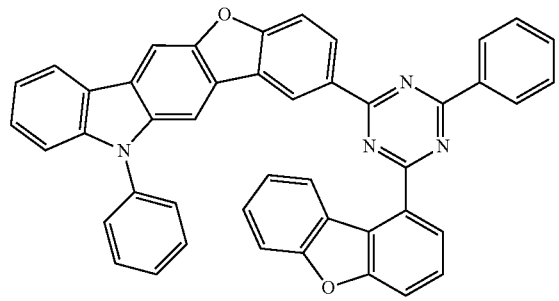
1D-2-42
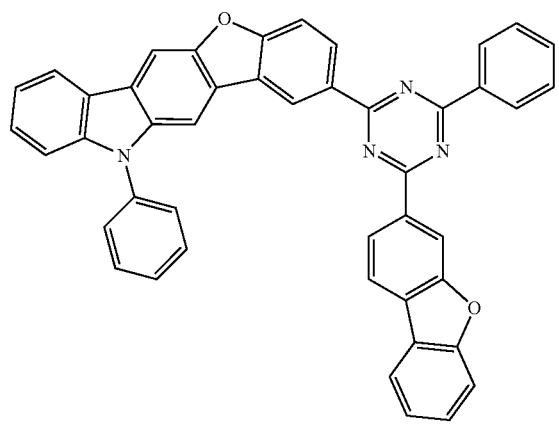
1D-2-43
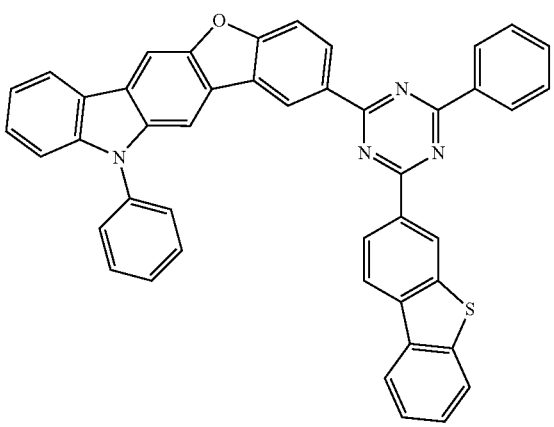
1D-2-44
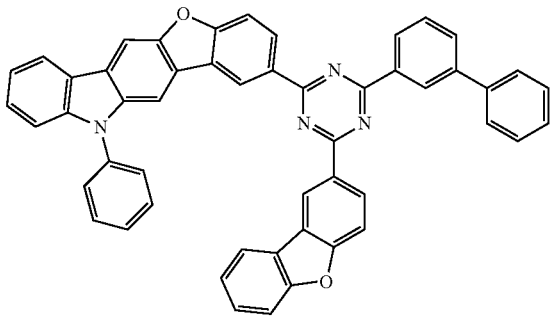
1D-2-45
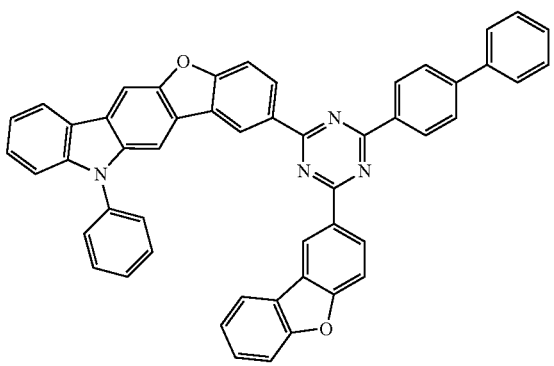
1D-2-46
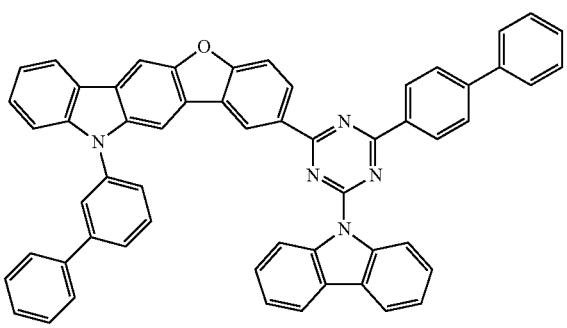

-continued
1D-2-47
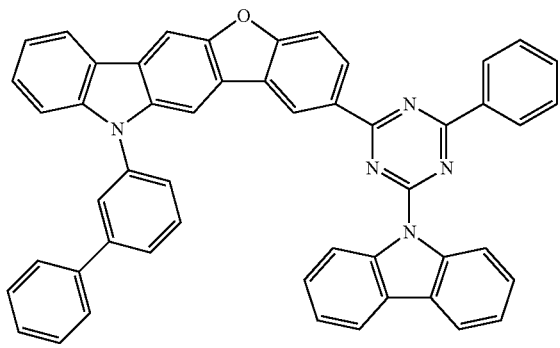
1D-2-48
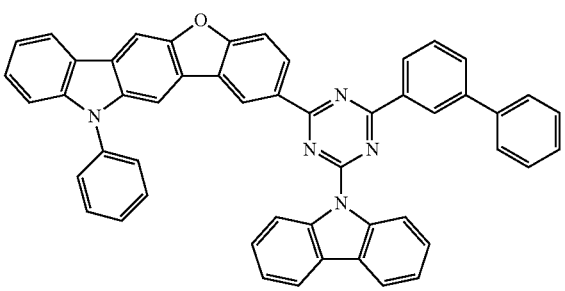
1D-2-49
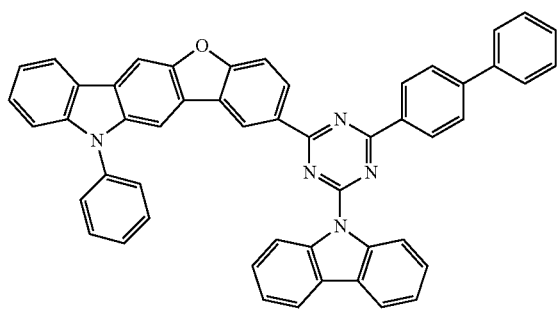
1D-2-50
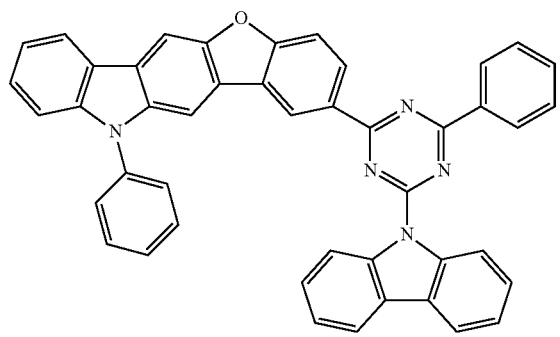
-continued
1D-2-51
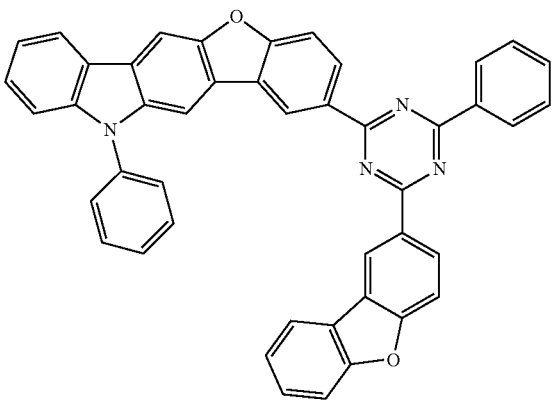
1D-2-52
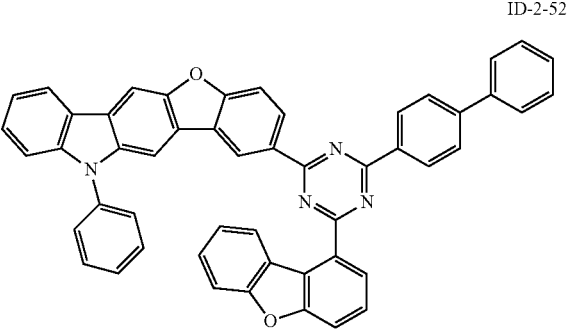
1D-2-53
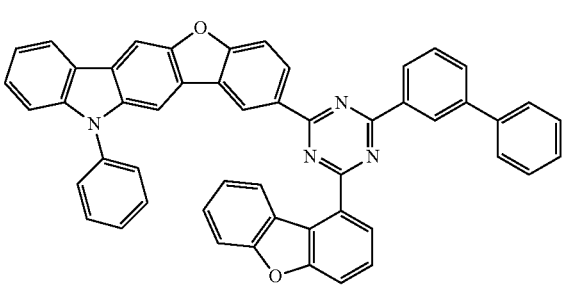
1D-2-54
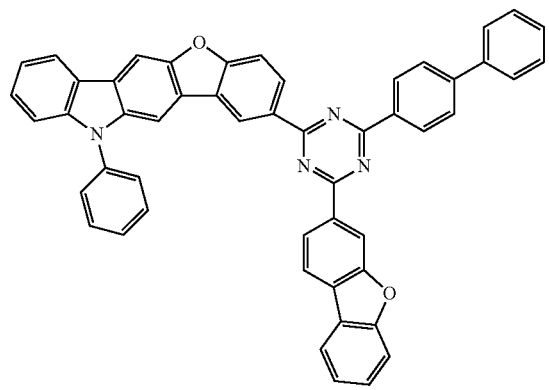

1D-2-55
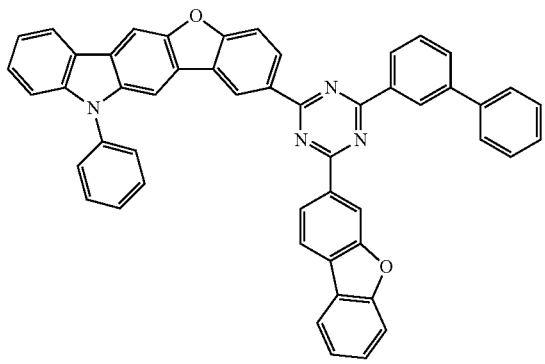
1D-2-56
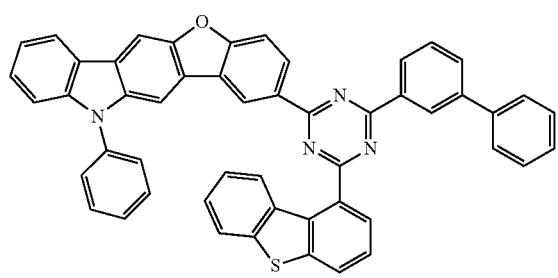
1D-2-57
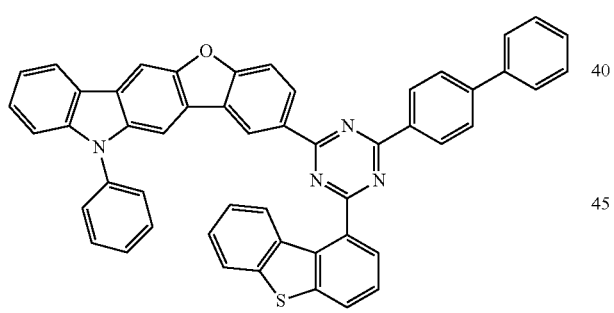
1D-2-58
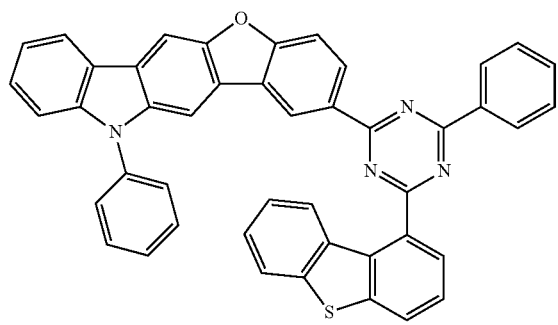
1D-2-59
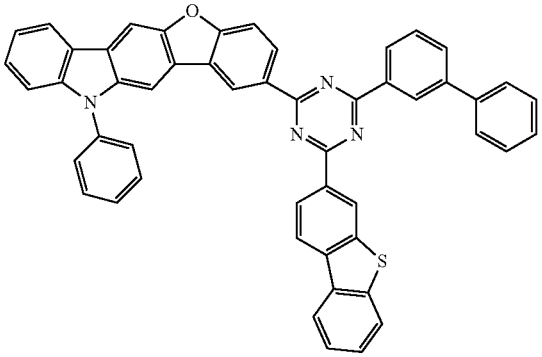
1D-2-60
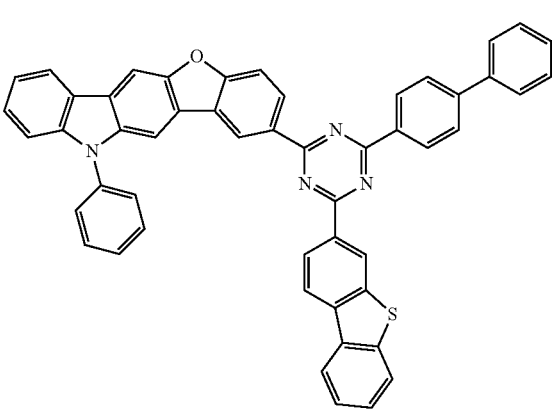
1D-2-61
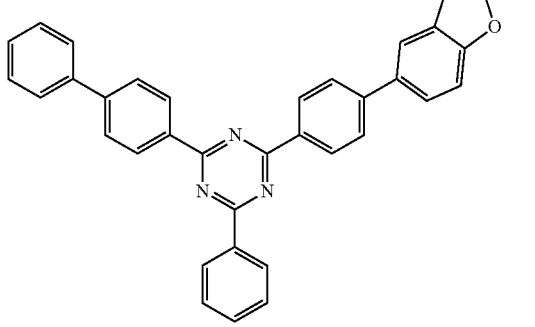

1D-2-62
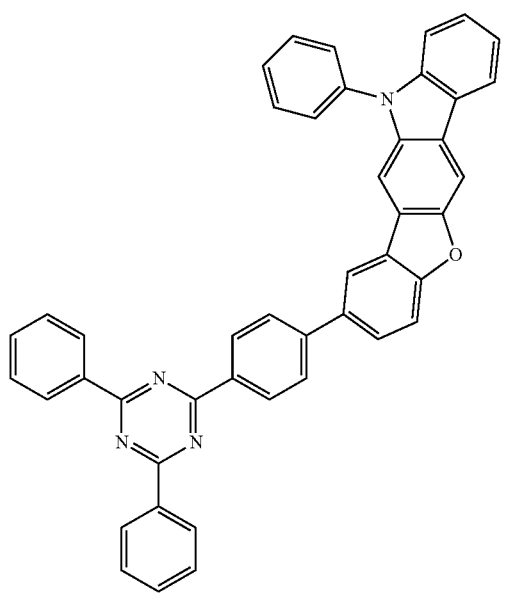
1D-2-64
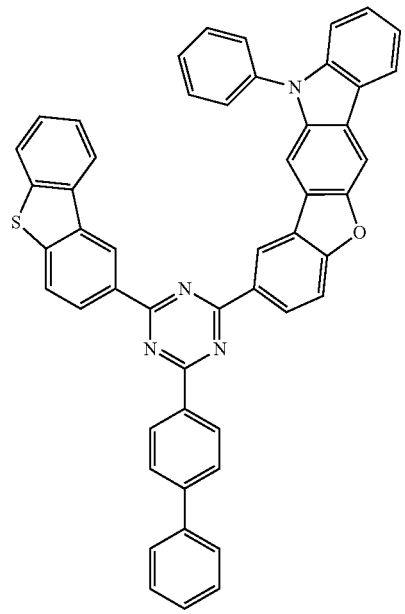
1D-2-63
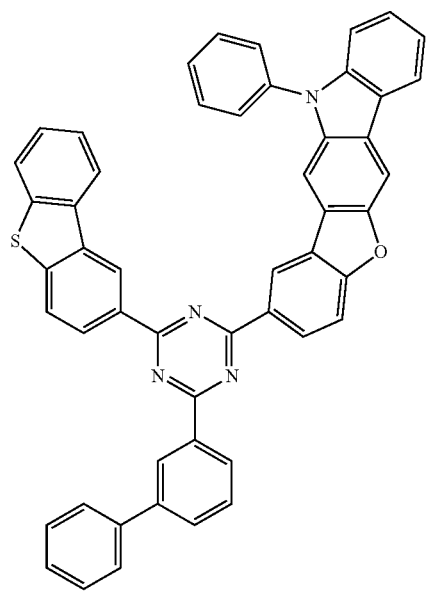
1D-2-65
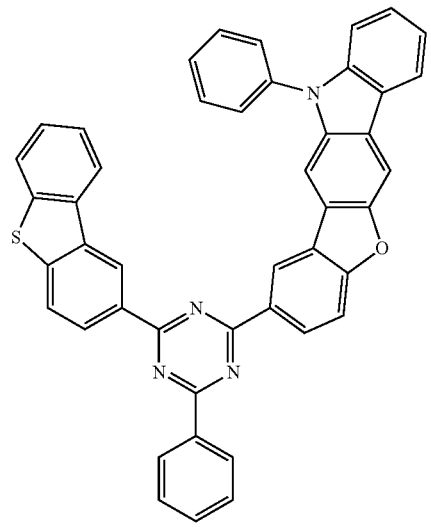

-continued
1D-2-66
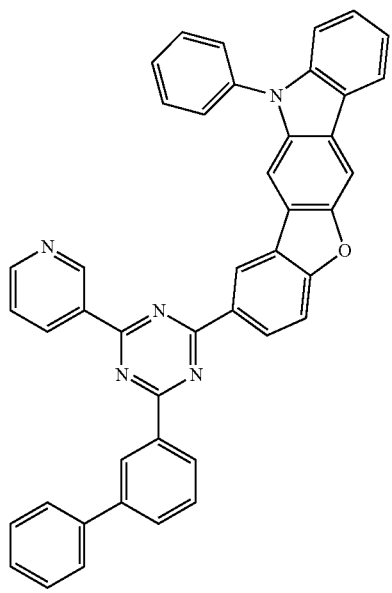
1D-2-68
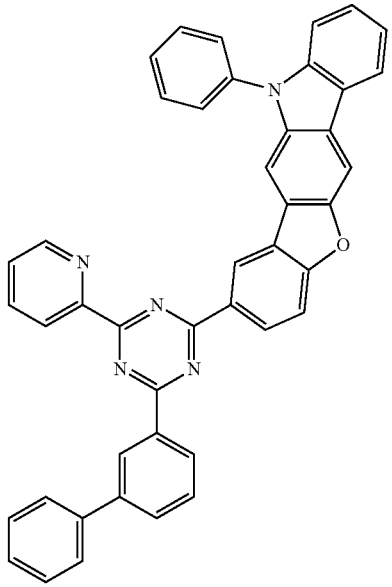
1D-2-67
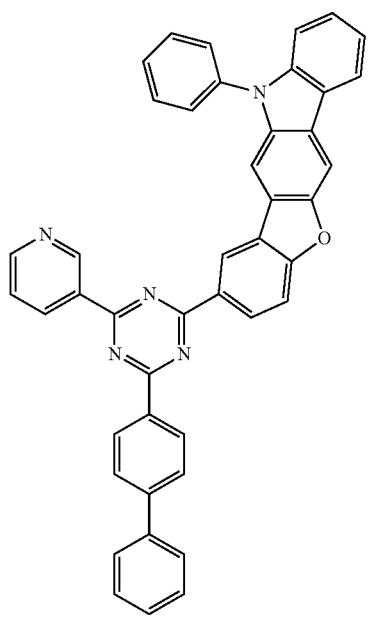
1D-2-69
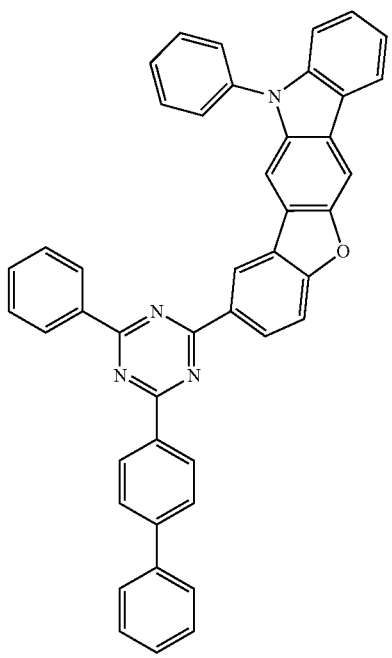

1D-2-70
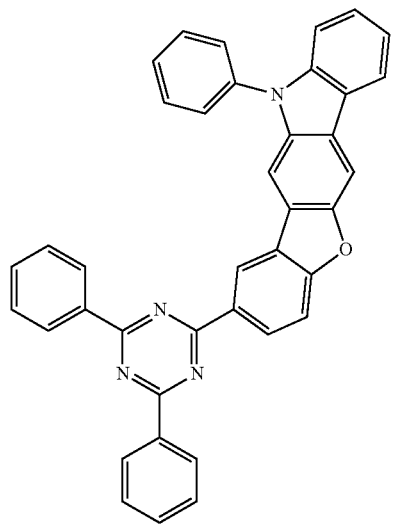
1D-2-71
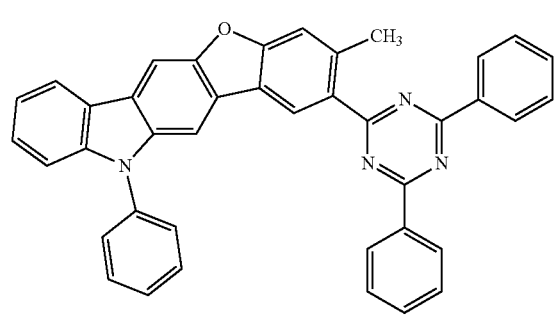
1D-2-72
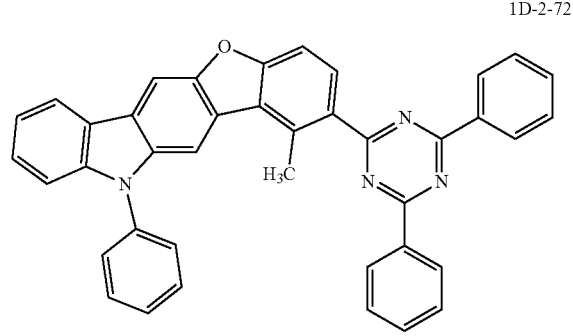
1D-2-73
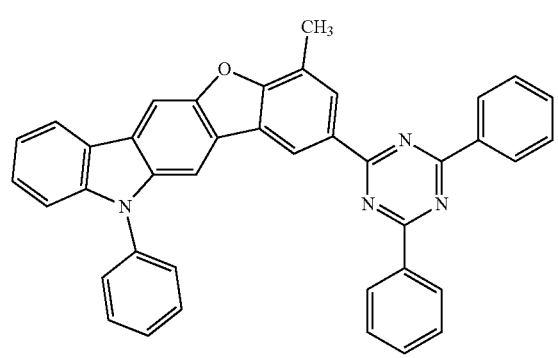
1D-2-74
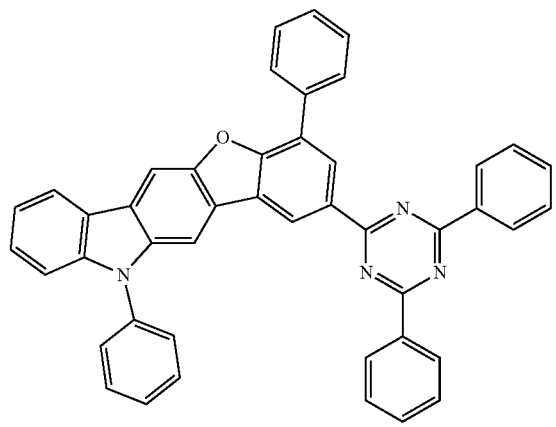
1D-2-75
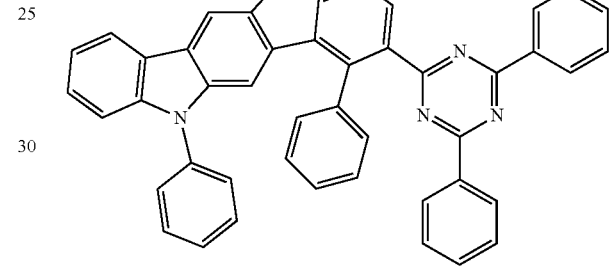
1D-2-76
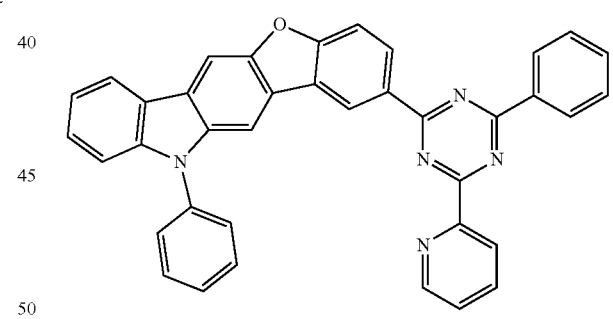
1D-2-77
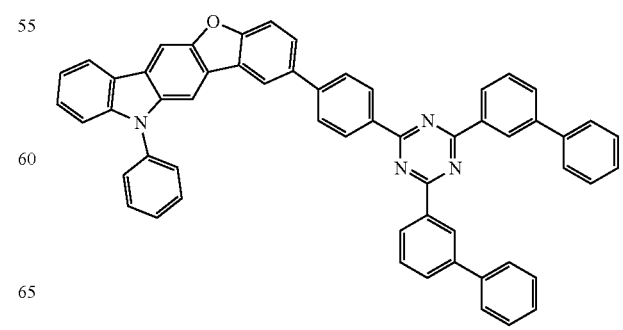

433
-continued
1D-2-78
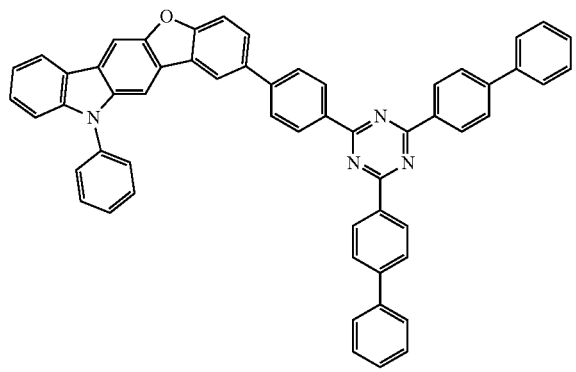
1D-2-79
1D-2-80
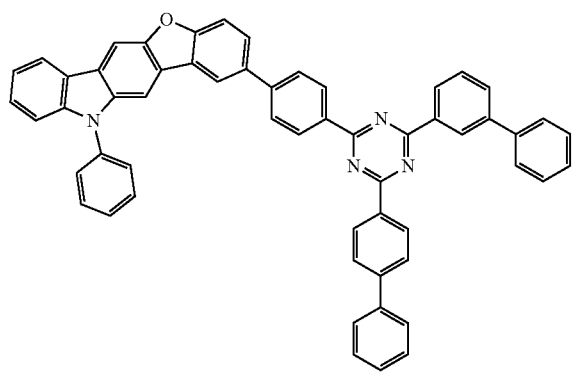
1D-2-81
434
-continued
1D-2-82
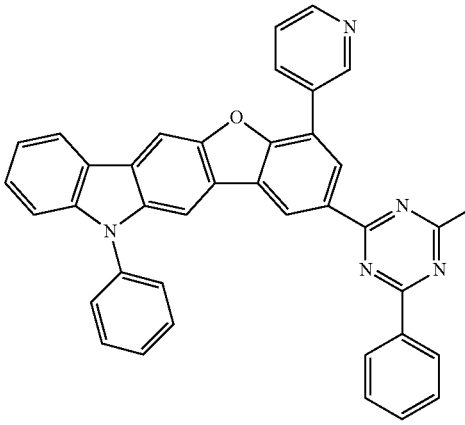
1D-2-83
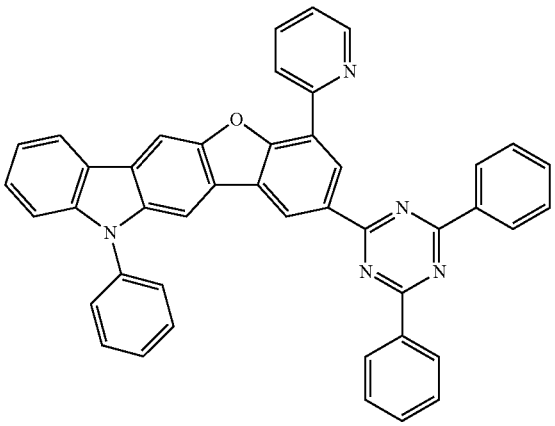
1D-3-1
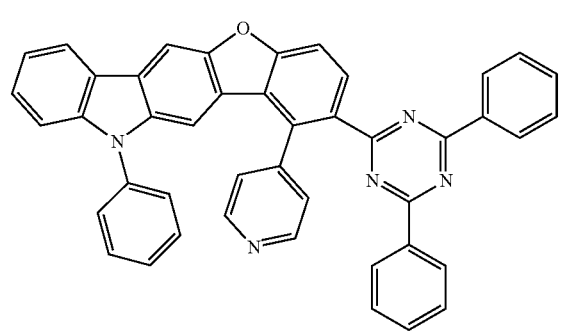
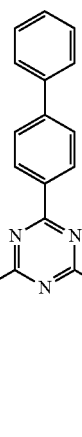

-continued
1D-3-2
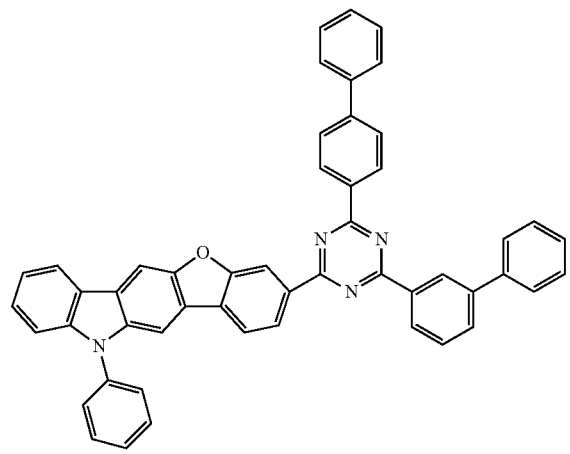
1D-3-3
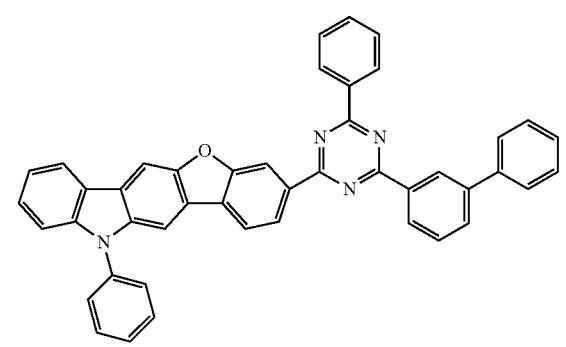
1D-3-4
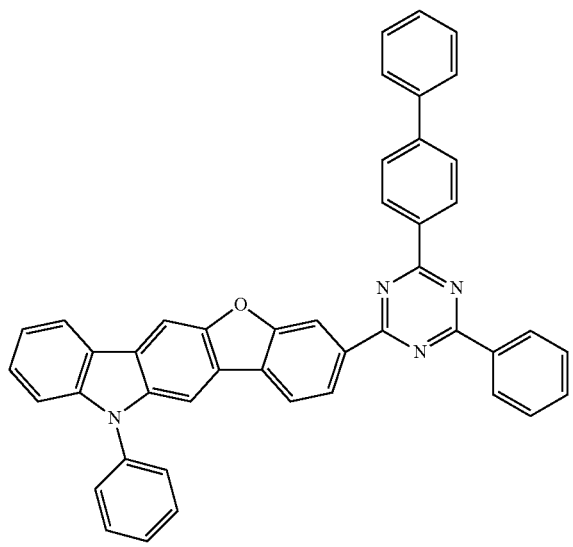
1D-3-5
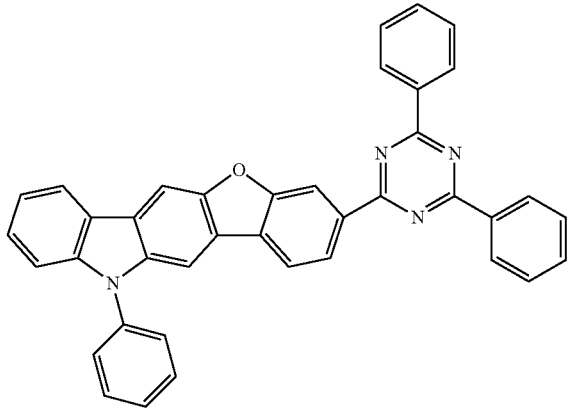
1D-3-6
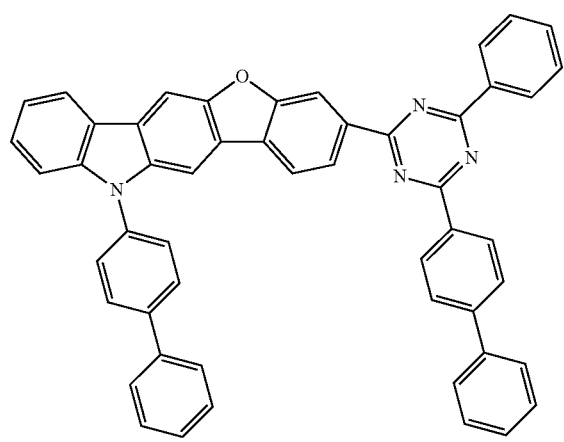
1D-3-7
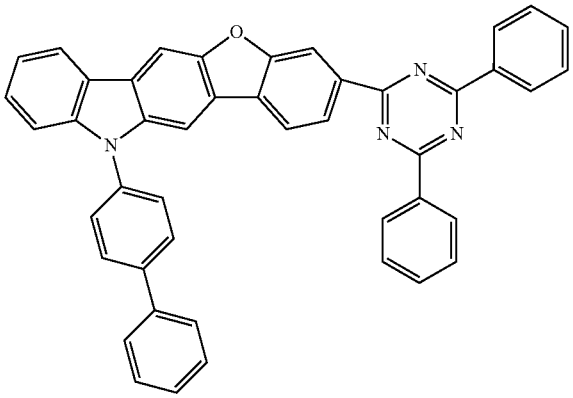
1D-3-8
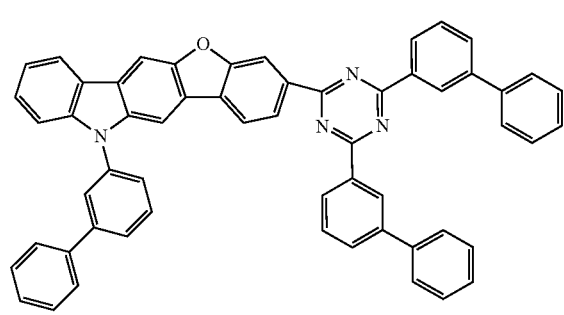

-continued
1D-3-9
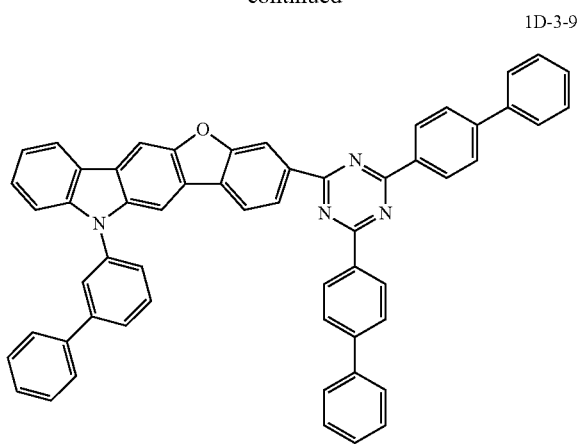
1D-3-10
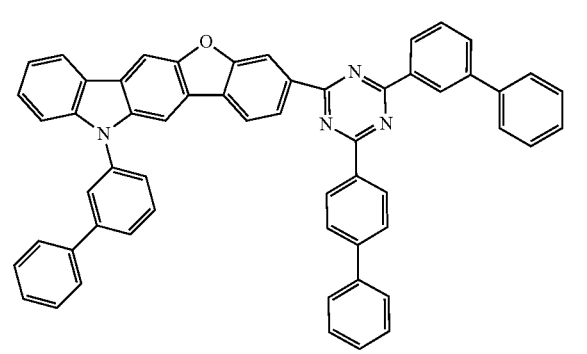
1D-3-11
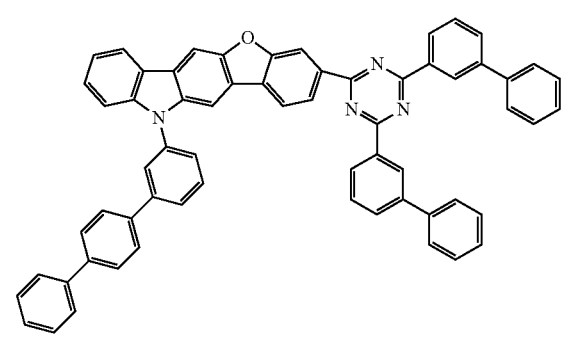
1D-3-12
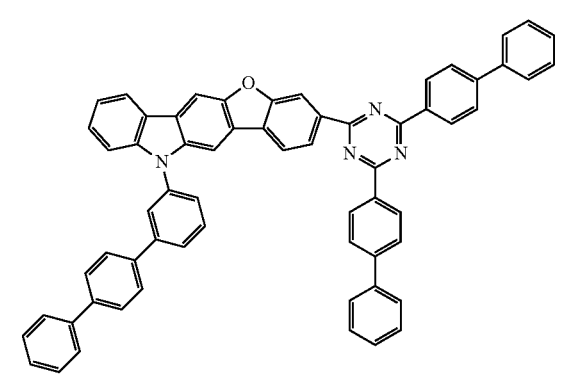
-continued
1D-3-13
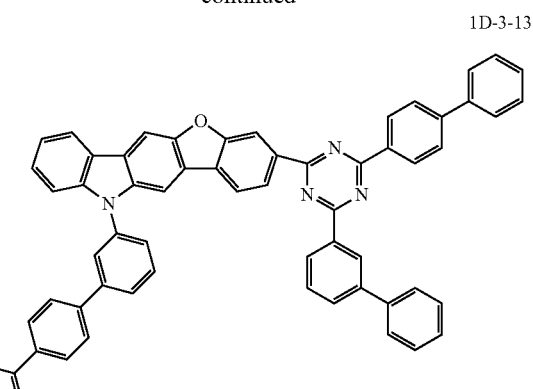
1D-3-14
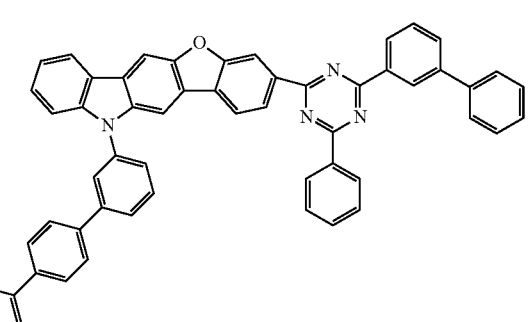
1D-3-15
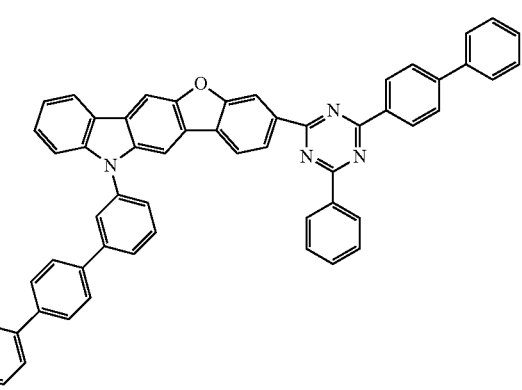
1D-3-16
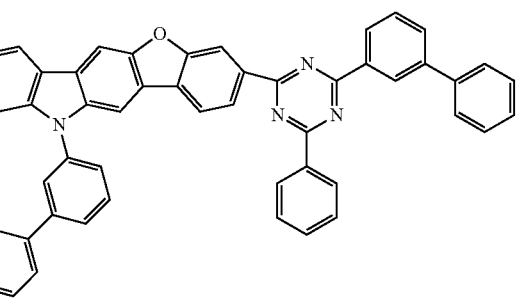

1D-3-17
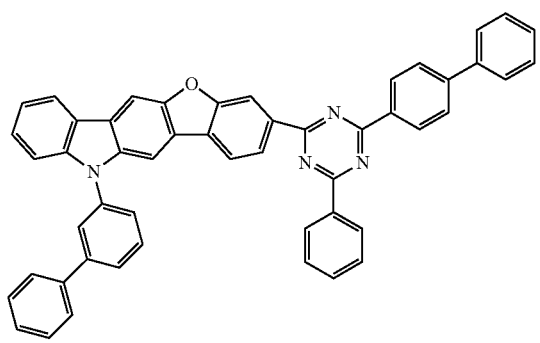
1D-3-21
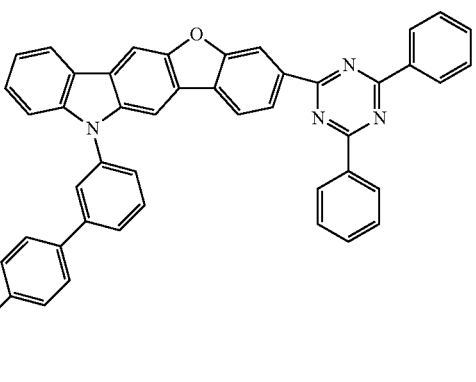
1D-3-18
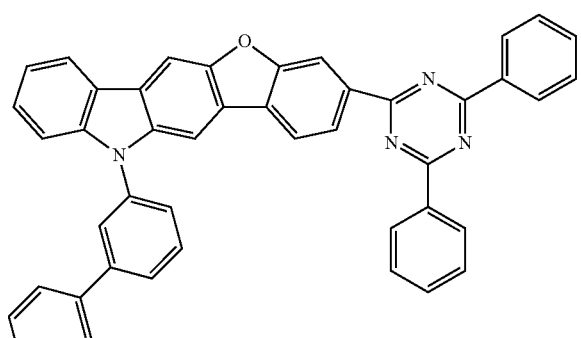
1D-3-22
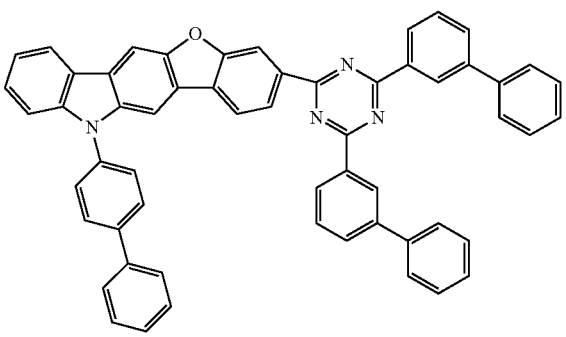
1D-3-19
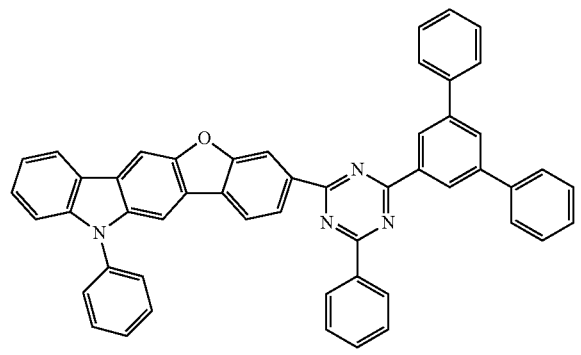
1D-3-23
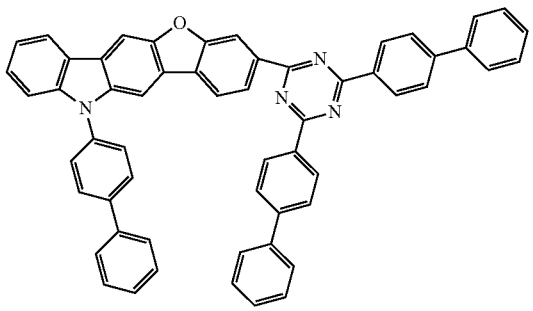
1D-3-20
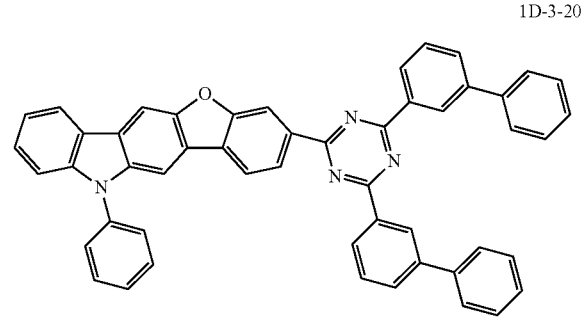
1D-3-24

1D-3-25
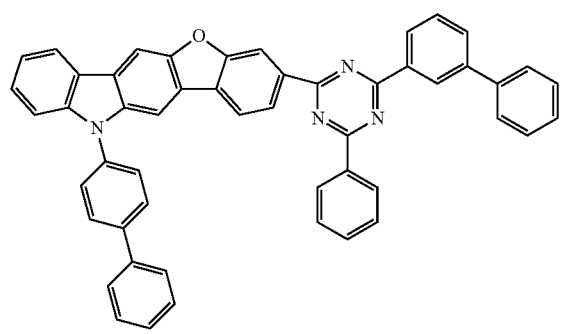
1D-3-26
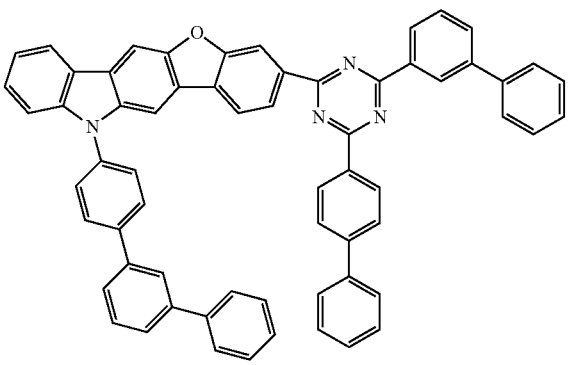
1D-3-27
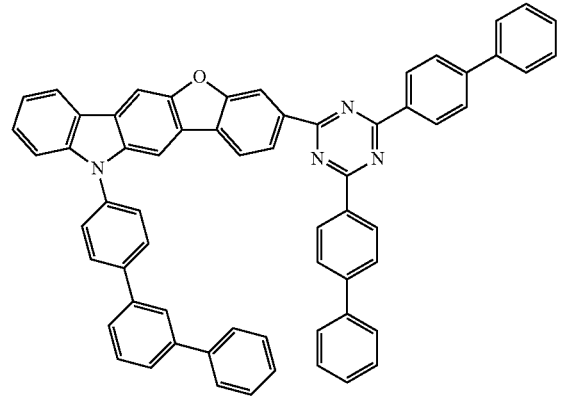
1D-3-28
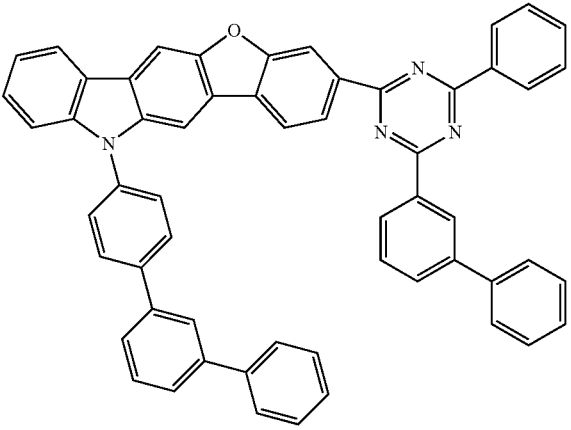
1D-3-29
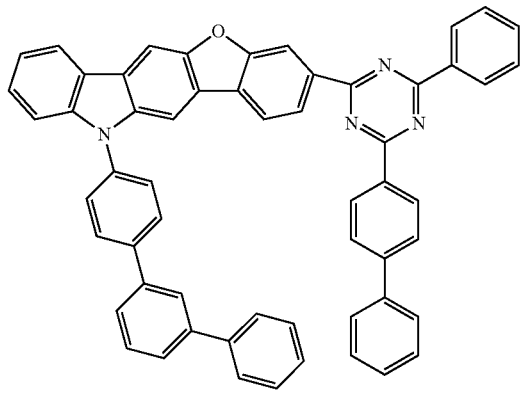
1D-3-30
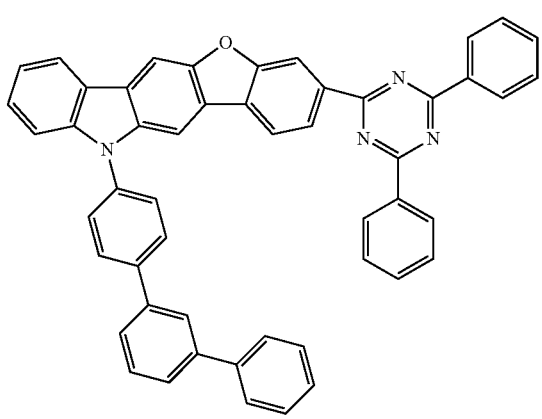
1D-3-31
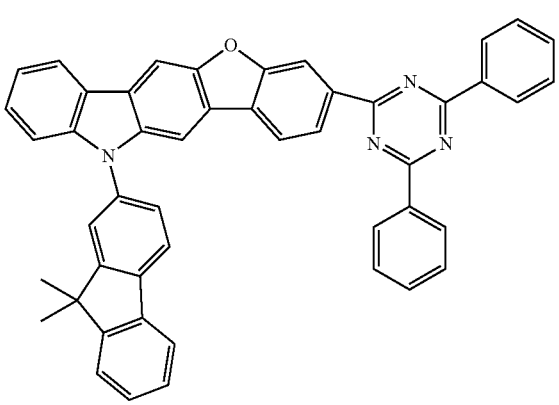

-continued
1D-3-32
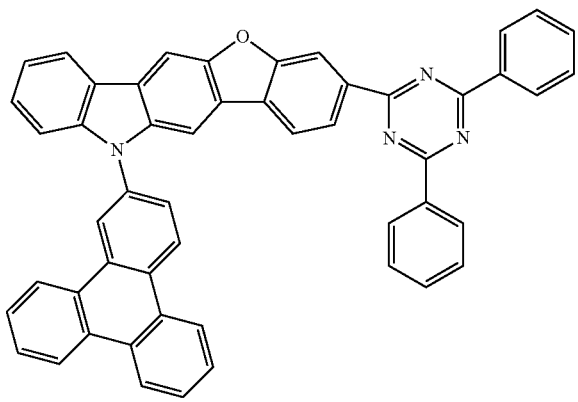
1D-3-33
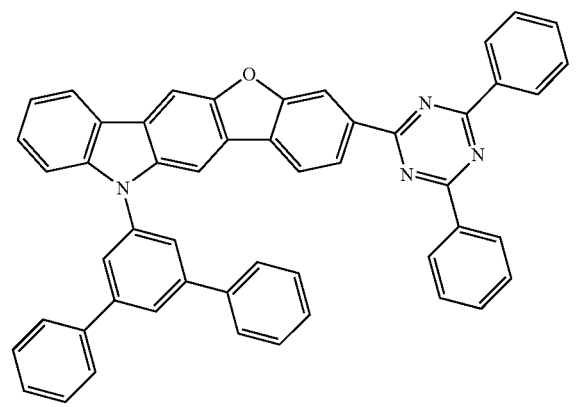
1D-3-34
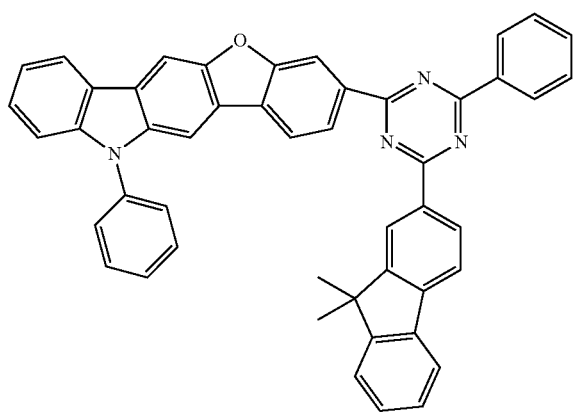
1D-3-35
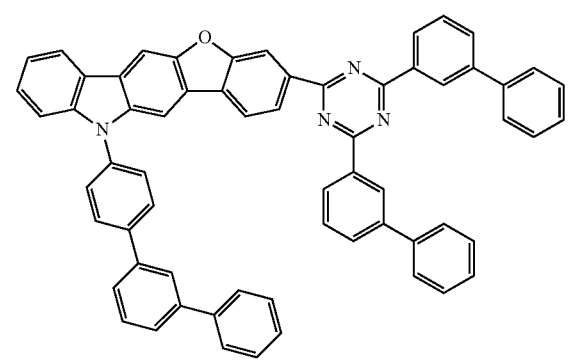
1D-3-36
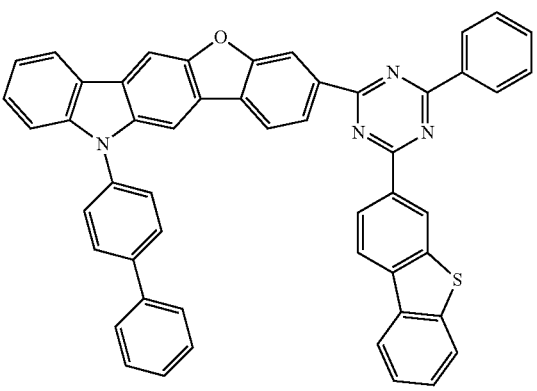
1D-3-37
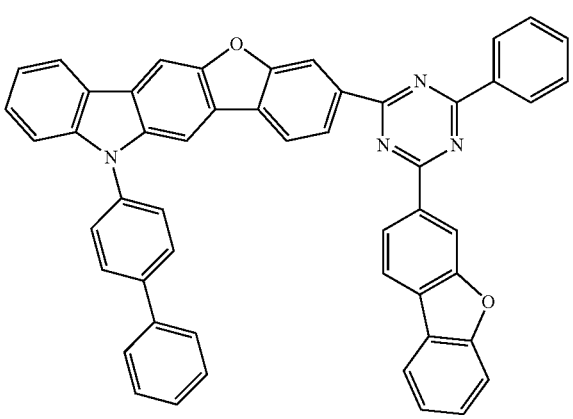
1D-3-38
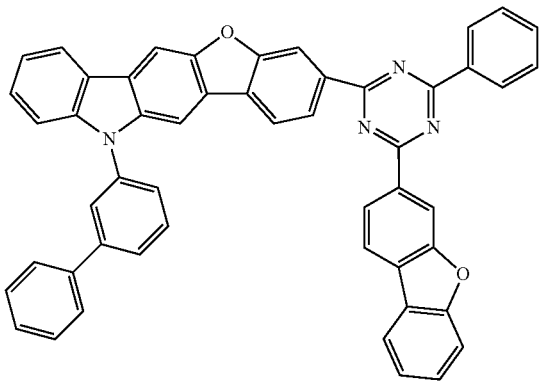
1D-3-39
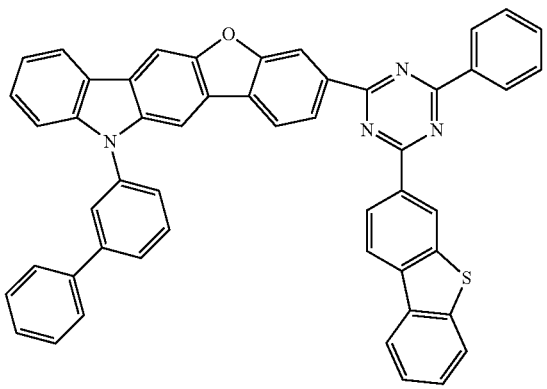

1D-3-40
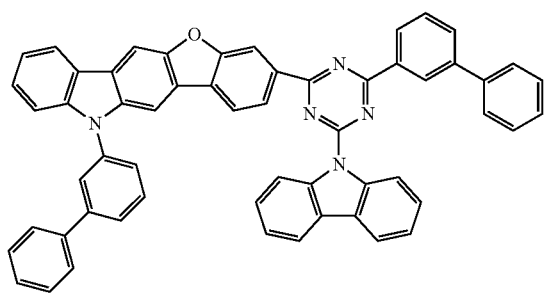
1D-3-41
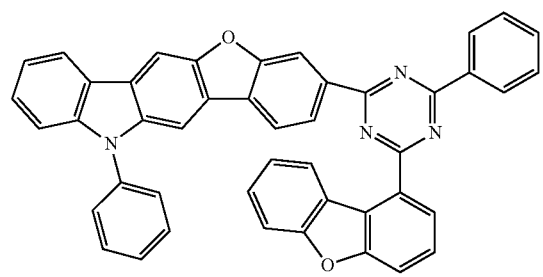
1D-3-42
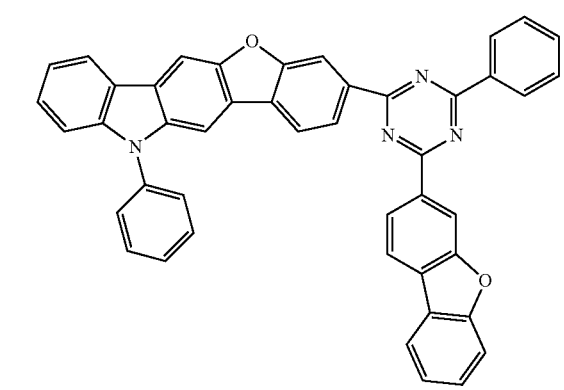
1D-3-43
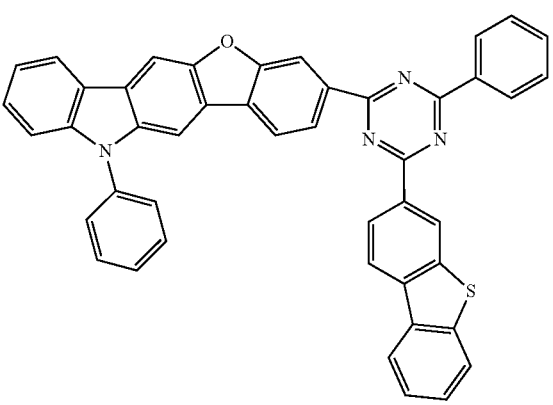
1D-3-44
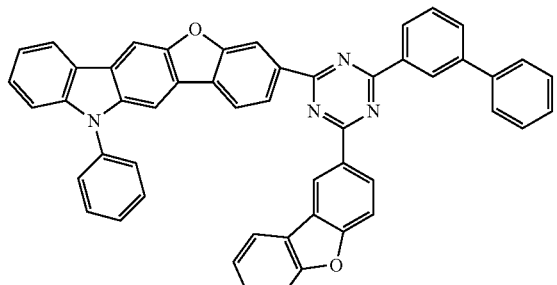
1D-3-45
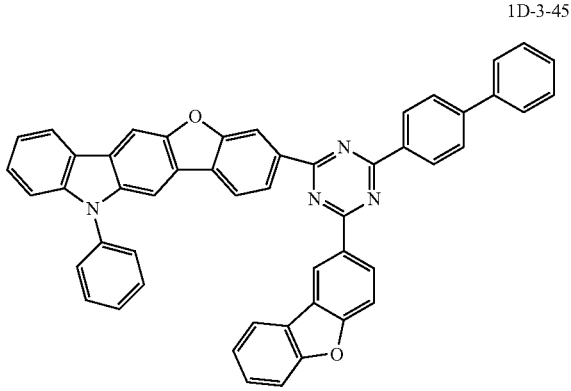
1D-3-46
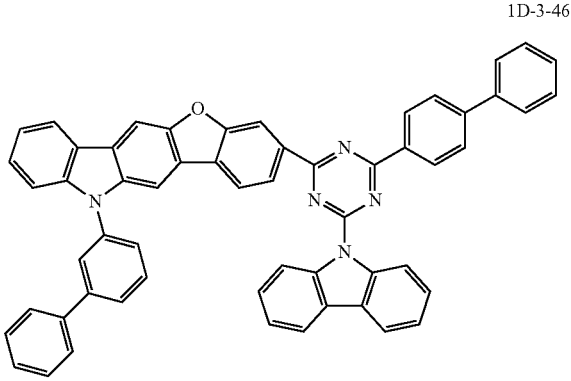
1D-3-47
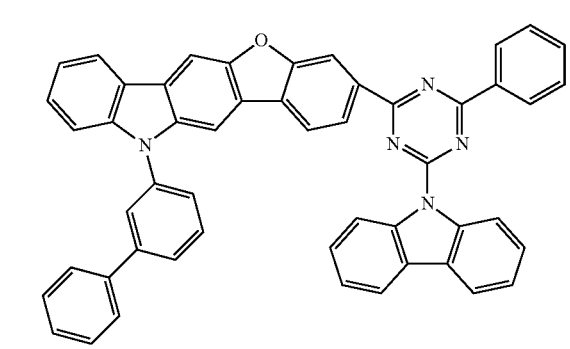

1D-3-48
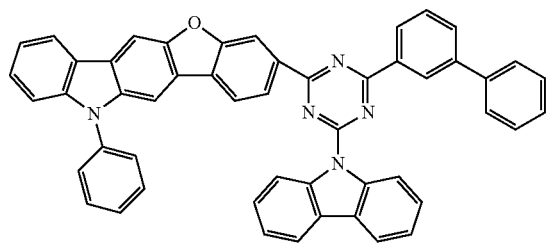
1D-3-49
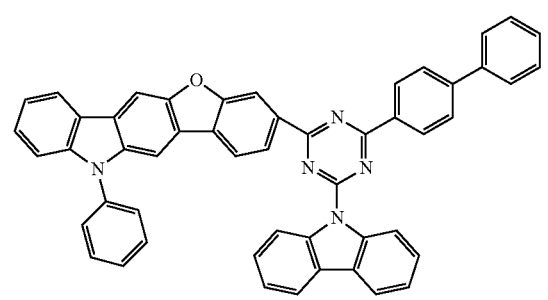
1D-3-50
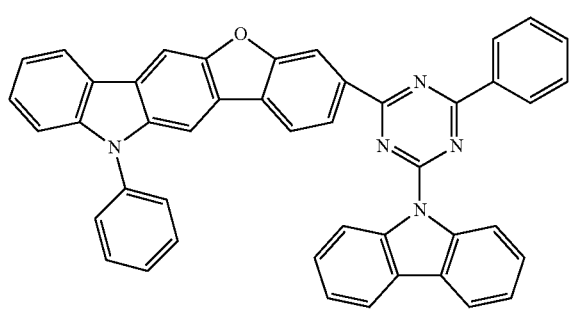
1D-3-51
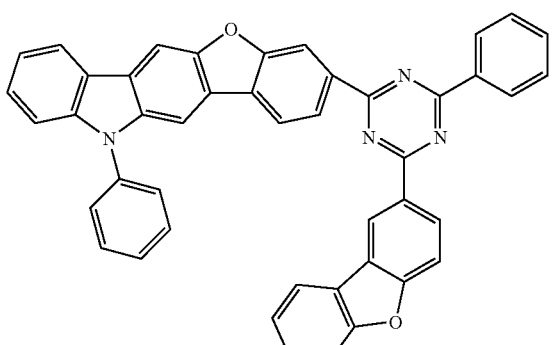
1D-3-52
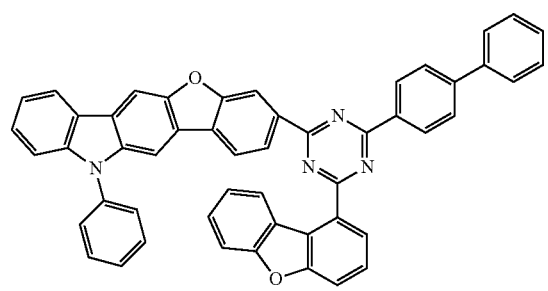
1D-3-53
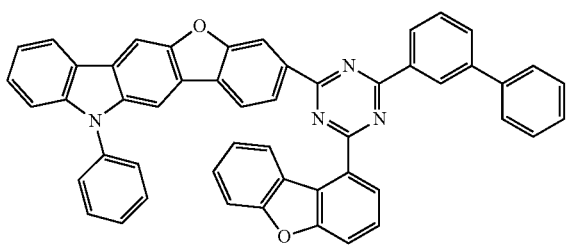
1D-3-54
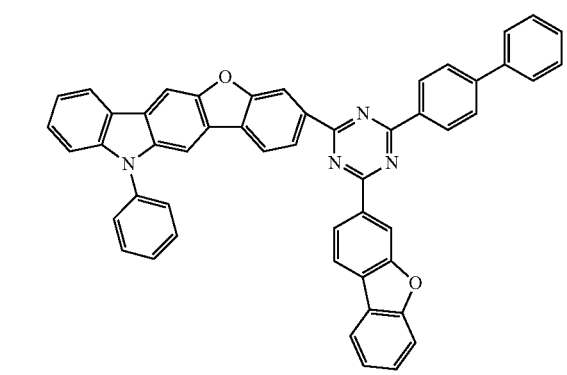
1D-3-55
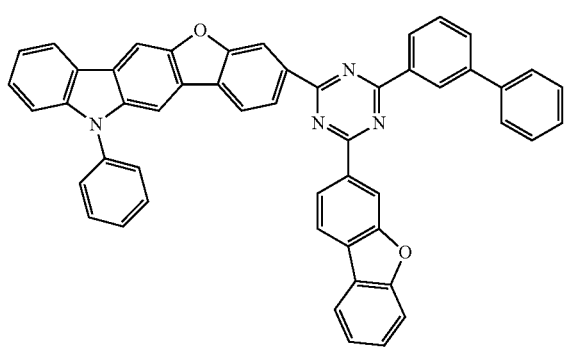
1D-3-56
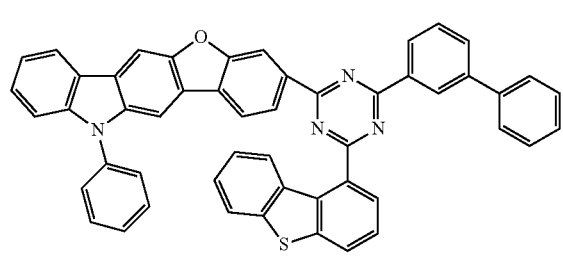
1D-3-57
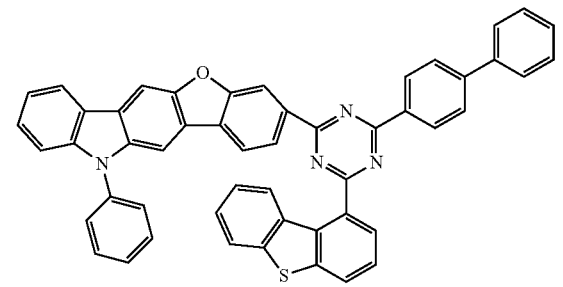

-continued
1D-3-58
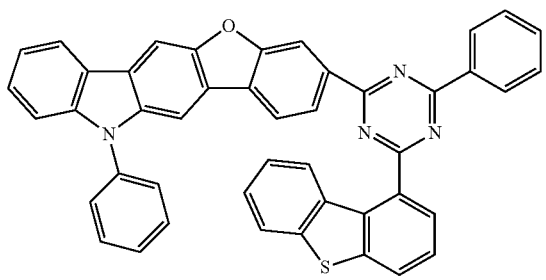
1D-3-59
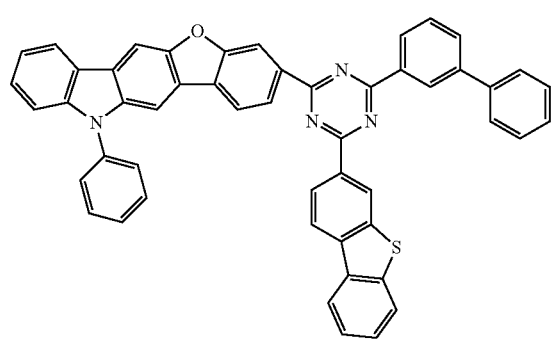
1D-3-60
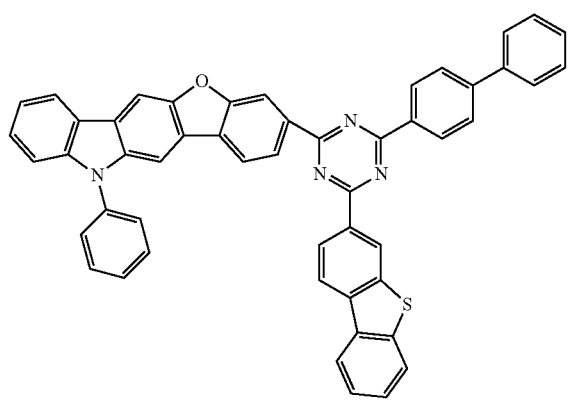
1D-3-61
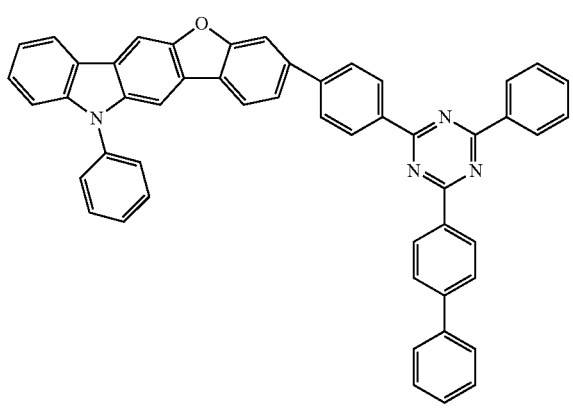
-continued
1D-3-62
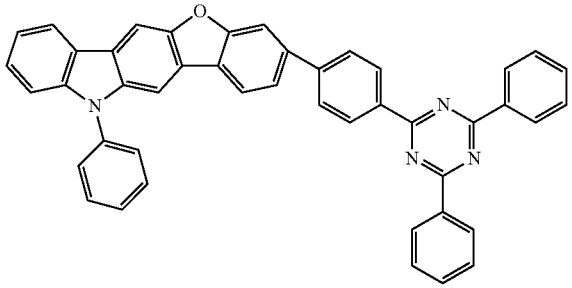
1D-3-63
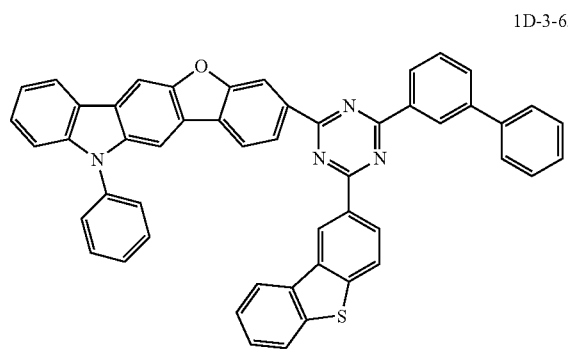
1D-3-64
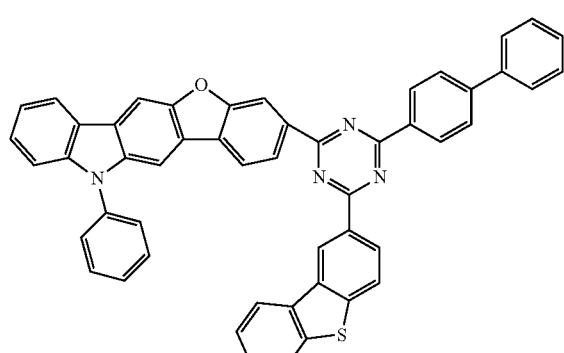
1D-3-65
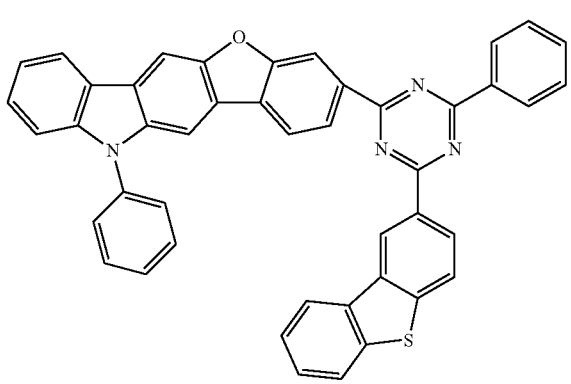

1D-3-66
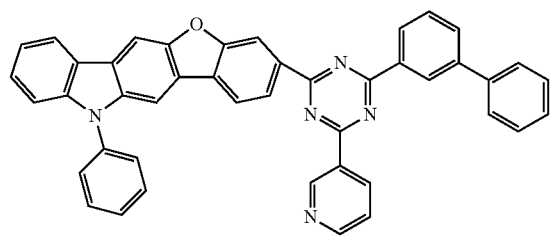
1D-3-67
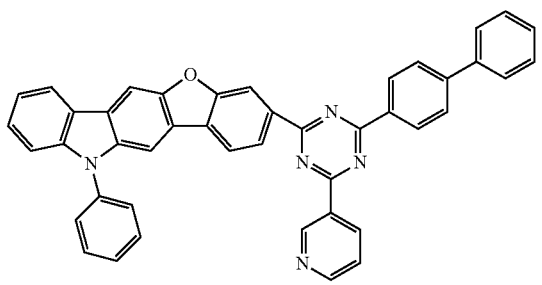
1D-3-68
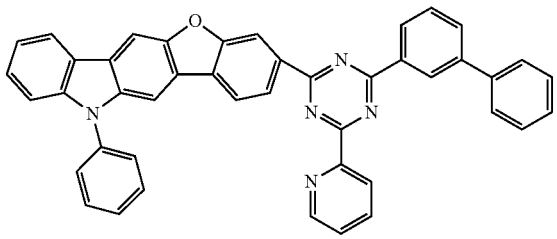
1D-3-69
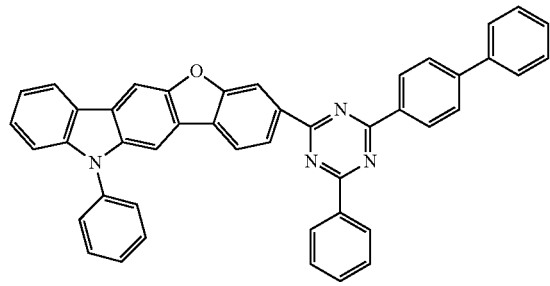
1D-3-70
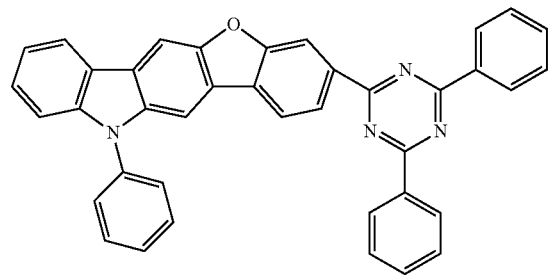
1D-3-71
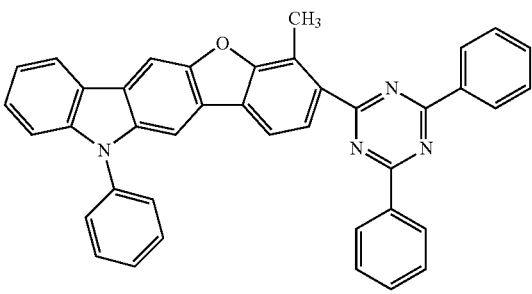
1D-3-72
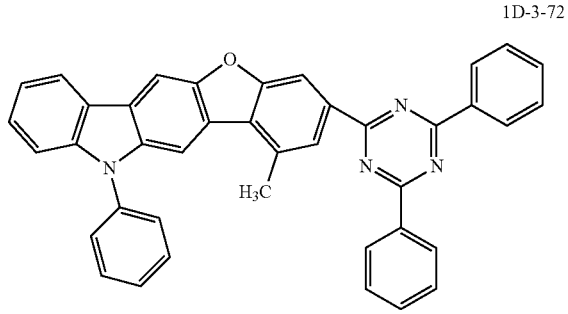
1D-3-73
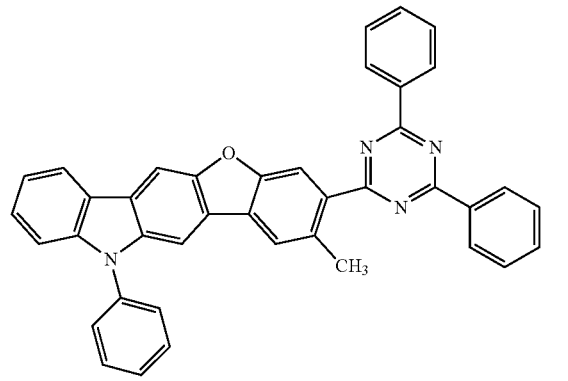
1D-3-74
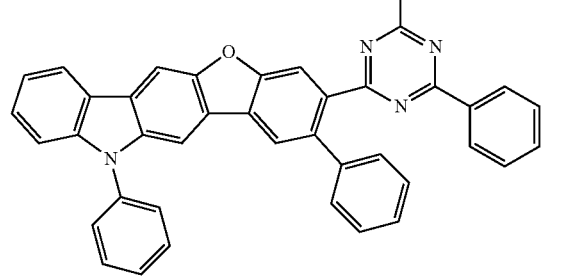

1D-3-75
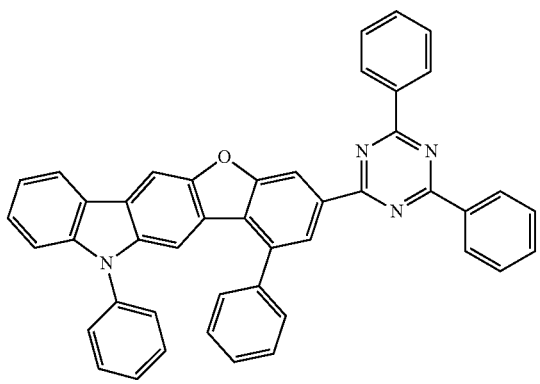
1D-3-76
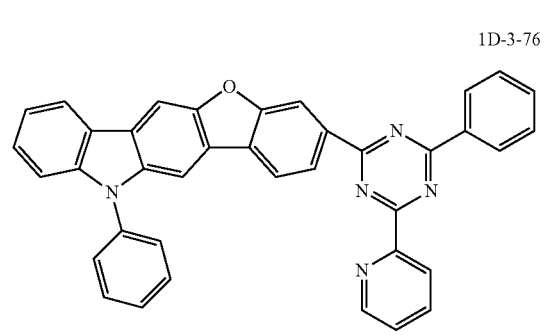
1D-3-77
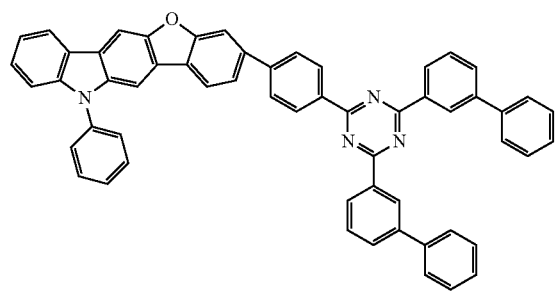
1D-3-78
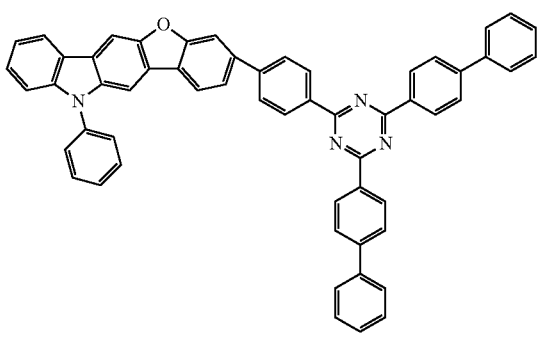
1D-3-79
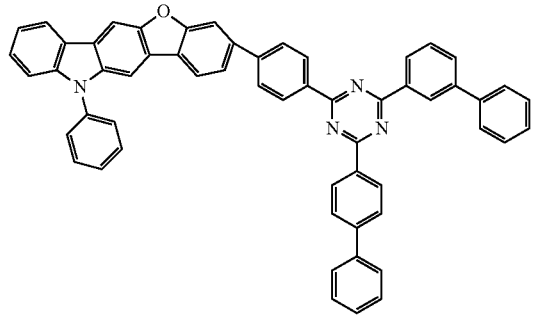
1D-3-80
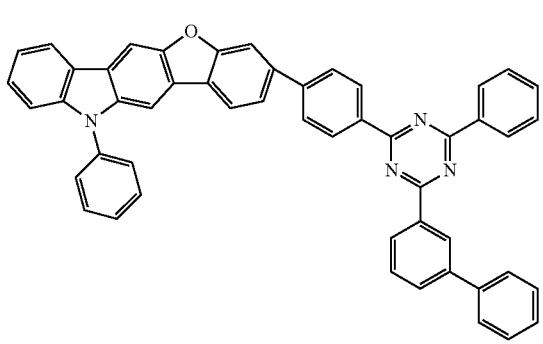
1D-3-81
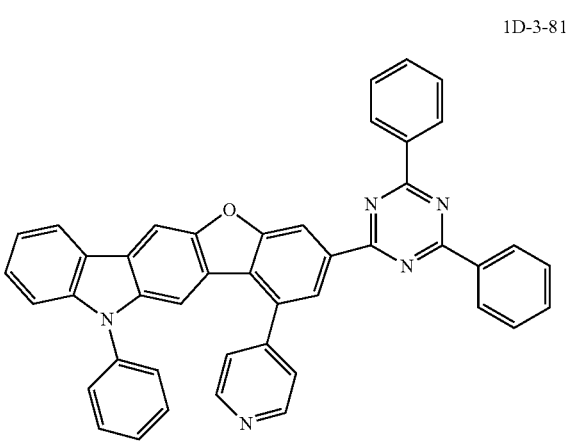
1D-3-82
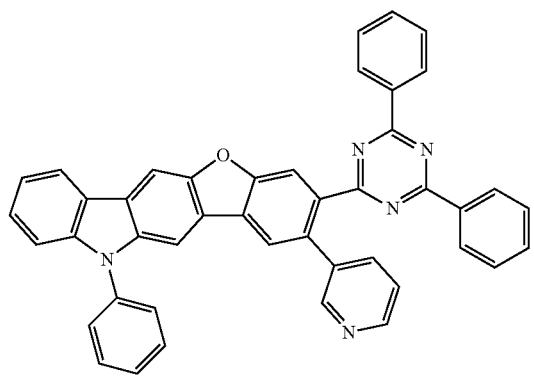

1D-3-83
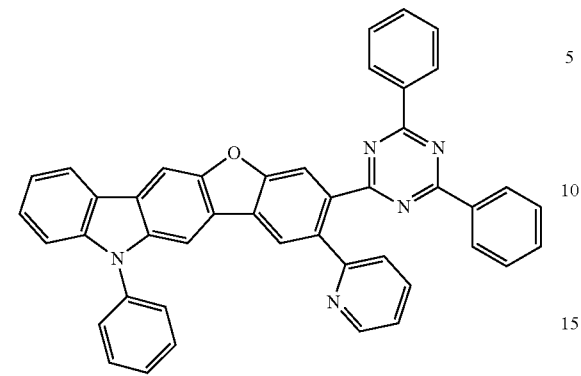
1D-4-1
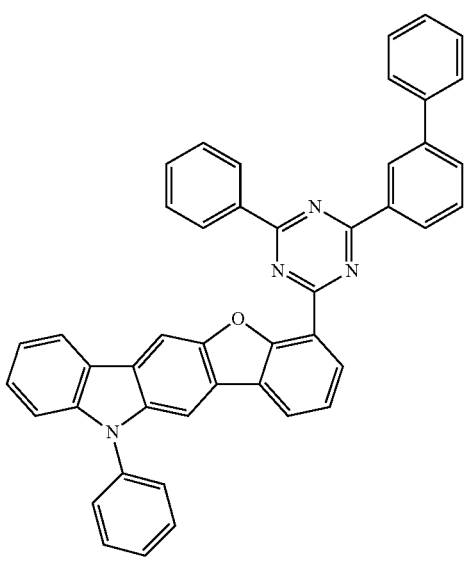
1D-4-2
1D-4-3
1D-4-4
1D-4-5
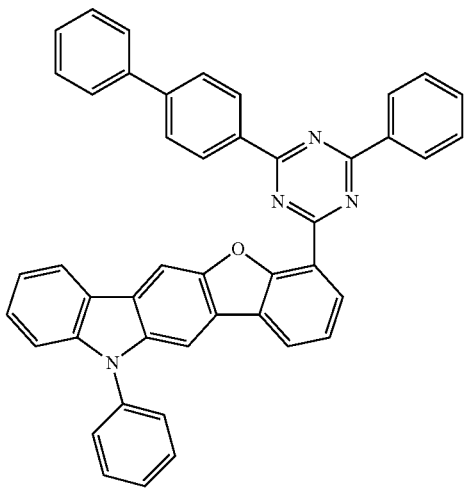
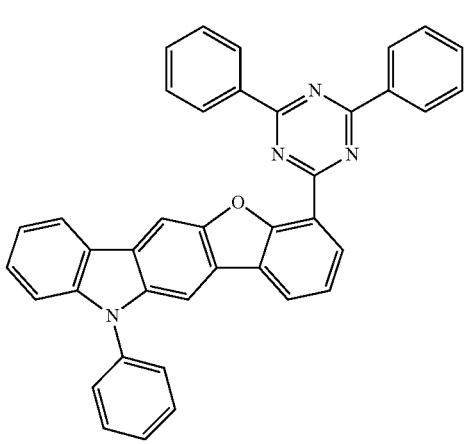

1D-4-6
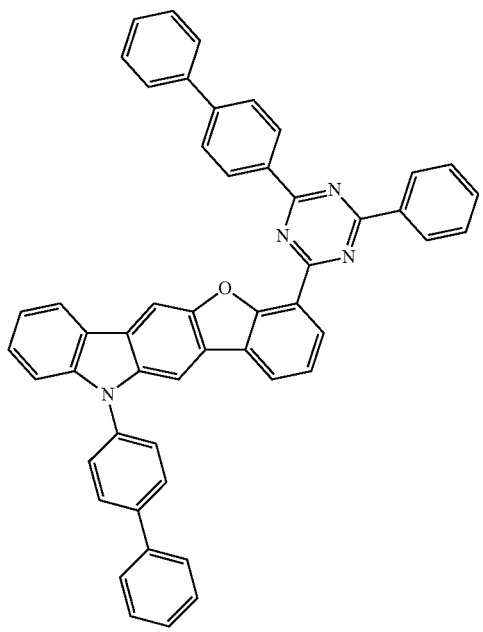
1D-4-8
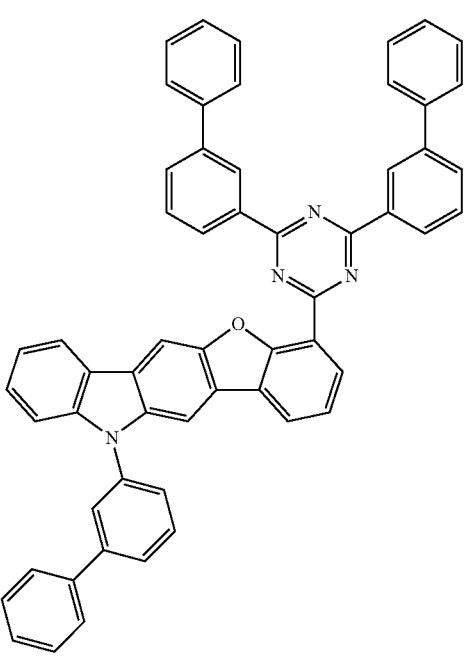
1D-4-7
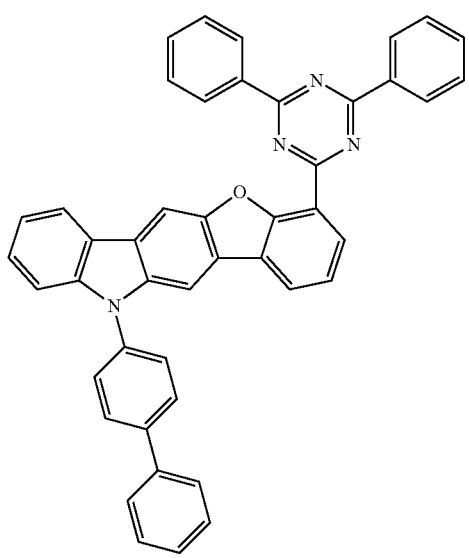
1D-4-9
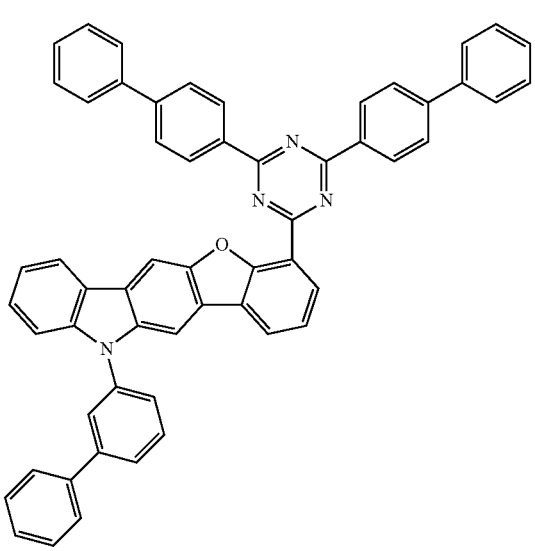

1D-4-10
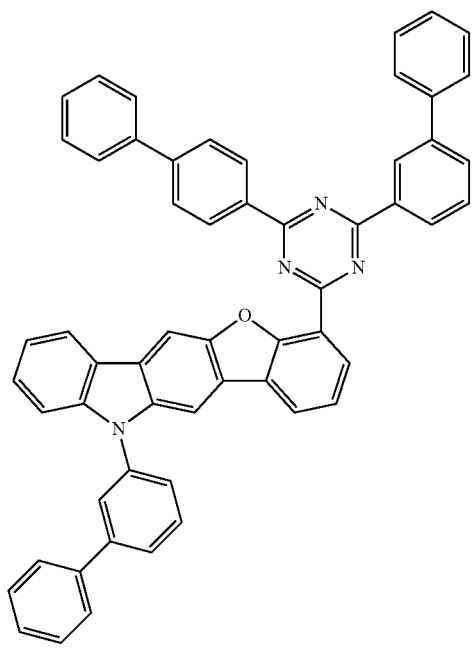
1D-4-12
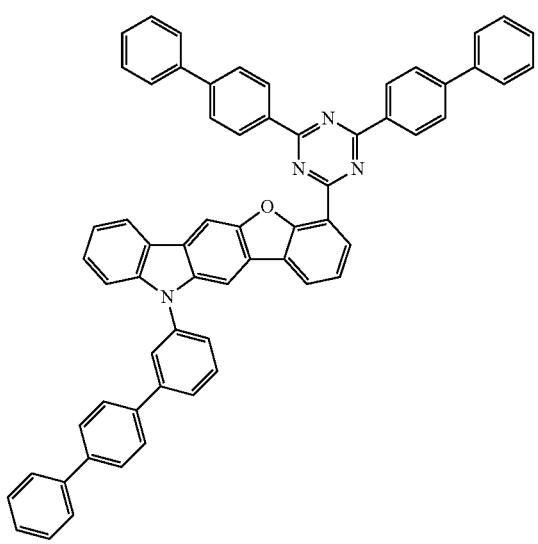
1D-4-11
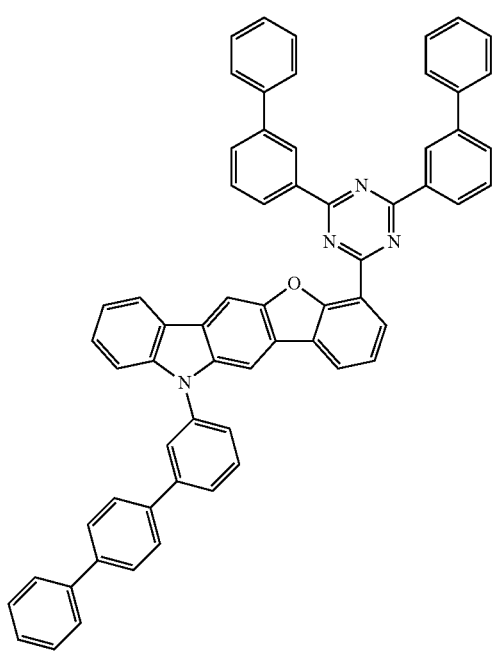
1D-4-13
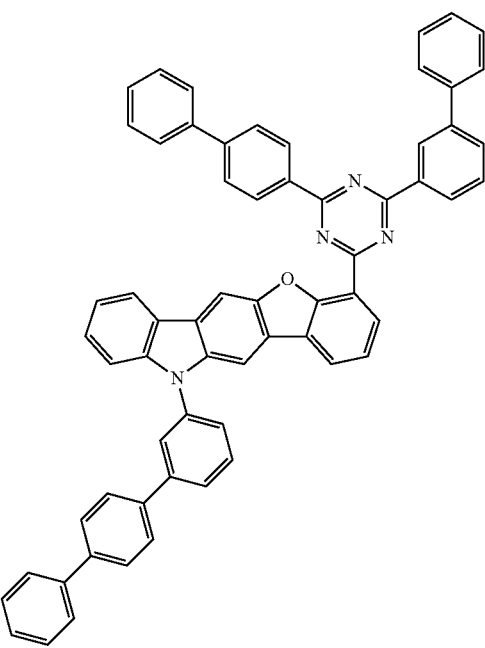

1D-4-14
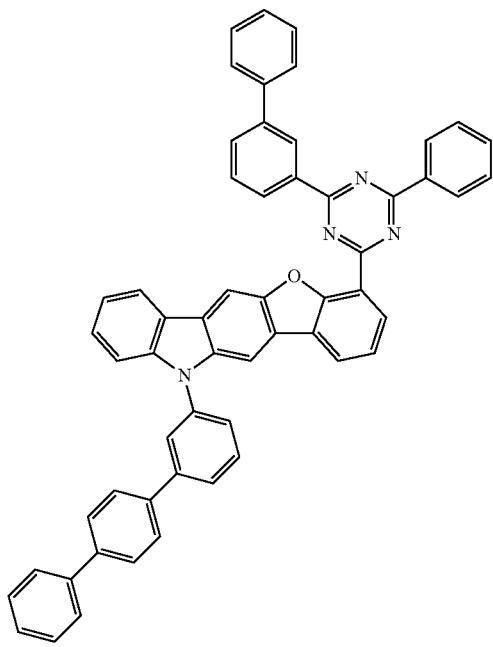
1D-4-15
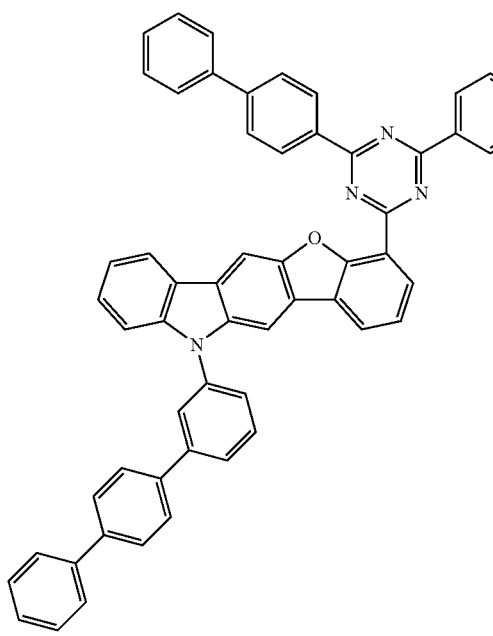
1D-4-16
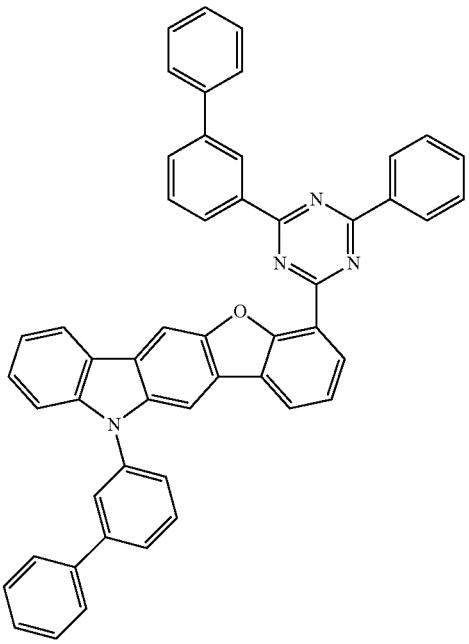
1D-4-17
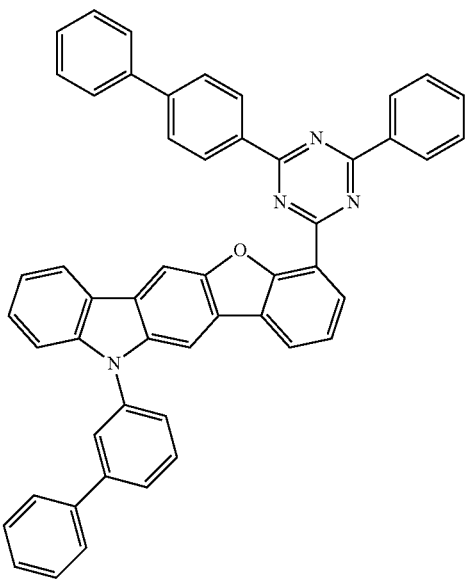

1D-4-18
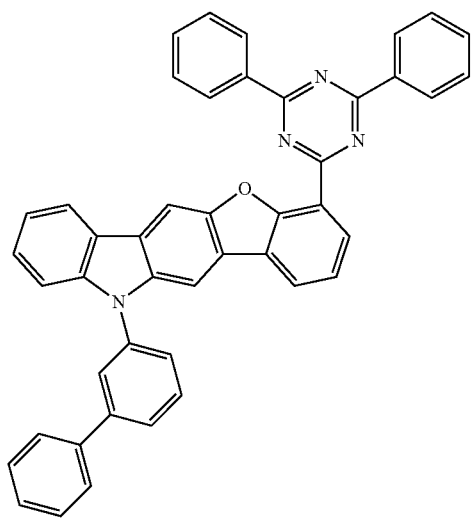
1D-4-20
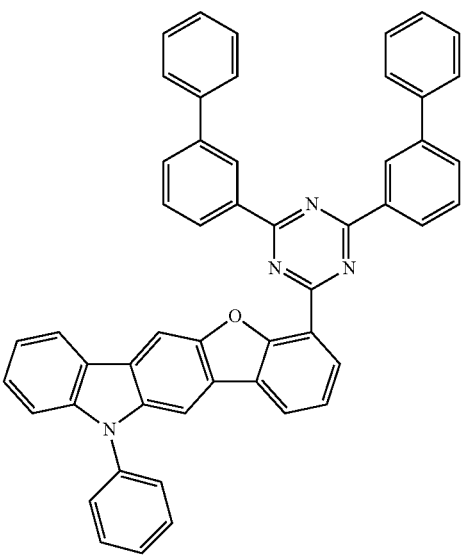
1D-4-19
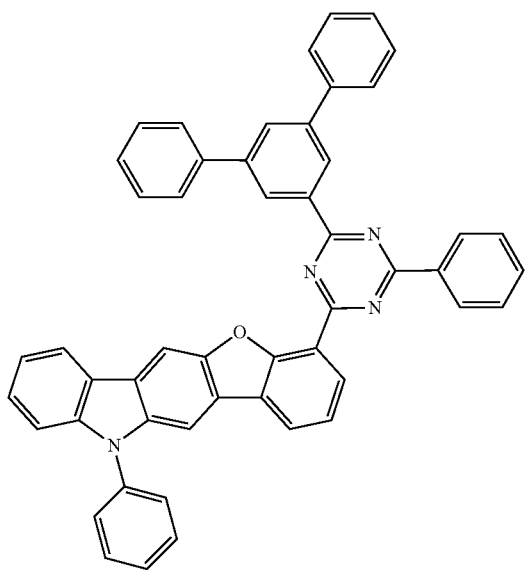
1D-4-21
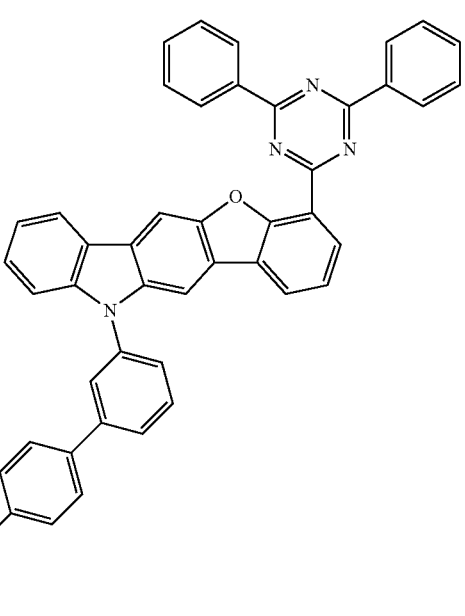

1D-4-22
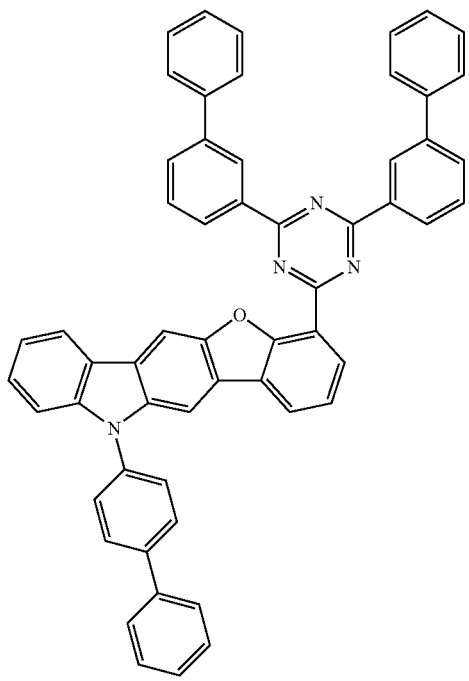
1D-4-24
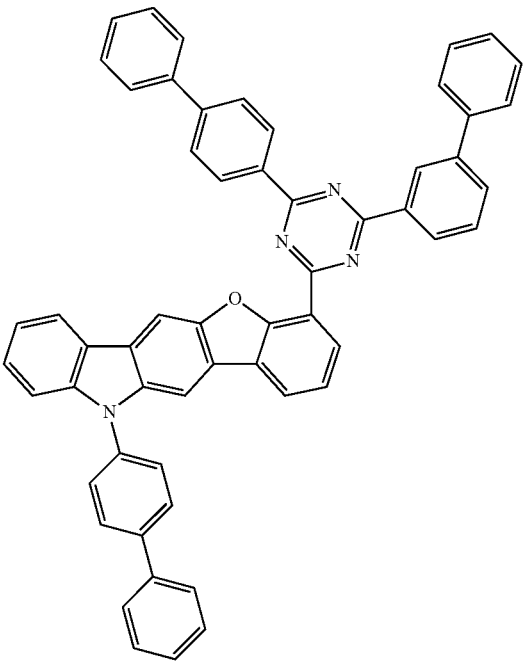
1D-4-23
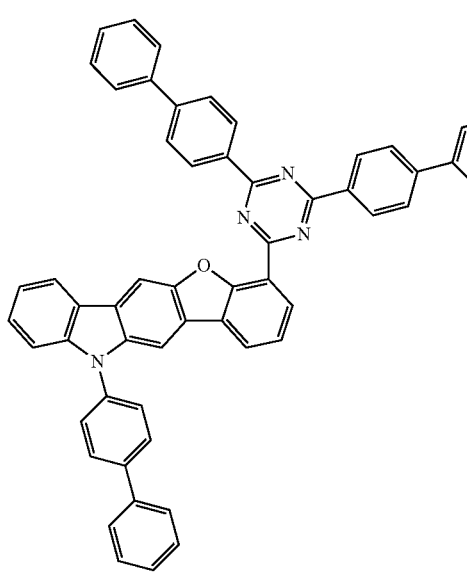
1D-4-25
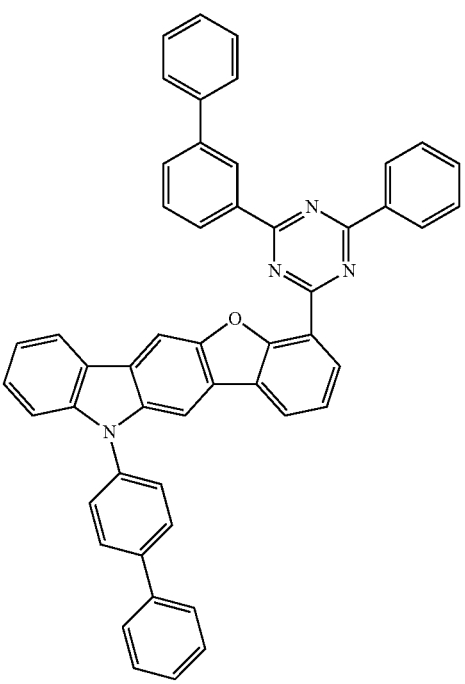

1D-4-26
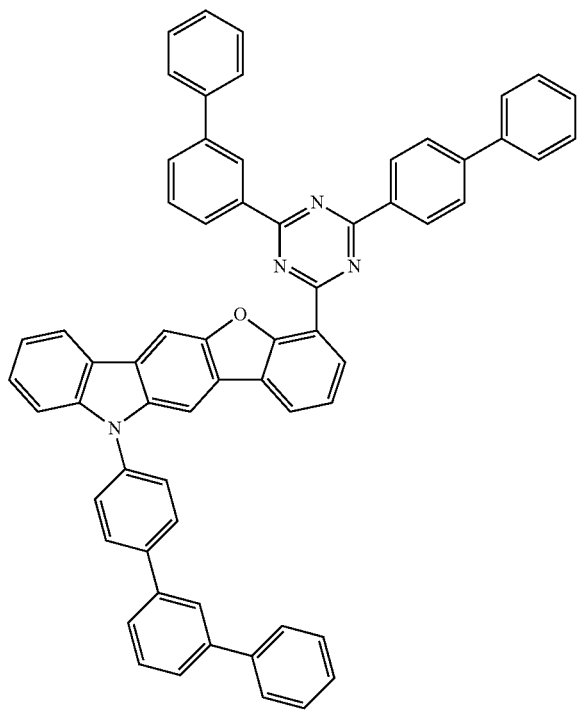
1D-4-28
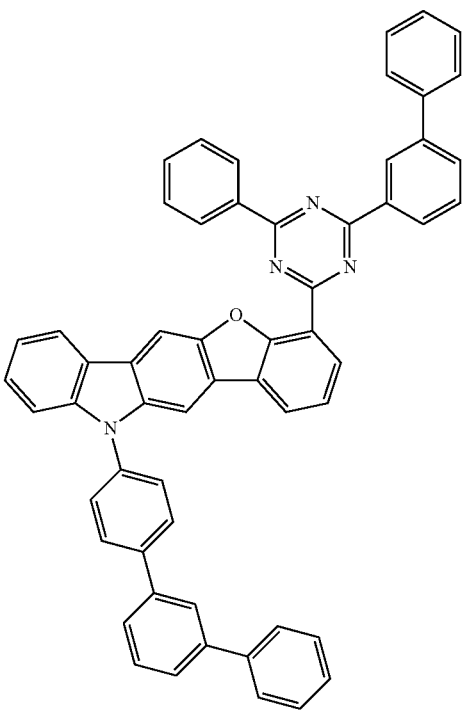
1D-4-27
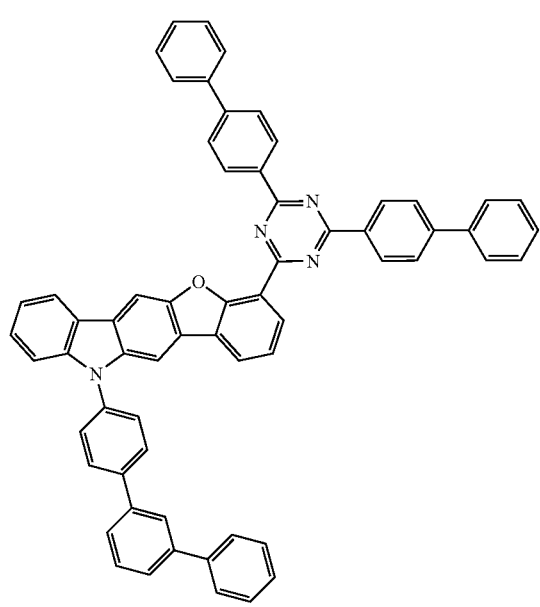
1D-4-29
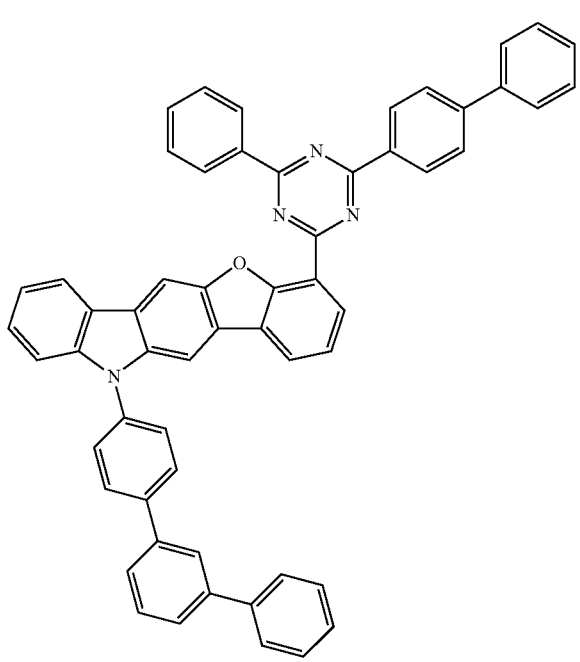

1D-4-30
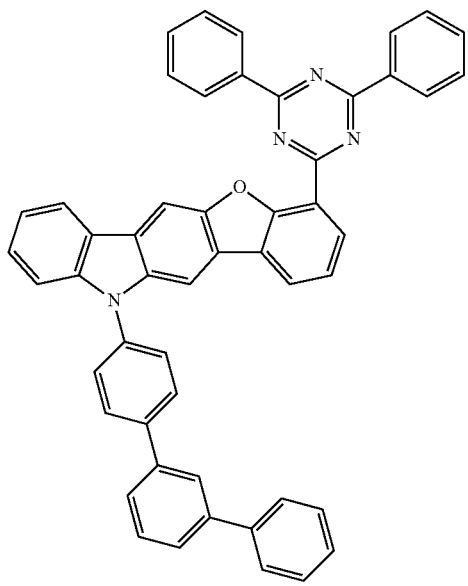
1D-4-31
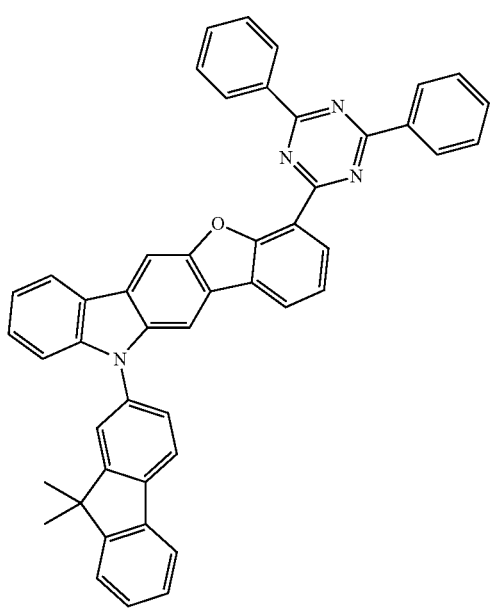
1D-4-32
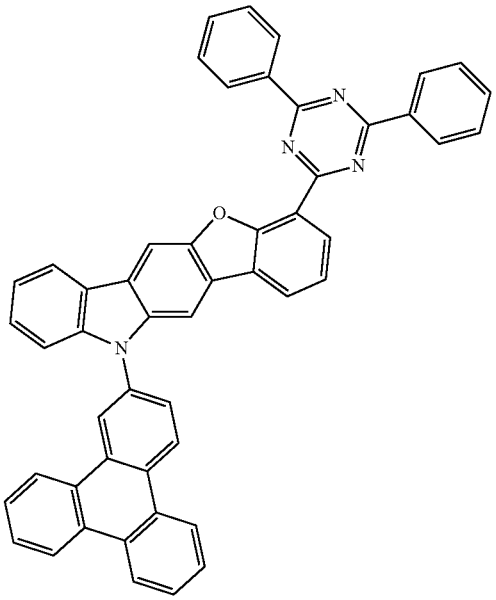
1D-4-33
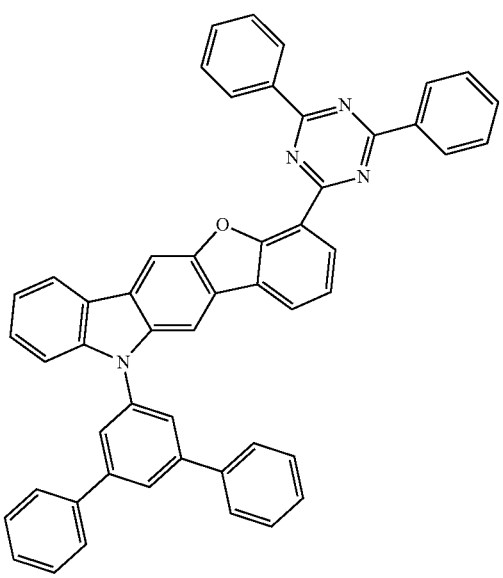

1D-4-34
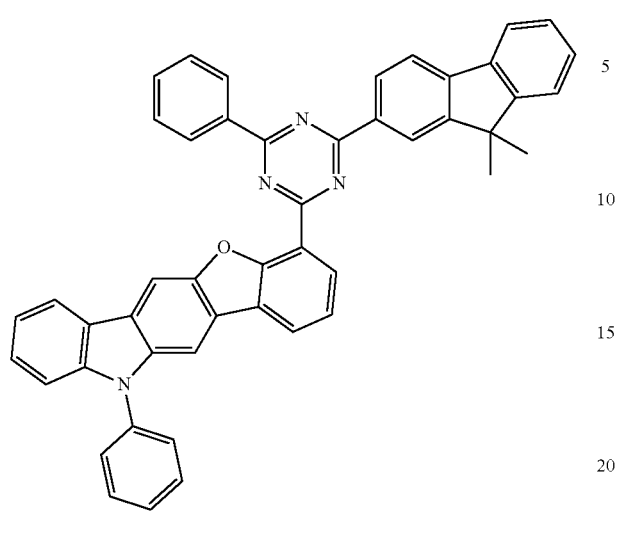
1D-4-36
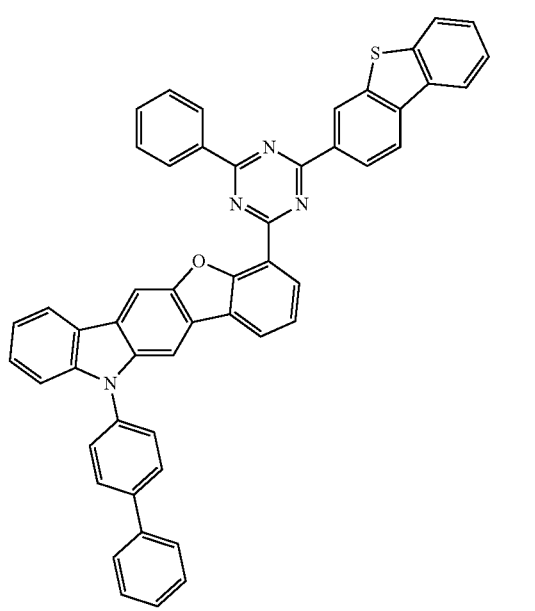
1D-4-35
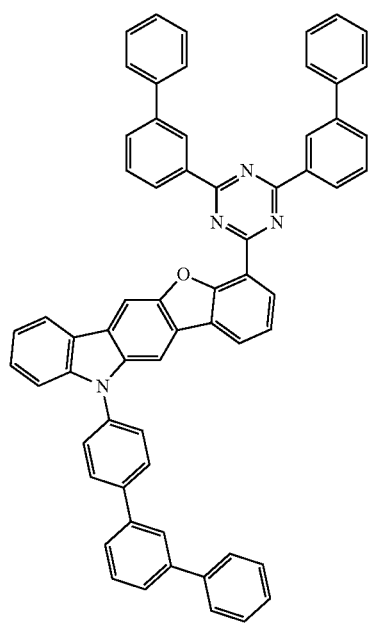
1D-4-37
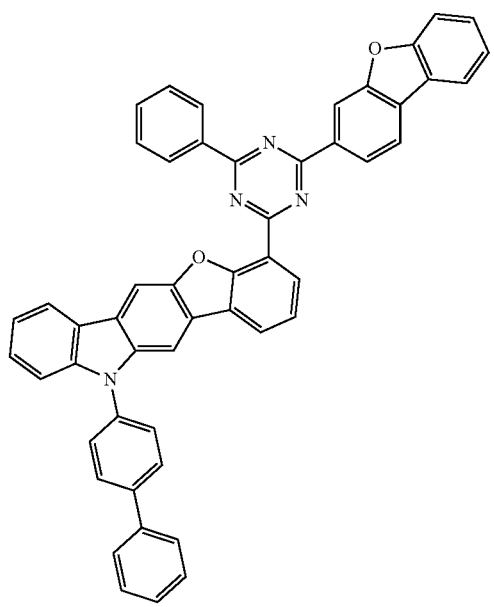

473
-continued
1D-4-38
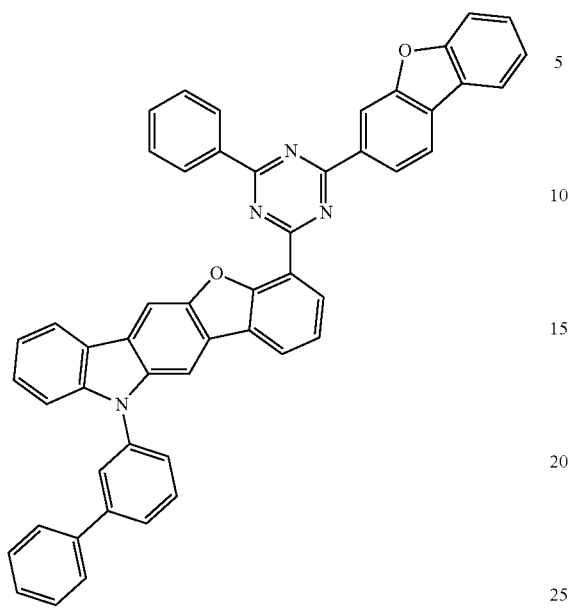
1D-4-39
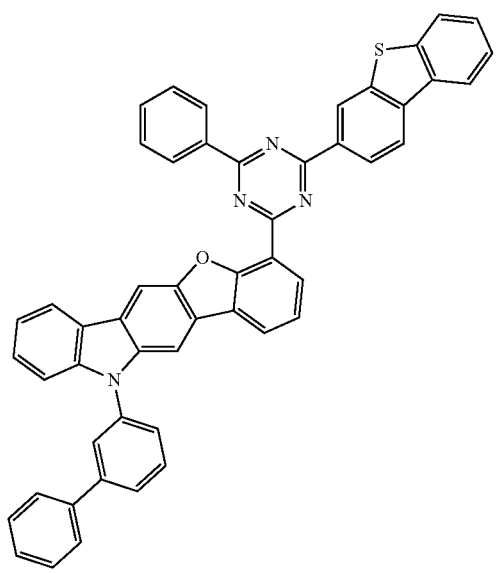
474
-continued
1D-4-40
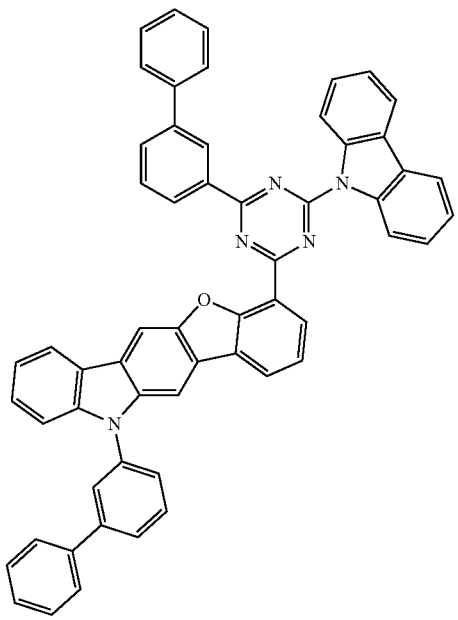
1D-4-41
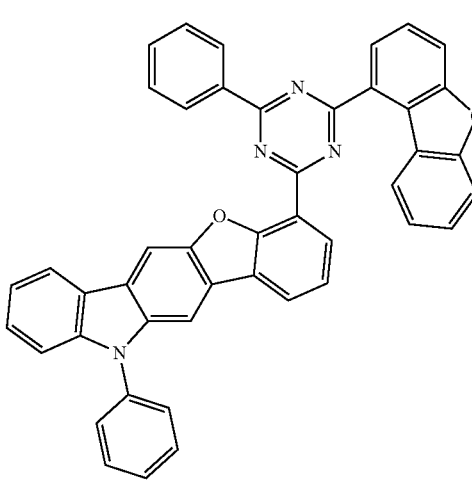

1D-4-42
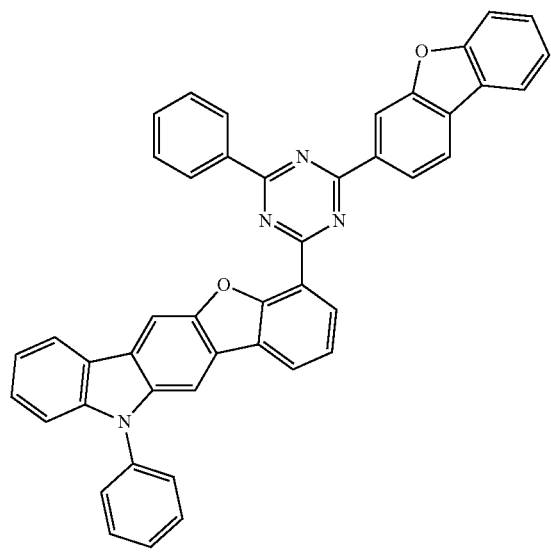
1D-4-44
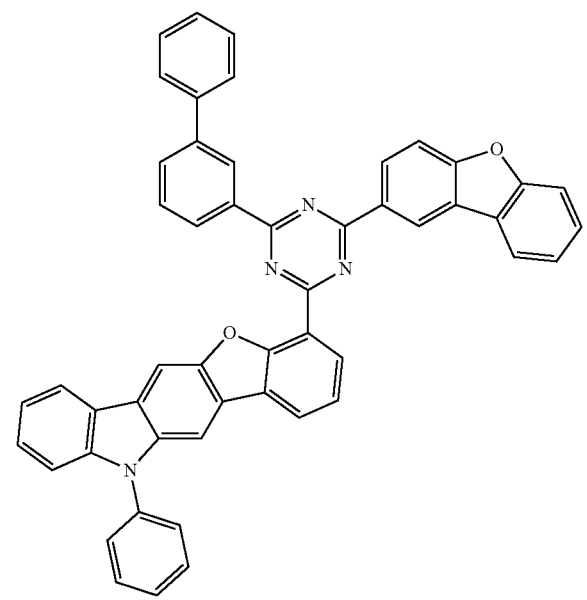
1D-4-43
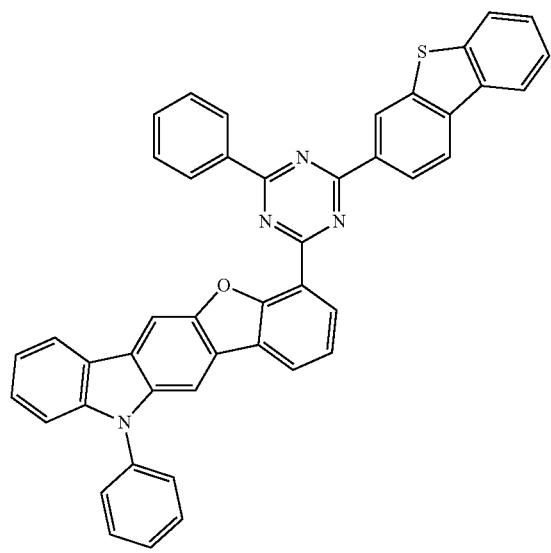
1D-4-45

1D-4-46
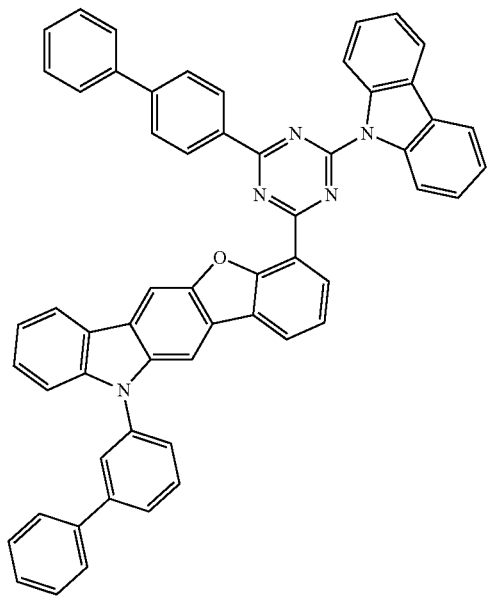
1D-4-47
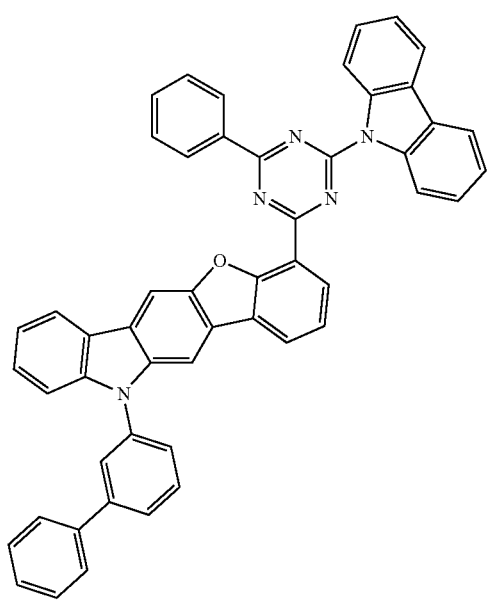
1D-4-48
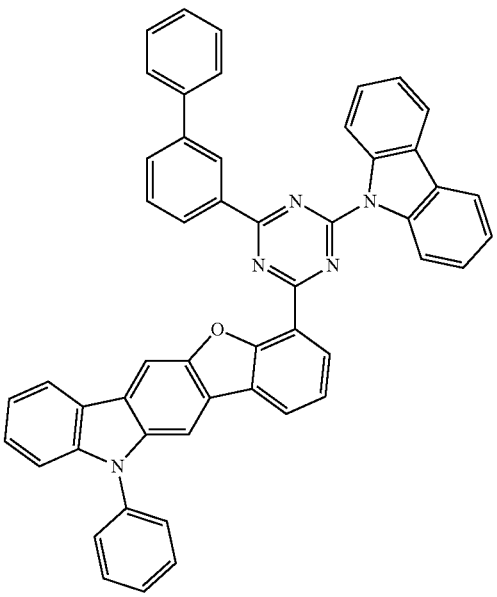
1D-4-49
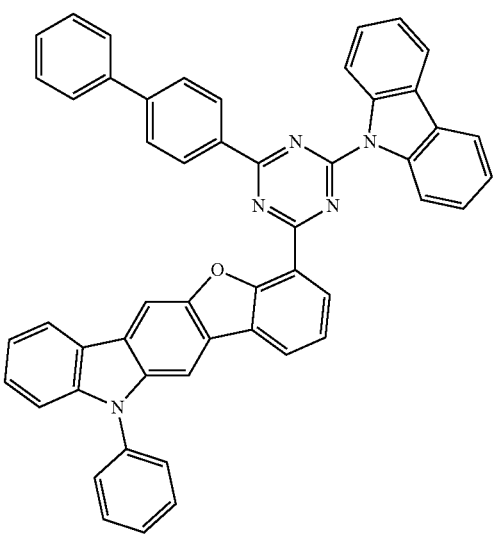

1D-4-50
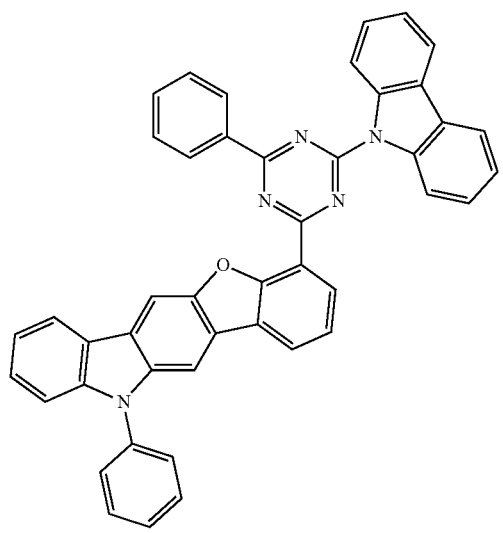
1D-4-51
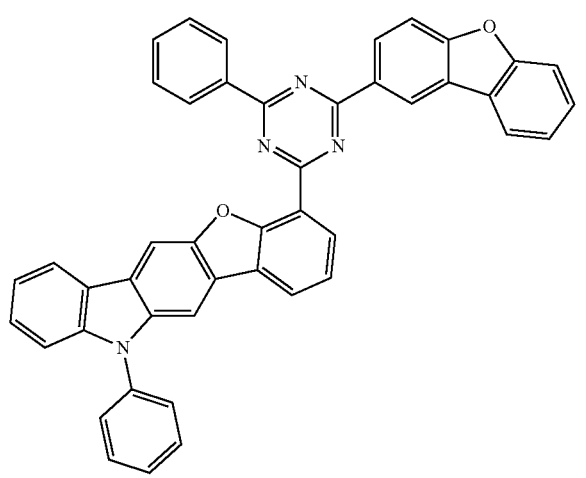
1D-4-52
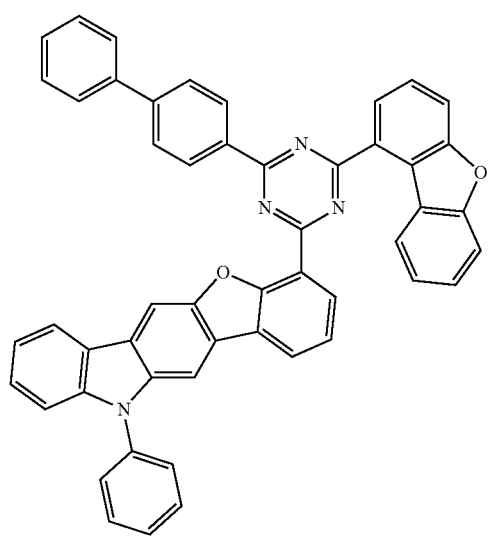
1D-4-53
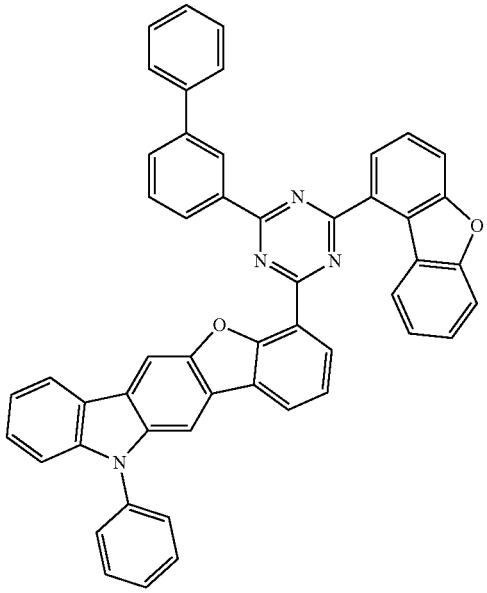
1D-4-54
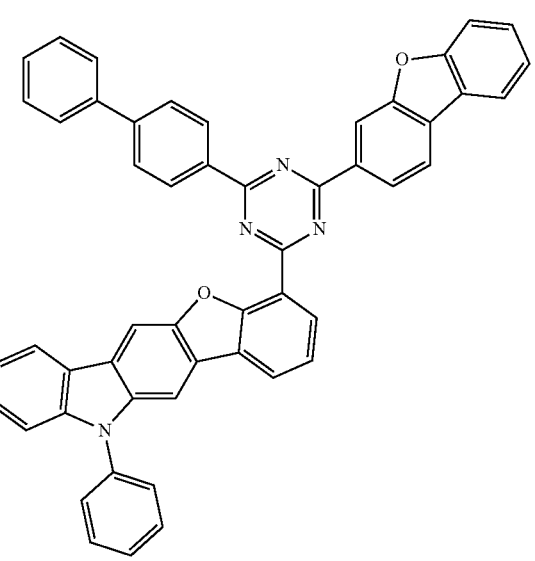

1D-4-55
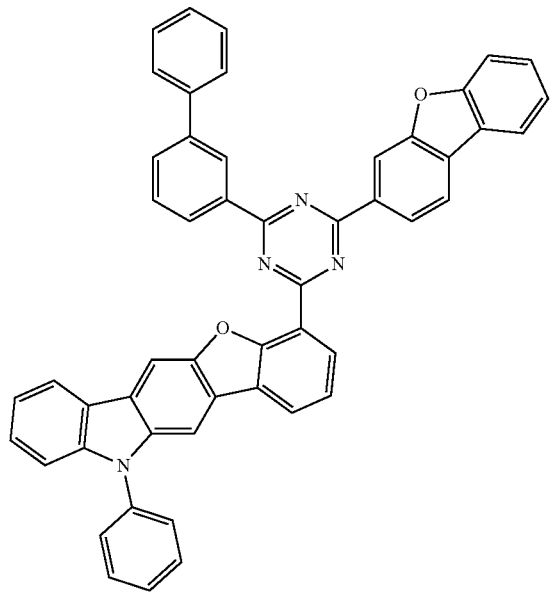
1D-4-56
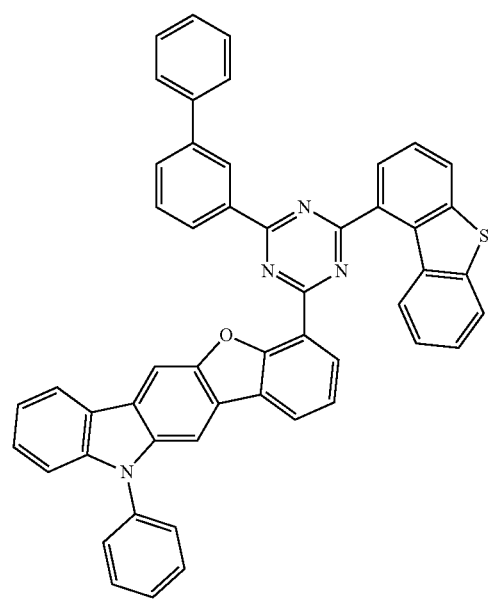
1D-4-57
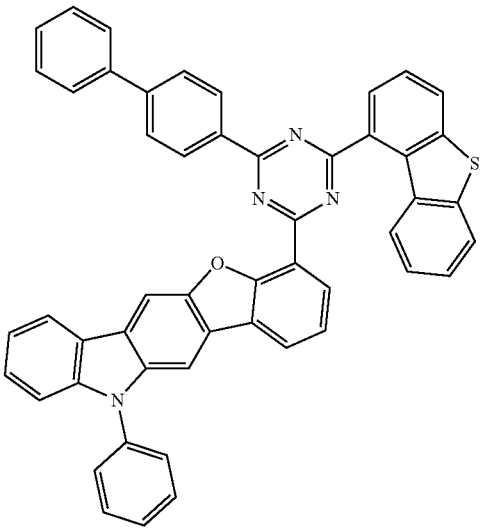
1D-4-58
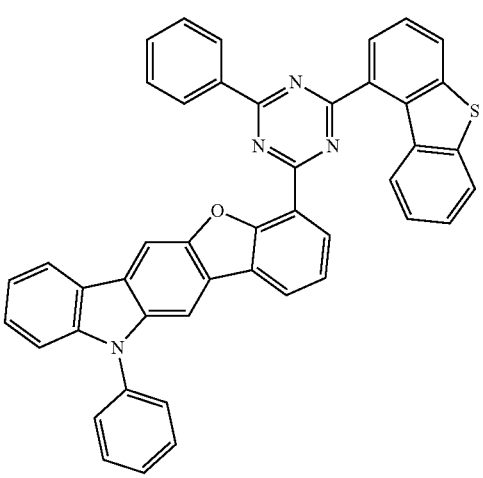
1D-4-59
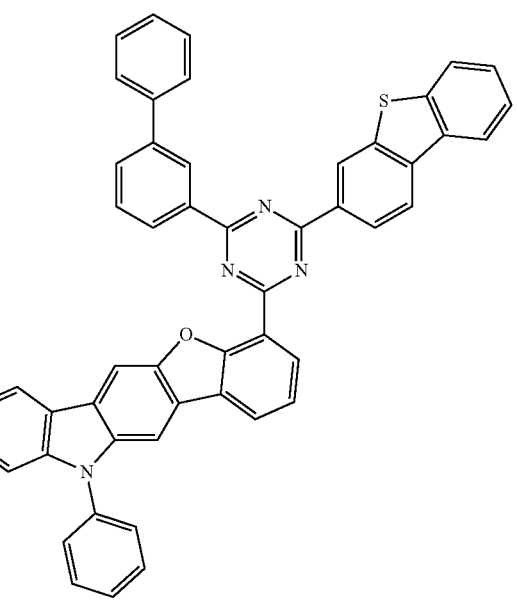

483
1D-4-60
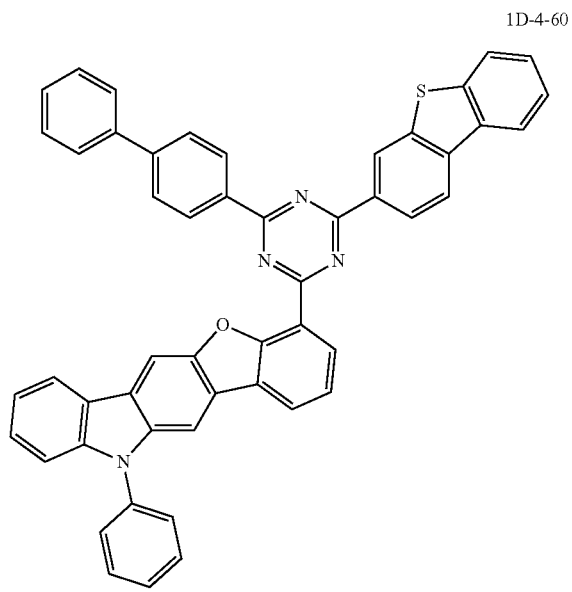
1D-4-61
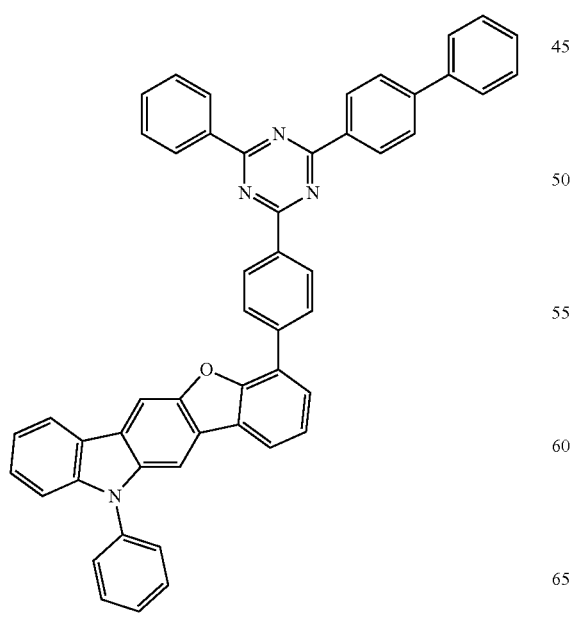
484
1D-4-62
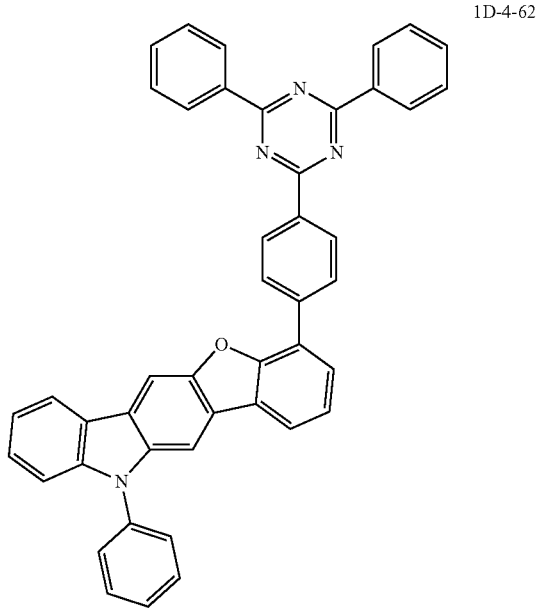
1D-4-63
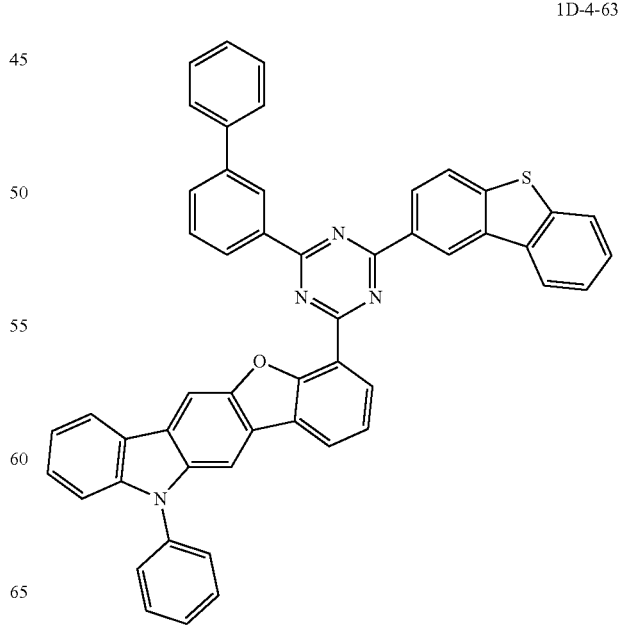

1D-4-64
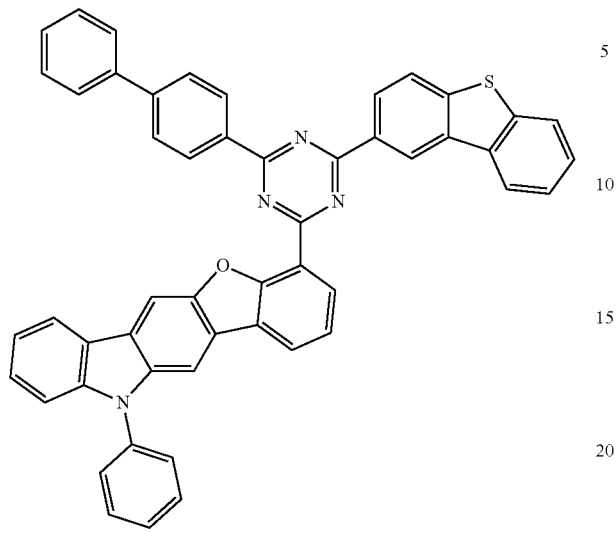
1D-4-65
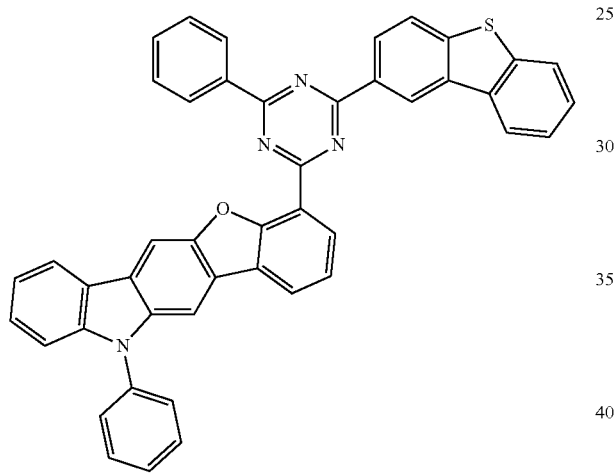
1D-4-66
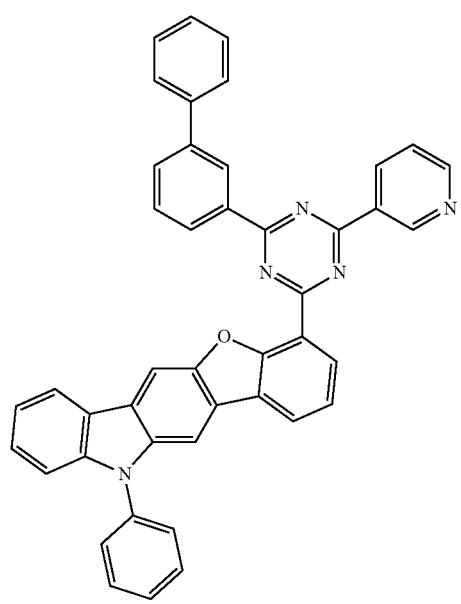
1D-4-67
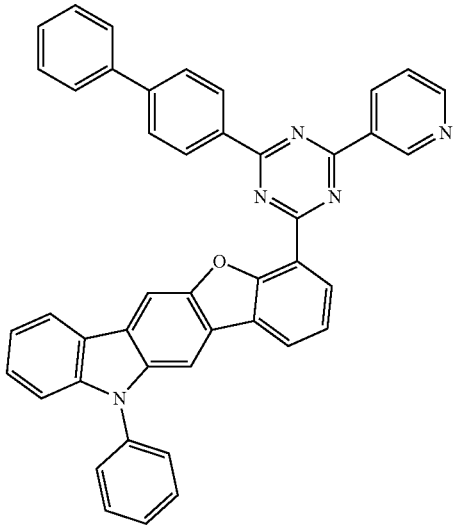
1D-4-68
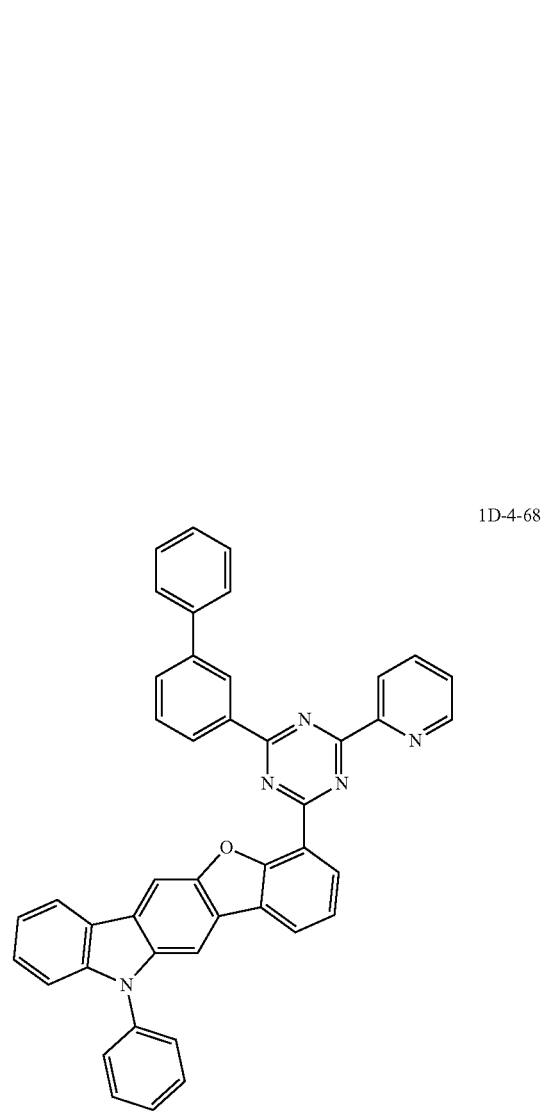

1D-4-69
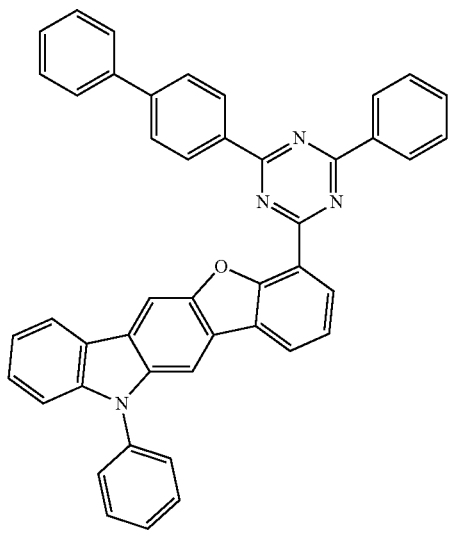
1D-4-72
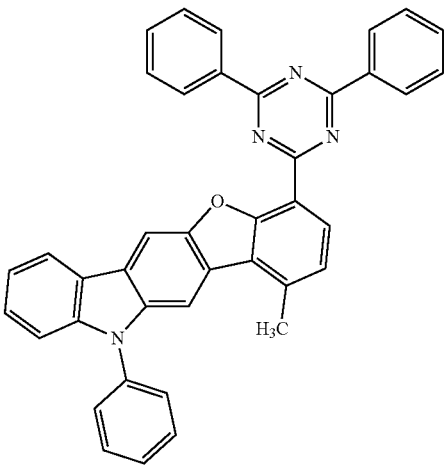
1D-4-70
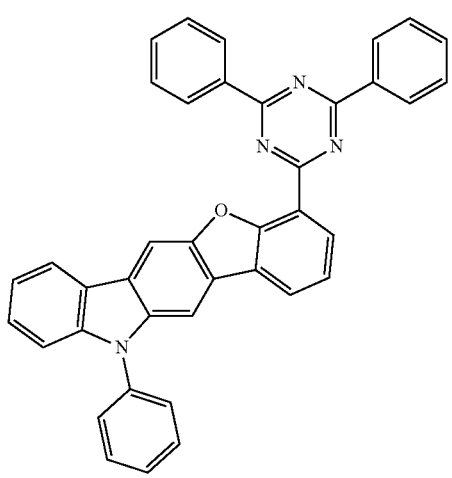
1D-4-73
1D-4-71
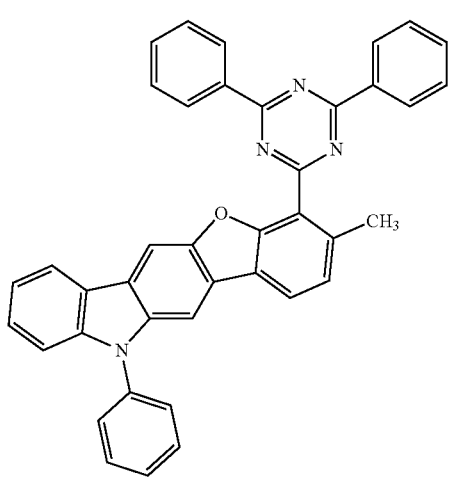
1D-4-74
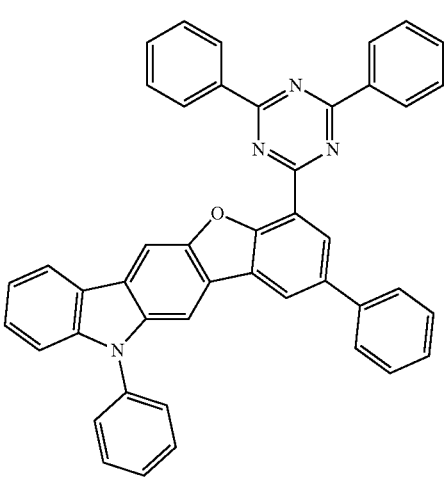

489
-continued
1D-4-75
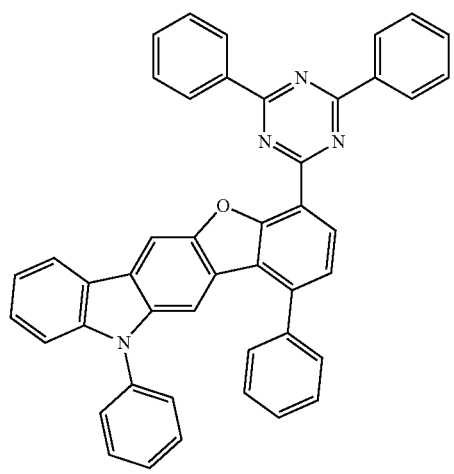
1D-4-76
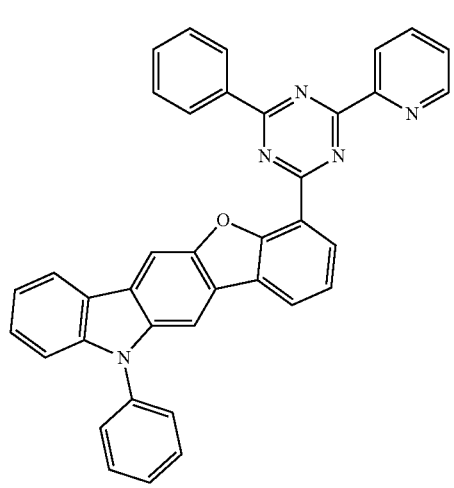
1D-4-77
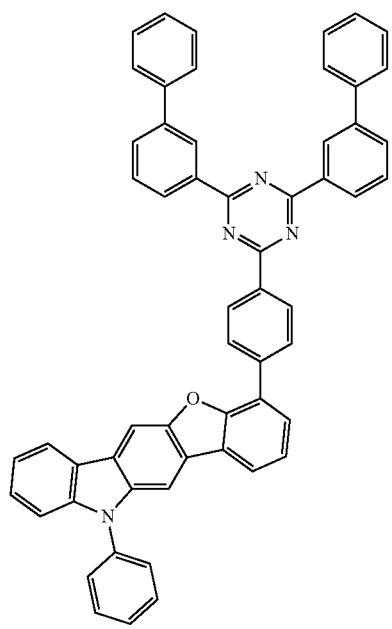
490
-continued
1D-4-78
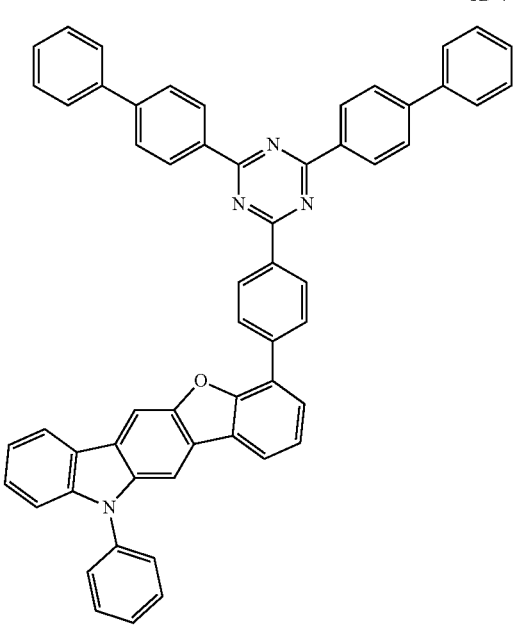
1D-4-79
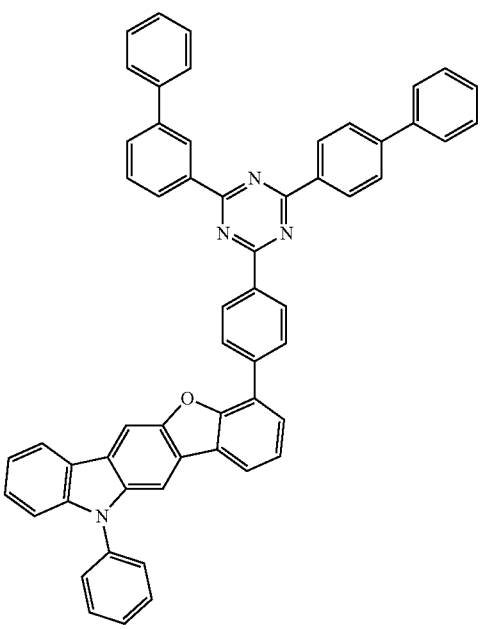

1D-4-80
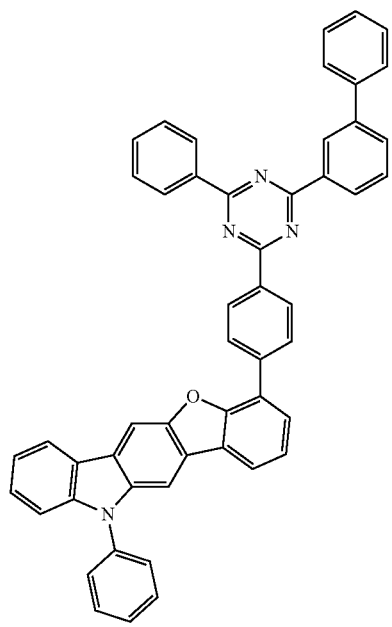
1D-4-83
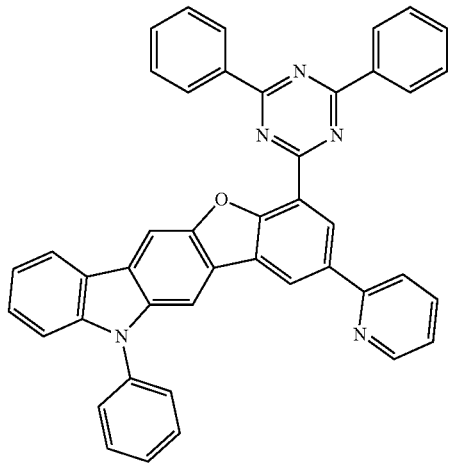
1D-4-81
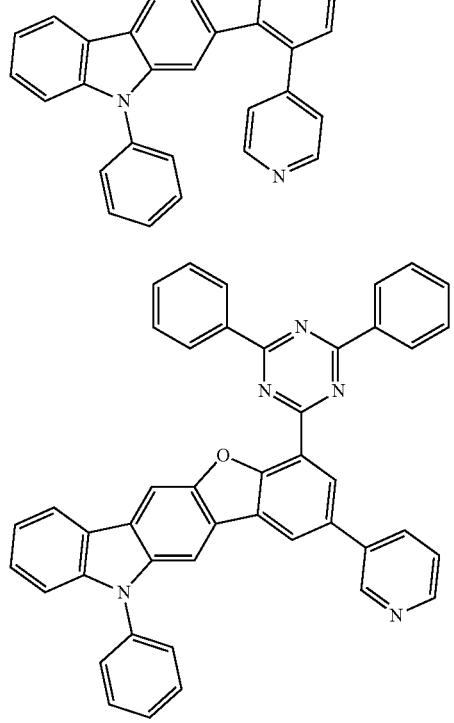
1E-1-1
1E-1-2
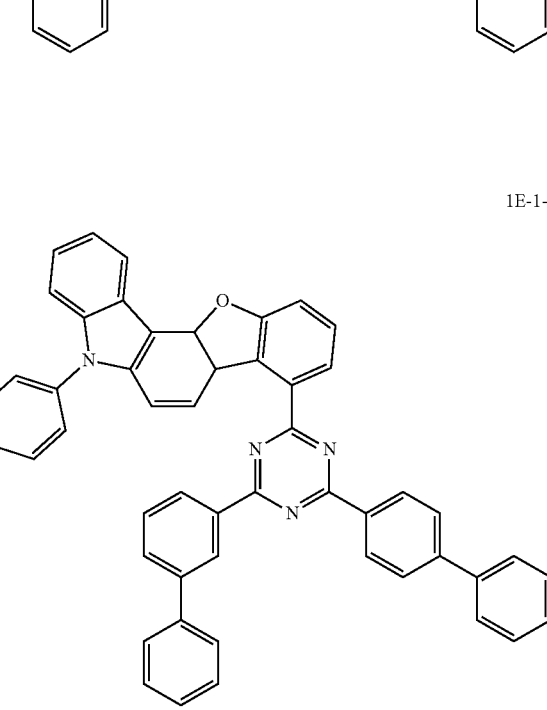
1D-4-82

1E-1-3
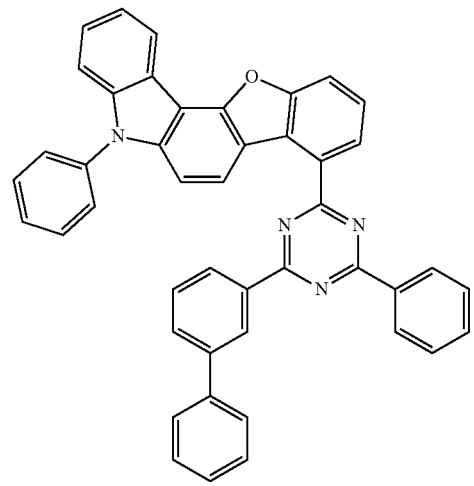
1E-1-4
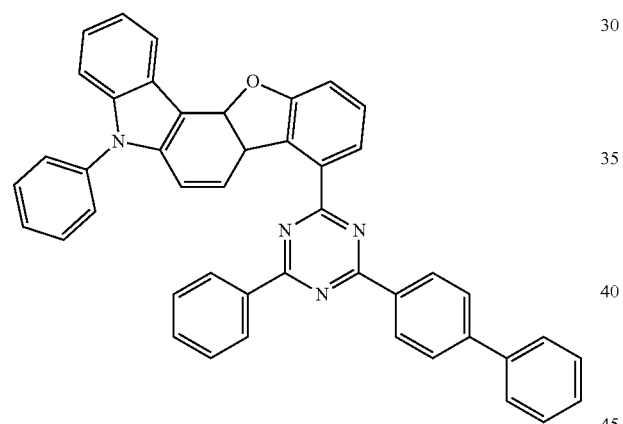
1E-1-5
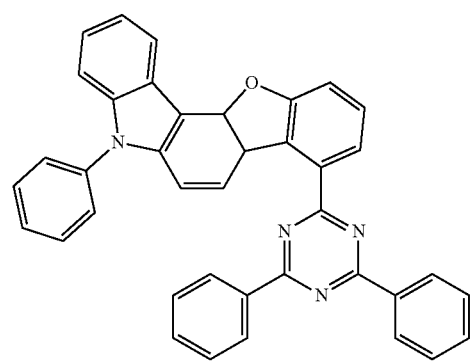
1E-1-6
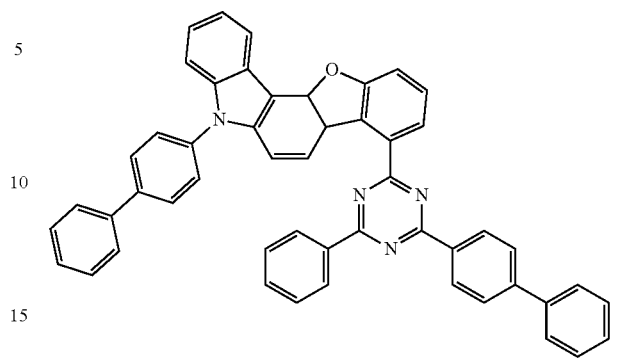
1E-1-7
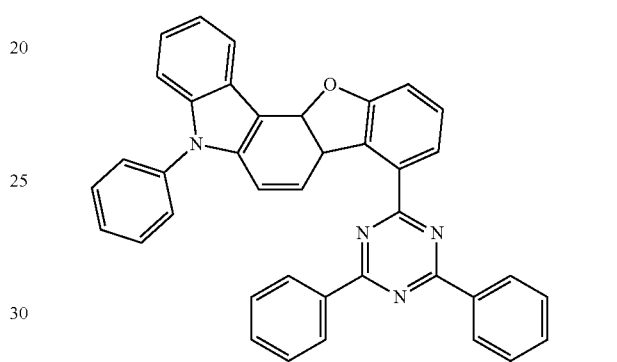
1E-1-8
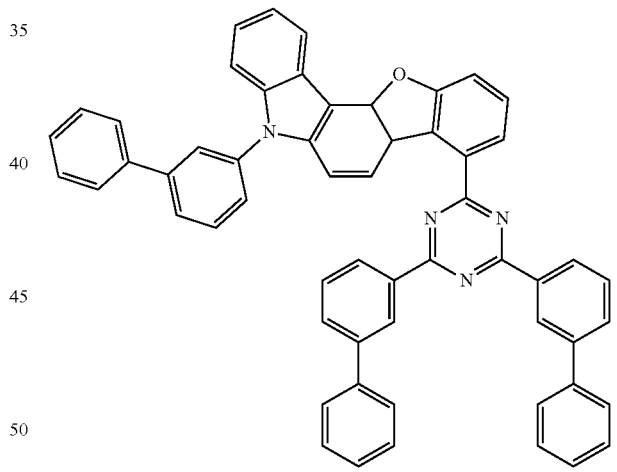
1E-1-9
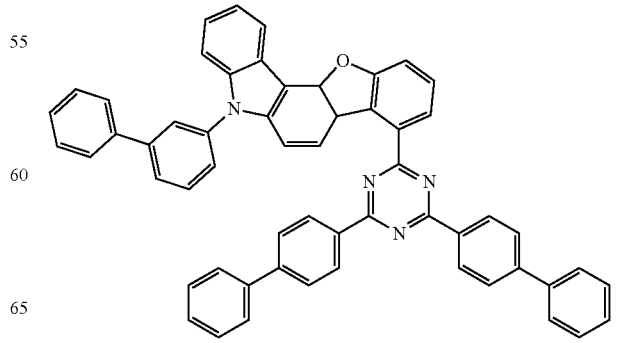

1E-1-10
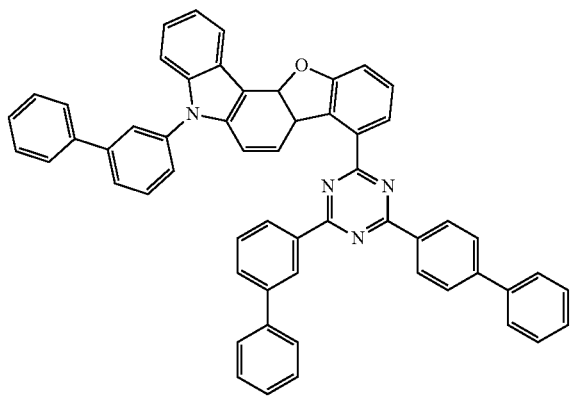
1E-1-11
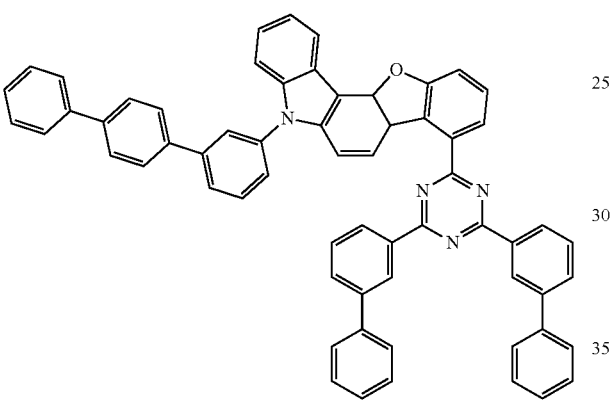
1E-1-12
1E-1-13
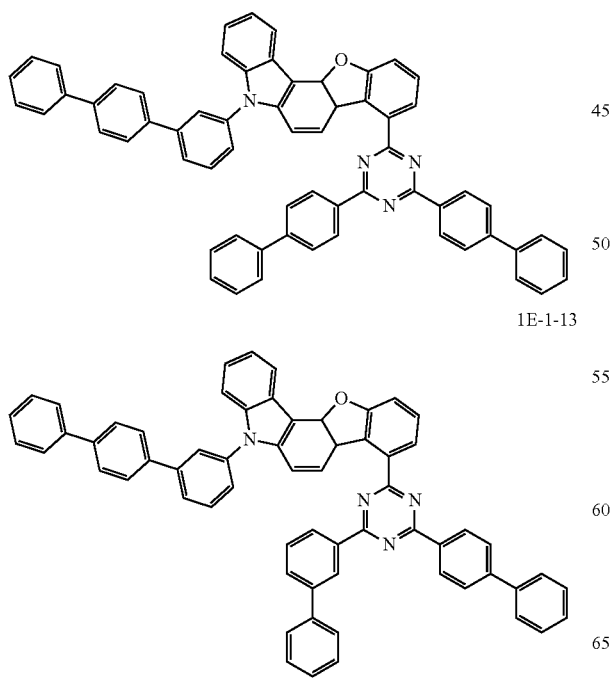
1E-1-14
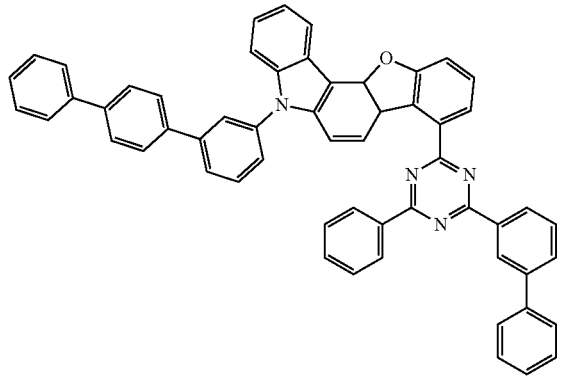
1E-1-15
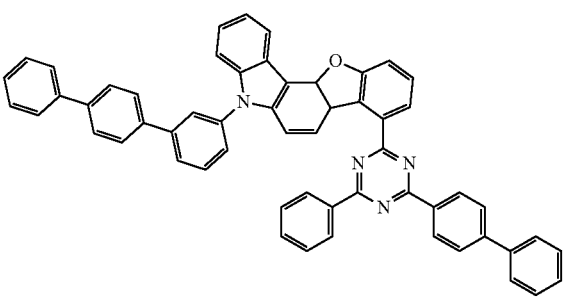
1E-1-16
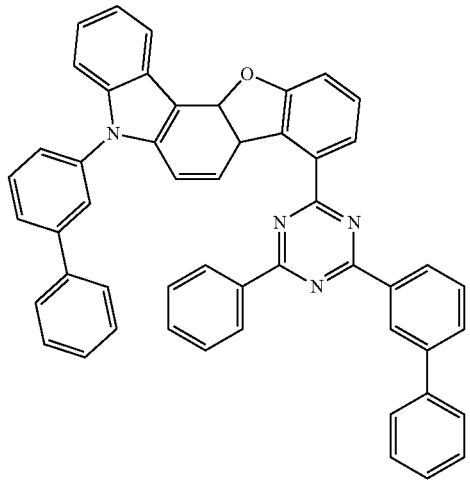

1E-1-17
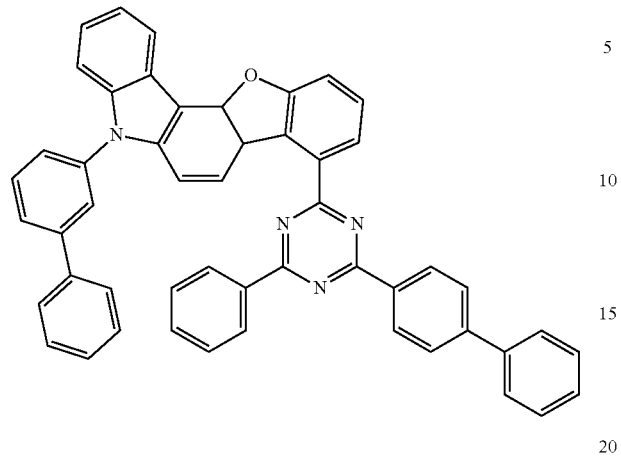
1E-1-20
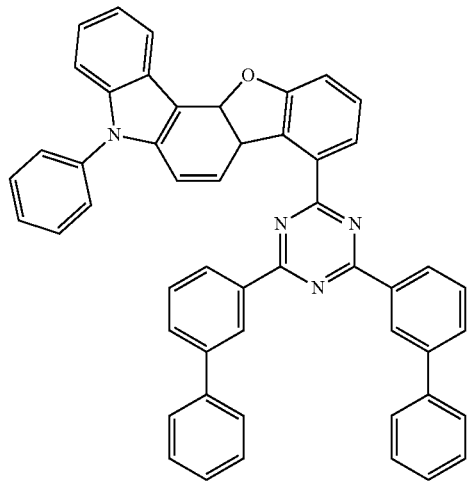
1E-1-18
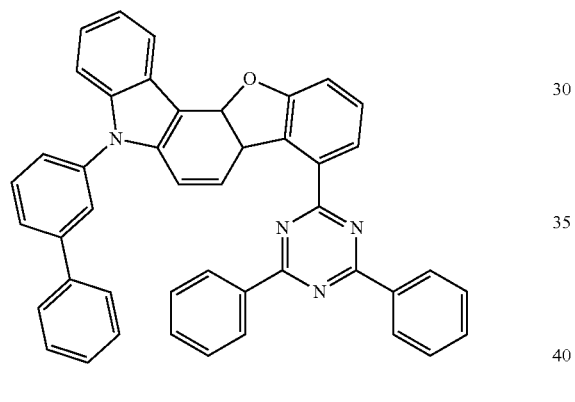
1E-1-21
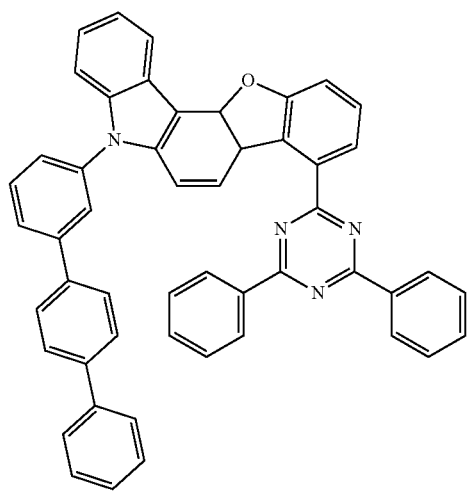
1E-1-19
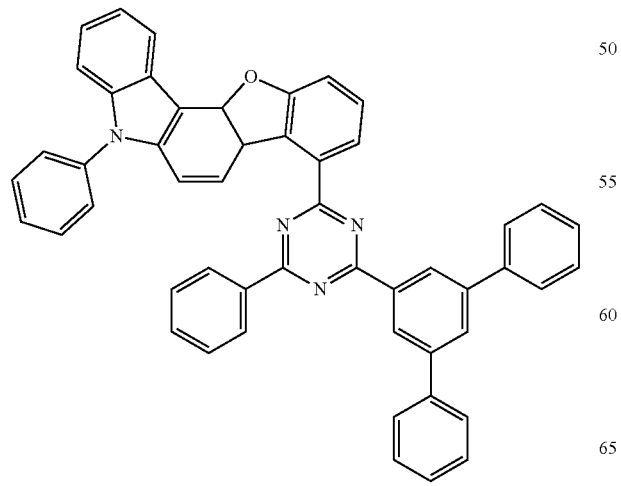
1E-1-22
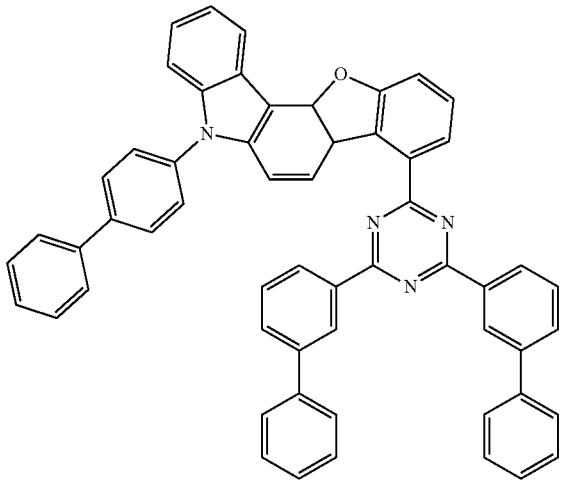

1E-1-23
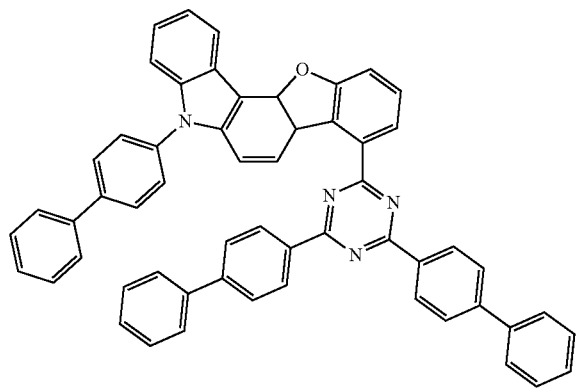
1E-1-26
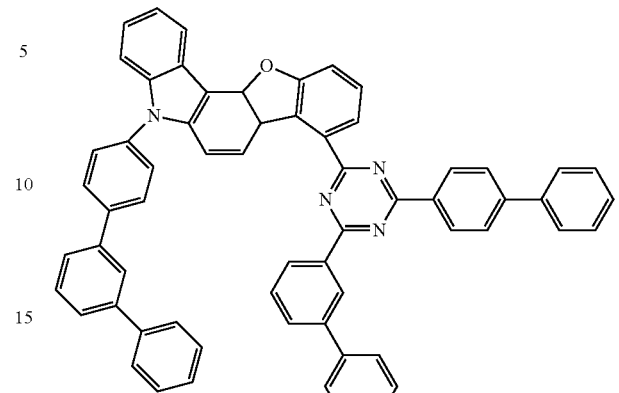
1E-1-24
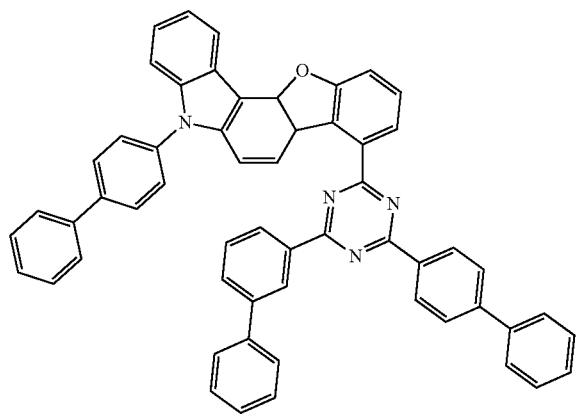
1E-1-27
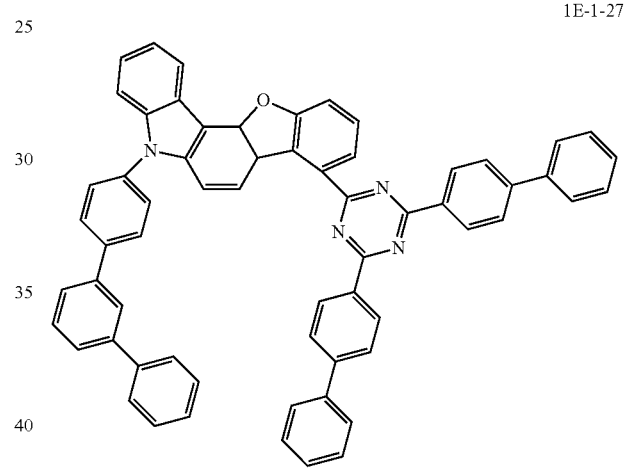
1E-1-25
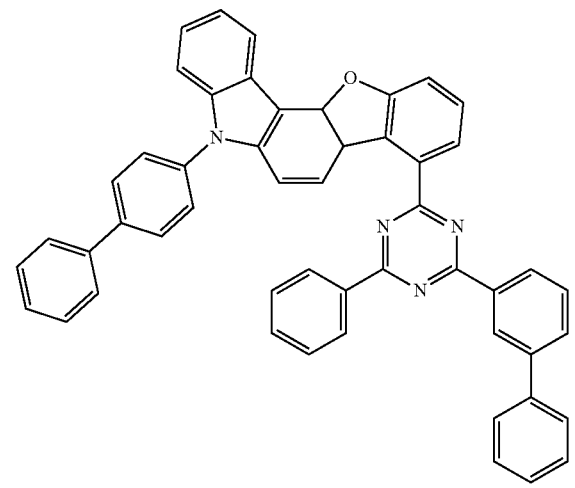
1E-1-28
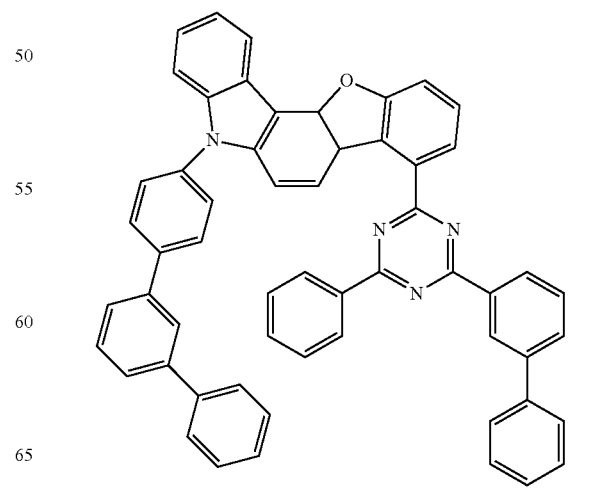

1E-1-29
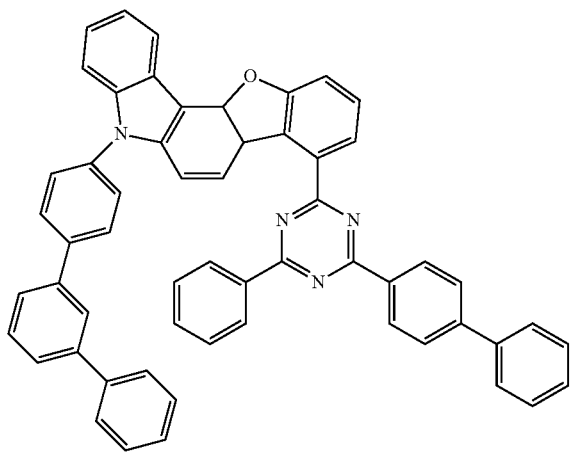
1E-1-30
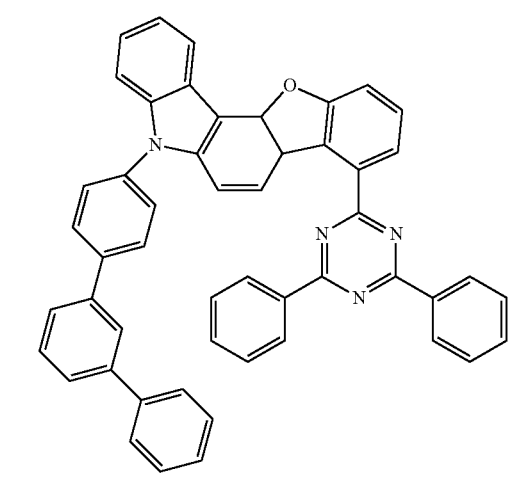
1E-1-31
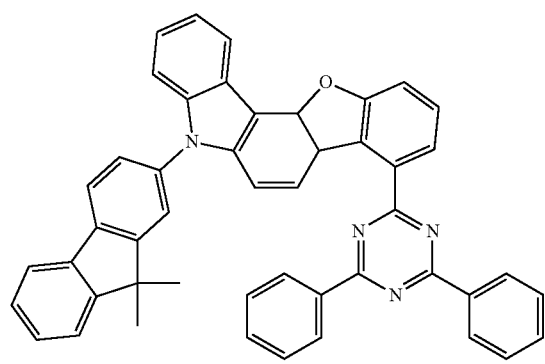
1E-1-32
1E-1-33
1E-1-34
1E-1-35
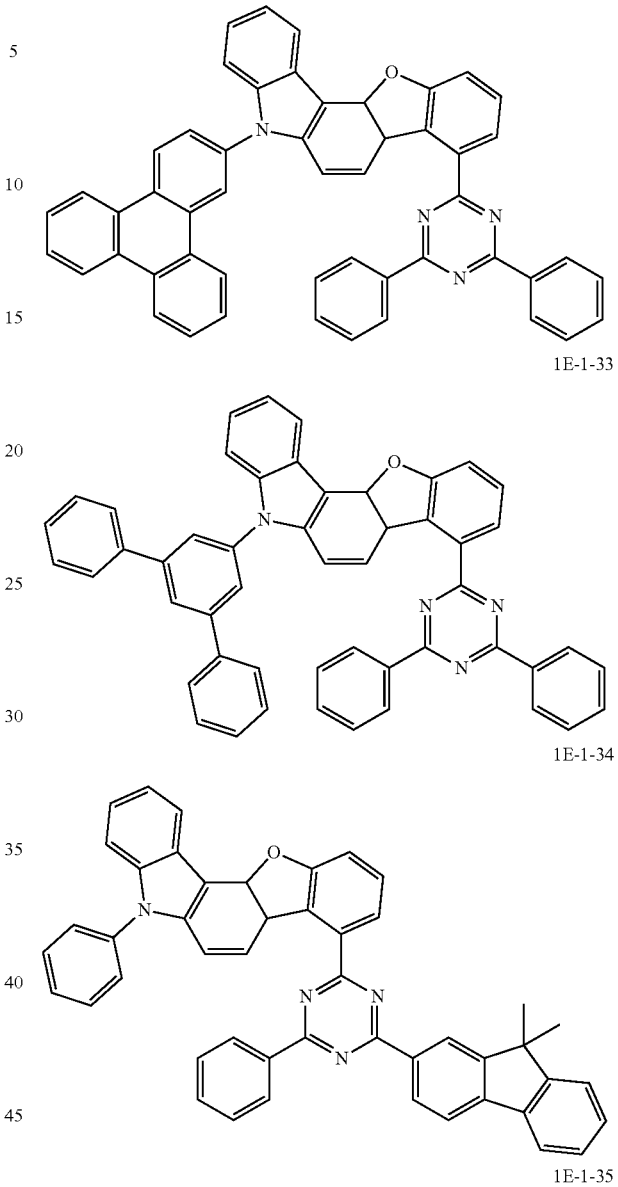
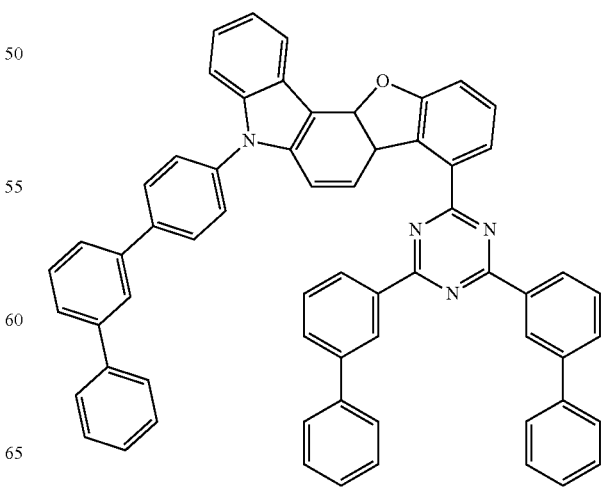

1E-1-36
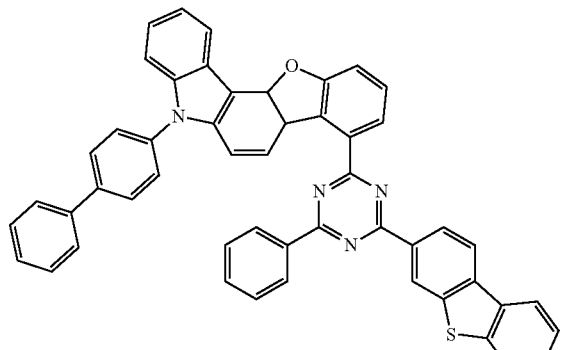
1E-1-37
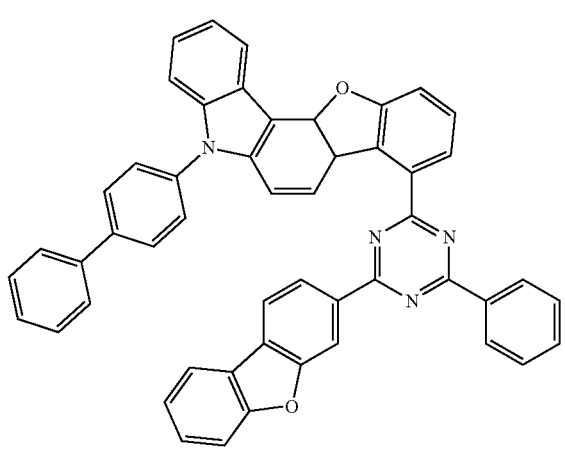
1E-1-38
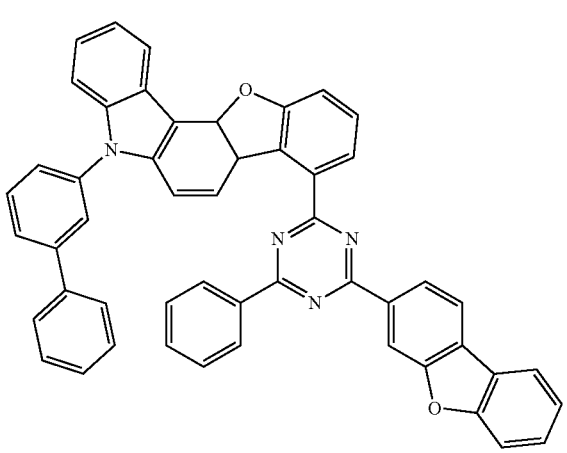
1E-1-39
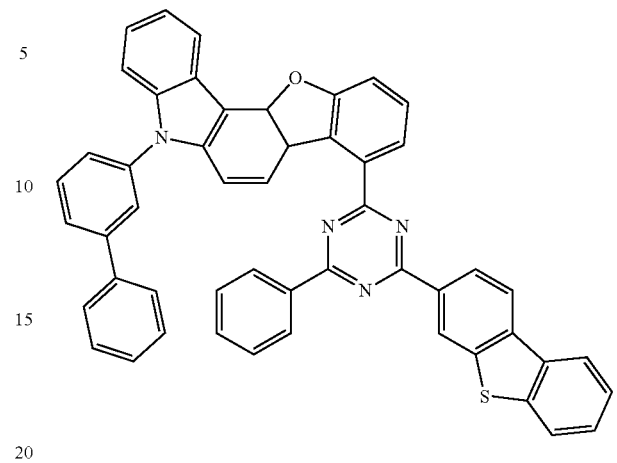
1E-1-40
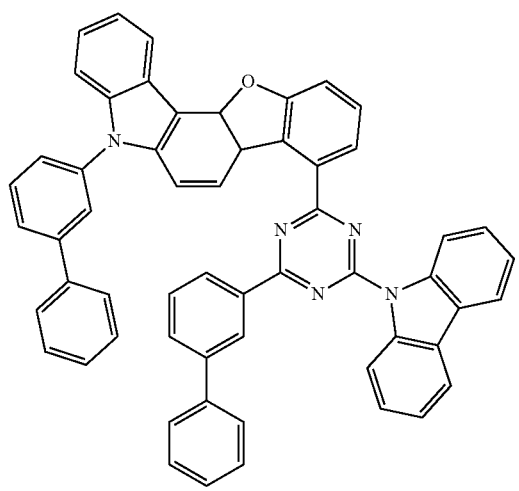
1E-1-41
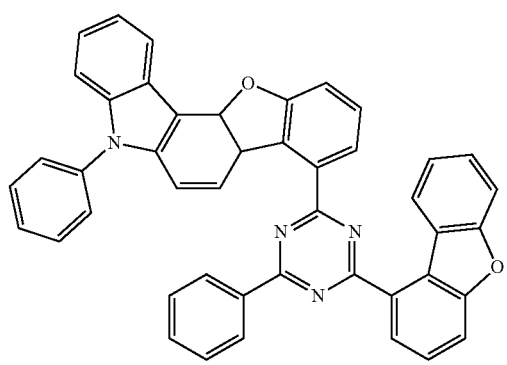

1E-1-42
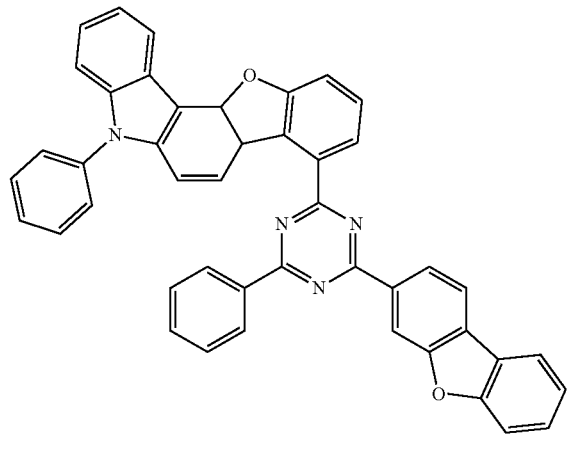
1E-1-45
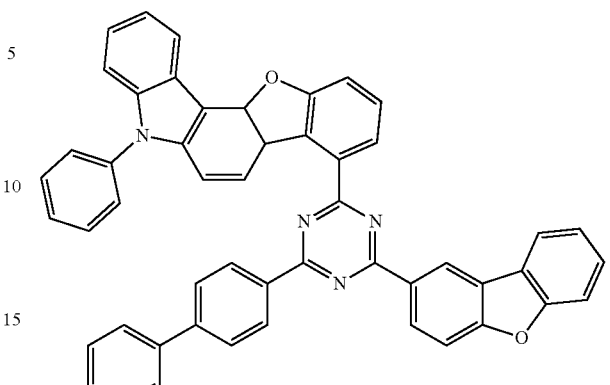
1E-1-43
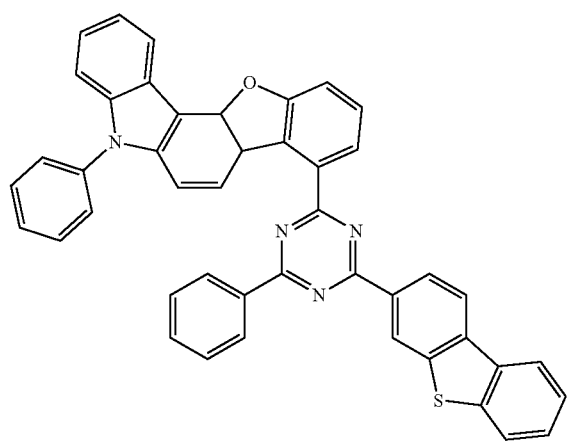
1E-1-46
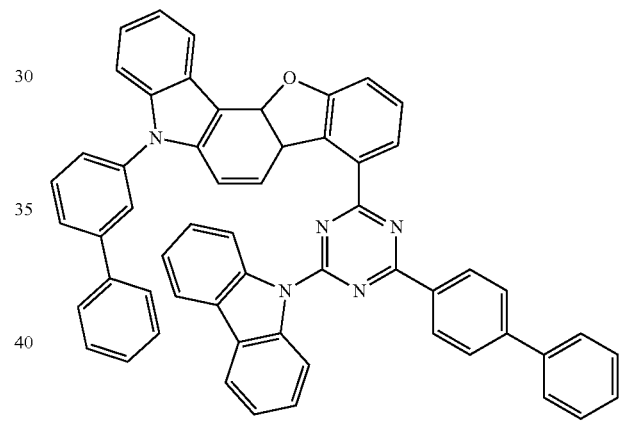
1E-1-44
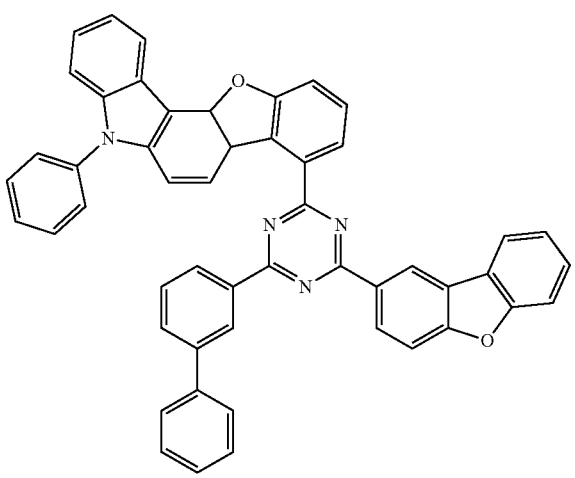
1E-1-47
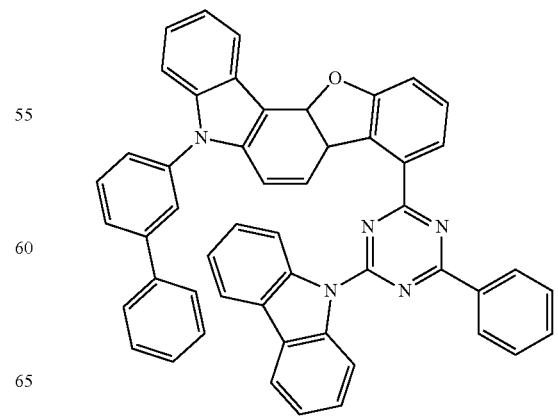

1E-1-48
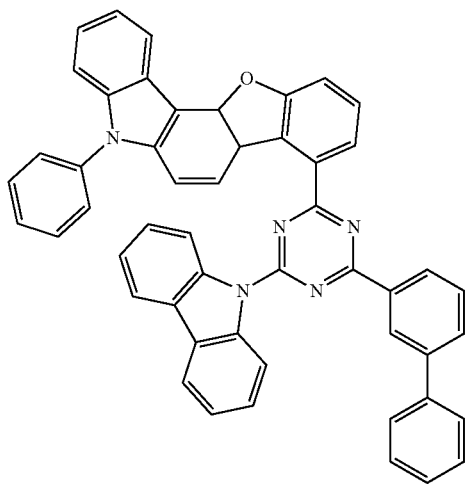
1E-1-51
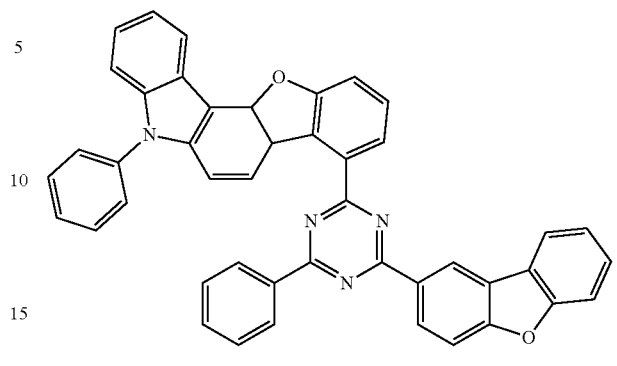
1E-1-49
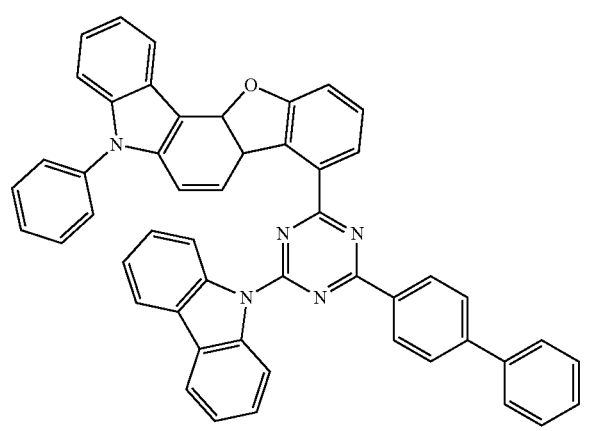
1E-1-52
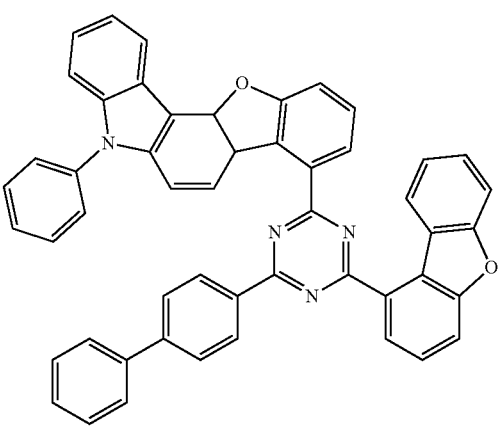
1E-1-50
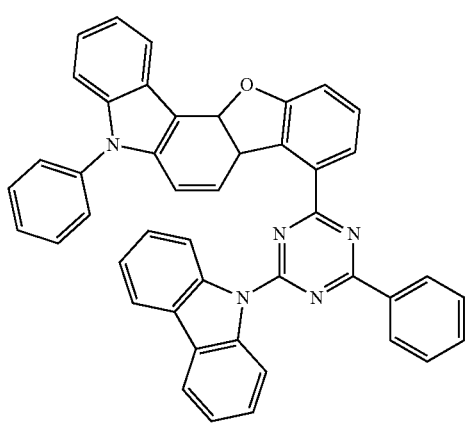
1E-1-53
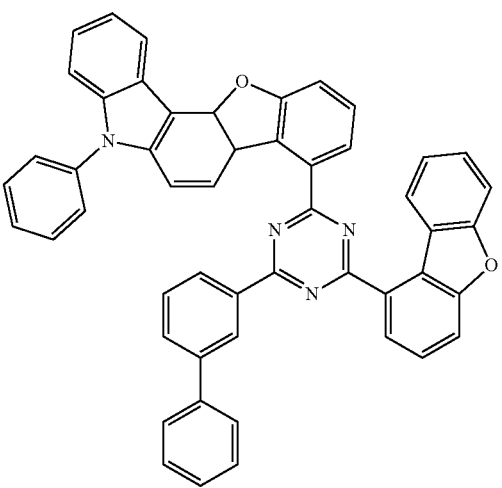

1E-1-54
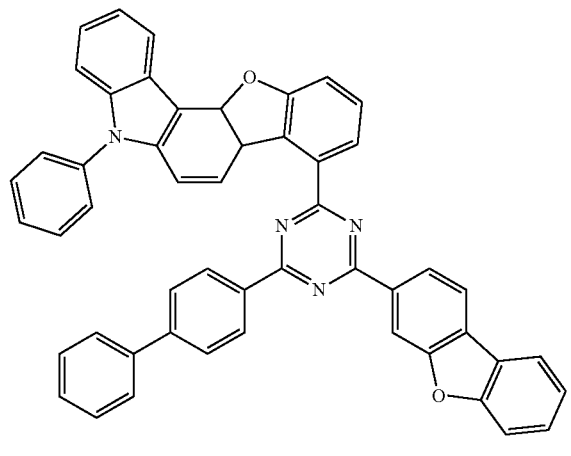
1E-1-55
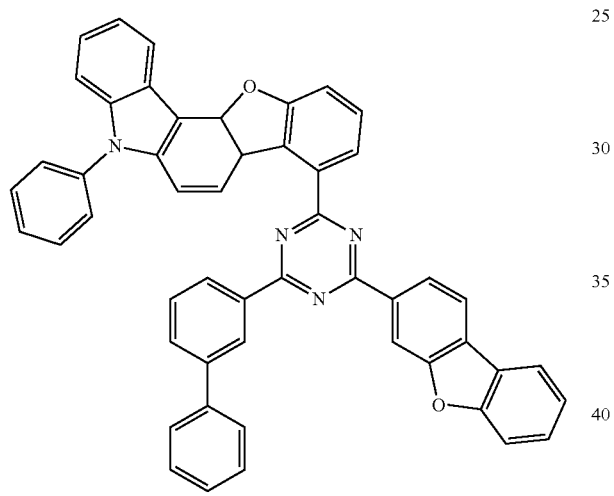
1E-1-57
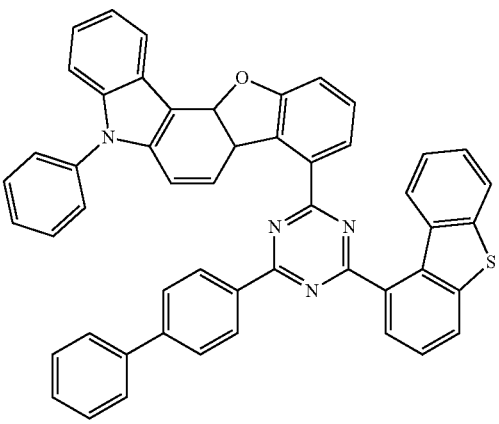
1E-1-58
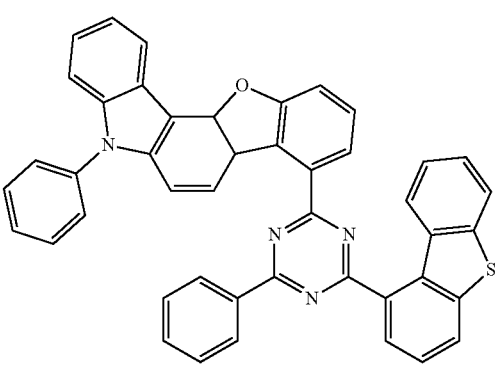
1E-1-56
1E-1-59
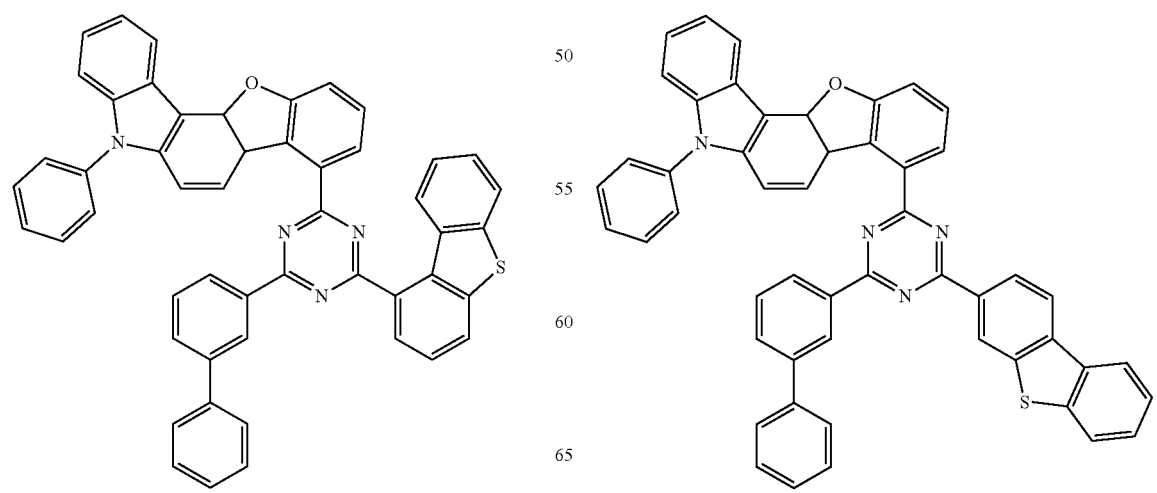

1E-1-60
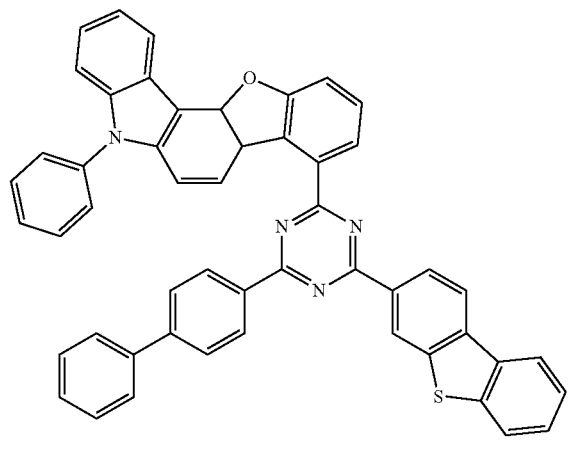
1E-1-63
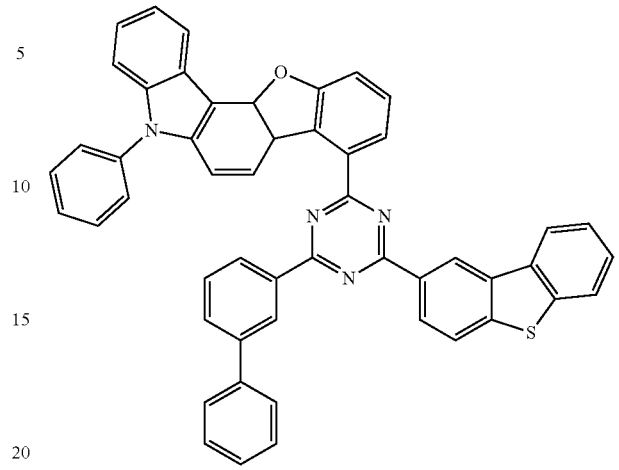
1E-1-61
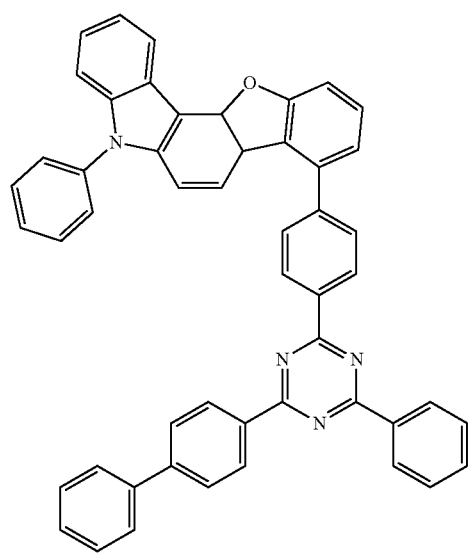
1E-1-64
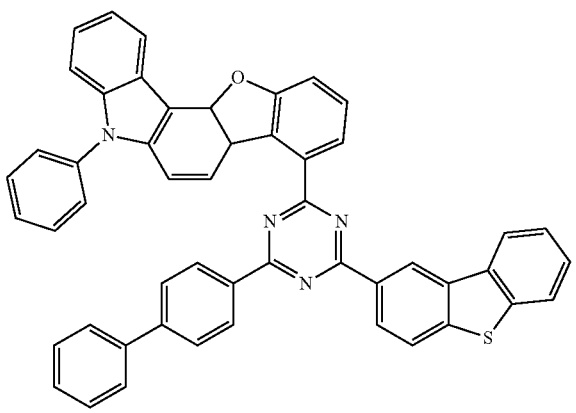
1E-1-62
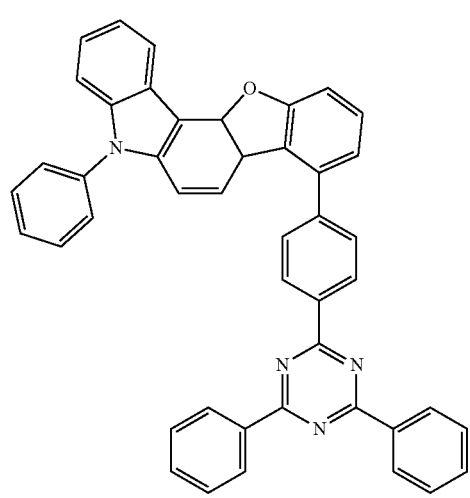
1E-1-65
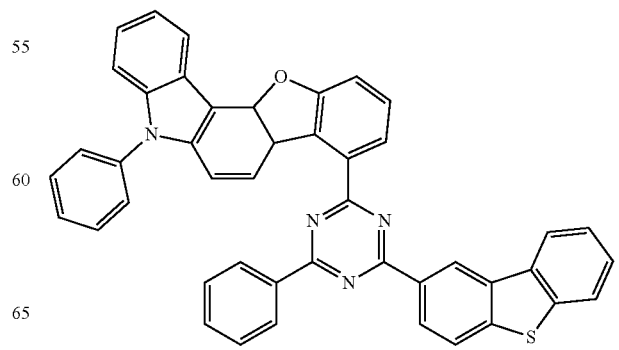

1E-1-66
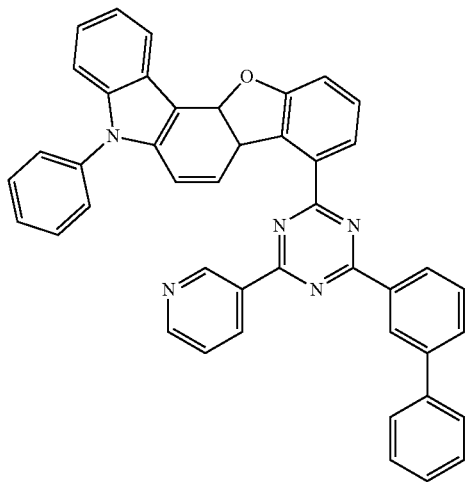
1E-1-67
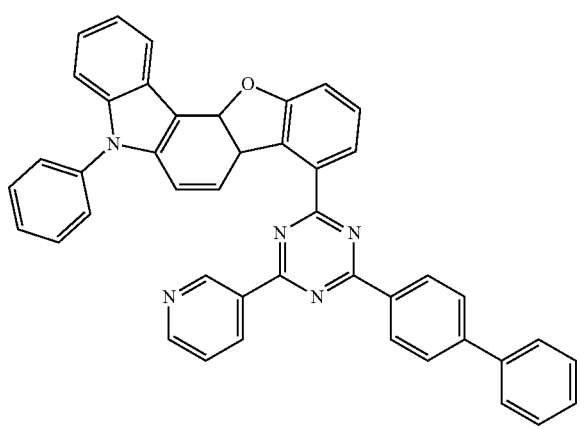
1E-1-68
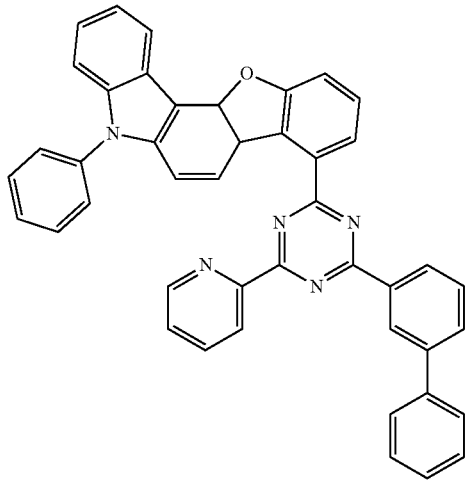
1E-1-69
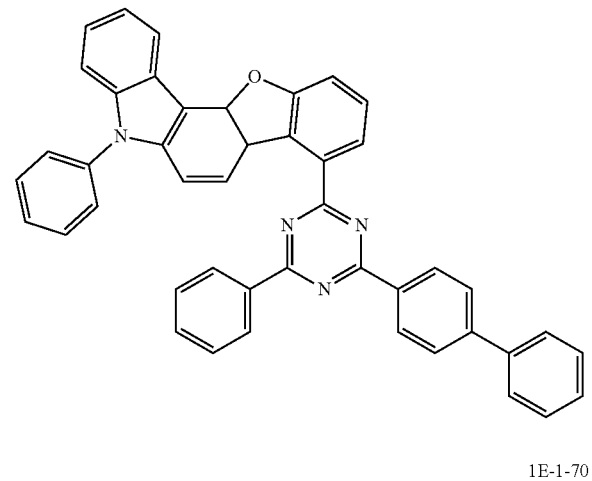
1E-1-70
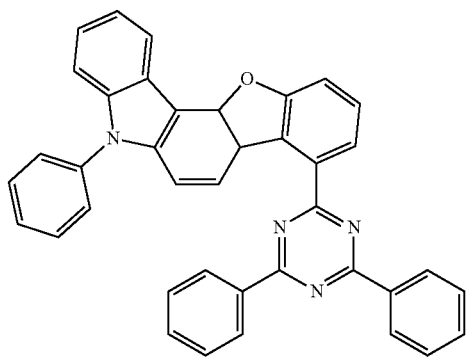
1E-1-71
1E-1-72
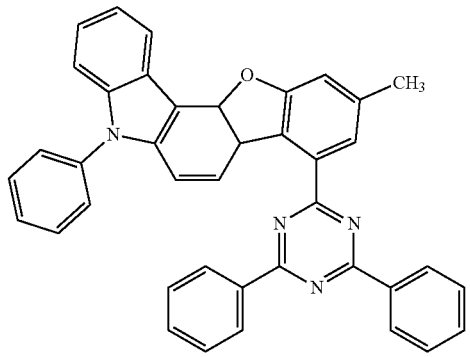

1E-1-73
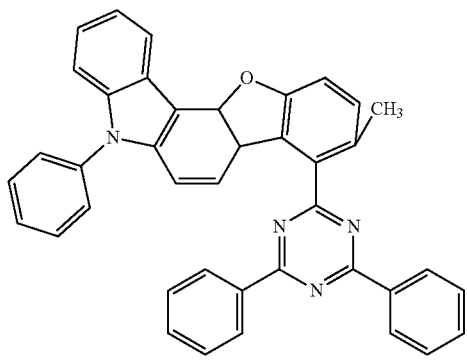
1E-1-74
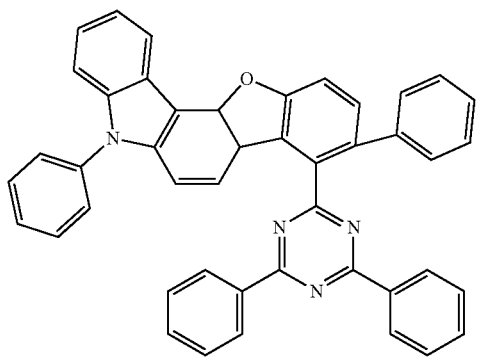
1E-1-75
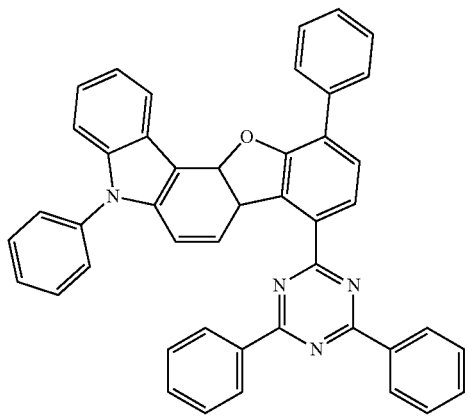
1E-1-76
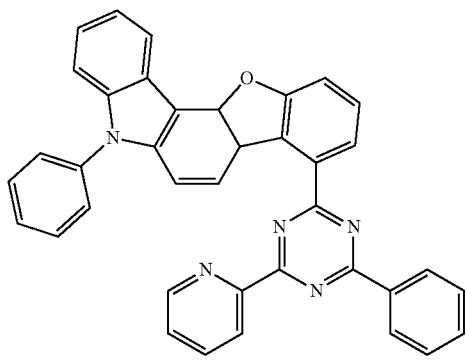
1E-1-77
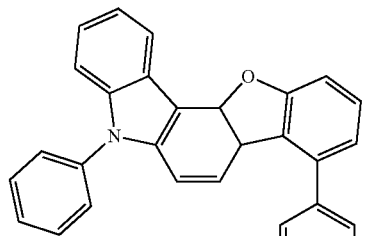
1E-1-78
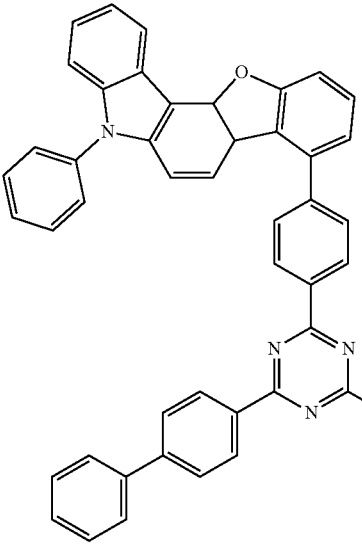

1E-1-79
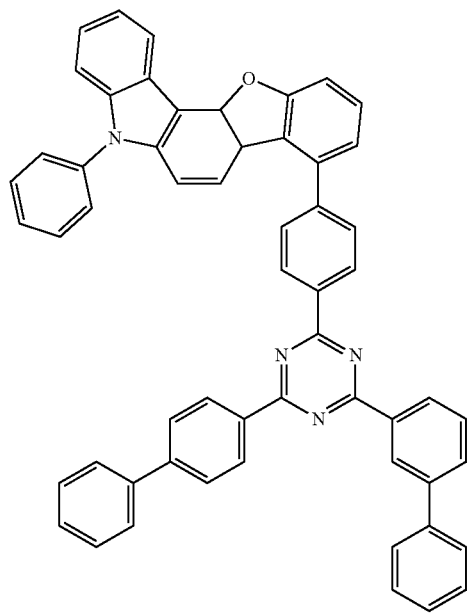
1E-1-81
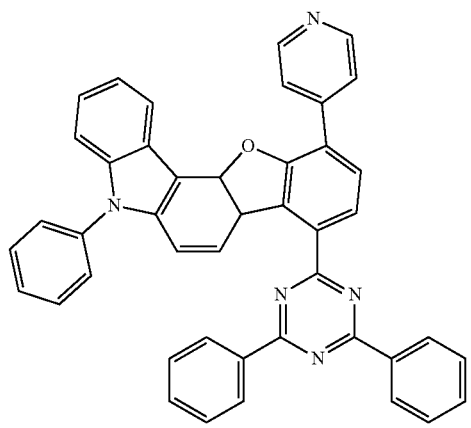
1E-1-82
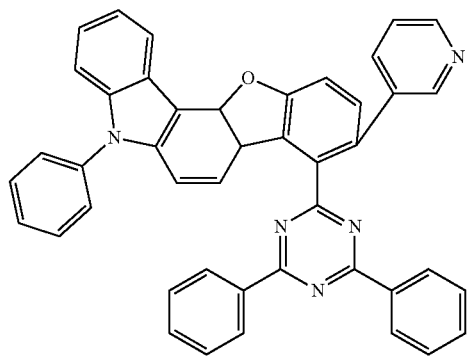
1E-1-80
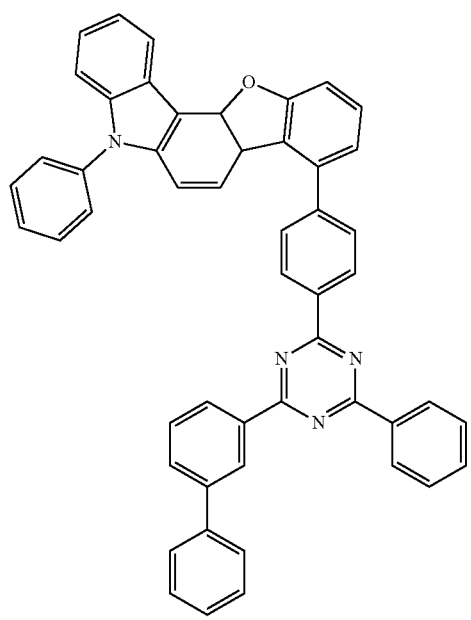
1E-1-83
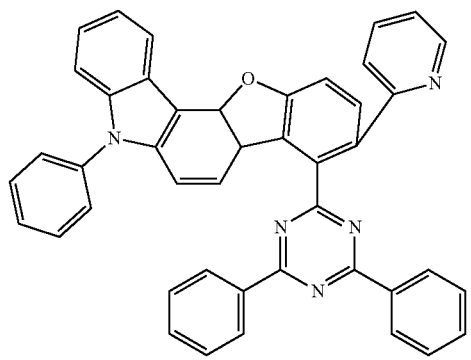

1E-2-1
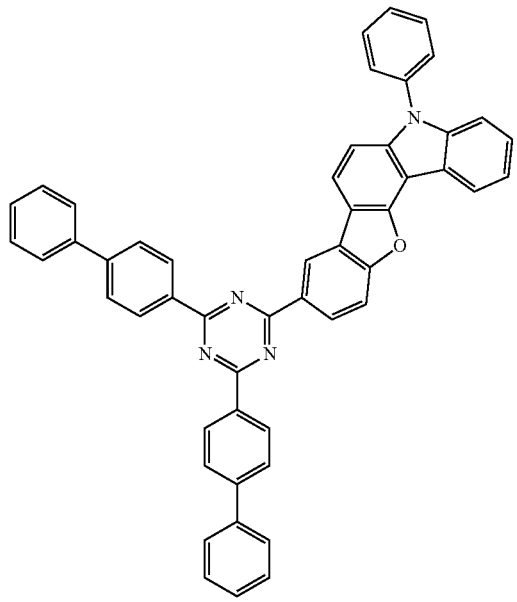
1E-2-3
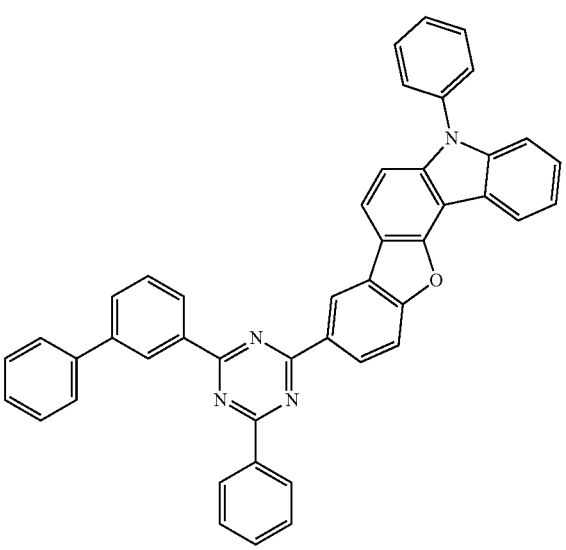
1E-2-2
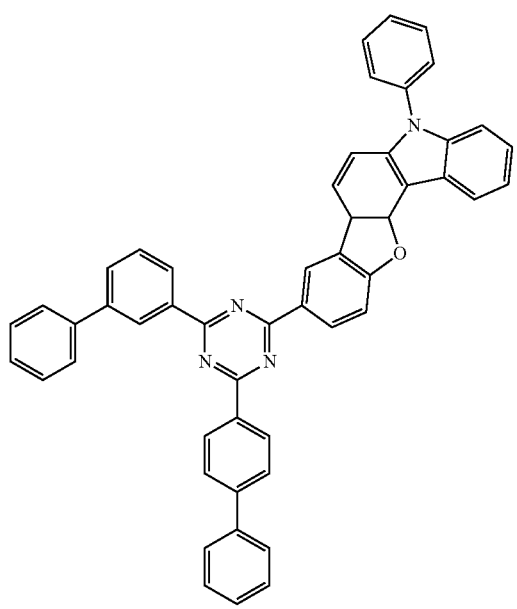
1E-2-4
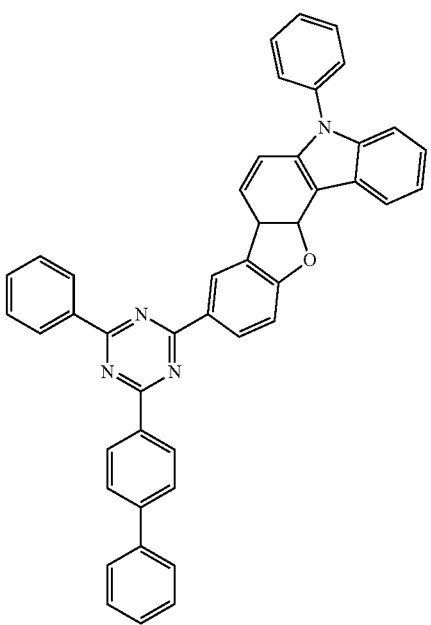

521
-continued
1E-2-5
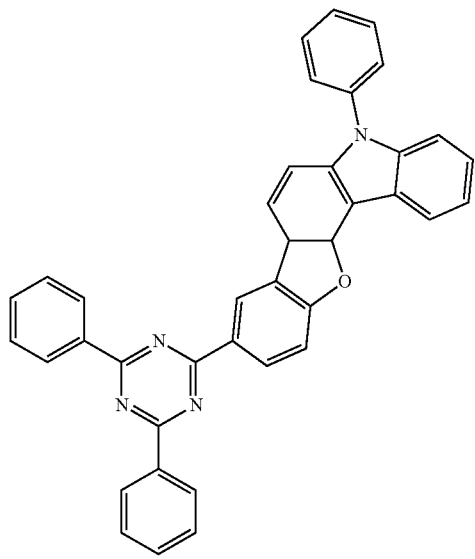
522
-continued
1E-2-7
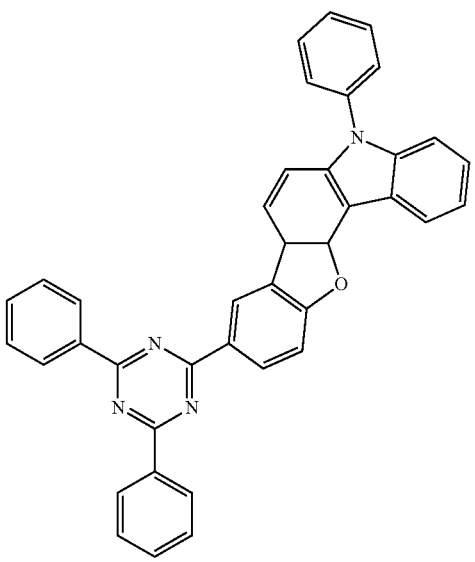
1E-2-6
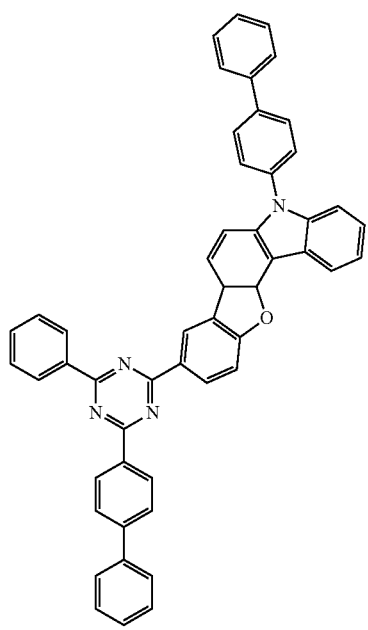
1E-2-8
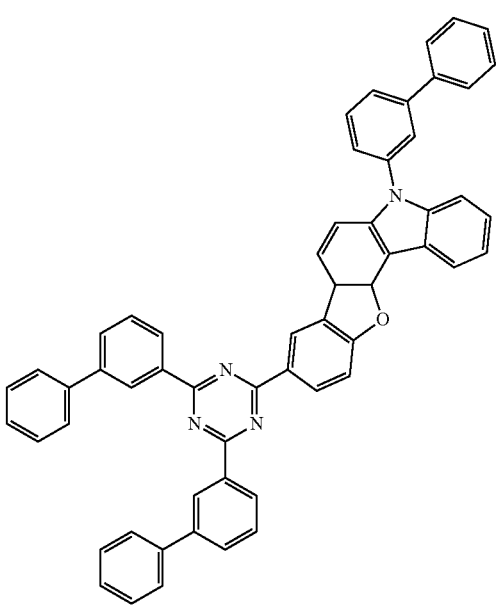

1E-2-9
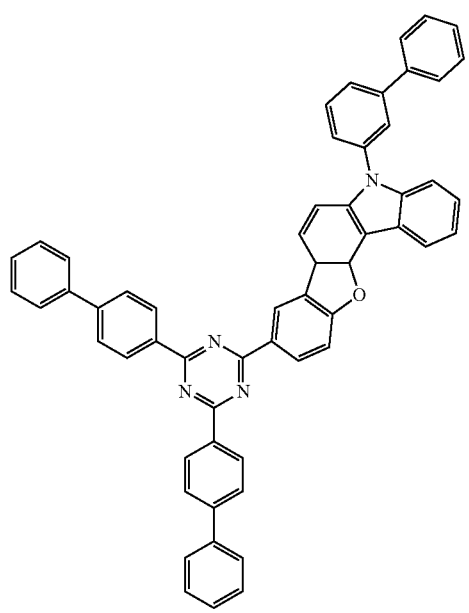
1E-2-10
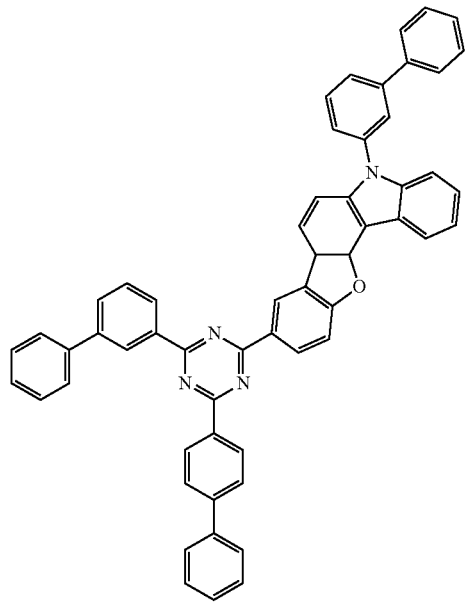
1E-2-11
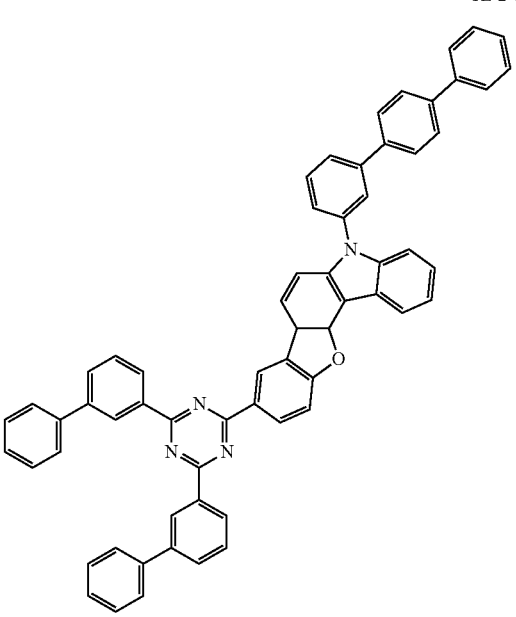
1E-2-12
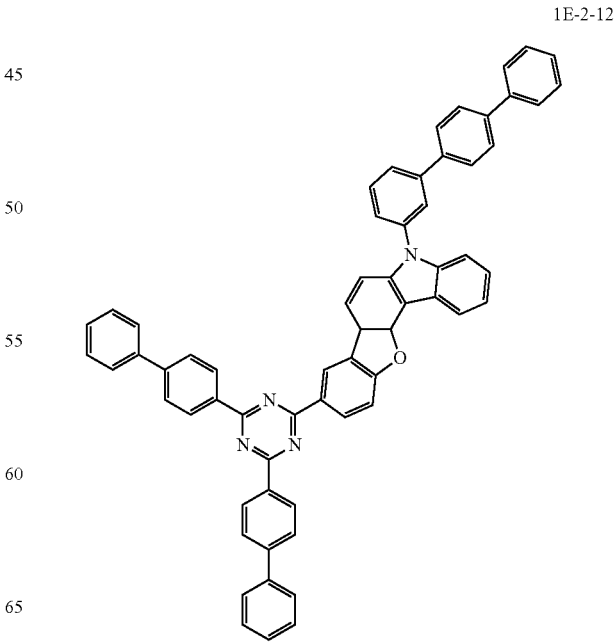

1E-2-13
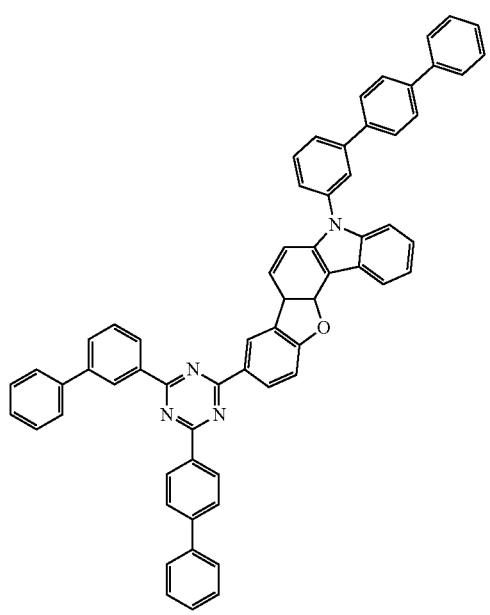
1E-2-15
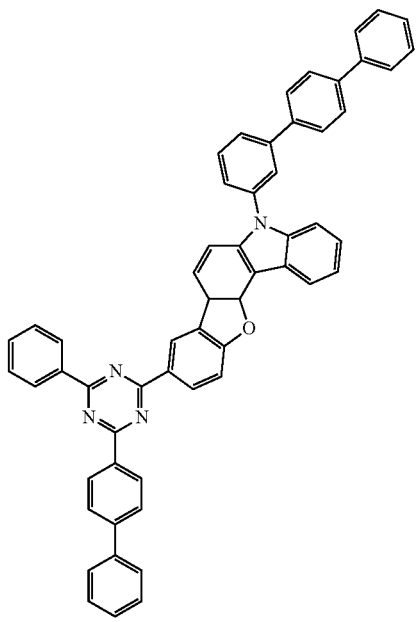
1E-2-14
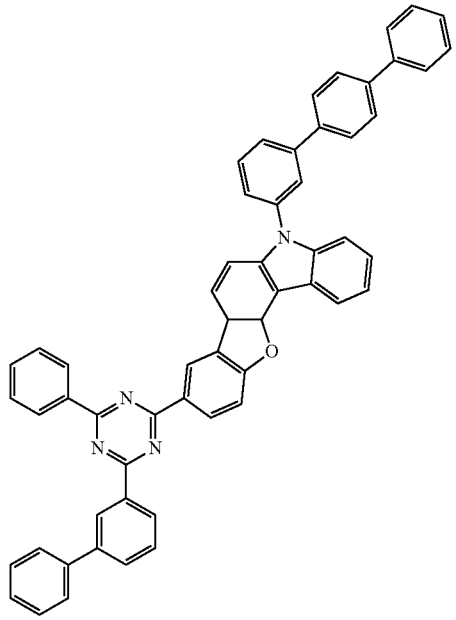
1E-2-16
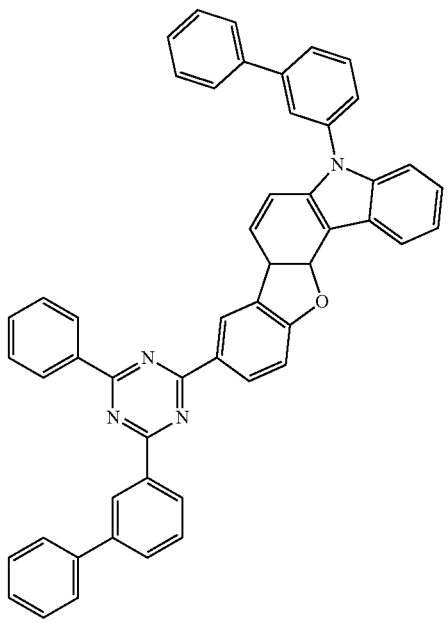

527
-continued
1E-2-17
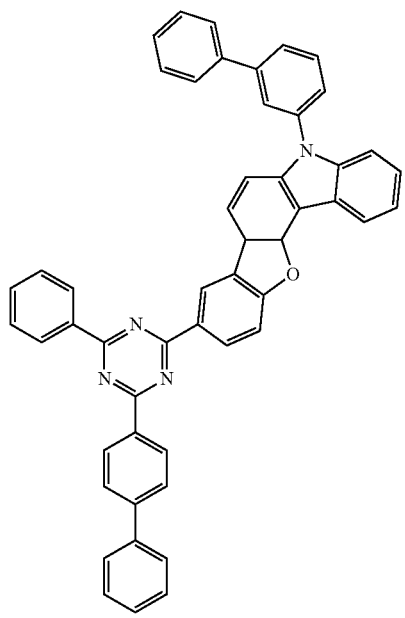
1E-2-18
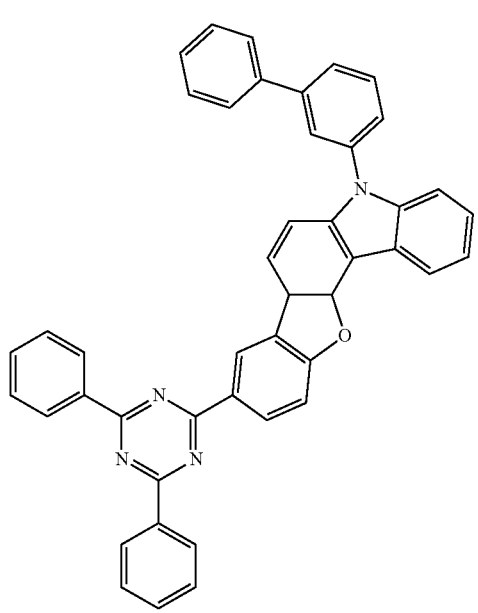
528
-continued
1E-2-19
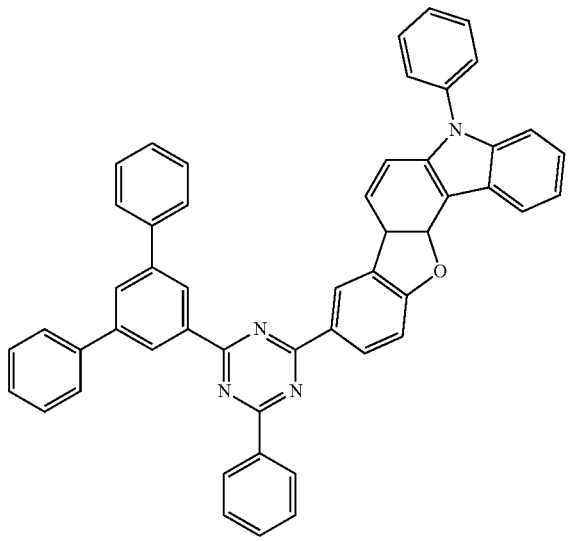
1E-2-20
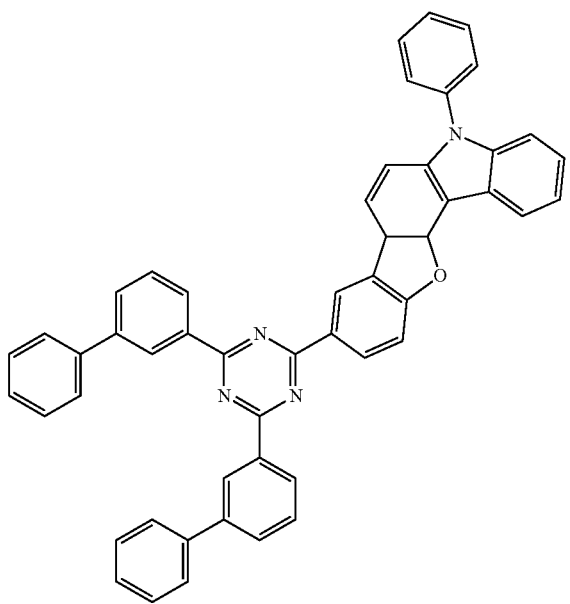

1E-2-21
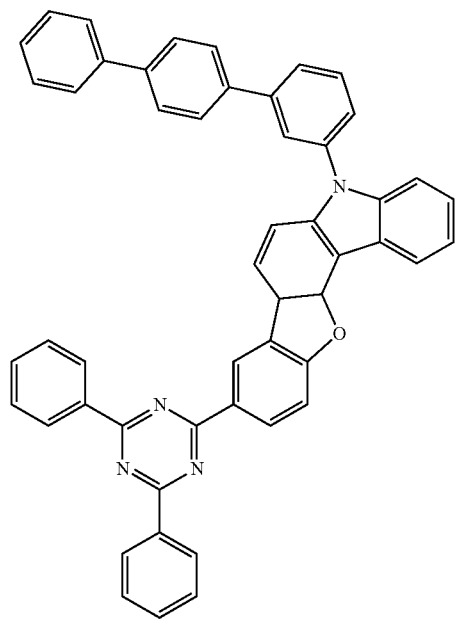
1E-2-22
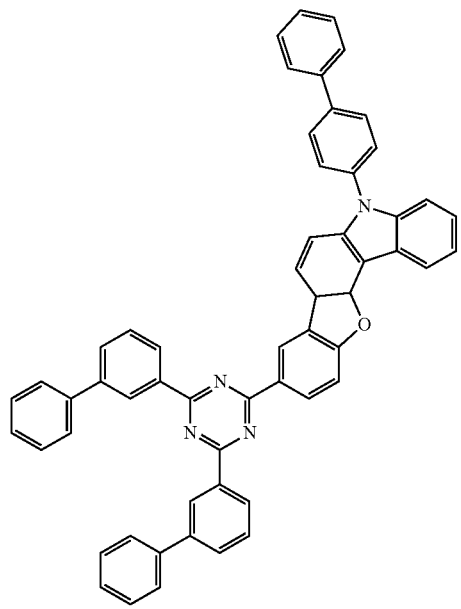
-continued
1E-2-23
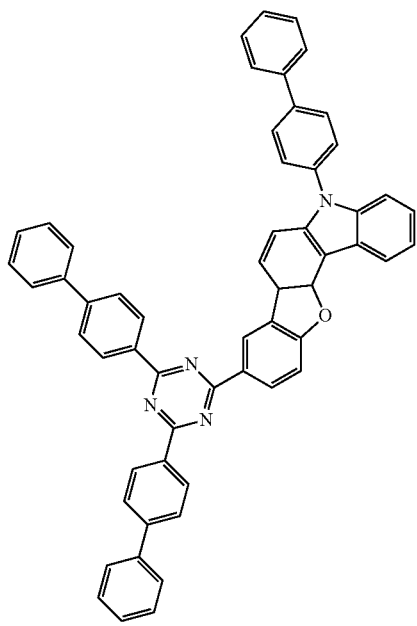
1E-2-24
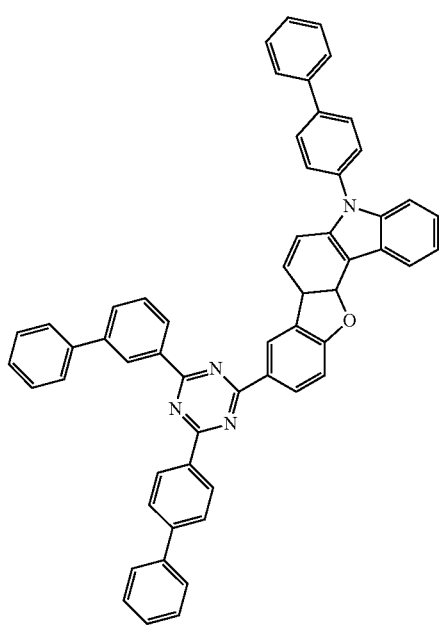

1E-2-25
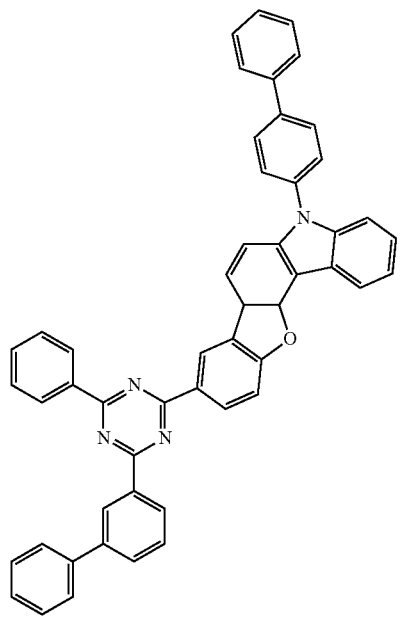
1E-2-27
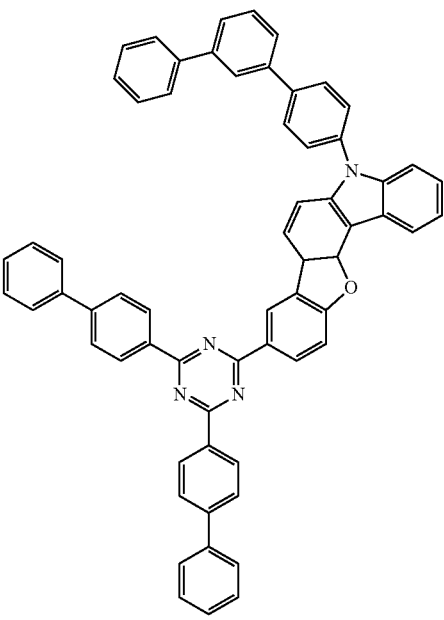
1E-2-26
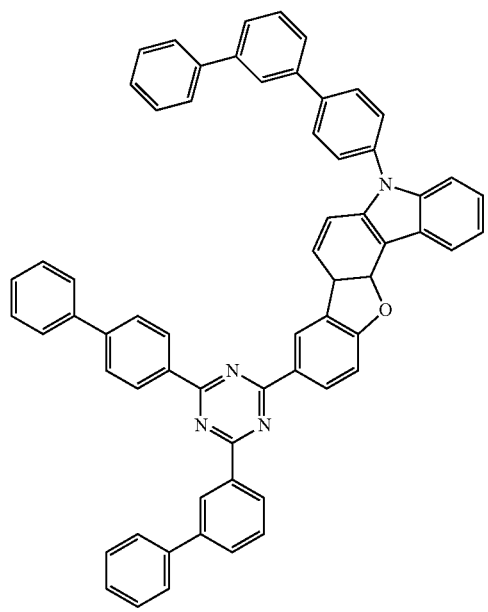
1E-2-28
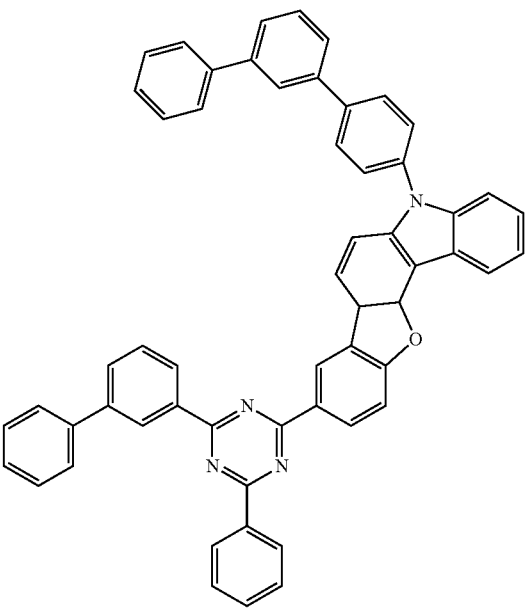

533
-continued
1E-2-29
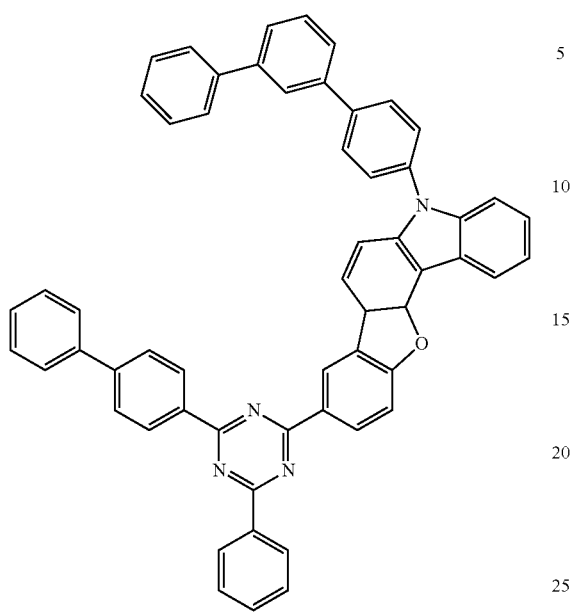
534
-continued
1E-2-31
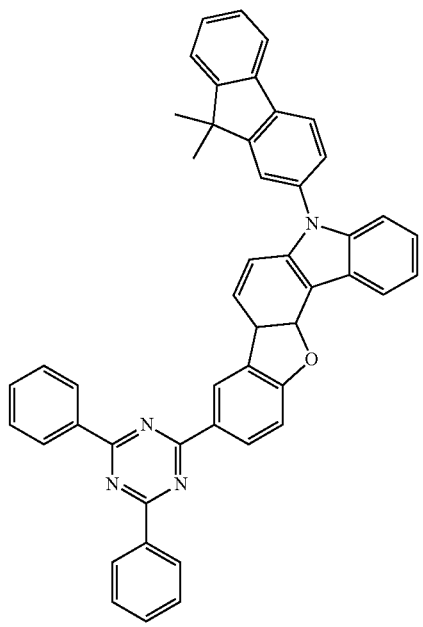
1E-2-30
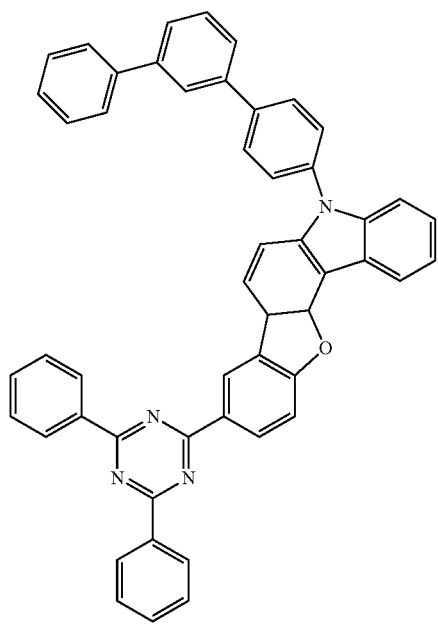
1E-2-32
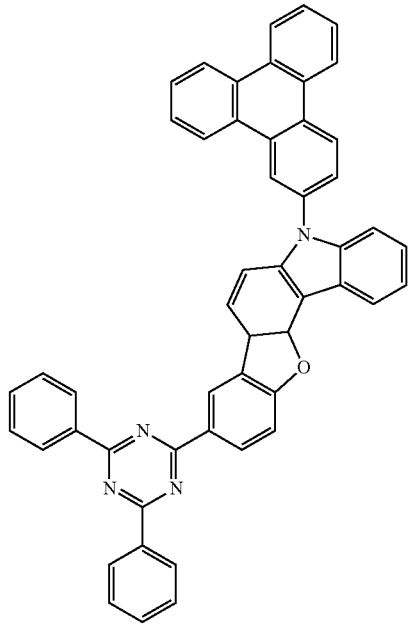

1E-2-32
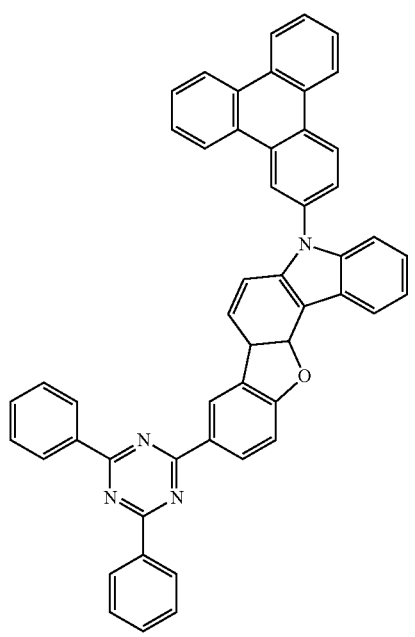
1E-2-34
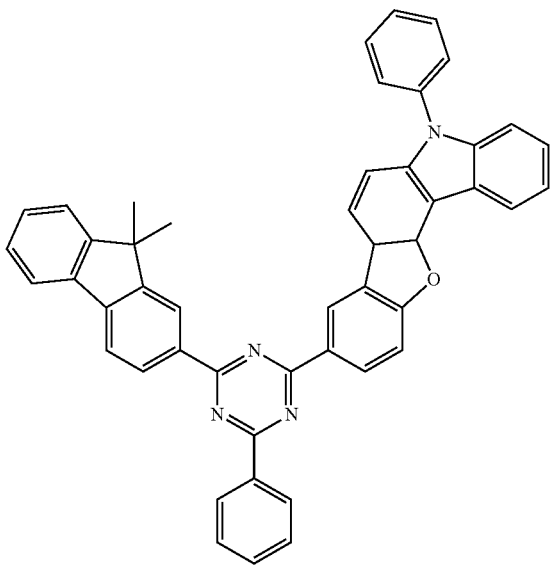
1E-2-33
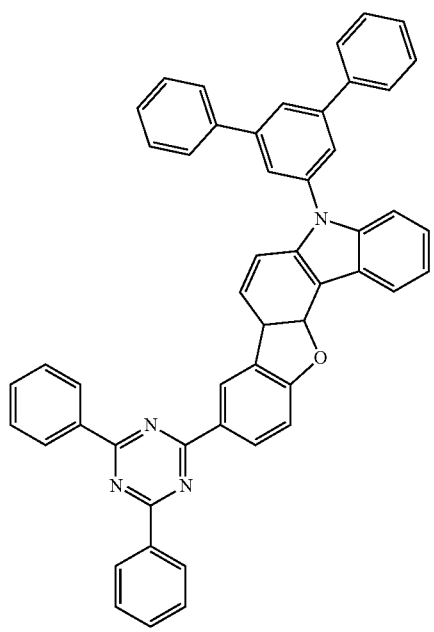
1E-2-35
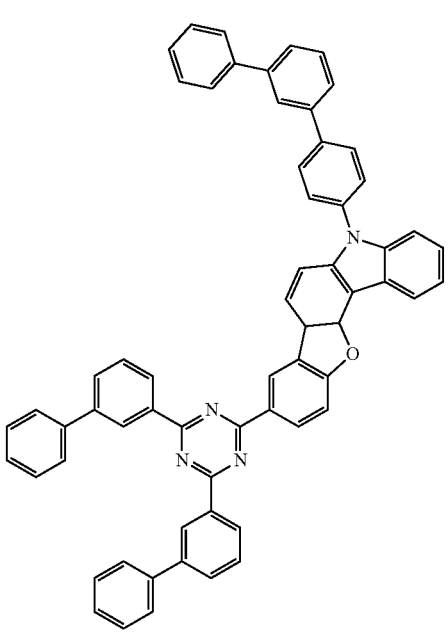

1E-2-36
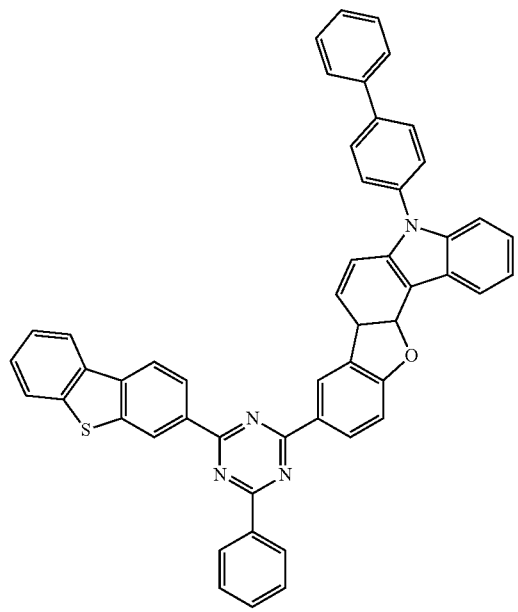
1E-2-38
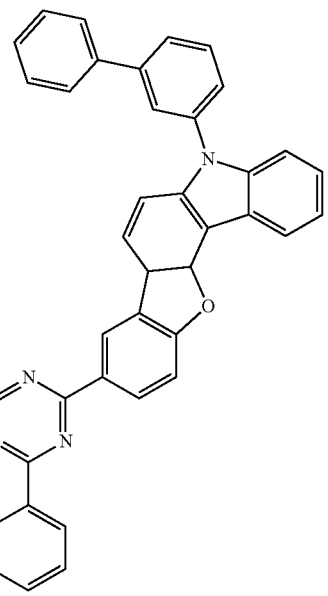
1E-2-37
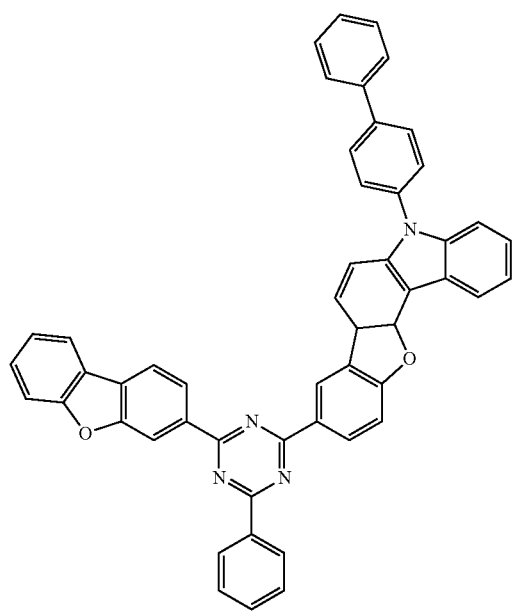
1E-2-39

1E-2-40
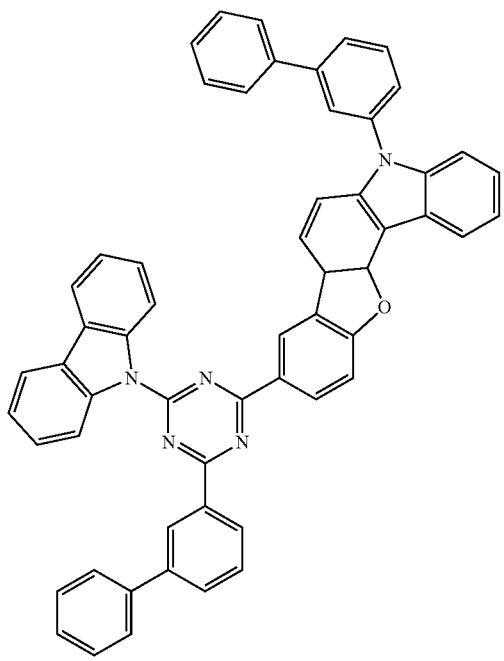
1E-2-41
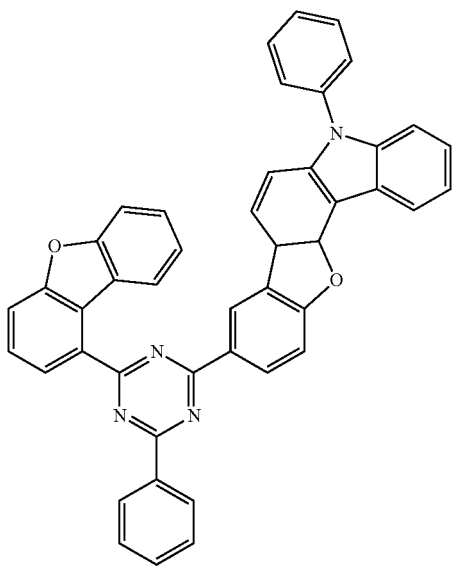
1E-2-42
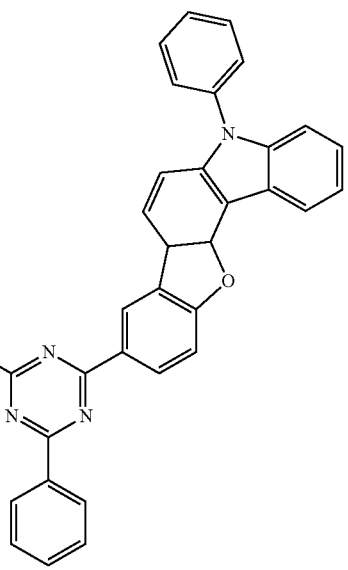
1E-2-43
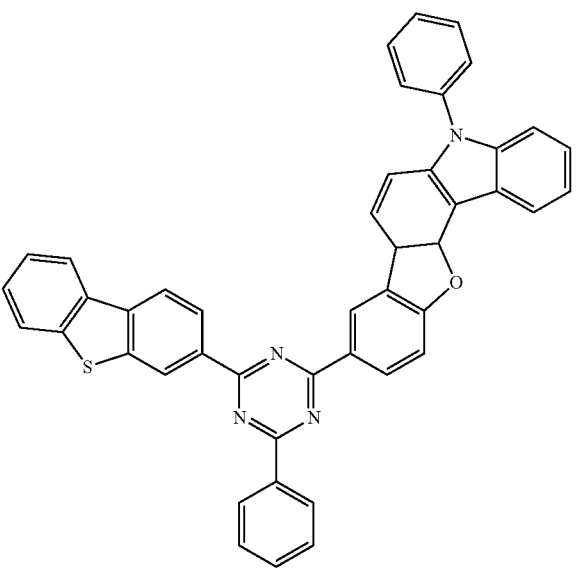

1E-2-44
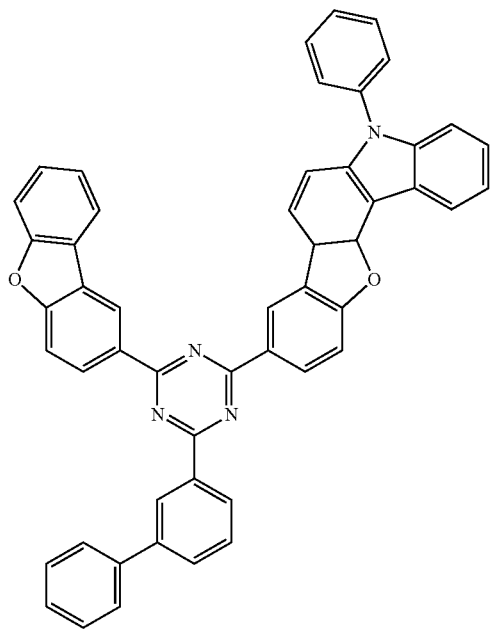
1E-2-46
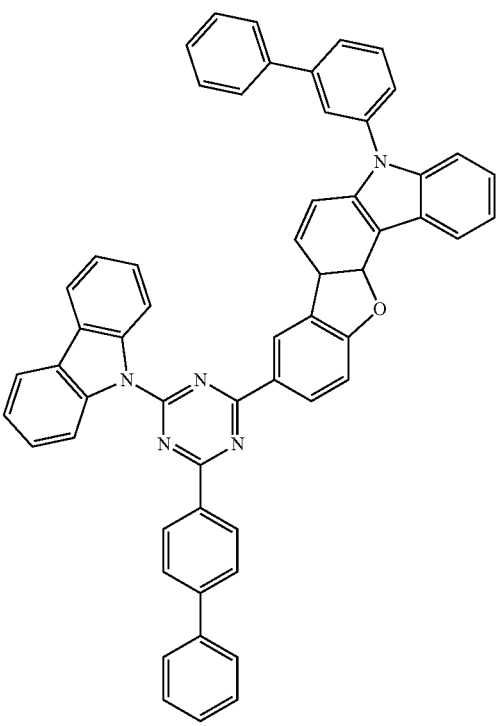
1E-2-45
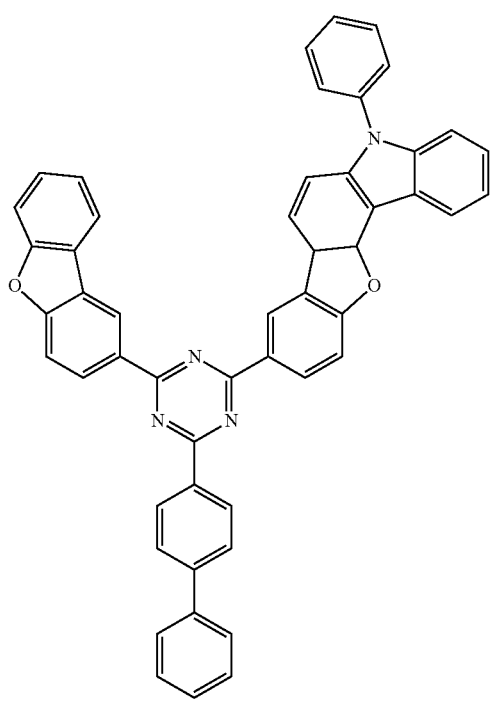
1E-2-47

1E-2-48
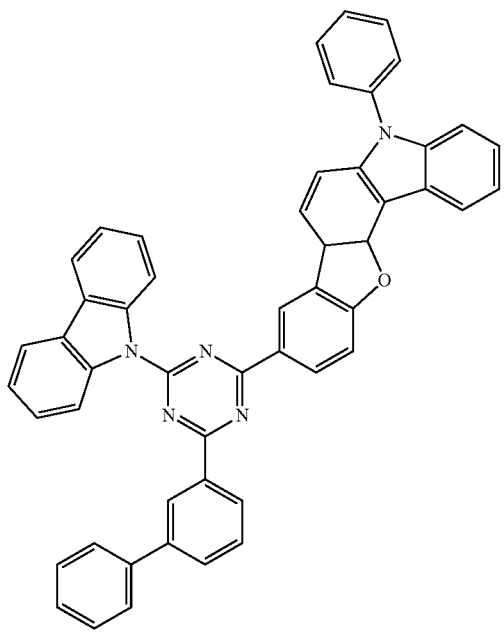
1E-2-50
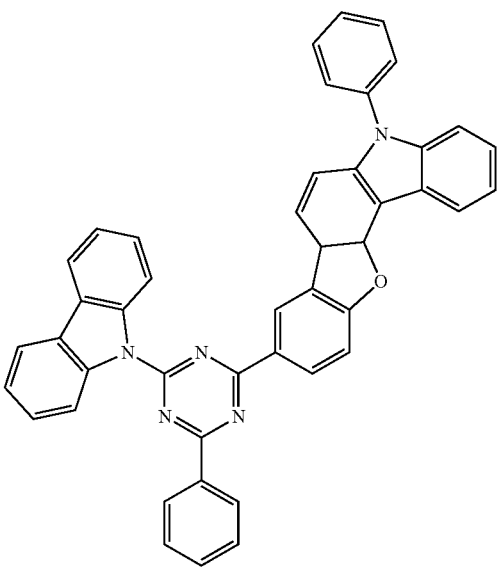
1E-2-49
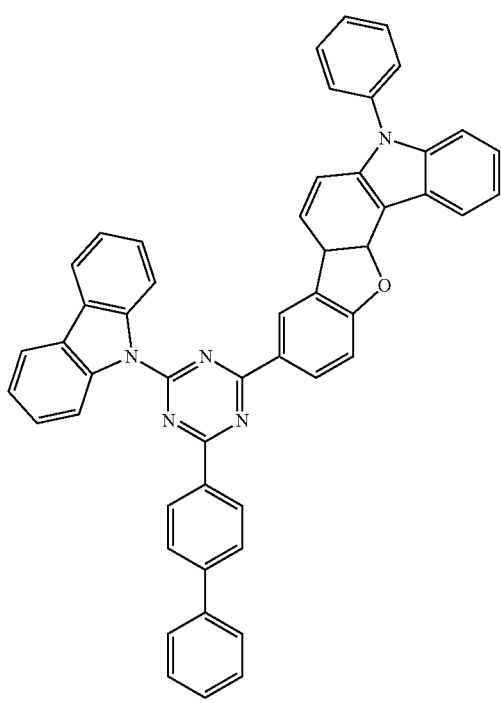
1E-2-51
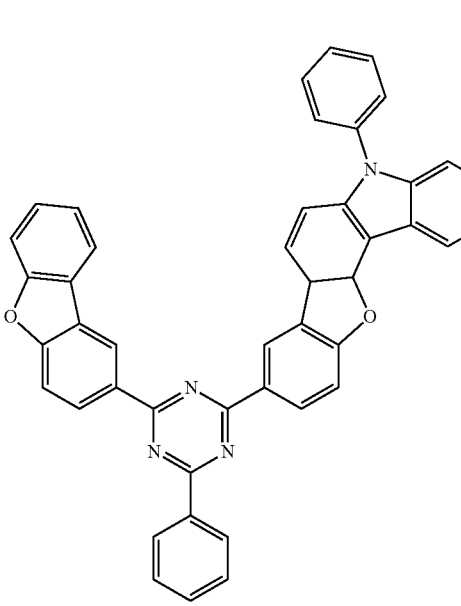

-continued
1E-2-52
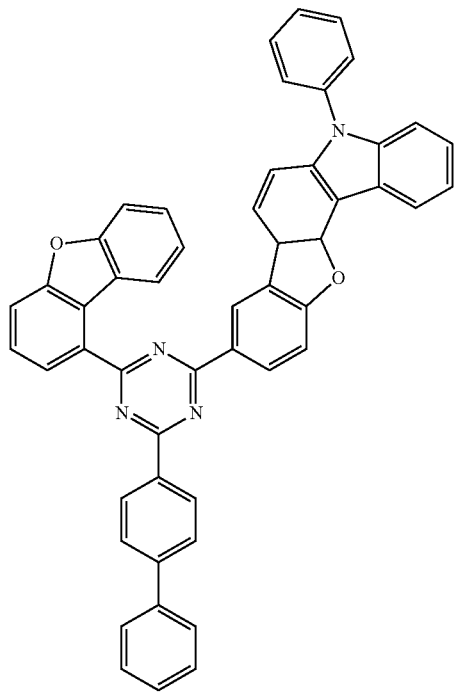
1E-2-54
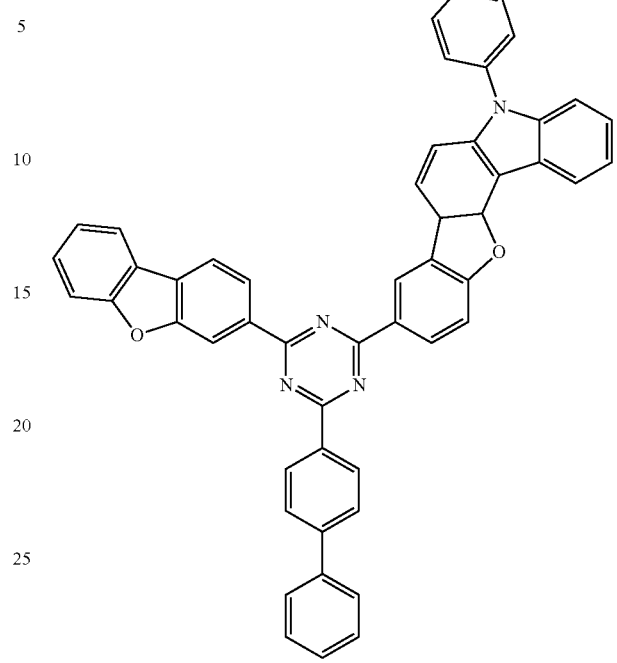
1E-2-53
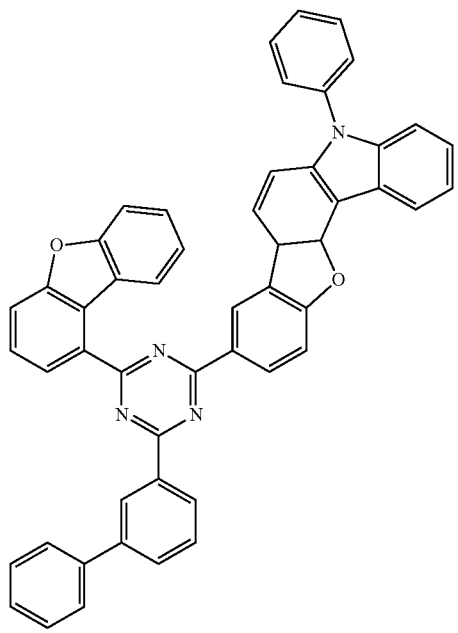
1E-2-55
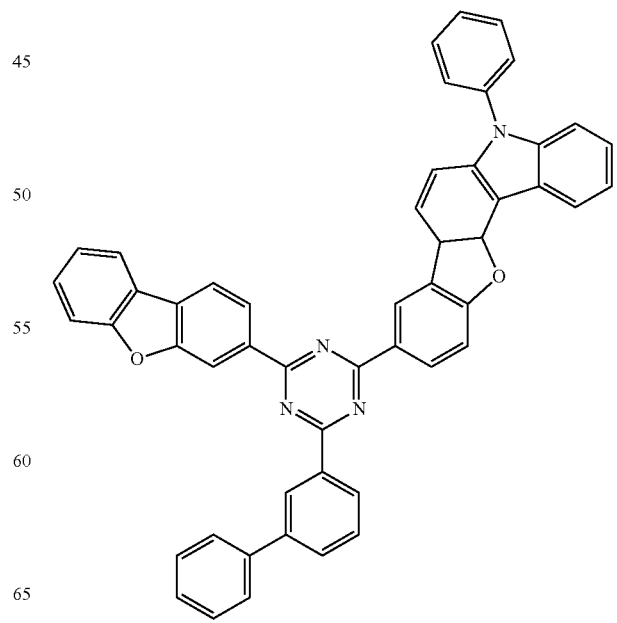

1E-2-56
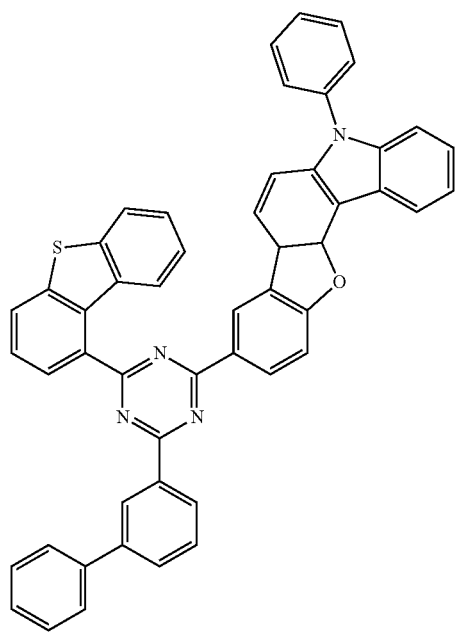
1E-2-58
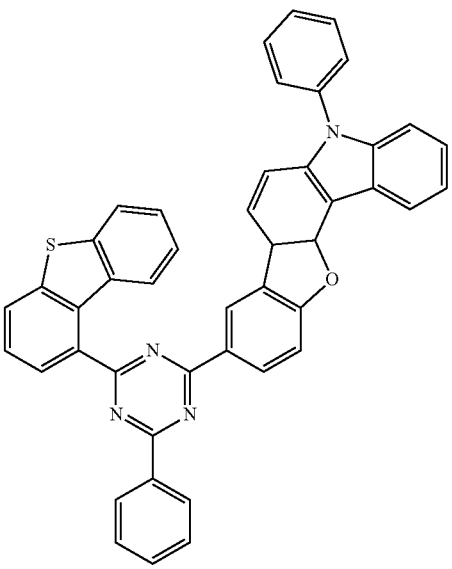
1E-2-57
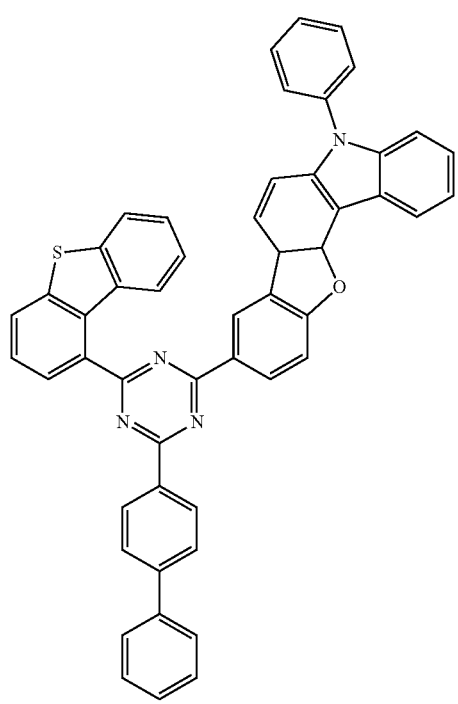
1E-2-59
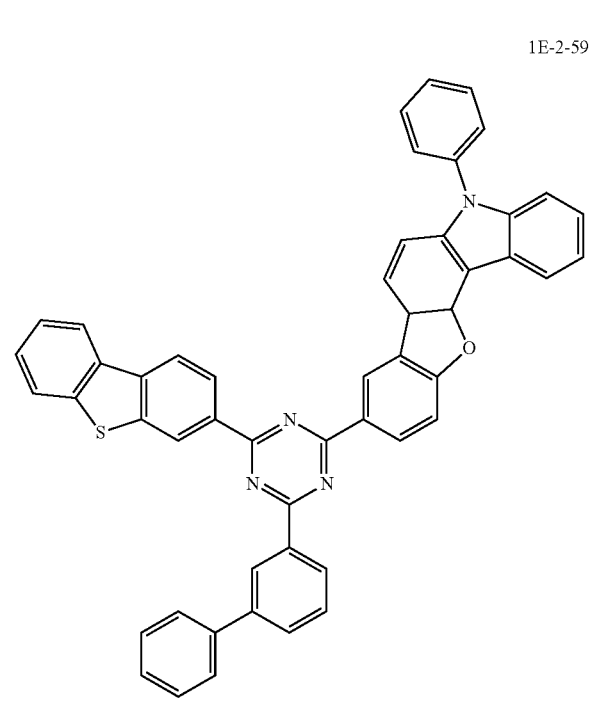

1E-2-60
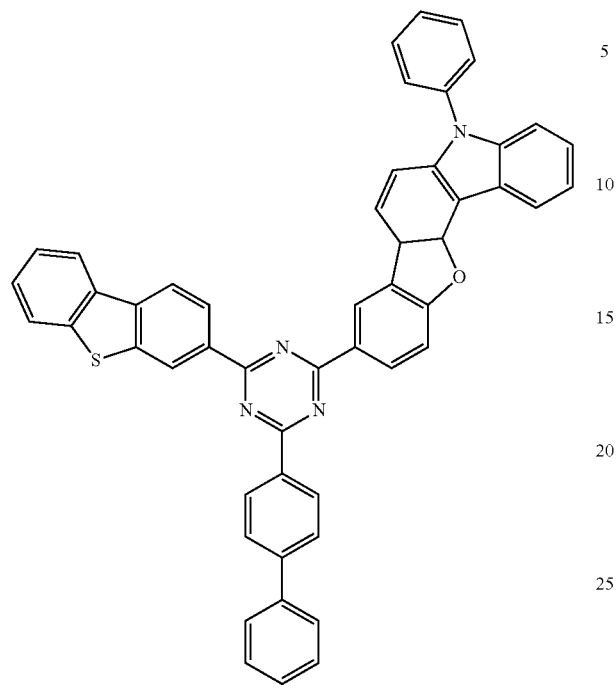
1E-2-62
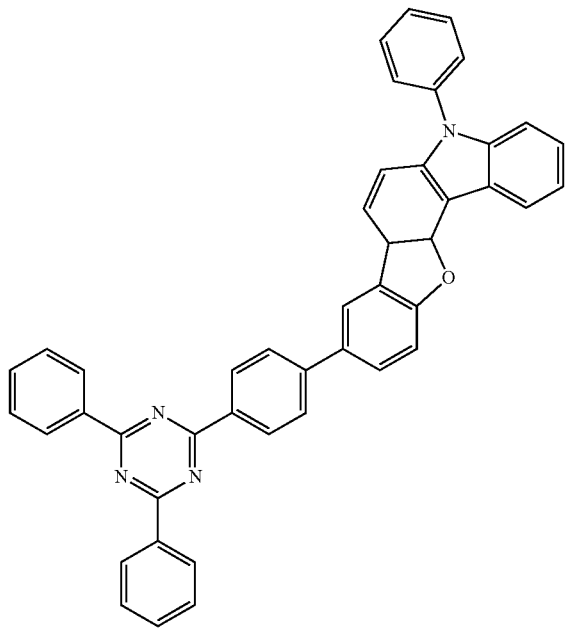
1E-2-61
1E-2-63
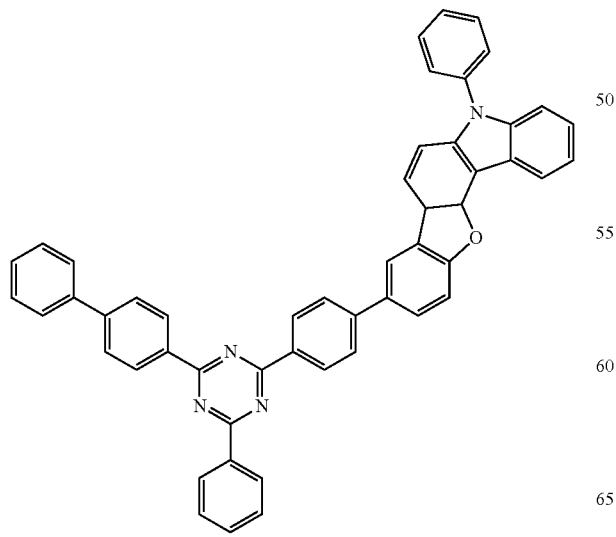

1E-2-64
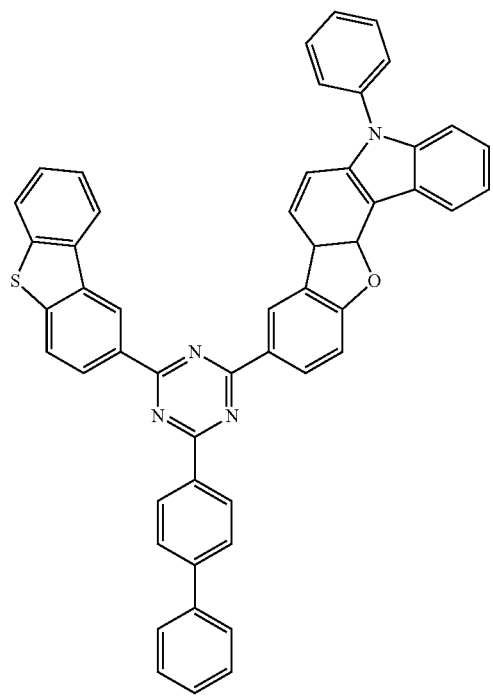
1E-2-66
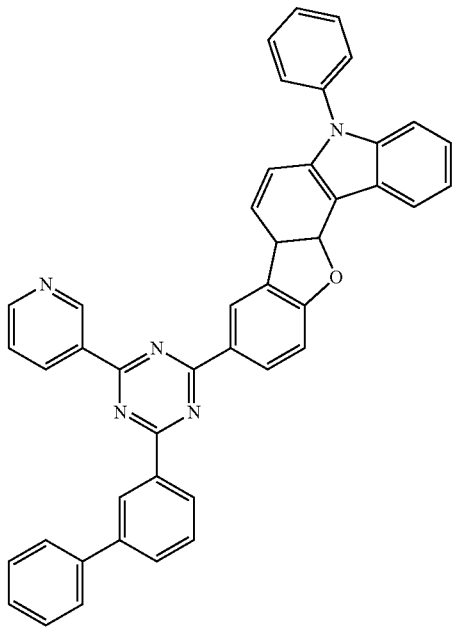
1E-2-65
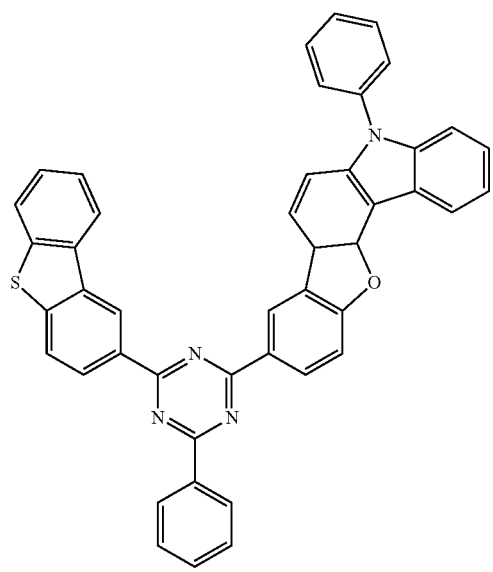
1E-2-67
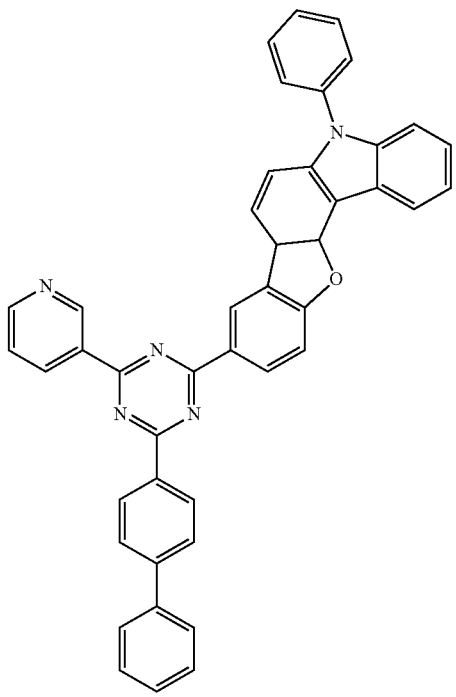

553
-continued
1E-2-68
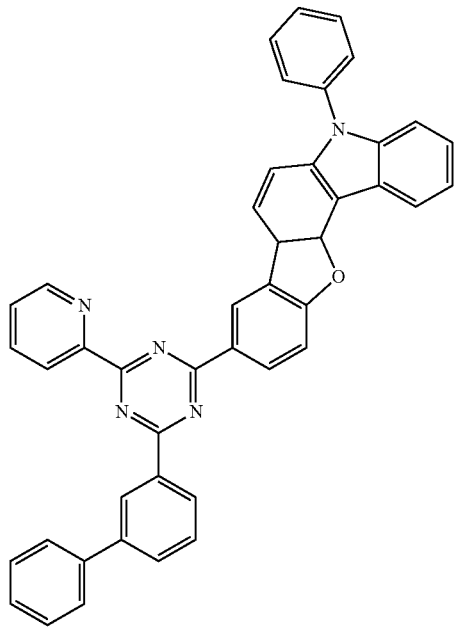
1E-2-69
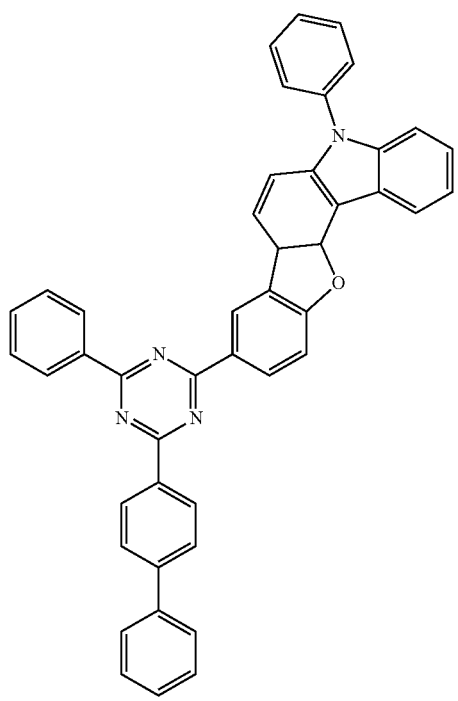
554
-continued
1E-2-70
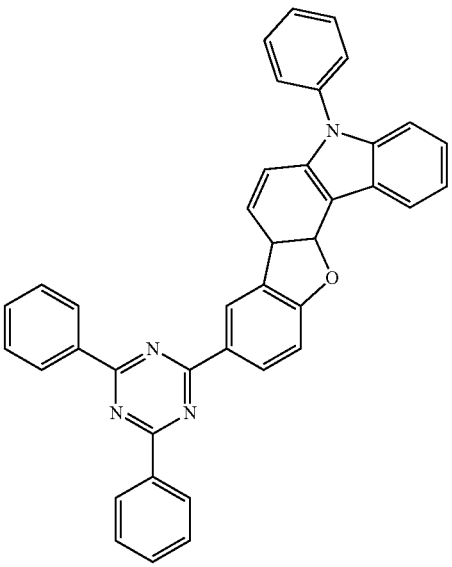
1E-2-71
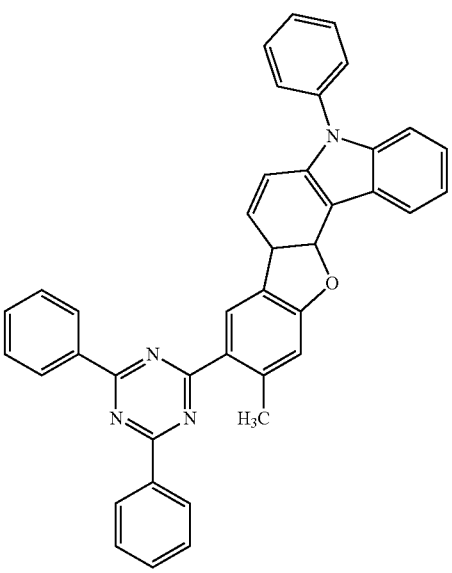

1E-2-72
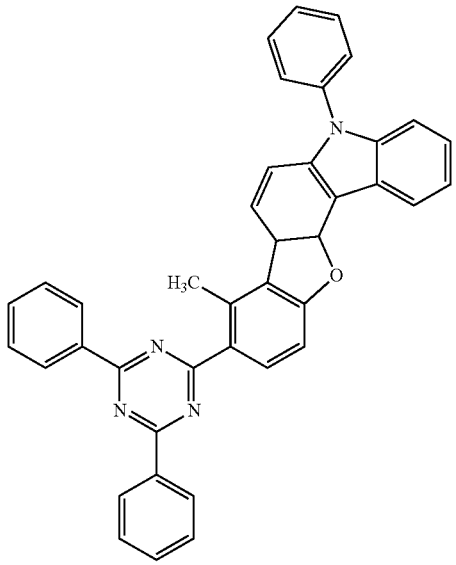
1E-2-74
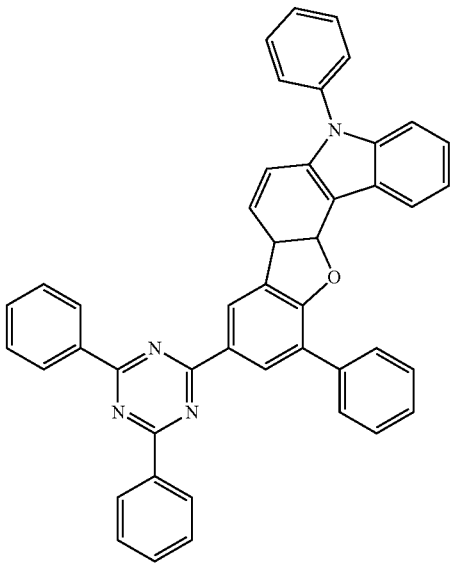
1E-2-73
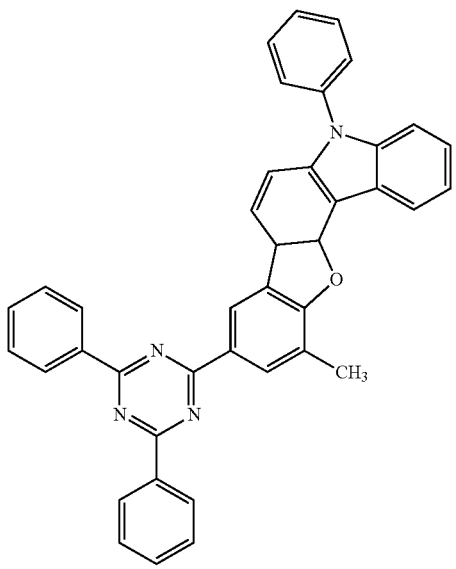
1E-2-75
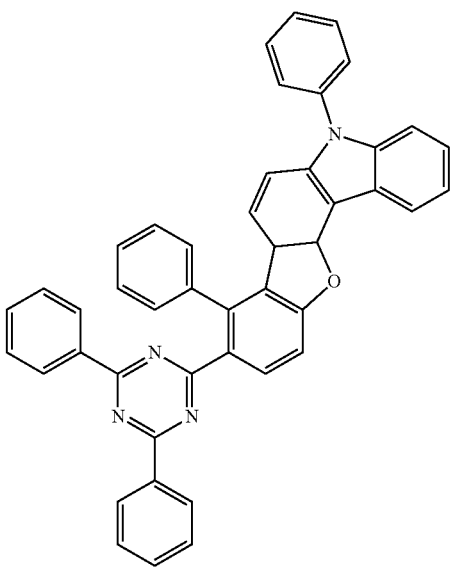

1E-2-76
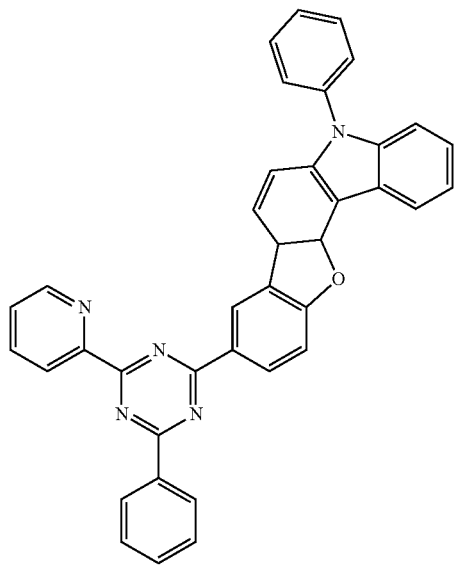
1E-2-78
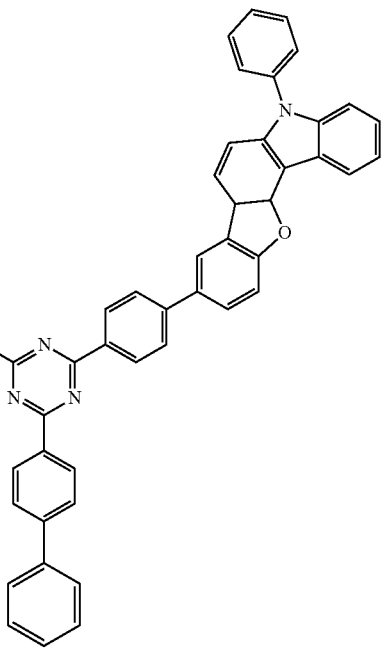
1E-2-77
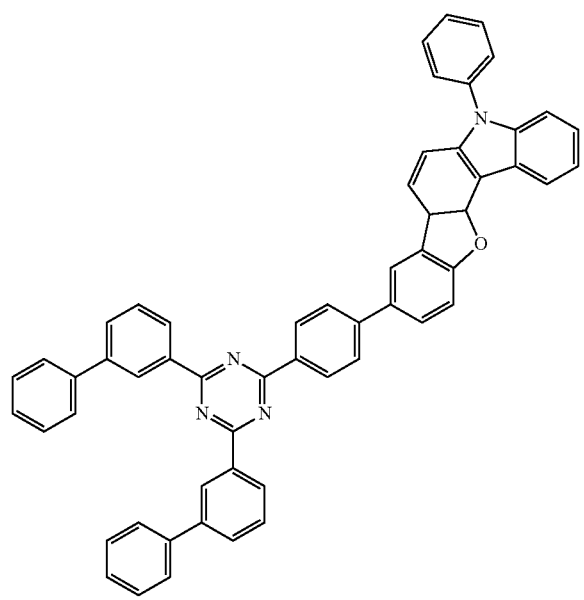
1E-2-79
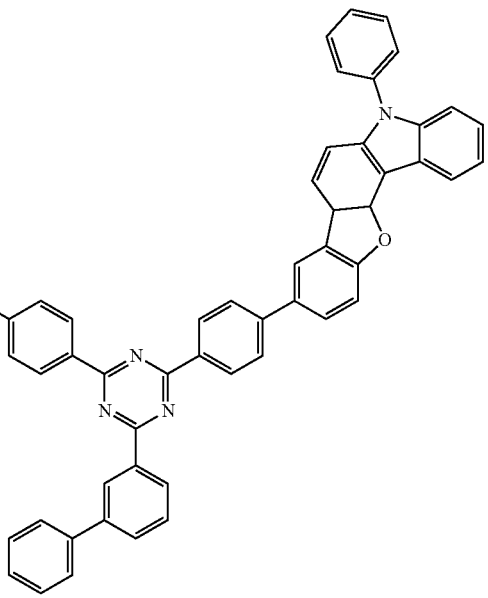

559
-continued
1E-2-80
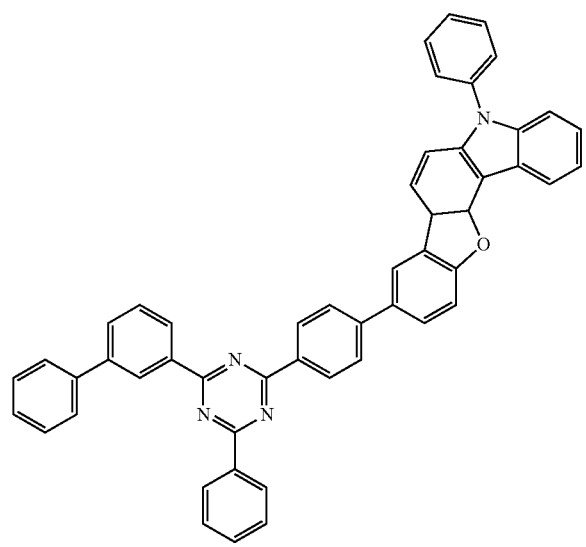
1E-2-81
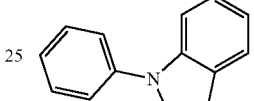
1E-2-82
560
-continued
1E-2-83
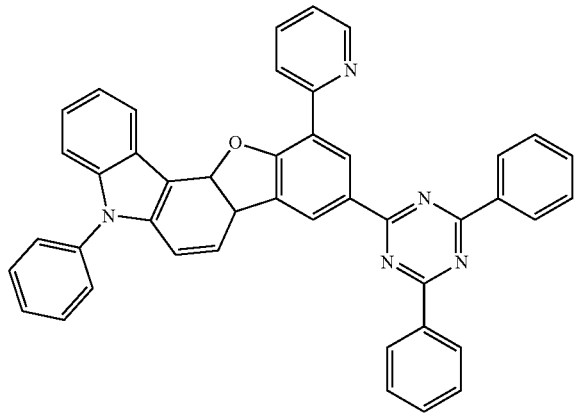
1E-3-1
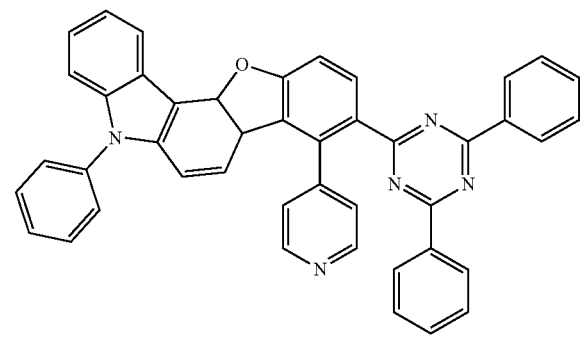
1E-3-2
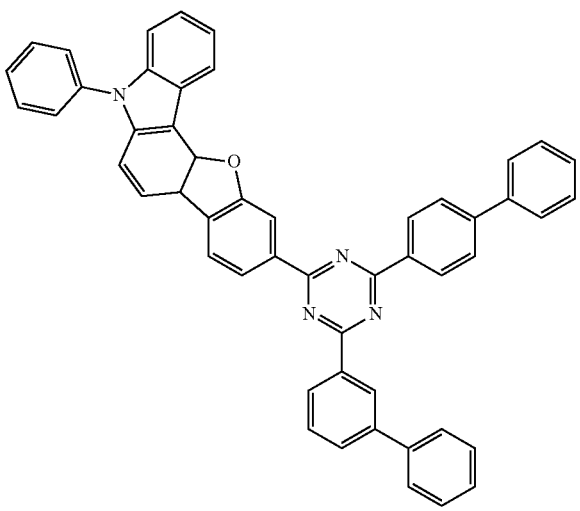

1E-3-3
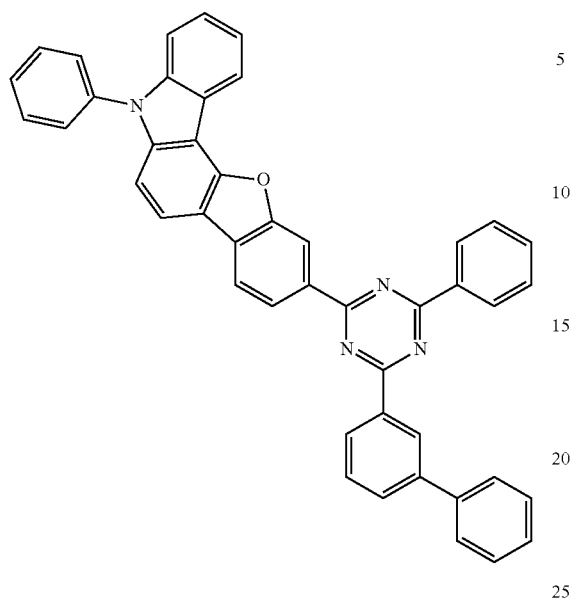
1E-3-6
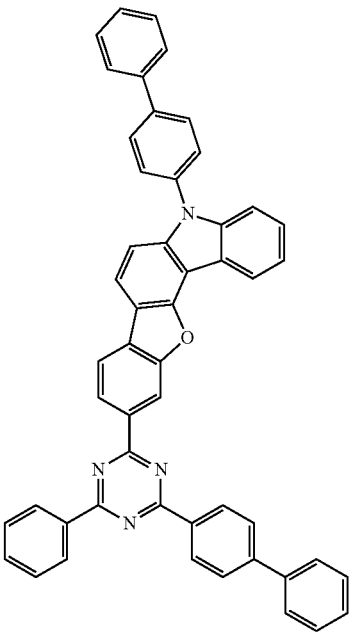
1E-3-4
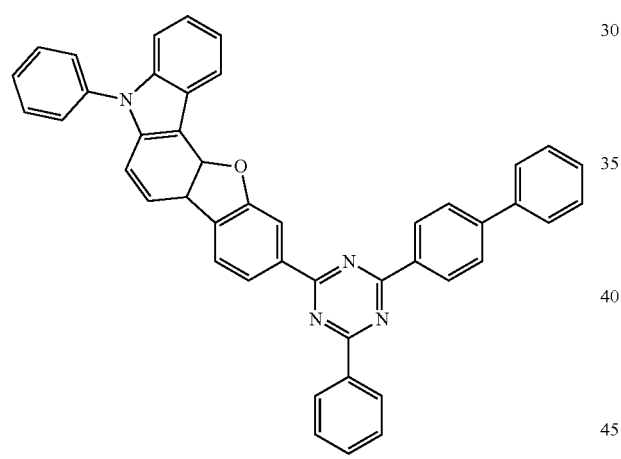
1E-3-5
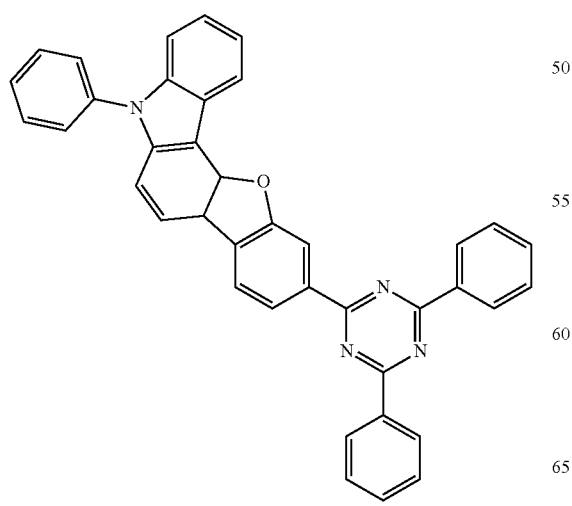
1E-3-7
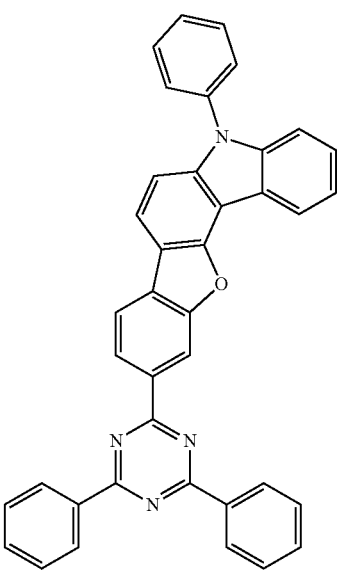

-continued
1E-3-8
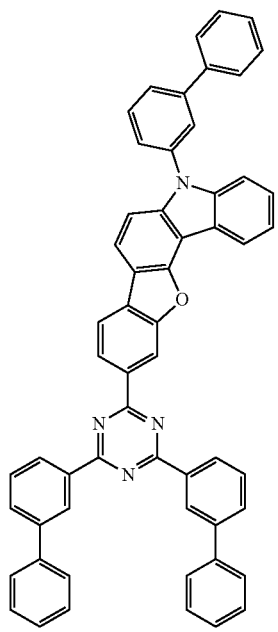
1E-3-9
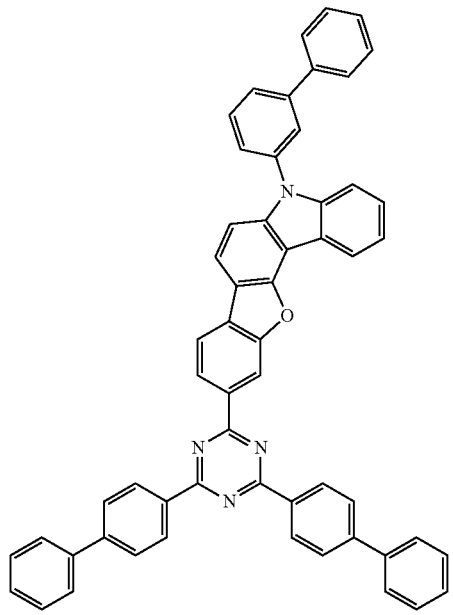
-continued
1E-3-10
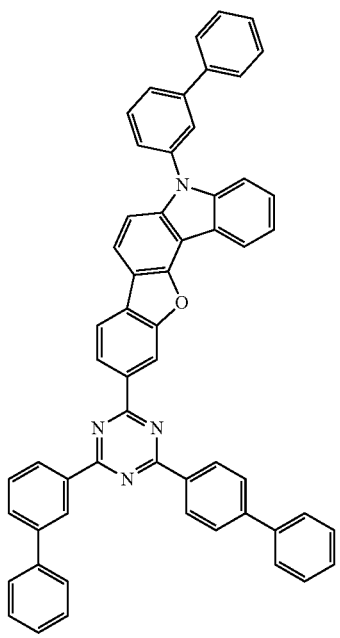
1E-3-11
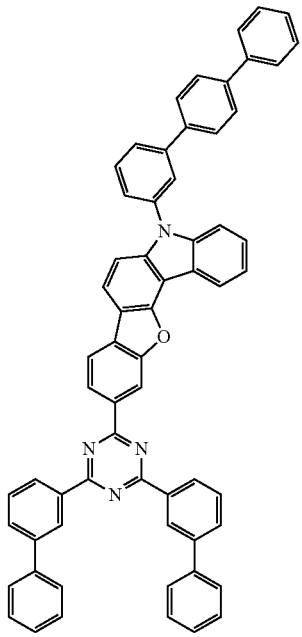

1E-3-12
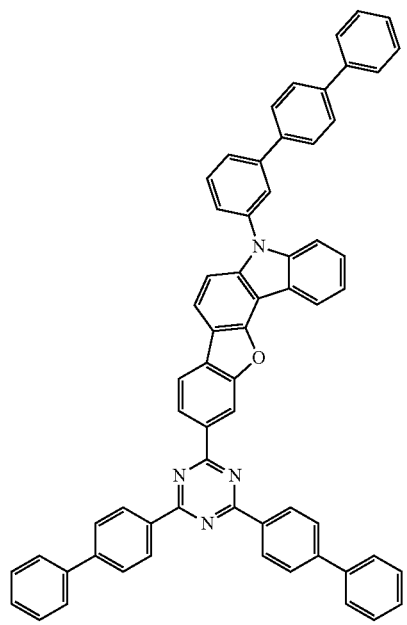
1E-3-14
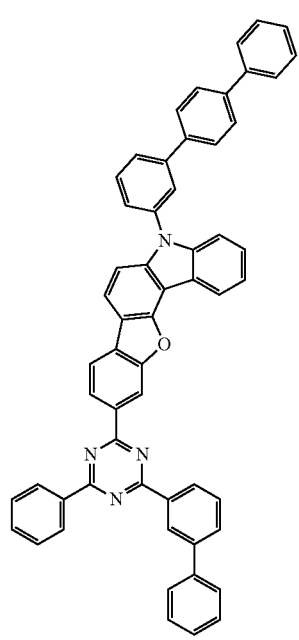
1E-3-13
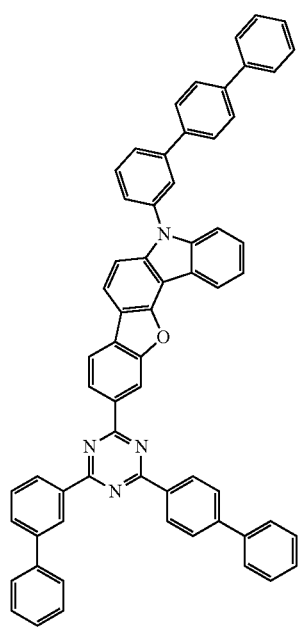
1E-3-15
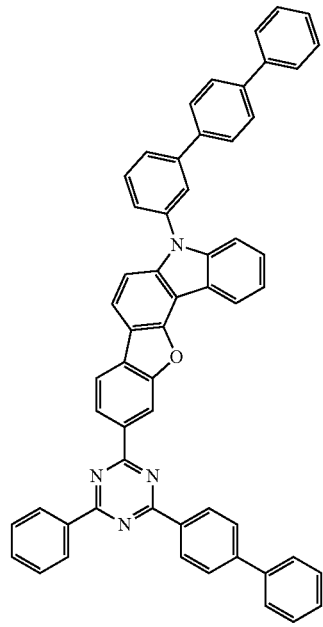

567
-continued
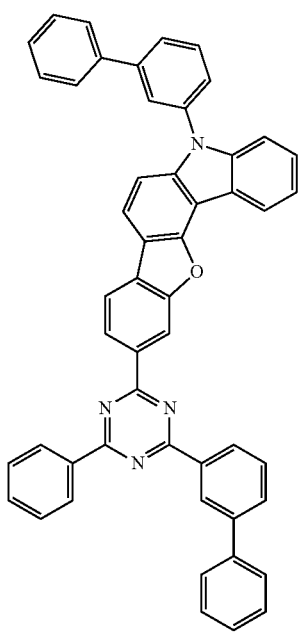
1E-3-16
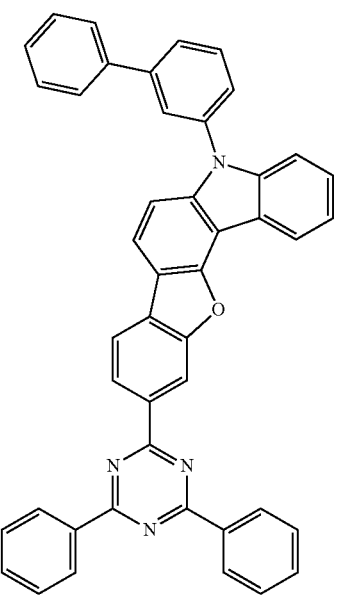
1E-3-18
568
-continued
1E-3-17
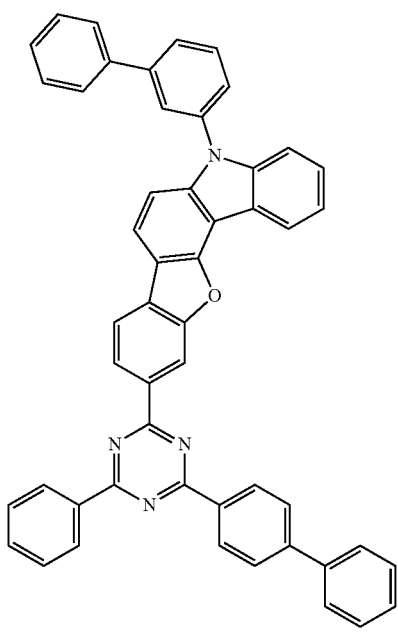
1E-3-19
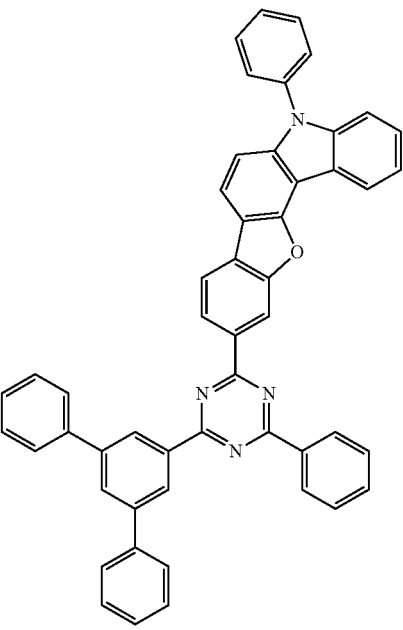

1E-3-20
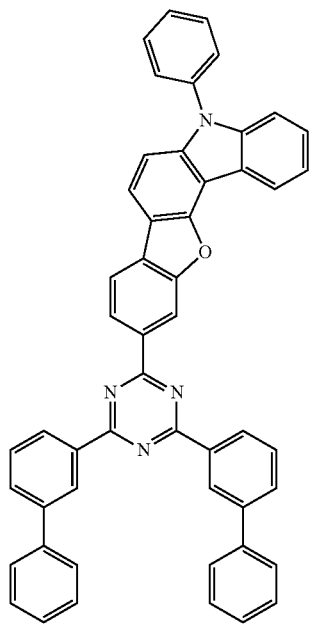
1E-3-21
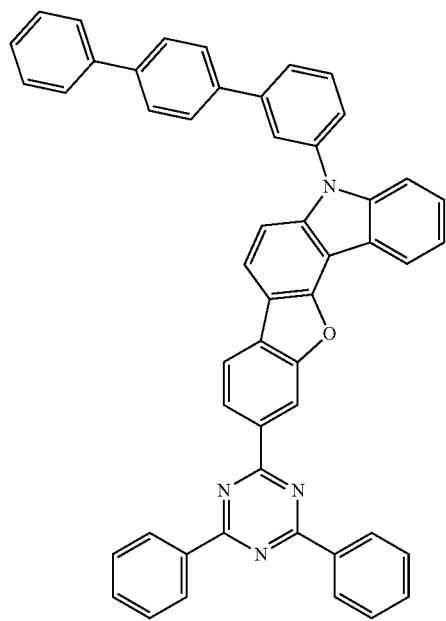
1E-3-22
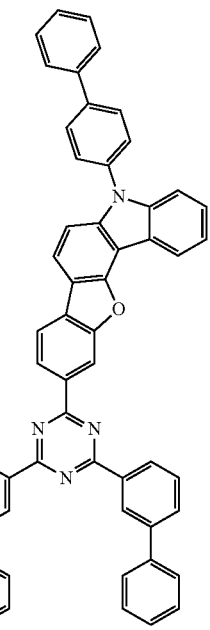
1E-3-23
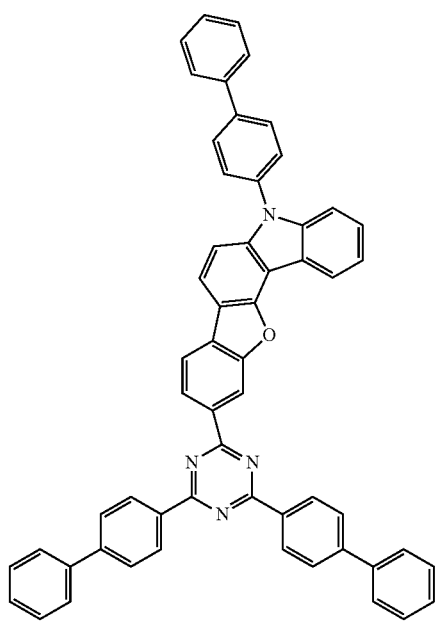

1E-3-24
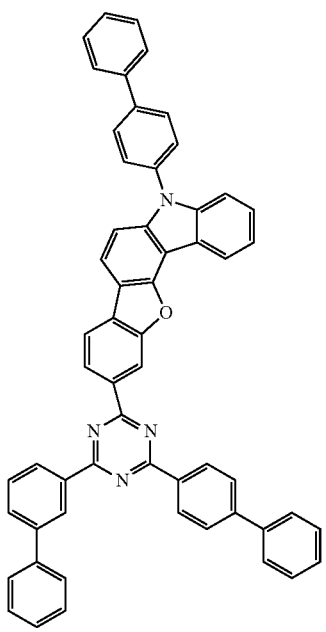
1E-3-26
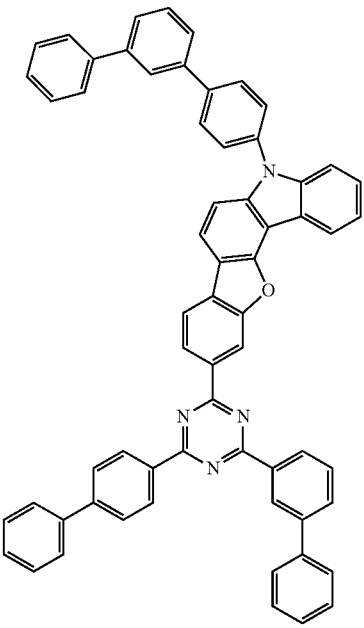
1E-3-25
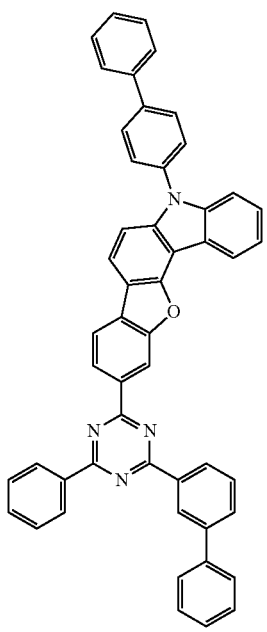
1E-3-27
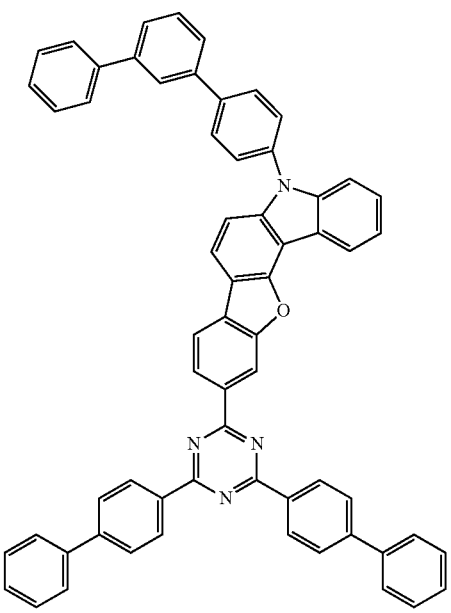

1E-3-28
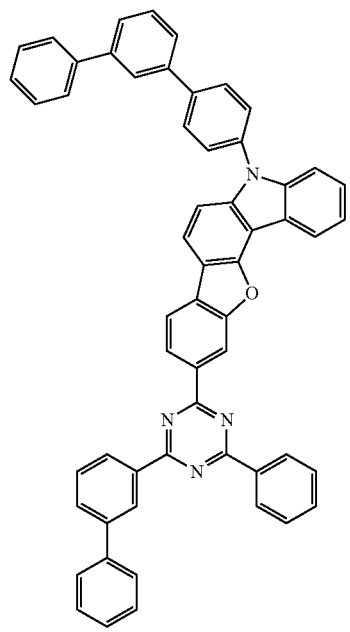
1E-3-30
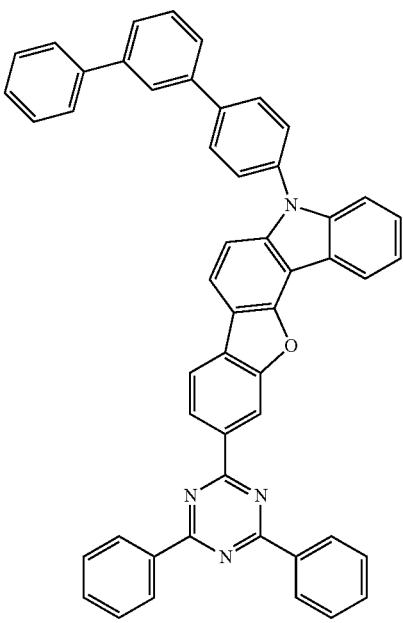
1E-3-29
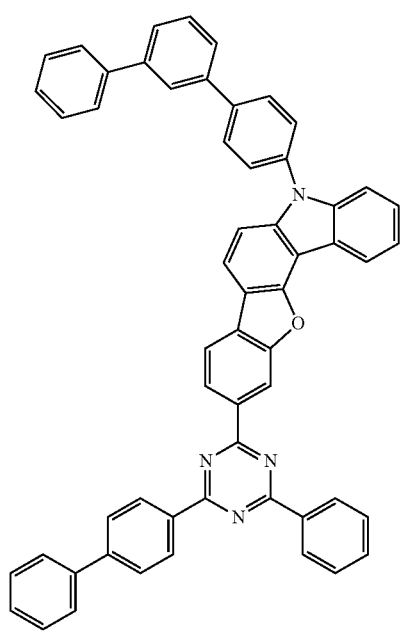
1E-3-31
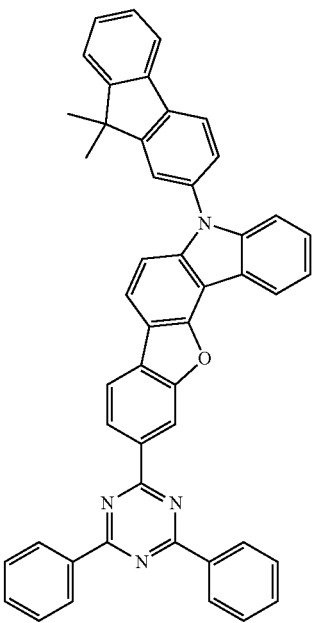

-continued
1E-3-32
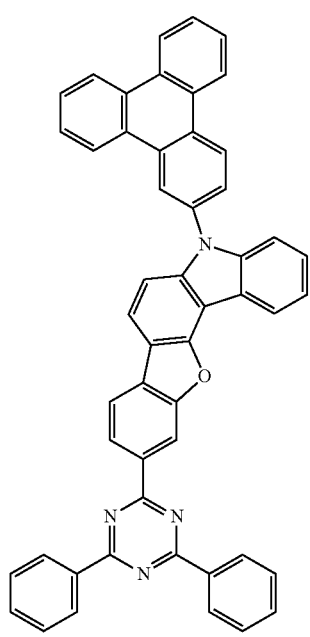
1E-3-34
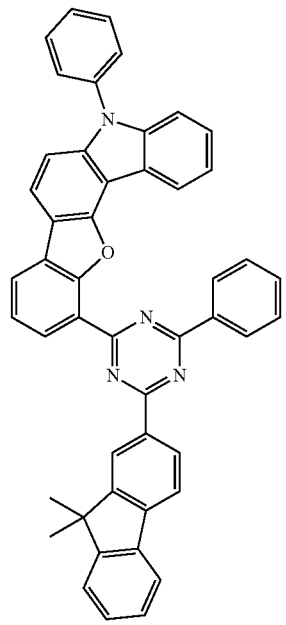
1E-3-33
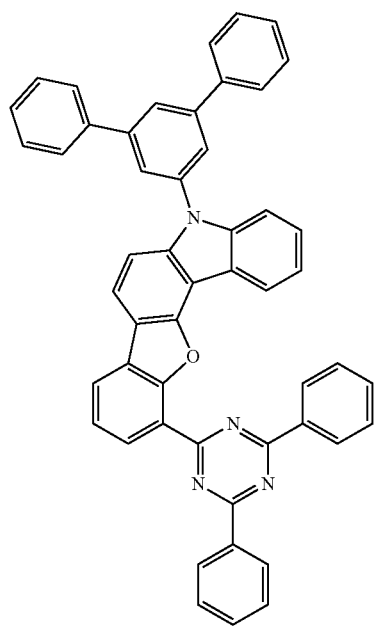
1E-3-35
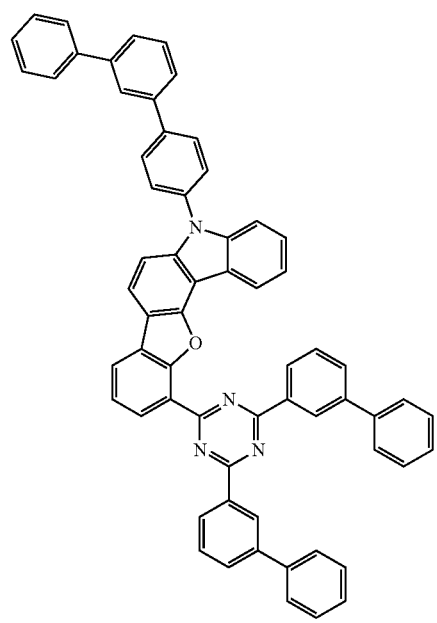

1E-3-36
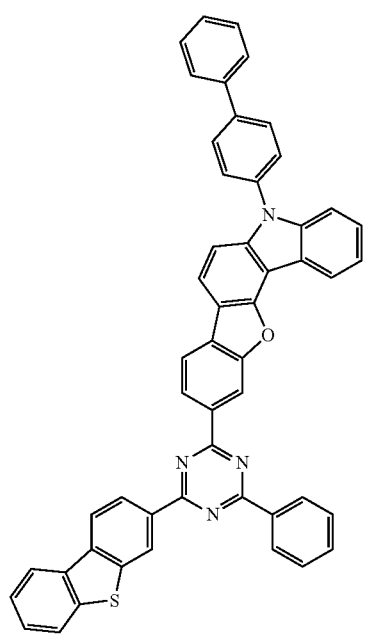
1E-3-38
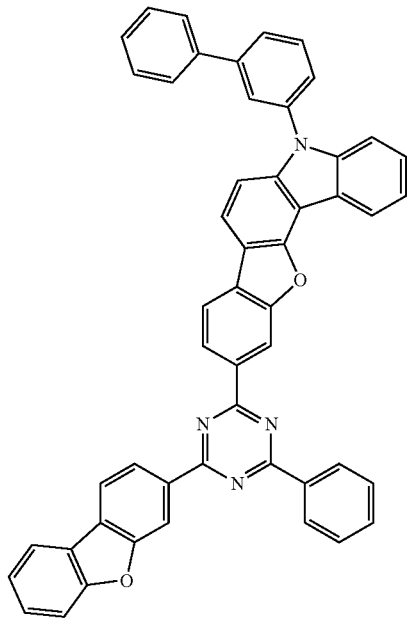
1E-3-37
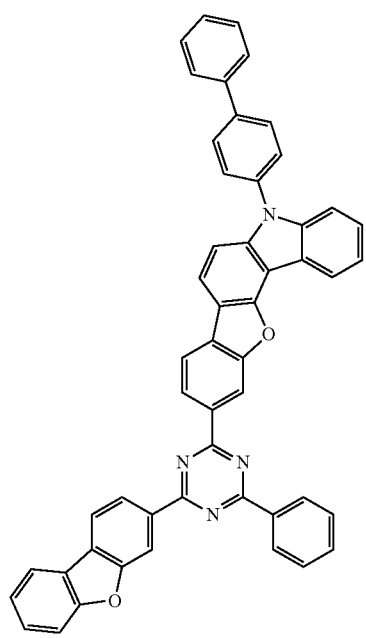
1E-3-39
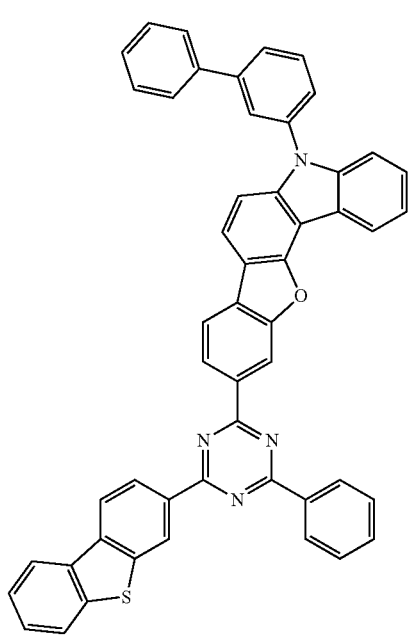

1E-3-40
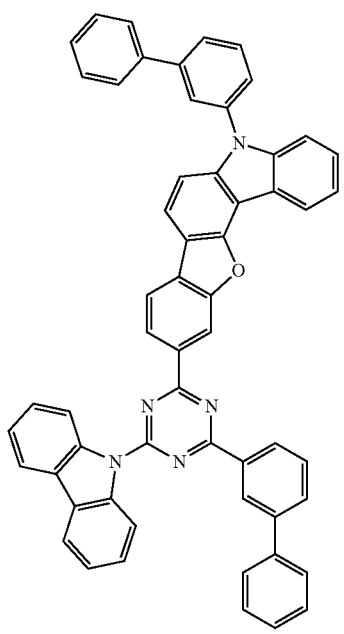
1E-3-41
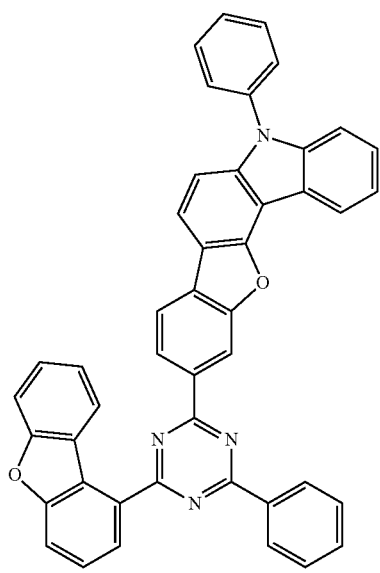
1E-3-42
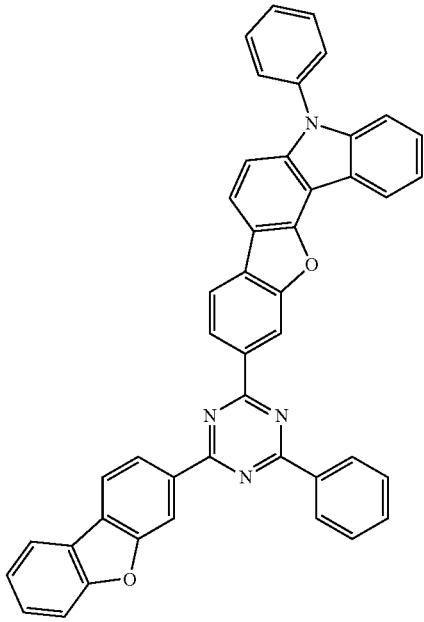
1E-3-43
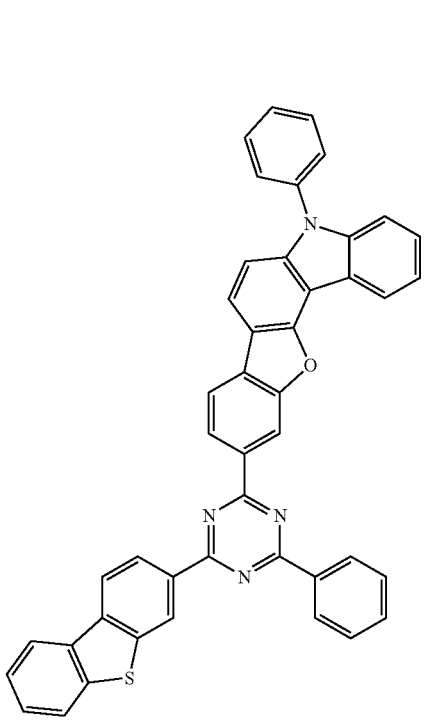

-continued
1E-3-44
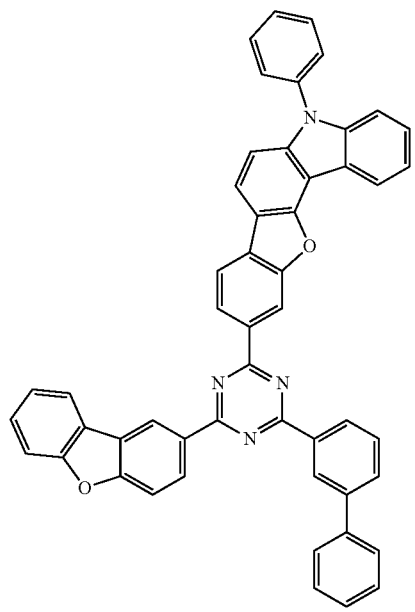
1E-3-45
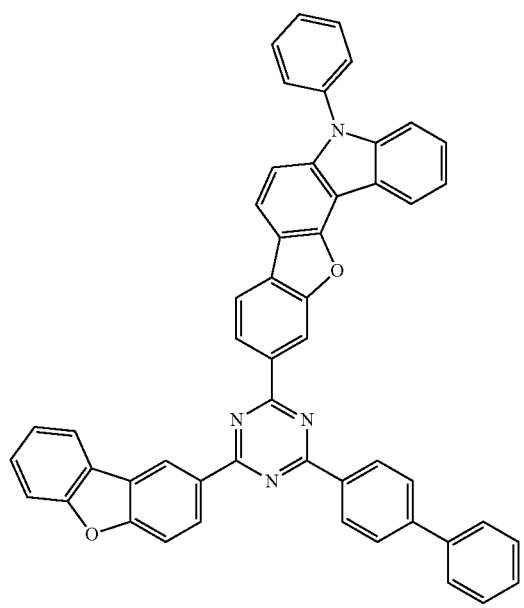
-continued
1E-3-46
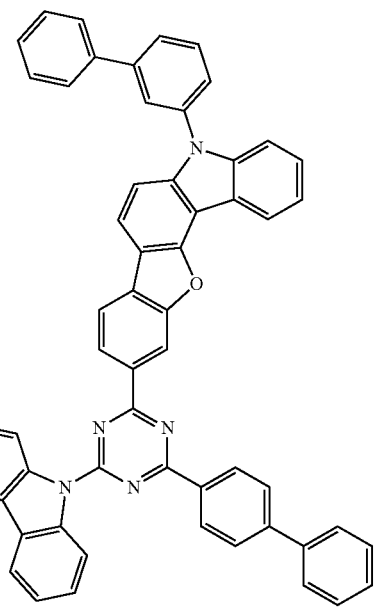
1E-3-47
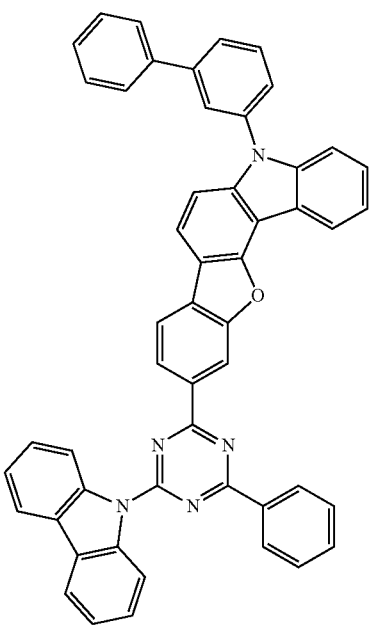

1E-3-48
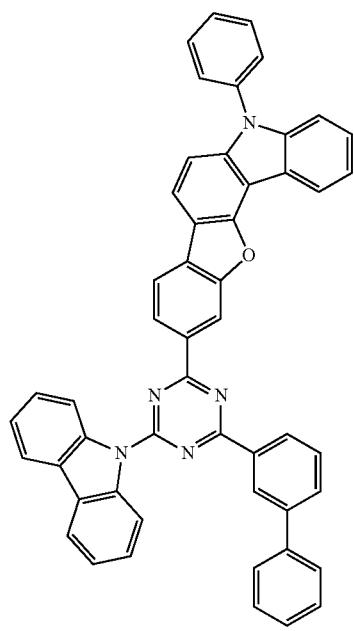
1E-3-49
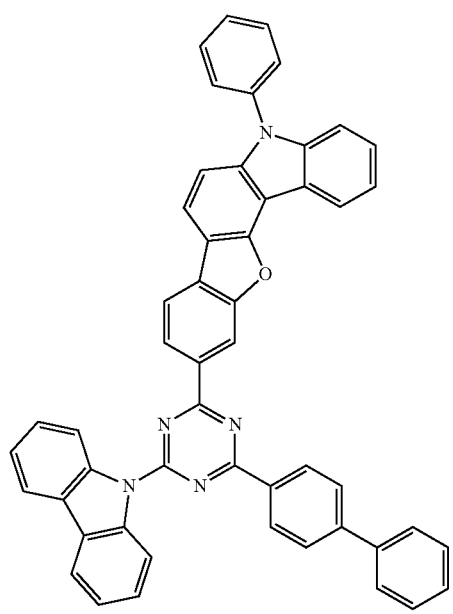
1E-3-50
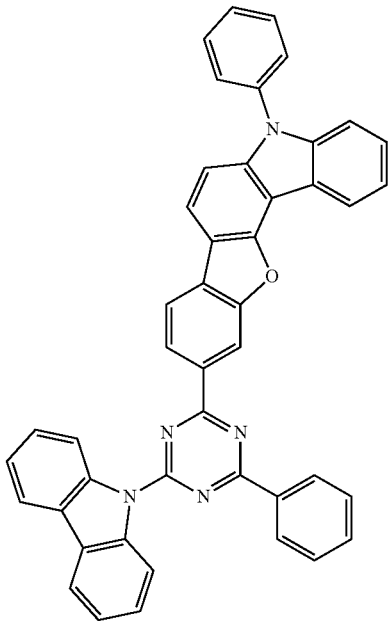
1E-3-51
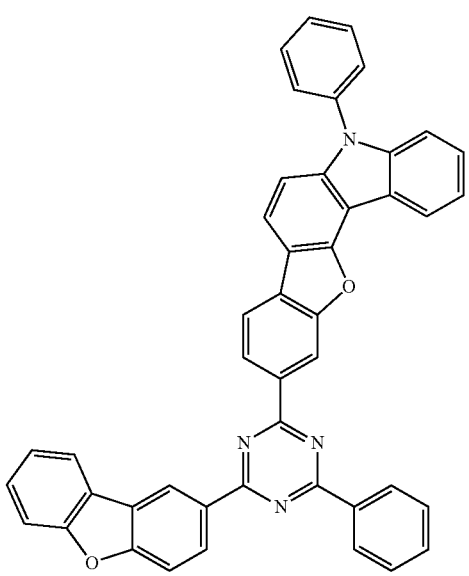

1E-3-52
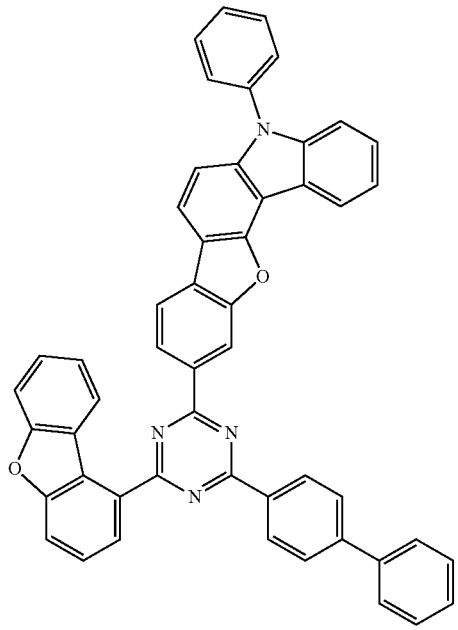
1E-3-53
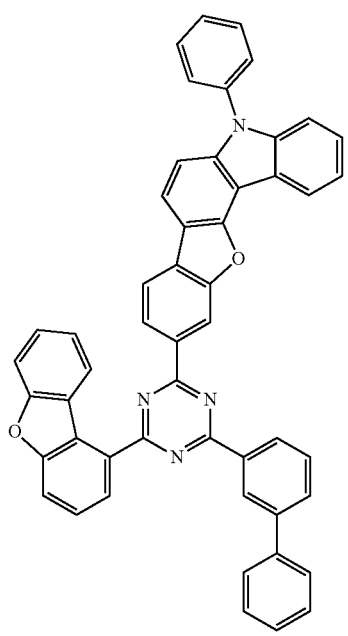
1E-3-54
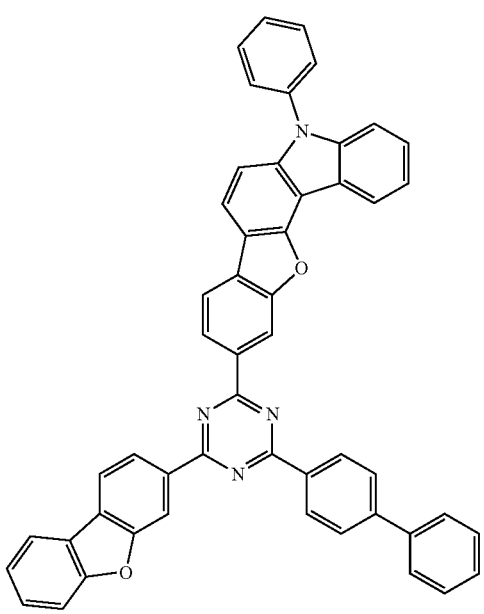
1E-3-55
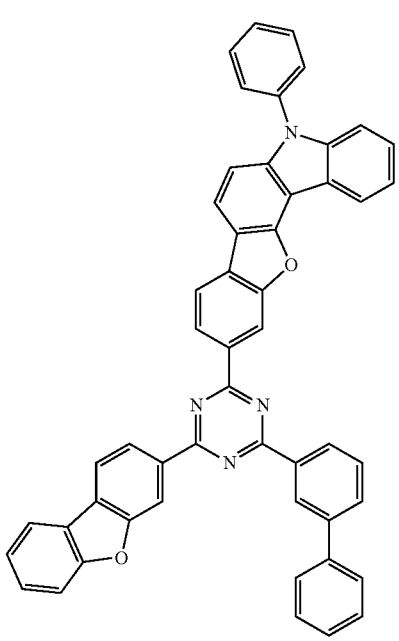

1E-3-56
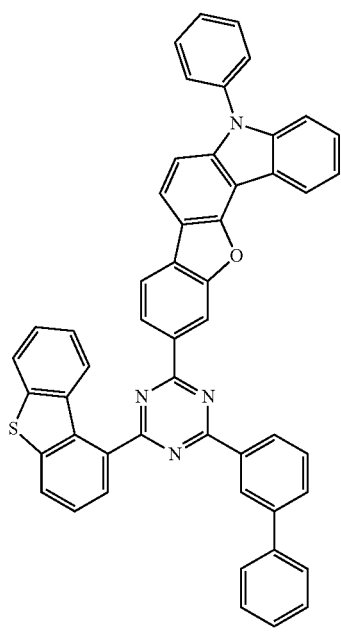
1E-3-58
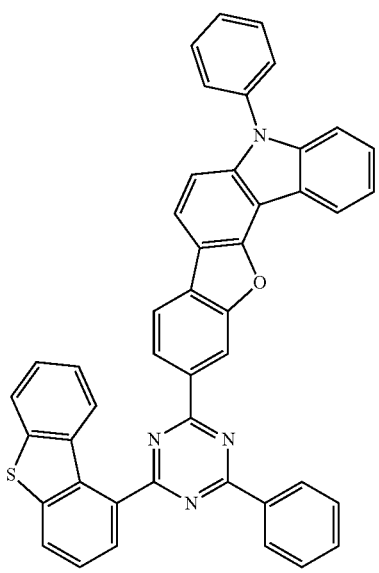
1E-3-57
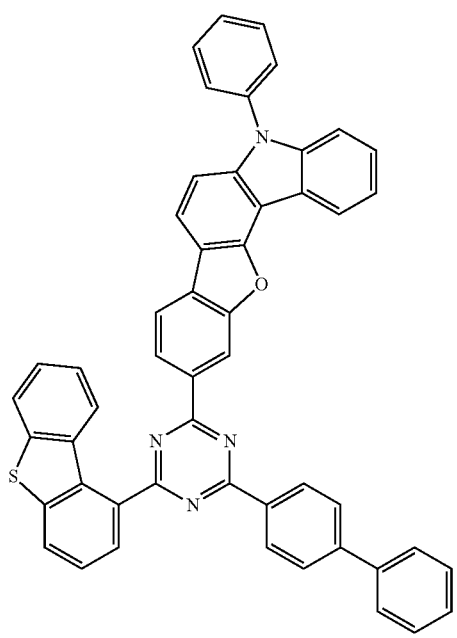
1E-3-59
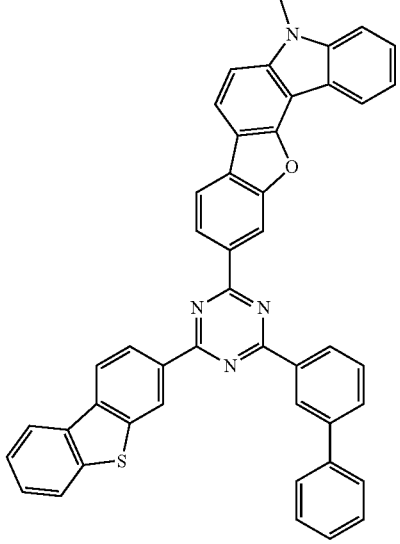

-continued
1E-3-60
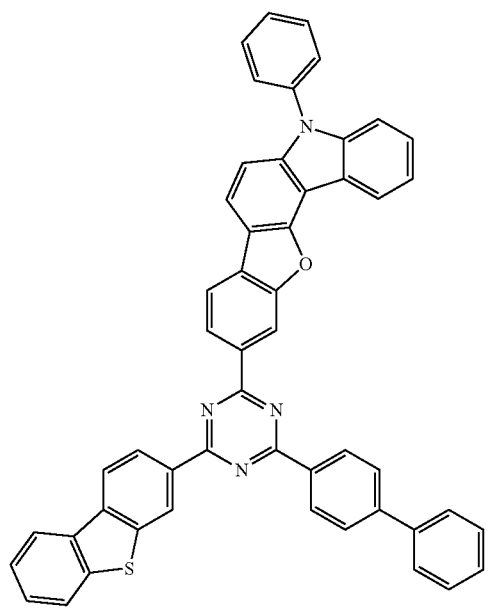
1E-3-61
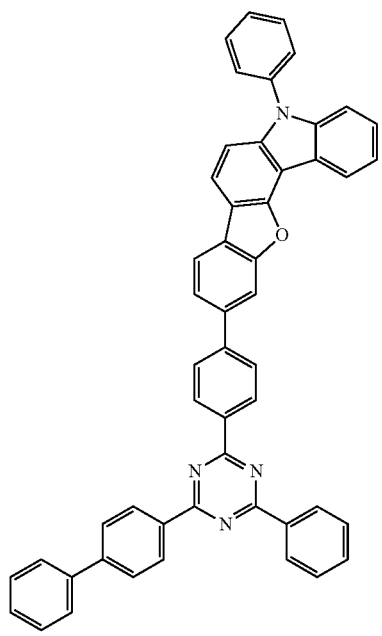
-continued
1E-3-62
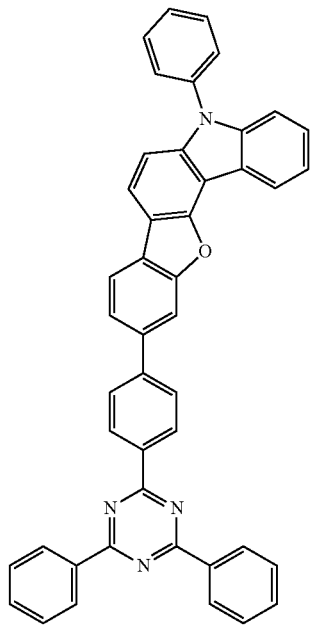
1E-3-63
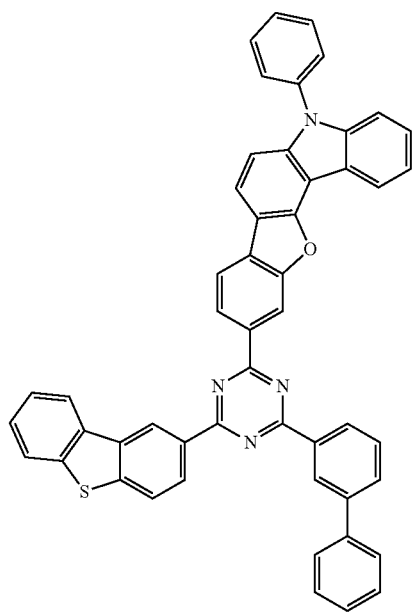

1E-3-64
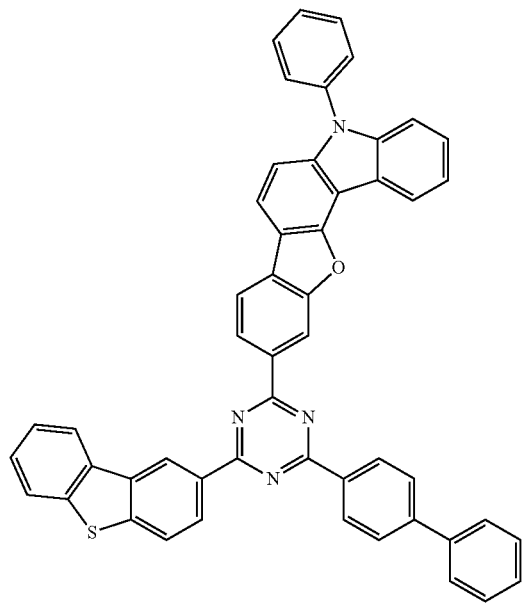
1E-3-65
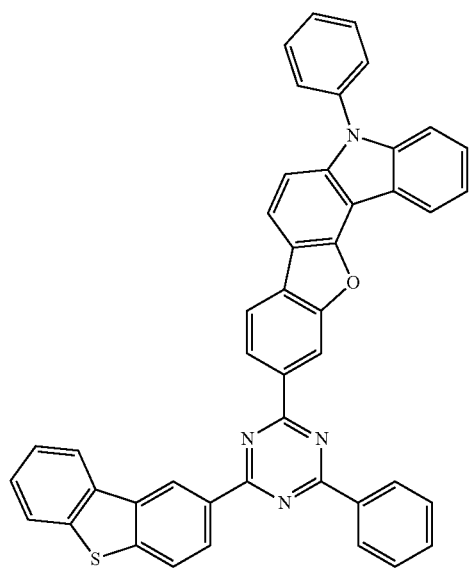
1E-3-66
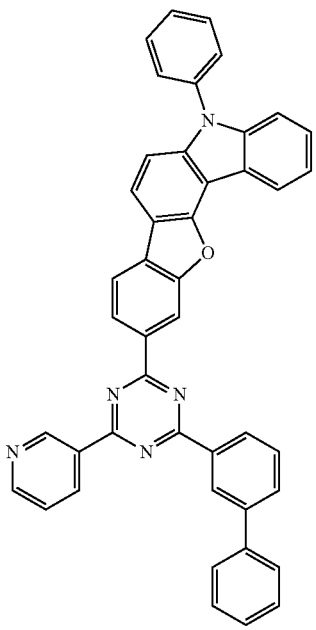
1E-3-67
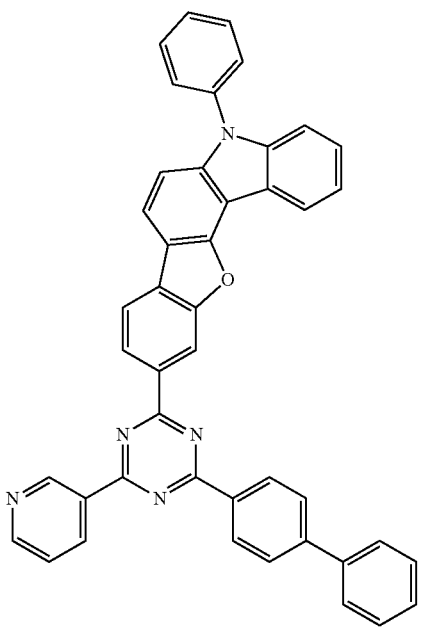

1E-3-68
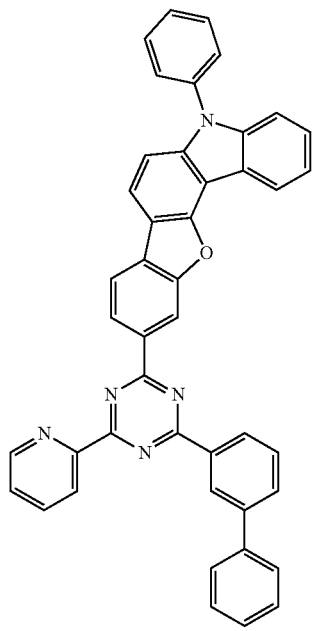
1E-3-69
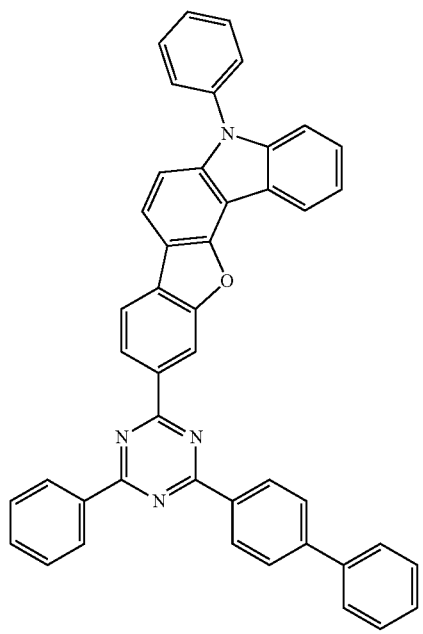
1E-3-70
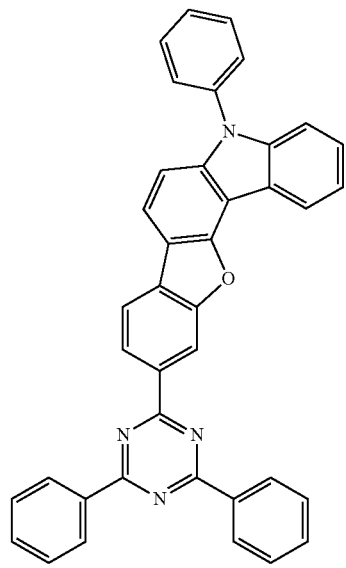
1E-3-71
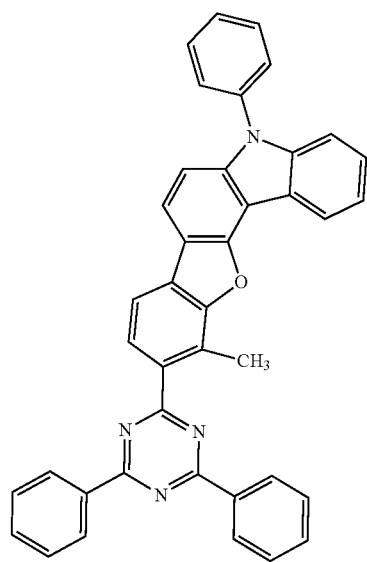

1E-3-72
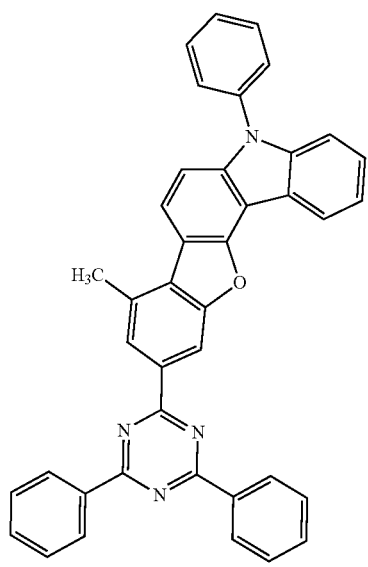
1E-3-74
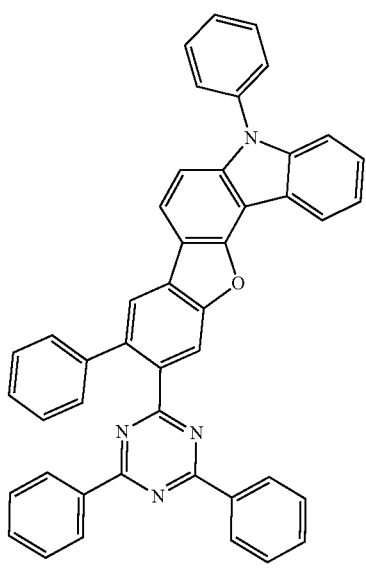
1E-3-73
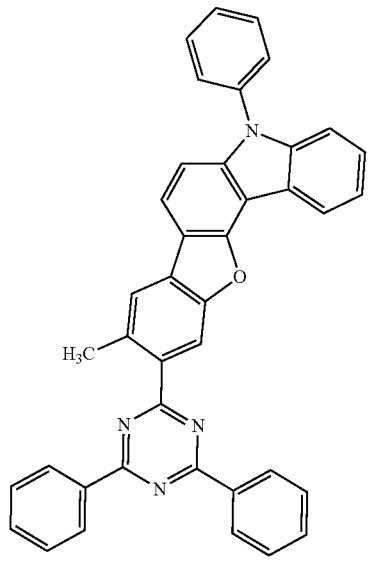
1E-3-75
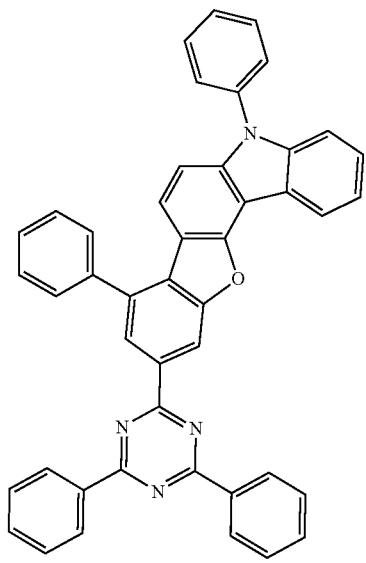

597
-continued
1E-3-76
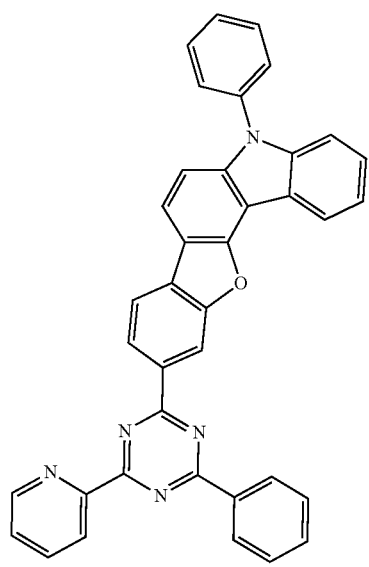
598
-continued
1E-3-78
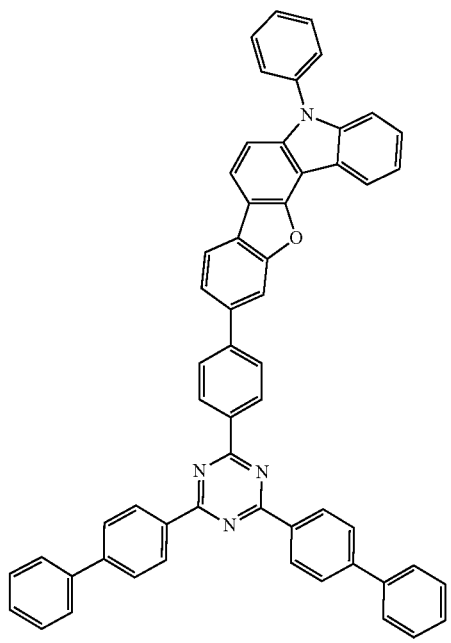
1E-3-77
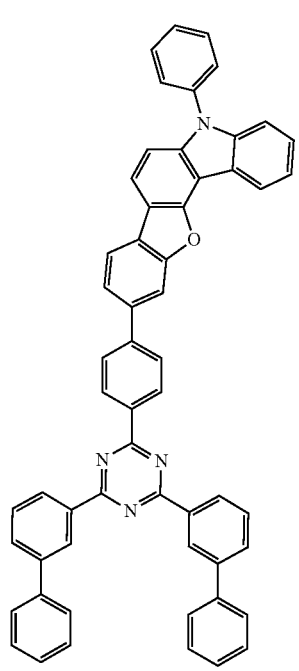
1E-3-79
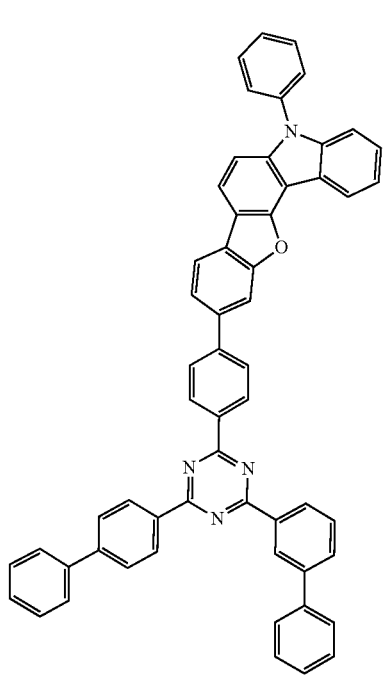

1E-3-80
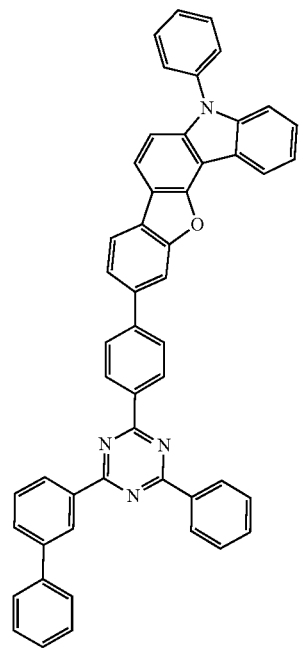
1E-3-81
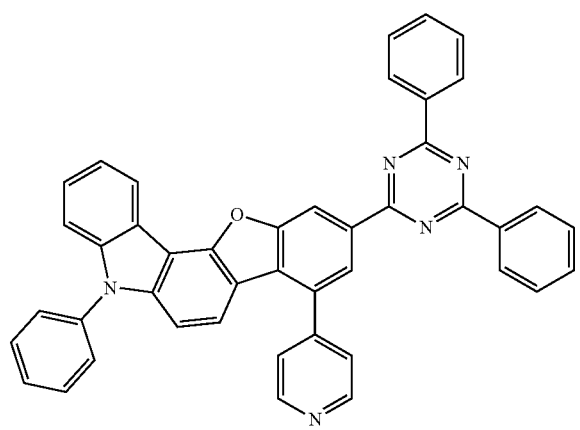
1E-3-82
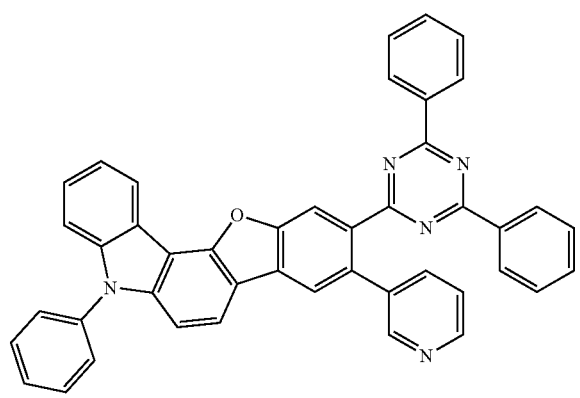
1E-3-83
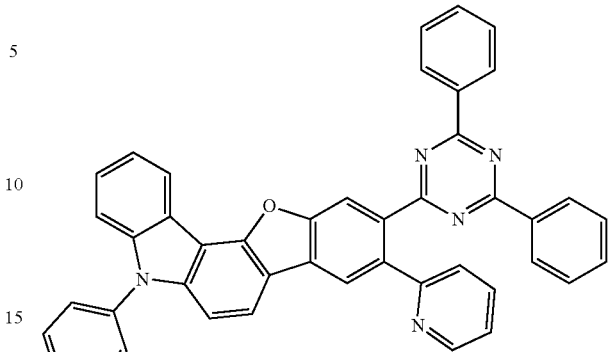
1E-4-1
1E-4-2

1E-4-3
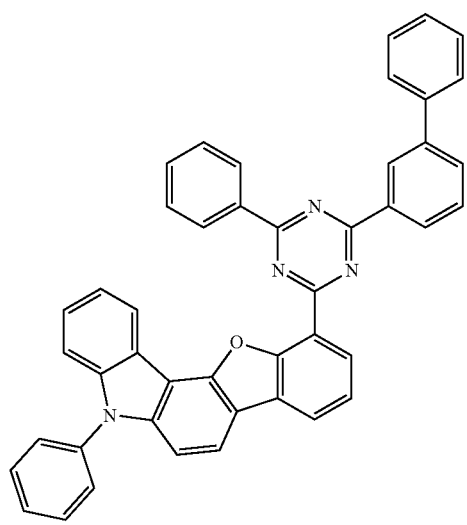
1E-4-4
1E-4-5
1E-4-6
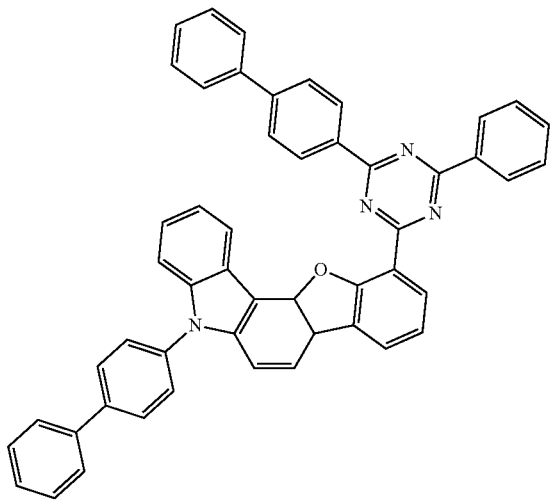
1E-4-7
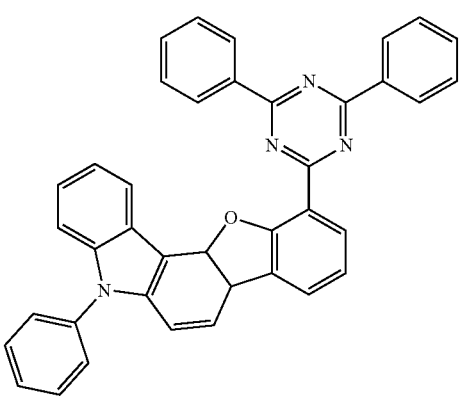
1E-4-8
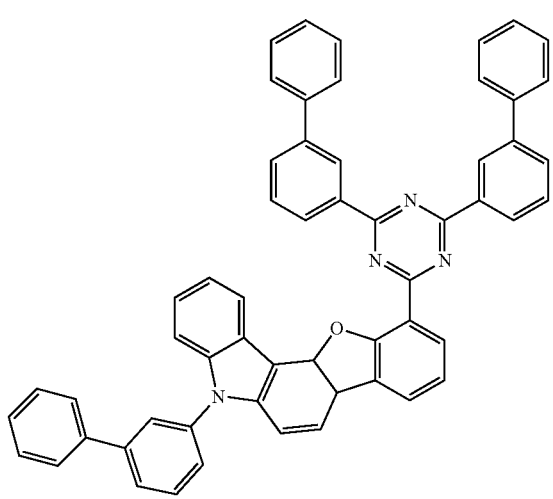

-continued
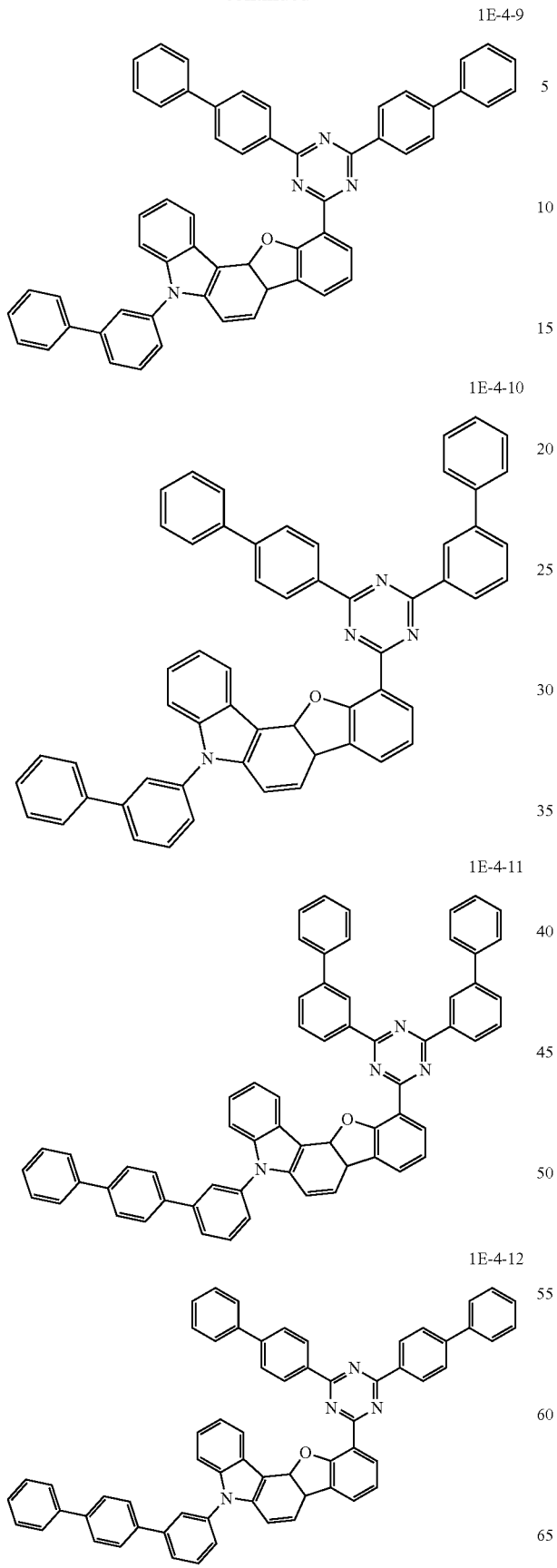
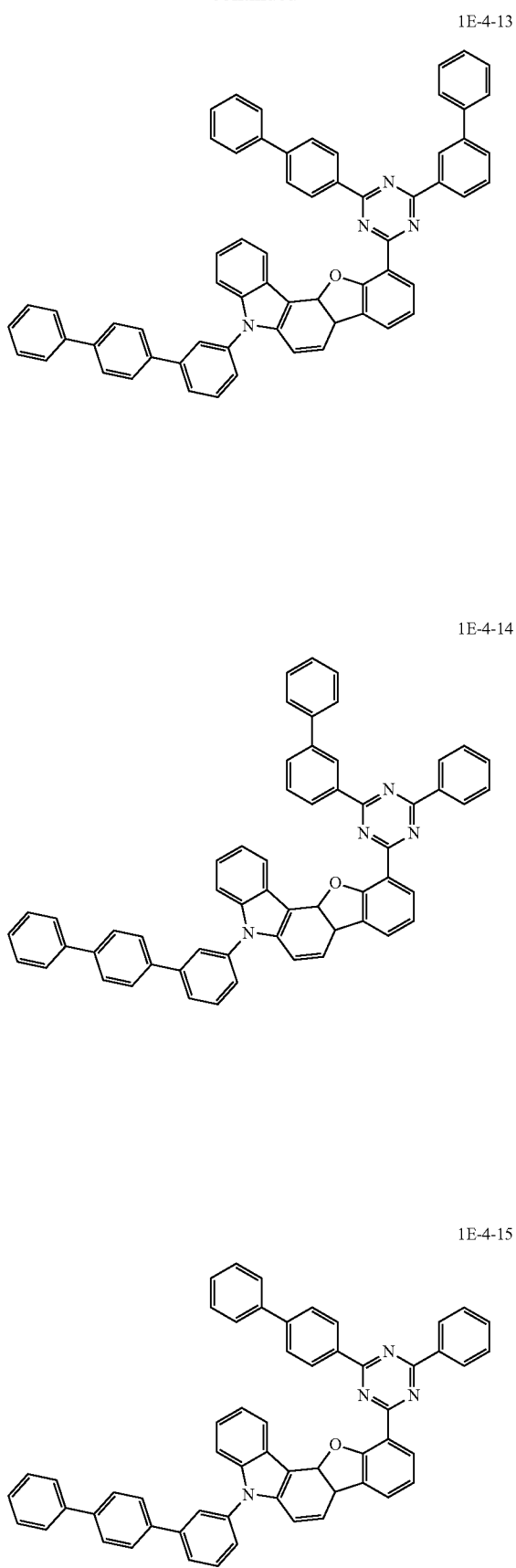

1E-4-16
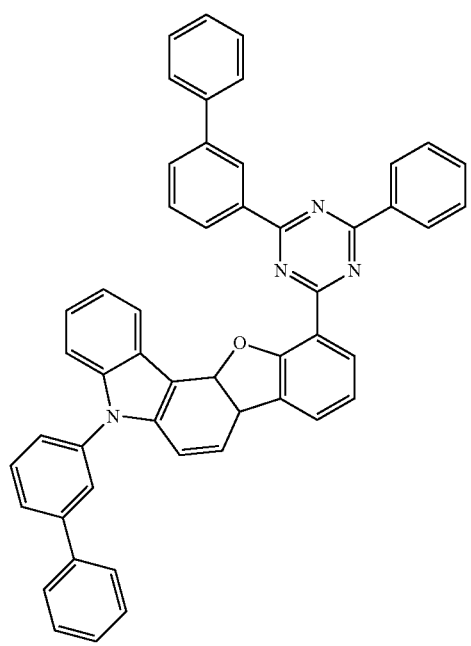
1E-4-17
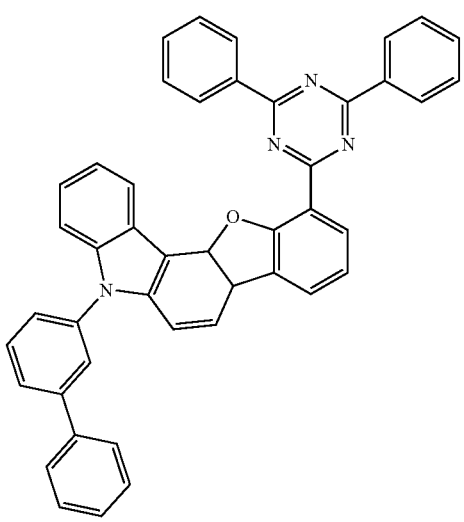
1E-4-18
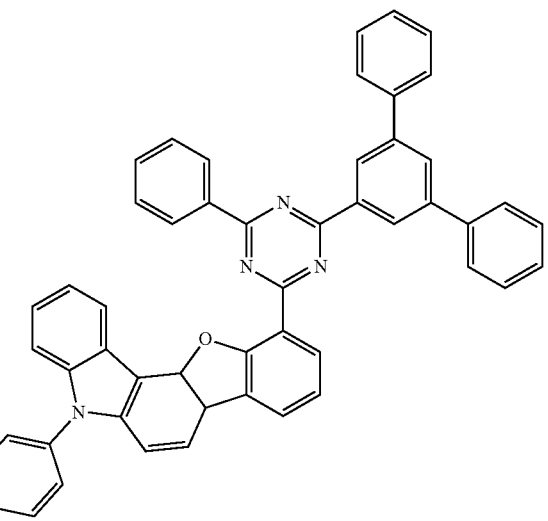
1E-4-19
1E-4-20
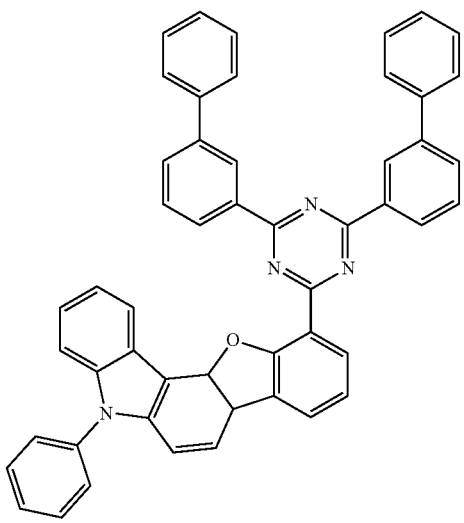

1E-4-21
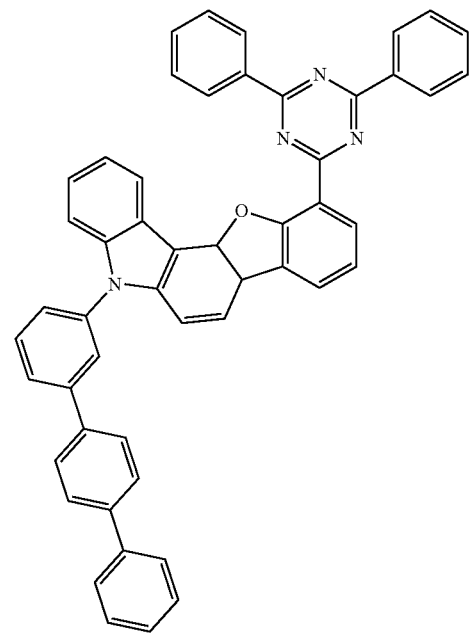
1E-4-22
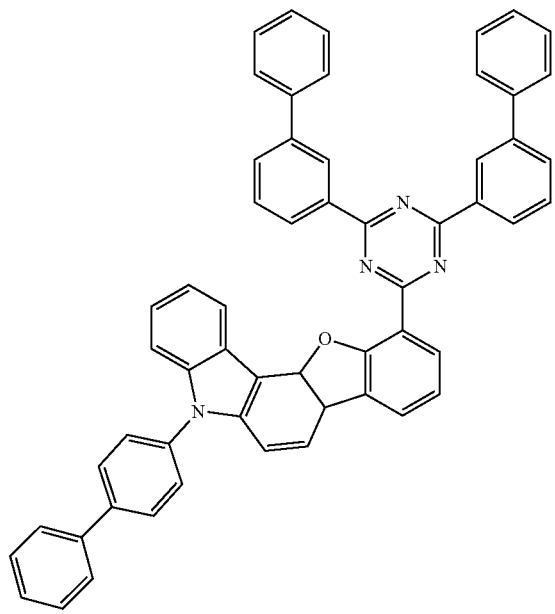
1E-4-23
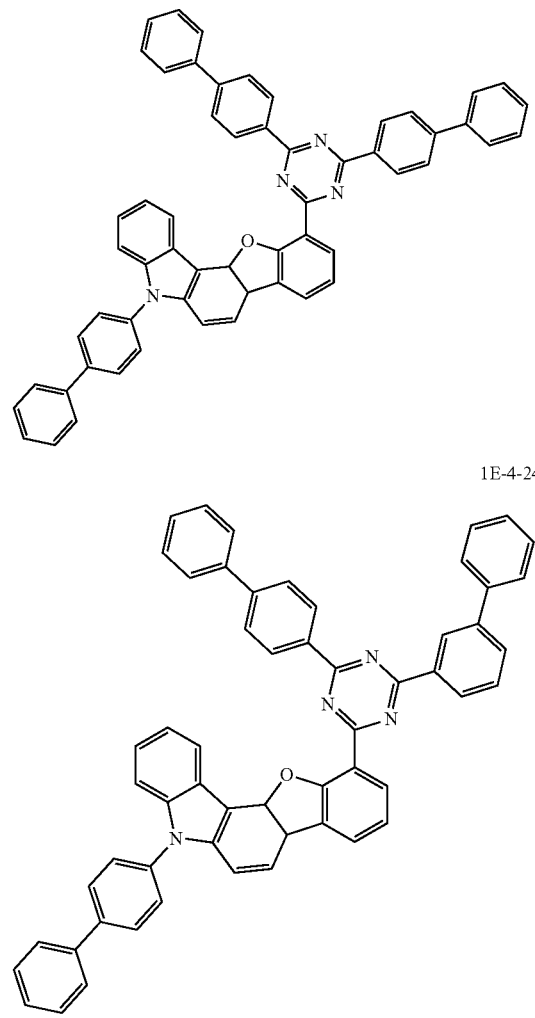
1E-4-24
1E-4-25
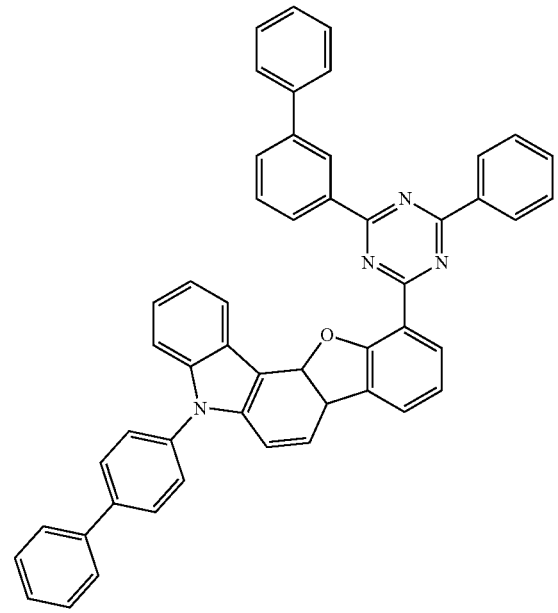

1E-4-26
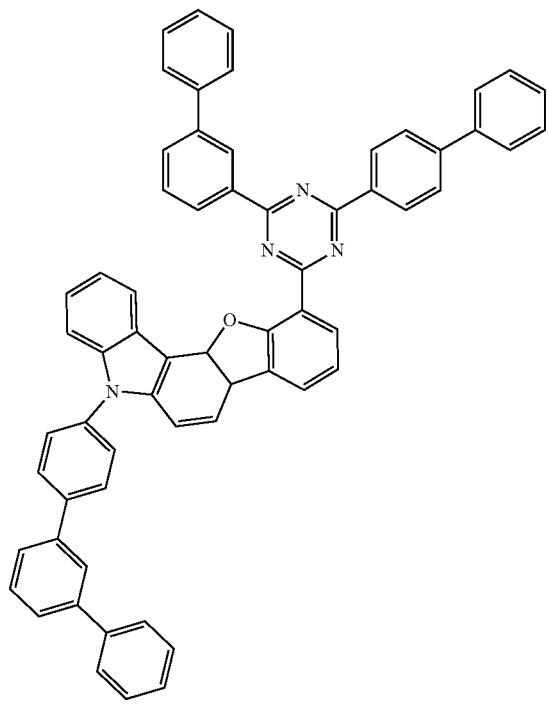
1E-4-28
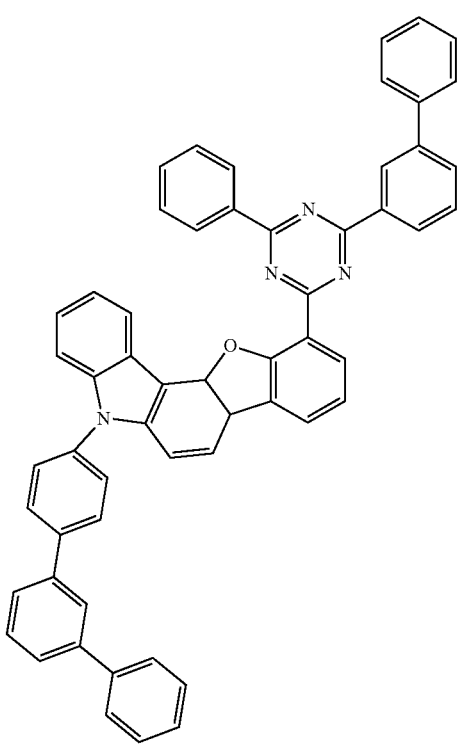
1E-4-27
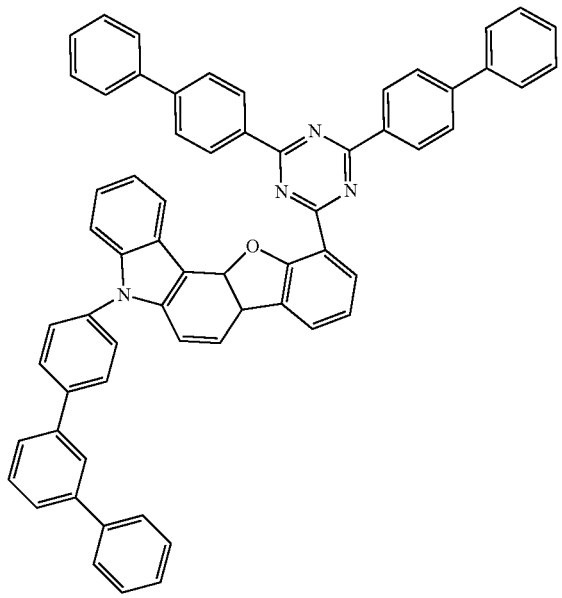
1E-4-29
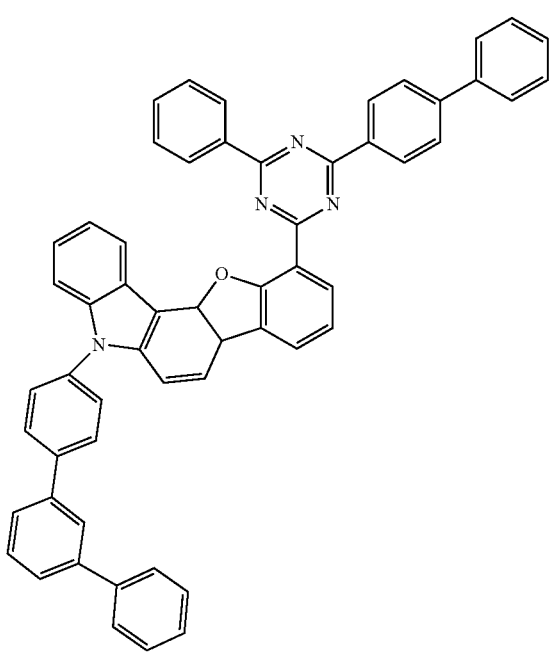

611
-continued
1E-4-30
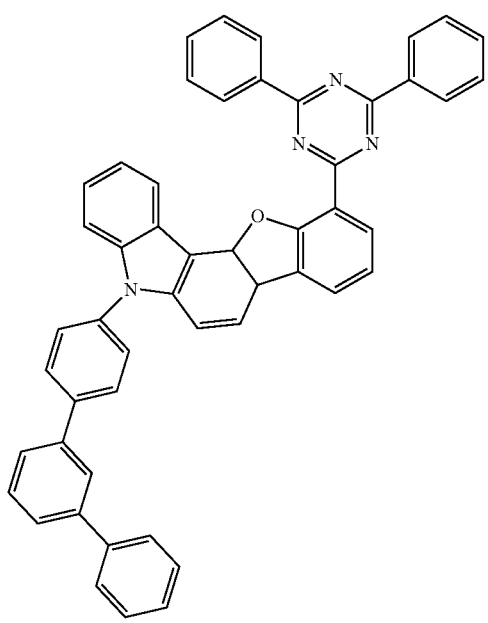
1E-4-31
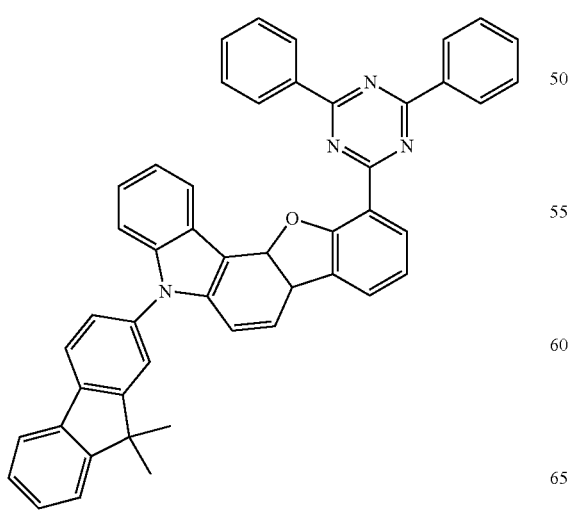
612
-continued
1E-4-32
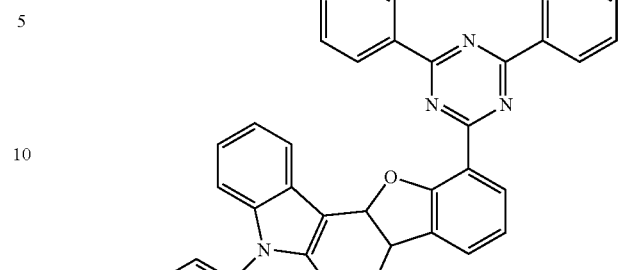
1E-4-33
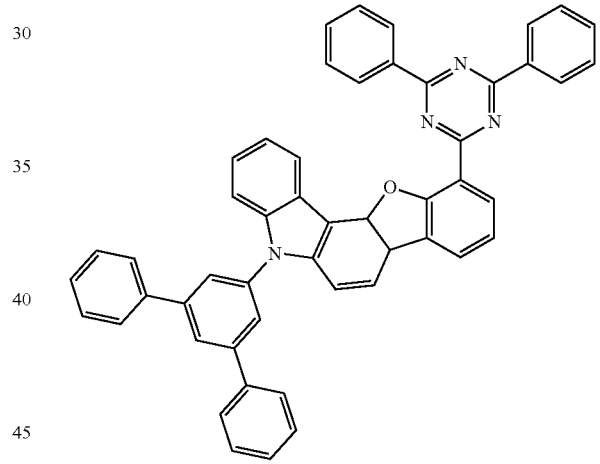
1E-4-34
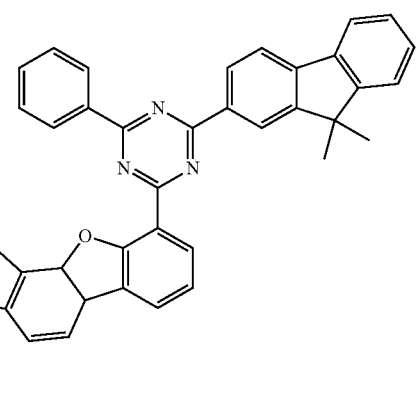

613
-continued
1E-4-35
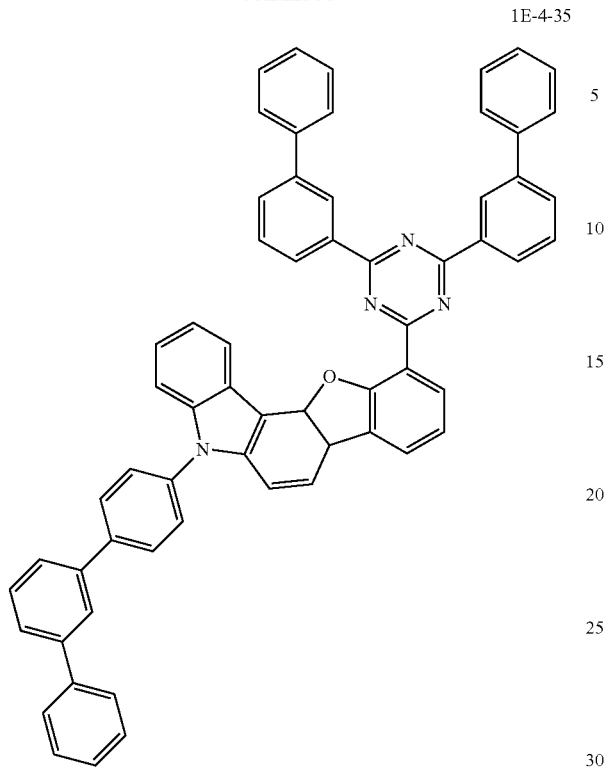
1E-4-36
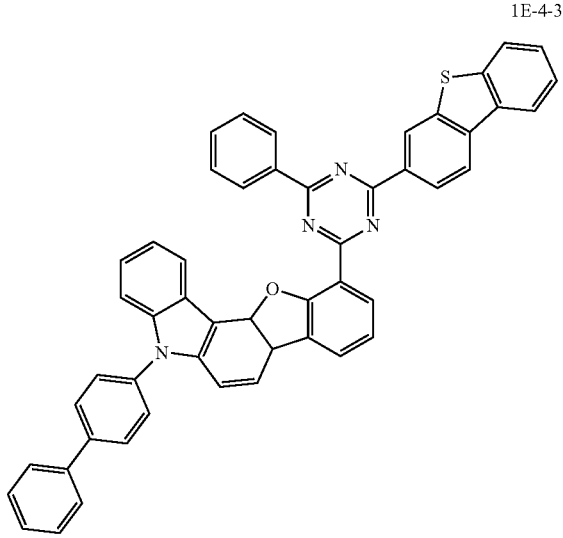
614
-continued
1E-4-37
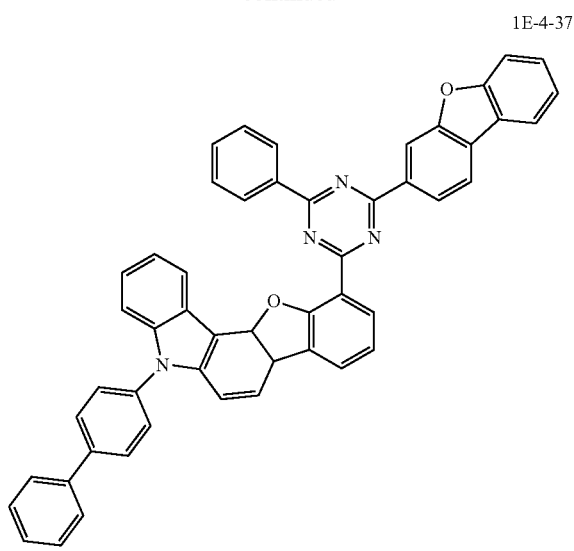
1E-4-38
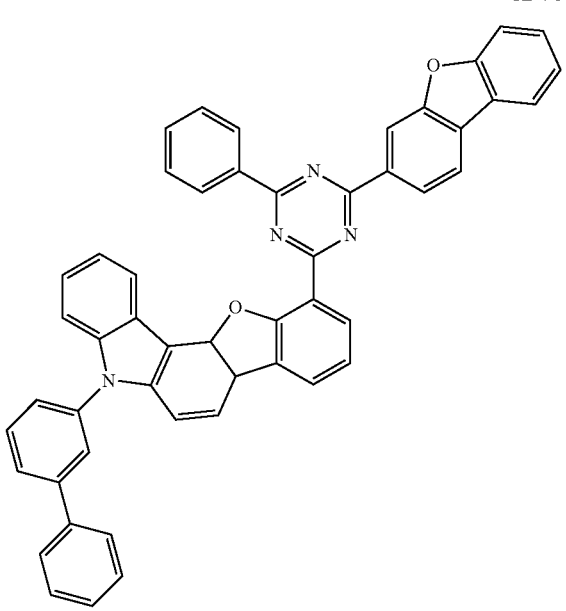

1E-4-39
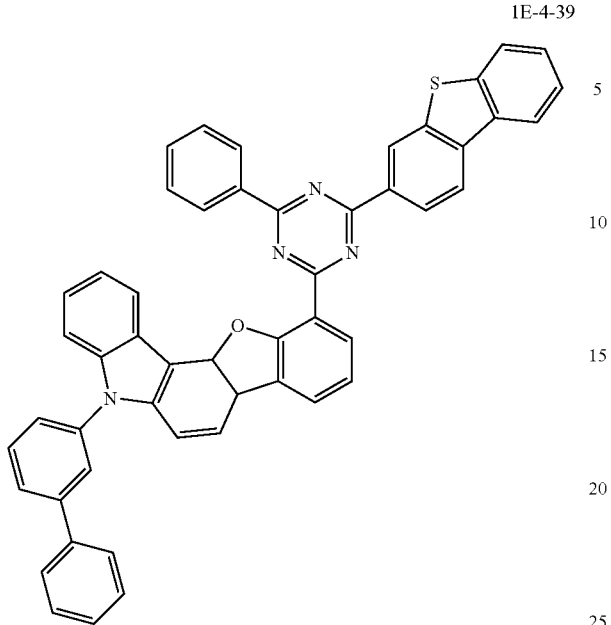
1E-4-41
1E-4-42
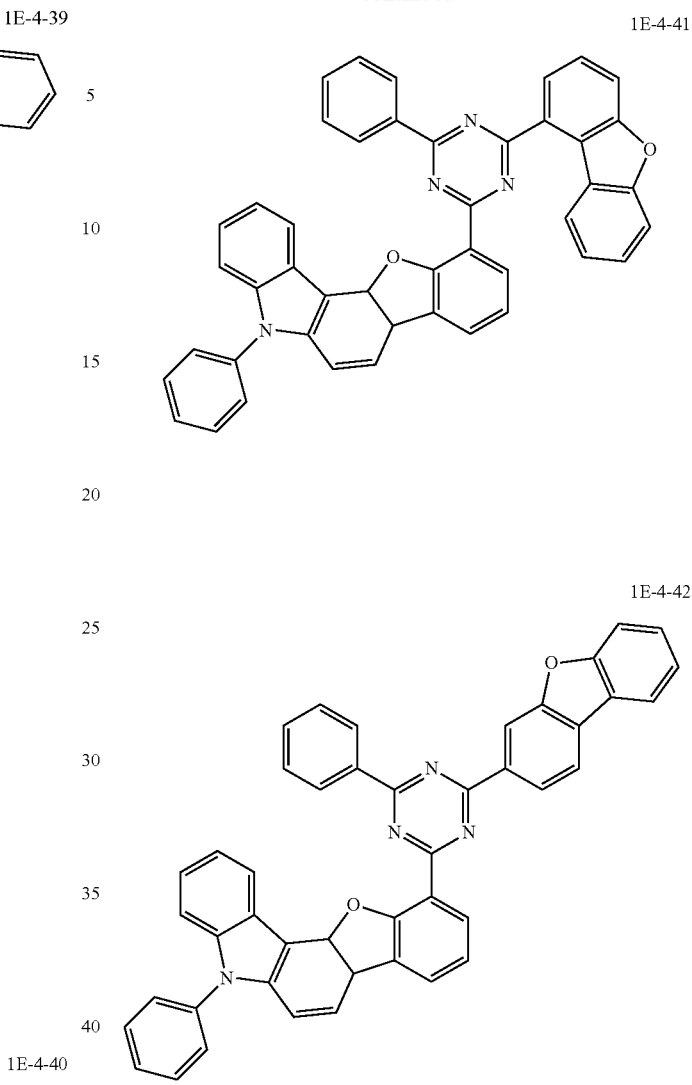
1E-4-40
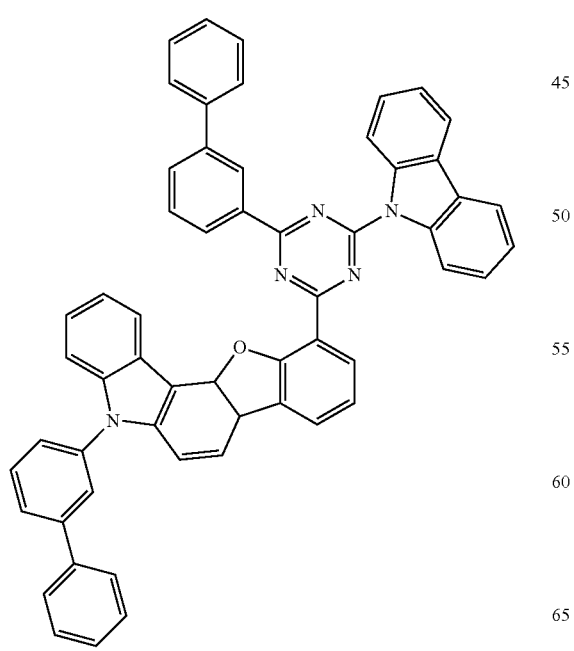
1E-4-43

1E-4-44
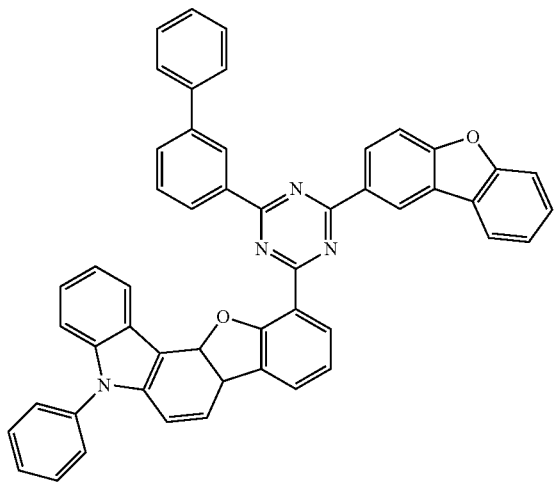
1E-4-45
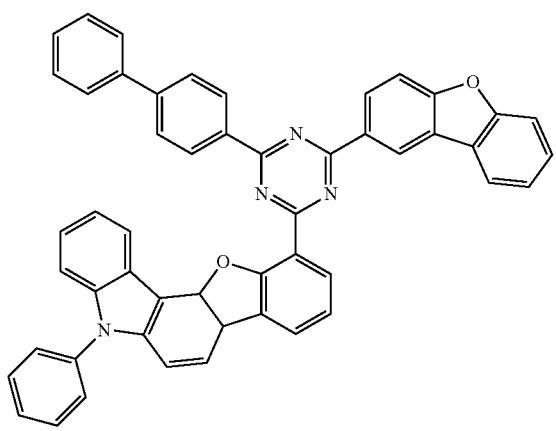
1E-4-46
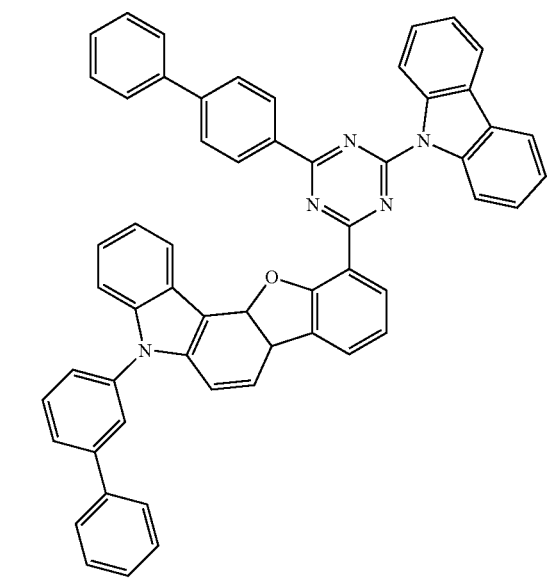
1E-4-47
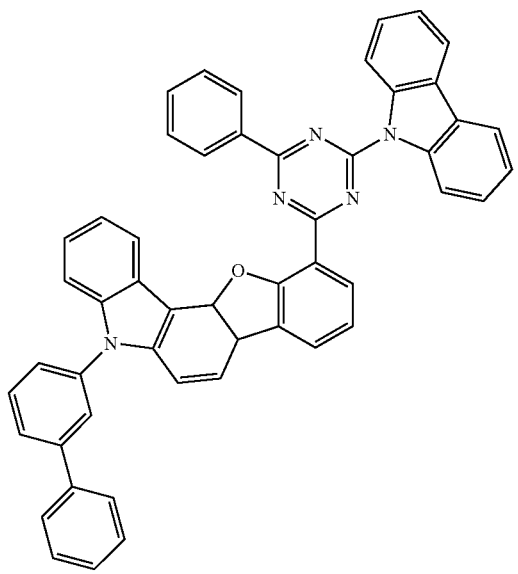
1E-4-48
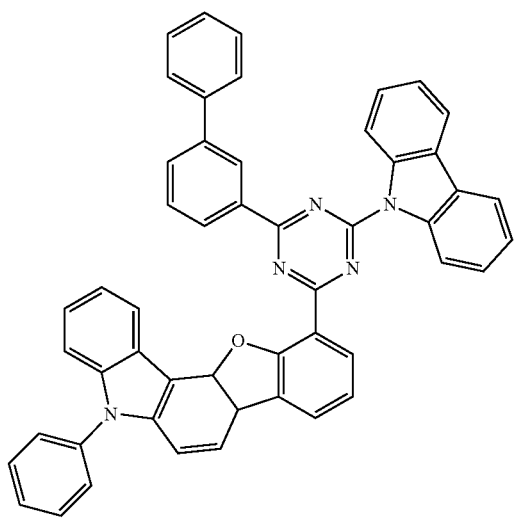
1E-4-49
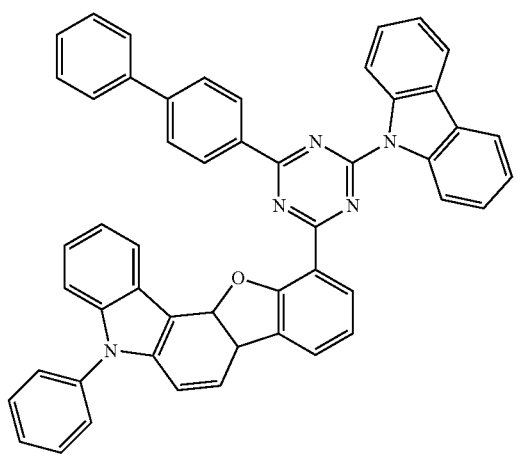

1E-4-50
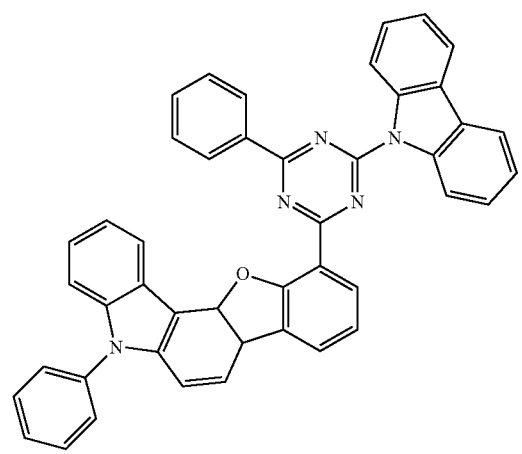
1E-4-53
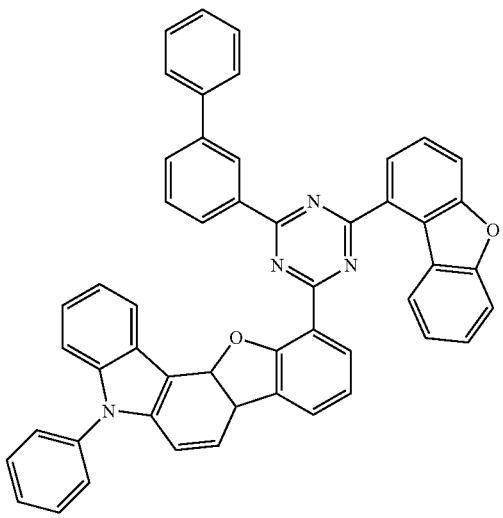
1E-4-51
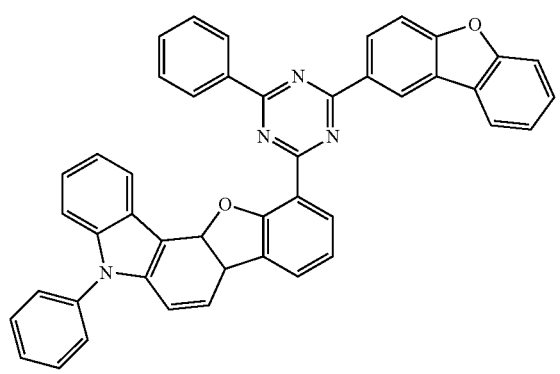
1E-4-54
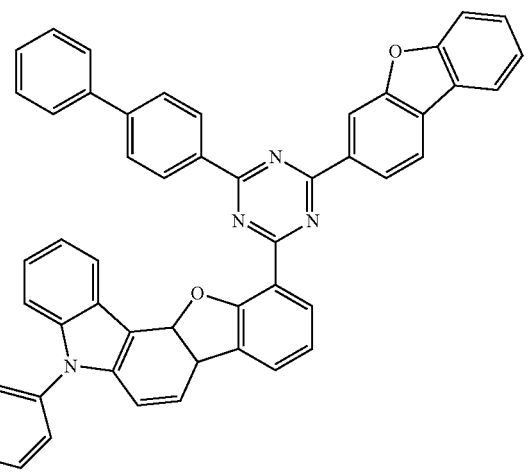
1E-4-52
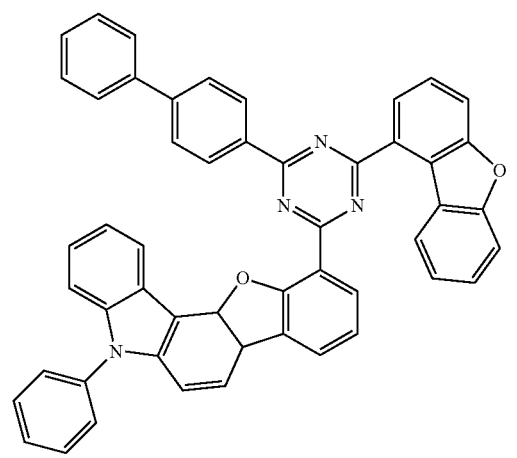
1E-4-55
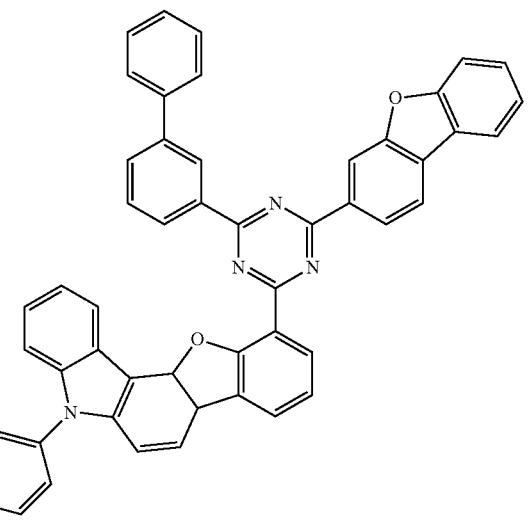

-continued
1E-4-56
1E-4-57
1E-4-58
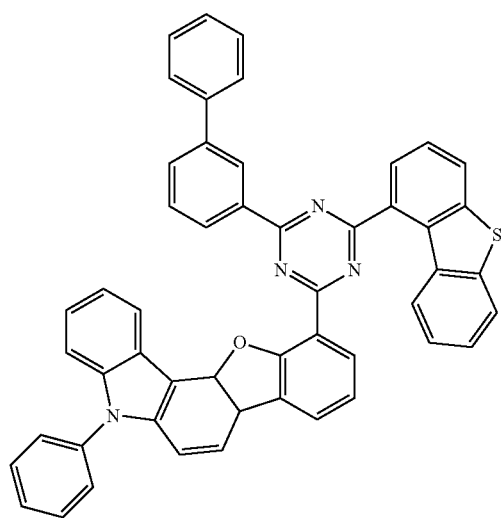
1E-4-59
1E-4-60
1E-4-61
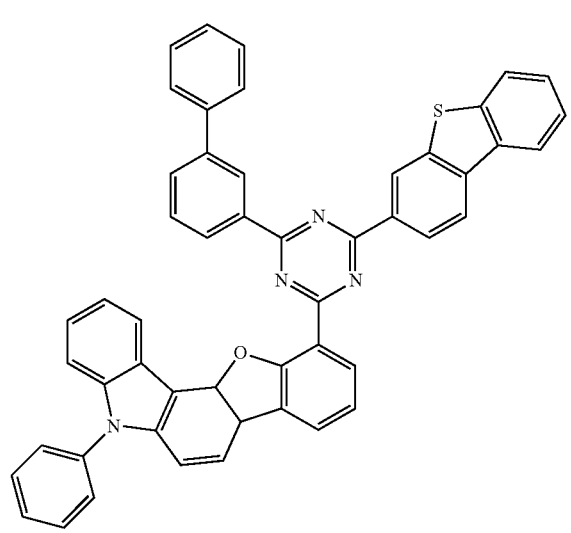

1E-4-62
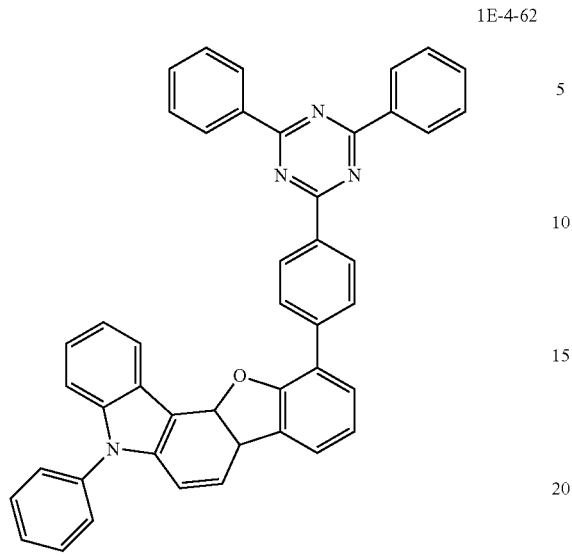
1E-4-63
1E-4-65
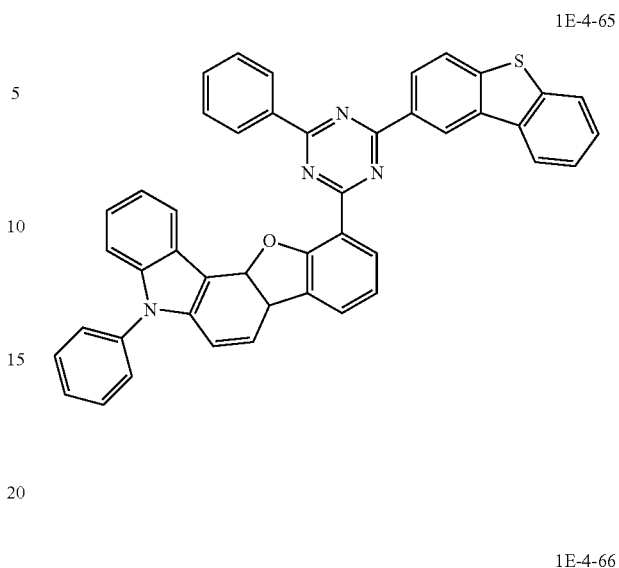
1E-4-66
1E-4-64
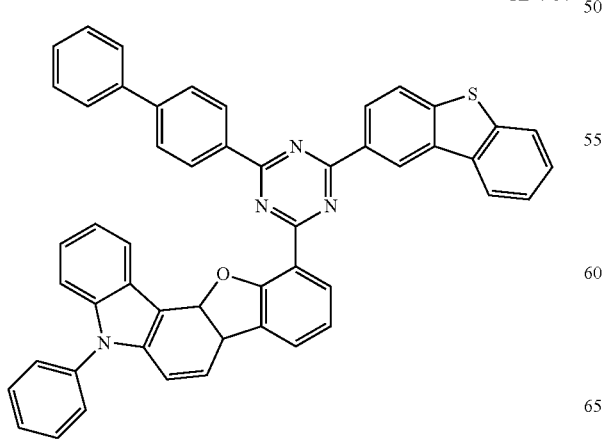
1E-4-67
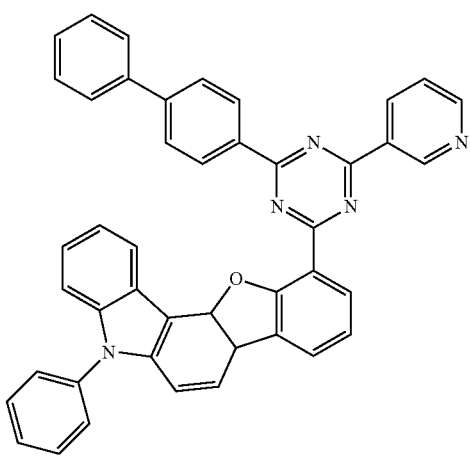

-continued
1E-4-68
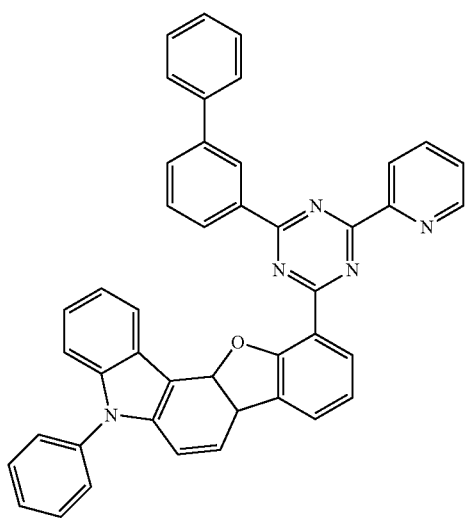
1E-4-69
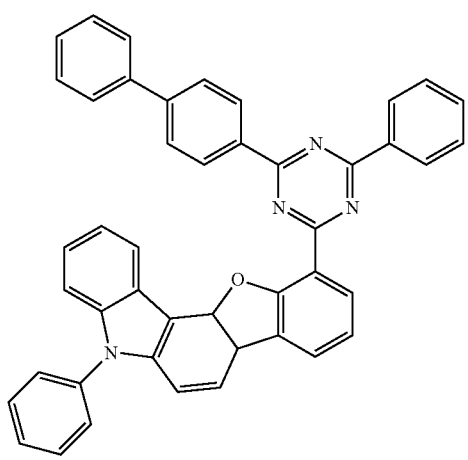
1E-4-70
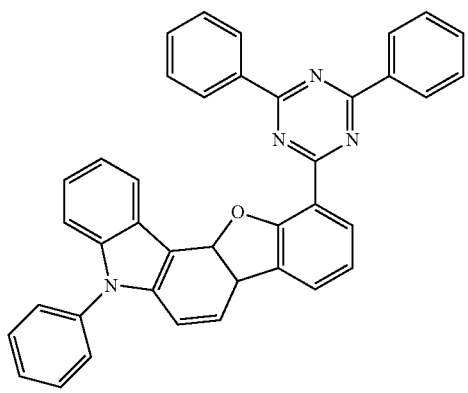
-continued
1E-4-71
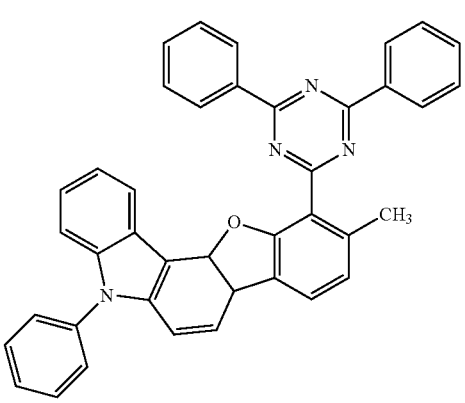
1E-4-72
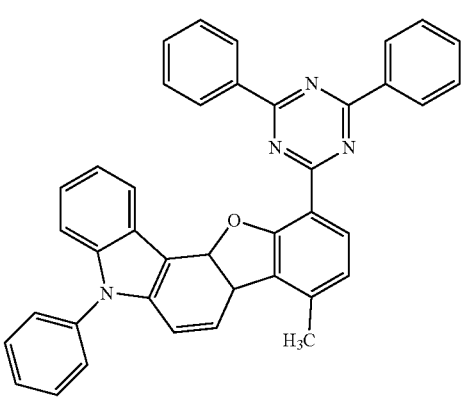
1E-4-73
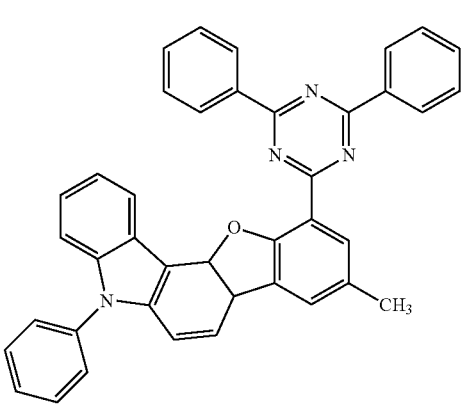
1E-4-74
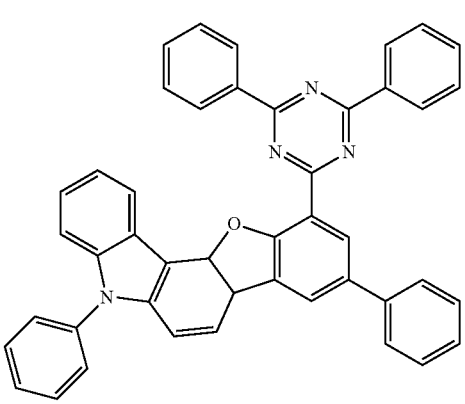

1E-4-75
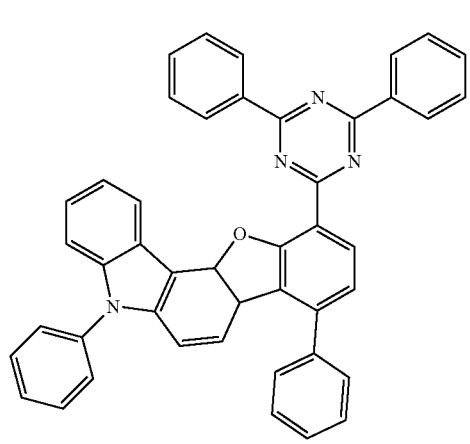
1E-4-78
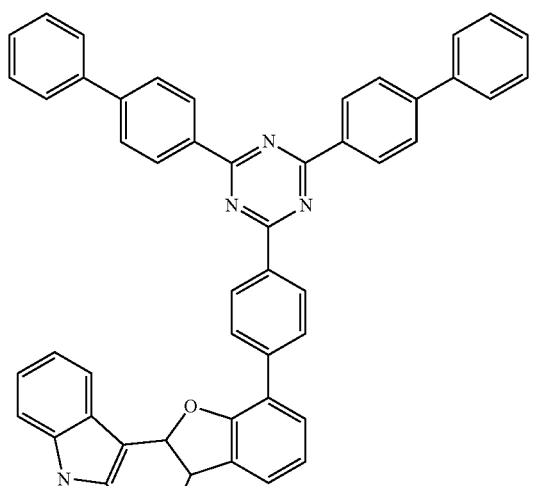
1E-4-76
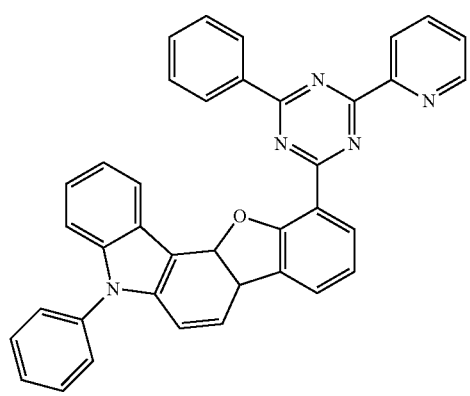
1E-4-77
1E-4-79
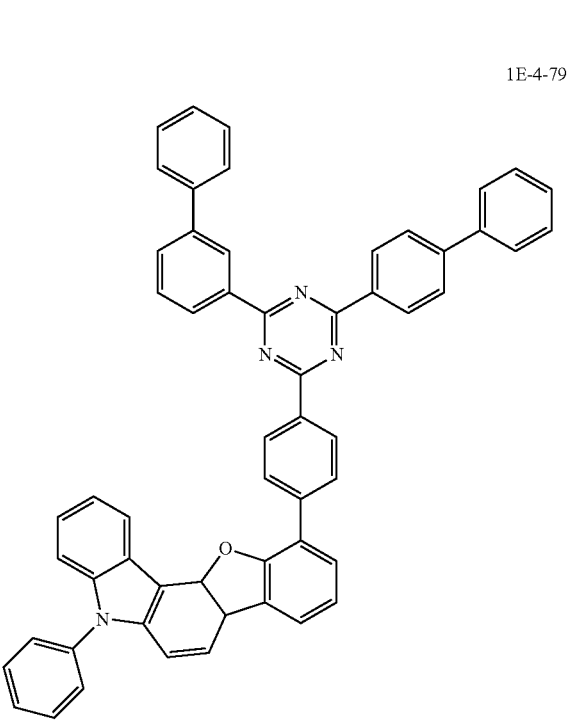

1E-4-80
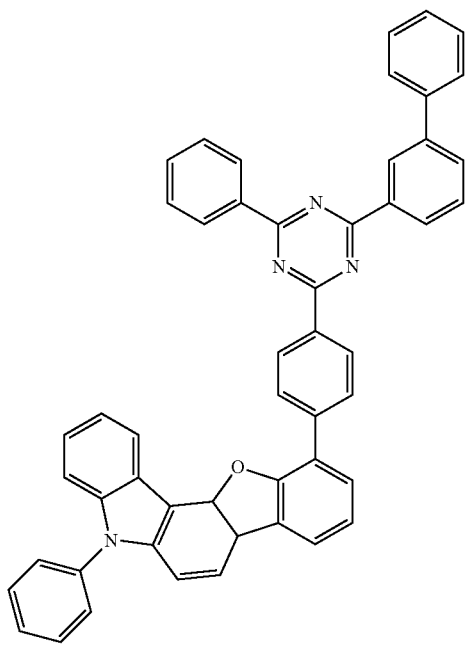
1E-4-81
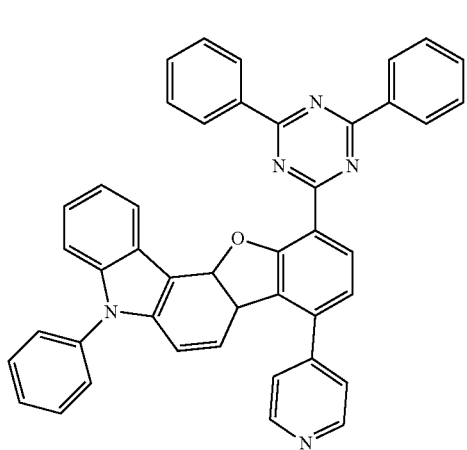
1E-4-82
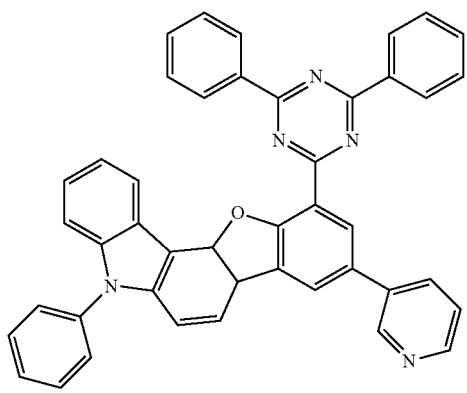
1E-4-83
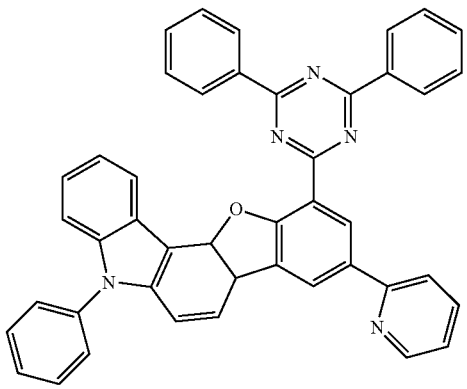
1F-1-1
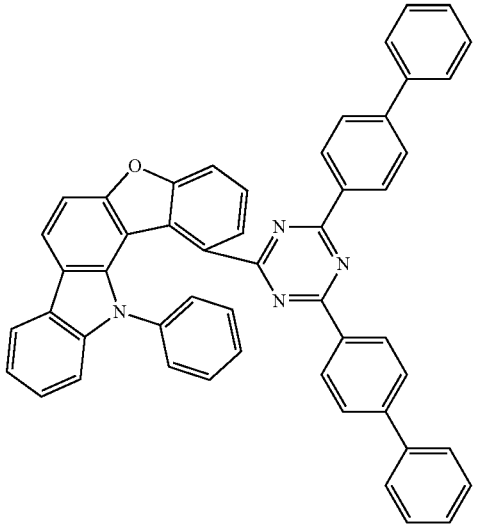
1F-1-2
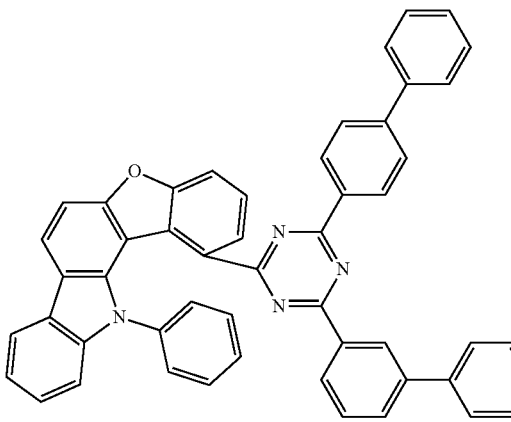

-continued
1F-1-3
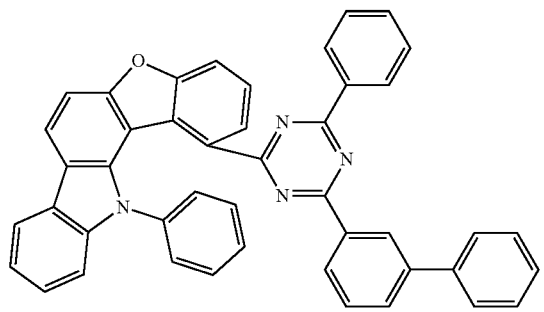
1F-1-4
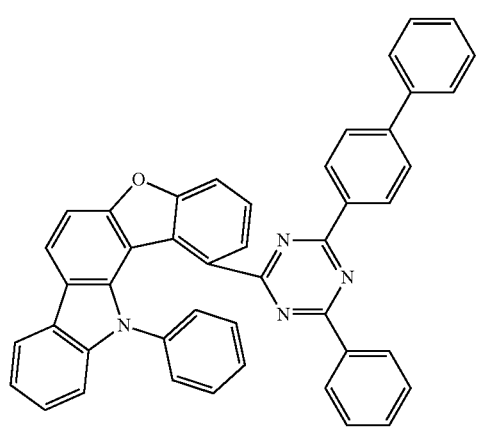
1F-1-5
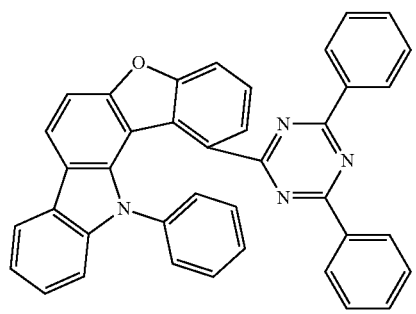
1F-1-6
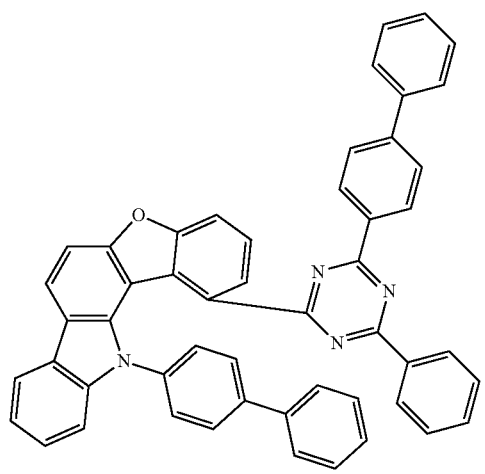
-continued
1F-1-7
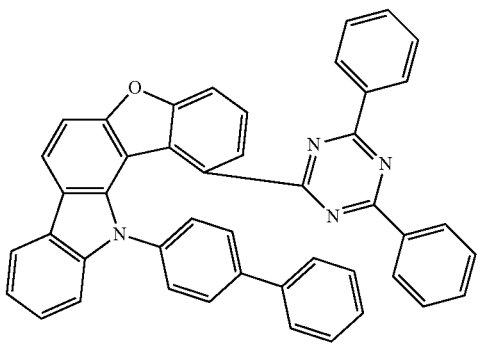
1F-1-8
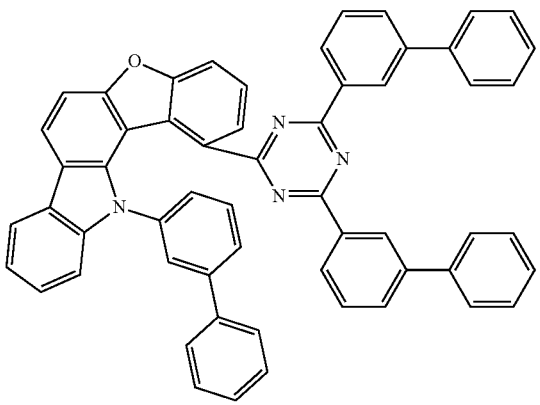
1F-1-9
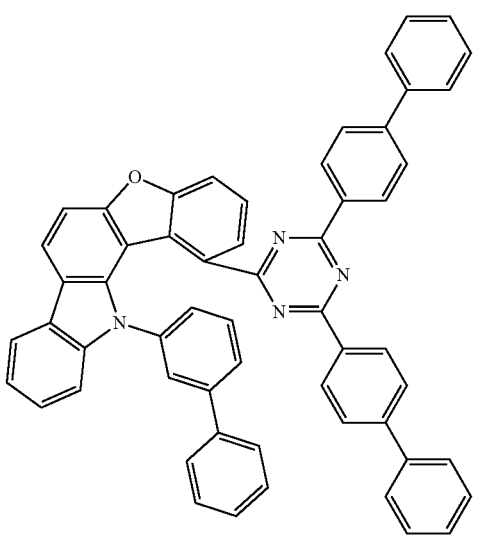

1F-1-10
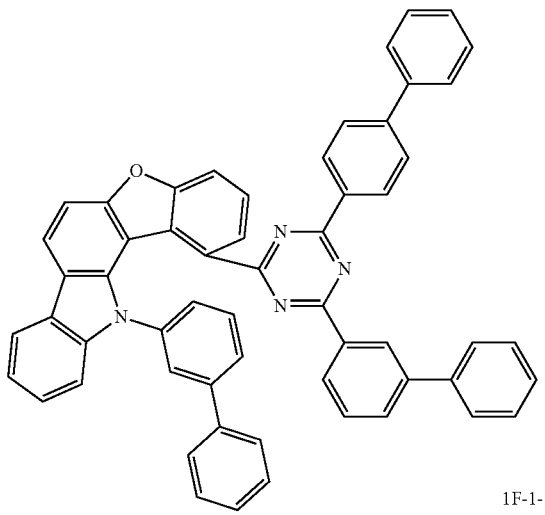
1F-1-11
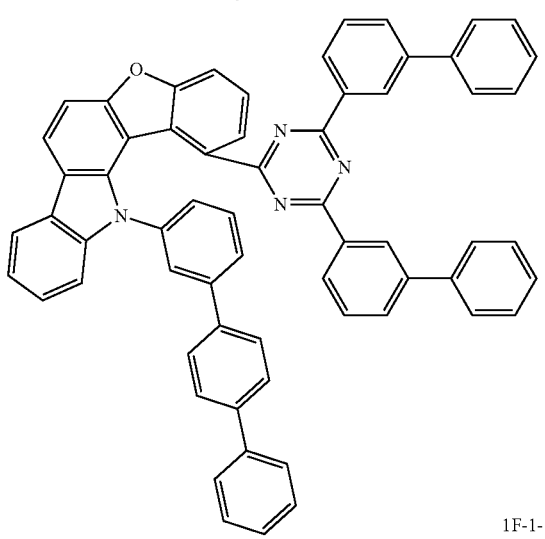
1F-1-12
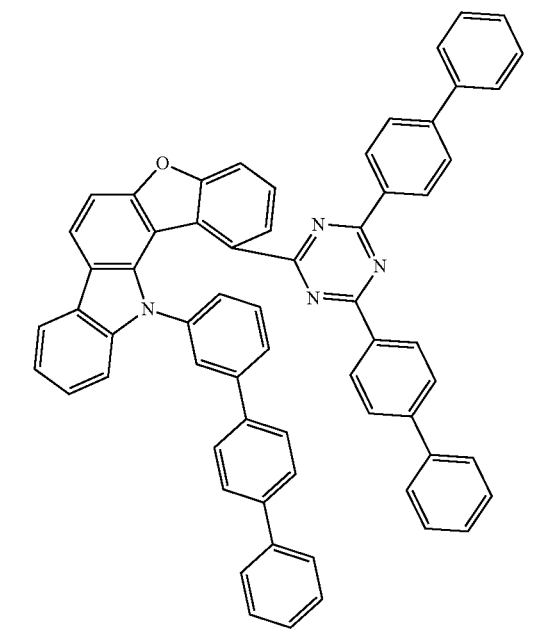
1F-1-13
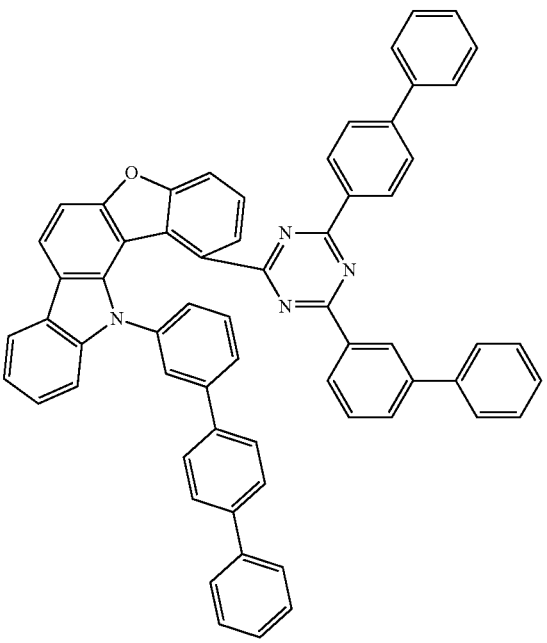
1F-1-14
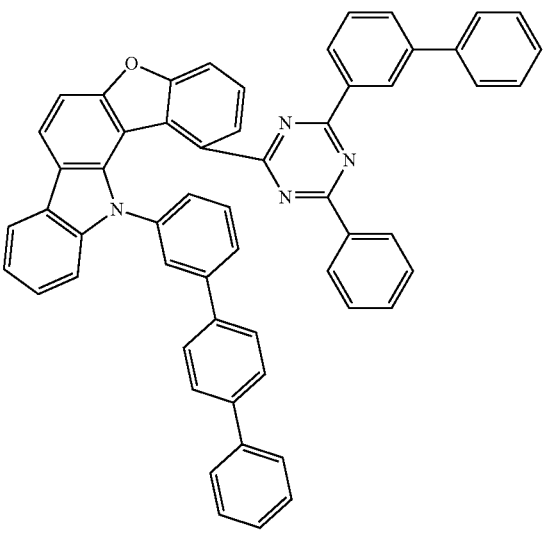

1F-1-15
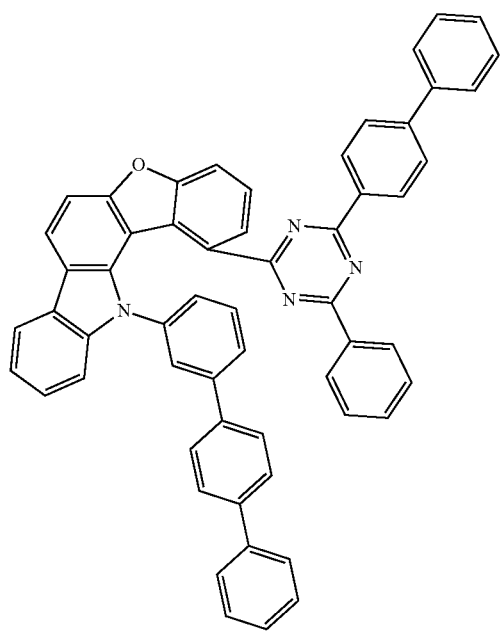
1F-1-16
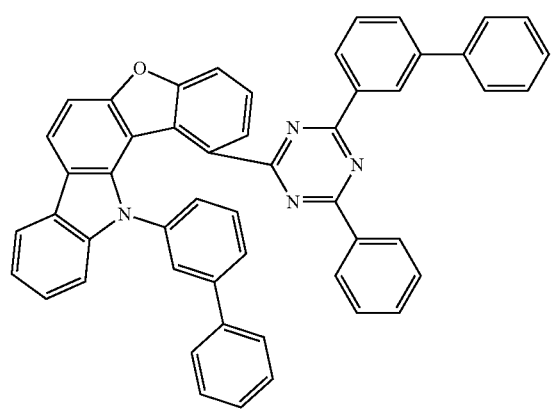
1F-1-17
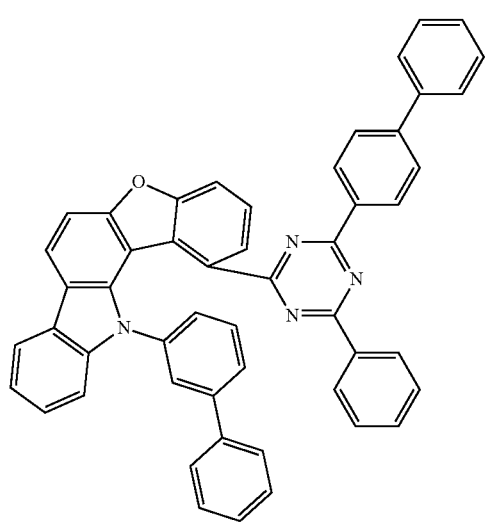
1F-1-18
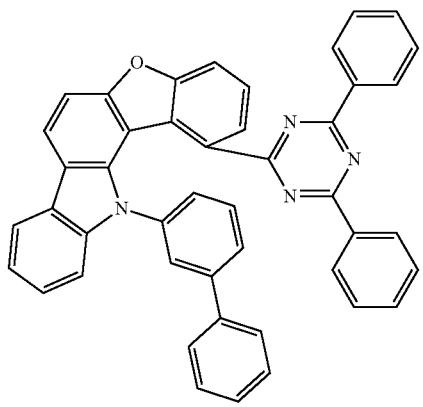
1F-1-19
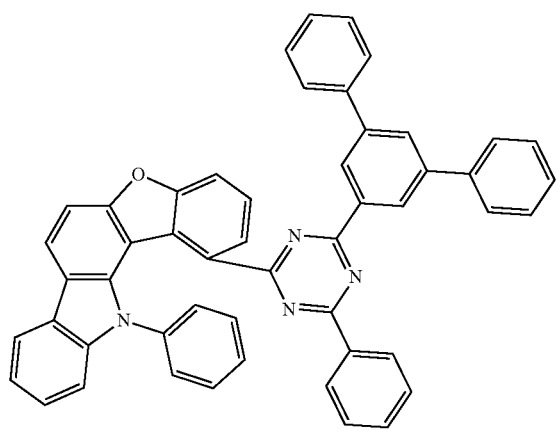
1F-1-20
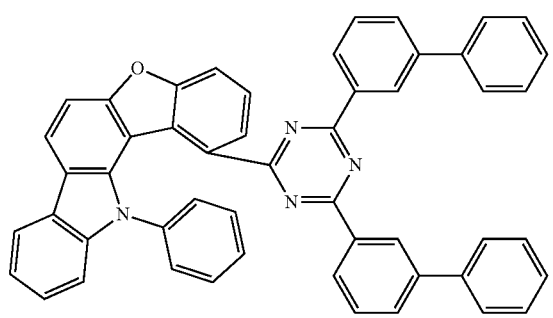

1F-1-21
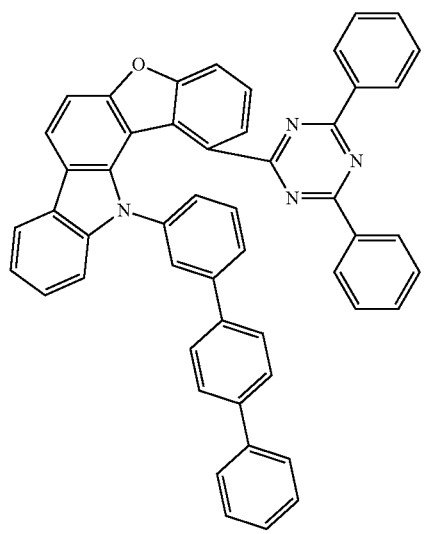
1F-1-22
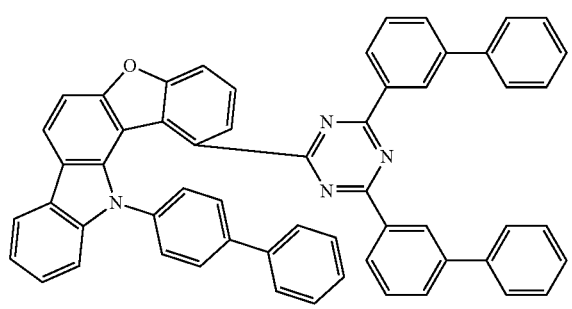
1F-1-23
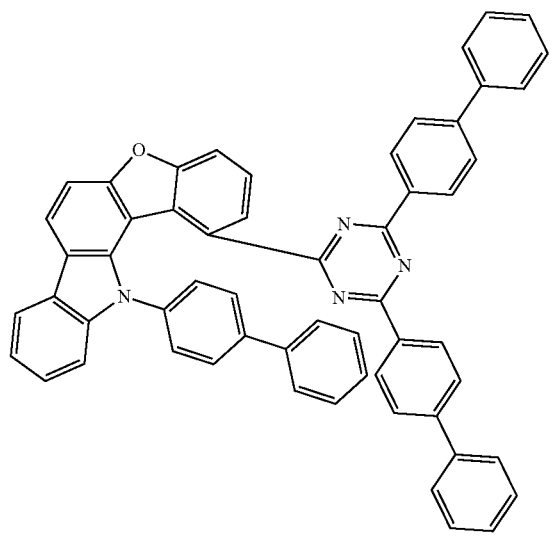
1F-1-24
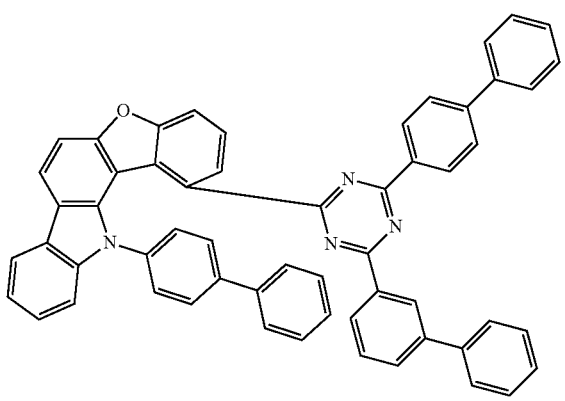
1F-1-25
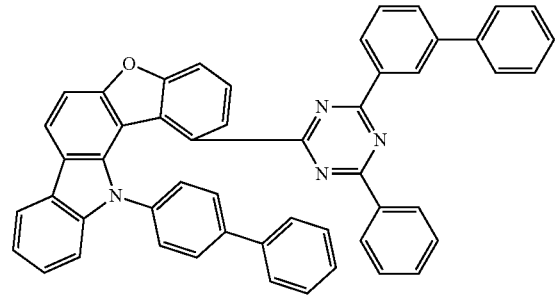
1F-1-26
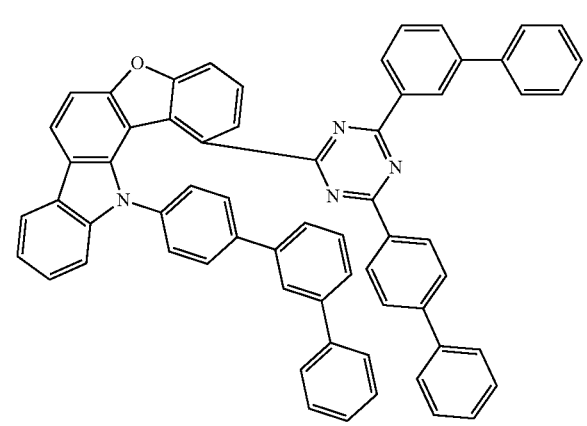

1F-1-27
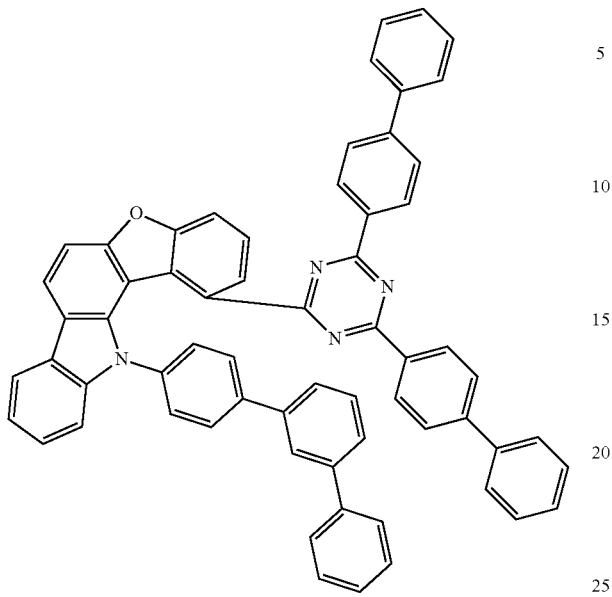
1F-1-28
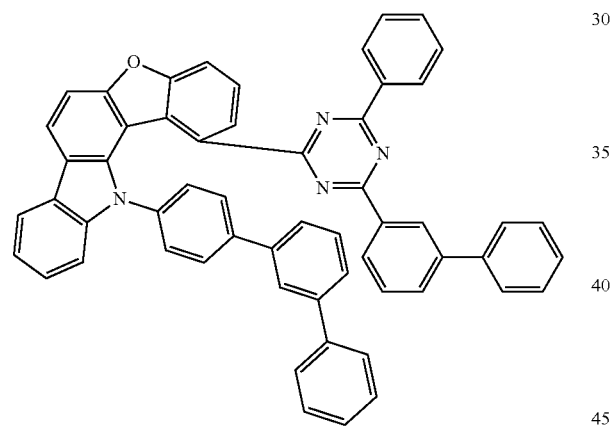
1F-1-29
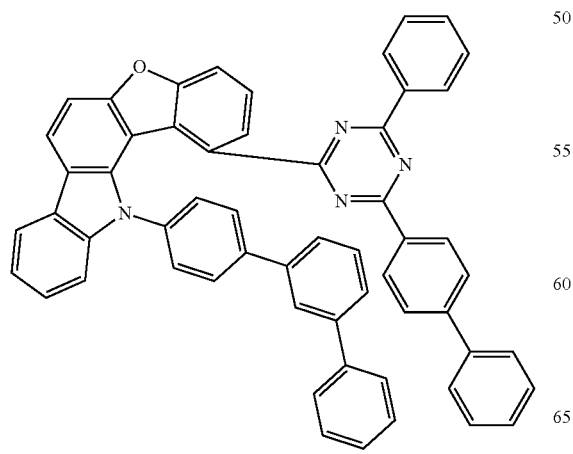
1F-1-30
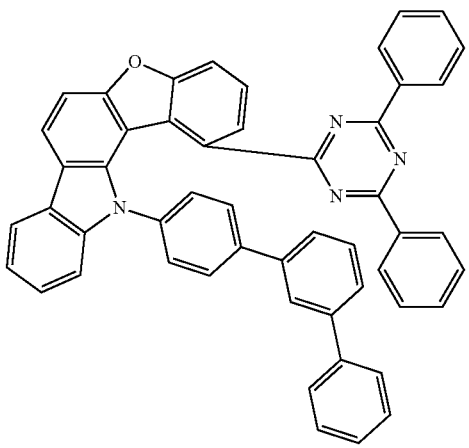
1F-1-31
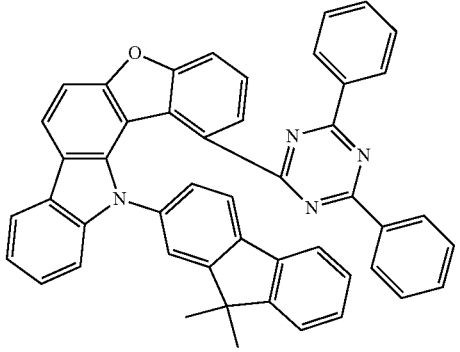
1F-1-32
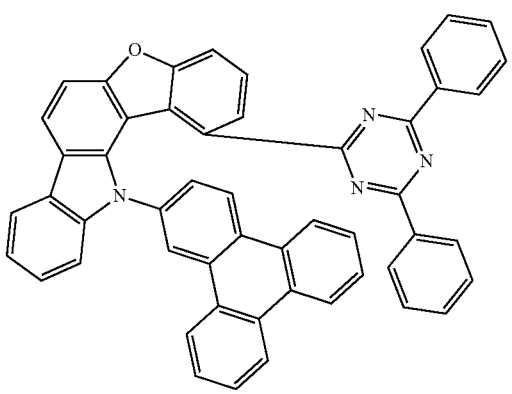

1F-1-33
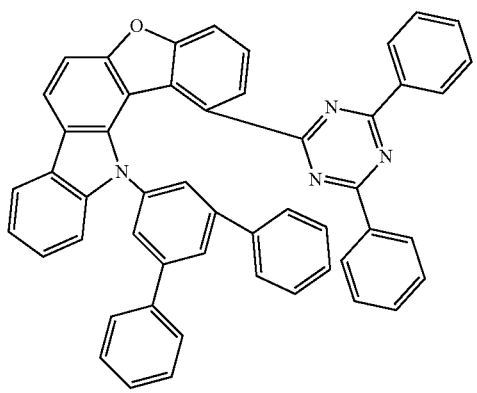
1F-1-36
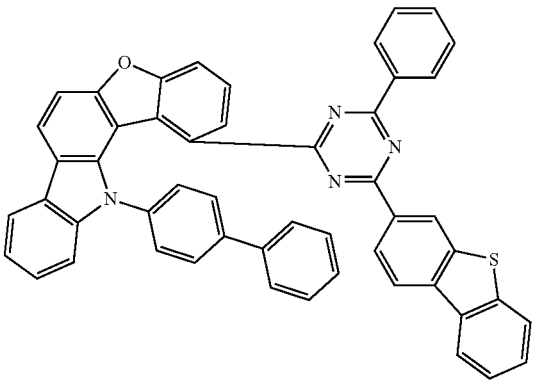
1F-1-34
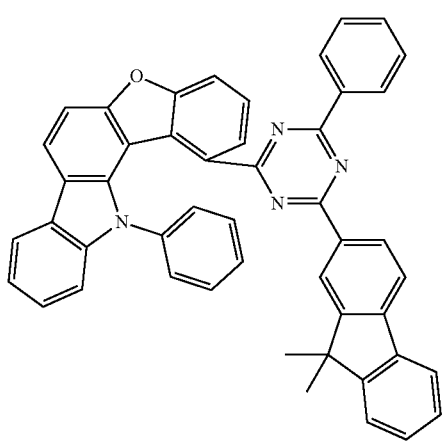
1F-1-37
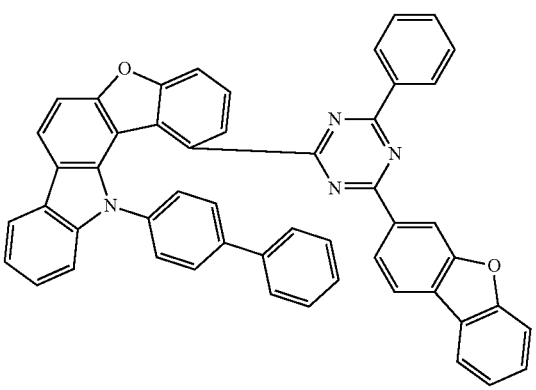
1F-1-35
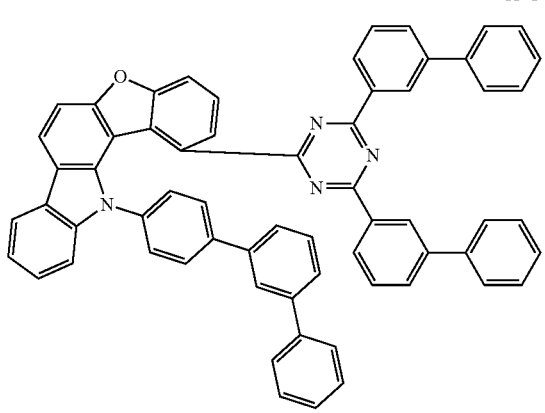
1F-1-38
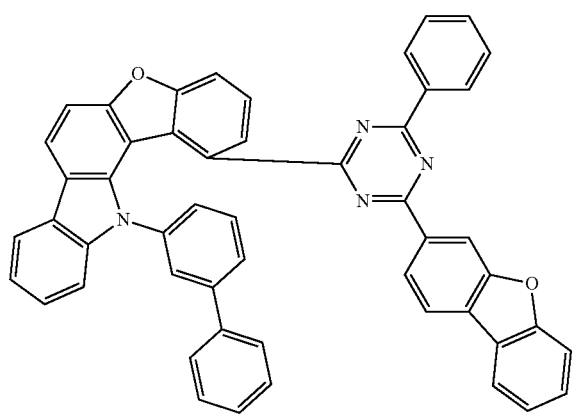

1F-1-39
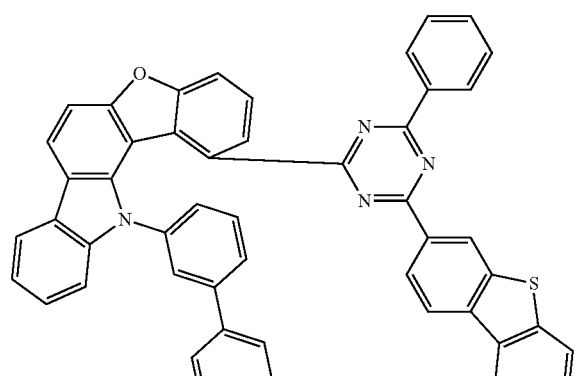
1F-1-40
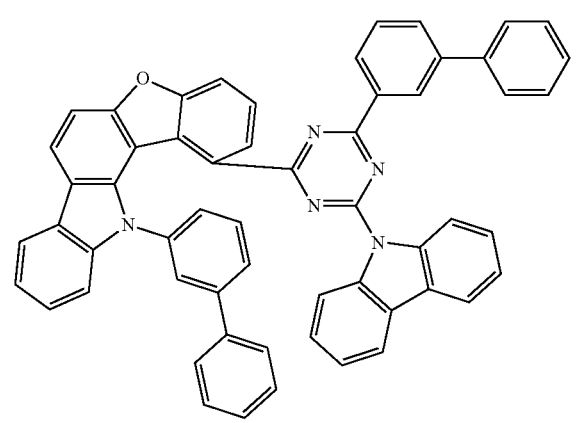
1F-1-41
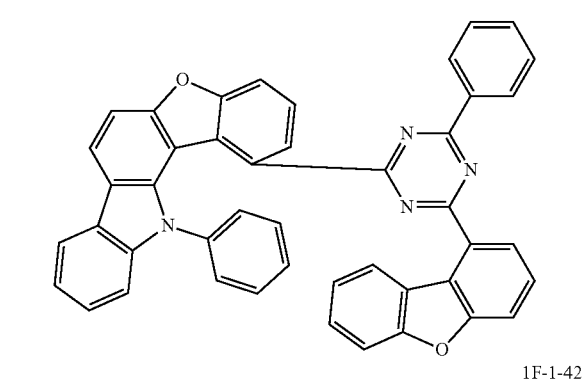
1F-1-42
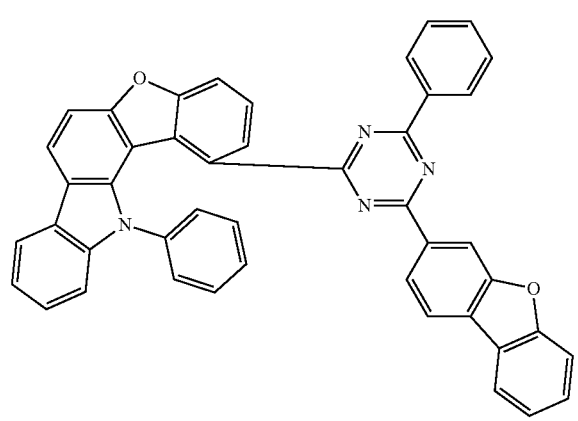
1F-1-43
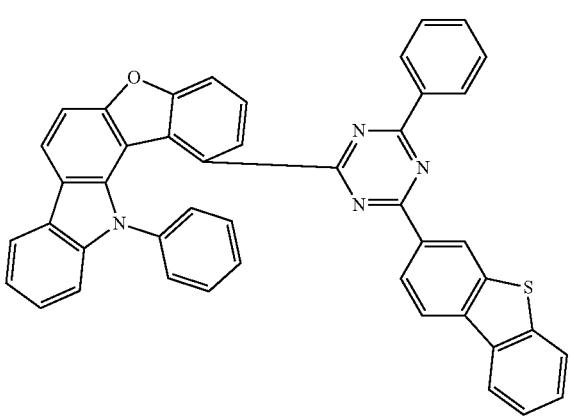
1F-1-44
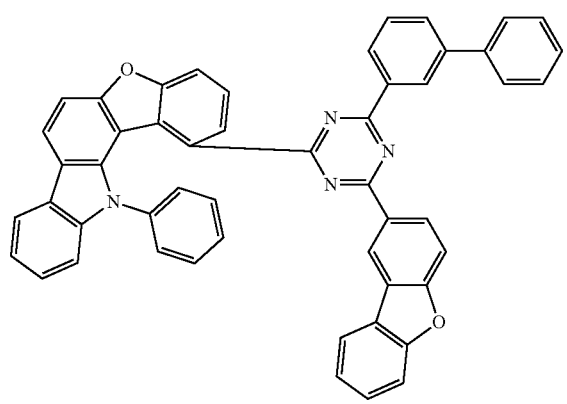
1F-1-45
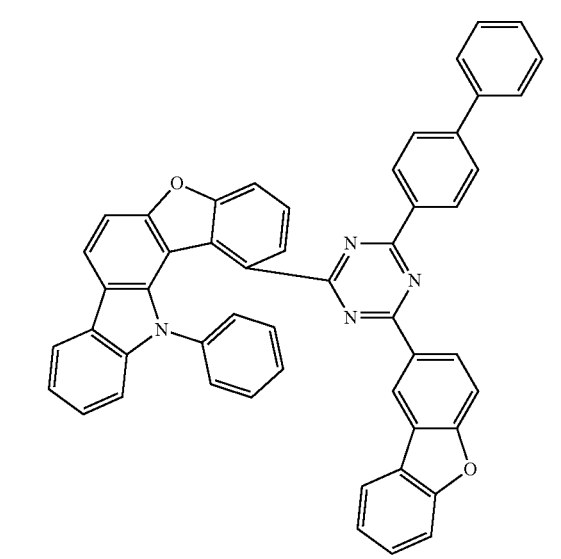

1F-1-46
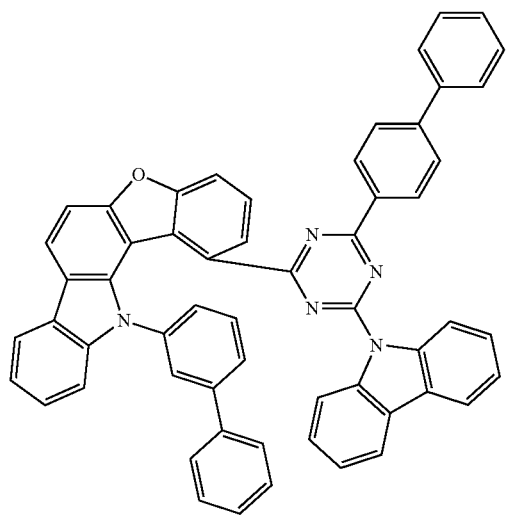
1F-1-49
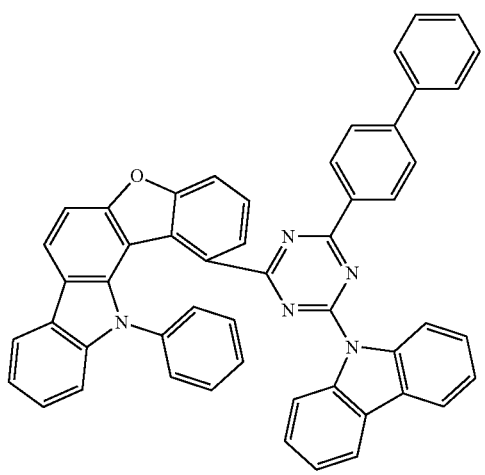
1F-1-47
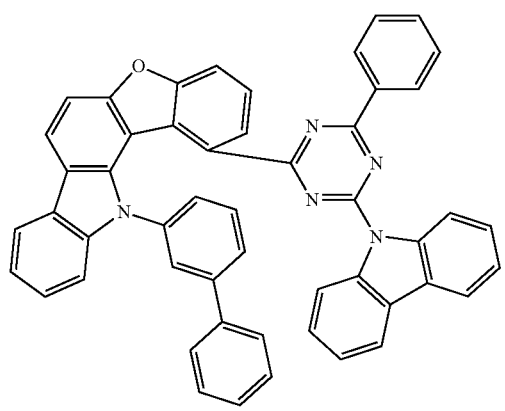
1F-1-50
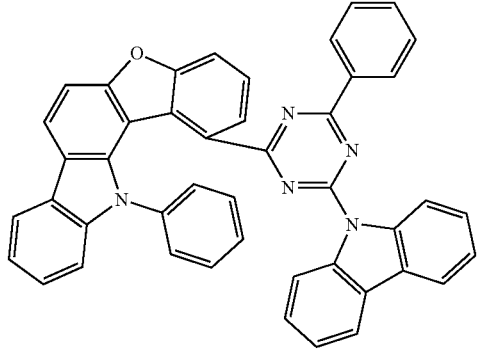
1F-1-48
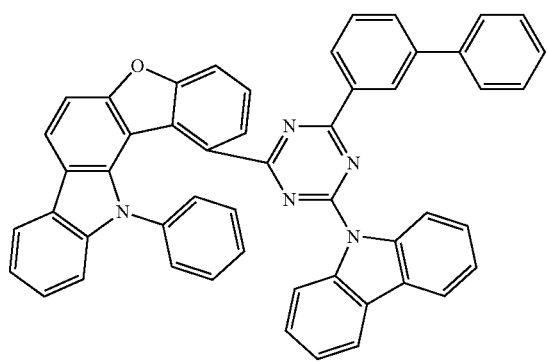
1F-1-51
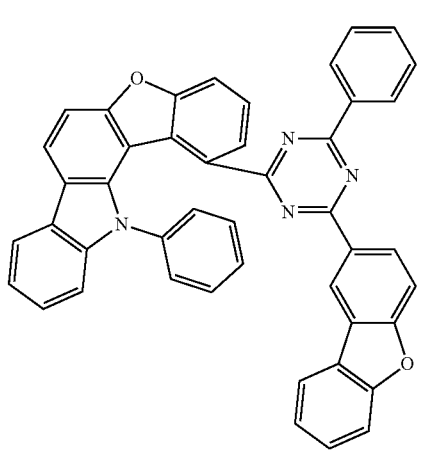

1F-1-52
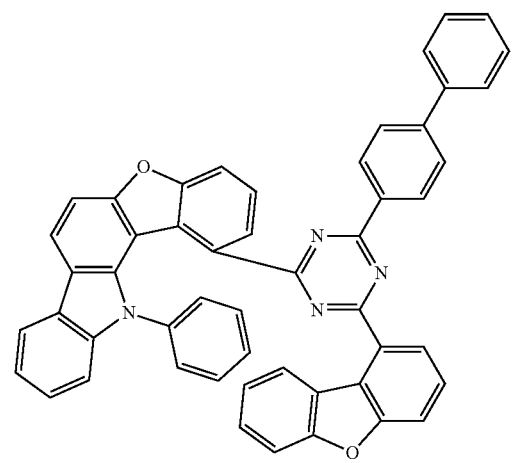
1F-1-53
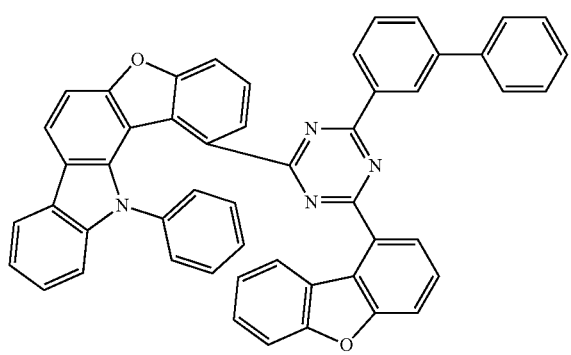
1F-1-54
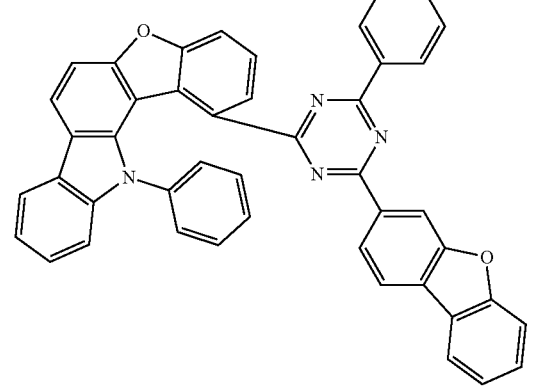
1F-1-55
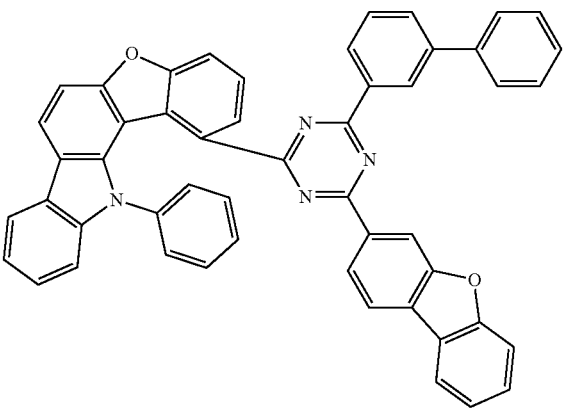
1F-1-56
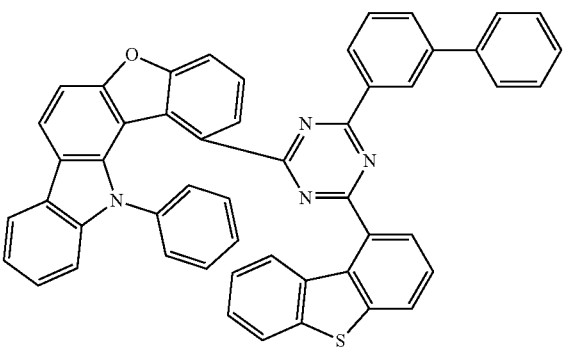
1F-1-57
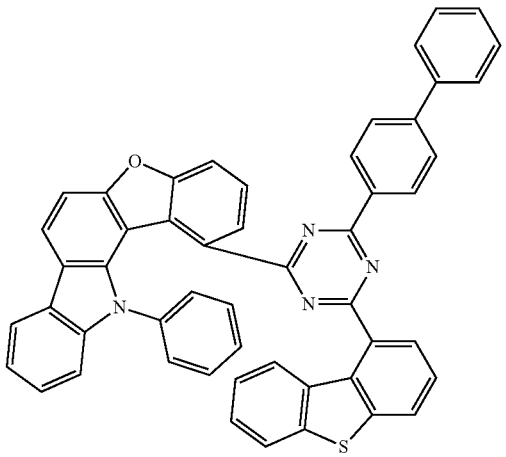
1F-1-58
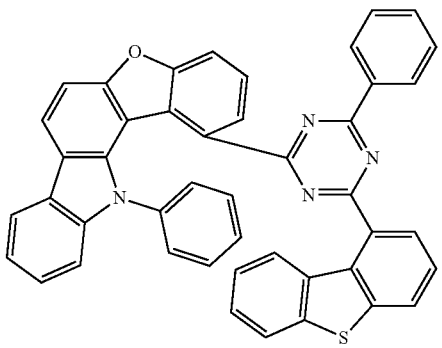

1F-1-59
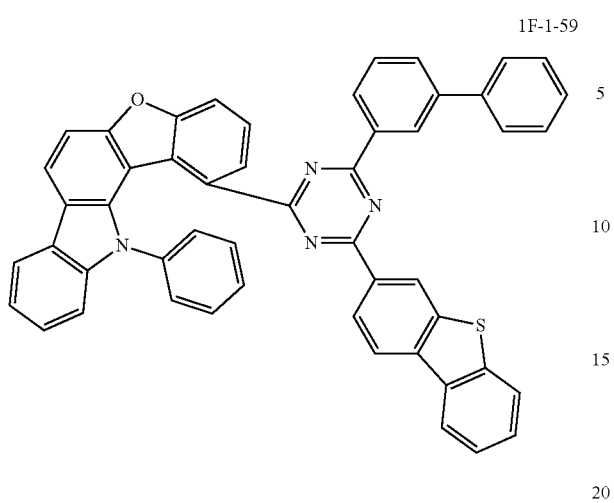
1F-1-62
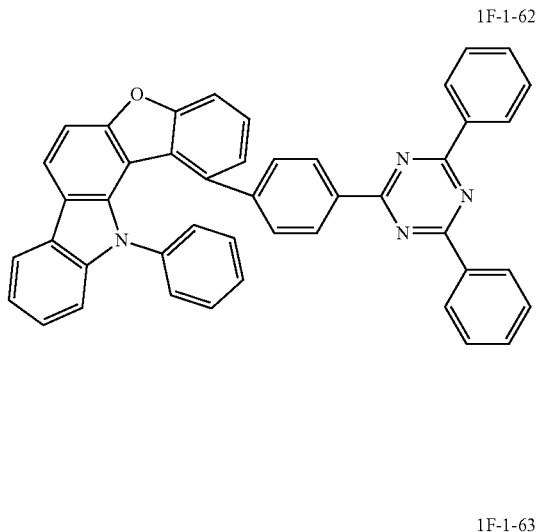
1F-1-60
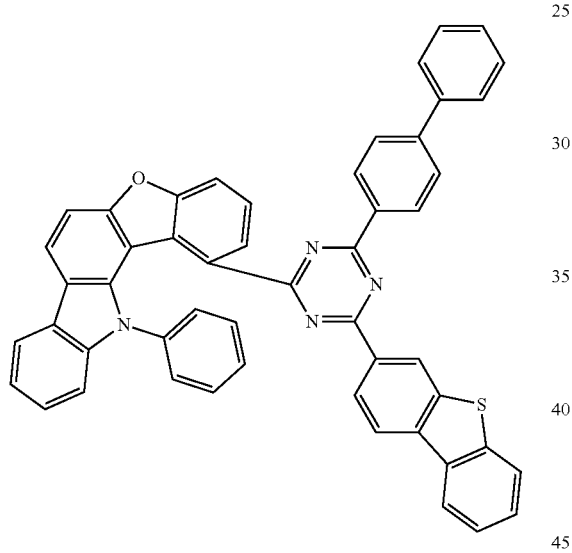
1F-1-63
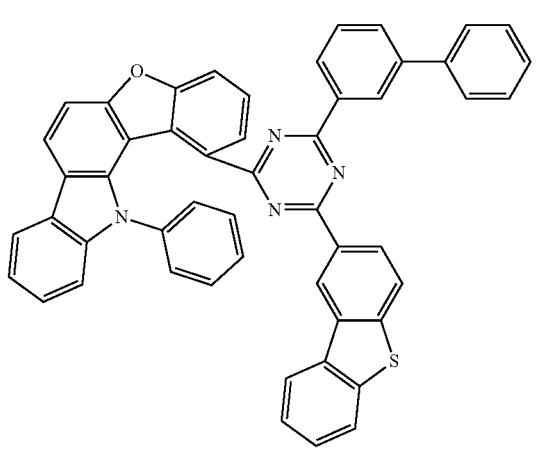
1F-1-61
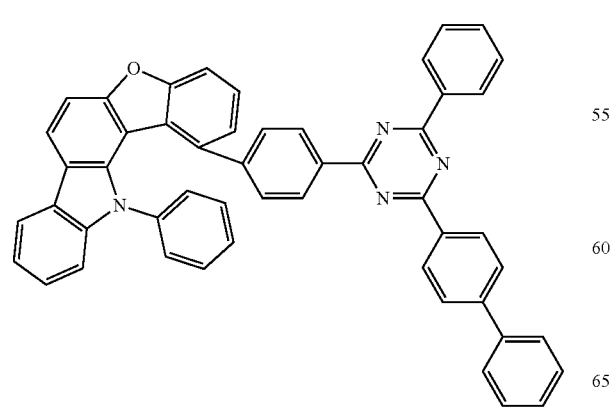
1F-1-64
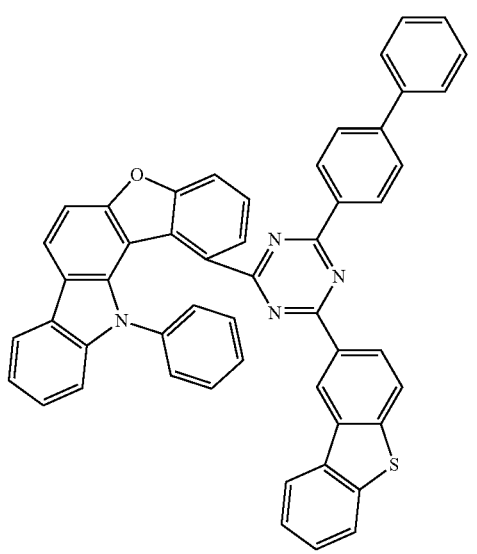

1F-1-65
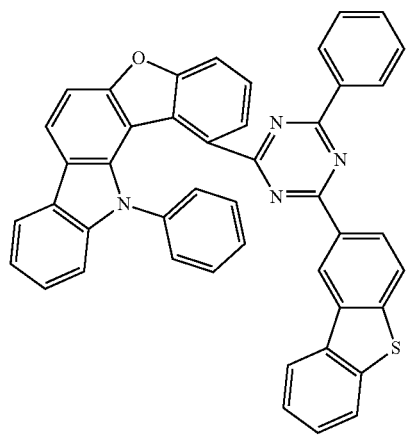
1F-1-69
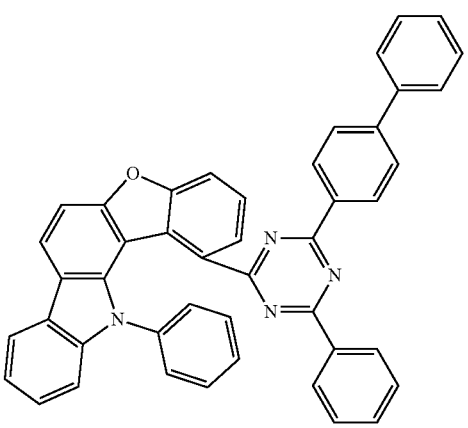
1F-1-66
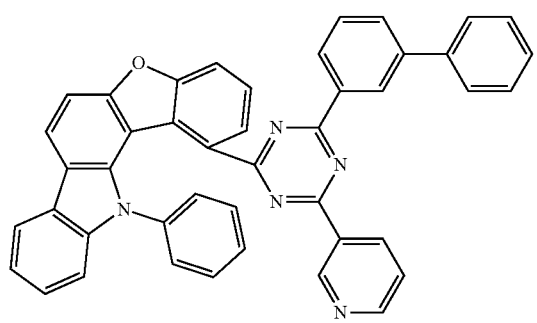
1F-1-70
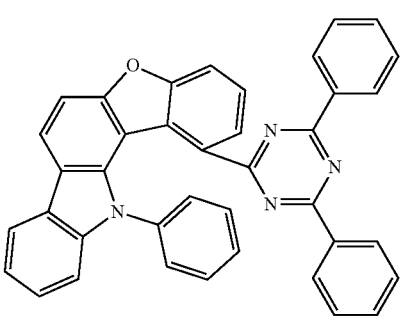
1F-1-67
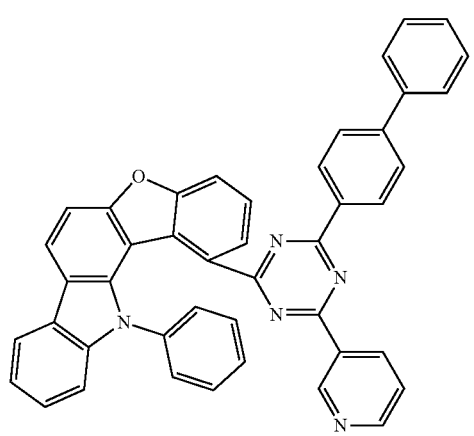
1F-1-71
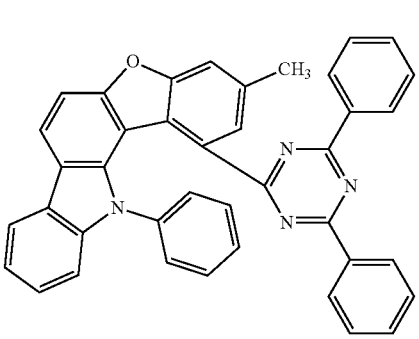
1F-1-68
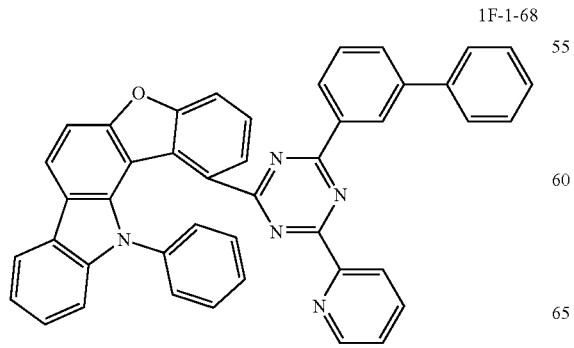
1F-1-72
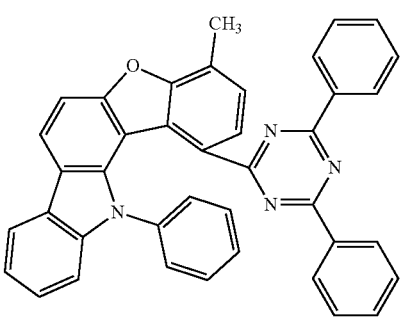

1F-1-73
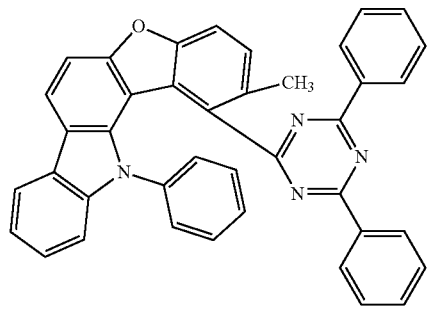
1F-1-74
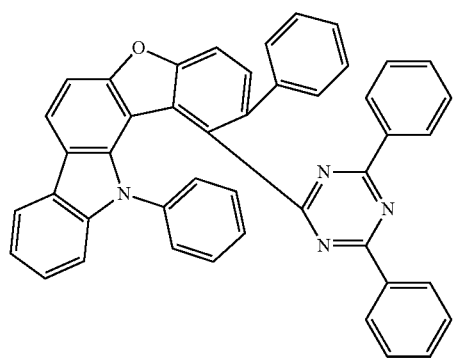
1F-1-75
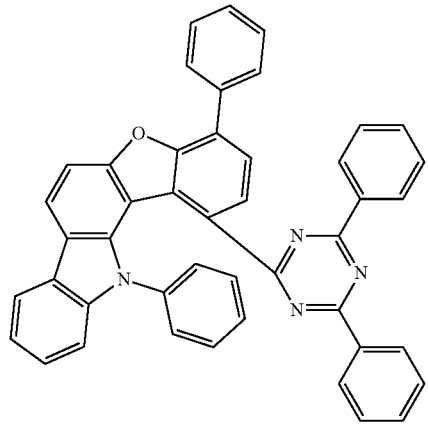
1F-1-76
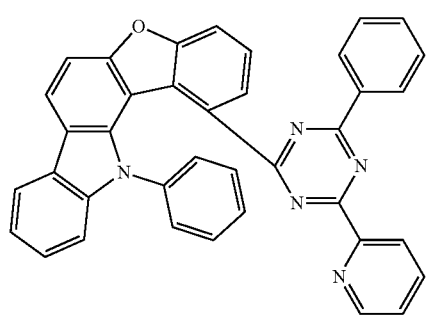
1F-1-77
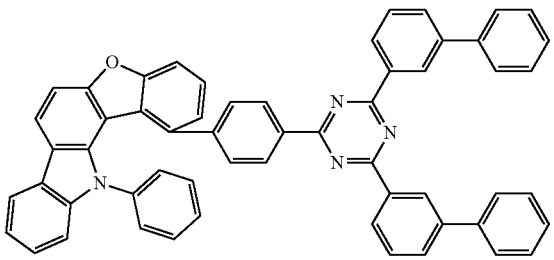
1F-1-78
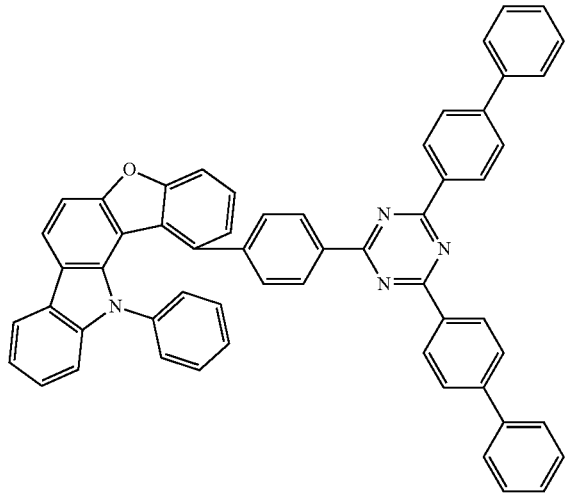
1F-1-79
1F-1-80
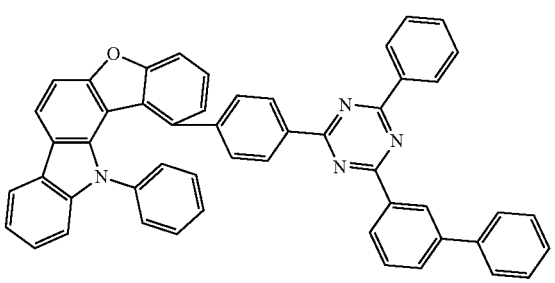

1E-1-81
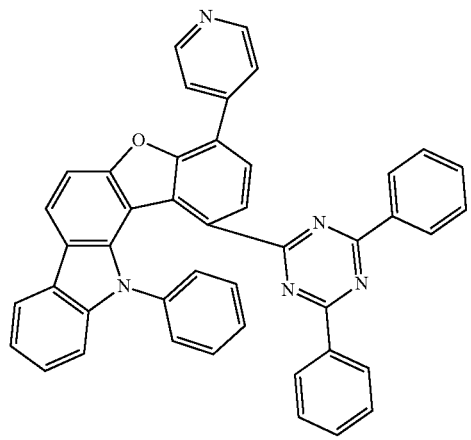
1F-2-1
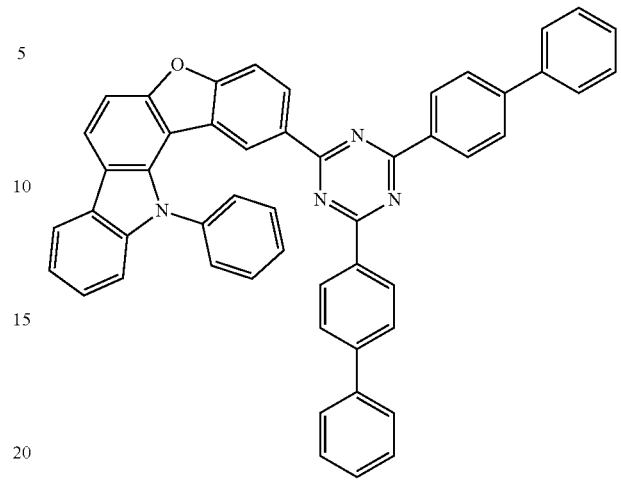
1E-1-82
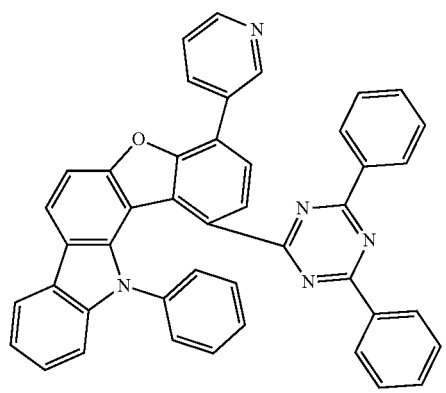
1F-2-2
1E-1-83
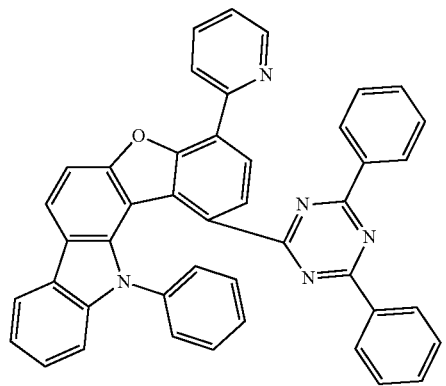
1F-2-3
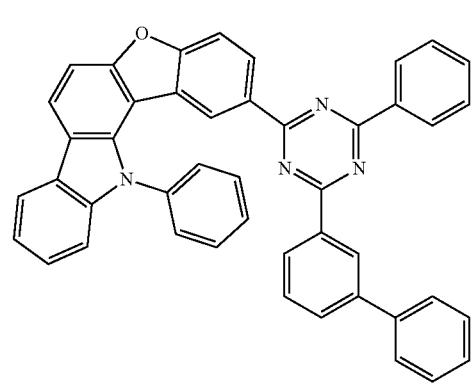

-continued
1F-2-4
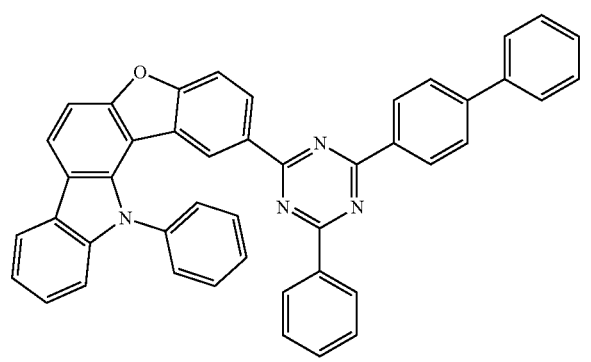
1F-2-5
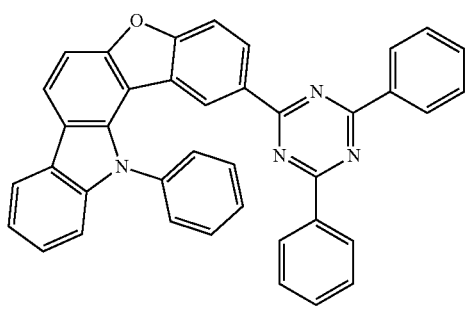
1F-2-6
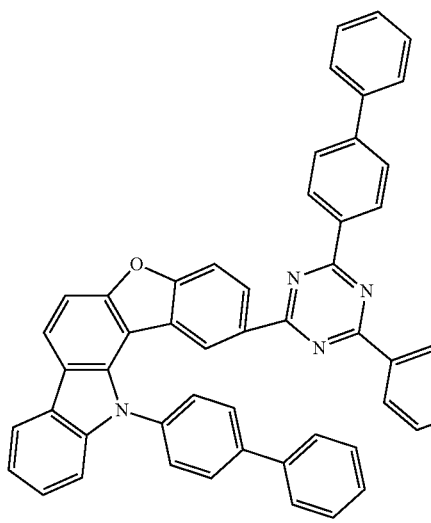
1F-2-7
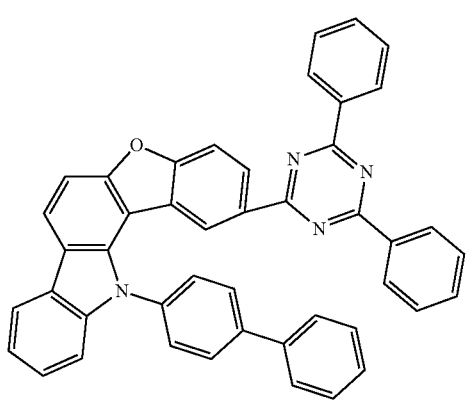
1F-2-8
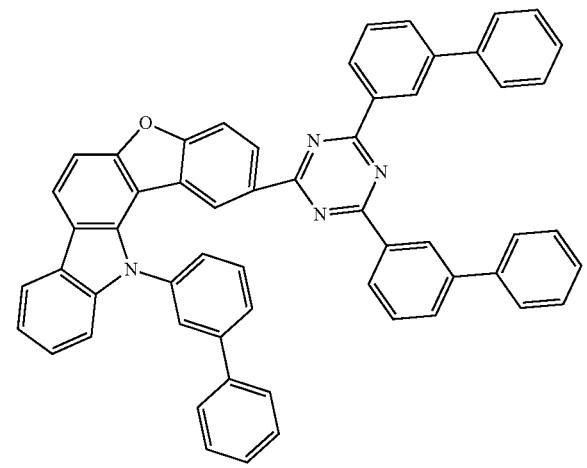
1F-2-9
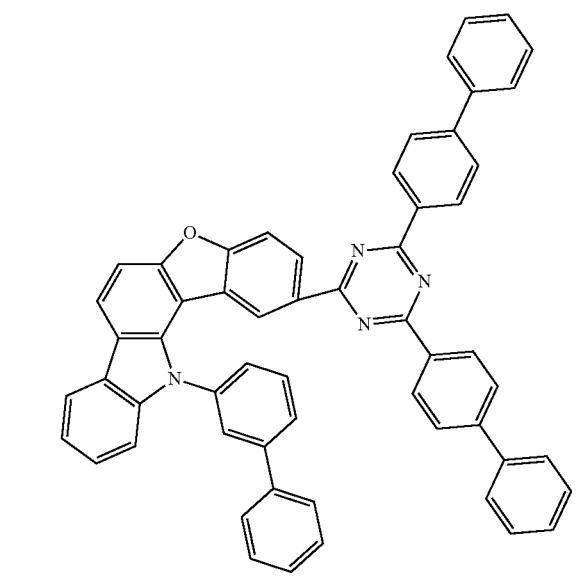
1F-2-10
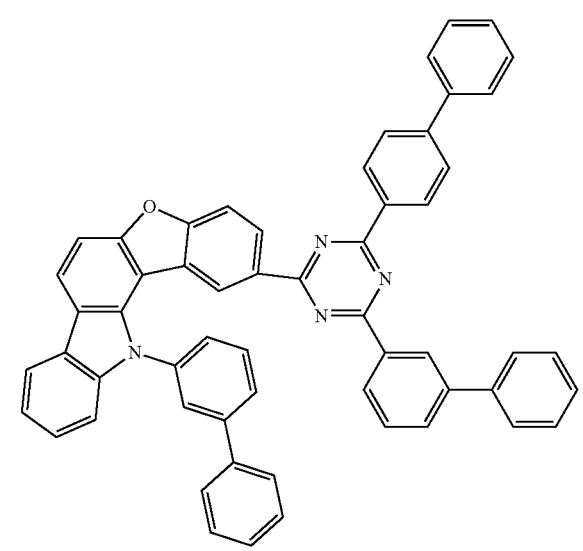

1F-2-11
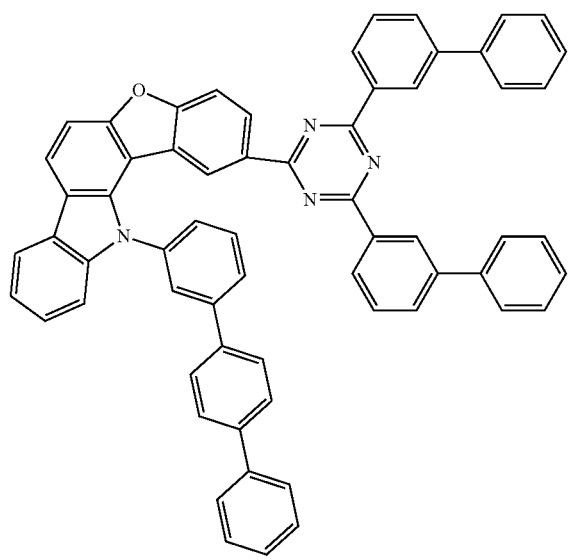
1F-2-13
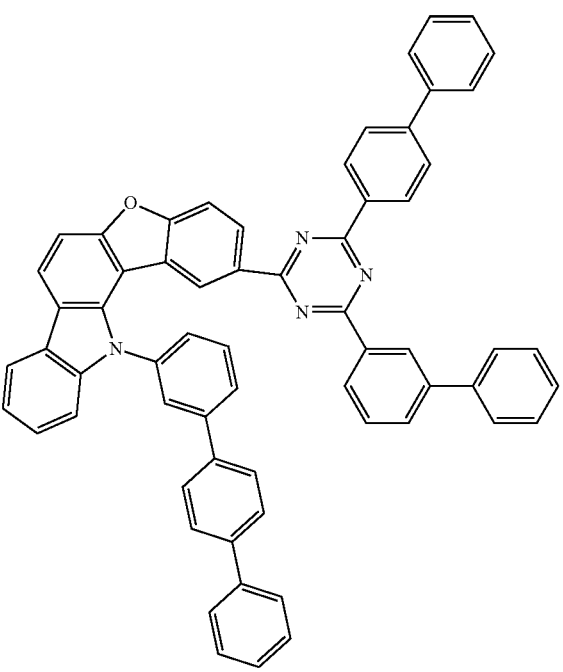
1F-2-12
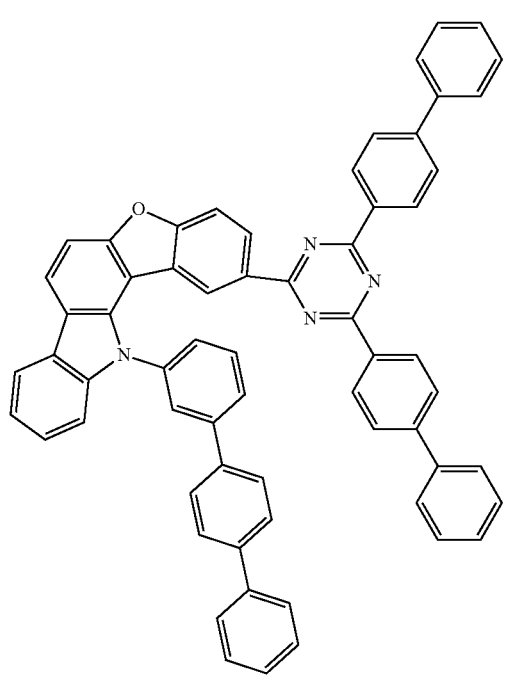
1F-2-14
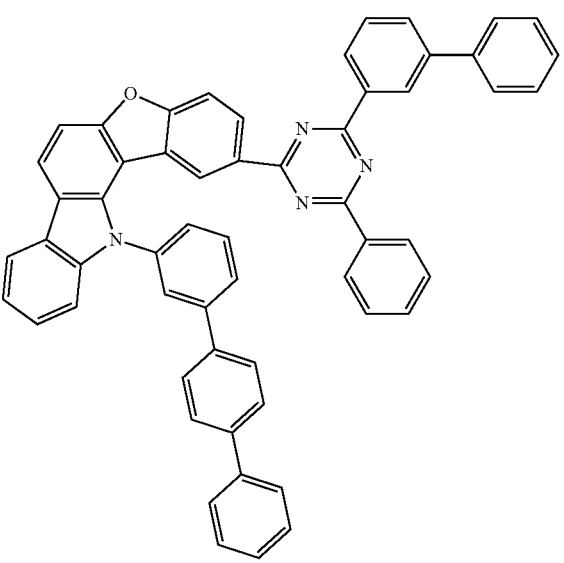

1F-2-15
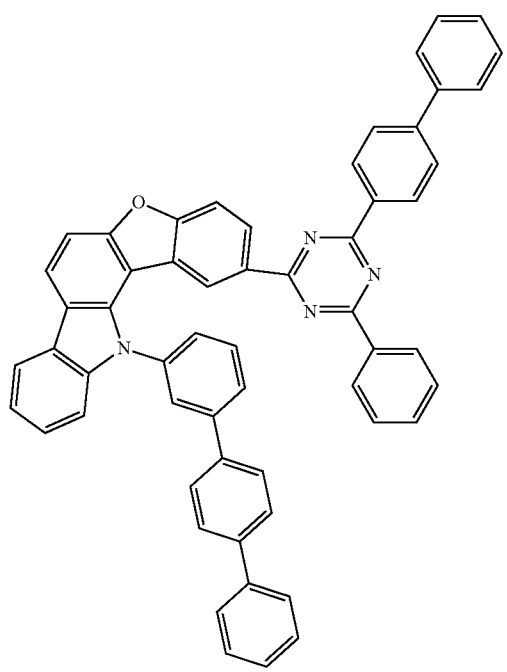
1F-2-17
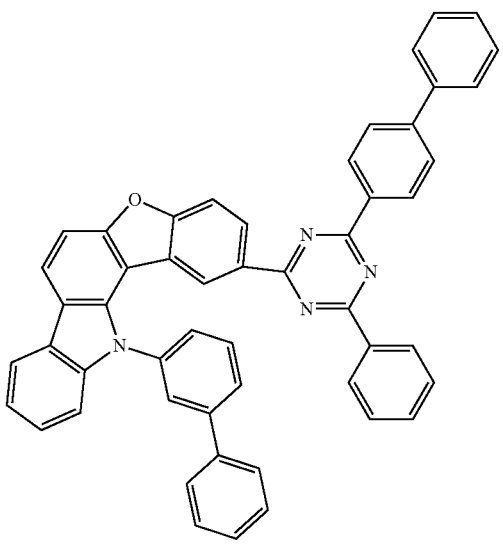
1F-2-18
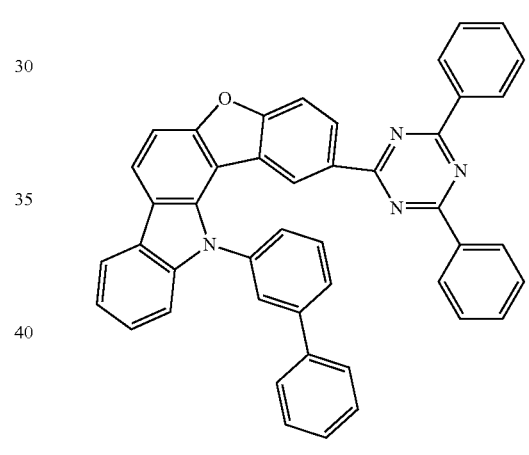
1F-2-16
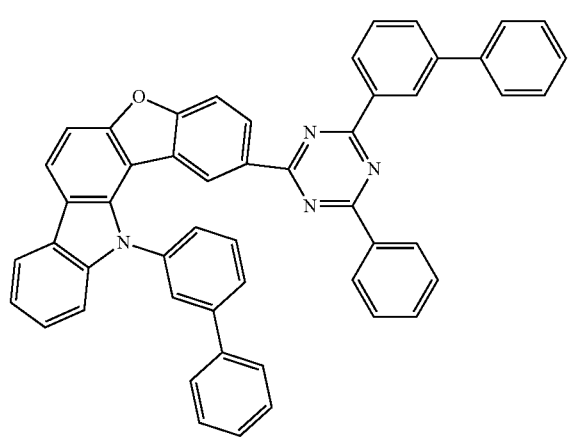
1F-2-19
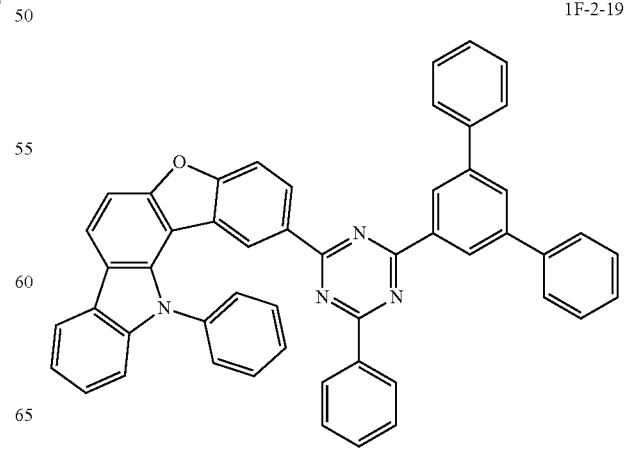

1F-2-20
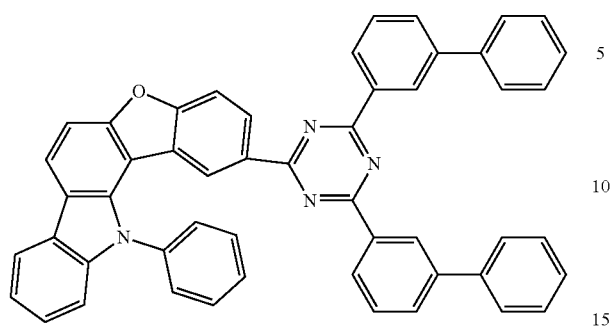
1F-2-21
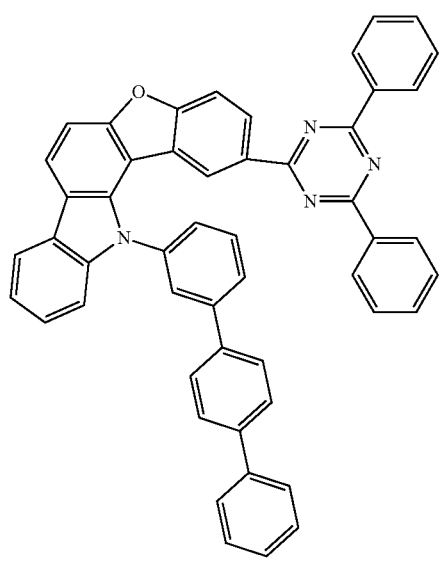
1F-2-22
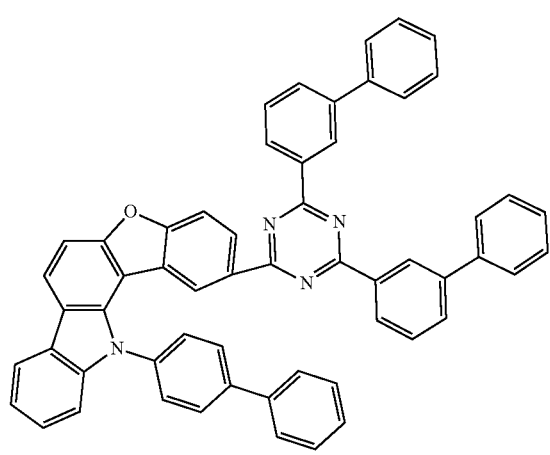
1F-2-23
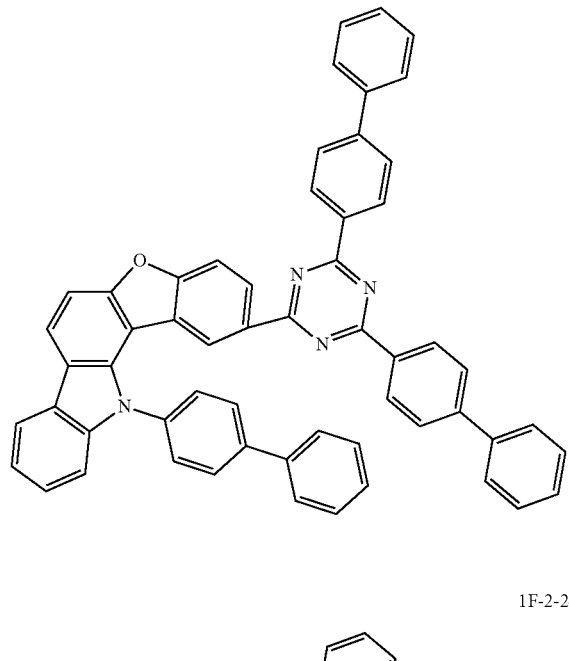
1F-2-24
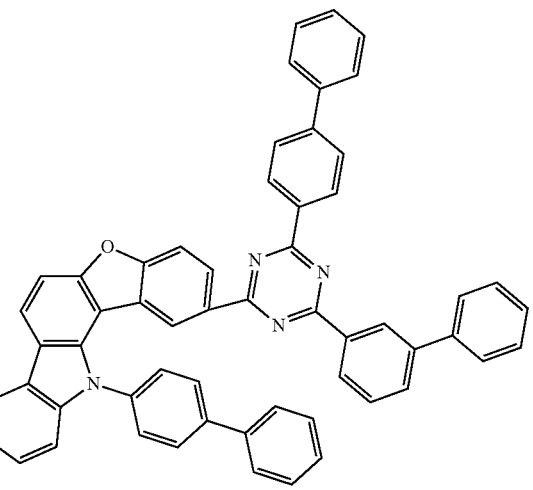
1F-2-25
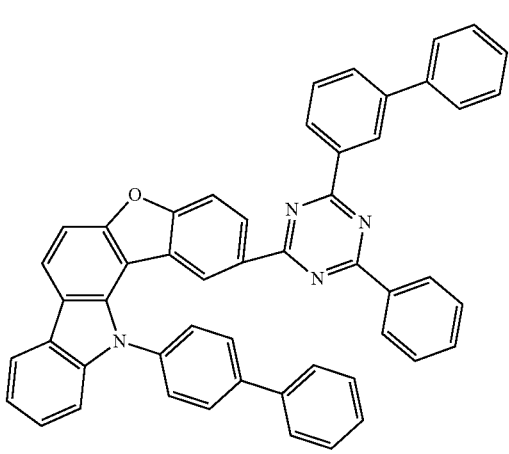

1F-2-26
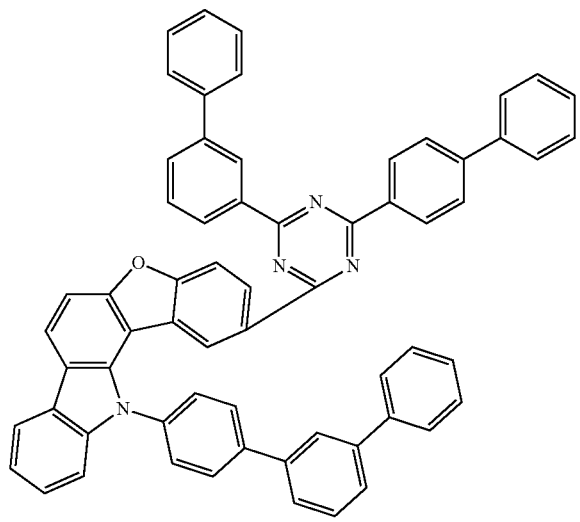
1F-2-29
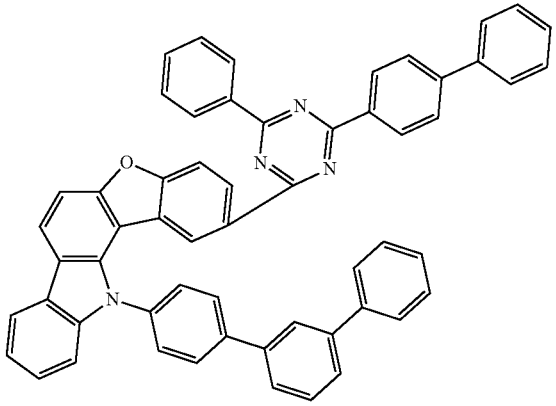
1F-2-27
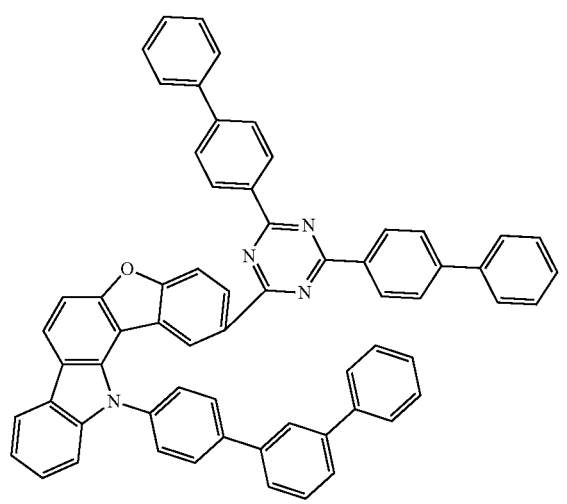
1F-2-30
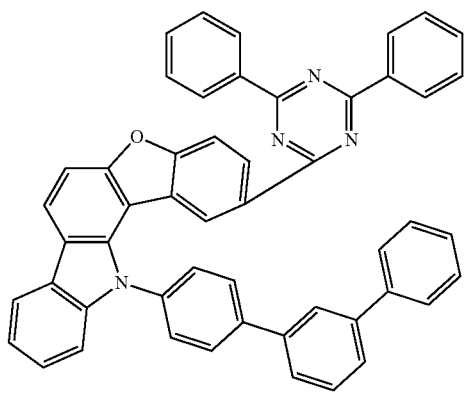
1F-2-28
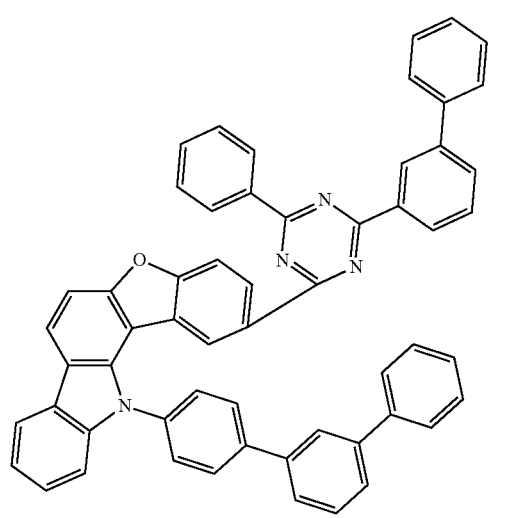
1F-2-31
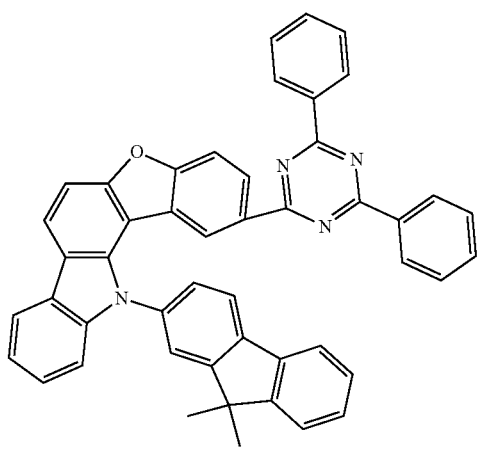

1F-2-32
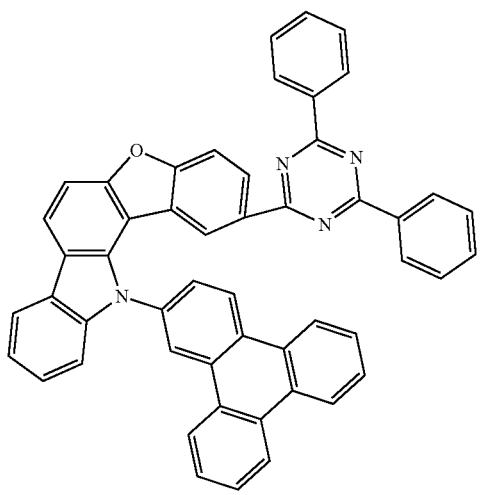
1F-2-33
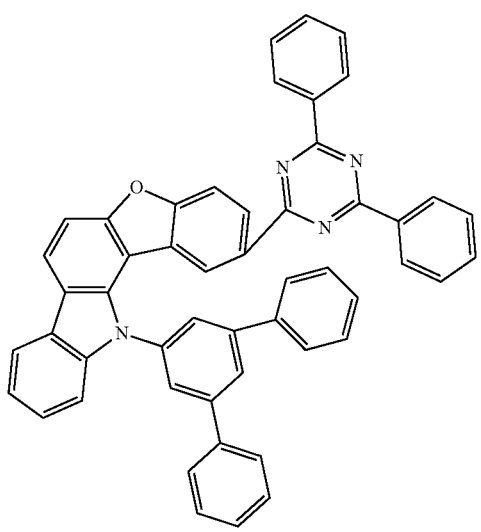
1F-2-34
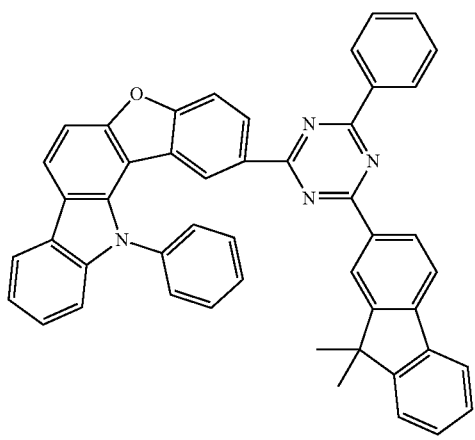
1F-2-35
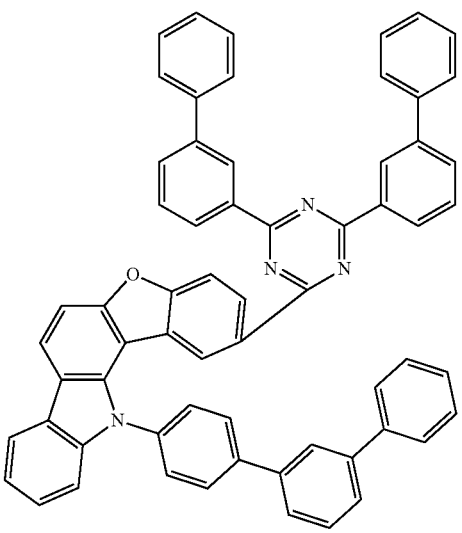
1F-2-36
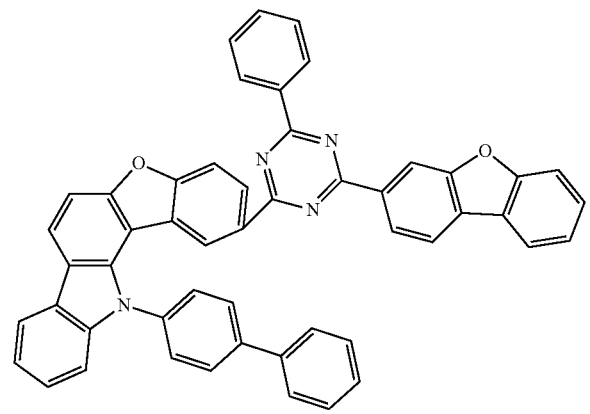
1F-2-37

1F-2-38
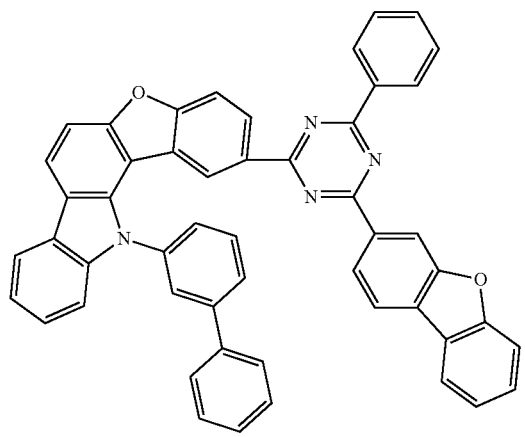
1F-2-41
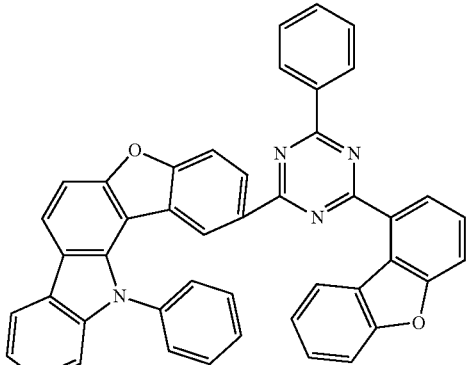
1F-2-39
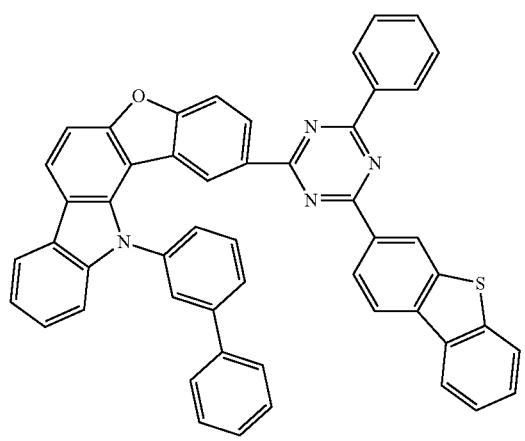
1F-2-42
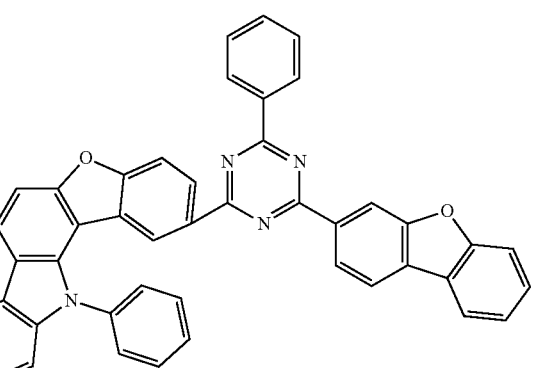
1F-2-40
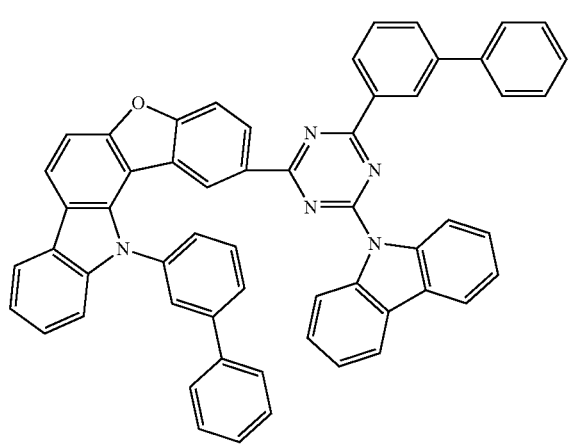
1F-2-43
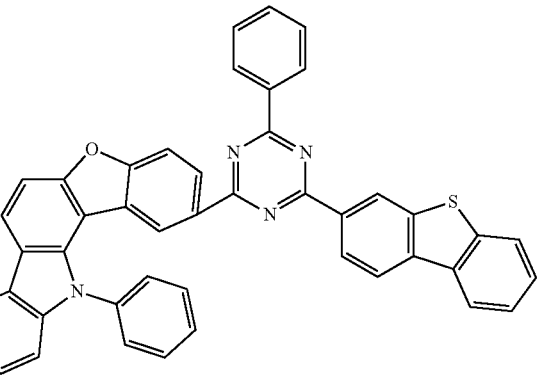

671
-continued
1F-2-44
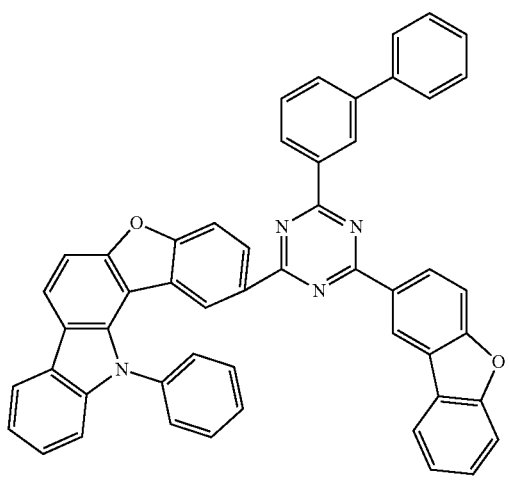
1F-2-45
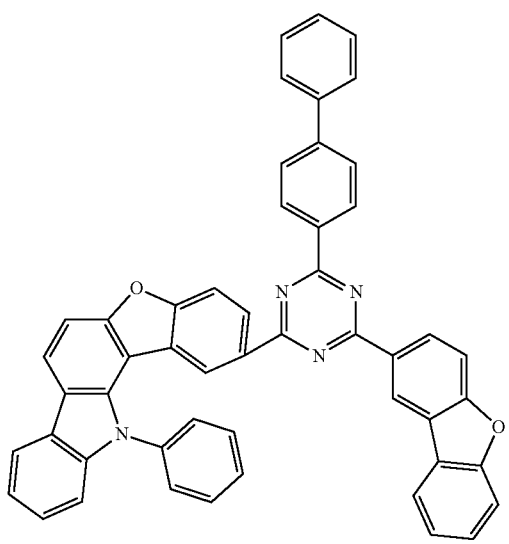
672
-continued
1F-2-46
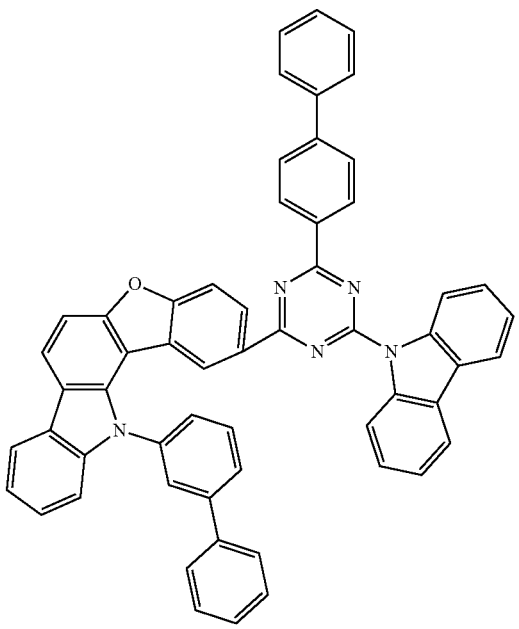
1F-2-47
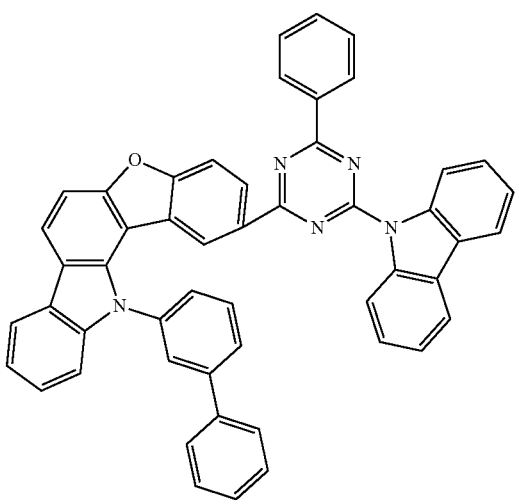
1F-2-48
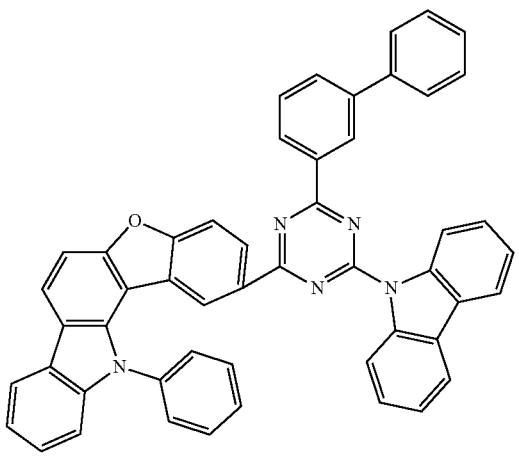

1F-2-49
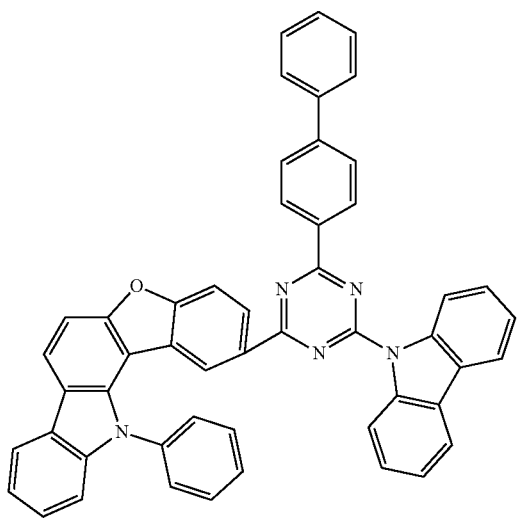
1F-2-50
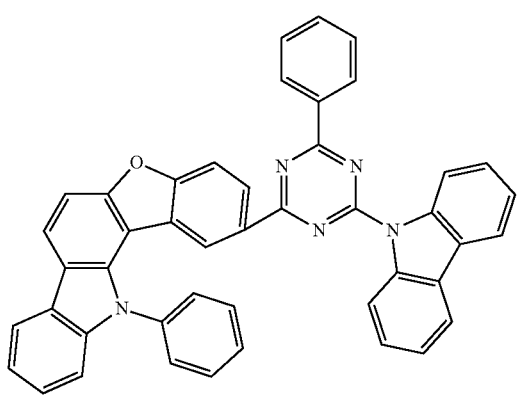
1F-2-51
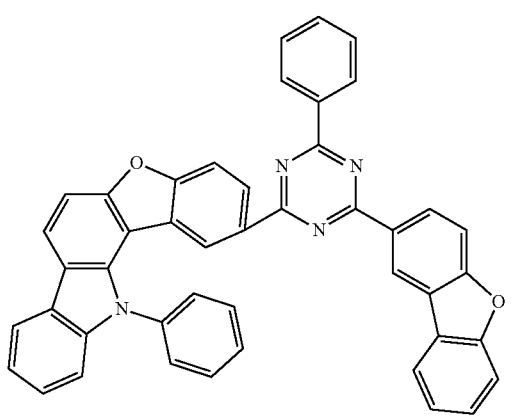
1F-2-52
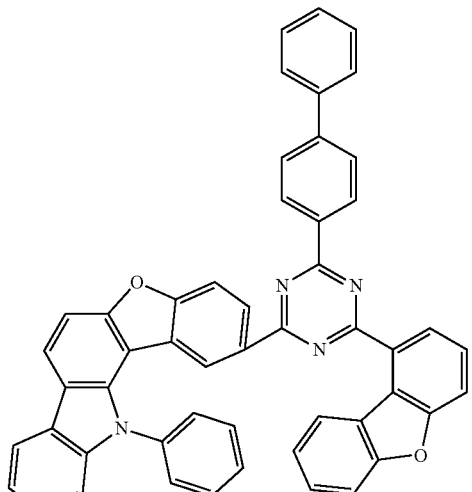
1F-2-53
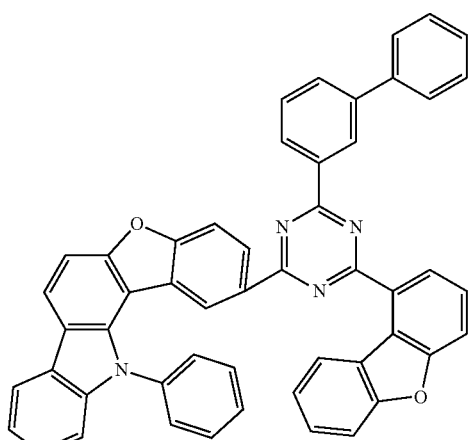
1F-2-54

1F-2-55
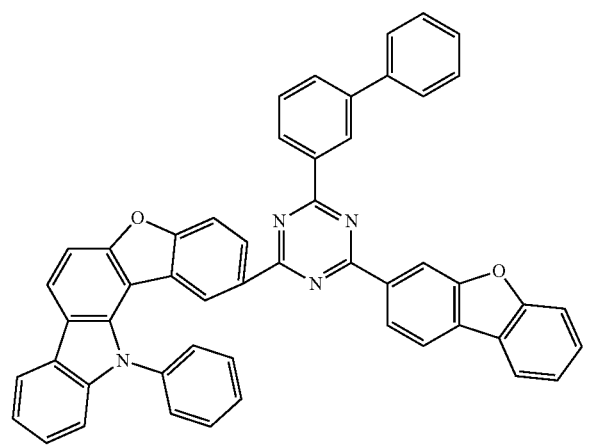
1F-2-58
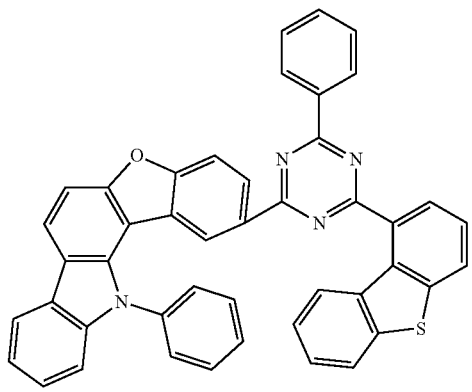
1F-2-56
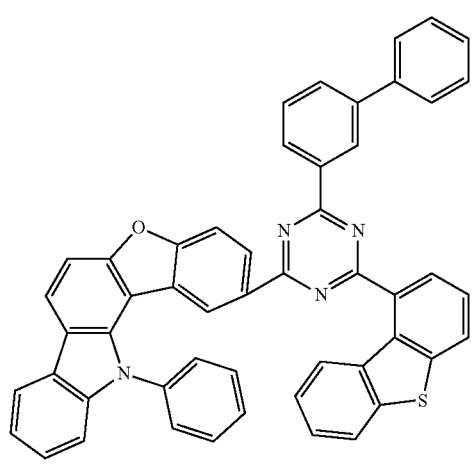
1F-2-59
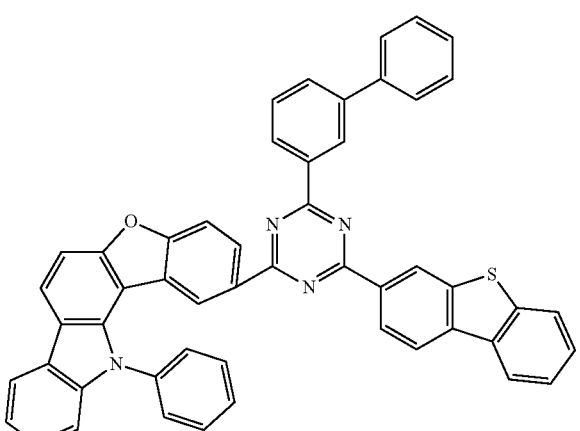
1F-2-57
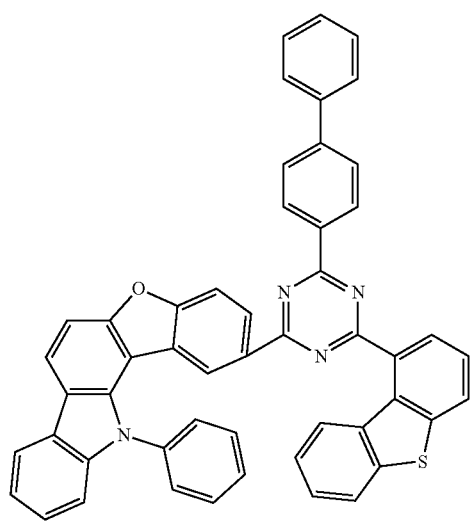
1F-2-60
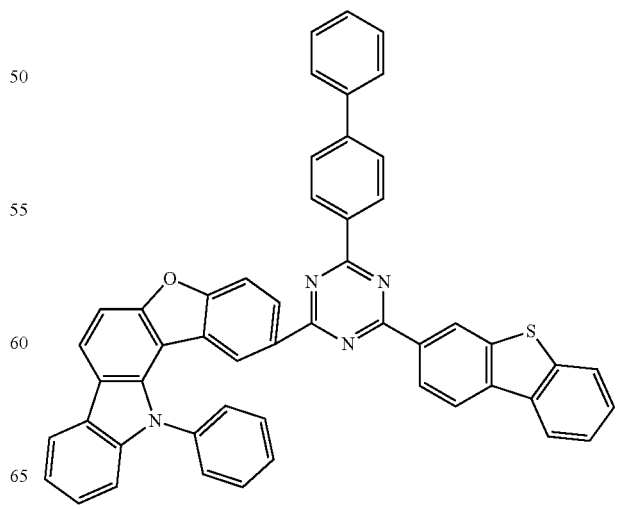

677
-continued
1F-2-61
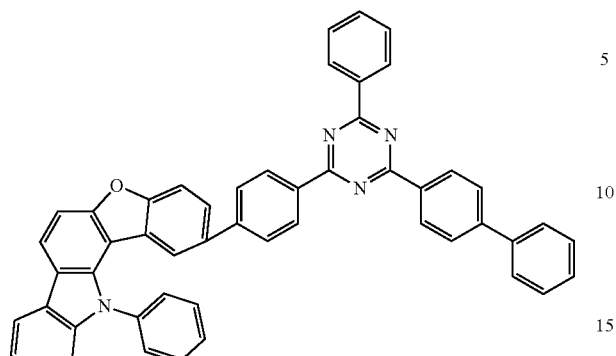
1F-2-62
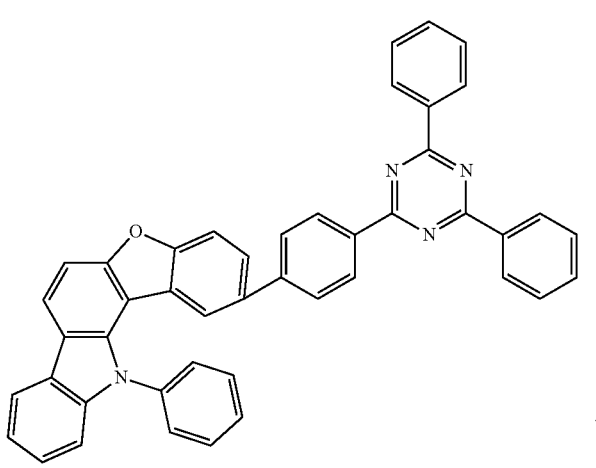
1F-2-63
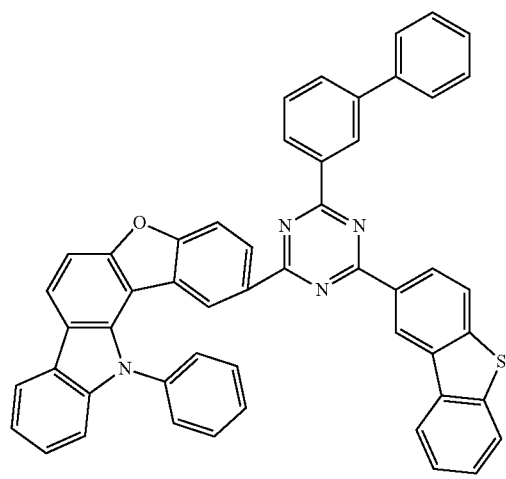
678
-continued
1F-2-64
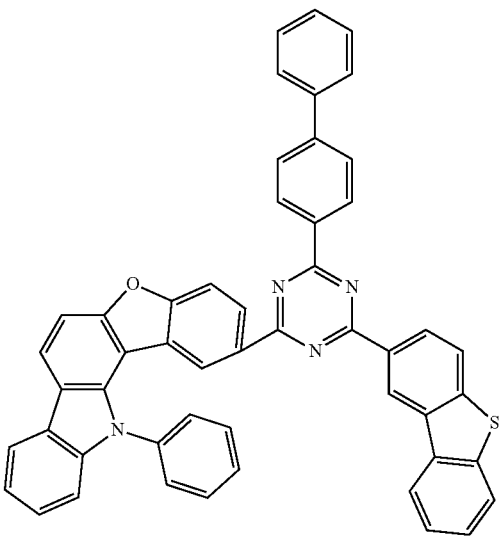
1F-2-65
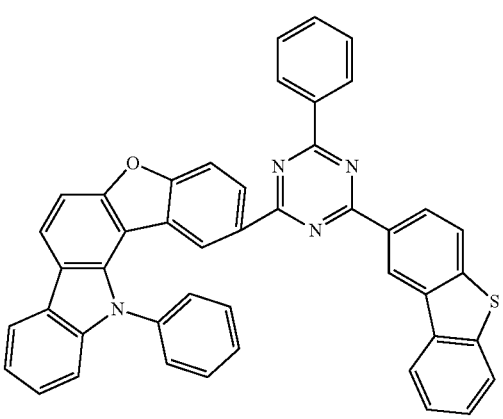
1F-2-66
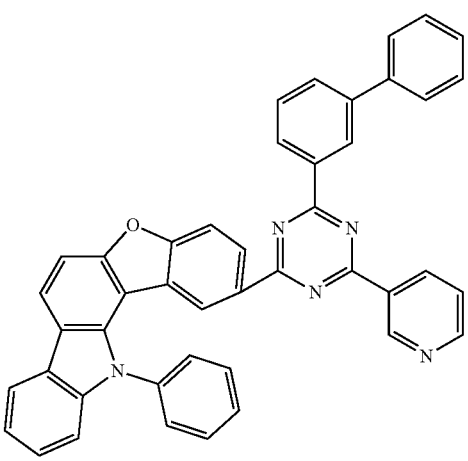

1F-2-67
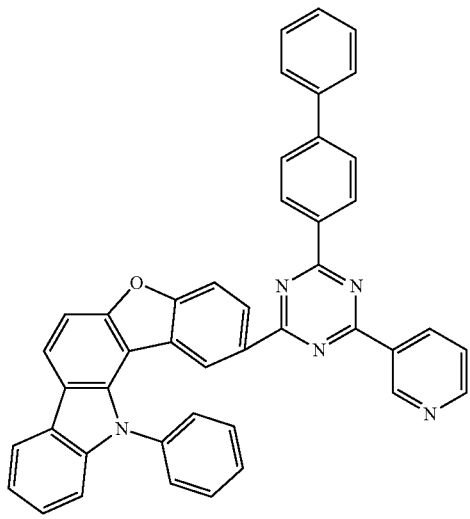
1F-2-68
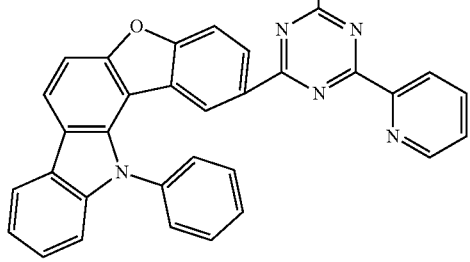
1F-2-69
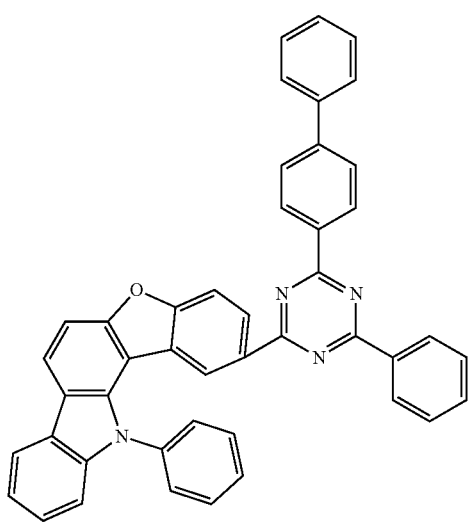
1F-2-70
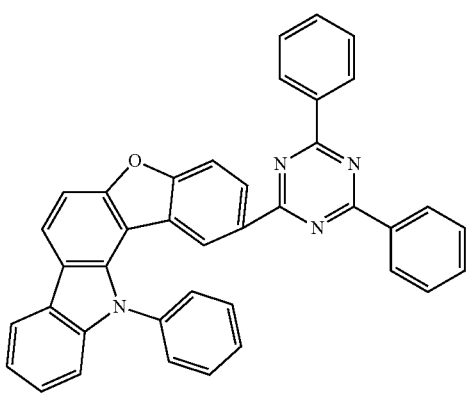
1F-2-71
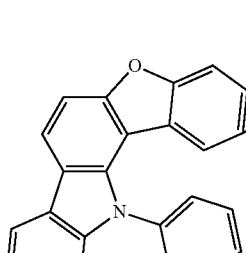
1F-2-72
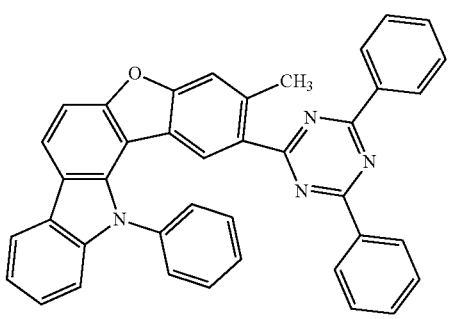
1F-2-73
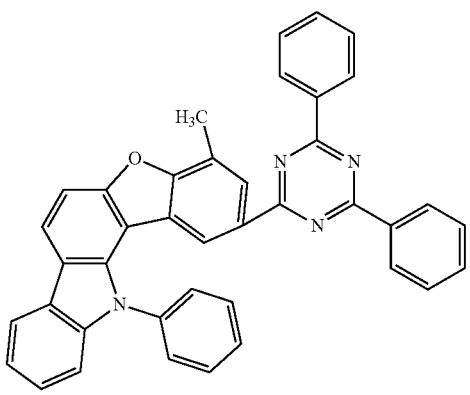

1F-2-74
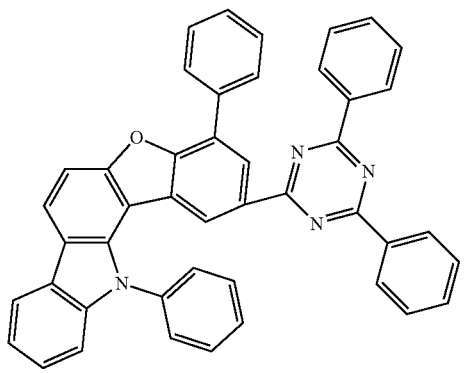
1F-2-77
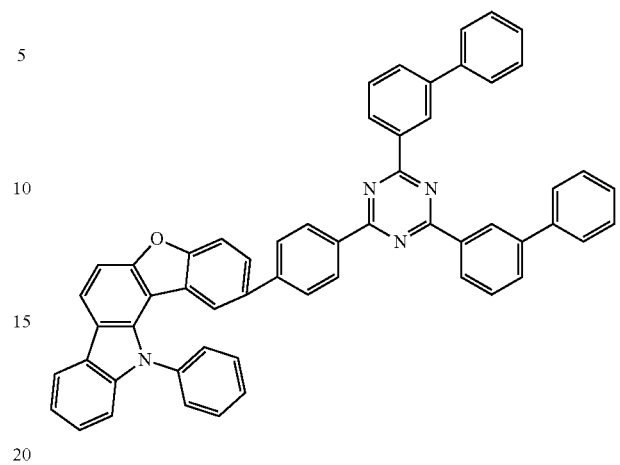
1F-2-75
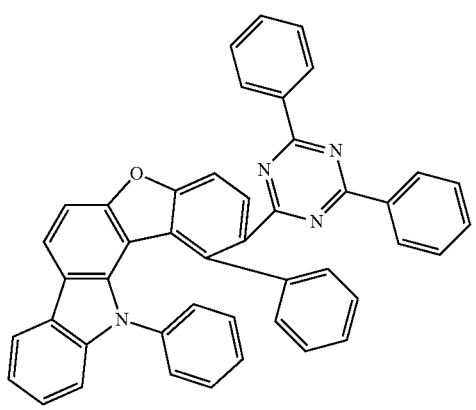
1F-2-78
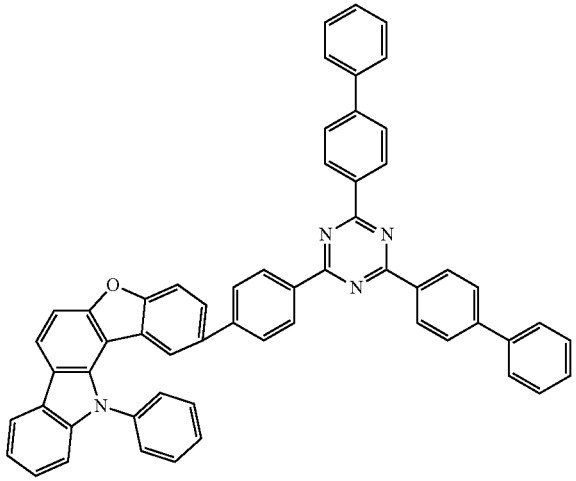
1F-2-76
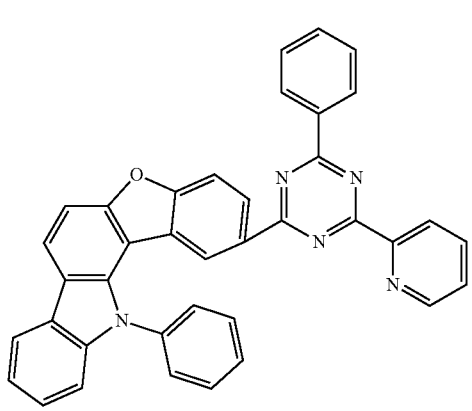
1F-2-79
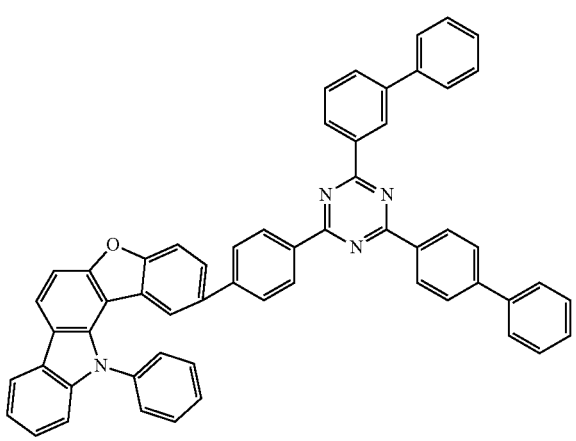

1F-2-80
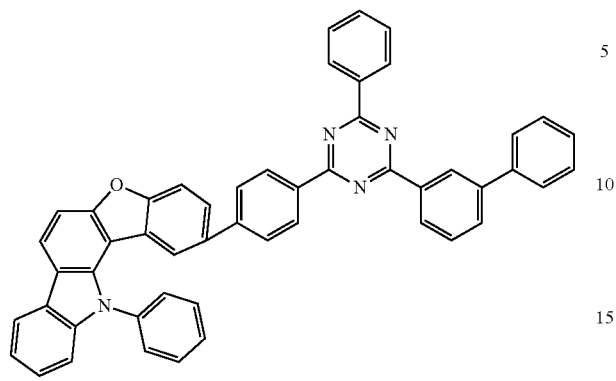
1F-2-81
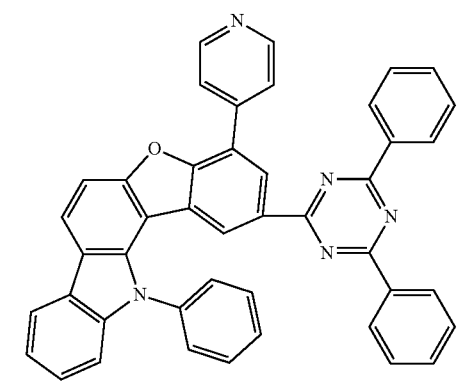
1F-2-82
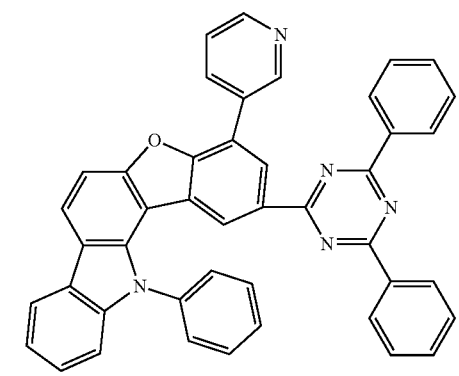
1F-2-83
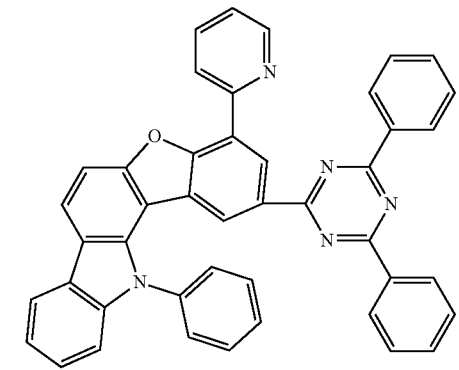
1F-3-1
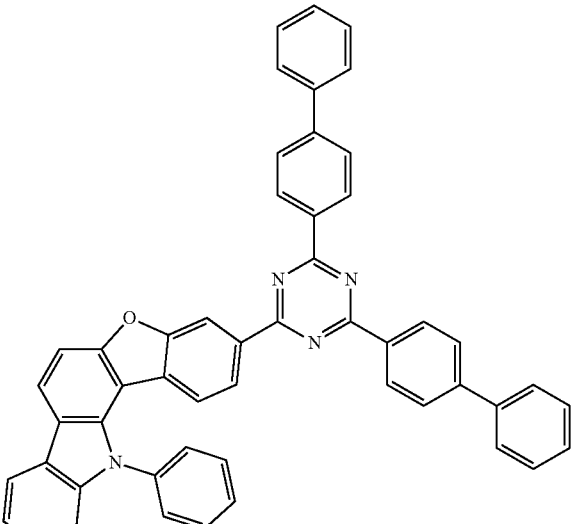
1F-3-2
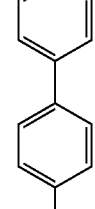
1F-3-3
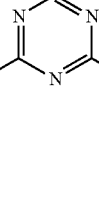

1F-3-4
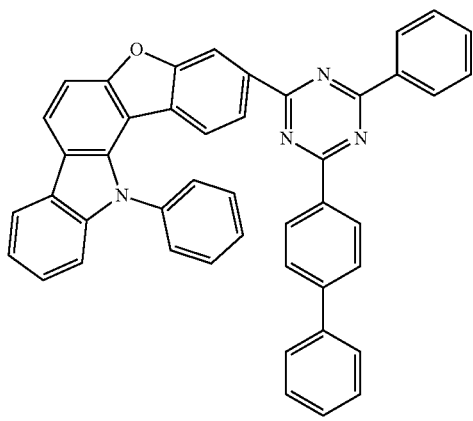
1F-3-5
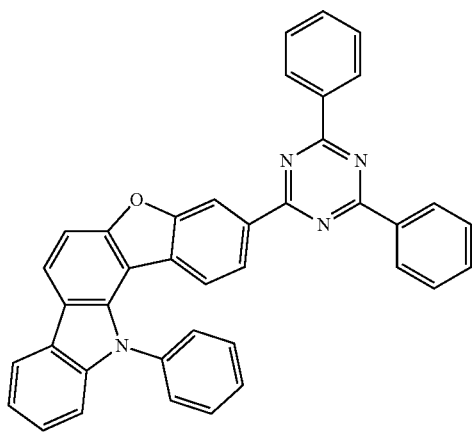
1F-3-6
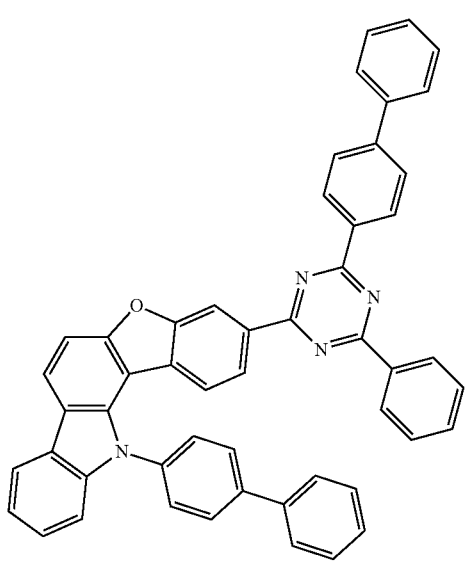
1F-3-7
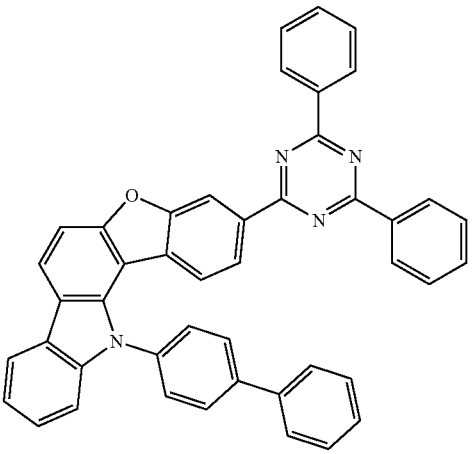
1F-3-8
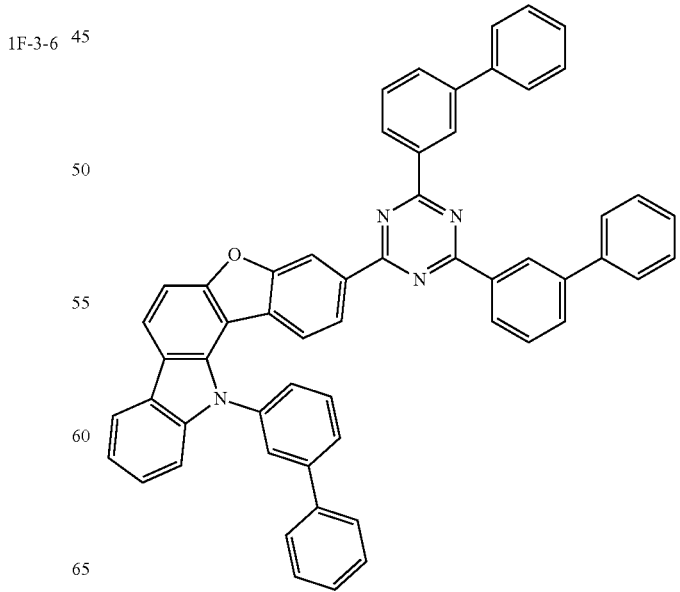

1F-3-9
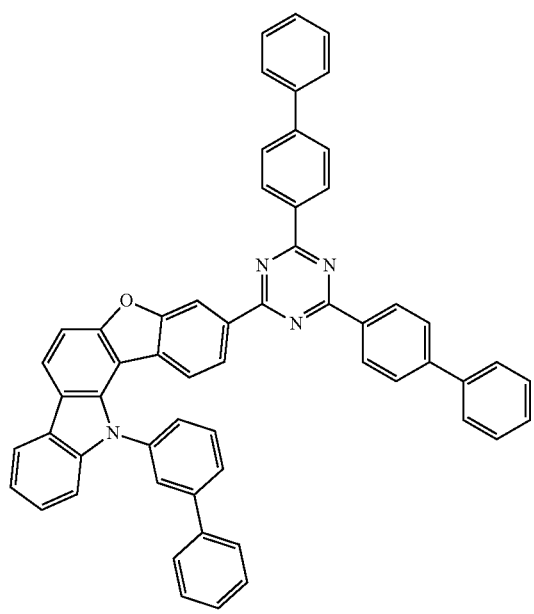
1F-3-11
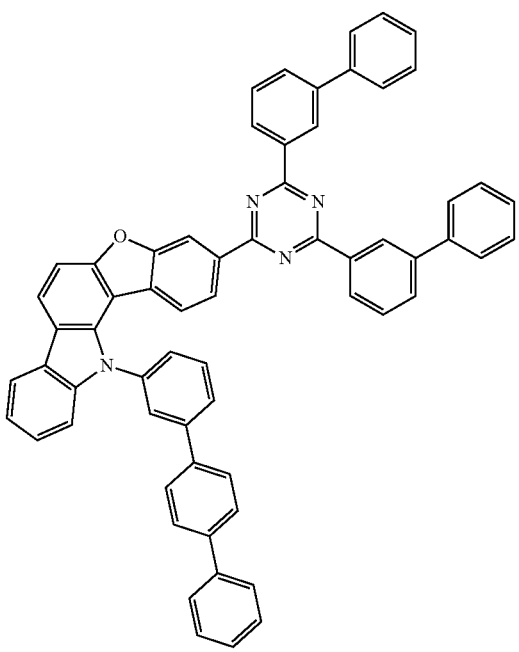
1F-3-10
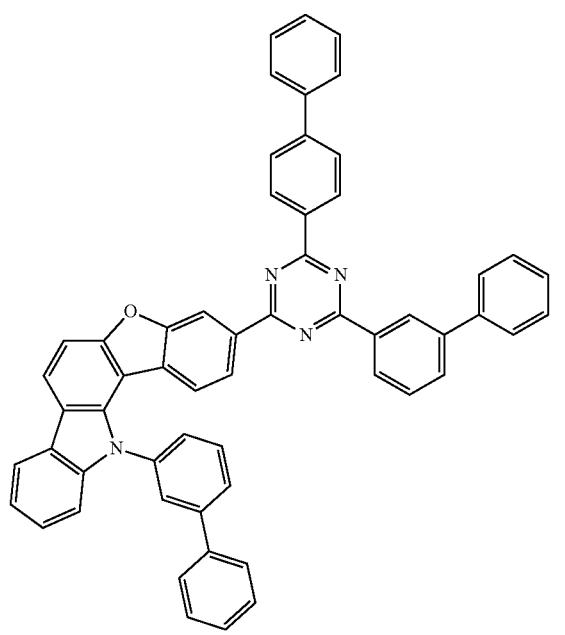
1F-3-12
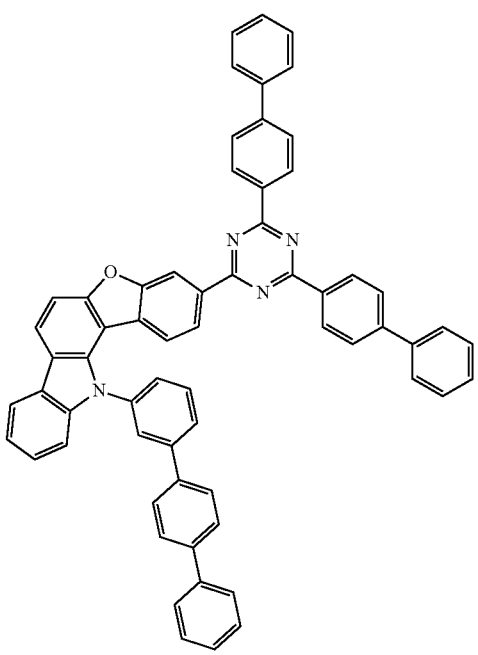

-continued
1F-3-13
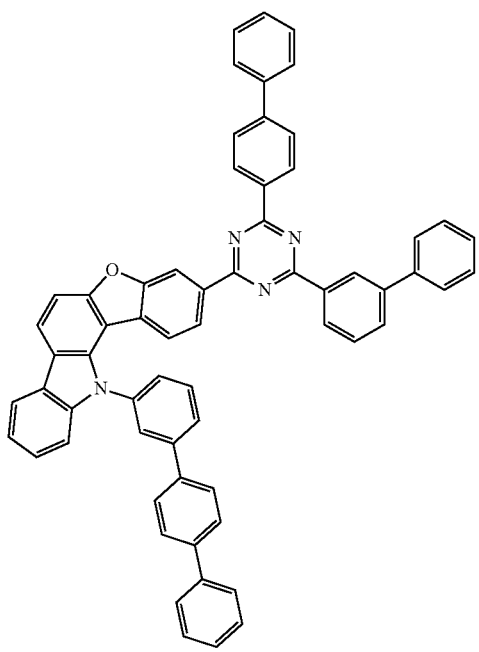
1F-3-15
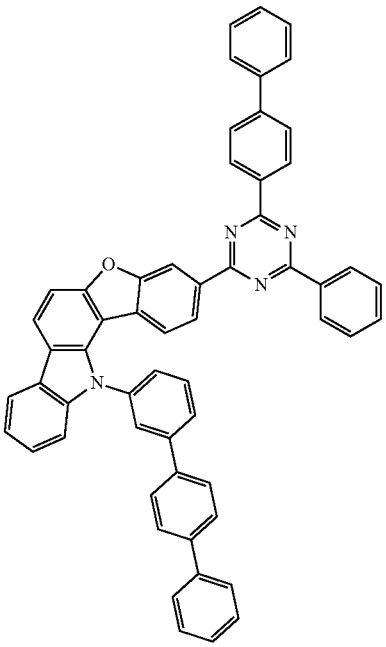
1F-3-14
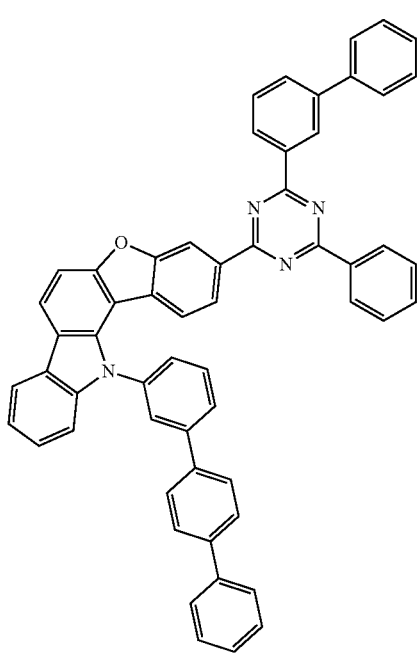
1F-3-16
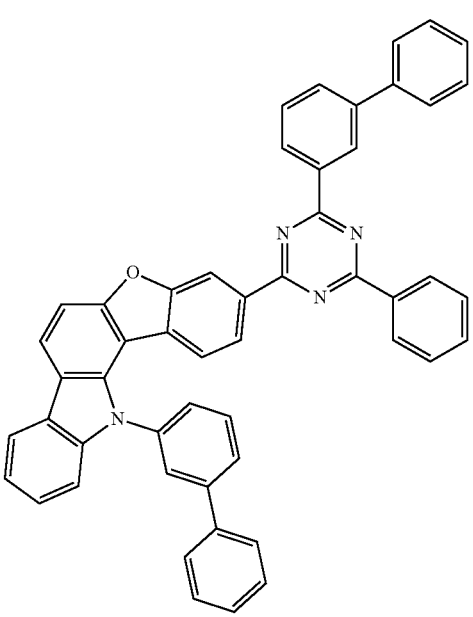

1F-3-17
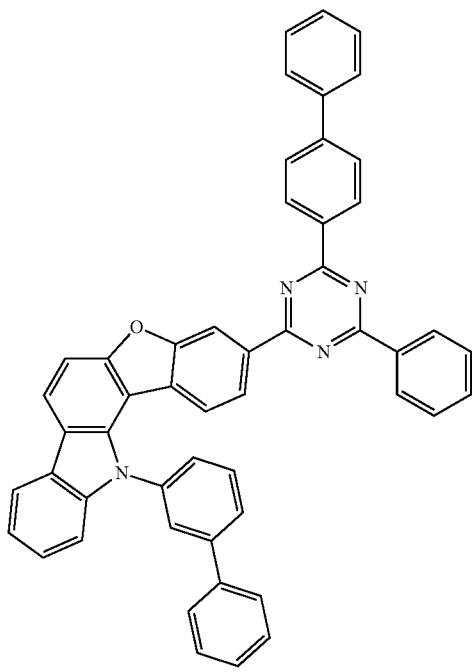
1F-3-19
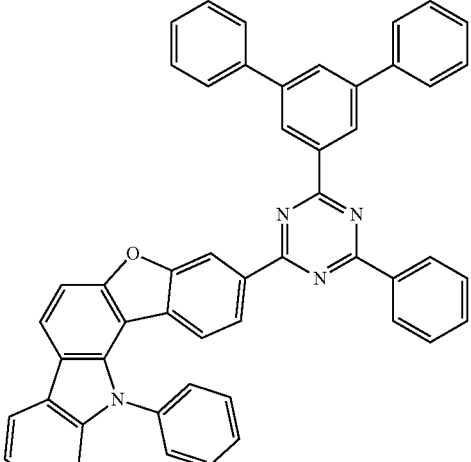
1F-3-20
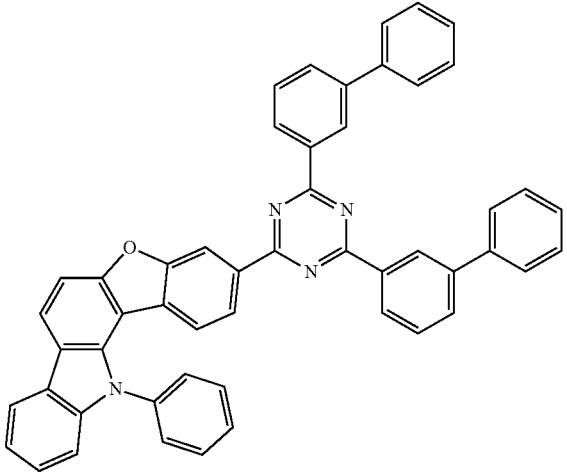
1F-3-18
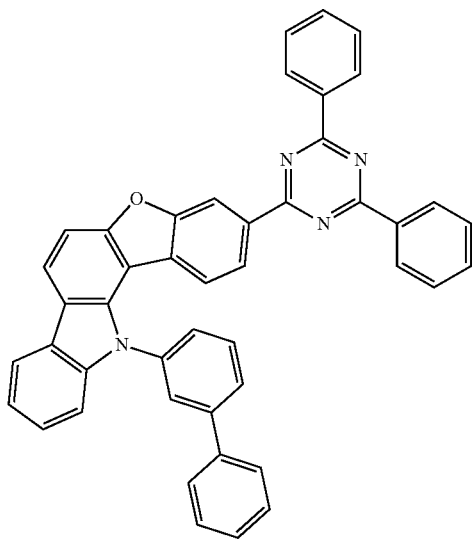
IE-3-21
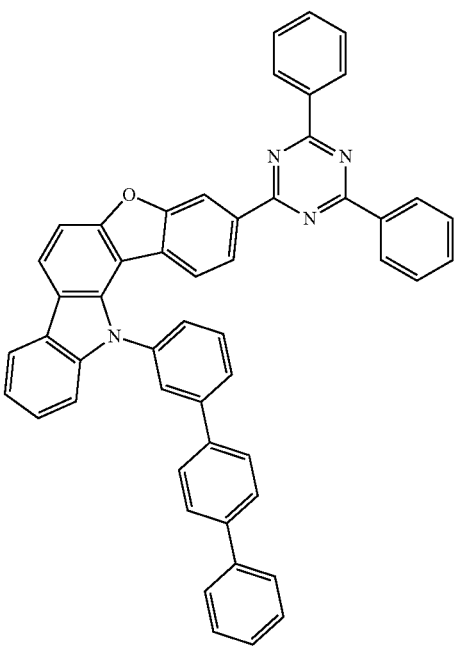

IE-3-22
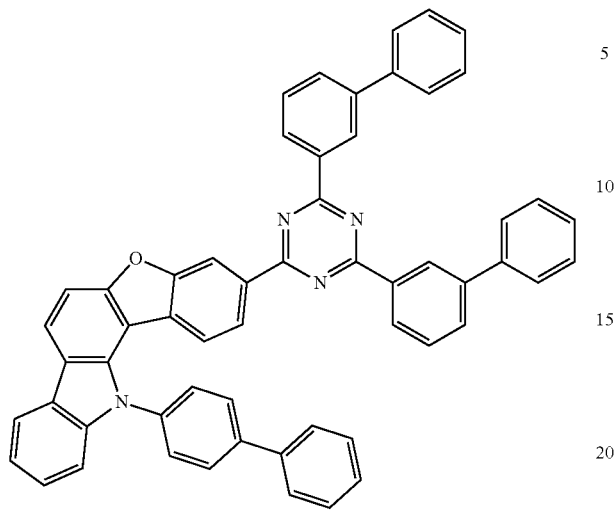
IE-3-25
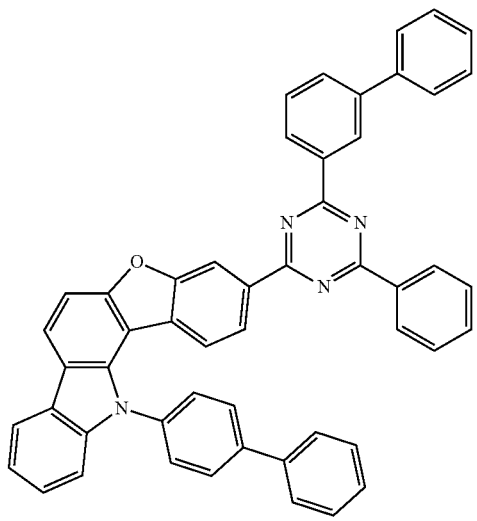
IE-3-23
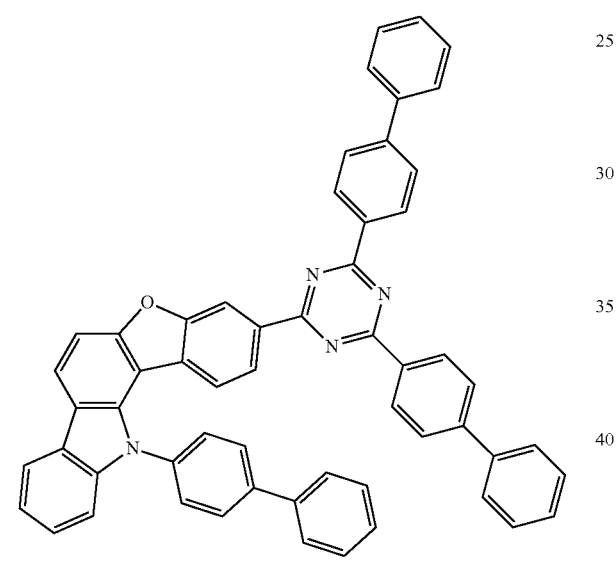
IE-3-24
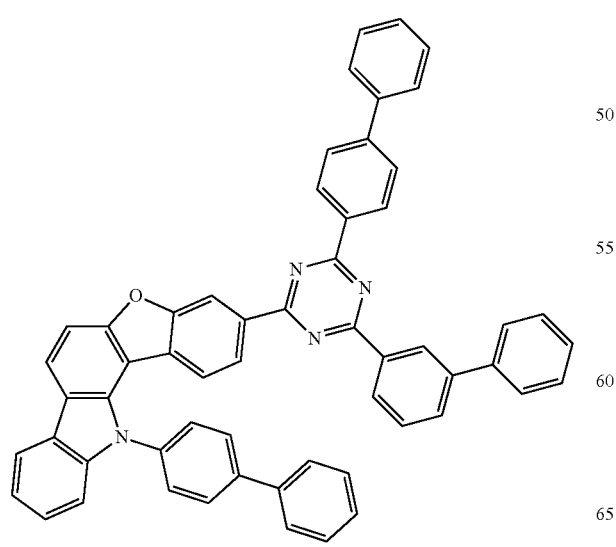
IF-3-26
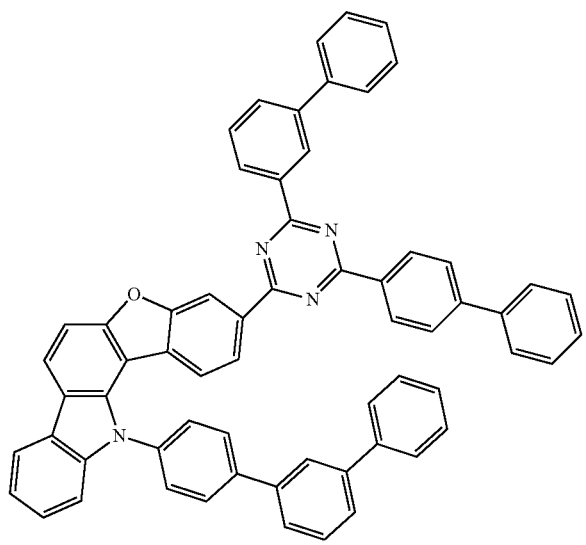

1F-3-27
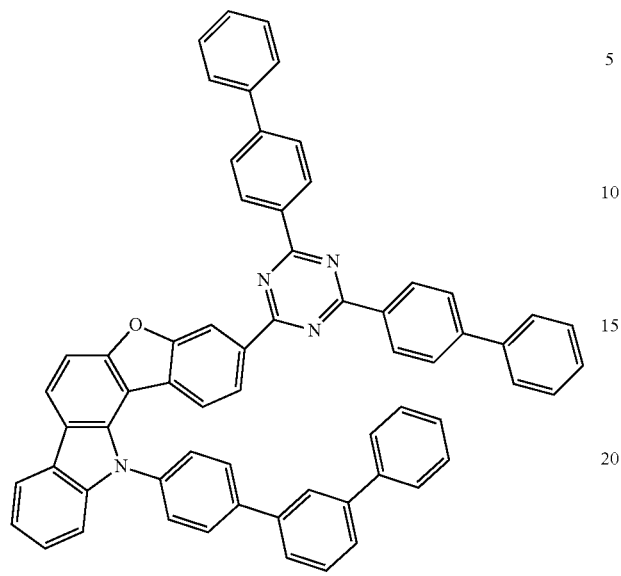
1F-3-28
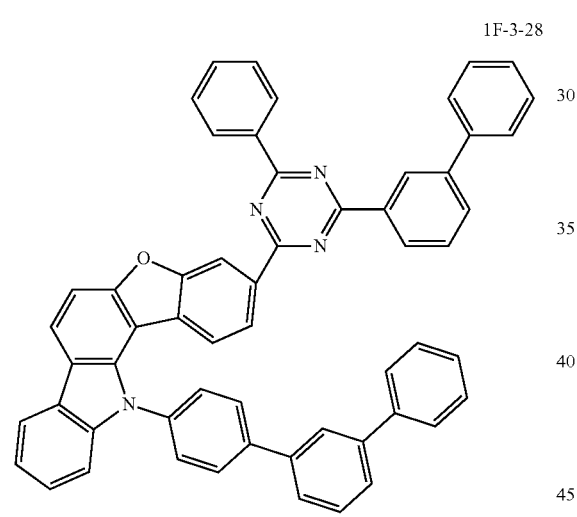
1F-3-29
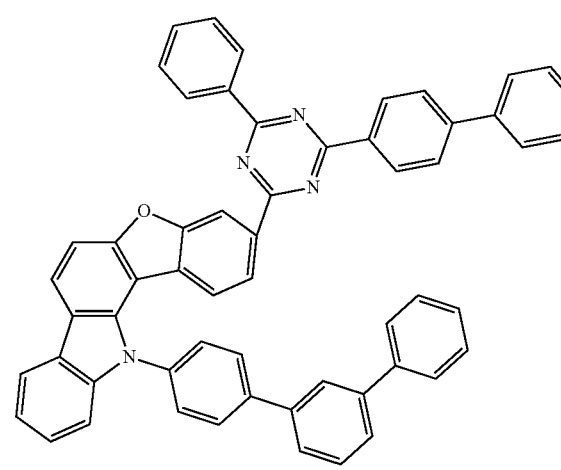
1F-3-30
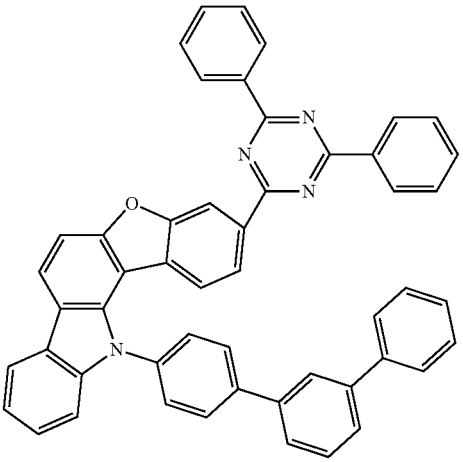
1F-3-31
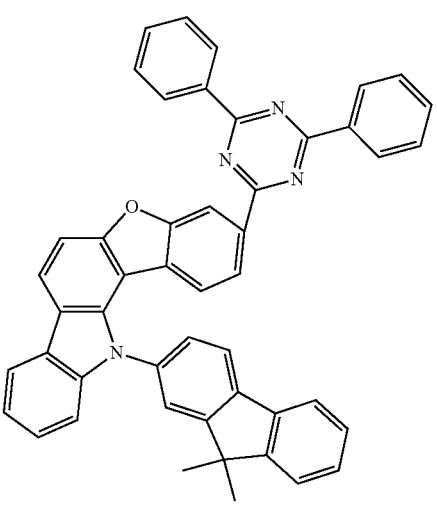
1F-3-32
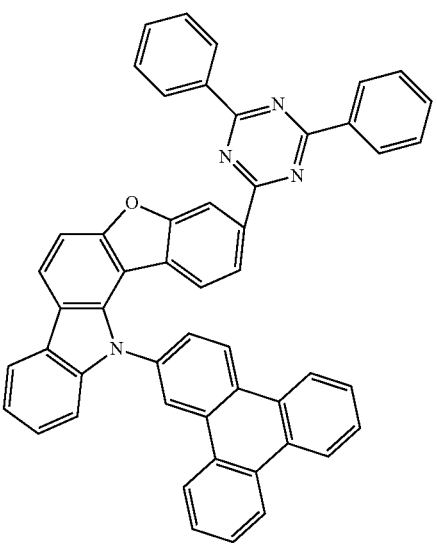

1F-3-33
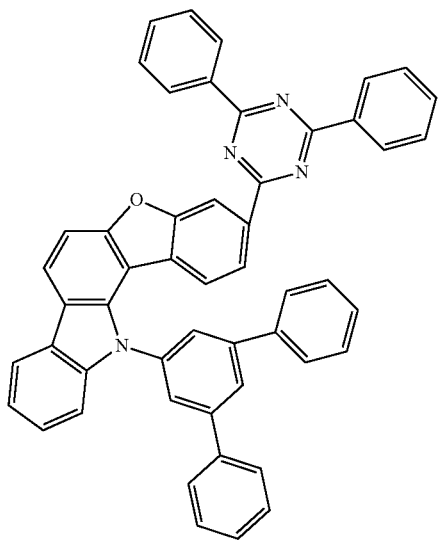
1F-3-34
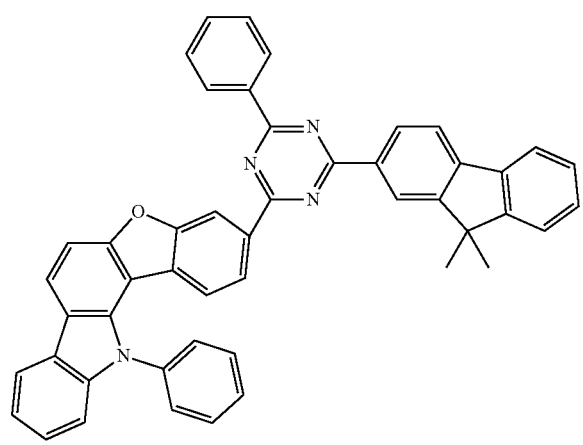
1F-3-35
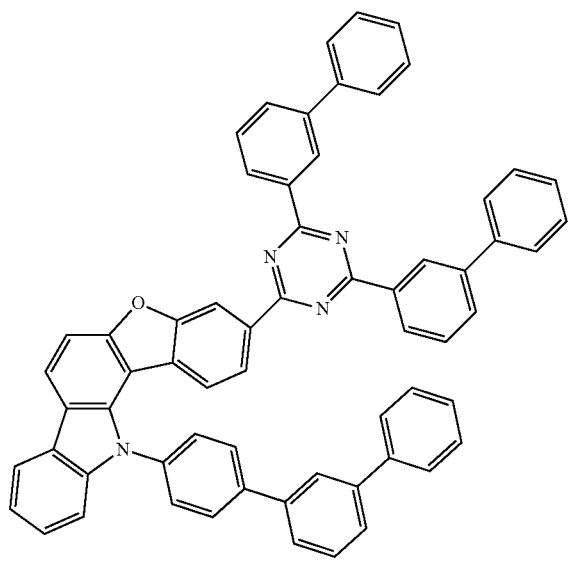
1F-3-36
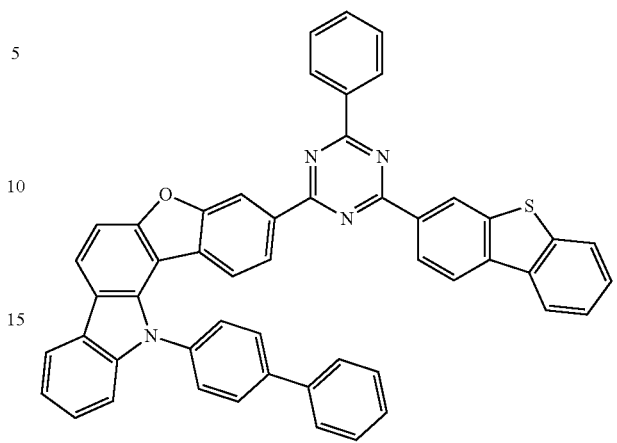
1F-3-37
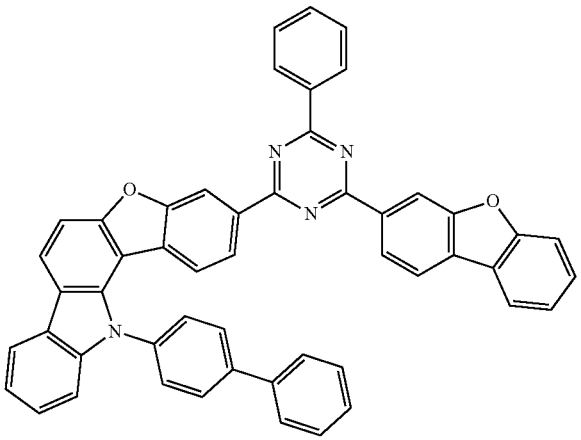
1F-3-38

1F-3-39
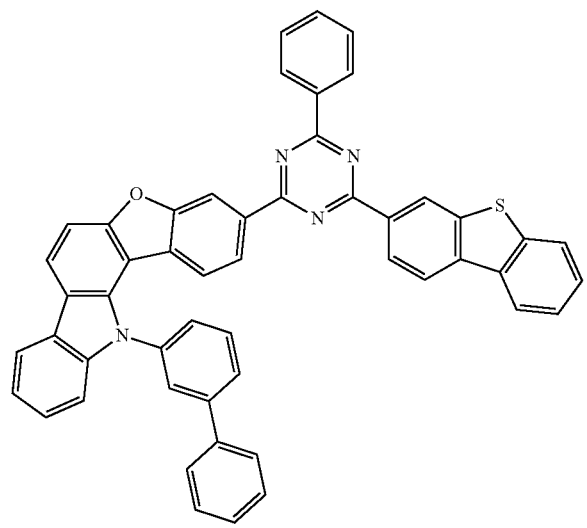
1F-3-40
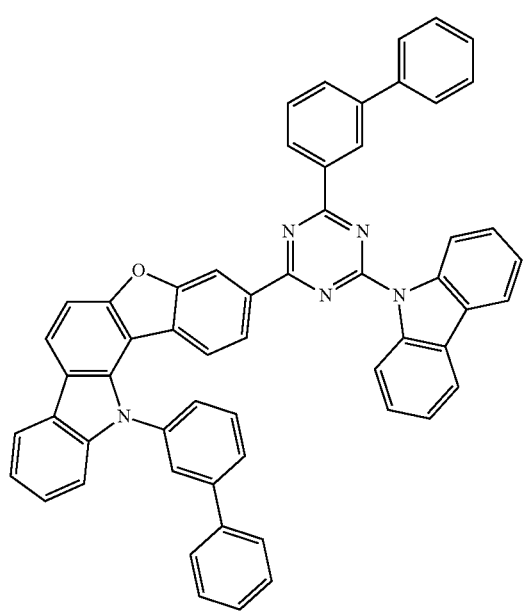
1F-3-41
1F-3-42
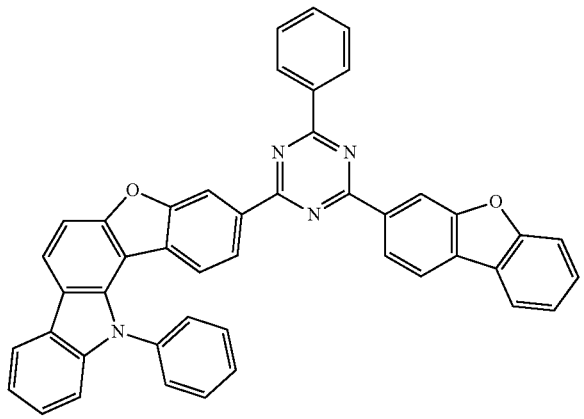
1F-3-43
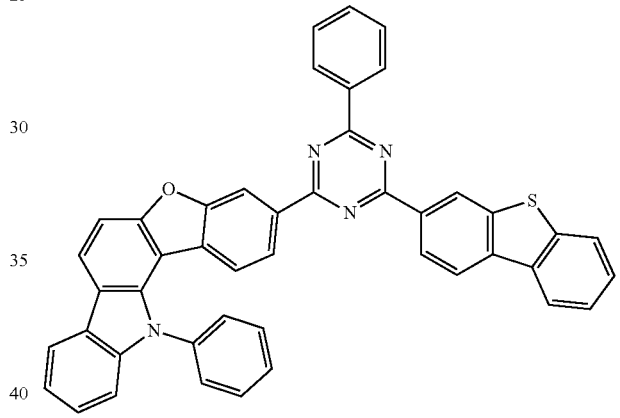
1F-3-44
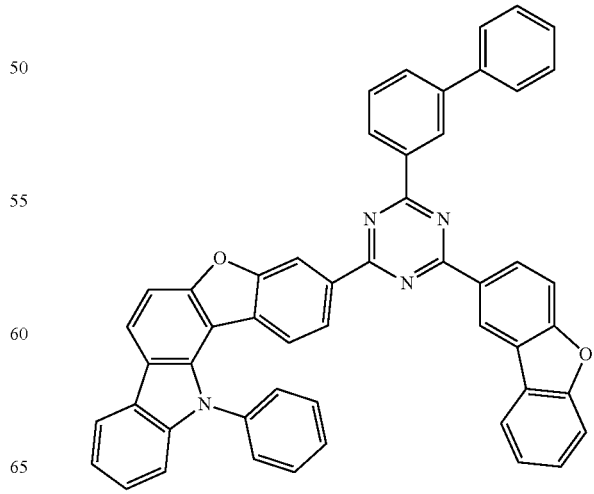

1F-3-45
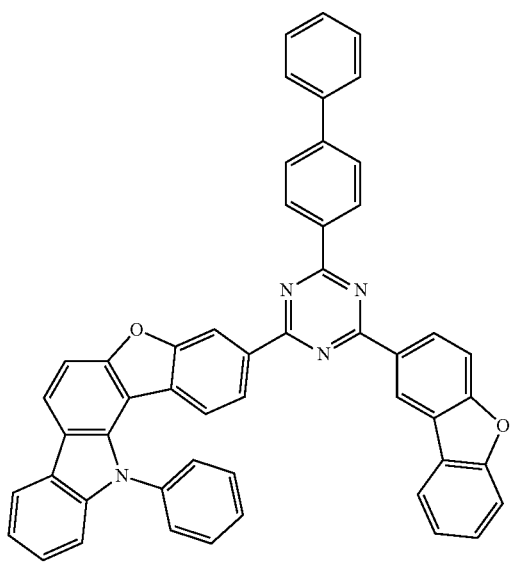
1F-3-47
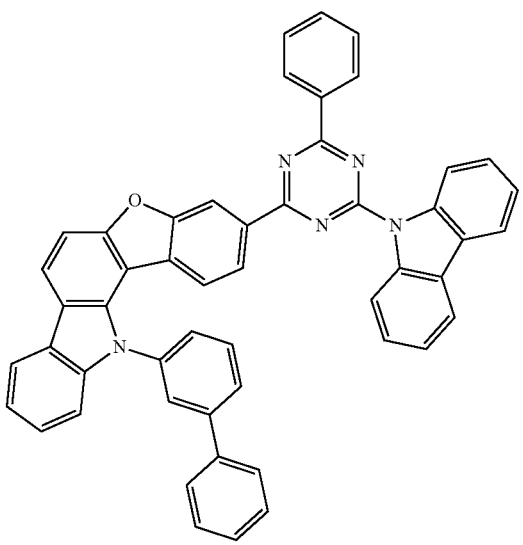
1F-3-48
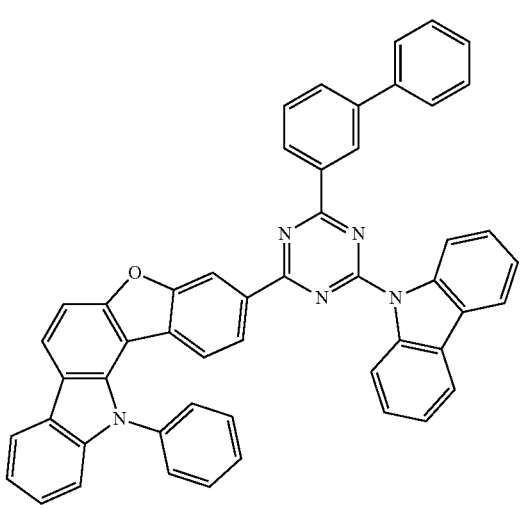
1F-3-46
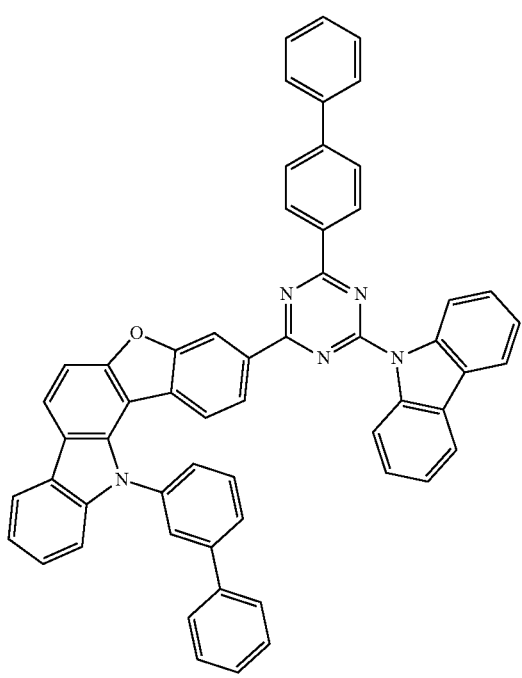
1F-3-49
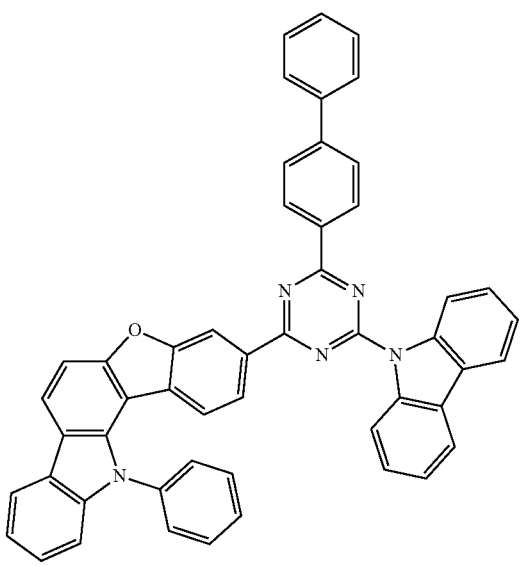

1F-3-50
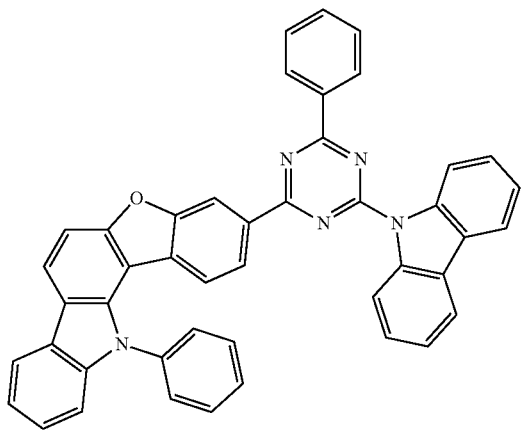
1F-3-51
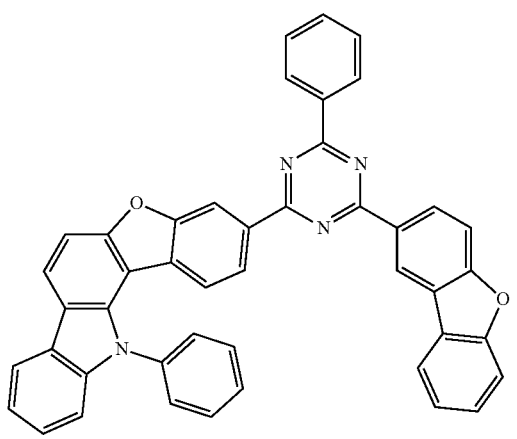
1F-3-52
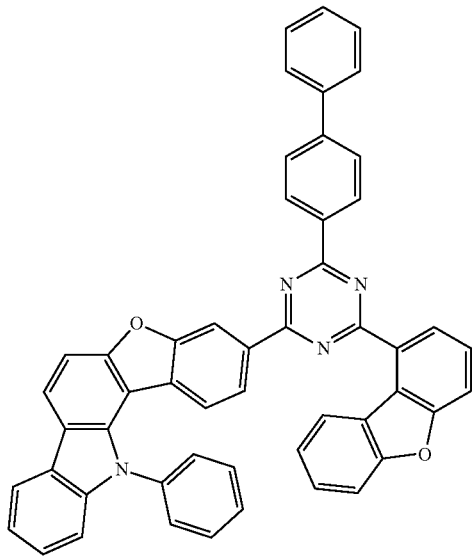
1F-3-53
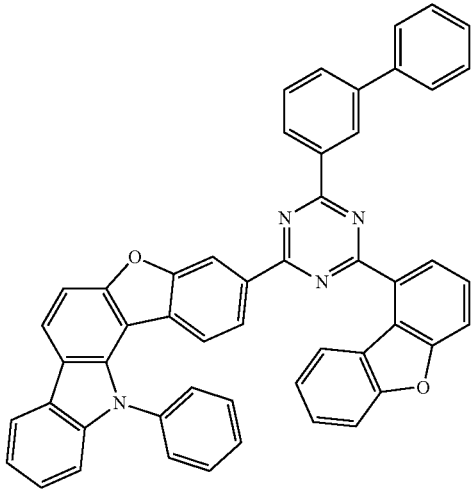
1F-3-54
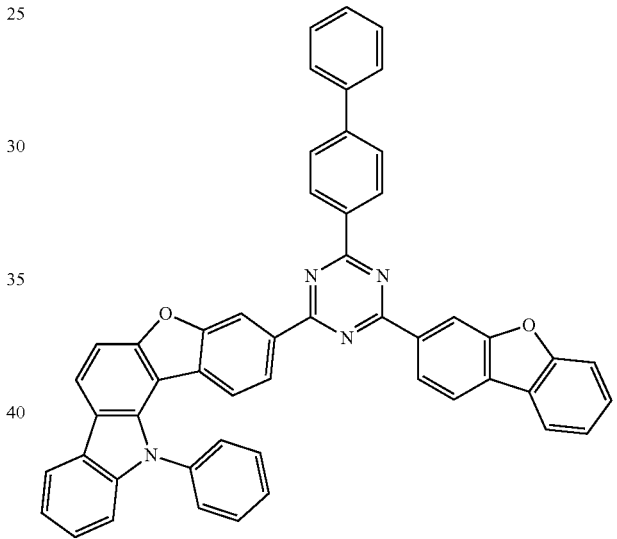
1F-3-55
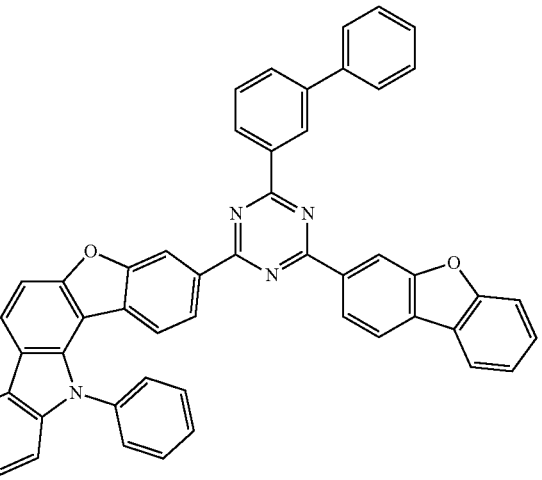

1F-3-56
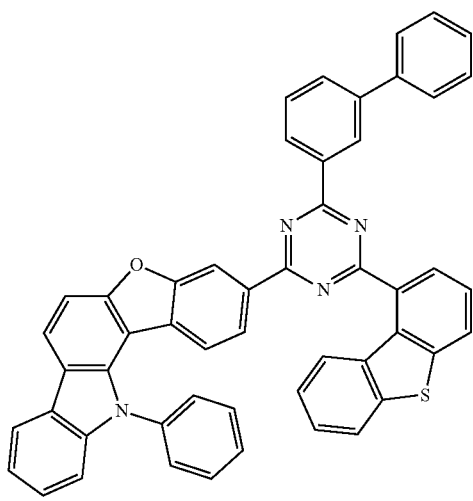
1F-3-57
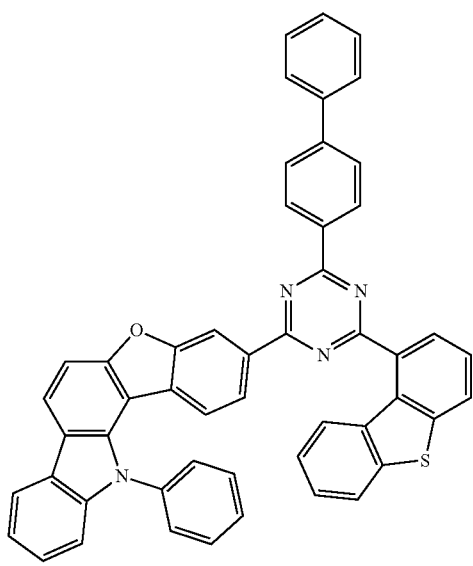
1F-3-58
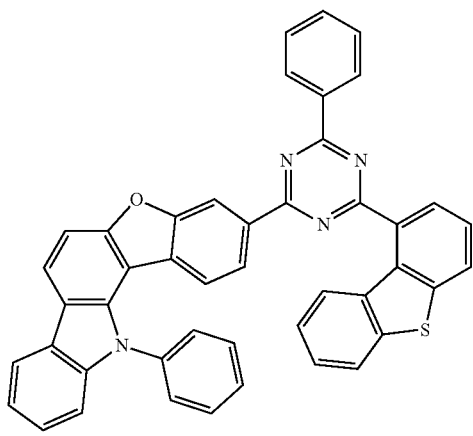
1F-3-59
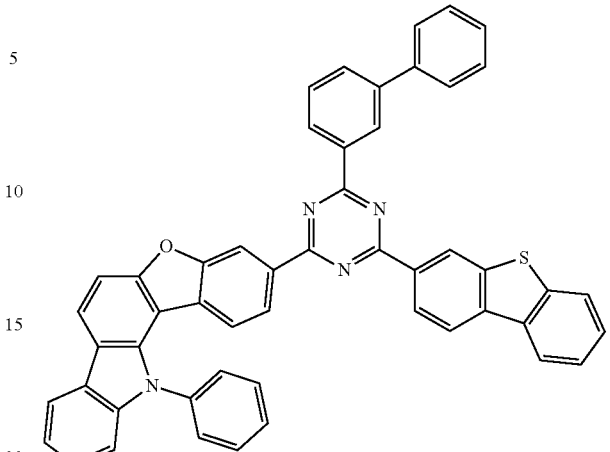
1F-3-60
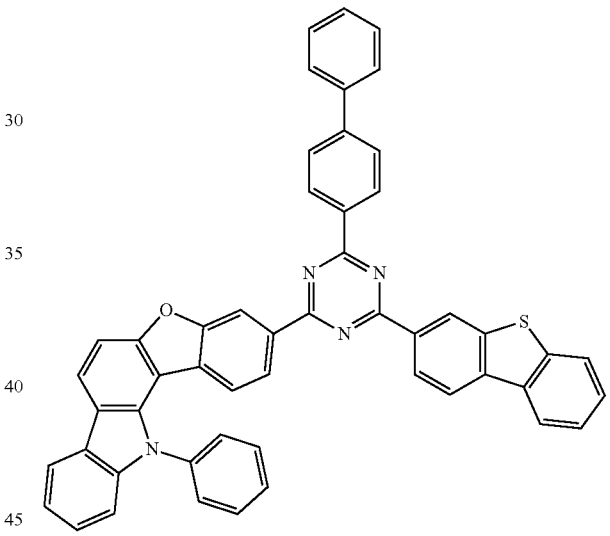
1F-3-61
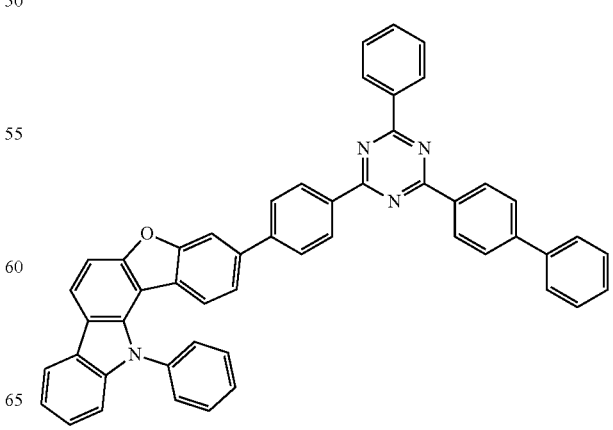

-continued
1F-3-62
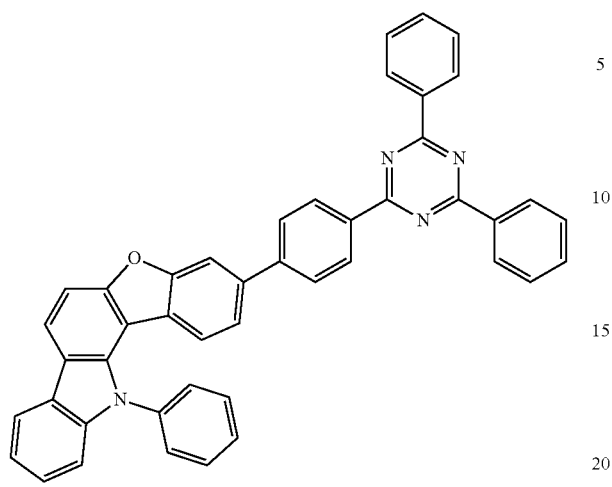
1F-3-63
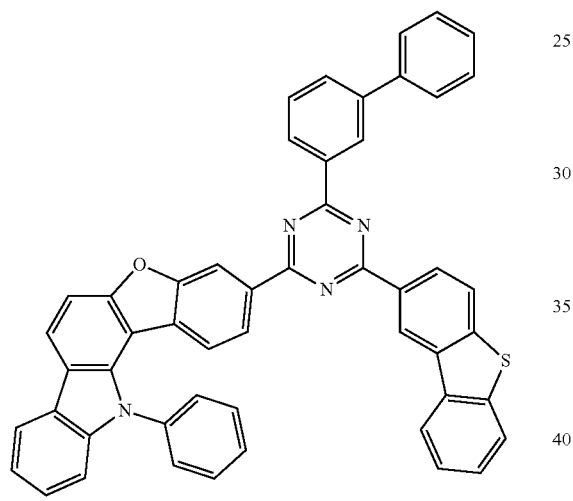
1F-3-64
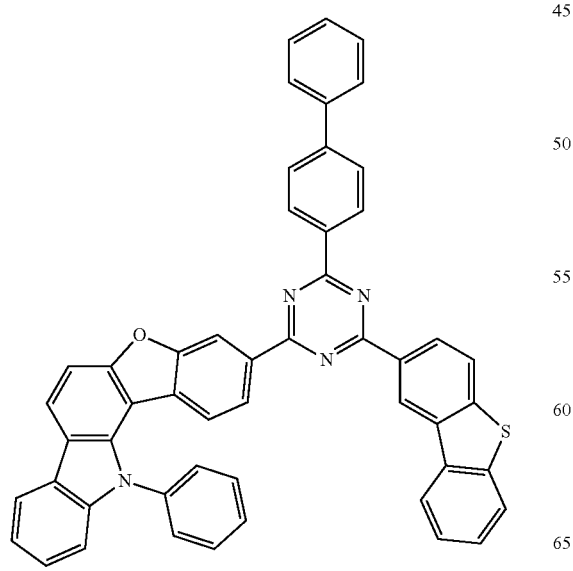
-continued
1F-3-65
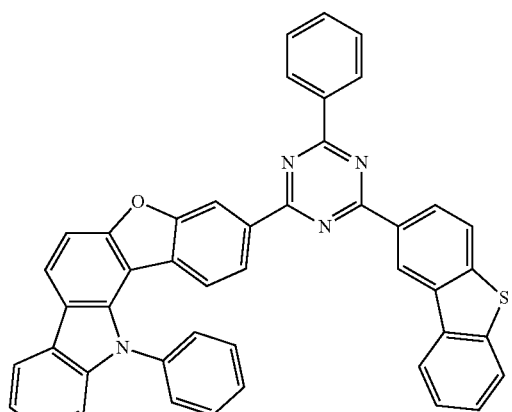
1F-3-66
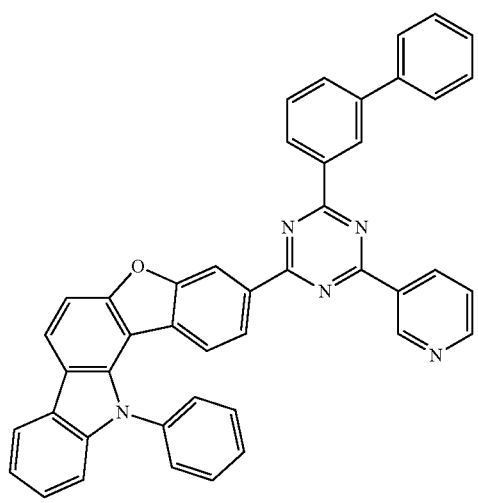
1F-3-67
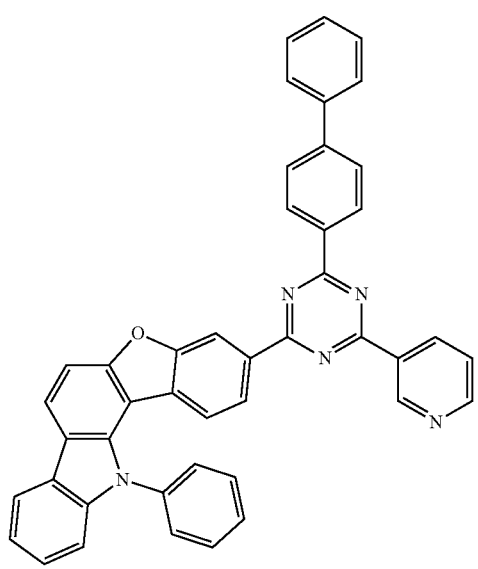

1F-3-68
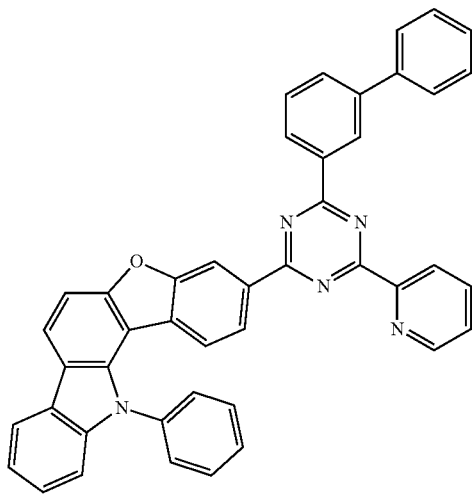
1F-3-69
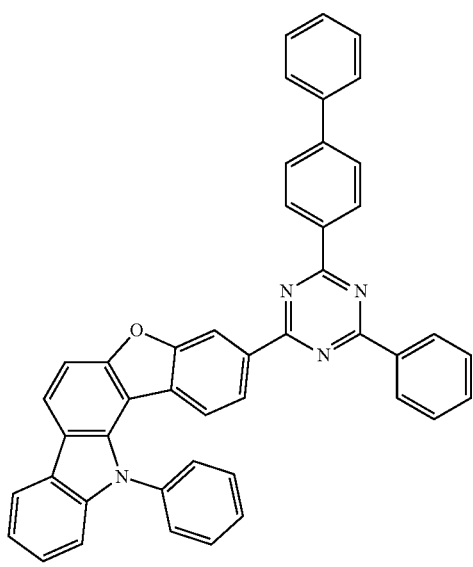
1F-3-70
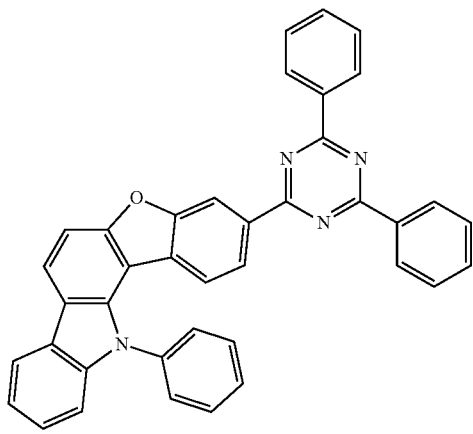
1F-3-71
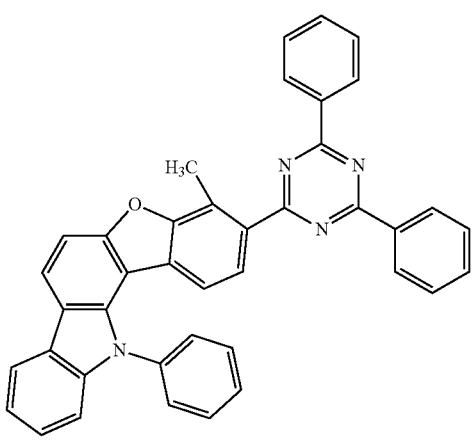
1F-3-72
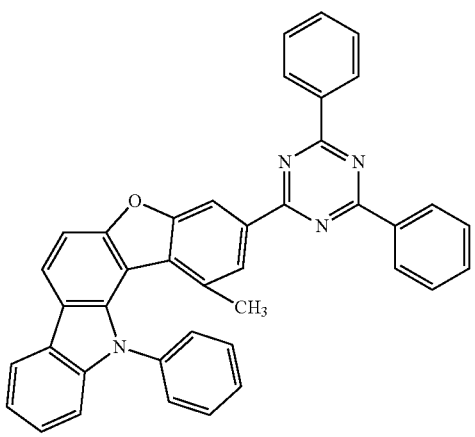
1F-3-73
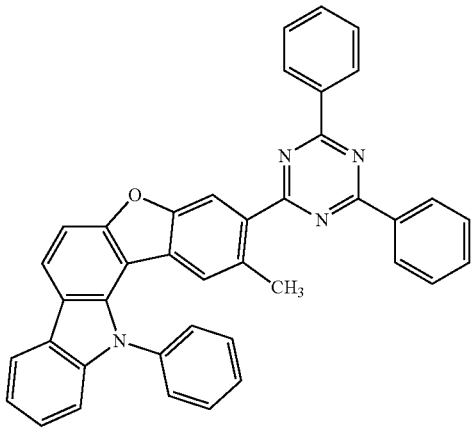

-continued
1F-3-74
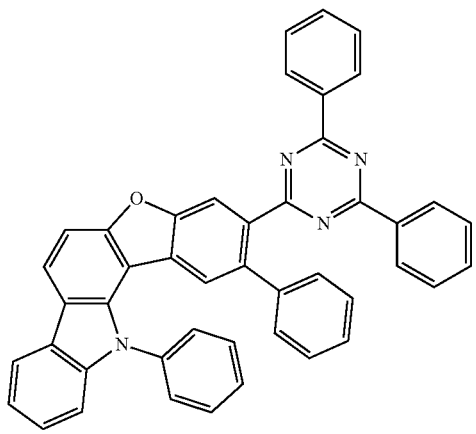
1F-3-75
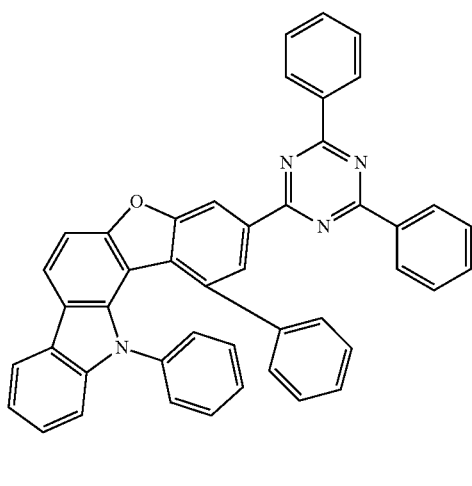
1F-3-76
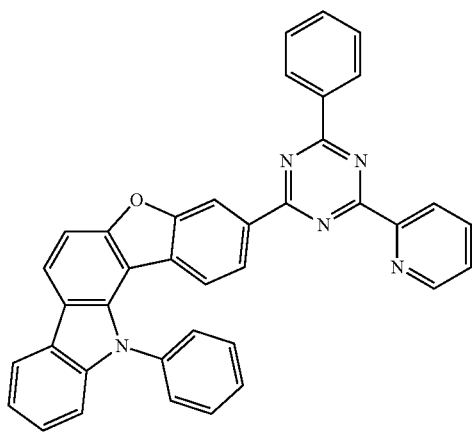
-continued
1F-3-77
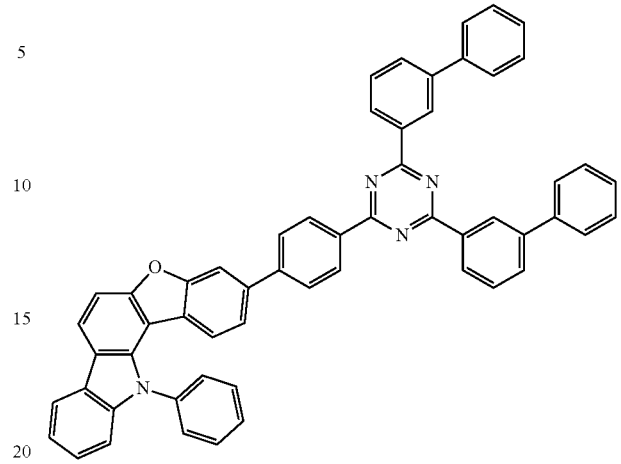
1F-3-78
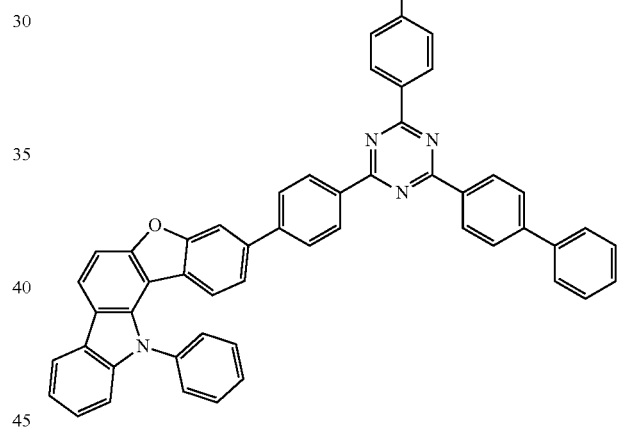
1F-3-79
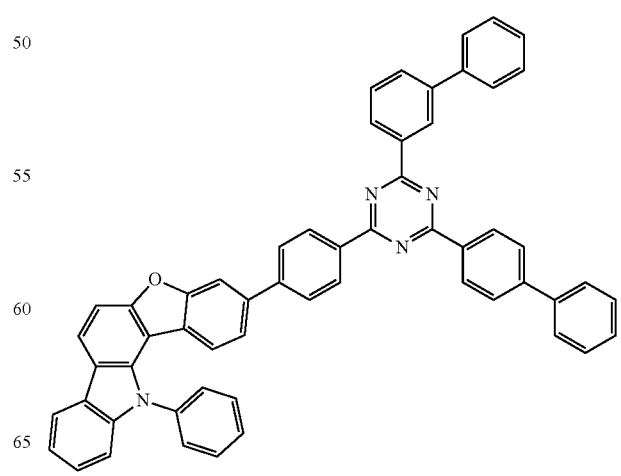

1F-3-80
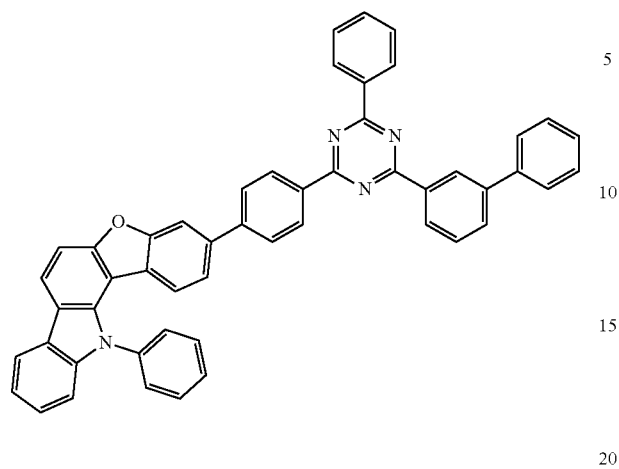
1F-3-83
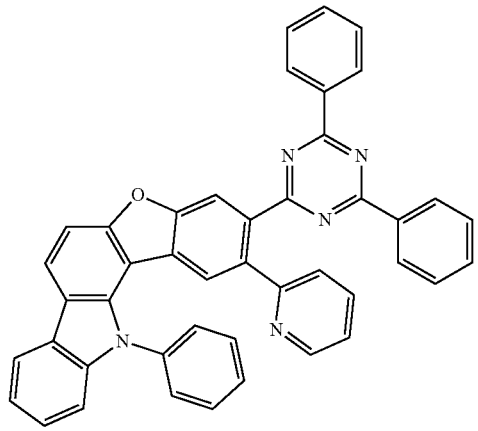
1F-3-81
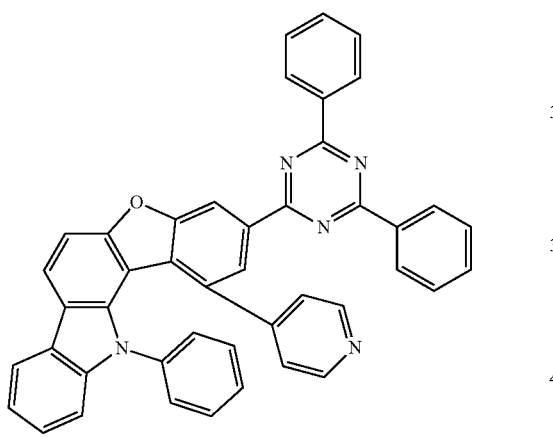
1F-4-1
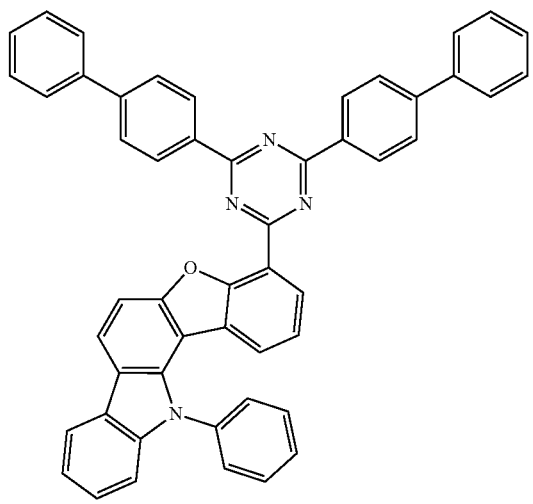
1F-3-82
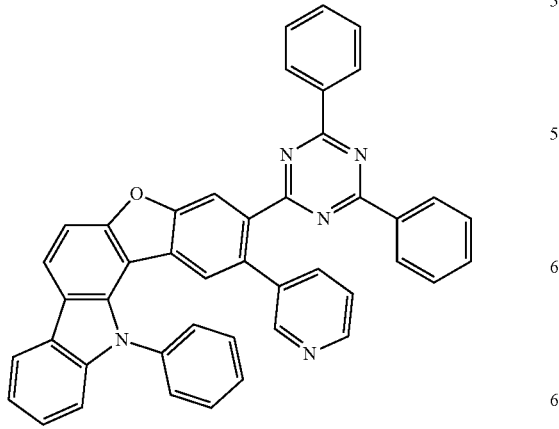
1F-4-2
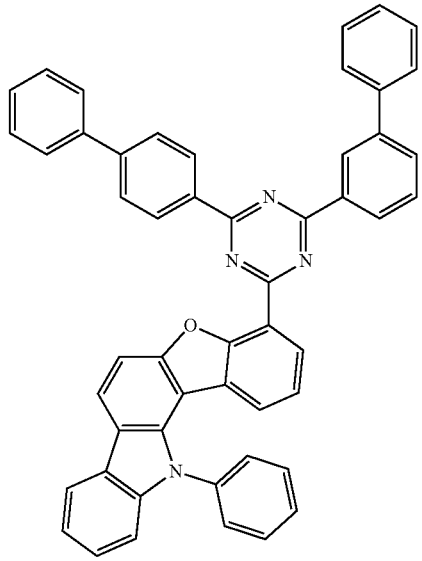

1F-4-3
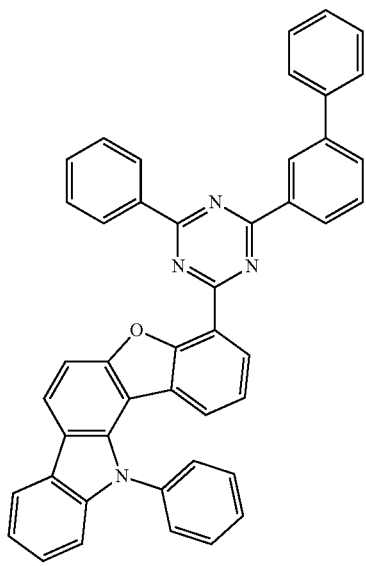
1F-4-4
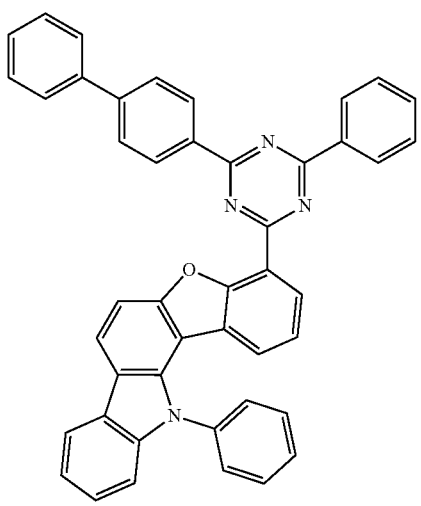
1F-4-5
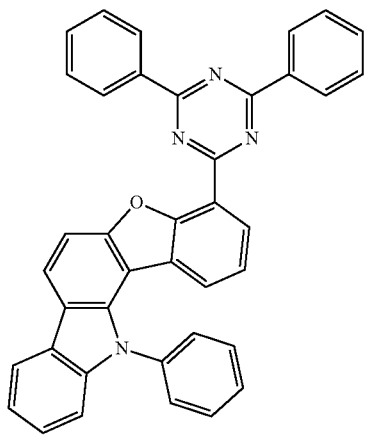
1F-4-6
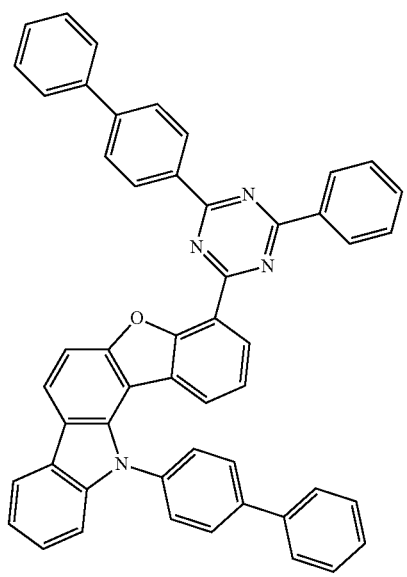
1F-4-7
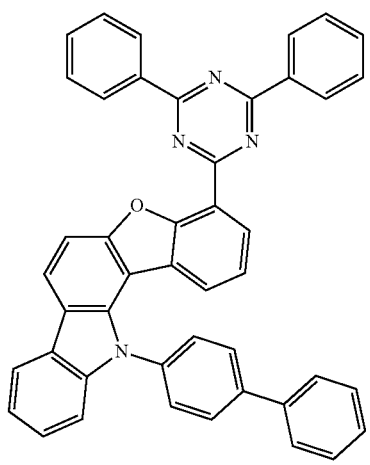

717
-continued
1F-4-8
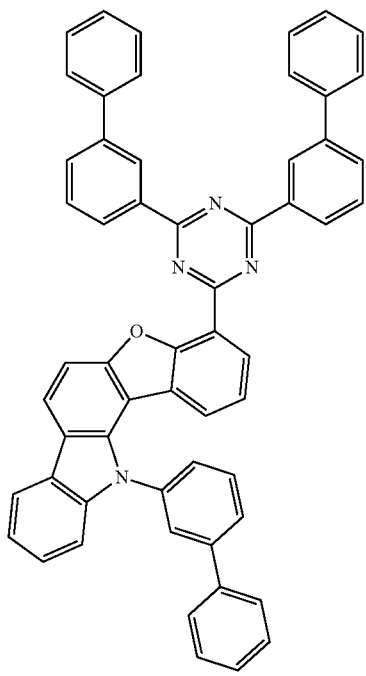
1F-4-9
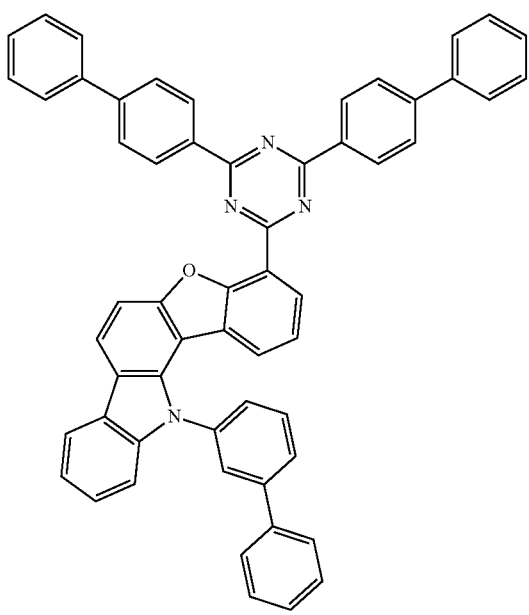
718
-continued
1F-4-10
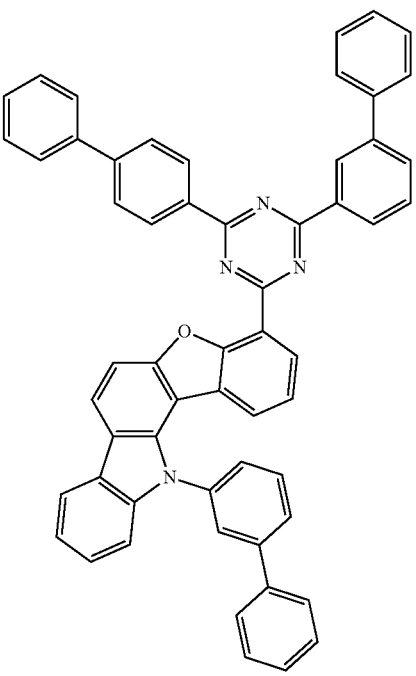
1F-4-11
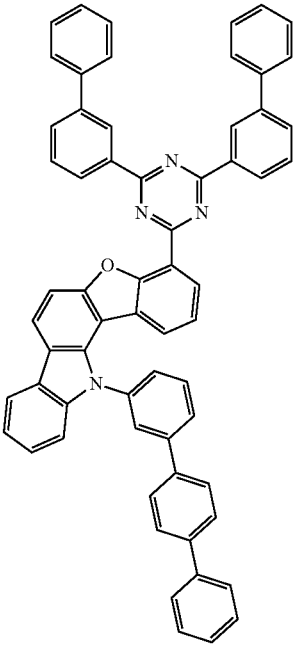

1F-4-12
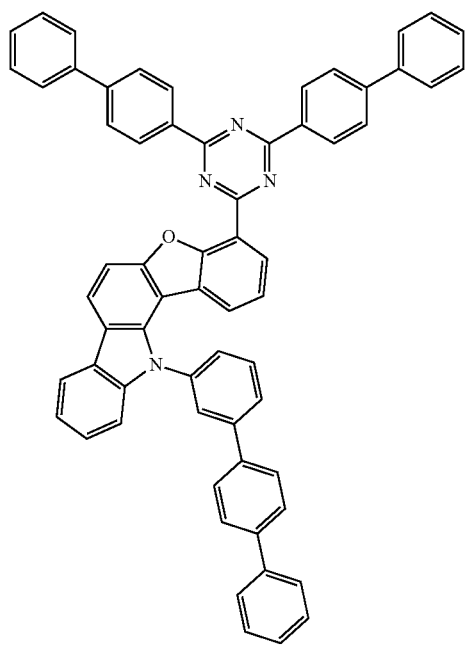
1F-4-13
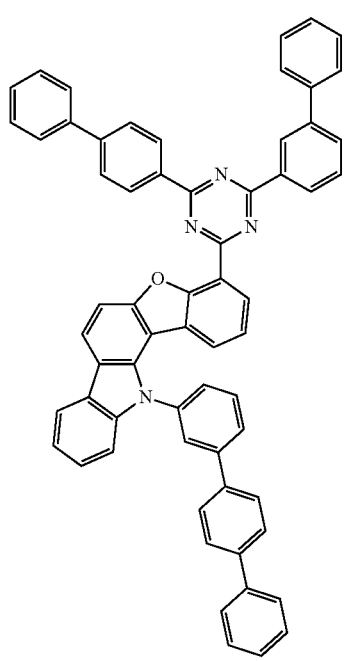
1F-4-14
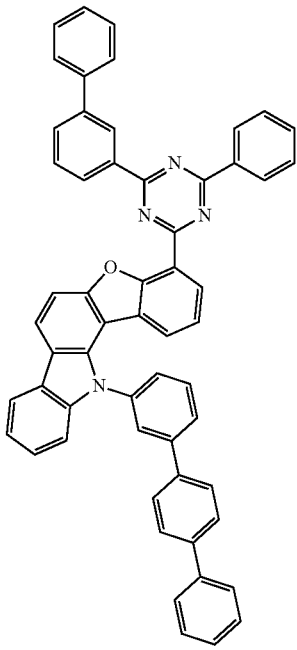
1F-4-15
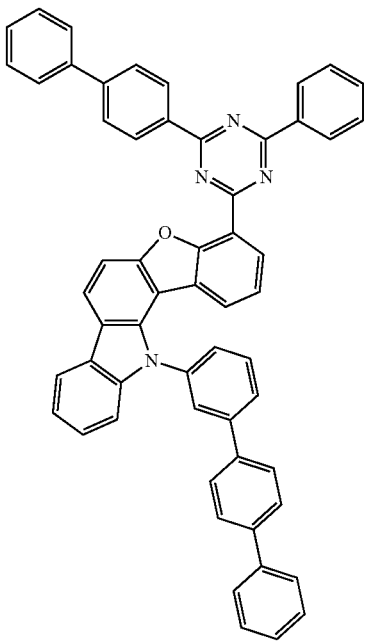

721
-continued
1F-4-16
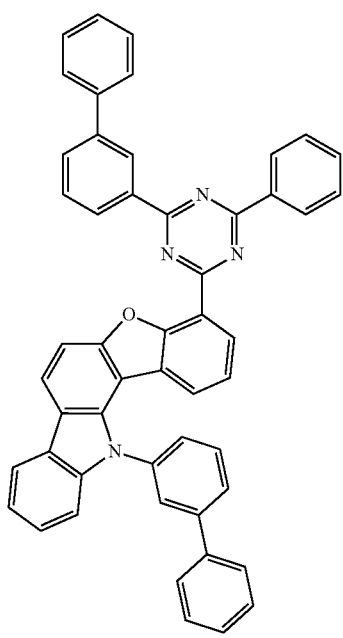
722
-continued
1F-4-18
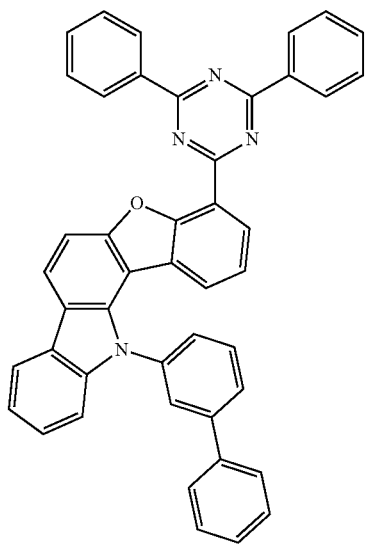
1F-4-17
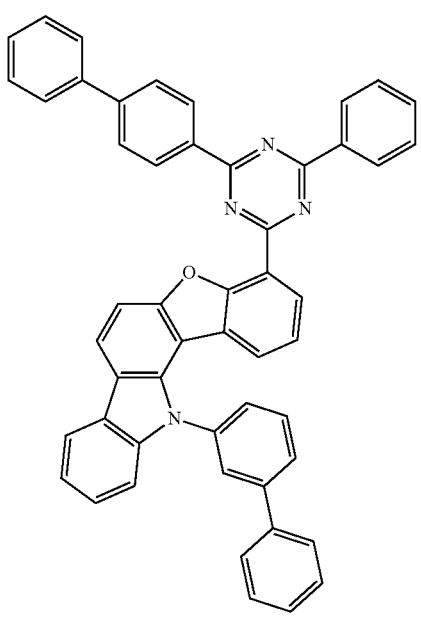
1F-4-19
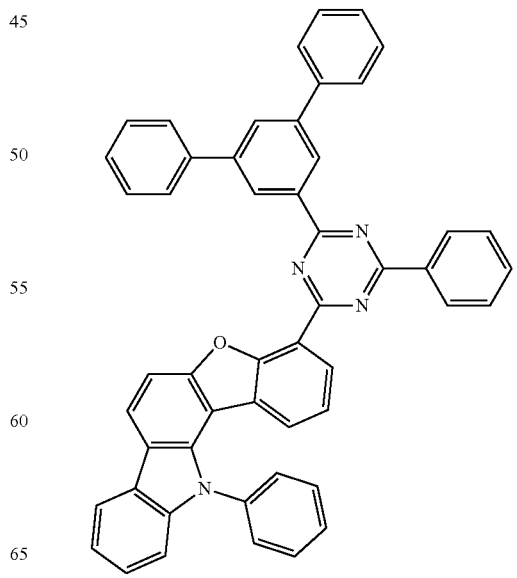

-continued
1F-4-20
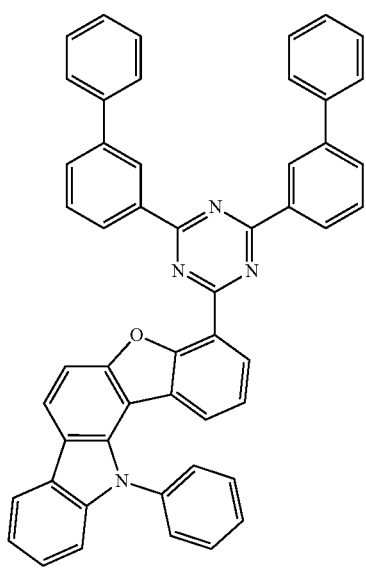
1F-4-21
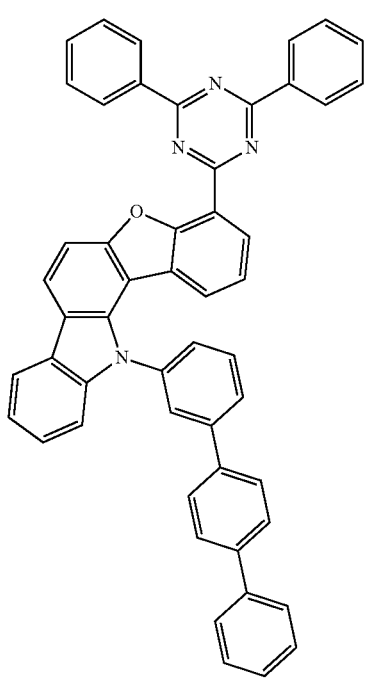
-continued
1F-4-22
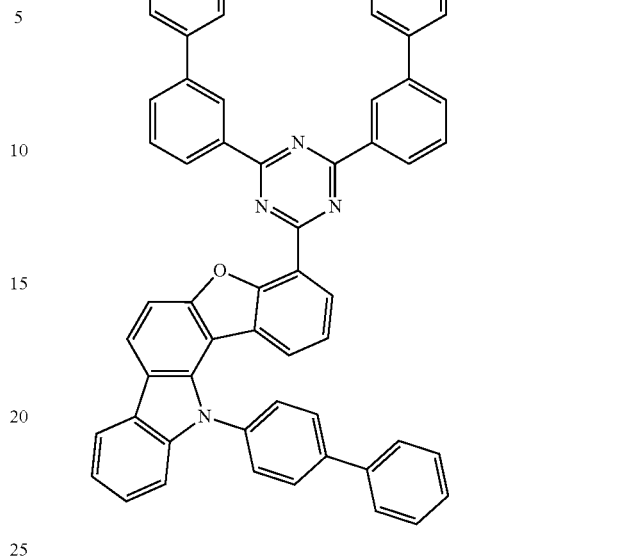
1F-4-23
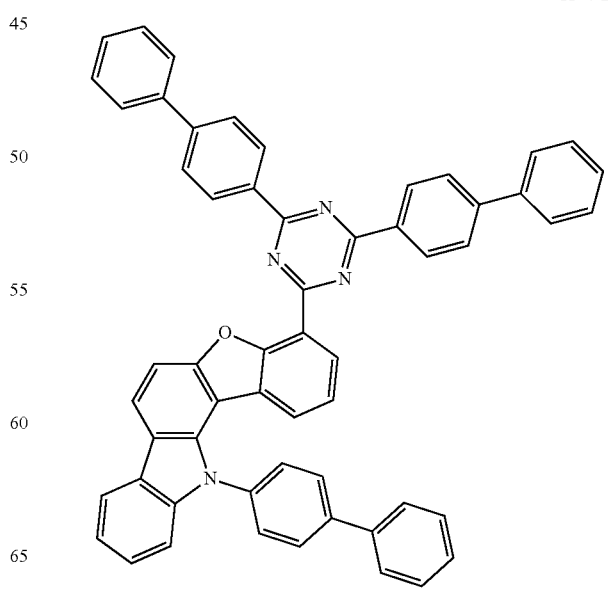

1F-4-24
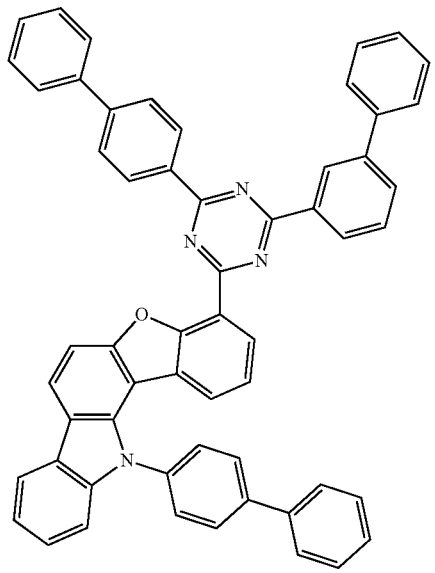
1F-4-26
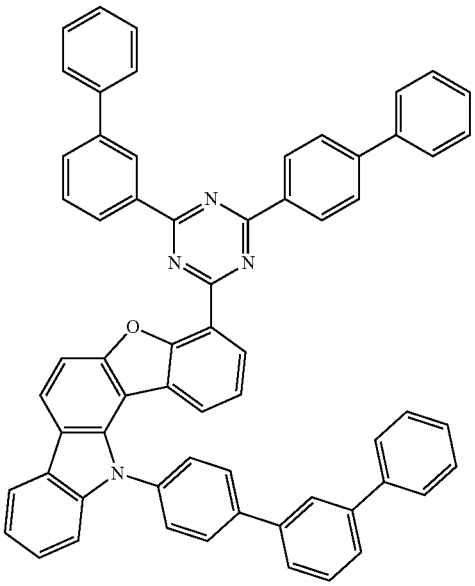
1F-4-25
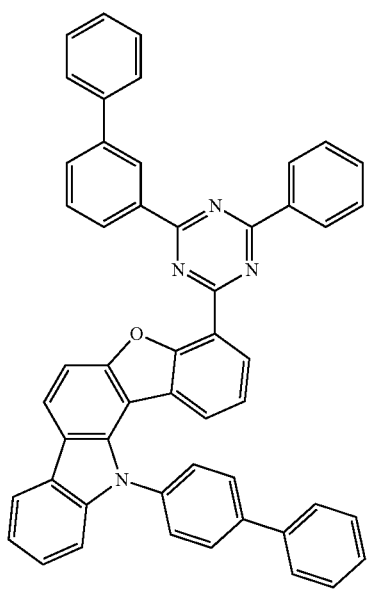
1F-4-27
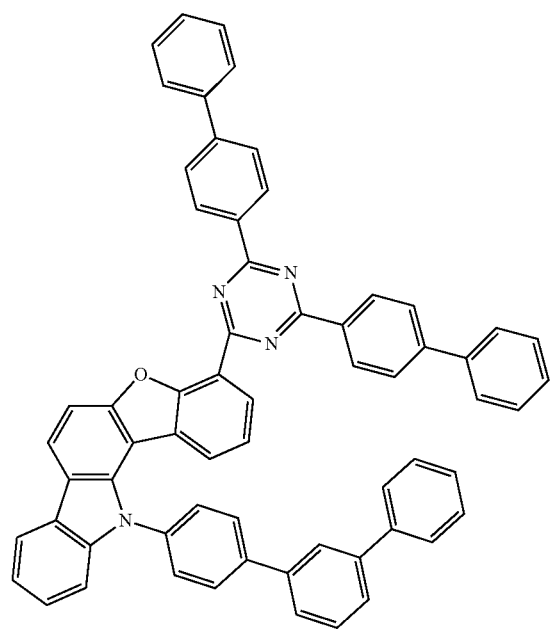

1F-4-28
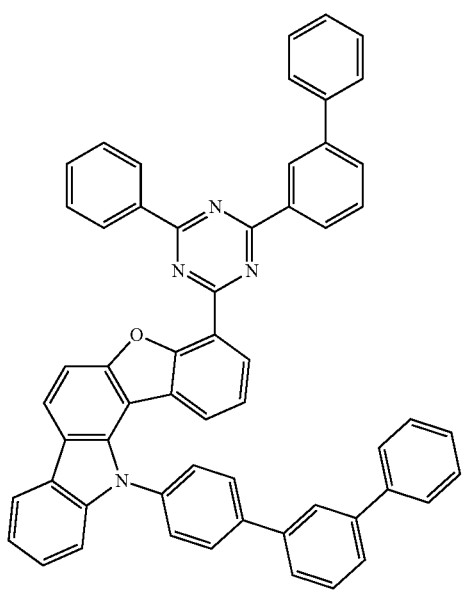
1F-4-29
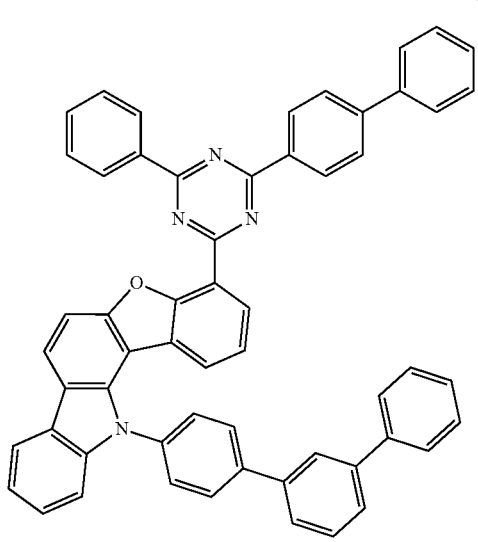
1F-4-30
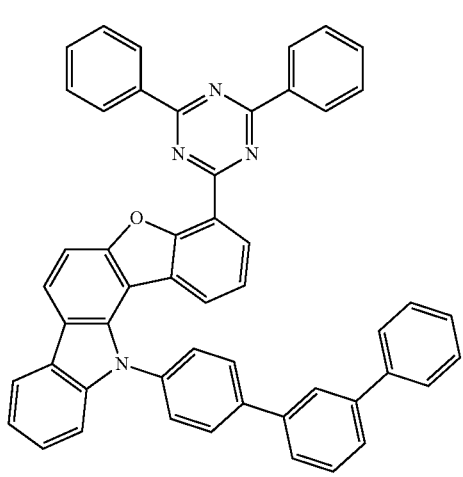
1F-4-31
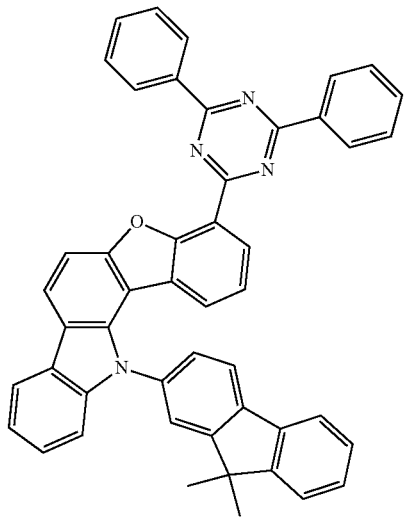
1F-4-32
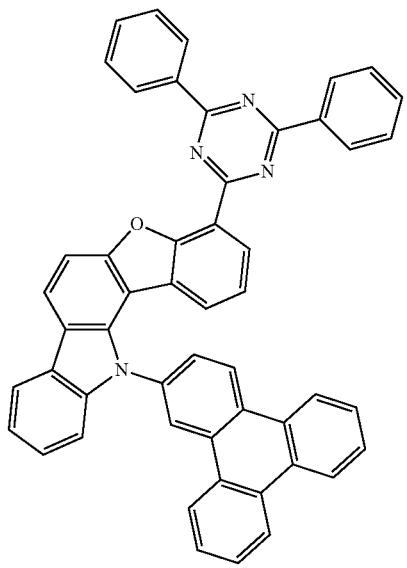
1F-4-33
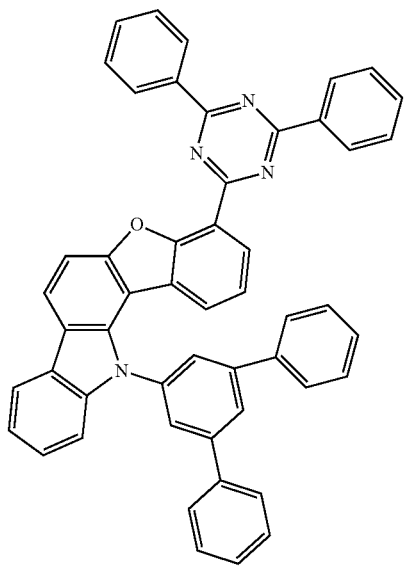

1F-4-34
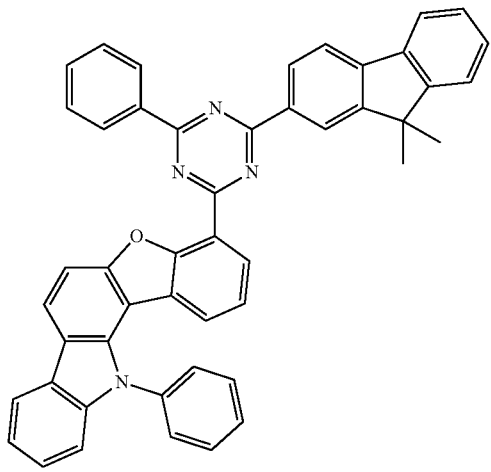
1F-4-35
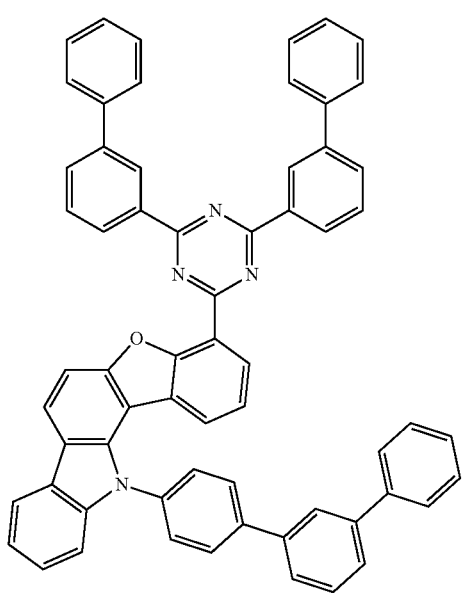
1F-4-36
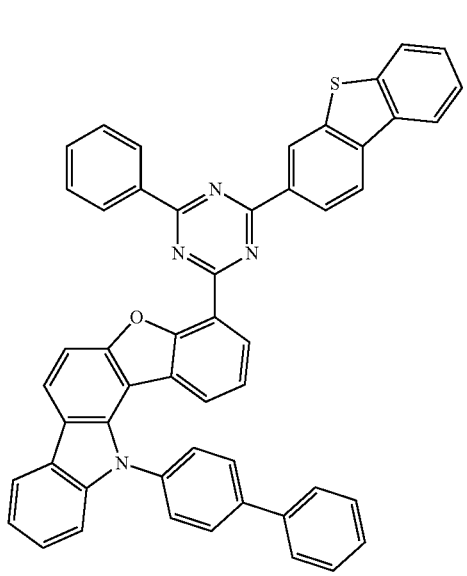
1F-4-37
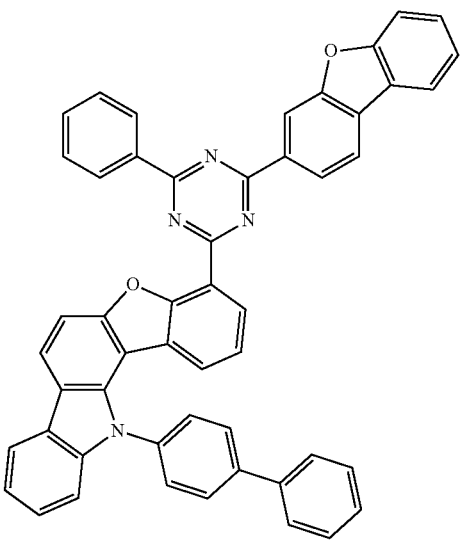
1F-4-38
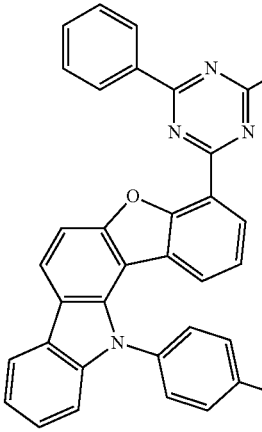

1F-4-39
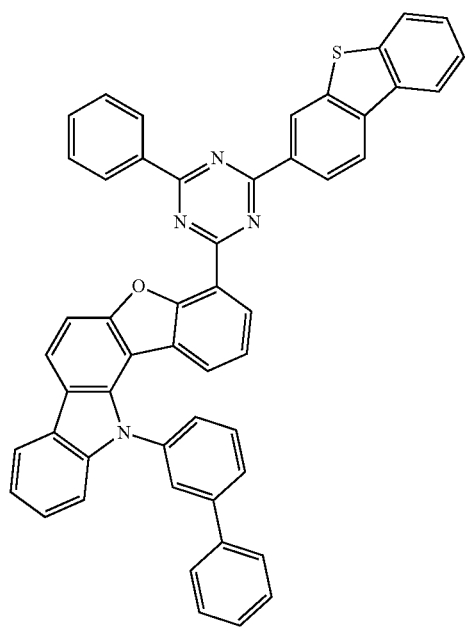
1F-4-40
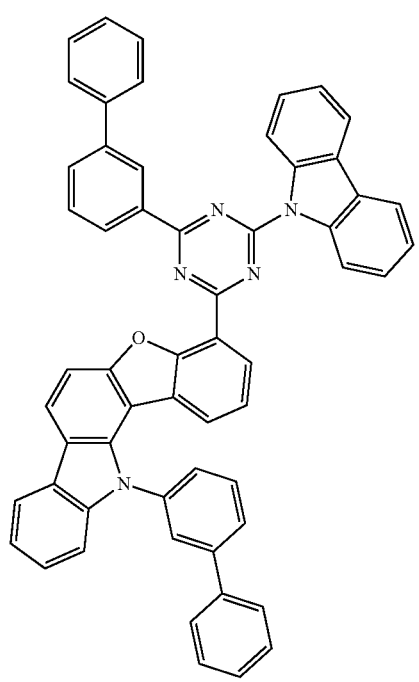
1F-4-41
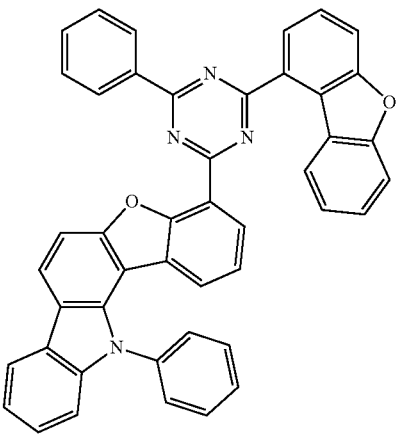
1F-4-42
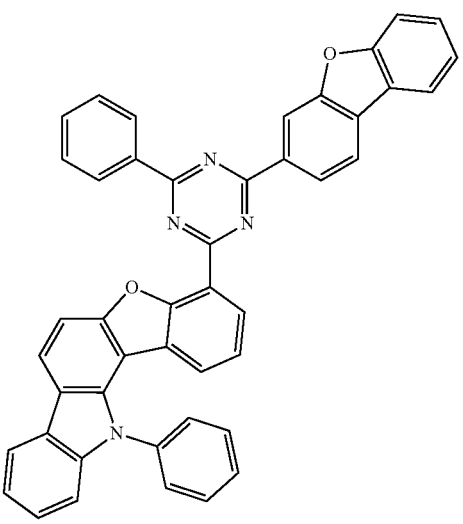
1F-4-43
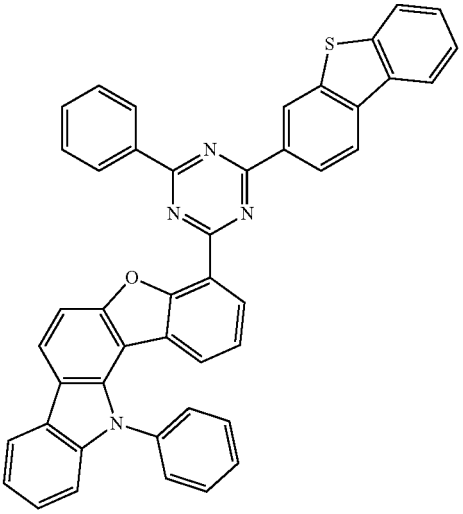

1F-4-44
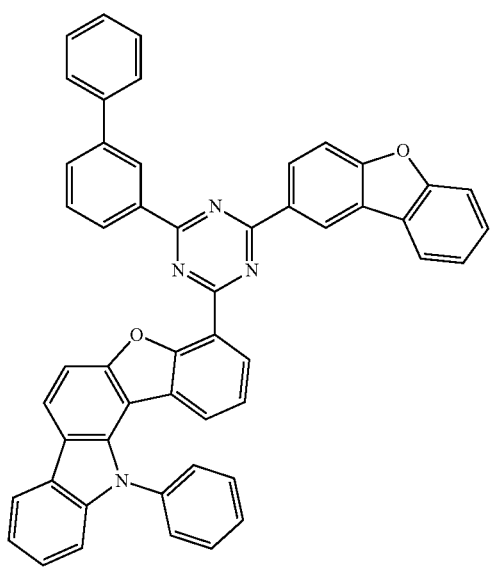
1F-4-45
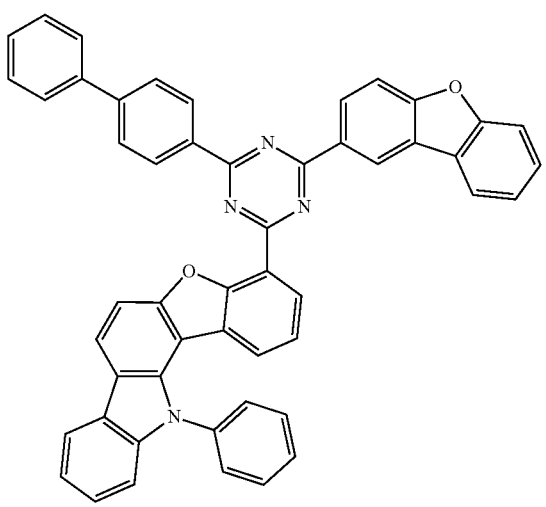
1F-4-46
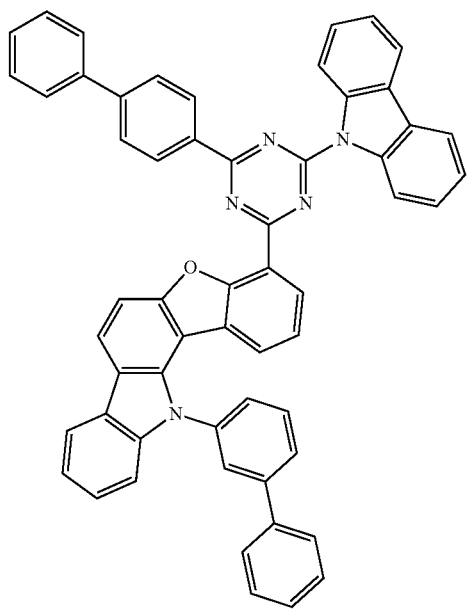
1F-4-47
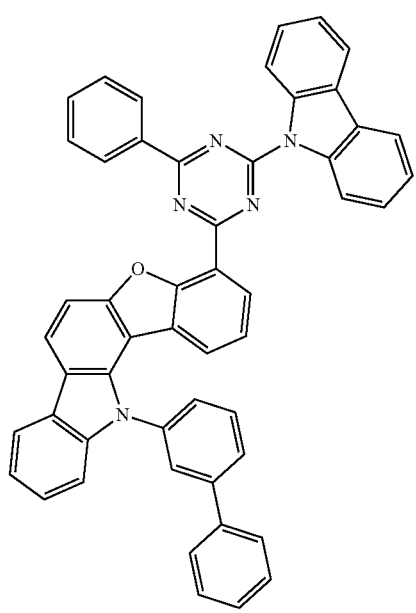

735
-continued
1F-4-48
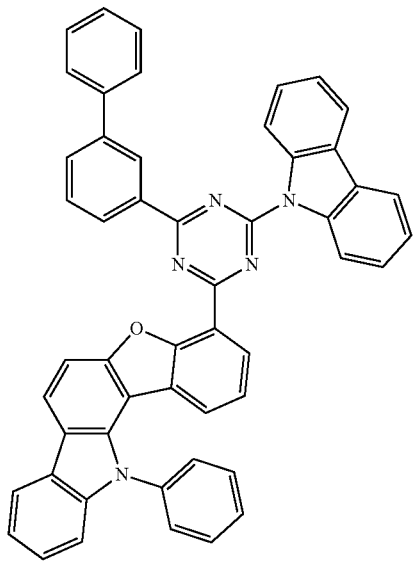
1F-4-49
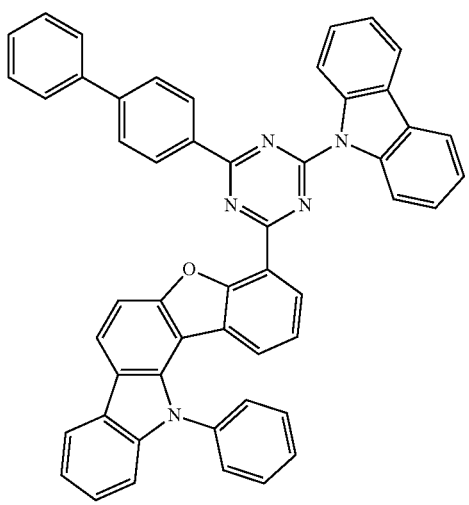
1F-4-50
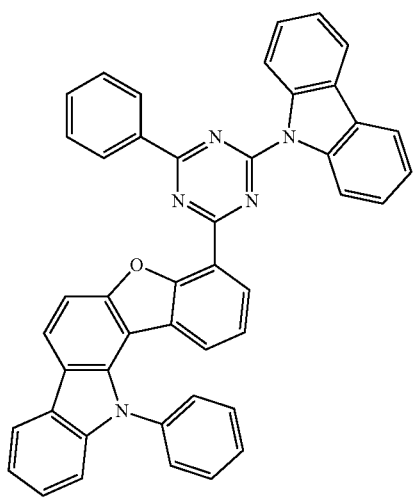
736
-continued
1F-4-51
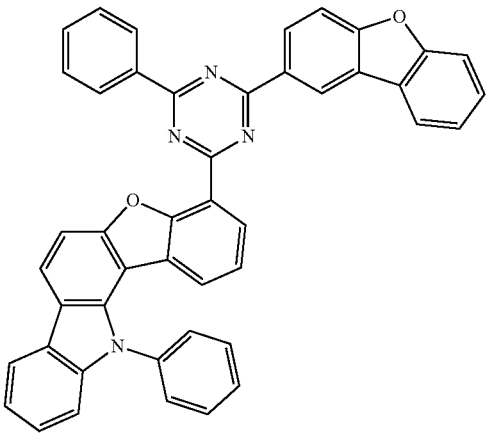
1F-4-52
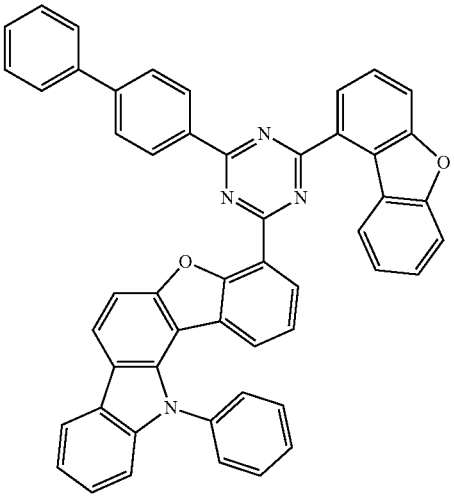
1F-4-53
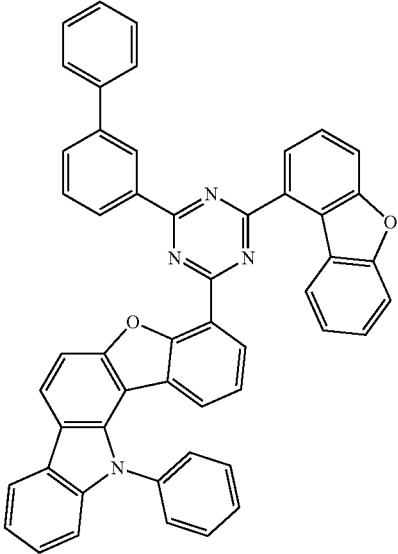

1F-4-54
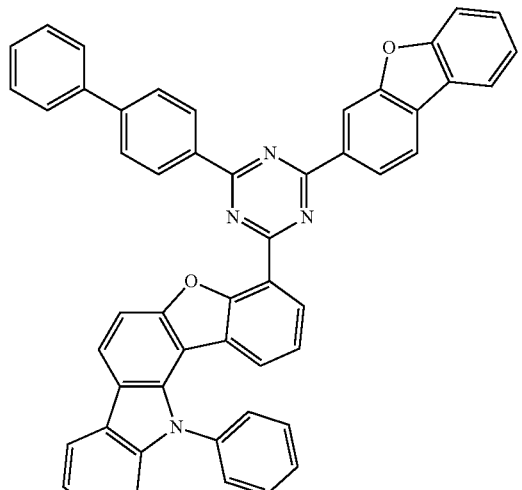
1F-4-55
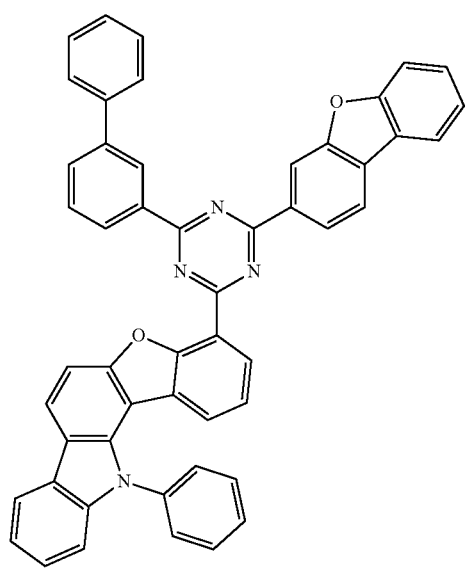
1F-4-56
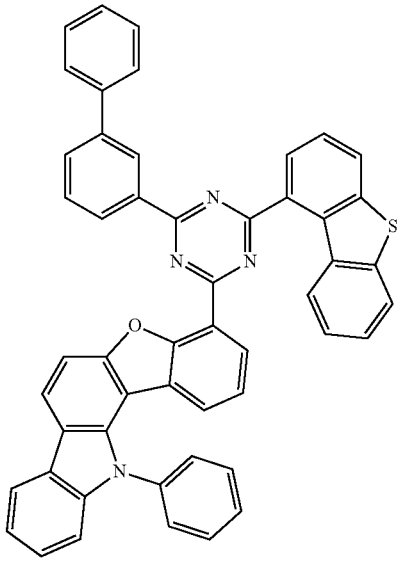
1F-4-57
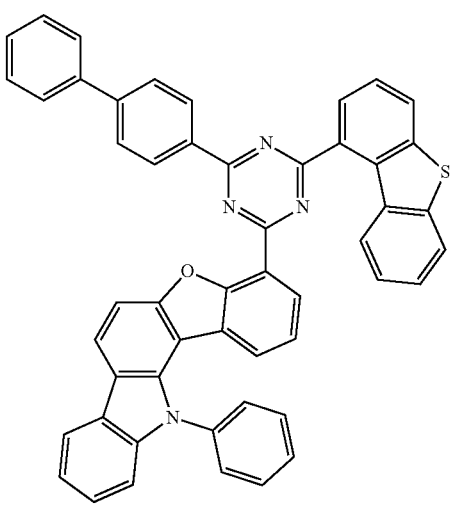
1F-4-58
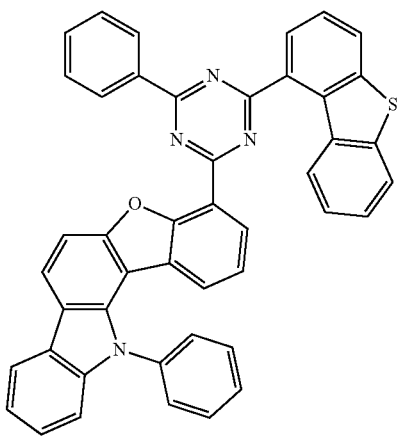

-continued
1F-4-59
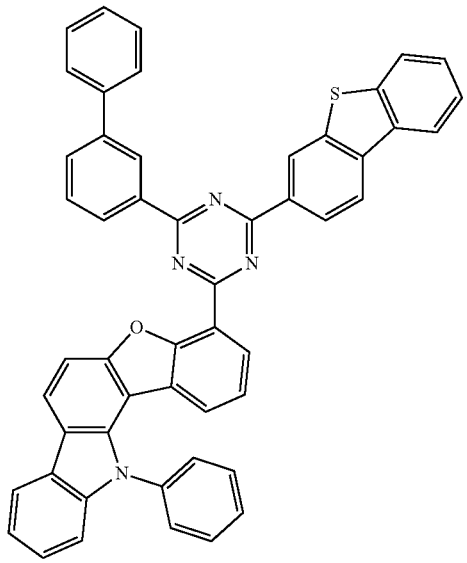
1F-4-60
1F-4-61
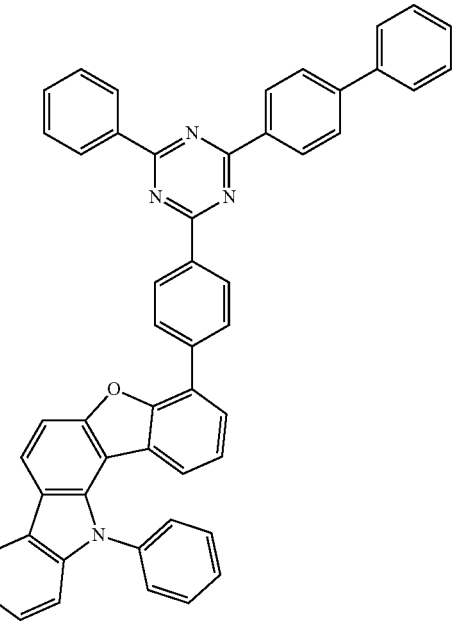
1F-4-62
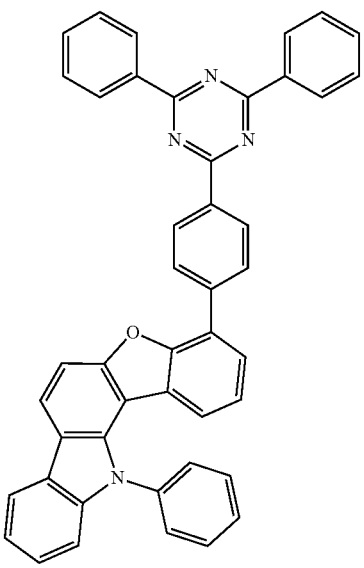

1F-4-63
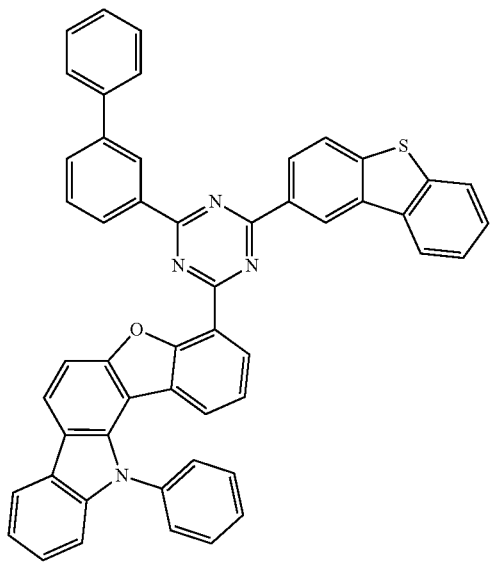
1F-4-64
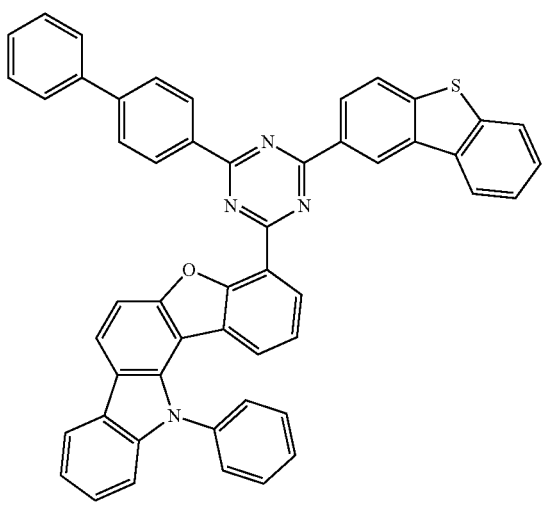
1F-4-65
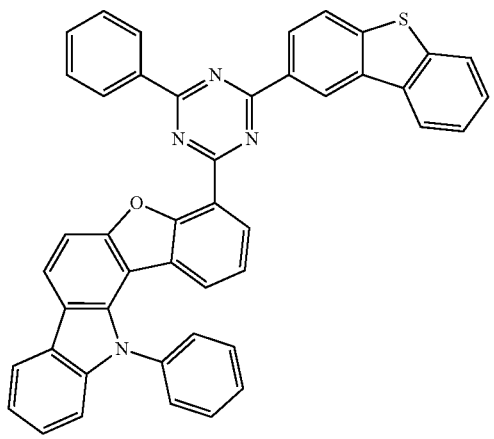
1F-4-66
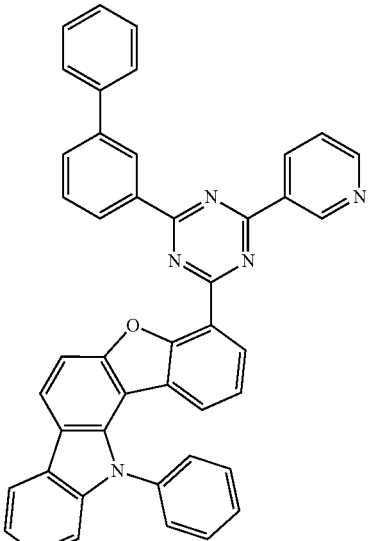
1F-4-67
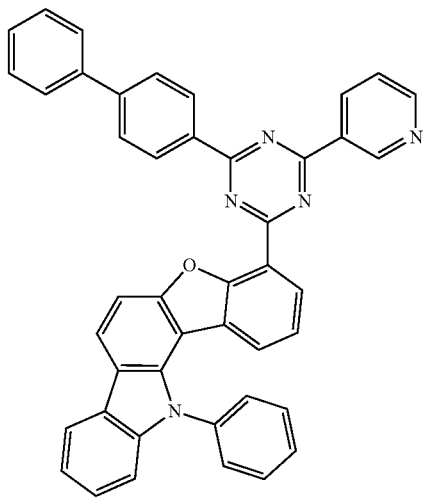
1F-4-68
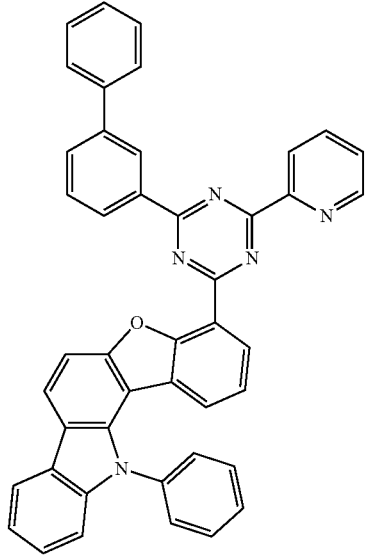

1F-4-69
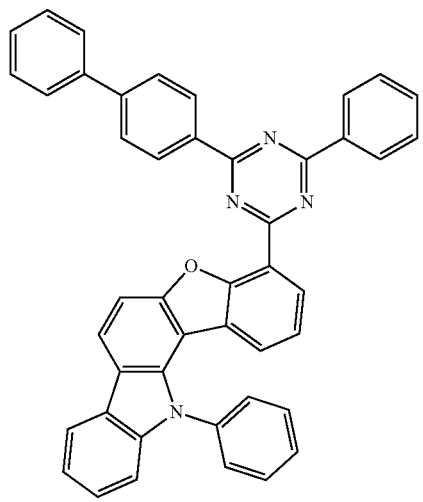
1F-4-70
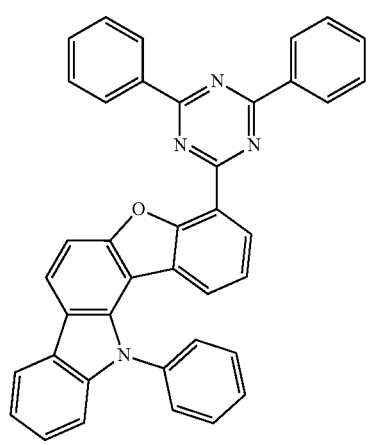
1F-4-71
1F-4-72
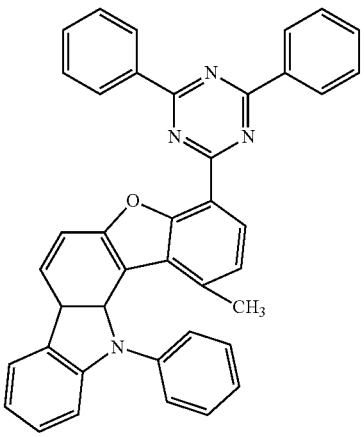
1F-4-73
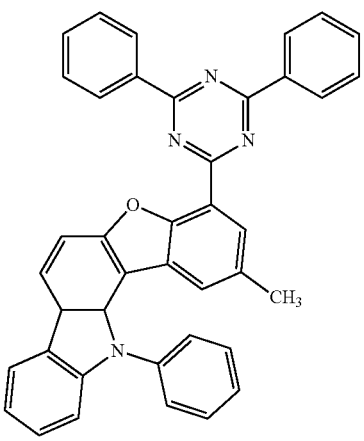
1F-4-74
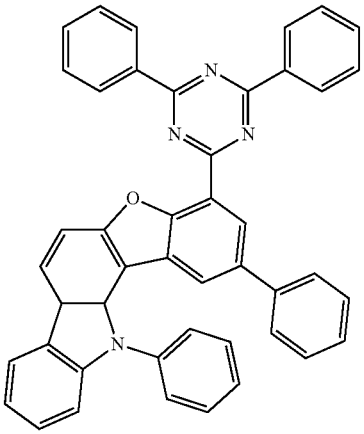

745
-continued
1F-4-75
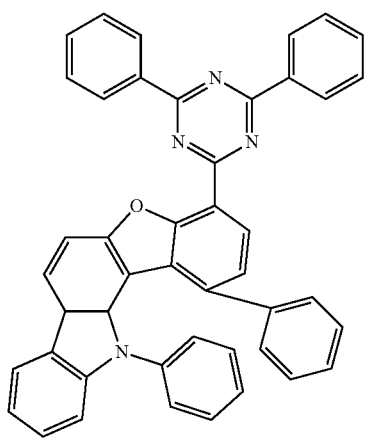
1F-4-76
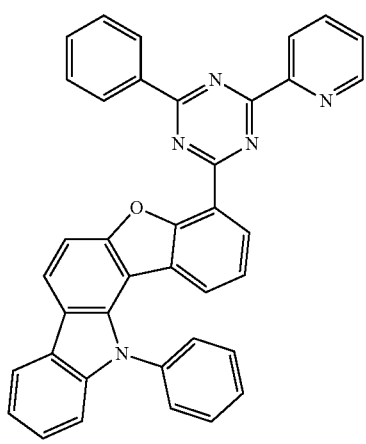
1F-4-77
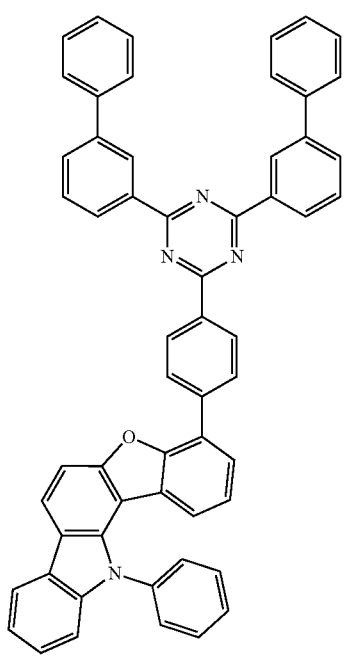
746
-continued
1F-4-78
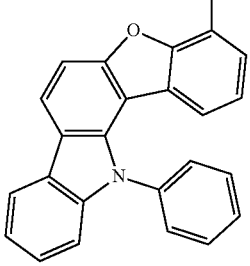
1F-4-79
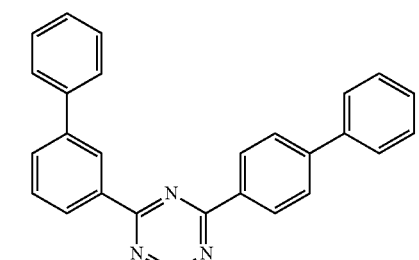
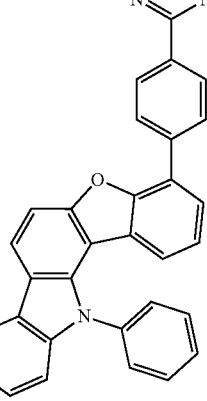

1F-4-80
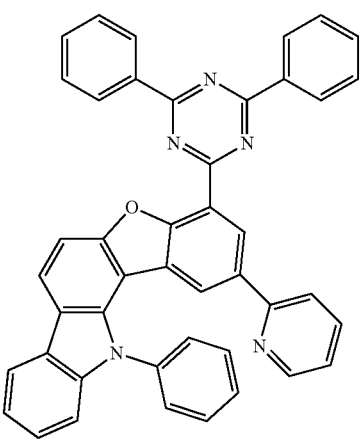
1F-4-83
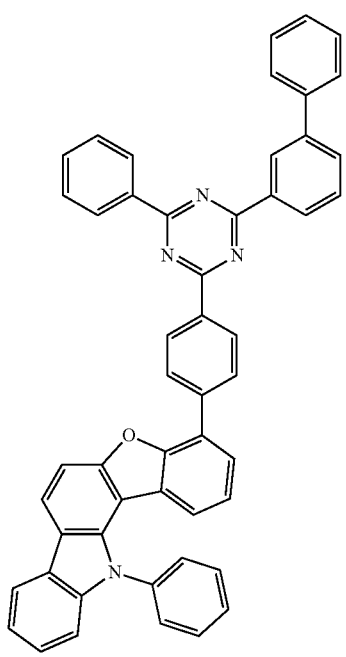
In an implementation, the second compound may include a skeleton represented by a combination of Chemical Formula 3 and Chemical Formula 4, and may be represented by, e.g., one of Chemical Formula 3A to Chemical Formula 3E according to the fusion position of Chemical Formula 3 and Chemical Formula 4.
[Chemical Formula 3A]
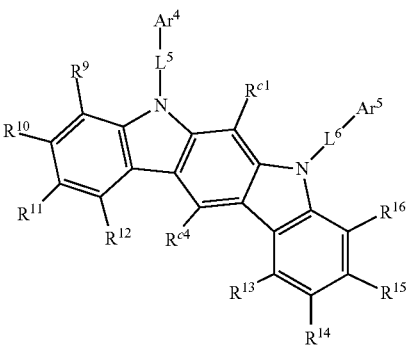
1F-4-81
1F-4-82
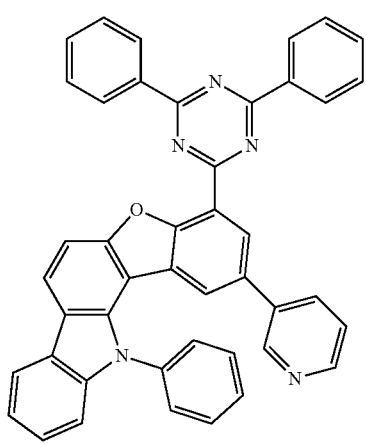
[Chemical Formula 3B]
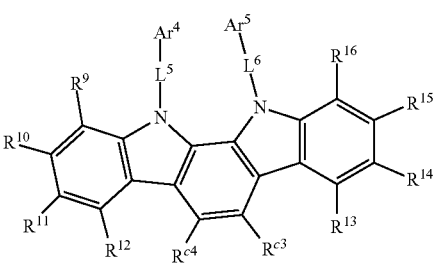

[Chemical Formula 3C]

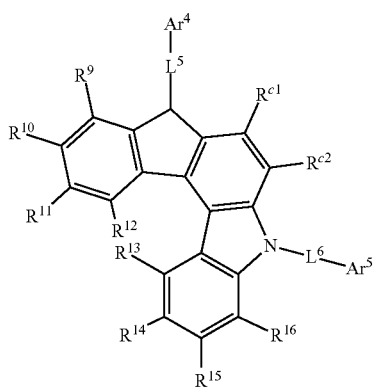

[Chemical Formula 3D]

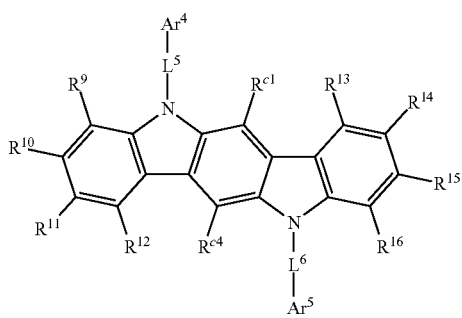

[Chemical Formula 3E]

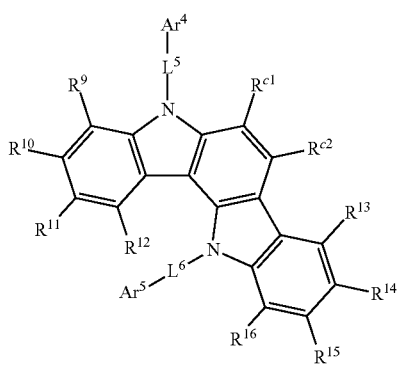

In Chemical Formula 3A to Chemical Formula 3E, $Ar^4$, $Ar^5$, $L^5$, $L^6$, and $R^9$ to $R^{16}$ may be defined the same as those described above, and $R^{c1}$ to $R^{c4}$ may each independently be defined the same as $R^c$.

In an implementation, $L^5$ and $L^6$ may each independently be, e.g., a single bond or a substituted or unsubstituted phenylene group.

In an implementation, $Ar^4$ and $Ar^5$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylene group.

In an implementation, moieties *-$L^5$-$Ar^4$ and *-$L^6$-$Ar^5$ may each independently be, e.g., a moiety of Group II.

[Group II]

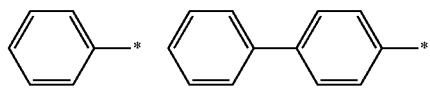

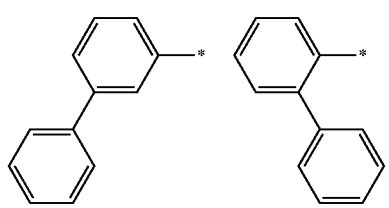

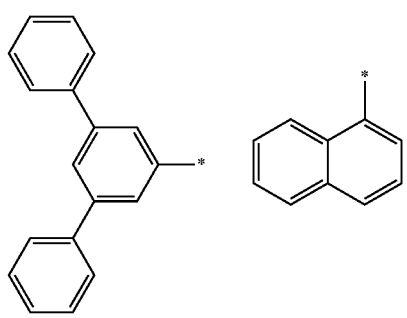

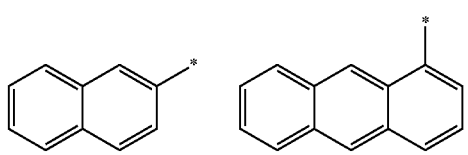

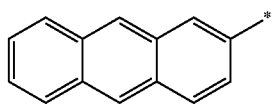

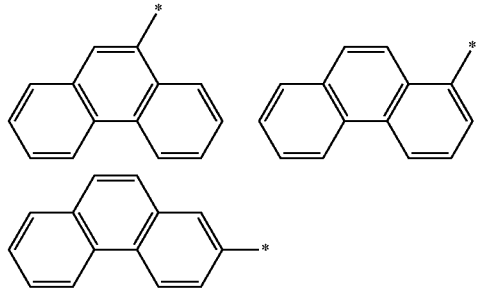

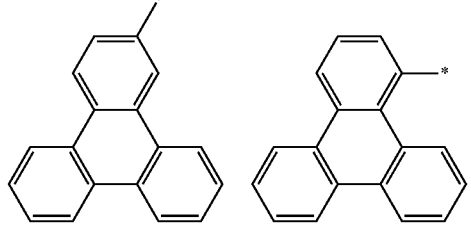

In Group II, * is a linking point.

In an implementation, the second compound may be, e.g., represented by Chemical Formula 3C.

In an implementation, the second compound may be, e.g., a compound of Group 2.

[Group 2]
[1]
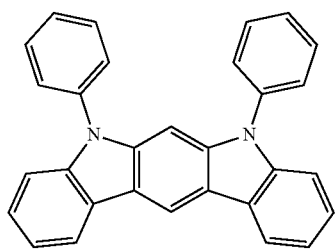
[2]
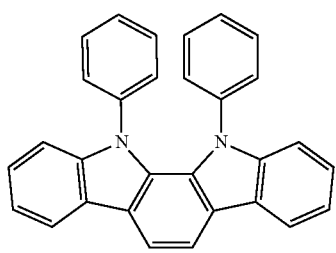
[3]
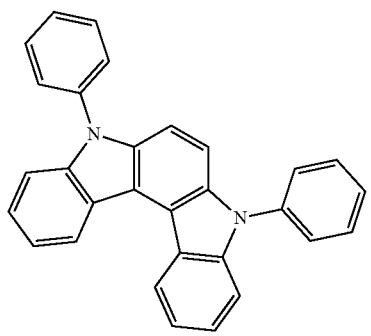
[4]
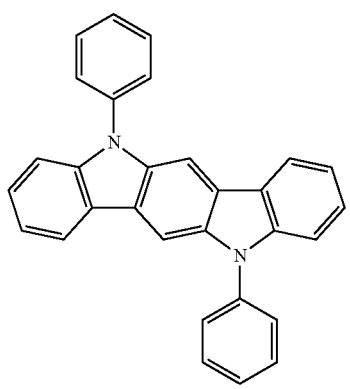
-continued
[5]
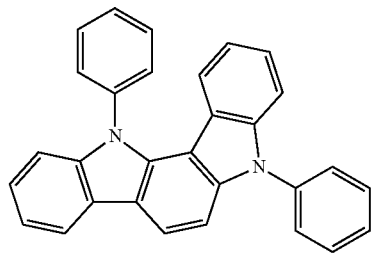
[6]
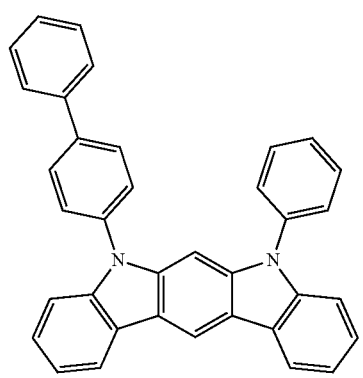
[7]
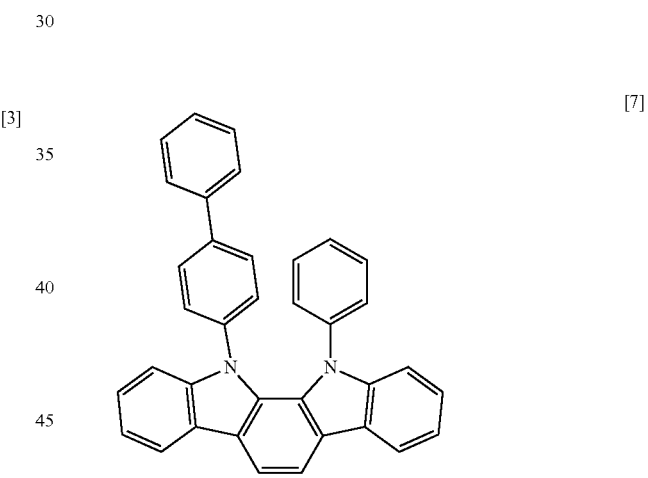
[8]
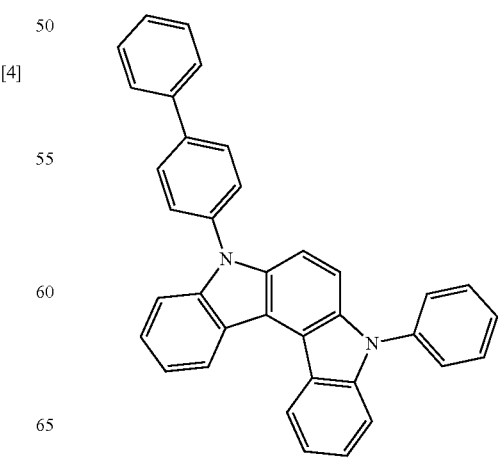

[9]
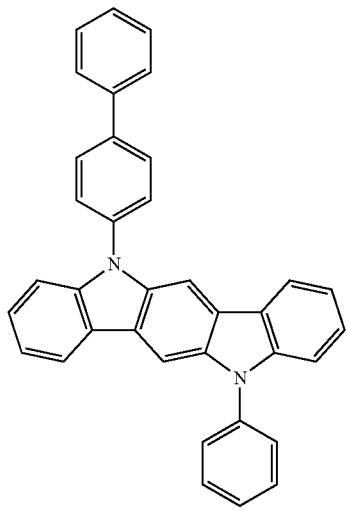
[10]
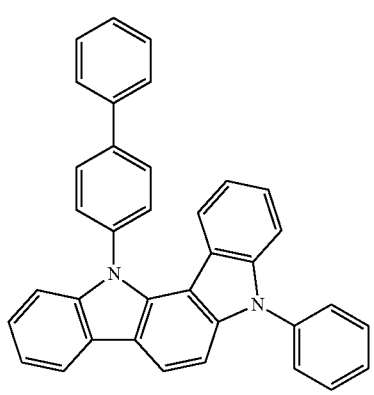
[11]
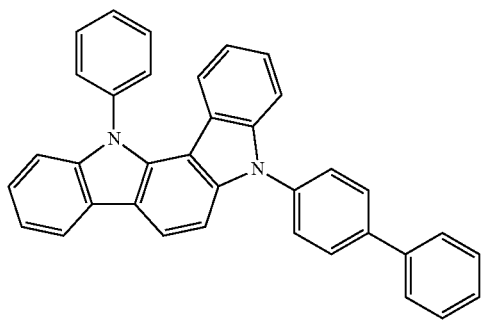
[12]
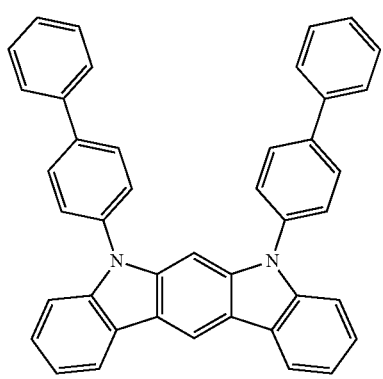
[13]
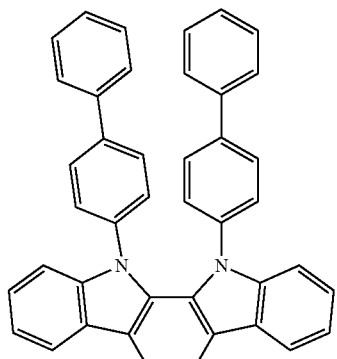
[14]
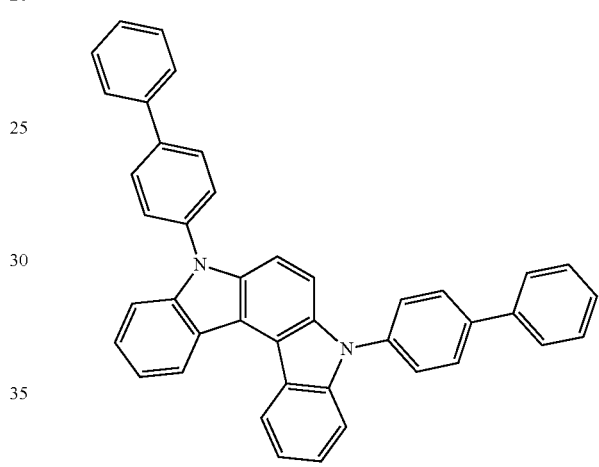
[15]
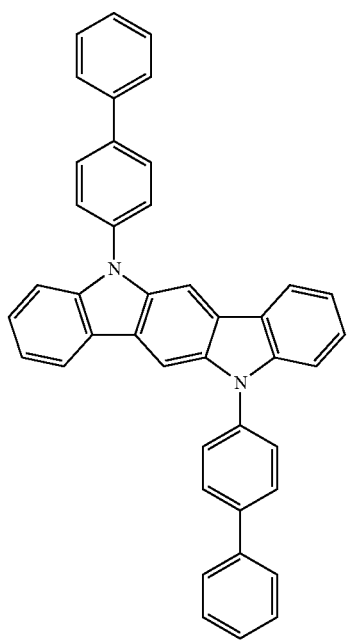

-continued
[16]
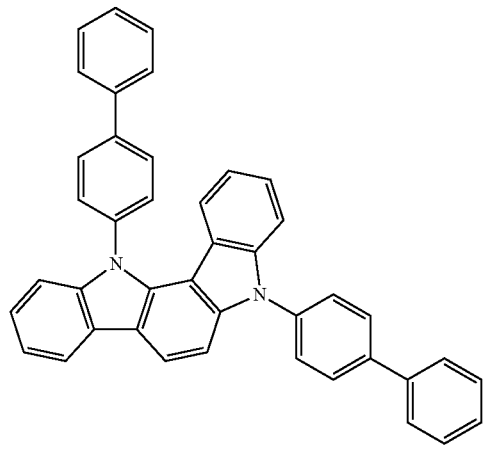
[17]
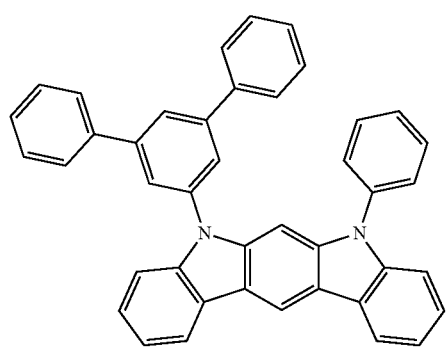
[18]
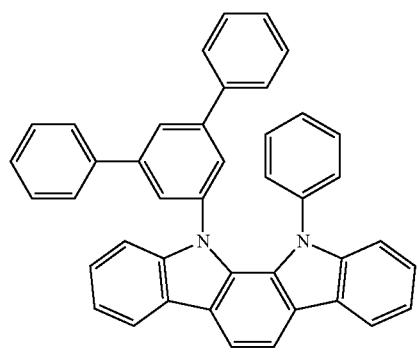
[19]
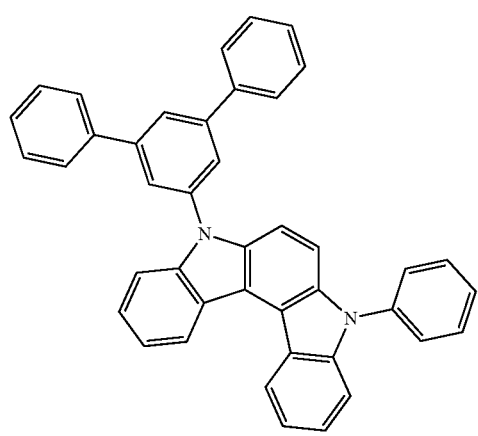
-continued
[20]
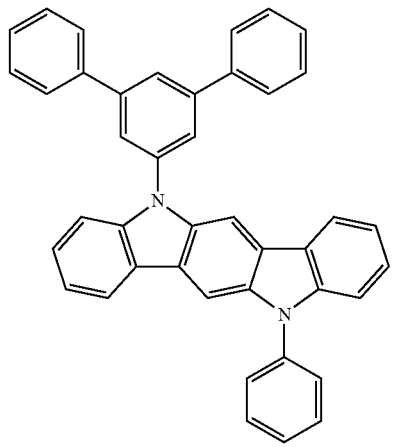
[21]
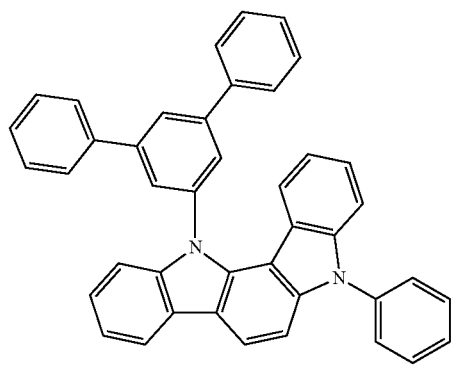
[22]
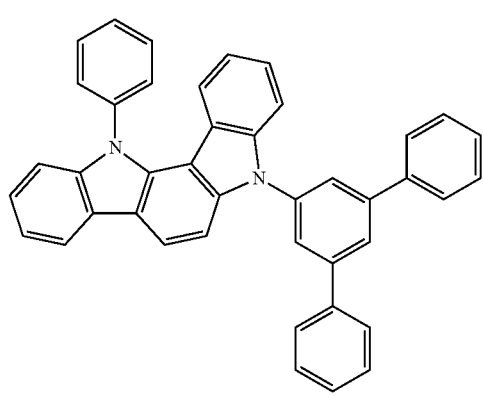
[23]
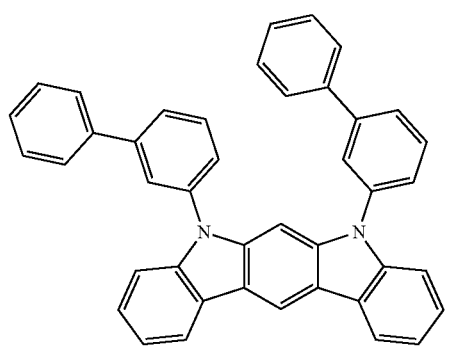

757
-continued
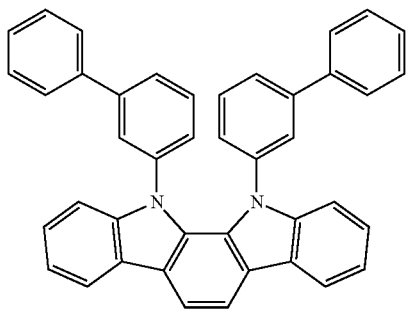
[24]
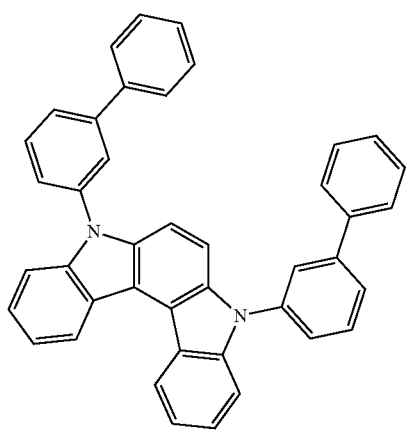
[25]
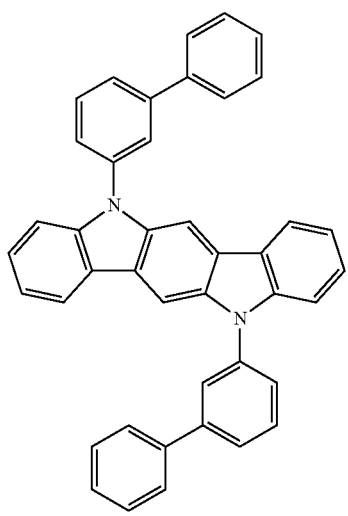
[26]
758
-continued
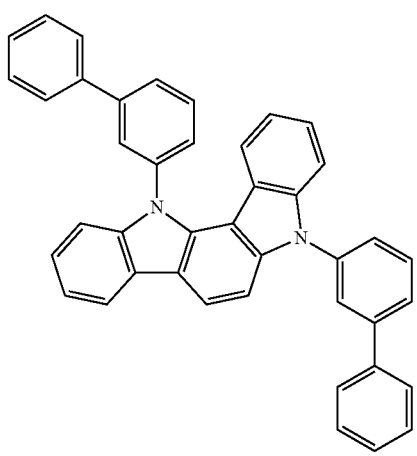
[27]
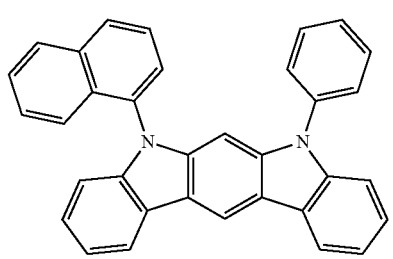
[28]
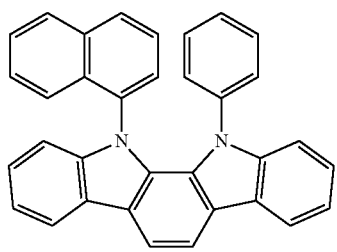
[29]
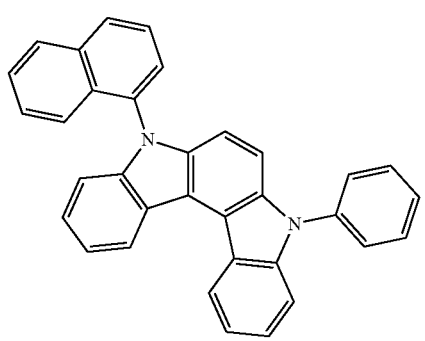
[30]

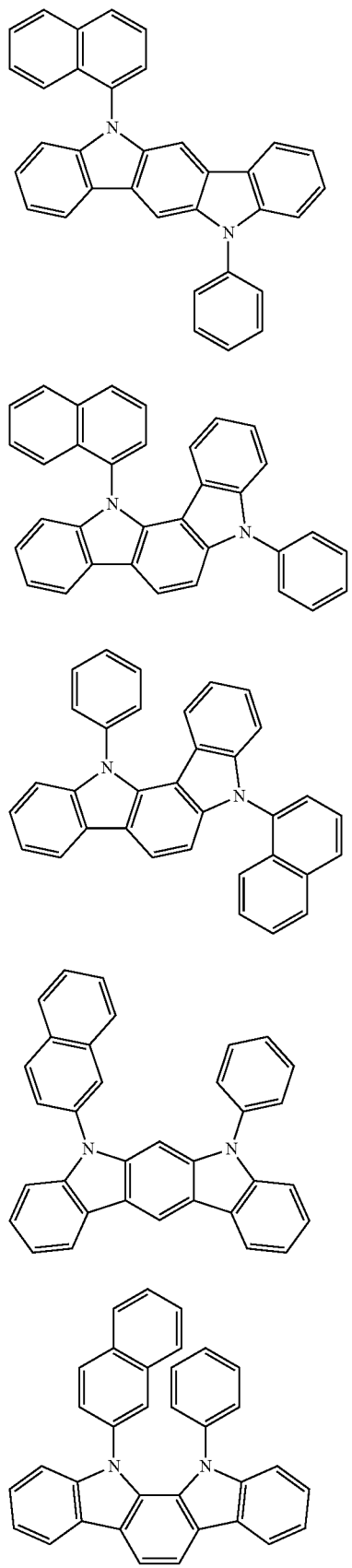
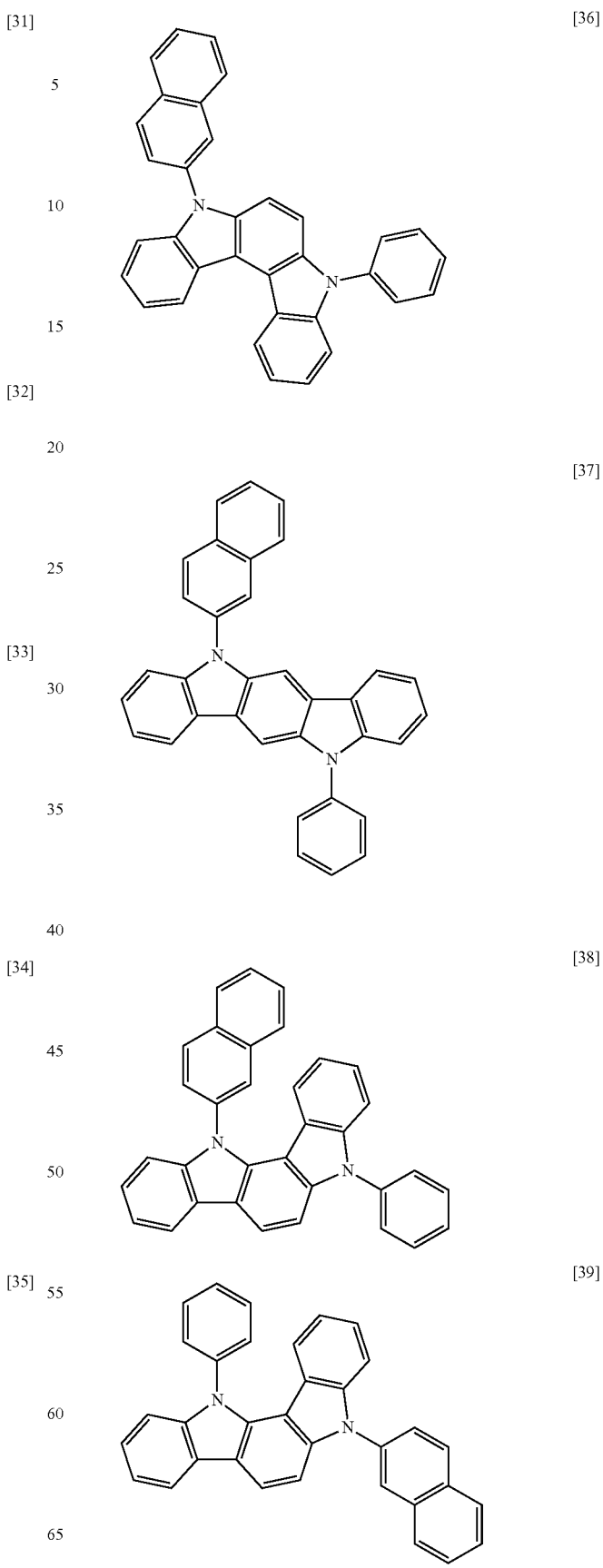

[40]
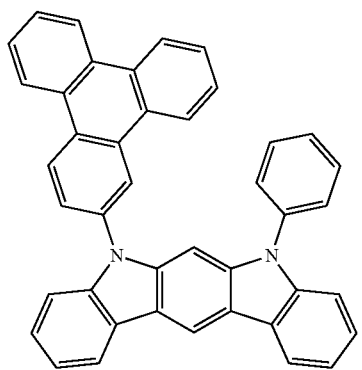
[41]
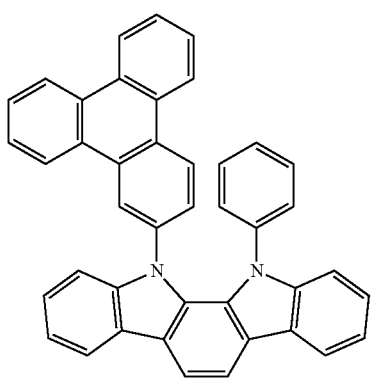
[42]
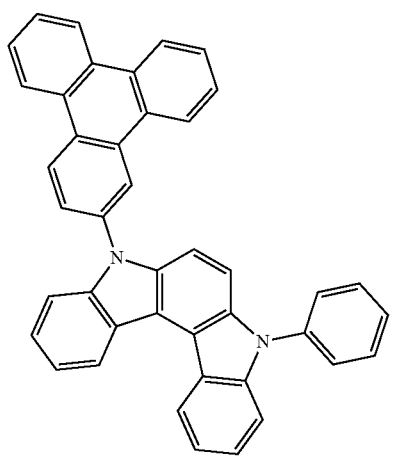
[43]
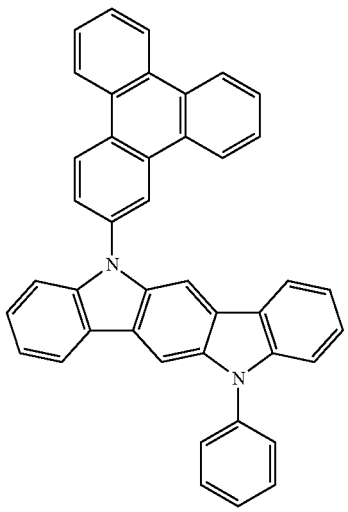
[44]
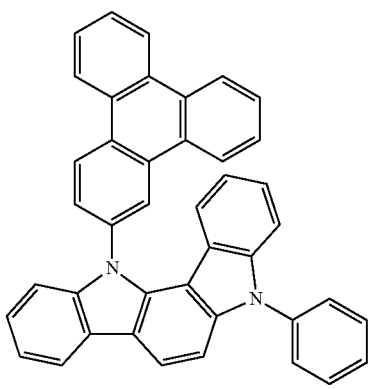
[45]
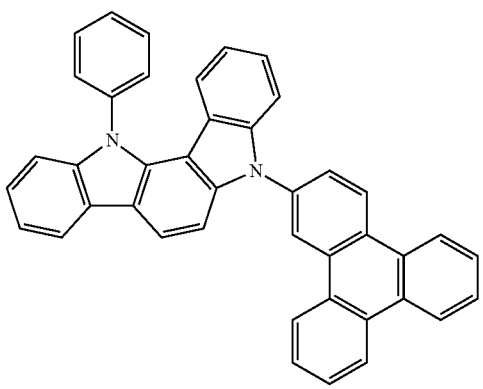

-continued
[46]
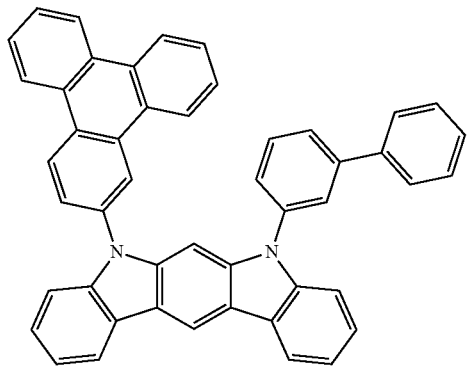
[47]
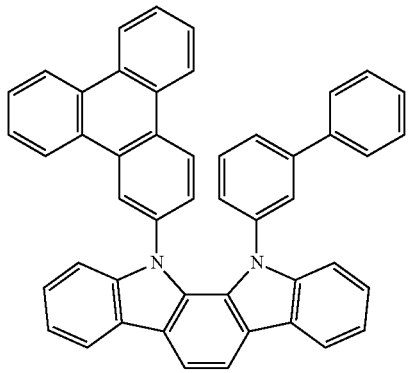
[48]
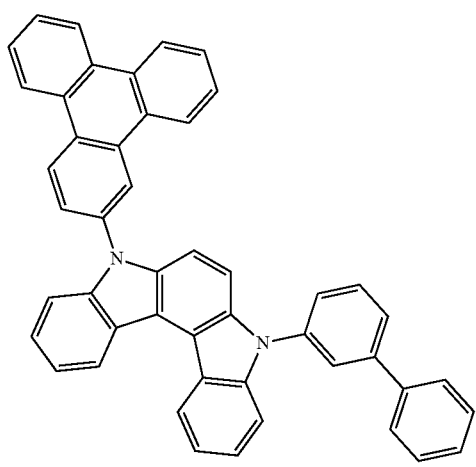
-continued
[49]
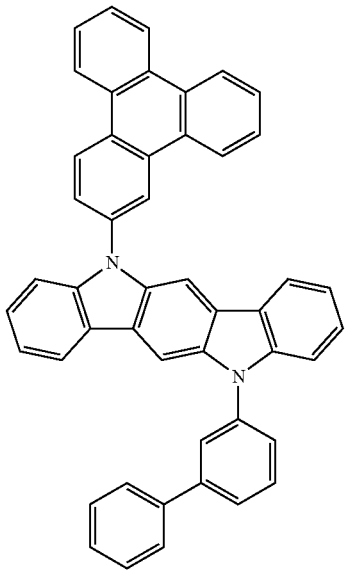
[50]
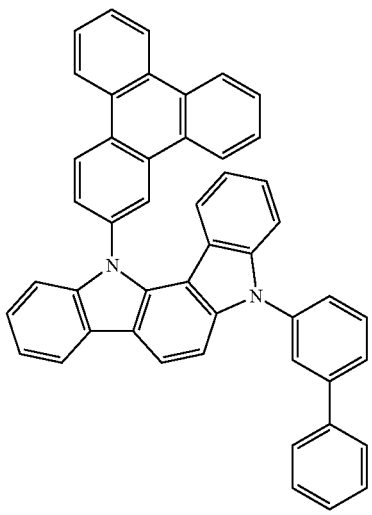
[51]
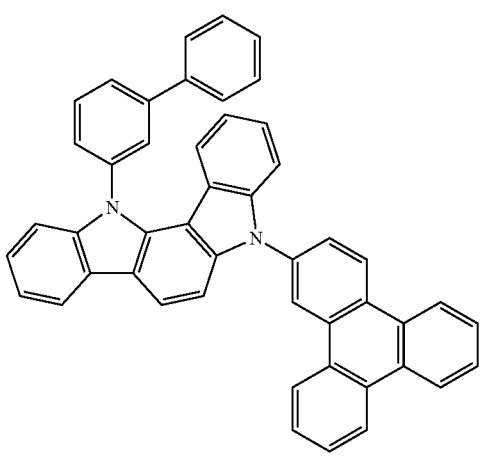

[52]
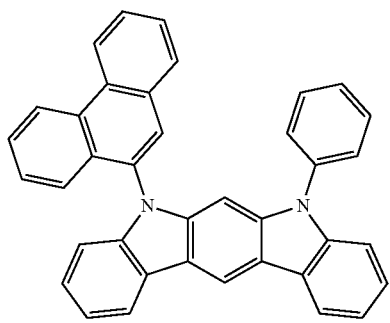
[53]
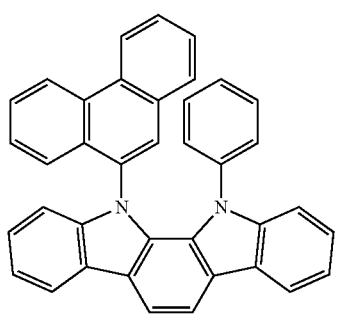
[54]
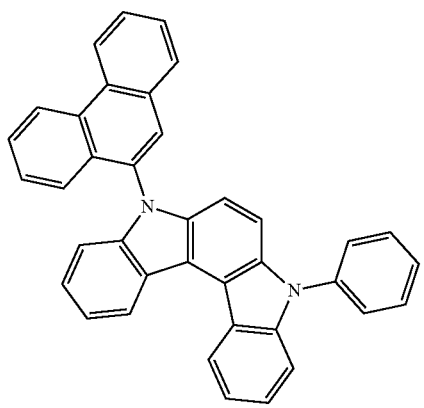
[55]
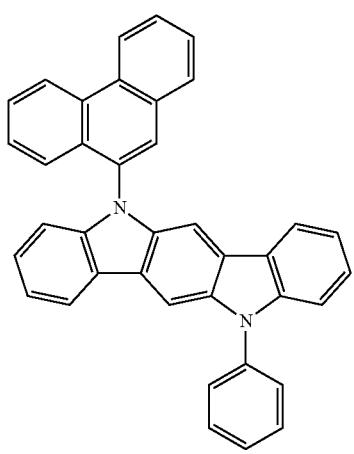
[56]
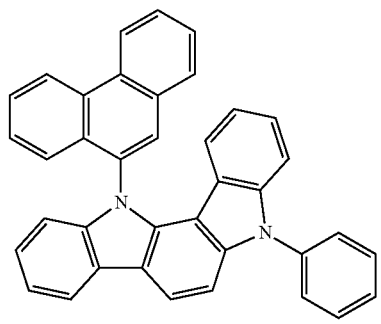
[57]
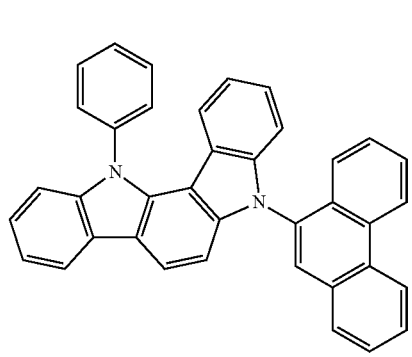
[58]
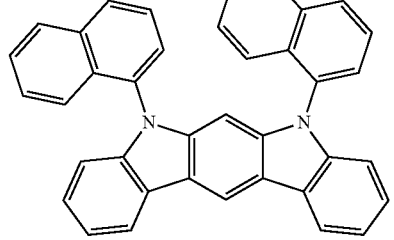
[59]
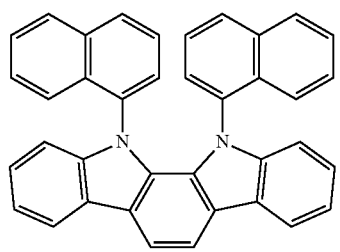
[60]
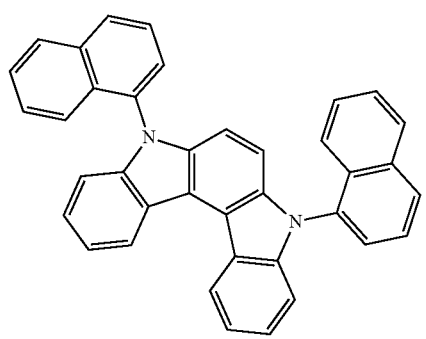

[61]
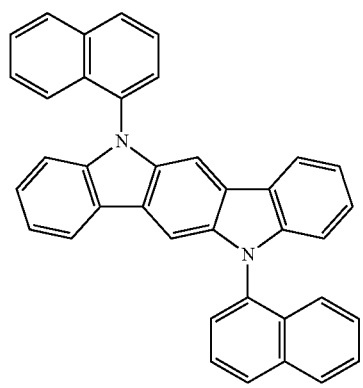
[62]
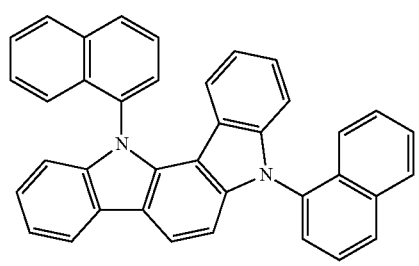
[63]
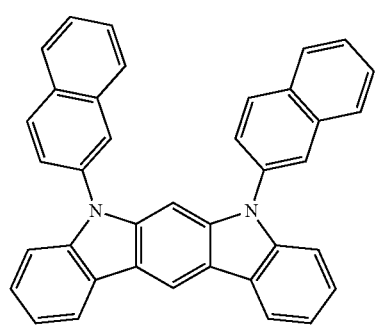
[64]
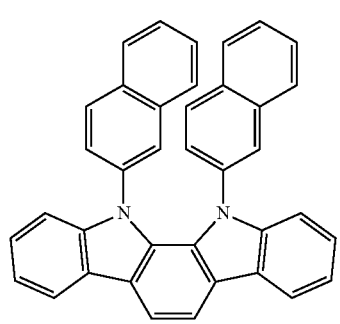
[65]
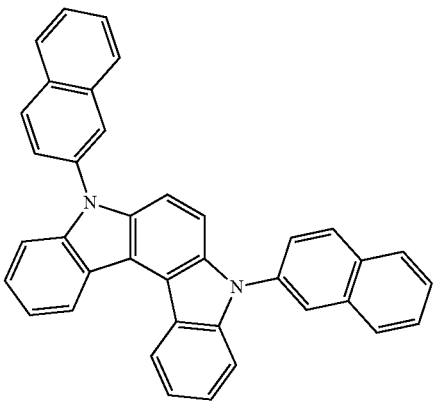
[66]
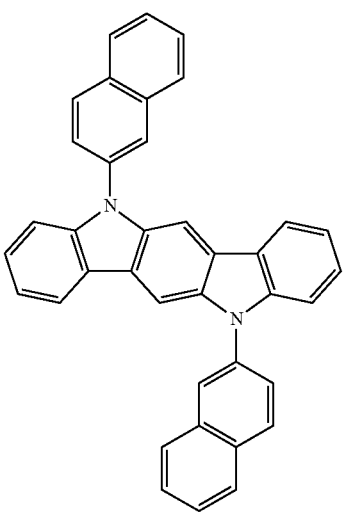
[67]
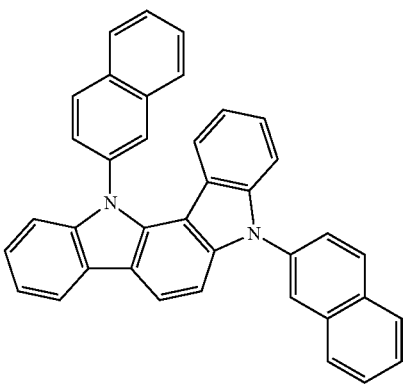

-continued

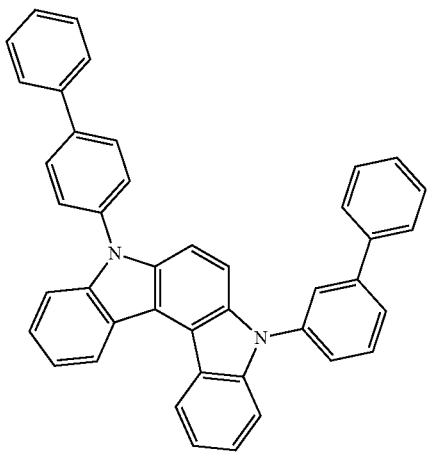

In an implementation, the composition for an organic optoelectronic device may include, e.g., a first compound represented by Chemical Formula 1B-4A and a second compound represented by Chemical Formula 3C-I.

[Chemical Formula 1B-4A]

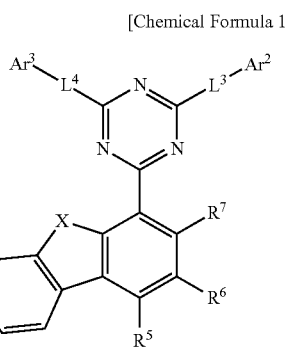

In Chemical Formula 1B-4A, $Ar^1$ to $Ar^3$ may each independently be, e.g., a substituted or unsubstituted phenyl group or a substituted or unsubstituted biphenyl group.

$L^3$ and $L^4$ may each independently be, e.g., a single bond or a substituted or unsubstituted phenylene group.

$R^1$ to $R^7$ may each independently be, e.g., hydrogen, deuterium, a substituted or unsubstituted C1 to C5 alkyl group or a substituted or unsubstituted C6 to C12 aryl group.

[Chemical Formula 3C-I]

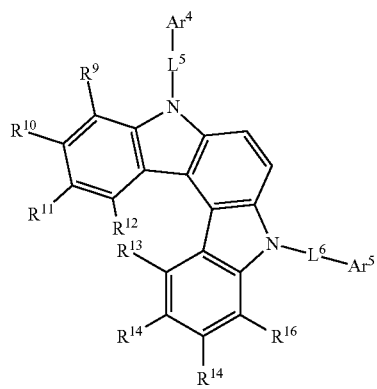

In Chemical Formula 3C-I, $Ar^4$ and $Ar^5$ may each independently be, e.g., a substituted or unsubstituted phenyl group or a substituted or unsubstituted biphenyl group.

$L^5$ and $L^6$ may each independently be, e.g., a single bond or a substituted or unsubstituted phenylene group.

$R^9$ to $R^{16}$ may each independently be, e.g., hydrogen, deuterium, a substituted or unsubstituted C1 to C5 alkyl group or a substituted or unsubstituted C6 to C12 aryl group.

In an implementation, the composition for an organic optoelectronic device may include, e.g., a first compound from Group 1-1 and a second compound from Group 2-1.

[Group 1-1]

1B-4-1

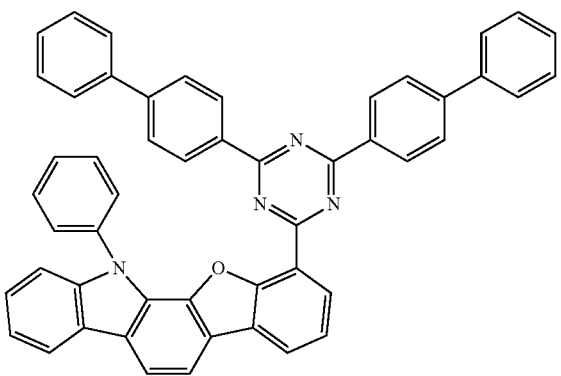

1B-4-2

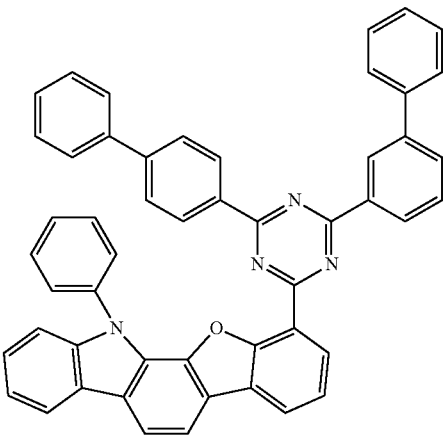

1B-4-3

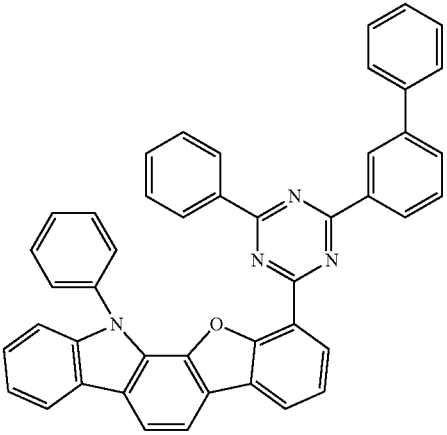

1B-4-4
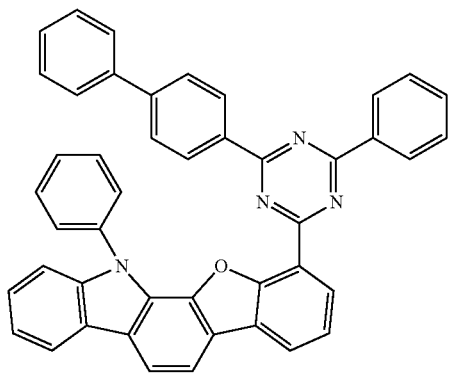
1B-4-8
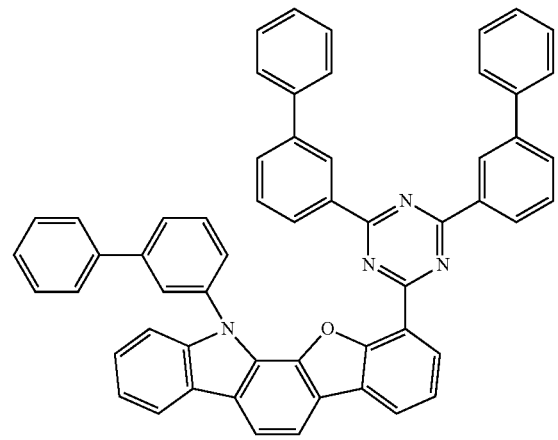
1B-4-5
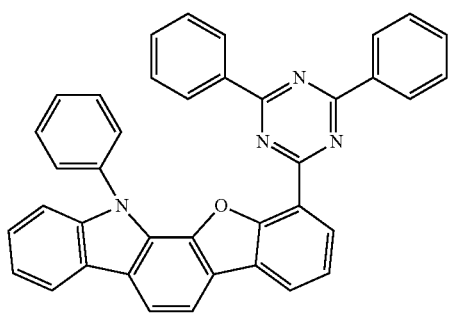
1B-4-6
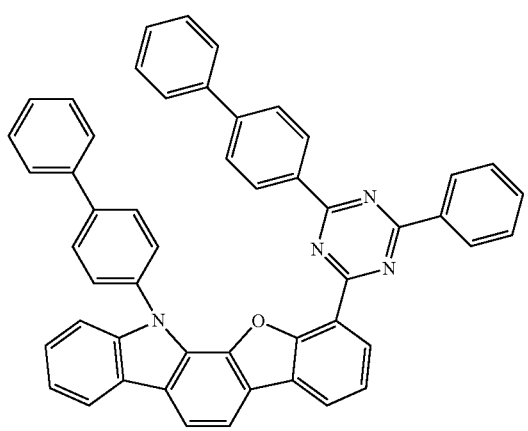
1B-4-9
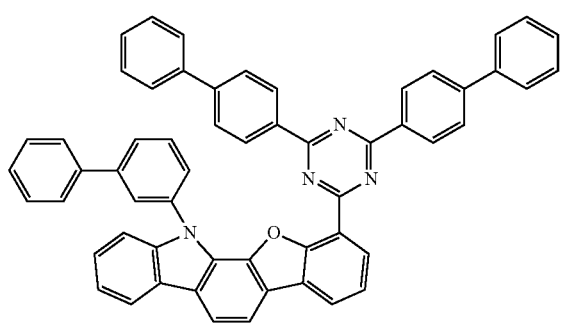
1B-4-7
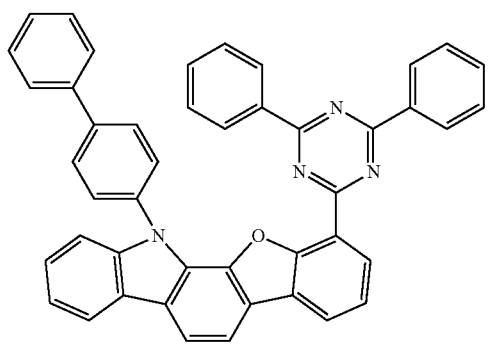
1B-4-10
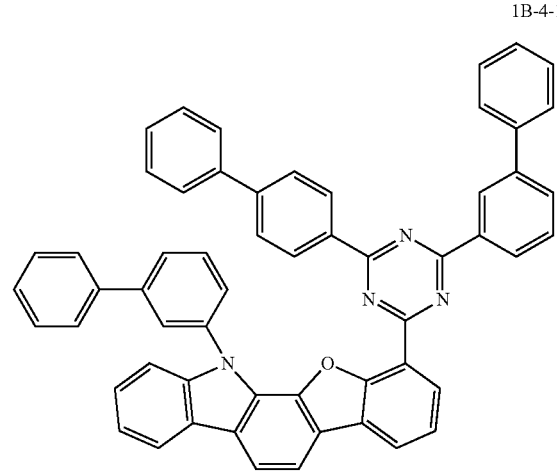

[Group 2-1]

[14]

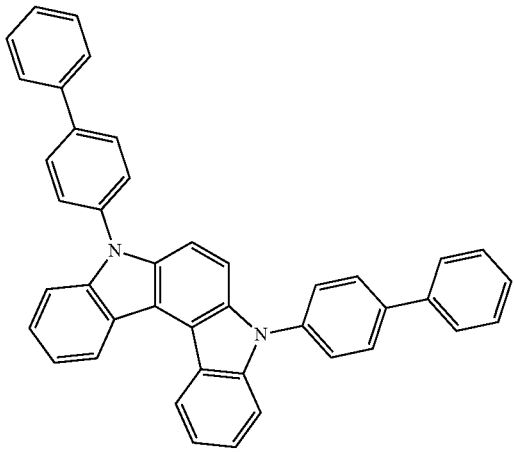

[68]

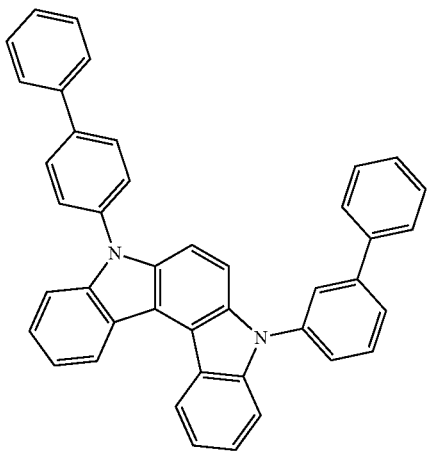

The first compound and the second compound may be included, e.g., as a mixture in a weight ratio of about 1:99 to about 99:1. Within the range, a weight ratio may be adjusted using an electron transport capability of the first compound and a hole transport capability of the second compound to realize bipolar characteristics and thus to improve efficiency and life-span. Within the range, they may be, e.g., included in a weight ratio of about 90:10 to about 10:90, about 90:10 to about 20:80, about 90:10 to about 30:70, about 90:10 to about 40:60, or about 90:10 to about 50:50. In an implementation, they may be included in a weight ratio of about 60:40 to about 50:50, e.g., about 60:40.

In an implementation, the first compound and the second compound may be included as a host of the light emitting layer, e.g., a phosphorescent host.

The aforementioned composition for an organic optoelectronic device may be formed by a dry film deposition method such as chemical vapor deposition.

Hereinafter, an organic optoelectronic device including the aforementioned composition for an organic optoelectronic device is described.

The organic optoelectronic device may be a suitable device to convert electrical energy into photoenergy and vice versa, e.g., an organic photoelectric device, an organic light emitting diode, an organic solar cell, or an organic photoconductor drum.

Herein, an organic light emitting diode as one example of an organic optoelectronic device is described referring to drawings.

FIGS. 1 to 4 are cross-sectional views showing organic light emitting diodes according to embodiments.

Referring to FIG. 1, an organic light emitting diode 100 according to an embodiment may include an anode 120 and a cathode 110 facing each other and an organic layer 105 disposed between the anode 120 and cathode 110.

The anode 120 may be made of a conductor having a large work function to facilitate hole injection, and may be, e.g., a metal, a metal oxide, or a conductive polymer. In an implementation, the anode 120 may include, e.g., a metal such as nickel, platinum, vanadium, chromium, copper, zinc, gold, or the like or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, or polyaniline.

The cathode 110 may be made of a conductor having a small work function to facilitate electron injection, and may be, e.g., a metal, a metal oxide, or a conductive polymer. In an implementation, the cathode 110 may include, e.g., a metal such as magnesium, calcium, sodium, potassium, titanium, indium, yttrium, lithium, gadolinium, aluminum silver, tin, lead, cesium, barium, or the like, or an alloy thereof; or a multi-layer structure material such as LiF/Al, $LiO_2$/Al, LiF/Ca, or $BaF_2$/Ca.

The organic layer 105 may include the aforementioned composition for an organic optoelectronic device.

The organic layer 105 may include the light emitting layer 130, and the light emitting layer 130 may include the aforementioned composition for an organic optoelectronic device.

The light emitting layer 130 may include, e.g., the aforementioned composition for an organic optoelectronic device as a phosphorescent host.

In an implementation, the light emitting layer may further include, e.g., one or more compounds in addition to the aforementioned host.

The light emitting layer may further include a dopant. The dopant may be, e.g., a phosphorescent dopant. In an implementation, the dopant may be, e.g., a phosphorescent dopant of red, green, or blue color.

The composition for an organic optoelectronic device further including a dopant may be, e.g., a green light-emitting composition.

The dopant may be a material mixed with the compound or composition for an organic optoelectronic device in a trace amount to cause light emission, and may be a material such as a metal complex that emits light by multiple excitation into a triplet or more. The dopant may be, e.g., an inorganic, organic, or organic-inorganic compound, and one or more types thereof may be used.

Examples of the dopant may include a phosphorescent dopant and examples of the phosphorescent dopant may include an organic metal compound including Ir, Pt, Os, Ti, Zr, Hf, Eu, Tb, Tm, Fe, Co, Ni, Ru, Rh, Pd, or a combination thereof. In an implementation, the phosphorescent dopant may be, e.g., a compound represented by Chemical Formula Z.

$L^7MX^2$ [Chemical Formula Z]

In Chemical Formula Z, M may be, e.g., a metal, and $L^7$ and $X^2$ may each independently be, e.g., a ligand to form a complex compound with M.

The M may be, e.g., Ir, Pt, Os, Ti, Zr, Hf, Eu, Tb, Tm, Fe, Co, Ni, Ru, Rh, Pd, or a combination thereof, and $L^7$ and $X^2$ may be, e.g., a bidendate ligand.

The organic layer may further include a charge transport region in addition to the light emitting layer.

Figure 2:
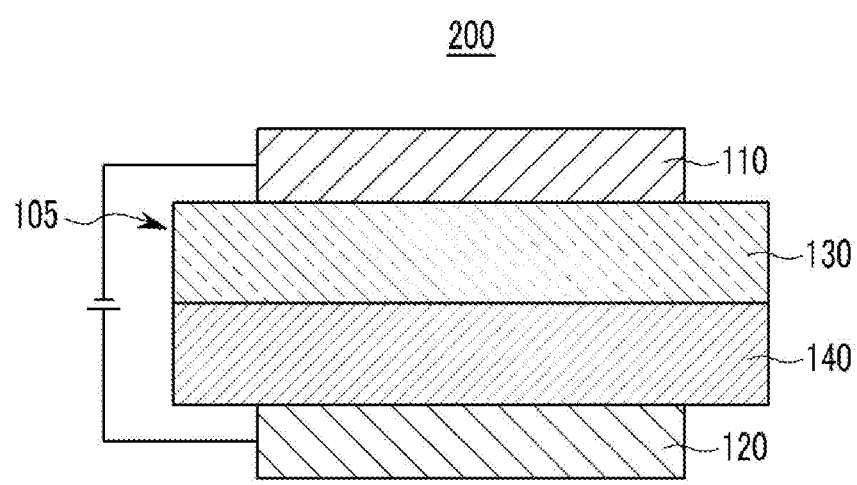

Referring to FIG. 2, an organic light emitting diode 200 may further include a hole transport region 140 in addition to the light emitting layer 130. The hole transport region 140 may further increase hole injection and/or hole mobility between the anode 120 and the light emitting layer 130 and block electrons. In an implementation, the hole transport region 140 may include a hole transport layer between the anode 120 and the light emitting layer 130, and a hole transport auxiliary layer between the light emitting layer 130 and the hole transport layer, and at least one of the compounds of Group A may be included in at least one of the hole transport layer and the hole transport auxiliary layer.

[Group A]

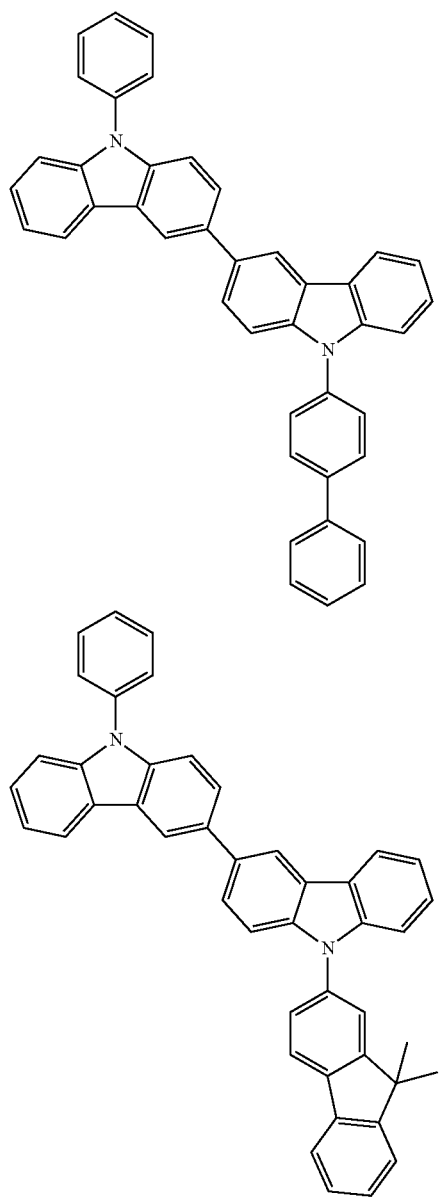

-continued

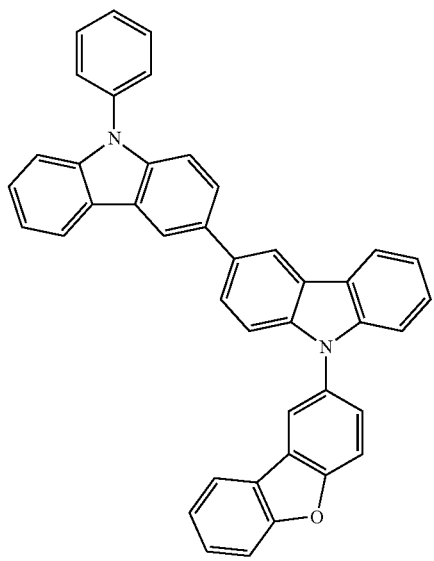

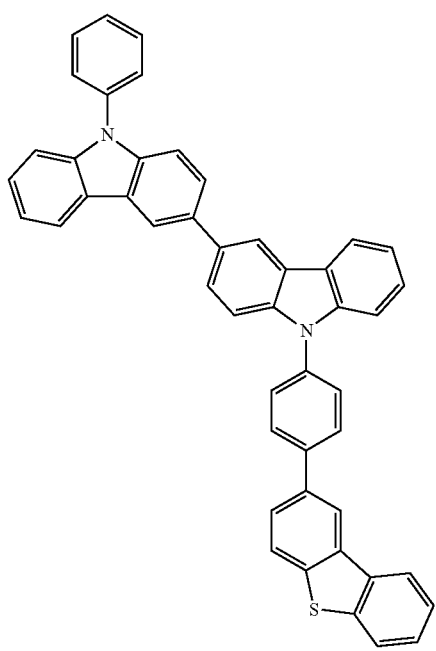

777
-continued
778
-continued
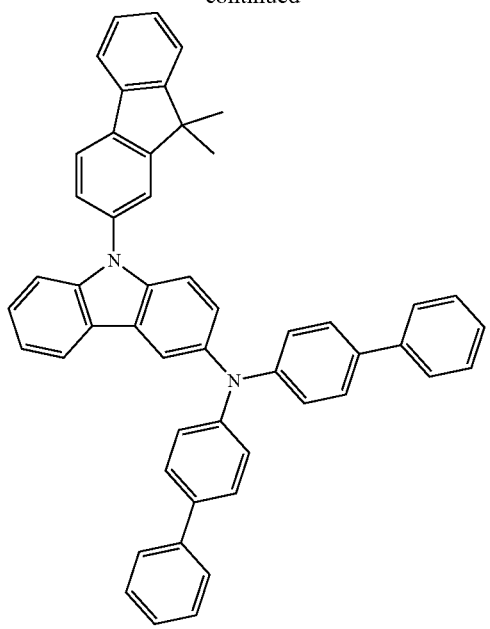
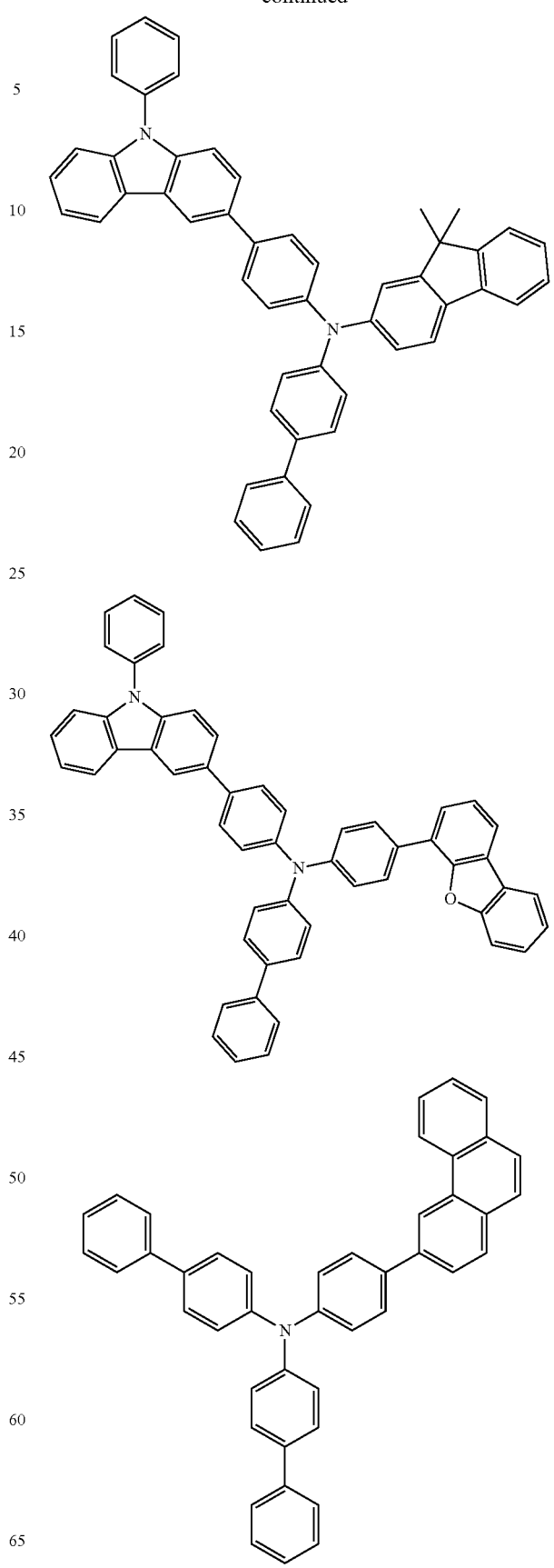

779
-continued
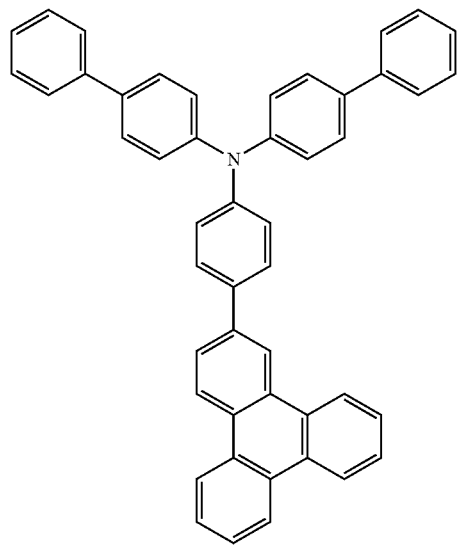
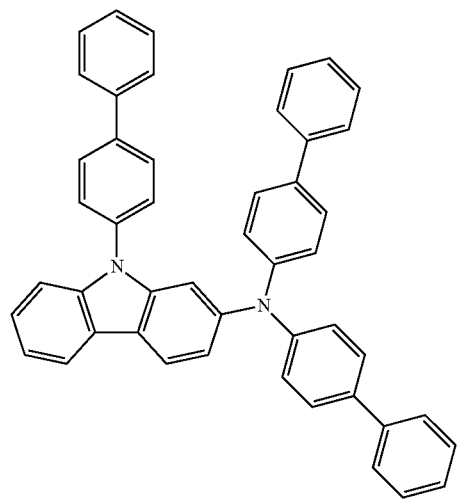
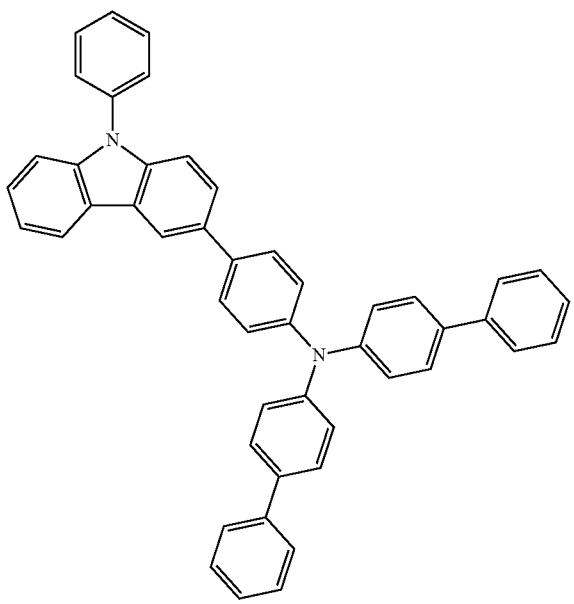
780
-continued
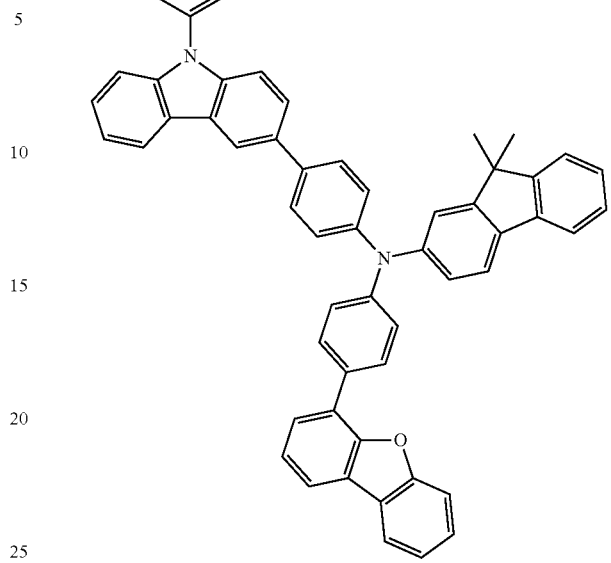
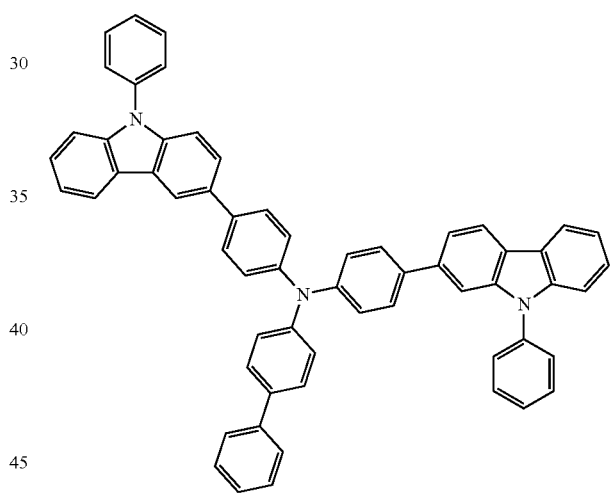
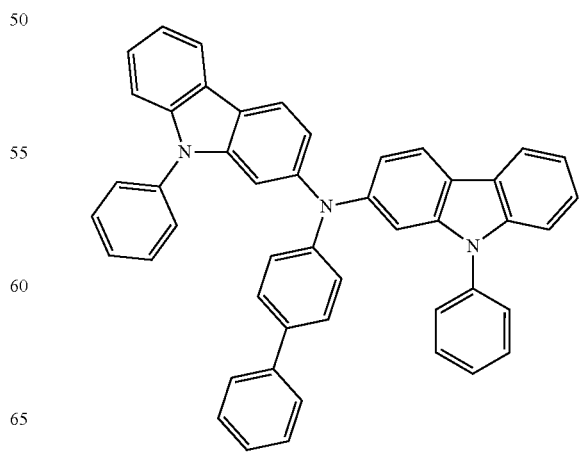

781
-continued
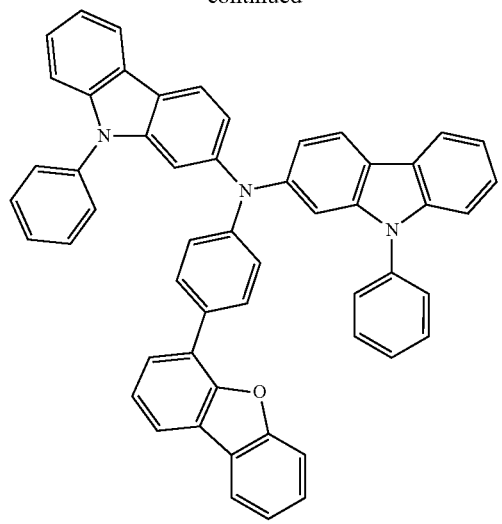
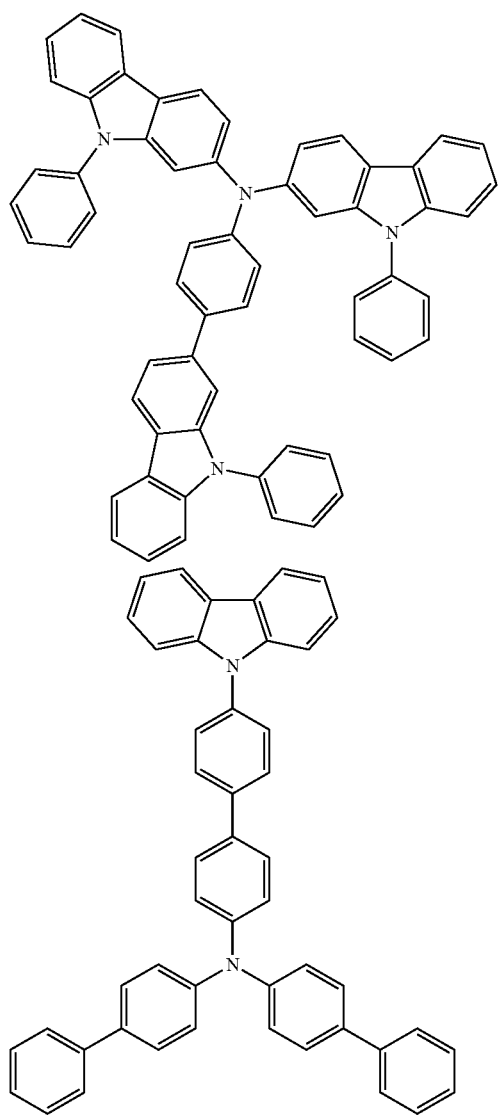
782
-continued
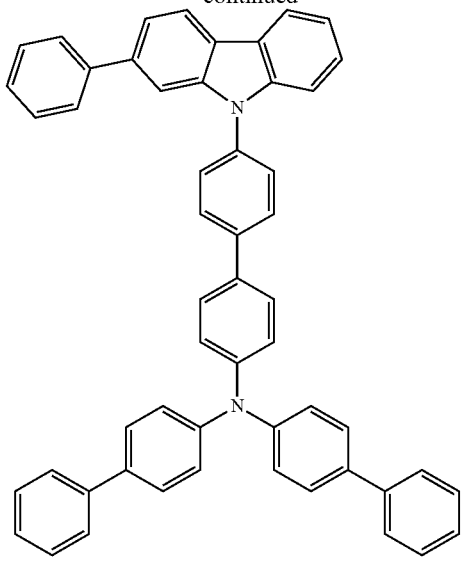
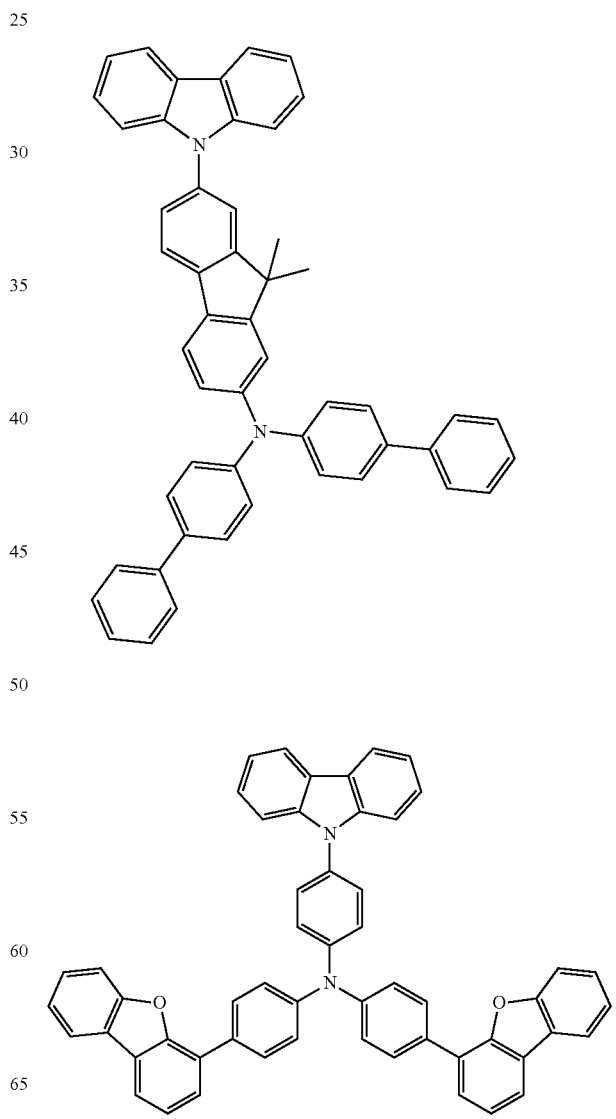

783
-continued
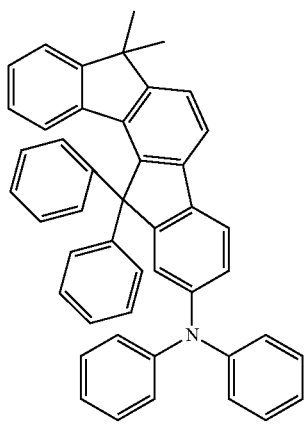
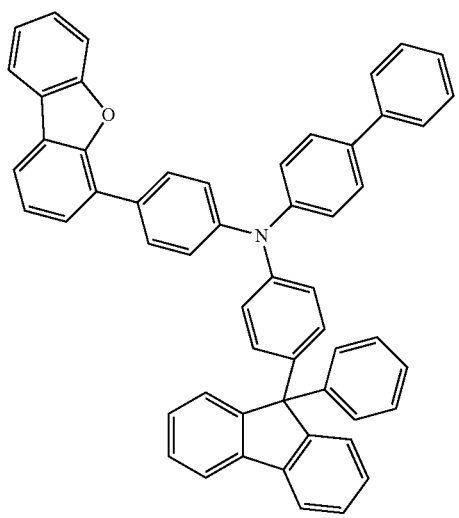
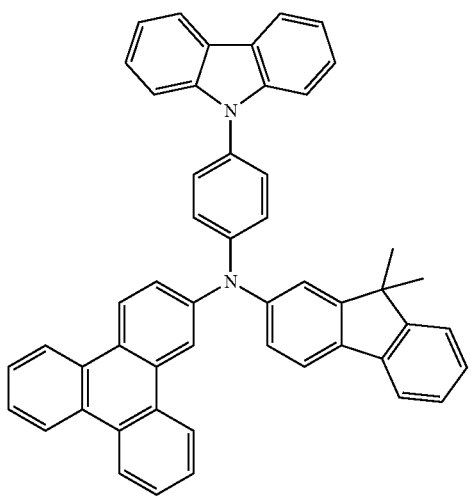
784
-continued
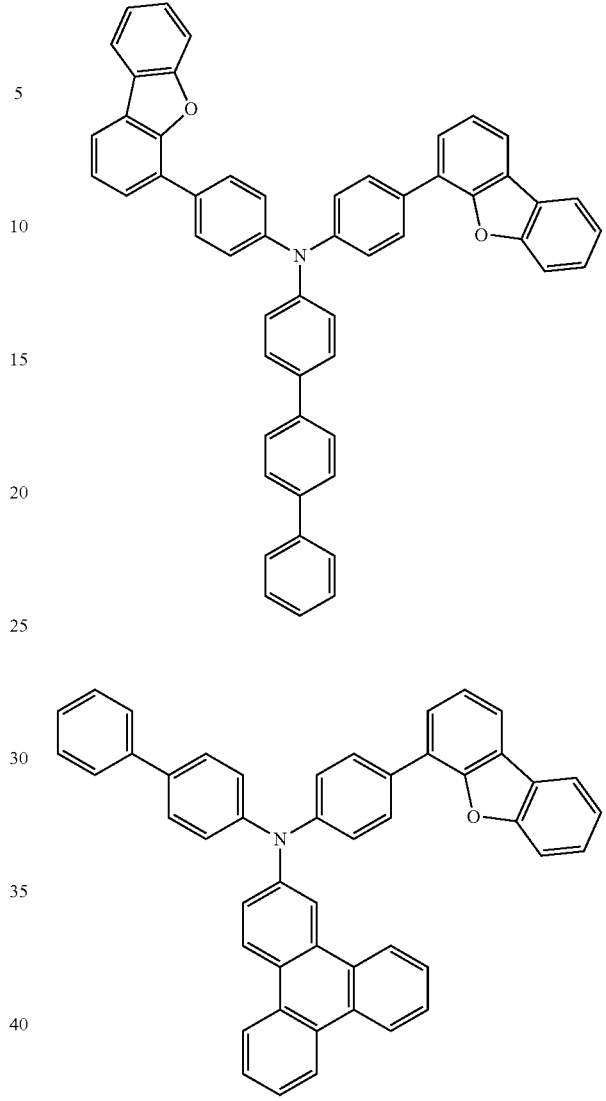
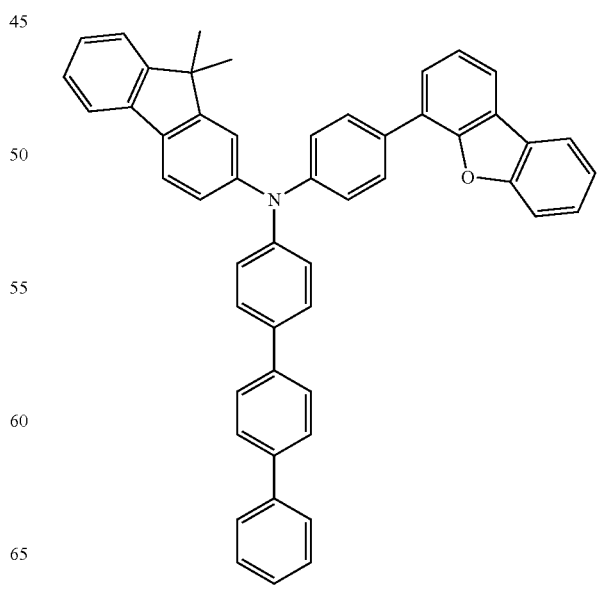

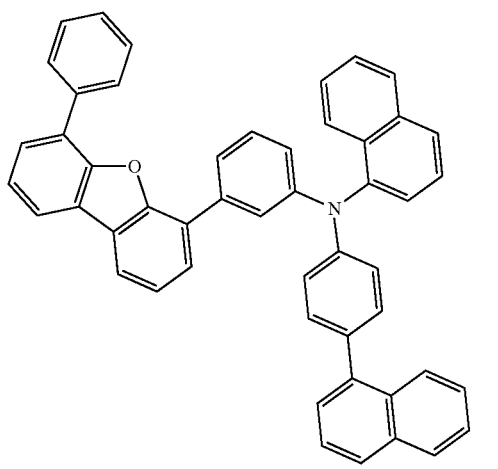
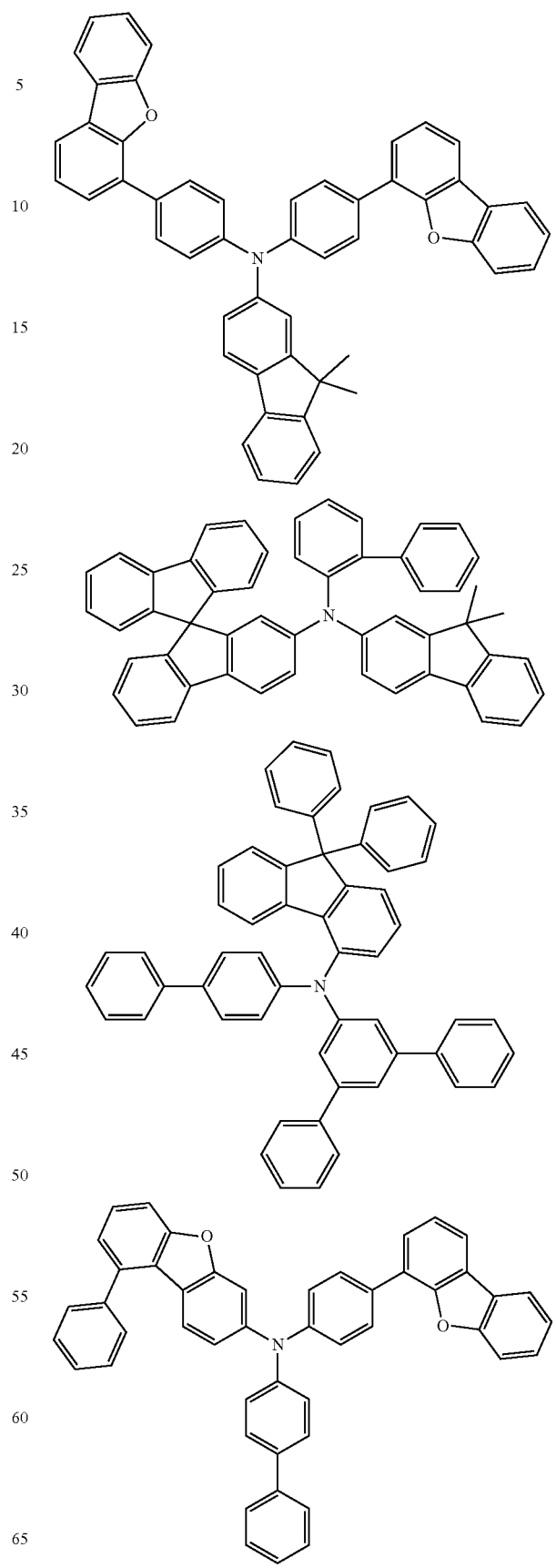

787
-continued
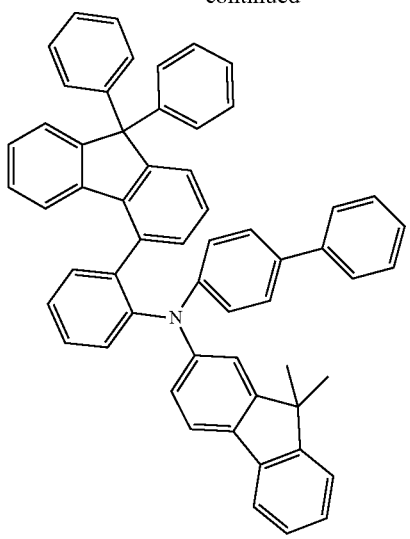
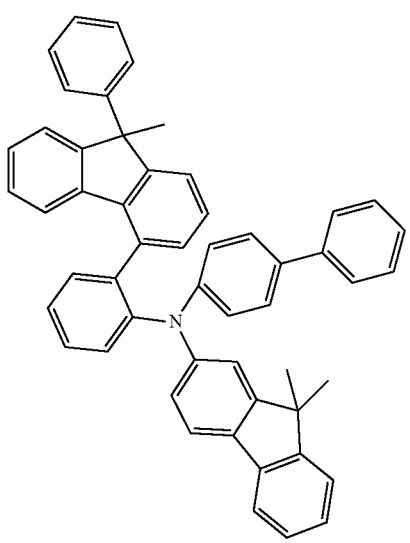
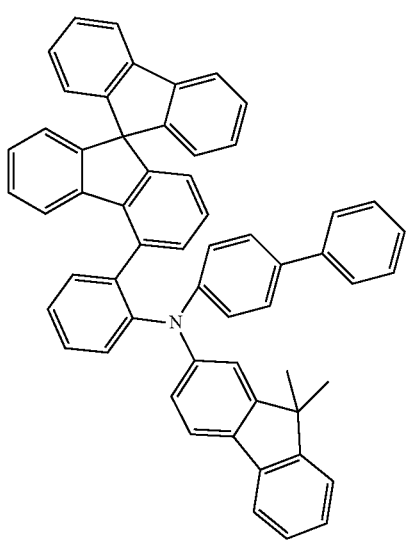
788
-continued
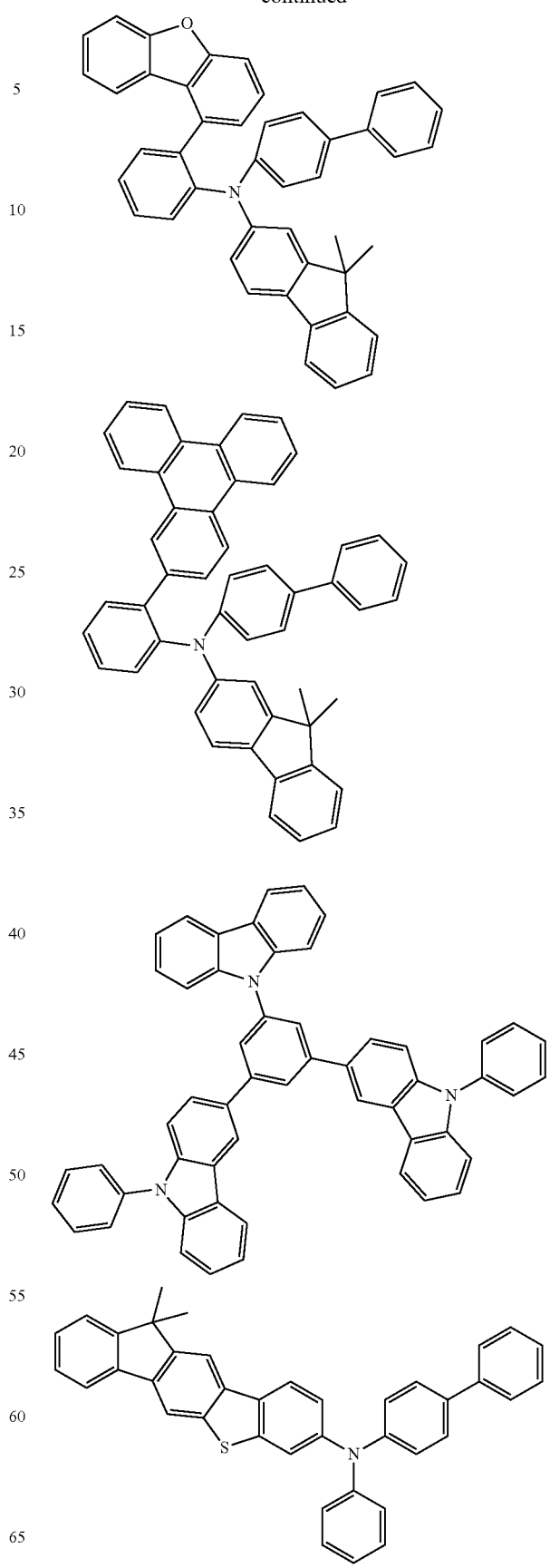

789
-continued
790
-continued
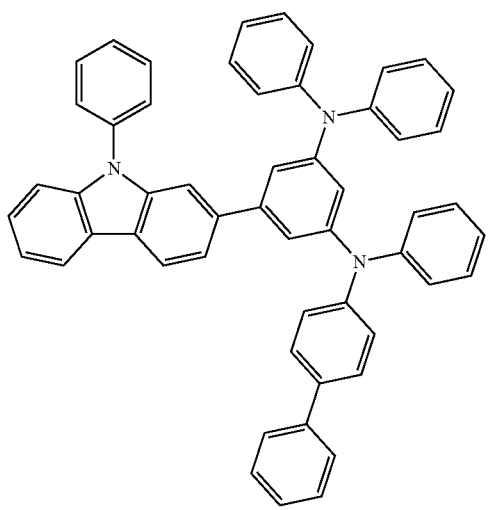
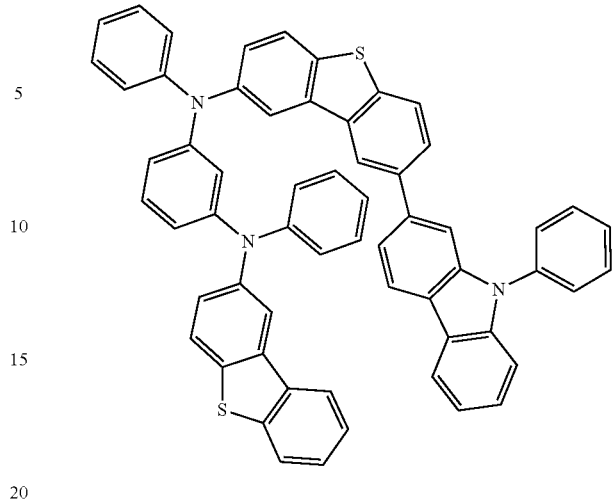
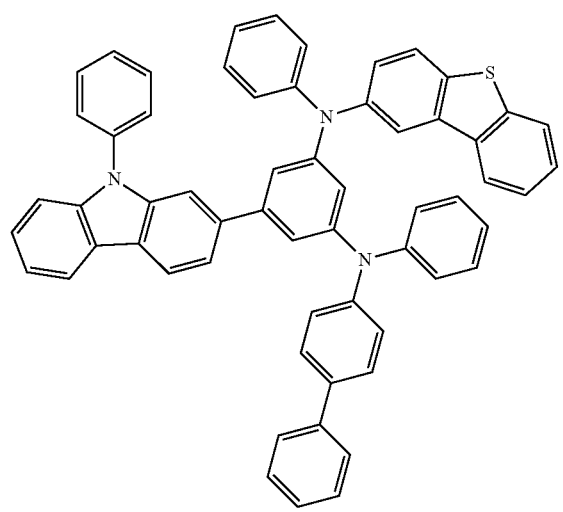
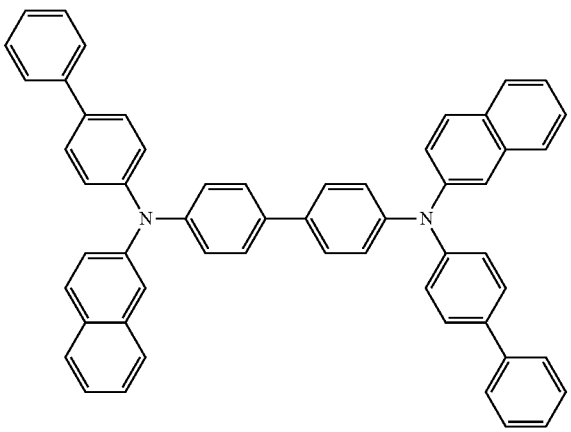
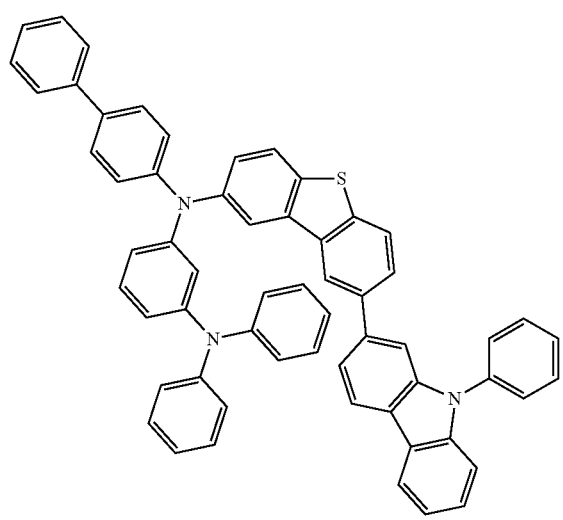
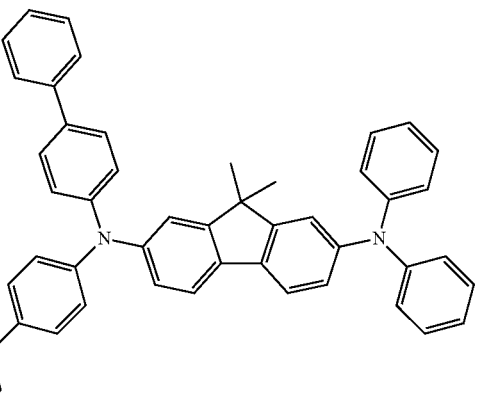

791
-continued
792
-continued
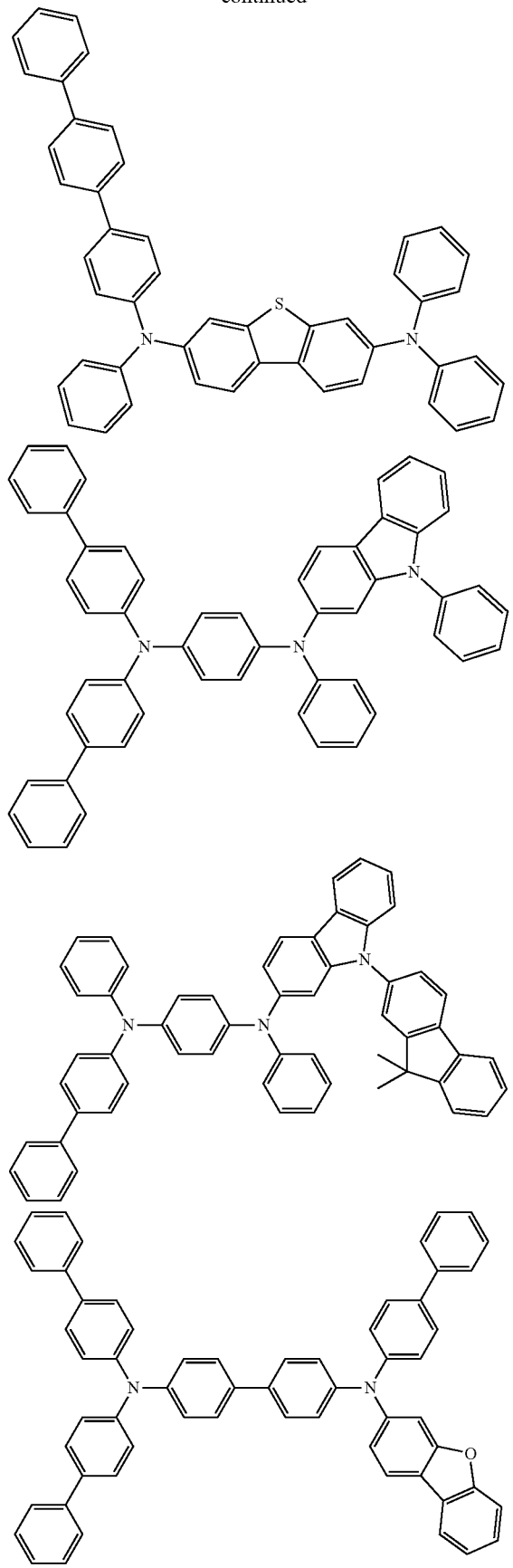
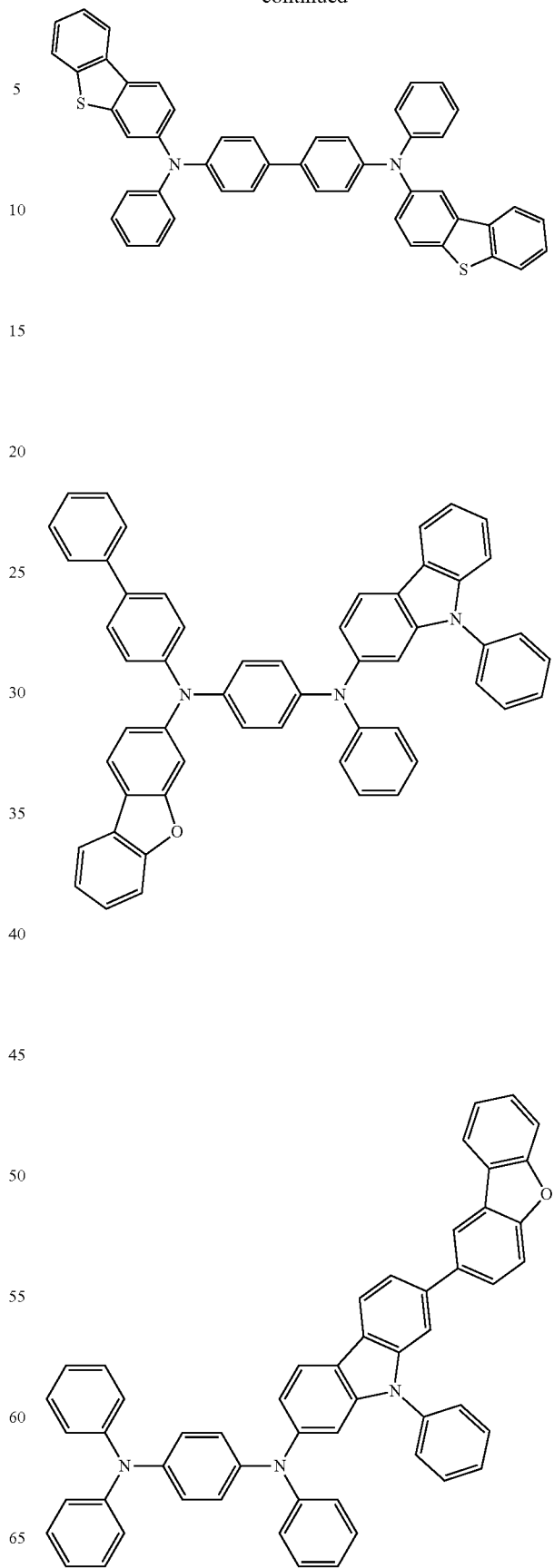

-continued
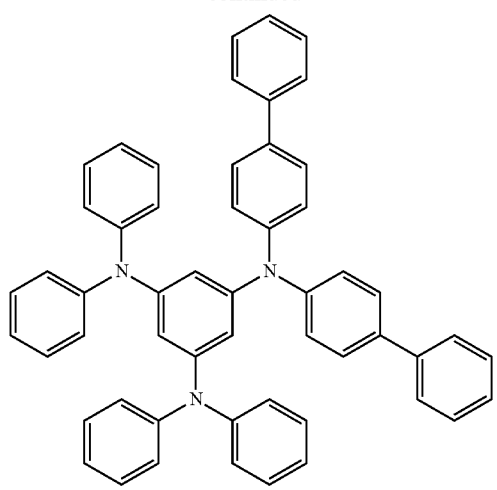
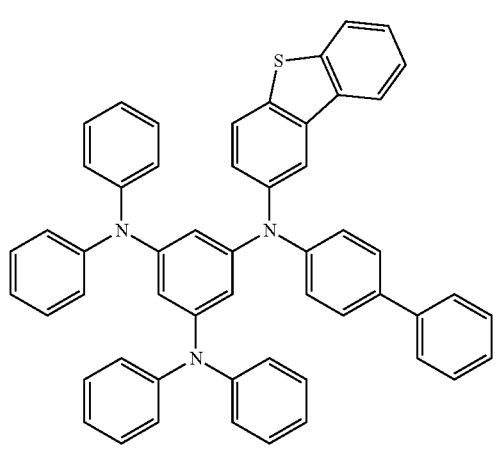
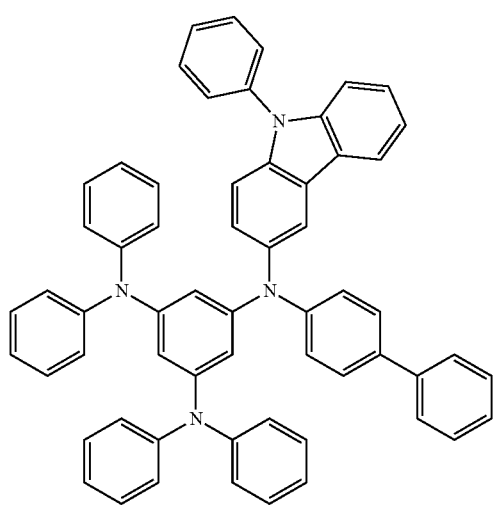
-continued
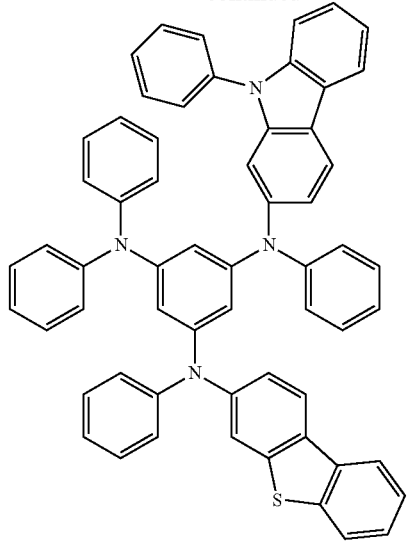
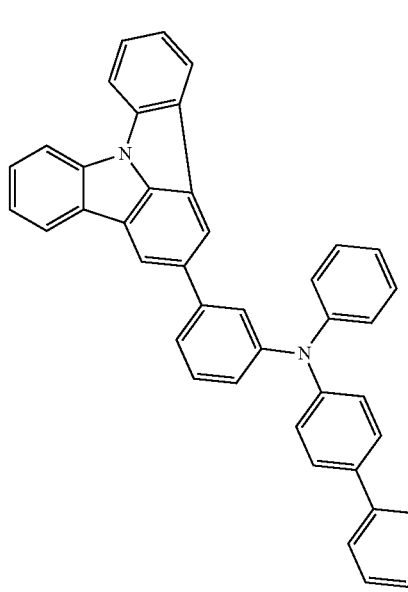
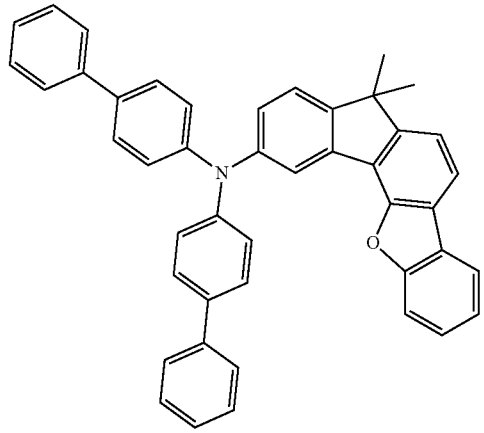

795
-continued
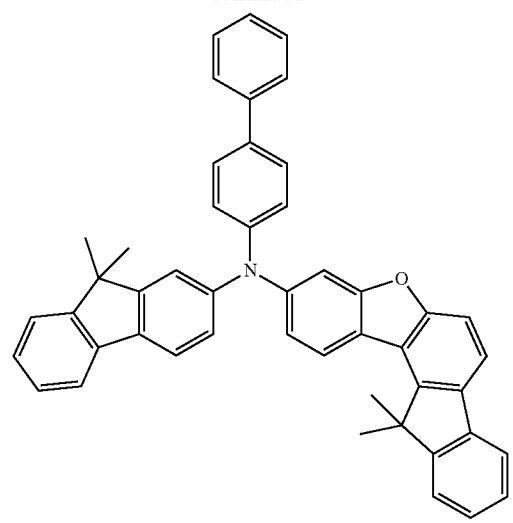
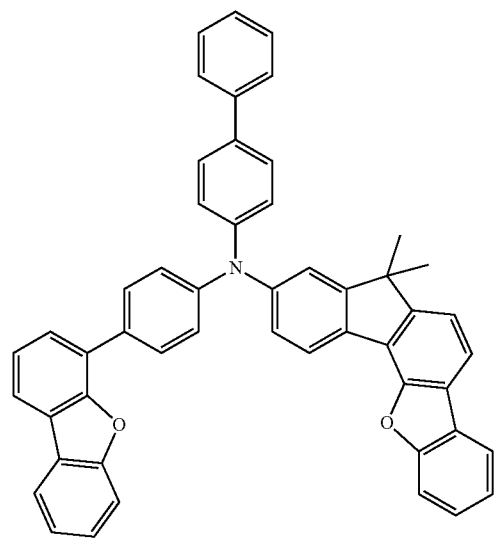
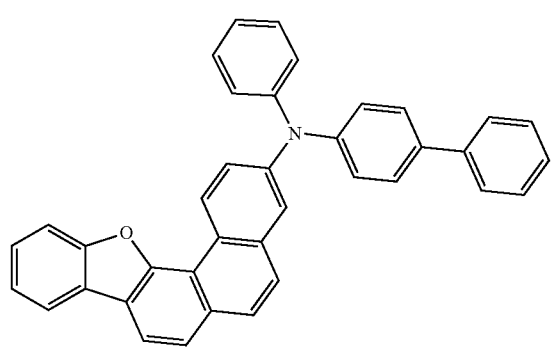
796
-continued
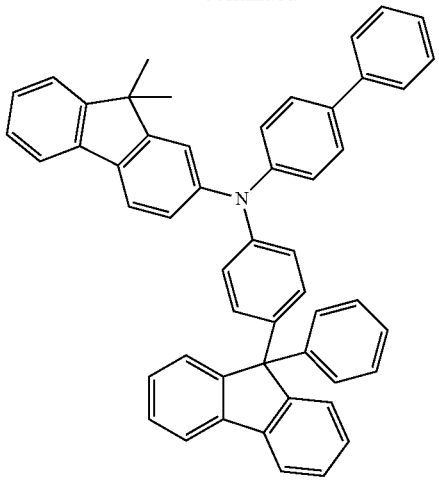
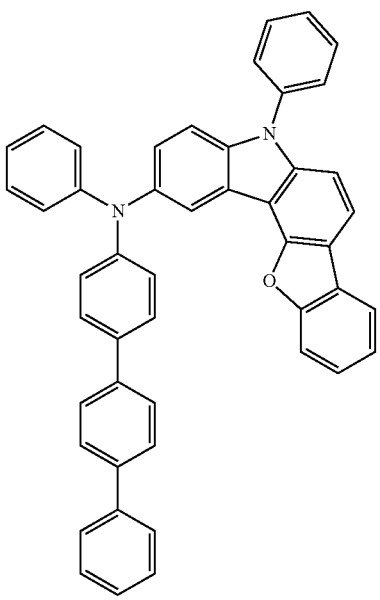

797
-continued
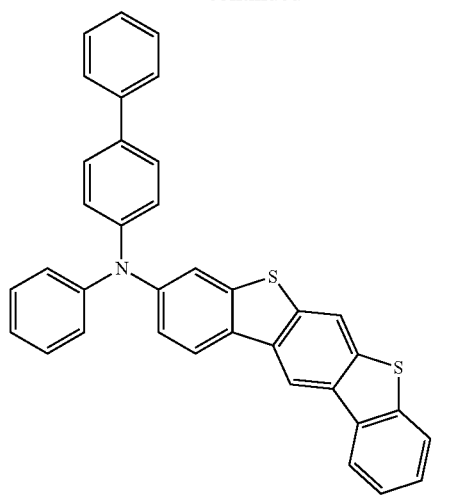
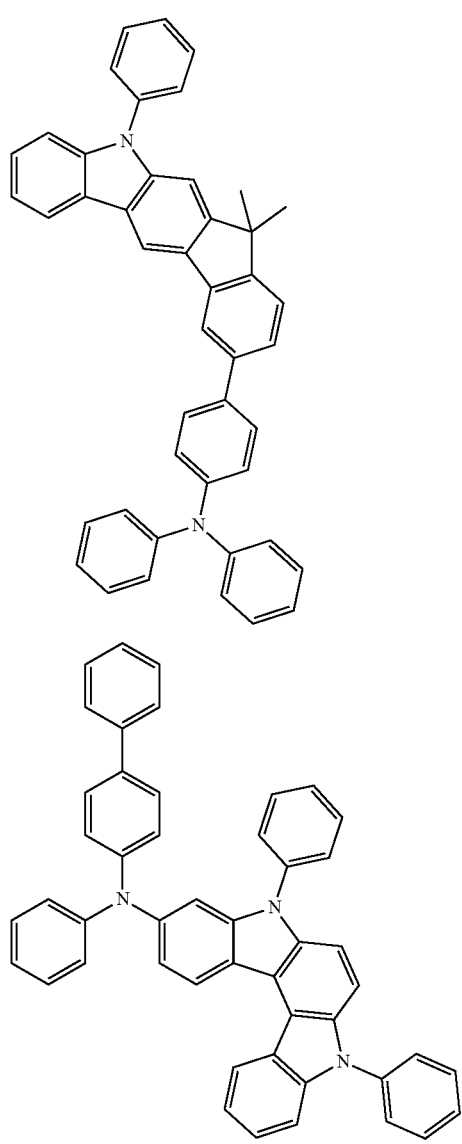
798
-continued
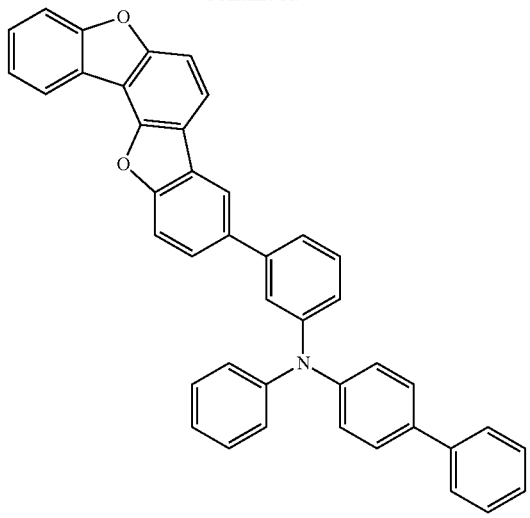
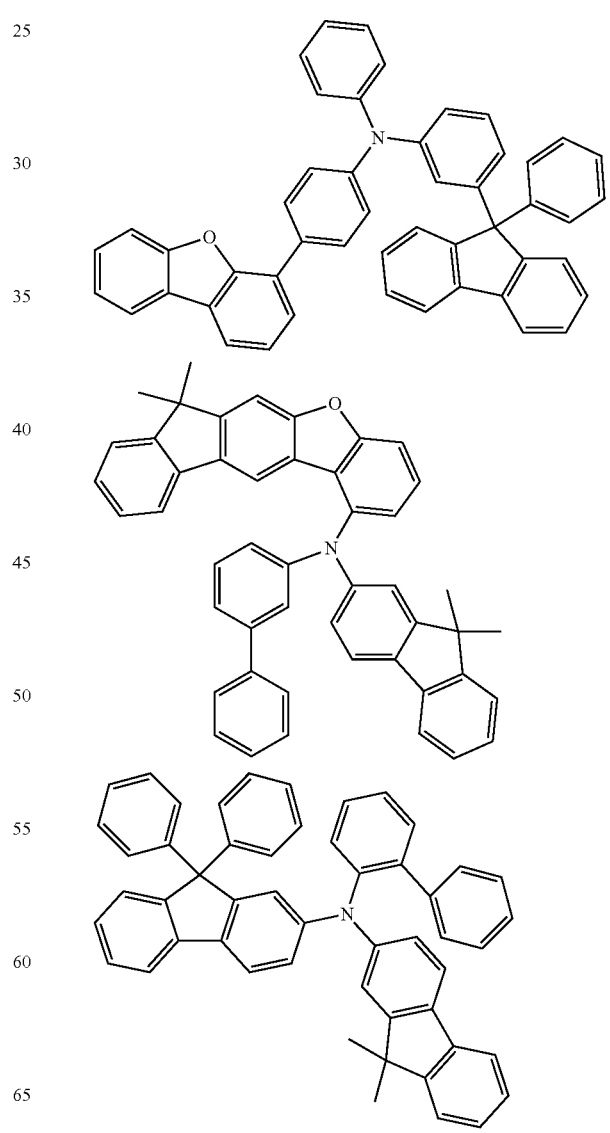

799
-continued
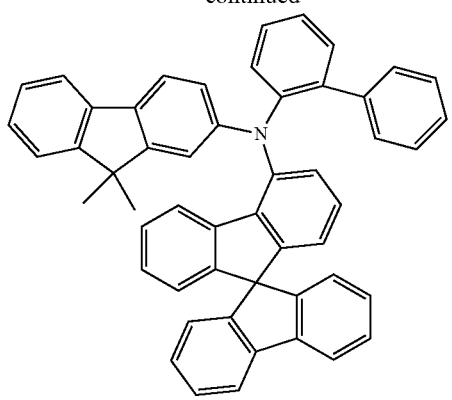
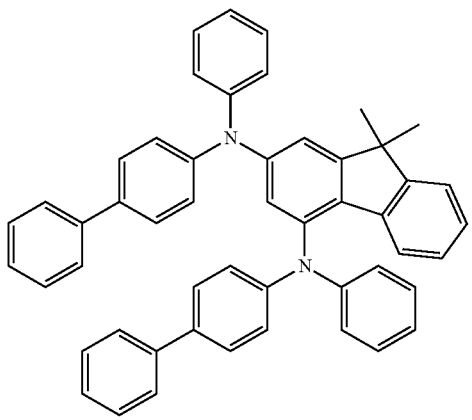
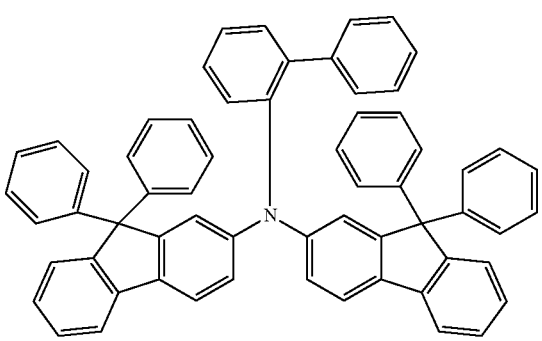
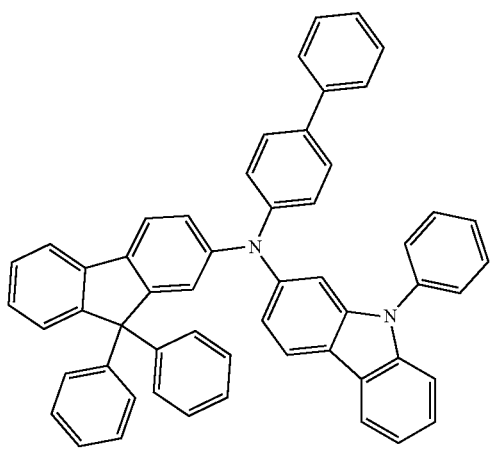
800
-continued
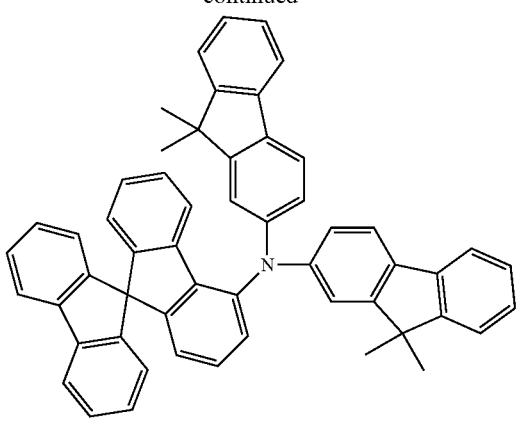
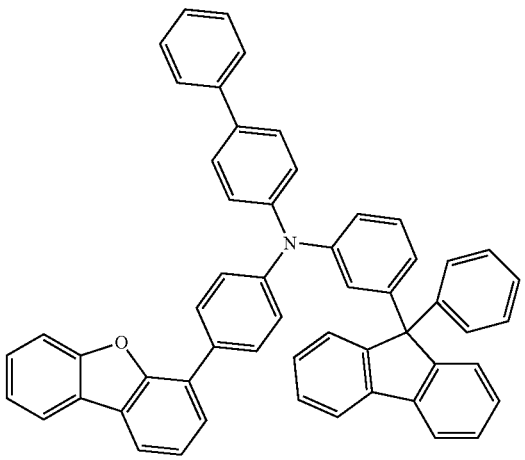
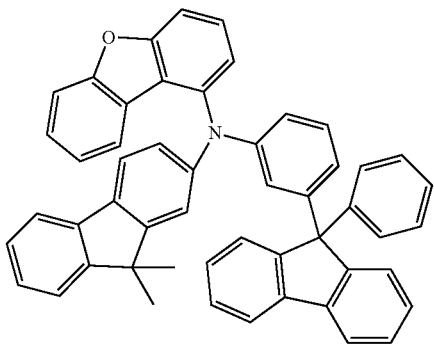

801
-continued
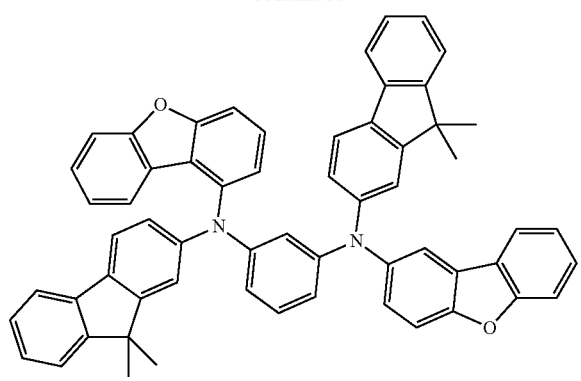
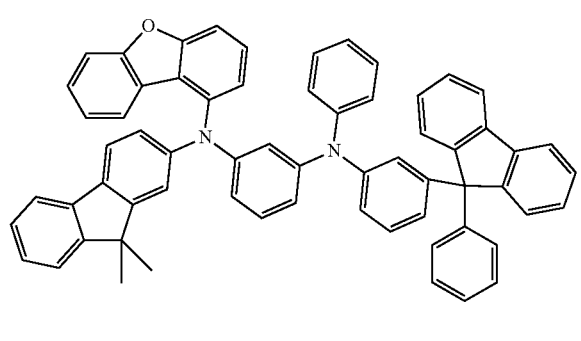
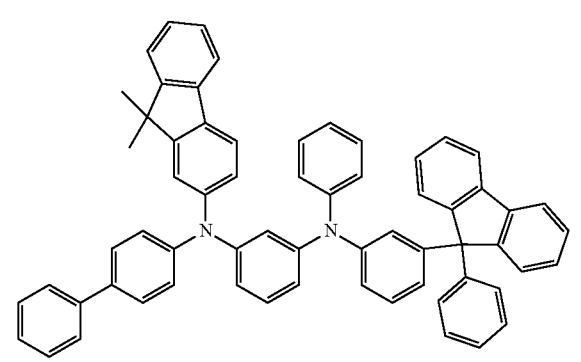
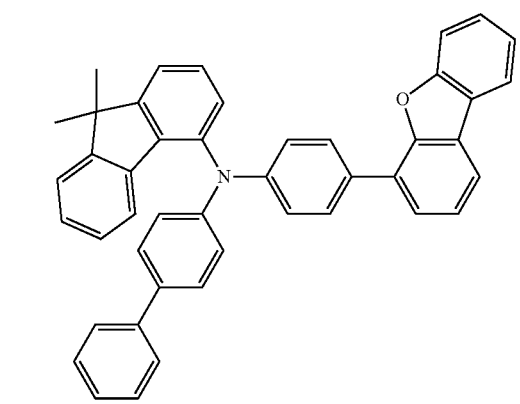
802
-continued
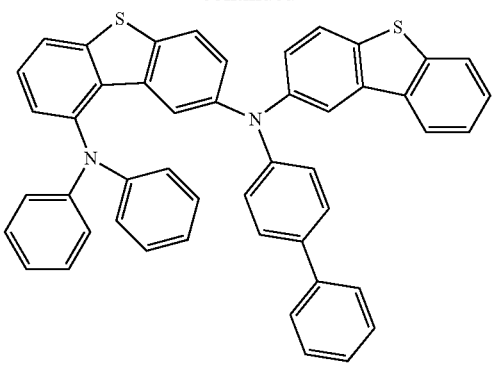
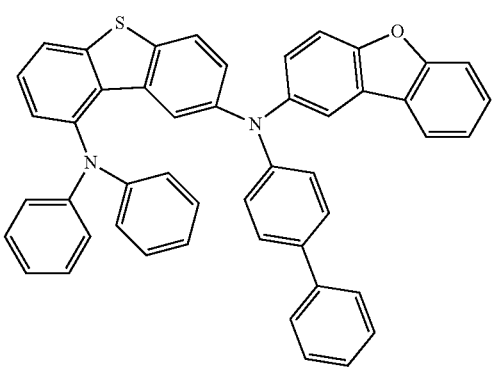
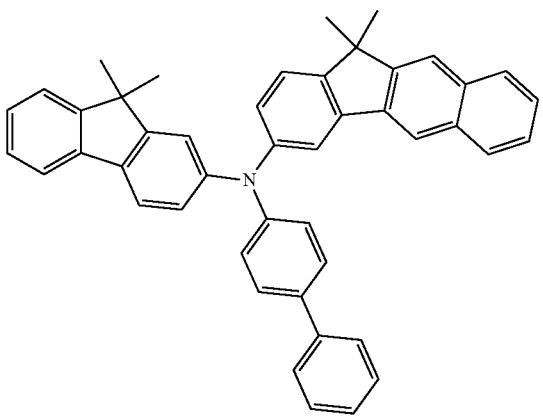

803
-continued

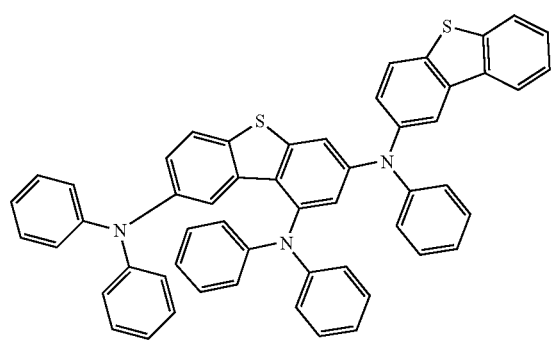

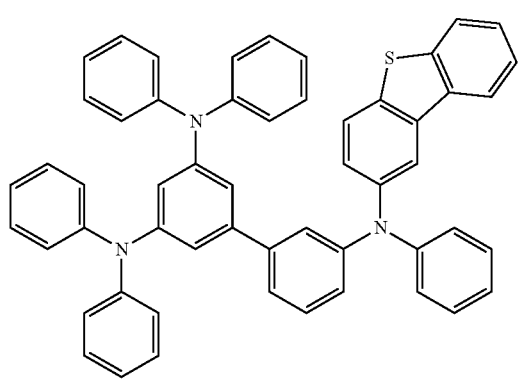

804
-continued

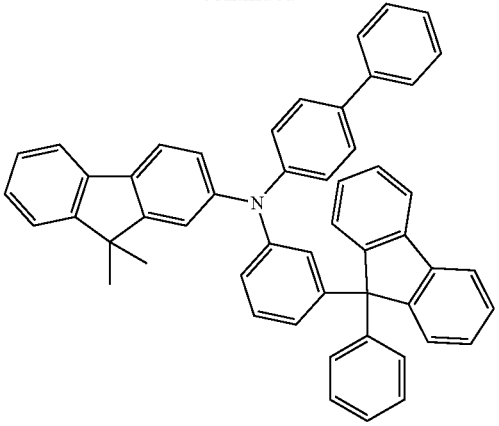

In the hole transport region, in addition to the compounds described above, other suitable compounds may also be used.

In an implementation, the charge transport region may be, e.g., an electron transport region.

Figure 3:
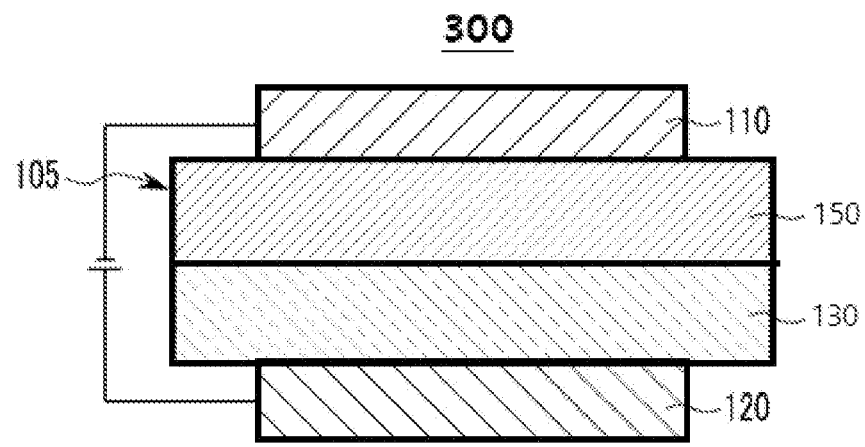

Referring to FIG. 3, the organic light emitting diode 300 may further include an electron transport region 150 in addition to the light emitting layer 130. The electron transport region 150 may help further increase electron injection and/or electron mobility between the cathode 110 and the light emitting layer 130 and block holes.

In an implementation, the electron transport region 150 may include an electron transport layer between the cathode 110 and the light emitting layer 130, and an electron transport auxiliary layer between the light emitting layer 130 and the electron transport layer. In an implementation, at least one compound of Group B may be included in at least one of the electron transport layer and the electron transport auxiliary layer.

[Group B]

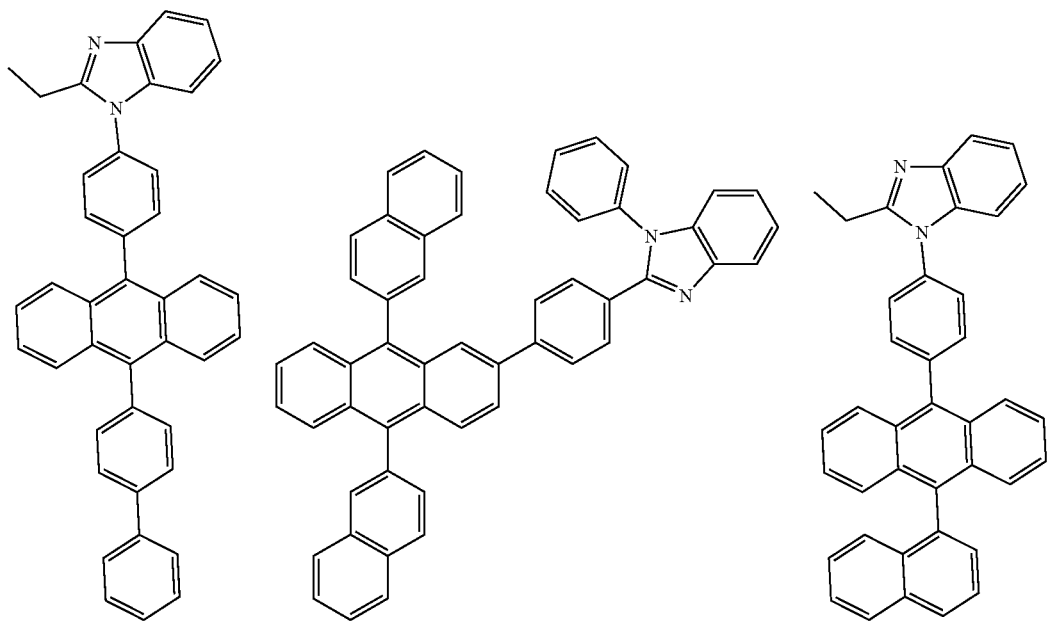

805
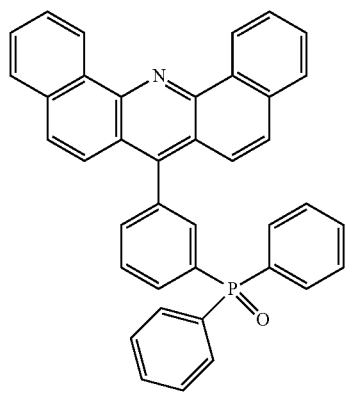
806
-continued
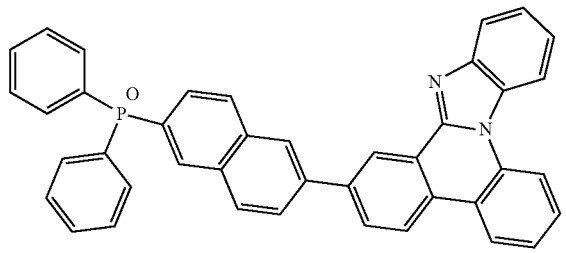
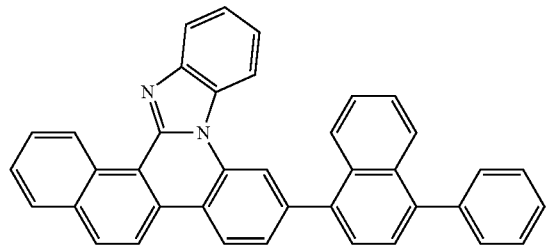
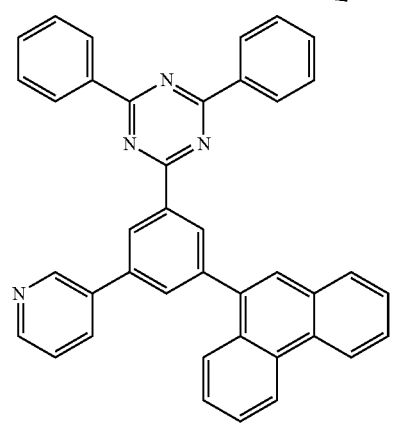
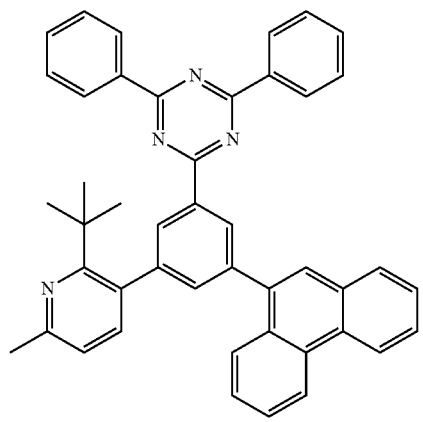
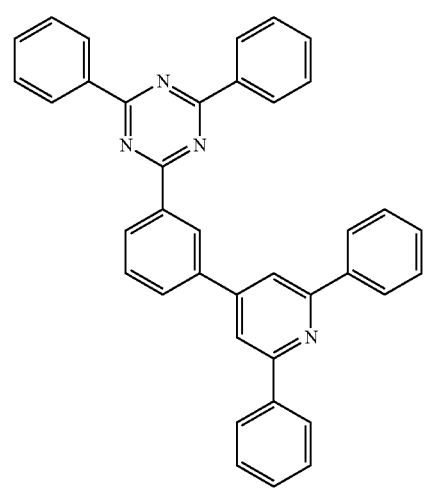
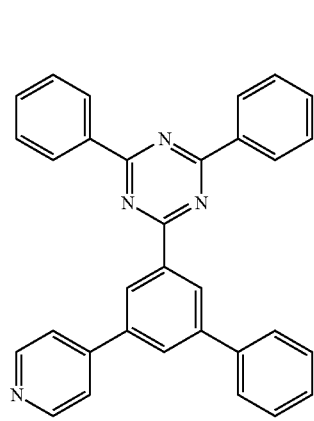
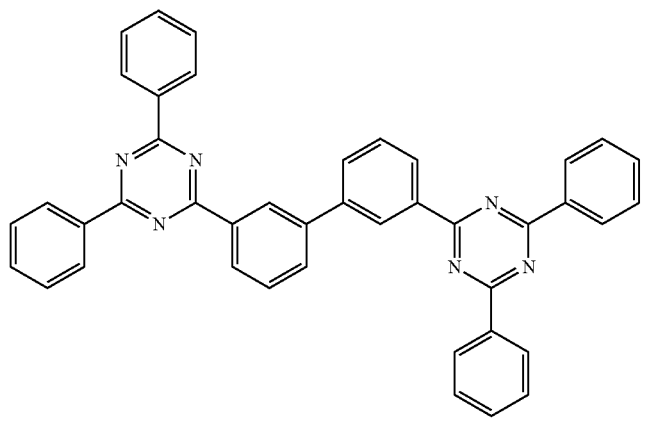

807
-continued
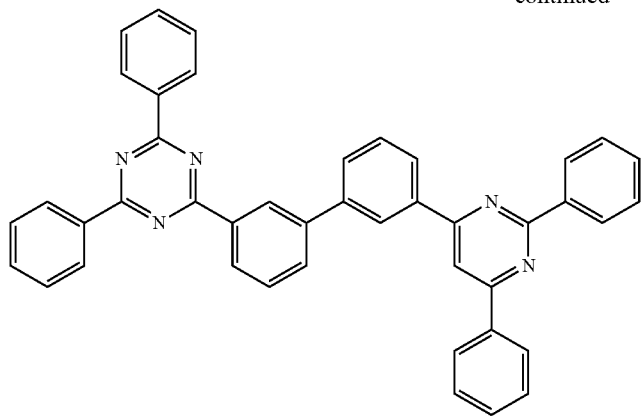
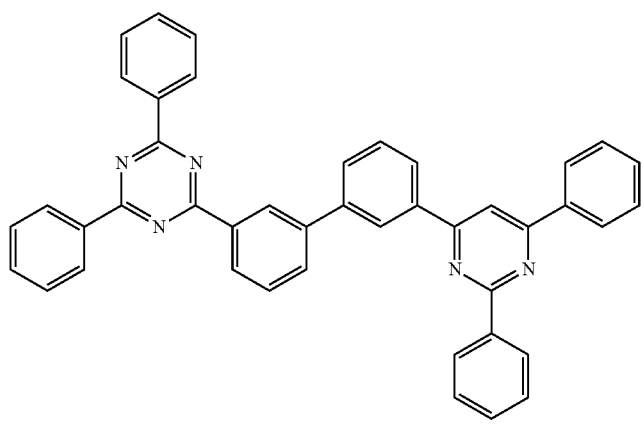
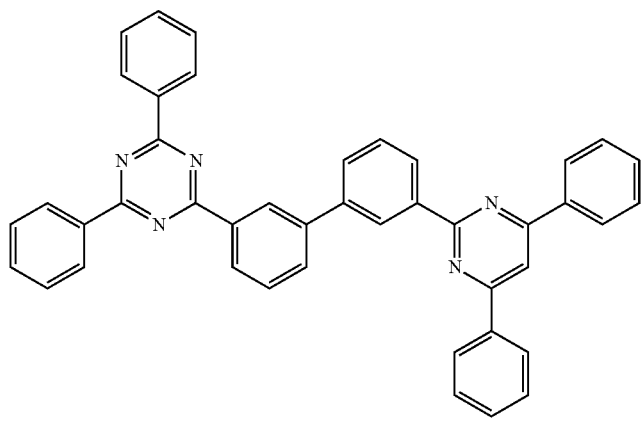
808
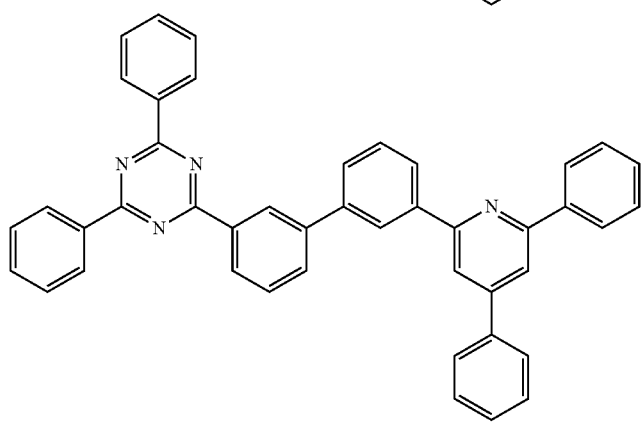

809
810
-continued
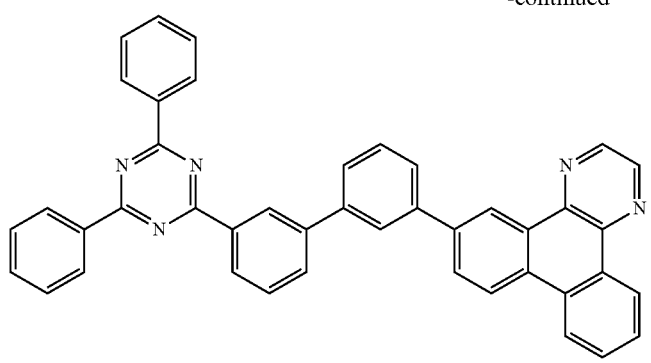
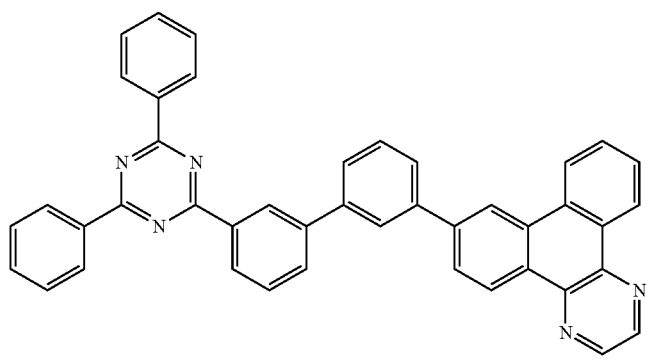
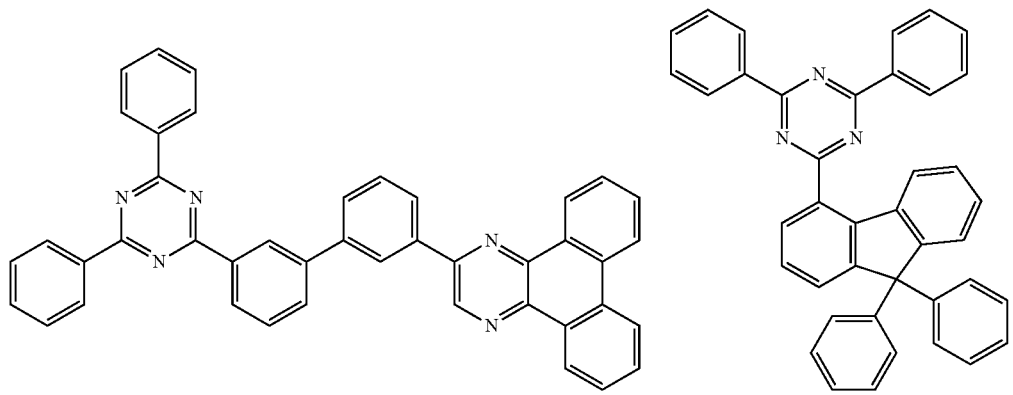
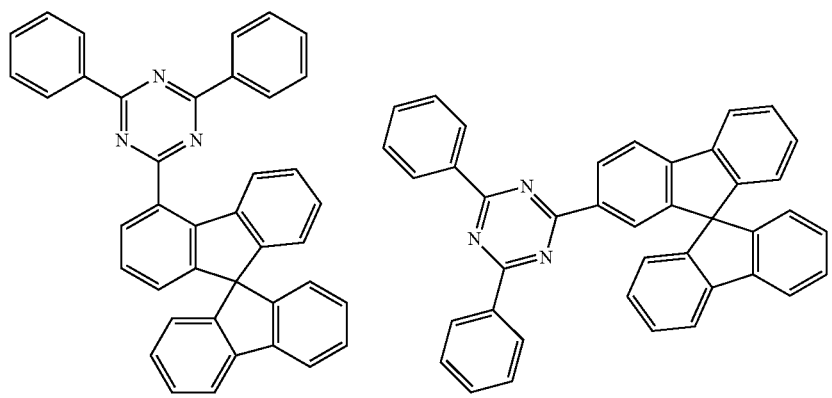

811
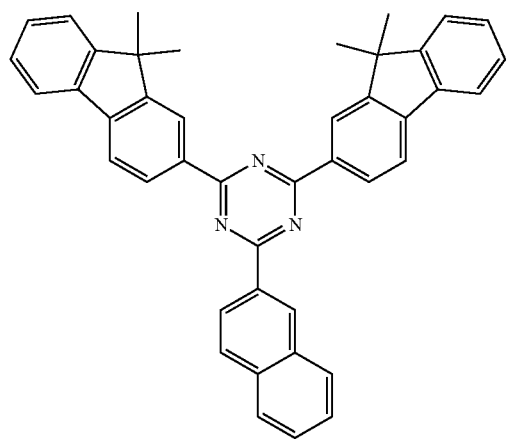
-continued
812
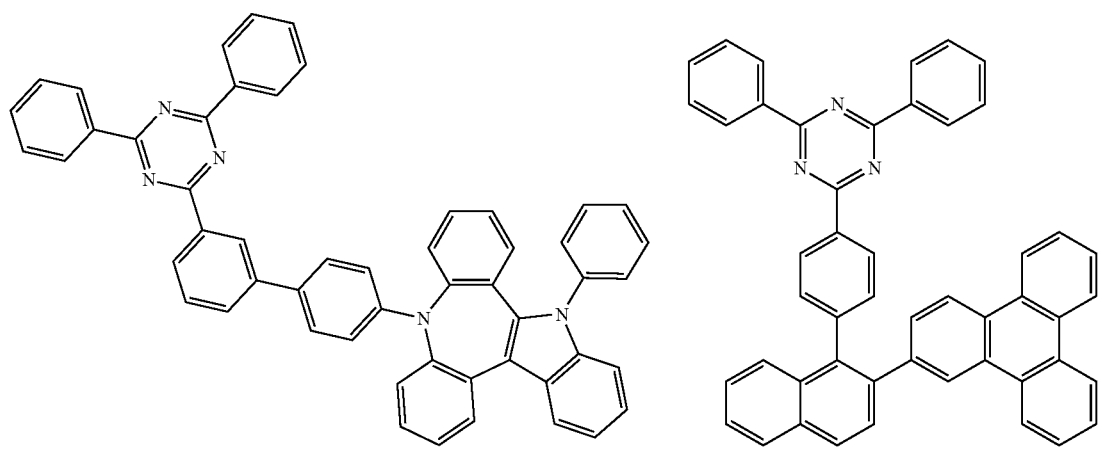
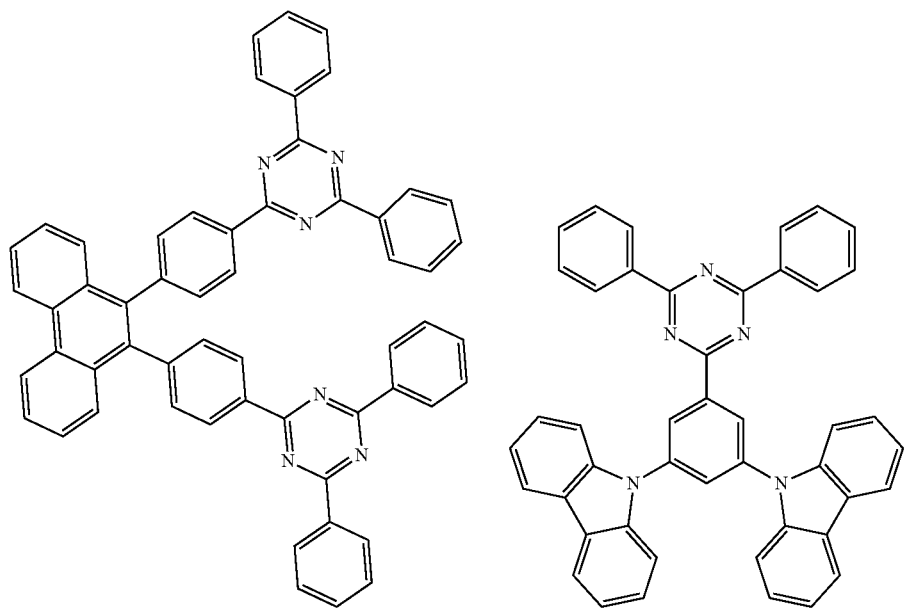

813
-continued
814
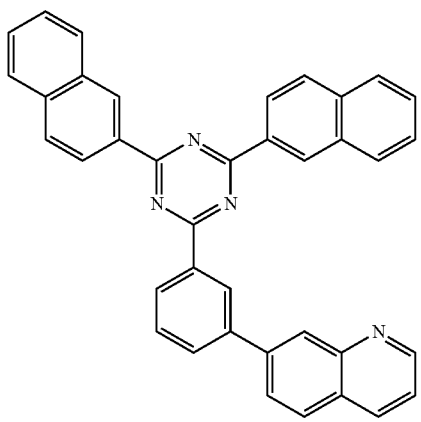
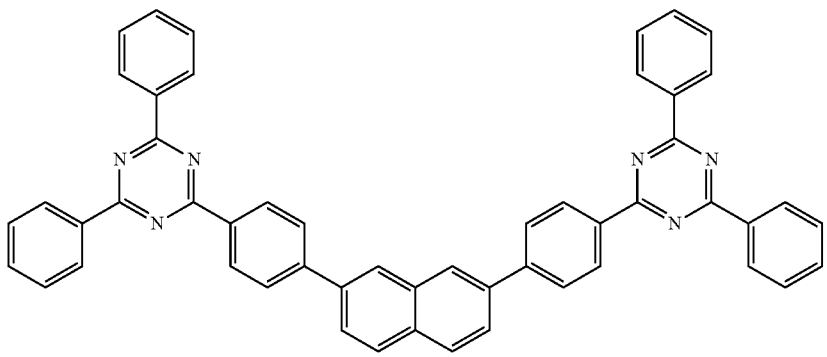
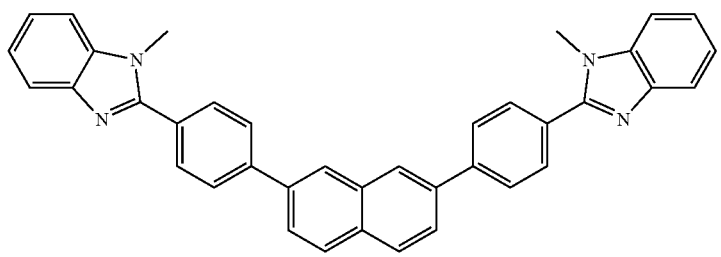
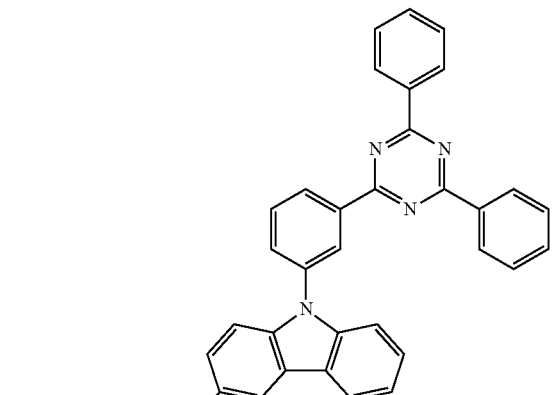
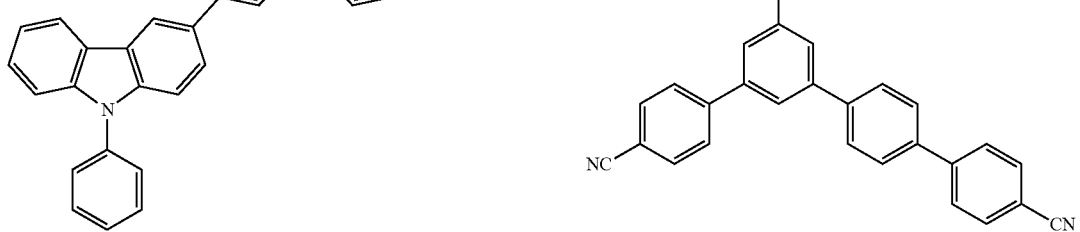

-continued
815
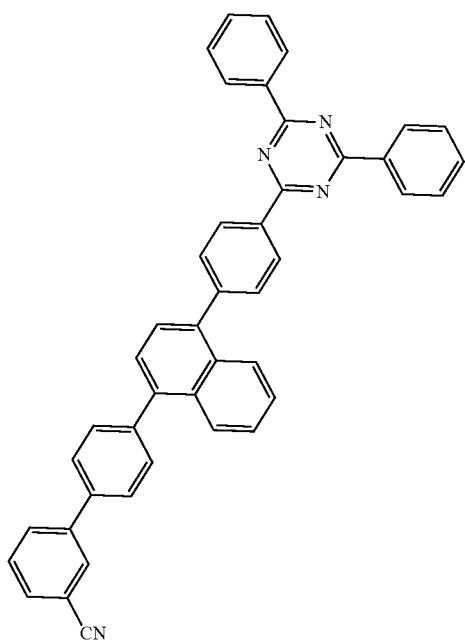
816
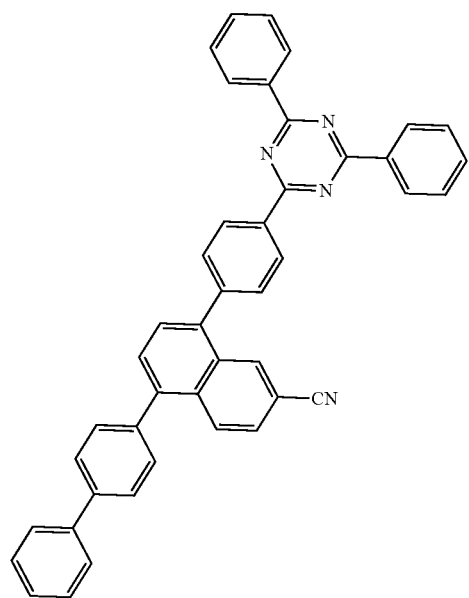
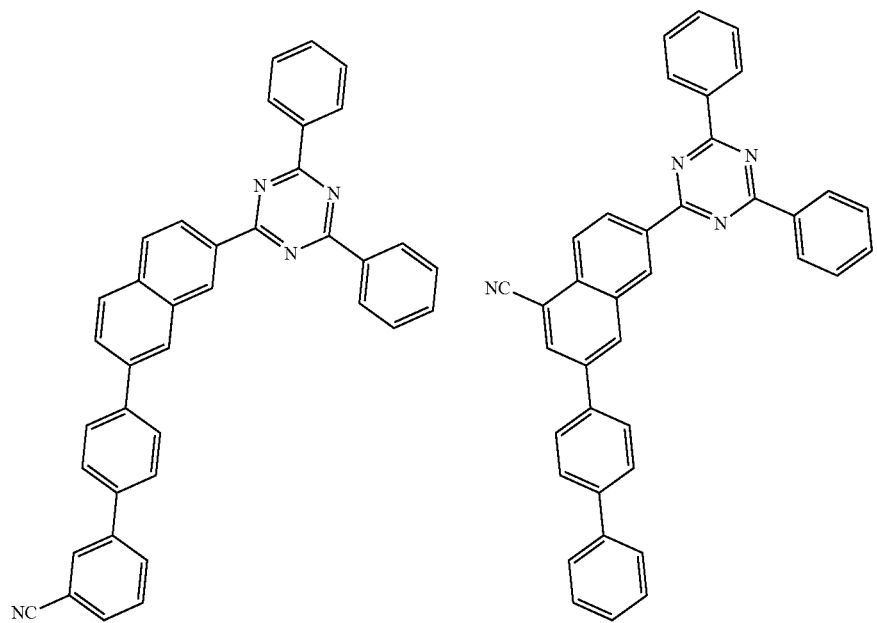

-continued
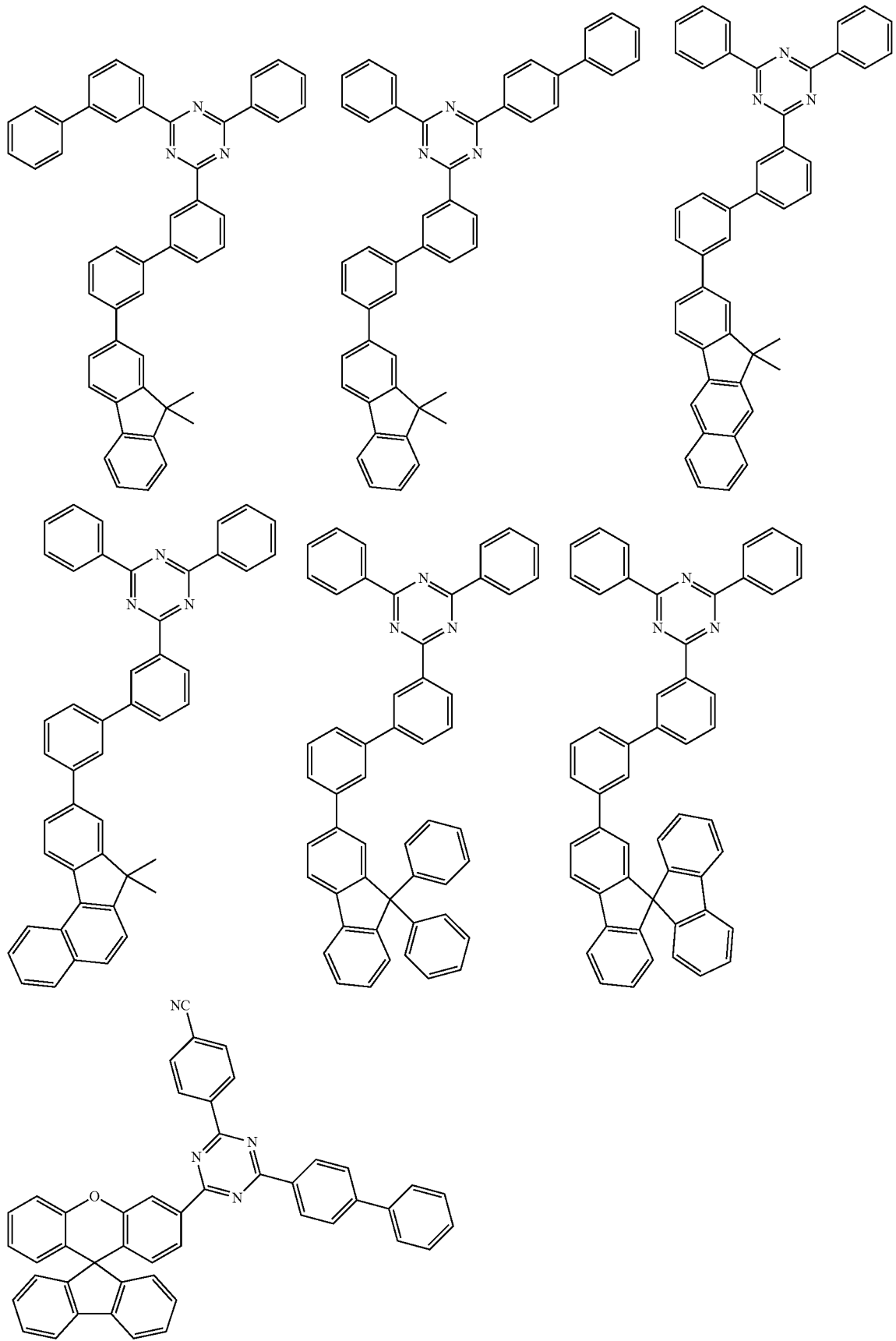

819 820
-continued

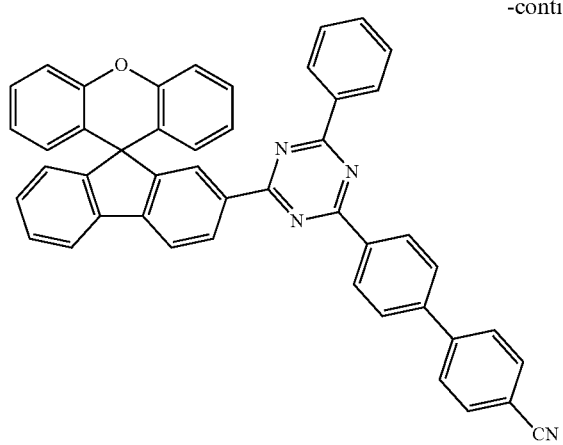
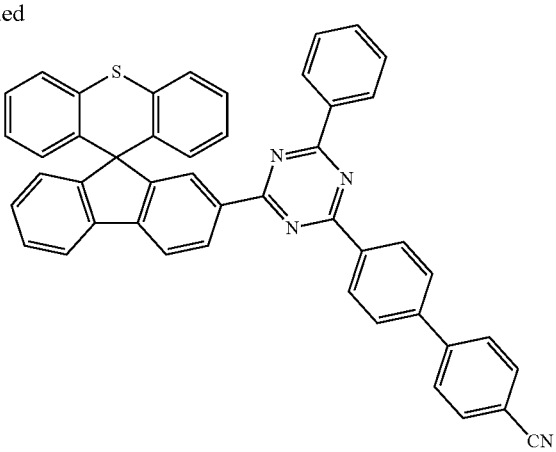
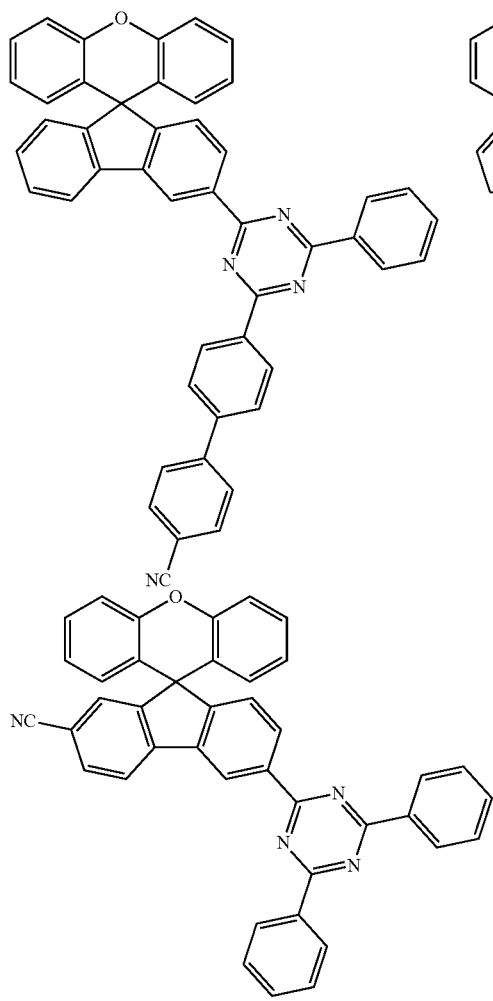
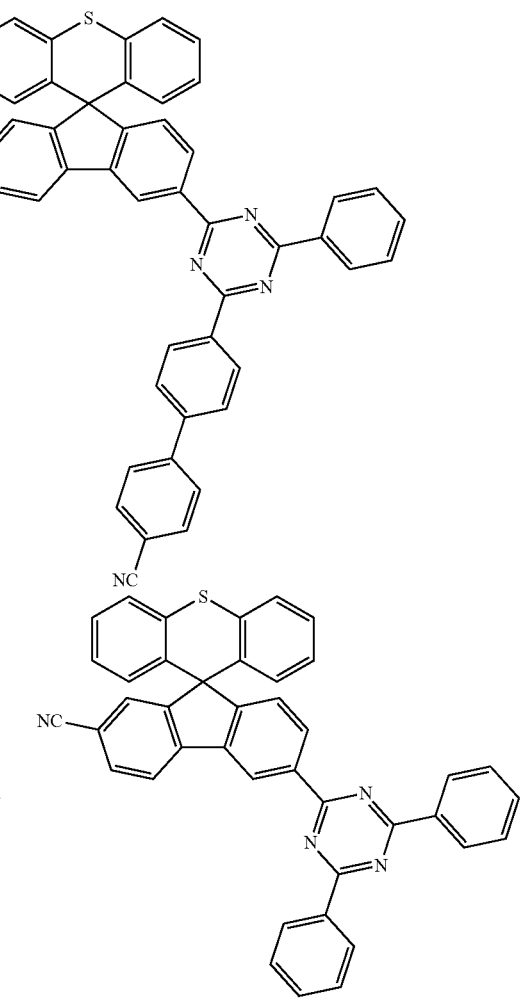

An embodiment may provide an organic light emitting diode including the light emitting layer 130 as the organic layer 105 as shown in FIG. 1.

Another embodiment may provide an organic light emitting diode including a hole transport region 140 in addition to the light emitting layer 130 as the organic layer 105, as shown in FIG. 2.

Another embodiment may provide an organic light emitting diode including an electron transport region 150 in addition to the light emitting layer 130 as the organic layer 105 as shown in FIG. 3.

Figure 4:
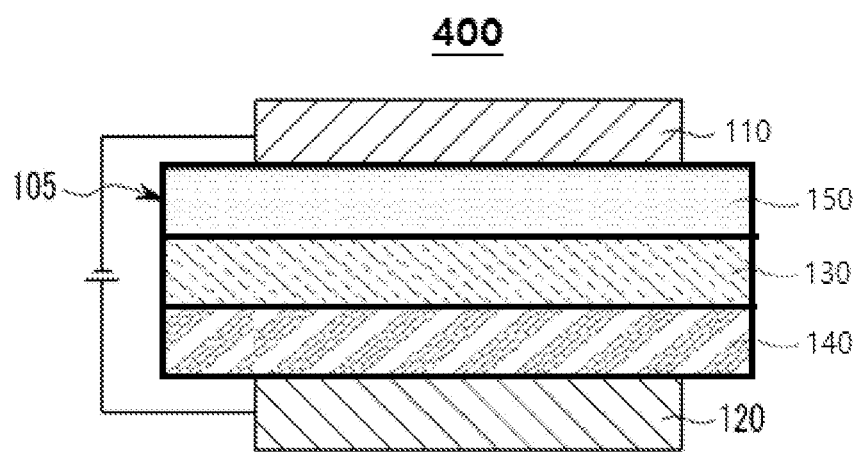

Another embodiment may provide an organic light emitting diode including a hole transport region 140 and an electron transport region 150 in addition to the light emitting layer 130 as the organic layer 105, as shown in FIG. 4.

In another embodiment, an organic light emitting diode may further include an electron injection layer, a hole injection layer, or the like, in addition to the light emitting layer 130 as the organic layer 105 in each of FIGS. 1 to 4.

The organic light emitting diodes 100, 200, 300, and 400 may be manufactured by forming an anode or a cathode on a substrate, and then forming an organic layer by a dry film method such as vacuum deposition, sputtering, plasma plating and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in examples and synthesis examples were purchased from Sigma-Aldrich Co. Ltd., TCI Inc., Tokyo chemical industry or P&H tech as far as there is no particular comment or were synthesized by suitable methods.

Preparation of Compound for Organic Optoelectronic Device

Compounds were synthesized through the following steps.

Synthesis of First Compound

Synthesis Example 1: Synthesis of Intermediate M-1

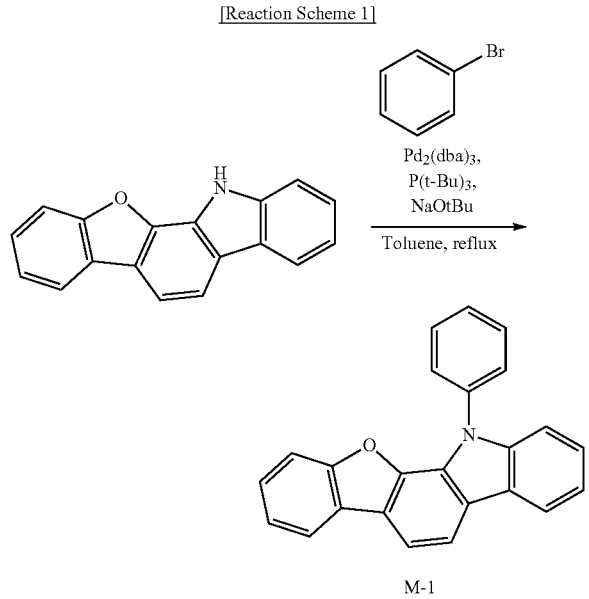

12H-benzofuro[2,3-a]carbazole (20 g, 77.73 mmol), bromobenzene (30.5 g, 194.33 mmol), NaOtBu (11.21 g, 116.6 mmol), and $Pd_2(dba)_3$ (3.56 g, 3.89 mmol) were added to 130 ml of toluene and suspended therein, and $P(t-Bu)_3$ (4.72 ml, 11.66 mmol) was added thereto and then, stirred under reflux for 12 hours under a nitrogen atmosphere. Subsequently, distilled water was added to the reaction solution, and a solid produced in an organic layer due to the distilled water was filtered and separated under a reduced pressure. The solid was dissolved in toluene and then, cooled down to ambient temperature and recrystallized, obtaining Intermediate M-1 (29.8 g, Yield: 80%).

LC-MS M+H: 334.12 g/mol,

Synthesis Example 2: Synthesis of Intermediate M-2

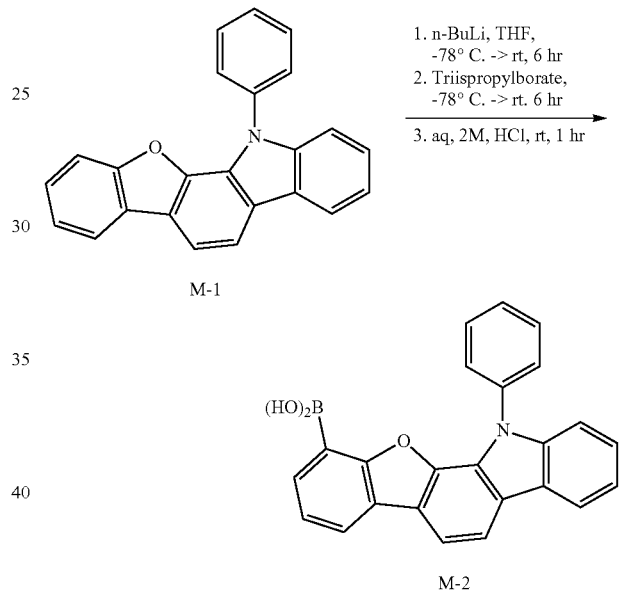

29.8 g (89.39 mmol) of Intermediate M-1 was added to 224 ml of tetrahydrofuran and dissolved therein and then, cooled down to −78° C. and stirred under a nitrogen atmosphere. Subsequently, 42.9 ml (107.26 mmol) of a 2.5 M n-BuLi (in n-Hexane) solution was slowly added thereto and then, stirred under a nitrogen atmosphere at ambient temperature for 6 hours, while slowly heating up. The reaction solution was cooled down to −78° C., and 25.22 g (134.08 mmol) of triisopropylborate was slowly added thereto and then, stirred under a nitrogen atmosphere for 6 hours, while slowly heating up to ambient temperature. Then, 223.5 ml of a 2.0 M hydrochloric acid aqueous solution was added thereto and then, stirred for 1 hour, and a solid produced therein was filtered and separated under a reduced pressure. The obtained solid was dissolved in methyl chloride and recrystallized, obtaining Intermediate M-2 (50 g, Yield: 55%).

LC-MS M+H: 378.12 g/mol

Synthesis Example 3: Synthesis of Compound 1B-4-4

[Reaction Scheme 3]

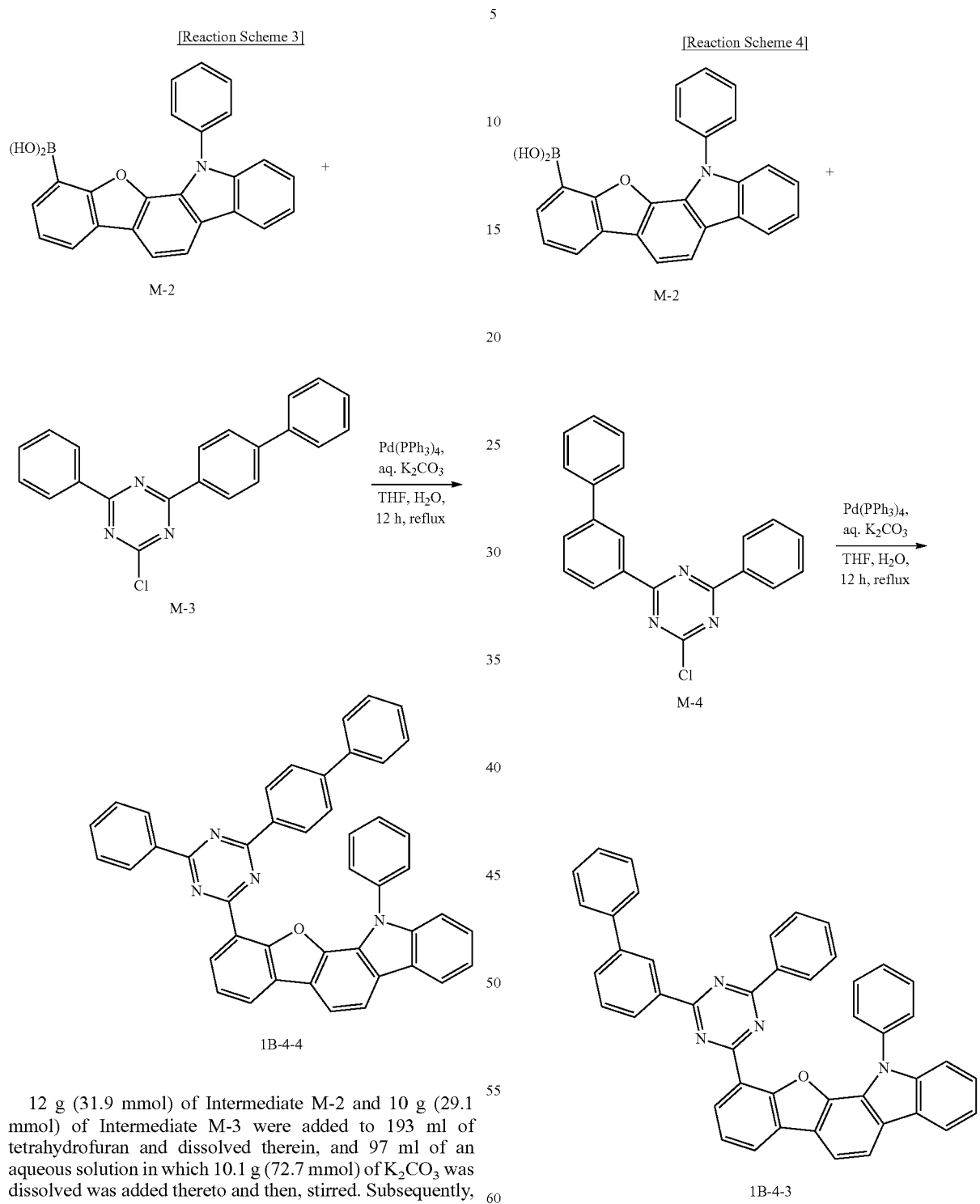

12 g (31.9 mmol) of Intermediate M-2 and 10 g (29.1 mmol) of Intermediate M-3 were added to 193 ml of tetrahydrofuran and dissolved therein, and 97 ml of an aqueous solution in which 10.1 g (72.7 mmol) of K₂CO₃ was dissolved was added thereto and then, stirred. Subsequently, 1.68 g (1.45 mmol) of Pd(PPh₃)₄ was added thereto and then, stirred under reflux for 12 hours under a nitrogen atmosphere. When a reaction was completed, a solid produced therein was filtered and separated under a reduced pressure, dissolved in toluene and recrystallized, obtaining Compound 1B-4-4 (14 g, Yield: 75%).

LC-MS M+H: 641.23 g/mol

Synthesis Example 4: Synthesis of Compound 1B-4-3

[Reaction Scheme 4]

Compound 1B-4-3 (20 g, Yield: 79%) was obtained according to the same method as Synthesis Example 3 except that 8.18 g (23.81 mmol) of Intermediate M-4 was used instead of Intermediate M-3.

LC-MS M+H: 640.33 g/mol

Comparative Synthesis Example 1: Synthesis of Compound G-1

[Reaction Scheme 5]

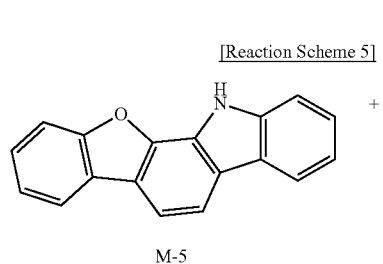

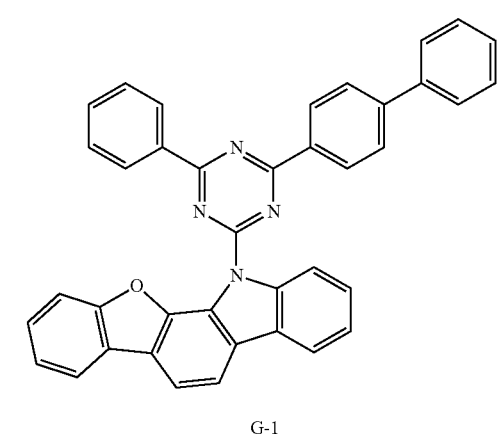

10 g (37.31 mmol) of Intermediate M-5, 14.75 g (42.91 mmol) of Intermediate M-3, and 2.09 g (52.24 mmol) of sodium hydride were added to 149 ml of DMF and dissolved therein and then, stirred for 4 hours at ambient temperature. When a reaction was completed, a solid produced by adding water thereto was filtered and separated under a reduced pressure and then, dissolved in 100 ml of a 1,2-dichlorobenzene solvent and made to pass silica to obtain a target compound in a liquid state, and 50 ml of n-hexane was added thereto and then, stirred for 4 hours. Subsequently, Compound G-1 (18 g, Yield: 85.5%) was obtained by performing recrystallization in the above method.

Comparative Synthesis Example 2: Synthesis of Intermediate M-6

[Reaction Scheme 6]

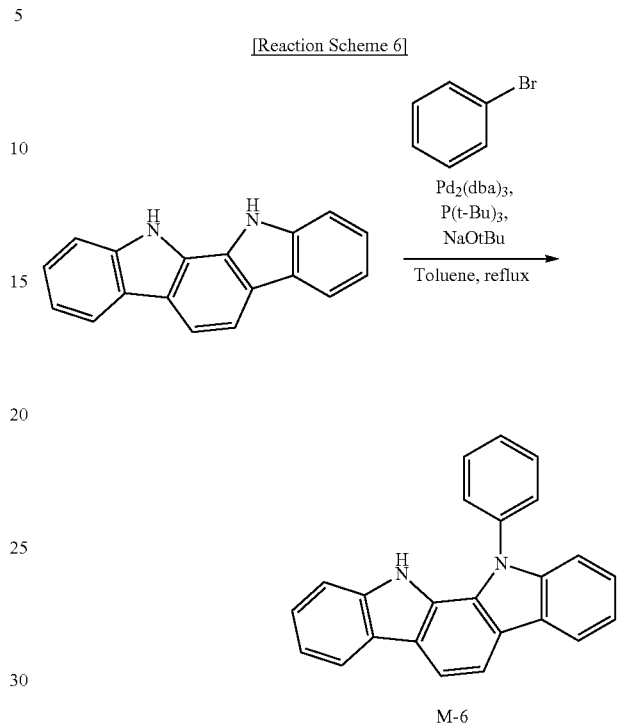

11,12-dihydroindolo[2,3-a]carbazole (48.97 g, 191.07 mmol), bromobenzene (30 g, 191.07 mmol), NaOtBu (27.54 g, 286.61 mmol), and Pd$_2$(dba)$_3$ (8.75 g, 9.55 mmol) were added to 636 ml of toluene and suspend therein, and P(t-Bu)$_3$ (11.6 g, 28.66 mmol) was added thereto and then, stirred under reflux for 12 hours under a nitrogen atmosphere. Subsequently, distilled water was added to the reaction solution, and a solid produced in an organic layer due to the distilled water was filtered and separated under a reduced pressure. The obtained solid was adsorbed in silica gel by using MC (methylene chloride) and then, column-purified, obtaining Intermediate M-6 (30.49 g, Yield: 48%).

LC-MS M+H: 333.13 g/mol,

Comparative Synthesis Example 3: Synthesis of Compound G-2

[Reaction Scheme 7]

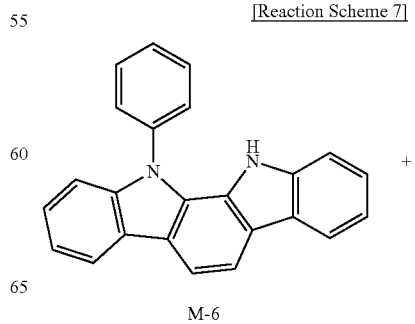

827

-continued

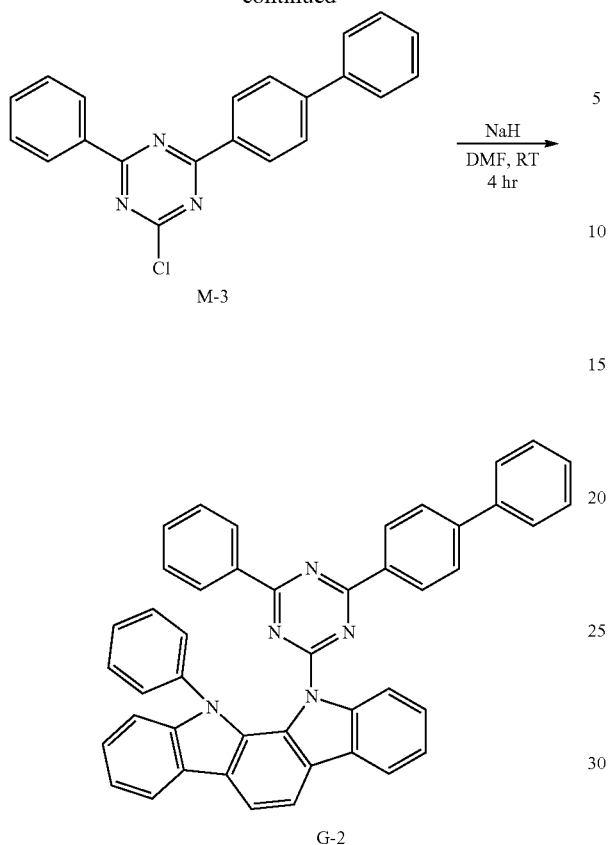

10 g (28.881 mmol) of Intermediate M-6, 11.42 g (33.21 mmol) of Intermediate M-3, and 1.62 g (40.43 mmol) of sodium hydride were added to 116 ml of DMF and dissolved therein and then, stirred for 4 hours at ambient temperature. When a reaction was completed, a solid produced by adding water thereto was filtered and separated under a reduced pressure, dissolved in 100 ml of a toluene solvent, and made to pass silica to obtain a target compound in a liquid state, and 50 ml of n-hexane was added thereto and then, stirred for 4 hours. A solid product obtained by performing recrystallization in the above method was heated and stirred in 100 ml of acetone, cooled down to ambient temperature, and stirred for 12 hours. Then, Compound G-2 (14.23 g, Yield: 77%) was obtained by performing second recrystallization.

Synthesis of Second Compound

Synthesis Example 5: Synthesis of Compound 68

[Reaction Scheme 8]

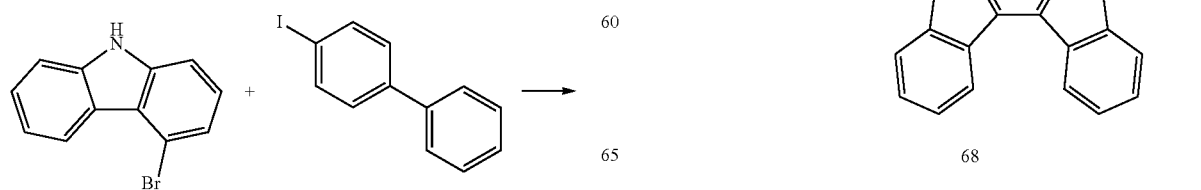

828

-continued

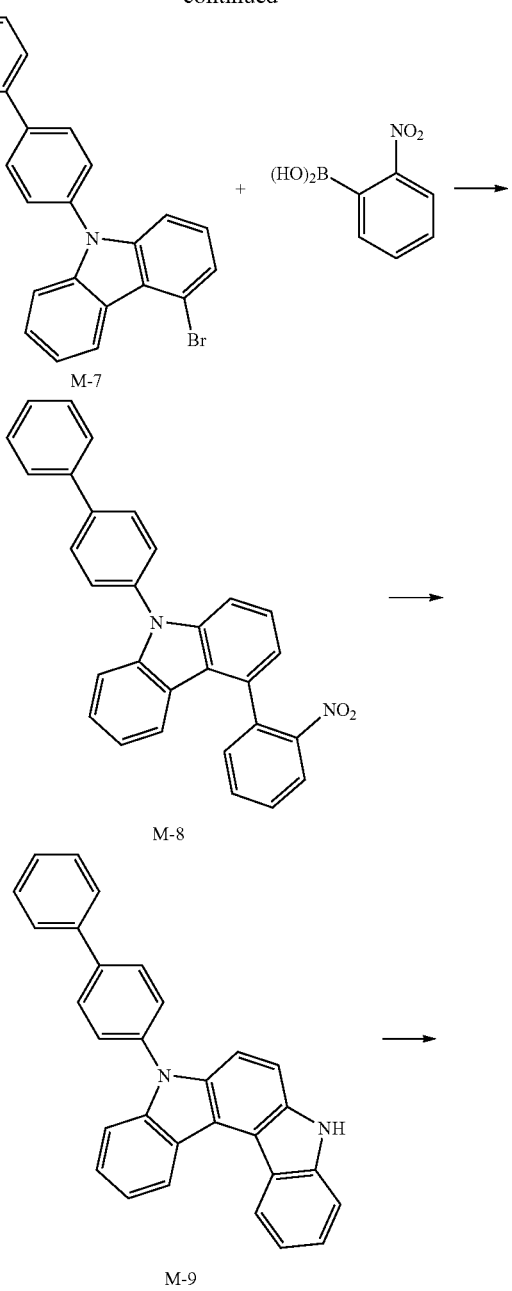

829

1st Step: Synthesis of Intermediate M-7

10.4 g (42.4 mmol) of 4-bromo-9H-carbazole, 11.9 g (42.4 mmol) of 4-iodo-1,1'-biphenyl, 0.39 g (0.42 mmol) of $Pd_2(dba)_3$, 0.21 g (0.85 mmol) of $P(t-Bu)_3$, and 6.1 g (63.6 mmol) of NaOt-Bu were suspended in 420 ml of toluene and then, stirred at 60° C. for 12 hours. When a reaction was completed, distilled water was added thereto, and the mixture was stirred for 30 minutes and then, extracted and treated through column chromatography (hexane:DCM (10%)), obtaining Intermediate M-7 (14.7 g, Yield: 87%).

2nd Step: Synthesis of Intermediate M-8

15.5 g (38.9 mmol) of Intermediate M-7, 7.2 g (42.8 mmol) of 2-nitrophenylboronic acid, 16.1 g (116.7 mmol) of $K_2CO_3$, and 1.4 g (1.2 mmol) of $Pd(PPh_3)_4$ were suspended in 150 ml of toluene and 70 ml of distilled water and then, stirred under reflux for 12 hours. An organic layer obtained therefrom by performing extraction with DCM and distilled water was silica gel-filtered. Subsequently, after removing an organic solution, a solid produced therein was recrystallized with DCM and hexane, obtaining Intermediate M-8 (13.7 g, Yield: 80%).

3rd Step: Synthesis of Intermediate M-9

22.5 g (51.0 mmol) of Intermediate M-8 was added to 52.8 ml of triethyl phosphite and then, substituted with nitrogen and stirred under reflux for 12 hours at 160° C. When a reaction was completed, 3 L of methanol was added thereto and then, stirred and filtered, and a filtrate therefrom was distilled a under reduced pressure. The resultant was treated through column chromatography (hexane:DCM (10%)), obtaining Intermediate M-9 (10.4 g, Yield: 50%).

4th Step: Synthesis of Compound 68

10 g (24.48 mmol) of Intermediate M-9, 6.17 g (22.03 mmol) of 3-Iodo-biphenyl, 0.67 g (0.73 mmol) of $Pd_2(dba)_3$, 1.49 g (3.67 mmol) of $P(t-Bu)_3$, and 2.35 g (24.48 mmol) of NaOt-Bu were suspended in 122 ml of toluene and then, stirred at 110° C. for 12 hours. When a reaction was completed, distilled water was added thereto, and the mixture was stirred for 30 minutes, extracted, and treated through column chromatography (hexane:DCM (10%)), synthesizing Compound 68 (7.96 g, Yield: 58%).

(LC/MS: theoretical value: 560.23 g/mol, measured value: 561.57 g/mol)

Synthesis Example 6: Synthesis of Compound 14

[Reaction Scheme 9]

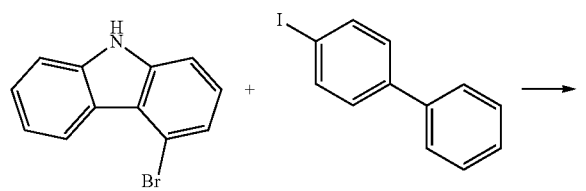

830
-continued

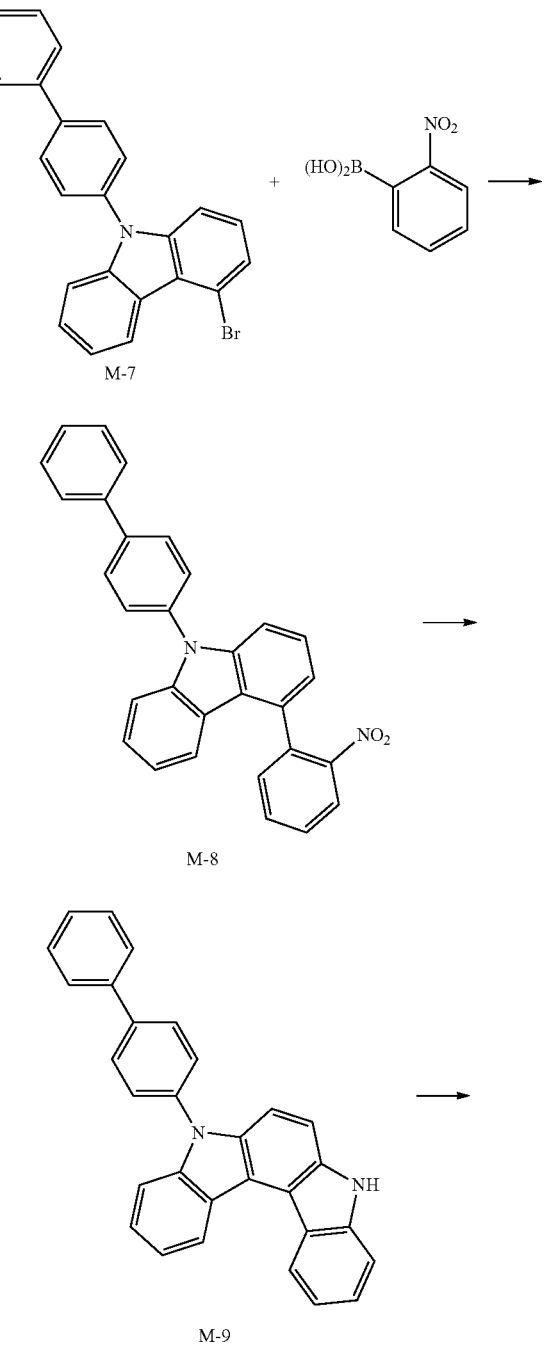

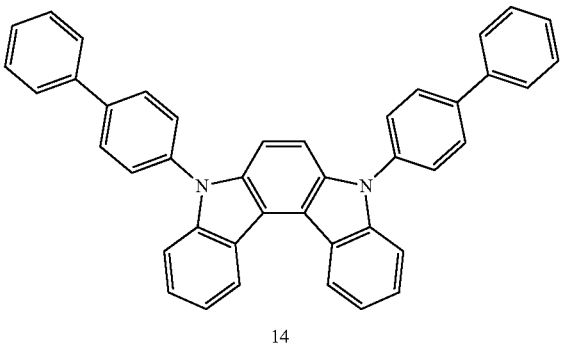 [SMILES: c1ccc(-c2ccc(-n3c4ccccc4c4c5c6ccccc6n(-c6ccc(-c7ccccc7)cc6)c5ccc43)cc2)cc1]

1st to 3rd Step: Synthesis of Compounds M-7, M-8, and M-9

A synthesis proceeded in the same method as 1 to 3 steps

4th Step: Synthesis of Compound 14

10 g (24.48 mmol) of Intermediate M-9, 6.17 g (22.03 mmol) of 4-Iodo-biphenyl, 0.67 g (0.73 mmol) of $Pd_2(dba)_3$, 1.49 g (3.67 mmol) of $P(t-Bu)_3$, and 2.35 g (24.48 mmol) of NaOt-Bu were suspended in 122 ml of toluene and then, stirred at 110° C. for 12 hours. When a reaction was completed, distilled water was added thereto, and the mixture was stirred for 30 minutes, extracted, and treated through column chromatography (hexane:DCM (10%)), synthesizing Compound 14 (7.96 g, Yield: 58%).

(LC/MS: theoretical value: 560.23 g/mol, measured value: 561.57 g/mol)

(Manufacture of Organic Light Emitting Diode)

Example 1

The glass substrate coated with 1,500 Å-thick ITO (indium tin oxide) was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 1,020 Å-thick to form a hole transport layer. On the hole transport layer, 400 Å-thick light emitting layer was formed by simultaneously using Compound 1B-4-4 of Synthesis Example 3 and Compound 68 of Synthesis Example 5 as a host and doping 10 wt % of PhGD as a dopant by a vacuum deposition. Herein, Compound 1B-4-4 and Compound 68 were used in a weight ratio of 3:7. Subsequently, on the light emitting layer, a 300 Å-thick electron transport layer was formed by simultaneously vacuum-depositing Compound D and Liq in a weight ratio of 1:1, and on the electron transport layer, Liq and Al were sequentially vacuum-deposited to be 15 Å-thick and 1,200 Å-thick, manufacturing an organic light emitting diode.

The organic light emitting diode had a five-layered organic thin layer, and specifically the following structure.

ITO/Compound A (700 Å)/Compound B (50 Å)/Compound C (1,020 Å)/EML[Compound 1B-4-4:Compound 68:PhGD (10 wt %)] (400 Å)/Compound D:Liq (300 Å)/Liq (15 Å)/Al (1,200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

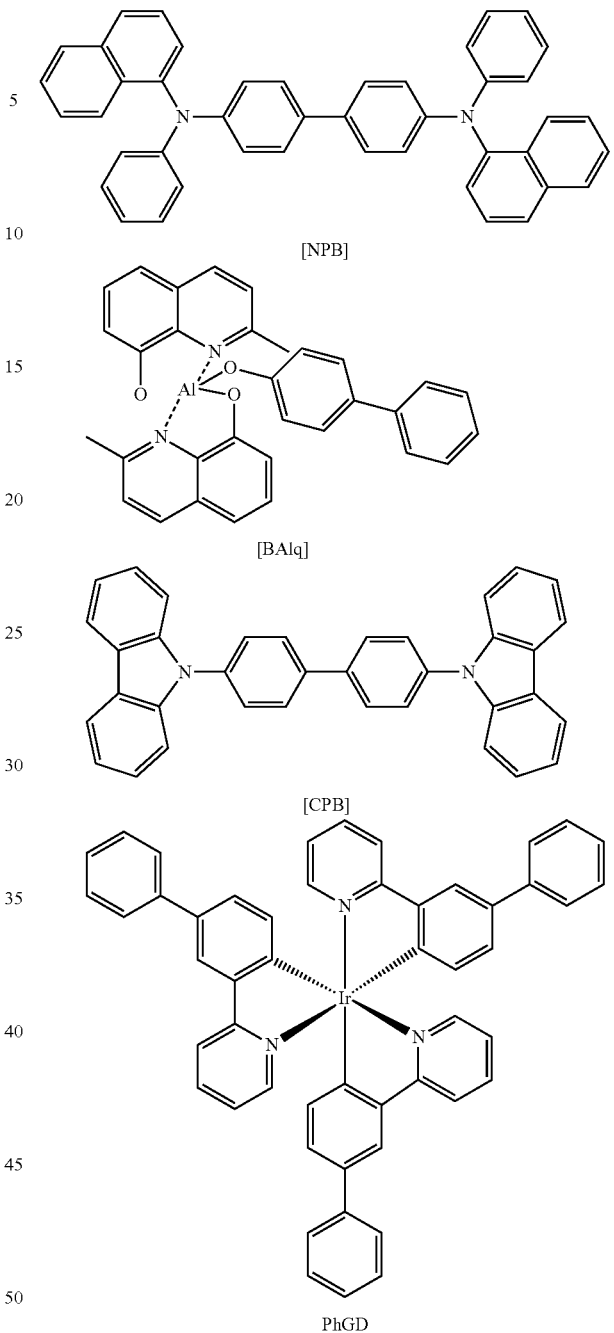

[NPB]

[BAlq]

[CPB]

PhGD

Examples 2 to 4 and Comparative Examples 1 and 2

Diodes of Example 2 and Comparative Examples 1 and 2 were manufactured in the same manner as in Example 1, except that the host was changed as shown in Tables 1 and 2.

Evaluation

Driving voltage and luminous efficiency of the organic light emitting diodes according to Examples 1 and 2 and Comparative Examples 1 and 2 were evaluated. Specific measurement methods are as follows, and the results are shown in Tables 1 and 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Luminous efficiency (cd/A) at the same current density (10 mA/cm$^2$) were calculated by using the luminance and current density from the items (1) and (2).

(4) Calculation of Luminous Efficiency Ratio (%)

The luminous efficiency ratio was evaluated relative to the luminous efficiency of Comparative Example 1 or Comparative Example 2.

(5) Measurement of Driving Voltage

A driving voltage of each diode was measured using a current-voltage meter (Keithley 2400) at 15 mA/cm$^2$.

(6) Calculation of Driving Voltage Ratio (%)

The driving voltage ratio was evaluated relative to the driving voltages of Comparative Example 1 or Comparative Example 2.

TABLE 1

| | First host | Second host | Driving voltage ratio (%) | Luminous efficiency ratio (%) |
|---|---|---|---|---|
| Example 1 | Compound 1B-4-4 | Compound 68 | 94.5 | 104.9 |
| Comparative Example 1 | Compound G-1 | Compound 68 | 100 | 100 |

TABLE 2

| | First host | Second host | Driving voltage ratio (%) | Luminous efficiency ratio (%) |
|---|---|---|---|---|
| Example 1 | Compound 1B-4-4 | Compound 68 | 93.9 | 114.1 |
| Example 2 | Compound 1B-4-3 | Compound 14 | 93.9 | 108.2 |
| Comparative Example 2 | Compound G-2 | Compound 68 | 100 | 100 |

Referring to Tables 1 and 2, the compositions according to the Examples exhibited significantly improved driving and efficiency compared with the compositions according to the Comparative Examples.

One or more embodiments may provide a composition for an organic optoelectronic device capable of implement an organic optoelectronic device having high efficiency and a long life-span.

An organic optoelectronic device having high efficiency and a long life-span may be realized.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A composition for an organic optoelectronic device, the composition comprising:
a first compound represented by a combination of Chemical Formula 1 and Chemical Formula 2, and
a second compound represented by a combination of Chemical Formula 3 and Chemical Formula 4:

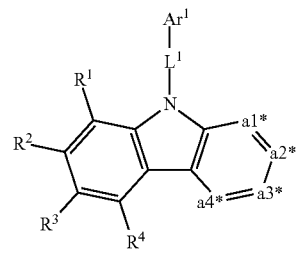

[Chemical Formula 1]

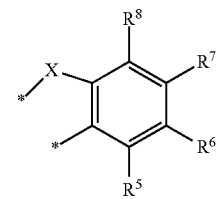

[Chemical Formula 2]

wherein, in Chemical Formula 1 and Chemical Formula 2,
X is O or S,
$Ar^1$ is a substituted or unsubstituted C6 to C30 aryl group or a substituted or unsubstituted C2 to C30 heterocyclic group,
two adjacent ones of a1* to a4* of Chemical Formula 1 are linking carbons linked at * of Chemical Formula 2, the remaining two of a1* to a4* of Chemical Formula 1, not linked at * of Chemical Formula 2, are $CR^a$,
$L^1$ is a single bond or a substituted or unsubstituted C6 to C30 arylene group,
$R^a$ and $R^1$ to $R^8$ are each independently hydrogen, deuterium, a substituted or unsubstituted C1 to C30 alkyl group, a substituted or unsubstituted C6 to C30 aryl group, or a substituted or unsubstituted C2 to C30 heterocyclic group, and
at least one of $R^5$ to $R^8$ is represented by Chemical Formula a, in which * is a linking point,

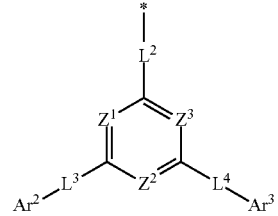

[Chemical Formula a]

wherein, in Chemical Formula a,
$Z^1$ to $Z^3$ are each independently N or $CR^b$,
at least two of $Z^1$ to $Z^3$ are N, $L^2$ to $L^4$ are each independently a single bond or a substituted or unsubstituted C6 to C30 arylene group, $Ar^2$ and $Ar^3$ are each independently a substituted or unsubstituted C6 to C30 aryl group or a substituted or unsubstituted C2 to C30 heterocyclic group, $R^b$ is hydrogen, deuterium, a substituted or unsubstituted C1 to C30 alkyl group, a substituted or unsubstituted C6 to C30 aryl group, or a substituted or unsubstituted C2 to C30 heterocyclic group, and is a linking point;

[Chemical Formula 3]

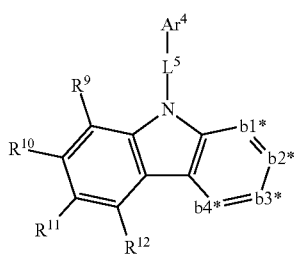

[Chemical Formula 4]

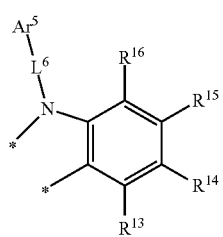

wherein, in Chemical Formula 3 and Chemical Formula 4, two adjacent ones of b1* to b4* of Chemical Formula 3 are linking carbons linked at * of Chemical Formula 4, the remaining two of b1* to b4* of Chemical Formula 3, not linked at * of Chemical Formula 4, are CRC, $Ar^4$ and $Ar^5$ are each independently a substituted or unsubstituted C6 to C30 aryl group, a substituted or unsubstituted carbazolyl group, a substituted or unsubstituted dibenzofuranyl group, or a substituted or unsubstituted dibenzothiophenyl group, $L^5$ and $L^6$ are each independently a single bond, or a substituted or unsubstituted C6 to C30 arylene group, and $R^c$ and $R^9$ to $R^{16}$ are each independently hydrogen, deuterium, a substituted or unsubstituted C1 to C30 alkyl group, or a substituted or unsubstituted C6 to C30 aryl group.

2. The composition as claimed in claim 1, wherein:
the first compound is represented by one of Chemical Formula 1A to Chemical Formula 1F:

[Chemical Formula 1A]

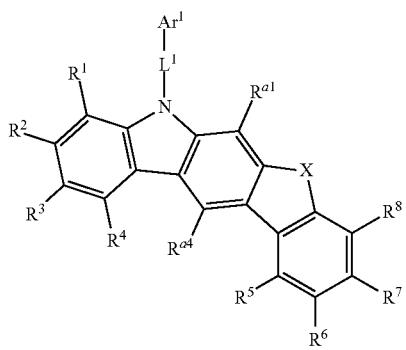

[Chemical Formula 1B]

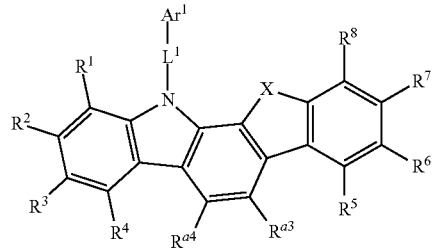

[Chemical Formula 1C]

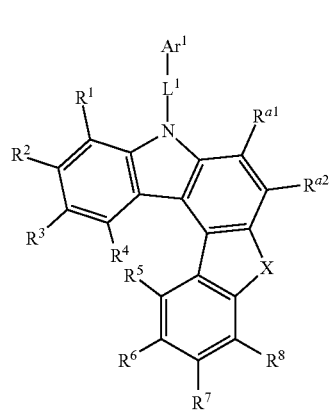

[Chemical Formula 1D]

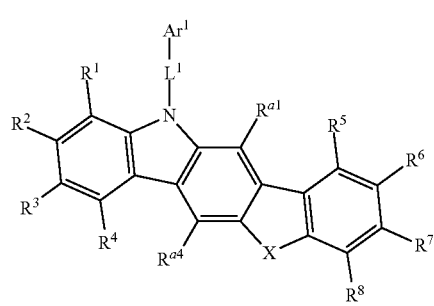

[Chemical Formula 1E]

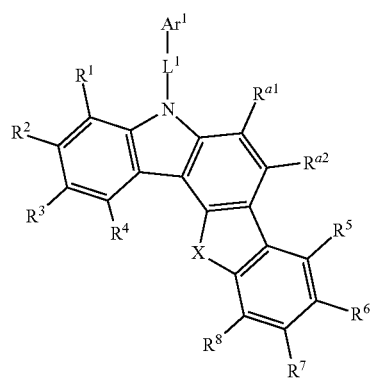

[Chemical Formula 1F]

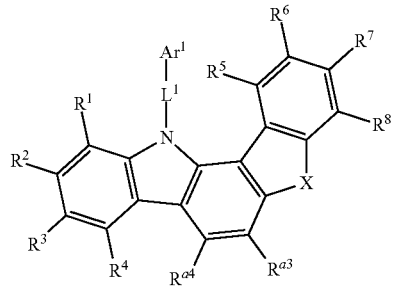

in Chemical Formula 1A to Chemical Formula 1F,
X, $L^1$, $Ar^1$, and $R^1$ to $R^8$ are defined the same as those of Chemical Formulae 1 and 2, and
$R^{a1}$ to $R^{a4}$ are each independently defined the same as $R^a$ of Chemical Formulae 1 and 2.

3. The composition as claimed in claim 1, wherein:
the first compound is represented by one of Chemical Formula 1A-1 to Chemical Formula 1A-4, Chemical Formula 1B-1 to Chemical Formula 1B-4, Chemical Formula 1C-1 to Chemical Formula 1C-4, Chemical Formula 1D-1 to Chemical Formula 1D-4, Chemical Formula 1E-1 to Chemical Formula 1E-4, and Chemical Formula 1F-1 to Chemical Formula 1F-4:

[Chemical Formula 1A-1]

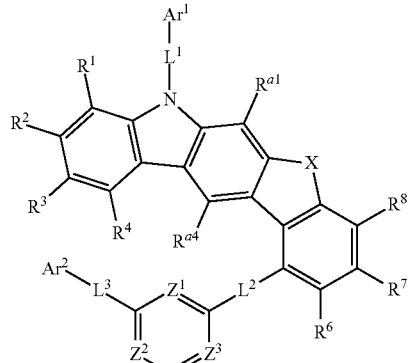

[Chemical Formula 1A-2]

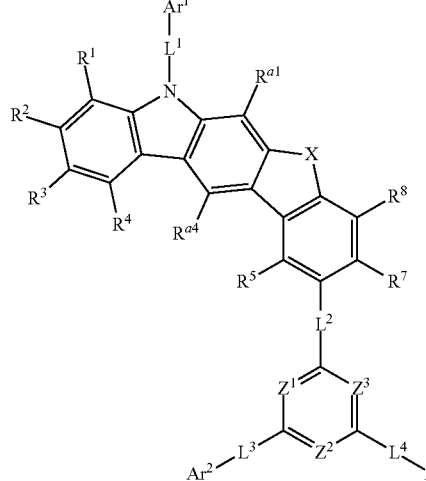

[Chemical Formula 1A-3]

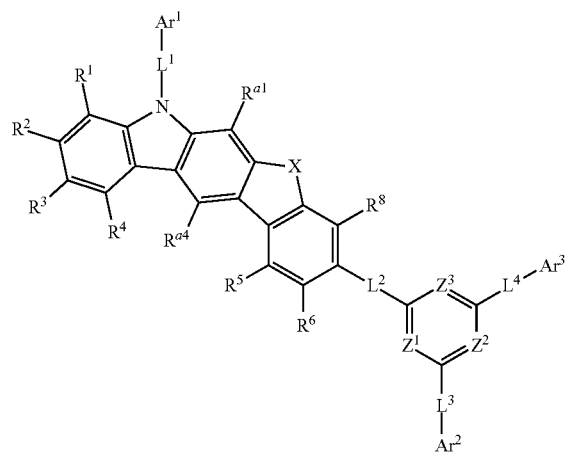

[Chemical Formula 1A-4]

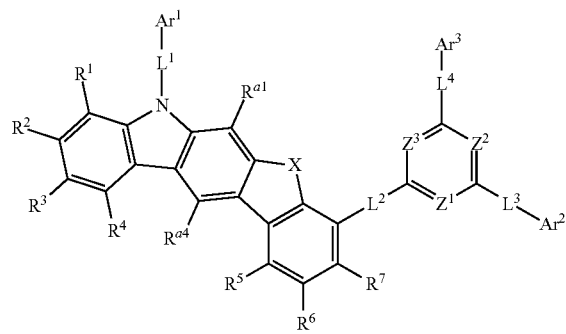

[Chemical Formula 1B-1]

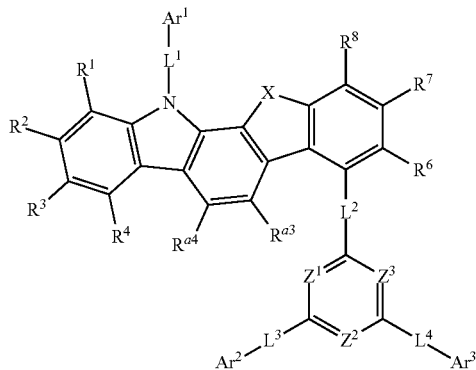

[Chemical Formula 1B-2]

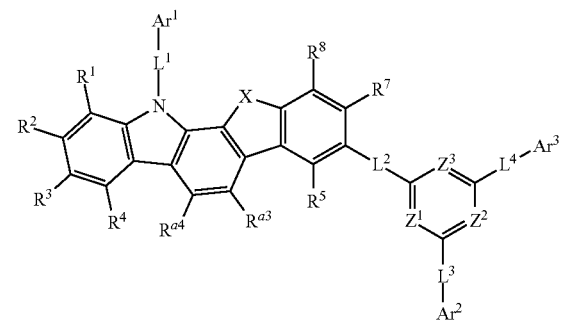

-continued
[Chemical Formula 1B-3]
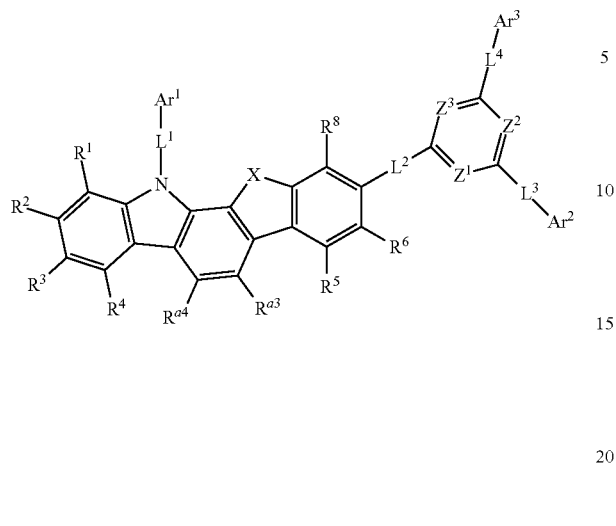
[Chemical Formula 1B-4]
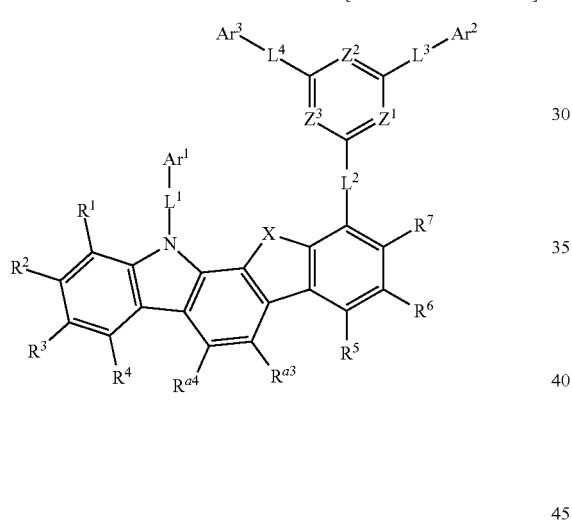
[Chemical Formula 1C-1]
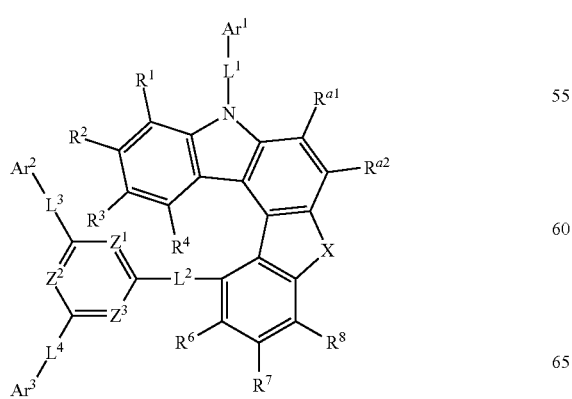
-continued
[Chemical Formula 1C-2]
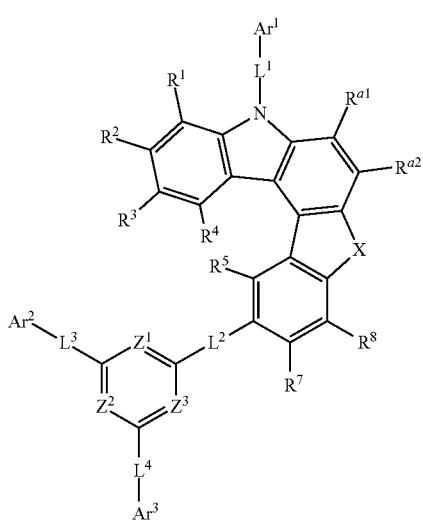
[Chemical Formula 1C-3]
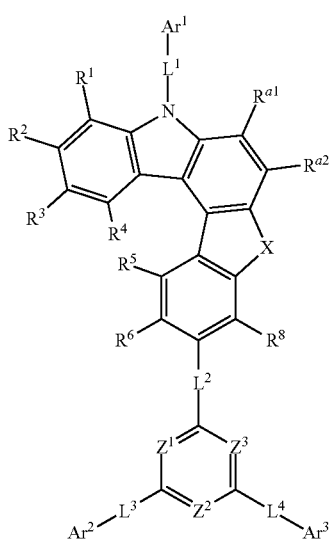
[Chemical Formula 1C-4]
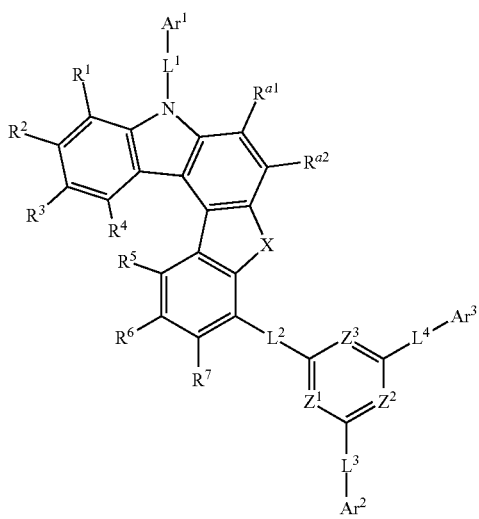

-continued
[Chemical Formula 1D-1]
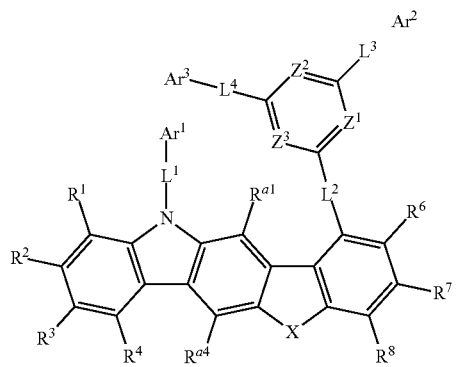
[Chemical Formula 1D-2]
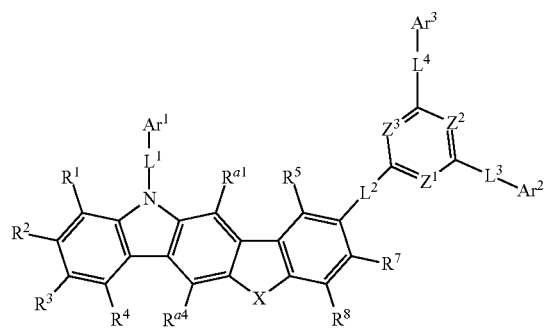
[Chemical Formula 1D-3]
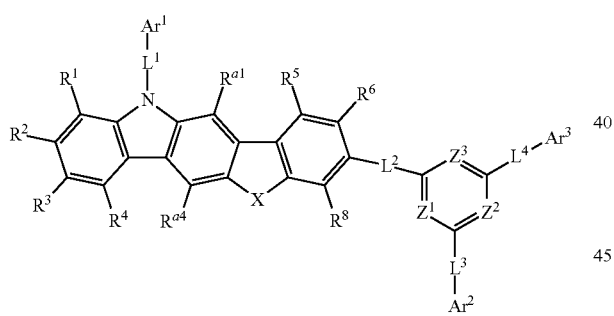
[Chemical Formula 1D-4]
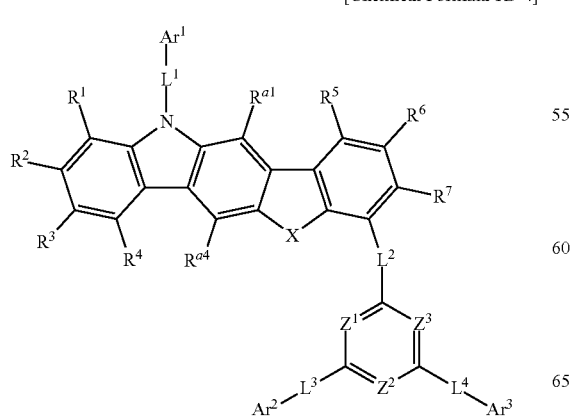
-continued
[Chemical Formula 1E-1]
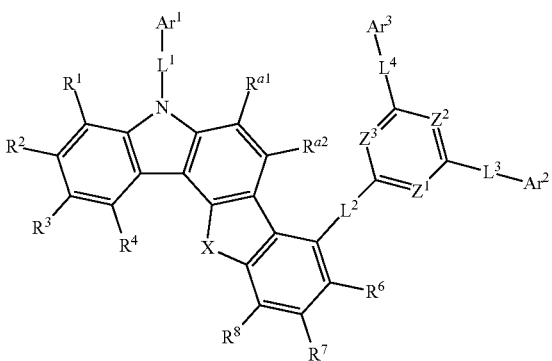
[Chemical Formula 1E-2]
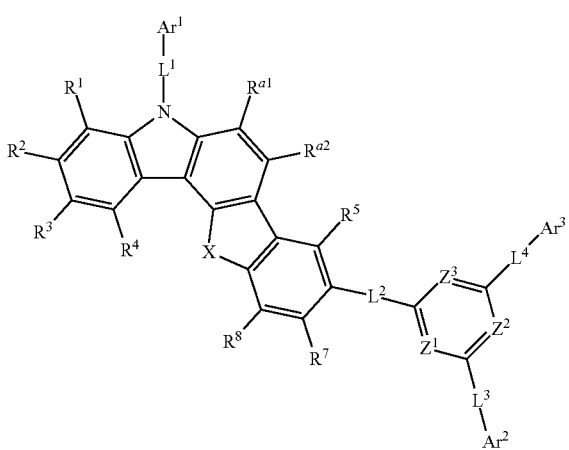
[Chemical Formula 1E-3]
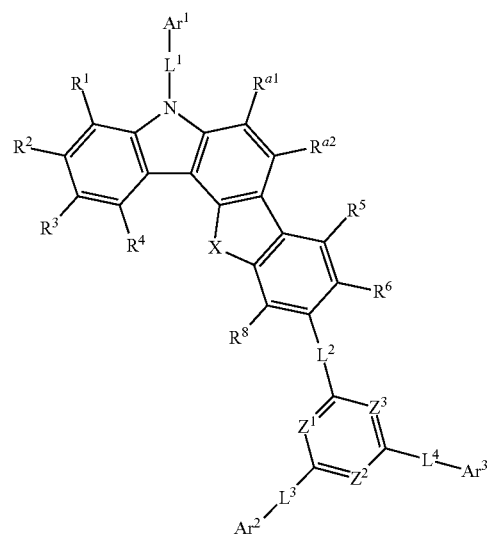

-continued

[Chemical Formula 1E-4]

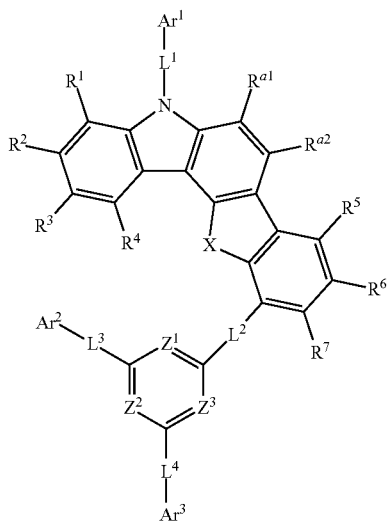

[Chemical Formula 1F-1]

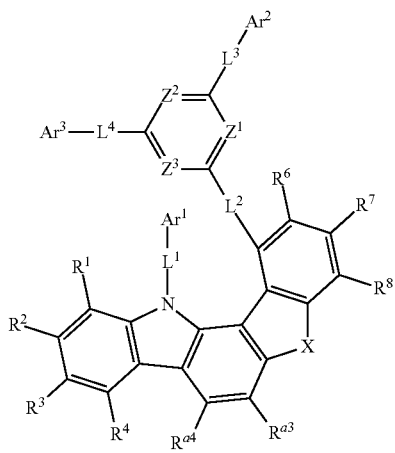

[Chemical Formula 1F-2]

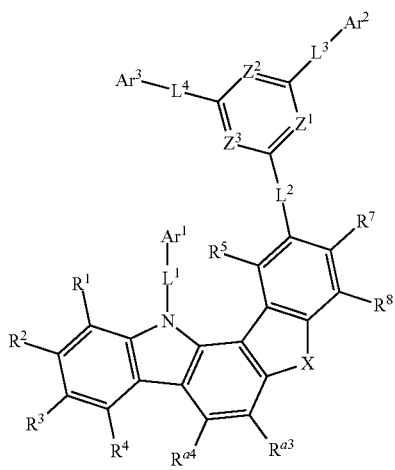

-continued

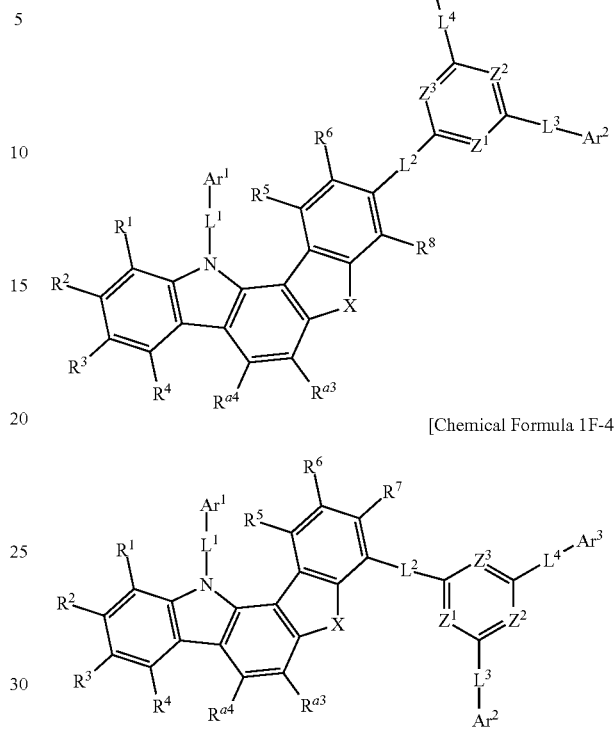

in Chemical Formula 1A-1 to Chemical Formula 1A-4, Chemical Formula 1B-1 to Chemical Formula 1B-4, Chemical Formula 1C-1 to Chemical Formula 1C-4, Chemical Formula 1D-1 to Chemical Formula 1D-4, Chemical Formula 1E-1 to Chemical Formula 1E-4, and Chemical Formula 1F-1 to Chemical Formula 1F-4, X, $Ar^1$ to $Ar^3$, $L^1$ to $L^4$ and $Z^1$ to $Z^3$ are defined the same as those of Chemical Formulae 1 and 2, and $R^{a1}$ to $R^{a4}$ and $R^1$ to $R^8$ are each independently hydrogen, deuterium, a substituted or unsubstituted C1 to C30 alkyl group, a substituted or unsubstituted C6 to C30 aryl group or a substituted or unsubstituted C2 to C20 heterocyclic group.

4. The composition as claimed in claim 1, wherein:

$Ar^1$ is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group or a substituted or unsubstituted fluorene group, and $Ar^2$ and $Ar^3$ are each independently a substituted or unsubstituted phenyl group, a substituted or unsubstituted biphenyl group, a substituted or unsubstituted terphenyl group, a substituted or unsubstituted fluorene group, a substituted or unsubstituted dibenzofuranyl group, a substituted or unsubstituted dibenzothiophenyl group, a substituted or unsubstituted carbazolyl group, or a substituted or unsubstituted pyridinyl group.

5. The composition as claimed in claim 1, wherein:
Chemical Formula a is a group of the following Group I,
[Group I]
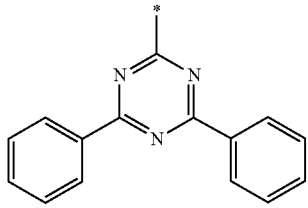
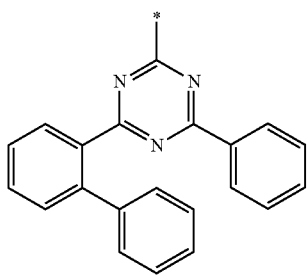
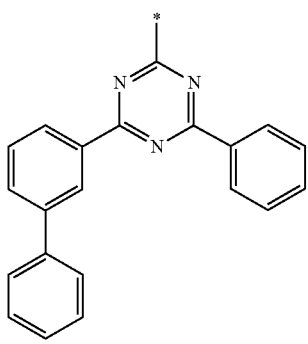
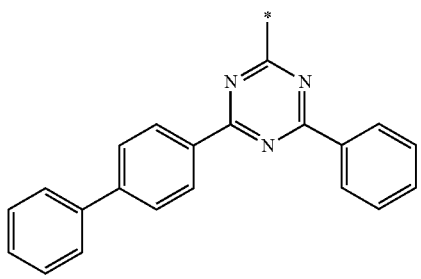
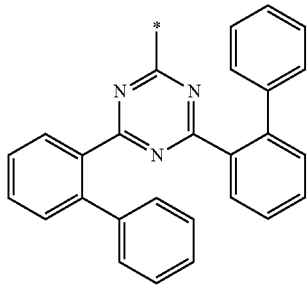
-continued
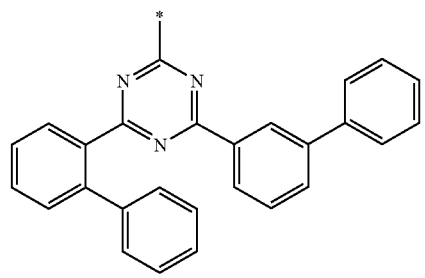
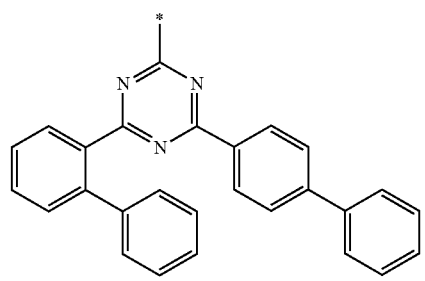
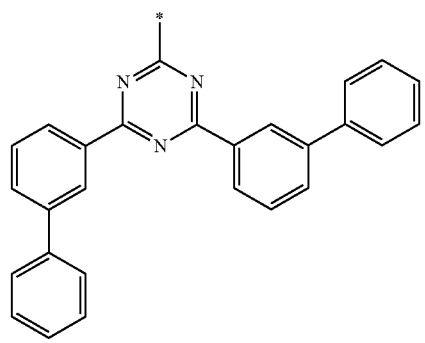
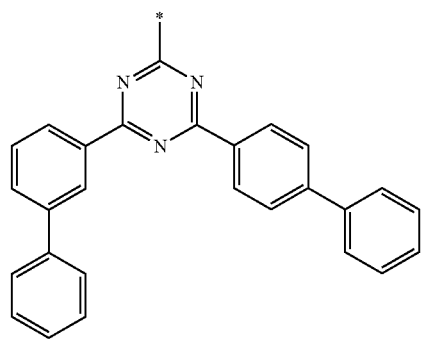
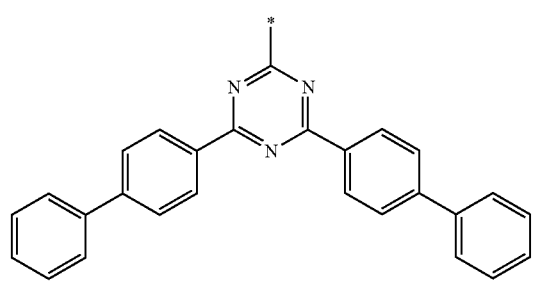

-continued
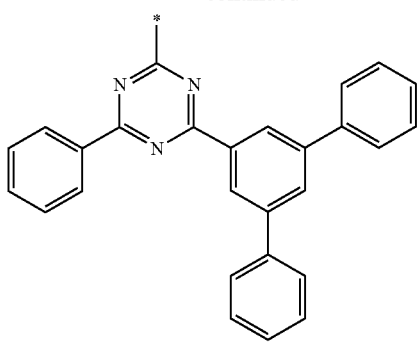
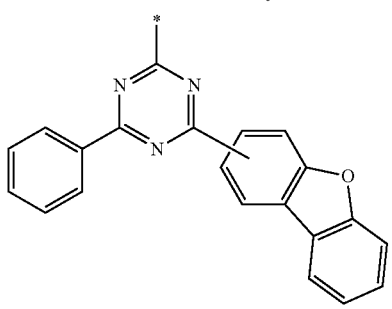
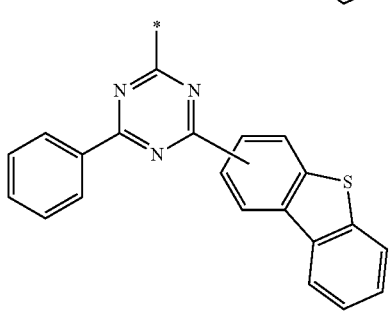
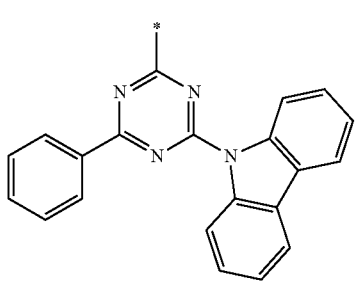
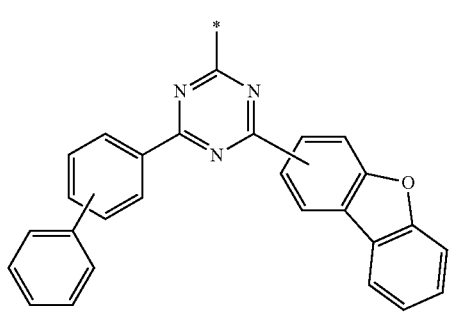
-continued
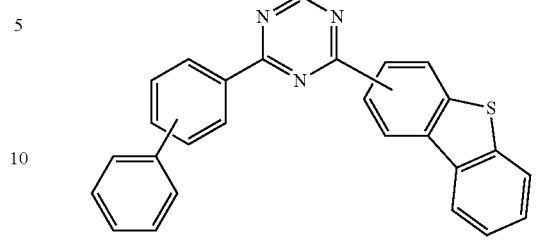
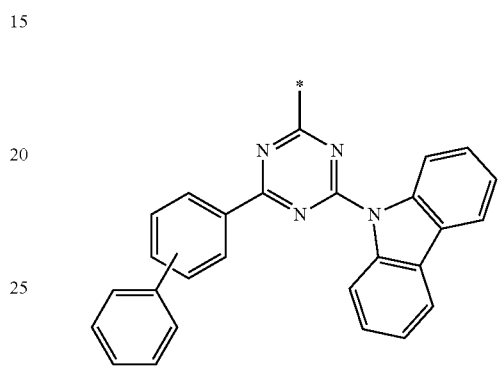
in Group I, * is a linking point.
6. The composition as claimed in claim 1, wherein:
the second compound is represented by one of Chemical Formula 3A to Chemical Formula 3E:
[Chemical Formula 3A]
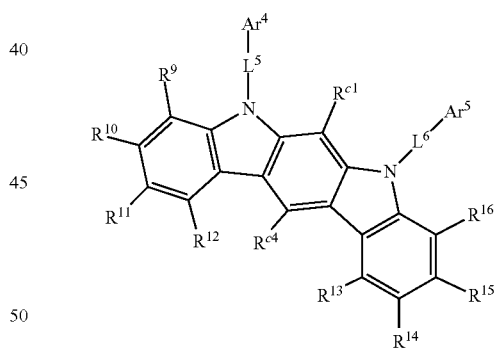
[Chemical Formula 3B]
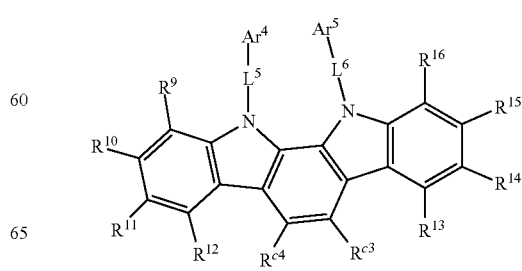

[Chemical Formula 3C]

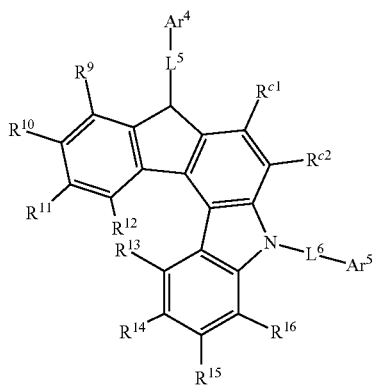

[Chemical Formula 3D]

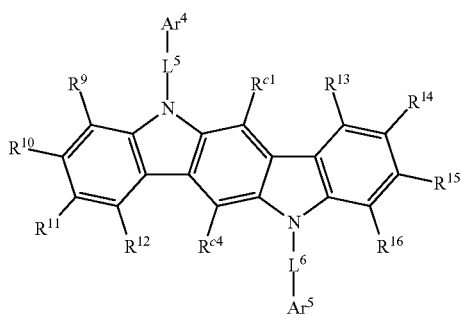

[Chemical Formula 3E]

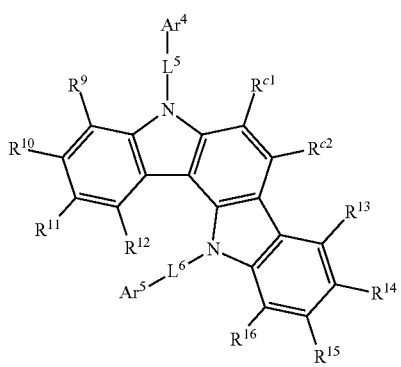

in Chemical Formula 3A to Chemical Formula 3E, $Ar^4$, $Ar^5$, $L^5$, $L^6$, and $R^9$ to $R^{16}$ are defined the same as those of Chemical Formulae 3 and 4, and $R^{c1}$ to $R^{c4}$ are each independently defined the same as $R^c$ of Chemical Formulae 3 and 4.

7. The composition as claimed in claim 1, wherein:

$L^5$ and $L^6$ are each independently a single bond, or a substituted or unsubstituted phenylene group, and $Ar^4$ and $Ar^5$ are each independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylene group.

8. The composition as claimed in claim 1, wherein:

moieties *-$L^5$-$Ar^4$ and *-$L^6$-$Ar^5$ of Chemical Formula 3 and Chemical Formula 4 are each independently a moiety of Group II,

[Group II]

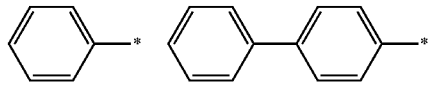

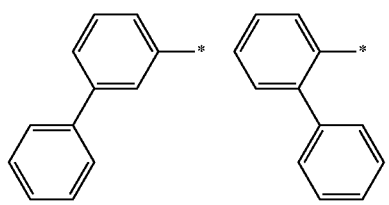

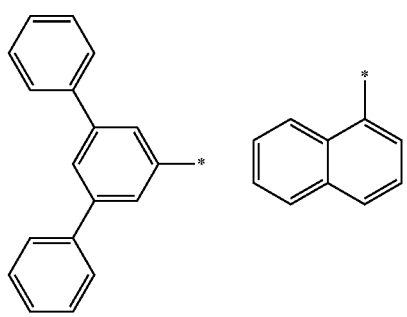

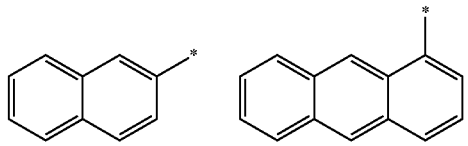

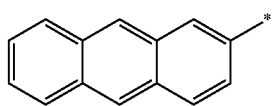

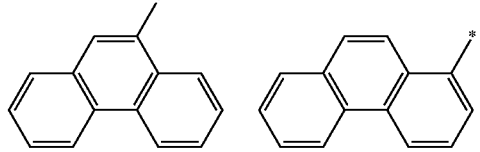

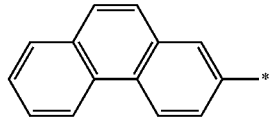

-continued

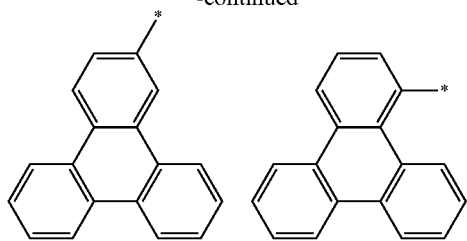

in Group II, * is a linking point.

9. The composition as claimed in claim 1, wherein:
the first compound is represented by Chemical Formula 1B-4A, and
the second compound is represented by Chemical Formula 3C-I:

[Chemical Formula 1B-4A]

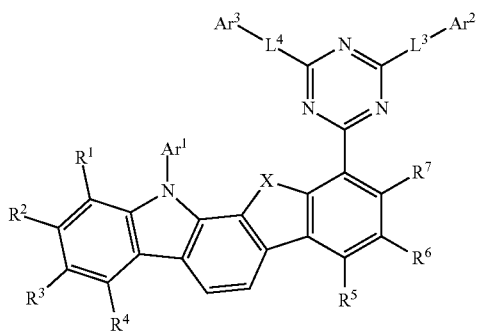

in Chemical Formula 1B-4A, $Ar^1$ to $Ar^3$ are each independently a substituted or unsubstituted phenyl group or a substituted or unsubstituted biphenyl group, X is O or S $L^3$ and $L^4$ are each independently a single bond or a substituted or unsubstituted phenylene group, and $R^1$ to $R^7$ are each independently hydrogen, deuterium, a substituted or unsubstituted C1 to C5 alkyl group or a substituted or unsubstituted C6 to C12 aryl group;

[Chemical Formula 3C-I]

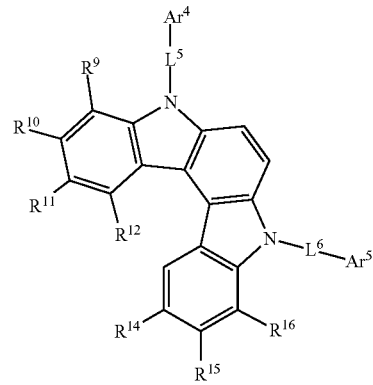

in Chemical Formula 3C-I, $Ar^4$ and $Ar^5$ are each independently a substituted or unsubstituted phenyl group or a substituted or unsubstituted biphenyl group, $L^5$ and $L^6$ are each independently a single bond or a substituted or unsubstituted phenylene group, and $R^9$ to $R^{16}$ are each independently hydrogen, deuterium, a substituted or unsubstituted C1 to C5 alkyl group or a substituted or unsubstituted C6 to C12 aryl group.

10. An organic optoelectronic device, comprising:
an anode and a cathode facing each other,
at least one organic layer between the anode and the cathode,
wherein:
the at least one organic layer includes a light emitting layer,
the light emitting layer includes the composition for an organic optoelectronic device as claimed in claim 1.

11. The organic optoelectronic device as claimed in claim 10, wherein the composition for an organic optoelectronic device is a host in the light emitting layer.

12. The organic optoelectronic device as claimed in claim 11, wherein the composition for an organic optoelectronic device includes the first compound and the second compound in a weight ratio of about 90:10 to about 10:90.

13. The organic optoelectronic device as claimed in claim 11, wherein the light emitting layer further includes a phosphorescent dopant.

14. A display device comprising the organic optoelectronic device as claimed in claim 10.

* * * * *